United States Patent
Balog et al.

(10) Patent No.: US 9,790,169 B2
(45) Date of Patent: Oct. 17, 2017

(54) IDO INHIBITORS

(71) Applicant: BRISTOL-MYERS SQUIBB COMPANY, Princeton, NJ (US)

(72) Inventors: James Aaron Balog, Lambertville, NJ (US); Emily Charlotte Cherney, Newtown, PA (US); Weiwei Guo, Lawrenceville, NJ (US); Audris Huang, New Hope, PA (US); Jay A. Markwalder, Lahaska, PA (US); Steven P. Seitz, Swarthmore, PA (US); Weifang Shan, Princeton, NJ (US); David K. Williams, Delran, NJ (US); Natesan Murugesan, Princeton Junction, NJ (US); Susheel Jethanand Nara, Bangalore (IN); Saumya Roy, Bangalore (IN); Soodamani Thangavel, Krishnagiri (IN); Ramesh Kumar Sistla, Bangalore (IN); Srinivas Cheruku, Bangalore (IN); Srinivasan Thangathirupathy, Hosur (IN); Yadagiri Kanyaboina, Bangalore (IN); Nagalakshmi Pulicharla, Bangalore (IN)

(73) Assignees: Bristol-Myers Squibb Company, Princeton, NJ (US); Syngene International Limited, Bangalore, Karnataka (IN); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/088,211

(22) Filed: Apr. 1, 2016

(65) Prior Publication Data
US 2016/0289171 A1 Oct. 6, 2016

Related U.S. Application Data

(60) Provisional application No. 62/142,589, filed on Apr. 3, 2015.

(51) Int. Cl.
| | | |
|---|---|---|
| *C07C 229/42* | (2006.01) | |
| *A61K 31/17* | (2006.01) | |
| *A61K 31/196* | (2006.01) | |
| *A61K 31/277* | (2006.01) | |
| *A61K 31/351* | (2006.01) | |
| *A61K 31/382* | (2006.01) | |
| *A61K 31/397* | (2006.01) | |
| *A61K 31/428* | (2006.01) | |
| *A61K 31/437* | (2006.01) | |
| *A61K 31/445* | (2006.01) | |
| *A61K 31/501* | (2006.01) | |
| *A61K 31/505* | (2006.01) | |
| *A61K 31/506* | (2006.01) | |
| *A61K 31/519* | (2006.01) | |
| *A61K 31/5375* | (2006.01) | |

(Continued)

(52) U.S. Cl.
CPC ............ *C07C 229/42* (2013.01); *A61K 31/17* (2013.01); *A61K 31/196* (2013.01); *A61K 31/277* (2013.01); *A61K 31/351* (2013.01); *A61K 31/382* (2013.01); *A61K 31/397* (2013.01); *A61K 31/428* (2013.01); *A61K 31/437* (2013.01); *A61K 31/445* (2013.01); *A61K 31/501* (2013.01); *A61K 31/505* (2013.01); *A61K 31/506* (2013.01); *A61K 31/519* (2013.01); *A61K 31/538* (2013.01); *A61K 31/5375* (2013.01); *A61K 31/5377* (2013.01); *A61K 39/3955* (2013.01); *C07C 235/38* (2013.01); *C07C 235/56* (2013.01); *C07C 255/57* (2013.01); *C07C 255/58* (2013.01); *C07C 275/40* (2013.01); *C07D 205/04* (2013.01); *C07D 207/08* (2013.01); *C07D 211/08* (2013.01); *C07D 211/14* (2013.01); *C07D 239/47* (2013.01); *C07D 265/30* (2013.01); *C07D 265/36* (2013.01); *C07D 277/64* (2013.01); *C07D 295/155* (2013.01); *C07D 307/22* (2013.01); *C07D 309/04* (2013.01); *C07D 309/14* (2013.01); *C07D 335/02* (2013.01); *C07D 401/12* (2013.01); *C07D 405/12* (2013.01); *C07D 405/14* (2013.01); *C07D 407/12* (2013.01); *C07D 409/12* (2013.01); *C07D 413/12* (2013.01); *C07D 417/12* (2013.01); *C07D 471/04* (2013.01); *C07D 487/04* (2013.01); *C07D 487/08* (2013.01)

(58) Field of Classification Search
None
See application file for complete search history.

(56) References Cited

FOREIGN PATENT DOCUMENTS

| EP | 2 009 005 A1 | 12/2008 |
|---|---|---|
| WO | WO03/099276 A1 | 12/2003 |

(Continued)

OTHER PUBLICATIONS

Pinedo et al. (2000).*

(Continued)

*Primary Examiner* — Paul V Ward
(74) *Attorney, Agent, or Firm* — Serena Farquharson-Torres; Maureen S. Gibbons

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

27 Claims, No Drawings

(51) Int. Cl.

| | | |
|---|---|---|
| A61K 31/5377 | (2006.01) | |
| A61K 31/538 | (2006.01) | |
| A61K 39/395 | (2006.01) | |
| C07C 255/58 | (2006.01) | |
| C07C 275/40 | (2006.01) | |
| C07D 205/04 | (2006.01) | |
| C07D 211/14 | (2006.01) | |
| C07D 239/47 | (2006.01) | |
| C07D 265/36 | (2006.01) | |
| C07D 277/64 | (2006.01) | |
| C07D 295/155 | (2006.01) | |
| C07D 309/04 | (2006.01) | |
| C07D 335/02 | (2006.01) | |
| C07D 401/12 | (2006.01) | |
| C07D 405/12 | (2006.01) | |
| C07D 405/14 | (2006.01) | |
| C07D 409/12 | (2006.01) | |
| C07D 413/12 | (2006.01) | |
| C07D 417/12 | (2006.01) | |
| C07D 471/04 | (2006.01) | |
| C07D 487/04 | (2006.01) | |
| C07D 309/14 | (2006.01) | |
| C07D 407/12 | (2006.01) | |
| C07D 487/08 | (2006.01) | |
| C07D 265/30 | (2006.01) | |
| C07D 207/08 | (2006.01) | |
| C07D 211/08 | (2006.01) | |
| C07D 307/22 | (2006.01) | |
| C07C 255/57 | (2006.01) | |
| C07C 235/38 | (2006.01) | |
| C07C 235/56 | (2006.01) | |

(56) References Cited

FOREIGN PATENT DOCUMENTS

| | | |
|---|---|---|
| WO | WO2005/030705 A1 | 4/2005 |
| WO | WO2006/029879 A2 | 3/2006 |
| WO | WO2006/105021 A2 | 10/2006 |
| WO | WO2006/122150 A1 | 11/2006 |
| WO | WO2007/005874 A2 | 1/2007 |
| WO | WO2007/075598 A2 | 7/2007 |
| WO | WO2008/036642 A2 | 3/2008 |
| WO | WO2008/036653 A2 | 3/2008 |
| WO | WO2008/132601 A1 | 11/2008 |
| WO | WO2009/009116 A2 | 1/2009 |
| WO | WO2009/044273 A2 | 4/2009 |
| WO | WO2009/073620 A2 | 6/2009 |
| WO | WO2010/019570 A2 | 2/2010 |
| WO | WO2010/077634 A1 | 7/2010 |
| WO | WO2011/028683 A1 | 3/2011 |
| WO | WO2011/056652 A1 | 5/2011 |
| WO | WO2011/070024 A1 | 6/2011 |
| WO | WO2011/107553 A1 | 9/2011 |
| WO | WO2011/109400 A2 | 9/2011 |
| WO | WO2011/131407 A1 | 10/2011 |
| WO | WO2011/140249 A2 | 11/2011 |
| WO | WO2012/032433 A1 | 3/2012 |
| WO | WO2012/142237 A1 | 10/2012 |
| WO | WO2012/145493 A1 | 10/2012 |
| WO | WO2013/079174 A1 | 6/2013 |
| WO | WO2013/087699 A1 | 6/2013 |
| WO | WO2013/119716 A1 | 8/2013 |
| WO | WO2013/132044 A1 | 9/2013 |
| WO | WO2013/169264 A1 | 11/2013 |
| WO | WO2014/008218 A1 | 1/2014 |
| WO | WO2014/036357 A1 | 3/2014 |
| WO | WO2014/150646 A1 | 9/2014 |
| WO | WO2014/150677 A1 | 9/2014 |

OTHER PUBLICATIONS

McMahon et al. (2000).*
Allen, L.V. Jr. et al., Remington: The Science and Practice of Pharmacy (2 Volumes) 22,d Edition (2012) Pharmaceutical Press.
Bundgaard, Hans, Editor, Design of Prodrugs, Elsevier (1985).
Bundgaard, Hans, "Means to Enhance Penetration, Prodrugs as a means to improve the delivery of peptide drugs", Advanced Drug Delivery Reviews, vol. 8, pp. 1-38 (1992).
Bundgaard, Hans, Editor, Chapter 5, "Design and Application of Prodrugs", A Textbook of Drug Design and Development, pp. 113-119 (1991).
Goldstein, N. et al., "Biological Efficacy of a Chimeric Antibody to the Epidermal Growth Factor Receptor in a Human Tumor Xenograft Model", Clinical Cancer Research, vol. 1, pp. 1311-1318 (1995).
Greene, T.W. et al., Protective Groups in Organic Synthesis, Third Edition, Wiley-Interscience, NY (1999).
Gross, E., The Peptides: Analysis, Synthesis, Biology, vol. 3, Academic Press, NY (1981).
Han, So-Yeop et al., "Recent development of peptide coupling reagents in organic synthesis", Tetrahedron. vol. 60, pp. 2447-2467 (2004).
Hayashi, T. et al., "Catalytic Cycle of Rhodium-Catalyzed Asymmetric 1,4-Addition of Organoboronic Acids. Arylrhodium, oxa-π-allylrhodium, and Hydroxorhodium Intermediates", J. Am. Chem Society, vol. 124, pp. 5052-5058 (2002).
House, H.O., Modern Synthetic Reactions, Second Edition, W.A. Benjamin Inc., Menlo Park CA, (1972).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Phar. Bull., vol. 32(2), pp. 692-698 (1984).
Katritzky, Alan R. et al. Eds. Comprehensive Organic Functional Group Transformations, Elsevier Science Inc Tarrytown NY 1995.
King, Frank, Editor, Medicinal Chemistry: Principles and Practice (2006).
Kohl, Nancy E. et al., "Inhibition of farnesyltransferase induces regression of mammary and salivary carcinomas in ras transgenic mice",Nature Medicine, vol. 1(8), pp. 792-797 (1995).
Larock, R.C., Comprehensive Organic Transformations, VCH Publishers, Inc. NY (1989).
March, J., Advanced Organic Chemistry: Reactions, Mechanisms, and Structure, Fourth Edition, New York, NY (1992).
Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77(4), p. 285 (1988).
Rautio, J. (Editor). Prodrugs and Targeted Delivery (Methods and Principles in Medicinal Chemistry), vol. 47, Wiley-VCH, (2011).
Sausville, Edward A., "Cyclin-Dependent Kinase Modulators Studied at the NCI: Pre-Clinical and Clinical Studies", Current Med. Chemistry-Anti-Cancer Agents, vol. 3, pp. 47-56 (2003).
Scheller, B. et al., "Paclitaxel Balloon Coating, a Novel Method for Prevention and Therapy of Restenosis", Circulation, vol. 110, pp. 810-814 (2004).
Sekulić, A. et al., "A Direct Linkage between the Phosphoinositide 3-Kinase-AKT Signaling Pathway and the Mammalian Target of Rapamycin in Mitogen-stimulated and Transformed Cells", Cancer Research, vol. 60, pp. 3504-3513 (2000).
Smith, M.B. et al., "March's Advanced Organic Chemistry Reactions, Mechanisms, and Structure", Fifth Edition, Wiley-Interscience, NY (2001.
Surry, D.S. et al., "Dialkylbiaryl phosphines in Pd-catalyzed amination: a user's guide", Chemical Science, vol. 2, pp. 2-50 (2011).
Testa, B. et al., Hydrolysis in Drug and Prodrug Metabolism, Chemistry, Biochemistry and Enzymology, VCHA and Wiley-VCH, Zurich, Switzerland (2003).
Trost, B.M.et al., eds., Comprehensive Organic Synthesis: Selectivity, Strategy & Efficiency in Modern Organic Chemistry, New York, NY (1991).

(56) References Cited

OTHER PUBLICATIONS

Vlahos, C. et al., "A Specific Inhibitor of Phosphatidylinositol 3-Kinase, 2-(4-Morpholinyl)-8-phenyl-4H-1-benzopyran-4-one (LY294002)", The J. of Biological Chemistry, vol. 269(7), pp. 5241-5248 (1994).
Wermuth, C.G. (Editor), *The Practice Medicinal Chemistry*, 3$^{rd}$ Edition, Academic Press, San Diego, CA (2008).
Widder, K. et al., Editor, *"Methods in Enzymology"*, vol. 112, pp. 309-396, Academic Press, (1985).
Wuts, P.G.M. and Greene, T. W. *Protecting Groups in Organic Synthesis*, 4th Edition, Wiley (2007).
CAPLUS—XP002757849, Xiang, Yuhong et al., "Studied on benzamide hydroxamic acid histone deacetylase inhibitors (HDAC) by molecular docking and CoMFA", Database accession No. 2010:152919.
CAPLUS—XP002757850, Rodrigues, Tiago et al., De novo design and optimization of Aurora A Kinase inhibitors, Database accession No. 2013:196001.

\* cited by examiner

IDO INHIBITORS

CROSS-REFERENCE TO RELATED APPLICATIONS

This application claims priority to U.S. Provisional Application Ser. No. 62/142,589, filed Apr. 3, 2015, the entire content of which is incorporated herein by reference.

FIELD OF THE INVENTION

The invention relates generally to compounds that modulate or inhibit the enzymatic activity of indoleamine-2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. Indoleamine-2,3-dioxygenase is a heme-containing intracellular enzyme that catalyzes the first and rate-determining step in the degradation of the essential amino acid L-tryptophan to N-formyl-kynurenine. N-formyl-kynurenine is then metabolized by multiple steps to eventually produce nicotinamide adenine dinucleotide (NAD+). Tryptophan catabolites produced from N-formyl-kynurenine, such as kynurenine, are known to be preferentially cytotoxic to T-cells. Thus, an overexpression of IDO can lead to increased tolerance in the tumor microenvironment. IDO overexpression has been shown to be an independent prognostic factor for decreased survival in patients with melanoma, pancreatic, colorectal and endometrial cancers, among others. Moreover, IDO has been found to be implicated in neurologic and psychiatric disorders including mood disorders as well as other chronic diseases characterized by IDO activation and tryptophan depletion, such as viral infections, for example, AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting the enzymatic function of IDO would be a most welcomed addition to the physician's armamentarium.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds. Compounds of the present invention have the following Formula I:

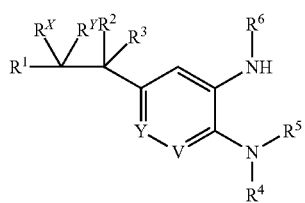

(I)

wherein:
Y is N, CH or CF;
V is N, CH or CF;
$R^1$ is —COOH, —COO$C_1$-$C_6$ alkyl, —CONH$_2$, —CN, optionally substituted heterocyclyl, optionally substituted heteroaryl, —NHCONHR$^{13}$, —CONHSO$_2$R$^{14}$, —CONHCOR$^{13}$, —SO$_2$NHCOR$^{13}$, —CONHSO$_2$NR$^{13}$R$^{14}$, —SO$_2$NHR$^{13}$, —NHCONHSO$_2$R$^{13}$, —CHCF$_3$OH, —COCF$_3$, —CR$^2$R$^3$OH, or —NHSO$_2$R$^{13}$;

$R^{13}$ is H, optionally substituted $C_1$-$C_{10}$ alkyl, optionally substituted $C_3$-$C_8$ cycloalkyl, optionally substituted $C_2$-$C_{10}$ alkenyl, optionally substituted $C_2$-$C_{10}$ alkynyl, optionally substituted heterocyclyl, optionally substituted phenyl, or optionally substituted heteroaryl;

$R^{14}$ is H, optionally substituted $C_1$-$C_{10}$ alkyl, phenyl, or $C_{3-8}$ cycloalkyl, $R^2$ and $R^3$ are independently -hydrogen, optionally substituted $C_1$-$C_{10}$ alkyl, optionally substituted $C_{3-8}$ cycloalkyl, or optionally substituted phenyl; or $R^2$ and $R^3$ are taken together with the carbon to which they are attached to form an optionally substituted 3- to 6-membered carbocyclic or heterocyclic ring;

$R^4$ and $R^5$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, optionally substituted $C_3$-$C_8$ cycloalkyl or optionally substituted heterocyclyl; or $R^4$ and $R^5$ are taken together with the nitrogen to which they are attached to form a 4- to 8-membered optionally substituted heterocyclic ring containing 0-3 additional heteroatoms selected from —N—, —S— and —O—; or $R^4$ and $R^5$ are taken together with the nitrogen to which they are attached to form a 6- to 10-membered optionally substituted heterobicyclic ring containing 0-3 additional heteroatoms selected from —N—, —S—, and —O—;

$R^6$ is optionally substituted aryl, optionally substituted heteroaryl, optionally substituted $C_3$-$C_8$ cycloalkyl optionally substituted heterocyclyl, or —COR$^7$;

$R^7$ is optionally substituted —CR$^2$R$^3$-aryl, optionally substituted —CR$^2$R$^3$-heteroaryl, —CR$^2$R$^3$-heterocyclyl, optionally substituted aryl, optionally substituted heteroaryl, optionally substituted $C_3$-$C_8$ cycloalkyl, or optionally substituted heterocyclyl; and $R^x$ and $R^y$ are each independently H, optionally substituted $C_1$-$C_{10}$ alkyl, optionally substituted $C_1$-$C_{10}$ alkoxy, or optionally substituted $C_3$-$C_8$ cycloalkyl; or $R^x$ and $R^y$ are taken together with the carbon to which they are attached to form a 3- to 7-membered heterocyclic ring containing 0-3 additional heteroatoms selected from —N—, —S— and —O—;

and/or a stereoisomer, a tautomer or a pharmaceutically acceptable salt thereof.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

The present invention provides compounds having the following Formula I:

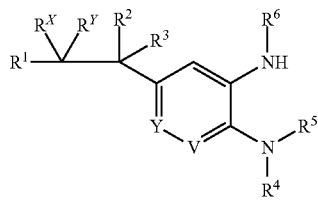

wherein:

Y is N, CH or CF;
V is N, CH or CF;
$R^1$ is —COOH, —COO$C_1$-$C_6$ alkyl, —CONH$_2$, —CN, optionally substituted heterocyclyl, optionally substituted heteroaryl, —NHCONHR$^{13}$, —CONHSO$_2$R$^{14}$, —CONHCOR$^{13}$, —SO$_2$NHCOR$^{13}$, —CONR$^{13}$, —CONHSO$_2$NR$^{13}$R$^{14}$, —SO$_2$NHR$^{13}$, —NHCONHSO$_2$R$^{13}$, —CHCF$_3$OH, —COCF$_3$, —CR$^2$R$^3$OH, or —NHSO$_2$R$^{13}$;
$R^{13}$ is H, optionally substituted $C_1$-$C_{10}$ alkyl, optionally substituted $C_3$-$C_8$ cycloalkyl, optionally substituted $C_2$-$C_{10}$ alkenyl, optionally substituted $C_2$-$C_{10}$ alkynyl, optionally substituted heterocyclyl, optionally substituted phenyl, or optionally substituted heteroaryl;
$R^{14}$ is H, optionally substituted $C_1$-$C_{10}$ alkyl, phenyl, or $C_{3-8}$ cycloalkyl;
$R^2$ and $R^3$ are independently -hydrogen, optionally substituted $C_1$-$C_{10}$ alkyl, optionally substituted $C_{3-8}$ cycloalkyl, or optionally substituted phenyl; or
$R^2$ and $R^3$ are taken together with the carbon to which they are attached to form an optionally substituted 3- to 6-membered carbocyclic or heterocyclic ring;
$R^4$ and $R^5$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, optionally substituted $C_3$-$C_8$ cycloalkyl or optionally substituted heterocyclyl; or
$R^4$ and $R^5$ are taken together with the nitrogen to which they are attached to form a 4- to 8-membered optionally substituted heterocyclic ring containing 0-3 additional heteroatoms selected from —N—, —S— and —O—; or
$R^4$ and $R^5$ are taken together with the nitrogen to which they are attached to form a 6- to 10-membered optionally substituted heterobicyclic ring containing 0-3 additional heteroatoms selected from —N—, —S—, and —O—;
$R^6$ is optionally substituted aryl, optionally substituted heteroaryl, optionally substituted $C_3$-$C_8$ cycloalkyl optionally substituted heterocyclyl, or —COR$^7$;
$R^7$ is optionally substituted —CR$^2$R$^3$-aryl, optionally substituted —CR$^2$R$^3$-heteroaryl, —CR$^2$R$^3$-heterocyclyl, optionally substituted aryl, optionally substituted heteroaryl, optionally substituted $C_3$-$C_8$ cycloalkyl, or optionally substituted heterocyclyl; and
$R^x$ and $R^y$ are each independently H, optionally substituted $C_1$-$C_{10}$ alkyl, optionally substituted $C_1$-$C_{10}$ alkoxy, or optionally substituted $C_3$-$C_8$ cycloalkyl; or
$R^x$ and $R^y$ are taken together with the carbon to which they are attached to form a 3- to 7-membered heterocyclic ring containing 0-3 additional heteroatoms selected from —N—, —S— and —O—;

and/or a stereoisomer, a tautomer or a pharmaceutically acceptable salt thereof.

According to the one embodiment of the present invention, Y is N, CH, or CF. In preferred aspects, Y is CH. In other aspects, Y is CF. In yet other aspects, Y is N.

According to one embodiment of the present invention, V is N, CH, or CF. In preferred aspects, V is CH. In other aspects, V is CF. In yet other aspects, V is N.

According to one embodiment of the present invention, $R^1$ is —COOH, —COO$C_1$-$C_6$ alkyl, —CONH$_2$, —CN, optionally substituted heterocyclyl, optionally substituted heteroaryl, —NHCONHR$^{13}$, —CONHSO$_2$R$^{14}$, —CONHCOR$^{13}$, —SO$_2$NHCOR$^{13}$, —CONR$^{13}$, —CONHSO$_2$NR$^{13}$R$^{14}$, —SO$_2$NHR$^{13}$, —NHCONHSO$_2$R$^{13}$, —CHCF$_3$OH, —COCF$_3$, —CR$^2$R$^3$OH, or —NHSO$_2$R$^{13}$. In a preferred embodiment, $R^1$ is —COOH, —COORC$_1$-$C_6$ alkyl, —CONHSO$_2$R$^{14}$, —NHSO$_2$R$^{14}$, —CHCF$_3$OH, or is selected from the group consisting of

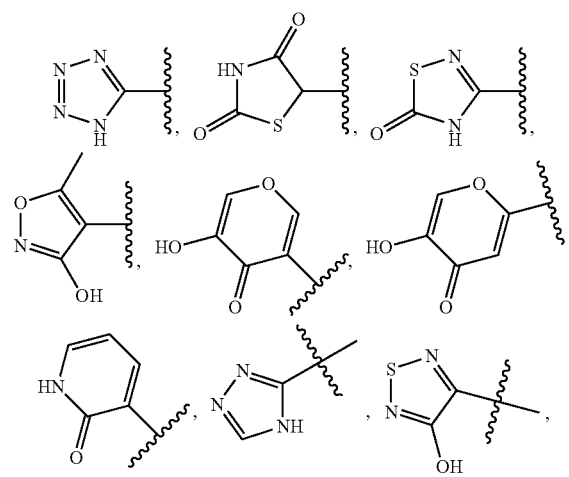

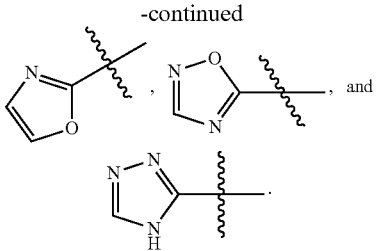

In a preferred embodiment of the present invention, is —COOH, —CONHSO$_2$R$^{14}$, —NHSO$_2$R$^{14}$, —CHCF$_3$OH,

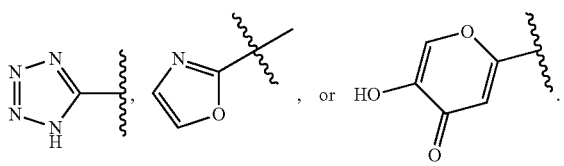

In one preferred embodiment of the present invention, R$^1$ is —COOH.

According to one embodiment of the present invention, R$^2$ is H, optionally substituted C$_1$-C$_{10}$ alkyl, optionally substituted C$_{3-6}$ cycloalkyl, optionally substituted heterocyclyl, or optionally substituted aryl. In preferred aspects, R$^2$ is H.

In other aspects, R$^2$ is C$_1$-C$_{10}$ alkyl, for example, methyl, ethyl, propyl, isopropyl, butyl, isobutyl, or t-butyl. In some aspects, R$^2$ is substituted C$_1$-C$_{10}$ alkyl, for example, substituted with 1, 2, or 3 independently selected substituents. When R$^2$ is substituted C$_1$-C$_{10}$ alkyl, the C$_1$-C$_{10}$ alkyl can be substituted with any substituent as defined herein. In preferred aspects, the substituted C$_1$-C$_{10}$ alkyl is substituted with a substituent selected from —OH, C$_{3-6}$ cycloalkyl, —OC$_{1-6}$ alkyl, —OC$_{1-6}$ haloalkyl, halo, and haloalkyl.

According to one preferred embodiment of the present invention, R$^2$ and R$^3$ are each independently H, methyl, ethyl, methoxymethyl, haloalkyl, or alkoxy.

In other aspects, R$^2$ is C$_{3-6}$ cycloalkyl, for example, cyclopropyl, cyclobutyl, cyclopentyl, or cyclohexyl. In other aspects, R$^2$ is substituted C$_{3-6}$ cycloalkyl, for example, substituted with 1, 2, or 3 independently selected substituents. When R$^2$ is substituted C$_{3-6}$ cycloalkyl the C$_{3-6}$ cycloalkyl can be substituted with any substituent as defined herein. In preferred aspects, the substituted C$_{3-6}$ cycloalkyl is substituted with a substituent selected from —OH, C$_1$-C$_{10}$ alkyl, C$_{3-6}$ cycloalkyl, —OC$_{1-6}$ alkyl, —OC$_{1-6}$ haloalkyl, halo, and haloalkyl.

In other aspects, R$^2$ is heterocyclyl. The heterocyclyl can be any heterocyclyl defined herein, with a preferred heterocyclyl being tetrahydropyranyl. In some aspects, the heterocyclyl is substituted heterocyclyl, for example, substituted with 1, 2, or 3 independently selected substituents. When R$^2$ is substituted heterocyclyl, the heterocyclyl can be substituted with any substituent as defined herein. In preferred aspects, the substituted heterocyclyl is substituted with a substituent selected from —OH, C$_1$-C$_{10}$ alkyl, C$_{3-6}$ cycloalkyl, —OC$_{1-6}$ alkyl, —OC$_{1-6}$ haloalkyl, halo, and haloalkyl.

In other aspects, R$^2$ is aryl, for example phenyl. In other aspects, R$^2$ is substituted aryl, for example, substituted with 1, 2, or 3 independently selected substituents. When R$^2$ is substituted aryl the aryl can be substituted with any substituent as defined herein. In preferred aspects, the substituted aryl is substituted with a substituent selected from —OH, C$_1$-C$_{10}$ alkyl, C$_{3-6}$ cycloalkyl, —OC$_{1-6}$ alkyl, —OC$_{1-6}$ haloalkyl, halo, and haloalkyl.

According to one aspect of the present invention, R$^3$ is H, optionally substituted C$_1$-C$_{10}$ alkyl, optionally substituted C$_{3-6}$ cycloalkyl, optionally substituted heterocyclyl, or optionally substituted aryl. In preferred aspects, R$^3$ is H.

In other aspects, R$^3$ is C$_1$-C$_{10}$ alkyl, for example, methyl, ethyl, propyl, isopropyl, butyl, isobutyl, or t-butyl. In some aspects, R$^3$ is substituted C$_1$-C$_{10}$ alkyl, for example, substituted with 1, 2, or 3 independently selected substituents. When R$^3$ is substituted C$_1$-C$_{10}$ alkyl, the C$_1$-C$_{10}$ alkyl can be substituted with any substituent as defined herein. In preferred aspects, the substituted C$_1$-C$_{10}$ alkyl is substituted with a substituent selected from —OH, C$_{3-6}$ cycloalkyl, —OC$_{1-6}$ alkyl, —OC$_{1-6}$ haloalkyl, halo, and haloalkyl.

In other aspects, R$^3$ is C$_{3-6}$ cycloalkyl, for example, cyclopropyl, cyclobutyl, cyclopentyl, or cyclohexyl. In other aspects, R$^2$ is substituted C$_{3-6}$ cycloalkyl, for example, substituted with 1, 2, or 3 independently selected substituents. When R$^3$ is substituted C$_{3-6}$ cycloalkyl the C$_{3-6}$ cycloalkyl can be substituted with any substituent as defined herein. In preferred aspects, the substituted C$_{3-6}$ cycloalkyl is substituted with a substituent selected from —OH, C$_1$-C$_{10}$ alkyl, C$_{3-6}$ cycloalkyl, —OC$_{1-6}$alkyl, —OC$_{1-6}$haloalkyl, halo, and haloalkyl.

In other aspects, R$^3$ is heterocyclyl. The heterocyclyl can be any heterocyclyl defined herein, with a preferred heterocyclyl being tetrahydropyranyl. In some aspects, the heterocyclyl is substituted heterocyclyl, for example, substituted with 1, 2, or 3 independently selected substituents. When R$^3$ is substituted heterocyclyl, the heterocyclyl can be substituted with any substituent as defined herein. In preferred aspects, the substituted heterocyclyl is substituted with a substituent selected from —OH, C$_1$-C$_{10}$ alkyl, C$_{3-6}$ cycloalkyl, —OC$_{1-6}$alkyl, —OC$_{1-6}$haloalkyl, halo, and haloalkyl.

In other aspects, R$^3$ is aryl, for example phenyl. In other aspects, R$^3$ is substituted aryl, for example, substituted with 1, 2, or 3 independently selected substituents. When R$^3$ is substituted aryl the aryl can be substituted with any substituent as defined herein. In preferred aspects, the substituted aryl is substituted with a substituent selected from —OH, C$_1$-C$_{10}$ alkyl, C$_{3-6}$ cycloalkyl, —OC$_{1-6}$alkyl, —OC$_{1-6}$haloalkyl, halo, and haloalkyl.

In alternative embodiments, R$^2$ and R$^3$ are taken together with the carbon to which they are attached to form a 3- to 6-membered carbocyclic ring, for example, R$^2$ and R$^3$ are taken together with the carbon to which they are attached to form a cyclopropyl, cyclobutyl, cyclopentyl, or cyclohexyl ring. In some embodiments, the 3- to 6-membered carbocyclic ring formed by the taking together of R$^2$ and R$^3$ is substituted, for example, with 1, 2, or 3 independently selected substituents. The 3- to 6-membered carbocyclic ring can be substituted with any substituent as defined herein. In preferred aspects, the 3- to 6-membered carbocyclic ring is substituted with a substituent selected from —OH, C$_1$-C$_{10}$ alkyl, C$_{3-6}$ cycloalkyl, —OC$_{1-6}$alkyl, —OC$_{1-6}$haloalkyl, halo, and haloalkyl.

In alternative embodiments, R$^2$ and R$^3$ are taken together with the carbon to which they are attached to form a 3- to 6-membered heterocyclic ring, for example, R$^2$ and R$^3$ are taken together with the carbon to which they are attached to form a 3- to 6-membered heterocyclic ring including at least one heteroatom selected from O, N, or S. In some embodiments, the 3- to 6-membered heterocyclic ring formed by the taking together of $R^2$ and $R^3$ is substituted, for example, with 1, 2, or 3 independently selected substituents. The 3- to 6-membered heterocyclic ring can be substituted with any substituent as defined herein. In preferred aspects, the 3- to 6-membered heterocyclic ring is substituted with a substituent selected from —OH, $C_1$-$C_{10}$ alkyl, $C_{3-6}$cycloalkyl, —$OC_{1-6}$alkyl, —$OC_{1-6}$haloalkyl, halo, and haloalkyl.

In preferred aspects, one of $R^2$ and $R^3$ is H and the other is optionally substituted $C_1$-$C_{10}$ alkyl, optionally substituted $C_{3-6}$ cycloalkyl, optionally substituted heterocyclyl, or optionally substituted aryl. In some preferred aspects, one of $R^2$ and $R^3$ is H and the other is $C_1$-$C_{10}$ alkyl, for example, methyl, ethyl, propyl, butyl, isobutyl, or t-butyl. In those embodiments wherein the $C_1$-$C_{10}$ alkyl is a substituted $C_1$-$C_{10}$ alkyl, the $C_1$-$C_{10}$ alkyl is substituted with 1 or 2 substituents independently selected from —$OC_{1-6}$alkyl (e.g., —$OCH_3$) and haloalkyl (e.g., —$CF_3$). In some preferred aspects, one of $R^2$ and $R^3$ is H and the other is $C_{3-6}$ cycloalkyl, for example cyclopropyl, cyclobutyl, cyclopentyl, cyclobutyl, cyclopenyl, or cyclohexyl. In those embodiments wherein the $C_{3-6}$ cycloalkyl is a substituted $C_{3-6}$ cycloalkyl, the $C_{3-6}$ cycloalkyl is substituted with 1 or 2 substituents independently selected from —OH, $C_1$-$C_{10}$alkyl (e.g., methyl, ethyl, and the like), —$OC_{1-6}$alkyl (e.g., —$OCH_3$), and haloalkyl (e.g., —$CF_3$).

In other preferred aspects, $R^2$ and $R^3$ are each independently $C_1$-$C_{10}$ alkyl, for example, methyl, ethyl, propyl, butyl, isobutyl, or t-butyl. In those embodiments wherein $R^2$ and $R^3$ are each independently a substituted $C_1$-$C_{10}$ alkyl, each $C_1$-$C_{10}$ alkyl is independently substituted with 1 or 2 substituents independently selected from —OH, —$OC_{1-6}$alkyl (e.g., —$OCH_3$) and haloalkyl (e.g., —$CF_3$).

According to one embodiment of the present invention, $R^4$ and $R^5$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, optionally substituted $C_3$-$C_8$ cycloalkyl or optionally substituted heterocyclyl. In one preferred embodiment, $R^4$ is optionally substituted $C_1$ to $C_6$ alkyl, optionally substituted $C_3$ to $C_6$ cycloalkyl; or selected from the group consisting of optionally substituted tetrahydropyranyl, optionally substituted azetidinyl, optionally substituted morpholinyl, optionally substituted piperidinyl, optionally substituted pyrrolidinyl, optionally substituted piperazinyl, or an optionally substituted heterocyclic ring selected from

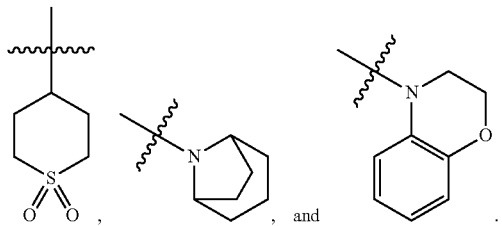 [SMILES: *C1CCS(=O)(=O)CC1 ; *N1C2CCCC1CC2 ; *N1CCOc2ccccc21]

In a preferred embodiment of the present invention, $R^4$ is optionally substituted $C_1$ to $C_6$ alkyl, such as methyl, ethyl, propyl, isopropyl, butyl, isobutyl, or isopentyl optionally substituted with hydroxyl or other substituents as described herein with respect to alkyl. In another preferred embodiment, $R^4$ is $C_3$ to $C_6$ cycloalkyl, such as cyclopropyl, cyclobutyl, or cyclohexyl, optionally substituted with 1 to 3 substituents selected from $C_1$ to $C_6$ alkyl, hydroxyl, and alkoxy, In another preferred embodiment of the present invention, $R^4$ is azetidinyl optionally substituted with up to 3 substituents selected from hydroxyl, halo, and alkoxy, such as methoxy. In one preferred embodiment of the present invention, $R^4$ is tetrahydropyranyl or morpholinyl optionally substituted with 1 to 3 $C_1$ to $C_6$ alkyl and/or phenyl. In one preferred embodiment of the present invention, $R^4$ is piperidinyl optionally substituted with 1 to 3 $C_1$ to $C_6$ alkyl, phenyl and/or benzyl. In one preferred embodiment of the present invention, $R^4$ is cyclohexyl.

According to another preferred embodiment of the present invention, $R^4$ is pyrrolidinyl optionally substituted with at least one of —OH, hydroxyalkyl, methoxyalkyl and/or haloalkyl.

According to another preferred embodiment of the present invention, $R^4$ is piperazinyl optionally substituted with at least one of $C_1$ to $C_4$ alkyl and/or —$COOR^{13}$.

In some embodiments of the present invention, $R^4$ is

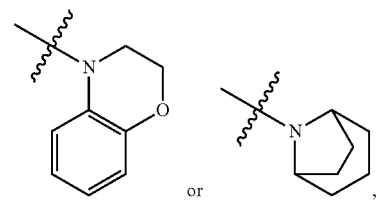

optionally substituted with phenyl, —$COOR_{13}$, alkyl, haloalkyl, or benzyl.

According to one preferred embodiment of the present invention, compounds of Formula I, as described above are presented, wherein $R^5$ is —H, optionally substituted $C_1$ to $C_6$ alkyl, or optionally substituted $C_3$ to $C_6$ cycloalkyl. In preferred embodiments, $R^5$ is H, methyl, ethyl, propyl or isobutyl. In preferred aspects, the substituted $C_1$-$C_6$ alkyl is substituted with 1, 2, or 3 substituents independently selected from —OH, $C_{3-6}$ cycloalkyl, —$OC_{1-6}$ alkyl, —$OC_{1-6}$haloalkyl, halo, and haloalkyl. In other preferred aspects, the substituted $C_1$-$C_6$ alkyl is substituted with 1 or 2 substituents independently selected from —OH, $C_{3-6}$ cycloalkyl and —$OC_{1-6}$ alkyl.

In alternative embodiments, $R^4$ and $R^5$ are taken together with the nitrogen to which they are attached to form a 4- to 8-membered heterocyclic ring containing 0-3 additional heteroatoms, preferably 1 or 2 additional heteroatoms, selected from —N—, —S— (wherein the —S— can be oxidized to SO or $SO_2$), and —O—, for example, the ring formed by the taking together of $R^4$ and $R^5$ is a pyrrolidinyl, piperidinyl, piperazinyl, morpholinyl, or thiomorpholinyl. In some aspects, the 4- to 8-membered heterocyclic ring is substituted, for example, substituted with 1, 2, or 3 independently selected substituents. The substituents can be any substituent defined herein. In preferred aspects, the substituted 4- to 8-membered heterocyclic ring is substituted with a substituent selected from —OH, $C_1$-$C_6$ alkyl, $C_{3-6}$ cycloalkyl, —$OC_{1-6}$alkyl, $OC_{1-6}$ haloalkyl, halo, haloalkyl, aryl, and alkaryl.

In alternative embodiments, $R^4$ and $R^5$ are taken together with the nitrogen to which they are attached to form a 6- to 10-membered optionally substituted heterobicyclic ring containing 0-3 additional heteroatoms, preferably 1 or 2 additional heteroatoms selected from —N—, —S— (wherein the —S— can be oxidized to SO or $SO_2$), and —O—. In some aspects, the 6- to 10-membered optionally substituted heterobicyclic ring is substituted, for example, substituted with 1, 2, or 3 independently selected substituents. The substituents can be any substituent defined herein. In preferred aspects, the substituted 6- to 10-membered optionally substituted heterobicyclic ring is substituted with a substituent selected from —OH, $C_1$-$C_6$ alkyl, $C_{3-6}$ cycloalkyl, —$OC_{1-6}$alkyl, —$OC_{1-6}$haloalkyl, halo, haloalkyl, aryl, and alkaryl. In a preferred embodiment of the present invention, $R^4$ and $R^5$ are taken together with the nitrogen to which they are attached to form an optionally substituted heterocyclyl selected from the group consisting of morpholinyl, piperidinyl, azetidinyl, piperazinyl,

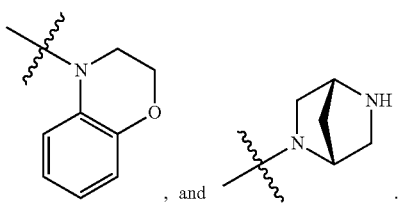 [SMILES: *N1CCOc2ccccc21 ; *N1C[C@H]2C[C@@H]1CN2]

, and .

In one preferred embodiment of the present invention, $R^4$ and $R^5$ are taken together with the nitrogen to which they are attached to form morpholinyl optionally substituted with at least one substituent, such as $C_1$ to $C_6$ alkyl and/or phenyl.

In another aspect of the present invention, $R^4$ and $R^5$ are taken together with the nitrogen to which they are attached to form piperidinyl or piperazinyl, either of which may be optionally substituted with at least one substituent, such as $C_1$ to $C_6$ alkyl and/or phenyl.

In another aspect of the present invention, $R^4$ and $R^5$ together with the nitrogen to which they are attached form pyrrolidinyl optionally substituted with at least one substituent such as $C_1$ to $C_6$ and/or $C_{1-6}$alkoxy$C_{1-6}$ alkyl.

According to one aspect of the present invention, compounds of Formula I, as described above, are provided wherein $R^6$ is optionally substituted aryl, optionally substituted heteroaryl, optionally substituted $C_3$-$C_8$ cycloalkyl, optionally substituted heterocyclyl, or —$COR^7$. In one preferred embodiment, $R^6$ is optionally substituted phenyl; optionally substituted pyrimidinyl; optionally substituted pyridyl; optionally substituted pyrazinyl, optionally substituted pyridazinyl, an optionally substituted heterocyclic ring selected from the group consisting of

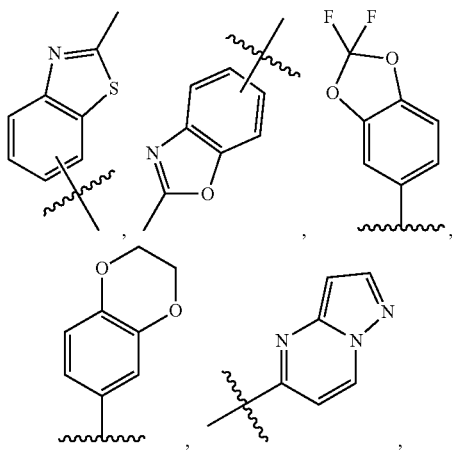

-continued

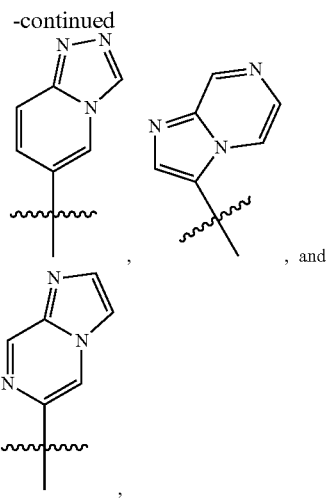

or —$COR^7$ wherein $R^7$ is optionally substituted benzyl, —$CF_2$phenyl, —$CH_2$-isoxalyl, or optionally substituted phenyl. According to one aspect of the present invention, $R^6$ is phenyl optionally substituted with 1 to 3 substituents selected from $C_1$ to $C_6$ alkyl, —CN, halo, hydroxyl, alkoxy, haloalkoxy, phenoxy, and/or —$SO_2$-alkyl.

In one preferred embodiment, $R^6$ is pyrimidinyl optionally substituted with at least one of $C_1$ to $C_6$ alkyl, $C_1$ to $C_6$ alkoxy, —CN, and/or amino.

In one preferred embodiment, $R^6$ is pyridyl, optionally substituted with at least one of alkoxy, amino, and/or $CONH_2$.

According to the one aspect of the present invention, $R^x$ is H, optionally substituted $C_1$-$C_{10}$ alkyl, optionally substituted $C_1$-$C_{10}$ alkoxy, or optionally substituted $C_3$-$C_8$ cycloalkyl. In preferred aspects, $R^x$ is H.

In other aspects, $R^x$ is $C_1$-$C_{10}$ alkyl, for example, methyl, ethyl, propyl, isopropyl, butyl, isobutyl, or t-butyl. In some aspects, $R^x$ is substituted $C_1$-$C_{10}$ alkyl, for example, substituted with 1, 2, or 3 independently selected substituents. When $R^x$ is substituted $C_1$-$C_{10}$ alkyl, the $C_1$-$C_{10}$ alkyl can be substituted with any substituent as defined herein. In preferred aspects, the substituted $C_1$-$C_{10}$ alkyl is substituted with a substituent selected from —OH, $C_{3-6}$ cycloalkyl, —$OC_{1-6}$alkyl, —$OC_{1-6}$haloalkyl, halo, and haloalkyl.

In other aspects, $R^x$ is $C_1$-$C_{10}$ alkoxy, for example, methoxy, ethoxy, propoxy, butoxy, and the like. In some aspects, $R^x$ is substituted $C_1$-$C_{10}$ alkoxy, for example, substituted with 1, 2, or 3 independently selected substituents. When $R^x$ is substituted $C_1$-$C_{10}$ alkoxy, the $C_1$-$C_{10}$ alkoxy can be substituted with any substituent as defined herein. In preferred aspects, the substituted $C_1$-$C_{10}$ alkoxy is substituted with a substituent selected from —OH, $C_{3-6}$ cycloalkyl, —$OC_{1-6}$alkyl, —$OC_{1-6}$haloalkyl, halo, and haloalkyl.

In other aspects, $R^x$ is $C_3$-$C_8$ cycloalkyl, for example, cyclopropyl, cyclobutyl, cyclopentyl, or cyclohexyl. In other aspects, $R^x$ is substituted $C_{3-6}$ cycloalkyl, for example, substituted with 1, 2, or 3 independently selected substituents. When $R^x$ is substituted $C_{3-6}$ cycloalkyl the $C_{3-6}$ cycloalkyl can be substituted with any substituent as defined herein. In preferred aspects, the substituted $C_3$-$C_8$ cycloalkyl is substituted with a substituent selected from —OH, $C_1$-$C_{10}$ alkyl, $C_{3-6}$ cycloalkyl, —$OC_{1-6}$alkyl, —$OC_{1-6}$ haloalkyl, halo, and haloalkyl. According to the disclosure, $R^y$ is H, optionally substituted $C_1$-$C_{10}$ alkyl, optionally substituted $C_1$-$C_{10}$ alkoxy, or optionally substituted $C_3$-$C_8$ cycloalkyl. In preferred aspects, $R^x$ is H.

According to the disclosure, $R^y$ is H, optionally substituted $C_1$-$C_{10}$ alkyl, optionally substituted $C_1$-$C_{10}$ alkoxy, or optionally substituted $C_3$-$C_8$ cycloalkyl. In preferred aspects, $R^y$ is H.

In other aspects, $R^y$ is $C_1$-$C_{10}$ alkyl, for example, methyl, ethyl, propyl, isopropyl, butyl, isobutyl, or t-butyl. In some aspects, $R^y$ is substituted $C_1$-$C_{10}$ alkyl, for example, substituted with 1, 2, or 3 independently selected substituents. When $R^y$ is substituted $C_1$-$C_{10}$ alkyl, the $C_1$-$C_{10}$ alkyl can be substituted with any substituent as defined herein. In preferred aspects, the substituted $C_1$-$C_{10}$ alkyl is substituted with a substituent selected from —OH, $C_{3-6}$ cycloalkyl, —$OC_{1-6}$alkyl, —$OC_{1-6}$haloalkyl, halo, and haloalkyl.

In other aspects, $R^y$ is $C_1$-$C_{10}$ alkoxy, for example, methoxy, ethoxy, propoxy, butoxy, and the like. In some aspects, $R^y$ is substituted $C_1$-$C_{10}$ alkoxy, for example, substituted with 1, 2, or 3 independently selected substituents. When $R^y$ is substituted $C_1$-$C_{10}$ alkoxy, the $C_1$-$C_{10}$ alkoxy can be substituted with any substituent as defined herein. In preferred aspects, the substituted $C_1$-$C_{10}$ alkoxy is substituted with a substituent selected from —OH, $C_{3-6}$cycloalkyl, —$OC_{1-6}$alkyl, —$OC_{1-6}$haloalkyl, halo, and haloalkyl.

In other aspects, $R^y$ is $C_3$-$C_8$ cycloalkyl, for example, cyclopropyl, cyclobutyl, cyclopentyl, or cyclohexyl. In other aspects, $R^y$ is substituted $C_{3-6}$cycloalkyl, for example, substituted with 1, 2, or 3 independently selected substituents. When $R^y$ is substituted $C_{3-6}$ cycloalkyl the $C_{3-6}$ cycloalkyl can be substituted with any substituent as defined herein. In preferred aspects, the substituted $C_3$-$C_8$ cycloalkyl is substituted with a substituent selected from —OH, $C_1$-$C_{10}$ alkyl, $C_{3-6}$ cycloalkyl, —$OC_{1-6}$alkyl, —$OC_{1-6}$ haloalkyl, halo, and haloalkyl.

In alternative aspects, $R^x$ and $R^y$ are taken together with the carbon to which they are attached to form a 3- to 6-membered carbocyclic ring.

In alternative aspects, $R^x$ and $R^y$ are taken together with the carbon to which they are attached to form a 3- to 7-membered heterocyclic ring containing 1-3 heteroatoms, preferably 1 heteroatom selected from —N—, —S— (wherein the —S— is optionally oxidized to SO or $SO_2$) and —O—.

In most preferred embodiments, $R^x$ and $R^y$ are each H.

According to the disclosure, $R^2$ is H, optionally substituted $C_1$-$C_{10}$ alkyl, optionally substituted $C_{3-6}$ cycloalkyl, optionally substituted heterocyclyl, or optionally substituted aryl. In preferred aspects, $R^2$ is H.

In other aspects, $R^2$ is $C_1$-$C_{10}$ alkyl, for example, methyl, ethyl, propyl, isopropyl, butyl, isobutyl, or t-butyl. In some aspects, $R^2$ is substituted $C_1$-$C_{10}$ alkyl, for example, substituted with 1, 2, or 3 independently selected substituents. When $R^2$ is substituted $C_1$-$C_{10}$ alkyl, the $C_1$-$C_{10}$ alkyl can be substituted with any substituent as defined herein. In preferred aspects, the substituted $C_1$-$C_{10}$ alkyl is substituted with a substituent selected from —OH, $C_{3-6}$ cycloalkyl, —$OC_{1-6}$alkyl, —$OC_{1-6}$haloalkyl, halo, and haloalkyl.

In other aspects, $R^2$ is $C_{3-6}$ cycloalkyl, for example, cyclopropyl, cyclobutyl, cyclopentyl, or cyclohexyl. In other aspects, $R^2$ is substituted $C_{3-6}$ cycloalkyl, for example, substituted with 1, 2, or 3 independently selected substituents. When $R^2$ is substituted $C_{3-6}$ cycloalkyl the $C_{3-6}$ cycloalkyl can be substituted with any substituent as defined herein. In preferred aspects, the substituted $C_{3-6}$ cycloalkyl is substituted with a substituent selected from —OH, $C_1$-$C_{10}$ alkyl, $C_{3-6}$ cycloalkyl, —$OC_{1-6}$alkyl, —$OC_{1-6}$ haloalkyl, halo, and haloalkyl.

In other aspects, $R^2$ is heterocyclyl. The heterocyclyl can be any heterocyclyl defined herein, with a preferred heterocyclyl being tetrahydropyranyl. In some aspects, the heterocyclyl is substituted heterocyclyl, for example, substituted with 1, 2, or 3 independently selected substituents. When $R^2$ is substituted heterocyclyl, the heterocyclyl can be substituted with any substituent as defined herein. In preferred aspects, the substituted heterocyclyl is substituted with a substituent selected from —OH, $C_1$-$C_{10}$ alkyl, $C_{3-6}$ cycloalkyl, —$OC_{1-6}$alkyl, —$OC_{1-6}$haloalkyl, halo, and haloalkyl.

In other aspects, $R^2$ is aryl, for example phenyl. In other aspects, $R^2$ is substituted aryl, for example, substituted with 1, 2, or 3 independently selected substituents. When $R^2$ is substituted aryl the aryl can be substituted with any substituent as defined herein. In preferred aspects, the substituted aryl is substituted with a substituent selected from —OH, $C_1$-$C_{10}$ alkyl, $C_{3-6}$ cycloalkyl, —$OC_{1-6}$alkyl, —$OC_{1-6}$haloalkyl, halo, and haloalkyl.

According to the disclosure, $R^3$ is H, optionally substituted $C_1$-$C_{10}$ alkyl, optionally substituted $C_{3-6}$ cycloalkyl, optionally substituted heterocyclyl, or optionally substituted aryl. In preferred aspects, $R^3$ is H.

In other aspects, $R^3$ is $C_1$-$C_{10}$ alkyl, for example, methyl, ethyl, propyl, isopropyl, butyl, isobutyl, or t-butyl. In some aspects, $R^3$ is substituted $C_1$-$C_{10}$ alkyl, for example, substituted with 1, 2, or 3 independently selected substituents. When $R^3$ is substituted $C_1$-$C_{10}$ alkyl, the $C_1$-$C_{10}$ alkyl can be substituted with any substituent as defined herein. In preferred aspects, the substituted $C_1$-$C_{10}$ alkyl is substituted with a substituent selected from —OH, $C_{3-6}$ cycloalkyl, —$OC_{1-6}$alkyl, —$OC_{1-6}$haloalkyl, halo, and haloalkyl.

In other aspects, $R^3$ is $C_{3-6}$ cycloalkyl, for example, cyclopropyl, cyclobutyl, cyclopentyl, or cyclohexyl. In other aspects, $R^2$ is substituted $C_{3-6}$ cycloalkyl, for example, substituted with 1, 2, or 3 independently selected substituents. When $R^3$ is substituted $C_{3-6}$ cycloalkyl the $C_{3-6}$ cycloalkyl can be substituted with any substituent as defined herein. In preferred aspects, the substituted $C_{3-6}$ cycloalkyl is substituted with a substituent selected from —OH, $C_1$-$C_{10}$ alkyl, $C_{3-6}$ cycloalkyl, —$OC_{1-6}$alkyl, —$OC_{1-6}$ haloalkyl, halo, and haloalkyl.

In other aspects, $R^3$ is heterocyclyl. The heterocyclyl can be any heterocyclyl defined herein, with a preferred heterocyclyl being tetrahydropyranyl. In some aspects, the heterocyclyl is substituted heterocyclyl, for example, substituted with 1, 2, or 3 independently selected substituents. When $R^3$ is substituted heterocyclyl, the heterocyclyl can be substituted with any substituent as defined herein. In preferred aspects, the substituted heterocyclyl is substituted with a substituent selected from —OH, $C_1$-$C_{10}$ alkyl, $C_{3-6}$ cycloalkyl, —$OC_{1-6}$alkyl, —$OC_{1-6}$haloalkyl, halo, and haloalkyl.

In other aspects, $R^3$ is aryl, for example phenyl. In other aspects, $R^3$ is substituted aryl, for example, substituted with 1, 2, or 3 independently selected substituents. When $R^3$ is substituted aryl the aryl can be substituted with any substituent as defined herein. In preferred aspects, the substituted aryl is substituted with a substituent selected from —OH, $C_1$-$C_{10}$ alkyl, $C_{3-6}$ cycloalkyl, —$OC_{1-6}$alkyl, —$OC_{1-6}$haloalkyl, halo, and haloalkyl.

In alternative embodiments, $R^2$ and $R^3$ are taken together with the carbon to which they are attached to form a 3- to 6-membered carbocyclic ring, for example, $R^2$ and $R^3$ are taken together with the carbon to which they are attached to form a cyclopropyl, cyclobutyl, cyclopentyl, or cyclohexyl ring. In some embodiments, the 3- to 6-membered carbocyclic ring formed by the taking together of R² and R³ is substituted, for example, with 1, 2, or 3 independently selected substituents. The 3- to 6-membered carbocyclic ring can be substituted with any substituent as defined herein. In preferred aspects, the 3- to 6-membered carbocyclic ring is substituted with a substituent selected from —OH, $C_1$-$C_{10}$ alkyl, $C_{3-6}$ cycloalkyl, —$OC_{1-6}$alkyl, —$OC_{1-6}$haloalkyl, halo, and haloalkyl.

In alternative embodiments, R² and R³ are taken together with the carbon to which they are attached to form a 3- to 6-membered heterocyclic ring, for example, R² and R³ are taken together with the carbon to which they are attached to form a 3- to 6-membered heterocyclic ring including at least one heteroatom selected from O, N, or S. In some embodiments, the 3- to 6-membered heterocyclic ring formed by the taking together of R² and R³ is substituted, for example, with 1, 2, or 3 independently selected substituents. The 3- to 6-membered heterocyclic ring can be substituted with any substituent as defined herein. In preferred aspects, the 3- to 6-membered heterocyclic ring is substituted with a substituent selected from —OH, $C_1$-$C_{10}$ alkyl, $C_{3-6}$ cycloalkyl, —$OC_{1-6}$alkyl, —$OC_{1-6}$ haloalkyl, halo, and haloalkyl.

In preferred aspects, one of R² and R³ is H and the other is optionally substituted $C_1$-$C_{10}$ alkyl, optionally substituted $C_{3-6}$ cycloalkyl, optionally substituted heterocyclyl, or optionally substituted aryl. In some preferred aspects, one of R² and R³ is H and the other is $C_1$-$C_{10}$ alkyl, for example, methyl, ethyl, propyl, butyl, isobutyl, or t-butyl. In those embodiments wherein the $C_1$-$C_{10}$ alkyl is a substituted $C_1$-$C_{10}$ alkyl, the $C_1$-$C_{10}$ alkyl is substituted with 1 or 2 substituents independently selected from —$OC_{1-6}$alkyl (e.g., —$OCH_3$) and haloalkyl (e.g., —$CF_3$). In some preferred aspects, one of R² and R³ is H and the other is $C_{3-6}$ cycloalkyl, for example cyclopropyl, cyclobutyl, cyclopentyl, cyclobutyl, cyclopenyl, or cyclohexyl. In those embodiments wherein the $C_{3-6}$cycloalkyl is a substituted $C_{3-6}$ cycloalkyl, the $C_{3-6}$ cycloalkyl is substituted with 1 or 2 substituents independently selected from —OH, $C_1$-$C_{10}$alkyl (e.g., methyl, ethyl, and the like), —$OC_{1-6}$ alkyl (e.g., —$OCH_3$), and haloalkyl (e.g., —$CF_3$).

In other preferred aspects, R² and R³ are each independently $C_1$-$C_{10}$ alkyl, for example, methyl, ethyl, propyl, butyl, isobutyl, or t-butyl. In those embodiments wherein R² and R³ are each independently a substituted $C_1$-$C_{10}$ alkyl, each $C_1$-$C_{10}$ alkyl is independently substituted with 1 or 2 substituents independently selected from —OH, —$OC_{1-6}$ alkyl (e.g., —$OCH_3$) and haloalkyl (e.g., —$CF_3$).

According to one aspect of the present invention, compounds of Formula I are provided wherein:

Y is CH or CF;

V is CH or CF;

R¹ is —COOH;

R² and R³ are independently hydrogen, optionally substituted $C_1$ to $C_6$ alkyl, $C_3$ to $C_6$ cycloalkyl, phenyl, or R² and R³ join together with the carbon to which they are attached to form tetrahydropyranyl;

R⁴ is H, optionally substituted $C_1$ to $C_6$ alkyl, tetrahydropyranyl, optionally substituted cyclohexyl,

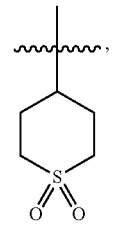

optionally substituted piperazinyl, optionally substituted piperidinyl, optionally substituted pyrrolidinyl, optionally substituted diazabicycloheptanyl, or furanyl; or R⁴ and R⁵ are taken together with the nitrogen to which they are attached to form optionally substituted morpholinyl, optionally substituted piperidinyl, optionally substituted piperazinyl, optionally substituted

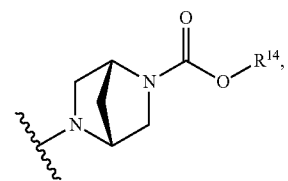

or optionally substituted pyrrolidinyl; and

R⁶ is optionally substituted phenyl, optionally substituted pyrimidinyl, morpholinyl; or —COR⁷ wherein R⁷ is optionally substituted phenyl.

In some preferred embodiments, R⁴ and R⁵ are independently H, $C_1$ to $C_6$ alkyl optionally substituted with at least one of halo and/or cyclopropyl; tetrahydropyranyl; cyclohexyl optionally substituted with alkoxy; tetrahydro-2H-1,1-dioxo-thiopyranyl; piperazinyl optionally substituted with at least one of alkyl and/or —COOR¹³, piperidinyl optionally substituted with phenylalkyl; pyrrolidinyl optionally substituted with $C_1$ to $C_6$ alkyl; diazabicycloheptanyl optionally substituted with phenylalkyl; or furanyl; or R⁴ and R⁵ are taken together with the nitrogen to which they are attached to form morpholinyl optionally substituted with at least one of $C_1$ to $C_6$ alkyl and/or phenyl; piperidinyl optionally substituted with at least one of $C_1$ to $C_6$ alkyl and/or phenyl; piperazinyl or

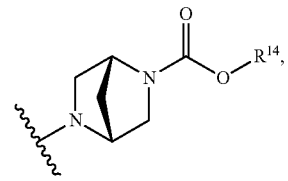

optionally substituted with phenyl; or pyrrolidinyl optionally substituted with at least one of alkyl and/or alkoxyalkyl.

According to some preferred embodiments of the present invention, R⁶ is phenyl optionally substituted with at least one of methyl, ethyl, propyl, —CN, —$OCH_2CF_3$, halo, or —$SO_2$-alkyl; pyrimidinyl optionally substituted with at least one of $C_1$ to $C_6$ alkyl, hydroxy, alkoxy, amino and/or morpholinyl; pyridyl optionally substituted with at least one of alkoxy, halo, amino, and/or —$CONH_2$; 2,2-difluorobenzo[d][1,3]dioxolyl; 2,3-dihydrobenzo[b][1,4]dioxinyl; 3,3a-dihydropyrazolo[1,5-a]pyridyl; or 3,3a-dihydropyrazolo[1, 5-a]pyrimidyl optionally substituted with at least one of halo and/or methyl; 3,8a-dihydro-[1,2,4]triazolo[4,3-a]pyridyl; or pyrazinyl optionally substituted with at least one of alkoxy and/or benzoxazo, or —COR⁷; and R⁷ is phenyl optionally substituted with at least one of alkoxy, methyl, and/or halo; —CH₂-phenyl or —CF₂-phenyl, wherein said phenyl is optionally substituted with at least one of methyl and/or phenoxy; or —CH₂-isoxalolyl.

According to one aspect of the present invention, compounds having the following Formula II, within the scope of Formula I are provided:

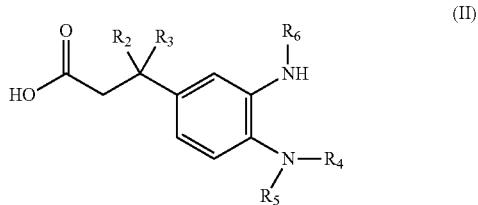

wherein $R^6$ is optionally substituted phenyl, optionally substituted pyrimidinyl, or optionally substituted pyridyl, $R^2$ and $R^3$ are each independently H, methyl or ethyl; $R^4$ is morpholinyl, tetrahydropyranyl, piperidinyl, or piperazinyl.

In another aspect, the invention provides a compound selected from any of the exemplified examples within the scope of the first aspect, or a pharmaceutically acceptable salt, tautomer or stereoisomer thereof.

In another aspect, the invention provides a compound selected from the exemplified examples that are within the scope of Formula I, or a pharmaceutically acceptable salt, tautomer or stereoisomer thereof.

In another embodiment, the compounds of the invention have human IDO $IC_{50}$ values>50 nM.

In another embodiment, the compounds of the invention have human IDO $IC_{50}$ values≤50 nM.

In another embodiment, the compounds of the invention have human IDO $IC_{50}$ values<5 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents,* 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of Formula I is administered with one or more immuno-oncology agents. The immuno-oncology agents used herein, also known as cancer immunotherapies, are effective to enhance, stimulate, and/or upregulate immune responses in a subject.

In one aspect, the Compound of Formula I is sequentially administered prior to administration of the immuno-oncology agent. In another aspect, the Compound of Formula I is administered concurrently with the immunology-oncology agent. In yet another aspect, the Compound of Formula I is sequentially administered after administration of the immuno-oncology agent.

In another aspect, the Compound of Formula I may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response. In one aspect, T cell responses can be stimulated by a combination of the Compound of Formula I and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of Formula I for the treatment of cancer include antagonists of inhibitory receptors on NK cells or agonists of activating receptors on NK cells. For example, the Compound of Formula I can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of Formula I can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., —SO$_2$NH$_2$, substituted sulfonamido, nitro, cyano, carboxy, carbamyl, e.g., —CONH$_2$, substituted carbamyl, e.g., —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol  is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of 5 to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

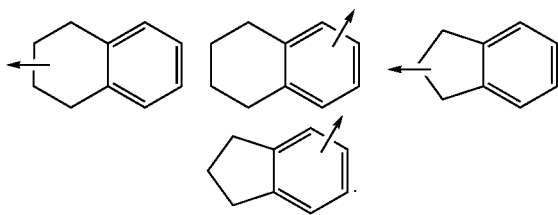

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluorom-ethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolo-pyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, Fourth Edition, Wiley (2007) and *The Peptides: Analysis, Synthesis, Biology*, Vol. 3, Academic Press, New York (1981). The disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012). The disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);

c) Bundgaard, H., *Adv. Drug Deliv. Rev.*, 8:1-38 (1992);

d) Nielsen, N. M. et al., *J. Pharm. Sci.*, 77:285 (1988);

e) Kakeya, N. et al., *Chem. Pharm. Bull.*, 32:692 (1984); and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "Tr" for retention time, "atm" for atmosphere, "psi" for pounds per square inch, "conc." For concentrate or concentrated, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
BOP (Benzotriazol-1-yloxy)tris(dimethylamino)phosphonium hexafluorophosphate
$CDCl_3$ deutero-chloroform
$CHCl_3$ chloroform
cDNA complimentary DNA
DMF dimethylformamide
DMSO dimethyl sulfoxide DIAD Diisopropyl azodicarboxylate
EDTA ethylenediaminetetraacetic acid
EtOAc ethyl acetate
Et$_2$O diethyl ether
AlCl$_3$ aluminum chloride
Boc tert-butyloxycarbonyl
CH$_2$Cl$_2$ dichloromethane
CH$_3$CN or ACN acetonitrile
Cs$_2$CO$_3$ cesium carbonate
HCl hydrochloric acid
H$_2$SO$_4$ sulfuric acid
Hunig's base diisopropylethylamine
K$_2$CO$_3$ potassium carbonate
mCPBA or m-CPBA meta-chloroperbenzoic acid
Pd/C palladium on carbon
PS polystyrene
SiO$_2$ silica oxide
SnCl$_2$ tin(II) chloride
TEA triethylamine
TFA trifluoroacetic acid
TFAA trifluoroacetic anhydride
THF tetrahydrofuran
TMSCHN$_2$ trimethylsilyldiazomethane
KOAc potassium acetate
LHMDS Lithium hexamethyldisilazide
MgSO$_4$ magnesium sulfate
NMP N-Methylpyrrolidone
MsOH or MSA methylsulfonic acid
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
LG leaving group
RT Room temperature
SFC Supercritical Fluid Chromatography The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula I may be prepared by the exemplary processes described in the following Schemes and working Examples, as well as relevant published literature procedures that are used by one skilled in the art. Exemplary reagents and procedures for these reactions appear hereinafter and in the working Examples. Protection and de-protection in the processes below may be carried out by procedures generally known in the art (see, for example, Greene, T. W. et al., *Protecting Groups in Organic Synthesis*, Third Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*, Fourth Edition, Wiley & Sons, New York, N.Y. (1992); Katritzky, A. R. et al., eds., *Comprehensive Organic Functional Groups Transformations*, First Edition, Elsevier Science Inc., Tarrytown, N.Y. (1995); Larock, R. C., *Comprehensive Organic Transformations*, VCH Publishers, Inc., New York, N.Y. (1989), and references therein.

Compounds (i), where X=F and Z can be Br, Cl and I are commercially available or can be prepared utilizing standard transformations known to those of ordinary proficiency in the art of organic/medicinal chemistry. Treatment of compounds (i), with amines HNR$^4$R$^5$ (Scheme 1) and a suitable base in a solvent such as THF, DMF, NMP, or the like affords intermediates (ii). Generally heating is required. Suitable bases include, but are not limited to aliphatic tertiary amines or an excess of the reacting primary or secondary amine HNR$^4$R$^5$. Treatment of compounds (ii) under standard Heck palladium coupling conditions such as a Pd$^{II}$ catalyst Pd(OAc)$_2$ and olefin containing compounds (iii) in a solvent such as THF, yields compounds (iv). Reduction of the olefin and the nitroaromatic found in compounds (iv) can be accomplished under reductive conditions such as but not limited to Pd/C under an atmosphere of H$_2$ and in a solvent such as ethyl acetate or methanol to afford saturated aniline compounds (v). Treatment of anilines (v) with an isocyanate R$^7$N=C=O, affords urea compounds (vi). Typically, this reaction is performed in a solvent such as THF at a temperature between ambient and the boiling point of the solvent. Esters (vi) may be converted to the corresponding carboxylic acids of the invention I under various conditions familiar to those of ordinary skill in the art. Generally this is effected using an alkali metal hydroxide (MOH) in aqueous solution, preferably with an organic co-solvent such as methanol or THF.

Scheme 1

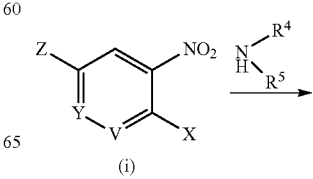

(i)

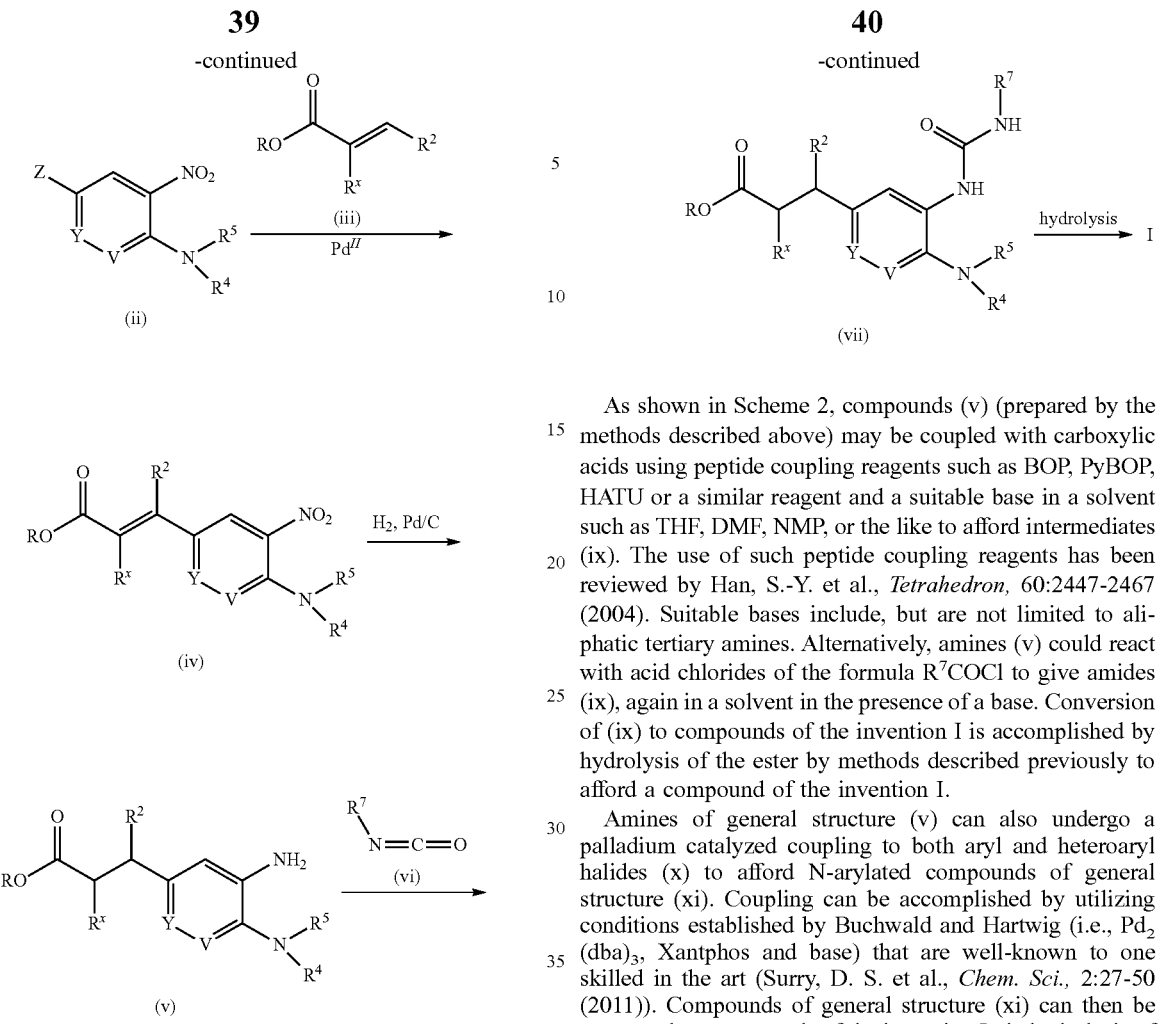

As shown in Scheme 2, compounds (v) (prepared by the methods described above) may be coupled with carboxylic acids using peptide coupling reagents such as BOP, PyBOP, HATU or a similar reagent and a suitable base in a solvent such as THF, DMF, NMP, or the like to afford intermediates (ix). The use of such peptide coupling reagents has been reviewed by Han, S.-Y. et al., *Tetrahedron*, 60:2447-2467 (2004). Suitable bases include, but are not limited to aliphatic tertiary amines. Alternatively, amines (v) could react with acid chlorides of the formula $R^7COCl$ to give amides (ix), again in a solvent in the presence of a base. Conversion of (ix) to compounds of the invention I is accomplished by hydrolysis of the ester by methods described previously to afford a compound of the invention I.

Amines of general structure (v) can also undergo a palladium catalyzed coupling to both aryl and heteroaryl halides (x) to afford N-arylated compounds of general structure (xi). Coupling can be accomplished by utilizing conditions established by Buchwald and Hartwig (i.e., $Pd_2(dba)_3$, Xantphos and base) that are well-known to one skilled in the art (Surry, D. S. et al., *Chem. Sci.*, 2:27-50 (2011)). Compounds of general structure (xi) can then be converted to compounds of the invention I via hydrolysis of the ester via methods already described herein (Scheme 2).

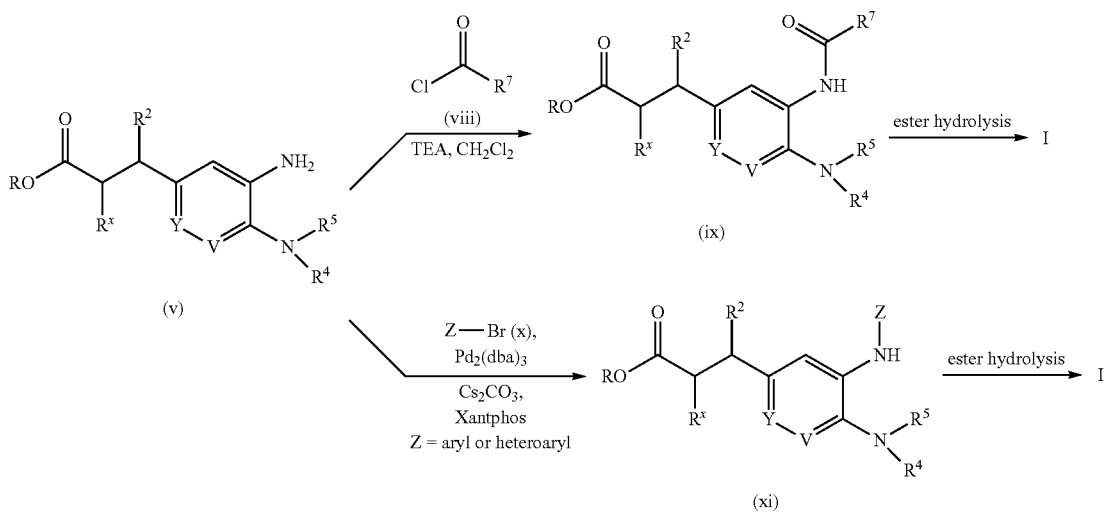

Treatment of carbonyl containing compounds (xii), where X=F and Z can be Br, Cl and I, with amines HNR⁴R⁵ (xiii) (Scheme 3) and a suitable base in a solvent such as THF, DMF, NMP, or the like affords intermediates (xiv). Generally heating is required. Suitable bases include, but are not limited to aliphatic tertiary amines or an excess of the reacting primary or secondary amine HNR⁴R⁵. Olefination of the carbonyl aldehyde or ketone can be accomplished by many methods that are well-known to those skilled in the art, such as Horner-Wadsworth-Emmons conditions as shown in Scheme 3. In practice the carbonyl compounds (xiv) can be treated with a phosphonic ester (xv) in the presence of a base such as sodium hexamethyldisilazane (NaHMDS) to afford olefins (iv). Olefins (iv) can be converted to compounds of the invention I by methods described in Scheme 1.

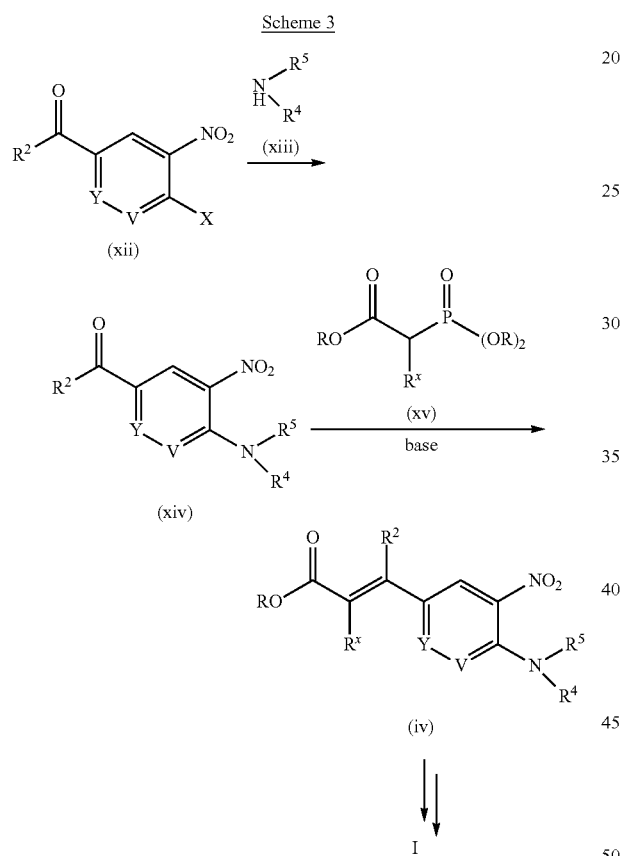

In Scheme 4 reduction of the nitro group in compounds (ii) to afford anilines (xvi) can be effected by various means including catalytic hydrogenation and dissolving metal reductions both in their various forms. See: House, H. O. et al., *Modern Synthetic Reactions*, Second Edition, Menlo Park, Calif. (1972). A preferred method for effecting this reduction without removal of the halogen substituent Z involves stirring a solution of (ii) in a wet alcoholic solvent with an acid such as ammonium chloride and finely divided zinc. The anilines (xvi) can be couple to the olefins (xvii) under standard Heck coupling conditions with a Pd$^{II}$ catalyst such as Pd(OAc)₂ to afford the olefins (xviii). The aniline compounds (xviii) can then be converted to compounds of the invention I by treatment previously described in Schemes 1 and 2.

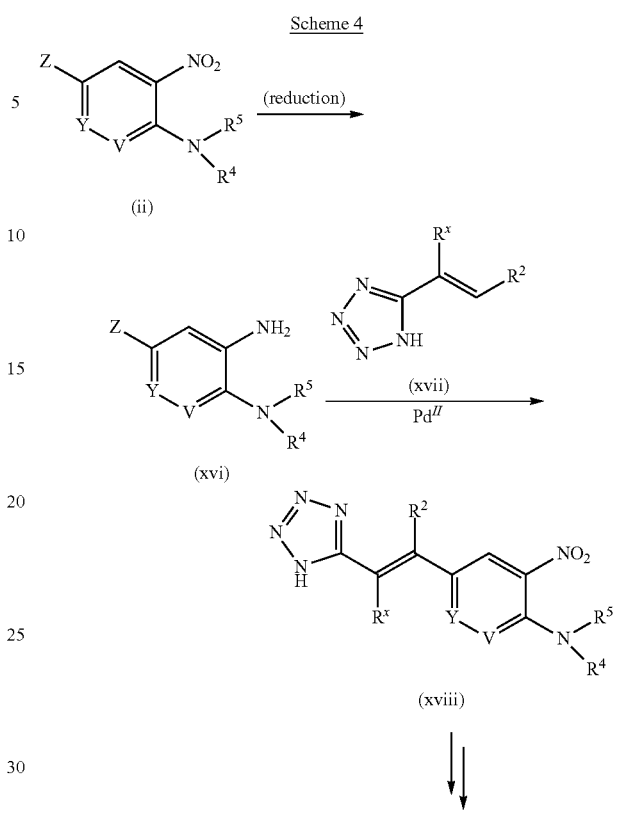

In Scheme 5, olefins (iv) may be treated with an appropriate organometallic, such as an alkyl cuprate, to afford compounds (xx) where R³ has been installed beta to the ester carbonyl. These reactions are well known to those skilled in the art and comprise an alkyl or aryl Grignard reagent such as R³—MgBr and a Cu$^I$ reagent such as copper(I)iodide. The cuprate that is so-formed can then add in a 1,4 sense to the unsaturated ester (iv) to give the compounds (xx) which can be converted to compounds of the invention I by methods described previously.

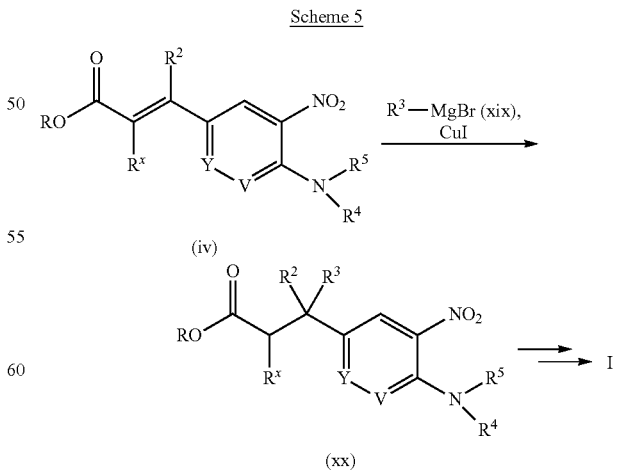

Scheme 6 below demonstrates the preparation of compounds of the invention I where R² and R³ have been joined to form a cyclopropane. The benzyl bromide (xxi) can be purchased or synthesized by one of ordinary skills in the art. Treatment of (xvii) with a cyanide anion source, such as potassium cyanide, in the presence of a base, such as potassium carbonate will afford the nitrile compounds (xxii). Treatment of (xxii) with HNR⁴R⁵, as described previously, will afford amines of general structure (xxiii). Cyclopropane formation can be accomplished by several methods known to one skilled in the art. One method uses 1-bromo-2-chloroethane in the presence of a strong base such as sodium hydride to afford the cyclopropane (xxiv). Hydrolysis of the nitrile (xxiv) can be accomplished by first treating with a strong base, such as potassium hydroxide, at elevated temperatures to afford the corresponding carboxylic acids (xxv). A one carbon homologation of the acid (xxv) can be accomplished by several methods known to one skilled in the art. Scheme 6 depicts a three step homologation process from (xxv) to produce the compounds of general structure (xxvi) (Qiao, J. et al., PCT Publication No. WO 2003/099276). The compounds of general structure (xxvi) can then be converted to compounds of the invention I by methods discussed previously.

Scheme 6

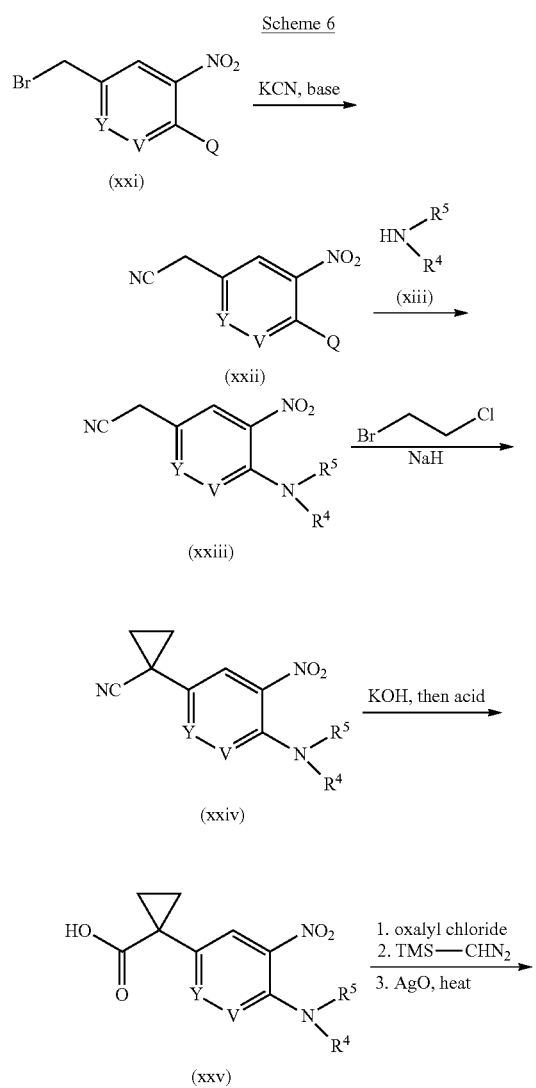

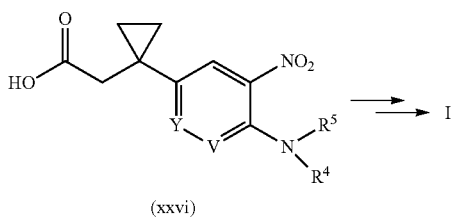

Scheme 7 below shows an alternative preparation of compounds of the invention I. The boronate (xxvii) can be prepared from the previously discussed aryl halide (ii) under standard condition utilizing a Pd catalyst such as Pd(PPh₃)₄ or 1,1'-bis(diphenylphosphino)ferrocenedichloro palladium (II). Rhodium catalyzed 1,4-conjugate addition of the boronic ester (xxvii) and an unsaturated ester (iii) are well known (Zou, G. et al., *Dalton Trans.*, 28:3055 (2007)) and can be accomplished using a rhodium$^I$ catalyst, for example, [Rh(COD)Cl]₂ in the presence of a strong base such as NaOH to afford saturated esters of the general structure (xxvii). The ester (xxvii) can then be converted to compounds of the invention I by methods previously described herein.

In another embodiment, the conjugate addition with boronates of general structure (xxvii), where R$^x$ is hydrogen, and the unsaturated ester (iii) can be accomplished with a chiral catalyst to give products of general structure (xxviii) with enhanced optical purity at the benzylic position (see Scheme 7 below). One can accomplish this transformation using the conditions developed by Hayashi whereby chlorobis(ethylene)rhodium(I)dimer is combined with (R)- or (S)-BINAP as the chiral ligand (Hayashi et al., *J. Am. Chem. Sci.*, 124:5052 (2002)). The desired stereochemistry at the benzylic position of compounds of general structure (xxviii) can be obtained by the appropriate choice of (R)- or (S)-BINAP used in the conjugate addition.

Scheme 7

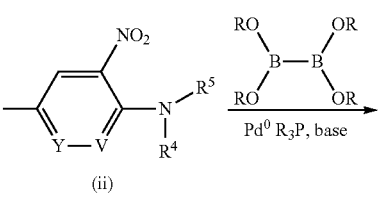

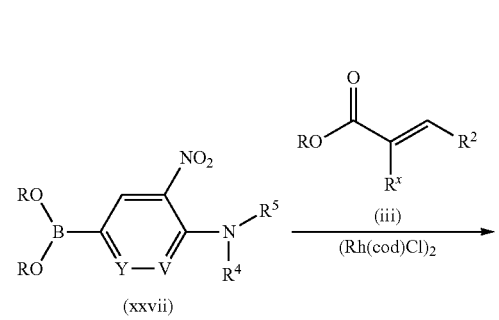

-continued

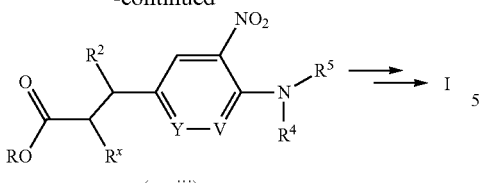
(xxviii)

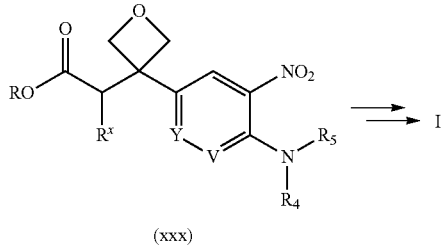
(xxx)

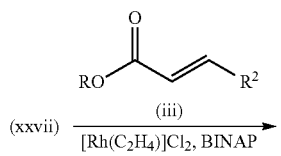
(xxvii)

In another embodiment shown in Scheme 9, an aryl halide of general structure (xxxi) can be treated with an amine of general structure (xiii) and a palladium catalyst under standard coupling conditions established by Buchwald and Hartwig (i.e., $Pd_2$ (dba)$_3$, Xantphos and base) that are well-known to one skilled in the art (Surry, D. S. et al., *Chem. Sci.*, 2:27-50 (2011)) to give the product of general structure (xxxii). This compound can then be converted to a compound of the invention I by methods already discussed herein.

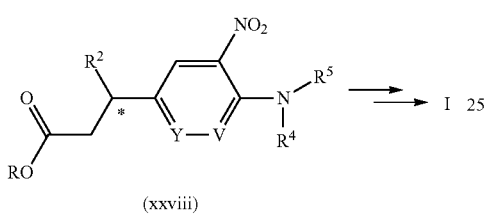
(xxviii)

Oxetanes of the invention I can also be prepared in a similar manner, as depicted in Scheme 8. Oxetan-3-one is commercially available and can be treated under standard Horner-Wadsworth Emmons olefination conditions using a phosphonate in the presence of a base such as lithium hexamethyldisilazane (LiHMDS) to afford the unsaturated ester (xxix). Rhodium catalyzed 1,4-conjugate addition of the boronic acid (xxvii) to the unsaturated ester (xxix) can then be accomplished using a rhodium$^I$ catalyst, for example, $[Rh(COD)Cl]_2$ in the presence of a strong base such as NaOH to afford the oxetanes (xxx). The oxetanes (xxx) can be converted to compounds of the invention I by methods previously described.

Scheme 9

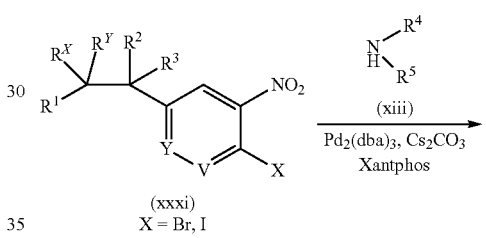
(xxxi)
X = Br, I

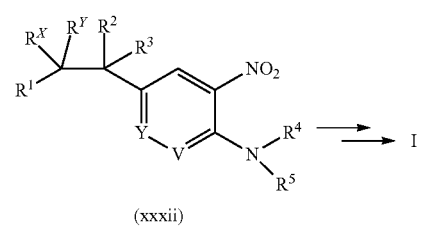
(xxxii)
X = Br, I

Scheme 10 shows another embodiment where the carboxylic acid of general structure (xxxiii) can be converted to an acyl sulfonamide of general structure (xxxv) by sequential treatment with an activating agent, such as CDI (carbonyl diimidazole), followed by addition of a sulfonamide (xxxiv) in the presence of a base such as DBU with or without heating. Numerous sulfonamides (xxxiv) are commercially available. The acylsulfonamide (xxxv) is a compound of the invention (I). The carboxylic acid (xxxiii) can also be treated under conditions known to affect a Curtius rearrangement, such as heating with DPPA in toluene, followed by a strong base such as LiOH, to afford an amine of general structure (xxxvi). The amine (xxxvi) can then be treated with a sulfonyl chloride of general structure (xxxvii) and a base, such as diisopropyl ethyl amine, to afford a sulfonamide a general structure (xxxviii) which is a compound of the invention I.

Scheme 8

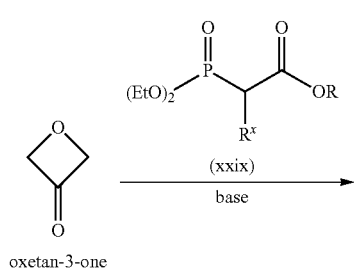
oxetan-3-one

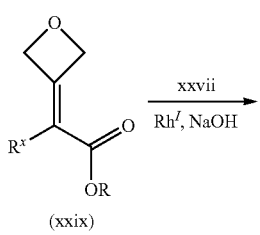
(xxix)

Scheme 10

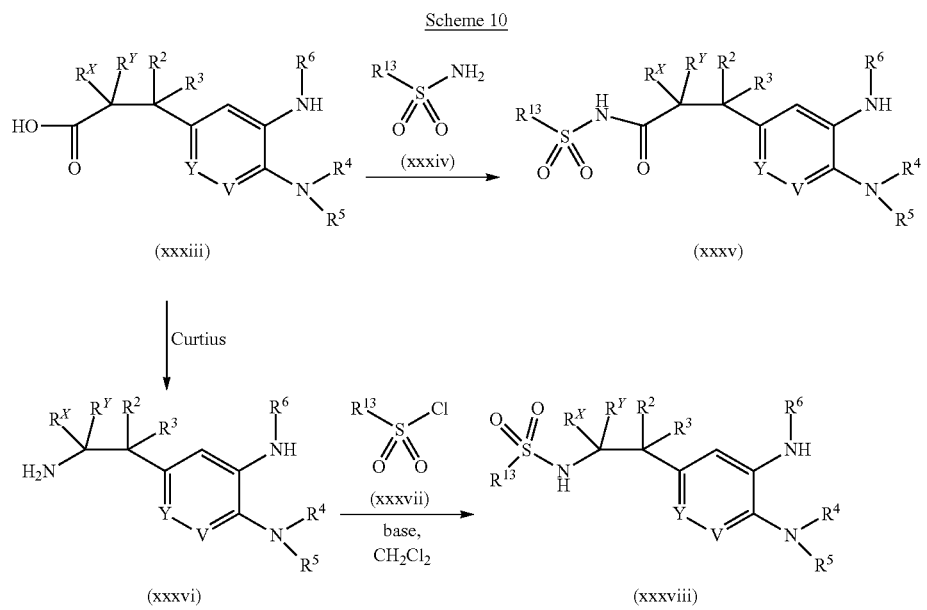

In another embodiment shown in Scheme 11, the carboxylic acid (xl) can be reduced to the corresponding primary alcohol by treatment with a reducing agent, such as borane.THF in a solvent such as THF at elevated temperatures. Subsequent oxidation of the resulting primary alcohol by an appropriate oxidant, such as Dess-Martin periodinane, in a solvent such as dichloromethane will afford the aldehyde of general structure (xli). Treatment of the aldehyde (xli) with an alkyl lithium or Grignard reagent in a solvent such as THF, will afford a secondary alcohol of general structure (xlii), which is a compound of the invention I.

Scheme 11

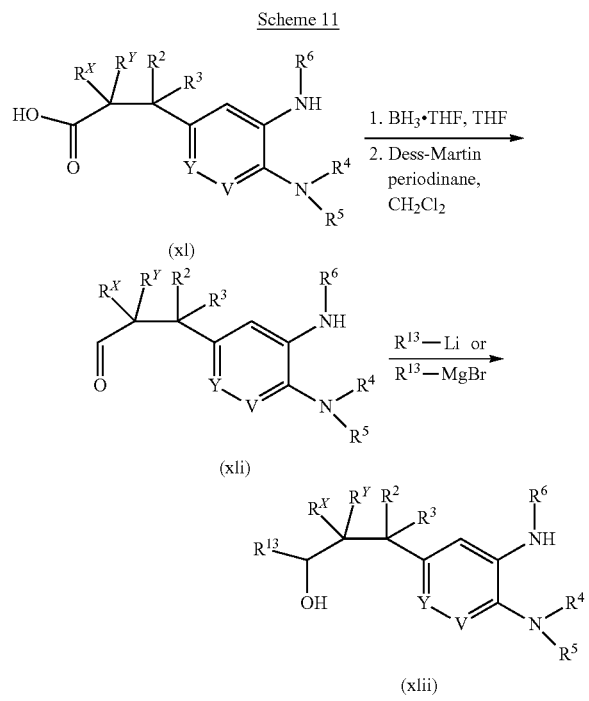

HPLC/MS and Preparatory/Analytical HPLC Methods Employed in Characterization or Purification of Examples Analytical HPLC/MS was performed using the following methods:

Method A: Waters Acquity SDS using the following method: Linear Gradient of 2% to 98% Solvent B over 1.00 min; UV visualization at 220 or 254 nm; Column: BEH C18 2.1 mm×50 mm; 1.7 µm particle (heated to temp. 50° C.); Flow rate: 0.8 ml/min; Mobile Phase A: 100% water, 0.05% TFA; Mobile Phase B: 100% acetonitrile, 0.05% TFA.

Method B: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.00 mL/min; Detection: UV at 220 nm.

Method C: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method D: Column: Waters XBridge C18, 4.6×150 mm, 3.5-µm particles; Mobile Phase A: 10 mM ammonium bicarbonate pH9.5/methanol 95/5; Mobile Phase B: 10 mM ammonium bicarbonate pH9.5/methanol 5/95; Temperature: 40° C.; Gradient: 10-100-100% B at 0-25-30 minutes; Flow: 1.0 mL/min; Detection: UV at 220 and 254 nm.

Analytical chiral SFC chromatography was performed on a Berger or Aurora Analytical SFC using the following method:

Method E: Aurora SFC, Column: WHELK-O1® Komosil 250×4.6 mm ID, 5 µm, Flow rate: 2.0 mL/min, Mobile Phase: 90/10 $CO_2$/MeOH.

Method F: Instrument: Berger SFC MGII; Column: PHENOMENEX® Lux Cellulose-2 Axia Pack 25×3 cm ID, 5

µm; Mobile Phase A: 88/12 $CO_2$/(MeOH/ACN 50/50); 85.0 mL/min; Detection: UV at 220; Sample Prep: 600⁴ of 30 mg dissolved in 5 mL MeOH.

Method G: Instrument: Aurora analytical SFC; Column: PHENOMENEX® Lux Cellulose-2 250×4.6 mm ID, 3 µm; Flow rate: 2.0 mL/min; Mobile Phase: 85/15 $CO_2$/(MeOH/ACN 50/50).

Method H: Column: WHELK-O1® (R,R), KROMASIL®, 250 mm×30 mm, 5µ. Mobile Phase: 85 mL/min. of 85:15 $CO_2$:MeOH.

Method I: Column: WHELK-O1® (R,R), KROMASIL®, 250 mm×30 mm, 5µ. Mobile Phase: 85 mL/min. of 93:7 $CO_2$:MeOH.

Method J: Column: WHELK-O1® (R,R), KROMASIL®, 250 mm×30 mm, 5µ. Mobile Phase: 85 mL/min. of 90:10 $CO_2$:MeOH.

Method K: Column: PHENOMENEX® Lux Cellulose-2, 250 mm×30 mm, 5µ. Mobile Phase: 85 mL/min. of 85:15 $CO_2$:MeOH.

Method L: Column: PHENOMENEX® Lux Cellulose-2, 250 mm×30 mm, 5µ. Mobile Phase: 85 mL/min. of 84:16 $CO_2$:MeOH+0.1% each of formic acid and diethylamine.

Method M: Column: PHENOMENEX® Lux Cellulose-2, 250 mm×30 mm, 5µ. Mobile Phase: 85 mL/min. of 92:8 $CO_2$:MeOH+0.1% each of formic acid and diethylamine.

Method N: Kinetex XB-C18 (75×3) mm, 2.6 µm; Mobile Phase A: 10 mM $NH_4OAc$ in water:acetonitrile (98:02); Mobile Phase B: 10 mM $NH_4OAc$ in water:acetonitrile (02:98); Gradient: 20-100% B over 4 minutes, Flow rate: 1 mL/min, then a 0.6 minute hold at 100% B Flow rate: 1.5 mL/min; then Gradient: 100-20% B over 0.1 minutes, Flow rate: 1.5 mL/min.

Method O: Column: Ascentis Express C18 (50×2.1) mm, 2.7 µm; Flow rate: 1.1 mL/min; Gradient time 3 min; Temperature: 50° C., 0% Solvent B to 100% Solvent B; monitoring at 220 nm (Solvent A: 95% water:5% acetonitrile; 10 mM $NH_4OAc$; Solvent B: 5% water:95% acetonitrile; 10 mM $NH_4OAc$).

Method P: Column: Ascentis Express C18 (50×4.6) mm, 2.7 µm, Flow rate: 4 mL/min; Gradient: 0 to 100% Solvent B over 4 min; Temperature: 50° C. Monitoring at 220 nm (Solvent A: 95:05 water:$CH_3CN$ with 10 mM $NH_4OAc$ and Solvent B: 05:95 water:$CH_3CN$ with 10 mM $NH_4OAc$).

Method Q: Column: Ascentis Express C18 (50×4.6) mm, 2.7 µm, Flow rate: 4 mL/min; Gradient: 0 to 100% Solvent B over 4 min; Temperature: 50° C.; monitoring at 220 nm (Solvent A: 95:05 water:$CH_3CN$ with 0.1% TFA and Solvent B: 05:95 water:$CH_3CN$ with 0.1% TFA).

Method R: Column: Ascentis Express C18 (50×2.1) mm, 2.7 µm, Flow rate: 1.1 mL/min; Gradient: 0 to 100% Solvent B over 3 min; Temperature: 50° C.; monitoring at 220 nm (Solvent A: 95:05 water:$CH_3CN$ with 0.1% TFA and Solvent B: 05:95 water:$CH_3CN$ with 0.1% TFA).

Method S: Column: CHIRALPAK® ASH (250×4.6) mm, 5.0 µm; Isocratic Mode, $CO_2$: Co-solvent (85:15), Co-solvent: 0.2% DEA in methanol; Co-solvent percentage: 15%, Column Temperature: 22.1° C.; Back Pressure: 100 bars; Total Flow: 3 g/min; $CO_2$ flow: 2.55 g/min; Co-solvent flow: 0.45 g/min.

Method T: Column: Acquity BEH C18 (2.1×50 mm) 1.7 µm; Mobile Phase A: Buffer: ACN (95:5); Mobile Phase B: Buffer: ACN (5:95), Buffer: 5 mM ammonium acetate; Gradient: 20-90% B over 1.1 minutes, then a 0.6 minute hold at 90% B, Flow rate: 0.5 mL/min.

Method U: Column: Kinetex XB-C18 (75×3) mm, 2.6 µm; Mobile Phase A: 10 mM $NH_4COOH$ in water:acetonitrile (98:02; Mobile Phase B: 10 mM $NH_4COOH$ in water:acetonitrile (02:98); Gradient: 20-100% B over 4 minutes, Flow rate: 1 mL/min, then a 0.6 minute hold at 100% B Flow rate: 1.5 mL/min; then Gradient: 100-20% B over 0.1 minutes, Flow rate: 1.5 mL/min.

Method V: Column: CHIRALPAK® ASH (250×4.6) mm, 5.0 µm; Isocratic Mode, Co-solvent: 0.2% DEA in methanol; Co-solvent percentage: 20%, Column Temperature: 20.2° C.; Back Pressure: 100 bars; Total Flow: 3 g/min; $CO_2$ flow: 2.4 g/min; Co-solvent flow: 0.6 g/min.

Method W: Column: CHIRALPAK® ASH (250×4.6) mm, 5.0 µm; Isocratic Mode, Co-solvent: 0.2% DEA in methanol; Co-solvent percentage: 30%, Column Temperature: 20.2° C.; Back Pressure: 100 bars; Total Flow: 3 g/min; $CO_2$ flow: 2.1 g/min; Co-solvent flow: 0.9 g/min.

Method X: Column: CHIRALPAK® ASH (250×4.6) mm, 5.0 µm; Isocratic Mode, Co-solvent: 0.2% DEA in methanol; Co-solvent percentage: 25%, Column Temperature: 24.3° C.; Back Pressure: 100 bars; Total Flow: 3 g/min; $CO_2$ flow: 2.5 g/min; Co-solvent flow: 0.75 g/min.

Method Y: Column: CHIRALPAK® ASH (250×4.6) mm, 5.0 µm; Isocratic Mode, Co-solvent: 0.2% DEA in methanol; Co-solvent percentage: 25%, Column Temperature: 27.1° C.; Back Pressure: 100 bars; Total Flow: 3 g/min; $CO_2$ flow: 2.25 g/min; Co-solvent flow: 0.75 g/min.

Method Z: Column: CHIRALCEL®-OJH (250×4.6) mm, 5.0 µm; Isocratic Mode, Co-solvent: 0.2% DEA in methanol; Co-solvent percentage: 30%, Column Temperature: 26° C.; Back Pressure: 100 bars; Total Flow: 3 g/min; $CO_2$ flow: 2.1 g/min; Co-solvent flow: 0.9 g/min.

Method AA: Column: Acquity BEH C18 (2.1×50 mm) 1.7 µm; Mobile Phase A: 0.1% TFA in water; Mobile Phase B: acetonitrile; Gradient: 2-98% B over 1 minute, then a 0.6 minute hold at 98% B.

Method AB: Column: Lux Cellulose-4 (250×4.6) mm, 5.0 µm; Isocratic Mode, Co-solvent: 0.2% DEA in methanol; Co-solvent percentage: 30%, Column Temperature: 24.2° C.; Back Pressure: 100 bars; Total Flow: 3 g/min; $CO_2$ flow: 2.1 g/min; Co-solvent flow: 0.9 g/min.

Method AC: Column: CHIRALCEL®-ASH (250×4.6) mm, 5.0 µm; Isocratic Mode, Co-solvent: 0.2% DEA in methanol; Co-solvent percentage: 30%, Column Temperature: 26° C.; Back Pressure: 100 bars; Total Flow: 3 g/min; $CO_2$ flow: 2.1 g/min; Co-solvent flow: 0.9 g/min.

Method AD: Kinetex XB-C18 (75×3) mm, 2.6 µm; Mobile Phase A: 0.1% HCOOH in water; Mobile Phase B: 100% acetonitrile; Gradient: 20-100% B over 4 minutes; Flow rate: 1 mL/min, then a 0.6 minute hold at 100% B Flow rate: 1.5 mL/min; Flow rate: 1.5 mL/min.

Method AE: Column: HP-5MS (Part Number: AGILENT® 19091S-433); (250×30) mm; 0.25 µm; Injection volume 3 µl, run time 17 min (GCMS).

Method AF: Column: CHIRALPAK® AD-H (250×4.6) mm, 5.0 µm; Isocratic Mode, Co-solvent: 0.25% DEA in methanol; Co-solvent percentage: 30%, Column Temperature: 25° C.; Back Pressure: 100 bars; Total Flow: 3 g/min; $CO_2$ flow: 2.1 g/min; Co-solvent flow: 0.9 g/min.

Method AG: Column: CHIRALCEL®-ASH (250×21) mm, 5.0 µm; Isocratic Mode, Co-solvent: 0.25% DEA in methanol; Co-solvent percentage: 45%, Column Temperature: 25° C.; Back Pressure: 100 bars; Total Flow: 75 g/min.

Method AH: Column: CHIRALCEL®-ASH (250×4.6) mm, 5.0 µm; Isocratic Mode, Co-solvent: 0.2% DEA in methanol; Co-solvent percentage: 40%, Column Temperature: 25° C.; Back Pressure: 100 bars; Total Flow: 4 g/min.

Method AI: Column: CHIRALCEL®-ASH (250×4.6) mm, 5.0 µm; Isocratic Mode, Co-solvent: 0.2% DEA in methanol; Co-solvent percentage: 30%, Column Temperature: 24.7° C.; Back Pressure: 95 bars; Total Flow: 4 g/min; $CO_2$ flow: 2.4 g/min; Co-solvent flow: 1.6 g/min.

Method AJ: Column: CHIRALPAK® AD-H (250×30) mm, 5.0 µm; Isocratic Mode, Co-solvent: 0.25% DEA in methanol; Co-solvent percentage: 30%, Column Temperature: 25° C.; Back Pressure: 100 bars; Total Flow: 120 g/min.

Method AK: Column: CHIRALPAK® AD-H (250×4.6) mm, 5.0 µm; Isocratic Mode, Co-solvent: 0.25% DEA in methanol; Co-solvent percentage: 40%, Column Temperature: 25° C.; Back Pressure: 100 bars; Total Flow: 4 g/min; $CO_2$ flow: 2.4 g/min; Co-solvent flow: 1.6 g/min.

Method AM: Column: CHIRALPAK® IA (250×4.6) mm, 5.0 µm; Isocratic Mode, Co-solvent: 0.2% DEA in methanol; Co-solvent percentage: 30%, Column Temperature: 21° C.; Back Pressure: 100 bars; Total Flow: 3 g/min; $CO_2$ flow: 2.1 g/min; Co-solvent flow: 0.9 g/min.

Method AN: Column: CHIRALPAK® IA (250×4.6) mm, 5.0 µm; Isocratic Mode, Co-solvent: 0.2% DEA in methanol; Co-solvent percentage: 20%, Column Temperature: 21° C.; Back Pressure: 100 bars; Total Flow: 3 g/min; $CO_2$ flow: 2.4 g/min; Co-solvent flow: 0.6 g/min.

Method AU: Column: XBridge C18 (50×3.0) mm, 1.7 µm; Flow rate: 1.0 mL/min; Gradient time 0 min 0% Solvent B to 2 min 100% Solvent B, then a 1.0 minute hold at 100% B, monitoring at 220 nm (Solvent A: 10 mM 98% ammonium formate, 2% acetonitrile; Solvent B: 10 mM 2% ammonium formate, 98% acetonitrile).

Method AV: Column: Acquity BEH C8 (2.1×50 mm) 1.7 µm; Mobile Phase A: Buffer: ACN (95:5); Mobile Phase B: Buffer: ACN (5:95), Buffer: 5 mM ammonium acetate; Gradient: 20-90% B over 1.1 minutes, then a 0.6 minute hold at 90% B, Flow rate: 0.5 mL/min.

Method AQ: Column: CHIRALPAK® OD-H (250×4.6) mm, 5.0 µm, Co-solvent: 0.2% DEA in methanol; Co-solvent percentage: 40%, Column Temperature: 30° C.; Back Pressure: 100 bars; Total Flow: 3 g/min.

Method AR: Column: Lux Cellulose-2 (250×4.6) mm, 5.0 µm; Isocratic Mode, Co-solvent: 0.2% DEA in methanol; Co-solvent percentage: 10%, Column Temperature: 30° C.; Back Pressure: 100 bars; Total Flow: 3 g/min.

Method AS: Column: Whelk-O1 (R,R) (4.6×250) mm, 5µ; Co-solvent: 0.2% DEA in IPA; Co-solvent percentage: 15%, Column Temperature: 20.6° C.; Back Pressure: 100 bars; Total Flow: 3 g/min.

Method AT: Column: Ascentis Express C18 (50×2.1) mm, 1.7 µm; Flow rate: 1.0 mL/min; Gradient time 0 min 20% Solvent B to 4 min 100% Solvent B, then a 0.6 minute hold at 100% B, monitoring at 220 nm (Solvent A: 10 mM 98% ammonium formate, 2% acetonitrile; Solvent B: 10 mM 2% ammonium formate, 98% acetonitrile).

Method AU: Column: Waters XBridge C18 (19×150) mm, 5-µm particles; Mobile Phase A: 10 mM ammonium acetate; Mobile Phase B: acetonitrile; Gradient: 5-45% B over 25 minutes, then a 5-minute hold at 100% B; Flow: 15 mL/min.

Method AV: Column: Lux Cellulose-2 (250×4.6) mm, 5.0 µm; Isocratic Mode, Co-solvent: 25% (0.2% DEA in methanol; Co-solvent percentage: 75%, Column Temperature: 30° C.; Back Pressure: 100 bars; Total Flow: 3 g/min; $CO_2$ flow: 2.1 g/min; Co-solvent flow: 0.9 g/min.

Method AW: Column: YMC Amylose SA (250×4.6) mm, 5.0 µm; Isocratic Mode, Co-solvent: (0.2% DEA in ethanol; Co-solvent percentage: 20%, Column Temperature: 30° C.; Back Pressure: 100 bars; Total Flow: 3 g/min; $CO_2$ flow: 2.1 g/min; Co-solvent flow: 0.9 g/min.

Method AX: Column: CHIRALPAK® IC (250×4.6) mm, 5.0 µm; Isocratic Mode, Co-solvent: 0.25% DEA in ethanol; Co-solvent percentage: 30%, Column Temperature: 30° C.; Back Pressure: 100 bars; Total Flow: 3 g/min; $CO_2$ flow: 2.1 g/min; Co-solvent flow: 0.9 g/min.

Method AY: Column: Acquity BEH C18 (3.0×50 mm) 1.7 µm; Mobile Phase A: Buffer: ACN (95:5); Mobile Phase B: Buffer: ACN (5:95), Buffer: 5 mM ammonium acetate; Gradient: 20-90% B over 1.1 minutes, then 1.7 minute hold at 90% B, Flow rate: 0.7 mL/min.

Method AZ: Column: CHIRALPAK® AD-H (250×30) mm, 5.0 µm; Isocratic Mode, Co-solvent: 0.2% DEA in methanol; Co-solvent percentage: 30%, Column Temperature: 25° C.; Back Pressure: 100 bars; Total Flow: 120 g/min.

Method BA: Column: Acquity UPLC BEH C18 (3×50 mm) 1.7 µm; Mobile Phase A: Buffer: ACN (95:5); Mobile Phase B: Buffer: ACN (5:95), Buffer: 5 mM ammonium acetate; Gradient: 20-90% B over 1.1 minutes, then a 0.6 minute hold at 90% B, Flow rate: 0.7 mL/min.

Method BB: Column: ZORBAX® SBC18 (4.6×50) mm, 5 µm; Mobile Phase A: 10 mM $NH_4COOH$ in water:acetonitrile (98:02); Mobile Phase B: 10 mM $NH_4COOH$ in water:acetonitrile (02:98); Gradient: 0-100% B over 4 minutes, Flow rate: 1.5 mL/min, then a 0.6 minute hold at 100% B Flow rate: 1.5 mL/min; then Gradient: 100-30% B over 0.1 minutes, Flow rate: 1.5 mL/min.

Method BC: Column: Acquity BEH C18 (2.1×50 mm) 1.7 µm; Mobile Phase A: 0.1% TFA in water; Mobile Phase B: 0.1% TFA in acetonitrile; Gradient: 10-90% B over 1.0 minutes, then a 0.6 minute hold at 90% B, Flow rate: 0.7 mL/min.

Method BD: Column: Kinetex SBC18 (4.6×50 mm—5 µm), Mobile Phase A: 10 mM $NH_4COOH$ in water:ACN (98:02), Mobile Phase B: 10 mM $NH_4COOH$ in water:ACN (02:98), Buffer: 10 mM ammonium acetate; Gradient: 30-100% B over 4.0 minutes, then a 0.6 minute hold at 100% B, Flow rate: 1.5 mL/min.

Method BE: Gemini-Kinetex nx-C18 (4.6×50 mm—5 µm), Mobile Phase A: 10 mM $NH_4COOH$ in water:ACN (98:02), Mobile Phase B: 10 mM $NH_4COOH$ in water:ACN (02:98), Buffer: 10 mM ammonium acetate; Gradient: 30-100% B over 4.0 minutes, then a 0.6 minute hold at 100% B, Flow rate: 1.5 mL/min.

Method BF: Column: CHIRALCEL®-OJH (250×4.6) mm, 5.0 µm; Co-solvent: 0.2% DEA in methanol; Co-solvent percentage: 20%, Column Temperature: 30° C.; Back Pressure: 100 bars; Total Flow: 3 g/min.

Method BG: Column: Whelk-O1 (R,R) (250×4.6) mm, 5µ; Co-solvent: 0.2% DEA in ethanol; Co-solvent percentage: 5%, Column Temperature: 22.2° C.; Back Pressure: 100 bars; Total Flow: 3 g/min.

Method BH: Column: CHIRALPAK® AD-H (250×4.6) mm, 5.0 µm; Co-solvent: 0.2% DEA in IPA; Co-solvent percentage: 15%, Column Temperature: 30° C.; Back Pressure: 100 bars; Total Flow: 3 g/min.

Method BI: Column: CHIRALPAK® AD-H (250×3.0) mm, 5.0 µm; Isocratic Mode, Co-solvent: 0.2% DEA in methanol; Co-solvent percentage: 30%, Column Temperature: 25° C.; Back Pressure: 100 bars.

Method BJ: Column: CHIRALPAK® AD-H (250×4.6) mm, 5.0 µm; Co-solvent: 0.2% DEA in methanol+IPA (1:1); Co-solvent percentage: 10%, Column Temperature: 30° C.; Back Pressure: 100 bars; Total Flow: 3 g/min.

Method BK: Column: CHIRALPAK® AD-H (250×4.6) mm, 5.0 µm; Co-solvent: 0.2% DEA in methanol; Co-solvent percentage: 10%, Column Temperature: 30° C.; Back Pressure: 100 bars; Total Flow: 3 g/min.

Method BL: Column: CHIRALPAK® OD-H (250×2.1) mm, 5.0 μm, Co-solvent: 0.2% DEA in IPA; Co-solvent percentage: 15%, Column Temperature: 30° C.

Method BM: Column: CHIRALPAK® AD-H (250×4.6) mm, 5.0 μm; Co-solvent: 0.2% DEA in methanol; Co-solvent percentage: 25%, Column Temperature: 30° C.; Back Pressure: 100 bars; Total Flow: 3 g/min.

Method BN: Column: CHIRALPAK® AD-H (250×4.6) mm, 5.0 μm; Co-solvent: 0.1% NH$_4$OH in IPA; Co-solvent percentage: 10%, Column Temperature: 30° C.; Back Pressure: 100 bars; Total Flow: 3 g/min.

Method BO: Column: Ascentis Express C18 (50×2.1 mm) 2.7 μm, Mobile Phase A: 10 mM NH$_4$COOH in water:ACN (98:02), Mobile Phase B: 10 mM NH$_4$COOH in water:ACN (02:98); Gradient: 0-100% B over 1.5 minutes, then a 1.7 minute hold at 100% B, Flow rate: 1.0 mL/min.

Method BP: Column: Whelk-O1 (R,R) (250×4.6) mm, 5μ; Co-solvent: 0.2% DEA in IPA; Co-solvent percentage: 10%, Column Temperature: 30° C.; Back Pressure: 100 bars; Total Flow: 3 g/min.

Method BQ: Column: CHIRALPAK® IC (250×4.6) mm, 5.0 μm; Isocratic Mode, Co-solvent: 0.2% DEA in methanol: IPA (1:1); Co-solvent percentage: 10%, Column Temperature: 30° C.; Back Pressure: 100 bars; Total Flow: 3 g/min.

Method BR: Column: CHIRALPAK® OJ-H (250×4.6 mm), 5μ; Mobile Phase: 0.2% TEA in n-hexane:EtOH (70:30), Flow: 1.0 mL/min.

Method BS: Column: CHIRALCEL®-OJH (250×4.6) mm, 5.0 μm; Co-solvent: 0.2% DEA in methanol; Co-solvent percentage: 25%, Column Temperature: 28° C.; Back Pressure: 100 bars; Total Flow: 3 g/min.

Method BT: Column: CHIRALCEL®-OJH (250×4.6) mm, 5.0 μm; Co-solvent: 0.2% DEA in methanol; Co-solvent percentage: 15%, Column Temperature: 30° C.; Back Pressure: 100 bars; Total Flow: 60 g/min.

Method BU: Column: CHIRALPAK® AD-H (250×4.6) mm, 5.0 μm; Isocratic Mode, Co-solvent: 0.2% DEA in IPA+ACN; Co-solvent percentage: 10%, Column Temperature: 25° C.; Back Pressure: 100 bars; Total Flow: 3 g/min.

Method BV: Column: Lux Amylose 2 (250×21.2) mm, Mobile Phase A: 0.2% DEA in hexane; Mobile Phase B: EtOH; Flow: 25 mL/min.

Method BW: Column: Lux Cellulose-2 (250×4.6) mm, 5.0 μm; Isocratic Mode, Co-solvent: 25% (0.1% NH$_4$OH in methanol); Co-solvent percentage: 75%, Column Temperature: 30° C.; Back Pressure: 100 bars; Total Flow: 3 g/min.

Method BX: Column: Lux Cellulose-2 (250×4.6) mm, 5.0 μm; Isocratic Mode, Co-solvent: 0.2% DEA in ethanol; Co-solvent percentage: 20%, Column Temperature: 30° C.; Back Pressure: 100 bars; Total Flow: 3 g/min.

Method BY: Column: CHIRALPAK® AD-H (250×4.6) mm, 5.0 μm; Isocratic Mode, Co-solvent: 0.2% DEA in ethanol; Co-solvent percentage: 25%, Column Temperature: 25.7° C.; Back Pressure: 100 bars; CO$_2$ Flow rate: 2.25 g/min; Co solvent Flow rate: 0.75 g/min; Total Flow: 3 g/min.

Method BZ: Column: CHIRALCEL®-OJH (250×4.6) mm, 5.0 μm; Co-solvent: 0.2% DEA in methanol; Co-solvent percentage: 10%, Column Temperature: 30° C.; Back Pressure: 100 bars; Total Flow: 3 mL/min.

Method CA: Column: YMC Amylose SA (250×4.6) mm, 5.0 μm; Isocratic Mode, Co-solvent: 0.2% DEA in IPA; Co-solvent percentage: 15%, Column Temperature: 35° C.; Back Pressure: 100 bars; Total Flow: 60.0 g/min.

Method CB: Column: CHIRALPAK® ASH (250×4.6) mm, 5.0 μm; Isocratic Mode, Co-solvent: 0.2% DEA in hexane:IPA (98:02); Total Flow: 1.0 mL/min.

Method CC: Column: Lux Cellulose-4 (250×4.6) mm, 5.0 μm; Isocratic Mode, Co-solvent: 30% (0.1% NH$_4$OH in methanol); Co-solvent percentage: 30%, Column Temperature: 30° C.; Back Pressure: 100 bars; Total Flow: 60 g/min.

Method CD: Column: CHIRALCEL®-OJH (250×4.6) mm, 5.0 μm; Co-solvent: 0.2% DEA in methanol; Co-solvent percentage: 30%, Column Temperature: 30° C.; Back Pressure: 100 bars; Total Flow: 3 mL/min.

Method CE: Column: CHIRALCEL®-OJH (250×2.1) mm, 5.0 μm; Co-solvent: 0.2% DEA in methanol; Co-solvent percentage: 20%, Column Temperature: 30° C.; Back Pressure: 100 bars; Total Flow: 60 mL/min.

Method CF: Column: CHIRALCEL®-OJH (250×4.6) mm, 5.0 μm; Co-solvent: 0.2% DEA in IPA:ACN (1:1); Co-solvent percentage: 20%, Column Temperature: 30° C.; Back Pressure: 100 bars; Total Flow: 3 mL/min.

Method CG: Column: CHIRALPAK® IC (250×3.0) mm, 5.0 μm; Co-solvent: 0.2% DEA in methanol: IPA (1:1); Co-solvent percentage: 10%, Column Temperature: 30° C.; Back Pressure: 100 bars; Total Flow: 110 g/min.

Method CH: Column: Lux Amylose 2 (250×4.6) mm, 5.0 μm; Mobile Phase A: 0.2% DEA in hexane; Mobile Phase B: EtOH; Flow: 1 mL/min.

Method CI: Column: Kineticsx 2.6μ, EVO c18 100 Au. Mobile Phase A; 5 mM NH$_4$COAC in water:ACN (95:05), Mobile Phase B: 5 mM NH$_4$COAC in water:ACN (05:95), Buffer: 5 mM ammonium acetate; Flow rate: 0.7 mL/min.

Method CJ: Column: CHIRALCEL®-OJH (250×4.6) mm, 5.0 μm; Co-solvent: 0.2% DEA in n-hexane:EtOH (98:2 Total Flow: 1 mL/min.

Method CK: Column: Lux Cellulose-4 (250×4.6) mm, 5.0 μm; Isocratic Mode, Co-solvent: 0.2% DEA in IPA; Co-solvent percentage: 15%, Column Temperature: 30° C.; Back Pressure: 100 bars; Total Flow: 3 g/min.

Method CL: Column: CHIRALPAK® AD-H (250×4.6) mm, 5.0 μm; Isocratic Mode, Co-solvent: 0.2% DEA in methanol; Co-solvent percentage: 30%, Column Temperature: 30° C.; Back Pressure: 100 bars; Total Flow: 4 g/min.

Method CM: Column: CHIRALPAK® AD-H (250×4.6) mm, 5.0 μm; Co-solvent: 0.2% DEA in IPA; Co-solvent percentage: 30%, Column Temperature: 30° C.; Back Pressure: 100 bars; Total Flow: 4 g/min.

Method CN: Column: CHIRALPAK® IC (250×4.6) mm, 5.0 μm; Isocratic Mode, Co-solvent: 0.2% DEA in methanol: ACN (1:1); Co-solvent percentage: 25%, Column Temperature: 30° C.; Back Pressure: 100 bars; Total Flow: 3 g/min.

Method CO: Column: Lux Cellulose-4 (250×4.6) mm, 5.0 μm; Co-solvent: 0.2% DEA in methanol; Co-solvent percentage: 10%, Column Temperature: 30° C.; Back Pressure: 100 bars; Total Flow: 3 g/min.

Method CP: Column: ZORBAX® AQ (4.6×50) mm, 5 μm; Mobile Phase A: 10 mM NH$_4$COOH in water:acetonitrile (98:02); Mobile Phase B: 10 mM NH$_4$COOH in water:acetonitrile (02:98); Gradient: 30-100% B over 4 minutes, Flow rate: 1.5 mL/min, then a 0.6 minute hold at 100% B Flow rate: 1.5 mL/min; then Gradient: 100-30% B over 0.1 minutes, Flow rate: 1.5 mL/min.

Method CQ: Column: Gemini nx-C18 (50×4.6) mm, 5 μm; Mobile Phase A: 10 mM NH$_4$COOH in water:acetonitrile (98:02); Mobile Phase B: 10 mM NH$_4$COOH in water: acetonitrile (02:98); Gradient: 30-100% B over 4 minutes, Flow rate: 1.5 mL/min, then a 0.6 minute hold at 100% B Flow rate: 1.5 mL/min; then Gradient: 100-30% B over 0.1 minutes, Flow rate: 1.5 mL/min.

Method CR: Column: CHIRALPAK® AD-H (250×4.6) mm, 5.0 μm; Co-solvent: 0.2% DEA in methanol; Co-solvent percentage: 20%, Column Temperature: 30° C.; Back Pressure: 100 bars; Total Flow: 3 g/min.

Method CS: Column: XBridge C18 (50×4.6) mm, 5 μm, Flow rate: 4.0 mL/min; Gradient: 0 to 100% Solvent B over 3 min; Temperature: 35° C.; monitoring at 220 nm (Solvent A: 95:05 water:$CH_3CN$ with 0.1% TFA and Solvent B: 05:95 water:$CH_3CN$ with 0.1% TFA).

Method CT: Column: CHIRALPAK® IA (250×4.6) mm, 5.0 μm; Co-solvent: 0.2% DEA in methanol; Co-solvent percentage: 15%, Column Temperature: 21.7° C.; Back Pressure: 96 bars; Total Flow: 3 g/min; $CO_2$ flow: 2.55 g/min; Co-solvent flow: 0.45 g/min.

Method CU: Column: CHIRALPAK® ASH (250×4.6) mm, 5.0 μm; Co-solvent: 0.2% DEA in IPA; Co-solvent percentage: 20%, Column Temperature: 30° C.; Back Pressure: 100 bars; Total Flow: 3 mL/min.

Method CV: Column: Lux Cellulose-4 (250×4.6) mm, 5.0 μm; Co-solvent: 0.2% DEA in IPA:methanol, (1:1); Co-solvent percentage: 10%, Column Temperature: 30° C.; Back Pressure: 100 bars; Total Flow: 3 g/min.

Method CW: Column: CHIRALPAK® AD-H (250×30) mm, 5.0 μm; Isocratic Mode, Co-solvent: 0.2% DEA in methanol; Co-solvent percentage: 30%, Column Temperature: 21.6° C.; Back Pressure: 104 bars; Total Flow: 3 g/min. $CO_2$ Flow rate: 2.1; Co solvent Flow rate: 0.9.

Method CX: Column: Lux Amylose-2 (250×4.6) mm, 5.0 μm; Isocratic Mode, Co-solvent: 15% (0.2% DEA in IPA; Column Temperature: 30° C.; Back Pressure: 101 bars; Total Flow: 3 g/min; $CO_2$ flow: 2.55 g/min; Co-solvent flow: 0.45 g/min.

Method CY: Column: Lux Cellulose-4 (250×4.6) mm, 5.0 μm; Mobile Phase: 0.2% TFA in n-hexane:methanol:ethanol (97:03), Flow rate: 1.0 mL/min.

Method CZ: Column: XBridge C18 (50×4.6) mm, 5.0 μm; Mobile Phase A: 0.1% TFA in water; Mobile Phase B: acetonitrile; Gradient: 5-95% B over 4 minutes, Temp: 35° C.; Flow Rate: 4.0 mL/min.

Method DA: Column: R,R-WHELK (250×4.6) mm, 5 μm, Mobile Phase: 0.2% EA in n-hexane:IPA (99:01), Flow: 1.0 mL/min.

Method DB: Column: Lux Cellulose-4 (250×4.6) mm, 5 μm, Co-solvent 0.2% DEA in methanol, Column Temperature 19.4° C., $CO_2$ Flow Rate 1.8 g/min, Co-solvent Flow Rate 1.2 g/min, Co-solvent 40%, Total Flow 3 g/min, Back Pressure 104 bars.

Method DC: Column: XBridge C18 (50×4.6) mm, 5 μm, Solvent A: 10 mM $NH_4OAc$, Solvent B: acetonitrile, Temp: 35° C., Gradient: 5-95% B over 4 minutes, Flow Rate: 4.0 ml/min.

Method DD: Column: CHIRALPAK® AD-H (250×4.6) mm, 5 μm, Co-solvent 0.2% DEA in methanol, Column Temperature 19.5° C., $CO_2$ Flow Rate 2.25 g/min, Co-solvent Flow Rate 0.75 g/min, Co-solvent 25%; Total Flow 3 g/min; Back Pressure 100 bars.

Method DE: Column: CHIRALPAK® AD-H (250×4.6) mm, 5 μm, Column Temperature 27° C., Co-solvent 0.2% DEA in methanol, $CO_2$ Flow Rate 2.25 g/min, Co-solvent Flow Rate 0.75 g/min, Co-solvent 25%, Total Flow 3 g/min, Back Pressure 98 bars.

Method DF: Column: CHIRALPAK® IA (250×4.6) mm, 5μ, Co-solvent 0.1% $NH_4OH$ in IPA, Column Temperature 19.3° C., $CO_2$ Flow Rate 1.8 g/min, Co-solvent Flow Rate 1.2 g/min, Co-solvent 40%, Total Flow 3 g/min, Back Pressure 100 bars.

Method DG: Column: CHIRALPAK® AD-H (250×4.6) mm, 5 μm, Co-solvent; 0.2% DEA in IPA, Column Temperature: 15.3° C., $CO_2$ Flow Rate: 2.4 g/min, Co-solvent Flow Rate: 3 g/min, Co-solvent: 99%, Back Pressure 100 bars.

Method DH: Column: CHIRALPAK® AD-H (250×4.6) mm, 5 μm, Co-solvent: 0.2% DEA in IPA, Column Temperature: 27.7° C., $CO_2$ Flow Rate: 2.4 g/min, Co-solvent Flow Rate: 0.6 g/min, Co-solvent: 20%, Total Flow; 3 g/min, Back Pressure; 100 bars.

Method DI: Column: CHIRALPAK® AD-H (250×4.6) mm, 5 μm, Co-solvent: 0.1% $NH_4OH$ in IPA, Column Temperature: 21.4° C., $CO_2$ Flow Rate: 2.25 g/min, Co-solvent Flow Rate: 0.75 g/min, Co-solvent: 25%, Total Flow: 3 g/min, Back Pressure: 102 bars.

Method DJ: Column: CHIRALPAK® AD-H (250×4.6) mm, 5 μm, Co-solvent: IPA, Column Temperature: 20.6° C., $CO_2$ Flow Rate: 2.7 g/min, Co-solvent Flow Rate: 0.3 g/min, Co-solvent: 10%, Total Flow: 3, Back Pressure: 100.

Method DK: Column: CHIRALPAK®-IA (250×4.6), 5 μm, Mobile Phase: −0.2% DEA in n-hexane:EtOH (60:40), Flow: 1.0 ml/min.

Method DL: Column: CHIRALPAK® AD-H (250×4.6) mm, 5.0 μm; Isocratic Mode, Co-solvent: 0.2% DEA in IPA+ACN; Co-solvent percentage: 10%, Column Temperature: 30° C.; Back Pressure: 100 bars; Total Flow: 3 g/min.

Method DM: Column: XBridge BEH C8 (2.1×50 mm) 2.5 μm; Mobile Phase A: Buffer: ACN (95:5); Mobile Phase B: Buffer: ACN (5:95), Buffer: 5 mM ammonium acetate; Gradient: 20-90% B over 1.1 minutes, then a 1.7 minute hold at 90% B, Flow rate: 0.5 mL/min.

Method DN: Column: CHIRALCEL®-OJH (250×4.6) mm, 5.0 μm; Isocratic Mode, Co-solvent: 0.2% DEA in ethanol; Co-solvent percentage: 10%, Column Temperature: 25.8° C.; Back Pressure: 100 bars; Total Flow: 3 g/min; $CO_2$ flow: 2.7 g/min; Co-solvent flow: 0.3 g/min.

Method DO: Column: Acquity BEH C18 (2.1×50 mm) 1.7 μm; Mobile Phase A: Buffer: ACN (95:5); Mobile Phase B: Buffer: ACN (5:95), Buffer: 5 mM ammonium acetate; Gradient: 20-90% B over 1.1 minutes, then a 0.6 minute hold at 90% B, Flow rate: 0.7 mL/min.

Method DP: Column: CHIRALCEL® OD-H (250×4.6) mm, 5 μm; Co-solvent: 0.2% DEA in MeOH; $CO_2$ Flow Rate: 2.4 g/min; Co-solvent Flow Rate: 0.6; Co-solvent 20%; Total Flow: g/mon3; Back Pressure: 100 bars.

Method DQ: Column: CHIRALCEL® IE (250×4.6) mm, 5 μm; Mobile Phase: 0.2% DEA in hexane:ethanol:methanol (1:1) (95:05) Flow: 1.0 ml/min.

Method DR: Kinetex C18 (75×3) mm, 2.6 μm; Mobile Phase A: 10 mM $NH_4OAc$ in water:acetonitrile (98:02); Mobile Phase B: 10 mM $NH_4OAc$ in water:acetonitrile (02:98); Gradient: 80-98% B over 2.5 minutes, Flow rate: 1 mL/min, then a 1.0 minute hold at 98% B Flow rate: 1.0 mL/min; then Gradient: 100-20% B over 0.1 minutes, Flow rate 1.0 mL/min.

Method DS: Column: CHIRALPAK® AD-H (250×4.6) mm, 5.0 μm; Co-solvent: 0.2% DEA in methanol; Co-solvent percentage: 15%, Column Temperature: 30° C.; Back Pressure: 100 bars; Total Flow: 3 g/min.

Method DT: Column: CHIRALPAK® AS, 250 mm×30 mm, 5μ. Mobile Phase: 85 mL/min. of 88:12 $CO_2$:MeOH.

Method DU: Column: WHELK-O1®) (R,R), KROMASIL®, 250 mm×4.6 mm, 5μ. Mobile Phase: 2 mL/min. of 85:15 $CO_2$:MeOH.

Method DV: Column: WHELK-O1®) (R,R), KROMASIL®, 250 mm×4.6 mm, 5μ. Mobile Phase: 2 mL/min. of 90:10 $CO_2$:MeOH.

Method DW: Column: PHENOMENEX® Lux Cellulose-2, 250 mm×4.6 mm, 5μ. Mobile Phase: 2 mL/min. of 85:15 CO$_2$:MeOH.

Method DX: Column: PHENOMENEX® Lux Cellulose-2, 250 mm×4.6 mm, 5μ. Mobile Phase: 2 mL/min. of 90:10 CO$_2$:MeOH+0.1% each of formic acid and diethylamine.

Method DY: Column: PHENOMENEX® Lux Cellulose-2, 250 mm×4.6 mm, 5μ. Mobile Phase: 2 mL/min. of 80:20 CO$_2$:MeOH+0.1% each of formic acid and diethylamine.

Method DZ: Column: CHIRALPAK® AS, 250 mm×4.6 mm, 5μ. Mobile Phase: 2 mL/min. of 90:10 CO$_2$:MeOH.

Example 1

3-(3-((4-Chlorophenyl)amino)-4-(ethyl(4-hydroxy-4-methylcyclohexyl)amino)phenyl)-3-methylbutanoic acid

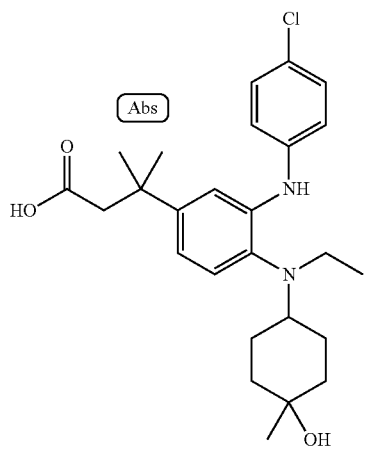 [SMILES: CCN(c1ccc(C(C)(C)CC(=O)O)cc1Nc1ccc(Cl)cc1)C1CCC(C)(O)CC1]

1A. 8-Methyl-1,4-dioxaspiro[4.5]decan-8-ol

A stirred solution of 1,4-dioxaspiro[4.5]decan-8-one (5 g, 32.0 mmol) in dry THF (70 mL) was cooled to −70° C. and methylmagnesium bromide (23.48 mL, 70.4 mmol) in ether was added dropwise over 10 min. The cooling bath was allowed to warm to room temperature and the mixture was stirred overnight. The mixture was quenched with sat. aq. NH$_4$Cl (75 mL) and extracted with diethyl ether (2×300 mL). The combined ether extracts were washed with brine (50 mL), dried over anhydrous sodium sulfate and concentrated under reduced pressure to afford 1A (yellow liquid, 5.1 g, 29.6 mmol, 92% yield) which was used in next step without further purification. $^1$H NMR (400 MHz, CDCl$_3$) δ 3.96-3.90 (m, 4H), 1.91-1.84 (m, 2H), 1.71-1.65 (m, 3H), 1.63-1.57 (m, 3H), 1.22 (s, 3H).

1B. 4-Hydroxy-4-methylcyclohexanone

Compound 1A (5.1 g, 29.6 mmol) was dissolved in THF (100 mL), followed by addition of 1N aqueous HCl (44.4 mL, 44.4 mmol) at room temperature. The resulting mixture was stirred at room temperature for 16 h. The resulting reaction liquid was concentrated under reduced pressure and then extracted with 10% MeOH/DCM (2×200 mL). The combined organic layer were washed with brine (50 mL), dried over anhydrous sodium sulfate and concentrated under reduced pressure to afford 1B (yellow liquid, 3.1 g, 24.19 mmol, 82% yield) which was used in next step without further purification. $^1$H NMR (300 MHz, CDCl$_3$) δ 2.81-2.65 (m, 2H), 2.32-2.15 (m, 2H), 2.01-1.75 (m, 4H), 1.36 (s, 3H).

1C. 4-(Ethylamino)-1-methylcyclohexanol (Diastereomeric Mixture)

To a stirred solution of 1B (3.2 g, 24.97 mmol), ethanamine (13.73 mL, 27.5 mmol) in dry MeOH (50 mL) under nitrogen atmosphere molecular sieves (5.0 g) was added and the reaction stirred at room temperature overnight. Reaction mixture was cooled to 0° C. and was added NaBH$_4$ (1.889 g, 49.9 mmol) in portionwise in 10 minutes. Reaction stirred at room temperature for 3 h. Reaction mixture was concentrated under reduced pressure to get semi-solid. To this was added sat. NaHCO$_3$ (100 mL) and was stirred overnight. Reaction mixture was dissolved in EtOAc (400 ml), washed with water (100 ml), brine (100 ml), dried over Na$_2$SO$_4$ and concentrated under reduced pressure to get 1C (light yellow liquid, 3.1 g, 19.71 mmol, 79% yield). $^1$H NMR (400 MHz, CDCl$_3$) δ 2.65 (q, J=7.2 Hz, 2H), 2.45-2.35 (m, 1H), 1.92-1.61 (m, 4H), 1.51-1.35 (m, 4H), 1.23 (s, 3H), 1.10 (t, J=7.2 Hz, 3H).

1D. Dimethyl 2-(2-(4-fluorophenyl) propan-2-yl) malonate

To a stirred solution of (4-fluorophenyl)magnesium bromide (54.1 mL, 54.1 mmol) in diethyl ether (70 mL) at −10° C. was added copper(I) chloride (2.68 g, 27.1 mmol). Then dimethyl 2-(propan-2-ylidene)malonate (6.99 g, 40.6 mmol) in 10 mL ether was added in dropwise over 2 min. Reaction mixture was stirred for 20 minutes at room temperature, followed by reflux for 3 h. Reaction mixture was cooled to room temperature and quenched with ice cold 1 N HCl. The aqueous layer was extracted with diethyl ether (50 mL), dried over sodium sulfate, concentrated under reduced pressure to give 1D (light yellow liquid, 495 mg, 1.856 mmol, 65% yield). $^1$H NMR (300 MHz, CDCl$_3$) δ 7.34-7.31 (m, 2H), 6.99-6.94 (m, 2H), 3.75 (s, 1H), 3.58 (s, 6H), 1.56 (s, 6H).

1E. Methyl 3-(4-fluorophenyl)-3-methylbutanoate

To a stirred solution of 1D (12.5 g, 46.6 mmol), in DMSO (5.0 mL) and water (0.15 mL) mixture, lithium chloride (3.95 g, 93 mmol) was added. Reaction mixture heated to 180° C. and stirred for 5 h. Reaction mixture was cooled to room temperature, partitioned between diethyl ether (50 mL) and water (25 mL). Aqueous layer was extracted with ethyl acetate (2×100 mL). The combined organic layer was washed with brine (25 mL), dried over anhydrous sodium sulfate, concentrated under reduced pressure to get crude compound. Purification via flash chromatography gave 1E (gummy liquid, 6.2 g, 29.5 mmol, 63% yield). $^1$H NMR (300 MHz, DMSO-d$_6$) δ 7.34-7281 (m, 2H), 7.02-6.94 (m, 2H), 3.52 (s, 3H), 2.60 (s, 2H), 1.48 (s, 6H).

1F. Methyl 3-(4-fluoro-3-nitrophenyl)-3-methylbutanoate

To a stirred solution of 1E (0.200 g, 0.892 mmol) in H$_2$SO$_4$ (2.0 mL) at 0° C., nitric acid (0.092 mL, 1.338 mmol) was slowly added under nitrogen atmosphere and maintained at same temperature for 1 h. Reaction mixture quenched with ice and extracted with DCM (2×10 mL). Organic layer dried over sodium sulfate and concentrated under reduced pressure to get light yellow liquid. Purification via flash chromatography gave 1F (colorless liquid, 100 mg, 0.392 mmol, 42% yield). $^1$H NMR (300 MHz, DMSO-d$_6$) δ 8.05-8.02 (m, 1H), 7.65-7.61 (m, 1H), 7.25-7.19 (m, 1H), 3.53 (s, 3H), 2.65 (s, 2H), 1.47 (s, 6H).

1G. Methyl 3-(4-(ethyl(4-hydroxy-4-methylcyclohexyl)amino)-3-nitrophenyl)-3-methylbutanoate (Diastereomeric Mixture)

To a solution of 1F (1.0 g, 3.92 mmol) in dioxane (10 mL) was added DIPEA (2.053 mL, 11.75 mmol), followed by 1C (0.924 g, 5.88 mmol). Reaction mixture was heated to 135° C. and was stirred overnight. LCMS indicated completion of reaction. Reaction mixture was concentrated under reduced pressure to afford a residue. The residue was purified via flash silica gel column chromatography (ethyl acetate in pet ether as eluent) to afford 1G (yellow liquid, 1.1 g, 2.354 mmol, 60.1% yield). LC-MS Anal. Calc'd. $C_{21}H_{32}N_2O_5$ for 392.2, found [M+H] 393.2, $T_r$=3.3 min (Method N).

1H. Methyl 3-(3-amino-4-(ethyl(4-hydroxy-4-methylcyclohexyl)amino)phenyl)-3-methylbutanoate The solution of methyl 1G (850 mg, 2.166 mmol) in ethyl acetate (10.0 mL) was charged to a sealable hydrogen flask. The solution was sequentially evacuated and purged with nitrogen gas. To this 10% Pd on carbon (157 mg, 0.147 mmol) was added under nitrogen atmosphere. The reaction mixture was stirred under hydrogen atmosphere (40 psi) at room temperature for 16 h. The reaction mixture was filtered through a CELITE® pad and the residue on the pad was thoroughly rinsed with MeOH (3×20 mL). The combined filtrate was concentrated under reduced pressure to afford 1H (diastereomer mixture). LC-MS Anal. Calc'd. $C_{21}H_{34}N_2O_3$ for 362.3, found [M+H] 363.4, $T_r$=2.68 min (Method U).

Chiral separation of diastereomeric mixture 1H (Method AM) gave Diastereomer 1 $T_r$=3.76 min (Method AM), Diastereomer 2 $T_r$=6.37 min (Method AM).

1H Diastereomer 1 (yellow liquid, 90 mg, 0.248 mmol, 12% yield): LC-MS Anal. Calc'd. $C_{21}H_{34}N_2O_3$ for 362.3, found [M+H] 363.4, $T_r$=2.79 min (Method U).

1H Diastereomer 2 (yellow liquid, 650 mg, 1.793 mmol, 83% yield): LC-MS Anal. Calc'd. $C_{21}H_{34}N_2O_3$ for 362.3, found [M+H] 363.4, $T_r$=2.96 min (Method U).

1I. Methyl 3-(3-((4-chlorophenyl)amino)-4-(ethyl(4-hydroxy-4-methylcyclohexyl)amino)phenyl)-3-methylbutanoate The mixture of 1H Diastereomer 2 (100 mg, 0.276 mmol), 1-bromo-4-chlorobenzene (58.1 mg, 0.303 mmol), Xantphos (31.9 mg, 0.055 mmol) and $Cs_2CO_3$ (270 mg, 0.828 mmol) in dioxane (2.0 mL) was stirred at room temperature. Argon gas was bubbled through the mixture for 10 min. Bis(dibenzylideneacetone)palladium (15.86 mg, 0.028 mmol) was added and argon gas was bubbled through the mixture for 5 min. The reaction mixture was sealed and placed in preheated oil bath at 110° C. for 18 h. The reaction mixture was cooled to room temperature and concentrated under reduced pressure to afford a residue. The residue was reconstituted in a mixture of DCM (50 mL) and water (10 mL). The organic layer was separated and was washed with water (10 mL), brine (10 mL), dried over anhydrous sodium sulfate and concentrated under reduced pressure to afford a residue of 1I (131 mg, 0.116 mmol, 42% yield) which was used in next step without further purification. LC-MS Anal. Calc'd. $C_{27}H_{37}ClN_2O_3$ for 472.3, found [M+H] 473.5, $T_r$=2.13 min (Method BA).

Example 1. 3-(3-((4-Chlorophenyl)amino)-4-(ethyl(4-hydroxy-4-methylcyclohexyl)amino)phenyl)-3-methylbutanoic acid To a stirred solution of above residue 1I (0.116 mmol) in mixture of THF (1.0 mL), MeOH (1.0 mL) and water (0.5 mL) was added $LiOH·H_2O$ (33.0 mg, 1.380 mmol). The reaction mixture was stirred at room temperature for 12 h. The reaction mixture was concentrated under reduced pressure. The aqueous residue so obtained was acidified with 1N HCl to pH~2. The aqueous layer was diluted with water (5 mL) and extracted with ethyl acetate (2×20 mL). Combined organic layer was washed with water (10 mL), brine (10 mL), dried over anhydrous sodium sulfate and concentrated under reduced pressure to afford a residue. The residue was purified via preparative LC/MS to afford Example 1 (17.9 mg, 0.039 mmol, 14% yield). LC-MS Anal. Calc'd. $C_{26}H_{35}ClN_2O_3$ for 458.234, found [M+H] 459.2, $T_r$=2.3 min (Method O). $^1$H NMR (400 MHz, DMSO-$d_6$) δ 7.61-7.52 (m, 3H), 7.22-7.19 (m, 2H), 6.76 (d, J=8.7 Hz, 2H), 3.71-3.50 (m, 3H), 2.70 (s, 2H), 1.83-1.73 (m, 6H), 1.45-1.31 (m, 8H), 1.19 (s, 3H), 1.05 (t, J=6.9 Hz, 3H).

Examples 2 to 4

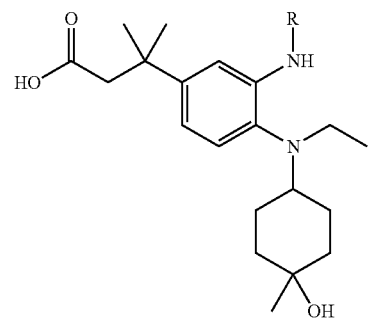

Examples 2 to 4 were prepared from 1H Diastereomer 2 and the corresponding halides following the procedure described for the synthesis of Example 1.

| Ex. No. | Name | R | $T_r$ (min) Method O | [M + H]$^+$ |
|---|---|---|---|---|
| 2 | 3-(4-(ethyl(4-hydroxy-4-methylcyclohexyl)amino)-3-((4-fluorophenyl)amino)phenyl)-3-methylbutanoic acid | F-C$_6$H$_4$- | 2.148 | 443.3 |

-continued

| Ex. No. | Name | R | T$_r$ (min) Method O | [M + H]$^+$ |
|---|---|---|---|---|
| 3 | 3-(3-((2-ethoxypyrimidin-5-yl)amino)-4-(ethyl(4-hydroxy-4-methylcyclohexyl)amino)phenyl)-3-methylbutanoic acid | 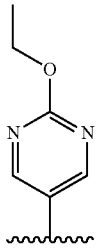 | 1.638 | 471.4 |
| 4 | 3-(3-((4-cyanophenyl)amino)-4-(ethyl(4-hydroxy-4-methylcyclohexyl)amino)phenyl)-3-methylbutanoic acid | 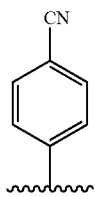 | 1.703 | 450.4 |

Example 5

3-(4-(Ethyl(4-hydroxy-4-methylcyclohexyl)amino)-3-(3-O-tolyl)ureido)phenyl)-3-methylbutanoic acid

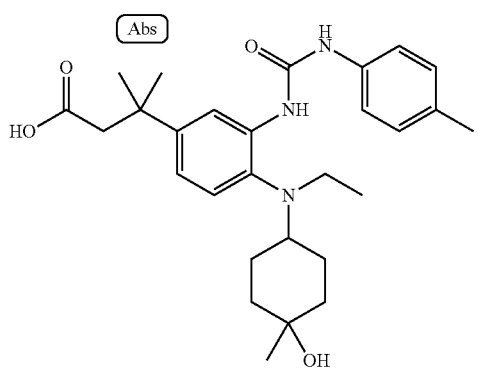 [SMILES: CCN(c1ccc(C(C)(C)CC(=O)O)cc1NC(=O)Nc1ccc(C)cc1)C1CCC(C)(O)CC1]

5A. Methyl 3-(4-(ethyl(4-hydroxy-4-methylcyclohexyl)amino)-3-(3-(p-tolyl)ureido)phenyl)-3-methylbutanoate To a stirred solution of 1H Diastereomer 2 (0.035 g, 0.097 mmol) in dry THF (1.0 mL), 1-isocyanato-4-methylbenzene (0.013 g, 0.097 mmol) was added at room temperature and was stirred for 12 h. Reaction mixture was diluted with DCM (50 mL), filtered through CELITE®, concentrated under reduced pressure to get the crude compound. The residue was purified via flash silica gel column chromatography (conditions: 0-10% MeOH/CHCl$_3$, 12 g silica gel column) to afford 5A (yellow liquid, 45 mg, 0.091 mmol, 94% yield). LC-MS Anal. Calc'd. C$_{29}$H$_{41}$N$_3$O$_4$ for 495.3, found [M+H] 496.3, T$_r$=1.52 min (Method BA).

Example 5. 3-(4-(Ethyl(4-hydroxy-4-methylcyclohexyl)amino)-3-(3-(p-tolyl)ureido)phenyl)-3-methylbutanoic acid Example 5 was prepared from 5A following the procedure described for the synthesis of Example 1 from 1I. LC-MS Anal. Calc'd. C$_{28}$H$_{39}$N$_3$O$_4$ [M+H] 482.3, T$_r$=1.893 min (Method O). $^1$H NMR (500 MHz, DMSO-d$_6$) δ 9.40 (s, 1H), 8.43 (s, 1H), 8.27 (s, 1H), 7.38-7.36 (m, 2H), 7.15-7.05 (m, 3H), 6.98-6.93 (m, 1H), 3.00 (s, 2H), 2.72-2.65 (m, 1H), 2.25 (s, 3H), 1.59-1.53 (m, 6H), 1.38 (s, 6H), 1.27-1.21 (m, 2H), 1.05 (s, 3H), 0.85-0.81 (m, 3H). (2H peak is buried under solvent peak).

Example 6

Enantiomer 1 and Enantiomer 2

3-(3-((4-Cyanophenyl)amino)-4-morpholinophenyl)pentanoic acid

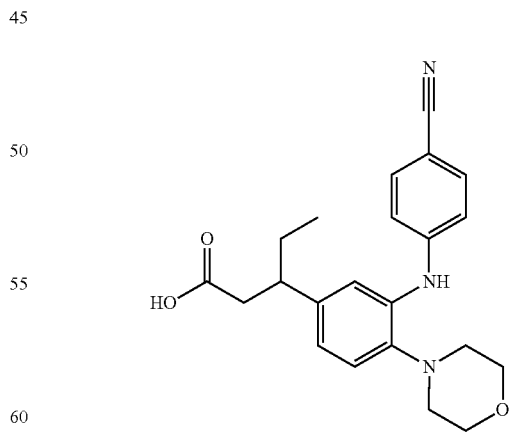

6A. Methyl 3-(4-morpholino-3-nitrophenyl)pentanoate

To a solution of 41B (2.0 g, 7.84 mmol) in NMP (15 mL) was added DIPEA (4.11 mL, 23.51 mmol), followed by morpholine (0.819 g, 9.40 mmol). Reaction mixture was heated to 120° C. and was stirred overnight. LCMS indicated completion of reaction. The reaction mixture was cooled to room temperature and diluted with diethyl ether. The organic layer was washed with 10% aq. AcOH solution, 10% NaHCO$_3$ solution, brine, dried over Na$_2$SO$_4$ and was concentrated under reduced pressure to afford a residue. The residue was purified via flash silica gel column chromatography (0-100% ethyl acetate in pet ether as eluent to afford 6A (orange liquid, 2.4 g, 7.45 mmol, 95% yield). LC-MS Anal. Calc'd. C$_{16}$H$_{22}$N$_2$O$_5$ for 322.2, found [M+H] 323.2, T$_r$=2.678 min (Method U).

6B. Methyl 3-(3-amino-4-morpholinophenyl)pentanoate

The solution of 6A (2.4 g, 7.45 mmol) in ethyl acetate (10.0 mL) was charged to a sealable hydrogen flask. The solution was sequentially evacuated and purged with nitrogen gas. To this 10% Pd on carbon (0.396 g, 0.372 mmol) was added under nitrogen atmosphere. The reaction mixture was stirred under hydrogen atmosphere (40 psi) at room temperature for 3 h. The reaction mixture was filtered through a CELITE® pad and the residue on the pad was thoroughly rinsed with MeOH (3×20 mL). The combined filtrate was concentrated under reduced pressure to afford 6B (enantiomeric mixture). LC-MS Anal. Calc'd. C$_{16}$H$_{24}$N$_2$O$_3$ for 292.2, found [M+H] 293.2, T$_r$=3.028 min (Method BE).

Chiral separation of Enantiomeric mixture 6B (Method AF) gave Enantiomer 1 T$_r$=5.12 min (Method AF), Enantiomer 2 T$_r$=5.79 min (Method AF).

6B Enantiomer 1 (brown semi-solid, 0.8 g, 2.72 mmol, 36.6% yield): LC-MS Anal. Calc'd. C$_{16}$H$_{24}$N$_2$O$_3$ for 292.2, found [M+H] 293.2, T$_r$=2.064 min (Method BE).

6B Enantiomer 2 (brown semi-solid, 0.85 g, 2.75 mmol, 36.9% yield); LC-MS Anal. Calc'd. C$_{16}$H$_{24}$N$_2$O$_3$ for 292.2, found [M+H] 293.2, T$_r$=2.067 min (Method BE).

6C. Methyl 3-(3-((4-cyanophenyl)amino)-4-morpholinophenyl)pentanoate

Compound 6C was prepared from 6B Enantiomer 1 and 4-bromobenzonitrile following the procedure described for the synthesis of 1I. LC-MS Anal. Calc'd. C$_{23}$H$_{27}$N$_3$O$_3$, 393.2, found [M+H] 394.2, T$_r$=1.41 min (Method BA).

Example 6 Enantiomer 1. 3-(3-((4-Cyanophenyl)amino)-4-morpholinophenyl)pentanoic acid Example 6 Enantiomer 1 was prepared from 6C following the procedure described for the synthesis of Example 1 from 1I. LC-MS Anal. Calc'd. C$_{22}$H$_{25}$N$_3$O$_3$ for 379.2, found [M+H] 380.2, T$_r$=1.527 min (Method O). $^1$H NMR (400 MHz, DMSO-d$_6$) δ 8.14 (s, 1H), 7.53 (d, J=6.4 Hz, 2H), 7.04-6.92 (m, 5H), 3.56-3.55 (m, 4H), 2.80-2.79 (m, 5H), 2.58-2.39 (m, 2H), 1.65-1.45 (m, 2H), 0.73 (t, J=7.2 Hz, 3H).

Example 6 Enantiomer 2. 3-(3-((4-Cyanophenyl)amino)-4-morpholinophenyl)pentanoic acid Example 6 Enantiomer 2 was prepared from 6B Enantiomer 2 following the procedure described for the synthesis of Example 6 Enantiomer 1. LC-MS Anal. Calc'd. C$_{22}$H$_{25}$N$_3$O$_3$ for 379.2, found [M+H] 380.2, T$_r$=1.527 min (Method O). $^1$H NMR (400 MHz, DMSO-d$_6$) δ 8.16 (s, 1H), 7.53 (d, J=6.4 Hz, 2H), 7.04-6.92 (m, 5H), 3.56-3.55 (m, 4H), 2.80-2.79 (m, 5H), 2.58-2.39 (m, 2H), 1.65-1.45 (m, 2H), 0.73 (t, J=7.2 Hz, 3H).

Example 7

Enantiomer 1 and Enantiomer 2

3-(3-((2-Ethoxypyrimidin-5-yl)amino)-4-morpholinophenyl)pentanoic acid

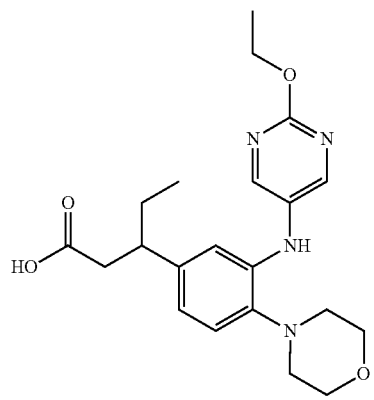 [SMILES: CCOc1ncc(Nc2cc(C(CC)CC(=O)O)ccc2N2CCOCC2)cn1]

Example 7 Enantiomer 1. 3-(3-((2-Ethoxypyrimidin-5-yl)amino)-4-morpholinophenyl)pentanoic acid Example 7 Enantiomer 1 was prepared from 6B Enantiomer 1 and 5-bromo-2-ethoxypyrimidine following the procedure described for the synthesis of Example 6 Enantiomer 1. LC-MS Anal. Calc'd. C$_{21}$H$_{28}$N$_4$O$_4$ for 400.2, found [M+H] 401.3, T$_r$=1.113 min (Method O). $^1$H NMR (400 MHz, DMSO-d$_6$) δ 8.25 (s, 2H), 7.33 (s, 1H), 6.98 (d, J=1.6 Hz, 1H), 6.72-6.71 (m, 2H), 4.30 (q, J=7.2 Hz, 2H), 3.60-3.55 (m, 4H), 2.81-2.72 (m, 5H), 2.52-2.34 (m, 2H), 1.57-1.4 (m, 2H), 1.31 (t, J=7.2 Hz, 3H), 0.70 (t, J=7.2 Hz, 3H).

Example 7 Enantiomer 2. 3-(3-((2-Ethoxypyrimidin-5-yl)amino)-4-morpholinophenyl)pentanoic acid Example 7 Enantiomer 2 was prepared from 6B Enantiomer 2 and 5-bromo-2-ethoxypyrimidine following the procedure described for the synthesis of Example 6 Enantiomer 1. LC-MS Anal. Calc'd. C$_{21}$H$_{28}$N$_4$O$_4$ for 400.2, found [M+H] 401.3, T$_r$=1.113 min (Method O). $^1$H NMR (400 MHz, DMSO-d$_6$) δ 8.26 (s, 2H), 7.33 (s, 1H), 6.97 (d, J=1.6 Hz, 1H), 6.77-6.71 (m, 2H), 4.30 (q, J=7.2 Hz, 2H), 3.60-3.55 (m, 4H), 2.81-2.72 (m, 6H), 2.52-2.34 (m, 2H), 1.56-1.4 (m, 2H), 1.31 (t, J=7.2 Hz, 3H), 0.70 (t, J=7.2 Hz, 3H).

Example 8

Enantiomer 1 and Enantiomer 2

3-(4-Morpholino-3-(3-(p-tolyl)ureido)phenyl)pentanoic acid

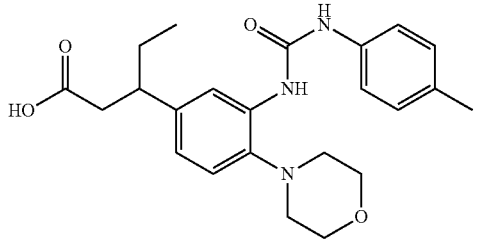 [SMILES: CCC(CC(=O)O)c1ccc(N2CCOCC2)c(NC(=O)Nc2ccc(C)cc2)c1]

Example 8 Enantiomer 1. 3-(4-Morpholino-3-(3-(p-tolyl)ureido)phenyl)pentanoic acid Example 8 Enantiomer 1 was prepared from 6B Enantiomer 1 and 1-isocyanato-4-methylbenzene following the procedure described for the synthesis of Example 5. LC-MS Anal. Calc'd. $C_{23}H_{29}N_3O_4$ for 411.2, found [M+H] 412.2, $T_r$=1.524 min (Method O). $^1$H NMR (400 MHz, DMSO-$d_6$) δ 9.43 (s, 1H), 8.07 (s, 1H), 7.96 (d, J=2.0 Hz, 1H), 7.36 (d, J=8.4 Hz, 2H), 7.11-7.08 (m, 3H), 6.79 (dd, J=8.4, 2.0 Hz, 1H), 3.82-3.80 (m, 4H), 2.82-2.75 (m, 5H), 2.53-2.44 (m, 2H), 2.25 (s, 3H), 1.63-1.60 (m, 1H), 1.55-1.48 (m, 1H), 0.73 (t, J=7.2 Hz, 3H).

Example 8 Enantiomer 2. 3-(4-Morpholino-3-(3-(p-tolyl)ureido)phenyl)pentanoic acid Example 8 Enantiomer 2 was prepared from 6B Enantiomer 2 and 1-isocyanato-4-methylbenzene following the procedure described for the synthesis of Example 5. LC-MS Anal. Calc'd. $C_{23}H_{29}N_3O_4$ for 411.2, found [M+H] 412.2, $T_r$=1.274 min (Method O). $^1$H NMR (400 MHz, MeOD) δ 8.00 (d, J=2.0 Hz, 1H), 7.35 (d, J=8.4 Hz, 2H), 7.17-7.14 (m, 3H), 6.88 (dd, J=8.4, 2.0 Hz, 1H), 3.86-3.84 (m, 4H), 2.96-2.83 (m, 5H), 2.66-2.32 (m, 2H), 2.32 (s, 3H), 1.75-1.66 (m, 1H), 1.65-1.62 (m, 1H), 0.82 (t, J=7.2 Hz, 3H).

Example 9

Enantiomer 1

(S)-3-(4-(Diisobutylamino)-3-((2-methylbenzo[d]thiazol-6-yl)amino)phenyl)pentanoic acid

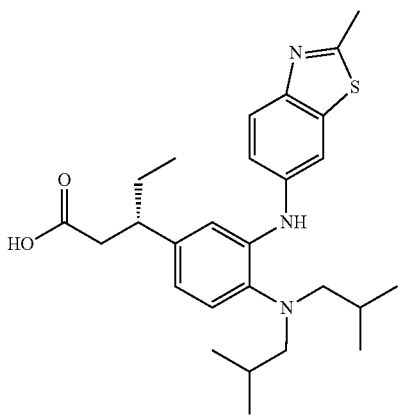 [SMILES: CC[C@@H](CC(=O)O)c1ccc(N(CC(C)C)CC(C)C)c(Nc2ccc3nc(C)sc3c2)c1]

9A. N,N-Diisobutyl-2-nitro-4-(4,4,5,5-tetramethyl-1,3,2-dioxaborolan-2-yl)aniline The mixture of 4-bromo-N,N-diisobutyl-2-nitroaniline (1 g, 3.04 mmol), bis(pinacolato)diboron (1.018 g, 4.01 mmol) and potassium acetate (0.894 g, 9.11 mmol) in DMSO (10 mL) was stirred at room temperature. Argon gas was bubbled through the mixture for 5 min. $PdCl_2$ (dppf).$CH_2Cl_2$ Adduct (0.074 g, 0.091 mmol) was added and argon gas was bubbled through the mixture for 5 min. The reaction mixture was heated at 80° C. for 6 h. The reaction mixture was cooled to room temperature and diluted with dichloromethane (200 mL). The organic layer was washed with water (2×50 mL), dried over anhydrous sodium sulfate and concentrated under reduced pressure to afford a residue. The residue was purified via flash silica gel column chromatography (conditions: 0-100% ethyl acetate in pet ether or gradient of ethyl acetate in pet ether) to afford 9A (gummy, 1.0 g, 2.66 mmol, 87% yield). LC-MS Anal. Calc'd. for $C_{20}H_{33}BN_2O_4$ 376.253, found [M+H] 377.3, $T_r$=4.48 min (Method U).

9B. (S)-Methyl 3-(4-(diisobutylamino)-3-nitrophenyl)pentanoate

In a pressure tube equipped with Teflon cap, 9A (200 mg, 0.531 mmol), 1,4-dioxane (5.0 mL) were added followed by (E)-methyl pent-2-enoate (72.8 mg, 0.638 mmol), (R)-BINAP (7.28 mg, 0.012 mmol) and 1M solution of sodium hydroxide (0.485 mL, 0.485 mmol). Argon gas was bubbled through the mixture for 10 min and chlorobis(ethylene)rhodium(I) dimer (3.10 mg, 7.97 μmol) was added at room temperature. Argon gas was bubbled through the mixture for 5 min. The tube was then screw-capped and heated at 50° C. for 3 h. The reaction mixture was cooled to room temperature, quenched with acetic acid (0.027 mL, 0.478 mmol) and was stirred for 5 minutes before it was diluted with water (10 mL). The aqueous layer was extracted with ethyl acetate (3×20 mL). Combined organic layer was washed with water (20 mL), brine (20 mL), dried over anhydrous sodium sulfate and concentrated under reduced pressure to afford a residue. The residue was purified via flash silica gel column chromatography (conditions: 0-100% ethyl acetate in pet ether or gradient of ethyl acetate in pet ether) to afford 9B (yellow liquid, 150 mg, 0.412 mmol, 77% yield). LC-MS Anal. Calc'd. for $C_{20}H_{32}N_2O_4$, 364.2, found [M+H] 365.4, $T_r$=4.12 min (Method U). (Absolute stereochemistry of the product assigned based on the expected product enantiomer from the use of (R)-BINAP in the conjugate addition).

9C. (S)-Methyl 3-(3-amino-4-(diisobutylamino)phenyl)pentanoate

The solution of 9B (0.150 g, 0.412 mmol) in ethyl acetate (20.0 mL) was charged to a sealable hydrogen flask. The solution was sequentially evacuated and purged with nitrogen gas. To this 10% Pd on carbon (0.030 g, 0.028 mmol) was added under nitrogen atmosphere. The reaction mixture was stirred under hydrogen atmosphere (40 psi) at room temperature for 4 h. The reaction mixture was filtered through a CELITE® pad and the residue on the pad was thoroughly rinsed with MeOH (3×20 mL). The combined filtrate was concentrated under reduced pressure to afford 9C (120 mg, 0.359 mmol, 87% yield). LC-MS Anal. Calc'd. $C_{20}H_{34}N_2O_2$ for 334.3, found [M+H] 335.3, $T_r$=1.90 min (Method BA).

Example 9. (S)-3-(4-(Diisobutylamino)-3-((2-methylbenzo[d]thiazol-6-yl)amino)phenyl)pentanoic acid The mixture of 9C (100 mg, 0.276 mmol), 6-bromo-2-methylbenzo[d]thiazole (32.7 mg, 0.143 mmol), Xantphos (41.5 mg, 0.072 mmol) and sodium tert-butoxide (41.4 mg, 0.430 mmol) in dioxane (2.0 mL) was stirred at room temperature. Argon gas was bubbled through the mixture for 10 min. Bis(dibenzylideneacetone)palladium (8.25 mg, 0.014 mmol) was added and argon gas was bubbled through the mixture for 5 min. The reaction mixture was sealed and placed in preheated oil bath at 110° C. for 18 h. The reaction mixture was cooled to room temperature and concentrated under reduced pressure to afford a residue. The residue was reconstituted in a mixture of DCM (50 mL) and water (10 mL). The organic layer was separated and was washed with water (10 mL), brine (10 mL), dried over anhydrous sodium sulfate and concentrated under reduced pressure to afford a residue. The residue was purified via preparative LC/MS to afford Example 9 (14.2 mg, 0.030 mmol, 21% yield). LC-MS Anal. Calc'd. $C_{27}H_{37}N_3O_2S$ for 467.3, found [M+H] 468.4, $T_r$=2.616 min (Method O). $^1$H NMR (400 MHz, DMSO-$d_6$) δ 12.0 (bs, 1H), 7.75 (d, J=8.8 Hz, 1H), 7.64 (s, 1H), 7.16-7.11 (m, 3H), 6.73 (dd, J=8.8, 2.0 Hz, 2H), 2.9-2.79 (m, 1H), 2.72 (s, 3H), 2.61-2.40 (m, 6H), 1.71-1.63 (m, 3H), 1.61-1.45 (m, 1H), 0.84-0.83 (m, 12H), 0.73 (t, J=7.2 Hz, 3H).

Example 10

Enantiomer 2

(R)-3-(4-(Diisobutylamino)-3-((2-methylbenzo[d]thiazol-6-yl)amino)phenyl)pentanoic acid

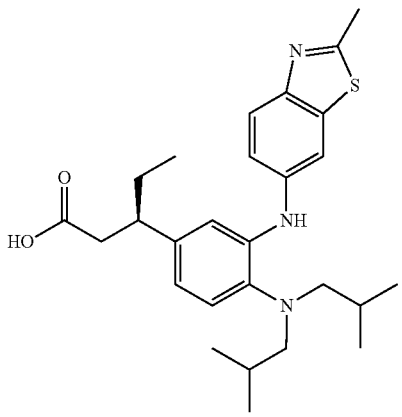 [SMILES: CC[C@H](CC(=O)O)c1ccc(N(CC(C)C)CC(C)C)c(Nc2ccc3nc(C)sc3c2)c1]

10A. (R)-Methyl 3-(4-(diisobutylamino)-3-nitrophenyl)pentanoate 10A was prepared from 9A and (S)-BINAP following the procedure described for the synthesis of 9B. LC-MS Anal. Calc'd. for $C_{20}H_{32}N_2O_4$, 364.2, found [M+H] 365.4. $T_r$=4.2 min (Method U). (Absolute stereochemistry of the product assigned based on the expected product enantiomer from the use of (S)-BINAP in the conjugate addition).

10B. (R)-Methyl 3-(3-amino-4-(diisobutylamino)phenyl)pentanoate 10B was prepared from 10A following the procedure described for the synthesis of 9C. LC-MS Anal. Calc'd. $C_{20}H_{34}N_2O_2$ for 334.3, found [M+H] 335.3, $T_r$=1.87 min (Method BA). Chiral purity $T_r$=18.9 min with ee 90% (Method CY) as single enantiomer.

Example 10. (R)-3-(4-(Diisobutylamino)-3-((2-methylbenzo[d]thiazol-6-yl)amino)phenyl)pentanoic acid Example 10 was prepared from 10B following the procedure described for the synthesis of Example 9. LC-MS Anal. Calc'd. $C_{27}H_{37}N_3O_2S$ for 467.3, found [M+H] 468.4, $T_r$=2.616 min (Method O). $^1$H NMR (400 MHz, DMSO-$d_6$) δ 12.0 (br. s., 1H), 7.75 (d, J=8.8 Hz, 1H), 7.63 (s, 1H), 7.16-7.11 (m, 3H), 6.73 (d, J=8.8 Hz, 2H), 2.9-2.79 (m, 1H), 2.72 (s, 3H), 2.61-2.40 (m, 6H), 1.71-1.63 (m, 3H), 1.61-1.45 (m, 1H), 0.84-0.83 (m, 12H), 0.73 (t, J=7.2 Hz, 3H).

Example 11

Enantiomer 1

(S)-3-(3-((4-Chlorophenyl)amino)-4-(diisobutylamino)phenyl)pentanoic acid

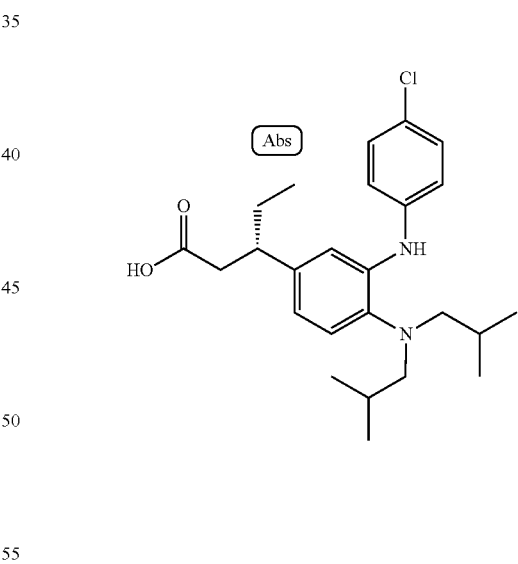

Example 11 was prepared from 9C and 1-bromo-4-chlorobenzene following the procedure described for the synthesis of Example 9. LC-MS Anal. Calc'd. $C_{25}H_{35}ClN_2O_2$ for 430.2, found [M+H] 431.2, $T_r$=2.862 min (Method O). $^1$H NMR (400 MHz, DMSO-$d_6$) δ 12.0 (bs, 1H), 7.26 (d, J=8.8 Hz, 2H), 7.19 (s, 1H), 7.13 (d, J=8.0 Hz, 1H), 7.04-7.02 (m, 3H), 6.73 (dd, J=8.4, 1.6 Hz, 1H), 2.82-2.76 (m, 1H), 2.66-2.32 (m, 6H), 1.67-1.57 (m, 3H), 1.52-1.46 (m, 1H), 0.82 (d, J=6.4 Hz, 12H), 0.72 (t, J=7.2 Hz, 3H).

Example 12

Enantiomer 1 and Enantiomer 2

3-(3-((4-Cyanophenyl)amino)-4-((1,1-dioxidotetrahydro-2H-thiopyran-4-yl)(propyl)amino)phenyl)pentanoic acid

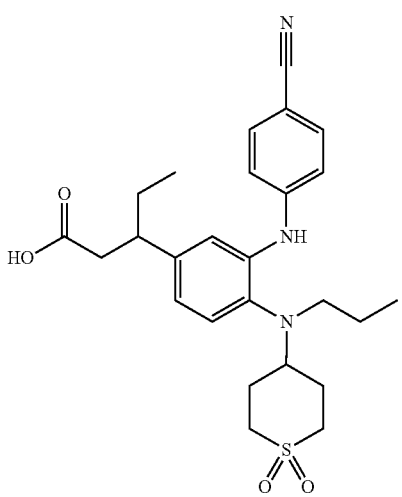 [SMILES: CCCN(c1ccc(C(CC)CC(=O)O)cc1Nc1ccc(C#N)cc1)C1CCS(=O)(=O)CC1]

12A. N-Propyltetrahydro-2h-thiopyran-4-amine

To a stirred solution of dihydro-2H-thiopyran-4(3H)-one (5.0 g, 43.0 mmol) in dry MeOH (80 mL), propan-1-amine (2.80 g, 47.3 mmol) was added. Then molecular sieves (5.0 g) were added to the reaction mixture. Reaction mixture was stirred at RT overnight. Reaction mixture was cooled to 0° C. and added NaBH$_4$ (3.26 g, 86 mmol) portionwise in 10 minutes. It was stirred at room temperature for 3 h. Reaction mixture was concentrated under reduced pressure to get semi-solid. To this was added sat. aq. NaHCO$_3$ (200 mL) and was stirred overnight. Mixture was extracted with EtOAc (400 mL), washed with water (100 mL), brine (100 mL), dried over Na$_2$SO$_4$ and concentrated under reduced pressure to get 12A (light yellow liquid, 5.5 g, 34.5 mmol, 80% yield). $^1$H NMR (300 MHz, CDCl$_3$) δ 2.74-2.51 (m, 6H), 2.49-2.35 (m, 1H), 2.21-2.1 (m, 2H), 1.56-1.41 (m, 4H), 0.90 (t, J=7.2 Hz, 3H).

12B. Methyl 3-(3-nitro-4-(propyl(tetrahydro-2H-thiopyran-4-yl)amino)phenyl)pentanoate To a solution of 41B (2.0 g, 7.84 mmol) in NMP (20 mL) was added DIPEA (4.11 mL, 23.51 mmol), followed by 12A (1.872 g, 11.75 mmol). Reaction mixture was heated to 135° C. and was stirred overnight. Reaction mixture was cooled to RT and was diluted with EtOAc (100 mL), washed with water (20 mL), brine (20 mL), dried over Na$_2$SO$_4$ and concentrated to get crude compound as yellow liquid. The residue was purified via flash silica gel column chromatography (conditions: 0-100% ethyl acetate in pet ether or gradient of ethyl acetate in pet ether) to afford 12B (yellow liquid, 0.6 g, 1.521 mmol, 20% yield). LC-MS Anal. Calc'd. for C$_{20}$H$_{30}$N$_2$O$_4$S, 394.2, found [M+H] 395.2. T$_r$=3.75 min (Method BE).

12C. Methyl 3-(4-((1,1-dioxidotetrahydro-2H-thiopyran-4-yl)(propyl)amino)-3-nitrophenyl)pentanoate To a stirred solution of 12B (0.6 g, 1.521 mmol) in acetonitrile (7.0 mL), water (5.38 mL) at 0° C. was added sodium bicarbonate (1.278 g, 15.21 mmol), followed by OXONE® (2.337 g, 3.80 mmol). The mixture was stirred at the same temperature for 20 min and at RT. The reaction mixture was diluted with ethyl acetate (100 mL) and filtered through CELITE®. The filtrate was concentrated under reduced pressure and diluted with ethyl acetate (25 mL), washed with water (10 mL), dried over sodium sulfate, concentrated under reduced pressure to get orange liquid. The residue was purified via flash silica gel column chromatography (conditions: 0-100% ethyl acetate in pet ether or gradient of ethyl acetate in pet ether) to afford 12C (yellow liquid, 500 mg, 1.172 mmol, 77% yield). LC-MS Anal. Calc'd. for C$_{20}$H$_{30}$N$_2$O$_6$S, 426.2, found [M+H] 427.2. T$_r$=2.65 min (Method BE).

12D. Methyl 3-(3-amino-4-((1,1-dioxidotetrahydro-2H-thiopyran-4-yl)(propyl)amino)phenyl)pentanoate The solution of methyl 12C (450 mg, 1.055 mmol) in ethyl acetate (10.0 mL) was charged to a sealable hydrogen flask. The solution was sequentially evacuated and purged with nitrogen gas. To this 10% Pd on carbon (76 mg, 0.072 mmol) was added under nitrogen atmosphere. The reaction mixture was stirred under hydrogen atmosphere (40 psi) at room temperature for 16 h. The reaction mixture was filtered through a CELITE® pad and the residue on the pad was thoroughly rinsed with MeOH (3×20 mL). The combined filtrate was concentrated under reduced pressure to afford 12D. LC-MS Anal. Calc'd. C$_{20}$H$_{32}$N$_2$O$_4$S for 396.2, found [M+H] 397.4, T$_r$=1.27 min (Method BA).

Chiral separation of mixture 12D (Method BS) gave Diastereomer 1 T$_r$=3.43 min (Method BS), Diastereomer 2 T$_r$=7.73 min (Method BS).

12D Enantiomer 1 (absolute stereochemistry unknown, yellow liquid, 130 mg, 0.328 mmol, 31.1% yield): LC-MS Anal. Calc'd. C$_{20}$H$_{32}$N$_2$O$_4$S for 396.2, found [M+H] 397.4, T$_r$=1.27 min (Method BA).

12D Enantiomer 2 (absolute stereochemistry unknown, yellow liquid, 130 mg, 0.328 mmol, 31.1% yield): LC-MS Anal. Calc'd. C$_{20}$H$_{32}$N$_2$O$_4$S for 396.2, found [M+H] 397.4, T$_r$=1.27 min (Method BA).

Example 12 Enantiomer 1. 3-(3-((4-Cyanophenyl)amino)-4-((1,1-dioxidotetrahydro-2H-thiopyran-4-yl)(propyl)amino)phenyl)pentanoic acid Example 12 Enantiomer 1 was prepared from 12D Enantiomer 1 following the procedure described for the synthesis of Example 9 (absolute stereochemistry unknown). LC-MS Anal. Calc'd. C$_{26}$H$_{33}$N$_3$O$_4$S [M+H] 484.3, T$_r$=1.463 min (Method Q). $^1$H NMR (400 MHz, MeOD) δ 7.55 (d, J=8.4 Hz, 2H), 7.24 (d, J=8.0 Hz, 2H), 7.15 (d, J=8.0 Hz, 2H), 6.96-6.93 (m, 1H), 3.21-3.16 (m, 1H), 3.01-2.96 (m, 7H), 2.68-2.64 (m, 1H), 2.57-2.53 (m, 1H), 2.17-2.13 (m, 4H), 1.74-1.60 (m, 2H), 1.38-1.30 (m, 2H), 0.86-0.83 (m, 6H).

Example 12 Enantiomer 2. 3-(3-((4-Cyanophenyl)amino)-4-((1,1-dioxidotetrahydro-2H-thiopyran-4-yl)(propyl)amino)phenyl)pentanoic acid Example 12 Enantiomer 2 was prepared from 12D Enantiomer 2 following the procedure described for the synthesis of Example 9 (absolute stereochemistry unknown). LC-MS Anal. Calc'd. $C_{26}H_{33}N_3O_4S$ [M+H] 484.3, $T_r$=2.015 min (Method O). $^1$H NMR (400 MHz, DMSO-$d_6$) δ 7.90 (s, 1H), 7.55 (d, J=8.0 Hz, 2H), 7.17-7.11 (m, 2H), 7.15 (d, J=8.0 Hz, 2H), 6.92-6.90 (m, 1H), 3.21-3.16 (m, 1H), 3.05-2.81 (m, 7H), 2.61-2.42 (m, 2H), 2.06-1.91 (m, 4H), 1.62-1.45 (m, 2H), 1.23-1.18 (m, 2H), 0.75-0.71 (m, 6H).

Example 13

Enantiomer 1 and Enantiomer 2

3-(4-((1,1-Dioxidotetrahydro-2h-thiopyran-4-yl)(propyl)amino)-3-((2-ethoxypyrimidin-5-yl)amino)phenyl)pentanoic acid

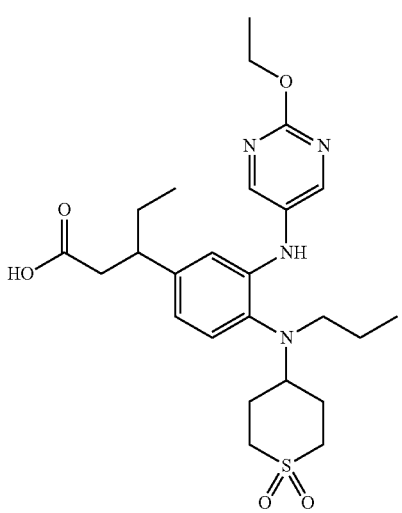 [SMILES: CCCN(c1ccc(C(CC)CC(=O)O)cc1Nc1cnc(OCC)nc1)C1CCS(=O)(=O)CC1]

Example 13 Enantiomer 1. 3-(4-((1,1-Dioxidotetrahydro-2h-thiopyran-4-yl)(propyl)amino)-3-((2-ethoxypyrimidin-5-yl)amino)phenyl)pentanoic acid Example 13 Enantiomer 1 was prepared from 12D Enantiomer 1 and 5-bromo-2-ethoxypyrimidine following the procedure described for the synthesis of Example 1 (absolute stereochemistry unknown). LC-MS Anal. Calc'd. $C_{25}H_{36}N_4O_5S$ for 504.241, found [M+H] 504.3, $T_r$=1.619 min (Method O). $^1$H NMR (400 MHz, DMSO-$d_6$) δ 8.41 (s, 2H), 7.22 (s, 1H), 7.11 (d, J=8.0 Hz, 1H), 6.76-6.75 (m, 1H), 6.66-6.64 (m, 1H), 4.30 (q, J=7.2 Hz, 2H), 3.30-3.01 (m, 5H), 2.91-2.85 (m, 2H), 2.8-2.72 (m, 1H), 2.52-2.41 (m, 2H), 2.2-1.9 (m, 4H), 1.64-1.46 (m, 2H), 1.28 (t, J=7.2 Hz, 3H), 1.27-1.22 (m, 2H), 0.77 (t, J=7.2 Hz, 3H), 0.69 (t, J=7.2 Hz, 3H).

Example 13 Enantiomer 2. 3-(4-((1,1-Dioxidotetrahydro-2h-thiopyran-4-yl)(propyl)amino)-3-((2-ethoxypyrimidin-5-yl)amino)phenyl)pentanoic acid Example 13 Enantiomer 2 was prepared from 12D Enantiomer 2 and 5-bromo-2-ethoxypyrimidine following the procedure described for the synthesis of Example 1 (absolute stereochemistry unknown). LC-MS Anal. Calc'd. $C_{25}H_{36}N_4O_5S$ for 504.241, found [M+H] 505.1, $T_r$=1.955 min (Method O). $^1$H NMR (400 MHz, MeOD) δ 8.41 (s, 2H), 7.21 (d, J=8.0 Hz, 1H), 6.82 (d, J=1.6 Hz, 1H), 6.75 (dd, J=8.0, 1.6 Hz, 1H), 4.43 (q, J=7.2 Hz, 2H), 3.33-3.25 (m, 3H), 3.08-2.95 (m, 4H), 2.9-2.82 (m, 1H), 2.12-1.92 (m, 2H), 2.31-2.21 (m, 4H), 1.69-1.51 (m, 2H), 1.45-1.30 (m, 5H), 0.86 (t, J=7.2 Hz, 3H), 0.79 (t, J=7.2 Hz, 3H).

Example 14

Enantiomer 1 and Enantiomer 2

3-(4-((1,1-Dioxidotetrahydro-2h-thiopyran-4-yl)(propyl)amino)-3-(3-(p-tolyl)ureido)phenyl)pentanoic acid

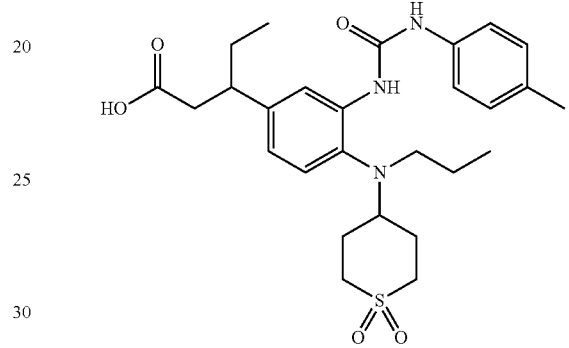

Example 14 Enantiomer 1. 3-(4-((1,1-Dioxidotetrahydro-2h-thiopyran-4-yl)(propyl)amino)-3-(3-(p-tolyl)ureido)phenyl)pentanoic acid Example 14 Enantiomer 1 was prepared from 12D Enantiomer 1 and 1-isocyanato-4-methylbenzene following the procedure described for the synthesis of Example 5 (absolute stereochemistry unknown). LC-MS Anal. Calc'd. $C_{27}H_{37}N_3O_5S$ for 515.3, found [M+H] 516.4, $T_r$=1.7 min (Method O). $^1$H NMR (400 MHz, MeOD) δ 8.08 (d, J=2.0 Hz, 1H), 7.32 (d, J=8.4 Hz, 2H), 7.22-7.15 (m, 3H), 6.90 (dd, J=8.4, 2.0 Hz, 1H), 3.20-3.05 (m, 5H), 2.96-2.93 (m, 3H), 2.63-2.53 (m, 2H), 2.33 (s, 3H), 2.23-2.20 (m, 2H), 2.11 2.06 (m, 2H), 1.77-1.62 (m, 2H), 1.34-1.28 (m, 2H), 0.85-0.81 (m, 6H).

Example 14 Enantiomer 2. 3-(4-((1,1-Dioxidotetrahydro-2h-thiopyran-4-yl)(propyl)amino)-3-(3-(p-tolyl)ureido)phenyl)pentanoic acid Example 14 Enantiomer 2 was prepared from 12D Enantiomer 2 and 1-isocyanato-4-methylbenzene following the procedure described for the synthesis of Example 5 (absolute stereochemistry unknown). LC-MS Anal. Calc'd. $C_{27}H_{37}N_3O_5S$ for 515.3, found [M+H] 516.4, $T_r$=1.427 min (Method O). $^1$H NMR (400 MHz, DMSO-$d_6$) δ 9.41 (s, 1H), 8.34 (s, 1H), 8.10 (d, J=2.0 Hz, 1H), 7.36 (d, J=8.4 Hz, 2H), 7.16 (d, J=8.4 Hz, 1H), 7.09 (d, J=8.4 Hz, 2H), 6.79 (dd, J=8.4, 2.0 Hz, 1H), 3.17-3.05 (m, 5H), 2.90-2.86 (m, 3H), 2.53-2.44 (m, 2H), 2.24-2.18 (m, 5H), 1.9-1.81 (m, 2H), 1.69-1.59 (m, 1H), 1.55-1.46 (m, 1H), 1.23-1.17 (m, 2H), 0.77 (t, J=7.2 Hz, 3H), 0.70 (t, J=7.2 Hz, 3H).

Example 15

3-(3-((4-Chlorophenyl)amino)-4-((2-methoxyethyl)(tetrahydro-2H-pyran-4-yl)amino)phenyl)-3-methylbutanoic acid

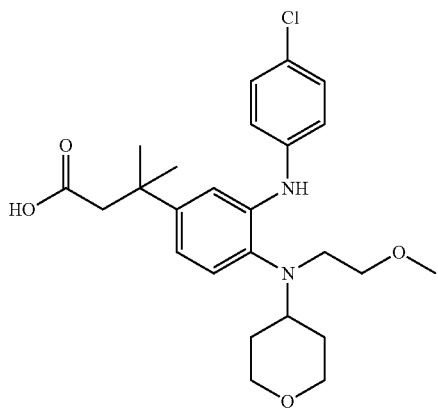 [SMILES: COCCN(c1ccc(C(C)(C)CC(=O)O)cc1Nc1ccc(Cl)cc1)C1CCOCC1]

15A. Diethyl 2-(2-(4-fluorophenyl)propan-2-yl)malonate

To a stirred solution of magnesium (0.139 g, 5.71 mmol) and pinch of iodine in dry diethyl ether (5.0 mL), 1-bromo-4-fluorobenzene (0.500 g, 2.86 mmol) in 2 mL THF was added at room temperature. Reaction was stirred for 30 minutes at room temperature. Reaction mixture was cooled to −10° C. and diethyl isopropylidenemalonate (1.144 g, 5.71 mmol) dissolved in 1 mL THF was added dropwise over 2 minutes. Reaction mixture was stirred for 20 minutes at room temperature, followed by reflux for 3 h. Reaction mixture was cooled to rt and quenched with ice cold 1 N HCl. The aqueous layer was extracted with diethyl ether (50 mL), dried over sodium sulfate, concentrated under reduced pressure to give 15A (light yellow liquid, 550 mg, 1.856 mmol, 65% yield). LC-MS Anal. Calc'd. for $C_{16}H_{21}FO_4$, 296.14, found [M+H] 297.2, $T_r$=1.47 min (Method BA).

15B. Ethyl 3-(4-fluorophenyl)-3-methylbutanoate

To a stirred solution of 15A (0.500 g, 1.687 mmol), in DMSO (5.0 mL), water (0.15 mL) mixture lithium chloride (0.143 g, 3.37 mmol) was added. Reaction mixture heated to 180° C. and stirred for 12 h. Reaction mixture was cooled to room temperature, partitioned between diethyl ether (50 mL) and water (25 mL). Aqueous layer was extracted with ether (2×25 mL). The combined organic layer was washed with brine (25 mL), dried over anhydrous sodium sulfate, concentrated under reduced pressure to get crude compound. Purification via flash chromatography gave 15B (light yellow liquid, 255 mg, 1.137 mmol, 67% yield). LC-MS Anal. Calc'd. for $C_{13}H_{17}FO_2$, 224.12, found [M+H] 225.2, $T_r$=2.87 min (Method N).

15C. Ethyl 3-(4-fluoro-3-nitrophenyl)-3-methylbutanoate

To a stirred solution of 15B (0.200 g, 0.892 mmol) in $H_2SO_4$ (2.0 mL) at 0° C. nitric acid (0.092 mL, 1.338 mmol) was slowly added under nitrogen atmosphere and maintained at same temperature for 1 h. Reaction mixture quenched with ice and extracted with DCM (2×10 mL). Organic layer dried over sodium sulfate and concentrated under reduced pressure to get light yellow liquid. Purification via flash chromatography gave 15C (colorless liquid, 210 mg, 0.780 mmol, 87% yield). LC-MS Anal. Calc'd. for $C_{13}H_{16}FNO_4$, 269.10, found [M+H] 270.2, $T_r$=2.967 min (Method N).

15D. N-(2-Methoxyethyl)tetrahydro-2H-pyran-4-amine

To a stirred solution of dihydro-2H-pyran-4(3H)-one (27.7 mL, 300 mmol) in methanol (300 mL) under nitrogen atmosphere was added 2-methoxyethanamine (25.8 mL, 300 mmol), followed by 4 Å molecular sieves (2 g). The reaction mixture was stirred for 12 h at room temperature. To this was added $NaBH_4$ (34.0 g, 899 mmol) portionwise at 0° C. and the reaction mixture was stirred at room temperature for 3 h. Reaction mixture was quenched with water (10 mL) and concentrated under reduced pressure to get semi-solid which was quenched with 10% sodium bicarbonate (500 mL) and it was extracted with ethyl acetate (2×200 mL). The combined organic layer was washed with brine (100 mL), dried over anhydrous sodium sulfate, concentrated under reduced pressure to get 15D (yellow liquid, 30 g, 188 mmol, 62% yield). $^1$H NMR (400 MHz, DMSO-$d_6$) δ 3.89-3.56 (m, 6H), 3.37 (s, 3H), 2.86-2.67 (m, 3H), 1.98-1.67 (m, 4H).

15E. Ethyl 3-(4-((2-methoxyethyl)(tetrahydro-2H-pyran-4-yl)amino)-3-nitrophenyl)-3-methylbutanoate In a sealed tube 15C (2 g, 7.43 mmol) in N-methyl-2-pyrrolidinone (10 mL) were added DIPEA (3.89 mL, 22.28 mmol) and 15D (2.365 g, 14.86 mmol). The reaction mixture was stirred at 135° C. for 36 h. TLC indicated completion of reaction. Reaction mixture was cooled to room temperature, quenched with water (20 mL) and was extracted with MTBE (3×30 mL). The combined organic layer was washed with brine (20 mL), dried over anhydrous sodium sulfate, concentrated under reduced pressure to get crude compound. Purification via flash chromatography gave 15E (yellow liquid, 810 mg, 1.923 mmol, 25% yield). LC-MS Anal. Calc'd. for $C_{21}H_{32}N_2O_6$, 408.22, found [M+H] 409.5, $T_r$=1.41 min. (Method AY).

15F. Ethyl 3-(3-amino-4-((2-methoxyethyl)(tetrahydro-2H-pyran-4-yl)amino)phenyl)-3-methylbutanoate The solution of 15E (0.810 g, 1.983 mmol) in ethyl acetate (8 mL) was charged to a sealable hydrogen flask. The solution was sequentially evacuated and purged with nitrogen gas. To this 10% Pd on carbon (0.106 g, 0.099 mmol) was added under nitrogen atmosphere. The reaction mixture was stirred under hydrogen atmosphere (40 psi). The reaction mixture was stirred at room temperature for 3 h. The reaction mixture was filtered through a CELITE® pad and the residue on the pad was thoroughly rinsed with ethyl acetate (3×15 mL). The combined filtrate was concentrated under reduced pressure to get crude compound. Purification via flash chromatography gave 15F (yellow liquid, 500 mg, 1.281 mmol, 64% yield). LC-MS Anal. Calc'd. for $C_{21}H_{34}N_2O_4$, 378.26, found [M+H] 379.3, $T_r$=1.34 min (Method AY).

15G. Ethyl 3-(3-((4-chlorophenyl)amino)-4-((2-methoxyethyl)(tetrahydro-2H-pyran-4-yl)amino)phenyl)-3-methylbutanoate The mixture of 15F (0.050 g, 0.132 mmol), 1-bromo-4-chlorobenzene (0.030 g, 0.159 mmol), 4,5-bis(diphenylphosphino)-9,9-dimethylxanthene (7.64 mg, 0.013 mmol) and $Cs_2CO_3$ (0.065 g, 0.198 mmol) in 1,4-dioxane (1.5 mL) was stirred at room temperature. Argon gas was bubbled through the mixture for 5 min. Bis(dibenzylideneacetone)palladium (3.80 mg, 6.60 µmol) was added and argon gas was bubbled through the mixture for another 5 min. The reaction mixture was sealed and placed in preheated oil bath at 110° C. for 12 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography to afford 15G (yellow liquid, 50 mg, 0.082 mmol, 61% yield). LC-MS Anal. Calc'd. for $C_{27}H_{37}ClN_2O_4$, 488.2, found [M+H] 489.4, $T_r$=1.84 min. (Method AY).

Example 15. 3-(3-((4-Chlorophenyl)amino)-4-((2-methoxyethyl)(tetrahydro-2H-pyran-4-yl)amino)phenyl)-3-methylbutanoic acid To a stirred solution of 15G (0.050 g, 0.102 mmol) in mixture of THF (0.7 mL), methanol (0.7 mL) and water (0.1 mL) was added $LiOH.H_2O$ (0.017 g, 0.409 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 15 (16.7 mg, 0.036 mmol, 35% yield). LC-MS Anal. Calc'd. for $C_{25}H_{33}ClN_2O_4$, 460.2, found [M+H] 461.1, $T_r$=2.13 min. (Method O). $^1$H NMR (400 MHz, DMSO-$d_6$) δ 7.49 (s, 1H), 7.13-7.30 (m, 3H), 7.18 (m, 1H), 7.09 (m, 2H), 6.91 (m, 1H), 3.67-3.85 (m, 4H), 3.07-3.22 (m, 7H), 2.89-3.03 (m, 1H), 2.26-2.40 (m, 2H), 1.65 (m, 4H), 1.27-1.44 (m, 6H).

Examples 16 and 17

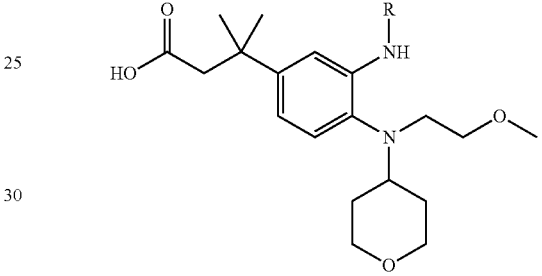

Examples 16 and 17 were prepared following the procedure for Example 15 by using the corresponding halides.

| Ex. No. | Name | R | $T_r$ (min) Method O | [M + H]$^+$ |
|---|---|---|---|---|
| 16 | 3-(3-((4-cyanophenyl)amino)-4-((2-methoxyethyl)(tetrahydro-2H-pyran-4-yl)amino)phenyl)-3-methylbutanoic acid | CN (4-cyanophenyl) | 1.766 | 452.1 |
| 17 | 3-(3-((2-ethoxypyrimidin-5-yl)amino)-4-((2-methoxyethyl)(tetrahydro-2H-pyran-4-yl)amino)phenyl)-3-methylbutanoic acid | 2-ethoxypyrimidin-5-yl | 1.619 | 473.1 |

Example 18

3-(4-((2-Methoxyethyl)(tetrahydro-2H-pyran-4-yl)amino)-3-(3-(p-tolyl)ureido)phenyl)-3-methylbutanoic acid

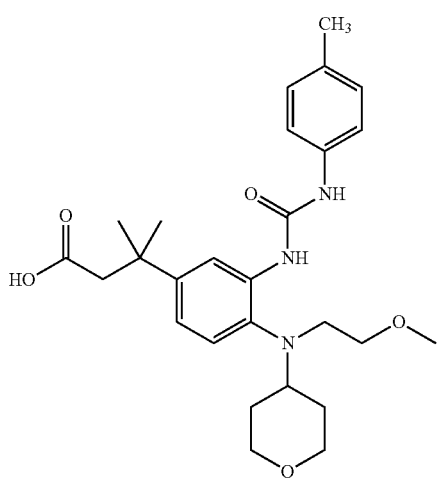 [SMILES: COCCN(c1ccc(C(C)(C)CC(=O)O)cc1NC(=O)Nc1ccc(C)cc1)C1CCOCC1]

18A. Ethyl 3-(4-((2-methoxyethyl)(tetrahydro-2H-pyran-4-yl)amino)-3-(3-(p-tolyl)ureido)phenyl)-3-methylbutanoate

To a stirred solution of 15F (0.035 g, 0.092 mmol) in tetrahydrofuran (1 mL) was added 1-isocyanato-4-methylbenzene (0.015 g, 0.111 mmol). The reaction mixture was stirred at room temperature for 12 h. LCMS indicated completion of reaction. The reaction mixture was concentrated under reduced pressure to get 18A (yellow liquid, 45 mg, 0.069 mmol, 75% yield). LC-MS Anal. Calc'd. for $C_{29}H_{41}N_3O_5$, 511.3, found [M+H] 512.5, $T_r$=1.53 min. (Method AY).

Example 18. 3-(4-((2-Methoxyethyl)(tetrahydro-2H-pyran-4-yl)amino)-3-(3-(p-tolyl)ureido)phenyl)-3-methylbutanoic acid

Example 18 was prepared from 18A following the procedure described for the synthesis of Example 15 from 15G. LC-MS Anal. Calc'd. for $C_{27}H_{37}N_3O_5$, 483.3, found [M+H] 484.1. $T_r$=1.71 min. (Method O). $^1$H NMR (400 MHz, DMSO-$d_6$) δ 9.36 (s, 1H), 8.40 (s, 1H), 8.20-8.31 (m, 1H), 7.36 (d, J=8.2 Hz, 2H), 7.15-7.23 (m, 1H), 7.09 (d, J=8.2 Hz, 2H), 6.87-7.01 (m, 1H), 4.13-4.20 (m, 4H), 3.05-3.14 (m, 5H), 2.88-3.02 (m, 2H), 2.64-2.74 (m, 1H), 2.30-2.39 (m, 2H), 2.17-2.27 (m, 3H), 1.69 (m, 4H), 1.32-1.42 (m, 6H).

Examples 19 and 20

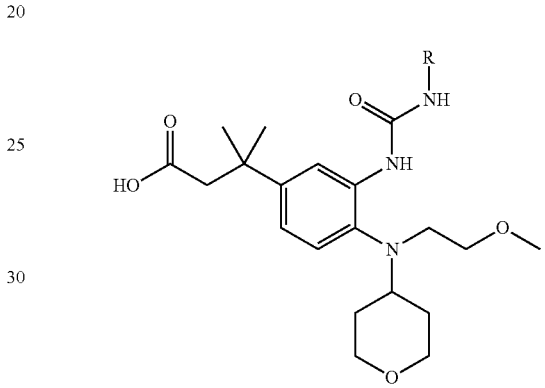

Examples 19 and 20 were prepared following the procedure for Example 18 by using the corresponding isocyanates.

| Ex. No. | Name | R | $T_r$ (min) Method O | [M + H]$^+$ |
|---|---|---|---|---|
| 19 | 3-(3-(3-(4-cyanophenyl)ureido)-4-((2-methoxyethyl)(tetrahydro-2H-pyran-4-yl)amino)phenyl)-3-methylbutanoic acid | CN-C₆H₄- | 1.56 | 495.3 |
| 20 | 3-(3-(3-(4-chloro-2-fluorophenyl)ureido)-4-((2-methoxyethyl)(tetrahydro-2H-pyran-4-yl)amino)phenyl)-3-methylbutanoic acid | 4-Cl-2-F-C₆H₃- | 2.02 | 522.1 |

Example 21

3-(3-((4-Chlorophenyl)amino)-4-(propyl(tetrahydro-2H-pyran-4-yl)amino)phenyl)-3-methylbutanoic acid

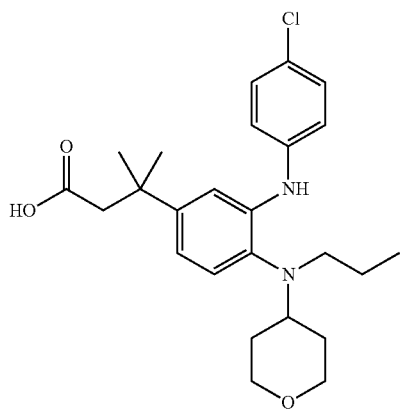 [SMILES: CCCN(c1ccc(C(C)(C)CC(=O)O)cc1Nc1ccc(Cl)cc1)C1CCOCC1]

21A. N-Propyltetrahydro-2H-pyran-4-amine

To a stirred solution of dihydro-2H-pyran-4(3H)-one (9.26 mL, 100 mmol) in tetrahydrofuran (100 mL), methanol (100 mL) under nitrogen atmosphere was added propan-1-amine (8.25 mL, 100 mmol), followed by 4 Å molecular sieves (4 g). The reaction mixture was stirred for 12 h at room temperature. To this was added NaBH$_4$ (11.34 g, 300 mmol) portionwise at 0° C. and the reaction mixture was stirred at room temperature for 3 h. Reaction mixture was quenched with water (10 mL) and concentrated under reduced pressure to get semi-solid which was quenched with 10% sodium bicarbonate (500 mL) and it was extracted with ethyl acetate (2×200 mL). The combined organic layer was washed with brine (100 mL), dried over anhydrous sodium sulfate, concentrated under reduced pressure to give 21A (yellow liquid, 8.4 g, 58.6 mmol, 58% yield). $^1$H NMR (400 MHz, DMSO-d$_6$) δ 3.82-3.27 (m, 4H), 2.49 (m, 1H), 2.56 (m, 2H), 1.73-1.63 (m, 4H), 1.41 (m, 2H), 0.87 (t, J=7.2 Hz, 3H).

21B. Methyl 3-methyl-3-(3-nitro-4-(propyl(tetrahydro-2H-pyran-4-yl)amino)phenyl)butanoate In a sealed tube 15C (0.600 g, 2.351 mmol) in N-methyl-2-pyrrolidinone (3 mL) were added DIPEA (1.232 mL, 7.05 mmol) and 21A (0.673 g, 4.70 mmol). The reaction mixture was stirred at 135° C. for 15 h. LCMS indicated completion of reaction. Reaction mixture was cooled to room temperature, quenched with water (20 mL) and it was extracted with MTBE (2×30 mL). The combined organic layer was washed with brine (20 mL), dried over anhydrous sodium sulfate, concentrated under reduced pressure to get crude compound. Purification via flash chromatography gave 21B (yellow liquid, 230 mg, 0.608 mmol, 25% yield). LC-MS Anal. Calc'd. for $C_{20}H_{30}N_2O_5$, 378.21, found [M+H] 379.5, $T_r$=1.55 min (Method AY).

21C. Methyl 3-(3-amino-4-(propyl(tetrahydro-2H-pyran-4-yl)amino)phenyl)-3-methylbutanoate The solution of 21B (0.230 g, 0.608 mmol) in ethyl acetate (3 mL) was charged to a sealable hydrogen flask. The solution was sequentially evacuated and purged with nitrogen gas. To this 10% Pd on carbon (0.032 g, 0.030 mmol) was added under nitrogen atmosphere. The reaction mixture was stirred under hydrogen atmosphere (40 psi). The reaction mixture was stirred at room temperature for 3 h. The reaction mixture was filtered through a CELITE® pad and the residue on the pad was thoroughly rinsed with ethyl acetate (3×15 mL). The combined filtrate was concentrated under reduced pressure to get 21C (yellow liquid, 160 mg, 0.459 mmol, 76% yield). LC-MS Anal. Calc'd. for $C_{20}H_{32}N_2O_3$, 348.2, found [M+H] 349.6, $T_r$=1.52 min. (Method AY).

21D. Methyl 3-(3-((4-chlorophenyl)amino)-4-(propyl(tetrahydro-2H-pyran-4-yl)amino)phenyl)-3-methylbutanoate The mixture of 21C (0.050 g, 0.143 mmol), 1-bromo-4-chlorobenzene (0.033 g, 0.172 mmol), 4,5-bis(diphenylphosphino)-9,9-dimethylxanthene (0.042 g, 0.072 mmol) and Cs$_2$CO$_3$ (0.140 g, 0.430 mmol) in 1,4-dioxane (2 mL) was stirred at room temperature. Argon gas was bubbled through the mixture for 5 min. Bis(dibenzylideneacetone) palladium (8.25 mg, 0.014 mmol) was added and argon gas was bubbled through the mixture for 5 min. The reaction mixture was sealed and placed in preheated oil bath at 110° C. for 12 h. The reaction mixture was cooled to room temperature and concentrated under reduced pressure to afford residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography gave 21D (yellow liquid, 60 mg, 0.131 mmol, 91% yield). LC-MS Anal. Calc'd. for $C_{26}H_{35}ClN_2O_3$, 458.2, found [M+H] 459.6, $T_r$=2.20 min. (Method AY).

Example 21. 3-(3-((4-Chlorophenyl)amino)-4-(propyl(tetrahydro-2H-pyran-4-yl)amino)phenyl)-3-methylbutanoic acid To a stirred solution of 21D (0.060 g, 0.131 mmol) in mixture of tetrahydrofuran (1 mL), methanol (1 mL) and water (0.2 mL) was added LiOH.H$_2$O (0.022 g, 0.523 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 21 (14.4 mg, 0.031 mmol, 23% yield). LC-MS Anal. Calc'd. for $C_{25}H_{33}ClN_2O_3$, 444.2, found [M+H] 445.2, $T_r$=2.39 min. (Method O). $^1$H NMR (400 MHz, DMSO-d$_6$) δ 7.49 (s, 1H), 7.13-7.30 (m, 3H), 7.18 (m, 1H), 7.09 (m, 2H), 6.91 (m, 1H), 3.67-3.85 (m, 4H), 3.07-3.22 (m, 4H), 2.89-3.03 (m, 1H), 2.26-2.40 (m, 2H), 1.65 (m, 4H), 1.27-1.44 (m, 6H), 0.79 (t, J=7.2 Hz, 3H).

Examples 22 to 24

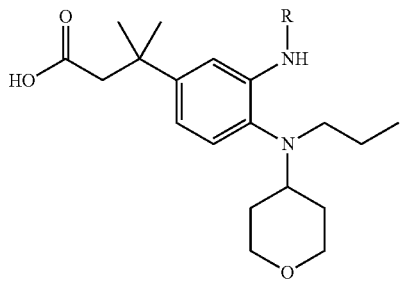

Examples 22 to 24 were prepared following the procedure for Example 21 by using the corresponding halides.

| Ex. No. | Name | R | $T_r$ (min) Method O | $[M+H]^+$ |
|---|---|---|---|---|
| 22 | 3-(3-((4-cyanophenyl)amino)-4-(propyl(tetrahydro-2H-pyran-4-yl)amino)phenyl)-3-methylbutanoic acid | CN ⟨phenyl⟩ | 2.036 | 436.2 |
| 23 | 3-(3-((2-methoxypyrimidin-5-yl)amino)-4-(propyl(tetrahydro-2H-pyran-4-yl)amino)phenyl)-3-methylbutanoic acid | ⟨methoxypyrimidine⟩ | 1.766 | 443.3 |
| 24 | 3-(3-((2-ethoxypyrimidin-5-yl)amino)-4-(propyl(tetrahydro-2H-pyran-4-yl)amino)phenyl)-3-methylbutanoic acid | ⟨ethoxypyrimidine⟩ | 1.879 | 457.3 |

Example 25

3-Methyl-3-(4-(propyl(tetrahydro-2H-pyran-4-yl)amino)-3-(3-(p-tolyl)ureido)phenyl)butanoic acid

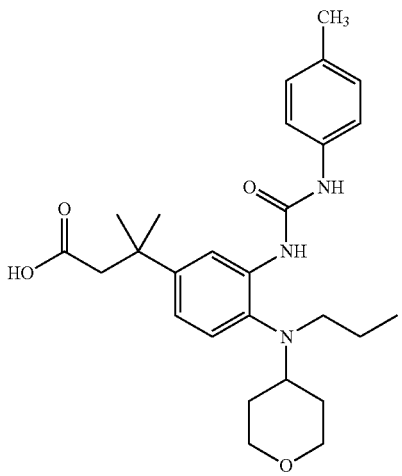 [SMILES: CCCN(c1ccc(C(C)(C)CC(=O)O)cc1NC(=O)Nc1ccc(C)cc1)C1CCOCC1]

25A. Ethyl 3-(4-((2-methoxyethyl)(tetrahydro-2H-pyran-4-yl)amino)-3-(3-(p-tolyl)ureido)phenyl)-3-methylbutanoate Compound 25A was prepared from 15F and 1-isocyanato-4-methylbenzene following the procedure described for the synthesis of 18A. LC-MS Anal. Calc'd. for $C_{29}H_{41}N_3O_5$, 511.3, found [M+H] 512.5, $T_r$=1.53 min. (Method AY).

Example 25. 3-Methyl-3-(4-(propyl(tetrahydro-2H-pyran-4-yl)amino)-3-(3-(p-tolyl)ureido)phenyl)butanoic acid Example 25 was prepared from 25A following the procedure described for the synthesis of Example 15 from 15G. LC-MS Anal. Calc'd. for $C_{27}H_{37}N_3O_4$, 467.26, found [M+H] 468.3, $T_r$=1.91 min. (Method O). $^1$H NMR (400 MHz, DMSO-d$_6$) δ 9.33-9.43 (m, 1H), 8.38 (s, 1H), 8.28 (m, 1H), 7.37 (m, 2H), 7.06-7.18 (m, 3H), 6.90-7.00 (m, 1H), 3.84 (m, 2H), 3.13-3.20 (m, 2H), 2.63-2.71 (m, 3H), 2.29-2.37 (m, 4H), 2.24 (s, 3H), 1.98-2.11 (m, 2H), 1.34-1.41 (m, 6H), 1.18-1.26 (m, 2H), 0.72-0.83 (t, J=7.2 Hz, 3H).

Example 26

3-(3-((4-Chlorophenyl)amino)-4-(ethyl(tetrahydro-2H-pyran-4-yl)amino)phenyl)-3-ethylpentanoic acid

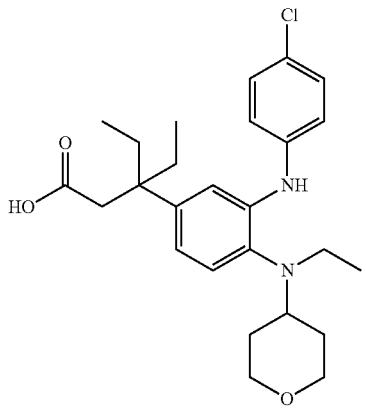 [SMILES: CCN(c1ccc(C(CC)(CC)CC(=O)O)cc1Nc1ccc(Cl)cc1)C1CCOCC1]

26A. Diethyl 2-(pentan-3-ylidene)malonate

To a stirred solution of diethyl malonate (15.24 mL, 100 mmol), pentan-3-one (10.62 mL, 100 mmol) and pyridine (11.31 mL, 140 mmol) in tetrahydrofuran (480 mL) at 0° C. was added titanium tetrachloride (1M in DCM) (140 mL, 140 mmol) in dropwise (10 min) manner. The reaction mixture was allowed to rise to room temperature and stirred at room temperature for 24 h. Reaction mixture was quenched with water (150 mL). The mixture was extracted with diethyl ether (150 mL). The organic layer was separated and the aqueous layer was extracted with ethyl acetate (150 mL). The organic layers were combined, dried over anhydrous sodium sulfate, concentrated under reduced pressure to get crude compound. Purification via flash silica gel column chromatography gave 26A (yellow liquid, 5.8 g, 25.4 mmol, 25% yield). LC-MS Anal. Calc'd. for $C_{12}H_{20}O_4$, 228.1, found [M+H] 229.3, $T_r$=1.43 min. (Method AY).

26B. Diethyl 2-(3-(4-fluorophenyl)pentan-3-yl)malonate

To a stirred solution of (4-fluorophenyl)magnesium bromide (89 mL, 89 mmol) in dry diethyl ether (76 mL), cooled to –10° C., was added copper(I) chloride (2.2 g, 22.22 mmol). Then 26A (7.61 g, 33.3 mmol) in diethyl ether (7.6 mL) was added dropwise for 5 minutes. Reaction mixture was stirred for 20 minutes at room temperature and then refluxed for 12 h. LCMS indicated completion of reaction. Reaction mixture was cooled to 0° C., quenched with ice cold 1 N HCl. Aqueous layer was extracted with ether (2×100 mL). The combined organic layer was washed with brine (50 mL), dried over anhydrous sodium sulfate, concentrated under reduced pressure to get crude compound. Purification via flash silica gel column chromatography gave 26B (yellow liquid, 7.5 g, 21.73 mmol, 98% yield). LC-MS Anal. Calc'd. for $C_{18}H_{25}FO_4$, 324.2, found [M+H] 325.3, $T_r$=1.65 min. (Method AY).

26C. Ethyl 3-ethyl-3-(4-fluorophenyl)pentanoate

To a stirred solution of 26B (7.5 g, 23.12 mmol) in DMSO (75 mL), water (3.75 mL), was added lithium chloride (1.960 g, 46.2 mmol). The reaction mixture was heated at 180° C. for 12 h. TLC indicated completion of reaction. Reaction mixture was cooled to 0° C. and it was quenched with water (60 mL). It was extracted with ethyl acetate (2×60 mL). The combined organic layer was washed with brine (40 mL), dried over anhydrous sodium sulfate, concentrated under reduced pressure to get crude compound. Purification via flash silica gel column chromatography gave 26C (yellow liquid, 4.7 g, 16.02 mmol, 69% yield). LC-MS Anal. Calc'd. for $C_{15}H_{21}FO_2$, 252.1, found [M+H] 253.3, $T_r$=1.64 min. (Method AY).

26D. Ethyl 3-ethyl-3-(4-fluoro-3-nitrophenyl)pentanoate

To a stirred solution of 26C (4.7 g, 18.63 mmol) in $H_2SO_4$ (47 mL) at 0° C. was added potassium nitrate (1.883 g, 18.63 mmol). The reaction mixture was stirred at 0° C. for 15 min. TLC indicated completion of reaction. Reaction mixture was poured into ice and it was extracted with ethyl acetate (2×50 mL). The combined organic layer was washed with brine (20 mL), dried over anhydrous sodium sulfate, concentrated under reduced pressure to get crude compound. Purification via flash silica gel column chromatography gave 26D (yellow liquid, 2 g, 6.73 mmol, 36% yield). $^1$H NMR (300 MHz, $CDCl_3$) δ 8.05 (s, 1H), 7.64 (m, 1H), 7.29 (m, 1H), 4.05 (q, J=7.2 Hz, 2H), 2.74 (s, 2H), 1.89-1.94 (m, 4H), 1.17 (t, J=7.2 Hz, 3H), 0.82 (m, 6H).

26E. N-Ethyltetrahydro-2H-pyran-4-amine

Compound 26E was prepared from dihydro-2H-pyran-4(3H)-one and ethanamine following the procedure described for the synthesis of 15D. $^1$H NMR (300 MHz, $CDCl_3$) δ 3.97 (m, 2H), 3.41 (m, 2H), 2.67 (m, 1H), 2.63 (m, 2H), 1.89-1.77 (m, 4H), 1.09 (t, J=7.2 Hz, 3H).

26F. Ethyl 3-ethyl-3-(4-(ethyl(tetrahydro-2H-pyran-4-yl)amino)-3-nitrophenyl)pentanoate In a sealed tube 26D (2 g, 6.73 mmol) in N-methyl-2-pyrrolidinone (10 mL) were added DIPEA (3.52 mL, 20.18 mmol) and 26E (1.738 g, 13.45 mmol). The reaction mixture was stirred at 135° C. for 15 h. TLC indicated completion of reaction. Reaction mixture was cooled to room temperature, quenched with water (20 mL) and it was extracted with MTBE (3×30 mL). The combined organic layer was washed with brine (20 mL), dried over anhydrous sodium sulfate, concentrated under reduced pressure to get crude compound. Purification via flash silica gel column chromatography gave compound 26F (gummy liquid, 1.2 g, 2.83 mmol, 42% yield). LC-MS Anal. Calc'd. for $C_{22}H_{34}N_2O_5$, 406.2, found [M+H] 407.2, $T_r$=1.64 min. (Method AY).

26G. Ethyl 3-(3-amino-4-(ethyl(tetrahydro-2H-pyran-4-yl)amino)phenyl)-3-ethylpentanoate The solution of 26F (1.2 g, 2.95 mmol) in ethyl acetate (12 mL) was charged to a sealable hydrogen flask. The solution was sequentially evacuated and purged with nitrogen gas. To this 10% Pd on carbon (0.157 g, 0.148 mmol) was added under nitrogen atmosphere. The reaction mixture was stirred under hydrogen atmosphere (40 psi). The reaction mixture was stirred at room temperature for 3 h. The reaction mixture was filtered through a CELITE® pad and the residue on the pad was thoroughly rinsed with ethyl acetate (3×15 mL). The combined filtrate was concentrated under reduced pressure to get crude compound. Purification via flash chromatography gave 26G (yellow liquid, 900 mg, 2.271 mmol, 77% yield). LC-MS Anal. Calc'd. for $C_{22}H_{36}N_2O_3$, 376.3, found [M+H] 377.3, $T_r$=1.65 min. (Method AY).

26H. Ethyl 3-(3-((4-chlorophenyl)amino)-4-(ethyl(tetrahydro-2H-pyran-4-yl)amino)phenyl)-3-ethylpentanoate The mixture of 26G (0.050 g, 0.133 mmol), 1-bromo-4-chlorobenzene (0.031 g, 0.159 mmol), 4,5-bis(diphenylphosphino)-9,9-dimethylxanthene (7.68 mg, 0.013 mmol) and $Cs_2CO_3$ (0.065 g, 0.199 mmol) in 1,4-dioxane (1.5 mL) was stirred. Argon gas was bubbled through the mixture for 5 min. Bis(dibenzylideneacetone)palladium (3.82 mg, 6.64 µmol) was added and argon gas was bubbled through the mixture for 5 min. The reaction mixture was sealed and placed in preheated oil bath at 110° C. for 12 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography gave 26H (gummy liquid, 50 mg, 0.050 mmol, 37% yield). LC-MS Anal. Calc'd. for $C_{28}H_{39}ClN_2O_3$, 486.3, found [M+H] 487.5, $T_r$=2.31 min. (Method AY).

Example 26. 3-(3-((4-Chlorophenyl)amino)-4-(ethyl(tetrahydro-2H-pyran-4-yl)amino)phenyl)-3-ethylpentanoic acid To a stirred solution of 26H (0.050 g, 0.103 mmol) in mixture of THF (1 mL), methanol (1 mL) and water (0.1 mL) was added $LiOH·H_2O$ (0.017 g, 0.411 mmol). The reaction mixture was stirred at 50° C. for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS gave Example 26 (13.7 mg, 0.030 mmol, 28% yield). LC-MS Anal. Calc'd. for $C_{26}H_{35}ClN_2O_3$, 458.2, found [M+H] 459.1, $T_r$=2.67 min. (Method O). $^1$H NMR (400 MHz, DMSO-$d_6$) δ 7.36 (s, 1H), 7.20-7.29 (m, 2H), 7.06-7.17 (m, 4H), 6.85 (m, 1H), 3.79 (m, 2H), 3.11-3.23 (m, 2H), 2.91-3.04 (m, 3H), 2.56 (s, 2H), 1.69-1.81 (m, 4H), 1.64 (m, 2H), 1.41 (m, 2H), 0.80 (t, J=7.2 Hz, 3H), 0.66 (m, 6H).

Examples 27 to 29

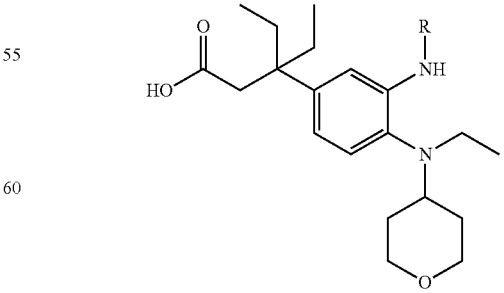

Examples 27 to 29 were prepared following the procedure for Example 26 by using the corresponding halides.

| Ex. No. | Name | R | $T_r$ (min) Method O | $[M + H]^+$ |
|---|---|---|---|---|
| 27 | 3-(3-((4-cyanophenyl)amino)-4-(ethyl (tetrahydro-2H-pyran-4-yl)amino) phenyl)-3-ethylpentanoic acid | CN-C6H4- | 2.267 | 450.1 |
| 28 | 3-ethyl-3-(4-(ethyl(tetrahydro-2H-pyran-4-yl)amino)-3-((2-methoxypyrimidin-5-yl)amino)phenyl) pentanoic acid | 2-methoxypyrimidin-5-yl | 1.989 | 457.1 |
| 29 | 3-(3-((2-ethoxypyrimidin-5-yl)amino)-4-(ethyl(tetrahydro-2H-pyran-4-yl)amino)phenyl)-3-ethylpentanoic acid | 2-ethoxypyrimidin-5-yl | 2.149 | 471.1 |

Example 30

3-Ethyl-3-(4-(ethyl(tetrahydro-2H-pyran-4-yl) amino)-3-(3-(p-tolyl)ureido)phenyl)pentanoic acid

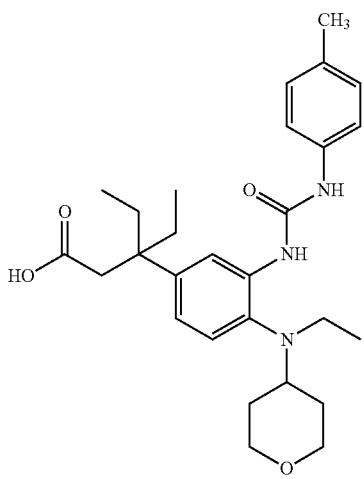 [SMILES: CCN(c1ccc(C(CC)(CC)CC(=O)O)cc1NC(=O)Nc1ccc(C)cc1)C1CCOCC1]

30A. Ethyl 3-ethyl-3-(4-(ethyl(tetrahydro-2H-pyran-4-yl)amino)-3-(3-(p-tolyl)ureido)phenyl)pentanoate To a stirred solution of 26G (0.035 g, 0.093 mmol) in tetrahydrofuran (1 mL) was added 1-isocyanato-4-methylbenzene (0.015 g, 0.112 mmol). The reaction mixture was stirred at room temperature for 12 h. LCMS indicated completion of reaction. The reaction mixture was concentrated under reduced pressure to get 30A (gummy liquid, 45 mg, 0.071 mmol, 76% yield). LC-MS Anal. Calc'd. for $C_{30}H_{43}N_3O_4$, 509.32, found [M+H] 510.4. $T_r$=1.74 min. (Method AY).

Example 30. 3-Ethyl-3-(4-(ethyl(tetrahydro-2H-pyran-4-yl)amino)-3-(3-(p-tolyl)ureido)phenyl)pentanoic acid To a stirred solution of 30A (0.045 g, 0.088 mmol) in mixture of tetrahydrofuran (1 mL), methanol (1 mL) and water (0.1 mL), was added LiOH.H$_2$O (0.015 g, 0.353 mmol). The reaction mixture was stirred at 50° C. for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 30 (25 mg, 0.051 mmol, 58% yield). LC-MS Anal. Calc'd. for $C_{28}H_{39}N_3O_4$, 481.2, found [M+H] 482.2, $T_r$=2.21 min. (Method R). $^1$H NMR (400 MHz, DMSO-d$_6$) δ 9.43 (s, 1H), 8.45-8.56 (m, 1H), 8.15-8.30 (m, 1H), 7.31-7.45 (m, 2H), 7.16 (d, J=8.2 Hz, 1H), 7.09 (d, J=8.2 Hz, 2H), 6.79-6.93 (m, 1H), 3.83 (m, 2H), 3.13-3.31 (m, 2H), 2.87-3.05 (m, 3H), 2.59 (s, 2H), 2.25 (s, 3H), 1.63-1.86 (m, 6H), 1.39 (m, 2H), 0.79 (t, J=7.2 Hz, 3H), 0.64 (m, 6H).

Examples 31 and 32

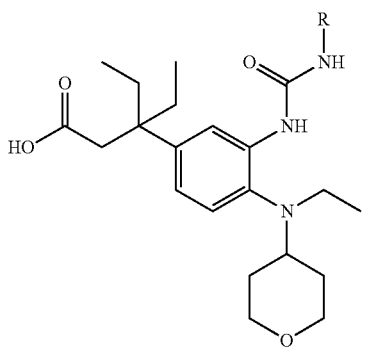

Examples 31 and 32 were prepared following the procedure for Example 30 by using the corresponding isocyanates.

| Ex. No. | Name | R | $T_r$ (min) Method O | $[M + H]^+$ |
|---|---|---|---|---|
| 31 | 3-(3-(3-(4-cyanophenyl)ureido)-4-(ethyl(tetrahydro-2H-pyran-4-yl)amino)phenyl)-3-ethylpentanoic acid | CN-C6H4- | 2.04 | 493.1 |
| 32 | 3-(3-(3-(4-chloro-2-fluorophenyl)ureido)-4-(ethyl(tetrahydro-2H-pyran-4-yl)amino)phenyl)-3-ethylpentanoic acid | 4-Cl-2-F-C6H3- | 2.04 | 520.3 |

Example 33

Enantiomer 1 and Enantiomer 2

3-(3-((4-Chlorophenyl)amino)-4-(ethyl(tetrahydro-2H-pyran-4-yl)amino)phenyl)-3-cyclopropylpropanoic acid

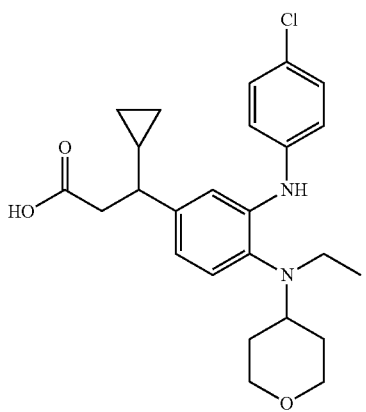 [SMILES: CCN(c1ccc(C(CC(=O)O)C2CC2)cc1Nc1ccc(Cl)cc1)C1CCOCC1]

33A. N-(4-Bromo-2-nitrophenyl)-N-ethyltetrahydro-2H-pyran-4-amine

In a sealed tube containing 4-bromo-1-fluoro-2-nitrobenzene (5.6 g, 25.5 mmol) was added 26E. The reaction mixture was heated at 135° C. for 12 h. LCMS indicated completion of reaction. Purification via flash chromatography gave 33A (yellow liquid, 7.3 g, 21.73 mmol, 85% yield). LC-MS Anal. Calc'd. for $C_{13}H_{17}BrN_2O_3$, 328.0, found [M+2] 330.2, $T_r$=3.10 min. (Method U).

33B. N-Ethyl-N-(2-nitro-4-(4,4,5,5-tetramethyl-1,3,2-dioxaborolan-2-yl)phenyl)tetrahydro-2H-pyran-4-amine To a stirred solution of 33A (2.6 g, 7.90 mmol), bis(pinacolato)diboron (3.01 g, 11.85 mmol) and potassium acetate (2.325 g, 23.69 mmol) in 1,4-dioxane (26 mL) was purged with argon for 10 min. To this $PdCl_2$ (dppf).$CH_2Cl_2$ Adduct (0.322 g, 0.395 mmol) was added and purged with argon for 5 min. The reaction mixture was heated at 90° C. for 5 h. LCMS indicated completion of reaction. Reaction mixture was cooled to room temperature and quenched with water (30 mL). Aqueous layer was extracted with ethyl acetate (3×30 mL). The combined organic layer was washed with brine (20 mL), dried over anhydrous sodium sulfate, concentrated under reduced pressure to get crude compound. Purification via flash chromatography gave 33B (yellow solid, 2.8 g, 7.44 mmol, 91% yield). LC-MS Anal. Calc'd. for $C_{19}H_{29}BN_2O_5$, 376.2, found [M+H] 377.4, $T_r$=3.63 min. (Method U).

33C. (E)-Methyl 3-cyclopropylacrylate

To a stirred suspension of lithium chloride (18.15 g, 428 mmol) in acetonitrile (80 mL) under nitrogen atmosphere was added trimethyl phosphonoacetate (55.4 mL, 342 mmol), 1,8-diazabicyclo[5.4.0]undec-7-ene (86 mL, 571 mmol) and followed by cyclopropanecarbaldehyde (21.32 mL, 285 mmol) at 0° C. The reaction mixture was stirred for 12 h at room temperature. TLC indicated completion of reaction. Reaction mixture was quenched with water (300 mL) and it was extracted with ethyl acetate (300 mL). Aqueous layer was extracted with ethyl acetate (2×100 mL). The combined organic layer was washed with 1N HCl (50 mL) and brine (50 mL), dried over anhydrous sodium sulfate, concentrated under reduced pressure to get crude compound. Purification via flash chromatography gave 33C (yellow liquid, 11 g, 87 mmol, 30% yield). $^1$H NMR (300 MHz, CDCl$_3$) δ 6.46 (m, 1H), 5.87 (m, 1H), 3.72 (s, 3H), 1.68 (m, 1H), 0.98 (m, 2H), 0.66 (m, 2H).

33D. Methyl 3-cyclopropyl-3-(4-(ethyl(tetrahydro-2H-pyran-4-yl)amino)-3-nitrophenyl)propanoate In a sealed tube, the suspension of 33B, 33C and sodium hydroxide (8.98 mL, 8.98 mmol) in 1,4-dioxane (37 mL) was purged with argon for 10 min. To this chloro(1,5-cyclooctadiene)rhodium(I) dimer (0.242 g, 0.492 mmol) was added and purged with argon for 5 min. The reaction mixture was heated at 50° C. for 6 h. LCMS indicated completion of reaction. Reaction mixture was cooled to room temperature and quenched with acetic acid (0.563 mL) and it was stirred for 5 minutes before it was partitioned between ethyl acetate (40 mL) and water (20 mL). Aqueous layer was extracted with ethyl acetate (30 mL). The combined organic layer was washed with brine (30 mL), dried over anhydrous sodium sulfate, concentrated under reduced pressure to get crude compound. Purification via flash chromatography gave 33D (yellow solid, 2.1 g, 5.24 mmol, 53% yield). LC-MS Anal. Calc'd. for $C_{20}H_{28}N_2O_5$, 376.2, found [M+H] 377.4, $T_r$=1.53 min. (Method AY).

33E. Methyl 3-(3-amino-4-(ethyl(tetrahydro-2H-pyran-4-yl)amino)phenyl)-3-cyclopropylpropanoate The solution of 33D (2.1 g, 5.58 mmol) in ethyl acetate (21 mL) was charged to a sealable hydrogen flask. The solution was sequentially evacuated and purged with nitrogen gas. To this 10% Pd on carbon (0.297 g, 0.279 mmol) was added under nitrogen atmosphere. The reaction mixture was stirred under hydrogen atmosphere (40 psi). The reaction mixture was stirred at room temperature for 3 h. The reaction mixture was filtered through a CELITE® pad and the residue on the pad was thoroughly rinsed with ethyl acetate (3×15 mL). The combined filtrate was concentrated under reduced pressure to get crude compound Racemate 33E (yellow solid, 1.5 g). LC-MS Anal. Calc'd. for $C_{20}H_{30}N_2O_3$, 346.2, found [M+H] 347.2, $T_r$=1.46 min. (Method AY).

Chiral separation of Racemate 33E (Method BK) gave Enantiomer 1 and Enantiomer 2 as single enantiomers. Enantiomer 1 $T_r$=2.89 min (Method BK) and Enantiomer 2 $T_r$=3.61 min (Method BK).

33E Enantiomer 1 (yellow liquid, 390 mg, 1.126 mmol, 20% yield): LC-MS Anal. Calc'd. for $C_{20}H_{30}N_2O_3$, 346.2, found [M+H] 347.2, $T_r$=2.17 min (Method BB).

33E Enantiomer 2 (yellow liquid, 440 mg, 1.245 mmol, 22% yield): LC-MS Anal. Calc'd. for $C_{20}H_{30}N_2O_3$, 346.2, found [M+H] 347.2, $T_r$=2.17 min (Method BB).

33F. Methyl 3-(3-((4-chlorophenyl)amino)-4-(ethyl (tetrahydro-2H-pyran-4-yl)amino)phenyl)-3-cyclopropylpropanoate The mixture of 33E Enantiomer 1 (0.050 g, 0.144 mmol), 1-bromo-4-chlorobenzene (0.033 g, 0.173 mmol), 4,5-bis (diphenylphosphino)-9,9-dimethylxanthene (0.042 g, 0.072 mmol) and Cs$_2$CO$_3$ (0.141 g, 0.433 mmol) in 1,4-dioxane (2 mL) was stirred at room temperature. Argon gas was bubbled through the mixture for 5 min. Bis(dibenzylideneacetone)palladium (8.30 mg, 0.014 mmol) was added and argon gas was bubbled through the mixture for 5 min. The reaction mixture was sealed and placed in preheated oil bath at 110° C. for 5 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography to afford 33F (yellow liquid, 50 mg, 0.048 mmol, 33% yield). LC-MS Anal. Calc'd. for $C_{26}H_{33}ClN_2O_3$, 456.2, found [M+H] 457.4, $T_r$=1.31 min. (Method AY).

Example 33 Enantiomer 1. 3-(3-((4-Chlorophenyl)amino)-4-(ethyl(tetrahydro-2H-pyran-4-yl)amino) phenyl)-3-cyclopropylpropanoic acid To a stirred solution of 33F (0.050 g, 0.109 mmol) in mixture of tetrahydrofuran (1 mL), methanol (1 mL) and water (0.2 mL) was added LiOH.H$_2$O (0.018 g, 0.438 mmol). The reaction mixture was stirred at room temperature for 12 h. The reaction mixture was concentrated under reduced pressure. The aqueous residue so obtained was acidified with aqueous citric acid The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 33 Enantiomer 1 (20.4 mg, 0.046 mmol, 41% yield). LC-MS Anal. Calc'd. for $C_{25}H_{31}ClN_2O_3$, 442.2, found [M+H] 443.2, $T_r$=2.15 min. (Method O). $^1$H NMR (400 MHz, DMSO-d$_6$) δ 7.40 (m, 1H), 7.04-7.20 (m, 2H), 7.08-7.18 (m, 4H), 6.95 (m, 1H), 3.79 (m, 2H), 3.10-3.22 (m, 2H), 2.98 (m, 3H), 2.57-2.72 (m, 2H), 2.33 (m, 1H), 1.63 (m, 2H), 1.43 (m, 2H), 0.94-1.08 (m, 1H), 0.83 (t, J=7.2 Hz, 3H), 0.44-0.58 (m, 1H), 0.31-0.40 (m, 1H), 0.19-0.28 (m, 1H), 0.06-0.18 (m, 1H).

Example 33 Enantiomer 2. 3-(3-((4-Chlorophenyl)amino)-4-(ethyl(tetrahydro-2H-pyran-4-yl)amino) phenyl)-3-cyclopropylpropanoic acid Example 33 Enantiomer 2 was prepared following the same procedure for Example 33 Enantiomer 1 by utilizing compound 33E Enantiomer 2. LC-MS Anal. Calc'd. for $C_{25}H_{31}ClN_2O_3$, 442.2, found [M+H] 443.1, $T_r$=2.15 min. (Method O). $^1$H NMR (400 MHz, DMSO-d$_6$) δ 7.35-7.43 (m, 1H), 7.22-7.28 (m, 2H), 7.08-7.18 (m, 4H), 6.71-6.87 (m, 1H), 3.79 (m, 2H), 3.10-3.22 (m, 2H), 2.91-3.05 (m, 3H), 2.56-2.70 (m, 2H), 2.17-2.26 (m, 1H), 1.65 (m, 2H), 1.32-1.47 (m, 2H), 0.95-1.06 (m, 1H), 0.83 (t, J=7.2 Hz, 3H), 0.45-0.55 (m, 1H), 0.30-0.40 (m, 1H), 0.22 (m, 1H), 0.06-0.18 (m, 1H).

Examples 34 to 36

Enantiomer 1

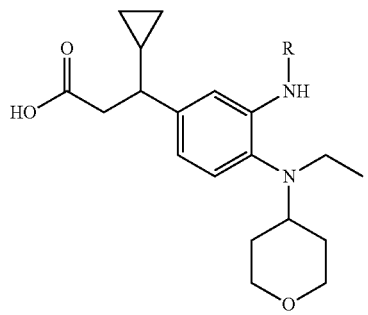

Examples 37 to 39

Enantiomer 2

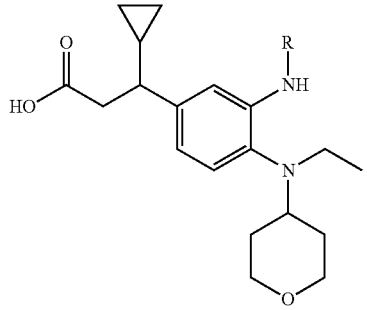

Examples 34 to 36 was prepared from 33E Enantiomer 1 and corresponding halides following the procedure described for the synthesis of Example 33 Enantiomer 1 (absolute stereochemistry unknown).

Examples 37 to 39 was prepared from 33E Enantiomer 2 and corresponding halides following the procedure described for the synthesis of Example 33 Enantiomer 1.

| Ex. No. | Name | R | $T_r$ (min) | $[M + H]^+$ |
|---|---|---|---|---|
| 34 | 3-(3-((4-cyanophenyl)amino)-4-(ethyl(tetrahydro-2H-pyran-4-yl)amino)phenyl)-3-cyclopropylpropanoic acid | CN-phenyl | 1.62 (Method O) | 434.3 |
| 35 | 3-cyclopropyl-3-(4-(ethyl(tetrahydro-2H-pyran-4-yl)amino)-3-((2-methoxypyrimidin-5-yl)amino)phenyl)propanoic acid | 2-methoxypyrimidin-5-yl | 1.34 (Method O) | 441.3 |
| 36 | 3-cyclopropyl-3-(3-((2-ethoxypyrimidin-5-yl)amino)-4-(ethyl(tetrahydro-2H-pyran-4-yl)amino)phenyl)propanoic acid | 2-ethoxypyrimidin-5-yl | 1.15 (Method R) | 455.3 |

| Ex. No. | Name | R | $T_r$ (min) | $[M + H]^+$ |
|---|---|---|---|---|
| 37 | 3-(3-((4-cyanophenyl)amino)-4-(ethyl(tetrahydro-2H-pyran-4-yl)amino)phenyl)-3-cyclopropylpropanoic acid | CN-C6H4- | 1.81 (Method O) | 434.2 |
| 38 | 3-cyclopropyl-3-(4-(ethyl(tetrahydro-2H-pyran-4-yl)amino)-3-((2-methoxypyrimidin-5-yl)amino)phenyl)propanoic acid | 2-methoxypyrimidin-5-yl | 1.55 (Method O) | 441.2 |
| 39 | 3-cyclopropyl-3-(3-((2-ethoxypyrimidin-5-yl)amino)-4-(ethyl(tetrahydro-2H-pyran-4-yl)amino)phenyl)propanoic acid | 2-ethoxypyrimidin-5-yl | 1.15 (Method R) | 455.4 |

Example 40

Enantiomer 1 and Enantiomer 2

3-Cyclopropyl-3-(4-(ethyl(tetrahydro-2H-pyran-4-yl)amino)-3-(3-(p-tolyl)ureido)phenyl)propanoic acid

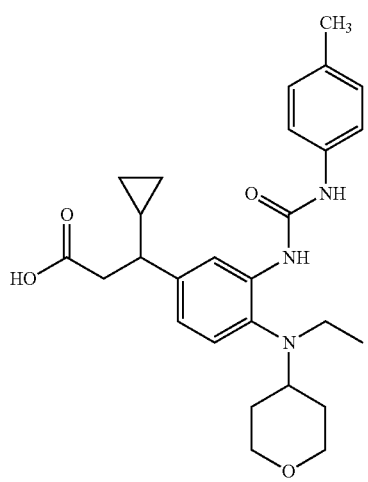 [SMILES: CCN(c1ccc(C(CC(=O)O)C2CC2)cc1NC(=O)Nc1ccc(C)cc1)C1CCOCC1]

40A. Methyl 3-cyclopropyl-3-(4-(ethyl(tetrahydro-2H-pyran-4-yl)amino)-3-(3-(p-tolyl)ureido)phenyl) propanoate To a stirred solution of 33E Enantiomer 1 (0.035 g, 0.101 mmol) in tetrahydrofuran (1.5 mL) was added 1-isocyanato-4-methylbenzene (0.032 g, 0.242 mmol). The reaction mixture was stirred at room temperature for 12 h. LCMS indicated completion of reaction. The reaction mixture was concentrated under reduced pressure to get 40A (yellow liquid, 45 mg, 0.057 mmol, 56% yield). LC-MS Anal. Calc'd. for $C_{28}H_{37}N_3O_4$, 479.3, found [M+H] 480.4, $T_r$=1.12 min. (Method AY).

Example 40 Enantiomer 1. 3-Cyclopropyl-3-(4-(ethyl(tetrahydro-2H-pyran-4-yl)amino)-3-(3-(p-tolyl)ureido)phenyl)propanoic acid To a stirred solution of compound 40A (0.045 g, 0.094 mmol) in mixture of tetrahydrofuran (1.5 mL), methanol (1.5 mL) and water (0.5 mL) was added LiOH.H$_2$O (0.016 g, 0.375 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 40 Enantiomer 1 (22.5 mg, 0.047 mmol, 50% yield). LC-MS Anal. Calc'd. for $C_{27}H_{35}N_3O_4$, 465.2, found [M+H] 466.4, $T_r$=1.54 min. (Method O). $^1$H NMR (400 MHz, DMSO-d$_6$) δ 9.63-9.73 (m, 1H), 8.67-8.80 (m, 1H), 8.34-8.42 (m, 1H), 7.58-7.68 (m, 2H), 7.30-7.43 (m, 3H), 6.85 (m, 1H), 4.08 (m, 2H), 3.39-3.55 (m, 2H), 3.24 (q, J=6.4 Hz, 2H), 2.80-2.95 (m, 3H), 2.44-2.57 (m, 4H), 1.61-1.73 (m, 2H), 1.20-1.31 (m, 2H) 1.06 (t, J=7.2 Hz, 1H), 0.82 (t, J=7.2 Hz, 3H), 0.76 (t, J=7.2 Hz, 1H), 0.55-0.68 (m, 1H), 0.49 (m, 1H), 0.38 (m, 1H).

Example 40 Enantiomer 2. 3-Cyclopropyl-3-(4-(ethyl(tetrahydro-2H-pyran-4-yl)amino)-3-(3-(p-tolyl)ureido)phenyl)propanoic acid Example 40 Enantiomer 2 was prepared from 33E Enantiomer 2 following the procedure described for the synthesis of Example 40 Enantiomer 1. LC-MS Anal. Calc'd. for $C_{27}H_{35}N_3O_4$, 465.2, found [M+H] 466.3, $T_r$=1.75 min. (Method O). $^1$H NMR (400 MHz, DMSO-$d_6$) δ 9.40 (s, 1H), 8.47 (s, 1H), 8.13 (m, 1H), 7.37 (m, 2H), 7.04-7.18 (m, 3H), 6.84 (m, 1H), 3.76-3.91 (m, 2H), 3.39-3.55 (m, 2H), 3.24 (q, J=6.4 Hz, 2H), 2.89-3.03 (m, 3H), 2.63-2.74 (m, 4H), 1.64-1.77 (m, 2H), 1.33-1.45 (m, 2H), 0.92-1.02 (m, 1H), 0.73-0.85 (t, J=7.2 Hz, 3H), 0.43-0.56 (m, 2H), 0.29-0.38 (m, 2H).

Example 41

Enantiomer 1 and Enantiomer 2

3-(3-((4-Cyanophenyl)amino)-4-(4-methylpiperidin-1-yl)phenyl)pentanoic acid

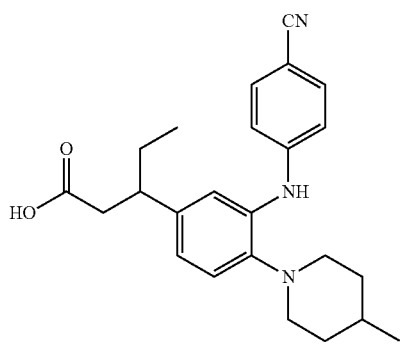 [SMILES: CCC(CC(=O)O)c1ccc(N2CCC(C)CC2)c(Nc2ccc(C#N)cc2)c1]

41A. 2-(4-Fluoro-3-nitrophenyl)-4,4,5,5-tetramethyl-1,3,2-dioxaborolane

To a stirred solution of 4-bromo-1-fluoro-2-nitrobenzene (10 g, 45.5 mmol), 4,4,4',4',5,5,5',5'-octamethyl-2,2'-bi(1,3,2-dioxaborolane) (16.16 g, 63.6 mmol), potassium acetate (13.38 g, 136 mmol) in dioxane (100 mL). The reaction mixture was purged with argon for 5 min. After 5 min, $PdCl_2$ (dppf).$CH_2Cl_2$ Adduct (3.71 g, 4.55 mmol) was added to the reaction mixture under argon and heated to 108° C. for 12 h. The reaction mixture was allowed to cool to rt, filtered through CELITE® pad, washed with ethyl acetate (100 mL). The organic layer was washed with water (50 mL) and the aqueous layer was separated and re-extracted with ethyl acetate (2×100 mL). Combined the organic extracts were washed with brine, dried over sodium sulfate and solvent was removed under reduced pressure to give the crude product as a brown colored oil. The oily compound was purified by silica gel column chromatography eluting with pet ether/ethyl acetate to afford 41A (light yellow solid, 10.4 g, 38.9 mmol, 86% yield). LC-MS Anal. Calc'd. for $C_{12}H_{15}BFNO_4$, 267.108, found [M+NH$_4$] 285.2, $T_r$=1.07 (Method AY).

41B. Methyl 3-(4-fluoro-3-nitrophenyl)pentanoate

To a stirred solution of 41A (5 g, 18.72 mmol) in dioxane (80 mL), to this (E)-methyl pent-2-enoate (5.34 g, 46.8 mmol) was added followed by NaOH (1M) (16.85 mL, 16.85 mmol). The reaction mixture was purged with argon for 15 mins. To the above reaction mixture was charged with chloro(1,5-cyclooctadiene)rhodium(I) dimer (0.462 g, 0.936 mmol) and the argon purge cycle was repeated. The reaction suspension was stirred at 50° C. for 6 h. The reaction mixture was allowed to cool to room temperature and quenched with AcOH (0.965 mL, 16.85 mmol) and it was stirred for 5 minutes before it was partitioned between ethyl acetate (100 mL) and water (80 mL). The aqueous layer was re-extracted with ethyl acetate (2×100 mL). Combined organic extracts was washed with brine (80 mL), dried over anhydrous sodium sulfate, filtered and concentrated under reduced pressure to afford a residue. The residue was purified by silica gel column chromatography using pet ether/ethyl acetate to afford 41B (brown oil, 4.0 g, 15.74 mmol, 84% yield). LC-MS Anal. Calc'd. for $C_{12}H_{14}FNO_4$, 255.09, found [M+NH$_4$] 273.0, $T_r$=2.751 (Method U).

41C. Methyl 3-(4-(4-methylpiperidin-1-yl)-3-nitrophenyl)pentanoate

In a sealed tube 41B (1.5 g, 5.88 mmol) in N-methyl-2-pyrrolidinone (15 mL) were added DIPEA (3.08 mL, 17.63 mmol) and 4-methylpiperidine (1.166 g, 11.75 mmol). The reaction mixture was stirred at 135° C. for 12 h. TLC indicated completion of reaction. Reaction mixture was cooled to room temperature, quenched with water (20 mL) and it was extracted with MTBE (3×30 mL). The combined organic layer was washed with brine (20 mL), dried over anhydrous sodium sulfate, concentrated under reduced pressure to get crude compound. Purification via flash chromatography gave 41C (yellow liquid, 1.8 g, 5.38 mmol, 86% yield). LC-MS Anal. Calc'd. for $C_{18}H_{26}N_2O_4$, 334.2, found [M+2] 336.6, $T_r$=1.69 min. (Method AY).

41D. Methyl 3-(3-amino-4-(4-methylpiperidin-1-yl)phenyl)pentanoate

The solution of 41C (1.8 g, 5.38 mmol) in ethyl acetate (18 mL) was charged to a sealable hydrogen flask. The solution was sequentially evacuated and purged with nitrogen gas. To this 10% Pd on carbon (0.286 g, 0.269 mmol) was added under nitrogen atmosphere. The reaction mixture was stirred under hydrogen atmosphere (40 psi). The reaction mixture was stirred at room temperature for 4 h. The reaction mixture was filtered through a CELITE® pad and the residue on the pad was thoroughly rinsed with ethyl acetate (3×15 mL). The combined filtrate was concentrated under reduced pressure to get crude compound 41D (yellow solid, 1.2 g). LC-MS Anal. Calc'd. for $C_{18}H_{28}N_2O_2$, 3 304.2, found [M+H] 305.2, $T_r$=1.67 min. (Method AY).

Chiral separation of Racemate 41D (Method BU) gave Enantiomer 1 and Enantiomer 2 as single enantiomers. 41D Enantiomer 1, $T_r$=4.25 min (Method BU) and 41D Enantiomer 2, $T_r$=5.4 min (Method BU).

41D Enantiomer 1 (yellow liquid, 350 mg, 1.138 mmol, 21% yield): LC-MS Anal. Calc'd. for $C_{18}H_{28}N_2O_2$, 304.2, found [M+H] 305.2. $T_r$=3.54 min (Method BE).

41D Enantiomer 2 (yellow liquid, 350 mg, 1.138 mmol, 21% yield): LC-MS Anal. Calc'd. for $C_{18}H_{28}N_2O_2$, 304.2, found [M+H] 305.2. $T_r$=3.53 min (Method BE).

41E. Methyl 3-(3-((4-cyanophenyl)amino)-4-(4-methylpiperidin-1-yl)phenyl)pentanoate The mixture of 41D Enantiomer 1 (0.050 g, 0.164 mmol), 4-bromobenzonitrile (0.036 g, 0.197 mmol), 4,5-bis(diphenylphosphino)-9,9-dimethylxanthene (9.50 mg, 0.016 mmol) and Cs$_2$CO$_3$ (0.080 g, 0.246 mmol) in 1,4-dioxane (1.5 mL) was stirred. Argon gas was bubbled through the mixture for 5 min. Bis(dibenzylideneacetone)palladium (4.72 mg, 8.21 μmol) was added and argon gas was bubbled through the mixture for 5 min. The reaction mixture was sealed and placed in preheated oil bath at 110° C. for 4 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography (conditions: 50% ethyl acetate in pet ether) to afford 41E (yellow liquid, 50 mg, 0.112 mmol, 68% yield). LC-MS Anal. Calc'd. for C$_{25}$H$_{31}$N$_3$O$_2$, 405.2, found [M+H] 406.5, T$_r$=1.85 min. (Method AY).

Example 41 Enantiomer 1. 3-(3-((4-Cyanophenyl)amino)-4-(4-methylpiperidin-1-yl)phenyl)pentanoic acid To a stirred solution of 41E in mixture of tetrahydrofuran (1 mL), methanol (1 mL) and water (0.1 mL) was added LiOH.H$_2$O (0.021 g, 0.493 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 41 Enantiomer 1 (16.7 mg, 0.036 mmol, 35% yield). LC-MS Anal. Calc'd. for C$_{24}$H$_{29}$N$_3$O$_2$, 391.2, found [M+H] 392.3. T$_r$=1.97 min. (Method O). $^1$H NMR (400 MHz, DMSO-d$_6$) δ 7.94-8.06 (s, 1H), 7.47-7.58 (m, 2H), 6.98 (m, 5H), 3.17 (s, 1H), 3.04 (m, 4H), 2.81 (m, 1H), 2.28-2.42 (m, 1H), 1.46-1.68 (m, 5H), 1.17-1.34 (m, 2H), 0.88 (m, 3H), 0.73 (t, J=7.2 Hz, 3H).

Example 41 Enantiomer 2. 3-(3-((4-Cyanophenyl)amino)-4-(4-methylpiperidin-1-yl)phenyl)pentanoic acid Example 41 Enantiomer 2 was prepared from 41D Enantiomer 2 following the procedure described for the synthesis of Example 41 Enantiomer 1. LC-MS Anal. Calc'd. for C$_{24}$H$_{29}$N$_3$O$_2$, 391.2, found [M+H] 392.3. T$_r$=1.98 min. (Method O). $^1$H NMR (400 MHz, DMSO-d$_6$) δ 8.00 (s, 1H), 7.46-7.59 (m, 2H), 6.85-7.09 (m, 5H), 3.17 (s, 1H), 3.04 (m, 4H), 2.81 (m, 1H), 2.37-2.46 (m, 1H), 1.46-1.68 (m, 5H), 1.10-1.24 (m, 2H), 0.88 (m, 3H), 0.73 (t, J=7.2 Hz, 3H).

Examples 42 and 43

Enantiomer 1

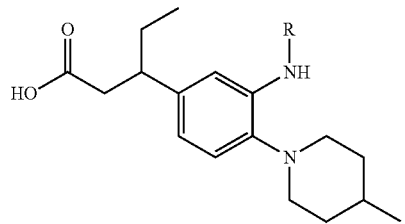

Examples 42 and 43 was prepared from 41D Enantiomer 1 and corresponding halides following the procedure described for the synthesis of Example 41 Enantiomer 1.

| Ex. No. | Name | R | T$_r$ (min) | [M + H]$^+$ |
|---|---|---|---|---|
| 42 | 3-(3-((2-methoxypyrimidin-5-yl)amino)-4-(4-methylpiperidin-1-yl)phenyl)pentanoic acid | | 1.68 (Method O) | 399.3 |
| 43 | 3-(3-((2-ethoxypyrimidin-5-yl)amino)-4-(4-methylpiperidin-1-yl)phenyl)pentanoic acid | | 1.42 (Method R) | 413.3 |

Examples 44 and 45

Enantiomer 2

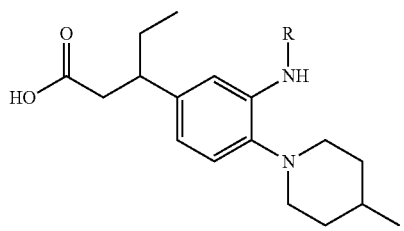

Examples 44 and 45 was prepared from 41D Enantiomer 2 and corresponding halides following the procedure described for the synthesis of Example 41 Enantiomer 1.

| Ex. No. | Name | R | $T_r$ (min) Method R | $[M + H]^+$ |
|---|---|---|---|---|
| 44 | 3-(3-((2-methoxypyrimidin-5-yl)amino)-4-(4-methylpiperidin-1-yl)phenyl)pentanoic acid | | 1.95 | 399.1 |
| 45 | 3-(3-((2-ethoxypyrimidin-5-yl)amino)-4-(4-methylpiperidin-1-yl)phenyl)pentanoic acid | | 1.41 | 413.3 |

Example 46

Enantiomer 1 and Enantiomer 2

3-(4-(4-Methylpiperidin-1-yl)-3-(3-(p-tolyl)ureido)phenyl)pentanoic acid

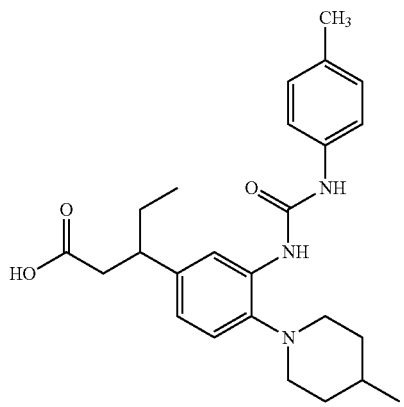 [SMILES: CCC(CC(=O)O)c1ccc(N2CCC(C)CC2)c(NC(=O)Nc2ccc(C)cc2)c1]

46A. Methyl 3-(4-(4-methylpiperidin-1-yl)-3-(3-(p-tolyl)ureido)phenyl)pentanoate To a stirred solution of 41D Enantiomer 1 (0.035 g, 0.115 mmol) in tetrahydrofuran (1.5 mL) was added 1-isocyanato-4-methylbenzene (0.018 g, 0.138 mmol). The reaction mixture was stirred at room temperature for 12 h. LCMS indicated completion of reaction. The reaction mixture was concentrated under reduced pressure to get compound 46A (yellow liquid, 50 mg, 0.075 mmol, 65% yield). LC-MS Anal. Calc'd. for $C_{26}H_{35}N_3O_3$, 437.2, found [M+H] 438.5. $T_r$=1.76 min. (Method AY).

Example 46 Enantiomer 1. 3-(4-(4-Methylpiperidin-1-yl)-3-(3-(p-tolyl)ureido)phenyl)pentanoic acid To a stirred solution of 46A (0.050 g, 0.114 mmol) in mixture of tetrahydrofuran (1 mL), methanol (1 mL) and water (0.1 mL) was added LiOH.H$_2$O (0.019 g, 0.457 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 46 Enantiomer 1 (13.3 mg, 0.031 mmol, 27% yield). LC-MS Anal. Calc'd. for $C_{25}H_{33}N_3O_3$, 423.3, found [M+H] 424.3. $T_r$=2.24 min. (Method O). $^1$H NMR (400 MHz, DMSO-d$_6$) δ 9.41 (s, 1H), 7.87-8.04 (m, 2H), 7.37 (m, 2H), 7.01-7.18 (m, 3H), 6.67-6.85 (m, 1H), 2.87-2.96 (m, 3H), 2.56-2.64 (m, 2H), 2.36-2.45 (m, 1H), 2.14-2.29 (m, 4H), 1.58-1.77 (m, 3H), 1.36-1.54 (m, 4H), 0.99 (m, 3H), 0.73 (t, J=7.2 Hz, 3H).

Example 46 Enantiomer 2. 3-(4-(4-Methylpiperidin-1-yl)-3-(3-(p-tolyl)ureido)phenyl)pentanoic acid Example 46 Enantiomer 2 was prepared following the same procedure for Example 46 Enantiomer 1 by utilizing 41D Enantiomer 2. LC-MS Anal. Calc'd. for $C_{25}H_{33}N_3O_3$, 423.2, found [M+H] 424.3. $T_r$=2.15 min. (Method O). $^1$H NMR (400 MHz, DMSO-d$_6$) δ 9.41 (s, 1H), 7.84-8.04 (m, 2H), 7.31-7.46 (m, 2H), 6.98-7.17 (m, 3H), 6.77 (m, 1H), 2.75-2.96 (m, 3H), 2.54-2.67 (m, 2H), 2.35-2.45 (m, 1H), 2.19-2.30 (m, 4H), 1.56-1.77 (m, 3H), 1.34-1.53 (m, 4H), 0.99 (m, 3H), 0.73 (t, J=7.2 Hz, 3H).

Example 47 Enantiomer 1 and Enantiomer 2

3-(3-((2-Ethoxypyrimidin-5-yl)amino)-4-(4-phenylpiperidin-1-yl)phenyl)pentanoic acid

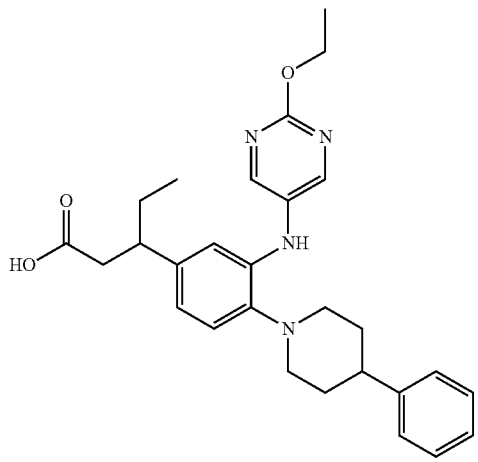 [SMILES: CCOc1ncc(Nc2cc(C(CC)CC(=O)O)ccc2N2CCC(c3ccccc3)CC2)cn1]

47A. Methyl 3-(3-nitro-4-(4-phenylpiperidin-1-yl)phenyl)pentanoate

Compound 47A was prepared from 41B and 4-phenylpiperidine following the procedure described for the synthesis of 41C. LC-MS Anal. Calc'd. for C$_{23}$H$_{28}$N$_2$O$_4$, 396.2, found [M+H] 397.4, $T_r$=1.73 min. (Method AY).

47B. Methyl 3-(3-amino-4-(4-phenylpiperidin-1-yl)phenyl)pentanoate

Compound 47B was prepared from 47A following the procedure described for the synthesis of 41D. LC-MS Anal. Calc'd. for C$_{23}$H$_{30}$N$_2$O$_2$, 366.2, found [M+H] 367.2, $T_r$=1.72 min (Method AY).

47C. Methyl 3-(3-((2-ethoxypyrimidin-5-yl)amino)-4-(4-phenylpiperidin-1-yl)phenyl)pentanoate Compound 47C was prepared from 47B following the procedure described for the synthesis of 41E. LC-MS Anal. Calc'd. for C$_{29}$H$_{36}$N$_4$O$_3$, 488.3, found [M+H] 489.5, $T_r$=1.83 min (Method AY).

Racemate Example 47. 3-(3-((2-Ethoxypyrimidin-5-yl)amino)-4-(4-phenylpiperidin-1-yl)phenyl)pentanoic acid Racemate Example 47 was prepared from 47C following the procedure described for the synthesis of Example 41 Enantiomer 1. LC-MS Anal. Calc'd. for C$_{28}$H$_{34}$N$_4$O$_3$, 474.3, found [M+H] 475.5, $T_r$=1.40 min (Method AY).

Chiral separation of Racemic Example 47 (Method BF) gave Enantiomer 1 and Enantiomer 2 as single enantiomers. Enantiomer 1, $T_r$=5.22 min and Enantiomer 2, $T_r$=6.76 min (Method BF).

Example 47 Enantiomer 1: LC-MS Anal. Calc'd. for C$_{28}$H$_{34}$N$_4$O$_3$, 474.3, found [M+H] 475.4, $T_r$=1.98 min (Method O). $^1$H NMR (400 MHz, DMSO-d$_6$) δ 8.25 (s, 2H), 7.45 (s, 1H), 7.25-7.33 (m, 2H), 7.14-7.23 (m, 3H), 7.01 (m, 1H), 6.83 (m, 1H), 6.75 (m, 1H), 4.30 (q, J=7.2 Hz, 2H), 3.12-3.26 (m, 3H), 2.73-2.85 (m, 1H), 2.61-2.71 (m, 2H), 2.37-2.46 (m, 2H), 1.65-1.80 (m, 2H), 1.42-1.62 (m, 4H), 1.34 (m, 3H), 0.61-0.77 (t, J=7.2 Hz, 3H).

Example 47 Enantiomer 2: LC-MS Anal. Calc'd. for C$_{28}$H$_{34}$N$_4$O$_3$, 474.3, found [M+H] 475.4, $T_r$=1.98 min (Method O). $^1$H NMR (400 MHz, DMSO-d$_6$) δ 8.25 (s, 2H), 7.45 (s, 1H), 7.27-7.28 (m, 2H), 7.17-7.20 (m, 3H), 7.01 (m, 1H), 6.82 (m, 1H), 6.75 (m, 1H), 4.32 (q, J=7.2 Hz, 2H), 3.12-3.26 (m, 3H), 2.79-2.85 (m, 1H), 2.61-2.71 (m, 2H), 2.37-2.46 (m, 2H), 1.65-1.80 (m, 2H), 1.56-1.62 (m, 4H), 1.34 (m, 3H), 0.72 (t, J=7.2 Hz, 3H).

Example 48

Enantiomer 1 and Enantiomer 2

3-(3-((4-Chlorophenyl)amino)-4-(cyclohexyl(2-hydroxy-2-methylpropyl)amino)phenyl)butanoic acid

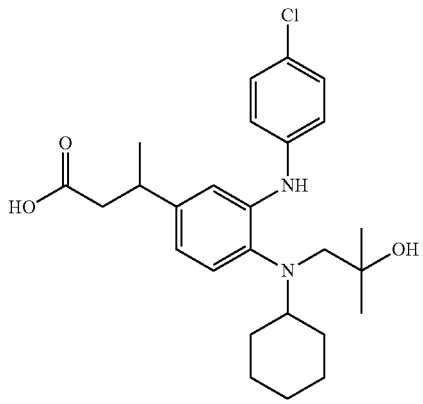 [SMILES: CC(CC(=O)O)c1ccc(N(CC(C)(C)O)C2CCCCC2)c(Nc2ccc(Cl)cc2)c1]

48A. 1-(Cyclohexylamino)-2-methylpropan-2-ol

To a stirred solution of cyclohexanone (10.0 g, 102 mmol), 1-amino-2-methylpropan-2-ol (9.08 g, 102 mmol) in dry THF (100 mL), MeOH (100 mL), were added 3.0 g molecular sieves under nitrogen atmosphere. Reaction mixture was stirred at room temperature for 16 h. Reaction cooled to 0° C. and added NaBH$_4$ (11.56 g, 306 mmol) portionwise in 60 minutes. Reaction mixture was stirred at room temperature for 3 h. Reaction mixture was quenched with water (20 mL) at 0° C. Concentrated under reduced pressure to remove methanol completely to get semi-solid and it was quenched with 10% sodium bicarbonate (100 mL). Aqueous layer extracted with ethyl acetate (2×100 mL). Organic layer separated and washed with brine (50 mL). Organic layer dried over sodium sulfate, concentrated under reduced pressure to get liquid compound. Purification via flash chromatography gave 48A (light yellow liquid, 13.5 g, 102 mmol, 78% yield). $^1$H NMR (400 MHz, DMSO-d$_6$) δ 4.10 (br. s., 1H), 2.40 (s, 2H), 2.33-2.30 (m, 1H), 1.90-1.20 (m, 11H), 1.16 (s, 6H).

48B. 1-((4-Bromo-2-nitrophenyl)(cyclohexyl)amino)-2-methylpropan-2-ol

To a stirred solution of NaH (2.182 g, 54.5 mmol) in dry DMF (60.0 mL), 48A (12.46 g, 72.7 mmol) was added at 0° C. and maintained for 30 minutes at same temperature. 4-Bromo-1-fluoro-2-nitrobenzene (8.0 g, 36.4 mmol) was added at 0° C. Reaction stirred at room temperature for 4 h. Reaction mixture cooled to 0° C. and quenched with 3 mL water and stirred for 10 minutes at room temperature. Reaction mixture was diluted with ethyl acetate (20 mL) washed with water (10 mL), organic layer separated and aqueous layer extracted with ethyl acetate (2×20 mL). Organic layer combined together dried over sodium sulfate, concentrated under reduced pressure to get orange liquid. Purification via flash chromatography gave 48B (orange liquid, 0.7 g, 1.65 mmol, 93% yield). LC-MS Anal. Calc'd. for $C_{16}H_{23}BrN_2O_3$, 370.2, found [M+2] 372.2, $T_r$=3.58 min (Method N).

48C. 1-(Cyclohexyl(2-nitro-4-(4,4,5,5-tetramethyl-1,3,2-dioxaborolan-2-yl)phenyl)amino)-2-methylpropan-2-ol To a stirred solution of 48B (5.0 g, 13.47 mmol), 4,4,4',4',5,5,5',5'-octamethyl-2,2'-bi(1,3,2-dioxaborolane) (4.10 g, 16.16 mmol), potassium acetate (3.97 g, 40.4 mmol) in dry DMSO (50.0 mL) purged argon for 10 minutes added PdCl$_2$(dppf).CH$_2$Cl$_2$ Adduct (0.550 g, 0.673 mmol). Reaction placed on preheated oil bath at 80° C. and maintained for 2 h. Reaction mixture cooled to room temperature, diluted with ethyl acetate (50 mL) washed with water (25 mL) and organic layer separated, aqueous layer back extracted with ethyl acetate (2×50 mL). Organic layers mixed together dried over sodium sulfate, concentrated completely to get brown liquid. Purification via flash chromatography gave 48C (orange semi-solid, 4.5 g, 10.76 mmol, 80% yield). LC-MS Anal. Calc'd. for $C_{22}H_{35}BN_2O_5$, 418.2, found [M+H] 419.2, $T_r$=4.00 min (Method N).

48D. Methyl 3-(4-(cyclohexyl(2-hydroxy-2-methylpropyl)amino)-3-nitrophenyl)butanoate Compound 48D was prepared from methyl crotonate following the procedure described for the synthesis of 33D. LC-MS Anal. Calc'd. for $C_{21}H_{32}N_2O_5$, 392.2, found [M+H] 393.4, $T_r$=3.66 min (Method N).

48E. Methyl 3-(3-amino-4-(cyclohexyl(2-hydroxy-2-methylpropyl)amino)phenyl)butanoate The solution of 48D (1.8 g, 4.59 mmol) in ethyl acetate (30 mL) was charged to a sealable hydrogen flask. The solution was sequentially evacuated and purged with nitrogen gas. To this 10% Pd on carbon (0.332 g, 0.312 mmol) was added under nitrogen atmosphere. The reaction mixture was stirred under hydrogen atmosphere (40 psi). The reaction mixture was stirred at room temperature for 4 h. The reaction mixture was filtered through a CELITE® pad and the residue on the pad was thoroughly rinsed with ethyl acetate (3×15 mL). The combined filtrate was concentrated under reduced pressure to get crude compound Racemate 48E (yellow solid, 1.4 g). LC-MS Anal. Calc'd. for $C_{21}H_{34}N_2O_3$, 362.2, found [M+H] 363.3, $T_r$=3.06 min (Method N).

Chiral separation of Racemate 48E (Method AE) to get Enantiomer 1 and Enantiomer 2 as single enantiomers (Method AE) Enantiomer 1, $T_r$=3.15 min and Enantiomer 2, $T_r$=5.12 min (Method AE).

48E Enantiomer 1 (yellow liquid, 450 mg, 1.241 mmol, 26% yield): LC-MS Anal. Calc'd. for $C_{21}H_{34}N_2O_3$, 362.2, found [M+H] 363.2. $T_r$=3.18 min (Method BO).

48E Enantiomer 2 (yellow liquid, 450 mg, 1.241 mmol, 26% yield): LC-MS Anal. Calc'd. for $C_{21}H_{34}N_2O_3$, 362.2, found [M+H] 363.5. $T_r$=3.81 min (Method U).

48F. Methyl 3-(3-((4-chlorophenyl)amino)-4-(cyclohexyl(2-hydroxy-2-methylpropyl)amino)phenyl)butanoate The mixture of 48E Enantiomer 1 (0.050 g, 0.138 mmol), 1-bromo-4-chlorobenzene (0.032 g, 0.166 mmol), 4,5-bis(diphenylphosphino)-9,9-dimethylxanthene (0.040 g, 0.069 mmol) and Cs$_2$CO$_3$ (0.135 g, 0.414 mmol) in 1,4-dioxane (1.5 mL) was stirred. Argon gas was bubbled through the mixture for 5 min. Bis(dibenzylideneacetone)palladium (7.93 mg, 0.014 mmol) was added and argon gas was bubbled through the mixture for 5 min. The reaction mixture was sealed and placed in preheated oil bath at 110° C. for 12 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography gave 48F (yellow liquid, 50 mg, 0.037 mmol, 26% yield). LC-MS Anal. Calc'd. for $C_{27}H_{37}ClN_2O_3$, 472.2, found [M+H] 473.5, $T_r$=2.03 min. (Method AY).

Example 48 Enantiomer 1. 3-(3-((4-Chlorophenyl)amino)-4-(cyclohexyl(2-hydroxy-2-methylpropyl)amino)phenyl)butanoic acid To a stirred solution of 48F (0.050 g, 0.106 mmol) in mixture of tetrahydrofuran (1 mL), methanol (1 mL) and water (0.1 mL) was added LiOH.H$_2$O (0.018 g, 0.423 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS gave Example 48 Enantiomer 1 (20.6 mg, 0.045 mmol, 42% yield). LC-MS Anal. Calc'd. for $C_{26}H_{35}ClN_2O_3$, 458.2, found [M+H] 459.3, $T_r$=2.24 min. (Method O). $^1$H NMR (400 MHz, DMSO-d$_6$) δ 7.48 (s, 1H), 7.22-7.31 (m, 2H), 7.02-7.17 (m, 4H), 6.73 (m, 1H), 3.05 (m, 2H), 2.95 (br. s., 2H), 2.31-2.46 (m, 3H), 1.76-1.89 (m, 2H), 1.61 (m, 2H), 1.42 (m, 1H), 1.08-1.22 (m, 5H), 0.91 (m, 9H).

Example 48 Enantiomer 2. 3-(3-((4-Chlorophenyl)amino)-4-(cyclohexyl(2-hydroxy-2-methylpropyl)amino)phenyl)butanoic acid Example 48 Enantiomer 2 was prepared from 48E Enantiomer 2 following the procedure described for the synthesis of Example 48 Enantiomer 1. LC-MS Anal. Calc'd. for $C_{26}H_{35}ClN_2O_3$, 458.2, found [M+H] 459.2, $T_r$=2.24 min (Method O). $^1$H NMR (400 MHz, DMSO-d$_6$) δ 7.48 (s, 1H), 7.26 (m, 2H), 7.10-7.17 (m, 3H), 7.01-7.09 (m, 1H), 6.73 (m, 1H), 3.05-3.18 (m, 2H), 2.95 (m, 2H), 2.49

(m, 3H), 1.97-2.10 (m, 2H), 1.62 (m, 2H), 1.43 (m, 1H), 1.06-1.26 (m, 5H), 0.90 (m, 9H).

Examples 49 to 52

Enantiomer 1

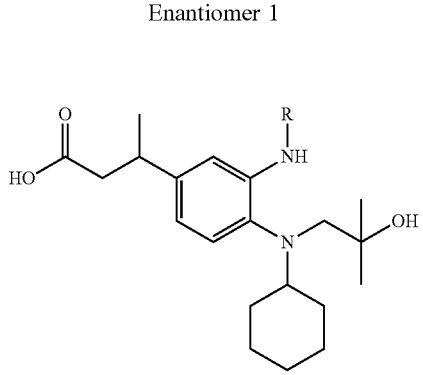

Examples 49 to 52 was prepared from 48E Enantiomer 1 and corresponding halides following the procedure described for the synthesis of Example 48 Enantiomer 1.

Examples 53 to 56

Enantiomer 2

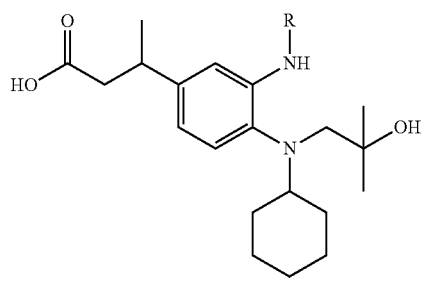

Examples 53 to 56 was prepared from 48E Enantiomer 2 and corresponding halides following the procedure described for the synthesis of Example 48 Enantiomer 1.

| Ex. No. | Name | R | $T_r$ (min) Method O | $[M + H]^+$ |
|---|---|---|---|---|
| 49 | 3-(4-(cyclohexyl(2-hydroxy-2-methylpropyl)amino)-3-((2,2-difluorobenzo[d][1,3]dioxol-5-yl)amino)phenyl)butanoic acid | | 2.32 | 505.3 |
| 50 | 3-(4-(cyclohexyl(2-hydroxy-2-methylpropyl)amino)-3-((2-ethoxypyrimidin-5-yl)amino)phenyl)butanoic acid | | 1.81 | 471.3 |
| 51 | 3-(3-((4-chloro-3-(2,2,2-trifluoroethoxy)phenyl)amino)-4-(cyclohexyl(2-hydroxy-2-methylpropyl)amino)phenyl)butanoic acid | | 2.40 | 557.3 |
| 52 | 3-(4-(cyclohexyl(2-hydroxy-2-methylpropyl)amino)-3-((4-ethoxy-2-fluorophenyl)amino)phenyl)butanoic acid | | 2.23 | 487.3 |

| Ex. No. | Name | R | T_r (min) Method O | [M + H]+ |
|---|---|---|---|---|
| 53 | 3-(4-(cyclohexyl(2-hydroxy-2-methylpropyl)amino)-3-((2,2-difluorobenzo[d][1,3]dioxol-5-yl)amino)phenyl)butanoic acid | | 2.35 | 505.3 |
| 54 | 3-(4-(cyclohexyl(2-hydroxy-2-methylpropyl)amino)-3-((2-ethoxypyrimidin-5-yl)amino)phenyl)butanoic acid | | 1.79 | 471.3 |
| 55 | 3-(3-((4-chloro-3-(2,2,2-trifluoroethoxy)phenyl)amino)-4-(cyclohexyl(2-hydroxy-2-methylpropyl)amino)phenyl)butanoic acid | | 2.42 | 557.2 |
| 56 | 3-(4-(cyclohexyl(2-hydroxy-2-methylpropyl)amino)-3-((4-ethoxy-2-fluorophenyl)amino)phenyl)butanoic acid | | 2.28 | 487.3 |

Example 59

Diastereomer 1 and Diastereomer 2

3-(3-((4-Chlorophenyl)amino)-4-(ethyl(tetrahydro-2H-pyran-3-yl)amino)phenyl)pentanoic acid

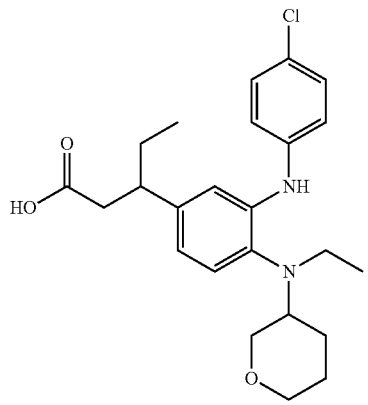 [SMILES: CCC(CC(=O)O)c1ccc(N(CC)C2CCCOC2)c(Nc2ccc(Cl)cc2)c1]

59A. N-Ethyltetrahydro-2H-pyran-3-amine

To a stirred solution of dihydro-2H-pyran-3(4H)-one (10 g, 100 mmol) in tetrahydrofuran (100 mL), methanol (100 mL) under nitrogen atmosphere was added ethanamine (2M in THF) (49.9 mL, 100 mmol), followed by 4 Å molecular sieves (4 g). The reaction mixture was stirred for 12 h at room temperature. To this was added NaBH$_4$ (11.34 g, 300 mmol) portionwise at 0° C. and the reaction mixture was stirred at room temperature for 3 h. Reaction mixture was quenched with water (10 mL) and concentrated under reduced pressure to get semi-solid which was quenched with 10% sodium bicarbonate (500 mL). It was extracted with ethyl acetate (2×200 mL), washed with brine (100 mL). Organic layer was dried over anhydrous sodium sulfate, concentrated under reduced pressure to get 59A (yellow liquid, 11 g, 85 mmol, 85% yield). $^1$H NMR (400 MHz, DMSO-d$_6$) δ 3.74-3.65 (m, 4H), 2.70 (m, 1H), 2.67 (m, 2H), 1.98-1.57 (m, 4H), 1.02 (t, J=7.2 Hz 3H).

59B. N-(4-Bromo-2-nitrophenyl)-N-ethyltetrahydro-2H-pyran-3-amine

In a sealed tube 4-bromo-1-fluoro-2-nitrobenzene (4 g, 18.18 mmol) was added 59A (3.52 g, 27.3 mmol). The reaction mixture was heated at 135° C. for 12 h. LCMS indicated completion of reaction. Purification via flash chromatography gave 59B (yellow liquid, 3.5 g, 10.63 mmol, 58% yield). LC-MS Anal. Calc'd. $C_{13}H_{17}BrN_2O_3$, 328.0, found [M+H] 329.2. $T_r$=3.10 min. (Method U).

59C. 4-Bromo-N1-ethyl-N1-(tetrahydro-2H-pyran-3-yl)benzene-1,2-diamine

To a stirred solution of 59B (6.8 g, 20.66 mmol) in acetic acid (68 mL) under nitrogen atmosphere at 0° C. was added iron (4.61 g, 83 mmol). The reaction mixture was stirred at room temperature for 12 h. LCMS indicated completion of reaction. Reaction mixture was concentrated under reduced pressure to get residue which was basified to pH~9 by using 10% sodium bicarbonate and it was extracted with ethyl acetate (4×50 mL). The combined organic layer was washed with brine (30 mL), dried over anhydrous sodium sulfate, concentrated under reduced pressure to get crude compound 59C (yellow solid, 5 g). LC-MS Anal. Calc'd. for $C_{13}H_{19}BrN_2O$, 298.06, found [M+2] 301.3. $T_r$=1.46 min (Method AY).

Chiral separation of Racemate 59C gave Enantiomer 1 and Enantiomer 2 as single enantiomers (Method AR). 59C Enantiomer 1, $T_r$=4.27 min and 59C Enantiomer 2, $T_r$=5.33 min (Method AR).

59C Enantiomer 1 (yellow liquid, 2 g, 6.68 mmol, 32% yield): LC-MS Anal. Calc'd. for $C_{13}H_{19}BrN_2O$, 298.06, found [M+H] 299.2, $T_r$=2.874 min (Method U).

59C Enantiomer 2 (yellow liquid, 1.5 g, 5.01 mmol, 24% yield): LC-MS Anal. Calc'd. for $C_{13}H_{19}BrN_2O$, 298.06, found [M+H] 299.2, $T_r$=2.876 min (Method U).

59D. N1-Ethyl-N1-(tetrahydro-2H-pyran-3-yl)-4-(4,4,5,5-tetramethyl-1,3,2-dioxaborolan-2-yl)benzene-1,2-diamine To a stirred solution of 59C Enantiomer 1 (1.9 g, 6.35 mmol), bis(pinacolato)diboron (2.419 g, 9.53 mmol) and potassium acetate (1.870 g, 19.05 mmol) in 1,4-dioxane (19 mL) was purged with argon for 10 min. To this $PdCl_2$(dppf).$CH_2Cl_2$ Adduct (0.259 g, 0.318 mmol) was added and purged with argon for 5 min. The reaction mixture was heated at 90° C. for 5 h. LCMS indicated completion of reaction. Reaction mixture was cooled to room temperature and quenched with water (30 mL). Aqueous layer was extracted with ethyl acetate (3×30 mL). The combined organic layer was washed with brine (20 mL), dried over anhydrous sodium sulfate, concentrated under reduced pressure to get crude compound. Purification via flash chromatography gave 59D (yellow liquid, 2.0 g, 5.78 mmol, 91% yield). LC-MS Anal. Calc'd. for $C_{19}H_{31}BN_2O_3$, 346.2, found [M+H] 347.6, $T_r$=1.56 min. (Method AY).

59E. Methyl 3-(3-amino-4-(ethyl(tetrahydro-2H-pyran-3-yl)amino)phenyl)pentanoate In a pressure tube equipped with Teflon cap, compound 59D (1 g, 2.89 mmol), 1,4-dioxane (10 mL) were added followed by (E)-methyl pent-2-enoate (0.989 g, 8.66 mmol), (S)-(−)-2,2'-bis(diphenylphosphino)-1,1'-binaphthyl (0.036 g, 0.058 mmol) and 1M solution of sodium hydroxide (2.60 mL, 2.60 mmol). Argon gas was bubbled through the mixture for 10 min and chloro(1,5-cyclooctadiene)rhodium (I) dimer (0.014 g, 0.029 mmol) was added at room temperature. Argon gas was bubbled through the mixture for 5 min. The tube was then screw-capped and heated at 50° C. for 2 h. The reaction mixture was cooled to room temperature, quenched with acetic acid (0.165 mL) and was stirred for 5 minutes before it was diluted with water (15 mL). The aqueous layer was extracted with ethyl acetate (3×20 mL). Combined organic layer was washed with water (15 mL), brine (15 mL), dried over anhydrous sodium sulfate and concentrated under reduced pressure to afford a residue. The residue was purified via flash silica gel column chromatography to afford 59E (yellow solid, 800 mg). LC-MS Anal. Calc'd. for $C_{19}H_{30}N_2O_3$, 334.2, found [M+H] 335.8, $T_r$=1.48 min (Method AY).

Chiral separation of 59E (Method BY) gave 59E Diastereomer 1 $T_r$=2.78 min (Method BY) and 59E Diastereomer 2 $T_r$=3.51 min (Method BY)

59E Diastereomer 1 (yellow liquid, 240 mg): LC-MS Anal. Calc'd. for $C_{19}H_{30}N_2O_3$, 334.2, found [M+H] 335.2, $T_r$=3.26 min (Method U).

59E Diastereomer 2 (yellow liquid, 265 mg): LC-MS Anal. Calc'd. for $C_{19}H_{30}N_2O_3$, 334.2, found [M+2] 335.2, $T_r$=3.26 min (Method U).

59F. Methyl 3-(3-((4-chlorophenyl)amino)-4-(ethyl(tetrahydro-2H-pyran-3-yl)amino)phenyl)pentanoate The mixture of 59E Diastereomer 1 (0.050 g, 0.149 mmol), 1-bromo-4-chlorobenzene (0.034 g, 0.179 mmol), 4,5-bis(diphenylphosphino)-9,9-dimethylxanthene (0.043 g, 0.075 mmol) and $Cs_2CO_3$ (0.146 g, 0.448 mmol) in 1,4-dioxane (2 mL) was stirred. Argon gas was bubbled through the mixture for 5 min. Bis(dibenzylideneacetone)palladium (8.60 mg, 0.015 mmol) was added and argon gas was bubbled through the mixture for 5 min. The reaction mixture was sealed and placed in preheated oil bath at 110° C. for 12 h. The reaction mixture was cooled to room temperature and concentrated under reduced pressure to afford a residue. The residue was reconstituted in a mixture of ethyl acetate (15 mL) and water (15 mL). The combined organic layer was washed with water (10 mL), brine (10 mL), dried over anhydrous sodium sulfate and concentrated under reduced pressure to afford a residue. The residue was purified via flash silica gel column chromatography to afford 59F (yellow liquid, 60 mg, 0.082 mmol, 55% yield). LC-MS Anal. Calc'd. for $C_{25}H_{33}ClN_2O_3$, 444.2, found [M+H] 445.5, $T_r$=2.06 min. (Method AY).

Example 59. Diastereomer 1. 3-(3-((4-Chlorophenyl)amino)-4-(ethyl(tetrahydro-2H-pyran-3-yl)amino)phenyl)pentanoic acid To a stirred solution of 59F (0.060 g, 0.135 mmol) in mixture of tetrahydrofuran (1 mL), methanol (1 mL) and water (0.2 mL) was added $LiOH.H_2O$ (0.023 g, 0.539 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 59 Diastereomer 1 (16.3 mg, 0.037 mmol, 27% yield). LC-MS Anal. Calc'd. for $C_{24}H_{31}ClN_2O_3$, 430.2, found [M+H] 431.2, $T_r$=2.33 min. (Method O). $^1$H NMR (400 MHz, DMSO-$d_6$) δ 7.36 (s, 1H), 7.22-7.29 (m, 2H), 7.09-7.16 (m, 3H), 7.03 (m, 1H), 6.68-6.78 (m, 1H), 3.79 (m, 1H), 3.60-3.69 (m, 3H), 3.10-3.21 (m, 2H), 2.92-3.03

(m, 1H), 2.81 (m, 1H), 2.38-2.47 (m, 2H), 1.54-1.70 (m, 4H), 1.33-1.47 (m, 2H), 0.79 (t, J=7.2 Hz, 3H), 0.73 (t, J=7.2 Hz, 3H).

Example 59. Diastereomer 2. 3-(3-((4-Chlorophenyl)amino)-4-(ethyl(tetrahydro-2H-pyran-3-yl)amino)phenyl)pentanoic acid Example 59 Diastereomer 2 was prepared from 59E Diastereomer 2 following the procedure described for the synthesis of Example 59 Diastereomer 1. LC-MS Anal. Calc'd. for $C_{24}H_{31}ClN_2O_3$, 430.2, found [M+H] 431.2, $T_r$=2.32 min. (Method O). $^1$H NMR (400 MHz, DMSO-$d_6$) δ 7.36 (s, 1H), 7.21-7.29 (m, 2H), 7.08-7.17 (m, 3H), 7.03 (m, 1H), 6.74 (m, 1H), 3.79 (m, 1H), 3.59-3.71 (m, 3H), 3.09-3.22 (m, 2H), 2.93-3.03 (m, 1H), 2.77-2.90 (m, 1H), 2.38-2.48 (m, 2H), 1.55-1.67 (m, 4H), 1.45-1.54 (m, 2H), 0.79 (t, J=7.2 Hz, 3H), 0.73 (t, J=7.2 Hz, 3H).

Example 60

3-(3-((4-Chlorophenyl)amino)-4-(ethyl(tetrahydro-2H-pyran-3-yl)amino)phenyl)pentanoic acid (Diastereomer 3 and Diastereomer 4)

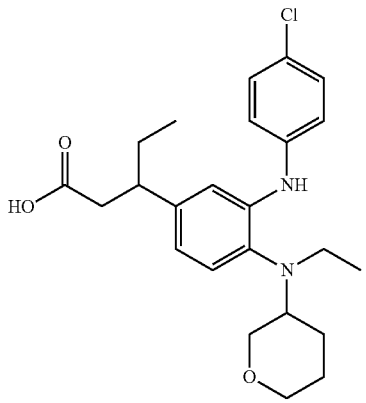 [SMILES: CCC(CC(=O)O)c1ccc(N(CC)C2CCCOC2)c(Nc2ccc(Cl)cc2)c1]

60A. N1-Ethyl-N1-(tetrahydro-2H-pyran-3-yl)-4-(4,4,5,5-tetramethyl-1,3,2-dioxaborolan-2-yl)benzene-1,2-diamine To a stirred solution of 59C Enantiomer 2 (1.9 g, 6.35 mmol), bis(pinacolato)diboron (2.419 g, 9.53 mmol) and potassium acetate (1.870 g, 19.05 mmol) in 1,4-dioxane (19 mL) was purged with argon for 10 min. To this PdCl$_2$(dppf).CH$_2$Cl$_2$ Adduct (0.259 g, 0.318 mmol) was added and purged with argon for 5 min. The reaction mixture was heated at 90° C. for 5 h. LCMS indicated completion of reaction. Reaction mixture was cooled to room temperature and quenched with water (30 mL). Aqueous layer was extracted with ethyl acetate (3×30 mL). The combined organic layer was washed with brine (20 mL), dried over anhydrous sodium sulfate, concentrated under reduced pressure to get crude compound. Purification via flash chromatography gave 60A (yellow liquid, 1.5 g, 4.33 mmol, 93% yield). LC-MS Anal. Calc'd. for $C_{19}H_{31}BN_2O_3$, 346.2, found [M+H] 347.6, $T_r$=1.56 min. (Method AY).

60B. Methyl 3-(3-amino-4-(ethyl(tetrahydro-2H-pyran-3-yl)amino)phenyl)pentanoate Compound 60B was prepared from 60A following the procedure described for the synthesis of 59E. LC-MS Anal. Calc'd. for $C_{19}H_{30}N_2O_3$, 334.2, found [M+H] 335.8, $T_r$=1.48 min (Method AY).
Chiral separation of 60B (Method DN) gave 60B Diastereomer 3 $T_r$=2.3 min (Method DN) and 60B Diastereomer 4 $T_r$=3.08 min (Method DN).
60B Diastereomer 3: LC-MS Anal. Calc'd. for $C_{19}H_{30}N_2O_3$, 334.2, found [M+H] 335.2, $T_r$=3.26 min (Method U).
60B Diastereomer 4: LC-MS Anal. Calc'd. for $C_{19}H_{30}N_2O_3$, 334.2, found [M+2] 335.2, $T_r$=3.42 min (Method U).

60C. Methyl 3-(3-((4-chlorophenyl)amino)-4-(ethyl(tetrahydro-2H-pyran-3-yl)amino)phenyl)pentanoate The mixture of 60B Diastereomer 3 (0.050 g, 0.149 mmol), 1-bromo-4-chlorobenzene (0.034 g, 0.179 mmol), 4,5-bis(diphenylphosphino)-9,9-dimethylxanthene (0.043 g, 0.075 mmol) and Cs$_2$CO$_3$ (0.146 g, 0.448 mmol) in 1,4-dioxane (2 mL) was stirred. Argon gas was bubbled through the mixture for 5 min. Bis(dibenzylideneacetone)palladium (8.60 mg, 0.015 mmol) was added and argon gas was bubbled through the mixture for 5 min. The reaction mixture was sealed and placed in preheated oil bath at 110° C. for 12 h. The reaction mixture was cooled to room temperature and concentrated under reduced pressure to afford a residue. The residue was reconstituted in a mixture of ethyl acetate (15 mL) and water (15 mL). The combined organic layer was washed with water (10 mL), brine (10 mL), dried over anhydrous sodium sulfate and concentrated under reduced pressure to afford a residue. The residue was purified via flash silica gel column chromatography to afford 60C (yellow liquid, 55 mg, 0.054 mmol, 36% yield). LC-MS Anal. Calc'd. for $C_{25}H_{33}ClN_2O_3$, 444.2, found [M+H] 445.4, $T_r$=2.08 min. (Method AY).

Example 60. Diastereomer 3. 3-(3-((4-Chlorophenyl)amino)-4-(ethyl(tetrahydro-2H-pyran-3-yl)amino)phenyl)pentanoic acid To a stirred solution of 60C (0.060 g, 0.135 mmol) in mixture of tetrahydrofuran (1 mL), methanol (1 mL) and water (0.2 mL) was added LiOH.H$_2$O (0.023 g, 0.539 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 60 Diastereomer 3 (15 mg, 0.033 mmol, 26% yield). LC-MS Anal. Calc'd. for $C_{24}H_{31}ClN_2O_3$, 430.2, found [M+H] 431.2, $T_r$=2.32 min. (Method O). $^1$H NMR (400 MHz, DMSO-$d_6$) δ 7.36 (s, 1H), 7.25 (m, 2H), 7.09-7.18 (m, 3H), 6.98-7.06 (m, 1H), 6.74 (m, 1H), 3.77-3.84 (m, 1H), 3.62-3.70 (m, 3H), 3.10-3.23 (m, 2H), 2.98 (m, 1H), 2.76-2.92 (m, 1H), 2.35-2.47 (m, 2H), 1.58-1.69 (m, 4H), 1.35-1.45 (m, 2H), 0.79 (t, J=7.2 Hz, 3H), 0.73 (t, J=7.2 Hz, 3H).

Example 60. Diastereomer 4. 3-(3-((4-Chlorophenyl)amino)-4-(ethyl(tetrahydro-2H-pyran-3-yl)amino)phenyl)pentanoic acid Example 60 Diastereomer 4 was prepared from 60B Diastereomer 4 following the procedure described for the synthesis of Example 60 Diastereomer 3. LC-MS Anal. Calc'd. for $C_{24}H_{31}ClN_2O_3$, 430.2, found [M+H] 431.2, $T_r$=2.24 min. (Method O). $^1$H NMR (400 MHz, DMSO-$d_6$) δ 7.35 (s, 1H), 7.24 (d, J=8.2 Hz, 2H), 7.00-7.17 (m, 4H), 6.67-6.88 (m, 1H), 3.79 (m, 1H), 3.60-3.69 (m, 3H), 3.10-3.21 (m, 2H), 2.92-3.03 (m, 1H), 2.81 (m, 1H), 2.38-2.47 (m, 2H), 1.54-1.70 (m, 4H), 1.33-1.47 (m, 2H), 0.79 (t, J=7.2 Hz, 3H), 0.73 (t, J=7.2 Hz, 3H).

Examples 61 to 63

Diastereomer 1

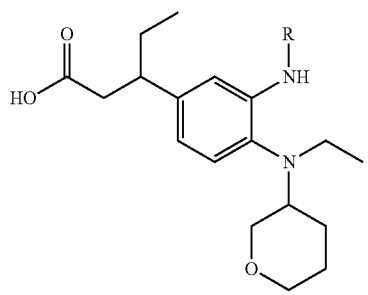

Examples 61 to 63 was prepared from 59E Diastereomer 1 and the corresponding halides following the procedure described for the synthesis of Example 59 Diastereomer 1.

| Ex. No. | Name | R | $T_r$ (min) Method O | [M + H]$^+$ |
|---|---|---|---|---|
| 61 | 3-(3-((4-cyanophenyl)amino)-4-(ethyl(tetrahydro-2H-pyran-3-yl)amino)phenyl)pentanoic acid |  | 1.96 | 422.2 |
| 62 | 3-(4-(ethyl(tetrahydro-2H-pyran-3-yl)amino)-3-((2-methoxypyrimidin-5-yl)amino)phenyl)pentanoic acid |  | 1.67 | 429.2 |
| 63 | 3-(3-((2-ethoxypyrimidin-5-yl)amino)-4-(ethyl(tetrahydro-2H-pyran-3-yl)amino)phenyl)pentanoic acid | 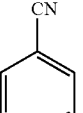 | 1.78 | 443.2 |

Examples 64 to 66

Diastereomer 2

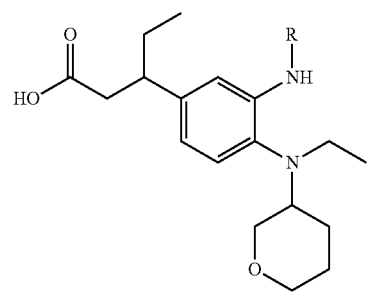

Examples 64 to 66 was prepared from 59E Diastereomer 2 and the corresponding halides following the procedure described for the synthesis of Example 59 Diastereomer 1.

| Ex. No. | Name | R | $T_r$ (min) Method O | [M + H]$^+$ |
|---|---|---|---|---|
| 64 | 3-(3-((4-cyanophenyl)amino)-4-(ethyl(tetrahydro-2H-pyran-3-yl)amino)phenyl)pentanoic acid | 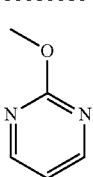 | 1.95 | 422.2 |
| 65 | 3-(4-(ethyl(tetrahydro-2H-pyran-3-yl)amino)-3-((2-methoxypyrimidin-5-yl)amino)phenyl)pentanoic acid | 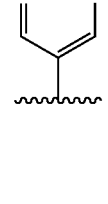 | 1.68 | 429.2 |
| 66 | 3-(3-((2-ethoxypyrimidin-5-yl)amino)-4-(ethyl(tetrahydro-2H-pyran-3-yl)amino)phenyl)pentanoic acid | 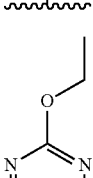 | 1.78 | 443.2 |

Examples 67 to 69

Diastereomer 3

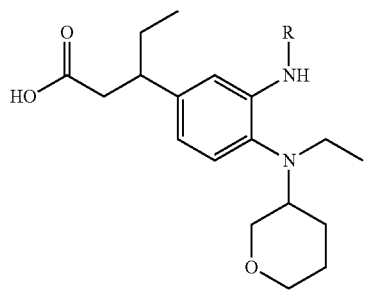

Examples 67 to 69 was prepared from 60B Diastereomer 3 and the corresponding halides following the procedure described for the synthesis of Example 60 Diastereomer 3.

| Ex. No. | Name | R | $T_r$ (min) Method O | $[M + H]^+$ |
|---|---|---|---|---|
| 67 | 3-(3-((4-cyanophenyl)amino)-4-(ethyl(tetrahydro-2H-pyran-3-yl)amino)phenyl)pentanoic acid | CN-C6H4- | 1.95 | 422.2 |
| 68 | 3-(4-(ethyl(tetrahydro-2H-pyran-3-yl)amino)-3-((2-methoxypyrimidin-5-yl)amino)phenyl)pentanoic acid | 2-methoxypyrimidin-5-yl | 1.69 | 429.2 |
| 69 | 3-(3-((2-ethoxypyrimidin-5-yl)amino)-4-(ethyl(tetrahydro-2H-pyran-3-yl)amino)phenyl)pentanoic acid | 2-ethoxypyrimidin-5-yl | 1.82 | 443.3 |

Examples 70 to 72

Diastereomer 4

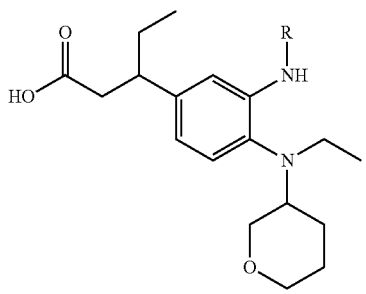

Examples 70 to 72 was prepared from 60B Diastereomer 4 and the corresponding halides following the procedure described for the synthesis of Example 60 Diastereomer 3.

| Ex. No. | Name | R | $T_r$ (min) Method O | $[M + H]^+$ |
|---|---|---|---|---|
| 70 | 3-(3-((4-cyanophenyl)amino)-4-(ethyl(tetrahydro-2H-pyran-3-yl)amino)phenyl)pentanoic acid | CN-C6H4- | 1.92 | 422.2 |
| 71 | 3-(4-(ethyl(tetrahydro-2H-pyran-3-yl)amino)-3-((2-methoxypyrimidin-5-yl)amino)phenyl)pentanoic acid | 2-methoxypyrimidin-5-yl | 1.62 | 429.3 |
| 72 | 3-(3-((2-ethoxypyrimidin-5-yl)amino)-4-(ethyl(tetrahydro-2H-pyran-3-yl)amino)phenyl)pentanoic acid | 2-ethoxypyrimidin-5-yl | 1.79 | 443.2 |

Example 73

Diastereomer 1, Diastereomer 2, Diastereomer 3, Diastereomer 4

3-(4-(Ethyl(tetrahydro-2H-pyran-3-yl)amino)-3-(3-(p-tolyl)ureido)phenyl)pentanoic acid

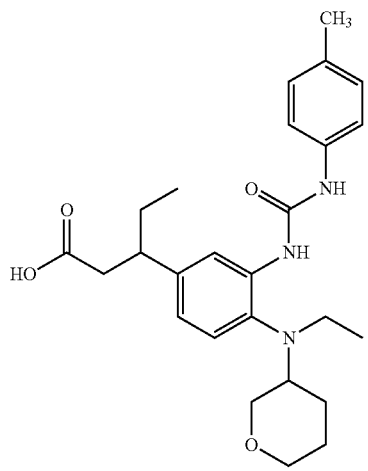 [SMILES: CCC(CC(=O)O)c1ccc(N(CC)C2CCCOC2)c(NC(=O)Nc2ccc(C)cc2)c1]

73A. Methyl 3-(4-(ethyl(tetrahydro-2H-pyran-3-yl)amino)-3-(3-(p-tolyl)ureido)phenyl)pentanoate To a stirred solution of 59E Diastereomer 1 (0.035 g, 0.105 mmol) in tetrahydrofuran (1.5 mL) was added 1-isocyanato-4-methylbenzene (0.017 g, 0.126 mmol). The reaction mixture was stirred at room temperature for 12 h. LCMS indicated completion of reaction. The reaction mixture was concentrated under reduced pressure to get 73A (yellow liquid, 45 mg, 0.069 mmol, 66% yield). LC-MS Anal. Calc'd. for $C_{27}H_{37}N_3O_4$, 467.3, found [M+H] 468.5. $T_r$=1.63 min. (Method AY).

Example 73. Diastereomer 1. 3-(4-(Ethyl(tetrahydro-2H-pyran-3-yl)amino)-3-(3-(p-tolyl)ureido)phenyl)pentanoic acid To a stirred solution of 73A (0.045 g, 0.096 mmol) in mixture of tetrahydrofuran (1.5 mL), methanol (1.5 mL) and water (0.5 mL) was added LiOH.H$_2$O (0.016 g, 0.385 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 73 Diastereomer 1 (25 mg, 0.056 mmol, 57% yield). LC-MS Anal. Calc'd. for $C_{26}H_{35}N_3O_4$, 453.2, found [M+H] 454.2, $T_r$=1.85 min. (Method O). $^1$H NMR (400 MHz, DMSO-d$_6$) δ 9.40 (s, 1H), 8.40 (s, 1H), 8.08 (s, 1H), 7.38 (m, 2H), 7.05-7.19 (m, 3H), 6.69-6.85 (m, 1H), 3.94 (m, 1H), 3.65-3.77 (m, 1H), 3.07-3.21 (m, 2H), 2.94-3.05 (m, 2H), 2.80-2.91 (m, 2H), 2.33 (m, 2H), 2.25 (s, 3H), 1.91 (m, 1H), 1.56-1.74 (m, 2H), 1.39-1.54 (m, 2H), 1.21-1.36 (m, 1H), 0.79 (t, J=7.2 Hz, 3H), 0.63-0.74 (t, J=7.2 Hz, 3H).

Example 73. Diastereomer 2. 3-(4-(Ethyl(tetrahydro-2H-pyran-3-yl)amino)-3-(3-(p-tolyl)ureido)phenyl)pentanoic acid Example 73 Diastereomer 2 was prepared from 59E Diastereomer 2 following the procedure described for the synthesis of Example 73 Diastereomer 1. LC-MS Anal. Calc'd. for $C_{26}H_{35}N_3O_4$, 453.2, found [M+H] 454.2, $T_r$=1.85 min. (Method O). $^1$H NMR (400 MHz, DMSO-d$_6$) δ 9.40 (s, 1H), 8.40 (s, 1H), 8.08 (s, 1H), 7.38 (m, 2H), 7.05-7.20 (m, 3H), 6.71 (s, 1H), 3.85-4.00 (m, 1H), 3.62-3.77 (m, 1H), 3.06-3.18 (m, 2H), 2.93-3.05 (m, 2H), 2.78-2.92 (m, 2H), 2.33 (m, 2H), 2.26 (s, 3H), 1.91 (m, 1H), 1.57-1.73 (m, 2H), 1.38-1.52 (m, 2H), 1.15-1.35 (m, 1H), 0.79 (t, J=7.2 Hz, 3H), 0.63-0.74 (t, J=7.2 Hz, 3H).

Example 73. Diastereomer 3. 3-(4-(Ethyl(tetrahydro-2H-pyran-3-yl)amino)-3-(3-(p-tolyl)ureido)phenyl)pentanoic acid Example 73 Diastereomer 3 was prepared from 60B Diastereomer 3 following the procedure described for the synthesis of Example 73 Diastereomer 1. LC-MS Anal. Calc'd. for $C_{26}H_{35}N_3O_4$, 453.2, found [M+H] 454.2. $T_r$=1.84 min. (Method O). $^1$H NMR (400 MHz, DMSO-d$_6$) δ 9.34-9.46 (m, 1H), 8.36-8.45 (m, 1H), 8.02-8.12 (m, 1H), 7.34-7.44 (m, 2H), 7.16 (m, 1H), 7.03-7.12 (m, 2H), 6.80 (m, 1H), 3.88-3.98 (m, 1H), 3.71 (m, 1H), 3.06-3.20 (m, 2H), 2.94-3.03 (m, 2H), 2.80-2.92 (m, 2H), 2.33 (m, 2H), 2.24 (s, 3H), 1.91 (m, 1H), 1.56-1.71 (m, 2H), 1.39-1.54 (m, 2H), 1.20-1.34 (m, 1H), 0.79 (m, 3H), 0.62-0.75 (m, 3H).

Example 73. Diastereomer 4. 3-(4-(Ethyl(tetrahydro-2H-pyran-3-yl)amino)-3-(3-(p-tolyl)ureido)phenyl)pentanoic acid Example 73 Diastereomer 4 was prepared from 60B Diastereomer 4 following the procedure described for the synthesis of Example 73 Diastereomer 1. LC-MS Anal. Calc'd. for $C_{26}H_{35}N_3O_4$, 453.2, found [M+H] 454.3, $T_r$=1.85 min. (Method O). $^1$H NMR (400 MHz, DMSO-d$_6$) δ 9.47 (m, 1H), 8.36-8.51 (m, 1H), 8.01-8.15 (m, 1H), 7.38 (m, 2H), 7.16 (m, 1H), 7.10 (m, 2H), 6.73-6.85 (m, 1H), 3.94 (m, 1H), 3.64-3.80 (m, 1H), 3.07-3.20 (m, 2H), 2.94-3.05 (m, 2H), 2.79-2.92 (m, 2H), 2.34 (m, 2H), 2.26 (s, 3H), 1.84-1.98 (m, 1H), 1.56-1.74 (m, 2H), 1.38-1.54 (m, 2H), 1.29 (m, 1H), 0.79 (t, J 7.2 Hz, 3H), 0.73 (t, J=7.2 Hz, 3H).

Example 74

Diastereomer 1

(S)-3-(4-((S)-3-Isopropylmorpholino)-3-(3-(p-tolyl)ureido)phenyl)pentanoic acid

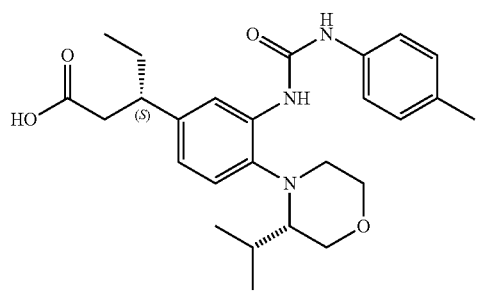

74A. (S)-5-Isopropylmorpholin-3-one

To an ice cold suspension of 60% NaH (8.92 g, 223 mmol) in toluene (300 mL) was added L-Valinol (10 g, 97 mmol) in toluene (200 mL) in a dropwise manner. The reaction mixture was slowly warmed to room temperature and was added ethyl 2-chloroacetate (11.88 g, 97 mmol) in toluene (50 mL) in a dropwise manner. The reaction mixture was heated to reflux for 20 h. Reaction mass was cooled to room temperature, quenched with 20 mL of water and concentrated under reduced pressure. The crude was purified by flash chromatography (120 g silica gel column; 2% MeOH: CHCl$_3$) to afford 74A (off-white solid, 10 g, 69.8 mmol, 72.0% yield). LC-MS Anal. Calc'd. for C$_7$H$_{13}$NO$_2$, 143.1, found [M+H] 144.2, T$_r$=0.6 min (Method U).

74B. (S)-3-Isopropylmorpholine

To a solution of LiAlH$_4$ (2.4 M in THF, 58.2 mL, 140 mmol) in THF (100 mL) cooled to 0° C. and was added 74A (10 g, 69.8 mmol) in THF (50 mL) in a dropwise manner. Then reaction mass was heated to reflux overnight. Reaction mass was cool to 0° C., quenched with water (5 mL) followed by 2M NaOH solution (10 mL). Reaction mixture was stirred at room temperature for 1 h. The solids were filtered and washed with ethyl acetate. The filtrate was concentrated under reduced pressure to afford 74B (brown oil, 8.5 g, 65.8 mmol, 94% yield). LC-MS Anal. Calc'd. for C$_7$H$_{15}$NO, 129.2, found [M+H] 130.2, T$_r$=0.33 min (Method U).

74C. (S)-4-(4-Bromo-2-nitrophenyl)-3-isopropylmorpholine

To a solution of 4-bromo-1-fluoro-2-nitrobenzene (9.02 g, 41.0 mmol) in NMP (30 mL) was added DIPEA (21.49 mL, 123 mmol), followed by 74B (5.3 g, 41.0 mmol) and heated to 120° C. overnight. Reaction mixture was diluted with water (100 mL) and extracted with MTBE (2×100 mL). The combined organic layer was dried over sodium sulfate and concentrated under reduced pressure to get crude which was purified by flash chromatography (5% EA:hexane; 40 g silica gel column) to afford 74C (brown gummy, 3.8 g, 11.43 mmol, 27.9% yield). LC-MS Anal. Calc'd. for C$_{13}$H$_{17}$BrN$_2$O$_3$, 328.04, found [M+H] 329.2, T$_r$=3.23 min (Method U).

74D. (S)-4-(4-(5,5-Dimethyl-1,3,2-dioxaborinan-2-yl)-2-nitrophenyl)-3-isopropylmorpholine To a solution of 74C (1.1 g, 3.34 mmol) in DMSO (25 mL) were added 5,5,5',5'-tetramethyl-2,2'-bi(1,3,2-dioxaborinane) (1.510 g, 6.68 mmol) and potassium acetate (1.476 g, 15.04 mmol). The reaction mixture was purged with nitrogen for 10 minutes. Then was added PdCl$_2$(dppf).CH$_2$Cl$_2$ Adduct (0.136 g, 0.167 mmol) and heated to 80° C. for 5 h. Reaction mixture was cooled to room temperature, diluted with ethyl acetate (50 mL) and washed with brine solution (10×50 mL). The organic layer was dried over sodium sulfate and concentrated under reduced pressure to afford 74D (brown solid, 1.4 g, 2.435 mmol, 72.9% yield). LC-MS Anal. Calc'd. for C$_{18}$H$_{27}$BN$_2$O$_5$, 362.2, found [M+H] 295.2 for parent boronic acid, T$_r$=2.05 min (Method U).

74E. (S)-Methyl 3-(4-((S)-3-isopropylmorpholino)-3-nitrophenyl)pentanoate

To a solution of 74D (1.4 g, 3.86 mmol) in dioxane (20 mL) was added 1 N sodium hydroxide (3.48 mL, 3.48 mmol) and purged with nitrogen for 10 minutes. Then were added (E)-methyl pent-2-enoate (2.206 g, 19.32 mmol), (R)-(+)-2,2'-bis(diphenylphosphino)-1,1'-binaphthyl (0.072 g, 0.116 mmol) and chlorobis(ethylene) rhodium(I) dimer (0.023 g, 0.058 mmol). Round bottomed flask was closed with septum and stirred at 35° C. for 2 h. Reaction mixture was cooled to room temperature, diluted with ethyl acetate (50 mL) and washed with water (30 mL) followed by brine solution (2×30 mL). The organic layer was dried over sodium sulfate and concentrated under reduced pressure to get crude was purified by flash chromatography (15% EA:hexane; 24 g silica gel column) to afford 74E (brown gummy, 0.7 g, 1.748 mmol, 37% yield). LC-MS Anal. Calc'd. for C$_{19}$H$_{28}$N$_2$O$_5$, 364.2, found [M+H] 365.2, T$_r$=3.08 min (Method U). (Absolute stereochemistry of the product assigned based on the expected product enantiomer from the use of (R)-BINAP in the conjugate addition).

74F. (S)-Methyl 3-(3-amino-4-((S)-3-isopropylmorpholino)phenyl)pentanoate

To a solution of 74E (0.65 g, 1.784 mmol) in ethyl acetate (10 mL) was added 10% Pd/C (0.15 g, 0.141 mmol) and stirred under hydrogen bladder pressure for 4 h. Reaction mixture was filtered through CELITE® and concentrated under reduced pressure to get crude which was purified by flash chromatography (15% EA:hexane; 40 g silica gel column) to afford Diastereomer mixture of 74F.

Chiral separation of diastereomer mixture (91:9) 74F yielded 74F Diastereomer 1 T$_r$=6.9 min, 74F Diastereomer 2 T$_r$=7.2 min (Method BK).

74F Diastereomer 1 (brown solid, 230 mg, 0.681 mmol, 38.2% yield): LC-MS Anal. Calc'd. for C$_{19}$H$_{30}$N$_2$O$_3$, 334.2, found 335.2, T$_r$=3.55 min (Method U).

74G. (S)-Methyl 3-(4-((S)-3-isopropylmorpholino)-3-(3-(p-tolyl)ureido)phenyl)pentanoate To a solution of 74F Diastereomer 1 (15 mg, 0.045 mmol) in THF (1 mL) was added 1-isocyanato-4-methylbenzene (11.94 mg, 0.090 mmol) and stirred at room temperature overnight. Reaction mass was diluted with ethyl acetate (10 mL) and washed with brine solution (2×10 mL). The organic layer was dried over sodium sulfate and concentrated under reduced pressure to get 74G (30 mg, 0.022 mmol, 50.1% yield) as white solid. LC-MS Anal. Calc'd. for C$_{27}$H$_{37}$N$_3$O$_4$, 467.2, found 468.2, T$_r$=4.01 min (Method U).

Example 74. (S)-3-(4-((S)-3-Isopropylmorpholino)-3-(3-(p-tolyl)ureido)phenyl)pentanoic acid To a solution of 74G (30 mg, 0.064 mmol) in THF (2 mL) and MeOH (0.5 mL) was added LiOH.H$_2$O (13.45 mg, 0.321 mmol) in water (1 mL) and stirred at room temperature overnight. Reaction mass was concentrated under reduced pressure. To that residue water (10 mL) was added and acidified (pH~4) with solid citric acid and extracted with ethyl acetate (2×25 mL). The combined organic layer was dried over sodium sulfate and concentrated under reduced pressure to get crude was purified by prep HPLC to obtain Example 74 (11.3 mg, 0.025 mmol, 38.4% yield). LC-MS Anal. Calc'd. for C$_{26}$H$_{35}$N$_3$O$_4$, 453.2, found 454.2, T$_r$=4.01 min (Method O). $^1$H NMR (400 MHz, DMSO-d$_6$) δ 9.42 (s, 1H), 8.38 (s, 1H), 8.10 (d, J=2.0 Hz, 1H), 7.37 (d, J=8.4 Hz, 2H), 7.16 (d, J=8.4 Hz, 1H), 7.10 (d, J=8.4 Hz, 2H), 6.79 (dd, J=2.0, 8.0 Hz, 1H), 3.74-3.88 (m, 3H), 3.50-3.55 (m, 1H), 3.01 (d, J=9.6 Hz, 1H), 2.81-2.84 (m, 1H), 2.62-2.64 (m, 2H), 2.43-2.45 (m, 1H), 2.25 (s, 3H), 1.60-1.62 (m, 2H), 1.59-1.60 (m, 1H), 0.80 (d, J=7.2 Hz, 3H), 0.67-0.74 (m, 6H) (Note: 1H buried under solvent peak).

Examples 75 and 76

Diastereomer 1

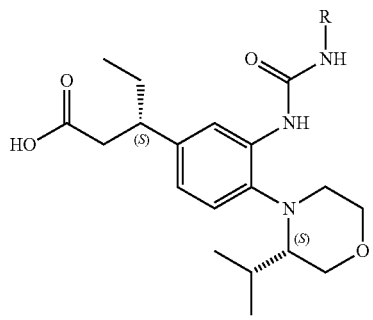

Examples 75 and 76 was prepared from 74F Diastereomer 1 and corresponding isocyanates following the procedure described for the synthesis of Example 74.

| Ex. No. | Name | R | $T_r$ (min) Method O | $[M + H]^+$ |
|---|---|---|---|---|
| 75 | (S)-3-(3-(3-(4-chloro-2-fluorophenyl)ureido)-4-((S)-3-isopropylmorpholino)phenyl)pentanoic acid | | 1.85 | 492.2 |
| 76 | (S)-3-(3-(3-(2-fluoro-4-methoxyphenyl)ureido)-4-((S)-3-isopropylmorpholino)phenyl)pentanoic acid | | 1.5 | 488.2 |

Example 77

Diastereomer 1

(S)-3-(4-((S)-3-Isopropylmorpholino)-3-(3-(5-methylisoxazol-3-yl)ureido)phenyl)pentanoic acid

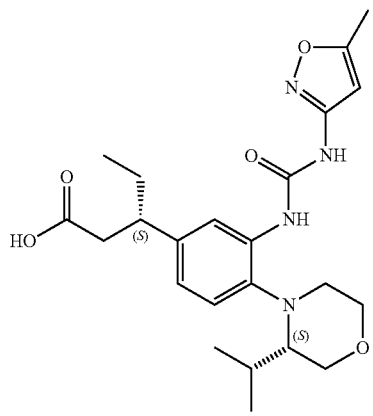

77A. (S)-Methyl 3-(4-((S)-3-isopropylmorpholino)-3-(3-(5-methylisoxazol-3-yl)ureido)phenyl)pentanoate To a solution of 74F Diastereomer 1 (15 mg, 0.045 mmol) in THF (2 mL) was added 4-nitrophenyl chloroformate (9.04 mg, 0.045 mmol) and stirred at room temperature for 2 h. To the reaction mass was added 5-methylisoxazol-3-amine (5.28 mg, 0.054 mmol) followed by pyridine (3.63 µl, 0.045 mmol), cat. amount of DMAP and stirred at 50° C. overnight. Reaction mass was diluted with ethyl acetate (20 mL) and washed with water (2×10 mL) followed by brine solution (2×15 mL). The organic layer was dried over sodium sulfate and concentrated under reduced pressure to afford 77A (brown gummy, 30 mg, 9.16 µmol, 20% yield). LC-MS Anal. Calc'd. for $C_{24}H_{34}N_4O_5$, 458.2, found 459.2. $T_r$=1.49 min (Method AY).

Example 77. (S)-3-(4-((S)-3-Isopropylmorpholino)-3-(3-(5-methylisoxazol-3-yl)ureido)phenyl)pentanoic acid Example 77 was prepared from 77A following the procedure described for the synthesis of Example 74 from 74G. LC-MS Anal. Calc'd. for $C_{23}H_{32}N_4O_5$, 444.2, found 445.2, $T_r$=1.42 min (Method O). $^1$H NMR (400 MHz, DMSO-$d_6$) δ 10.35 (s, 1H), 9.50 (s, 1H), 8.15 (s, 1H), 7.21 (d, J=8.4 Hz, 1H), 6.86 (dd, J=2.00, 8.00 Hz, 1H), 6.38 (s, 1H), 3.87-3.89 (m, 2H), 3.72 (d, J=10.40 Hz, 1H), 3.56-3.59 (m, 2H), 3.04 (d, J=10.40 Hz, 1H), 2.79-2.84 (m, 1H), 2.62-2.65 (m, 1H), 2.51-2.54 (m, 1H), 2.43-2.46 (m, 1H), 2.37 (d, J=0.80 Hz, 3H), 1.48-1.59 (m, 3H), 0.80 (d, J=7.20 Hz, 3H), 0.72 (t, J=7.60 Hz, 3H), 0.66 (d, J=7.20 Hz, 3H).

Example 78

Diastereomer 1

(S)-3-(3-((4-Chlorophenyl)amino)-4-((S)-3-isopropylmorpholino)phenyl)pentanoic acid

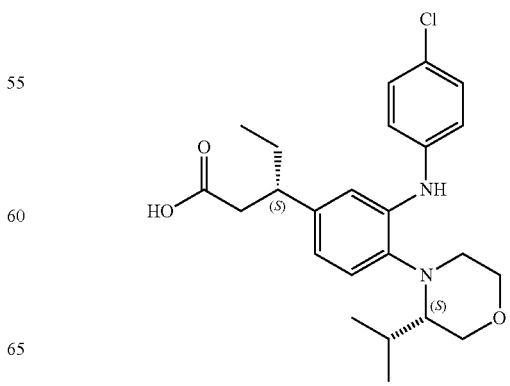

78A. (S)-Methyl 3-(3-((4-chlorophenyl)amino)-4-((S)-3-isopropylmorpholino)phenyl)pentanoate To a solution of 74F Diastereomer 1 (25 mg, 0.075 mmol) in 1,4-dioxane (2 mL) were added 1-bromo-4-chlorobenzene (17.17 mg, 0.090 mmol), $Cs_2CO_3$ (73.1 mg, 0.224 mmol). The reaction mixture was purged with nitrogen for 15 minutes. Then was added Xantphos (21.63 mg, 0.037 mmol) followed by bis(dibenzylideneacetone)palladium (4.30 mg, 7.47 µmol) and heated to 110° C. overnight. Reaction mixture was diluted with ethyl acetate (20 mL) and washed with water (2×15 mL) followed by brine solution (2×15 mL). The organic layer was dried over sodium sulfate and concentrated under reduced pressure to obtained 78A (brown gummy, 45 mg, 0.029 mmol, 39.2% yield). LC-MS Anal. Calc'd. for $C_{25}H_{33}ClN_2O_3$, 444.2, found 445.2, $T_r$=4.07 min (Method U).

Example 78. (S)-3-(3-((4-Chlorophenyl)amino)-4-((S)-3-isopropylmorpholino)phenyl)pentanoic acid To a solution of 78A (40 mg, 0.090 mmol) in THF (2 mL) and MeOH (0.5 mL) was added $LiOH.H_2O$ (18.84 mg, 0.449 mmol) in water (1 mL) and stirred at rt overnight. Reaction mixture was concentrated under reduced pressure. To that residue water (10 mL) was added and acidified (pH~4) with solid citric acid and extracted with ethyl acetate (2×25 mL). The combined organic layer was dried over sodium sulfate and concentrated under reduced pressure to get crude was purified by prep HPLC to obtain Example 78 (5.8 mg, 0.013 mmol, 15% yield). LC-MS Anal. Calc'd. for $C_{24}H_{31}ClN_2O_3$, 430.2, found 431.2, $T_r$=2.17 min (Method O). $^1$H NMR (400 MHz, DMSO-$d_6$) δ 7.45 (s, 1H), 7.27 (d, J=8.80 Hz, 2H), 7.14 (d, J=8.80 Hz, 3H), 7.02 (s, 1H), 6.73 (d, J=9.60 Hz, 1H), 3.69-3.76 (m, 3H), 3.46-3.49 (m, 1H), 3.01-3.04 (m, 1H), 2.67-2.72 (m, 3H), 2.52-2.55 (m, 1H), 2.41-2.44 (m, 1H), 1.70-1.73 (m, 1H), 1.58-1.62 (m, 1H), 1.46-1.52 (m, 1H), 0.71-0.78 (m, 6H), 0.66 (d, J=7.20 Hz, 3H).

Examples 79 to 82

Diastereomer 1

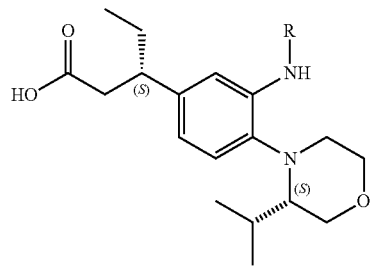

Examples 79 to 82 were prepared from 74F Diastereomer 1 and corresponding aryl halides following the procedure described for the synthesis of Example 78.

| Ex. No. | Name | R | $T_r$ (min) Method O | $[M + H]^+$ |
|---|---|---|---|---|
| 79 | (S)-3-(3-((2-ethoxypyrimidin-5-yl)amino)-4-((S)-3-isopropylmorpholino)phenyl)pentanoic acid | | 1.69 | 443.3 |
| 80 | (S)-3-(4-((S)-3-isopropylmorpholino)-3-((2-methylbenzo[d]thiazol-6-yl)amino)phenyl)pentanoic acid | | 1.95 | 468.2 |
| 81 | (S)-3-(3-((2,2-difluorobenzo[d][1,3]dioxol-5-yl)amino)-4-((S)-3-isopropylmorpholino)phenyl)pentanoic acid | | 2.26 | 477.2 |
| 82 | (S)-3-(3-((4-ethoxyphenyl)amino)-4-((S)-3-isopropylmorpholino)phenyl)pentanoic acid | | 2.1 | 441.3 |

Example 83

Diastereomer 1

(S)-3-(3-((4-Cyanophenyl)amino)-4-((S)-3-isopropylmorpholino)phenyl)pentanoic acid

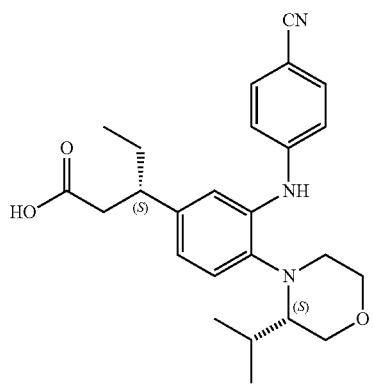

83A. (S)-Methyl 3-(3-((4-cyanophenyl)amino)-4-((S)-3-isopropylmorpholino)phenyl)pentanoate Compound 83A was prepared from 74F Diastereomer 1 and 4-bromobenzonitrile following the procedure described for the synthesis of 78A. LC-MS Anal. Calc'd. for $C_{26}H_{33}N_3O_3$, 435.2, found 436.2. $T_r$=3.58 min (Method U).

Example 83. (S)-3-(3-((4-Cyanophenyl)amino)-4-((S)-3-isopropylmorpholino)phenyl)pentanoic acid To a solution of 83A (40 mg, 0.092 mmol) in THF (2 mL) and MeOH (0.5 mL) was added LiOH.H$_2$O (19.25 mg, 0.459 mmol) and stirred at room temperature overnight. Reaction mixture was concentrated under reduced pressure. To that residue water (10 mL) was added and acidified (pH~4) with solid citric acid and extracted with ethyl acetate (2×25 mL). The combined organic layer was dried over sodium sulfate and concentrated under reduced pressure to get crude. The crude mixture was purified by prep HPLC to obtain Example 83 (8.4 mg, 0.020 mmol, 22% yield). LC-MS Anal. Calc'd. for $C_{25}H_{31}N_3O_3$, 421.2, found 422.2, $T_r$=1.93 min (Method O). $^1$H NMR (400 MHz, DMSO-d$_6$) δ 8.00 (s, 1H), 7.56 (d, J=8.40 Hz, 2H), 7.15 (d, J=8.00 Hz, 1H), 7.09 (d, J=8.80 Hz, 3H), 6.89 (dd, J=2.00, 8.20 Hz, 1H), 3.63-3.68 (m, 3H), 3.48-3.51 (m, 1H), 3.01-3.03 (m, 1H), 2.82-2.86 (m, 2H), 2.69-2.72 (m, 1H), 2.51-2.58 (m, 1H), 2.41-2.44 (m, 1H), 1.78-1.81 (m, 1H), 1.61-1.64 (m, 1H), 1.45-1.50 (m, 1H), 0.71-0.74 (m, 6H), 0.64 (d, J=6.80 Hz, 3H).

Example 84

Diastereomer 1

(S)-3-(3-((4-Fluorophenyl)amino)-4-((S)-3-isopropylmorpholino)phenyl)pentanoic acid

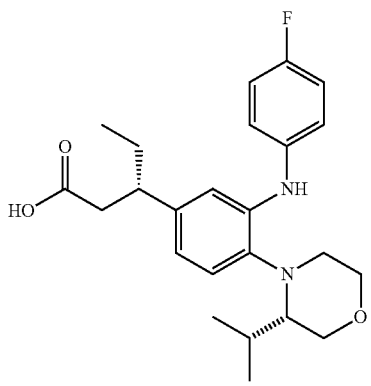 [SMILES: CC[C@@H](CC(=O)O)c1ccc(N2CCOC[C@@H]2C(C)C)c(Nc2ccc(F)cc2)c1]

To a solution of 74F Diastereomer 1 (25 mg, 0.075 mmol) in 1,4-dioxane (2 mL) were added 1-bromo-4-fluorobenzene (15.70 mg, 0.090 mmol), sodium tert-butoxide (21.55 mg, 0.224 mmol). The reaction mixture was purged with nitrogen for 15 minutes. Then Xantphos (21.63 mg, 0.037 mmol) was added followed by bis(dibenzylideneacetone)palladium (4.30 mg, 7.47 μmol) and heated to 110° C. overnight. Reaction mass was cooled to room temperature and was concentrated under reduced pressure. To that residue water (10 mL) was added and acidified (pH~4) with solid citric acid. The reaction mixture was extracted with ethyl acetate (2×25 mL). The combined organic layer was dried over sodium sulfate and concentrated under reduced pressure to get crude which was purified by prep HPLC to obtain Example 84 (pale yellow solid, 3.5 mg, 8.27 μmol, 11.07% yield). LC-MS Anal. Calc'd. for $C_{24}H_{31}FN_2O_3$, 414.2, found 415.2, $T_r$=2.0 min (Method O). $^1$H NMR (400 MHz, DMSO-d$_6$) δ 7.31 (s, 1H), 7.07-7.16 (m, 5H), 6.93 (d, J=2.00 Hz, 1H), 6.66 (dd, J=1.60, 8.00 Hz, 1H), 3.78-3.81 (m, 1H), 3.69-3.71 (m, 2H), 3.02-3.05 (m, 1H), 2.65-2.70 (m, 3H), 2.35-2.40 (m, 1H), 1.70-1.71 (m, 1H), 1.57-1.58 (m, 1H), 1.47-1.49 (m, 1H), 0.78 (d, J=6.80 Hz, 3H), 0.65-0.73 (m, 6H), (1H buried under solvent peak and 1H buried under moisture peak).

Example 85

Diastereomer 2

(R)-3-(4-((S)-3-Isopropylmorpholino)-3-(3-(p-tolyl)ureido)phenyl)pentanoic acid

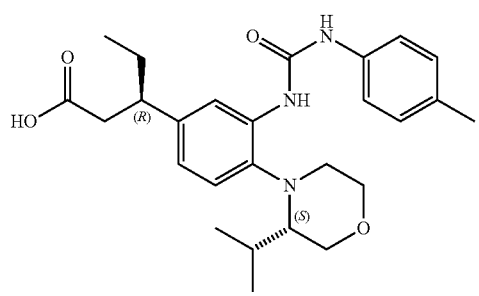

85A. (R)-Methyl 3-(4-((S)-3-isopropylmorpholino)-3-nitrophenyl)pentanoate

To a solution of 74D (1.25 g, 3.45 mmol) in dioxane (20 mL) was added 1 N sodium hydroxide (3.11 mL, 3.11 mmol) and purged with nitrogen for 10 minutes. Then were added (E)-methyl pent-2-enoate (1.969 g, 17.25 mmol), (S)-(−)-2,2'-bis(diphenylphosphino)-1,1'-binaphthyl (0.107 g, 0.173 mmol) and chlorobis(ethylene)rhodium(I) dimer (0.027 g, 0.069 mmol). The RB was closed with septum and stirred at 35° C. for 2 h. Reaction mixture was cooled to room temperature, diluted with ethyl acetate (50 mL) and washed with water (30 mL) followed by brine solution (2×30 mL). The organic layer was dried over sodium sulfate and concentrated under reduced pressure to get crude was purified by flash chromatography (15% EA:hexane; 24 g silica gel column) to afford 85A (brown gummy, 0.7 g, 1.748 mmol, 37.2% yield). LC-MS Anal. Calc'd. for $C_{19}H_{28}N_2O_5$, 364.2, found 365.2. $T_r$=3.3 min (Method U). (Absolute stereochemistry of the product assigned based on the expected product enantiomer from the use of (S)-BINAP in the conjugate addition).

85B. (R)-Methyl 3-(3-amino-4-((S)-3-isopropylmorpholino)phenyl)pentanoate

Compound 85B (diastereomer mixture) was prepared from 85A following the procedure described for the synthesis of 74F.

Chiral separation of Diastereomer mixture (10:90) 85B yielded 85B Diastereomer 1, $T_r$=6.9 min, 85B Diastereomer 2, $T_r$=7.2 min (Method BK).

85B Diastereomer 2: LC-MS Anal. Calc'd. for $C_{19}H_{30}N_2O_3$, 334.2, found 335.2. $T_r$=3.55 min (Method U).

Example 85. (R)-3-(4-((S)-3-Isopropylmorpholino)-3-(3-(p-tolyl)ureido)phenyl)pentanoic acid Example 85 was prepared from 85B Diastereomer 2 following the procedure described for the synthesis of Example 74. LC-MS Anal. Calc'd. for $C_{26}H_{35}N_3O_4$ 453.2, found 454.2, $T_r$=1.7 min (Method O). $^1$H NMR (400 MHz, DMSO-$d_6$) δ 9.42 (s, 1H), 8.38 (s, 1H), 8.10 (d, J=2.00 Hz, 1H), 7.37 (d, J=8.40 Hz, 2H), 7.16 (d, J=8.40 Hz, 1H), 7.10 (d, J=8.40 Hz, 2H), 6.79 (dd, J=2.00, 8.00 Hz, 1H), 3.74-3.88 (m, 3H), 3.50-3.55 (m, 1H), 3.01 (d, J=9.60 Hz, 1H), 2.81-2.84 (m, 1H), 2.62-2.64 (m, 2H), 2.43-2.45 (m, 1H), 2.25 (s, 3H), 1.60-1.62 (m, 2H), 1.59-1.60 (m, 1H), 0.80 (d, J=7.20 Hz, 3H), 0.67-0.74 (m, 6H) (Note: 1H buried under solvent peak).

Examples 86 to 88

Diastereomer 2

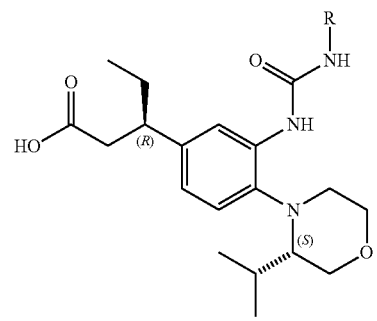

Examples 86 and 87 was prepared from 85B Diastereomer 2 and corresponding isocyanates following the procedure described for the synthesis of Example 85.

Example 88 was prepared from 85B Diastereomer 2 and corresponding amine following the procedure described for the synthesis of Example 77.

| Ex. No. | Name | R | $T_r$ (min) Method O | [M + H]$^+$ |
|---|---|---|---|---|
| 86 | (R)-3-(3-(3-(4-chloro-2-fluorophenyl)ureido)-4-((S)-3-isopropylmorpholino)phenyl)pentanoic acid | 4-chloro-2-fluorophenyl | 1.85 | 492.2 |
| 87 | (R)-3-(3-(3-(2-fluoro-4-methoxyphenyl)ureido)-4-((S)-3-isopropylmorpholino)phenyl)pentanoic acid | 2-fluoro-4-methoxyphenyl | 1.64 | 488.2 |
| 88 | (R)-3-(4-((S)-3-isopropylmorpholino)-3-(3-(5-methylisoxazol-3-yl)ureido)phenyl)pentanoic acid | 5-methylisoxazol-3-yl | 1.58 | 445.2 |

Examples 89 to 91

Diastereomer 2

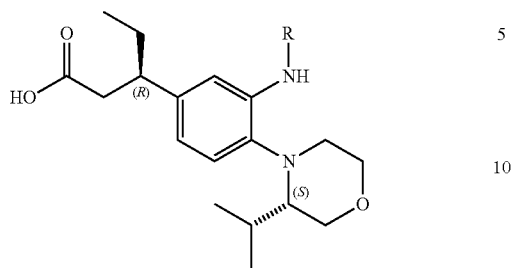

Examples 89 to 91 was prepared from 85B Diastereomer 2 and corresponding aryl halides following the procedure described for the synthesis of Example 84.

| Ex. No. | Name | R | $T_r$ (min) Method O | $[M + H]^+$ |
|---|---|---|---|---|
| 89 | (R)-3-(3-((4-chlorophenyl)amino)-4-((S)-3-isopropylmorpholino)phenyl) pentanoic acid | 4-Cl-C6H4 | 2.18 | 431.2 |
| 90 | (R)-3-(3-((4-fluorophenyl)amino)-4-((S)-3-isopropylmorpholino)phenyl) pentanoic acid | 4-F-C6H4 | 1.9 | 415.2 |
| 91 | (R)-3-(3-((4-ethylphenyl)amino)-4-((S)-3-isopropylmorpholino)phenyl) pentanoic acid | 4-Et-C6H4 | 2.31 | 425.3 |

Examples 92 to 94

Diastereomer 2

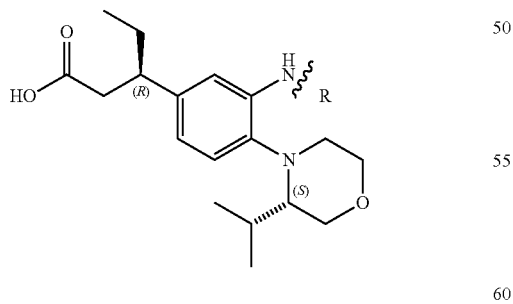

Example 92 was prepared from 85B Diastereomer 2 and corresponding aryl halide following the procedure described for the synthesis of Example 83.

Examples 93 and 94 was prepared from 85B Diastereomer 2 and corresponding aryl halides following the procedure described for the synthesis of Example 78.

| Ex. No. | Name | R | $T_r$ (min) | Method | [M + H]+ |
|---|---|---|---|---|---|
| 92 | (R)-3-(3-((4-cyanophenyl)amino)-4-((S)-3-isopropylmorpholino)phenyl)pentanoic acid | 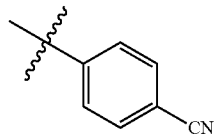 [SMILES: *c1ccc(C#N)cc1] | 2.32 | R | 422.2 |
| 93 | (R)-3-(3-((2,2-difluorobenzo[d][1,3]dioxol-5-yl)amino)-4-((S)-3-isopropylmorpholino)phenyl)pentanoic acid | 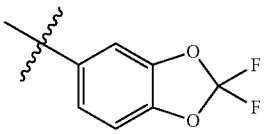 [SMILES: *c1ccc2c(c1)OC(F)(F)O2] | 2.25 | O | 477.2 |
| 94 | (R)-3-(3-((2-ethoxypyrimidin-5-yl)amino)-4-((S)-3-isopropylmorpholino)phenyl)pentanoic acid | 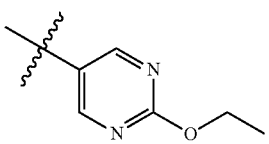 [SMILES: *c1cnc(OCC)nc1] | 2.23 | R | 443.3 |

Example 95

Enantiomer 1

3-(4-(Diisobutylamino)-3-fluoro-5-((2-methylbenzo[d]thiazol-6-yl)amino)phenyl)pentanoic acid

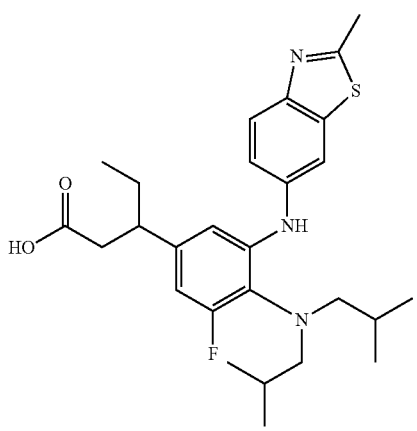 [SMILES: CCC(CC(=O)O)c1cc(F)c(N(CC(C)C)CC(C)C)c(Nc2ccc3nc(C)sc3c2)c1]

95A. 4-Bromo-2-fluoro-N,N-diisobutyl-6-nitroaniline

A solution of 5-bromo-1,2-difluoro-3-nitrobenzene (1 g, 4.20 mmol) and diisobutylamine (1.629 g, 12.61 mmol) was placed under nitrogen and heated at 130° C. for 2 h. The reaction was diluted with ether and washed with 5% HOAc then brine. The org. phase was dried, stripped, and chromatographed on silica gel (EtOAc-hexane) to afford 95A (1.28 g, 83% yield) as an orange oil. MS(ES): m/z=347 [M+H]+, $T_r$=1.34 min (Method A).

95B. 4-(5,5-Dimethyl-1,3,2-dioxaborinan-2-yl)-2-fluoro-N,N-diisobutyl-6-nitroaniline A solution of 5,5,5',5'-tetramethyl-2,2'-bi(1,3,2-dioxaborinane) (1.015 g, 4.49 mmol) and 95A (1.2 g, 3.46 mmol) and potassium acetate (1.018 g, 10.37 mmol) in degassed DMSO (4.94 ml) was treated with 1,1'-bis(diphenylphosphino)ferrocenedichloro palladium(II) dichloromethane complex (0.126 g, 0.173 mmol). This dark solution was placed under nitrogen and heated to 80° C. for 2 h then cooled to RT. The reaction was purified by flash chromatography (EtOAc-hexane). Concentration of the appropriate fractions afforded 95B (1.23 g, 89% yield) as an orange oil. MS(ES): m/z=313 [M+H]+ for parent boronic acid. $T_r$=1.11 min (Method A).

95C. (+/−)-Methyl 3-(4-(diisobutylamino)-3-fluoro-5-nitrophenyl)pentanoate

A reaction vial was charged with 95B (1.2 g, 3.16 mmol). The SM was dissolved in dioxane (10 mL), and (E)-methyl pent-2-enoate (1.081 g, 9.47 mmol) was added followed by 1M aq. sodium hydroxide (2.84 mL, 2.84 mmol). The sample was degassed by freezing under vacuum then thawing under nitrogen twice. The reaction was charged with chloro(1,5-cyclooctadiene)rhodium(I) dimer (0.078 g, 0.158 mmol), and the freeze/thaw purge cycle was repeated. The reaction was stirred 4.5 h at 50° C., treated with acetic acid (0.361 mL, 6.31 mmol) then applied to a flash column and eluted with 5-15% EtOAc-hexane. Concentration of the appropriate fractions afforded 95C (0.81 g, 64% yield) as an orange oil. MS(ES): m/z=383 [M+H]+. $T_r$=1.29 min (Method A).

95D. Methyl 3-(3-amino-4-(diisobutylamino)-5-fluorophenyl)pentanoate

Racemate 95D was prepared from 95C following the procedure described for the synthesis of 1H. MS(ES): m/z=353 [M+H]+. $T_r$=1.22 min (Method A).

Chiral separation of Racemate 95D gave Enantiomer 1 $T_r$=8.31 min and Enantiomer 2 $T_r$=8.98 min (Method BG).

95D Enantiomer 1: LC-MS Anal. Calc'd. for $C_{20}H_{33}FN_2O_2$, 352.2, found [M+H] 353.4. $T_r$=4.13 min (Method U).

95D Enantiomer 2: LC-MS Anal. Calc'd. for $C_{20}H_{33}FN_2O_2$, 352.2, found [M+H] 353.4. $T_r$=4.12 min (Method U).

95E. Methyl 3-(4-(diisobutylamino)-3-fluoro-5-((2-methylbenzo[d]thiazol-6-yl)amino)phenyl)pentanoate To a solution of methyl 95D Enantiomer 1 (50 mg, 0.142 mmol) in 1,4-dioxane (2 mL) were added 6-bromo-2-methylbenzo[d]thiazole (38.8 mg, 0.170 mmol), Cs$_2$CO$_3$ (139 mg, 0.426 mmol). The reaction mixture was purged with nitrogen for 15 minutes. Then was added Xantphos (41.0 mg, 0.071 mmol) followed by bis(dibenzylideneacetone)palladium (8.16 mg, 0.014 mmol) and heated to 110° C. overnight. Reaction mixture was diluted with ethyl acetate (20 mL) and washed with water (2×15 mL) followed by brine solution (2×15 mL). The organic layer was dried over sodium sulfate and concentrated under reduced pressure get crude was purified by flash chromatography (15% EA:hexane; 12 g silica gel column) to afford 95E (brown gummy, 50 mg, 0.093 mmol, 65.6% yield). LC-MS Anal. Calc'd. for C$_{28}$H$_{38}$FN$_3$O$_2$S, 499.2, found 500.2, T$_r$=4.67 min (Method U).

Example 95. 3-(4-(Diisobutylamino)-3-fluoro-5-((2-methylbenzo[d]thiazol-6-yl)amino)phenyl)pentanoic acid Example 95 was prepared from 95E following the procedure described for the synthesis of Example 78. LC-MS Anal. Calc'd. for C$_{27}$H$_{36}$FN$_3$O$_2$S, 485.2, found 486.2, T$_r$=2.65 min (Method O). $^1$H NMR (400 MHz, DMSO-d$_6$) δ 7.81 (d, J=8.40 Hz, 1H), 7.77 (s, 1H), 7.53 (s, 1H), 7.19 (d, J=10.40 Hz, 1H), 6.92 (s, 1H), 6.52 (d, J=13.20 Hz, 1H), 2.67-2.86 (m, 8H), 2.55-2.57 (m, 1H), 2.39-2.45 (m, 1H), 1.45-1.67 (m, 4H), 0.87 (d, J=6.40 Hz, 12H), 0.73 (t, J=7.60 Hz, 3H).

Examples 96 to 107

Enantiomer 1

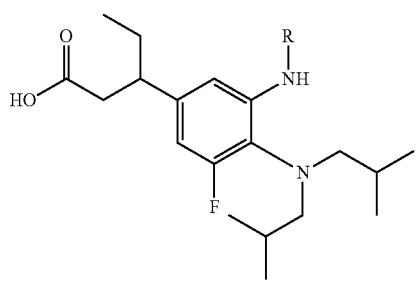

Examples 96 to 106 were prepared from Intermediate 95D Enantiomer 1 and corresponding halides following the procedure described for the synthesis of Example 95.

Example 107 was prepared from 95D Enantiomer 1 and corresponding halides following the procedure described for the synthesis of Example 83.

| Ex. No. | Name | R | T$_r$ (min) | Method | [M + H]$^+$ |
|---|---|---|---|---|---|
| 96 | 3-(4-(diisobutylamino)-3-((4-ethylphenyl)amino)-5-fluorophenyl)pentanoic acid | 4-ethylphenyl | 3.0 | O | 443.3 |
| 97 | 3-(4-(diisobutylamino)-3-((4-ethoxyphenyl)amino)-5-fluorophenyl)pentanoic acid | 4-ethoxyphenyl | 2.86 | O | 459.3 |
| 98 | 3-(4-(diisobutylamino)-3-fluoro-5-((4-(2,2,2-trifluoroethoxy)phenyl)amino)phenyl)pentanoic acid | 4-(2,2,2-trifluoroethoxy)phenyl | 2.86 | O | 513.3 |
| 99 | 3-(3-((4-chlorophenyl)amino)-4-(diisobutylamino)-5-fluorophenyl)pentanoic acid | 4-chlorophenyl | 2.95 | O | 449.2 |
| 100 | 3-(4-(diisobutylamino)-3-fluoro-5-((4-fluorophenyl)amino)phenyl)pentanoic acid | 4-fluorophenyl | 2.89 | O | 433.3 |

-continued

| Ex. No. | Name | R | $T_r$ (min) | Method | $[M + H]^+$ |
|---|---|---|---|---|---|
| 101 | 3-(3-((2,2-difluorobenzo[d][1,3]dioxol-5-yl)amino)-4-(diisobutylamino)-5-fluorophenyl)pentanoic acid | 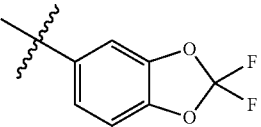 [SMILES: *c1ccc2c(c1)OC(F)(F)O2] | 3.08 | O | 495.2 |
| 102 | 3-(3-((4-chloro-3-(2,2,2-trifluoroethoxy)phenyl)amino)-4-(diisobutylamino)-5-fluorophenyl)pentanoic acid | 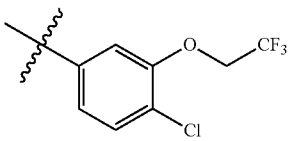 [SMILES: *c1ccc(Cl)c(OCC(F)(F)F)c1] | 3.08 | O | 547.2 |
| 103 | 3-(4-(diisobutylamino)-3-((2-ethoxypyrimidin-5-yl)amino)-5-fluorophenyl)pentanoic acid | 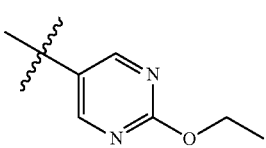 | 2.99 | R | 461.3 |
| 104 | 3-(4-(diisobutylamino)-3-fluoro-5-((2-methoxypyrimidin-5-yl)amino)phenyl)pentanoic acid | 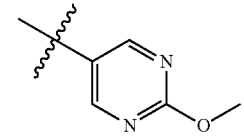 [SMILES: *c1cnc(OC)nc1] | 2.35 | O | 447.3 |
| 105 | 3-(4-(diisobutylamino)-3-fluoro-5-((2-morpholinopyrimidin-4-yl)amino)phenyl)pentanoic acid | 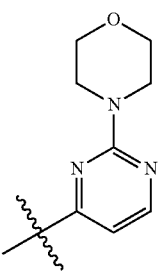 [SMILES: *c1ccnc(N2CCOCC2)n1] | 2.46 | O | 502.3 |
| 106 | 3-(3-((4-(cyclopropylmethoxy)phenyl)amino)-4-(diisobutylamino)-5-fluorophenyl)pentanoic acid | 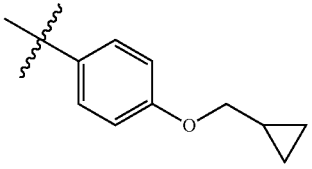 [SMILES: *c1ccc(OCC2CC2)cc1] | 2.97 | O | 485.3 |
| 107 | 3-(3-((4-cyanophenyl)amino)-4-(diisobutylamino)-5-fluorophenyl)pentanoic acid | 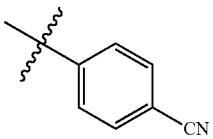 | 2.66 | O | 440.3 |

Examples 111 to 123

Enantiomer 2

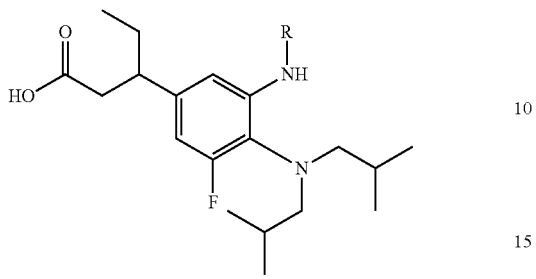

Examples 111 to 122 was prepared from 95D Enantiomer 2 and corresponding halides following the procedure described for the synthesis of Example 95.

Example 123 was prepared from 95D Enantiomer 2 and corresponding halides following the procedure described for the synthesis of Example 83.

| Ex. No. | Name | R | $T_r$ (min) | Method | $[M + H]^+$ |
|---|---|---|---|---|---|
| 111 | 3-(4-(diisobutylamino)-3-fluoro-5-((2-methylbenzo[d]thiazol-6-yl)amino)phenyl)pentanoic acid | | 2.65 | O | 486.2 |
| 112 | 3-(4-(diisobutylamino)-3-((4-ethylphenyl)amino)-5-fluorophenyl)pentanoic acid | | 3.0 | O | 443.3 |
| 113 | 3-(4-(diisobutylamino)-3-((4-ethoxyphenyl)amino)-5-fluorophenyl)pentanoic acid | | 2.86 | O | 459.3 |
| 114 | 3-(4-(diisobutylamino)-3-fluoro-5-((4-(2,2,2-trifluoroethoxy)phenyl)amino)phenyl)pentanoic acid | | 2.85 | O | 513.3 |
| 115 | 3-(3-((4-chlorophenyl)amino)-4-(diisobutylamino)-5-fluorophenyl)pentanoic acid | | 2.95 | O | 449.2 |
| 116 | 3-(4-(diisobutylamino)-3-fluoro-5-((4-fluorophenyl)amino)phenyl)pentanoic acid | | 2.81 | O | 433.3 |

| Ex. No. | Name | R | $T_r$ (min) | Method | [M + H]$^+$ |
|---|---|---|---|---|---|
| 117 | 3-(3-((2,2-difluorobenzo[d][1,3]dioxol-5-yl)amino)-4-(diisobutylamino)-5-fluorophenyl)pentanoic acid | 2,2-difluorobenzo[d][1,3]dioxol-5-yl | 3.12 | O | 495.3 |
| 118 | 3-(3-((4-chloro-3-(2,2,2-trifluoroethoxy)phenyl)amino)-4-(diisobutylamino)-5-fluorophenyl)pentanoic acid | 4-chloro-3-(2,2,2-trifluoroethoxy)phenyl | 3.14 | Q | 547.2 |
| 119 | 3-(4-(diisobutylamino)-3-((2-ethoxypyrimidin-5-yl)amino)-5-fluorophenyl)pentanoic acid | 2-ethoxypyrimidin-5-yl | 2.65 | O | 461.3 |
| 120 | 3-(4-(diisobutylamino)-3-fluoro-5-((2-methoxypyrimidin-5-yl)amino)phenyl)pentanoic acid | 2-methoxypyrimidin-5-yl | 2.34 | O | 447.3 |
| 121 | 3-(4-(diisobutylamino)-3-fluoro-5-((2-morpholinopyrimidin-4-yl)amino)phenyl)pentanoic acid | 2-morpholinopyrimidin-4-yl | 2.46 | O | 502.3 |
| 122 | 3-(3-((4-(cyclopropylmethoxy)phenyl)amino)-4-(diisobutylamino)-5-fluorophenyl)pentanoic acid | 4-(cyclopropylmethoxy)phenyl | 2.97 | O | 485.3 |
| 123 | 3-(3-((4-cyanophenyl)amino)-4-(diisobutylamino)-5-fluorophenyl)pentanoic acid | 4-cyanophenyl | 2.66 | O | 440.3 |

Example 127

Enantiomer 1

3-(3-(4-Chlorobenzamido)-4-(diisobutylamino)-5-fluorophenyl)pentanoic acid

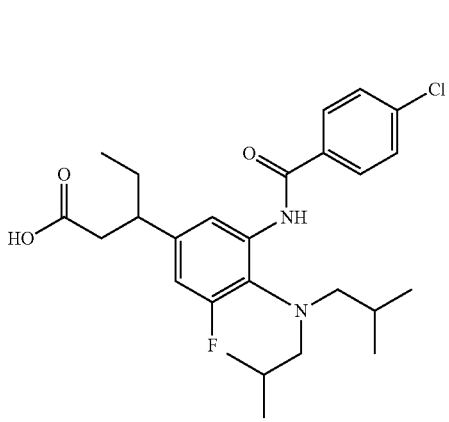 [SMILES: CCC(CC(=O)O)c1cc(F)c(N(CC(C)C)CC(C)C)c(NC(=O)c2ccc(Cl)cc2)c1]

127A. Methyl 3-(3-(4-chlorobenzamido)-4-(diisobutylamino)-5-fluorophenyl)pentanoate To a solution of 4-chlorobenzoic acid (48.9 mg, 0.312 mmol) in DMF (1 mL) was added HATU (108 mg, 0.284 mmol) and DIPEA (0.149 mL, 0.851 mmol) stirred at rt for 30 minutes. Then was added 95D Enantiomer 1 (100 mg, 0.284 mmol) in DMF (1 mL) and stirred at room temperature overnight. Reaction mass was concentrated under reduced pressure. To that residue sodium bicarbonate (10%) solution (20 mL) was added and extracted with ethyl acetate (2×20 mL). The combined organic layer was dried over sodium sulfate and concentrated under reduced pressure to afford 127A (brown gummy, 150 mg, 0.079 mmol, 28.0% yield). LC-MS Anal. Calc'd. for $C_{27}H_{36}ClFN_2O_3$ 490.2, found 491.2, $T_r$=4.62 min (Method U).

Example 127. 3-(3-(4-Chlorobenzamido)-4-(diisobutylamino)-5-fluorophenyl)pentanoic acid Example 127 was prepared from 127A following the procedure described for the synthesis of Example 74. LC-MS Anal. Calc'd. for $C_{26}H_{34}ClFN_2O_3$, 476.2, found 477.2. $T_r$=2.62 min (Method O). $^1$H NMR (400 MHz, DMSO-$d_6$) δ 9.61 (s, 1H), 8.07 (s, 1H), 7.84 (d, J=8.80 Hz, 2H), 7.66 (d, J=8.40 Hz, 2H), 6.88 (d, J=13.20 Hz, 1H), 2.88-2.90 (m, 1H), 2.73-2.75 (m, 4H), 2.55-2.58 (m, 1H), 2.44-2.49 (m, 1H), 1.50-1.67 (m, 4H), 0.82 (d, J=6.40 Hz, 12H), 0.74 (t, J=7.20 Hz, 3H).

Example 128

Enantiomer 2

3-(3-(4-Chlorobenzamido)-4-(diisobutylamino)-5-fluorophenyl)pentanoic acid

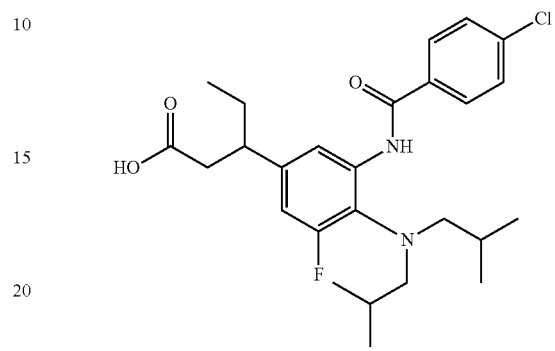

Example 128 was prepared from 95D Enantiomer 2 following the procedure described for the synthesis of Example 127. LC-MS Anal. Calc'd. for $C_{26}H_{34}ClFN_2O_3$, 476.2, found 477.2, $T_r$=2.62 min (Method O). $^1$H NMR (400 MHz, DMSO-$d_6$) δ 9.61 (s, 1H), 8.07 (s, 1H), 7.84 (d, J=8.80 Hz, 2H), 7.66 (d, J=8.40 Hz, 2H), 6.88 (d, J=13.20 Hz, 1H), 2.88-2.90 (m, 1H), 2.73-2.75 (m, 4H), 2.55-2.58 (m, 1H), 2.44-2.49 (m, 1H), 1.50-1.67 (m, 4H), 0.82 (d, J=6.40 Hz, 12H), 0.74 (t, J=7.20 Hz, 3H).

Example 129

Enantiomer 1

3-(3-((4-Chlorophenyl)amino)-4-(diisobutylamino)-5-fluorophenyl)-3-phenylpropanoic acid

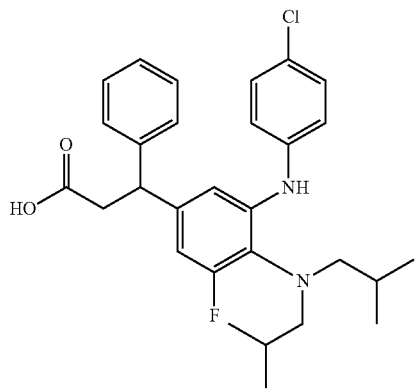 [SMILES: CC(C)CN(CC(C)C)c1c(F)cc(C(CC(=O)O)c2ccccc2)cc1Nc1ccc(Cl)cc1]

129A. Methyl 3-(4-(diisobutylamino)-3-fluoro-5-nitrophenyl)-3-phenylpropanoate To a solution of 95B (0.45 g, 1.183 mmol) in dioxane (15 mL) was added methyl cinnamate (0.384 g, 2.367 mmol) followed by 1M sodium hydroxide (1.065 mL, 1.065 mmol). The reaction mixture was purged with argon for 10 min, then was added chloro(1,5-cyclooctadiene)rhodium(I) dimer (0.029 g, 0.059 mmol). Then reaction mixture was heated to 50° C. and stirred overnight. Reaction mass was cooled to room temperature, diluted with ethyl acetate (50 mL) and washed with water (2×50 mL) followed by brine solution (2×50 mL). The organic layer was dried over sodium sulfate and concentrated under reduced pressure to get crude which was purified by flash chromatography (5% EA:hexane; 40 g silica gel column) to afford 129A (brown gummy, 0.4 g, 0.892 mmol, 75% yield). LC-MS Anal. Calc'd. for $C_{24}H_{31}FN_2O_4$, 430.2, found 431.2, $T_r$=4.3 min (Method U).

129B. Methyl 3-(3-amino-4-(diisobutylamino)-5-fluorophenyl)-3-phenylpropanoate To a solution of 129A (80 mg, 0.186 mmol) in ethyl acetate (2 mL) was added Pd/C (39.6 mg, 0.037 mmol) and stirred under hydrogen pressure at 40 psi in tiny clave for 2.5 h. Reaction mass was filtered through CELITE® and concentrated under reduced pressure to get 129B (brown gummy, 0.07 g, 0.15 mmol, 80% yield). LC-MS Anal. Calc'd. for $C_{24}H_{33}FN_2O_2$, 400.2, found 401.2, $T_r$=4.23 min (Method U).

Chiral separation of Racemate 129B gave Enantiomer 1, $T_r$=4.5 min and Enantiomer 2, $T_r$=5.0 min (Method BN).

129B Enantiomer 1 (0.02 g, 0.085 mmol, 27.1% yield): LC-MS Anal. Calc'd. for $C_{24}H_{33}FN_2O_2$, 400.2, found 401.2, $T_r$=4.248 min (Method U).

129B Enantiomer 2 (0.02 g, 0.085 mmol, 27.1% yield): LC-MS Anal. Calc'd. for $C_{24}H_{33}FN_2O_2$, 400.2, found 401.2, $T_r$=4.248 min (Method U).

129C. Methyl 3-(3-((4-chlorophenyl)amino)-4-(diisobutylamino)-5-fluorophenyl)-3-phenylpropanoate To a solution of 129B Enantiomer 1 (40 mg, 0.100 mmol) in 1,4-dioxane (2 mL) were added 1-bromo-4-chlorobenzene (27.3 mg, 0.120 mmol), $Cs_2CO_3$ (98 mg, 0.300 mmol). The reaction mixture was purged with nitrogen for 15 minutes. Then was added Xantphos (28.9 mg, 0.050 mmol) followed by bis(dibenzylideneacetone)palladium (5.74 mg, 9.99 µmol) and heated to 110° C. overnight. Reaction mixture was diluted with ethyl acetate (20 mL) and washed with water (2×15 mL) followed by brine solution (2×15 mL). The organic layer was dried over sodium sulfate and concentrated under reduced pressure to afford 129C (brown gummy, 50 mg, 0.030 mmol, 30.2% yield). LC-MS Anal. Calc'd. for $C_{30}H_{36}ClFN_2O_2$, 510.2, found 511.2, $T_r$=4.79 min (Method U).

Example 129. 3-(3-((4-Chlorophenyl)amino)-4-(diisobutylamino)-5-fluorophenyl)-3-phenylpropanoic acid Example 129 was prepared from 129C following the procedure described for the synthesis of Example 74 from 74G. LC-MS Anal. Calc'd. for $C_{29}H_{34}ClFN_2O_2$ 496.2, found 497.2. $T_r$=2.99 min (Method O). $^1$H NMR (400 MHz, DMSO-d$_6$) δ 7.42 (s, 1H), 7.27-7.34 (m, 6H), 7.17-7.20 (m, 1H), 7.07-7.10 (m, 2H), 6.95 (s, 1H), 6.60 (dd, J=1.60, 13.20 Hz, 1H), 4.35 (t, J=8.00 Hz, 1H), 2.96-2.99 (m, 2H), 2.67-2.68 (m, 4H), 1.54-1.60 (m, 2H), 0.83 (d, J=6.80 Hz, 12H).

Example 130

Enantiomer 1

3-(4-(Diisobutylamino)-3-fluoro-5-((2-methylbenzo[d]thiazol-6-yl)amino)phenyl)-3-phenylpropanoic acid

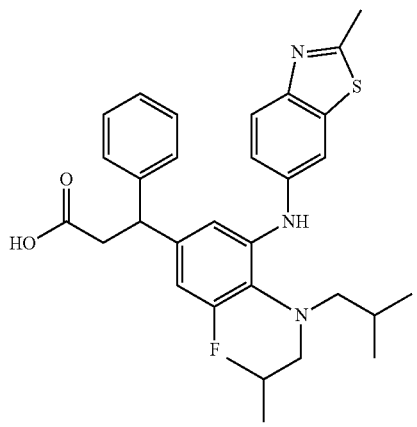 [SMILES: Cc1nc2ccc(Nc3cc(C(CC(=O)O)c4ccccc4)cc(F)c3N(CC(C)C)CC(C)C)cc2s1]

Example 130 was prepared from 129B Enantiomer 1 and 6-bromo-2-methylbenzo[d]thiazole following the procedure described for the synthesis of Example 129. LC-MS Anal. Calc'd. for $C_{31}H_{36}FN_3O_2S$, 533.2, found 534.2, $T_r$=2.7 min (Method O). $^1$H NMR (400 MHz, DMSO-d$_6$) δ7.79 (d, J=8.80 Hz, 1H), 7.68 (d, J=2.40 Hz, 1H), 7.52 (s, 1H), 7.34 (d, J=7.20 Hz, 2H), 7.29 (t, J=7.60 Hz, 2H), 7.18-7.21 (m, 1H), 7.13 (dd, J=2.40, 8.80 Hz, 1H), 7.01 (s, 1H), 6.60 (dd, J=1.60, 13.20 Hz, 1H), 4.37 (t, J=7.60 Hz, 1H), 2.97-3.00 (m, 2H), 2.75 (s, 3H), 2.67-2.70 (m, 4H), 1.56-1.63 (m, 2H), 0.85 (d, J=6.80 Hz, 12H).

Examples 131 and 132

Enantiomer 2

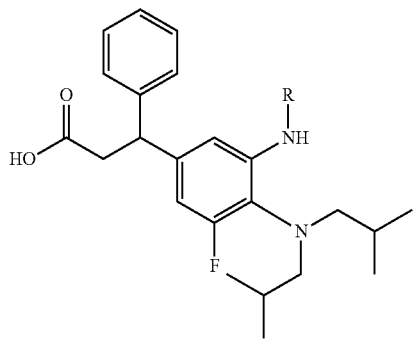

Examples 131 and 132 were prepared from 129B Enantiomer 2 and corresponding halide by following the procedure described for the synthesis of Example 129.

| Ex. No. | Name | R | $T_r$ (min) | Method | [M + H]⁺ |
|---|---|---|---|---|---|
| 131 | 3-(3-((4-chlorophenyl)amino)-4-(diisobutylamino)-5-fluorophenyl)-3-phenylpropanoic acid | 4-chlorophenyl | 2.94 | O | 497.2 |
| 132 | 3-(4-(diisobutylamino)-3-fluoro-5-((2-methylbenzo[d]thiazol-6-yl)amino)phenyl)-3-phenylpropanoic acid | 2-methylbenzo[d]thiazol-6-yl | 2.7 | O | 534.3 |

Example 133

Enantiomer 1

3-(3-((4-Chlorophenyl)amino)-4-(ethyl(tetrahydro-2H-pyran-4-yl)amino)-5-fluorophenyl)pentanoic acid

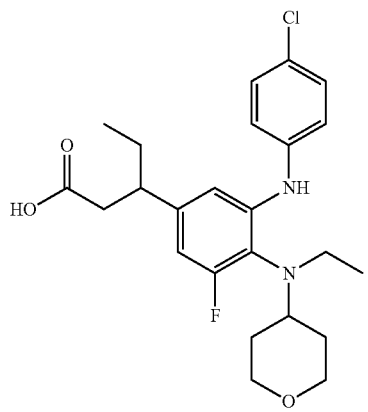 [SMILES: CCC(CC(=O)O)c1cc(F)c(N(CC)C2CCOCC2)c(Nc2ccc(Cl)cc2)c1]

133A. N-(4-Bromo-2-fluoro-6-nitrophenyl)-N-ethyl-tetrahydro-2H-pyran-4-amine

Compound 133A was prepared from 5-bromo-1,2-difluoro-3-nitrobenzene and N-ethyltetrahydro-2H-pyran-4-amine following the procedure described for the synthesis of 74C. LC-MS Anal. Calc'd. for $C_{13}H_{16}BrFN_2O$, 346.03, found (M+2) 348.2, $T_r$=3.28 (Method U). ¹H NMR (400 MHz, DMSO-$d_6$) δ 8.02 (d, J=1.60 Hz, 1H), 7.91 (dd, J=2.00, 11.00 Hz, 1H), 3.82 (dd, J=3.20, 11.20 Hz, 2H), 3.23 (t, J=10.00 Hz, 2H), 3.11-3.17 (m, 1H), 3.01-3.06 (m, 2H), 1.58 (d, J=8.00 Hz, 2H), 1.29-1.39 (m, 2H), 0.83 (t, J=7.20 Hz, 3H).

133B. Methyl 3-(4-(ethyl(tetrahydro-2H-pyran-4-yl)amino)-3-fluoro-5-nitrophenyl)pent-2-enoate To a solution of 133A (2.1 g, 6.05 mmol) in DMF (40 mL) were added (E)-methyl pent-2-enoate (2.071 g, 18.15 mmol), TEA (2.53 mL, 18.15 mmol) followed by tetrabutylammonium bromide (0.390 g, 1.210 mmol). Then reaction mixture was purged with nitrogen for 10 minutes. Then was added dichlorobis(tri-o-tolylphosphine)palladium(II) (0.238 g, 0.302 mmol) and heated to 120° C. overnight. Reaction mixture was diluted with ethyl acetate (30 mL) and washed with water (20 mL) followed by brine solution (2×20 mL). The organic layer was dried over sodium sulfate and concentrated under reduced pressure to get crude which was purified by flash chromatography (15% EA:hexane; 40 g silica gel column) to afford 133B (brown gummy 420 mg, 0.773 mmol, 12.78% yield). LC-MS Anal. Calc'd. for $C_{19}H_{25}FN_2O_5$, 380.17, found 381.2, $T_r$=3.41 min (Method U).

133C. Methyl 3-(3-amino-4-(ethyl(tetrahydro-2H-pyran-4-yl)amino)-5-fluorophenyl)pentanoate To a solution of 133B (400 mg, 1.051 mmol) in ethyl acetate (10 mL) was added 10% Pd/C (224 mg, 0.210 mmol) and stirred at room temperature under hydrogen bladder pressure for 12 h. Reaction mixture was filtered through CELITE® and concentrated under reduced pressure to get crude which purified by flash chromatography to afford Racemate 133C. LC-MS Anal. Calc'd. for $C_{19}H_{29}FN_2O_3$, 352.21, found 353.2, $T_r$=3.07 min (Method U).

Chiral separation of Racemate 133C gave Enantiomer 1 $T_r$=11.56 min and Enantiomer 2 $T_r$=16.43 min (Method BV).

133C Enantiomer 1 (brown gummy, 64 mg, 0.154 mmol, 14.67% yield): LC-MS Anal. Calc'd. for $C_{19}H_{29}FN_2O_3$, 352.21, found 353.2, $T_r$=3.12 min (Method U).

133C Enantiomer 2 (brown gummy, 57 mg, 0.145 mmol, 13.82% yield): LC-MS Anal. Calc'd. for $C_{19}H_{29}FN_2O_3$, 352.21, found 353.2, $T_r$=3.06 min (Method U).

Example 133. 3-(3-((4-Chlorophenyl)amino)-4-(ethyl(tetrahydro-2H-pyran-4-yl)amino)-5-fluorophenyl)pentanoic acid Example 133 was prepared from 133C Enantiomer 1 following the procedure described for the synthesis of Example 84. LC-MS Anal. Calc'd. for $C_{24}H_{30}ClFN_2O_3$, 448.19, found 449.2, $T_r$=2.35 min (Method R). ¹H NMR (400 MHz, DMSO-$d_6$) δ12.05 (s, 1H), 7.56 (s, 1H), 7.30 (dd, J=2.00, 6.80 Hz, 2H), 7.20 (dd, J=2.40, 6.80 Hz, 2H), 6.82 (d, J=1.60 Hz, 1H), 6.51 (dd, J=1.60, 12.80 Hz, 1H), 3.79 (s, 2H), 3.21-3.24 (m, 2H), 3.13-3.15 (m, 1H), 3.01-3.04 (m, 2H), 2.73-2.75 (m, 1H), 2.66-2.68 (m, 1H), 2.40-2.44 (m, 1H), 1.14-1.60 (m, 6H), 0.84 (t, J=7.44 Hz, 3H), 0.72 (t, J=7.20 Hz, 3H).

Examples 134 to 138

Enantiomer 1

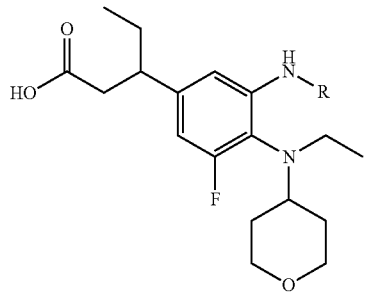

Examples 134 to 137 were prepared from 133C Enantiomer 1 and corresponding aryl halides following the procedure described for the synthesis of Example 78.

Example 138 was prepared from 133C Enantiomer 1 and corresponding aryl halides following the procedure described for the synthesis of Example 83.

Examples 139 to 144

Enantiomer 2

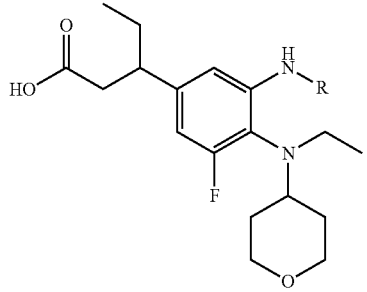

Examples 139 to 142 were prepared from 133C Enantiomer 2 and corresponding aryl halide following the procedure described for the synthesis of Example 78.

Example 143 was prepared from 133C Enantiomer 2 and corresponding aryl halide following the procedure described for the synthesis of Example 83.

Example 144 was prepared from 133C Enantiomer 2 and corresponding aryl halide following the procedure described for the synthesis of Example 133.

| Ex. No. | Name | R | $T_r$ (min) | Method | $[M + H]^+$ |
|---|---|---|---|---|---|
| 134 | 3-(3-((2-ethoxypyrimidin-5-yl)amino)-4-(ethyl(tetrahydro-2H-pyran-4-yl)amino)-5-fluorophenyl)pentanoic acid | | 1.55 | O | 461.4 |
| 135 | 3-(4-(ethyl(tetrahydro-2H-pyran-4-yl)amino)-3-fluoro-5-((2-methoxypyrimidin-5-yl)amino)phenyl)pentanoic acid | | 1.42 | O | 447.3 |
| 136 | 3-(3-((2-(cyclopropylmethoxy)pyrimidin-5-yl)amino)-4-(ethyl(tetrahydro-2H-pyran-4-yl)amino)-5-fluorophenyl)pentanoic acid | | 1.93 | O | 487.4 |
| 137 | 3-(4-(ethyl(tetrahydro-2H-pyran-4-yl)amino)-3-fluoro-5-((6-methoxypyridin-3-yl)amino)phenyl)pentanoic acid | | 1.61 | O | 446.3 |
| 138 | 3-(3-((5-cyanopyridin-2-yl)amino)-4-(ethyl(tetrahydro-2H-pyran-4-yl)amino)-5-fluorophenyl)pentanoic acid | | 1.79 | O | 441.3 |

| Ex. No. | Name | R | $T_r$, min | Method | (M + H) |
|---|---|---|---|---|---|
| 139 | 3-(3-((2-ethoxypyrimidin-5-yl)amino)-4-(ethyl(tetrahydro-2H-pyran-4-yl)amino)-5-fluorophenyl)pentanoic acid | | 1.95 | R | 461.3 |
| 140 | 3-(4-(ethyl(tetrahydro-2H-pyran-4-yl)amino)-3-fluoro-5-((2-methoxypyrimidin-5-yl)amino)phenyl)pentanoic acid | | 1.39 | O | 447.3 |
| 141 | 3-(3-((2-(cyclopropylmethoxy)pyrimidin-5-yl)amino)-4-(ethyl(tetrahydro-2H-pyran-4-yl)amino)-5-fluorophenyl)pentanoic acid | | 1.71 | O | 487.4 |
| 142 | 3-(4-(ethyl(tetrahydro-2H-pyran-4-yl)amino)-3-fluoro-5-((6-methoxypyridin-3-yl)amino)phenyl)pentanoic acid | | 1.59 | O | 446.4 |
| 143 | 3-(3-((5-cyanopyridin-2-yl)amino)-4-(ethyl(tetrahydro-2H-pyran-4-yl)amino)-5-fluorophenyl)pentanoic acid | | 1.54 | O | 441.3 |
| 144 | 3-(3-((4-chlorophenyl)amino)-4-(ethyl(tetrahydro-2H-pyran-4-yl)amino)-5-fluorophenyl)pentanoic acid | | 1.97 | O | 449.3 |

Example 145

3-(3-((4-Chlorophenyl)amino)-4-(diisobutylamino)phenyl)-3-methylbutanoic acid

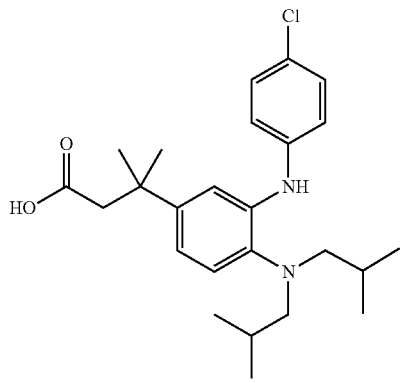 [SMILES: CC(C)CN(CC(C)C)c1ccc(C(C)(C)CC(=O)O)cc1Nc1ccc(Cl)cc1]

145A. Diethyl 2-(2-(4-fluorophenyl) propan-2-yl) malonate

To a stirred solution of magnesium (0.139 g, 5.71 mmol) in dry diethyl ether (5.0 mL), 1-bromo-4-fluorobenzene (0.500 g, 2.86 mmol) and pinch of iodine was added at room temperature. Reaction mixture was stirred for 30 minutes at room temperature. Reaction mixture was cooled to −10° C. and diethyl isopropylidenemalonate (1.144 g, 5.71 mmol) was added in dropwise over 2 minutes and stirred for 20 minutes at room temperature. The reaction mixture was then refluxed for 3 h. Reaction mixture was quenched with ice cold 1 N HCl (5 mL). Organic layer separated and aqueous layer extracted with diethyl ether (2×10 mL). The organic phases were combined, dried over anhydrous $Na_2SO_4$, and the solvent was evaporated to give 145A (light yellow liquid, 550 mg, 1.856 mmol, 65% yield). LC-MS Anal. Calc'd. for $C_{16}H_{21}FO_4$, 296.14, found [M+H] 297.2, $T_r$=1.47 min (Method BA).

145B. Ethyl 3-(4-fluorophenyl)-3-methylbutanoate

To a stirred solution of 145A (0.500 g, 1.687 mmol), in DMSO (5.0 mL), water (0.15 mL) mixture lithium chloride (0.143 g, 3.37 mmol) was added. Reaction mixture was heated to 180° C. and stirred for 12 h. Reaction mixture was cooled to room temperature, partitioned between diethyl ether (50 mL) and water (25 mL). Aqueous layer was extracted with ether (2×25 mL). The combined organic layer was washed with brine (25 mL). The organic phase were dried over anhydrous $Na_2SO_4$, filtered and concentrated to give crude compound. Purification via flash chromatography gave 145B (light yellow liquid, 255 mg, 1.137 mmol, 67% yield). LC-MS Anal. Calc'd. for $C_{13}H_{17}FO_2$ 224.12, found [M+H] 225.2, $T_r$=2.87 min (Method N).

145C. Ethyl 3-(4-fluoro-3-nitrophenyl)-3-methylbutanoate

To a 25 mL round bottomed flask at 0° C. was charged with 145B (0.200 g, 0.892 mmol) in $H_2SO_4$ (2.0 mL). Nitric acid (0.092 mL, 1.338 mmol) was added under nitrogen atmosphere and maintained at same temperature for 1 h. Reaction mixture was added to the ice and extracted with DCM (2×10 mL). The organic phase were dried over anhydrous $Na_2SO_4$, filtered and concentrated to give crude compound. Purification via flash chromatography gave 145C (colorless liquid, 210 mg, 0.780 mmol, 87% yield). LC-MS Anal. Calc'd. for $C_{13}H_{16}FNO_4$, 269.10, found [M+H] 270.2, $T_r$=1.02 min (Method BC).

145D. Ethyl 3-(4-(diisobutylamino)-3-nitrophenyl)-3-methylbutanoate

To a 5 mL pressure tube was charged with 145C (200 mg, 0.743 mmol), diisobutylamine (192 mg, 1.486 mmol) and heated to 130° C. temperature for 12 h. Reaction mixture was concentrated completely under reduced pressure to get crude reaction mixture. Purification via flash chromatography gave 145D (orange liquid, 255 mg, 0.674 mmol, 91% yield). LC-MS Anal. Calc'd. for $C_{21}H_{34}N_2O_4$, 378.2, found [M+H] 379.2, $T_r$=4.29 min (Method N).

145E. Ethyl 3-(3-amino-4-(diisobutylamino)phenyl)-3-methylbutanoate

The solution of 145D (255 mg, 0.674 mmol) in ethyl acetate (15 mL) was charged to a sealable hydrogen flask. The solution was sequentially evacuated and purged with nitrogen gas. To this 10% Pd/C (25 mg, 0.023 mmol) was charged under flow of nitrogen. The resulting mixture was sequentially evacuated then purged with nitrogen before the flask was pressured to 40 psi of hydrogen pressure and stirred at ambient temperature for 4 h. The reaction mixture was filtered through a pad of CELITE® which was then thoroughly rinsed with ethyl acetate (2×20 mL). The combined filtrates were concentrated under reduced pressure to afford 145E (230 mg, 0.660 mmol, 98% yield). LC-MS Anal. Calc'd. for $C_{21}H_{36}N_2O_2$, 348.2, found [M+H] 349.2, $T_r$=4.22 min (Method N).

145F. Ethyl 3-(3-((4-chlorophenyl)amino)-4-(diisobutylamino)phenyl)-3-methylbutanoate To a stirred solution of 145E (0.040 g, 0.115 mmol) in dry dioxane (2.0 mL), 1-bromo-4-chlorobenzene (0.022 g, 0.115 mmol), cesium carbonate (0.112 g, 0.344 mmol) was added and argon was purged for 10 minutes. 4,5-Bis(diphenylphosphino)-9,9-dimethylxanthene (0.013 g, 0.023 mmol), and bis(dibenzylideneacetone)palladium (6.60 mg, 0.011 mmol) was added under argon atmosphere. The lid of tube was closed and placed on parallel synthesizer at 100° C. temperature for 16 h. The reaction mixture was filtered through pad of CELITE®, washed with EtOAc (2×10 mL). The filtrate was concentrated under reduced pressure to get crude reaction mixture. Purification via flash chromatography gave 145F (off-white solid, 42 mg, 0.091 mmol, 80% yield). LC-MS Anal. Calc'd. for $C_{27}H_{39}ClN_2O_2$, 458.2, found [M+H] 459.1, $T_r$=1.71 min (Method BC).

Example 145. 3-(3-((4-Chlorophenyl)amino)-4-(diisobutylamino)phenyl)-3-methylbutanoic acid To a solution of 145F (0.040 g, 0.087 mmol) in THF (1.0 mL), MeOH (1.0 mL), water (0.5 mL) mixture LiOH (10.43 mg, 0.436 mmol) was added and was stirred at RT for 12 h. Solvent was concentrated under reduced pressure and the crude pH was adjusted to ~2 with 1.5 (N) HCl solution. The aqueous layer was extracted with dichloromethane (2×25 mL). The combined organic layer was dried over anhydrous sodium sulfate and concentrated under reduced pressure. Purification via preparative LC/MS gave Example 145 (36.4 mg, 0.083 mmol, 95% yield). LC-MS Anal. Calc'd. for $C_{25}H_{35}ClN_2O_2$ 430.2, found [M+H] 431.2. $T_r$=3.09 min (Method O). $^1$H NMR (400 MHz, DMSO-$d_6$) δ11.90 (br. s., 1H), 7.27-7.20 (m, 2H), 7.14-7.12 (m, 1H), 7.05-7.04 (m, 2H), 7.03-7.02 (m, 2H), 6.93-6.90 (m, 1H), 2.67-2.50 (m, 4H), 1.69-1.61 (m, 2H), 1.34 (s, 6H), 0.83 (m, 12H) (Note: one multiplet CH$_2$ buried under solvent peak).

Examples 146 to 148

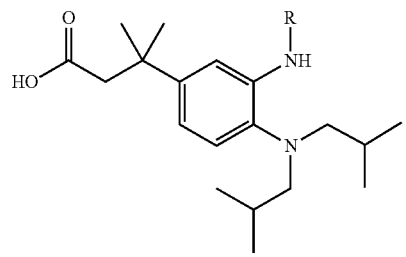

Examples 146 to 148 were prepared from 145E and corresponding aryl halides following the procedure described for the synthesis of Example 145.

| Ex. No. | Name | R | $T_r$ (min) Method O | (M + H)$^+$ |
|---|---|---|---|---|
| 146 | 3-(4-(diisobutylamino)-3-((2-methylbenzo[d]thiazol-6-yl)amino)phenyl)-3-methylbutanoic acid | | 2.807 | 468.3 |

-continued

| Ex. No. | Name | R | $T_r$ (min) Method O | $(M + H)^+$ |
|---|---|---|---|---|
| 147 | 3-(3-((2,2-difluorobenzo[d][1,3]dioxol-5-yl)amino)-4-(diisobutylamino)phenyl)-3-methylbutanoic acid | | 3.138 | 477.3 |
| 148 | 3-(4-(diisobutylamino)-3-((2-ethoxypyrimidin-5-yl)amino)phenyl)-3-methyl butanoic acid | | 2.624 | 443.4 |

Example 153

2-(4-(3-((2-Ethoxypyrimidin-5-yl)amino)-4-(ethyl(tetrahydro-2H-pyran-4-yl)amino)phenyl)tetrahydro-2H-pyran-4-yl)acetic acid

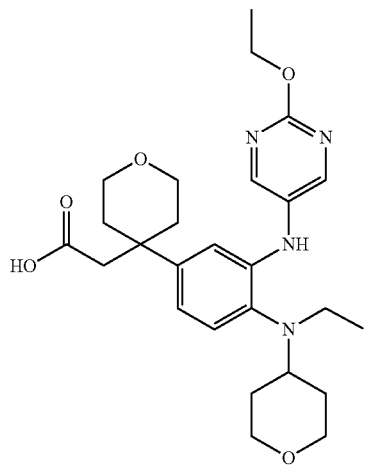 [SMILES: CCOc1ncc(Nc2cc(C3(CC(=O)O)CCOCC3)ccc2N(CC)C2CCOCC2)cn1]

153A. Ethyl 2-cyano-2-(dihydro-2H-pyran-4(3H)-ylidene)acetate

To a stirred solution of dihydro-2H-pyran-4(3H)-one (5.0 g, 49.9 mmol), ethyl 2-cyanoacetate (5.65 g, 49.9 mmol) in dry toluene (50.0 mL), ammonium acetate (0.770 g, 9.99 mmol), acetic acid (2.45 ml, 42.8 mmol) and piperidine (0.00494 mL, 0.050 mmol) were added at room temperature. Reaction mixture was heated to reflux at 110° C. for 3 h. Reaction mixture cooled to room temperature and toluene was evaporated under reduced pressure to get brown liquid. Above liquid was diluted with ethyl acetate (300 mL) and washed with water (100 mL), saturated bicarbonate solution (100 mL) and brine (100 mL). The organic phases were combined and the solvent was dried over anhydrous sodium sulfate, concentrated under reduced pressure to give off-white semi-solid. Purification by flash chromatography gave 153A (off-white solid, 7.65 g, 39.2 mmol, 78% yield). LC-MS Anal. Calc'd. for $C_{10}H_{13}NO_3$, 195.2, found [M–H] 194.2, $T_r$=0.96 min (Method BA).

153B. Ethyl 2-cyano-2-(4-(4-fluorophenyl)tetrahydro-2H-pyran-4-yl)acetate

To a stirred solution of 153A (2.5 g, 12.87 mmol), in dry diethyl ether (60 mL), (4-fluorophenyl)magnesium bromide (15.45 mL, 15.45 mmol) was added slowly in 20 min under nitrogen atmosphere at room temperature. A thick suspension of resulting mixture was refluxed at 40° C. for 5 h. Reaction mixture cooled to 0° C. and quenched with 1N HCl (25 mL). Aqueous layer extract with diethyl ether (2×50 mL). The organic phases were combined and the solvent was evaporated under reduced pressure to give brown liquid. Purification by flash chromatography gave 153B (light yellow liquid, 3.0 g, 10.30 mmol, 80% yield). LC-MS Anal. Calc'd. for $C_{16}H_{18}FNO_3$, 291.12, found [M–H] 290.4, $T_r$=1.15 min (Method BA).

153C. 2-(4-(4-Fluorophenyl)tetrahydro-2H-pyran-4-yl)acetic acid

To a stirred solution of 153B (2.9 g, 9.95 mmol) in ethylene glycol (50 mL), KOH (4.55 g, 81 mmol) and water (10.0 mL, 555 mmol) were added. Reaction mixture was heated to 180° C. and maintained for 16 h. Reaction mixture cooled to room temperature, diluted with water (100 mL) and pH was adjusted about to 3 with con. HCl. Aqueous layer extracted with dichloromethane (3×50 mL). The organic phases were combined and the solvent dried over sodium sulfate, concentrated under reduced pressure to give 153C (light yellow liquid, 2.1 g, 8.81 mmol, 89.0% yield). LC-MS Anal. Calc'd. for $C_{13}H_{15}FO_3$, 238.1, found [M+H] 239.2, $T_r$=0.48 min (Method U).

153D. Methyl 2-(4-(4-fluorophenyl)tetrahydro-2H-pyran-4-yl)acetate

To a stirred solution of 153C in MeOH (20.0 mL), $H_2SO_4$ (0.045 mL, 0.839 mmol) was added at room temperature.

Reaction mixture was heated to reflux for 6 h. Reaction mixture was cooled to room temperature, concentrated under reduced pressure to get light yellow liquid. Purification by flash chromatography gave 153D (light yellow liquid, 1.25 g, 4.95 mmol, 59.0% yield). LC-MS Anal. Calc'd. for $C_{14}H_{17}FO_3$ 252.1, found [M+H] 253.2, $T_r$=1.89 min (Method BE).

153E. Methyl 2-(4-(4-fluoro-3-nitrophenyl)tetrahydro-2H-pyran-4-yl)acetate

In a 50 mL round bottomed flask with 153D (0.750 g, 2.97 mmol) at 0° C., $H_2SO_4$ (3.0 ml, 56.3 mmol) was slowly added, followed by potassium nitrate (0.301 g, 2.97 mmol) under nitrogen atmosphere. The reaction mixture was stirred at same temperature for 15 min. Reaction mixture was poured in ice slowly for 20 minutes. Aqueous layer was extracted with ethyl acetate (2×10 mL). The organic phases were combined, dried over sodium sulfate and concentrated under reduced pressure to give light yellow liquid. Purification by flash chromatography gave 153E (light yellow liquid, 785 mg, 2.64 mmol, 89% yield). $^1$H NMR (400 MHz, $CDCl_3$) δ 8.01-7.99 (m, 1H), 7.61-7.57 (m, 1H), 7.33-7.26 (m, 1H), 3.83-3.64 (m, 4H), 3.46 (s, 3H), 2.69 (s, 2H), 2.23-2.04 (m, 4H).

153F. Methyl 2-(4-(4-(ethyl(tetrahydro-2H-pyran-4-yl)amino)-3-nitrophenyl)tetrahydro-2H-pyran-4-yl)acetate To a stirred solution of 153E (1.0 g, 3.36 mmol), N-ethyltetrahydro-2H-pyran-4-amine (0.652 g, 5.05 mmol) in NMP (10.0 mL), DIPEA (1.763 mL, 10.09 mmol) was added and heated to 135° C. for 36 h. Reaction mixture was cooled to room temperature, diluted with MTBE (50.0 mL). Organic layer was washed with water (2×25 mL). Aqueous layer was extracted with MTBE (2×30 mL). The organic phases were combined and the solvent was dried over sodium sulfate concentrated to give light yellow liquid. Purification by flash chromatography gave 153F (light orange liquid, 1.1 g, 2.71 mmol, 80% yield). LC-MS Anal. Calc'd. for $C_{21}H_{30}N_2O_6$, 406.2, found [M+H] 407.2, $T_r$=2.64 min (Method N).

153G. Methyl 2-(4-(3-amino-4-(ethyl(tetrahydro-2H-pyran-4-yl)amino)phenyl)tetrahydro-2H-pyran-4-yl)acetate To a stirred solution of 153F (1.0 g, 2.460 mmol), in dry ethyl acetate (7.5 mL), 10% Pd/C (0.100 g, 0.094 mmol) was added under nitrogen atmosphere. The resulting mixture was sequentially evacuated then purged with nitrogen before the flask was pressured to 40 psi of hydrogen and stirred at ambient temperature for 16 h. The reaction mixture was filtered through a pad of CELITE® which was then thoroughly rinsed with ethyl acetate. The combined filtrates were concentrated under reduced pressure to afford 153G (light yellow liquid, 900 mg, 2.391 mmol, 97% yield). LC-MS Anal. Calc'd. for $C_{21}H_{32}N_2O_4$, 376.2, found [M+H] 377.3, $T_r$=2.79 min (Method N).

153H. Methyl 2-(4-(3-((2-ethoxypyrimidin-5-yl)amino)-4-(ethyl(tetrahydro-2H-pyran-4-yl)amino)phenyl)tetrahydro-2H-pyran-4-yl)acetate To a degassed solution of 153G (0.075 g, 0.199 mmol), 5-bromo-2-ethoxypyrimidine (0.040 g, 0.199 mmol), cesium carbonate (0.097 g, 0.299 mmol) in dry dioxane (2.0 mL) purged argon for 15 minutes. 4,5-Bis(diphenylphosphino)-9,9-dimethylxanthene (0.012 g, 0.020 mmol), bis(dibenzylideneacetone)palladium (5.73 mg, 9.96 μmol) was added, the pressure tube lid was closed and placed on an oil bath. Reaction mixture was heated to 110° C. temperature and maintained for 4 h. The reaction mixture was filtered through pad of CELITE®, washed with EtOAc (2×10 mL). The filtrate was concentrated under reduced pressure. Purification via flash chromatography gave 153H (off-white solid, 78 mg, 0.156 mmol, 79% yield). LC-MS Anal. Calc'd. for $C_{27}H_{38}N_4O_5$, 498.2, found [M+H] 499.4. $T_r$=2.75 min (Method N).

Example 153. 2-(4-(3-((2-Ethoxypyrimidin-5-yl)amino)-4-(ethyl(tetrahydro-2H-pyran-4-yl)amino)phenyl)tetrahydro-2H-pyran-4-yl)acetic acid Example 153 was prepared from 153H following the procedure described for the synthesis of Example 145 from 145F. LC-MS Anal. Calc'd. for $C_{26}H_{36}N_4O_5$, 484.2, found [M+H] 485.1, $T_r$=1.51 min (Method O). $^1$H NMR (400 MHz, DMSO-$d_6$) δ11.9 (br. s., 1H), 8.41 (s, 2H), 7.28 (s, 1H), 7.15-7.12 (d, J=8.4 Hz, 1H), 6.97 (d, J=2.0 Hz, 1H), 6.84-6.82 (m, 1H), 4.29-4.27 (m, 2H), 3.80-3.76 (m, 2H), 3.64-3.63 (m, 2H), 3.49-3.47 (m, 2H), 3.23-3.16 (m, 3H), 3.00-2.96 (m, 2H), 2.53-2.49 (m, 2H), 2.06-1.92 (m, 4H), 1.68-1.65 (m, 2H), 1.42-1.40 (m, 2H), 1.33 (m, 3H), 0.82 (t, J=7.2 Hz, 3H).

Examples 154 to 156

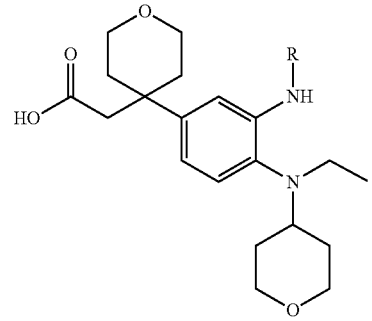

Examples 154 to 156 were prepared from 153G and corresponding aryl halides following the procedure described for the synthesis of Example 153.

| Ex. No. | Name | R | $T_r$ (min) Method O | $(M + H)^+$ |
|---|---|---|---|---|
| 154 | 2-(4-(3-((4-cyanophenyl)amino)-4-(ethyl(tetrahydro-2H-pyran-4-yl)amino)phenyl)tetrahydro-2H-pyran-4-yl)acetic acid | CN<br>⌬ | 1.659 | 464.1 |

-continued

| Ex. No. | Name | R | $T_r$ (min) Method O | $(M + H)^+$ |
|---|---|---|---|---|
| 155 | 2-(4-(3-((4-chlorophenyl)amino)-4-(ethyl(tetrahydro-2H-pyran-4-yl)amino)phenyl)tetrahydro-2H-pyran-4-yl)acetic acid | 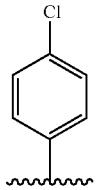 | 1.991 | 473.1 |
| 156 | 2-(4-(4-(ethyl(tetrahydro-2H-pyran-4-yl)amino)-3-(((6-methoxypyridin-3-yl)amino)phenyl)tetrahydro-2H-pyran-4-yl)acetic acid | 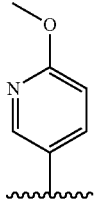 [SMILES: *c1ccc(OC)nc1] | 1.592 | 470.1 |

Example 157

2-(4-(4-(Ethyl(tetrahydro-2H-pyran-4-yl)amino)-3-(3-(p-tolyl)ureido)phenyl)tetrahydro-2H-pyran-4-yl)acetic acid

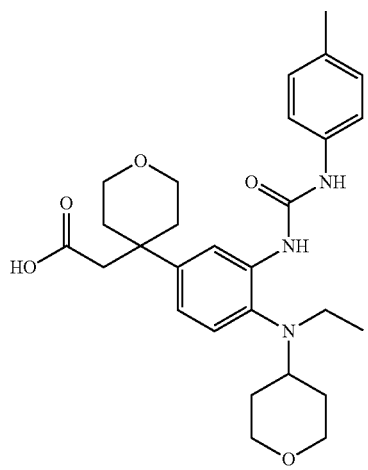 [SMILES: CCN(c1ccc(C2(CC(=O)O)CCOCC2)cc1NC(=O)Nc1ccc(C)cc1)C1CCOCC1]

157A. Methyl 2-(4-(4-(ethyl(tetrahydro-2H-pyran-4-yl)amino)-3-(3-(p-tolyl)ureido)phenyl)tetrahydro-2H-pyran-4-yl)acetate Compound 157A was prepared from 153G and 1-isocyanato-4-methylbenzene following the procedure described for the synthesis of 5A. LC-MS Anal. Calc'd. for $C_{29}H_{39}N_3O_5$, 509.2, found [M+H] 510.5, $T_r$=1.36 min (Method BA).

Example 157. 2-(4-(4-(Ethyl(tetrahydro-2H-pyran-4-yl)amino)-3-(3-(p-tolyl)ureido)phenyl)tetrahydro-2H-pyran-4-yl)acetic acid Example 157 was prepared from 157A following the procedure described for the synthesis of Example 145 from 145F. LC-MS Anal. Calc'd. for $C_{28}H_{37}N_3O_5$, 495.2, found [M+H] 496.1, $T_r$=1.59 min (Method O). $^1$H NMR (400 MHz, DMSO-d$_6$) δ 9.40 (s, 1H), 8.48 (s, 1H), 8.28 (s, 1H), 7.38-7.36 (d, J=8.4 Hz, 2H), 7.18-7.16 (m, 1H), 7.10-7.08 (m, 2H), 6.95-6.93 (m, 1H), 3.90-3.82 (m, 2H), 3.71-3.68 (m, 2H), 3.52-3.50 (m, 2H), 3.34-3.17 (m, 4H), 3.00-2.96 (m, 3H), 2.25 (s, 3H), 2.07-1.99 (m, 4H), 1.72-1.69 (m, 2H), 1.39-1.38 (m, 2H), 0.80 (t, J=6.8 Hz, 3H).

Example 158

2-(4-(3-(3-(4-Chloro-2-fluorophenyl)ureido)-4-(ethyl(tetrahydro-2H-pyran-4-yl)amino)phenyl)tetrahydro-2H-pyran-4-yl)acetic acid

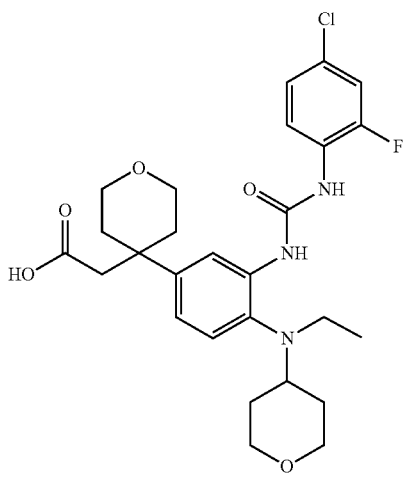 [SMILES: CCN(c1ccc(C2(CC(=O)O)CCOCC2)cc1NC(=O)Nc1ccc(Cl)cc1F)C1CCOCC1]

158A. Methyl 2-(4-(3-(3-(4-chloro-2-fluorophenyl)ureido)-4-(ethyl(tetrahydro-2H-pyran-4-yl)amino)phenyl)tetrahydro-2H-pyran-4-yl)acetate Compound 158A was prepared from 153G and 4-chloro-2-fluoro-1-isocyanatobenzene following the procedure described for the synthesis of 5A. LC-MS Anal. Calc'd. for $C_{28}H_{35}ClFN_3O_5$, 547.2, found [M+H] 548.4, $T_r$=1.44 min (Method BA).

Example 158. 2-(4-(3-(3-(4-Chloro-2-fluorophenyl) ureido)-4-(ethyl(tetrahydro-2H-pyran-4-yl)amino) phenyl)tetrahydro-2H-pyran-4-yl)acetic acid Example 158 was prepared from 158A following the procedure described for the synthesis of Example 145 from 145F. LC-MS Anal. Calc'd. for $C_{27}H_{33}ClFN_3O_5$ 533.2, found [M+H] 534.0, $T_r$=1.71 min (Method O). $^1$H NMR (400 MHz, DMSO-d$_6$) δ 9.51 (s, 1H), 8.86 (s, 1H), 8.23 (d, J=2.0 Hz, 1H), 8.16-8.11 (m, 1H), 7.45-7.24 (dd, J=2.4 Hz, 2.4 Hz, 1H), 7.22-7.16 (m, 2H), 6.98-6.96 (dd, J=2.0 Hz, 2.0 Hz, 1H), 3.89-3.82 (m, 2H), 3.68-3.66 (m, 2H), 3.50-3.46 (m, 2H), 3.34-3.17 (m, 2H), 3.00-2.96 (m, 3H), 2.53-2.50 (m, 2H), 2.07-1.90 (m, 4H), 1.72-1.69 (m, 2H), 1.41-1.38 (m, 2H), 0.80 (t, J=7.2 Hz, 3H).

Example 159

3-(3-((2-Ethoxypyrimidin-5-yl)amino)-4-(ethyl(tetrahydro-2H-pyran-4-yl)amino)phenyl)-3-methylbutanoic acid

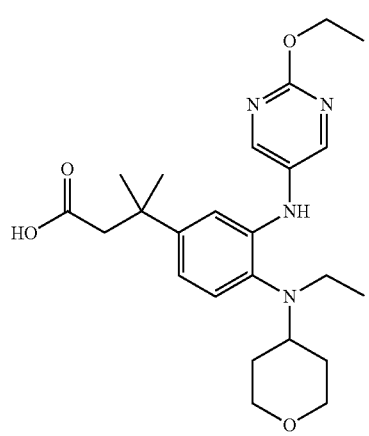 [SMILES: CCOc1ncc(Nc2cc(C(C)(C)CC(=O)O)ccc2N(CC)C2CCOCC2)cn1]

159A. Ethyl 3-(4-(ethyl(tetrahydro-2H-pyran-4-yl) amino)-3-nitrophenyl)-3-methylbutanoate To a stirred solution of 145C (2.0 g, 7.43 mmol) and N-ethyltetrahydro-2H-pyran-4-amine (1.439 g, 11.14 mmol) in NMP (5.0 mL) solvent, DIPEA (3.89 mL, 22.28 mmol) was added. Reaction mixture was heated to 135° C. for 16 h. Reaction mixture cooled to room temperature, diluted with MTBE (20 mL), washed with water (10 mL). Organic layer was separated and aqueous layer was back extracted with MTBE (2×20 mL). The organic phases were combined, dried over sodium sulfate and concentrated under reduced pressure to give light yellow liquid. Purification by flash chromatography gave 159A (520 mg, 1.374 mmol, 18.50% yield). LC-MS Anal. Calc'd for $C_{20}H_{30}N_2O_5$, 378.2, found [M+H] 379.2, $T_r$=3.374 min (Method N).

159B. Ethyl 3-(3-amino-4-(ethyl(tetrahydro-2H-pyran-4-yl)amino)phenyl)-3-methylbutanoate 159B was prepared from 159A following the procedure described for the synthesis of 145E. LC-MS Anal. Calc'd. for $C_{20}H_{32}N_2O_3$, 348.2, found [M+H] 349.2. $T_r$=3.05 min (Method N).

159C. Ethyl 3-(3-((2-ethoxypyrimidin-5-yl)amino)-4-(ethyl(tetrahydro-2H-pyran-4-yl)amino)phenyl)-3-methylbutanoate Compound 159C was prepared from 159B and 5-bromo-2-ethoxypyrimidine following the procedure described for the synthesis of 145F. LC-MS Anal. Calc'd. for $C_{26}H_{38}N_4O_4$, 470.2, found [M+H] 471.2, $T_r$=3.684 min (Method N).

Example 159. 3-(3-((2-Ethoxypyrimidin-5-yl) amino)-4-(ethyl(tetrahydro-2H-pyran-4-yl)amino) phenyl)-3-methylbutanoic acid Example 159 was prepared from 159C following the procedure described for the synthesis of Example 145 from 145F. LC-MS Anal. Calc'd. for $C_{24}H_{34}N_4O_4$, 442.2, found [M+H] 443.4, $T_r$=2.39 min. (Method N). $^1$H NMR (400 MHz, DMSO-d$_6$) δ11.90 (br. s., 1H), 8.43 (s, 2H), 7.29 (s, 1H), 7.11 (d, J=8.40 Hz, 1H), 7.02 (m, 1H), 6.86 (m, 1H), 4.27 (m, 2H), 3.83-3.80 (m, 2H), 3.25-2.97 (m, 4H), 2.99-2.98 (m, 3H), 1.51-1.50 (m, 2H), 1.48 (m, 2H), 1.44 (m, 9H), 0.77-0.82 (m, 3H).

Examples 160 to 165

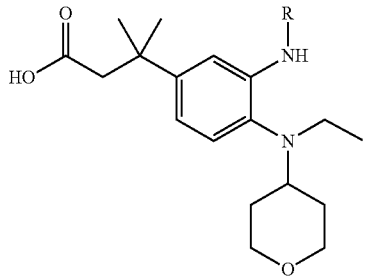

Examples 160 to 165 were prepared from 159B and the corresponding aryl halides following the procedure described for the synthesis of Example 145.

| Ex. No. | Name | R | T$_r$ (min) Method O | (M + H)$^+$ |
|---|---|---|---|---|
| 160 | 3-(3-((4-cyanophenyl)amino)-4-(ethyl(tetrahydro-2H-pyran-4-yl)amino)phenyl)-3-methylbutanoic acid | 4-cyanophenyl | 1.814 | 422.3 |
| 161 | 3-(3-((2,2-difluorobenzo[d][1,3]dioxol-5-yl)amino)-4-(ethyl(tetrahydro-2H-pyran-4-yl)amino)phenyl)-3-methylbutanoic acid | 2,2-difluorobenzo[d][1,3]dioxol-5-yl | 1.814 | 477.2 |
| 162 | 3-(4-(ethyl(tetrahydro-2H-pyran-4-yl)amino)-3-((2-methoxypyrimidin-5-yl)amino)phenyl)-3-methylbutanoic acid | 2-methoxypyrimidin-5-yl | 1.51 | 429.2 |
| 163 | 3-(3-((2-(cyclopropylmethoxy)pyrimidin-5-yl)amino)-4-(ethyl(tetrahydro-2H-pyran-4-yl)amino)phenyl)-3-methylbutanoic acid | 2-(cyclopropylmethoxy)pyrimidin-5-yl | 1.98 | 469.3 |
| 164 | 3-(4-(ethyl(tetrahydro-2H-pyran-4-yl)amino)-3-((2-methylbenzo[d]thiazol-6-yl)amino)phenyl)-3-methylbutanoic acid | 2-methylbenzo[d]thiazol-6-yl | 2.00 | 468.2 |
| 165 | 3-(3-((4-chlorophenyl)amino)-4-(ethyl(tetrahydro-2H-pyran-4-yl)amino)phenyl)-3-methylbutanoic acid | 4-chlorophenyl | 2.32 | 431.2 |

Example 166

3-(3-(3-(4-Ethoxyphenyl)ureido)-4-(ethyl(tetrahydro-2H-pyran-4-yl)amino)phenyl)-3-methylbutanoic acid

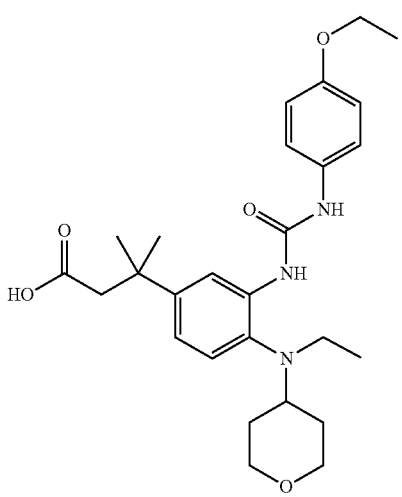 [SMILES: CCOc1ccc(NC(=O)Nc2cc(C(C)(C)CC(=O)O)ccc2N(CC)C2CCOCC2)cc1]

166A. Ethyl 3-(3-(3-(4-ethoxyphenyl)ureido)-4-(ethyl(tetrahydro-2H-pyran-4-yl)amino)phenyl)-3-methylbutanoate Compound 166A was prepared from 159B and 1-ethoxy-4-isocyanatobenzene following the procedure described for the synthesis of 5A. LC-MS Anal. Calc'd. for $C_{29}H_{41}N_3O_5$, 511.305, found [M+H] 512.6, $T_r$=1.20 min (Method BC).

Example 166. 3-(3-(3-(4-Ethoxyphenyl)ureido)-4-(ethyl(tetrahydro-2H-pyran-4-yl)amino)phenyl)-3-methylbutanoic acid Example 166 was prepared from 166A following the procedure described for the synthesis of Example 145 from 145F. LC-MS Anal. Calc'd. $C_{27}H_{37}N_3O_5$ for 483.2, found [M+H] 484.3, $T_r$=1.64 min (Method O). $^1$H NMR (400 MHz, DMSO-d$_6$) δ 9.28 (s, 1H), 8.32-8.31 (m, 2H), 7.36-7.34 (d, J=8.8 Hz, 1H), 7.14-7.12 (d, J=8.0 Hz, 2H), 6.97-6.94 (m, 1H), 6.86-6.84 (m, 2H), 4.03-3.95 (m, 2H), 3.45-2.90 (m, 7H), 2.18-2.15 (m, 2H), 1.87-1.85 (m, 2H), 1.36-1.32 (m, 9H), 0.79 (t, J=6.8 Hz, 3H) (Note: one —CH$_2$ peak buried under solvent peak).

Example 167

3-(4-(Ethyl(tetrahydro-2H-pyran-4-yl)amino)-3-(3-(p-tolyl)ureido)phenyl)-3-methylbutanoic acid

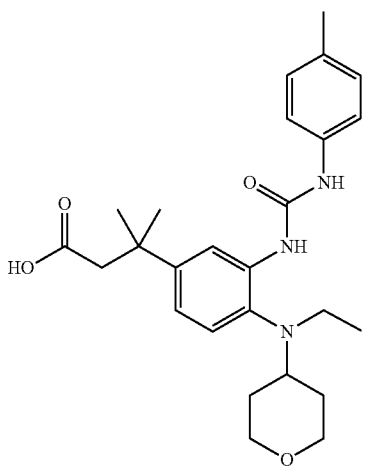 [SMILES: CCN(c1ccc(C(C)(C)CC(=O)O)cc1NC(=O)Nc1ccc(C)cc1)C1CCOCC1]

167A. Ethyl 3-(4-(ethyl(tetrahydro-2H-pyran-4-yl)amino)-3-(3-(p-tolyl)ureido)phenyl)-3-methylbutanoate Compound 167A was prepared from 159B and 1-isocyanato-4-methylbenzene following the procedure described for the synthesis of 5A. LC-MS Anal. Calc'd. for $C_{28}H_{39}N_3O_4$, 481.294, found [M+H] 482.5, $T_r$=1.23 min (Method CI).

Example 167. 3-(4-(Ethyl(tetrahydro-2H-pyran-4-yl)amino)-3-(3-(p-tolyl)ureido)phenyl)-3-methylbutanoic acid Example 167 was prepared from 167A following the procedure described for the synthesis of Example 145 from 145F. LC-MS Anal. Calc'd. $C_{26}H_{35}N_3O_4$ for 453.263, found [M+H] 454.3, $T_r$=1.806 min (Method O). $^1$H NMR (400 MHz, DMSO-d$_6$) δ11.8 (br. s., 1H), 9.4 (s, 1H), 8.46 (s, 1H), 8.31 (d, J=2.0 Hz, 1H), 7.38 (d, J=8.4 Hz, 2H), 7.14-7.08 (m, 3H), 6.97-6.76 (m, 1H), 3.83-3.81 (m, 2H), 3.37-3.23 (m, 4H), 2.99-2.94 (m, 3H), 2.25 (s, 3H), 1.72-1.69 (m, 2H), 1.41-1.37 (m, 8H), 0.79 (t, J=6.8 Hz, 3H).

Example 168

Enantiomer 1 and Enantiomer 2

3-(4-((1,1-Dioxidotetrahydro-2H-thiopyran-4-yl)(ethyl)amino)-3-((2-methoxypyrimidin-5-yl)amino)phenyl)-4-methoxybutanoic acid

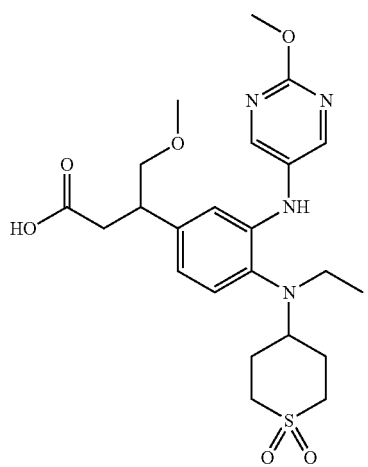 [SMILES: CCN(c1ccc(C(COC)CC(=O)O)cc1Nc1cnc(OC)nc1)C1CCS(=O)(=O)CC1]

168A. (E)-Methyl 4-methoxybut-2-enoate

To stirred solution of (E)-methyl 4-bromobut-2-enoate (3 g, 16.76 mmol) in methanol (1.5 mL), silver oxide (3.11 g, 13.41 mmol) was added and stirred at room temperature for 24 h. The reaction mixture was diluted with ethyl acetate (30 mL) filtered through CELITE® bed and washed with ethyl acetate (2×30 mL). The filtrate was evaporated to dryness under reduced pressure to get crude. Purification via flash chromatography gave 168A (yellow liquid, 0.7 g, 5.00 mmol, 29.8% yield). $^1$H NMR (400 MHz, DMSO-d$_6$) δ 6.93-6.85 (m, 1H), 6.02-5.95 (m, 1H), 4.08-4.06 (m, 2H), 3.66 (s, 3H), 3.29 (s, 3H).

168B. 2-(4-Fluorophenyl)-5,5-dimethyl-1,3,2-dioxaborinane

To a stirred solution of 1-bromo-4-fluorobenzene (20 g, 114 mmol), bis(neopentyl glycolato)diboron (31.0 g, 137 mmol) and potassium acetate (33.6 g, 343 mmol) in toluene (200 mL) was purged argon for 20 min. PdCl$_2$(dppf).CH$_2$Cl$_2$ Adduct (2.80 g, 3.43 mmol) was added and purged argon for 5 min. The reaction mixture was heated to 80° C. and maintained for 2 h. Reaction mixture was cooled to room temperature and it was concentrated under reduced pressure. The crude was dissolved in EtOAc (300 mL), filtered through a pad of CELITE® and rinsed with EtOAc (100 mL), filtrate was washed with water (200 mL) followed by brine (100 mL). The organic layers were mixed and dried over anhydrous sodium sulfate. Organic layer was concentrated under reduced pressure. Purification via flash chromatography gave 168B (off-white solid, 21 g, 96 mmol, 84% yield). $^1$H NMR (400 MHz, DMSO-d$_6$) δ 7.75-7.71 (m, 2H), 7.18-7.13 (m, 2H), 3.75 (s, 4H), 0.95 (s, 6H).

168C. Methyl 3-(4-fluorophenyl)-4-methoxybutanoate

In a sealed tube 168B (1.877 g, 14.42 mmol), 168A (1.877 g, 14.42 mmol) and sodium hydroxide solution (8.65 mL, 8.65 mmol) in 1,4-dioxane (20.0 mL) was purged argon for 30 min. To this chloro(1,5-cyclooctadiene)rhodium(I) dimer (0.237 g, 0.481 mmol) was added and purged argon for 10 min. The reaction mixture was heated at 50° C. for 2 h. Reaction mixture was cooled to room temperature and quenched with acetic acid (0.495 mL, 8.65 mmol) and it was stirred for 5 minutes. Reaction mixture was partitioned between ethyl acetate (50 mL) and water (20 mL). Aqueous layer was extracted with ethyl acetate (2×25 mL). The combined organic layer was washed with brine, dried over anhydrous sodium sulfate, concentrated under reduced pressure to get crude compound. Purification via flash chromatography gave Racemate 168C (light yellow liquid, 1.25 g, 5.53 mmol, 57.5% yield). $^1$H NMR (400 MHz, CDCl$_3$) δ 7.21-7.16 (m, 2H), 7.00-6.95 (m, 2H), 3.59 (s, 3H), 3.51-3.38 (m, 3H), 3.31 (s, 3H), 2.84-2.60 (m, 1H), 2.60-2.52 (m, 1H).

168D. Methyl 3-(4-fluoro-3-nitrophenyl)-4-methoxybutanoate

Compound 168D was prepared from 168C following the procedure described for the synthesis of 145C. LC-MS Anal. Calc'd. for C$_{12}$H$_{14}$FNO$_5$, 271.1, found [M+H] 272.2, T$_r$=2.28 min (Method U).

168E. N-Ethyltetrahydro-2H-thiopyran-4-amine

To a stirred solution of dihydro-2H-thiopyran-4(3H)-one (6.0 g, 51.6 mmol) in dry MeOH (50 mL), ethanamine (28.4 mL, 56.8 mmol) was added. Then molecular sieves (5.0 g) were added to the reaction mixture and stirred at room temperature overnight. Reaction mixture was cooled to 0° C. and NaBH$_4$ (3.91 g, 103 mmol) was added portionwise in 10 minutes. Reaction mixture was stirred at room temperature for 3 h. Reaction mixture was concentrated under reduced pressure to get semi-solid. To this was added sat. aq. NaHCO$_3$ (200 mL) and was stirred overnight. Mixture was extracted with EtOAc (2×200 mL). Combined organic layer was washed with water (100 mL), brine (100 mL), dried over Na$_2$SO$_4$ and concentrated under reduced pressure to get 168E (light yellow liquid, 6.4 g, 44.1 mmol, 85% yield). $^1$H NMR (400 MHz, CDCl$_3$) δ 2.69-2.59 (m, 6H), 2.49-2.43 (m, 1H), 2.21-2.15 (m, 2H), 1.55-1.41 (m, 2H), 1.10 (t, J=7.2 Hz, 3H).

168F. Methyl 3-(4-(ethyl(tetrahydro-2H-thiopyran-4-yl)amino)-3-nitrophenyl)-4-methoxybutanoate Compound 168F was prepared from 168D and 168E following the procedure described for the synthesis of 153F. LC-MS Anal. Calc'd. for C$_{19}$H$_{28}$N$_2$O$_5$S, 396.17, found [M+H] 397.2, T$_r$=3.108 min (Method U).

168G. Methyl 3-(4-((1,1-dioxidotetrahydro-2H-thiopyran-4-yl)(ethyl)amino)-3-nitrophenyl)-4-methoxybutanoate To a stirred solution of 168F (0.7 g, 1.765 mmol) in acetonitrile (7.0 mL), water (5.38 mL) mixture OXONE® (2.71 g, 4.41 mmol), sodium bicarbonate (1.483 g, 17.65 mmol) was added at 0° C. The reaction mixture was stirred at the same temperature for 20 minutes and continued at ambient temperature for 1 h. The resulting precipitates was diluted with acetonitrile and filtered through a pad of CELITE®. The filtrate was concentrated under reduced pressure and dilute with ethyl acetate (25 mL) washed with water (10 mL). Organic layer separated and dried over sodium sulfate, concentrated under reduced pressure to get orange liquid. Purification via flash chromatography gave Racemic 168G (orange liquid, 0.7 g, 1.65 mmol, 93% yield). LC-MS Anal. Calc'd. for $C_{19}H_{28}N_2O_7S$, 428.1, found [M+H] 429.1, $T_r$=2.58 min (Method U).

168H. Methyl 3-(3-amino-4-((1,1-dioxidotetrahydro-2H-thiopyran-4-yl)(ethyl)amino)phenyl)-4-methoxybutanoate 168H was prepared from 168G following the procedure described for the synthesis of 145E. LC-MS Anal. Calc'd. for $C_{19}H_{30}N_2O_5S$, 398.1, found [M+H] 399.2, $T_r$=1.94 min (Method U).

Chiral separation of Racemic 168H (Method Z) gave 168H Enantiomer 1 $T_r$=4.24 min (Method Z) and 168H Enantiomer 2 $T_r$=2.91 min (Method Z) as single enantiomers.

168H Enantiomer 1 (brown semi-solid, 0.15 g, 0.376 mmol, 23% yield): LC-MS Anal. Calc'd. for $C_{19}H_{30}N_2O_5S$, 398.1, found [M+H] 399.2, $T_r$=1.94 min (Method N).

168H Enantiomer 2 (brown semi-solid, 0.15 g, 0.376 mmol, 23% yield): LC-MS Anal. Calc'd. for $C_{19}H_{30}N_2O_5S$, 398.1, found [M+H] 399.2, $T_r$=1.94 min (Method N).

168I Enantiomer 1. Methyl 3-(4-((1,1-dioxidotetrahydro-2H-thiopyran-4-yl)(ethyl)amino)-3-((2-methoxypyrimidin-5-yl)amino)phenyl)-4-methoxybutanoate 168I Enantiomer 1 was prepared from 168H Enantiomer 1 and 5-bromo-2-methoxypyrimidine following the procedure described for the synthesis of 145F. LC-MS Anal. Calc'd. for $C_{24}H_{34}N_4O_6S$, 506.2, found [M+H] 507.4, $T_r$=1.13 min (Method BA).

Example 168 Enantiomer 1. 3-(4-((1,1-Dioxidotetrahydro-2H-thiopyran-4-yl)(ethyl)amino)-3-((2-methoxypyrimidin-5-yl)amino)phenyl)-4-methoxybutanoic acid Example 168 Enantiomer 1 was prepared from 168I Enantiomer 1 following the procedure described for the synthesis of Example 145 from 145F. LC-MS Anal. Calc'd. for $C_{23}H_{32}N_4O_6S$, 492.2, found [M+H] 493.2, $T_r$=1.13 min (Method O). $^1$H NMR (400 MHz, DMSO-$d_6$) δ 8.45 (s, 2H), 7.34 (s, 1H), 7.11-7.09 (d, J=8.0 Hz, 1H), 6.84 (m, 1H), 6.71-6.68 (dd, J=1.6, 2.0 Hz, 1H), 3.89 (s, 3H), 3.30 (s, 3H), 3.28-3.15 (m, 5H), 3.10-2.94 (m, 5H), 2.60-2.40 (m, 2H), 2.13-1.96 (m, 4H), 0.87-0.83 (t, J=6.80 Hz, 3H).

Example 168 Enantiomer 2. 3-(4-((1,1-Dioxidotetrahydro-2H-thiopyran-4-yl)(ethyl)amino)-3-((2-methoxypyrimidin-5-yl)amino)phenyl)-4-methoxybutanoic acid Example 168 Enantiomer 2 was prepared from 168H Enantiomer 2 following the procedure described for the synthesis of Example 168 Enantiomer 1. LC-MS Anal. Calc'd. for $C_{23}H_{32}N_4O_6S$, 492.2, found [M+H] 493.2, $T_r$=1.13 min (Method O). $^1$H NMR (400 MHz, DMSO-$d_6$) δ 8.45 (s, 2H), 7.34 (s, 1H), 7.11-7.09 (d, J=8.0 Hz, 1H), 6.84 (m, 1H), 6.71-6.68 (dd, J=1.6, 2.0 Hz, 1H), 3.89 (s, 3H), 3.30 (s, 3H), 3.28-3.15 (m, 5H), 3.10-2.94 (m, 5H), 2.60-2.40 (m, 2H), 2.13-1.96 (m, 4H), 0.87-0.83 (t, J=6.80 Hz, 3H).

Examples 169 to 172

Enantiomer 1

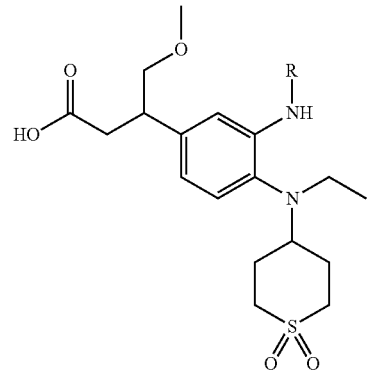

Examples 169 to 172 were prepared from 168H Enantiomer 1 and the corresponding aryl halides following the procedure described for the synthesis of Example 168 Enantiomer 1.

| Ex. No. | Name | R | $T_r$ (min) Method O | (M + H)$^+$ |
|---|---|---|---|---|
| 169 | 3-(3-((4-cyanophenyl)amino)-4-((1,1-dioxidotetrahydro-2H-thiopyran-4-yl)(ethyl)amino)phenyl)-4-methoxybutanoic acid | CN-C₆H₄- | 1.341 | 486.2 |
| 170 | 3-(3-((4-chlorophenyl)amino)-4-((1,1-dioxidotetrahydro-2H-thiopyran-4-yl)(ethyl)amino)phenyl)-4-methoxybutanoic acid | Cl-C₆H₄- | 1.580 | 495.2 |

-continued

| Ex. No. | Name | R | T$_r$ (min) Method O | (M + H)$^+$ |
|---|---|---|---|---|
| 171 | 3-(4-((1,1-dioxidotetrahydro-2H-thiopyran-4-yl)(ethyl)amino)-3-((2-ethoxypyrimidin-5-yl)amino)phenyl)-4-methoxybutanoic acid | (2-ethoxypyrimidin-5-yl) | 1.06 | 507.3 |
| 172 | 3-(4-((1,1-dioxidotetrahydro-2H-thiopyran-4-yl)(ethyl)amino)-3-((4-fluorophenyl)amino)phenyl)-4-methoxybutanoic acid | 4-fluorophenyl | 1.393 | 479.0 |

Examples 173 to 176

Enantiomer 2

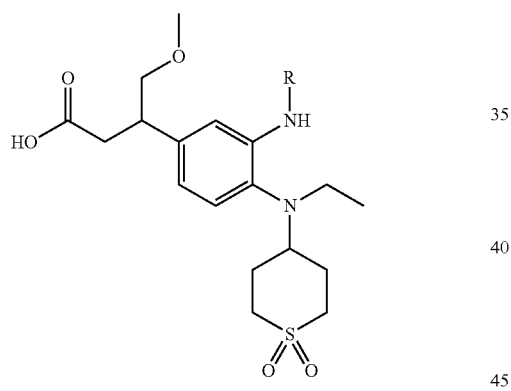

Examples 173 to 176 were prepared from 168H Enantiomer 2 and the corresponding aryl halides following the procedure described for the synthesis of Example 168 Enantiomer 1.

| Ex. No. | Name | R | T$_r$ (min) Method O | (M + H)$^+$ |
|---|---|---|---|---|
| 173 | 3-(3-((4-cyanophenyl)amino)-4-((1,1-dioxidotetrahydro-2H-thiopyran-4-yl)(ethyl)amino)phenyl)-4-methoxybutanoic acid | CN | 1.333 | 486.2 |

| Ex. No. | Name | R | T$_r$ (min) Method O | (M + H)$^+$ |
|---|---|---|---|---|
| 174 | 3-(3-((4-chlorophenyl)amino)-4-((1,1-dioxidotetrahydro-2H-thiopyran-4-yl)(ethyl)amino)phenyl)-4-methoxybutanoic acid | (4-chlorophenyl) | 1.369 | 495.3 |
| 175 | 3-(4-((1,1-dioxidotetrahydro-2H-thiopyran-4-yl)(ethyl)amino)-3-((2-ethoxypyrimidin-5-yl)amino)phenyl)-4-methoxybutanoic acid | (2-ethoxypyrimidin-5-yl) | 1.063 | 507.3 |
| 176 | 3-(4-((1,1-dioxidotetrahydro-2H-thiopyran-4-yl)(ethyl)amino)-3-((4-fluorophenyl)amino)phenyl)-4-methoxybutanoic acid | (4-fluorophenyl) | 1.389 | 479.1 |

Example 177

3-(4-((1,1-Dioxidotetrahydro-2H-thiopyran-4-yl)(ethyl)amino)-3-((2-ethoxypyrimidin-5-yl)amino)phenyl)-3-methylbutanoic acid

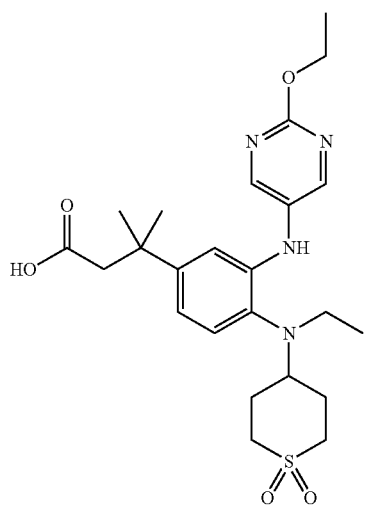 [SMILES: CCOc1ncc(Nc2cc(C(C)(C)CC(=O)O)ccc2N(CC)C2CCS(=O)(=O)CC2)cn1]

177A. N-Ethyltetrahydro-2H-thiopyran-4-amine

To a stirred solution of dihydro-2H-thiopyran-4(3H)-one (6.0 g, 51.6 mmol) in dry MeOH (50 mL), ethanamine (28.4 mL, 56.8 mmol) was added. Then molecular sieves (5.0 g) were added to the reaction mixture and were stirred at RT overnight. Reaction mixture was cooled to 0° C. and NaBH$_4$ (3.91 g, 103 mmol) was added portionwise in 10 minutes. It was stirred at room temperature for 3 h. Reaction mixture was concentrated under reduced pressure to get semi-solid. To this was added sat. aq. NaHCO$_3$ (200 mL) and was stirred overnight. Mixture was extracted with EtOAc (2×200 mL). Combined organic layer was washed with water (100 mL), brine (100 mL), dried over Na$_2$SO$_4$ and concentrated under reduced pressure to get 177A (light yellow liquid, 6.4 g, 44.1 mmol, 85% yield). $^1$H NMR (400 MHz, CDCl$_3$) δ 2.69-2.59 (m, 6H), 2.49-2.43 (m, 1H), 2.21-2.15 (m, 2H), 1.55-1.41 (m, 2H), 1.10 (t, J=7.2 Hz, 3H).

177B. Ethyl 3-(4-(ethyl(tetrahydro-2H-thiopyran-4-yl)amino)-3-nitrophenyl)-3-methylbutanoate Compound 177B was prepared from 145C and 177A following the procedure described for the synthesis of 159A. LC-MS Anal. Calc'd. for C$_{20}$H$_{30}$N$_2$O$_4$S, 394.2, found [M+H] 395.2, T$_r$=3.67 min (Method N).

177C. Ethyl 3-(4-((1,1-dioxidotetrahydro-2H-thiopyran-4-yl)(ethyl)amino)-3-nitrophenyl)-3-methylbutanoate Compound 177C was prepared from 177B following the procedure described for the synthesis of 168G. LC-MS Anal. Calc'd. for C$_{20}$H$_{30}$N$_2$O$_6$S, 426.2, found [M+H] 427.2, T$_r$=2.945 min (Method N).

177D. Ethyl 3-(3-amino-4-((1,1-dioxidotetrahydro-2H-thiopyran-4-yl)(ethyl)amino)phenyl)-3-methylbutanoate Compound 177D was prepared from 177C following the procedure described for the synthesis of 145E. LC-MS Anal. Calc'd. for $C_{20}H_{32}N_2O_4S$, 396.2, found [M+H] 397.4, $T_r$=2.669 min (Method N).

177E. Ethyl 3-(4-((1,1-dioxidotetrahydro-2H-thiopyran-4-yl)(ethyl)amino-3-((2-ethoxypyrimidin-5-yl)amino)phenyl)-3-methylbutanoate Compound 177E was prepared from 177D and 5-bromo-2-ethoxypyrimidine following the procedure described for the synthesis of 145F. LC-MS Anal. Calc'd. for $C_{26}H_{38}N_4O_5S$, 518.2, found [M+H] 519.5, $T_r$=1.43 min (Method BC).

Example 177. 3-(4-((1,1-Dioxidotetrahydro-2H-thiopyran-4-yl)(ethyl)amino)-3-((2-ethoxypyrimidin-5-yl)amino)phenyl)-3-methylbutanoic acid Example 177 was prepared from 177E following the procedure described for the synthesis of Example 145 from 145F. LC-MS Anal. Calc'd. for $C_{24}H_{34}N_4O_5S$, 490.2, found [M+H] 491.2, $T_r$=2.104 min (Method N). $^1$H NMR (400 MHz, DMSO-$d_6$) δ11.72 (br. s., 1H) 8.43 (s, 2H) 7.31 (m, 1H), 7.11-7.08 (m, 1H), 6.95 (m, 1H), 6.84-6.81 (m, 1H) 4.27 (m, 2H), 3.33-3.05 (m, 2H), 3.00-2.95 (m, 2H), 2.90 (m, 2H), 2.50 (m, 3H), 1.95-2.10 (m, 4H), 1.50-1.51 (m, 9H), 0.87 (m, 3H).

Examples 178 to 180

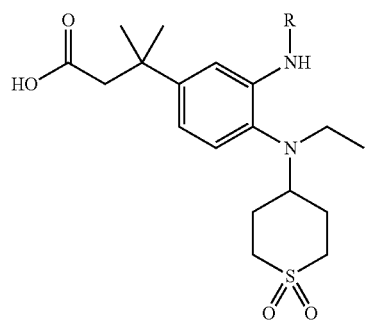

Examples 178 to 180 were prepared from 177D and the corresponding aryl halides following the procedure described for the synthesis of Example 177.

| Ex. No. | Name | R | $T_r$ (min) Method O | (M + H)⁺ |
|---|---|---|---|---|
| 178 | 3-(3-((4-cyanophenyl)amino)-4-((1,1-dioxidotetrahydro-2H-thiopyran-4-yl)(ethyl)amino)phenyl)-3-melhylbutanoic acid | CN (4-cyanophenyl) | 1.679 | 470.2 |
| 179 | 3-(3-((2,2-difluorobenzo[d][1,3]dioxol-5-yl)amino)-4-((1,1-dioxido tetrahydro-2H-thiopyran-4-yl)(ethyl)amino)phenyl)-3-methylbutanoic acid | 2,2-difluorobenzo[d][1,3]dioxol-5-yl | 2.067 | 525.2 |
| 180 | 3-(3-((4-chlorophenyl)amino)-4-((1,1-dioxido tetrahydro-2H-thiopyran-4-yl)(ethyl)amino)phenyl)-3-methylbutanoic acid | 4-chlorophenyl | 1.971 | 479.2 |

Example 181

3-(4-((1,1-Dioxidotetrahydro-2H-thiopyran-4-yl)(ethyl)amino)-3-(3-(4-ethoxyphenyl)ureido)phenyl)-3-methylbutanoic acid

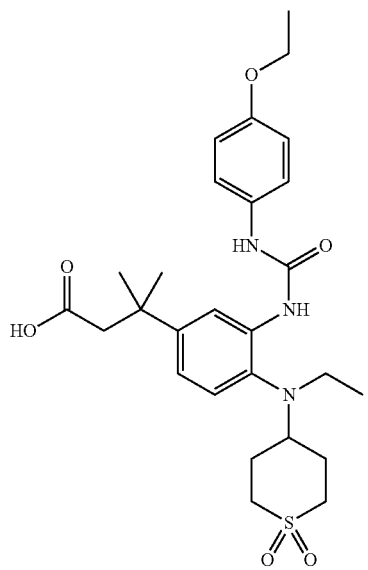 [SMILES: CCOc1ccc(NC(=O)Nc2cc(C(C)(C)CC(=O)O)ccc2N(CC)C2CCS(=O)(=O)CC2)cc1]

181A. Ethyl 3-(4-((1,1-dioxidotetrahydro-2H-thiopyran-4-yl)(ethyl)amino)-3-(3-(4-ethoxyphenyl)ureido)phenyl)-3-methylbutanoate Compound 181A was prepared from 177D and 1-ethoxy-4-isocyanatobenzene following the procedure described for the synthesis of 5A. LC-MS Anal. Calc'd. for $C_{29}H_{41}N_3O_6S$, 559.2, found [M+H] 560.2, $T_r$=0.95 min (Method BC).

Example 181. 3-(4-((1,1-Dioxidotetrahydro-2H-thiopyran-4-yl)(ethyl)amino)-3-(3-(4-ethoxyphenyl)ureido)phenyl)-3-methylbutanoic acid Example 181 was prepared from 181A following the procedure described for the synthesis of Example 145 from 145F. LC-MS Anal. Calc'd. for $C_{27}H_{37}N_3O_6S$, 531.2, found [M+H] 532.3, $T_r$=1.49 min (Method O). $^1$H NMR (400 MHz, DMSO-$d_6$) δ 9.28 (s 1H), 8.32-8.31 (m, 2H), 7.36-7.34 (d, J=8.8 Hz, 2H), 7.14-7.12 (d, J=8.8 Hz, 1H), 6.97-6.94 (m, 1H), 6.86-6.84 (m, 2H), 4.00-3.95 (m, 2H), 3.37-2.96 (s, 9H), 2.18-2.16 (m, 2H), 1.88-1.85 (m, 2H), 1.36 (s, 6H), 1.32-1.28 (m, 3H), 0.83-0.79 (m, 3H).

Example 182

Enantiomer 1 and Enantiomer 2

3-(3-((4-Cyanophenyl)amino)-4-((1,1-dioxidotetrahydro-2H-thiopyran-4-yl)(propyl)amino)phenyl)-4-methoxybutanoic acid

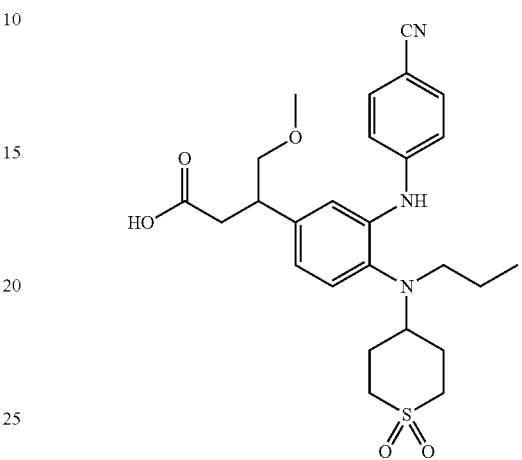

182A. N-Propyltetrahydro-2H-thiopyran-4-amine

To a stirred solution of dihydro-2H-thiopyran-4(3H)-one (5.0 g, 43.0 mmol) in dry MeOH (80 mL), propan-1-amine (2.80 g, 47.3 mmol) was added. Then molecular sieves (5.0 g) was added to the reaction mixture. Reaction mixture was stirred at RT overnight. Reaction mixture was cooled to 0° C. and added NaBH$_4$ (3.26 g, 86 mmol) portionwise in 10 minutes. It was stirred at room temperature for 3 h. Reaction mixture was concentrated under reduced pressure to get semi-solid. To this was added sat. aq. NaHCO$_3$ (200 mL) and was stirred overnight. Mixture was extracted with EtOAc (400 mL), washed with water (100 mL), brine (100 mL), dried over Na$_2$SO$_4$ and concentrated under reduced pressure to get 182A (light yellow liquid, 5.5 g, 34.5 mmol, 80% yield). $^1$H NMR (300 MHz, CDCl$_3$) δ 2.74-2.51 (m, 6H), 2.49-2.35 (m, 1H), 2.21-2.1 (m, 2H), 1.56-1.41 (m, 4H), 0.90 (t, J=7.2 Hz, 3H).

182B. N-(4-Bromo-2-nitrophenyl)-N-propyltetrahydro-2H-thiopyran-4-amine

To a solution of 4-bromo-1-fluoro-2-nitrobenzene (2.0 g, 9.09 mmol) in NMP (15 mL) was added DIPEA (4.76 mL, 27.3 mmol), followed by 182A (2.172 g, 13.64 mmol). Reaction mixture was heated to 135° C. and was stirred overnight. Reaction mixture was cooled to RT and was diluted with EtOAc (100 mL), washed with water (20 mL), brine (20 mL), dried over Na$_2$SO$_4$ and concentrated under reduced pressure to get crude compound as yellow liquid. The residue was purified via flash silica gel column chromatography to afford 182B (yellow liquid, 2.8 g, 7.79 mmol, 86% yield). LC-MS Anal. Calc'd. for $C_{14}H_{19}BrN_2O_2S$, 358.035, found [M+H] 359.2, $T_r$=3.75 min (Method U).

182C. N-(4-(5,5-Dimethyl-1,3,2-dioxaborinan-2-yl)-2-nitrophenyl)-N-propyltetrahydro-2H-thiopyran-4-amine Compound 182C was prepared from 182B following the procedure described for the synthesis of 168B. LC-MS Anal.

Calc'd. for $C_{19}H_{29}BN_2O_4S$, 392.2, found [M+H] 325.2 for parent boronic acid. $T_r$=2.74 min (Method N).

182D. Methyl 4-methoxy-3-(3-nitro-4-(propyl(tetrahydro-2H-thiopyran-4-yl)amino)phenyl)butanoate Compound 182D was prepared from 182C and (E)-methyl 4-methoxybut-2-enoate following the procedure described for the synthesis of 168C. LC-MS Anal. Calc'd. for $C_{20}H_{30}N_2O_5S$, 410.2, found [M+H] 411.2, $T_r$=3.40 min (Method BD).

182E. Methyl 3-(4-((1,1-dioxidotetrahydro-2H-thiopyran-4-yl)(propyl)amino)-3-nitrophenyl)-4-methoxybutanoate Compound 182E was prepared from 182D following the procedure described for the synthesis of 168G. LC-MS Anal. Calc'd. for $C_{20}H_{30}N_2O_7S$, 442.2, found [M+H] 443.2, $T_r$=2.17 min (Method BD).

182F. Methyl 3-(3-amino-4-((1,1-dioxidotetrahydro-2H-thiopyran-4-yl)(propyl)amino)phenyl)-4-methoxybutanoate Compound 182F was prepared from 182E following the procedure described for the synthesis of 145E. LC-MS Anal. Calc'd. for $C_{20}H_{32}N_2O_5S$, 412.2, found [M+H] 413.2, $T_r$=0.78 min (Method BC).

Chiral separation of racemic Example 182F (Method Z) gave 182F Enantiomer 1 $T_r$=3.14 min (Method Z) and 182F Enantiomer 2 $T_r$=5.85 min (Method Z) as single enantiomers.

182F Enantiomer 1 (brown semi-solid, 0.060 g, 0145 mmol, 6.44% yield): LC-MS Anal. Calc'd. for $C_{20}H_{32}N_2O_5S$, 412.2, found [M+H] 413.2, $T_r$=0.78 min (Method BC).

182F Enantiomer 2 (brown semi-solid, 0.050 g, 0121 mmol, 5.36% yield): LC-MS Anal. Calc'd. for $C_{20}H_{32}N_2O_5S$, 412.2, found [M+H] 413.2, $T_r$=0.78 min (Method BC).

182G Enantiomer 1. Methyl 3-(3-((4-cyanophenyl)amino)-4-((1,1-dioxidotetrahydro-2H-thiopyran-4-yl)(propyl)amino)phenyl)-4-methoxybutanoate 182G Enantiomer 1 was prepared from 182F Enantiomer 1 and 4-bromobenzonitrile following the procedure described for the synthesis of 145F. LC-MS Anal. Calc'd. for $C_{27}H_{35}N_3O_5S$, 513.2, found [M+H] 514.3, $T_r$=1.29 min (Method BA).

Example 182 Enantiomer 1. 3-(3-((4-Cyanophenyl)amino)-4-((1,1-dioxidotetrahydro-2H-thiopyran-4-yl)(propyl)amino)phenyl)-4-methoxybutanoic acid Example 182 Enantiomer 1 was prepared from 182G Enantiomer 1 following the procedure described for the synthesis of Example 145 from 145F. LC-MS Anal. Calc'd. for $C_{26}H_{33}N_3O_5S$, 499.2, found [M+H] 500.1, $T_r$=1.48 min (Method O). $^1$H NMR (400 MHz, DMSO-d$_6$) δ 7.88 (s, 1H), 7.57-7.52 (m, 2H), 7.18-7.14 (m, 2H), 7.06-7.04 (d, J=8.8 Hz, 2H), 6.97-6.94 (m, 1H), 3.40-3.23 (m, 6H), 3.19-3.10 (m, 4H), 3.05-2.90 (m, 2H), 2.85-2.36 (m, 3H), 2.07-1.90 (m, 4H), 1.25-1.21 (m, 2H), 0.81 (t, J=7.2 Hz, 3H).

Example 182 Enantiomer 2. 3-(3-((4-Cyanophenyl)amino)-4-((1,1-dioxidotetrahydro-2H-thiopyran-4-yl)(propyl)amino)phenyl)-4-methoxybutanoic acid Example 182 Enantiomer 2 was prepared from 182F Enantiomer 2 following the procedure described for the synthesis of Example 182 Enantiomer 1. LC-MS Anal. Calc'd. for $C_{26}H_{33}N_3O_5S$, 499.2, found [M+H] 500.1, $T_r$=1.47 min (Method O). $^1$H NMR (400 MHz, DMSO-d$_6$) δ 7.88 (s, 1H), 7.58-7.55 (m, 2H), 7.18-7.15 (m, 2H), 7.06-7.04 (d, J=8.8 Hz, 2H), 6.98-6.95 (m, 1H), 3.43-3.21 (m, 6H), 3.17-3.10 (m, 4H), 3.05-2.90 (m, 2H), 2.88-2.36 (m, 3H), 2.07-1.90 (m, 4H), 1.25-1.21 (m, 2H), 0.75 (t, J=7.2 Hz, 3H).

Examples 183 and 184

Enantiomer 1

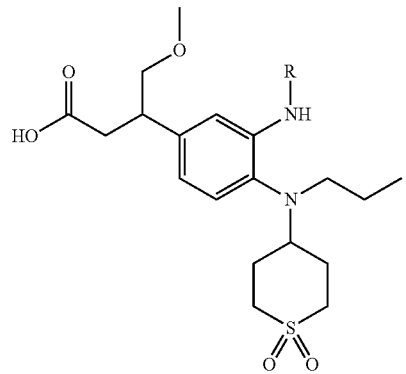

Examples 183 and 184 were prepared from 182F Enantiomer 1 and the corresponding aryl halides following the procedure described for the synthesis of Example 182 Enantiomer 1.

| Ex. No. | Name | R | $T_r$ (min) Method O | (M + H)$^+$ |
|---|---|---|---|---|
| 183 | 3-(3-((4-chlorophenyl)amino)-4-((1,1-dioxidotetrahydro-2H-thiopyran-4-yl)(propyl)amino)phenyl)-4-methoxybutanoic acid | Cl—⌬—⁓ | 1.663 | 509.0 |
| 184 | 3-(4-((1,1-dioxido-tetrahydro-2H-thiopyran-4-yl)(propyl)amino)-3-((4-fluorophenyl)amino)phenyl)-4-methoxybutanoic acid | F—⌬—⁓ | 1.530 | 493.0 |

Examples 185 and 186

Enantiomer 2

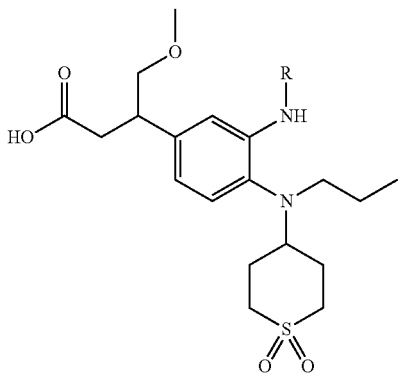

Examples 185 and 186 were prepared from 182F Enantiomer 2 and the corresponding aryl halides following the procedure described for the synthesis of Example 182 Enantiomer 1.

| Ex. No. | Name | R | $T_r$ (min) Method O | $(M + H)^+$ |
|---|---|---|---|---|
| 185 | 3-(3-((4-chlorophenyl) amino)-4-((1,1-dioxidotetrahydro-2H-thiopyran-4-yl)(propyl)amino)phenyl)-4-methoxybutanoic acid | Cl ⟨4-Cl-C6H4⟩ | 1.652 | 509.0 |
| 186 | 3-(4-((1,1-dioxido-tetrahydro-2H-thiopyran-4-yl)(propyl)amino)-3-((4-fluorophenyl)amino)phenyl)-4-methoxybutanoic acid | F ⟨4-F-C6H4⟩ | 1.53 | 493.3 |

Example 187

3-(3-((4-Cyanophenyl)amino)-4-((1,1-dioxidotetrahydro-2H-thiopyran-4-yl)(propyl)amino)phenyl)-3-methylbutanoic acid

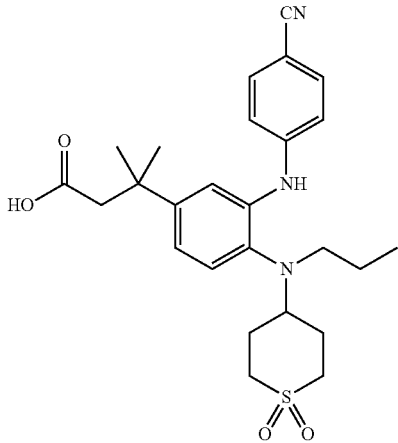 [SMILES: CCCN(c1ccc(C(C)(C)CC(=O)O)cc1Nc1ccc(C#N)cc1)C1CCS(=O)(=O)CC1]

187A. N-Propyltetrahydro-2H-thiopyran-4-amine

To a stirred solution of dihydro-2H-thiopyran-4(3H)-one (5.0 g, 43.0 mmol) in dry MeOH (80 mL), propan-1-amine (2.80 g, 47.3 mmol) was added. Then molecular sieves (5.0 g) were added to the reaction mixture. Reaction mixture was stirred at RT overnight. Reaction mixture was cooled to 0° C. and added $NaBH_4$ (3.26 g, 86 mmol) portionwise in 10 minutes. It was stirred at room temperature for 3 h. Reaction mixture was concentrated under reduced pressure to get semi-solid. To this was added sat. aq. $NaHCO_3$ (200 mL) and was stirred overnight. Reaction mixture was extracted with EtOAc (400 mL), washed with water (100 mL), brine (100 mL), dried over $Na_2SO_4$ and concentrated under reduced pressure to get 187A (light yellow liquid, 5.5 g, 34.5 mmol, 80% yield). $^1$H NMR (300 MHz, $CDCl_3$) δ 2.74-2.51 (m, 6H), 2.49-2.35 (m, 1H), 2.21-2.1 (m, 2H), 1.56-1.41 (m, 4H), 0.90 (t, J=7.2 Hz, 3H).

187B. Ethyl 3-methyl-3-(3-nitro-4-(propyl(tetrahydro-2H-thiopyran-4-yl)amino)phenyl)butanoate Compound 187B was prepared from 145C and 187A following the procedure described for the synthesis of 159A. LC-MS Anal. Calc'd. for $C_{21}H_{32}N_2O_4S$, 408.2, found [M+H] 409.2, $T_r$=4.108 min (Method N).

187C. Ethyl 3-(4-((1,1-dioxidotetrahydro-2H-thiopyran-4-yl)(propyl)amino)-3-nitrophenyl)-3-methylbutanoate Compound 187C was prepared from 187B following the procedure described for the synthesis of 168G. LC-MS Anal. Calc'd. for $C_{21}H_{32}N_2O_6S$, 440.2, found [M+H] 441.2, $T_r$=3.672 min (Method N).

187D. Ethyl 3-(3-amino-4-((1,1-dioxidotetrahydro-2H-thiopyran-4-yl)(propyl)amino)phenyl)-3-methylbutanoate 187D was prepared from 187C following the procedure described for the synthesis of 145E. LC-MS Anal. Calc'd. for $C_{21}H_{34}N_2O_4S$, 410.2, found [M+H] 411.2, $T_r$=3.48 min (Method N).

187E. Ethyl 3-(3-((4-cyanophenyl)amino)-4-((1,1-dioxidotetrahydro-2H-thiopyran-4-yl)(propyl)amino)phenyl)-3-methylbutanoate Compound 187E was prepared from 187D and 4-bromobenzonitrile following the procedure described for the synthesis of 145F. LC-MS Anal. Calc'd. for $C_{28}H_{37}N_3O_4S$, 511.2, found [M+H] 512.3, $T_r$=1.47 min (Method BA).

Example 187. 3-(3-((4-Cyanophenyl)amino)-4-((1,1-dioxidotetrahydro-2H-thiopyran-4-yl)(propyl) amino)phenyl)-3-methylbutanoic acid Example 187 was prepared from 187E following the procedure described for the synthesis of Example 145 from 145F. LC-MS Anal. Calc'd. for $C_{26}H_{33}N_3O_4S$, 483.2, found [M+H] 484.0, $T_r$=1.72 min (Method O). $^1$H NMR (400 MHz, DMSO-$d_6$) δ 7.88 (s, 1H), 7.55-7.52 (d, J=8.8 Hz, 2H), 7.25-7.20 (m, 1H), 7.16-7.10 (m, 2H), 7.08-7.00 (m, 2H), 3.17-3.02 (m, 2H), 2.99-2.87 (m, 5H), 2.53-2.51 (m, 2H), 1.97-1.91 (m, 4H), 1.33 (s, 6H), 1.19 (m, 2H), 0.75 (m, 3H).

Examples 188 and 189

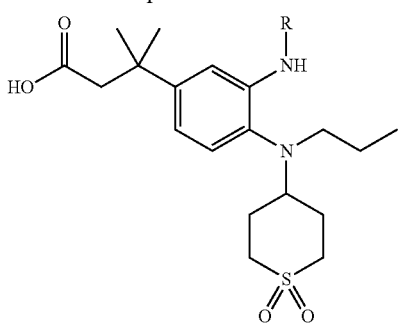

Examples 188 and 189 were prepared from 187D and the corresponding aryl halides following the procedure described for the synthesis of Example 187.

| Ex. No. | Name | R | $T_r$ (min) Method O | $(M + H)^+$ |
|---|---|---|---|---|
| 188 | 3-(4-((1,1-dioxidotetrahydro-2H-thiopyran-4-yl)(propyl)amino)-3-((2-ethoxypyrimidin-5-yl)amino)phenyl)-3-methylbutanoic acid | | 1.619 | 505.1 |
| 189 | 3-(4-((1,1-dioxidotetrahydro-2H-thiopyran-4-yl)(propyl)amino)-3-((2-methoxypyrimidin-5-yl)amino)phenyl)-3-methylbutanoic acid | | 1.482 | 491.1 |

Example 190

3-(3-(3-(4-Cyanophenyl)ureido)-4-((1,1-dioxidotetrahydro-2H-thiopyran-4-yl)(propyl)amino)phenyl)-3-methylbutanoic acid

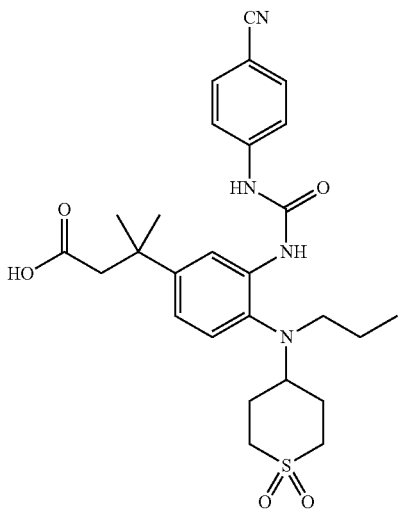 [SMILES: CCCN(c1ccc(C(C)(C)CC(=O)O)cc1NC(=O)Nc1ccc(C#N)cc1)C1CCS(=O)(=O)CC1]

190A. Ethyl 3-(3-(3-(4-cyanophenyl)ureido)-4-((1,1-dioxidotetrahydro-2H-thiopyran-4-yl)(propyl)amino)phenyl)-3-methylbutanoate 190A was prepared from 187D and 4-isocyanatobenzonitrile following the procedure described for the synthesis of 5A. LC-MS Anal. Calc'd. for $C_{29}H_{38}N_4O_5S$, 554.25, found [M+H] 555.3, $T_r$=1.39 min (Method BC).

Example 190. 3-(3-(3-(4-Cyanophenyl)ureido)-4-((1,1-dioxidotetrahydro-2H-thiopyran-4-yl)(propyl)amino)phenyl)-3-methylbutanoic acid Example 190 was prepared from 190A following the procedure described for the synthesis of Example 145 for 145F. LC-MS Anal. Calc'd. for $C_{27}H_{34}N_4O_5S$, 526.2, found [M+H] 527.1, $T_r$=1.66 min (Method O). $^1$H NMR (400 MHz, DMSO-$d_6$) δ10.02 (s, 1H), 8.50 (s, 1H), 8.30 (d, J=2.0 Hz, 1H), 7.76-7.63 (m, 5H), 7.20-7.18 (m, 1H), 7.03-6.98 (m, 1H), 3.20-2.95 (m, 7H), 2.50-2.40 (m, 2H), 2.24-2.21 (m, 2H), 1.92-1.86 (m, 2H), 1.37 (s, 6H), 1.20-1.19 (m, 2H), 0.81 (t, J=7.60 Hz, 3H).

Example 191

Enantiomer 1

3-(3-((2-Ethoxypyrimidin-5-yl)amino)-4-((2-hydroxy-2-methylpropyl)(tetrahydro-2H-pyran-4-yl)amino)phenyl)butanoic acid

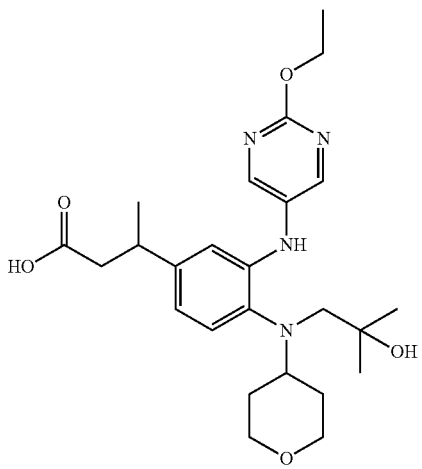 [SMILES: CCOc1ncc(Nc2cc(C(C)CC(=O)O)ccc2N(CC(C)(C)O)C2CCOCC2)cn1]

191A. 2-Methyl-1-((tetrahydro-2H-pyran-4-yl)amino)propan-2-ol

Compound 191A was prepared from dihydro-2H-pyran-4(3H)-one and 1-amino-2-methylpropan-2-ol following the procedure described for the synthesis of 168E. $^1$H NMR (400 MHz, CDCl$_3$) δ 3.90-3.80 (m, 2H), 3.45-3.30 (m, 2H), 2.55-2.50 (m, 1H), 2.40 (m, 2H), 1.90-1.83 (m, 2H), 1.45-1.30 (m, 2H), 1.14 (s, 6H).

191B. 1-((4-Bromo-2-nitrophenyl)(tetrahydro-2H-pyran-4-yl)amino)-2-methyl propan-2-ol To a stirred solution of NaH (0.818 g, 20.45 mmol) in dry DMF (20.0 mL), 191A (4.73 g, 27.3 mmol) was added at 0° C. and stirred for 30 minutes at same temperature. 4-Bromo-1-fluoro-2-nitrobenzene (3.0 g, 13.64 mmol) was added at 0° C. Reaction stirred at room temperature for 4 h. Reaction mixture quenched with 3 mL water at 0° C. and was diluted with ethyl acetate (50 mL). Organic layer washed with water (10 mL) and aqueous layer extract with ethyl acetate (2×20 mL). Organic layer dried over sodium sulfate, concentrated under reduced pressure to get orange liquid. Purification via flash chromatography gave 191B (orange semi-solid, 3.5 g, 9.38 mmol, 69% yield). LC-MS Anal. Calc'd. for C$_{15}$H$_{21}$BrN$_2$O$_4$, 372.06, found [M+H] 373.4.1, T$_r$=1.31 min (Method BA).

191C. 1-((4-(5,5-Dimethyl-1,3,2-dioxaborinan-2-yl)-2-nitrophenyl)(tetrahydro-2H-pyran-4-yl)amino)-2-methylpropan-2-ol Compound 191C was prepared from 191B following the procedure described for the synthesis of 168B. LC-MS Anal. Calc'd. for C$_{20}$H$_{313}$N$_2$O$_6$, 406.2, found [M+H] 339.0 for parent boronic acid, T$_r$=0.50 min (Method BA).

191D. Methyl 3-(4-((2-hydroxy-2-methylpropyl)(tetrahydro-2H-pyran-4-yl)amino)-3-nitrophenyl)butanoate 191D was prepared from 191C and methyl but-2-enoate following the procedure described for the synthesis of 168C. LC-MS Anal. Calc'd. for C$_{20}$H$_{30}$N$_2$O$_6$, 394.20, found [M+H] 395.5, T$_r$=1.22 min (Method BC).

191E. Methyl 3-(3-amino-4-((2-hydroxy-2-methylpropyl)(tetrahydro-2H-pyran-4-yl)amino)phenyl)butanoate 191E was prepared from 191D following the procedure described for the synthesis of 145E. LC-MS Anal. Calc'd. for C$_{20}$H$_{32}$N$_2$O$_4$, 364.20, found [M+H] 365.5, T$_r$=1.14 min (Method BC).

Chiral separation of racemic 191E (Method AM) gave 191E Enantiomer 1 T$_r$=4.24 min (Method AM) and 191E Enantiomer 2 T$_r$=9.14 min (Method AM) as single enantiomers.

191E Enantiomer 1 (light yellow semi-solid, 0.350 g, 0145 mmol, 18.4% yield): LC-MS Anal. Calc'd. for C$_{20}$H$_{32}$N$_2$O$_4$, 364.2, found [M+H] 365.2, T$_r$=2.09 min (Method N).

191E Enantiomer 2 (light yellow semi-solid, 0.350 g, 0145 mmol, 18.4% yield): LC-MS Anal. Calc'd. for C$_{20}$H$_{32}$N$_2$O$_4$, 364.2, found [M+H] 365.2, T$_r$=2.10 min (Method N).

191F Enantiomer 1. Methyl 3-(3-((2-ethoxypyrimidin-5-yl)amino)-4-((2-hydroxy-2-methylpropyl)(tetrahydro-2H-pyran-4-yl)amino)phenyl)butanoate 191F Enantiomer 1 was prepared from 191E Enantiomer 1 and 5-bromo-2-ethoxypyrimidine following the procedure described for the synthesis of 145F. LC-MS Anal. Calc'd. for C$_{26}$H$_{38}$N$_4$O$_5$ 486.2 found [M+H] 487.6, T$_r$=1.09 min (Method BC).

Example 191 Enantiomer 1. 3-(3-((2-Ethoxypyrimidin-5-yl)amino)-4-((2-hydroxy-2-methylpropyl)(tetrahydro-2H-pyran-4-yl)amino)phenyl)butanoic acid Example 191 Enantiomer 1 was prepared from 191F Enantiomer 1 and 5-bromo-2-ethoxypyrimidine following the procedure described for the synthesis of Example 145 from 145F. LC-MS Anal. Calc'd. for C$_{25}$H$_{36}$N$_4$O$_5$, 472.2, found [M+H] 473.4, T$_r$=1.08 min (Method O). $^1$H NMR (400 MHz, DMSO-d$_6$) δ 8.45 (s, 2H), 7.44 (br. s., 1H) 7.21-7.13 (m, 1H), 6.95 (m, 1H), 6.69-6.67 (m, 1H), 4.35-4.30 (m, 2H), 3.84-3.80 (m, 4H), 3.15-2.90 (m, 5H), 2.99 (m, 1H), 2.44 (m, 1H), 1.77 (m, 2H), 1.50 (m, 2H), 1.36-1.32 (t, J=7.20 Hz, 3H), 1.16-1.15 (d, J=6.80 Hz, 3H), 0.96 (m, 6H).

Examples 192 to 194

Enantiomer 1

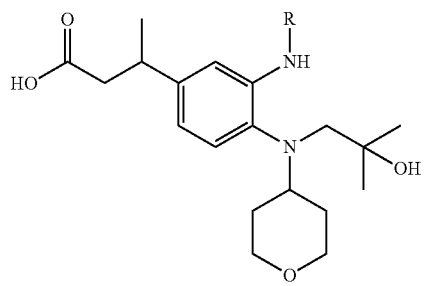

Examples 192 to 194 were prepared from 191E Enantiomer 1 and the corresponding aryl halides following the procedure described for the synthesis of Example 191 Enantiomer 1.

| Ex. No. | Name | R | $T_r$ (min) Method O | (M + H)+ |
|---|---|---|---|---|
| 192 | 3-(4-((2-hydroxy-2-methylpropyl)(tetrahydro-2H-pyran-4-yl)amino)-3-((2-methoxypyrimidin-5-yl)amino)phenyl)butanoic acid | | 1.202 | 459.4 |
| 193 | 3-(3-((4-chlorophenyl)amino)-4-((2-hydroxy-2-methylpropyl)(tetrahydro-2H-pyran-4-yl)amino)phenyl)butanoic acid | Cl | 1.420 | 461.3 |
| 194 | 3-(3-((4-cyanophenyl)amino)-4-((2-hydroxy-2-methylpropyl)(tetrahydro-2H-pyran-4-yl)amino)phenyl)butanoic acid | CN | 1.17 | 452.3 |

Example 195

Enantiomer 2

3-(3-((2-Ethoxypyrimidin-5-yl)amino)-4-((2-hydroxy-2-methylpropyl)(tetrahydro-2H-pyran-4-yl)amino)phenyl)butanoic acid

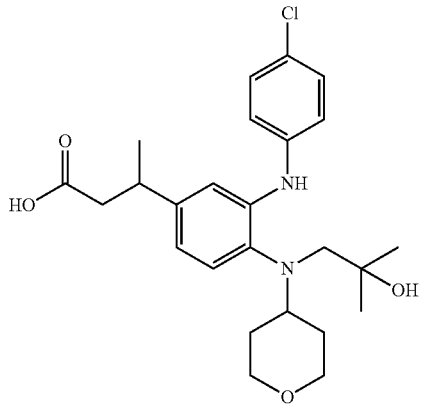 [SMILES: CC(CC(=O)O)c1ccc(N(CC(C)(C)O)C2CCOCC2)c(Nc2ccc(Cl)cc2)c1]

195A. Methyl 3-(3-((4-chlorophenyl)amino)-4-((2-hydroxy-2-methylpropyl)(tetrahydro-2H-pyran-4-yl)amino)phenyl)butanoate 195A was prepared from 191E Enantiomer 2 and 1-bromo-4-chlorobenzene following the procedure described for the synthesis of 145F. LC-MS Anal. Calc'd. for $C_{26}H_{35}ClN_2O_4$ 474.2 found [M+H] 475.6, $T_r$=1.38 min (Method BC).

Example 195 Enantiomer 2. 3-(3-((4-Chlorophenyl)amino)-4-((2-hydroxy-2-methylpropyl)(tetrahydro-2H-pyran-4-yl)amino)phenyl)butanoic acid Example 195 Enantiomer 2 was prepared from 195A following the procedure described for the synthesis of Example 145 from 145F. LC-MS Anal. Calc'd. for $C_{25}H_{33}ClN_2O_4$ 460.2 found [M+H] 461.3, $T_r$=1.43 min (Method O). $^1$H NMR (400 MHz, DMSO-$d_6$) δ11.80 (br. s., 1H), 7.61 (s, 1H) 7.29-7.26 (m, 2H), 7.17-7.11 (m, 4H), 7.07-7.06 (m, 1H), 6.76-6.73 (dd, J=2.0, 2.0 Hz, 1H), 3.09-2.90 (m, 3H), 2.68-2.54 (m, 3H), 2.52-2.30 (m, 2H), 1.71 (m, 2H), 1.46 (m, 2H), 1.16-1.15 (d, J=6.80 Hz, 3H), 0.93 (m, 6H) (Note: 2 proton buried under solvent peak).

Example 196

Enantiomer 2

3-(3-((4-Cyanophenyl)amino)-4-((2-hydroxy-2-methylpropyl)(tetrahydro-2H-pyran-4-yl)amino)phenyl)butanoic acid

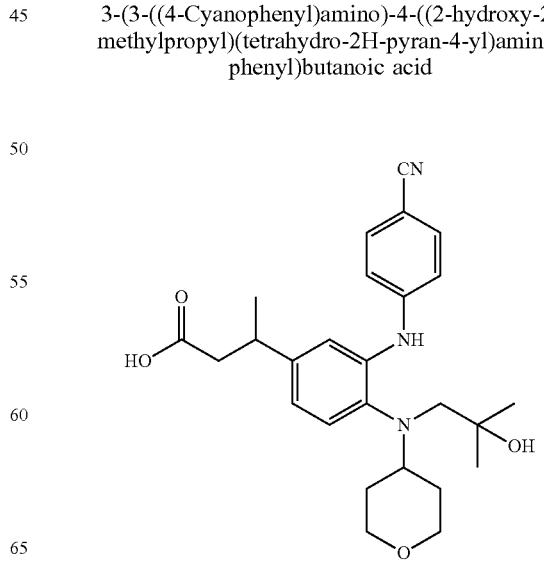

196A. Methyl 3-(3-((4-cyanophenyl)amino)-4-((2-hydroxy-2-methylpropyl)(tetrahydro-2H-pyran-4-yl)amino)phenyl)butanoate 196A was prepared from 191E Enantiomer 2 and 4-bromobenzonitrile following the procedure described for the synthesis of 145F. LC-MS Anal. Calc'd. for $C_{27}H_{35}N_3O_4$ 465.2 found [M+H] 466.6, $T_r$=1.25 min (Method BC).

Example 196 Enantiomer 2. 3-(3-((4-Cyanophenyl)amino)-4-((2-hydroxy-2-methylpropyl)(tetrahydro-2H-pyran-4-yl)amino)phenyl)butanoic acid Example 196 Enantiomer 2 was prepared from 196A following the procedure described for the synthesis of Example 145 for 145F. LC-MS Anal. Calc'd. for $C_{26}H_{33}N_3O_4$ 451.2 found [M+H] 452.3, $T_r$=1.19 min (Method O). $^1$H NMR (400 MHz, DMSO-d$_6$) δ12.10 (br. s., 1H), 8.15 (s, 1H) 7.62-7.59 (m, 2H), 7.24-7.19 (m, 2H), 7.13-7.08 (m, 2H), 6.95-6.90 (dd, J=2.0, 2.0 Hz, 1H), 3.10-2.90 (m, 5H), 2.68-2.54 (m, 4H), 1.63 (m, 2H), 1.46 (m, 2H), 1.22-1.15 (m, 3H), 0.94 (m, 6H) (Note: 2 proton buried under solvent peak).

Example 197

Enantiomer 1

(S)-3-(3-((2-Ethoxypyrimidin-5-yl)amino)-4-((2-hydroxy-2-methylpropyl)(tetrahydro-2H-pyran-4-yl)amino)phenyl)pentanoic acid

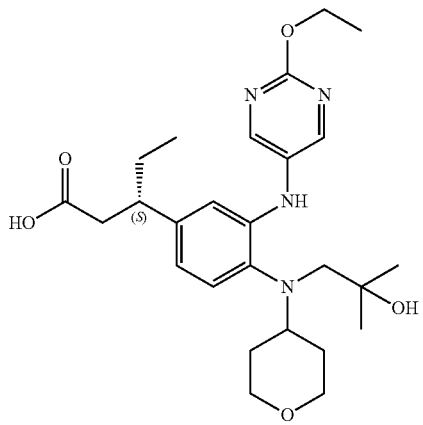

197A. (S)-Methyl 3-(4-((2-hydroxy-2-methylpropyl)(tetrahydro-2H-pyran-4-yl)amino)-3-nitrophenyl)pentanoate 197A was prepared from 191C, chlorobis(ethylene)rhodium(I) dimer and (R)-BINAP following the procedure described for the synthesis of 9B. LC-MS Anal. Calc'd. for $C_{21}H_{32}N_2O_6$, 408.2, found [M+H] 409.2, $T_r$=2.55 min (Method N). (Absolute stereochemistry of the product assigned based on the expected product enantiomer from the use of (R)-BINAP in the conjugate addition).

197B. (S)-Methyl 3-(3-amino-4-((2-hydroxy-2-methylpropyl)(tetrahydro-2H-pyran-4-yl)amino)phenyl)pentanoate 197B was prepared from 197A following the procedure described for the synthesis of 145E. LC-MS Anal. Calc'd. for $C_{21}H_{34}N_2O_4$, 378.2, found [M+H] 379.2, $T_r$=2.20 min (Method N). Analytical chiral HPLC; Chiral Purity, ee=100%, $T_r$=2.92 Min. (Method AM).

197C. (S)-Methyl 3-(3-((2-ethoxypyrimidin-5-yl)amino)-4-((2-hydroxy-2-methylpropyl)(tetrahydro-2H-pyran-4-yl)amino)phenyl)pentanoate 197C was prepared from 197B and 5-bromo-2-ethoxypyrimidine following the procedure described for the synthesis of 145F. LC-MS Anal. Calc'd. for $C_{27}H_{40}N_4O_5$, 500.3, found [M+H] 501.6, $T_r$=1.39 min (Method AY).

Example 197. (S)-3-(3-((2-Ethoxypyrimidin-5-yl)amino)-4-((2-hydroxy-2-methylpropyl)(tetrahydro-2H-pyran-4-yl)amino)phenyl)pentanoic acid Example 197 was prepared from 197C following the procedure described for the synthesis of Example 145 from 145F. LC-MS Anal. Calc'd. for $C_{26}H_{38}N_4O_5$ 486.2 found [M+H] 487.3, $T_r$=1.320 min (Method O). $^1$H NMR (400 MHz, DMSO-d$_6$) δ11.95 (br. s., 1H), 8.42 (s, 2H) 7.42 (s, 1H), 7.15-7.13 (d, J=8.0 Hz, 1H), 6.75 (m, 1H), 6.64-6.62 (dd, J=2.0, 2.0 Hz, 1H), 4.39-4.30 (m, 2H), 3.82-3.78 (m, 2H), 3.15 (m, 2H), 2.98 (m, 2H), 2.68-2.54 (m, 3H), 2.52-2.40 (m, 2H), 1.71 (m, 2H), 1.62-1.45 (m, 4H), 1.34-1.31 (m, 3H), 0.98 (s, 6H), 0.69-0.65 (d, J=8.0 Hz, 3H).

Examples 198 to 201

Enantiomer 1

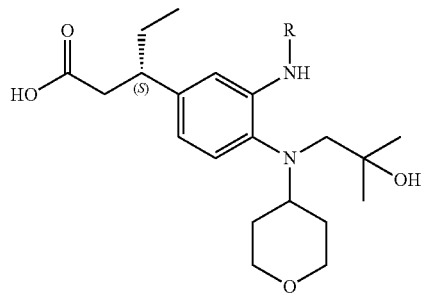

Examples 198 to 201 was prepared from 197B and the corresponding aryl halides following the procedure described for the synthesis of Example 197.

| Ex. No. | Name | R | T_r (min) Method O | (M + H)+ |
|---|---|---|---|---|
| 198 | (S)-3-(3-((4-chlorophenyl)amino)-4-((2-hydroxy-2-methylpropyl)(tetrahydro-2H-pyran-4-yl)amino)phenyl)pentanoic acid | 4-chlorophenyl | 2.014 | 475.2 |
| 199 | (S)-3-(3-((2,2-difluorobenzo[d][1,3]dioxol-5-yl)amino)-4-((2-hydroxy-2-methylpropyl)(tetrahydro-2H-pyran-4-yl)amino)phenyl)pentanoic acid | 2,2-difluorobenzo[d][1,3]dioxol-5-yl | 2.140 | 521.2 |
| 200 | (S)-3-(3-((4-chloro-3-(2,2,2-trifluoroethoxy)phenyl)amino)-4-((2-hydroxy-2-methylpropyl)(tetrahydro-2H-pyran-4-yl)amino)phenyl)pentanoic acid | 4-chloro-3-(2,2,2-trifluoroethoxy)phenyl | 2.267 | 573.3 |
| 201 | (S)-3-(3-((4-ethoxy-2-fluorophenyl)amino)-4-((2-hydroxy-2-methylpropyl)(tetrahydro-2H-pyran-4-yl)amino)phenyl)pentanoic acid | 4-ethoxy-2-fluorophenyl | 1.810 | 503.3 |

Example 202

Enantiomer 2

(R)-3-(3-((2-Ethoxypyrimidin-5-yl)amino)-4-((2-hydroxy-2-methylpropyl)(tetrahydro-2H-pyran-4-yl)amino)phenyl)pentanoic acid

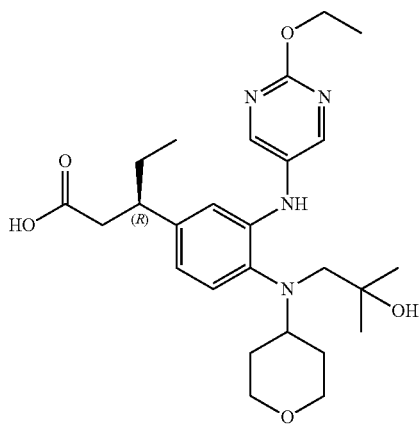

202A. (R)-Methyl 3-(4-((2-hydroxy-2-methylpropyl)(tetrahydro-2H-pyran-4-yl)amino)-3-nitrophenyl)pentanoate 202A was prepared from 191C, chlorobis(ethylene)rhodium(I) dimer and (S)-BINAP following the procedure described for the synthesis of 9B. LC-MS Anal. Calc'd. for $C_{21}H_{32}N_2O_6$, 408.2, found [M+H] 409.2, $T_r$=2.55 min (Method N). (Absolute stereochemistry of the product assigned based on the expected product enantiomer from the use of (S)-BINAP in the conjugate addition).

202B. (R)-Methyl 3-(3-amino-4-((2-hydroxy-2-methylpropyl)(tetrahydro-2H-pyran-4-yl)amino)phenyl)pentanoate 202B was prepared from 202A following the procedure described for the synthesis of 145E. LC-MS Anal. Calc'd. for $C_{21}H_{34}N_2O_4$, 378.2, found [M+H] 379.4, $T_r$=2.18 min (Method N). Chiral purity $T_r$=4.53 min with 99% ee (Method AN) as single enantiomer.

202C. (R)-Methyl 3-(3-((2-ethoxypyrimidin-5-yl)amino)-4-((2-hydroxy-2-methylpropyl)(tetrahydro-2H-pyran-4-yl)amino)phenyl)pentanoate 202C was prepared from 202B and 5-bromo-2-ethoxypyrimidine following the procedure described for the synthesis of 145F. LC-MS Anal. Calc'd. for $C_{27}H_{40}N_4O_5$, 500.3, found [M+H] 501.6, $T_r$=1.39 min (Method AY).

Example 202. (R)-3-(3-((2-Ethoxypyrimidin-5-yl)amino)-4-((2-hydroxy-2-methylpropyl)(tetrahydro-2H-pyran-4-yl)amino)phenyl)pentanoic acid Example 202 was prepared from 202C following the procedure described for the synthesis of Example 145 from 145F. LC-MS Anal. Calc'd. for $C_{26}H_{38}N_4O_5$ 486.2 found [M+H] 487.3, $T_r$=1.32 min (Method O). $^1$H NMR (400 MHz, DMSO-$d_6$) δ11.95 (br. s., 1H), 8.42 (s, 2H) 7.42 (s, 1H), 7.15-7.13 (d, J=8.0 Hz, 1H), 6.75 (m, 1H), 6.64-6.62 (dd, J=2.0, 2.0 Hz, 1H), 4.39-4.30 (m, 2H), 3.82-3.78 (m, 2H), 3.15 (m, 2H), 2.98 (m, 2H), 2.68-2.54 (m, 3H), 2.52-2.40 (m, 2H), 1.71 (m, 2H), 1.62-1.45 (m, 4H), 1.34-1.31 (m, 3H), 0.98 (s, 6H), 0.69-0.65 (d, J=8.0 Hz, 3H).

Examples 203 to 206

Enantiomer 2

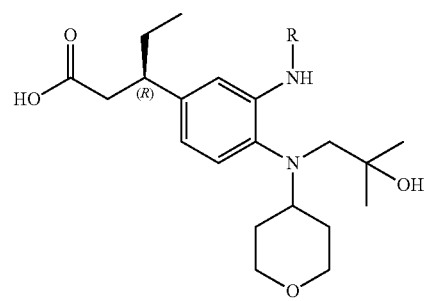

Examples 203 to 206 were prepared from 202B and the corresponding aryl halides following the procedure described for the synthesis of Example 202.

| Ex. No. | Name | R | $T_r$ (min) Method O | $(M + H)^+$ |
|---|---|---|---|---|
| 203 | (R)-3-(3-((4-chlorophenyl)amino)-4-((2-hydroxy-2-methylpropyl)(tetrahydro-2H-pyran-4-yl)amino)phenyl)pentanoic acid | 4-Cl-C6H4 | 2.00 | 475.3 |
| 204 | (R)-3-(3-((2,2-difluorobenzo[d][1,3]dioxol-5-yl)amino)-4-((2-hydroxy-2-methylpropyl)(tetrahydro-2H-pyran-4-yl)amino)phenyl)pentanoic acid | 2,2-difluorobenzo[d][1,3]dioxol-5-yl | 2.139 | 521.2 |
| 205 | (R)-3-(3-((4-chloro-3-(2,2,2-trifluoroethoxy)phenyl)amino)-4-((2-hydroxy-2-methylpropyl)(tetrahydro-2H-pyran-4-yl)amino)phenyl)pentanoic acid | 4-chloro-3-(2,2,2-trifluoroethoxy)phenyl | 2.274 | 573.3 |
| 206 | (R)-3-(3-((4-ethoxy-2-fluorophenyl)amino)-4-((2-hydroxy-2-methylpropyl)(tetrahydro-2H-pyran-4-yl)amino)phenyl)pentanoic acid | 4-ethoxy-2-fluorophenyl | 2.105 | 503.3 |

Example 207

Enantiomer 1

(S)-3-(4-((2-Hydroxy-2-methylpropyl)(tetrahydro-2H-pyran-4-yl)amino)-3-(3-(p-tolyl)ureido)phenyl)pentanoic acid

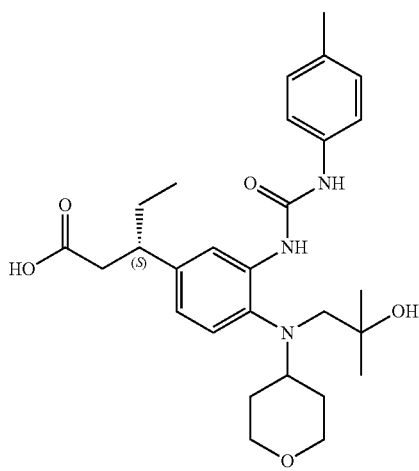

207A. (S)-Methyl 3-(4-((2-hydroxy-2-methylpropyl)(tetrahydro-2H-pyran-4-yl)amino)-3-(3-(p-tolyl)ureido)phenyl)pentanoate 207A was prepared from 197B and 1-isocyanato-4-methylbenzene following the procedure described for the synthesis of 5A. LC-MS Anal. Calc'd. for $C_{29}H_{41}N_3O_5$, 511.65, found [M+H] 512.4, $T_r$=2.78 min (Method Q).

Example 207. (S)-3-(4-((2-Hydroxy-2-methylpropyl)(tetrahydro-2H-pyran-4-yl)amino)-3-(3-(p-tolyl)ureido)phenyl)pentanoic acid Example 207 was prepared from 207A following the procedure described for the synthesis of Example 145 from 145F. LC-MS Anal. Calc'd. for $C_{28}H_{39}N_3O_5$, 497.6, found [M+H] 498.3. $T_r$=1.49 min (Method O). $^1$H NMR (400 MHz, DMSO-$d_6$) δ11.90 (br. s., 1H), 9.25 (s, 1H), 8.14 (s, 1H), 8.00 (s, 1H), 7.38-7.35 (m, 2H), 7.20-7.08 (m, 3H), 6.79-6.77 (m, 1H), 3.98-3.95 (m, 2H), 3.10-3.05 (m, 2H), 2.95-2.80 (m, 3H), 2.54-2.41 (m, 2H), 2.31 (s, 3H), 1.82-1.76 (m, 4H), 1.65-1.45 (m, 3H), 1.20-1.19 (m, 1H), 0.89 (s, 6H), 0.70 (t, J=7.20 Hz, 3H).

Example 208

Enantiomer 2

(R)-3-(4-((2-Hydroxy-2-methylpropyl)(tetrahydro-2H-pyran-4-yl)amino)-3-(3-(p-tolyl)ureido)phenyl)pentanoic acid

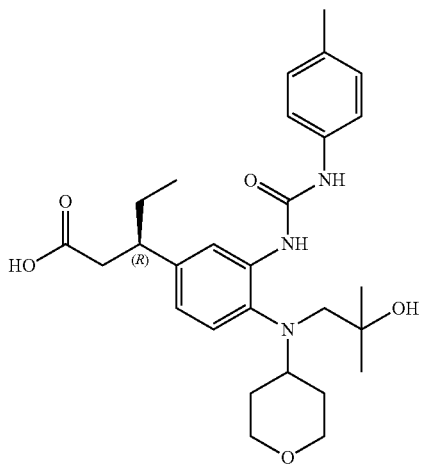

Example 208 was prepared from 202B and 1-isocyanato-4-methylbenzene following the procedure described for the synthesis of Example 207. LC-MS Anal. Calc'd. for $C_{28}H_{39}N_3O_5$, 497.6, found [M+H] 498.3. $T_r$=1.49 min (Method O). $^1$H NMR (400 MHz, DMSO-$d_6$) δ11.90 (br. s., 1H), 9.25 (s, 1H), 8.15 (s, 1H), 8.00 (s, 1H), 7.38-7.36 (m, 2H), 7.19-7.09 (m, 3H), 6.80-6.78 (m, 1H), 3.98-3.95 (m, 2H), 3.16-3.05 (m, 2H), 2.95-2.80 (m, 4H), 2.54-2.41 (m, 2H), 2.31 (s, 3H), 1.82-1.76 (m, 4H), 1.65-1.45 (m, 3H), 1.20-1.19 (m, 1H), 0.89 (s, 6H), 0.70 (t, J=7.20 Hz, 3H).

Example 209

Enantiomer 1

(R)-3-(4-((1,1-Dioxidotetrahydro-2H-thiopyran-4-yl)(isobutyl)amino)-3-(3-(p-tolyl)ureido)phenyl)pentanoic acid

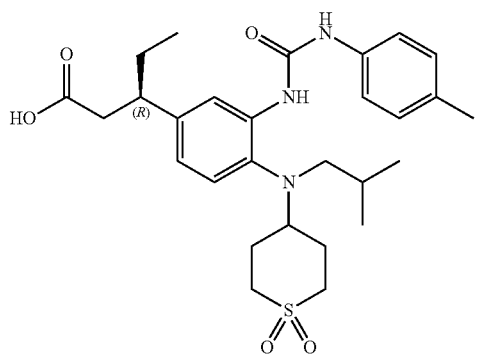

209A. N-Isobutyltetrahydro-2H-thiopyran-4-amine.HCl

To a stirred solution of dihydro-2H-thiopyran-4(3H)-one (10.0 g, 86 mmol), isobutylamine (9.36 mL, 95 mmol) in dry THF (100 mL), MeOH (100 mL) mixture under nitrogen atmosphere molecular sieves (3.0 g) was added to the reaction mixture and was stirred at RT overnight. Reaction mixture was cooled to 0° C. and NaBH$_4$ (3.91 g, 103 mmol) was added portionwise in 10 minutes. It was stirred at room temperature for 3 h. Reaction mixture was concentrated under reduced pressure to get semi-solid. To this was added sat. aq. NaHCO$_3$ (200 mL) and was stirred overnight. Mixture was extracted with EtOAc (2×200 mL). Combined organic layer was washed with water (100 mL), brine (100 mL), dried over Na$_2$SO$_4$ and concentrated under reduced pressure to get light yellow liquid. Above liquid dissolved in ether and acidified by using 4N HCl in dioxane to make HCl salt. Solid was filtered and dried under reduced pressure to give 209A (off-white solid, 14.5 g, 69.1 mmol, 80% yield). $^1$H NMR (400 MHz, DMSO-d$_6$) δ 8.69 (br. s., 1H), 3.10 (m, 1H), 2.90-2.70 (m, 5H), 2.52-2.43 (m, 2H), 2.05-1.90 (m, 1H), 1.73-1.68 (m, 2H), 1.10-0.90 (m, 6H).

209B. N-(4-Bromo-2-nitrophenyl)-N-isobutyltetrahydro-2H-thiopyran-4-amine 209B was prepared from 209A and 4-bromo-1-fluoro-2-nitrobenzene following the procedure described for the synthesis of 153F. LC-MS Anal. Calc'd. for C$_{15}$H$_{21}$BrN$_2$O$_2$S, 372.0, found [M+2] 374.4, T$_r$=1.69 min (Method AP).

209C. N-(4-(5,5-Dimethyl-1,3,2-dioxaborinan-2-yl)-2-nitrophenyl)-N-isobutyltetrahydro-2H-thiopyran-4-amine 209C was prepared from 209B following the procedure described for the synthesis of 168B. LC-MS Anal. Calc'd. for C$_{20}$H$_{31}$BN$_2$O$_4$S, 406.2, found [M+H] 339.2 for parent boronic acid. T$_r$=2.91 min (Method N).

209D. (R)-Methyl 3-(4-(isobutyl(tetrahydro-2H-thiopyran-4-yl)amino)-3-nitrophenyl)pentanoate 209D was prepared from 209C and (S)-BINAP following the procedure described for the synthesis of 197A. LC-MS Anal. Calc'd. for C$_{21}$H$_{32}$N$_2$O$_4$S, 408.2, found [M+H] 409.6, T$_r$=1.33 min (Method BC). (Absolute stereochemistry of the product assigned based on the expected product enantiomer from the use of (S)-BINAP in the conjugate addition)

209E. (R)-Methyl 3-(4-((1,1-dioxidotetrahydro-2H-thiopyran-4-yl)(isobutyl)amino)-3-nitrophenyl)pentanoate 209E was prepared from 209D following the procedure described for the synthesis of 168G. LC-MS Anal. Calc'd. for C$_{21}$H$_{32}$N$_2$O$_6$S, 440.2, found [M+H] 441.5, T$_r$=1.40 min (Method BA). Chiral purity T$_r$=2.92 min with 87% ee (Method BS).

209F. (R)-Methyl 3-(3-amino-4-((1,1-dioxidotetrahydro-2H-thiopyran-4-yl)(isobutyl)amino)phenyl)pentanoate 209F was prepared from 209E following the procedure described for the synthesis of 145E. LC-MS Anal. Calc'd. for C$_{21}$H$_{32}$N$_2$O$_6$S, 410.2, found [M+H] 411.2, T$_r$=2.87 min (Method N).

209G. (R)-Methyl 3-(4-((1,1-dioxidotetrahydro-2H-thiopyran-4-yl)(isobutyl)amino)-3-(3-(p-tolyl)ureido)phenyl)pentanoate 209G was prepared from 209F and 1-isocyanato-4-methylbenzene following the procedure described for the synthesis of 5A. LC-MS Anal. Calc'd. for C$_{29}$H$_{41}$N$_3$O$_5$S, 543.2, found [M+H] 544.6, T$_r$=1.14 min (Method BC).

Example 209. (R)-3-(4-((1,1-Dioxidotetrahydro-2H-thiopyran-4-yl)(isobutyl)amino)-3-(3-(p-tolyl)ureido)phenyl)pentanoic acid Example 209 was prepared from 209G following the procedure described for the synthesis of Example 145 for 145F. LC-MS Anal. Calc'd. for C$_{28}$H$_{39}$N$_3$O$_5$S, 529.2, found [M+H] 530.3, T$_r$=1.79 min (Method O). $^1$H NMR (400 MHz, DMSO-d$_6$) δ 9.40 (s, 1H) 8.05-7.98 (m, 2H), 7.37-7.35 (d, J=8.4 Hz, 2H), 7.14-7.08 (m, 3H), 6.79 (m, 1H), 3.33-3.10 (m, 4H), 3.05-2.95 (m, 2H), 2.60-2.50 (m, 3H), 2.40 (m, 1H), 2.32 (s, 3H), 2.22-2.15 (m, 2H), 1.92-1.85 (m, 2H), 1.74-1.21 (m, 3H), 0.82 (m, 6H), 0.72-0.69 (t, J=7.2 Hz, 3H).

Example 210

Enantiomer 2

(S)-3-(4-((1,1-Dioxidotetrahydro-2H-thiopyran-4-yl)(isobutyl)amino)-3-(3-(p-tolyl)ureido)phenyl)pentanoic acid

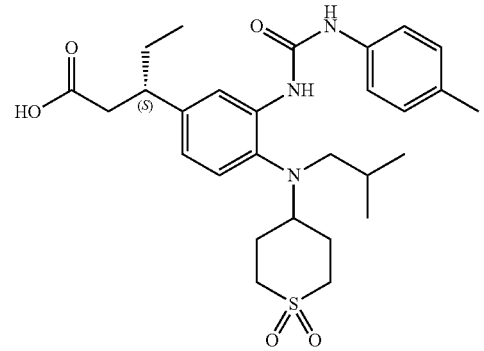

210A. (S)-Methyl 3-(4-(isobutyl(tetrahydro-2H-thiopyran-4-yl)amino)-3-nitrophenyl)pentanoate 210A was prepared from 209C and R(+) BINAP following the procedure described for the synthesis of 9B. LC-MS Anal. Calc'd. for C$_{21}$H$_{32}$N$_2$O$_4$S, 408.2, found [M+H] 409.2, T$_r$=1.33 min (Method BC). (Absolute stereochemistry of the product assigned based on the expected product enantiomer from the use of (R)-BINAP in the conjugate addition).

210B. (S)-Methyl 3-(4-((1,1-dioxidotetrahydro-2H-thiopyran-4-yl)(isobutyl)amino)-3-nitrophenyl)pentanoate 210B was prepared from 210A following the procedure described for the synthesis of 168G. LC-MS Anal. Calc'd. for $C_{21}H_{32}N_2O_6S$, 440.2, found [M+H] 441.2, $T_r$=1.40 min (Method BA). Chiral purity $T_r$=2.92 min with 98% ee (Method BS).

210C. (S)-Methyl 3-(3-amino-4-((1,1-dioxidotetrahydro-2H-thiopyran-4-yl)(isobutyl)amino)phenyl)pentanoate 210C was prepared from 210B following the procedure described for the synthesis of 145E. LC-MS Anal. Calc'd. for $C_{21}H_{34}N_2O_6S$, 410.2, found [M+H] 411.2, $T_r$=2.87 min (Method N).

210D. (S)-Methyl 3-(4-((1,1-dioxidotetrahydro-2H-thiopyran-4-yl)(isobutyl)amino)-3-(3-(p-tolyl)ureido)phenyl)pentanoate 210D was prepared from 210C and 1-isocyanato-4-methylbenzene following the procedure described for the synthesis of 5A. LC-MS Anal. Calc'd. for $C_{29}H_{41}N_3O_5S$, 543.2, found [M+H] 544.5, $T_r$=1.48 min (Method BC).

Example 210. (S)-3-(4-((1,1-Dioxidotetrahydro-2H-thiopyran-4-yl)(isobutyl)amino)-3-(3-(p-tolyl)ureido)phenyl)pentanoic acid Example 210 was prepared from 210D following the procedure described for the synthesis of Example 145 for 145F. LC-MS Anal. Calc'd. for $C_{28}H_{39}N_3O_5S$, 529.2, found [M+H] 530.3, $T_r$=1.79 min (Method O). $^1$H NMR (400 MHz, DMSO-$d_6$) δ 9.40 (s, 1H) 8.05-7.98 (m, 2H), 7.37-7.35 (d, J=8.4 Hz, 2H), 7.14-7.08 (m, 3H), 6.79 (m, 1H), 3.33-3.10 (m, 4H), 3.05-2.95 (m, 2H), 2.60-2.50 (m, 3H), 2.40 (m, 1H), 2.32 (s, 3H), 2.22-2.15 (m, 2H), 1.92-1.85 (m, 2H), 1.74-1.21 (m, 3H), 0.82 (m, 6H), 0.72-0.69 (t, J=7.2 Hz, 3H).

Examples 211 to 213

Enantiomer 1

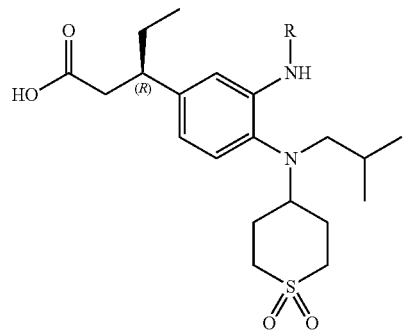

Examples 211 to 213 were prepared from 209F and the corresponding isocyanates following the procedure described for the synthesis of Example 210.

| Ex. No. | Name | R | $T_r$ (min) Method O | (M + H)$^+$ |
|---|---|---|---|---|
| 211 | (R)-3-(4-((1,1-dioxidotetrahydro-2H-thiopyran-4-yl)(isobutyl)amino)-3-(3-(2-fluoro-4-methoxyphenyl)ureido)phenyl)pentanoic acid | | 1.798 | 564.4 |
| 212 | (R)-3-(4-((1,1-dioxidotetrahydro-2H-thiopyran-4-yl)(isobutyl)amino)-3-(3-(4-ethoxyphenyl)ureido)phenyl)pentanoic acid | | 1.895 | 560.4 |

| Ex. No. | Name | R | T$_r$ (min) Method O | (M + H)$^+$ |
|---|---|---|---|---|
| 213 | (R)-3-(4-((1,1-dioxidotetrahydro-2H-thiopyran-4-yl)(isobutyl)amino)-3-(3-(5-methylisoxazol-3-yl)ureido)phenyl)pentanoic acid | 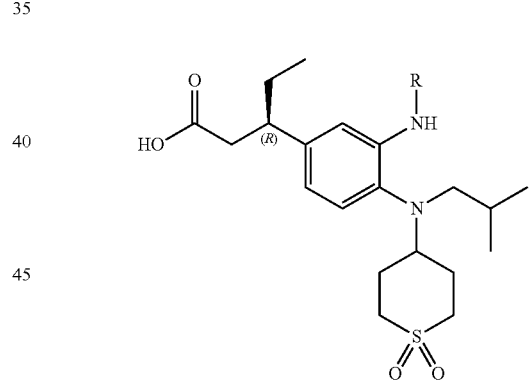 | 521.4 | 1.347 |

Example 214

Enantiomer 1

3-(4-((1,1-Dioxidotetrahydro-2H-thiopyran-4-yl)(isobutyl)amino)-3-((2-methylbenzo[d] thiazol-5-yl)amino)phenyl)pentanoic acid

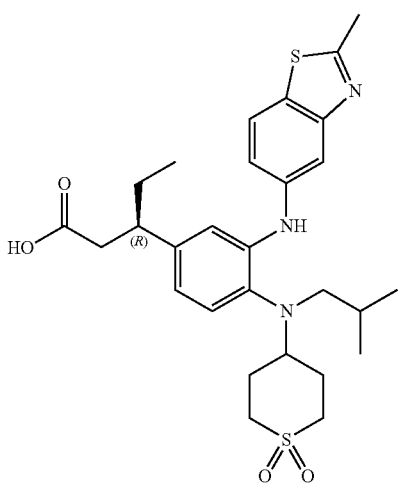

To a vial containing 209F (20 mg, 0.049 mmol), cesium carbonate (31.7 mg, 0.097 mmol), and 5-bromo-2-methyl-benzo[d]thiazole (12 mg, 0.073 mmol), was added 1,4-dioxane (1 mL). The mixture was degasified with nitrogen for 10 minutes. Xantphos (6.88 mg, 0.012 mmol) and bis(dibenzylideneacetone)palladium (1.401 mg, 2.436 µmol) were added and the reaction mixture was stirred to 110° C. for 6 h. The solvent was removed under reduced pressure. The crude residue was dissolved with DCM (0.5 mL) and treated with 1.5 N HCl until pH is acidic. The aqueous layer was extracted with DCM (1×20 mL) and concentrated under reduced pressure to get crude. To this LiOH (11.67 mg, 0.487 mmol) and MeOH (1 mL) were added. Reaction mixture was stirred at RT overnight. Purified by reverse phase prep HPLC to give Example 214 (off-white solid, 12 mg, 0.048 mmol, 42% yield). LC-MS Anal. Calc'd. for $C_{28}H_{37}N_3O_4S_2$, 543.7, found [M+H] 544.4, T$_r$=1.95 min (Method O). $^1$H NMR (400 MHz, DMSO-d$_6$) δ11.92 (s, 1H), 9.34 (s, 1H), 8.07-7.98 (m, 2H), 7.37-7.35 (m, 2H), 7.15-7.08 (m, 2H), 6.80-6.70 (m, 1H), 3.33-3.10 (m, 2H), 3.05-2.95 (m, 3H), 2.60-2.50 (m, 3H), 2.40 (m, 1H), 2.32 (s, 3H), 2.22-2.15 (m, 2H), 1.92-1.85 (m, 2H), 1.74-1.21 (m, 3H), 0.82 (m, 6H). 0.72-0.69 (t, J=7.2 Hz, 3H).

Example 215

Enantiomer 1

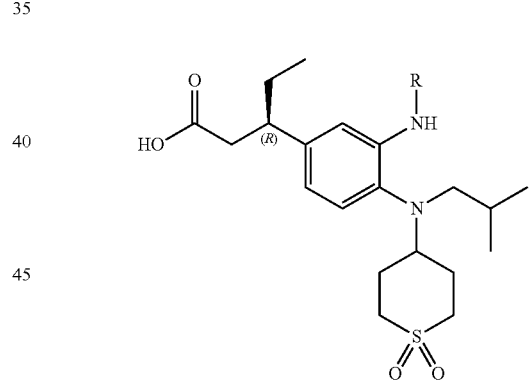

Example 215 was prepared from 209F and 5-bromo-2,2-difluorobenzo[d][1,3] dioxole following the procedure described for the synthesis of Example 214.

| Ex. No. | Name | R | T$_r$ (min) Method O | (M + H)$^+$ |
|---|---|---|---|---|
| 215 | (R)-3-(3-((2,2-difluorobenzo[d][1,3]dioxol-5-yl)amino)-4-((1,1-dioxidotetrahydro-2H-thiopyran-4-yl)(isobutyl)amino)phenyl)pentanoic acid |  | 1.961 | 553.3 |

Examples 216 to 218

Enantiomer 2

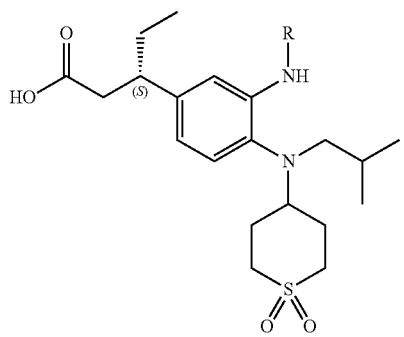

Examples 216 to 218 were prepared from 210C and the corresponding isocyanates following the procedure described for the synthesis of Example 210.

Examples 219 and 220

Enantiomer 2

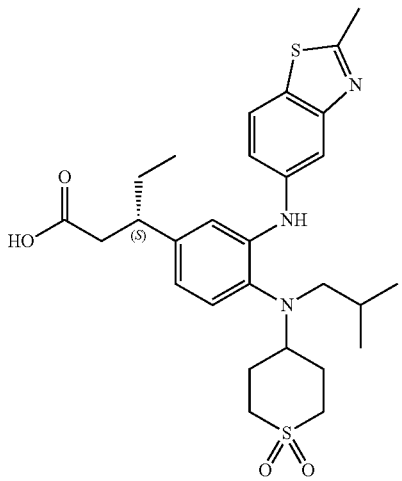

| Ex. No. | Name | R | $T_r$ (min) Method O | $(M + H)^+$ |
|---|---|---|---|---|
| 216 | (S)-3-(4-((1,1-dioxidotetrahydro-2H-thiopyran-4-yl)(isobutyl)amino)-3-(3-(2-fluoro-4-methoxyphenyl)ureido)phenyl)pentanoic acid | 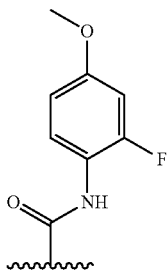 [SMILES: *C(=O)Nc1ccc(OC)cc1F] | 1.603 | 564.2 |
| 217 | (S)-3-(4-((1,1-dioxidotetrahydro-2H-thiopyran-4-yl)(isobutyl)amino)-3-(3-(4-ethoxyphenyl)ureido)phenyl)pentanoic acid | 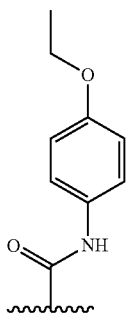 [SMILES: *C(=O)Nc1ccc(OCC)cc1] | 1.698 | 560.4 |
| 218 | (S)-3-(4-((1,1-dioxidotetrahydro-2H-thiopyran-4-yl)(isobutyl)amino)-3-(3-(5-methylisoxazol-3-yl)ureido)phenyl)pentanoic acid | 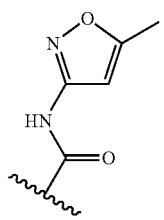 [SMILES: *C(=O)Nc1cc(C)on1] | 1.538 | 521.4 |

Examples 219 and 220 were prepared from 210C the corresponding aryl halides following the procedure described for the synthesis of Example 214.

| Ex. No. | Name | R | $T_r$ (min) Method O | $(M + H)^+$ |
|---|---|---|---|---|
| 219 | (S)-3-(4-((1,1-dioxidotetrahydro-2H-thiopyran-4-yl)(isobutyl)amino)-3-((2-methylbenzo[d]thiazol-5-yl)amino)phenyl)pentanoic acid | [2-methylbenzo[d]thiazol-5-yl structure] | 1.804 | 544.4 |
| 220 | (S)-3-(3-((2,2-difluorobenzo[d][1,3]dioxol-5-yl)amino)-4-((1,1-dioxidotetrahydro-2H-thiopyran-4-yl)(isobutyl)amino)phenyl)pentanoic acid | [2,2-difluorobenzo[d][1,3]dioxol-5-yl structure] | 2.117 | 553.3 |

Example 221

Enantiomer 1

(S)-3-(4-(Cyclohexyl(2-hydroxy-2-methylpropyl)amino)-3-(3-(p-tolyl)ureido)phenyl)pentanoic acid

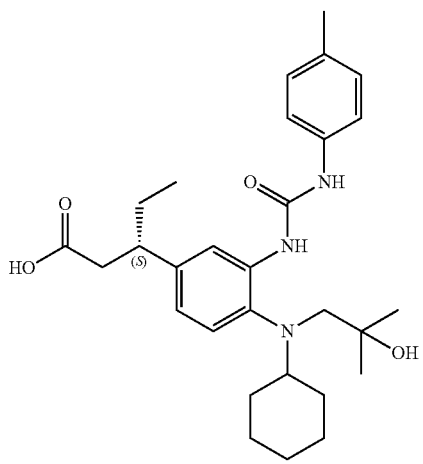

221A. 1-(Cyclohexylamino)-2-methylpropan-2-ol

To a stirred solution of cyclohexanone (10.0 g, 102 mmol), 1-amino-2-methylpropan-2-ol (9.08 g, 102 mmol) in dry THF (100 mL), MeOH (100 mL), added 3.0 g molecular sieves under nitrogen atmosphere. Reaction mixture was stirred at room temperature for 16 h. Reaction cooled to 0° C. and added NaBH$_4$ (11.56 g, 306 mmol) portionwise in 60 minutes. Reaction mixture was stirred at room temperature for 3 h. Reaction mixture was quenched with water (20 mL) at 0° C. Concentrated under reduced pressure to remove methanol completely to get semi-solid and it was quenched with 10% sodium bicarbonate (100 mL). Aqueous layer extracted with ethyl acetate (2×100 mL). Organic layer separated and washed with brine (50 mL). Organic layer dried over sodium sulfate, concentrated under reduced pressure to get liquid compound. Purification via flash chromatography gave 221A (light yellow liquid, 13.5 g, 102 mmol, 78% yield). $^1$H NMR (400 MHz, DMSO-d$_6$) δ 4.10 (br. s., 1H), 2.40 (s, 2H), 2.33-2.30 (m, 1H), 1.90-1.20 (m, 9H), 1.16 (s, 6H).

221B. 1-((4-Bromo-2-nitrophenyl)(cyclohexyl)amino)-2-methylpropan-2-ol

To a stirred solution of NaH (2.182 g, 54.5 mmol) in dry DMF (60.0 mL), 221A (12.46 g, 72.7 mmol) was added at 0° C. and maintained for 30 minutes at same temperature. 4-Bromo-1-fluoro-2-nitrobenzene (8.0 g, 36.4 mmol) was added at 0° C. Reaction stirred at room temperature for 4 h. Reaction mixture was cooled to 0° C. and quenched with 3 mL water and stirred for 10 minutes at room temperature. Reaction mixture dilute with ethyl acetate (20 mL) washed with water (10 mL), organic layer separated and aqueous layer extract with ethyl acetate (2×20 mL). Organic layer combined together dried over sodium sulfate, concentrated under reduced pressure to get orange liquid. Purification via flash chromatography gave 221B (orange liquid, 0.7 g, 1.65 mmol, 93% yield). LC-MS Anal. Calc'd. for C$_{16}$H$_{23}$BrN$_2$O$_3$, 370.2, found [M+2] 372.2, $T_r$=3.58 min (Method N).

221C. 1-(Cyclohexyl(2-nitro-4-(4,4,5,5-tetramethyl-1,3,2-dioxaborolan-2-yl)phenyl)amino)-2-methylpropan-2-ol To a stirred solution of 221B (5.0 g, 13.47 mmol), 4,4,4',4',5,5,5',5'-octamethyl-2,2'-bi(1,3,2-dioxaborolane) (4.10 g, 16.16 mmol), potassium acetate (3.97 g, 40.4 mmol) in dry DMSO (50.0 mL) purged argon for 10 minutes added PdCl$_2$ (dppf).CH$_2$Cl$_2$ Adduct (0.550 g, 0.673 mmol). Reaction placed on preheated oil bath at 80° C. and maintained for 2 h. Reaction mixture was cooled to room temperature, diluted with ethyl acetate (50 mL) washed with water (25 mL) and organic layer separated, aqueous layer back extracted with ethyl acetate (2×50 mL). Organic layers mixed together dried over sodium sulfate, concentrated completely to get brown liquid. Purification via flash chromatography gave 221C (orange semi-solid, 4.5 g, 10.76 mmol, 80% yield). LC-MS Anal. Calc'd. for $C_{22}H_{35}BN_2O_5$, 418.2, found [M+H] 419.2, $T_r$=4.00 min (Method N).

221D. (S)-Methyl 3-(4-(cyclohexyl(2-hydroxy-2-methylpropyl)amino)-3-nitrophenyl)pentanoate In a 100 mL round bottom flask 1,4-dioxane (50.0 mL), chlorobis(ethylene)rhodium(I) dimer (0.021 g, 0.054 mmol), (R)-BINAP (0.049 g, 0.079 mmol) bubbled with argon for 10 minutes, 221C (1.5 g, 3.59 mmol) and methyl pent-2-enoate (0.491 g, 4.30 mmol), sodium hydroxide (1 molar solution) (3.27 mL, 3.27 mmol) were added respectively and bubbled argon for another 5 minutes. The reaction mixture was heated at 50° C. for 1 h. Reaction mixture was cooled to room temperature and quenched with acetic acid (0.185 mL, 3.23 mmol) and it was stirred for 5 minutes. Reaction mixture was partitioned between ethyl acetate (25 mL) and water (25 mL). Aqueous layer was back extracted with ethyl acetate (2×25 mL). The combined organic layers were washed with brine, dried over anhydrous sodium sulfate, concentrated under reduced pressure to get crude compound. Purification via flash chromatography gave 221D (orange semi-solid, 0.9 g, 2.214 mmol, 62% yield). LC-MS Anal. Calc'd. for $C_{22}H_{34}N_2O_5$, 406.2, found [M+H] 407.2, $T_r$=3.58 min (Method N). (Absolute stereochemistry of the product assigned based on the expected product enantiomer from the use of (R)-BINAP in the conjugate addition).

221E. (S)-Methyl 3-(3-amino-4-(cyclohexyl(2-hydroxy-2-methylpropyl)amino)phenyl)pentanoate To sealable hydrogen stirring flask, 221D (0.900 g, 2.214 mmol), Pd/C (0.160 g, 0.151 mmol) charged in dry ethyl acetate (20.0 mL) under flow of nitrogen. The resulting mixture was sequentially evacuated then purged with nitrogen before the flask was pressured to 40 psi of hydrogen and stirred at ambient temperature for 4 hours. The reaction mixture was filtered through a pad of CELITE® which was then thoroughly rinsed with ethyl acetate (10 mL). The combined filtrates were concentrated in vacuo to afford orange semi-solid. Purification via flash chromatography gave 221E (orange semi-solid, 0.9 g, 2.214 mmol, 62% yield). LC-MS Anal. Calc'd. for $C_{22}H_{36}N_2O_3$, 376.2, found [M+H] 377.2, $T_r$=3.38 min (Method N). Chiral purity=94% ee, $T_r$=31.48 min (Method DA).

221F. (S)-Methyl 3-(4-(cyclohexyl(2-hydroxy-2-methylpropyl)amino)-3-(3-(p-tolyl)ureido)phenyl)pentanoate To a stirred solution of 221E (0.025 g, 0.066 mmol) in dry THF (1.0 mL) 1-isocyanato-4-methylbenzene (8.84 mg, 0.066 mmol) was added and stirred for 1 h at room temperature. Purification via flash chromatography gave 221F. LC-MS Anal. Calc'd. for $C_{30}H_{43}N_3O_4$, 509.3, found [M+H] 510.6, $T_r$=1.11 min (Method BC).

Example 221. (S)-3-(4-(Cyclohexyl(2-hydroxy-2-methylpropyl)amino)-3-(3-(p-tolyl)ureido)phenyl)pentanoic acid To a stirred solution of 221F (0.034 g, 0.067 mmol) in THF (1.0 mL), MeOH (0.667 mL), water (0.333 mL) mixture LiOH.H$_2$O (7.99 mg, 0.334 mmol) was added and stirred for 16 h at room temperature. Reaction mixture was concentrated under reduced pressure to get crude material. The crude pH was adjusted to ~2 with 1.5 N HCl solution and the aqueous layer was extracted with dichloromethane (2×15 mL). The combined organic layers were dried over anhydrous sodium sulfate and concentrated under reduced pressure to get crude product. Purification via preparative LC/MS gave Example 221 (off-white solid, 25.7 mg, 0.048 mmol, 72% yield). LC-MS Anal. Calc'd. for $C_{29}H_{41}N_3O_4$, 495.3, found [M+H] 496.3, $T_r$=1.72 Min (Method O). $^1$H NMR (400 MHz, DMSO-d$_6$) δ9.34 (s, 1H), 8.24 (m, 1H), 7.93 (d, J=2.0 Hz, 1H), 7.39-7.35 (m, 2H), 7.17-7.04 (m, 3H), 6.77-6.75 (m, 1H), 4.10 (br. s., 1H), 3.08-2.90 (m, 2H), 2.88-2.08 (m, 1H), 2.49-2.40 (m, 2H), 2.25 (s, 3H), 1.98-1.80 (m, 2H), 1.75-1.60 (m, 4H), 1.58-1.40 (m, 2H), 1.20-1.05 (m, 6H), 0.88 (m, 6H), 0.69 (t, J=8.00 Hz, 3H).

Examples 225 to 231

Enantiomer 1

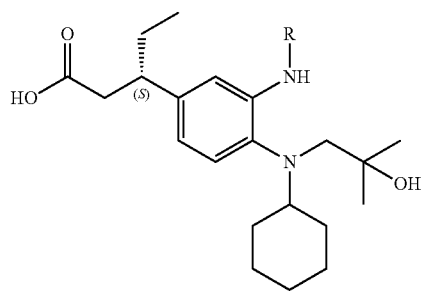

Examples 225 to 231 were prepared from 221E and corresponding aryl halides following the procedure described for the synthesis of Example 214.

| Ex. No. | Name | R | $T_r$ (min) Method O | (M + H)$^+$ |
|---|---|---|---|---|
| 225 | (S)-3-(4-(cyclohexyl(2-hydroxy-2-methylpropyl)amino)-3-((4-fluorophenyl)amino)phenyl)pentanoic acid | ![F-phenyl] | 1.633 | 457.4 |

-continued

| Ex. No. | Name | R | T_r (min) Method O | (M + H)+ |
|---|---|---|---|---|
| 226 | (S)-3-(4-(cyclohexyl(2-hydroxy-2-methylpropyl)amino)-3-((4-(difluoromethoxy)phenyl)amino)phenyl)pentanoic acid | 4-(OCHF₂)-phenyl | 1.698 | 505.4 |
| 227 | (S)-3-(3-((4-cyanophenyl)amino)-4-(cyclohexyl(2-hydroxy-2-methylpropyl)amino)phenyl)pentanoic acid | 4-CN-phenyl | 1.720 | 464.4 |
| 228 | (S)-3-(4-(cyclohexyl(2-hydroxy-2-mehtylpropyl)amino)-3-((4-ethylphenyl)amino)phenyl)pentanoic acid | 4-ethylphenyl | 2.199 | 467.5 |
| 229 | (S)-3-(4-(cyclohexyl(2-hydroxy-2-methylpropyl)amino)-3-((2-ethoxypyrimidin-5-yl)amino)phenyl)pentanoic acid | 2-ethoxypyrimidin-5-yl | 1.617 | 485.4 |
| 230 | (S)-3-(4-(cyclohexyl(2-hydroxy-2-methylpropyl)amino)-3-((5-ethylpyrimidin-2-yl)amino)phenyl)pentanoic acid | 5-ethylpyrimidin-2-yl | 1.723 | 469.4 |
| 231 | (S)-3-(3-((4-chlorophenyl)amino)-4-(cyclohexyl(2-hydroxy-2-methylpropyl)amino)phenyl)pentanoic acid | 4-Cl-phenyl | 2.080 | 473.4 |

Example 232

Enantiomer 2

(R)-3-(4-(Cyclohexyl(2-hydroxy-2-methylpropyl)amino)-3-(3-(p-tolyl)ureido)phenyl)pentanoic acid

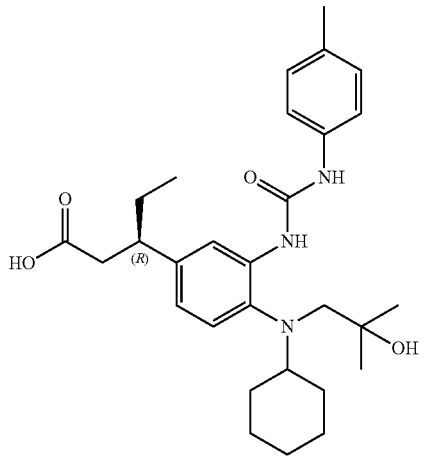

232A. (R)-Methyl 3-(4-(cyclohexyl(2-hydroxy-2-methylpropyl)amino)-3-nitrophenyl)pentanoate 232A was prepared from 221C and (S)-BINAP following the procedure described for the synthesis of 221D. LC-MS Anal. Calc'd. for $C_{22}H_{34}N_2O_5$, 406.2, found [M+H] 407.4, $T_r$=3.742 min (Method N). (Absolute stereochemistry of the product assigned based on the expected product enantiomer from the use of (S)-BINAP in the conjugate addition)

232B. (R)-Methyl 3-(3-amino-4-(cyclohexyl(2-hydroxy-2-methylpropyl)amino)phenyl)pentanoate 232B was prepared from 232A following the procedure described for the synthesis of 221E. LC-MS Anal. Calc'd. for $C_{22}H_{36}N_2O_3$, 376.2, found [M+H] 377.2, $T_r$=3.38 min (Method N). Chiral purity 83% ee, $T_r$=29.39 min (Method DA).

232C. Methyl 3-(4-(cyclohexyl(2-hydroxy-2-methylpropyl)amino)-3-(3-(p-tolyl)ureido)phenyl)pentanoate 232C was prepared from 232B and 1-isocyanato-4-methylbenzene following the procedure described for the synthesis of 221F. LC-MS Anal. Calc'd. for $C_{30}H_{43}N_3O_4$, 509.3, found [M+H] 510.6, $T_r$=1.11 min (Method BC).

Example 232. (R)-3-(4-(Cyclohexyl(2-hydroxy-2-methylpropyl)amino)-3-(3-(p-tolyl)ureido)phenyl) pentanoic acid Example 232 was prepared from 232C following the procedure described for the synthesis of Example 221 for 221F. LC-MS Anal. Calc'd. for $C_{29}H_{41}N_3O_4$, 495.3, found [M+H] 496.3, $T_r$=1.72 min (Method O). $^1$H NMR (400 MHz, DMSO-$d_6$) δ 9.34 (s, 1H), 8.24 (m, 1H), 7.93 (d, J=2.0 Hz, 1H), 7.39-7.35 (m, 2H), 7.17-7.04 (m, 3H), 6.77-6.75 (m, 1H), 4.10 (br. s., 1H), 3.08-2.90 (m, 2H), 2.88-2.08 (m, 1H), 2.49-2.40 (m, 2H), 2.25 (s, 3H), 1.98-1.80 (m, 2H), 1.75-1.60 (m, 4H), 1.58-1.40 (m, 2H), 1.20-1.05 (m, 6H), 0.88 (m, 6H), 0.69 (t, J=8.00 Hz, 3H).

examples 236 to 242

Enantiomer 2

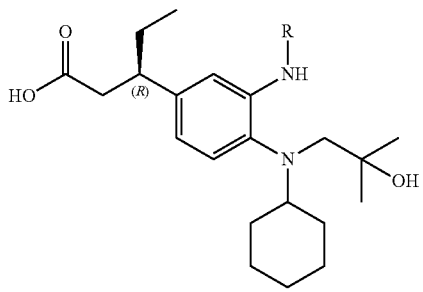

Examples 236 to 242 were prepared from 232B and corresponding aryl halides following the procedure described for the synthesis of Example 214.

| Ex. No. | Name | R | $T_r$ (min) Method O | (M + H)⁺ |
|---|---|---|---|---|
| 236 | (R)-3-(4-(cyclohexyl(2-hydroxy-2-methylpropyl)amino)-3-((4-fluorophenyl)amino)phenyl)pentanoic acid | 4-F-C₆H₄– | 1.944 | 457.4 |

-continued

| Ex. No. | Name | R | T$_r$ (min) Method O | (M + H)$^+$ |
|---|---|---|---|---|
| 237 | (R)-3-(4-(cyclohexyl(2-hydroxy-2-methylpropyl)amino)-3-((4-(difluoromethoxy)phenyl)amino)phenyl)pentanoic acid | 4-(OCHF$_2$)-phenyl | 2.022 | 505.4 |
| 238 | (R)-3-(3-((4-cyanophenyl)amino)-4-(cyclohexyl(2-hydroxy-2-methylpropyl)amino)phenyl)pentanoic acid | 4-CN-phenyl | 1.787 | 464.4 |
| 239 | (R)-3-(4-(cyclohexyl(2-hydroxy-2-methylpropyl)amino)-3-((4-ethylphenyl)amino)phenyl)pentanoic acid | 4-ethylphenyl | 2.241 | 467.5 |
| 240 | (R)-3-(4-(cyclohexyl(2-hydroxy-2-methylpropyl)amino)-3-((2-ethoxypyrimidin-5-yl)amino)phenyl)pentanoic acid | 2-ethoxypyrimidin-5-yl | 1.676 | 485.4 |
| 241 | (R)-3-(4-(cyclohexyl(2-hydroxy-2-methylpropyl)amino)-3-((5-ethylpyrimidin-2-yl)amino)phenyl)pentanoic acid | 5-ethylpyrimidin-2-yl | 1.786 | 469.4 |
| 242 | (R)-3-(3-((4-chlorophenyl)amino)-4-(cyclohexyl(2-hydroxy-2-methylpropyl)amino)phenyl)pentanoic acid | 4-Cl-phenyl | 1.828 | 473.4 |

Example 243

Enantiomer 1

3-(3-((4-Cyanophenyl)amino)-4-((2S,6R)-2,6-dimethylmorpholino)phenyl)-3-cyclopropylpropanoic acid

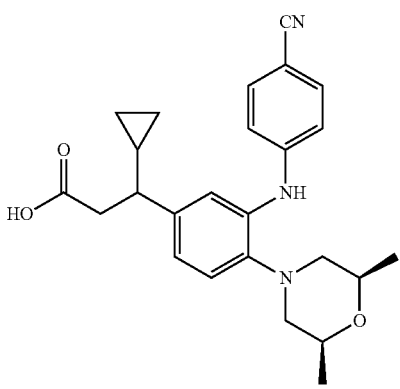 [SMILES: C[C@@H]1CN(c2ccc(C(CC(=O)O)C3CC3)cc2Nc2ccc(C#N)cc2)C[C@H](C)O1]

243A. (2S,6R)-4-(4-Bromo-2-nitrophenyl)-2,6-dimethylmorpholine

To a solution of 4-bromo-1-fluoro-2-nitrobenzene (2.8 g, 12.73 mmol) and (2R,6S)-2,6-dimethylmorpholine (1.466 g, 12.73 mmol) in NMP (10 mL) was added DIPEA (6.67 mL, 38.2 mmol). Reaction mixture heated to 135° C. for 16 h. The reaction mixture was cooled to RT and diluted with diethyl ether. The organic layer was washed with 10% aq. AcOH solution followed by 10% $NaHCO_3$ solution and brine solution. Organic layer dried over $Na_2SO_4$ and concentrated under reduced pressure to give crude sample. Purification via flash chromatography gave 243A (orange liquid, 3.5 g, 10.47 mmol, 82% yield). LC-MS Anal. Calc'd. for $C_{12}H_{15}BrN_2O_3$, 315.163, found [M+2] 317.0. $T_r$=3.191 min (Method N).

243B. (2S,6R)-4-(4-(5,5-Dimethyl-1,3,2-dioxaborinan-2-yl)-2-nitrophenyl)-2,6-dimethylmorpholine The mixture of 243A (2.5 g, 7.93 mmol), bis(neopentyl glycolato)diboron (2.365 g, 10.47 mmol) and potassium acetate (2.336 g, 23.80 mmol) in dioxane (30 mL) was stirred at room temperature. Argon gas was bubbled through the mixture for 5 min. $PdCl_2$ (dppf).$CH_2Cl_2$ Adduct (0.194 g, 0.238 mmol) was added and argon gas was bubbled through the mixture for 5 min. The reaction mixture was heated at 80° C. for 6 h. The reaction mixture was cooled to room temperature and diluted with dichloromethane (100 mL). The organic layer was washed with water (50 m), dried over anhydrous sodium sulfate and concentrated under reduced pressure. Purification via flash chromatography gave 243B (yellow solid, 2.4 g, 6.76 mmol, 85% yield). $^1$H NMR (400 MHz, $CDCl_3$) δ 8.18 (d, J=1.60 Hz, 1H), 7.83 (dd, J=1.60, 8.40 Hz, 1H), 7.02 (d, J=8.40 Hz, 1H), 3.82-3.87 (m, 2H), 3.75 (s, 4H), 3.09 (dd, J=2.00, 9.60 Hz, 2H), 2.60 (dd, J=10.40, 12.00 Hz, 2H), 1.19 (d, J=6.00 Hz, 6H), 1.01 (s, 6H).

243C. Methyl 3-cyclopropyl-3-(4-((2S,6R)-2,6-dimethylmorpholino)-3-nitrophenyl)propanoate In a pressure tube equipped with Teflon cap, 243B (2.0 g, 5.74 mmol), 1,4-dioxane (40 mL) were added followed by (E)-methyl 3-cyclopropylacrylate (0.870 g, 6.89 mmol), sodium hydroxide (5.17 mL, 5.17 mmol). Argon gas was bubbled through the mixture for 10 min and chloro(1,5-cyclooctadiene)rhodium(I) dimer (0.042 g, 0.086 mmol) was added at room temperature. Argon gas was bubbled through the mixture for 5 min. The tube was then screw-capped and heated at 50° C. for 1 h. The reaction mixture was cooled to room temperature, quenched with acetic acid (0.2 mL) and was stirred for 5 minutes before it was diluted with water (50 mL). The aqueous layer was extracted with ethyl acetate (3×100 mL). Combined organic layer were washed with water (50 mL), brine (50 mL), dried over anhydrous sodium sulfate and concentrated under reduced pressure to get crude product. Purification via flash chromatography gave 243C (yellow liquid, 2.0 g, 5.13 mmol, 89% yield). LC-MS Anal. Calc'd. for $C_{19}H_{26}N_2O_5$ 362.420, found [M+H] 363.0. $T_r$=1.47 min (Method BA).

243D. Methyl 3-(3-amino-4-((2S,6R)-2,6-dimethylmorpholino)phenyl)-3-cyclopropylpropanoate The solution of 243C (2.4 g, 6.62 mmol) in ethyl acetate (100 mL) was charged to a sealable hydrogen flask. The solution was sequentially evacuated and purged with nitrogen gas. To this 10% Pd on carbon (0.352 g, 0.331 mmol) was added under nitrogen atmosphere. The reaction mixture was stirred under hydrogen atmosphere (40 psi). The reaction mixture was stirred at room temperature for 3 h. The reaction mixture was filtered through a CELITE® pad and the residue on the pad was thoroughly rinsed with MeOH (3×100 mL). The combined filtrate was concentrated under reduced pressure. Purification via flash chromatography gave 243D. LC-MS Anal. Calc'd. for $C_{19}H_{28}N_2O_3$, 332.437, found [M+H] 333.3. $T_r$=1.33 min (Method BA).

Chiral separation of Racemate 243D (Method BZ) 243D Enantiomer 1, $T_r$=3.46 min (Method BZ), 243D Enantiomer 2, $T_r$=4.13 min (Method BZ).

243D Enantiomer 1: (brown semi-solid, 0.65 g, 1.955 mmol, 29.5% yield). LC-MS Anal. Calc'd. for $C_{19}H_{28}N_2O_3$, 332.437, found [M+H] 333.3. $T_r$=3.38 min (Method N).

243D Enantiomer 2: (brown semi-solid 0.7 g, 2.069 mmol, 31.2% yield). LC-MS Anal. Calc'd. for $C_{19}H_{28}N_2O_3$, 332.437, found [M+H] 333.3. $T_r$=3.37 min (Method N).

243E. Methyl 3-(3-((4-cyanophenyl)amino)-4-((2R,6S)-2,6-dimethylmorpholino)phenyl)-3-cyclopropylpropanoate To degassed solution of 243D Enantiomer 1 and 4-bromobenzonitrile (0.027 g, 0.150 mmol), cesium carbonate (0.074 g, 0.226 mmol) in dry dioxane (2.0 mL) purged argon for 15 minutes. 4,5-bis(diphenylphosphino)-9,9-dimethylxanthene (8.70 mg, 0.015 mmol). Bis(dibenzylideneacetone) palladium (4.32 mg, 7.52 μmol). Reaction heated to 110° C. temperature and maintained for 4 h. The reaction mixture was filtered through pad of CELITE®, washed with EtOAc. The filtrate was concentrated under reduced pressure. Purification via flash chromatography gave 243E (brown semi-solid, 52 mg, 0.120 mmol, 80% yield). LC-MS Anal. Calc'd. for $C_{26}H_{31}N_3O_3$, 433.2, found [M+H] 434.4. $T_r$=1.53 min (Method BA).

Example 243. 3-(3-((4-Cyanophenyl)amino)-4-((2R,6S)-2,6-dimethylmorpholino)phenyl)-3-cyclopropyl-propanoic acid To stirred solution of 243E (0.050 g, 0.115 mmol) in dry THF (1.0 mL), MeOH (1.0 mL) mixture lithium hydroxide monohydrate (0.024 g, 0.577 mmol) was added at room temperature. Reaction mixture was stirred at room temperature for 16 h. Reaction mixture concentrated under reduced pressure, added water (2 mL) washed with diethyl ether (5 mL). Aqueous layer separated and acidified with saturated citric acid. Aqueous layer extract with DCM (3×5 mL). Combined organic layers were dried over sodium sulfate and concentrated to get semi-solid product. Purification via preparative LCMS method gave Example 243 (off-white solid, 18.2 mg, 0.042 mmol, 36% yield). LC-MS Anal. Calc'd. for $C_{25}H_{29}N_3O_3$, 419.2, found [M+H] 420.3, $T_r$=1.50 min (Method O). $^1$H NMR (400 MHz, DMSO-$d_6$) δ 8.18 (s, 1H) 7.53-7.51 (d, J=8.8 Hz, 2H), 7.09 (m, 1H), 7.01-6.99 (m, 2H), 6.98-6.96 (d, J=8.4 Hz, 2H), 3.51-3.45 (m, 2H), 2.99-2.97 (m, 2H), 2.64-2.59 (m, 2H), 2.26-2.22 (m, 3H), 1.10-0.99 (m, 7H), 0.49-0.47 (m, 1H), 0.35-0.33 (m, 1H), 0.23-0.21 (m, 1H), 0.14-0.12 (m, 1H).

Examples 244 to 246

Enantiomer 1

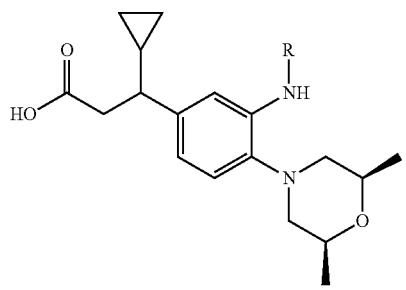

Examples 244 to 246 were prepared from 243D Enantiomer 1 and the corresponding aryl halides by following the procedure described for the synthesis of Example 243.

| Ex. No. | Name | R | $T_r$ (min) Method O | (M + H)$^+$ |
|---|---|---|---|---|
| 244 | 3-(3-((4-chlorophenyl)amino)-4-((2R,6S)-2,6-dimethylmorpholino)phenyl)-3-cyclopropylpropanoic acid | 4-chlorophenyl | 2.194 | 429.2 |
| 245 | 3-cyclopropyl-3-(4-((2R,6S)-2,6-dimethylmorpholino)-3-((2-ethoxypyrimidin-5-yl)amino)phenyl)propanoic acid | 2-ethoxypyrimidin-5-yl | 1.344 | 441.3 |
| 246 | 3-cyclopropyl-3-(4-((2R,6S)-2,6-dimethylmorpholino)-3-((6-methoxypyridin-3-yl)amino)phenyl)propanoic acid | 6-methoxypyridin-3-yl | 1.454 | 426.3 |

Example 247

Enantiomer 2

3-(3-((4-Cyanophenyl)amino)-4-((2R,6S)-2,6-dimethylmorpholino)phenyl)-3-cyclopropylpropanoic acid

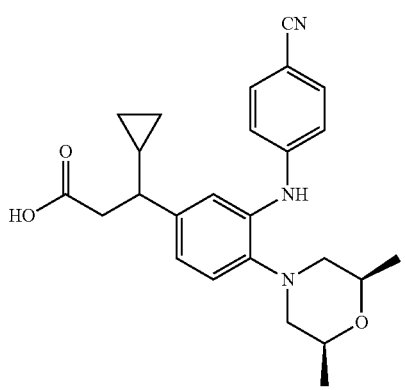 [SMILES: C[C@@H]1CN(c2ccc(C(CC(=O)O)C3CC3)cc2Nc2ccc(C#N)cc2)C[C@H](C)O1]

247A. Methyl 3-(3-((4-cyanophenyl)amino)-4-((2R,6S)-2,6-dimethylmorpholino)phenyl)-3-cyclopropyl-propanoate 247A was prepared from 243D Enantiomer 2 and 4-bromobenzonitrile following the procedure described for the synthesis of 145F. LC-MS Anal. Calc'd. for $C_{26}H_{31}N_3O_3$, 433.2, found [M+H] 434.5. $T_r$=1.53 min (Method BA).

Example 247. 3-(3-((4-Cyanophenyl)amino)-4-((2R,6S)-2,6-dimethylmorpholino)phenyl)-3-cyclopropyl-propanoic acid Example 247 was prepared from 247A following the procedure described for the synthesis of Example 145 for 145F. LC-MS Anal. Calc'd. for $C_{25}H_{29}N_3O_3$, 419.2, found [M+H] 420.3, $T_r$=1.52 min (Method O). $^1$H NMR (400 MHz, DMSO-d$_6$) δ 8.18 (s, 1H) 7.53-7.51 (d, J=8.8 Hz, 2H), 7.09 (m, 1H), 7.01-6.99 (m, 2H), 6.98-6.96 (d, J=8.4 Hz, 2H), 2.99-2.97 (m, 2H), 2.64-2.59 (m, 2H), 2.26-2.22 (m, 3H), 1.10-0.99 (m, 7H), 0.49-0.47 (m, 1H), 0.35-0.33 (m, 1H), 0.23-0.21 (m, 1H), 0.14-0.12 (m, 1H) (Note: 2 proton buried under solvent peak).

Examples 248 to 250

Enantiomer 2

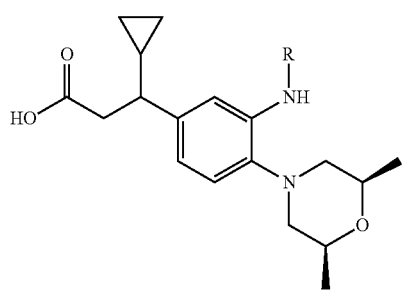

Examples 248 to 250 were prepared from 243D Enantiomer 2 and the corresponding aryl halides following the procedure described for the synthesis of Example 243.

| Ex. No. | Name | R | $T_r$ (min) Method O | (M + H)$^+$ |
|---|---|---|---|---|
| 248 | 3-(3-((4-chlorophenyl)amino)-4-((2R,6S)-2,6-dimethylmorpholino)phenyl)-3-cyclopropylpropanoic acid | 4-Cl-C6H4- | 1.87 | 429.3 |
| 249 | 3-cyclopropyl-3-(4-((2R,6S)-2,6-dimethylmorpholino)-3-((2-ethoxypyrimidin-5-yl)amino)phenyl)propanoic acid | 2-ethoxypyrimidin-5-yl | 1.357 | 441.3 |
| 250 | 3-cyclopropyl-3-(4-((2R,6S)-2,6-dimethylmorpholino)-3-((2-ethoxypyrimidin-5-yl)amino)phenyl)propanoic acid | 2-methoxypyridin-5-yl | 1.453 | 426.3 |

Example 251

Enantiomer 1 and Enantiomer 2

3-Cyclopropyl-3-(4-((2R,6S)-2,6-dimethylmorpholino)-3-(3-(p-tolyl)ureido)phenyl)propanoic acid

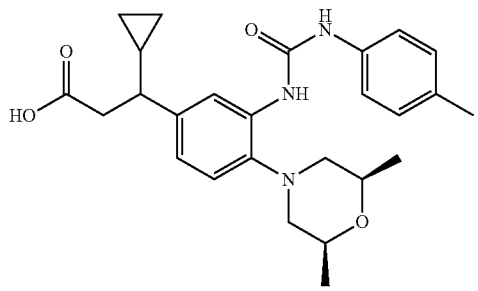 [SMILES: Cc1ccc(NC(=O)Nc2cc(C(CC(=O)O)C3CC3)ccc2N2C[C@@H](C)O[C@@H](C)C2)cc1]

251A. Methyl 3-cyclopropyl-3-(4-((2R,6S)-2,6-dimethylmorpholino)-3-(3-(p-tolyl)ureido)phenyl)propanoate 251A was prepared from 243D Enantiomer 1 and 1-isocyanato-4-methylbenzene following the procedure described for the synthesis of 5A. LC-MS Anal. Calc'd. for $C_{27}H_{35}N_3O_4$, 465.2, found [M+H] 466.4. $T_r$=1.49 min (Method BA).

Example 251 Enantiomer 1. 3-Cyclopropyl-3-(4-((2R,6S)-2,6-dimethylmorpholino)-3-(3-(p-tolyl)ureido)phenyl)propanoic acid Example 251 Enantiomer 1 was prepared from 251A following the procedure described for the synthesis of Example 145 from 145F (absolute stereochemistry unknown). LC-MS Anal. Calc'd. for $C_{26}H_{33}N_3O_4$, 451.2, found [M+H] 452.3, $T_r$=1.76 min (Method O). $^1$H NMR (400 MHz, DMSO-$d_6$) δ 9.42 (s, 1H), 8.09 (s, 1H), 8.01 (d, J=1.6 Hz, 1H), 7.36 (m, 1H), 7.34 (m, 1H), 7.10-7.05 (m, 3H), 6.84-6.82 (m, 1H), 3.91-3.88 (m, 2H), 2.76-2.60 (m, 2H), 2.49-2.35 (m, 2H), 2.33-2.30 (m, 2H), 2.23-2.15 (s, 3H), 2.10-2.05 (m, 1H), 1.09-1.07 (d, J=6.0 Hz, 6H), 0.93-0.08 (m, 1H), 0.49-0.47 (m, 1H), 0.32-0.30 (m, 1H), 0.23-0.19 (m, 1H), 0.09-0.05 (m, 1H).

Example 251 Enantiomer 2. 3-Cyclopropyl-3-(4-((2R,6S)-2,6-dimethylmorpholino)-3-(3-(p-tolyl)ureido)phenyl)propanoic acid Example 251 Enantiomer 2 was prepared from 243D Enantiomer 2 and 1-isocyanato-4-methylbenzene following the procedures described for the synthesis of Example 251 Enantiomer 1 (absolute stereochemistry unknown). LC-MS Anal. Calc'd. for $C_{26}H_{33}N_3O_4$, 451.2, found [M+H] 452.3, $T_r$=1.45 min (Method O). $^1$H NMR (400 MHz, DMSO-$d_6$) δ 9.42 (s, 1H), 8.09 (s, 1H), 8.01 (d, J=1.6 Hz, 1H), 7.36 (m, 1H), 7.34 (m, 1H), 7.10-7.05 (m, 3H), 6.84-6.82 (m, 1H), 3.91-3.88 (m, 2H), 2.76-2.60 (m, 2H), 2.49-2.35 (m, 2H), 2.33-2.30 (m, 2H), 2.23-2.15 (s, 3H), 2.10-2.05 (m, 1H), 1.09-1.07 (d, J=6.0 Hz, 6H), 0.93-0.08 (m, 1H), 0.49-0.47 (m, 1H), 0.32-0.30 (m, 1H), 0.23-0.19 (m, 1H), 0.09-0.05 (m, 1H).

Example 252

Enantiomer 1

3-(3-(3-(4-Chloro-2-fluorophenyl)ureido)-4-((2R,6S)-2,6-dimethylmorpholino)phenyl)-3-cyclopropylpropanoic acid

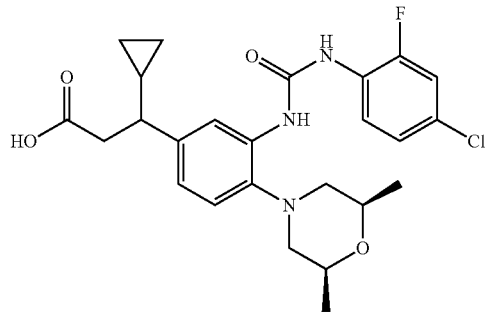 [SMILES: C[C@@H]1CN(c2ccc(C(CC(=O)O)C3CC3)cc2NC(=O)Nc2ccc(Cl)cc2F)C[C@H](C)O1]

252A. Methyl 3-(3-(3-(4-chloro-2-fluorophenyl)ureido)-4-((2R,6S)-2,6-dimethylmorpholino)phenyl)-3-cyclopropylpropanoate 252A was prepared from 243D Enantiomer 1 and 4-chloro-2-fluoro-1-isocyanatobenzene following the procedure described for the synthesis of 5A. LC-MS Anal. Calc'd. for $C_{26}H_{31}ClFN_3O_4$, 503.19, found [M+H] 504.4, $T_r$=1.57 min (Method BA).

Example 252 Enantiomer 1. 3-(3-(3-(4-Chloro-2-fluorophenyl)ureido)-4-((2R,6S)-2,6-dimethylmorpholino)phenyl)-3-cyclopropylpropanoic acid Example 252 Enantiomer 1 was prepared from 252A following the procedure described for the synthesis of Example 145 from 145F (absolute stereochemistry unknown). LC-MS Anal. Calc'd. for $C_{25}H_{29}ClFN_3O_4$, 489.18, found [M+H] 490.3, $T_r$=1.59 min (Method O). $^1$H NMR (400 MHz, DMSO-$d_6$) δ 9.52 (s, 1H), 8.50 (s, 1H), 8.15-8.10 (t, J=8.8 Hz, 1H), 7.94-7.93 (m, 1H), 7.47-7.44 (m, 1H), 7.25-7.22 (m, 1H), 7.08-7.06 (d, J=8.4 Hz, 1H), 6.89-6.87 (m, 1H), 3.94-3.89 (m, 2H), 2.81-2.76 (m, 2H), 2.59-2.51 (m, 2H), 2.36-2.31 (m, 2H), 2.22-2.20 (m, 1H), 1.09-1.07 (d, J=6.0 Hz, 6H), 0.94-0.93 (m, 1H), 0.49-0.47 (m, 1H), 0.32-0.30 (m, 1H), 0.23-0.19 (m, 1H), 0.09-0.05 (m, 1H).

Example 253

Enantiomer 2

3-(3-(3-(4-Chloro-2-fluorophenyl)ureido)-4-((2R,6S)-2,6-dimethylmorpholino)phenyl)-3-cyclopropylpropanoic acid

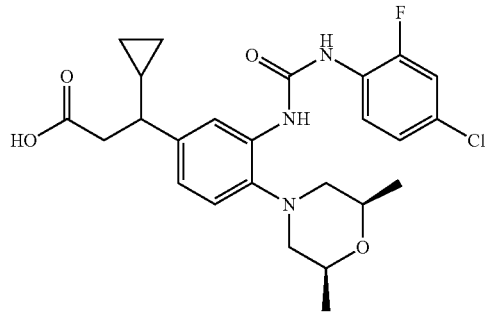 [SMILES: C[C@@H]1CN(c2ccc(C(CC(=O)O)C3CC3)cc2NC(=O)Nc2ccc(Cl)cc2F)C[C@H](C)O1]

253A. Methyl 3-(3-(3-(4-chloro-2-fluorophenyl)ureido)-4-((2R,6S)-2,6-dimethylmorpholino)phenyl)-3-cyclopropylpropanoate 253A was prepared from 243D Enantiomer 2 and 4-chloro-2-fluoro-1-isocyanatobenzene following the procedure described for the synthesis of 5A. LC-MS Anal. Calc'd. for $C_{26}H_{31}ClFN_3O_4$, 503.19, found [M+H] 504.4, $T_r$=1.57 min (Method BA).

Example 253 Enantiomer 2. 3-(3-(3-(4-Chloro-2-fluorophenyl)ureido)-4-((2R,6S)-2,6-dimethylmorpholino)phenyl)-3-cyclopropylpropanoic acid Example 253 Enantiomer 2 was prepared from 253A following the procedure for Example 145 from 145F (absolute stereochemistry unknown). LC-MS Anal. Calc'd. for $C_{25}H_{29}ClFN_3O_4$, 489.18, found [M+H] 490.3, $T_r$=1.59 min. (Method O). $^1$H NMR (400 MHz, DMSO-$d_6$) δ 9.52 (s, 1H), 8.50 (s, 1H), 8.15-8.10 (t, J=8.8 Hz, 1H), 7.94-7.93 (m, 1H), 7.47-7.44 (m, 1H), 7.25-7.22 (m, 1H), 7.08-7.06 (d, J=8.4 Hz, 1H), 6.89-6.87 (m, 1H), 3.94-3.89 (m, 2H), 2.81-2.76 (m, 2H), 2.59-2.51 (m, 2H), 2.36-2.31 (m, 2H), 2.22-2.20 (m, 1H), 1.09-1.07 (d, J=6.0 Hz, 6H), 0.94-0.93 (m, 1H), 0.49-0.47 (m, 1H), 0.32-0.30 (m, 1H), 0.23-0.19 (m, 1H), 0.09-0.05 (m, 1H).

Example 254

3-(4-((1,1-Dioxidotetrahydro-2H-thiopyran-4-yl)(ethyl)amino)-3-(3-(p-tolyl)ureido)phenyl)-3-methylbutanoic acid

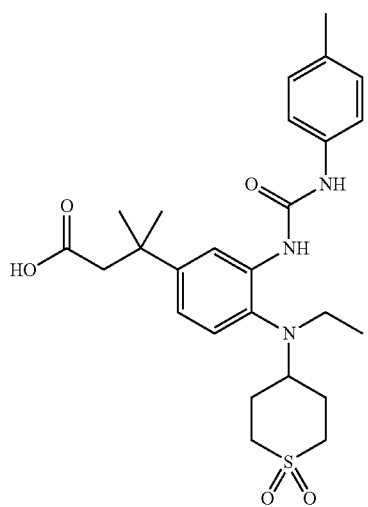 [SMILES: CCN(c1ccc(C(C)(C)CC(=O)O)cc1NC(=O)Nc1ccc(C)cc1)C1CCS(=O)(=O)CC1]

254A. Ethyl 3-(4-((1,1-dioxidotetrahydro-2H-thiopyran-4-yl)(ethyl)amino)-3-(3-(p-tolyl)ureido)phenyl)-3-methylbutanoate Compound 254A was prepared from 177D and 1-isocyanato-4-methylbenzene following the procedure described for the synthesis of 5A. LC-MS Anal. Calc'd. for $C_{28}H_{39}N_3O_5S$, 529.2, found [M+H] 530.2, $T_r$=0.97 min (Method BC).

Example 254. 3-(4-((1,1-Dioxidotetrahydro-2H-thiopyran-4-yl)(ethyl)amino)-3-(3-(p-tolyl)ureido)phenyl)-3-methylbutanoic acid Example 254 was prepared from 254A following the procedure described for the synthesis of Example 145 from 145F. LC-MS Anal. Calc'd. for $C_{26}H_{35}N_3O_5S$, 501.2, found [M+H] 502.3, $T_r$=1.50 min (Method O). $^1$H NMR (400 MHz, DMSO-$d_6$) δ 9.39 (s, 1H), 8.36-8.33 (m, 2H), 7.37-7.35 (d, J=8.4 Hz, 2H), 7.22-7.07 (m, 3H), 6.98-6.95 (m, 1H), 3.42-2.97 (m, 6H), 2.24 (s, 3H), 2.20-2.16 (m, 2H), 1.88-1.85 (m, 2H), 1.36 (s, 6H), 1.27-1.20 (m, 1H), 0.83-0.80 (m, 3H) (Note: one multiplet $CH_2$ buried under solvent peak).

Example 255

Enantiomer 1 and Enantiomer 2

3-(3-(3-(4-Cyanophenyl)ureido)-4-(ethyl(tetrahydro-2H-pyran-4-yl)amino)phenyl)-3-cyclopropylpropanoic acid

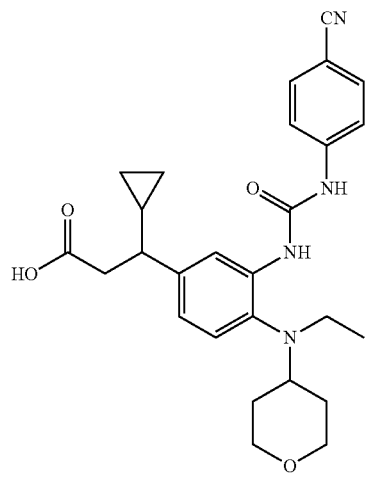 [SMILES: CCN(c1ccc(C(CC(=O)O)C2CC2)cc1NC(=O)Nc1ccc(C#N)cc1)C1CCOCC1]

255A. Methyl 3-(3-(3-(4-cyanophenyl)ureido)-4-(ethyl(tetrahydro-2H-pyran-4-yl)amino)phenyl)-3-cyclopropylpropanoate To a stirred solution of 33E Enantiomer 1 (0.035 g, 0.101 mmol) in tetrahydrofuran (1.5 mL) was added 4-isocyanatobenzonitrile (0.017 g, 0.121 mmol). The reaction mixture was stirred at room temperature for 12 h. LCMS indicated completion of reaction. The reaction mixture was concentrated under reduced pressure to afford 255A (yellow liquid, 45 mg, 0.076 mmol, 75% yield). LC-MS Anal. Calc'd. for $C_{28}H_{34}N_4O_4$, 490.25, found [M+H] 491.4. $T_r$=1.41 min. (Method AY).

Example 255 Enantiomer 1. 3-(3-(3-(4-Cyanophenyl)ureido)-4-(ethyl(tetrahydro-2H-pyran-4-yl)amino)phenyl)-3-cyclopropylpropanoic acid To a stirred solution of compound 255A (0.045 g, 0.076 mmol) in mixture of tetrahydrofuran (1.5 mL), methanol (1.5 mL) and water (0.5 mL) was added LiOH.H$_2$O (0.015 g, 0.367 mmol). The reaction mixture was stirred at room

223 temperature for 12 h. The reaction mixture was concentrated under reduced pressure. The aqueous residue so obtained was acidified with aqueous citric acid to pH~2. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 255 Enantiomer 1 (absolute stereochemistry unknown) (26 mg, 0.056 mmol, 60% yield). LC-MS Anal. Calc'd. for $C_{27}H_{32}N_4O_4$ 476.2, found [M+H] 477.1. $T_r$=1.60 min. (Method O). $^1$H NMR (400 MHz, DMSO-$d_6$) δ 8.55-8.92 (m, 1H), 8.02-8.32 (m, 1H), 7.55-7.87 (m, 5H), 7.05-7.28 (m, 1H), 6.68-6.97 (m, 1H), 3.82 (m, 4H), 3.08-3.23 (m, 2H), 2.84-3.05 (m, 1H), 2.67 (m, 1H), 2.25-2.41 (m, 2H), 1.87-2.15 (m, 4H), 0.82 (t, J=7.2 Hz, 3H), 0.54-0.79 (m, 5H).

Example 255 Enantiomer 2. 3-(3-(3-(4-Cyanophenyl)ureido)-4-(ethyl(tetrahydro-2H-pyran-4-yl)amino)phenyl)-3-cyclopropylpropanoic acid Example 255 Enantiomer 2 was prepared following the same procedure for Example 255 Enantiomer 1 by utilizing 33E Enantiomer 2 (absolute stereochemistry unknown). LC-MS Anal. Calc'd. for $C_{27}H_{32}N_4O_4$, 476.2, found [M+H] 477.0. $T_r$=1.58 min. (Method O). $^1$H NMR (400 MHz, DMSO-$d_6$) δ 8.55-8.92 (m, 1H), 8.02-8.32 (m, 1H), 7.55-7.87 (m, 5H), 7.05-7.28 (m, 1H), 6.68-6.97 (m, 1H), 3.82 (m, 4H), 3.08-3.23 (m, 2H), 2.84-3.05 (m, 1H), 2.67 (m, 1H), 2.25-2.41 (m, 2H), 1.87-2.15 (m, 4H), 0.82 (t, J=7.2 Hz, 3H), 0.54-0.79 (m, 5H).

Example 256

Enantiomer 1 and Enantiomer 2

3-(3-((4-Chlorophenyl)amino)-4-((2-methoxyethyl)(tetrahydro-2H-pyran-4-yl)amino)phenyl)-4-methoxybutanoic acid

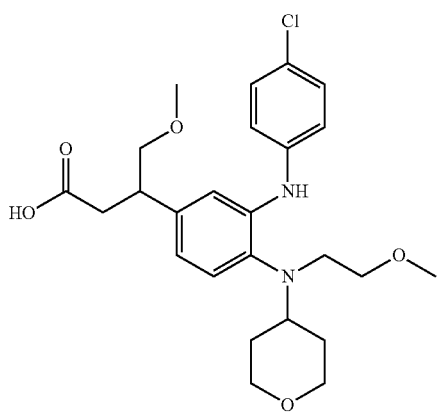

224

256A. N-(2-Methoxyethyl)tetrahydro-2H-pyran-4-amine

Compound 256A was prepared from 2-methoxyethanamine following the procedure described for the synthesis of 15D. $^1$H NMR (400 MHz, DMSO-$d_6$) δ3.89-3.55 (m, 6H), 3.37 (s, 3H), 2.86 (m, 2H), 2.68 (m, 1H), 1.98-1.61 (m, 4H).

256B. N-(4-Bromo-2-nitrophenyl)-N-(2-methoxyethyl)tetrahydro-2H-pyran-4-amine 256B was prepared from 256A following the procedure described for the synthesis of 15E. LC-MS Anal. Calc'd. for $C_{14}H_{19}BrN_2O_4$, 358.05, found [M+H] 361.2. $T_r$=1.37 min. (Method AY).

256C. N-(4-(5,5-Dimethyl-1,3,2-dioxaborinan-2-yl)-2-nitrophenyl)-N-(2-methoxyethyl)tetrahydro-2H-pyran-4-amine Compound 256C was prepared from 256B following the procedure described for the synthesis of 41A. LC-MS Anal. Calc'd. for $C_{19}H_{29}BN_2O_6$, 392.21, found MS(ES): m/z=325.3 [M+H]$^+$ for parent boronic acid. $T_r$=0.91 min. (Method AY).

256D. (E)-Ethyl 4-methoxybut-2-enoate

To a solution of ethyl but-2-ynoate (70 g, 624 mmol) in dry toluene (350 mL) then was added methanol (30.3 mL, 749 mmol), triphenylphosphine (8.19 g, 31.2 mmol), catalytic amount of acetic acid (7.15 mL, 125 mmol) was added at RT, and the reaction mixture allowed to stir for 10 minutes. Reaction mixture was heated at 110° C. for 20 h. Reaction mixture was cooled to room temperature, then added water (50 mL) and extracted with ethyl acetate (3×50 mL). The combined organic layer was dried over sodium sulfate and concentrated to give yellow oil. Above oil was purified via flash silica gel column chromatography gave 256D (35 g, 243 mmol, 38.9% yield) as light yellow liquid. $^1$H NMR (400 MHz, DMSO-$d_6$) δ6.84-6.91 (m, 1H), 5.94-5.99 (m, 1H), 4.07-4.15 (m, 4H), 3.29 (s, 3H), 1.22 (t, J=7.2 Hz, 3H).

256E. Ethyl 4-methoxy-3-(4-((2-methoxyethyl)(tetrahydro-2H-pyran-4-yl)amino)-3-nitrophenyl)butanoate Compound 256E was prepared from 256C and 256D following the procedure described for the synthesis of 59E. LC-MS Anal. Calc'd. for $C_{21}H_{32}N_2O_7$, 424.2, found [M+H] 425.4. $T_r$=1.29 min (Method AY).

256F. Ethyl 3-(3-amino-4-((2-methoxyethyl)(tetrahydro-2H-pyran-4-yl)amino)phenyl)-4-methoxybutanoate Compound 256F was prepared from 256E following the procedure described for the synthesis of 33E. LC-MS Anal. Calc'd. for $C_{21}H_{34}N_2O_3$, 394.2, found [M+H] 395.4. $T_r$=1.17 min (Method AY).

Chiral separation of 256F (Method CK) to get Enantiomer 1 and Enantiomer 2 as single enantiomers (Method CK) Enantiomer 1 $T_r$=7.6 min and Enantiomer 2 $T_r$=8.8 min (Method CK).

256F Enantiomer 1 (yellow liquid, 110 mg, 0.279 mmol, 39% yield): LC-MS Anal. Calc'd. for $C_{21}H_{34}N_2O_3$, 394.2, found [M+H] 395.2. $T_r$=1.80 min (Method BB).

256F Enantiomer 2 (yellow liquid, 110 mg, 0.279 mmol, 39% yield): LC-MS Anal. Calc'd. for $C_{21}H_{34}N_2O_3$, 394.2, found [M+H] 395.2. $T_r$=1.80 min (Method BB).

256G. Ethyl 3-(3-((4-chlorophenyl)amino)-4-((2-methoxyethyl)(tetrahydro-2H-pyran-4-yl)amino) phenyl)-4-methoxybutanoate Compound 256G was prepared from 256F Enantiomer 1 following the procedure described for the synthesis of 33F. LC-MS Anal. Calc'd. for $C_{27}H_{37}ClN_2O_5$, 504.2, found [M+H] 505.2. $T_r$=1.65 min (Method AY).

Example 256 Enantiomer 1. 3-(3-((4-Chlorophenyl) amino)-4-((2-methoxyethyl)(tetrahydro-2H-pyran-4-yl)amino)phenyl)-4-methoxybutanoic acid Example 256 Enantiomer 1 was prepared from 256G following the procedure described for the synthesis of Example 1 from 1I (absolute stereochemistry unknown). LC-MS Anal. Calc'd. for $C_{25}H_{33}ClN_2O_5$, 476.2, found [M+H] 477.1. $T_r$=1.60 min (Method O). $^1$H NMR (400 MHz, DMSO-$d_6$) δ 7.53 (s, 1H), 7.27 (d, J=8.80 Hz, 2H), 7.18 (d, J=8.0 Hz, 1H), 7.04-7.13 (m, 3H), 6.70-6.85 (m, 1H), 3.78 (m, 4H), 3.42-3.51 (m, 6H), 3.05-3.23 (m, 7H), 2.97 (m, 1H), 2.59-2.71 (m, 2H), 1.66 (m, 2H), 1.27-1.47 (m, 2H).

Example 256 Enantiomer 2. 3-(3-((4-Chlorophenyl) amino)-4-((2-methoxyethyl)(tetrahydro-2H-pyran-4-yl)amino)phenyl)-4-methoxybutanoic acid Example 256 Enantiomer 2 was prepared from 256F Enantiomer 2 following the procedure described for the synthesis of Example 256 Enantiomer 1 from 256F Enantiomer 1 (absolute stereochemistry unknown). LC-MS Anal. Calc'd. for $C_{25}H_{33}ClN_2O_5$, 476.2, found [M+H] 477.1. $T_r$=1.60 min (Method O). $^1$H NMR (400 MHz, DMSO-$d_6$) δ 7.53 (s, 1H), 7.32 (m, 2H), 7.18 (m, 1H), 7.13 (m, 3H), 6.77 (m, 1H), 3.78 (m, 4H), 3.42-3.51 (m, 6H), 3.05-3.23 (m, 7H), 2.97 (m, 1H), 2.65 (m, 2H), 1.65 (m, 2H), 1.24-1.47 (m, 2H).

examples 257 and 258

Enantiomer 1

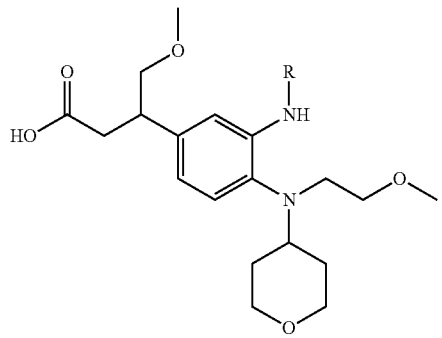

Examples 257 and 258 were prepared from 256F Enantiomer 1 and corresponding halides following the procedure described for the synthesis of Example 256 Enantiomer 1 (absolute stereochemistry unknown).

| Ex. No. | Name | R | $T_r$ (min) (Method O) | [M + H]$^+$ |
|---|---|---|---|---|
| 257 | 3-(3-((4-cyanophenyl)amino)-4-((2-methoxyethyl)(tetrahydro-2H-pyran-4-yl)amino)phenyl)-4-methoxybutanoic acid | CN-C₆H₄- | 1.23 | 468.3 |
| 258 | 3-(3-((4-fluorophenyl)amino)-4-((2-methoxyethyl)(tetrahydro-2H-pyran-4-yl)amino)phenyl)-4-methoxybutanoic acid | F-C₆H₄- | 1.51 | 461.2 |

Examples 259 and 260

Enantiomer 2

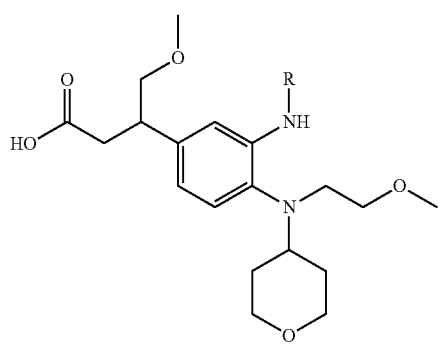

Examples 259 and 260 was prepared from 256F Enantiomer 2 and corresponding halides following the procedure described for the synthesis of Example 256 Enantiomer 1 (absolute stereochemistry unknown).

| Ex. No. | Name | R | $T_r$ (min) (Method O) | [M + H]+ |
|---|---|---|---|---|
| 259 | 3-(3-((4-cyanophenyl)amino)-4-((2-methoxyethyl)(tetrahydro-2H-pyran-4-yl)amino)phenyl)-4-methoxybutanoic acid | 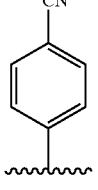 | 1.23 | 468.3 |
| 260 | 3-(3-((4-fluorophenyl)amino)-4-((2-methoxyethyl)(tetrahydro-2H-pyran-4-yl)amino)phenyl)-4-methoxybutanoic acid | 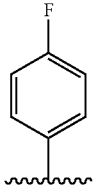 [SMILES: *c1ccc(F)cc1] | 1.51 | 461.2 |

Example 261

Enantiomer 1 and Enantiomer 2

4-Methoxy-3-(4-((2-methoxyethyl)(tetrahydro-2H-pyran-4-yl)amino)-3-(3-(p-tolyl)ureido)phenyl)butanoic acid

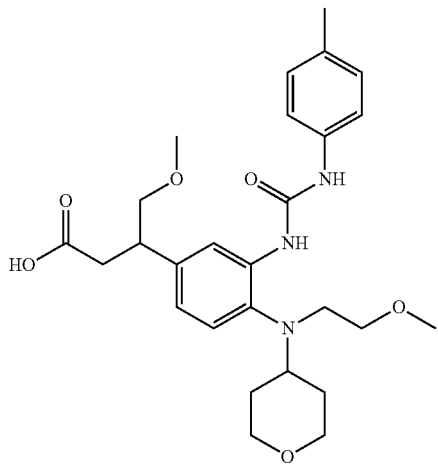 [SMILES: COCCN(c1ccc(C(COC)CC(=O)O)cc1NC(=O)Nc1ccc(C)cc1)C1CCOCC1]

261A. Ethyl 4-methoxy-3-(4-((2-methoxyethyl)(tetrahydro-2H-pyran-4-yl)amino)-3-(3-(p-tolyl)ureido)phenyl)butanoate To a stirred solution of 256F Enantiomer 1 (0.025 g, 0.063 mmol) in tetrahydrofuran (1 mL) was added 1-isocyanato-4-methylbenzene (10.13 mg, 0.076 mmol). The reaction mixture was stirred at room temperature for 12 h. LCMS indicated completion of reaction. The reaction mixture was concentrated under reduced pressure to get 261A (yellow liquid, 30 mg, 0.044 mmol, 77% yield). LC-MS Anal. Calc'd. for $C_{29}H_{41}N_3O_6$, 527.3, found [M+H] 528.0. $T_r$=1.41 min. (Method AY).

Example 261 Enantiomer 1. Ethyl 4-methoxy-3-(4-((2-methoxyethyl)(tetrahydro-2H-pyran-4-yl)amino)-3-(3-(p-tolyl)ureido)phenyl)butanoate To a stirred solution of compound 261A (0.030 g, 0.057 mmol) in mixture of tetrahydrofuran (1.5 mL), methanol (1.5 mL) and water (0.5 mL) was added LiOH.H$_2$O (9.54 mg, 0.227 mmol). The reaction mixture was stirred at room temperature for 12 h. The reaction mixture was concentrated under reduced pressure. The aqueous residue so obtained was acidified with aqueous citric acid to pH~2. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 261 Enantiomer 1 (absolute stereochemistry unknown) (7.3 mg, 0.014 mmol, 25% yield). LC-MS Anal. Calc'd. for $C_{27}H_{37}N_3O_6$ 499.2, found [M+H] 500.1. $T_r$=1.37 min (Method O). $^1$H NMR (400 MHz, DMSO-d$_6$) δ 9.39 (s, 1H), 8.41 (s, 1H), 8.04-8.13 (m, 1H), 7.38 (m, 2H), 7.18 (m, 1H), 7.04-7.13 (m, 2H), 6.78-6.88 (m, 1H), 3.83 (m, 4H), 3.20-3.28 (m, 6H), 3.68-3.71 (m, 7H), 2.58-2.72 (m, 1H), 2.37-2.45 (m, 2H), 2.25 (s, 3H), 1.64-1.80 (m, 2H), 1.31-1.46 (m, 2H).

Example 261 Enantiomer 2. Ethyl 4-methoxy-3-(4-((2-methoxyethyl)(tetrahydro-2H-pyran-4-yl)amino)-3-(3-(p-tolyl)ureido)phenyl)butanoate Example 261 Enantiomer 2 was prepared from 256F Enantiomer 2 following the procedure described for the synthesis of Example 261 Enantiomer 1 (absolute stereochemistry unknown). LC-MS Anal. Calc'd. for $C_{27}H_{37}N_3O_6$, 499.2, found [M+H] 500.1. $T_r$=1.37 min (Method O). $^1$H NMR (400 MHz, DMSO-d$_6$) δ 9.31-9.44 (m, 1H), 8.41 (s, 1H), 8.10 (m, 1H), 7.38 (m, 2H), 7.19 (m, 1H), 7.10 (m, 2H), 6.71-6.88 (m, 1H), 3.83 (m, 4H), 3.21-3.30 (m, 6H), 3.68-3.71 (m, 7H), 2.66 (m, 1H), 2.47 (m, 2H), 2.25 (s, 3H), 1.70 (m, 2H), 1.32-1.48 (m, 2H).

Example 262

Enantiomer 1

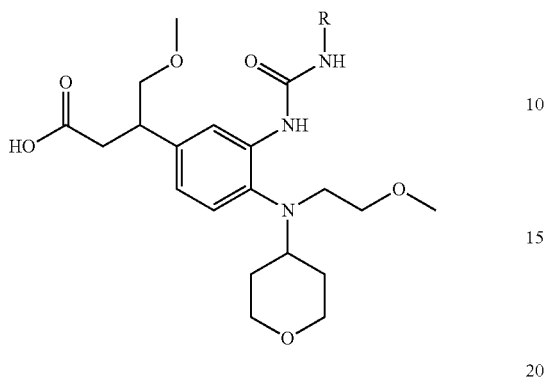

Example 262 was prepared from 256F Enantiomer 1 and corresponding isocyanate following the procedure described for the synthesis of Example 261 Enantiomer 1 (absolute stereochemistry unknown).

| Ex. No. | Name | R | $T_r$ (min) (Method O) | $[M + H]^+$ |
|---|---|---|---|---|
| 262 | 3-(3-(3-(4-chloro-2-fluorophenyl) ureido)-4-((2-methoxyethyl) (tetrahydro-2H-pyran-4-yl)amino) phenyl)-4-methoxybutanoic acid | 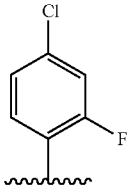 [SMILES: *c1ccc(Cl)cc1F] | 1.35 | 538.3 |

Example 263

Enantiomer 2

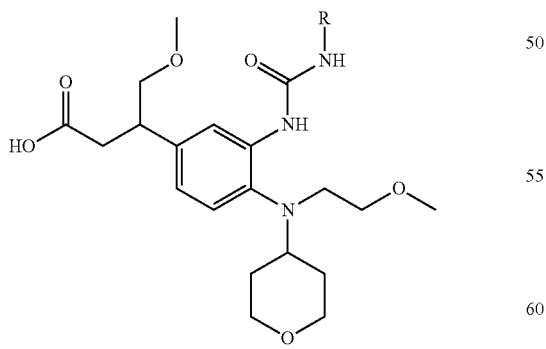

Example 263 was prepared from 256F Enantiomer 2 following the procedure described for the synthesis of Example 261 Enantiomer 1 (absolute stereochemistry unknown).

| Ex. No. | Name | R | $T_r$ (min) (Method O) | [M + H]$^+$ |
|---|---|---|---|---|
| 263 | 3-(3-(3-(4-chloro-2-fluorophenyl)ureido)-4-((2-methoxyethyl)(tetrahydro-2H-pyran-4-yl)amino)phenyl)-4-methoxybutanoic acid | | 1.36 | 538.3 |

Example 264

Diastereomer 1 and Diastereomer 2

3-(3-((4-Cyanophenyl)amino)-4-(ethyl(tetrahydro-2H-pyran-3-yl)amino)phenyl)-4-methoxybutanoic acid

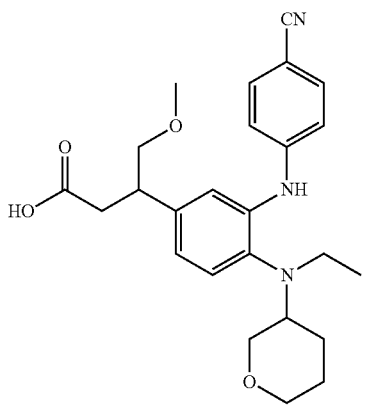 [SMILES: CCN(c1ccc(C(COC)CC(=O)O)cc1Nc1ccc(C#N)cc1)C1CCCOC1]

264A. Ethyl 3-(3-amino-4-(ethyl(tetrahydro-2H-pyran-3-yl)amino)phenyl)-4-methoxybutanoate Compound 264A was prepared from (E)-ethyl 4-methoxybut-2-enoate and 59D following the procedure described for the synthesis of 59E. LC-MS Anal. Calc'd. for $C_{20}H_{32}N_2O_4$, 364.2, found [M+H] 365.3. $T_r$=1.31 min (Method AY).

Chiral separation of 264A (Method CL) gave 264A Diastereomer 1 $T_r$=2.09 min (Method CL), and 264A Diastereomer 2 $T_r$=2.85 min (Method CL).

264A Diastereomer 1 (yellow liquid, 100 mg, 32%): LC-MS Anal. Calc'd. for $C_{20}H_{32}N_2O_4$, 364.2, found [M+H] 365.3. $T_r$=2.42 min (Method BB).

264A Diastereomer 2 (yellow liquid, 100 mg, 32%): LC-MS Anal. Calc'd. for $C_{20}H_{32}N_2O_4$, 364.2, found [M+H] 365.3. $T_r$=2.43 min (Method BB).

264B. Ethyl 3-(3-((4-cyanophenyl)amino)-4-(ethyl(tetrahydro-2H-pyran-3-yl)amino)phenyl)-4-methoxybutanoate The mixture of 264A Diastereomer 1 (0.050 g, 0.137 mmol), 4-bromobenzonitrile (0.030 g, 0.165 mmol), $Cs_2CO_3$ (0.067 g, 0.206 mmol) and 4,5-bis(diphenylphosphino)-9,9-dimethylxanthene (7.94 mg, 0.014 mmol) in 1,4-dioxane (2 mL) was stirred. Argon gas was bubbled through the mixture for 5 min. Bis(dibenzylideneacetone)palladium (3.94 mg, 6.86 µmol) was added and argon gas was bubbled through the mixture for 5 min. The reaction mixture was sealed and placed in preheated oil bath at 110° C. for 3 h. The reaction mixture was cooled to room temperature and concentrated under reduced pressure to afford a residue. The residue was reconstituted in a mixture of ethyl acetate (15 mL) and water (15 mL). The combined organic layer was washed with water (10 mL), brine (10 mL), dried over anhydrous sodium sulfate and concentrated under reduced pressure to afford a residue. The residue was purified via flash silica gel column chromatography to afford 264B (yellow liquid, 60 mg, 0.108 mmol, 79% yield). LC-MS Anal. Calc'd. for $C_{27}H_{35}N_3O_4$, 465.2, found [M+H] 466.3. $T_r$=2.06 min. (Method AY).

Example 264. Diastereomer 1. 3-(3-((4-Cyanophenyl)amino)-4-(ethyl(tetrahydro-2H-pyran-3-yl)amino)phenyl)-4-methoxybutanoic acid To a stirred solution of 264B (0.060 g, 0.135 mmol) in mixture of tetrahydrofuran (1 mL), methanol (1 mL) and water (0.2 mL) was added LiOH.H$_2$O (0.023 g, 0.539 mmol). The reaction mixture was stirred at room temperature for 12 h. The reaction mixture was concentrated under reduced pressure. The aqueous residue so obtained was acidified with aqueous citric acid to pH~2. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 264 Diastereomer 1 (absolute and relative stereochemistry unknown) (20.2 mg, 0.046 mmol, 35% yield). LC-MS Anal. Calc'd. for $C_{25}H_{31}N_3O_4$, 437.2, found [M+H] 438.1. $T_r$=1.56 min. (Method O). $^1$H NMR (400 MHz, DMSO-d$_6$) δ7.91 (s, 1H), 7.56 (d, J=8.74 Hz, 2H), 7.06-7.21 (m, 4H), 6.93 (m, 1H), 3.73-3.90 (m, 4H), 3.20-3.28 (s, 3H), 3.09-3.18 (m, 4H), 3.00 (m, 1H), 2.79-2.91 (m, 1H), 2.60 (m, 1H), 2.46 (m, 1H), 1.73-1.82 (m, 1H), 1.51-1.62 (m, 1H), 1.38-1.47 (m, 1H), 1.27-1.36 (m, 1H), 0.81 (t, J=6.8 Hz, 3H).

Example 264. Diastereomer 2. 3-(3-((4-Cyanophenyl)amino)-4-(ethyl(tetrahydro-2H-pyran-3-yl)amino)phenyl)-4-methoxybutanoic acid Example 264 Diastereomer 2 was prepared from 264A Diastereomer 2 following the procedure described for the synthesis of Example 264 Diastereomer 1 (absolute and relative stereochemistry unknown). LC-MS Anal. Calc'd. for $C_{25}H_{31}N_3O_4$, 437.2, found [M+H] 438.1. $T_r$=1.61 min.

(Method O). ¹H NMR (400 MHz, DMSO-$d_6$) δ 7.93 (s, 1H), 7.56 (m, 2H), 7.04-7.14 (m, 4H), 6.87-7.01 (m, 1H), 3.74 (m, 4H), 3.20-3.28 (s, 3H), 3.03-3.19 (m, 4H), 3.00 (m, 1H), 2.79-2.91 (m, 1H), 2.60 (m, 1H), 2.28-2.39 (m, 1H), 1.73-1.82 (m, 1H), 1.57 (m, 1H), 1.40-1.49 (m, 1H), 1.28-1.38 (m, 1H), 0.82 (t, J=7.2 Hz, 3H).

Example 265

Diastereomer 3 and Diastereomer 4

3-(3-((4-Cyanophenyl)amino)-4-(ethyl(tetrahydro-2H-pyran-3-yl)amino)phenyl)-4-methoxybutanoic acid

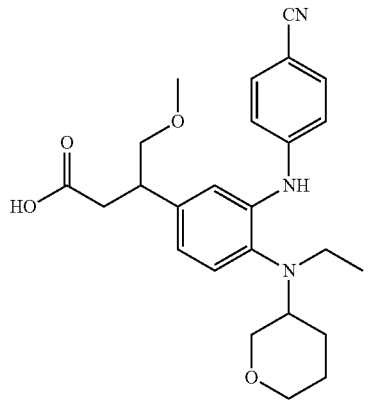 [SMILES: CCN(c1ccc(C(COC)CC(=O)O)cc1Nc1ccc(C#N)cc1)C1CCCOC1]

265A. N1-Ethyl-N1-(tetrahydro-2H-pyran-3-yl)-4-(4,4,5,5-tetramethyl-1,3,2-dioxaborolan-2-yl)benzene-1,2-diamine To a stirred solution of 59C Enantiomer 2 (800 mg, 2.67 mmol), bis(pinacolato)diboron (1.018 g, 4.01 mmol) and potassium acetate (0.787 g, 8.02 mmol) in 1,4-dioxane (8 mL) was purged with argon for 10 min. To this $PdCl_2$ (dppf).$CH_2Cl_2$ Adduct (0.109 g, 0.134 mmol) was added and purged with argon for 5 min. The reaction mixture was heated at 90° C. for 5 h. LCMS indicated completion of reaction. Reaction mixture was cooled to room temperature and quenched with water (30 mL). Aqueous layer was extracted with ethyl acetate (3×30 mL). The combined organic layer was washed with brine (20 mL), dried over anhydrous sodium sulfate, concentrated under reduced pressure to get crude compound. Purification via flash chromatography gave 265A (yellow liquid, 0.410 g, 1.184 mmol, 44% yield). LC-MS Anal. Calc'd. for $C_{19}H_{31}BN_2O_3$, 346.2, found [M+H] 347.0. $T_r$=1.52 min. (Method AY).

265B. Ethyl 3-(3-amino-4-(ethyl(tetrahydro-2H-pyran-3-yl)amino)phenyl)-4-methoxybutanoate Compound 265B was prepared from 265A and E-4-methoxybut-2-enoate following the procedure described for the synthesis of 59E. LC-MS Anal. Calc'd. for $C_{20}H_{32}N_2O_4$, 364.2, found [M+H] 365.3. $T_r$=1.43 min (Method AY).

Chiral separation of 265B (Method CM) gave 265B Diastereomer 3 $T_r$=1.62 min (Method CM), and 265B diastereomer 4 $T_r$=2.09 min (Method CM).

265B Diastereomer 3 (yellow liquid, 100 mg, 44%): LC-MS Anal. Calc'd. for $C_{20}H_{32}N_2O_4$, 364.2, found [M+H] 365.3. $T_r$=1.43 min (Method BB).

265B Diastereomer 4 (yellow liquid, 100 mg, 44%): LC-MS Anal. Calc'd. for $C_{20}H_{32}N_2O_4$, 364.2, found [M+H] 365.3. $T_r$=1.43 min (Method BB).

265C. Ethyl 3-(3-((4-cyanophenyl)amino)-4-(ethyl(tetrahydro-2H-pyran-3-yl)amino)phenyl)-4-methoxybutanoate The mixture of 265B Diastereomer 3 (0.050 g, 0.137 mmol), 4-bromobenzonitrile (0.030 g, 0.165 mmol), 4,5-bis(diphenylphosphino)-9,9-dimethylxanthene (7.94 mg, 0.014 mmol) and $Cs_2CO_3$ (0.067 g, 0.206 mmol) in 1,4-dioxane (2 mL) was stirred. Argon gas was bubbled through the mixture for 5 min. Bis(dibenzylideneacetone)palladium (3.94 mg, 6.86 µmol) was added and argon gas was bubbled through the mixture for 5 min. The reaction mixture was sealed and placed in preheated oil bath at 110° C. for 3 h. The reaction mixture was cooled to room temperature and concentrated under reduced pressure to afford a residue. The residue was reconstituted in a mixture of ethyl acetate (15 mL) and water (15 mL). The combined organic layer was washed with water (10 mL), brine (10 mL), dried over anhydrous sodium sulfate and concentrated under reduced pressure to afford a residue. The residue was purified via flash silica gel column chromatography to afford 265C (yellow liquid, 60 mg, 0.104 mmol, 76% yield). LC-MS Anal. Calc'd. for $C_{27}H_{35}N_3O_4$, 465.2, found [M+H] 466.3. $T_r$=1.56 min. (Method AY).

Example 265. Diastereomer 3. 3-(3-((4-Cyanophenyl)amino)-4-(ethyl(tetrahydro-2H-pyran-3-yl)amino)phenyl)-4-methoxybutanoic acid To a stirred solution of 265C (0.060 g, 0.129 mmol) in mixture of tetrahydrofuran (1 mL), methanol (1 mL) and water (0.2 mL) was added LiOH.$H_2O$ (0.022 g, 0.515 mmol). The reaction mixture was stirred at room temperature for 12 h. The reaction mixture was concentrated under reduced pressure. The aqueous residue so obtained was acidified with aqueous citric acid to pH~2. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LCMS to afford Example 265 Diastereomer 3 (absolute and relative stereochemistry unknown) (15 mg, 0.034 mmol, 26% yield). LC-MS Anal. Calc'd. for $C_{25}H_{31}N_3O_4$ 437.2, found [M+H] 438.1. $T_r$=1.56 min. (Method O). ¹H NMR (400 MHz, DMSO-$d_6$) δ 7.91 (s, 1H), 7.50-7.64 (m, 2H), 7.05-7.22 (m, 4H), 6.82-6.99 (m, 1H), 3.69-3.78 (m, 4H), 3.20-3.26 (m, 3H), 3.10-3.18 (m, 4H), 2.94-3.05 (m, 1H), 2.81-2.91 (m, 1H), 2.60 (m, 1H), 2.46 (m, 1H), 1.73-1.82 (m, 1H), 1.54-1.65 (m, 1H), 1.40-1.49 (m, 1H), 1.27-1.38 (m, 1H), 0.81 (t, J=7.2 Hz, 3H).

Example 265. Diastereomer 4. 3-(3-((4-Cyanophenyl)amino)-4-(ethyl(tetrahydro-2H-pyran-3-yl)amino)phenyl)-4-methoxybutanoic acid Example 265 Diastereomer 4 was prepared from 265B Diastereomer 4 following the procedure described for the synthesis of Example 265 Diastereomer 3 (absolute stereochemistry unknown). LC-MS Anal. Calc'd. for $C_{25}H_{31}N_3O_4$, 437.2, found [M+H] 438.1. $T_r$=1.56 min.

(Method O). ¹H NMR (400 MHz, DMSO-d₆) δ 7.91 (s, 1H), 7.56 (d, J=8.74 Hz, 2H), 7.06-7.22 (m, 4H), 6.83-7.00 (m, 1H), 3.72 (m, 4H), 3.20-3.28 (s, 3H), 3.08-3.17 (m, 4H), 2.94-3.05 (m, 1H), 2.86 (m, 1H), 2.65 (m, 1H), 2.46 (d, J=8.68 Hz, 1H), 1.73-1.82 (m, 1H), 1.51-1.60 (m, 1H), 1.38-1.49 (m, 1H), 1.27-1.38 (m, 1H), 0.81 (t, J=7.2 Hz, 3H).

Example 266

3-(3-((4-Chlorophenyl)amino)-4-((S)-3-hydroxypyrrolidin-1-yl)phenyl)pentanoic acid

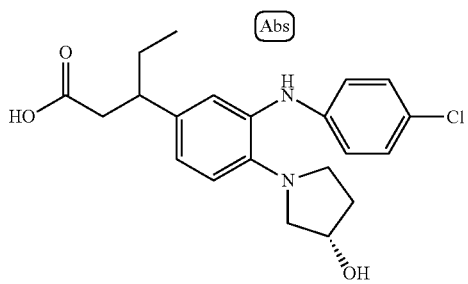 [SMILES: CCC(CC(=O)O)c1ccc(N2CC[C@H](O)C2)c(Nc2ccc(Cl)cc2)c1]

266A. 2-(4-Fluorophenyl)-5,5-dimethyl-1,3,2-dioxaborinane

A stirred solution of 1-bromo-4-fluorobenzene (10 g, 57.1 mmol), bis(pinacolato)diboron (19.36 g, 86 mmol) and potassium acetate (16.82 g, 171 mmol) in toluene (100 mL) was purged with argon for 10 min. To this PdCl₂(dppf).CH₂Cl₂ Adduct (1.400 g, 1.714 mmol) was added and purged with argon for 5 min. The reaction mixture was heated at 80° C. for 2 h. LCMS indicated completion of reaction. Reaction mixture was cooled to room temperature and quenched with water (30 mL). Aqueous layer was extracted with DCM (3×50 mL). The combined organic layer was washed with brine (20 mL), dried over anhydrous sodium sulfate, concentrated under reduced pressure to get crude compound. Purification via flash chromatography gave 266A (off-white solid, 10 g, 48.1 mmol, 84% yield). ¹H NMR (300 MHz, CDCl₃) δ 7.80-7.76 (m, 2H), 7.05-6.99 (m, 2H), 3.76 (s, 4H), 1.02 (s, 6H).

266B. Methyl 3-(4-fluorophenyl)pentanoate

In a pressure tube equipped with Teflon cap, compound 266A (1 g, 2.89 mmol), 1,4-dioxane (10 mL) were added followed by (E)-methyl pent-2-enoate (0.549 g, 4.81 mmol), (R)-(+)-2,2'-bis(diphenylphosphino)-1,1'-binaphthyl (0.066 g, 0.106 mmol) and 1M solution of sodium hydroxide (4.33 mL, 4.33 mmol). Argon gas was bubbled through the mixture for 10 min and chloro(1,5-cyclooctadiene)rhodium (I) dimer (0.028 g, 0.072 mmol) was added at room temperature. Argon gas was bubbled through the mixture for 5 min. The tube was then screw-capped and heated at 50° C. for 4 h. The reaction mixture was cooled to room temperature, quenched with acetic acid (0.2 mL) and was stirred for 5 minutes before it was diluted with water (15 mL). The aqueous layer was extracted with ethyl acetate (3×20 mL). Combined organic layer was washed with water (15 mL), brine (15 mL), dried over anhydrous sodium sulfate and concentrated under reduced pressure to afford a residue. The residue was purified via flash silica gel column chromatography to afford 266B (liquid, 0.8 g, 3.81 mmol, 79% yield). ¹H NMR (400 MHz, CDCl₃) δ 7.14-7.10 (m, 2H), 6.99-6.95 (m, 2H), 3.57 (s, 3H), 3.05-2.95 (m, 1H), 2.65-2.52 (m, 2H), 1.75-1.52 (m, 2H), 0.78 (t, J=7.2 Hz, 3H).

266C. Methyl 3-(4-fluoro-3-nitrophenyl)pentanoate

To a stirred solution of 266B (0.1 g, 0.476 mmol) in H₂SO₄ (3 mL, 56.3 mmol) at 0° C., nitric acid (0.031 mL, 0.476 mmol) was slowly added under nitrogen atmosphere and maintained at same temperature for 1 h. Reaction mixture quenched with ice and extracted with ethyl acetate (2×50 mL). Organic layer dried over sodium sulfate and concentrated under reduced pressure to get light yellow liquid. Purification via flash chromatography gave 266C (yellow liquid, 0.07 g, 0.274 mmol, 57.7% yield). ¹H NMR (400 MHz, CDCl₃) δ 7.88-7.86 (m, 1H), 7.48-7.45 (m, 1H), 7.26-7.19 (m, 1H), 3.57 (s, 3H), 3.15-3.05 (m, 1H), 2.71-2.52 (m, 2H), 1.81-1.52 (m, 2H), 0.82 (t, J=7.2 Hz, 3H).

266D. Methyl 3-(4-((S)-3-hydroxypyrrolidin-1-yl)-3-nitrophenyl)pentanoate

Compound 266D was prepared from 266C and (S)-pyrrolidin-3-ol following the procedure described for the synthesis of 1G. LC-MS Anal. Calc'd. C₁₆H₂₂N₂O₅ for 322.2, found [M+H] 323.2, T_r=3.012 min (Method U).

266E. Methyl 3-(3-amino-4-((S)-3-hydroxypyrrolidin-1-yl)phenyl)pentanoate

Compound 266E was prepared from 266D following the procedure described for the synthesis of 1H. LC-MS Anal. Calc'd. C₁₆H₂₄N₂O₃ for 292.2, found [M+H] 293.2, T_r=1.892 min (Method U).

266F. Methyl 3-(3-((4-chlorophenyl)amino)-4-((S)-3-hydroxypyrrolidin-1-yl)phenyl)pentanoate Compound 266F was prepared from 266E and 1-bromo-4-chlorobenzene following the procedure described for the synthesis of H. LC-MS Anal. Calc'd. C₂₂H₂₇ClN₂O₃ for 402.2, found [M+H] 403.5, T_r=1.55 min (Method T).

Example 266. 3-(3-((4-Chlorophenyl)amino)-4-((S)-3-hydroxypyrrolidin-1-yl)phenyl)pentanoic acid Example 266 was prepared from 266F following the procedure described for the synthesis of Example 1 from 1I (homochiral, stereochemistry at the benzylic position unknown) LC-MS Anal. Calc'd. C₂₁H₂₅ClN₂O₃ for 388.2, found [M+H] 389.2, T_r=1.560 min (Method O). ¹H NMR (400 MHz, DMSO-d₆) δ 7.42 (s, 1H), 7.11 (d, J=8.8 Hz, 2H), 6.88-6.76 (m, 3H), 6.67 (d, J=8.8 Hz, 2H), 4.79 (d, J=4.0 Hz, 1H), 4.25-4.15 (m, 1H), 3.37-3.16 (m, 2H), 3.07-3.06 (m, 1H), 2.68-2.53 (m, 2H), 2.40-2.33 (m, 2H), 1.95-1.85 (m, 1H), 1.75-1.35 (m, 3H), 0.72 (t, J=7.2 Hz, 3H).

Example 267

Enantiomer 1

(S)-3-(3-((4-Chlorophenyl)amino)-4-((cyclopropylmethyl)(2-hydroxy-2-methylpropyl)amino)phenyl)pentanoic acid

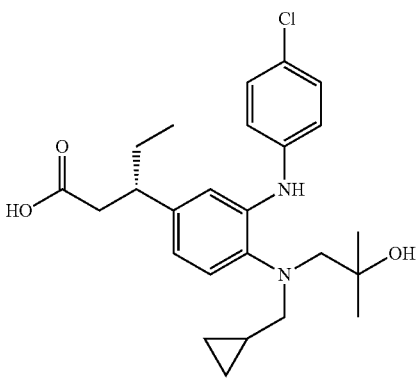 [SMILES: CC[C@@H](CC(=O)O)c1ccc(N(CC2CC2)CC(C)(C)O)c(Nc2ccc(Cl)cc2)c1]

267A. 1-((Cyclopropylmethyl)amino)-2-methylpropan-2-ol

To a stirred solution of cyclopropanecarbaldehyde (5 g, 71.3 mmol) in methanol (50 mL) under nitrogen was added 1-amino-2-methylpropan-2-ol (6.36 g, 71.3 mmol), followed by 4 Å molecular sieves (4 g). The reaction mixture was stirred for 12 h at RT. To the above mixture NaBH$_4$ (8.10 g, 214 mmol) was added portionwise at 0° C. The reaction mixture was stirred at RT for 3 h. Then quenched with ice water and removed volatiles under reduced pressure. The aqueous was diluted with 10% NaHCO$_3$ solution, extracted with EtOAc (2×200 mL). The combined organic layer was washed with brine solution, dried over anhydrous sodium sulfate and concentrated under reduced pressure to afford 267A (pale yellow oil, 6 g, 37.7 mmol, 52.9% yield). $^1$H NMR (400 MHz, DMSO-d$_6$): δ 4.18 (s, 1H), 2.40-2.27 (m, 4H), 1.08 (s, 6H), 0.87-0.85 (m, 1H), 0.41-0.37 (m, 2H), 0.09-0.07 (m, 2H).

267B. 1-((4-Bromo-2-nitrophenyl)(cyclopropylmethyl)amino)-2-methylpropan-2-ol To a solution of 4-bromo-1-fluoro-2-nitrobenzene (5 g, 22.73 mmol) in NMP (20 mL) was added 267A (3.26 g, 22.73 mmol) followed by DIPEA (9.92 mL, 56.8 mmol). Then the reaction mixture was heated to 120° C. for 5 h. The reaction mixture was cooled to RT and poured into water extracted with EtOAc (2×100 mL). The combined organic layer was washed with brine, dried over anhydrous sodium sulfate and concentrated under reduced pressure. Purified via flash chromatography to afford 267B (red color oil, 7.5 g, 19.67 mmol, 87% yield). LC-MS Analysis Calc'd. for C$_{14}$H$_{19}$BrN$_2$O$_3$, 343.2, found [M+2H] 345.1, T$_r$=1.12 min (Method BC).

267C. 1-((Cyclopropylmethyl)(4-(5,5-dimethyl-1,3,2-dioxaborinan-2-yl)-2-nitrophenyl)amino)-2-methylpropan-2-ol A mixture of 267B (7.5 g, 21.85 mmol), bis(neopentyl glycolato)diboron (6.42 g, 28.4 mmol) and potassium acetate (6.43 g, 65.6 mmol) in 1,4-dioxane (30 mL), at room temperature in a sealable flask, was purged with argon for 20 minutes before PdCl$_2$ (dppf).CH$_2$Cl$_2$ Adduct (0.535 g, 0.656 mmol) was added, the flask was sealed and the reaction heated at 80° C. for 6 h. The reaction mixture was cooled to RT and poured into water, extracted with EtOAc (2×150 mL). The combined organic layer was washed with brine, dried over anhydrous sodium sulfate and concentrated under reduced pressure. The crude sample was purified via flash chromatography to afford 267C (red color oil, 7 g, 17.67 mmol, 81% yield). LC-MS Analysis Calc'd. for C$_{19}$H$_{29}$BN$_2$O$_5$, 376.2, found [M-68] 309.1 for parent boronic acid, T$_r$=0.81 min (Method BC).

267D. Methyl (S)-3-(3-((4-chlorophenyl)amino)-4-((cyclopropylmethyl)(2-hydroxy-2-methylpropyl)amino)phenyl)pentanoate To a stirring and argon bubbling solution of 267C (2 g, 5.32 mmol) and (E)-methyl pent-2-enoate (1.820 g, 15.95 mmol) in 1,4-dioxane (20 mL) was added sodium hydroxide (1.0 molar) (4.85 mL, 4.85 mmol) and (R)-BINAP (0.073 g, 0.117 mmol), bubbling continued, then chlorobis(ethylene)rhodium(I) dimer (0.031 g, 0.080 mmol) was added and bubbled argon for another 5 minutes. The reaction mixture was heated at 50° C. for 1 h in sealed tube. Reaction mixture was cooled to room temperature and quenched with acetic acid (0.274 mL, 4.78 mmol) and it was stirred for 5 minutes before partitioned between ethyl acetate and water. Aqueous layer was extracted with ethyl acetate. The combined organic layer was washed with brine, dried over anhydrous sodium sulfate, concentrated under reduced pressure. The crude sample was purified via flash chromatography to afford 267D (pale yellow oil, 0.85 g, 2.134 mmol, 40.1% yield). LC-MS Analysis Calc'd. for C$_{20}$H$_{30}$N$_2$O$_5$, 378.2, found [M+H] 379.2, T$_r$=1.01 min (Method BC).

267E. Methyl (S)-3-(3-amino-4-((cyclopropylmethyl)(2-hydroxy-2-methylpropyl)amino)phenyl)pentanoate To a stirred solution of 267D (0.8 g, 2.114 mmol) in MeOH (15 mL) was carefully added Pd/C (10%) (0.112 g, 0.106 mmol). The flask was sequentially evacuated then purged with nitrogen before being pressurized to 15 psi of hydrogen for 6 h. The reaction mixture was filtered through a CELITE® bed, and the filtrate was concentrated under reduced pressure to afford 267E.

Chiral separation of 267E Enantiomeric mixture (93:7) yielded 267E Enantiomer 1 T$_r$=3.6 Min, 267E Enantiomer 2 T$_r$=4.86 min (Method CX).

267E Enantiomer 1: (pale yellow oil, 0.45 g, 1.227 mmol, 58.0% yield). LC-MS Analysis Calc'd. for C$_{20}$H$_{32}$N$_2$O$_3$, 348.2, found [M+H] 349.5, T$_r$=1.45 min (Method AY).

267F. Methyl (S)-3-(3-((4-chlorophenyl)amino)-4-((cyclopropylmethyl)(2-hydroxy-2-methylpropyl)amino)phenyl)pentanoate To a degassing solution of 267E Enantiomer 1 (0.03 g, 0.086 mmol) in 1,4-dioxane (2 mL) was added 1-bromo-4-chlorobenzene (0.020 g, 0.103 mmol), 4,5-bis(diphenylphosphino)-9,9-dimethylxanthene (9.96 mg, 0.017 mmol), cesium carbonate (0.084 g, 0.258 mmol) then bis(dibenzylideneacetone)palladium (4.95 mg, 8.61 µmol). Then the reaction temperature was raised to 110° C. for 5 h in a sealed tube. The reaction mixture was filtered through a CELITE® plug and the plug was washed with EtOAc. The filtrate was concentrated under reduced pressure to afford 267F (0.035 g, 0.076 mmol, 89% yield) as crude. The crude was taken further without purification. LC-MS Analysis Calc'd. for $C_{26}H_{35}ClN_2O_3$, 458.2, found [M+H] 459.2, $T_r$=0.93 min (Method BC).

Example 267 Enantiomer 1. (S)-3-(3-((4-Chlorophenyl)amino)-4-((cyclopropylmethyl)(2-hydroxy-2-methylpropyl)amino)phenyl)pentanoic acid To a solution of 267F (0.04 g, 0.052 mmol) in mixture of THF (1 mL), MeOH (1 mL) and water (1 mL) was added LiOH.H$_2$O (5.01 mg, 0.209 mmol) at RT and stirred for 5 h. Removed the volatiles under reduced pressure. The crude pH was adjusted to ~2 with 1.5N HCl solution. Aqueous solution was extracted with DCM (2×10 mL). The combined organic layer was washed with brine solution, dried over anhydrous sodium sulfate and concentrated under reduced pressure. The crude was purified via prep HPLC to afford Example 267 Enantiomer 1 (off-white solid, 0.006 g, 0.013 mmol, 26% yield). LC-MS Analysis Calc'd. for $C_{25}H_{33}ClN_2O_3$, 444.2, found [M+H] 445.2, $T_r$=2.134 min (Method O). $^1$H NMR (400 MHz, MeOD) δ 7.25-7.21 (m, 3H), 7.15-7.11 (m, 2H), 7.08 (d, J=2.00 Hz, 1H), 6.75 (dd, J=2.00, 7.60 Hz, 1H), 3.13 (s, 2H), 2.92-2.85 (m, 1H), 2.82 (d, J=6.80 Hz, 2H), 2.66-2.60 (m, 1H), 2.54-2.51 (m, 1H), 1.75-1.55 (m, 2H), 1.12 (s, 6H), 0.84-0.80 (m, 4H), 0.31-0.28 (m, 2H), −0.07-−0.88 (m, 2H).

Examples 268 to 270

Enantiomer 1

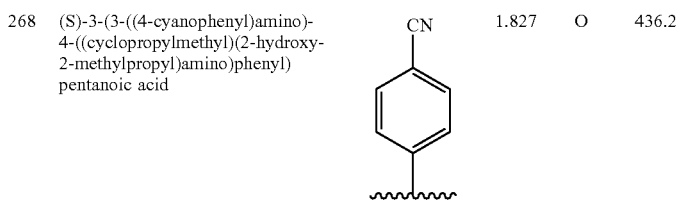

Examples 268 to 270 were prepared from 267E Enantiomer 1 and corresponding halides following the procedures described for the synthesis of Example 267.

| Ex. No. | Name | R | $T_r$ min | Method | (M + H) |
|---|---|---|---|---|---|
| 268 | (S)-3-(3-((4-cyanophenyl)amino)-4-((cyclopropylmethyl)(2-hydroxy-2-methylpropyl)amino)phenyl)pentanoic acid | 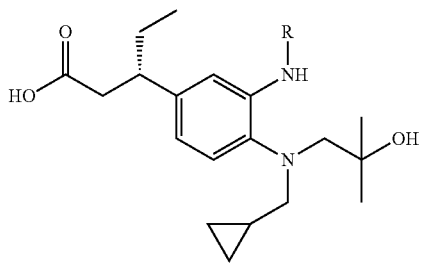 | 1.827 | O | 436.2 |
| 269 | (S)-3-(4-((cyclopropylmethyl)(2-hydroxy-2-methylpropyl)amino)-3-((4-fluorophenyl)amino)phenyl)pentanoic acid | 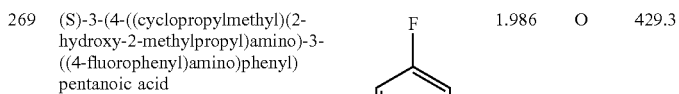 | 1.986 | O | 429.3 |
| 270 | (S)-3-(4-((cyclopropylmethyl)(2-hydroxy-2-methylpropyl)amino)-3-((2-ethoxypyrimidin-5-yl)amino)phenyl)pentanoic acid | 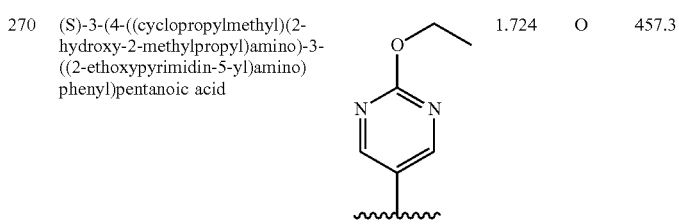 | 1.724 | O | 457.3 |

Example 271

Enantiomer 2

(R)-3-(3-((4-Chlorophenyl)amino)-4-((cyclopropylmethyl)(2-hydroxy-2-methylpropyl)amino)phenyl)pentanoic acid

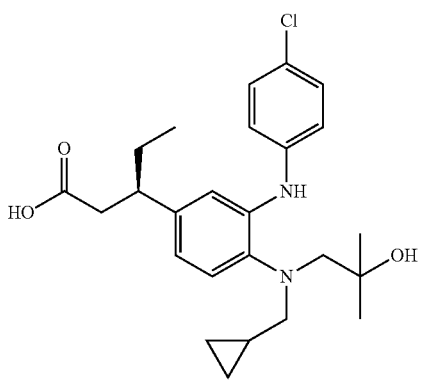 [SMILES: CC[C@H](CC(=O)O)c1ccc(N(CC2CC2)CC(C)(C)O)c(Nc2ccc(Cl)cc2)c1]

271A. Methyl (R)-3-(3-((4-chlorophenyl)amino)-4-((cyclopropylmethyl)(2-hydroxy-2-methylpropyl)amino)phenyl)pentanoate 271A was prepared using S-BINAP and 267C following the procedure described for the synthesis of 267D. LC-MS Analysis Calc'd. for $C_{20}H_{30}N_2O_5$, 378.2, found [M+H] 379.2, $T_r$=1.06 min (Method BC).

271B. Methyl (R)-3-(3-amino-4-((cyclopropylmethyl)(2-hydroxy-2-methylpropyl)amino)phenyl)pentanoate 271B was prepared using 271A following the procedure described for the synthesis of 267E.

Chiral separation of 271B Enantiomeric mixture (9:91) yielded 271B Enantiomer 1 $T_r$=3.6 min, 271B Enantiomer 2 $T_r$=4.8 min (Method CX).

271B Enantiomer 2: (pale yellow oil, 0.45 g, 1.227 mmol, 58.0% yield). LC-MS Analysis Calc'd. for $C_{20}H_{32}N_2O_3$, 348.2, found [M+H] 349.5, $T_r$=1.45 min (Method AY).

271C. Methyl (R)-3-(3-((4-chlorophenyl)amino)-4-((cyclopropylmethyl)(2-hydroxy-2-methylpropyl)amino)phenyl)pentanoate 271C was prepared using 271B Enantiomer 2 and 1-bromo-4-chlorobenzene following the procedure described for the synthesis of 267F. LC-MS Analysis Calc'd. for $C_{26}H_{35}ClN_2O_3$ 458.2 found [M+H] 459.2. $T_r$=0.93 min (Method BC).

Example 271 Enantiomer 2. (R)-3-(3-((4-Chlorophenyl)amino)-4-((cyclopropylmethyl)(2-hydroxy-2-methylpropyl)amino)phenyl)pentanoic acid Example 271 Enantiomer 2 was prepared using the 271C following the procedure described for the synthesis of Example 267 Enantiomer 1. LC-MS Analysis Calc'd. for $C_{25}H_{33}ClN_2O_3$, 444.2, found [M+H] 445.2, $T_r$=2.136 min (Method O). $^1$H NMR (400 MHz, MeOD) δ 7.25-7.21 (m, 3H), 7.15-7.11 (m, 2H), 7.08 (d, J=2.00 Hz, 1H), 6.75 (dd, J=2.00, 7.60 Hz, 1H), 3.13 (s, 2H), 2.92-2.85 (m, 1H), 2.82 (d, J=6.80 Hz, 2H), 2.66-2.60 (m, 1H), 2.54-2.51 (m, 1H), 1.75-1.55 (m, 2H), 1.12 (s, 6H), 0.84-0.80 (m, 4H), 0.31-0.28 (m, 2H), −0.07-−0.88 (m, 2H).

Examples 272 to 274

Enantiomer 2

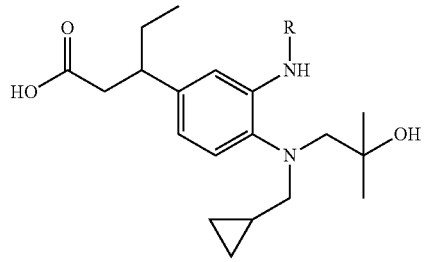

Examples 272 to 274 were prepared using 271B Enantiomer 2 and corresponding halides following the procedure described for the synthesis of Example 271

| Ex. No. | Name | R | | $T_r$ min | Method | (M + H) |
|---|---|---|---|---|---|---|
| 272 | (R)-3-(3-((4-cyanophenyl)amino)-4-((cyclopropylmethyl)(2-hydroxy-2-methylpropyl)amino)phenyl)pentanoic acid | CN | 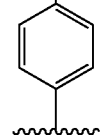 | 1.823 | O | 436.2 |
| 273 | (R)-3-(4-((cyclopropylmethyl)(2-hydroxy-2-methylpropyl)amino)-3-((4-fluorophenyl)amino)phenyl)pentanoic acid | F | 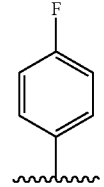 [SMILES: *c1ccc(F)cc1] | 2.066 | O | 429.3 |

| Ex. No. | Name | R | T$_r$ min | Method | (M + H) |
|---|---|---|---|---|---|
| 274 | (R)-3-(4-((cyclopropylmethyl)(2-hydroxy-2-methylpropyl)amino)-3-((2-ethoxypyrimidin-5-yl)amino)phenyl)pentanoic acid | 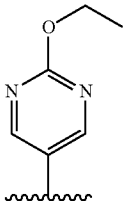 [SMILES: *c1cnc(OCC)nc1] | 1.700 | O | 457.3 |

Example 279

Enantiomer 1

(S)-3-(3-((4-Chlorophenyl)amino)-4-(cyclohexyl(ethyl)amino)phenyl)pentanoic acid

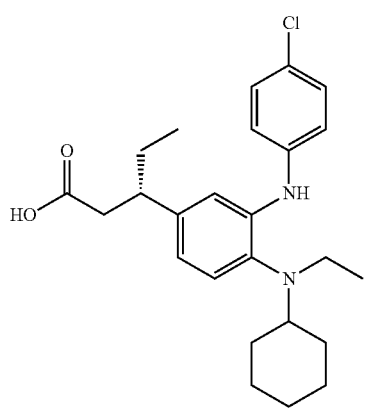 [SMILES: CC[C@@H](CC(=O)O)c1ccc(N(CC)C2CCCCC2)c(Nc2ccc(Cl)cc2)c1]

279A. N-Ethylcyclohexanamine, HCl

To a solution of ethanamine (2.53 g, 56.0 mmol) in MeOH (50 mL) was added cyclohexanone (5 g, 50.9 mmol) under nitrogen with 4 Å molecular sieves (2 g) at RT. Then the reaction mixture was stirred overnight. To the above mixture sodium borohydride (5.78 g, 153 mmol) was added portionwise, at 0° C. Then the reaction mixture was slowly allowed to RT and stirred for 2 h. The reaction mixture was quenched with satd. aq. Na$_2$CO$_3$ solution, extracted with diethyl ether (2×100 mL). The combined organic layer was dried over anhydrous sodium sulfate and concentrated under reduced pressure at lower temperature (35° C.). The resultant oil was dissolved in 10 mL of diethyl ether and slowly treated with 4M HCl in dioxane. The resultant precipitate was filtered and dried under vacuum to afford 279A (white solid, 3 g, 17.41 mmol, 34.2% yield). $^1$H NMR (400 MHz, DMSO-d$_6$) δ2.92-2.89 (m, 3H), 2.02-1.99 (m, 2H), 1.76-1.73 (m, 2H), 1.62-1.58 (m, 2H), 1.35-1.27 (m, 4H), 1.22 (t, J=8.40 Hz, 3H).

279B. 4-Bromo-N-cyclohexyl-N-ethyl-2-nitroaniline

To a solution of 4-bromo-1-fluoro-2-nitrobenzene (3 g, 13.64 mmol) in NMP (12 mL) at RT was added 279A (2.455 g, 15.00 mmol) followed by the addition of DIPEA (7.15 mL, 40.9 mmol). The reaction was sealed and heated at 120° C. for 16 h. The reaction mixture was cooled, poured into water and extracted with MTBE (2×150 mL). The combined organic layer was washed with brine solution, dried over anhydrous sodium sulfate and concentrated under reduced pressure. The crude sample was purified by flash chromatography using silica gel and 0-2% EtOAc in pet ether as eluent. The compound containing fractions were evaporated to afford 279B (red color oil, 2.5 g, 7.26 mmol, 53.2% yield). LC-MS Anal. Calc'd. for C$_{14}$H$_{19}$BrN$_2$O$_2$, 326.1, found [M+H] 329.2, T$_r$=1.96 min (Method T).

279C. N-Cyclohexyl-N-ethyl-2-nitro-4-(4,4,5,5-tetramethyl-1,3,2-dioxaborolan-2-yl)aniline To a stirred solution of 279B (2 g, 6.11 mmol), bis(pinacolato)diboron (2.328 g, 9.17 mmol) and potassium acetate (1.800 g, 18.34 mmol) in DMSO (20 mL) was purged with argon for 10 min. To this PdCl$_2$ (dppf).CH$_2$Cl$_2$ Adduct (0.250 g, 0.306 mmol) was added and purged with argon for another 5 min. The reaction mixture was heated at 80° C. for 4 h. Reaction mixture was cooled to RT and poured into water (100 mL), extracted with EtOAc (2×100 mL). The combined organic layer was dried over anhydrous sodium sulfate, filtered and concentrated under reduced pressure. The crude sample was purified by flash chromatography using silica gel and 0-10% EtOAc in pet ether as eluent. The compound containing fractions were evaporated to afford 279C (pale yellow oil, 2 g, 4.81 mmol, 79% yield). LC-MS Anal. Calc'd. for C$_{20}$H$_{31}$BN$_2$O$_4$, 374.2, found [M+H] 275.2, T$_r$=1.48 min (Method AA).

279D. Methyl (S)-3-(4-(cyclohexyl(ethyl)amino)-3-nitrophenyl)pentanoate (E1)

To a stirring and bubbling with argon solution of 1,4-dioxane (20 mL), added the chlorobis(ethylene)rhodium(I) dimer (7.79 mg, 0.020 mmol), (R)-BINAP (0.018 g, 0.029 mmol) bubbled with argon for 10 minutes, 279C (0.5 g, 1.336 mmol), (E)-methyl pent-2-enoate (0.183 g, 1.603 mmol), sodium hydroxide (1.220 mL, 1.220 mmol) were added respectively and bubbled argon for another 5 minutes. The reaction mixture was heated at 50° C. for 3 h in sealed tube. Reaction mixture was cooled to room temperature and quenched with acetic acid (0.069 mL, 1.202 mmol) and it was stirred for 5 minutes before partitioned between ethyl acetate and water. Aqueous layer was extracted with ethyl acetate. The combined organic layer was washed with brine, dried over anhydrous sodium sulfate, filtered and concentrated under reduced pressure. The crude sample was purified by flash chromatography using silica gel and 0-5%

EtOAc in pet ether as eluent. The compound containing fractions were evaporated to afford 279D (pale yellow oil, 0.35 g, 0.966 mmol, 72.3% yield). LC-MS Anal. Calc'd. for $C_{20}H_{30}N_2O_4$, 362.2, found [M+H] 363.6, $T_r$=1.26 min (Method AA).

279E. Methyl (S)-3-(3-amino-4-(cyclohexyl(ethyl) amino)phenyl)pentanoate

To a sealable hydrogen stirring flask, charged with 279D (0.35 g, 0.966 mmol) and Pd/C (10%) (0.051 g, 0.048 mmol) was carefully added ethyl acetate (15 mL). The flask was sequentially evacuated then purged with nitrogen before being pressurized to 40 psi of hydrogen for 4 h. The reaction mixture was filtered through CELITE® bed, washed with methanol (2×15 ml). The combined filtrate was concentrated under reduced pressure to get 279E (gummy solid, 0.28 g, 0.800 mmol, 83% yield). LC-MS Anal. Calc'd. for $C_{20}H_{32}N_2O_2$, 332.2, found [M+H] 333.6, $T_r$=0.87 min (Method AA).

Chiral purity for 279E Enantiomer 1 found to be enantiomerically pure (95:5) which was taken further without purification. (279E Enantiomer 1, $T_r$=3.07; 279E Enantiomer 2, $T_r$=4.02; Method BH).

279F. Methyl (S)-3-(3-((4-chlorophenyl)amino)-4 (cyclohexyl(ethyl)amino)phenyl)pentanoate To a degasified solution of 279E Enantiomer 1 (0.035 g, 0.180 mmol) in 1,4-dioxane (2 mL) was added $Cs_2CO_3$ (0.147 g, 0.451 mmol) and 4,5-bis(diphenylphosphino)-9,9-dimethylxanthene (0.044 g, 0.075 mmol) followed by bis (dibenzylideneacetone)palladium (8.65 mg, 0.015 mmol). Then the reaction was heated to 110° C. for 16 h. The reaction mixture was cooled to RT and filtered through CELITE® bed; the filtrate was concentrated under reduced pressure. The crude sample was purified by flash chromatography using silica gel and 0-50% EtOAc in pet ether as eluent. The compound containing fractions were evaporated to afford 279F (pale yellow oil, 0.04 g, 0.072 mmol, 48.0% yield). LC-MS Analysis Calc'd. for $C_{26}H_{35}ClN_2O_2$ 442.2, found [M+H] 443.6, $T_r$=1.02 min (Method BC).

Example 279 Enantiomer 1. (S)-3-(3-((4-Chlorophenyl)amino)-4-cyclohexyl(ethyl)amino)phenyl) pentanoic acid To a solution of 279F (0.04 g, 0.090 mmol) in mixture of THF (1 mL), MeOH (1 mL) and water (1 mL) was added NaOH (0.014 g, 0.361 mmol) at RT and stirred for 1 h. Removed the volatiles under reduced pressure, the crude was dissolved in 10 mL of water and acidified with 1.5N HCl solution, extracted with EtOAc (2×20 mL). The combined organic layer was dried over anhydrous sodium sulfate and concentrated under reduced pressure. The compound was purified by prep HPLC to afford Example 279 Enantiomer 1 (off-white solid, 0.27 g, 0.060 mmol, 66.9% yield). LC-MS Analysis Calc'd. for $C_{25}H_{33}ClN_2O_2$, 428.2, found [M+H] 429.2, $T_r$=2.392 min (Method O). $^1$H NMR (400 MHz, DMSO-$d_6$) δ 7.29 (s, 1H), 7.25-7.21 (m, 2H), 7.11-7.07 (m, 3H), 7.02 (d, J=2.00 Hz, 1H), 6.73-6.71 (m, 1H), 2.99-2.92 (m, 2H), 2.86-2.75 (m, 1H), 2.60-2.54 (m, 2H), 2.49-2.43 (m, 1H), 1.62-1.61 (m, 2H), 1.65-1.63 (m, 2H), 1.52-1.57 (m, 2H), 1.27-1.12 (m, 3H), 1.02-1.00 (m, 3H), 0.81 (t, J=7.20 Hz, 3H), 0.73 (t, J=6.80 Hz, 3H).

Examples 280 to 284

Enantiomer 1

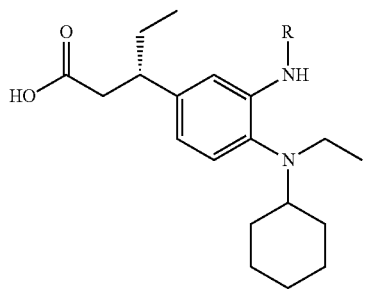

Examples 280 to 284 were prepared using 279E Enantiomer 1 and corresponding halides following the procedure described for the synthesis of Example 279.

| Ex. No. | Name | R | $T_r$ min | Method | (M + H) |
|---|---|---|---|---|---|
| 280 | (S)-3-(4-(cyclohexyl)(ethyl)amino)-3-((5-ethylpyrimidin-2-yl)amino)phenyl)pentanoic acid | 5-ethylpyrimidin-2-yl | 2.245 | O | 425.4 |
| 281 | (S)-3-(4-(cyclohexyl(ethyl)amino)-3-((2-ethoxypyrimidin-5-yl)amino)phenyl)pentanoic acid | 2-ethoxypyrimidin-5-yl | 2.079 | O | 441.4 |

-continued

| Ex. No. | Name | R | $T_r$ min | Method | (M + H) |
|---|---|---|---|---|---|
| 282 | (S)-3-(4-(cyclohexyl(ethyl)amino)-3-((4-ethylphenyl)amino)phenyl)pentanoic acid | | 2.733 | O | 423.4 |
| 283 | (S)-3-(3-((4-cyanophenyl)amino)-4-(cyclohexyl(ethyl)amino)phenyl)pentanoic acid | | 1.405 | R | 420.4 |
| 284 | (S)-3-(4-(cyclohexyl(ethyl)amino)-3-((4-(difluoromethoxy)phenyl)amino)phenyl)pentanoic acid | | 2.450 | O | 461.4 |

Example 285

Enantiomer 2

3-(3-((4-Chlorophenyl)amino)-4-(cyclohexyl(ethyl)amino)phenyl)pentanoic acid

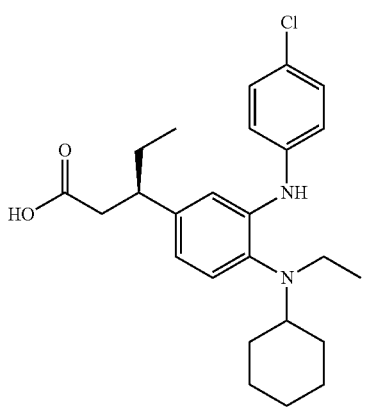 [SMILES: CC[C@H](CC(=O)O)c1ccc(N(CC)C2CCCCC2)c(Nc2ccc(Cl)cc2)c1]

285A. Methyl (R)-3-(4-(cyclohexyl(ethyl)amino)-3-nitrophenyl)pentanoate 285A was prepared using S-BINAP and 279C following the procedure described for the synthesis of 279D. LC-MS Anal. Calc'd. for $C_{20}H_{30}N_2O_4$, 362.2, found [M+H] 363.6, $T_r$=1.26 min (Method AA).

285B. Methyl (R)-3-(3-amino-4-(cyclohexyl(ethyl)amino)phenyl)pentanoate 285B was prepared using 285A following the same procedure described for the synthesis of 279E Enantiomer 1 (gummy solid, 0.28 g, 0.800 mmol, 85% yield), LC-MS Anal. Calc'd. for $C_{20}H_{32}N_2O_2$, 332.2, found [M+H] 333.6. $T_r$=0.87 min (Method AA).

Chiral purity for 285B Enantiomer 2 found to be enantiomerically pure (5:95) which was taken further without purification. (285B Enantiomer 1: $T_r$=3.09; 285B Enantiomer 2: $T_r$=3.92; Method BH).

285C. Methyl (R)-3-(3-((4-chlorophenyl)amino)-4-(cyclohexyl(ethyl)amino)phenyl)pentanoate 285C was prepared using 285B Enantiomer 2 and 1-chloro-4-bromobenzene following the procedure described for the synthesis of 279F. LC-MS Analysis Calc'd. for $C_{26}H_{35}ClN_2O_2$, 442.2, found [M+H] 443.6, $T_r$=1.02 min (Method BC).

Example 285 Enantiomer 2. (R)-3-(3-((4-Chlorophenyl)amino)-4-(cyclohexyl(ethyl)amino)phenyl)pentanoic acid Example 285 Enantiomer 2 was prepared using 285C following the procedure described for the synthesis of Example 279 Enantiomer 1. LC-MS Analysis Calc'd. for $C_{25}H_{33}ClN_2O_2$, 428.2, found [M+H] 429.2, $T_r$=2.392 min (Method O). $^1$H NMR (400 MHz, DMSO-$d_6$) δ 7.29 (s, 1H), 7.25-7.21 (m, 2H), 7.11-7.07 (m, 3H), 7.02 (d, J=2.00 Hz, 1H), 6.73-6.71 (m, 1H), 2.99-2.92 (m, 2H), 2.86-2.75 (m, 1H), 2.60-2.54 (m, 2H), 2.49-2.43 (m, 1H), 1.62-1.61 (m, 2H), 1.65-1.63 (m, 2H), 1.52-1.57 (m, 2H), 1.27-1.12 (m, 3H), 1.02-1.00 (m, 3H), 0.81 (t, J=7.20 Hz, 3H), 0.73 (t, J=6.80 Hz, 3H).

Examples 286 to 290

Enantiomer 2

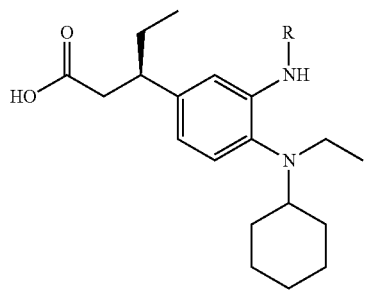

Examples 286 to 290 Enantiomer 2 were prepared using 285B Enantiomer 2 and corresponding halides following the procedure described for the synthesis of Example 285.

| Ex. No. | Name | R | $T_r$ min | Method | (M + H) |
|---|---|---|---|---|---|
| 286 | (R)-3-(4-(cyclohexyl(ethyl)amino)-3-((5-ethylpyrimidin-2-yl)amino)phenyl)pentanoic acid | 5-ethylpyrimidin-2-yl | 2.218 | O | 425.4 |
| 287 | (R)-3-(4-(cyclohexyl(ethyl)amino)-3-((2-ethoxypyrimidin-5-yl)amino)phenyl)pentanoic acid | 2-ethoxypyrimidin-5-yl | 2.206 | O | 441.4 |
| 288 | (R)-3-(4-(cyclohexyl(ethyl)amino)-3-((4-ethylphenyl)amino)phenyl)pentanoic acid | 4-ethylphenyl | 1.620 | R | 423.4 |
| 289 | (R)-3-(3-((4-cyanophenyl)amino)-4-(cyclohexyl(ethyl)amino)phenyl)pentanoic acid | 4-cyanophenyl | 2.128 | O | 420.4 |

-continued

| Ex. No. | Name | R | $T_r$, min | Method | (M + H) |
|---|---|---|---|---|---|
| 290 | (R)-3-(4-(cyclohexyl(ethyl)amino)-3-((4-(difluoromethoxy)phenyl)amino)phenyl)pentanoic acid | | 1.488 | R | 461.4 |

Example 299

Enantiomer 1

3-(4-(Cyclohexyl(isobutyl)amino)-3-((2,2-difluorobenzo[d][1,3]dioxol-5-yl)amino)phenyl)pentanoic acid

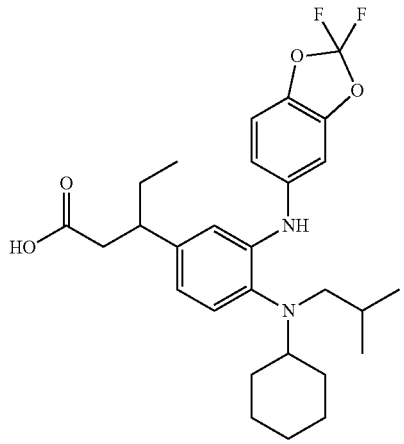 [SMILES: CCC(CC(=O)O)c1ccc(N(CC(C)C)C2CCCCC2)c(Nc2ccc3c(c2)OC(F)(F)O3)c1]

299A. Methyl 3-(4-(cyclohexyl(isobutyl)amino)-3-((2,2-difluorobenzo[d][1,3]dioxol-5-yl)amino)phenyl)pentanoate Racemic 3-(3-amino-4-(cyclohexyl(isobutyl)amino)phenyl)pentanoate 1073D was separated into individual antipodes by preparative chiral SFC on a CHIRALPAK® IC column with 10% acetonitrile/$CO_2$ (first peak, $T_R$=3.51 min on a 250 mm×4.6 mm CHIRALPAK® IC column with 3 g/min acetonitrile/$CO_2$, absolute stereochemistry unknown). To a degassing solution of resolved 3-(3-amino-4-(cyclohexyl(isobutyl)amino)phenyl)pentanoate (0.05 g, 0.139 mmol) in 1,4-dioxane (2 mL) was added 5-bromo-2,2-difluorobenzo[d][1,3]dioxole (0.039 g, 0.166 mmol), 4,5-bis(diphenylphosphino)-9,9-dimethylxanthene (0.016 g, 0.028 mmol), cesium carbonate (0.136 g, 0.416 mmol) followed by the addition of bis(dibenzylideneacetone)palladium (7.97 mg, 0.014 mmol). Then the reaction temperature was raised to 110° C. and stirred for 16 h in a sealed tube. The reaction mixture was filtered through CELITE® bed, washed with EtOAc (25 ml). The organic layer was washed with water (2×10 ml) followed by brine solution (10 ml), dried over anhydrous sodium sulfate, filtered and concentrated under reduced pressure to afford 299A (pale yellow oil, 0.05 g, 0.077 mmol, 55.8% yield). LC-MS Analysis Calc'd. for $C_{29}H_{38}F_2N_2O_4$, 516.2, found [M+H] 517.2, $T_r$=1.27 min (Method BC).

Example 299 Enantiomer 1. 3-(4-(Cyclohexyl(isobutyl)amino)-3-((2,2-difluorobenzo[d][1,3]dioxol-5-yl)amino)phenyl)pentanoic acid To a solution of 299A (0.05 g, 0.097 mmol) in mixture of THF (1 mL), MeOH (1 mL) and water (1 mL) was added NaOH (0.015 g, 0.387 mmol) at RT and stirred for 1 h. Removed the volatiles under reduced pressure, the salt was dissolved in 10 mL of water and acidified with 1.5 N HCl solution, extracted with EtOAc (2×20 mL). The combined organic layer was dried over anhydrous sodium sulfate, filtered and concentrated under reduced pressure. The crude was purified by prep HPLC to afford Example 299 Enantiomer 1 (absolute stereochemistry unknown, off-white solid, 0.047 g, 0.088 mmol, 91% yield). LC-MS Analysis Calc'd. for $C_{28}H_{36}F_2N_2O_4$, 502.2, found [M+H] 503.3, $T_r$=3.080 min (Method O). $^1$H NMR (400 MHz, DMSO-$d_6$) δ 7.23 (d, J=8.80 Hz, 1H), 7.11-7.10 (m, 4H), 6.83-6.80 (m, 1H), 6.73 (d, J=8.00 Hz, 1H), 2.81-2.73 (m, 3H), 2.59-2.56 (m, 1H), 2.45-2.40 (m, 2H), 1.78-1.72 (m, 2H), 1.68-1.61 (m, 3H), 1.50-1.44 (m, 2H), 1.33-1.25 (m, 3H), 1.02-0.94 (m, 3H), 0.80 (d, J=6.40 Hz, 6H), 0.72 (t, J=6.40 Hz, 3H).

Examples 300 to 314

Enantiomer 1

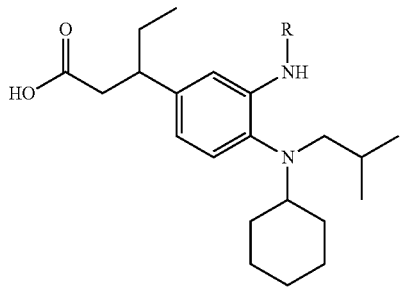

Examples 300 to 314 were prepared using 299A and the corresponding halides following the procedure described for the synthesis of Example 299 (absolute stereochemistry not determined).

| Ex. No. | Name | R | T,, min | Method | (M + H) |
|---|---|---|---|---|---|
| 300 | 3-(4-((1,1-dioxidotetrahydro-2H-thiopyran-4-yl)(ethyl)amino)-3-((4-fluorophenyl)amino)phenyl)-4-isopropoxybutanoic acid | 4-Cl, 3-(OCH$_2$CF$_3$)phenyl | 3.208 | O | 555.3 |
| 301 | 3-(4-(cyclohexyl(isobutyl)amino)-3-((2,3-dihydrobenzo[b][1,4]dioxin-6-yl)amino)phenyl)pentanoic acid | 2,3-dihydrobenzo[b][1,4]dioxin-6-yl | 2.162 | R | 481.3 |
| 302 | 3-(4-(cyclohexyl(isobutyl)amino)-3-((5-ethylpyrimidin-2-yl)amino)phenyl)pentanoic acid | 5-ethylpyrimidin-2-yl | 2.848 | O | 453.3 |
| 303 | 3-(4-(cyclohexyl(isobutyl)amino)-3-((2-ethoxypyrimidin-5-yl)maino)phenyl)pentanoic acid | 2-ethoxypyrimidin-5-yl | 2.127 | R | 469.3 |
| 304 | 3-(4-(cyclohexyl(isobutyl)amino)-3-(p-tolylamino)phenyl)pentanoic acid | p-tolyl | 2.044 | R | 437.4 |
| 305 | 3-(4-(cyclohexyl(isobutyl)amino)-3-((2-methylbenzo[d]thiazol-6-yl)amino)phenyl)pentanoic acid | 2-methylbenzo[d]thiazol-6-yl | 1.878 | R | 494.4 |
| 306 | 3-(4-(cylcohexyl(isobutyl)amino)-3-((3,4-difluorophenyl)amino)phenyl)pentanoic acid | 3,4-difluorophenyl | 2.080 | R | 459.4 |

| Ex. No. | Name | R | T$_r$, min | Method | (M + H) |
|---|---|---|---|---|---|
| 307 | 3-(3-((4-chloro-2-fluorophenyl)amino)-4-(cyclohexyl(isobutyl)amino)phenyl)pentanoic acid | 4-Cl, 2-F phenyl | 2.504 | R | 475.4 |
| 308 | 3-(3-((4-chlorophenyl)amino)-4-(cyclohexyl(isobutyl)amino)phenyl)pentanoic acid | 4-Cl phenyl | 2.975 | O | 457.4 |
| 309 | 3-(4-(cyclohexyl(isobutyl)amino)-3-((4-ethylphenyl)amino)phenyl)pentanoic acid | 4-ethylphenyl | 3.038 | O | 451.4 |
| 310 | 3-(3-((4-chloro-3-fluorophenyl)amino)-4-(cyclohexyl(isobutyl)amino)phenyl)pentanoic acid | 4-Cl, 3-F phenyl | 2.484 | O | 475.3 |
| 311 | 3-(4-(cyclohexyl(isobutyl)amino)-3-((4-fluorophenyl)amino)phenyl)pentanoic acid | 4-F phenyl | 1.989 | R | 441.4 |
| 312 | 3-(4-(cyclohexyl(isobutyl)amino)-3-((4-(trifluoromethoxy)phenyl)amino)phenyl)pentanoic acid | 4-OCF$_3$ phenyl | 2.985 | O | 507.4 |
| 313 | 3-(4-(cyclohexyl(isobutyl)amino)-3-((4-ethoxyphenyl)amino)phenyl)pentanoic acid | 4-ethoxyphenyl | 3.011 | O | 467.3 |

| Ex. No. | Name | R | $T_r$, min | Method | (M + H) |
|---|---|---|---|---|---|
| 314 | 3-(3-((4-cyanophenyl)amino)-4-(cyclohexyl(isobutyl)amino)phenyl)pentanoic acid | 4-cyanophenyl | 2.239 | O | 448.3 |

Example 315

Enantiomer 2

3-(4-(Cyclohexyl(isobutyl)amino)-3-((2,2-difluorobenzo[d][1,3]dioxol-5-yl)amino)phenyl)pentanoic acid

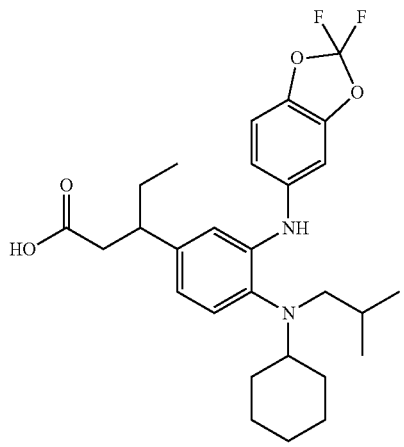 [SMILES: CCC(CC(=O)O)c1ccc(N(CC(C)C)C2CCCCC2)c(Nc2ccc3c(c2)OC(F)(F)O3)c1]

315A. Methyl 3-(4-(cyclohexyl(isobutyl)amino)-3-((2,2-difluorobenzo[d][1,3]dioxol-5-yl)amino)phenyl)pentanoate Racemic 3-(3-amino-4-(cyclohexyl(isobutyl)amino)phenyl)pentanoate 1073D was separated into individual antipodes by preparative chiral SFC on a CHIRALPAK® IC column with 10% acetonitrile/$CO_2$ (2nd peak, $T_R$=4.61 min on a 250 mm×4.6 mm CHIRALPAK® IC column with 3 g/min acetonitrile/$CO_2$, absolute stereochemistry unknown). Compound 315A was prepared using optically pure 3-(3-amino-4-(cyclohexyl(isobutyl)amino)phenyl)pentanoate (peak 2 above) and 5-bromo-2,2-difluorobenzo[d][1,3]dioxole following the procedure described for the synthesis of 299A. LC-MS Analysis Calc'd. for $C_{29}H_{38}F_2N_2O_4$, 516.2, found [M+H] 517.0, $T_r$=1.26 min (Method BC).

Example 315 Enantiomer 2. 3-(4-(Cyclohexyl(isobutyl)amino)-3-((2,2-difluorobenzo[d][1,3]dioxol-5-yl)amino)phenyl)pentanoic acid Example 315 Enantiomer 2 was prepared using 315A following the procedure described for the synthesis of Example 299 Enantiomer 1 (absolute stereochemistry unknown, off-white solid, 0.048 g, 0.096 mmol, 99% yield). LC-MS Analysis Calc'd. for $C_{28}H_{36}F_2N_2O_4$, 502.2, found [M+H] 503.3, $T_r$=3.208 min (Method O). $^1$H NMR (400 MHz, DMSO-$d_6$) δ 7.23 (d, J=8.80 Hz, 1H), 7.11-7.10 (m, 4H), 6.83-6.80 (m, 1H), 6.73 (d, J=8.00 Hz, 1H), 2.81-2.73 (m, 3H), 2.59-2.56 (m, 1H), 2.45-2.40 (m, 2H), 1.78-1.72 (m, 2H), 1.68-1.61 (m, 3H), 1.50-1.44 (m, 2H), 1.33-1.25 (m, 3H), 1.02-0.94 (m, 3H), 0.80 (d, J=6.40 Hz, 6H), 0.72 (t, J=6.40 Hz, 3H).

Examples 316 and 317

Enantiomer 2

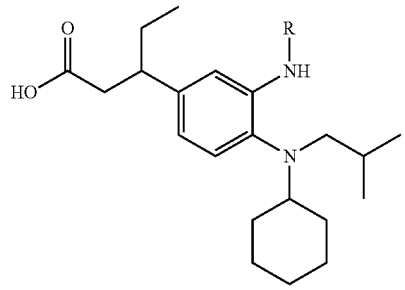

Examples 316 and 317 were prepared using optically pure 3-(3-amino-4-(cyclohexyl(isobutyl)amino)phenyl)pentanoate (peak 2 as described in 315A) and corresponding halides following the procedure described for the synthesis of Example 315 (absolute stereochemistry unknown).

| Ex. No. | Name | R | $T_r$, min | Method | (M + H) |
|---|---|---|---|---|---|
| 316 | 3-(4-((1,1-dioxidotetrahydro-2H-thiopyran-4-yl)(ethyl)amino)-3-((4-fluorophenyl)amino)phenyl)-4-isopropoxybutanoic acid | 2-chloro-5-(2,2,2-trifluoroethoxy)phenyl | 3.206 | O | 555.3 |

| Ex. No. | Name | R | $T_r$, min | Method | (M + H) |
|---|---|---|---|---|---|
| 317 | 3-(4-(cyclohexyl(isobutyl)amino)-3-((2,3-dihydrobenzo[b][1,4]dioxin-6-yl)amino)phenyl)pentanoic acid | | 2.196 | R | 481.3 |

Example 318

Enantiomer 1 and Enantiomer 2

3-(3-((4-Chlorophenyl)amino)-4-((2,2-difluoroethyl)(tetrahydro-2H-pyran-4-yl)amino)phenyl)pentanoic acid

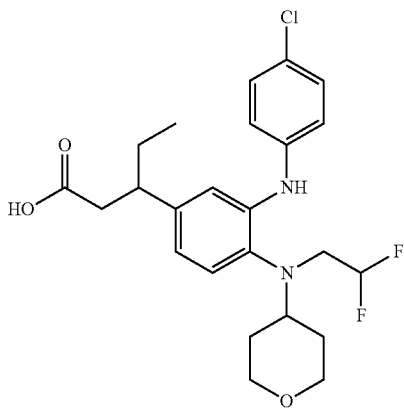 [SMILES: CCC(CC(=O)O)c1ccc(N(CC(F)F)C2CCOCC2)c(Nc2ccc(Cl)cc2)c1]

318A. 2-((Tetrahydro-2H-pyran-4-yl)amino)ethanol

A solution of dihydro-2H-pyran-4(3H)-one (5 g, 49.9 mmol) and 2-aminoethanol (3.66 g, 59.9 mmol) in ethanol (50 mL) was stirred for 2 h at RT. Then the reaction was cooled to ice bath and treated with sodium borohydride (2.83 g, 74.9 mmol) and stirred for 16 h at RT. The reaction mixture was quenched with saturated aqueous NaHCO₃ solution and extracted with DCM (2×100 mL). The combined organic layer was dried over anhydrous sodium sulfate, filtered and concentrated under reduced pressure to afford 318A (colorless oil, 5.3 g, 32.9 mmol, 65.8% yield). $^1$H NMR (300 MHz, DMSO-$d_6$) δ3.81 (dt, J=11.4, 3.5 Hz, 2H), 3.43 (q, J=5.7 Hz, 2H), 3.29-3.22 (m, 2H), 2.61-2.54 (m, 2H), 1.72-1.70 (m, 2H), 1.26-1.13, 1.08 (d, J=1.1 Hz, 1H), 1.07-1.00 (m, 2H).

318B. 2-((4-Bromo-2-nitrophenyl)(tetrahydro-2H-pyran-4-yl)amino)ethanol

To a solution of 4-bromo-1-fluoro-2-nitrobenzene (5 g, 22.73 mmol) in NMP (10 mL) was added 318A (3.30 g, 22.73 mmol) followed by DIPEA (9.92 mL, 56.8 mmol). Then the reaction mixture was heated to 120° C. for 16 h. The reaction mixture was poured into water and extracted with EtOAc (2×100 mL). The combined organic layer was dried over anhydrous sodium sulfate, filtered and concentrated under reduced pressure. The crude sample was purified by flash chromatography using silica gel and 0-40% EtOAc in pet ether as eluent. The compound containing fractions were evaporated to afford 318B (red color solid, 4 g, 11.01 mmol, 48.4% yield). LC-MS Anal. Calc'd. for $C_{13}H_{17}BrN_2O_4$, 344.1, found [M+H] 347.0, $T_r$=1.09 min (Method BA).

318C. 2-((4-Bromo-2-nitrophenyl)(tetrahydro-2H-pyran-4-yl)amino)acetaldehyde To a solution of 318B (3 g, 8.69 mmol) in DCM (60 mL) was added Dess-Martin periodinane (4.42 g, 10.43 mmol) at RT under nitrogen, stirred for 16 h. The crude was filtered through CELITE® bed, rinsed with DCM (60 ml). The filtrate was washed with NaHCO₃ solution (2×30 ml), brine (30 ml). The organic layers was dried over anhydrous sodium sulfate, filtered and concentrated under reduced pressure to afford 318C (pale yellow oil, 3 g, 7.87 mmol, 91% yield). The crude was taken further without purification. $^1$H NMR (400 MHz, DMSO-$d_6$) δ 9.44 (s, 1H), 8.10-8.05 (m, 1H), 7.82-7.76 (m, 1H), 7.48 (d, J=11.60 Hz, 1H), 4.00 (s, 2H), 3.81-3.85 (m, 2H), 3.27-3.10 (m, 2H), 2.93-2.89 (m, 1H), 1.33-1.21 (m, 4H).

318D. N-(4-Bromo-2-nitrophenyl)-N-(2,2-difluoroethyl)tetrahydro-2H-pyran-4-amine To a stirred solution of 318C (4 g, 11.66 mmol) in DCM (100 mL) was added DAST (3.85 mL, 29.1 mmol) slowly at −20° C. Then the reaction was allowed to RT for 16 h. The reaction mixture was cooled under ice bath and quenched with 10% NaHCO₃ solution (40 ml), aqueous was extracted with DCM (2×100 mL). The combined organic layers was washed with brine, dried over anhydrous sodium sulfate, filtered and concentrated under reduced pressure. The crude sample was purified by flash chromatography using silica gel and 0-30% EtOAc in pet ether as eluent to afford the pure fractions were concentrated under reduced pressure to afford 318D (yellow oil, 3.7 g, 9.12 mmol, 78% yield). $^1$H NMR (300 MHz, DMSO-$d_6$) δ 8.10-8.05 (m, 1H), 7.82-7.76 (m, 1H), 7.63 (d, J=8.7 Hz, 1H), 6.05-5.62 (m, 1H), 3.84 (dd, J=11.1, 4.0 Hz, 2H), 3.51 (td, J=15.1, 4.2 Hz, 2H), 3.19 (td, J=11.6, 2.1 Hz, 2H), 3.11-3.02 (m, 1H), 1.65-1.44 (m, 2H), 1.17 (d, J=7.2 Hz, 2H).

318E. N-(2,2-Difluoroethyl)-N-(4-(5,5-dimethyl-1,3,2-dioxaborinan-2-yl)-2-nitrophenyl)tetrahydro-2H-pyran-4-amine A mixture of 318D (2.5 g, 6.85 mmol), bis(neopentyl glycolato)diboron (2.010 g, 8.90 mmol) and potassium acetate (2.016 g, 20.54 mmol) in DMSO (50 mL), at room temperature in a sealable flask, was purged with argon for 20 minutes before PdCl$_2$(dppf).CH$_2$Cl$_2$ Adduct (0.168 g, 0.205 mmol) was added, the flask was sealed and the reaction heated at 80° C. for 6 hr. The reaction mixture was cooled to RT and poured into water (100 ml), extracted with EtOAc (2×150 mL). The combined organic layers were washed with brine, dried over anhydrous sodium sulfate, filtered and concentrated under reduced pressure. The crude sample was purified by flash chromatography using silica gel and 0-40% EtOAc in pet ether as eluent to afford the pure fractions were concentrated under reduced pressure to afford 318E (red color oil, 2.3 g, 5.20 mmol, 76% yield). LC-MS Anal. Calc'd. for C$_{18}$H$_{25}$BF$_2$N$_2$O$_5$, 398.2, found [M+H] 331 for parent boronic acid, T$_r$=0.98 min (Method BA).

318F. Methyl 3-(4-((2,2-difluoroethyl)(tetrahydro-2H-pyran-4-yl)amino)-3-nitrophenyl)pentanoate To a stirring and argon bubbling solution of 318E (0.5 g, 1.256 mmol) and (E)-methyl pent-2-enoate (0.430 g, 3.77 mmol) in 1,4-dioxane (10 mL) was added sodium hydroxide (1.146 mL, 1.146 mmol), bubbling continued, then chloro (1,5-cyclooctadiene)rhodium(I) dimer (0.012 g, 0.025 mmol) was added and bubbled argon for another 5 minutes. The reaction mixture was heated at 50° C. for 2 h in sealed tube. Reaction mixture was cooled to room temperature and quenched with acetic acid (0.065 mL, 1.130 mmol) and it was stirred for 5 minutes before partitioned between ethyl acetate (2×50 ml) and water (50 ml). Aqueous layer was extracted with ethyl acetate (50 ml). The combined organic layers were washed with brine, dried over anhydrous sodium sulfate, filtered and concentrated under reduced pressure. The crude sample was purified via flash chromatography using silica gel and 0-40% EtOAc in pet ether as eluent to afford the pure fractions were concentrated under reduced pressure to afford 318F (yellow oil, 0.4 g, 0.749 mmol, 59.7% yield). LC-MS Anal. Calc'd. for C$_{19}$H$_{26}$F$_2$N$_2$O$_5$, 400.1, found [M+H] 401.2. T$_r$=1.28 min (Method BA).

318G. Methyl 3-(3-amino-4-((2,2-difluoroethyl)(tetrahydro-2H-pyran-4-yl)amino)phenyl)-4-methoxybutanoate To a stirred solution of 318F (0.49 g, 1.224 mmol) in ethyl acetate (15 mL) was carefully added Pd/C (0.065 g, 0.061 mmol). The flask was sequentially evacuated then purged with nitrogen before being pressurized to 40 psi of hydrogen for 3 h. The reaction mixture was filtered through CELITE® bed, washed with methanol (30 ml) and the filtrate was concentrated under reduced pressure to get 318G racemic (0.23 g, 0.538 mmol, 45% yield).

Chiral separation of 318G racemic gave 318G Enantiomer 1 and 318G Enantiomer 2 as single enantiomers. Enantiomer 1 T$_r$=2.54 min and Enantiomer 2 T$_r$=2.92 min (Method CR).

318G Enantiomer 1 (absolute stereochemistry unknown). (0.11 g, 0.282 mmol, 23% yield). LC-MS Anal. Calc'd. for C$_{19}$H$_{28}$F$_2$N$_2$O$_3$, 370.2, found [M+H] 371.3, T$_r$=1.30 min (Method BA).

318G Enantiomer 2 (absolute stereochemistry unknown). (0.1 g, 0.256 mmol, 21% yield). LC-MS Anal. Calc'd. for C$_{19}$H$_{28}$F$_2$N$_2$O$_3$, 370.2, found [M+H] 371.3, T$_r$=1.30 min (Method BA).

318H. Methyl 3-(3-((4-chlorophenyl)amino)-4-((2,2-difluoroethyl)(tetrahydro-2H-pyran-4-yl)amino)phenyl)pentanoate To a degassing solution 318G Enantiomer 1 (0.031 g, 0.162 mmol), 1-chloro-4-bromobenzene (0.031 g, 0.162 mmol), 4,5-bis(diphenylphosphino)-9,9-dimethylxanthene (7.81 mg, 0.013 mmol), cesium carbonate (0.066 g, 0.202 mmol) by argon followed by the addition of bis(dibenzylideneacetone)palladium (3.88 mg, 6.75 µmol). The mixture bubbled with argon for another 5 minutes. Then the reaction was heated at 110° C. and stirred for 16 h. The reaction mixture was poured into water (10 ml) and extracted with EtOAc (2×25 mL). The combined organic layers were dried over anhydrous sodium sulfate, filtered and concentrated under reduced pressure to afford crude 318H (0.05 g, 0.078 mmol, 57.8% yield). The crude was taken further without purification. LC-MS Anal. Calc'd. for C$_{25}$H$_{31}$ClF$_2$N$_2$O$_3$, 480.1, found [M+H] 481.3, T$_r$=1.54 min (Method AA).

Example 318 Enantiomer 1. 3-(3-((4-Chlorophenyl)amino)-4-((2,2-difluoroethyl)(tetrahydro-2H-pyran-4-yl)amino)phenyl)pentanoic acid To a solution of 318H (0.05 g, 0.104 mmol) in mixture of THF (1 mL), MeOH (1 mL) and water (1 mL) was added LiOH.H$_2$O (9.96 mg, 0.416 mmol) at RT and stirred for 16 h. Removed the volatiles and the crude pH was adjusted to ~2 with saturated citric acid solution. The aqueous layer was extracted with DCM (2×10 mL). The combined organic layers were washed with brine, dried over anhydrous sodium sulfate, filtered and concentrated under reduced pressure. The crude sample was purified by prep HPLC to afford Example 318 Enantiomer 1 (absolute stereochemistry unknown) (off-white solid 0.017 g, 0.035 mmol, 34.6% yield). LC-MS Anal. Calc'd. for C$_{24}$H$_{29}$ClF$_2$N$_2$O$_3$ 466.1, found [M+H] 467.2, T$_r$=1.803 min (Method O). $^1$H NMR (400 MHz, DMSO-d$_6$) δ 7.28-7.25 (m, 3H), 7.20 (d, J=8.00 Hz, 1H), 7.11-7.08 (m, 2H), 7.02 (d, J=2.00 Hz, 1H), 6.75-6.72 (m, 1H), 6.04-5.76 (m, 1H), 3.81-3.77 (m, 2H), 3.39-3.36 (m, 3H), 3.17-3.19 (m, 2H), 3.00-2.96 (m, 1H), 2.91-2.89 (m, 2H), 2.50-2.40 (m, 2H), 1.68-1.61 (m, 2H), 1.39-1.36 (m, 2H), 0.72 (t, J=7.20 Hz, 3H).

Example 318 Enantiomer 2. 3-(3-((4-Chlorophenyl)amino)-4-((2,2-difluoroethyl)(tetrahydro-2H-pyran-4-yl)amino)phenyl)pentanoic acid Example 318 Enantiomer 2 was prepared using 318G Enantiomer 2 and 1-chloro-4-bromobenzene following the procedure described for the synthesis of Example 318 Enantiomer 1 (absolute stereochemistry unknown). LC-MS Anal. Calc'd. for C$_{24}$H$_{29}$ClF$_2$N$_2$O$_3$, 466.1, found [M+H] 467.1, T$_r$=2.049 min (Method O). $^1$H NMR (400 MHz, DMSO-d$_6$) δ 7.28-7.25 (m, 3H), 7.20 (d, J=8.00 Hz, 1H), 7.11-7.08 (m, 2H), 7.02 (d, J=2.00 Hz, 1H), 6.75-6.72 (m, 1H), 6.04-5.76 (m, 1H), 3.81-3.77 (m, 2H), 3.39-3.36 (m, 3H), 3.17-3.19 (m, 2H), 3.00-2.96 (m, 1H), 2.91-2.89 (m, 2H), 2.50-2.40 (m, 2H), 1.68-1.61 (m, 2H), 1.39-1.36 (m, 2H), 0.72 (t, J=7.20 Hz, 3H).

Example 319

Enantiomer 1

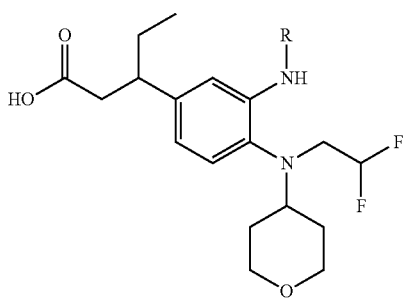

Example 319 was prepared using 318G Enantiomer 1 and corresponding halides following the procedure described for the synthesis Example 318 (absolute stereochemistry unknown).

| Ex. No. | Name | R | $T_r$, min | Method | (M + H) |
|---|---|---|---|---|---|
| 319 | methyl 3-(3-((4-chlorophenyl)amino)-4-((2,2-difluoroethyl)(tetrahydro-2H-pyran-4-yl)amino)phenyl)-4-methoxybutanoate | | 1.391 | O | 479.3 |

Example 320

Enantiomer 2

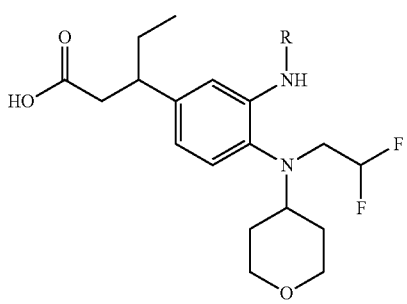

Example 320 (Enantiomer 2) was prepared using 318G Enantiomer 2 and corresponding halides following the procedure described for the synthesis of Example 318 (absolute stereochemistry unknown).

| Ex. No. | Name | R | $T_r$, min | Method | (M + H) |
|---|---|---|---|---|---|
| 320 | methyl 3-(3-((4-chlorophenyl)amino)-4-((2,2-difluoroethyl)(tetrahydro-2H-pyran-4-yl)amino)phenyl)-4-methoxybutanoate | | 1.389 | O | 479.3 |

Example 321

Enantiomer 1 and Enantiomer 2

3-(3-((4-Chlorophenyl)amino)-4-((2,2-difluoroethyl)(tetrahydro-2H-pyran-4-yl)amino)phenyl)-4-methoxybutanoic acid

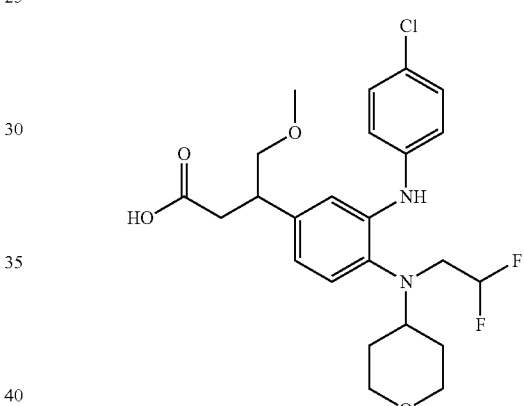

321A. Methyl 3-(4-((2,2-difluoroethyl)(tetrahydro-2H-pyran-4-yl)amino)-3-nitrophenyl)-4-methoxybutanoate To a stirring and argon bubbling solution of 318E (0.8 g, 2.009 mmol) and (E)-methyl 4-methoxybut-2-enoate 168A (0.784 g, 6.03 mmol) in 1,4-dioxane (16 mL) was added sodium hydroxide (1.834 mL, 1.834 mmol), bubbling continued, then chloro(1,5-cyclooctadiene)rhodium(I) dimer (0.020 g, 0.040 mmol) was added and bubbled argon for another 5 minutes. The reaction mixture was heated at 50° C. for 2 h in sealed tube. Reaction mixture was cooled to room temperature and quenched with acetic acid (0.104 mL, 1.808 mmol) and it was stirred for 5 minutes before partitioned between ethyl acetate (150 ml) and water (50 ml). Aqueous layer was extracted with ethyl acetate (2×50 ml). The combined organic layers were washed with brine, dried over anhydrous sodium sulfate, filtered and concentrated under reduced pressure to afford the crude material. The crude sample was purified via flash chromatography to afford 321A (red color oil 0.5 g, 1.081 mmol, 53.8% yield). $^1$H NMR (300 MHz, DMSO-$d_6$) δ 7.68 (d, J=1.9 Hz, 1H), 7.56-7.51 (m, 2H), 6.03-5.59 (m, 1H), 3.85-3.79 (m, 4H), 3.51 (s, 3H), 3.39 (s, 3H), 3.38-3.29 (m, 3H), 3.25-3.15 (m, 2H), 2.70-2.61 (m, 2H), 1.62-1.58 (m, 3H), 1.47 (d, J=9.4 Hz, 2H).

321B. Methyl 3-(3-amino-4-((2,2-difluoroethyl)(tetrahydro-2H-pyran-4-yl)amino)phenyl)-4-methoxybutanoate To a stirred solution of 321A (0.56 g, 1.345 mmol) in ethyl acetate (15 mL) was carefully added Pd/C (0.072 g, 0.067 mmol). The flask was sequentially evacuated then purged with nitrogen before being pressurized to 40 psi of hydrogen for 3 h. The reaction mixture was filtered through CELITE® bed, washed with methanol (50 ml) and the filtrate was concentrated under reduced pressure to get 321B racemic compound (0.23 g, 0.536 mmol, 40% yield).

Chiral separation of 321B racemic gave 321B Enantiomer 1 and 321B Enantiomer 2 as single enantiomers. Enantiomer 1 $T_r$=3.02 min and Enantiomer 2 $T_r$=3.62 min (Method CR).

321B Enantiomer 1 (absolute stereochemistry unknown): (0.12 g, 0.295 mmol, 22% yield). LC-MS Anal. Calc'd. for $C_{19}H_{28}F_2N_2O_4$, 386.2, found [M+H] 387.4, $T_r$=1.14 min (Method BA).

321B Enantiomer 2 (absolute stereochemistry unknown): (0.1 g, 0.241 mmol, 18% yield). LC-MS Anal. Calc'd. for $C_{19}H_{28}F_2N_2O_4$, 386.2, found [M+H] 387.4, $T_r$=1.14 min (Method BA).

321C. Methyl 3-(3-((4-chlorophenyl)amino)-4-((2,2-difluoroethyl)(tetrahydro-2H-pyran-4-yl)amino)phenyl)-4-methoxybutanoate To a degassing solution of 321B Enantiomer 1 (0.05 g, 0.129 mmol) in 1,4-dioxane (2 mL) was added 1-bromo-4-chlorobenzene (0.030 g, 0.155 mmol), 4,5-bis(diphenylphosphino)-9,9-dimethylxanthene (7.49 mg, 0.013 mmol), cesium carbonate (0.063 g, 0.194 mmol) followed by the addition of bis(dibenzylideneacetone)palladium (3.72 mg, 6.47 μmol). Then the reaction temperature was raised to 110° C. overnight in a sealed tube. The reaction mixture was poured into water (10 ml) and extracted with EtOAc (2×25 mL). The combined organic layers were dried over anhydrous sodium sulfate, filtered and concentrated under reduced pressure to afford crude 321C (0.05 g, 0.075 mmol, 58.3% yield). The crude was taken further without purification. LC-MS Anal. Calc'd. for $C_{25}H_{31}ClF_2N_2O_4$, 496.1, found [M+H] 497.3, $T_r$=1.53 min (Method BA).

Example 321 Enantiomer 1. 3-(3-((4-Chlorophenyl)amino)-4-((2,2-difluoroethyl)(tetrahydro-2H-pyran-4-yl)amino)phenyl)-4-methoxybutanoic acid To a solution of 321C (0.05 g, 0.101 mmol) in a mixture of THF (1 mL), MeOH (1 mL) and water (1 mL) was added LiOH.H₂O (9.64 mg, 0.402 mmol) at RT and stirred for 2 h. Removed the volatiles and the crude pH was adjusted to ~2 with saturated citric acid solution. The aqueous layer was extracted with DCM (2×10 mL). The combined organic layers were washed with brine, dried over anhydrous sodium sulfate, filtered and concentrated under reduced pressure. The crude sample was purified by prep HPLC to afford Example 321 Enantiomer 1 (absolute stereochemistry unknown) (off-white solid, 0.017 g, 0.035 mmol, 34.6% yield). LC-MS Anal. Calc'd. for $C_{24}H_{29}ClF_2N_2O_4$ 482.1, found [M+H] 483.2, $T_r$=1.165 min (Method BB). ¹H NMR (400 MHz, DMSO-$d_6$) δ 7.28 (d, J=2.40 Hz, 3H), 7.26 (d, J=2.40 Hz, 1H), 7.11-7.09 (m, 3H), 6.79-6.76 (m, 1H), 6.03-5.59 (m, 1H), 3.81-3.77 (m, 2H), 4.08-3.40 (m, 4H), 3.22 (s, 3H), 3.19-3.10 (m, 3H), 2.99-2.95 (m, 1H), 2.62-2.60 (m, 1H), 2.33-2.32 (m, 1H), 1.68-1.65 (m, 2H), 1.43-1.38 (m, 2H).

Example 321 Enantiomer 2. 3-(3-((4-Chlorophenyl)amino)-4-((2,2-difluoroethyl)(tetrahydro-2H-pyran-4-yl)amino)phenyl)-4-methoxybutanoic acid Example 321 Enantiomer 2 was prepared using 321B Enantiomer 2 and 1-bromo-4-chlorobenzene following the procedure described for the synthesis of Example 321 Enantiomer 1 (absolute stereochemistry unknown). LC-MS Anal. Calc'd. for $C_{24}H_{29}ClF_2N_2O_4$, 482.1, found [M+H] 483.2, $T_r$=1.171 min (Method BB). ¹H NMR (400 MHz, DMSO-$d_6$) δ 7.28 (d, J=2.40 Hz, 3H), 7.26 (d, J=2.40 Hz, 1H), 7.11-7.09 (m, 3H), 6.79-6.76 (m, 1H), 6.03-5.59 (m, 1H), 3.81-3.77 (m, 2H), 4.08-3.40 (m, 4H), 3.22 (s, 3H), 3.19-3.10 (m, 3H), 2.99-2.95 (m, 1H), 2.62-2.60 (m, 1H), 2.33-2.32 (m, 1H), 1.68-1.65 (m, 2H), 1.43-1.38 (m, 2H).

Example 322

Enantiomer 1

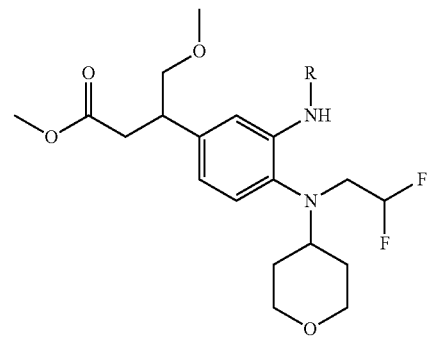

Example 322 was prepared using 321B Enantiomer 1 and corresponding halide following the procedure of described for the synthesis of Example 321 (absolute stereochemistry unknown).

| Ex. No. | Name | R | $T_r$ min | Method | (M + H) |
|---|---|---|---|---|---|
| 322 | 3-(3-((4-cyanophenyl)amino)-4-((2,2-difluoroethyl)(tetrahydro-2H-pyran-4-yl)amino)phenyl)-4-methoxybutanoic acid | CN-⬡- | 1.237 | O | 474.3 |

Example 323

Enantiomer 2

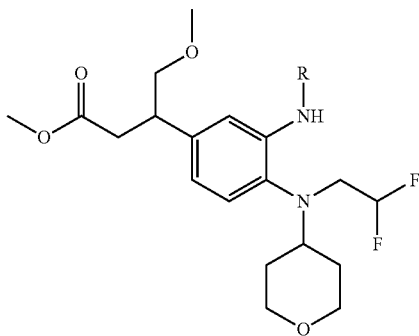

Example 323 was prepared using 321B Enantiomer 2 and corresponding halide following the procedure described for the synthesis of Example 321 (absolute stereochemistry unknown).

| Ex. No. | Name | R | $T_r$, min | Method | (M + H) |
|---|---|---|---|---|---|
| 323 | 3-(3-((4-cyanophenyl)amino)-4-((2,2-difluoroethyl)(tetrahydro-2H-pyran-4-yl)amino)phenyl)-4-methoxybutanoic acid | CN-C6H4- | 1.243 | O | 474.3 |

Example 324

Enantiomer 1

(S)-3-(3-((4-Cyanophenyl)amino)-4-(ethyl(tetrahydro-2H-pyran-4-yl)amino)phenyl)-4-isopropoxybutanoic acid

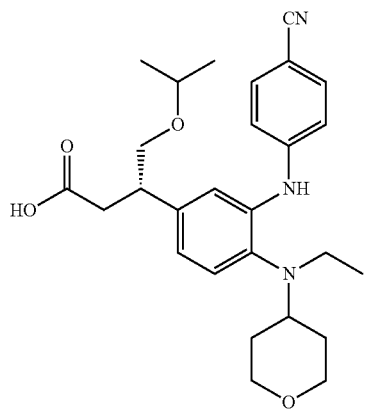 [SMILES: CCN(c1ccc([C@@H](COC(C)C)CC(=O)O)cc1Nc1ccc(C#N)cc1)C1CCOCC1]

324A. (E)-Methyl 4-isopropoxybut-2-enoate

To a stirred solution of (E)-methyl 4-bromobut-2-enoate (10 g, 55.9 mmol) in 2-propanol (50 mL) was added silver oxide (12.95 g, 55.9 mmol) at RT, and stirred for 16 h. Reaction mixture was filtered through the pad of CELITE®, washed with DCM (100 ml), filtrates were concentrated under reduced pressure. The crude was dissolved in diethylether (200 mL), washed with water, brine solution, dried over sodium sulfate, filtered and concentrated under reduced pressure. The crude sample was purified via flash chromatography to afford 324A (colorless oil, 8 g, 50.6 mmol, 91% yield). $^1$H NMR (400 MHz, DMSO-$d_6$) δ6.95-6.89 (m, 1H), 6.03-5.98 (m, 1H), 4.12 (d, J=2.00 Hz, 2H), 3.60 (s, 3H), 3.59-3.32 (m, 1H), 1.10 (d, J=4.40 Hz, 6H).

324B. Methyl (S)-3-(4-(ethyl(tetrahydro-2H-pyran-4-yl)amino)-3-nitrophenyl)-4-isopropoxybutanoate To a stirring and argon bubbling solution of N-(4-(5,5-dimethyl-1,3,2-dioxaborinan-2-yl)-2-nitrophenyl)-N-ethyl-tetrahydro-2H-pyran-4-amine (455C) (2 g, 5.52 mmol) and 324A (3.49 g, 22.09 mmol) in 1,4-dioxane (40 mL) was added sodium hydroxide (1.0 molar) (5.04 mL, 5.04 mmol) and (R)-BINAP (0.172 g, 0.276 mmol), bubbling with argon continued for 5 minutes, then chlorobis(ethylene)rhodium (I)dimer (0.043 g, 0.110 mmol) was added and bubbled argon for another 5 minutes. The reaction mixture was heated at 50° C. for 2 h in sealed tube. Then cooled to room temperature and quenched with acetic acid (0.284 mL, 4.97 mmol) and it was stirred for 5 minutes before partitioned between ethyl acetate (200 ml) and water (100 ml). Aqueous layer was extracted with ethyl acetate (2×50 ml). The combined organic layers were washed with brine, dried over anhydrous sodium sulfate, filtered and concentrated under reduced pressure. The crude sample was purified via flash chromatography to afford 324B (pale yellow oil, 0.85 g, 1.873 mmol, 33.9% yield). LC-MS Analysis Calc'd. for $C_{21}H_{32}N_2O_6$, 408.2, found [M+H] 409.6, $T_r$=1.46 min (Method AY).

324C. Methyl (S)-3-(3-amino-4-(ethyl(tetrahydro-2H-pyran-4-yl)amino)phenyl)-4-isopropoxybutanoate To a stirred solution of 324B (0.85 g, 2.081 mmol) in ethyl acetate (15 mL) was carefully added Pd/C (10%) (0.111 g, 0.104 mmol). The flask was sequentially evacuated then purged with nitrogen before being pressurized to 40 psi of hydrogen for 3 h. The reaction mixture was filtered through CELITE® bed, washed with methanol, filtrate was concentrated under reduced pressure to afford enantiomeric mixture 324C.

Chiral separation of enantiomeric mixture (94:6) of 324C yielded 324C Enantiomer 1, $T_r$=4.39 min, 324C Enantiomer 2, $T_r$=5.26 min (Method BK).

324C Enantiomer 1; (pale yellow oil, 0.65 g, 1.631 mmol, 78.0% yield) as. Calc'd. for $C_{21}H_{34}N_2O_4$, 378.2, found [M+H] 379.5, $T_r$=1.39 min (Method AY).

324D. Methyl (S)-3-(3-((4-cyanophenyl)amino)-4-(ethyl(tetrahydro-2H-pyran-4-yl)amino)phenyl)-4-isopropoxybutanoate To a degassing solution of 324C Enantiomer 1 (0.05 g, 0.132 mmol) in 2-propanol (2 mL) by argon was added 4-bromobenzonitrile (0.029 g, 0.159 mmol), 2-di-tert-butylphosphino-2',4',6'-triisopropylbiphenyl (5.61 mg, 0.013 mmol) and potassium acetate (0.039 g, 0.396 mmol) followed by the addition of tris(dibenzylideneacetone)dipalladium(0) (6.05 mg, 6.60 µmol). Then the reaction temperature was raised to 100° C. for 16 h in a sealed vial. The reaction mixture was poured into water (10 ml) and extracted with EtOAc (2×20 mL). The combined organic layers were washed with brine, dried over anhydrous sodium sulfate, filtered and concentrated under reduced pressure to afford crude 324D. The crude material was taken further without any purification. LC-MS Analysis Calc'd. for $C_{28}H_{37}N_3O_4$, 479.2, found [M+H] 480.3, $T_r$=1.04 min (Method AY).

Example 324 Enantiomer 1. (S)-3-(3-((4-Cyanophenyl)amino)-4-(ethyl(tetrahydro-2H-pyran-4-yl)amino)phenyl)-4-isopropoxybutanoic acid To a solution of 324D (0.03 g, 0.031 mmol) in mixture of THF (1 mL), MeOH (1 mL) and water (1 mL) was added LiOH.H₂O (3.00 mg, 0.125 mmol) at RT and stirred for 16 h. Removed the volatiles under reduced pressure and the crude pH as adjusted to ~2 with 1.5N HCl solution. The aqueous was extracted with DCM (2×10 mL). The combined organic layer was washed with brine, dried over anhydrous sodium sulfate, filtered and concentrated under reduced pressure. The crude sample was purified by prep HPLC to afford Example 324 Enantiomer 1 (off-white solid, 0.011 g, 0.022 mmol). LC-MS Analysis Calc'd. for $C_{27}H_{35}N_3O_4$, 465.2, found [M+H] 466.4, $T_r$=1.210 min (Method R). $^1$H NMR (400 MHz, DMSO-d₆) δ 7.94 (s, 1H), 7.54 (d, J=8.80 Hz, 2H), 7.18-7.10 (m, 4H), 6.94-6.92 (m, 1H), 3.78-3.75 (m, 2H), 3.51-3.48 (m, 3H), 3.19-3.10 (m, 3H), 2.97-2.95 (m, 3H), 2.69-2.66 (m, 1H), 2.48-2.45 (m, 1H), 1.57-1.54 (m, 2H), 1.44-1.41 (m, 2H), 1.03 (t, J=6.40 Hz, 6H), 0.80 (t, J=6.80 Hz, 3H).

Examples 325 to 328

Enantiomer 1

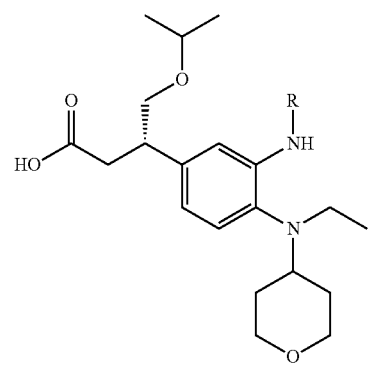

Examples 325 to 328 were prepared using 324C Enantiomer 1 and corresponding halides following the procedure described for the synthesis of Example 324.

| Ex. No. | Name | R | $T_r$ min | Method | (M + H) |
|---|---|---|---|---|---|
| 325 | (S)-3-(3-((4-chlorophenyl)amino)-4-((1,1-dioxidotetrahydro-2H-thiopyran-4-yl)(ethyl)amino)phenyl)-4-isopropoxybutanoic acid | Cl-C₆H₄- | 2.204 | O | 475.1 |
| 326 | (S)-3-(4-((1,1-dioxidotetrahydro-2H-thiopyran-4-yl)(ethyl)amino)-3-((4-fluorophenyl)amino)phenyl)-4-isopropoxybutanoic acid | F-C₆H₄- | 1.751 | O | 459.4 |
| 327 | (S)-3-(4-((1,1-dioxidotetrahydro-2H-thiopyran-4-yl)(ethyl)amino)-3-((2-methoxypyrimidin-5-yl)amino)phenyl)-4-isopropoxybutanoic acid | 2-methoxypyrimidin-5-yl | 1.603 | R | 473.1 |

| Ex. No. | Name | R | $T_r$, min | Method | (M + H) |
|---|---|---|---|---|---|
| 328 | (S)-3-(4-((1,1-dioxidotetrahydro-2H-thiopyran-4-yl)(ethyl)amino)-3-((2-ethoxypyrimidin-5-yl)amino)phenyl)-4-isopropoxybutanoic acid | (2-ethoxypyrimidin-5-yl) | 1.716 | O | 487.1 |

Example 329

Enantiomer 2

3-(3-((4-Cyanophenyl)amino)-4-(ethyl(tetrahydro-2H-pyran-4-yl)amino)phenyl)-4-isopropoxybutanoic acid

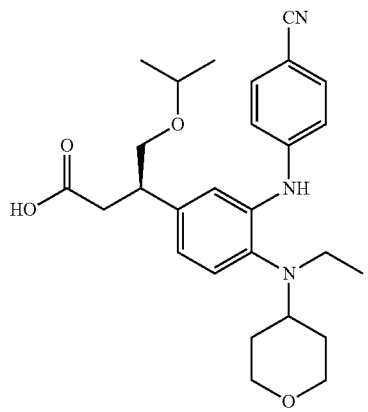 [SMILES: CCN(c1ccc([C@H](COC(C)C)CC(=O)O)cc1Nc1ccc(C#N)cc1)C1CCOCC1]

329A. Methyl (R)-3-(4-(ethyl(tetrahydro-2H-pyran-4-yl)amino)-3-nitrophenyl)-4-isopropoxybutanoate 329A was prepared using S-BINAP and 455C and following the procedure described for the synthesis of 324B. LC-MS Analysis Calc'd. for $C_{21}H_{32}N_2O_6$ 408.2 found [M+H] 409.6. $T_r$=1.46 min (Method AY).

329B. Methyl (R)-3-(3-amino-4-(ethyl(tetrahydro-2H-pyran-4-yl)amino)phenyl)-4-isopropoxybutanoate 329B was prepared using 329A following the procedure described for the synthesis of 324C.

Chiral separation of enantiomeric mixture 329B (6:94) yielded 329B Enantiomer 1 $T_r$=4.46 min, 329B Enantiomer 2 $T_r$=5.18 min (Method BK).

329B Enantiomer 2; (pale yellow oil, 0.67 g, 1.682 mmol, 68.7% yield). Calc'd. for $C_{21}H_{34}N_2O_4$, 378.2, found [M+H] 379.5, $T_r$=1.39 min (Method AY).

329C. Methyl (R)-3-(3-((4-cyanophenyl)amino)-4-(ethyl(tetrahydro-2H-pyran-4-yl)amino)phenyl)-4-isopropoxybutanoate 329C was prepared using 329B Enantiomer 2 and 4-bromo benzonitrile following the procedure described for the synthesis of 324D. LC-MS Analysis Calc'd. for $C_{28}H_{37}N_3O_4$, 479.2, found [M+H] 480.3, $T_r$=1.04 min (Method AY).

Example 329 Enantiomer 2. (R)-3-(3-((4-Cyanophenyl)amino)-4-(ethyl(tetrahydro-2H-pyran-4-yl)amino)phenyl)-4-isopropoxybutanoic acid Example 329 Enantiomer 2 was prepared using 329C following the procedure described for the synthesis of Example 324 Enantiomer 1. LC-MS Analysis Calc'd. for $C_{27}H_{35}N_3O_4$, 465.2, found [M+H] 466.4, $T_r$=1.218 min (Method R). $^1$H NMR (400 MHz, DMSO-$d_6$) δ 7.94 (s, 1H), 7.54 (d, J=8.80 Hz, 2H), 7.18-7.10 (m, 4H), 6.94-6.92 (m, 1H), 3.78-3.75 (m, 2H), 3.51-3.48 (m, 3H), 3.19-3.10 (m, 3H), 2.97-2.95 (m, 3H), 2.69-2.66 (m, 1H), 2.48-2.45 (m, 1H), 1.57-1.54 (m, 2H), 1.44-1.41 (m, 2H), 1.03 (t, J=6.40 Hz, 6H), 0.80 (t, J=6.80 Hz, 3H).

Examples 330 to 333

Enantiomer 2

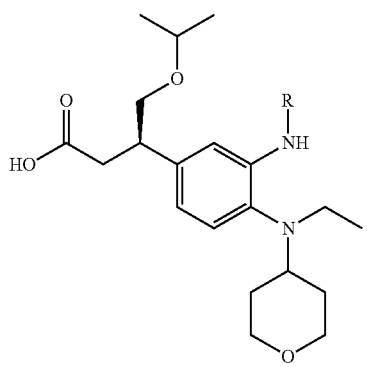

Examples 330 to 333 were prepared using 329B Enantiomer 2 and corresponding aryl halides following the procedure described for the synthesis of Example 329.

| Ex. No. | Name | R | $T_r$, min | Method | (M + H) |
|---|---|---|---|---|---|
| 330 | (R)-3-(3-((4-chlorophenyl)amino)-4-((1,1-dioxidotetrahydro-2H-thiopyran-4-yl)(ethyl)amino)phenyl)-4-isopropoxybutanoic acid | 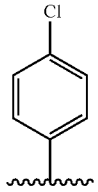 | 2.213 | O | 475.1 |
| 331 | (R)-3-(4-((1,1-dioxidotetrahydro-2H-thiopyran-4-yl)(ethyl)amino)-3-((4-fluorophenyl)amino)phenyl)-4-isopropoxybutanoic acid | 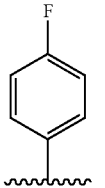 [SMILES: *c1ccc(F)cc1] | 1.758 | O | 459.4 |
| 332 | (R)-3-(4-((1,1-dioxidotetrahydro-2H-thiopyran-4-yl)(ethyl)amino)-3-((2-methoxypyrimidin-5-yl)amino)phenyl)-4-isopropoxybutanoic acid | 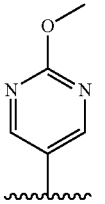 | 1.600 | O | 473.1 |
| 333 | (R)-3-(4-((1,1-dioxidotetrahydro-2H-thiopyran-4-yl)(ethyl)amino)-3-((2-ethoxypyrimidin-5-yl)amino)phenyl)-4-isopropoxybutanoic acid | 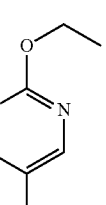 | 1.741 | O | 487.1 |

Example 334

Enantiomer 1 and Enantiomer 2

3-(3-((4-Chlorophenyl)amino)-4-((1,1-dioxidotetrahydro-2H-thiopyran-4-yl)(ethyl)amino)phenyl)pentanoic acid

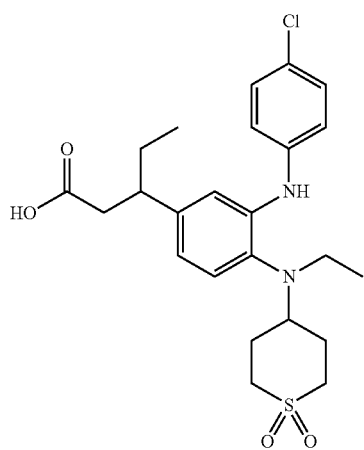 [SMILES: CCC(CC(=O)O)c1ccc(N(CC)C2CCS(=O)(=O)CC2)c(Nc2ccc(Cl)cc2)c1]

334A. N-Ethyltetrahydro-2H-thiopyran-4-amine

To a stirred solution of dihydro-2H-thiopyran-4(3H)-one (6.0 g, 51.6 mmol) and ethanamine (28.4 mL, 56.8 mmol) under nitrogen in dry THF (50 mL)-MeOH (50 mL) was added molecular sieves (5.0 g). The reaction was stirred at room temperature overnight. The reaction was cooled to 0° C. and treated with NaBH$_4$ (5.86 g, 155 mmol) portionwise over 10 minutes. The reaction was then stirred at room temperature for 3 h. The reaction mixture was concentrated under reduced pressure to afford a semi-solid. To this was added sat. NaHCO$_3$ (200 mL) and this mixture was stirred overnight. The resulting mixture was partitioned between EtOAc (400 ml) and water (100 ml). The organic extract was washed with brine (100 ml), dried over Na$_2$SO$_4$ and concentrated to afford N-ethyltetrahydro-2H-thiopyran-4-amine (6.5 g, 44.7 mmol, 87% yield) as light yellow liquid. $^1$H NMR (400 MHz, CDCl$_3$) δ 2.63-2.72 (m, 6H), 2.41-2.50 (m, 1H), 2.13-2.20 (m, 2H), 1.45-1.52 (m, 2H), 1.09 (t, J=7.2 Hz, 3H).

334B. Methyl 3-(4-(ethyl(tetrahydro-2H-thiopyran-4-yl)amino)-3-nitrophenyl)pentanoate To a stirred solution of methyl 3-(4-fluoro-3-nitrophenyl)pentanoate (443B) (0.5 g, 1.959 mmol), 334A (0.427 g, 2.94 mmol), DIPEA (1.026 mL, 5.88 mmol) in NMP (5 mL) stirred for 10 minutes at room temperature. Reaction heated to 135° C. and maintained for 48 h. The reaction mixture was poured into water (50 ml) and extracted with EtOAc (2×50 mL). The combined organic layers were washed with brine solution, dried over anhydrous sodium sulfate, filtered and concentrated under reduced pressure. The crude sample was purified by flash chromatography using silica gel and 0-10% EtOAc in pet ether as eluent. The compound containing fractions were evaporated to afford 334B (yellow oil, 0.5 g, 0.788 mmol, 40.2% yield). LC-MS Analysis Calc'd. for $C_{19}H_{28}N_2O_4S$, 380.1, found [M+H] 381.5, $T_r$=1.63 min (Method AY).

334C. Methyl 3-(4-((1,1-dioxidotetrahydro-2H-thiopyran-4-yl)(ethyl)amino)-3-nitrophenyl)pentanoate To a solution of 334B (0.4 g, 0.631 mmol) in acetonitrile (2 mL) and water (1.538 mL) was cooled to 0° C. and added OXONE® (1.163 g, 1.892 mmol) followed by sodium bicarbonate (0.530 g, 6.31 mmol). Then the reaction was slowly warmed to RT and stirred for 2 h. The reaction mixture was poured into water (50 ml) and extracted with EtOAc (2×50 mL). The combined organic layers were washed with brine, dried over anhydrous sodium sulfate, filtered and concentrated under reduced pressure. The crude sample was purified by flash chromatography using silica gel and 0-50% EtOAc in pet ether as eluent. The compound containing fractions were evaporated to afford 334C (yellow oil, 0.25 g, 0.576 mmol, 91% yield). LC-MS Analysis Calc'd. for $C_{19}H_{28}N_2O_6S$, 412.1, found [M+H] 413.5, $T_r$=0.87 min (Method BC).

334D. Methyl 3-(3-amino-4-((1,1-dioxidotetrahydro-2H-thiopyran-4-yl)(ethyl)amino)phenyl)pentanoate To a stirred solution of 334C (0.35 g, 0.848 mmol) in ethyl acetate (10 mL) was carefully added Pd/C (10%) (0.045 g, 0.042 mmol). The flask was sequentially evacuated then purged with nitrogen before being pressurized to 40 psi of hydrogen for 3 h. The reaction mixture was filtered through CELITE® bed, washed with methanol (50 ml). The combined filtrate was concentrated under reduced pressure to get crude compound 334D (0.28 g, 0.695 mmol, 80% yield).

Chiral separation of 334D racemic gave 334D Enantiomer 1 and 334D Enantiomer 2 as single enantiomers. Enantiomer 1 $T_r$=3.56 min and Enantiomer 2 $T_r$=5.87 min (Method BT).

334D Enantiomer 1 (absolute stereochemistry unknown): (0.14 g, 0.348 mmol, 41% yield). LC-MS Anal. Calc'd. for $C_{19}H_{30}N_2O_4S$, 382.1, found [M+H] 383.5, $T_r$=0.55 min (Method BC).

334D Enantiomer 2 (absolute stereochemistry unknown): (0.135 g, 0.335 mmol, 40% yield). LC-MS Anal. Calc'd. for $C_{19}H_{30}N_2O_4S$, 382.1, found [M+H] 383.5, $T_r$=0.55 min (Method BC).

334E. Methyl 3-(3-((4-chlorophenyl)amino)-4-((1,1-dioxidotetrahydro-2H-thiopyran-4-yl)(ethyl)amino)phenyl)pentanoate To a degassing solution of 334D Enantiomer 1 (0.025 g, 0.065 mmol) in 1,4-dioxane (2 mL) by argon was added 1-bromo-4-chlorobenzene (0.015 g, 0.078 mmol), 4,5-bis(diphenylphosphino)-9,9-dimethylxanthene (7.56 mg, 0.013 mmol), cesium carbonate (0.064 g, 0.196 mmol) followed by the addition of bis(dibenzylideneacetone)palladium (3.76 mg, 6.54 μmol). Then the reaction temperature was raised to 110° C. for 16 h in a sealed vessel. The reaction mixture was filtered through CELITE® plug, washed the plug with EtOAc (2×20 ml). The filtrate was concentrated under reduced pressure to afford crude 334E (0.03 g, 0.030 mmol, 46.5% yield). The crude was taken further without purification. LC-MS Analysis Calc'd. for $C_{25}H_{33}ClN_2O_4S$, 492.1, found [M+H] 493.5, $T_r$=1.72 min (Method AY).

Example 334 Enantiomer 1. 3-(3-((4-Chlorophenyl)amino)-4-((1,1-dioxidotetrahydro-2H-thiopyran-4-yl)(ethyl)amino)phenyl)pentanoic acid To a solution of 334E (0.04 g, 0.081 mmol) in mixture of THF (1 mL), MeOH (1 mL) and water (1 mL) was added LiOH.H$_2$O (7.77 mg, 0.325 mmol) at RT and stirred for 16 h. Removed the volatiles and the crude pH as adjusted to ~2 with 1.5N HCl solution. The aqueous was extracted with DCM (2×10 mL). The combined organic layers were washed with brine, dried over anhydrous sodium sulfate, filtered and concentrated under reduced pressure. The crude compound was purified by prep HPLC to afford Example 334 Enantiomer 1 (absolute stereochemistry unknown) (off-white solid, 0.011 g, 0.023 mmol, 32.8% yield) as. LC-MS Analysis Calc'd. for $C_{24}H_{31}ClN_2O_4S$, 478.1, found [M+H] 479.2, $T_r$=1.813 min (Method R). $^1$H NMR (400 MHz, MeOD) δ 7.27-7.24 (m, 2H), 7.19-7.10 (m, 4H), 6.77 (dd, J=1.60, 8.20 Hz, 1H), 3.28-3.26 (m, 1H), 3.14-3.07 (m, 4H), 3.01-2.98 (m, 3H), 2.63-2.62 (m, 1H), 2.54-2.50 (m, 1H), 2.22-2.17 (m, 4H), 1.72-1.69 (m, 1H), 1.72-1.56 (m, 1H), 0.95 (t, J=7.60 Hz, 3H), 0.83 (t, J=7.20 Hz, 3H).

Example 334 Enantiomer 2. 3-(3-((4-Chlorophenyl)amino)-4-((1,1-dioxidotetrahydro-2H-thiopyran-4-yl)(ethyl)amino)phenyl)pentanoic acid Example 334 Enantiomer 2 was prepared using compound 334D Enantiomer 2 and 1-bromo-4-chlorobenzene following the procedure described for the synthesis of Example 334 Enantiomer 1 (absolute stereochemistry unknown). LC-MS Analysis Calc'd. for $C_{24}H_{31}ClN_2O_4S$, 478.1, found [M+H] 479.2, $T_r$=1.812 min (Method R). $^1$H NMR (400 MHz, MeOD) δ 7.27-7.24 (m, 2H), 7.19-7.10 (m, 4H), 6.77 (dd, J=1.60, 8.20 Hz, 1H), 3.28-3.26 (m, 1H), 3.14-3.07 (m, 4H), 3.01-2.98 (m, 3H), 2.63-2.62 (m, 1H), 2.54-2.50 (m, 1H), 2.22-2.17 (m, 4H), 1.72-1.69 (m, 1H), 1.72-1.56 (m, 1H), 0.95 (t, J=7.60 Hz, 3H), 0.83 (t, J=7.20 Hz, 3H).

Examples 335 and 336

Enantiomer 1

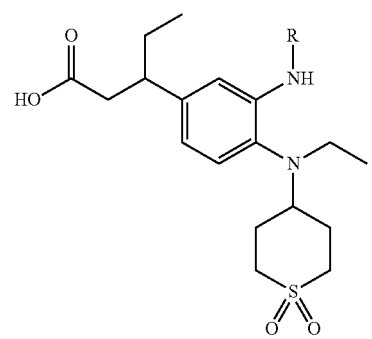

Examples 335 and 336 were prepared using 334D Enantiomer 1 and corresponding halides and following the procedure for Example 334 Enantiomer 1 (absolute stereochemistry unknown).

| Ex. No. | Name | R | T$_r$ min | Method | (M + H) |
|---|---|---|---|---|---|
| 335 | 3-(3-((4-cyanophenyl)amino)-4-((1,1-dioxidotetrahydro-2H-thiopyran-4-yl)(ethyl)amino)phenyl) pentanoic acid | 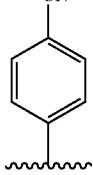 | 1.518 | O | 470.2 |
| 336 | 3-(4-((1,1-dioxidotetrahydro-2H-thiopyran-4-yl)(ethyl)amino)-3-((4-fluorophenyl)amino)phenyl)-4-isopropoxybutanoic acid | 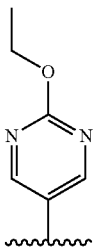 | 0.74 | BC | 491.5 |

Examples 337 and 338

Enantiomer 2

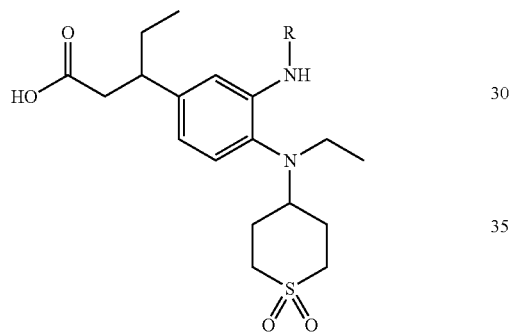

Examples 337 and 338 were prepared using 334D Enantiomer 2 and corresponding halides and following the procedure described for the synthesis of Example 334 Enantiomer 2 (absolute stereochemistry unknown).

| Ex. No. | Name | R | T$_r$ min | Method | (M + H) |
|---|---|---|---|---|---|
| 337 | 3-(3-((4-cyanophenyl)amino)-4-((1,1-dioxidotetrahydro-2H-thiopyran-4-yl)(ethyl)amino)phenyl) pentanoic acid | 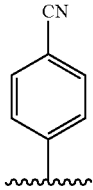 | 1.549 | O | 470.2 |
| 338 | 3-(4-((1,1-dioxidotetrahydro-2H-thiopyran-4-yl)(ethyl)amino)-3-((4-fluorophenyl)amino)phenyl)-4-isopropoxybutanoic acid | 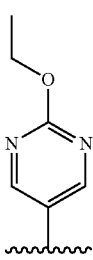 | 0.74 | BC | 491.5 |

Example 339

Enantiomer 1 and Enantiomer 2

3-(4-((1,1-Dioxidotetrahydro-2H-thiopyran-4-yl)(ethyl)amino)-3-((4-fluorophenyl)amino)phenyl)-4-isopropoxybutanoic acid

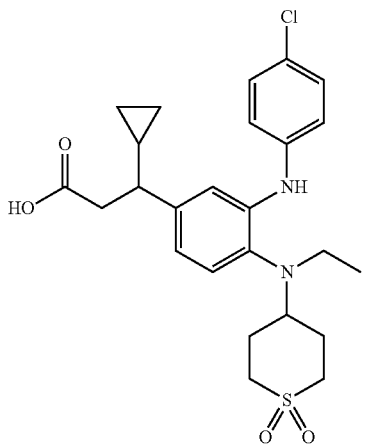 [SMILES: CCN(c1ccc(C(CC(=O)O)C2CC2)cc1Nc1ccc(Cl)cc1)C1CCS(=O)(=O)CC1]

339A. N-(4-Bromo-2-nitrophenyl)-N-ethyltetrahydro-2H-thiopyran-4-amine

To a solution of 4-bromo-1-fluoro-2-nitrobenzene (5 g, 22.73 mmol) in NMP (15 mL) at RT was added 334A (4.95 g, 34.1 mmol) followed by the addition of DIPEA (7.94 mL, 45.5 mmol). The reaction was sealed and heated at 130° C. for 16 h. The reaction mixture was poured into water (50 ml), extracted with EtOAc (2×100 mL). The combined organic layers were washed with brine, dried over anhydrous sodium sulfate, filtered and concentrated under reduced pressure. The crude sample was purified via flash chromatography to afford 339A (red color oil, 5.2 g, 14.31 mmol, 63.0% yield). LC-MS Analysis Calc'd. for $C_{13}H_{17}BrN_2O_2S$, 344.2, found [M+H] 347.1, $T_r$=1.66 min (Method AY).

339B. N-(4-(5,5-Dimethyl-1,3,2-dioxaborinan-2-yl)-2-nitrophenyl)-N-ethyltetrahydro-2H-thiopyran-4-amine A mixture of 339A (5 g, 14.48 mmol), bis(neopentyl glycolato)diboron (4.25 g, 18.83 mmol) and potassium acetate (4.26 g, 43.4 mmol) in DMSO (50 mL), at room temperature in a sealable flask, was purged with argon for 20 minutes before $PdCl_2$ (dppf).$CH_2Cl_2$ Adduct (0.355 g, 0.434 mmol) was added, the flask was sealed and the reaction heated at 80° C. for 6 h. The reaction mixture was cooled to RT and poured into water (500 ml), extracted with EtOAc (2×250 mL). The combined organic layers were washed with brine, dried over anhydrous sodium sulfate, filtered and concentrated under reduced pressure. The crude sample was purified via flash chromatography to afford 339B (red color oil, 4.5 g, 10.71 mmol, 73.9% yield). LC-MS Analysis Calc'd. for $C_{18}H_{27}BN_2O_4S$, 378.2, found [M+H] 311.2 for parent boronic acid, $T_r$=1.22 min (Method AY).

339C. Methyl 3-cyclopropyl-3-(4-(ethyl(tetrahydro-2H-thiopyran-4-yl)amino)-3-nitrophenyl)propanoate To a stirring and argon bubbling solution of 339B (2 g, 5.29 mmol) and (E)-methyl 3-cyclopropylacrylate (33C) (2.001 g, 15.86 mmol) in 1,4-dioxane (40 mL) was added sodium hydroxide (1.0 molar) (4.83 mL, 4.83 mmol), bubbling with argon continued for 5 minutes, then chloro(1,5-cyclooctadiene)rhodium(I) dimer (0.052 g, 0.106 mmol) was added and bubbled argon for another 5 minutes. The reaction mixture was heated at 50° C. for 2 h in sealed tube. Reaction mixture was cooled to room temperature and quenched with acetic acid (0.272 mL, 4.76 mmol) and it was stirred for 5 minutes before partitioned between ethyl acetate (100 ml) and water (50 ml). Aqueous layer was extracted with ethyl acetate (2×100 ml). The combined organic layers were washed with brine, dried over anhydrous sodium sulfate, filtered and concentrated under reduced pressure. The crude sample was purified via flash chromatography to afford 339C (yellow oil, 1.43 g, 3.28 mmol, 62.0% yield). LC-MS Analysis Calc'd. for $C_{20}H_{28}N_2O_4S$, 392.1, found [M+H] 393.3, $T_r$=1.56 min (Method AY).

339D. Methyl 3-cyclopropyl-3-(4-((1,1-dioxidotetrahydro-2H-thiopyran-4-yl)(ethyl)amino)-3-nitrophenyl)propanoate A solution of 339C (1.43 g, 3.64 mmol) in acetonitrile (15 mL) and water (11.54 mL) was cooled to 0° C. and treated with OXONE® (6.72 g, 10.93 mmol) followed by sodium bicarbonate (3.06 g, 36.4 mmol). Then the reaction was slowly warmed to RT and stirred for 2 h. The reaction mixture was poured into water (50 ml) and extracted with EtOAc (2×100 mL). The combined organic layers were washed with brine, dried over anhydrous sodium sulfate, filtered and concentrated under reduced pressure. The crude sample was purified via flash chromatography to afford 339D (yellow oil, 1 g, 2.238 mmol, 61.4% yield). LC-MS Analysis Calc'd. for $C_{20}H_{28}N_2O_6S$, 424.1, found [M+H] 425.2, $T_r$=1.22 min (Method AY).

339E. Methyl 3-(3-amino-4-((1,1-dioxidotetrahydro-2H-thiopyran-4-yl)(ethyl)amino)phenyl)-3-cyclopropylpropanoate To a stirred solution of 339D (0.9 g, 2.120 mmol) in ethyl acetate (20 mL) was carefully added Pd/C (10%) (0.113 g, 0.106 mmol). The flask was sequentially evacuated then purged with nitrogen before being pressurized to 40 psi of hydrogen for 3 h. The reaction mixture was filtered through CELITE® bed, washed with methanol (50 ml). The combined filtrate was concentrated under reduced pressure to get crude compound 339E (0.7 g, 1.686 mmol, 80% yield).

Chiral separation of 339E racemic gave 339E Enantiomer 1 and 339E Enantiomer 2 as single enantiomers (Method BS). Enantiomer 1 $T_r$=3.92 min and Enantiomer 2 $T_r$=5.53 min (Method BS).

339E Enantiomer 1 (absolute stereochemistry unknown): (0.35 g, 0.843 mmol, 40% yield). LC-MS Anal. Calc'd. for $C_{20}H_{30}N_2O_4S$, 394.5, found [M+H] 395.4, $T_r$=1.24 min (Method AY).

339E Enantiomer 2 (absolute stereochemistry unknown): (0.35 g, 0.843 mmol, 40% yield), LC-MS Anal. Calc'd. for $C_{20}H_{30}N_2O_4S$, 394.5, found [M+H] 395.4, $T_r$=1.24 min (Method AY).

339F. Methyl 3-(3-((4-chlorophenyl)amino)-4-((1,1-dioxidotetrahydro-2H-thiopyran-4-yl)(ethyl)amino)phenyl)-3-cyclopropylpropanoate To a degassing solution of 339E Enantiomer 1 (0.05 g, 0.127 mmol) in 1,4-dioxane (2 mL) by argon was added 1-bromo-4-chlorobenzene (0.029 g, 0.152 mmol), 4,5-bis(diphenylphosphino)-9,9-dimethylxanthene (7.33 mg, 0.013 mmol), cesium carbonate (0.062 g, 0.190 mmol) followed by bis(dibenzylideneacetone)palladium (3.64 mg, 6.34 µmol). Then the reaction temperature was raised to 110° C. overnight in a sealed tube. The reaction mixture was poured into water (25 ml) and extracted with EtOAc (2×25 mL). The combined organic layers were dried over anhydrous sodium sulfate, filtered and concentrated under reduced pressure to afford 339F (pale yellow oil, 0.06 g, 0.095 mmol, 80% yield). LC-MS Analysis Calc'd. for $C_{26}H_{33}ClN_2O_4S$, 504.1, found [M+H] 505.3, $T_r$=1.52 min (Method AY).

Example 339 Enantiomer 1. 3-(3-((4-Chlorophenyl)amino)-4-((1,1-dioxidotetrahydro-2H-thiopyran-4-yl)(ethyl)amino)phenyl)-3-cyclopropylpropanoic acid To a solution of 339F (0.05 g, 0.099 mmol) in mixture of THF (1 mL), MeOH (1 mL) and water (1 mL) was added LiOH.H₂O (9.48 mg, 0.396 mmol) at RT and stirred for 16 h. Removed the volatiles under reduced pressure and the crude pH as adjusted to ~2 with 1.5N HCl solution. The aqueous layer was extracted with DCM (2×10 mL). The combined organic layers were washed with brine, dried over anhydrous sodium sulfate, filtered and concentrated under reduced pressure. The crude was purified by prep HPLC to afford Example 339 Enantiomer 1 (absolute stereochemistry unknown): (off-white solid, 0.033 g, 0.066 mmol, 66.5% yield). LC-MS Analysis Calc'd. for $C_{25}H_{31}ClN_2O_4S$ 490.169, found [M+H] 491.0, $T_r$=1.855 min (Method O). ¹H NMR (400 MHz, DMSO-d₆) δ 7.42 (s, 1H), 7.27 (d, J=8.80 Hz, 2H), 7.16-7.10 (m, 4H), 6.81-6.79 (m, 1H), 3.29-3.21 (m, 2H), 3.18-3.13 (m, 2H), 3.09-2.94 (m, 4H), 2.28-2.26 (m, 1H), 2.23-2.21 (m, 1H), 2.15-2.06 (m, 2H), 1.96-1.94 (m, 2H), 1.02-0.96 (m, 1H), 0.85 (t, J=7.20 Hz, 3H), 0.49-0.39 (m, 2H), 0.24-0.13 (m, 2H).

Example 339 Enantiomer 2. 3-(3-((4-Chlorophenyl)amino)-4-((1,1-dioxidotetrahydro-2H-thiopyran-4-yl)(ethyl)amino)phenyl)-3-cyclopropylpropanoic acid Example 339 Enantiomer 2 was prepared using 339E Enantiomer 2 and 1-bromo-4-chlorobenzene following the procedure described for the synthesis of Example 339 Enantiomer 1 (absolute stereochemistry unknown). LC-MS Analysis Calc'd. for $C_{25}H_{31}ClN_2O_4S$, 490.169, found [M+H] 491.0, $T_r$=1.835 min (Method O). ¹H NMR (400 MHz, DMSO-d₆) δ 7.42 (s, 1H), 7.27 (d, J=8.80 Hz, 2H), 7.16-7.10 (m, 4H), 6.81-6.79 (m, 1H), 3.29-3.21 (m, 2H), 3.18-3.13 (m, 2H), 3.09-2.94 (m, 4H), 2.28-2.26 (m, 1H), 2.23-2.21 (m, 1H), 2.15-2.06 (m, 2H), 1.96-1.94 (m, 2H), 1.02-0.96 (m, 1H), 0.85 (t, J=7.20 Hz, 3H), 0.49-0.39 (m, 2H), 0.24-0.13 (m, 2H).

Examples 340 to 343

Enantiomer 1

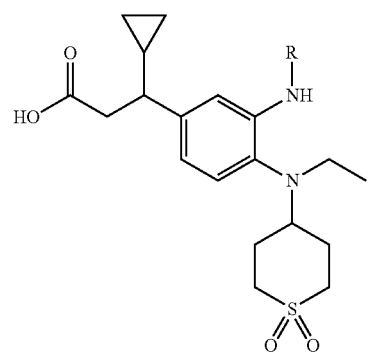

Examples 340 to 343 were prepared using 339E Enantiomer 1 and corresponding halides and following the procedure described for the synthesis of Example 339 (absolute stereochemistry unknown).

| Ex. No. | Name | R | $T_r$, min | Method | (M + H) |
|---|---|---|---|---|---|
| 340 | 3-(4-((1,1-dioxidotetrahydro-2H-thiopyran-4-yl)(ethyl)amino)-3-((4-fluorophenyl)amino)phenyl)-4-isopropoxybutanoic acid | CN-C₆H₄- | 1.567 | O | 482.1 |
| 341 | 3-(4-((1,1-dioxidotetrahydro-2H-thiopyran-4-yl)(ethyl)amino)-3-((4-fluorophenyl)amino)phenyl)-4-isopropoxybutanoic acid | isopropoxy-pyrimidinyl | 1.468 | O | 503.0 |
| 342 | 3-cyclopropyl-3-(4-((1,1-dioxidotetrahydro-2H-thiopyran-4-yl)(ethyl)amino)-3-((6-methoxypyridin-3-yl)amino)phenyl)propanoic acid | methoxypyridinyl | 1.312 | O | 488.3 |
| 343 | 3-cyclopropyl-3-(4-((1,1-dioxidotetrahydro-2H-thiopyran-4-yl)(ethyl)amino)-3-((4-fluorophenyl)amino)phenyl)propanoic acid | 4-F-C₆H₄- | 1.494 | O | 475.2 |

Examples 344 to 347

Enantiomer 2

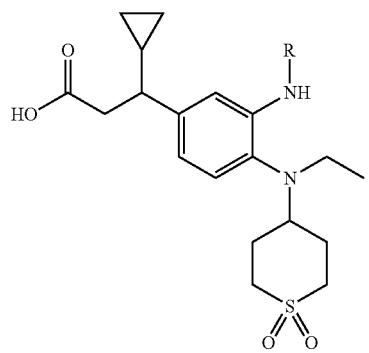

Examples 344 to 347 were prepared using 339E Enantiomer 2 and corresponding halides, following the procedure described for the synthesis of Example 339 (absolute stereochemistry unknown).

Example 348

Enantiomer 1 and Enantiomer 2

3-(3-(3-(4-Cyanophenyl)ureido)-4-((1,1-dioxidotetrahydro-2H-thiopyran-4-yl)(ethyl)amino)phenyl)-3-cyclopropylpropanoic acid

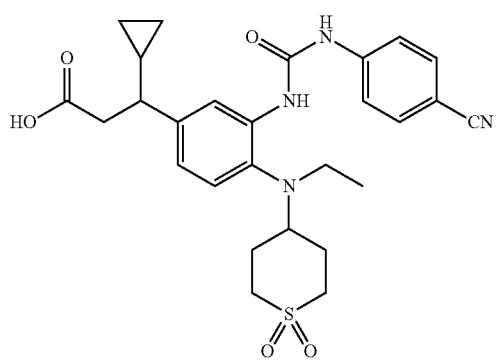 [SMILES: CCN(c1ccc(C(CC(=O)O)C2CC2)cc1NC(=O)Nc1ccc(C#N)cc1)C1CCS(=O)(=O)CC1]

| Ex. No. | Name | R | $T_r$ min | Method | (M + H) |
|---|---|---|---|---|---|
| 344 | 3-(4-((1,1-dioxidotetrahydro-2H-thiopyran-4-yl)(ethyl)amino)-3-((4-fluorophenyl)amino)phenyl)-4-isopropoxybutanoic acid | CN-C6H4- | 1.571 | O | 482.1 |
| 345 | 3-(4-((1,1-dioxidotetrahydro-2H-thiopyran-4-yl)(ethyl)amino)-3-((4-fluorophenyl)amino)phenyl)-4-isopropoxybutanoic acid | 2-ethoxypyrimidin-5-yl | 1.462 | O | 503.1 |
| 346 | 3-cyclopropyl-3-(4-((1,1-dioxidotetrahydro-2H-thiopyran-4-yl)(ethyl)amino)-3-((6-methoxypyridin-3-yl)amino)phenyl)propanoic acid | 6-ethoxypyridin-3-yl | 1.407 | O | 488.1 |
| 347 | 3-cyclopropyl-3-(4-((1,1-dioxidotetrahydro-2H-thiopyran-4-yl)(ethyl)amino)-3-((4-fluorophenyl)amino)phenyl)propanoic acid | 4-F-C6H4- | 1.499 | O | 475.2 |

348A. Methyl 3-(3-(3-(4-cyanophenyl)ureido)-4-((1,1-dioxidotetrahydro-2H-thiopyran-4-yl)(ethyl)amino)phenyl)-3-cyclopropylpropanoate To a solution of 339E Enantiomer 1 (0.025 g, 0.063 mmol) in THF (1 mL) was added 4-isocyanatobenzonitrile (10.96 mg, 0.076 mmol) under nitrogen. Then the reaction was stirred for 16 h at RT. Removed volatiles under reduced pressure to afford crude 348A (0.03 g, 0.050 mmol, 79% yield). LC-MS Analysis Calc'd. for $C_{28}H_{34}N_4O_5S$, 538.2, found [M+H] 539.3, $T_r$=1.26 min (Method AY).

Example 348 Enantiomer 1. 3-(3-(3-(4-Cyanophenyl)ureido)-4-((1,1-dioxidotetrahydro-2H-thiopyran-4-yl)(ethyl)amino)phenyl)-3-cyclopropylpropanoic acid To a solution of 348A (0.025 g, 0.046 mmol) in mixture of THF (1 mL), MeOH (1 mL) and water (1 mL) was added LiOH.H$_2$O (4.45 mg, 0.186 mmol) at RT and stirred for 16 h. Removed the volatiles under reduced pressure and the crude pH was adjusted to ~2 with 1.5N HCl solution. The aqueous layer was extracted with DCM (2×10 mL). The combined organic layer was washed with brine, dried over anhydrous sodium sulfate, filtered and concentrated under reduced pressure. The crude was purified by prep HPLC to afford Example 348 Enantiomer 1 (absolute stereochemistry unknown) (off-white solid, 0.005 g, 9.53 μmol, 20.3% yield). LC-MS Analysis Calc'd. for $C_{27}H_{32}N_4O_5S$, 524.2. Found [M+H] 525.1, $T_r$=1.454 min (Method O). $^1$H NMR (400 MHz, DMSO-d$_6$) δ10.06 (s, 1H), 8.61 (s, 1H), 8.16 (d, J=1.60 Hz, 1H), 7.74-7.67 (m, 4H), 7.19 (d, J=8.00 Hz, 1H), 6.93-6.91 (m, 1H), 3.23-3.14 (m, 3H), 3.07-3.01 (m, 4H), 2.64-2.57 (m, 2H), 2.30-2.24 (m, 3H), 1.91-1.86 (m, 2H), 1.01-0.99 (m, 1H), 0.83 (t, J=7.20 Hz, 3H), 0.55-0.35 (m, 2H), 0.25-0.14 (m, 2H).

348B. Methyl 3-(3-(3-(4-cyanophenyl)ureido)-4-((1,1-dioxidotetrahydro-2H-thiopyran-4-yl)(ethyl)amino)phenyl)-3-cyclopropylpropanoate 348B prepared using 339E Enantiomer 2 following the procedure described for the synthesis of 348A. LC-MS Analysis Calc'd. for $C_{28}H_{34}N_4O_5S$, 538.2 Found [M+H] 539.3. $T_r$=1.26 min (Method AY).

Example 348 Enantiomer 2. 3-(3-(3-(4-Cyanophenyl)ureido)-4-((1,1-di oxidotetrahydro-2H-thiopyran-4-yl)(ethyl)amino)phenyl)-3-cyclopropylpropanoic acid Example 348 Enantiomer 2 was prepared using 384B following the procedure described for the synthesis of Example 348 Enantiomer 1 (absolute stereochemistry unknown). LC-MS Analysis Calc'd. for $C_{27}H_{32}N_4O_5S$, 524.2, found [M+H] 525.1, $T_r$=1.454 min (Method O). $^1$H NMR (400 MHz, DMSO-d$_6$ ppm) δ 10.06 (s, 1H), 8.61 (s, 1H), 8.16 (d, J=1.60 Hz, 1H), 7.74-7.67 (m, 4H), 7.19 (d, J=8.00 Hz, 1H), 6.93-6.91 (m, 1H), 3.23-3.14 (m, 3H), 3.07-3.01 (m, 4H), 2.64-2.57 (m, 2H), 2.30-2.24 (m, 3H), 1.91-1.86 (m, 2H), 1.01-0.99 (m, 1H), 0.83 (t, J=7.20 Hz, 3H), 0.55-0.35 (m, 2H), 0.25-0.14 (m, 2H).

Example 349

Enantiomer 1 and Enantiomer 2

3-(3-((4-Cyanophenyl)amino)-4-(ethyl(tetrahydro-2H-pyran-4-yl)amino)phenyl)-4-methoxybutanoic acid

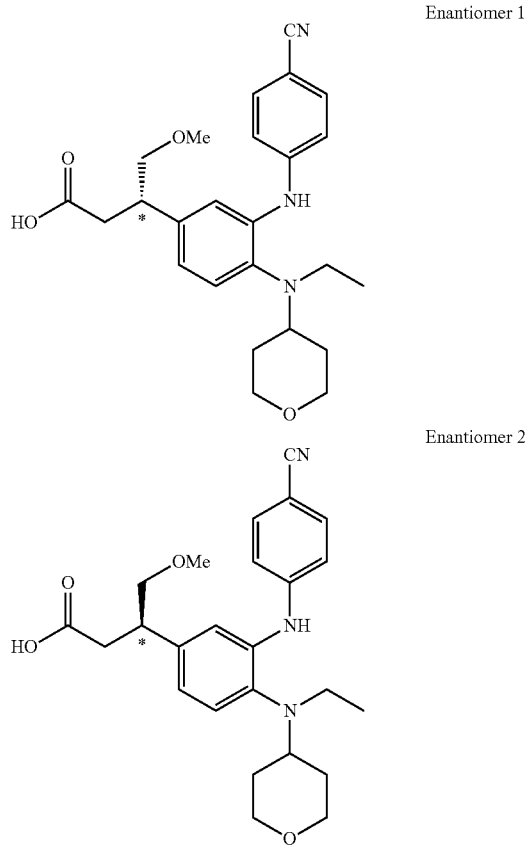

Enantiomer 1

Enantiomer 2

349A. Methyl 3-(4-(ethyl(tetrahydro-2H-pyran-4-yl)amino)-3-nitrophenyl)-4-methoxybutanoate In a pressure tube equipped with Teflon cap, 455C (5.5 g, 15.18 mmol) and 1,4-dioxane (60 ml) were added followed by sodium hydroxide (13.67 ml, 13.67 mmol). To it argon gas was passed through for 15 minutes and then (E)-methyl 4-methoxybut-2-enoate (5.3 g, 40.7 mmol) and chloro(1,5-cyclooctadiene)rhodium(I) dimer (0.374 g, 0.759 mmol) were added. Argon gas was further passed through it for 5 minutes. Reaction was screw-capped and heated at 50° C. for 3 h. To the reaction mixture 0.869 mL of acetic acid was added a followed by water (100 mL) and it was extracted with ethyl acetate (3×100 mL). The combined organic layers were dried over sodium sulfate and concentrated to afford the crude which was purified via flash silica gel column chromatography using ethyl acetate in pet ether (0-20%) as an eluant to afford 349A (orange oil, 5.25 g, 12.75 mmol, 84% yield). LC-MS Anal. Calc'd. for $C_{19}H_{28}N_2O_6$, 380.195, found [M+H] 381.2, $T_r$=3.009 min (Method U).

349B. Methyl 3-(3-amino-4-(ethyl(tetrahydro-2H-pyran-4-yl)amino)phenyl)-4-methoxybutanoate The solution of 349A (4.2 g, 11.04 mmol) in ethyl acetate (40 mL) was evacuated and purged with nitrogen for 3 times. Then carefully added Pd/C (0.47 g, 0.442 mmol) under nitrogen atmosphere and the suspension was hydrogenated (60 psi, autoclave) at RT for 4 h. The suspension was filtered through a pad of CELITE® and the filter cake was rinsed with ethyl acetate (200 mL). The combined filtrate was concentrated under reduced pressure to afford the racemic 349B (brown oil, 3.5 g, 9.97 mmol, 90%). LC-MS Anal. Calc'd. for $C_{19}H_{30}N_2O_4$, 350.221, found [M+H)] 351.2, $T_r$=2.4 min (Method U).

Chiral SFC separation of racemic 349B gave 349B Enantiomer 1 $T_r$=2.92 min (Method BZ) and 349B Enantiomer 2 $T_r$=3.76 min (Method BZ) as single enantiomers.

349B Enantiomer 1 (brown oil, 1.5 g, 4.24 mmol, 38.4% yield). LC-MS Anal. Calc'd. for $C_{19}H_{30}N_2O_4$, 350.221, found [M+H] 351.2, $T_r$=2.414 min (Method U).

349B Enantiomer 2 (brown oil, 1.5 g, 4.24 mmol, 38.4% yield). LC-MS Anal. Calc'd. for $C_{19}H_{30}N_2O_4$, 350.221, found [M+H] 351.2, $T_r$=2.304 min (Method U).

349C. Methyl (S)-3-(3-((4-cyanophenyl)amino)-4-(ethyl(tetrahydro-2H-pyran-4-yl)amino) phenyl)-4-methoxybutanoate To a solution of 349B Enantiomer 1 (1.5 g, 4.28 mmol) in 1,4-dioxane (15 mL) were added 4-bromobenzonitrile (0.935 g, 5.14 mmol), Xantphos (0.248 g, 0.428 mmol), $Cs_2CO_3$ (4.18 g, 12.84 mmol) in a sealed tube. Then argon was purged for 10 min, followed by the addition of bis(dibenzylideneacetone)palladium (0.123 g, 0.214 mmol). Argon was again purged for another 5 min. The reaction mixture was heated to 108° C. for 6 h. The reaction mixture was allowed to cool to room temperature and concentrated under reduced pressure to afford brown colored residue. The residue was purified via flash silica gel column chromatography using ethyl acetate in pet ether (0-30%) as an eluant to afford 349C Enantiomer 1 (light yellow semi-solid, 1.6 g, 3.40 mmol, 79% yield). LC-MS Anal. Calc'd. for $C_{26}H_{33}N_3O_4$, 451.247, found [M+H] 452.5, $T_r$=1.46 min (Method AY).

Example 349 Enantiomer 1. (S)-3-(3-((4-Cyanophenyl)amino)-4-(ethyl(tetrahydro-2H-pyran-4-yl)amino)phenyl)-4-methoxybutanoic acid To a stirred solution of 349C (130 mg, 0.288 mmol) in methanol (2 mL), water (2 mL) and THF (2 mL), LiOH (27.6 mg, 1.152 mmol) was added and stirred at RT for 4 h. The reaction mixture was concentrated and the aqueous solution was acidified with saturated citric acid solution (pH~4-5). The aqueous solution was extracted with ethyl acetate (3×20 mL). The combined organic layers were dried over sodium sulfate, filtered and concentrated to afford brown colored residue. The residue was purified by prep HPLC to afford Example 349 Enantiomer 1 (absolute stereochemistry confirmed as "S" by single crystal x-ray crystallography) (off-white solid, 74 mg, 0.169 mmol, 58.6% yield). LC-MS Anal. Calc'd. for $C_{25}H_{31}N_3O_4$, 437.231, found [M+H] 438.2, $T_r$=1.4648 min (Method U). $^1$H NMR (400 MHz, $CD_3OD$) δ 7.52-7.54 (m, 2H), 7.30 (d, J=2.00 Hz, 1H), 7.17-7.21 (m, 3H), 6.93-6.96 (m, 1H), 3.84-3.88 (m, 2H), 3.53-3.57 (m, 2H), 3.22-3.34 (m, 5H), 3.00-3.09 (m, 3H), 2.77-2.78 (m, 1H), 2.57-2.59 (m, 1H), 1.69-1.72 (m, 2H), 1.51-1.54 (m, 2H), 0.89 (t, J=7.2 Hz, 3H).

Example 349 Enantiomer 2. (R)-3-(3-((4-Cyanophenyl)amino)-4-(ethyl(tetrahydro-2H-pyran-4-yl)amino)phenyl)-4-methoxybutanoic acid Example 349 Enantiomer 2 was prepared utilizing 349B Enantiomer 2 and 4-bromobenzonitrile following the procedure described for the synthesis of Example 349 Enantiomer 2 (absolute stereochemistry inferred from Example 349 Enantiomer 1). LC-MS Anal. Calc'd. for $C_{25}H_{31}N_3O_4$, 437.231, found [M+H] 438.2, $T_r$=1.464 min (Method U). $^1$H NMR (400 MHz, $CD_3OD$) δ 7.51-7.55 (m, 2H), 7.30 (d, J=2.00 Hz, 1H), 7.17-7.21 (m, 3H), 6.94-6.96 (m, 1H), 3.84-3.88 (m, 2H), 3.53-3.57 (m, 2H), 3.22-3.34 (m, 5H), 2.99-3.07 (m, 3H), 2.75-2.76 (m, 1H), 2.56-2.57 (m, 1H), 1.69-1.72 (m, 2H), 1.50-1.53 (m, 2H), 0.89 (t, J=7.2 Hz, 3H).

Examples 350 to 386

Enantiomer 1

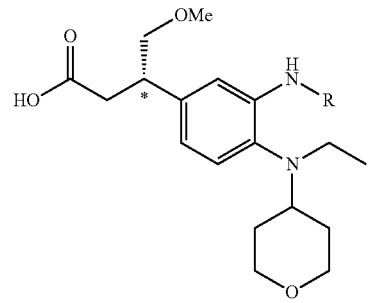

Examples 350 to 386 were prepared using the 349B Enantiomer 1 and corresponding aryl bromides following the procedure described for the synthesis of Example 349.

| Ex. No. | Name | R | $T_r$ (min) (Method O) | [M + H]$^+$ |
|---|---|---|---|---|
| 350 | (S)-3-(4-(ethyl(tetrahydro-2H-pyran-4-yl)amino)-3-((2-methoxypyrimidin-5-yl)amino)phenyl)-4-methoxybutanoic acid | ![pyrimidine-OMe] | 1.297 | 445.2 |

-continued

| Ex. No. | Name | R | $T_r$ (min) (Method O) | $[M + H]^+$ |
|---|---|---|---|---|
| 351 | (S)-3-(3-((2-ethoxypyrimidin-5-yl)amino)-4-(ethyl(tetrahydro-2H-pyran-4-yl)amino)phenyl)-4-methoxybutanoic acid | 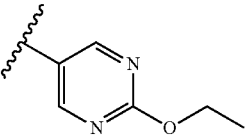 [SMILES: *c1cnc(OCC)nc1] | 1.418 | 459.2 |
| 352 | (S)-3-(3-((5-cyanopyridin-2-yl)amino)-4-(ethyl(tetrahydro-2H-pyran-4-yl)amino)phenyl)-4-methoxybutanoic acid | 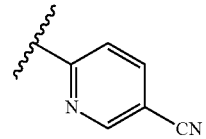 | 1.168 | 439.3 |
| 353 | (S)-3-(3-((4-cyano-3-fluorophenyl)amino)-4-(ethyl(tetrahydro-2H-pyran-4-yl)amino)phenyl)-4-methoxybutanoic acid | 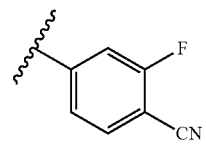 [SMILES: *c1ccc(C#N)c(F)c1] | 1.349 | 456.3 |
| 354 | (S)-3-(3-((4-cyano-3-methylphenyl)amino)-4-(ethyl(tetrahydro-2H-pyran-4-yl)amino)phenyl)-4-methoxybutanoic acid | 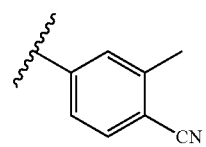 [SMILES: *c1ccc(C#N)c(C)c1] | 1.39 | 452.3 |
| 355 | (S)-3-(3-((4-cyano-2-fluorophenyl)amino)-4-(ethyl(tetrahydro-2H-pyran-4-yl)amino)phenyl)-4-methoxybutanoic acid | 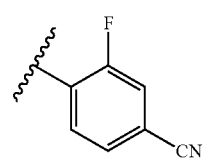 [SMILES: *c1ccc(C#N)cc1F] | 1.406 | 456.3 |
| 356 | (S)-3-(3-((5-chloropyridin-2-yl)amino)-4-(ethyl-(tetrahydro-2H-pyran-4-yl)amino)phenyl)-4-methoxybutanoic acid | 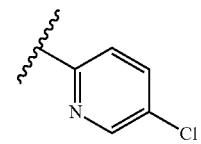 [SMILES: *c1ccc(Cl)cn1] | 1.657 | 448.1 |
| 357 | (S)-3-(3-((5-chloropyrimidin-2-yl)amino)-4-(ethyl-(tetrahydro-2H-pyran-4-yl)amino)phenyl)-4-methoxybutanoic acid | 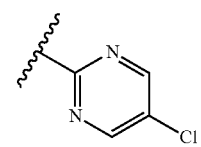 [SMILES: *c1ncc(Cl)cn1] | 1.581 | 449.0 |
| 358 | (S)-3-(3-((3,5-difluoropyridin-2-yl)amino)-4-(ethyl(tetrahydro-2H-pyran-4-yl)amino)phenyl)-4-methoxybutanoic acid | 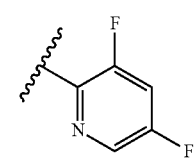 | 1.443 | 450.3 |
| 359 | (S)-3-(4-(ethyl(tetrahydro-2H-pyran-4-yl)amino)-3-((5-fluoropyrimidin-2-yl)amino)phenyl)-4-methoxybutanoic acid | 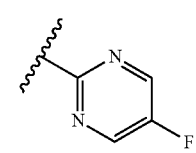 [SMILES: *c1ncc(F)cn1] | 1.164 | 433.3 |
| 360 | (S)-3-(4-(ethyl(tetrahydro-2H-pyran-4-yl)amino)-3-((3-(1,1,2,2-tetrafluoroethoxy)phenyl)amino)phenyl)-4-methoxybutanoic acid | 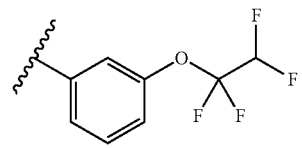 [SMILES: *c1cccc(OC(F)(F)C(F)F)c1] | 1.712 | 529.4 |

-continued

| Ex. No. | Name | R | T<sub>r</sub> (min) (Method O) | [M + H]+ |
|---|---|---|---|---|
| 361 | (S)-3-(4-(ethyl(tetrahydro-2H-pyran-4-yl)amino)-3-((3-(1,1,2,2-tetrafluoroethoxy)phenyl)amino)phenyl)-4-methoxybutanoic acid | 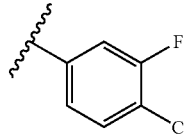 | 1.643 | 465.3 |
| 362 | (S)-3-(3-((4-chloro-2-fluorophenyl)amino)-4-(ethyl(tetrahydro-2H-pyran-4-yl)amino)phenyl)-4-methoxybutanoic acid | 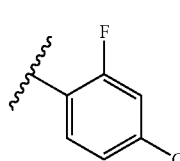 | 1.697 | 465.3 |
| 363 | (S)-3-(4-(ethyl(tetrahydro-2H-pyran-4-yl)amino)-3-((5-fluoropyridin-2-yl)amino)phenyl)-4-methoxybutanoic acid | 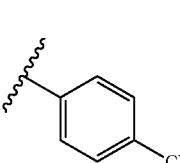 | 1.226 | 432.3 |
| 364 | (S)-3-(4-(ethyl(tetrahydro-2H-pyran-4-yl)amino)-3-((4-(trifluoromethyl)phenyl)amino)phenyl)-4-methoxybutanoic acid | 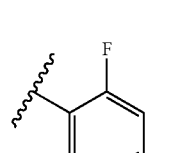 | 1.698 | 481.3 |
| 365 | (S)-3-(3-((2,4-difluorophenyl)amino)-4-(ethyl(tetrahydro-2H-pyran-4-yl)amino)phenyl)-4-methoxybutanoic acid | 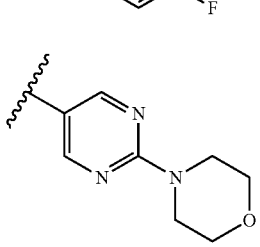 | 1.545 | 449.3 |
| 366 | (S)-3-(4-(ethyl(tetrahydro-2H-pyran-4-yl)amino)-3-((2-(tetrahydro-2H-pyran-4-yl)pyrimidin-5-yl)amino)phenyl)-4-methoxybutanoic acid | 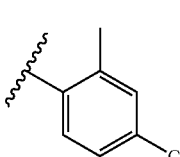 | 1.21 | 500.4 |
| 367 | (S)-3-(3-((4-cyano-2-methylphenyl)amino)-4-(ethyl(tetrahydro-2H-pyran-4-yl)amino)phenyl)-4-methoxybutanoic acid | 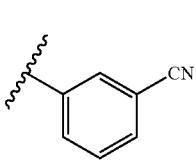 [SMILES: *c1cccc(C#N)c1] | 1.436 | 452.3 |
| 368 | (S)-3-(3-((3-cyanophenyl)amino)-4-(ethyl(tetrahydro-2H-pyran-4-yl)amino)phenyl)-4-methoxybutanoic acid | 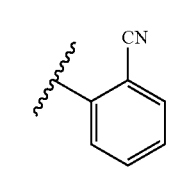 [SMILES: *c1ccccc1C#N] | 1.348 | 438.3 |
| 369 | (S)-3-(3-((2-cyanophenyl)amino)-4-(ethyl(tetrahydro-2H-pyran-4-yl)amino)phenyl)-4-methoxybutanoic acid | 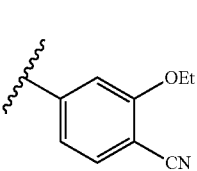 [SMILES: *c1ccc(C#N)c(C(F)(F)F)c1] | 1.335 | 438.3 |

-continued

| Ex. No. | Name | R | T_r (min) (Method O) | [M + H]+ |
|---|---|---|---|---|
| 370 | (S)-3-(3-((4-cyano-3-ethoxyphenyl)amino)-4-(ethyl(tetrahydro-2H-pyran-4-yl)amino)phenyl)-4-methoxybutanoic acid | 2,2-difluoroethoxy-4-cyanophenyl | 1.439 | 482.4 |
| 371 | (S)-3-(3-((4-cyano-3-(2,2-difluoroethoxy)phenyl)amino)-4-(ethyl(tetrahydro-2H-pyran-4-yl)amino)phenyl)-4-methoxybutanoic acid | 2,2,2-trifluoroethoxy-4-cyanophenyl | 1.431 | 518.4 |
| 372 | (S)-3-(3-((4-cyano-3-(2,2,2-trifluoroethoxy)phenyl)amino)-4-(ethyl(tetrahydro-2H-pyran-4-yl)amino)phenyl)-4-methoxybutanoic acid | p-tolyl | 1.536 | 536.3 |
| 373 | (S)-3-(4-(ethyl(tetrahydro-2H-pyran-4-yl)amino)-3-(p-tolylamino)phenyl)-4-methoxybutanoic acid | 4-ethylphenyl | 1.804 | 427.3 |
| 374 | (S)-3-(4-(ethyl(tetrahydro-2H-pyran-4-yl)amino)-3-((4-ethylphenyl)amino)phenyl)-4-methoxybutanoic acid | 4-fluorophenyl | 1.96 | 441.3 |
| 375 | (S)-3-(4-(ethyl(tetrahydro-2H-pyran-4-yl)amino)-3-((4-fluorophenyl)amino)phenyl)-4-methoxybutanoic acid | 4-chlorophenyl | 1.689 | 431.2 |
| 376 | (S)-3-(3-((4-chlorophenyl)amino)-4-(ethyl(tetrahydro-2H-pyran-4-yl)amino)phenyl)-4-methoxybutanoic acid | 2-methylbenzo[d]thiazol-6-yl | 1.831 | 447.2 |
| 377 | (S)-3-(4-(ethyl(tetrahydro-2H-pyran-4-yl)amino)-3-((2-methylbenzo[d]thiazol-6-yl)amino)phenyl)-4-methoxybutanoic acid | 2,2-difluorobenzo[d][1,3]dioxol-5-yl | 1.603 | 484.2 |
| 378 | (S)-3-(3-((2,2-difluorobenzo[d][1,3]dioxol-5-yl)amino)-4-(ethyl(tetrahydro-2H-pyran-4-yl)amino)phenyl)-4-methoxybutanoic acid | 2-methylpyrimidin-5-yl | 1.940 | 493.2 |

-continued

| Ex. No. | Name | R | T$_r$ (min) (Method O) | [M + H]$^+$ |
|---|---|---|---|---|
| 379 | (S)-3-(4-(ethyl(tetrahydro-2H-pyran-4-yl)amino)-3-((2-methylpyrimidin-5-yl)amino)phenyl)-4-methoxybutanoic acid | 4-CN, 3-OMe phenyl | 1.188 | 429.2 |
| 380 | (S)-3-(3-((4-cyano-3-ethoxyphenyl)amino)-4-(ethyl(tetrahydro-2H-pyran-4-yl)amino)phenyl)-4-methoxybutanoic acid | 4-CN, 3-Cl phenyl | 1.528 | 468.1 |
| 381 | (S)-3-(3-((3-chloro-4-cyanophenyl)amino)-4-(ethyl(tetrahydro-2H-pyran-4-yl)amino)phenyl)-4-methoxybutanoic acid | 2-methyl-3-CN pyridin-6-yl | 1.627 | 472.0 |
| 382 | (S)-3-(3-((5-cyano-6-methylpyridin-2-yl)amino)-4-(ethyl(tetrahydro-2H-pyran-4-yl)amino)phenyl)-4-methoxybutanoic acid | 4-CN, 3-CF$_3$ phenyl | 1.459 | 453.0 |
| 383 | (S)-3-(3-((4-cyano-3-(trifluoromethyl)phenyl)amino)-4-(ethyl(tetrahydro-2H-pyran-4-yl)amino)phenyl)-4-methoxybutanoic acid | 4-methyl-3-CN pyridin-6-yl | 1.701 | 506.1 |
| 384 | (S)-3-(3-((5-cyano-4-methylpyridin-2-yl)amino)-4-(ethyl(tetrahydro-2H-pyran-4-yl)amino)phenyl)-4-methoxybutanoic acid | 4-CONH$_2$ phenyl | 1.451 | 453.1 |
| 385 | (S)-3-(3-((4-carbamoylphenyl)amino)-4-(ethyl(tetrahydro-2H-pyran-4-yl)amino)phenyl)-4-methoxybutanoic acid | 4-(ethylsulfonyl)phenyl | 1.029 | 456.8 |
| 386 | (S)-3-(4-(ethyl(tetrahydro-2H-pyran-4-yl)amino)-3-((4-(ethylsulfonyl)phenyl)amino)phenyl)-4-methoxybutanoic acid | 2-methoxypyrimidin-5-yl | 1.390 | 505.1 |

Examples 387 to 421

Enantiomer 2

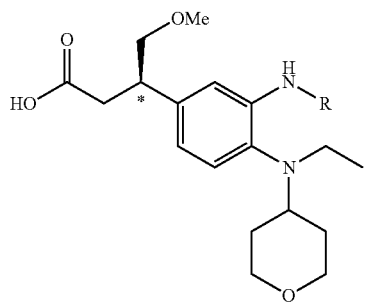

Examples 387 to 421 were prepared using 349B Enantiomer 2 and corresponding aryl bromides following the procedure described for the synthesis of Example 349.

| Ex. No. | Name | R | T$_r$ (min) (Method O) | [M + H]$^+$ |
|---|---|---|---|---|
| 387 | (R)-3-(4-(ethyl(tetrahydro-2H-pyran-4-yl)amino)-3-((2-methoxypyrimidin-5-yl)amino)phenyl)-4-methoxybutanoic acid | 2-methoxypyrimidin-5-yl | 1.300 | 445.2 |
| 388 | (R)-3-(3-((2-ethoxypyrimidin-5-yl)amino)-4-(ethyl(tetrahydro-2H-pyran-4-yl)amino)phenyl)-4-methoxybutanoic acid | 2-ethoxypyrimidin-5-yl | 1.420 | 459.2 |
| 389 | (R)-3-(3-((5-cyanopyridin-2-yl)amino)-4-(ethyl(tetrahydro-2H-pyran-4-yl)amino)phenyl)-4-methoxybutanoic acid | 5-cyanopyridin-2-yl | 1.422 | 439.2 |
| 390 | (R)-3-(3-((4-cyano-3-fluorophenyl)amino)-4-(ethyl(tetrahydro-2H-pyran-4-yl)amino)phenyl)-4-methoxybutanoic acid | 4-cyano-3-fluorophenyl | 1.551 | 456.1 |
| 391 | (R)-3-(3-((4-cyano-3-methylphenyl)amino)-4-(ethyl(tetrahydro-2H-pyran-4-yl)amino)phenyl)-4-methoxybutanoic acid | 6-methoxypyridin-3-yl (with CN) | 1.266 | 444.3 |
| 392 | (R)-3-(3-((4-cyano-2-fluorophenyl)amino)-4-(ethyl(tetrahydro-2H-pyran-4-yl)amino)phenyl)-4-methoxybutanoic acid | 4-cyano-2-fluorophenyl | 1.622 | 456.1 |

-continued

| Ex. No. | Name | R | T$_r$ (min) (Method O) | [M + H]$^+$ |
|---|---|---|---|---|
| 393 | (R)-3-(3-((5-chloropyridin-2-yl)amino)-4-(ethyl(tetrahydro-2H-pyran-4-yl)amino)phenyl)-4-methoxybutanoic acid | 2-pyridyl, 5-Cl | 1.672 | 448.1 |
| 394 | (R)-3-(3-((5-chloropyrimidin-2-yl)amino)-4-(ethyl(tetrahydro-2H-pyran-4-yl)amino)phenyl)-4-methoxybutanoic acid | 2-pyrimidinyl, 5-Cl | 1.567 | 449.1 |
| 395 | (R)-3-(3-((3-difluoropyridin-2-yl)amino)-4-(ethyl-(tetrahydro-2H-pyran-4-yl)amino)phenyl)-4-methoxybutanoic acid | 2-pyridyl, 3-F, 5-F | 1.704 | 450.1 |
| 396 | (R)-3-(4-(ethyl(tetrahydro-2H-pyran-4-yl)amino)-3-((5-fluoropyrimidin-2-yl)amino)phenyl)-4-methoxybutanoic acid | 2-pyrimidinyl, 5-F | 1.212 | 433.3 |
| 397 | (R)-3-(4-(ethyl(tetrahydro-2H-pyran-4-yl)amino)-3-((3-(1,1,2,2-tetrafluoroethoxy)phenyl)amino)phenyl)-4-methoxybutanoic acid | 3-(OCF$_2$CHF$_2$)phenyl | 1.994 | 529.1 |
| 398 | (R)-3-(4-(ethyl(tetrahydro-2H-pyran-4-yl)amino)-3-((3-(1,1,2,2-tetrafluoroethoxy)phenyl)amino)phenyl)-4-methoxybutanoic acid | 3-F, 4-Cl phenyl | 1.913 | 465.0 |
| 399 | (R)-3-(3-((4-chloro-2-fluorophenyl)amino)-4-(ethyl(tetrahydro-2H-pyran-4-yl)amino)phenyl)-4-methoxybutanoic acid | 2-F, 4-Cl phenyl | 1.969 | 465.0 |
| 400 | (R)-3-(4-(ethyl(tetrahydro-2H-pyran-4-yl)amino)-3-((5-fluoropyridin-2-yl)amino)phenyl)-4-methoxybutanoic acid | 2-pyridyl, 5-F | 1.470 | 432.1 |
| 401 | (R)-3-(4-(ethyl(tetrahydro-2H-pyran-4-yl)amino)-3-((4-trifluoromethyl)phenyl)amino)phenyl)-4-methoxybutanoic acid | 4-CF$_3$ phenyl | 1.964 | 481.1 |
| 402 | (R)-3-(3-((2,4-difluorophenyl)amino)-4-(ethyl(tetrahydro-2H-pyran-4-yl)amino)phenyl)-4-methoxybutanoic acid | 2-F, 4-F phenyl | 1.580 | 449.3 |

-continued

| Ex. No. | Name | R | T_r (min) (Method O) | [M + H]+ |
|---|---|---|---|---|
| 403 | (R)-3-(4-(ethyl(tetrahydro-2H-pyran-4-yl)amino)-3-((2-(tetrahydro-2H-pyran-4-yl)pyrimidin-5-yl)amino)phenyl)-4-methoxybutanoic acid | pyrimidin-morpholine | 1.248 | 500.4 |
| 404 | (R)-3-(3-((4-cyano-2-methylphenyl)amino)-4-(ethyl(tetrahydro-2H-pyran-4-yl)amino)phenyl)-4-methoxybutanoic acid | 4-cyano-2-methylphenyl | 1.682 | 452.1 |
| 405 | (R)-3-(3-((3-cyanophenyl)amino)-4-(ethyl(tetrahydro-2H-pyran-4-yl)amino)phenyl)-4-methoxybutanoic acid | 3-cyanophenyl | 1.382 | 438.3 |
| 406 | (R)-3-(3-((2-cyanophenyl)amino)-4-(ethyl(tetrahydro-2H-pyran-4-yl)amino)phenyl)-4-methoxybutanoic acid | 2-cyanophenyl | 1.362 | 438.3 |
| 407 | (R)-3-(3-((4-cyano-3-ethoxyphenyl)amino)-4-(ethyl(tetrahydro-2H-pyran-4-yl)amino)phenyl)-4-methoxybutanoic acid | 4-cyano-3-ethoxyphenyl | 1.454 | 482.4 |
| 408 | (R)-3-(3-((4-cyano-3-(2,2-difluoroethoxy)phenyl)amino)-4-(ethyl(tetrahydro-2H-pyran-4-yl)amino)phenyl)-4-methoxybutanoic acid | 4-cyano-3-(2,2-difluoroethoxy)phenyl | 1.445 | 518.4 |
| 409 | (R)-3-(3-((4-cyano-3-(2,2,2-trifluoroethoxy)phenyl)amino)-4-(ethyl(tetrahydro-2H-pyran-4-yl)amino)phenyl)-4-methoxybutanoic acid | 4-cyano-3-(2,2,2-trifluoroethoxy)phenyl | 1.536 | 536.3 |
| 410 | (R)-3-(4-(ethyl(tetrahydro-2H-pyran-4-yl)amino)-3-(p-tolylamino)phenyl)-4-methoxybutanoic acid | p-tolyl | 1.602 | 427.3 |
| 411 | (R)-3-(4-(ethyl(tetrahydro-2H-pyran-4-yl)amino)-3-((4-ethylphenyl)amino)phenyl)-4-methoxybutanoic acid | 4-ethylphenyl | 1.739 | 441.4 |

-continued

| Ex. No. | Name | R | $T_r$ (min) (Method O) | [M + H]$^+$ |
|---|---|---|---|---|
| 412 | (R)-3-(4-(ethyl(tetrahydro-2H-pyran-4-yl)amino)-3-((4-fluorophenyl)amino)phenyl)-4-methoxybutanoic acid | 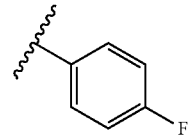 | 1.478 | 431.3 |
| 413 | (R)-3-(3-((4-chlorophenyl)amino)-4-(ethyltetrahydro-2H-pyran-4-yl)amino)phenyl)-4-methoxybutanoic acid | 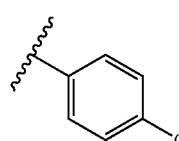 | 1.627 | 447.3 |
| 414 | (R)-3-(4-(ethyl(tetrahydro-2H-pyran-4-yl)amino)-3-((2-methylbenzo[d]thiazol-6-yl)amino)phenyl)-4-methoxybutanoic acid | 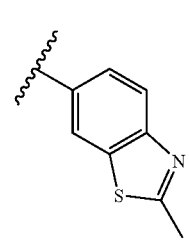 [SMILES: *c1ccc2nc(C)sc2c1] | 1.392 | 484.3 |
| 415 | (R)-3-(3-((2,2-difluorobenzo[d][1,3]dioxol-5-yl)amino)-4-(ethyl(tetrahydro-2H-pyran-4-yl)amino)phenyl)-4-methoxybutanoic acid | 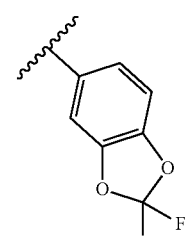 | 1.724 | 493.3 |
| 416 | (R)-3-(4-(ethyl(tetrahydro-2H-pyran-4-yl)amino)-3-((2-methylpyrimidin-5-yl)amino)phenyl)-4-methoxybutanoic acid | 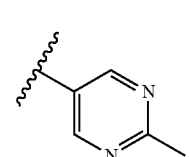 | 1.509 | 429.3 |
| 417 | (R)-3-(3-((4-cyano-3-methoxyphenyl)amino)-4-(ethyl(tetrahydro-2H-pyran-4-yl)amino)phenyl)-4-methoxybutanoic acid | 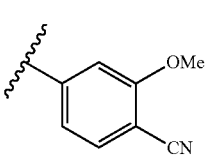 [SMILES: *c1ccc(C#N)c(OC)c1] | 1.509 | 468.1 |
| 418 | (R)-3-(3-((3-chloro-4-cyanophenyl)amino)-4-(ethyl(tetrahydro-2H-pyran-4-yl)amino)phenyl)-4-methoxybutanoic acid | 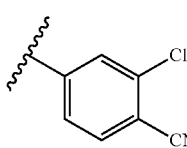 | 1.627 | 472.0 |
| 419 | (R)-3-(3-((5-cyano-6-methylpyridin-2-yl)amino)-4-(ethyl(tetrahydro-2H-pyran-4-yl)amino)phenyl)-4-methoxybutanoic acid | 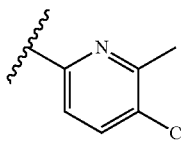 | 1.466 | 453.0 |
| 420 | (R)-3-(3-((4-cyano-3-(trifluoromethyl)phenyl)amino)-4-(ethyl(tetrahydro-2H-pyran-4-yl)amino)phenyl)-4-methoxybutanoic acid | 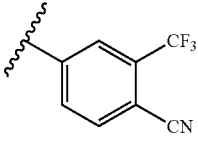 [SMILES: *c1ccc(C#N)c(C(F)(F)F)c1] | 1.710 | 506.1 |

| Ex. No. | Name | R | $T_r$ (min) (Method O) | [M + H]+ |
|---|---|---|---|---|
| 421 | (R)-3-(4-(ethyl(tetrahydro-2H-pyran-4-yl)amino)-3-((4-(ethylsulfonyl)phenyl)amino)phenyl)-4-methoxybutanoic acid | 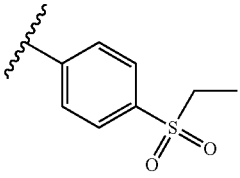 [SMILES: *c1ccc(S(=O)(=O)CC)cc1] | 1.404 | 505.1 |

Example 422

Enantiomer 1 and Enantiomer 2

3-(3-(3-(4-Cyanophenyl)ureido)-4-(ethyl(tetrahydro-2H-pyran-4-yl)amino)phenyl)-4-methoxybutanoic acid

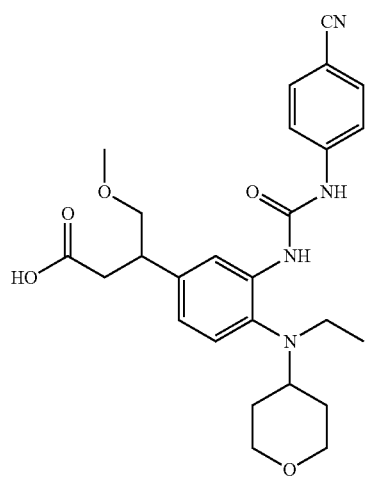 [SMILES: CCN(c1ccc(C(COC)CC(=O)O)cc1NC(=O)Nc1ccc(C#N)cc1)C1CCOCC1]

422A. Methyl (S)-3-(3-(3-(4-cyanophenyl)ureido)-4-(ethyl(tetrahydro-2H-pyran-4-yl)amino) phenyl)-4-methoxybutanoate To a stirred solution of 349B Enantiomer 1 (100 mg, 0.285 mmol) in DCM (5 mL), was added 4-isocyanatobenzonitrile (49.4 mg, 0.342 mmol) at room temperature. The reaction mixture was stirred at room temperature for 4 h. The solvent was removed under vacuum. The crude material was recrystallized from methanol to afford 422A (off-white solid, 104 mg, 0.210 mmol, 73.7% yield). LC-MS Anal. Calc'd. for $C_{27}H_{34}N_4O_5$, 494.253, found [M+H] 495.5, $T_r$=1.33 min (Method AY).

Example 422 Enantiomer 1. (S)-3-(3-(3-(4-Cyanophenyl)ureido)-4-(ethyl(tetrahydro-2H-pyran-4-yl) amino)phenyl)-4-methoxybutanoic acid To a stirred solution of 422A (100 mg, 0.202 mmol) in MeOH (5 mL), water (5 mL) and THF (5 mL) was added LiOH (19.37 mg, 0.809 mmol). The resulting mixture was stirred at room temperature for 4 h. The reaction mixture was concentrated and the aqueous solution was acidified with saturated citric acid solution (pH~4-5). The aqueous solution was extracted with ethyl acetate (3×20 mL). The combined organic layers were dried over sodium sulfate, filtered and concentrated to afford a brown colored residue. The residue was purified via preparative LC-MS to afford Example 422 Enantiomer 1 (off-white solid, 73.7 mg, 0.149 mmol, 73.6% yield). LC-MS Anal. Calc'd. for $C_{26}H_{32}N_4O_5$, 480.237, found [M+H] 481.3, $T_r$=1.253 min (Method O). $^1$H NMR (400 MHz, methanol-$d_4$) δ 8.16 (d, J=1.60 Hz, 1H), 7.64-7.72 (m, 4H), 7.22 (d, J=8.40 Hz, 1H), 6.97-7.00 (m, 1H), 3.91-3.94 (m, 2H), 3.58-3.61 (m, 2H), 3.33-3.43 (m, 6H), 3.05-3.10 (m, 3H), 2.75-2.76 (m, 1H), 2.59-2.60 (m, 1H), 1.79-1.82 (m, 2H), 1.51-1.54 (m, 2H), 0.90 (t, J=7.20 Hz, 3H).

Example 422 Enantiomer 2. (R)-3-(3-(3-(4-Cyanophenyl) ureido)-4-(ethyl(tetrahydro-2H-pyran-4-yl) amino)phenyl)-4-methoxybutanoic acid Example 422 Enantiomer 2 was prepared utilizing 349B Enantiomer 2 and 4-isocyanatobenzonitrile following the procedure described for the synthesis of Example 422 Enantiomer 1. LC-MS Anal. Calc'd. for $C_{26}H_{32}N_4O_5$, 480.237, found [M+H] 481.3, $T_r$=1.57 min (Method O). $^1$H NMR (400 MHz, CD$_3$OD) δ 8.16 (d, J=1.60 Hz, 1H), 7.64-7.72 (m, 4H), 7.21 (d, J=8.40 Hz, 1H), 6.95-7.00 (m, 1H), 3.91-3.93 (m, 2H), 3.59-3.62 (m, 2H), 3.33-3.44 m, 6H), 3.05-3.10 (m, 3H), 2.71-2.76 (m, 1H), 2.53-2.59 (m, 1H), 1.79-1.82 (m, 2H), 1.51-1.54 (m, 2H), 0.90 (t, J=7.20 Hz, 3H).

Examples 423 to 433

Enantiomer 1

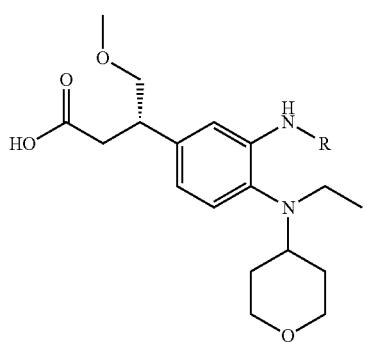

Examples 423 to 433 were prepared from 349B Enantiomer 1 and the corresponding isocyanates following the procedure described for the synthesis of Example 422.

| Ex. No. | Name | R | T_r (min) (Method O) | [M + H]+ |
|---|---|---|---|---|
| 423 | (S)-3-(3-(3-(4-chloro-2-fluorophenyl)ureido)-4-(ethyl(tetrahydro-2H-pyran-4-yl)amino)phenyl)-4-methoxybutanoic acid | | 1.699 | 508.2 |
| 424 | (S)-3-(4-(ethyl(tetrahydro-2H-pyran-4-yl)amino)-3-(3-(2-fluoro-4-methoxyphenyl)ureido)phenyl)-4-methoxybutanoic acid | | 1.457 | 504.3 |
| 425 | (S)-3-(3-(3-(4-(difluoromethoxy)phenyl)ureido)-4-(ethyl(tetrahydro-2H-pyran-4-yl)amino)phenyl)-4-methoxybutanoic acid | | 1.577 | 522.2 |
| 426 | (S)-3-(4-(ethyl(tetrahydro-2H-pyran-4-yl)amino)-3-(3-(6-methoxypyridin-3-yl)ureido)phenyl)-4-methoxybutanoic acid | | 1.268 | 487.2 |
| 427 | (S)-3-(4-(ethyl(tetrahydro-2H-pyran-4-yl)amino)-3-(3-(2-methylpyrimidin-5-yl)ureido)phenyl)-4-methoxybutanoic acid | | 1.1 | 472.3 |
| 428 | (S)-3-(4-(ethyl(tetrahydro-2H-pyran-4-yl)amino)-3-(3-(5-methylisoxazol-3-yl)ureido)phenyl)-4-methoxybutanoic acid | | 1.104 | 461.3 |
| 429 | (S)-3-(4-(ethyl(tetrahydro-2H-pyran-4-yl)amino)-3-(3-(3-methylisoxazol-5-yl)ureido)phenyl)-4-methoxybutanoic acid | | 1.281 | 461.3 |
| 430 | (S)-3-(3-(3-(2,4-dichlorophenyl)ureido)-4-(ethyl(tetrahydro-2H-pyran-4-yl)amino)phenyl)-4-methoxybutanoic acid | | 1.721 | 524.1 |
| 431 | (S)-3-(3-(3-(2,4-difluorophenyl)ureido)-4-(ethyl(tetrahydro-2H-pyran-4-yl)amino)phenyl)-4-methoxybutanoic acid | | 1.495 | 492.2 |
| 432 | (S)-3-(3-(3-(4-ethoxyphenyl)ureido)-4-(ethyl(tetrahydro-2H-pyran-4-yl)amino)phenyl)-4-methoxybutanoic acid | | 1.357 | 500.3 |

| Ex. No. | Name | R | T$_r$ (min) (Method O) | [M + H]$^+$ |
|---|---|---|---|---|
| 433 | (S)-3-(4-(ethyl(tetrahydro-2H-pyran-4-yl)amino)-3-(3-(p-tolyl)ureido)phenyl)-4-methoxybutanoic acid | 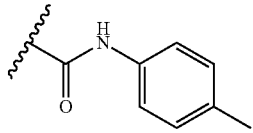 [SMILES: *C(=O)Nc1ccc(C)cc1] | 1.514 | 470.43 |

Examples 434 to 442

Enantiomer 2

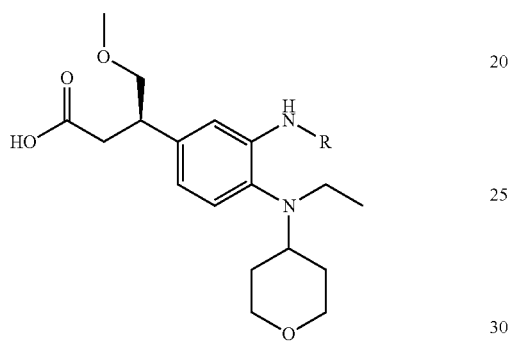

Examples 434 to 442 were prepared using 349B Enantiomer 2 and the corresponding isocyanates following the procedure described for the synthesis of Example 422 (absolute stereochemistry not determined).

| Ex. No. | Name | R | T$_r$ (min) (Method O) | [M + H]$^+$ |
|---|---|---|---|---|
| 434 | (R)-3-(3-(3-(4-chloro-2-fluorophenyl)ureido)-4-(ethyl(tetrahydro-2H-pyran-4-yl)amino)phenyl)-4-methoxybutanoic acid | 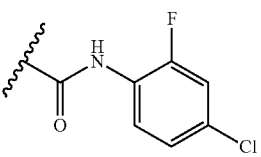 [SMILES: *C(=O)Nc1ccc(Cl)cc1F] | 1.700 | 508.1 |
| 435 | (R)-3-(4-(ethyl(tetrahydro-2H-pyran-4-yl)amino)-3-(3-(2-fluoro-4-methoxyphenyl)ureido)phenyl)-4-methoxybutanoic acid |  | 1.224 | 504.4 |
| 436 | (R)-3-(3-(3-(4-(difluoromethoxy)phenyl)ureido)-4-(ethyl(tetrahydro-2H-pyran-4-yl)amino)phenyl)-4-methoxybutanoic acid | 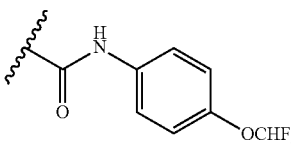 | 1.343 | 522.3 |
| 437 | (R)-3-(4-(ethyl(tetrahydro-2H-pyran-4-yl)amino)-3-(3-(6-methoxypyridin-3-yl)ureido)phenyl)-4-methoxybutanoic acid | 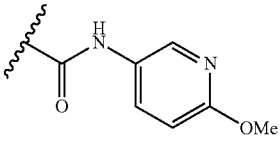 [SMILES: *C(=O)Nc1ccc(OC)nc1] | 1.067 | 487.3 |

| Ex. No. | Name | R | $T_r$ (min) (Method O) | $[M + H]^+$ |
|---|---|---|---|---|
| 438 | (R)-3-(4-(ethyl(tetrahydro-2H-pyran-4-yl)amino)-3-(3-(2-methylpyrimidin-5-yl)ureido)phenyl)-4-methoxybutanoic acid | | 0.906 | 472.4 |
| 439 | (R)-3-(4-(ethyl(tetrahydro-2H-pyran-4-yl)amino)-3-(3-(5-methylisoxazol-3-yl)ureido)phenyl)-4-methoxybutanoic acid | | 1.123 | 461.3 |
| 440 | (R)-3-(4-(ethyl(tetrahydro-2H-pyran-4-yl)amino)-3-(3-(3-methylisoxazol-5-yl)ureido)phenyl)-4-methoxybutanoic acid | | 1.297 | 461.2 |
| 441 | (R)-3-(3-(3-(2,4-dichlorophenyl)ureido)-4-(ethyl(tetrahydro-2H-pyran-4-yl)amino)phenyl)-4-methoxybutanoic acid | | 1.721 | 524.2 |
| 442 | (R)-3-(3-(3-(2,4-difluorophenyl)ureido)-4-(ethyl(tetrahydro-2H-pyran-4-yl)amino)phenyl)-4-methoxybutanoic acid | | 1.493 | 492.2 |

Example 443

Diastereomer 1 and Diastereomer 2

3-(4-((1S,4S)-5-(tert-Butoxycarbonyl)-2,5-diazabicyclo[2.2.1]heptan-2-yl)-3-((4-cyanophenyl)amino)phenyl)pentanoic acid

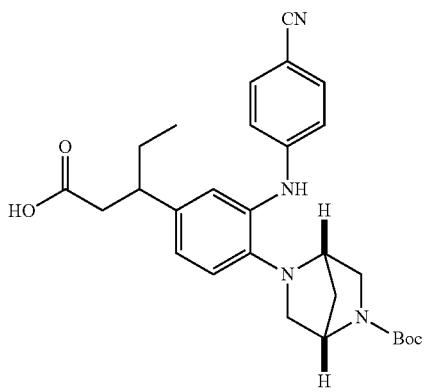 [SMILES: CCC(CC(=O)O)c1ccc(N2C[C@@H]3C[C@H]2CN3C(=O)OC(C)(C)C)c(Nc2ccc(C#N)cc2)c1]

443A. 2-(4-Fluoro-3-nitrophenyl)-4,4,5,5-tetramethyl-1,3,2-dioxaborolane

A stirred solution of 4-bromo-1-fluoro-2-nitrobenzene (10 g, 45.5 mmol), 4,4,4',4',5,5,5',5'-octamethyl-2,2'-bi(1,3,2-dioxaborolane) (16.16 g, 63.6 mmol), and potassium acetate (13.38 g, 136 mmol) in dioxane (100 mL), was purged with argon for 5 min. Then $PdCl_2$ (dppf).$CH_2Cl_2$ Adduct (3.71 g, 4.55 mmol) was added to the reaction mixture under argon and the mixture was heated to 108° C. for 12 h. The reaction mixture was allowed to cool to room temperature and then filtered through CELITE® pad and subsequently washed with ethyl acetate (100 mL). The organic layers were washed with water (50 mL) and the aqueous layer was separated and extracted with ethyl acetate (2×100 mL). The combined the organic layers were washed with brine, dried over sodium sulfate, filtered and evaporated under reduced pressure to give the crude product as a brown colored residue. The residue was purified via flash silica gel column chromatography using 30% ethyl acetate in pet ether to afford 443A (light yellow solid, 10.4 g, 38.9 mmol, 86% yield). LC-MS Anal. Calc'd. for $C_{12}H_{15}BFNO_4$, 267.108, found [M+NH$_4$] 285.2, $T_r$=1.07 (Method AY).

443B. Methyl 3-(4-fluoro-3-nitrophenyl)pentanoate

To a stirred solution of 443A (5 g, 18.72 mmol) in dioxane (80 mL) and (E)-methyl pent-2-enoate (5.34 g, 46.8 mmol) was added NaOH (16.85 mL, 16.85 mmol). The reaction mixture was then purged with argon gas for 15 min followed by addition of chloro(1,5-cyclooctadiene)rhodium(I) dimer (0.462 g, 0.936 mmol) and then purged again with argon for 5 minutes. The reaction suspension was stirred at 50° C. for 6 h followed by cooling to room temperature. The reaction was then quenched with AcOH (0.965 mL, 16.85 mmol) and it was stirred for 5 minutes before it was partitioned between ethyl acetate (100 mL) and water (80 mL). The aqueous layer was extracted with ethyl acetate (2×100 mL). The combined organic layers were washed with brine (80 mL), dried over anhydrous sodium sulfate, filtered and concentrated under reduced pressure to afford a residue. The residue was purified via flash silica gel column chromatography using ethyl acetate in pet ether as an eluant to afford Racemate 443B (brown oil, 4.0 g, 15.74 mmol, 84% yield). LC-MS Anal. Calc'd. for $C_{12}H_{13}FNO_4$, 255.091, found [M+NH$_4$] 273.0, $T_r$=2.751 (Method U).

Chiral separation of 443B racemic gave 443B Enantiomer 1 $T_r$=8.991 min (Method CB) and 443B Enantiomer 2 $T_r$=12.02 min (Method CB) as single enantiomers.

443B Enantiomer 1 (absolute stereochemistry not determined) (1.65 g, 6.23 mmol, 33.3% yield). LC-MS Anal. Calc'd. for $C_{12}H_{14}FNO_4$, 255.091, found [M+NH$_4$] 273.2, $T_r$=1.953 min (Method BB).

443B Enantiomer 2 (absolute stereochemistry not determined) (1.62 g, 5.99 mmol, 32.0% yield). LC-MS Anal. Calc'd. for $C_{12}H_{14}FNO_4$ 255.091 found [M+NH$_4$] 273.2, $T_r$=1.953 min (Method BB).

443C. (1S,4S)-tert-Butyl 5-(4-(1-methoxy-1-oxopentan-3-yl)-2-nitrophenyl)-2,5-diazabicyclo[2.2.1]heptane-2-carboxylate A stirred solution of 443B Enantiomer 1 (1 g, 3.92 mmol), (1S,4S)-tert-butyl 2,5-diazabicyclo[2.2.1]heptane-2-carboxylate (0.932 g, 4.70 mmol) and DIPEA (2.053 mL, 11.75 mmol) in NMP (10 mL) was heated at 120° C. for 6 h. The mixture was allowed to cool to room temperature and was partitioned between MTBE (50 mL) and water (50 mL). The layers were separated and the organic layers were washed with brine, dried over anhydrous sodium sulfate, filtered and concentrated under reduced pressure to afford the crude residue. The crude product was purified by silica gel column chromatography using ethyl acetate in pet ether as an eluant to afford 443C Diastereomer 1 (absolute and relative stereochemistry not confirmed, brown oil, 0.85 g, 1.961 mmol, 50.0% yield). LC-MS Anal. Calc'd. for $C_{22}H_{31}N_3O_6$, 433.221, found [M+H] 434.5, $T_r$=1.54 min (Method AY).

443D. (1S,4S)-tert-Butyl 5-(2-amino-4-(1-methoxy-1-oxopentan-3-yl)phenyl)-2,5-diazabicyclo[2.2.1]heptane-2-carboxylate To a stirred solution of 443C Diastereomer 1 (0.8 g, 1.845 mmol) in ethanol (10 mL) was added water (0.5 mL) followed by ammonium chloride (494 mg, 9.23 mmol). The mixture was stirred for 5 min, and then treated with zinc powder (121 mg, 1.845 mmol) at 0° C. The mixture was stirred at room temperature for 4 h. The reaction mixture was then concentrated under reduced pressure to afford the crude product. The crude material was diluted with ethyl acetate (30 mL), washed with water (30 mL), brine (30 mL), dried over sodium sulfate, filtered and concentrated to afford the crude residue. The residue was purified by silica gel column chromatography using ethyl acetate in pet ether as an eluant to afford 443D Diastereomer 1 (absolute and relative stereochemistry not determined, brown oil, 600 mg, 1.487 mmol, 81% yield). LC-MS Anal. Calc'd. for $C_{22}H_{33}N_3O_4$, 403.515, found [M+H] 406.4, $T_r$=3.019 min (Method U).

443E. (1S,4S)-tert-Butyl 5-(2-((4-cyanophenyl)amino)-4-(1-methoxy-1-oxopentan-3-yl)phenyl)-2,5-diazabicyclo[2.2.1]heptane-2-carboxylate A mixture of 443D Diastereomer 1 (160 mg, 0.397 mmol), 4-bromobenzonitrile (144 mg, 0.793 mmol), Xantphos (92 mg, 0.159 mmol), $Cs_2CO_3$ (646 mg, 1.983 mmol) in 1,4-dioxane (5 mL) was purged with argon gas for 5 minutes. Then the bis(dibenzylideneacetone)palladium (22.80 mg, 0.040 mmol) was added and the argon gas was bubbled through the mixture for 5 additional minutes. The reaction mixture was sealed and heated in microwave at 120° C. for 2 h. The reaction mixture was allowed to cool to room temperature and concentrated under reduced pressure to afford the residue. The residue was reconstituted in a mixture of ethyl acetate (20 mL) and water (20 mL). The organic layers were separated and the aqueous layers were extracted with ethyl acetate (2×20 mL). The combined organic layers were washed with water (20 mL), brine (20 mL), dried over anhydrous sodium sulfate, filtered and concentrated under reduced pressure to afford a residue. The residue was purified via flash silica gel column chromatography using ethyl acetate in pet ether as an eluant to afford 443E Diastereomer 1 (absolute and relative stereochemistry not determined, brown solid, 120 mg, 0.238 mmol, 60.0% yield). LC-MS Anal. Calc'd. for $C_{29}H_{36}N_4O_4$, 504.274, found [M+H] 505.3, $T_r$=1.40 (Method AA).

Example 443 Diastereomer 1. 3-(4-((1S,4S)-5-(tert-Butoxycarbonyl)-2,5-diazabicyclo[2.2.1]heptan-2-yl)-3-((4-cyanophenyl)amino)phenyl)pentanoic acid To a stirred solution of 443E Diastereomer 1 (50 mg, 0.099 mmol) in a mixture of MeOH (2 mL), THF (2 mL) and water (2 mL), was added LiOH (9.49 mg, 0.396 mmol). The resulting mixture was stirred at room temperature for 4 h. The reaction mixture was then concentrated and the aqueous solution was acidified with saturated citric acid solution (pH~4-5). The aqueous layer was diluted with water (5 mL) and extracted with ethyl acetate (2×10 mL). The combined organic layers were washed with water (10 mL), brine (10 mL), dried over anhydrous sodium sulfate, filtered and concentrated under reduced pressure to afford the residue. The residue was purified by preparative LCMS to afford Example 443 Diastereomer 1 (absolute and relative stereochemistry not confirmed, off-white solid, 14.2 mg, 0.029, 29.2% yield). LC-MS Anal. Calc'd. for $C_{28}H_{34}N_4O_4$, 490.258, found [M+H] 491.1, $T_r$=1.794 (Method O). $^1$H NMR (400 MHz, CD$_3$OD) δ 7.42-7.44 (m, 2H), 6.99-7.02 (m, 2H), 6.86-6.88 (m, 1H), 6.66-6.68 (m, 2H), 4.32-4.34 (m, 2H), 3.28-3.52 (m, 3H), 2.88-3.02 (m, 2H), 2.48-2.63 (m, 2H), 1.80-1.83 (m, 2H), 1.57-1.60 (m, 2H), 1.41 (s, 9H), 0.89 (t, J=7.2 Hz, 3H).

Example 443 Diastereomer 2. 3-(4-((1S,4S)-5-(tert-Butoxycarbonyl)-2,5-diazabicyclo[2.2.1]heptan-2-yl)-3-((4-cyanophenyl)amino)phenyl)pentanoic acid Example 443 Diastereomer 2 was prepared utilizing 443D Enantiomer 2 and 4-bromobenzonitrile following the procedure described for the synthesis of Example 443

Diastereomer 1 (absolute and relative stereochemistry not confirmed). LC-MS Anal. Calc'd. for $C_{28}H_{34}N_4O_4$, 490.258, found [M+H] 491.4, $T_r$=1.594 (Method O). $^1$H NMR (400 MHz, CD$_3$OD) δ 7.42-7.44 (m, 2H), 6.99-7.02 (m, 2H), 6.86-6.88 (m, 1H), 6.66-6.68 (m, 2H), 4.33-4.34 (m, 2H), 3.29-3.53 (m, 3H), 2.87-2.98 (m, 2H), 2.51-2.61 (m, 2H), 1.70-1.84 (m, 3H), 1.54-1.68 (m, 1H), 1.40-1.42 (m, 9H), 0.83 (t, J=7.20 Hz, 3H).

Examples 444 and 445

Diastereomer 1

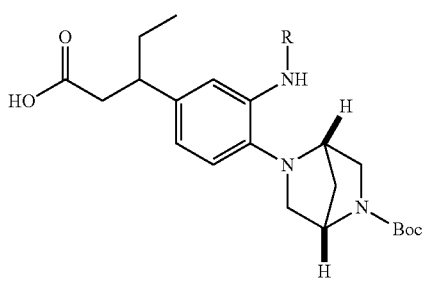

Examples 444 and 445 were prepared using 443D Diastereomer 1 and the corresponding aryl bromides following the procedure described for the synthesis of Example 443 absolute and relative stereochemistry not confirmed

| Ex. No. | Name | R | $T_r$ (min) | $[M + H]^+$ |
|---|---|---|---|---|
| 444 | 3-(4-((1S,4S)-5-(tert-butoxycarbonyl)-2,5-diazabicyclo[2.2.1]heptan-2-yl)-3-(phenylamino)phenyl)pentanoic acid | | 2.055 (Method O) | 466.2 |
| 445 | 3-(4-((1S,4S)-5-(tert-butoxycarbonyl)-2,5-diazabicyclo[2.2.1]heptan-2-yl)-3-(p-tolylamino)phenyl)pentanoic acid | | 2.202 (Method O) | 480.2 |

Examples 446 to 448

Diastereomer 2

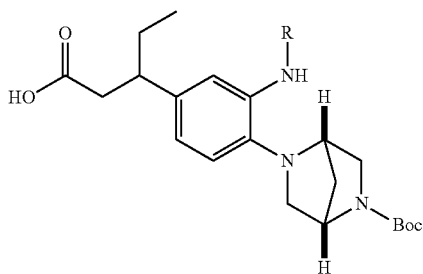

Examples 446 to 448 were prepared using the 443D Diastereomer 2 and corresponding aryl bromides following the procedure described for the synthesis of Example 443 (absolute and relative stereochemistry not confirmed).

| Ex. No. | Name | R | $T_r$ (min) | $[M + H]^+$ |
|---|---|---|---|---|
| 446 | 3-(4-((1S,4S)-5-(tert-butoxycarbonyl)-2,5-diazabicyclo[2.2.1]heptan-2-yl)-3-(phenylamino)phenyl)pentanoic acid | | 2.059 (Method O) | 466.3 |
| 447 | 3-(4-((1S,4S)-5-(tert-butoxycarbonyl)-2,5-diazabicyclo[2.2.1]heptan-2-yl)-3-(p-tolylamino)phenyl)pentanoic acid | | 2.201 (Method O) | 480.3 |
| 448 | 3-(4-((1S,4S)-5-(tert-butoxycarbonyl)-2,5-diazabicyclo[2.2.1]heptan-2-yl)-3-((2-ethoxypyrimidin-5-yl)amino)phenyl)pentanoic acid | | 1.866 (Method R) | 512.4 |

Example 449

Diastereomer 2

3-(3-((4-Cyanophenyl)amino)-4-((1S,4S)-5-(methoxycarbonyl)-2,5-diazabicyclo[2.2.1]heptan-2-yl)phenyl)pentanoic acid

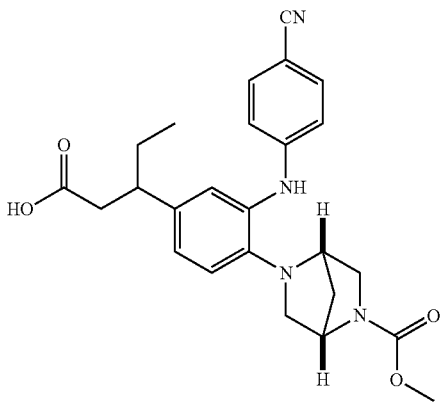 [SMILES: CCC(CC(=O)O)c1ccc(N2C[C@@H]3C[C@H]2CN3C(=O)OC)c(Nc2ccc(C#N)cc2)c1]

449A. Methyl 3-(4-((1S,4S)-2,5-diazabicyclo[2.2.1]heptan-2-yl)-3-((4-cyanophenyl)amino)phenyl)pentanoate A stirred solution of 443E Diastereomer 2 (150 mg, 0.297 mmol) in DCM (5 mL) was cooled at 0° C. To this was added TFA (0.115 mL, 1.486 mmol) dropwise and stirred at room temperature for 3 h. The reaction mixture was concentrated under reduced pressure to get brown colored semi-solid. The solid compound was partitioned between saturated aqueous sodium bicarbonate solution (20 mL) and ethyl acetate (20 mL). The organic layers were separated out and the aqueous layer was extracted with ethyl acetate (2×20 mL). The combined organic layers were dried over sodium sulfate, filtered and concentrated under reduced pressure to afford 449A Diastereomer 2 (brown solid, 90 mg, 0.222 mmol, 74.9%). LC-MS Anal. Calc'd. for $C_{24}H_{28}N_4O_2$, 404.221, found [M+H] 405.3, $T_r$=1.00 (Method AA).

449B. (1S,4S)-Methyl 5-(2-((4-cyanophenyl)amino)-4-(1-methoxy-1-oxopentan-3-yl)phenyl)-2,5-diazabicyclo[2.2.1]heptane-2-carboxylate A solution of 449A Diastereomer 2 (40 mg, 0.099 mmol), methyl carbonochloridate (14.02 mg, 0.148 mmol), DIPEA (0.052 mL, 0.297 mmol) in DCM (5 mL) was added DMAP (1.208 mg, 9.89 µmol). The resulting mixture was stirred at room temperature under nitrogen for 6 h. After evaporation of volatiles, the residue was diluted with DCM (10 mL), and washed with saturated NaHCO₃ (10 mL). The organic layers were dried over anhydrous sodium sulfate, filtered and evaporated under reduced pressure to afford the crude material. The crude residue was purified via silica gel flash chromatography using ethyl acetate in pet ether as an eluant to afford 449B Diastereomer 2 (absolute and relative stereochemistry not confirmed, brown solid, 38 mg, 0.082 mmol, 83% yield). LC-MS Anal. Calc'd. for $C_{26}H_{30}N_4O_4$, 462.227, found [M+H] 463.2, $T_r$=3.038 (Method AD).

449 Diastereomer 2. 3-(3-((4-Cyanophenyl)amino)-4-((1S,4S)-5-(methoxycarbonyl)-2,5-diazabicyclo[2.2.1]heptan-2-yl)phenyl)pentanoic acid Example 449 Diastereomer 2 was prepared by using the 449B following the procedure described for the synthesis of Example 443 (absolute and relative stereochemistry not confirmed). LC-MS Anal. Calc'd. for $C_{25}H_{28}N_4O_4$, 448.211, found [M+H] 449.1, $T_r$=1.517 (Method O). ¹H NMR (400 MHz, CD₃OD) δ 7.42-7.45 (m, 2H), 6.99-7.02 (m, 2H), 6.86-6.88 (m, 1H), 6.67-6.69 (m, 2H), 4.35-4.40 (m, 2H), 3.56-3.65 (m, 4H), 3.32-3.41 (m, 2H), 2.87-3.02 (m, 2H), 2.51-2.61 (m, 2H), 1.83-1.85 (m, 2H), 1.60-1.71 (m, 2H), 0.83 (t, J=7.20 Hz, 3H).

Example 450

Diastereomer 2

3-(3-((4-Cyanophenyl)amino)-4-((1S,4S)-5-(2,2-difluoroethyl)-2,5-diazabicyclo[2.2.1]heptan-2-yl)phenyl)pentanoic acid

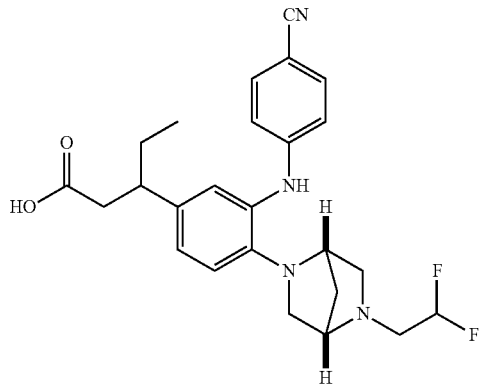 [SMILES: CCC(CC(=O)O)c1ccc(N2C[C@@H]3C[C@H]2CN3CC(F)F)c(Nc2ccc(C#N)cc2)c1]

450A. Methyl 3-(3-((4-cyanophenyl)amino)-4-((1S,4S)-5-(2,2-difluoroethyl)-2,5-diazabicyclo[2.2.1]heptan-2-yl)phenyl)pentanoate A stirred solution of 449A Diastereomer 2 (40 mg, 0.099 mmol) in ACN (5 mL) was cooled at 0° C. and DIPEA (0.052 mL, 0.297 mmol) was added followed by 2,2-difluoroethyl trifluoromethane sulfonate (31.8 mg, 0.148 mmol). The reaction suspension was stirred at room temperature for 4 h. After evaporation of volatiles, the residue was diluted with ethyl acetate (20 mL), and washed with brine (10 ml), dried over anhydrous sodium sulfate, filtered and evaporated under reduced pressure to afford the crude residue. The crude residue was purified via silica gel flash chromatography to afford 450A Diastereomer 2 (absolute and relative stereochemistry not confirmed, brown solid, 37 mg, 0.079 mmol, 80% yield). LC-MS Anal. Calc'd. for $C_{26}H_{30}F_2N_4O_2$, 468.234, found [M+H] 469.4, $T_r$=3.77 (Method U).

Example 450 Diastereomer 2. 3-(3-((4-Cyanophenyl)amino)-4-((1S,4S)-5-(2,2-difluoroethyl)-2,5-diazabicyclo[2.2.1]heptan-2-yl)phenyl)pentanoic acid Example 450 Diastereomer 2 were prepared using 450A Diastereomer 2 following the procedure described for the synthesis of Example 449 (absolute and relative stereochemistry not confirmed). LC-MS Anal. Calc'd. for $C_{25}H_{28}F_2N_4O_2$, 454.218, found [M+H] 455.0, $T_r$=1.632 (Method O). ¹H NMR (400 MHz, CD₃OD) δ 7.46-7.49 (m, 2H), 7.05-7.07 (m, 2H), 6.92-6.95 (m, 1H), 6.73-6.75 (m, 2H), 6.13-6.42 (m, 1H), 4.50 (s, 1H), 4.36 (s, 1H), 3.67-3.81 (m, 2H), 3.32-3.51 (m, 4H), 2.89-2.92 (m, 1H), 2.47-2.66 (m, 2H), 2.06-2.21 (m, 2H), 1.69-1.74 (m, 1H), 1.58-1.63 (m, 1H), 0.82 (t, J=7.2 Hz, 3H).

Example 451

Diastereomer 1 and Diastereomer 2

3-(4-((1S,4S)-5-(tert-Butoxycarbonyl)-2,5-diazabicyclo[2.2.1]heptan-2-yl)-3-((4-cyanophenyl)amino)phenyl)-4-methoxybutanoic acid

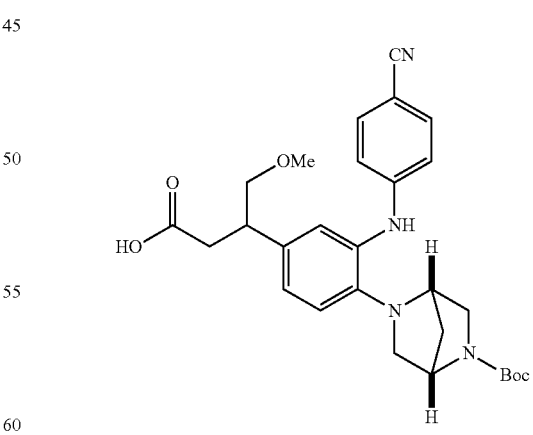

451A. Methyl 3-(4-fluoro-3-nitrophenyl)-4-methoxybutanoate 451A was prepared using the 443A and (E)-methyl 4-methoxybut-2-enoate following the procedure described for the synthesis of 443B. LC-MS Anal. Calc'd. for $C_{12}H_{14}FNO_5$, 271.086, found [M+H] 272.0, $T_r$=2.339 (Method U).

451B. (1S,4S)-tert-Butyl 5-(4-(1,4-dimethoxy-4-oxobutan-2-yl)-2-nitrophenyl)-2,5-diazabicyclo[2.2.1]heptane-2-carboxylate 451B was prepared using the 451A following the procedure described for the synthesis of 443C. LC-MS Anal. Calc'd. for $C_{22}H_{31}N_3O_7$, 449.216, found [M+H] 450.5, $T_r$=1.34 (Method AY).

451C. (1S,4S)-tert-Butyl 5-(2-amino-4-(1,4-dimethoxy-4-oxobutan-2-yl)phenyl)-2,5-diazabicyclo[2.2.1]heptane-2-carboxylate 451C was prepared using the 451B following the procedure described for the synthesis of 443D. LC-MS Anal. Calc'd. for $C_{22}H_{33}N_3O_5$, 419.242, found [M+H] 420.4, $T_r$=2.514 (Method U).
Separation of 451C diastereomeric mixture gave the 451C Diastereomer 1, $T_r$=4.0 min (Method CC) and 451C Diastereomer 2, $T_r$=5.0 min (Method CC) as single diastereomers.
451C Diastereomer 1 (absolute and relative stereochemistry not determined, brown solid, 0.25 g, 0.596 mmol, 32.7% yield). LC-MS Anal. Calc'd. for $C_{22}H_{33}N_3O_5$, 419.242, found [M+H] 420.5, $T_r$=1.27 (Method AY).
451C Diastereomer 2 (absolute and relative stereochemistry not determined, brown solid, 0.26 g, 0.620 mmol, 34.0% yield). LC-MS Anal. Calc'd. for $C_{22}H_{33}N_3O_5$, 419.242, found [M+H] 420.5, $T_r$=1.27 (Method AY).

451D. (1S,4S)-tert-Butyl 5-(2-((4-cyanophenyl)amino)-4-(1, 4-dimethoxy-4-oxobutan-2-yl)phenyl)-2,5-diazabicyclo[2.2.1]heptane-2-carboxylate 451D Diastereomer 1 was prepared using the 451C Diastereomer 1 and 4-bromobenzonitrile following the procedure described for the synthesis of 443E Diastereomer 1. LC-MS Anal. Calc'd. for $C_{29}H_{36}N_4O_5$, 520.269, found [M+H] 521.4, $T_r$=1.44 (Method AY).

Example 451 Diastereomer 1. 3-(4-((1S,4S)-5-(tert-Butoxycarbonyl)-2,5-diazabicyclo[2.2.1]heptan-2-yl)-3-((4-cyanophenyl)amino)phenyl)-4-methoxybutanoic acid Example 451 Diastereomer 1 were prepared using the 451D Diastereomer 1 following the procedure described for the synthesis of Example 443 Diastereomer 1 (absolute and relative stereochemistry not confirmed). LC-MS Anal. Calc'd. for $C_{28}H_{34}N_4O_5$, 506.253, found [M+H] 507.4, $T_r$=1.392 (Method O). $^1$H NMR (400 MHz, $CD_3OD$) δ 7.40-7.44 (m, 2H), 7.03-7.05 (m, 2H), 6.84-6.86 (m, 1H), 6.65-6.66 (m, 2H), 4.318 (s, 2H), 3.42-3.52 (m, 4H), 3.27-3.36 (m, 5H), 2.93-3.00 (m, 1H), 2.73-2.78 (m, 1H), 2.48-2.54 (m, 1H), 1.78-1.83 (m, 2H), 1.39 (s, 9H).

Example 451 Diastereomer 2. 3-(4-((1S,4S)-5-(tert-Butoxycarbonyl)-2,5-diazabicyclo[2.2.1]heptan-2-yl)-3-((4-cyanophenyl)amino)phenyl)-4-methoxybutanoic acid Example 451 Diastereomer 2 was prepared by using the 451C Diastereomer 2 and 4-bromobenzonitrile following the procedure described for the synthesis of Example 443 Diastereomer 1 (absolute and relative stereochemistry not confirmed). LC-MS Anal. Calc'd. for $C_{28}H_{34}N_4O_5$, 506.253, found [M+H] 507.4, $T_r$=1.379 (Method O). $^1$H NMR (400 MHz, $CD_3OD$) δ 7.40-7.42 (m, 2H), 7.03-7.05 (m, 2H), 6.84-6.86 (m, 1H), 6.64-6.66 (m, 2H), 4.32 (s, 2H), 3.47-3.51 (m, 4H), 3.27-3.37 (m, 5H), 2.91-2.96 (m, 1H), 2.71-2.76 (m, 1H), 2.45-2.53 (m, 1H), 1.78-1.81 (m, 2H), 1.39 (s, 9H).

Example 452

Racemate 3-(4-((2-Hydroxy-2-methylpropyl)(isobutyl)amino)-3-((2-methylbenzo[d]thiazol-6-yl)amino)phenyl)pentanoic acid

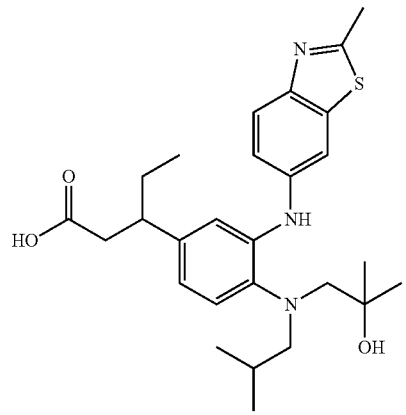 [SMILES: CCC(CC(=O)O)c1ccc(N(CC(C)C)CC(C)(C)O)c(Nc2ccc3nc(C)sc3c2)c1]

452A. 1-(Isobutylamino)-2-methylpropan-2-ol

To a solution of 1-amino-2-methylpropan-2-ol (10 g, 112 mmol) in THF (50 mL) and MeOH (50 mL) was added isobutyraldehyde (8.90 g, 123 mmol), followed by 4 Å molecular sieves (3 g). The reaction was stirred at room temperature for 6 h. The reaction mixture was cooled to 0° C. and $NaBH_4$ (12.73 g, 337 mmol) was added portionwise followed by stirring at RT for 2 h. The solvent was evaporated and the resultant residue was quenched with 10% $NaHCO_3$ solution (50 ml) and extracted with EtOAc (2×50 mL). The combined organic layers were washed with brine, dried over sodium sulfate, filtered and concentrated under reduced pressure to afford 452A (colorless oil, 11 g, 76 mmol, 67.5% yield). LC-MS Anal. Calc'd. for $C_8H_{19}NO$, 145.147, found [M+H] 146.4, $T_r$=0.44 (Method AY).

452B. 1-((4-Bromo-2-nitrophenyl)(isobutyl)amino)-2-methylpropan-2-ol

To sealable reaction flask containing 4-bromo-1-fluoro-2-nitrobenzene (5 g, 22.73 mmol), was added 452A (3.96 g, 27.3 mmol), DIPEA (11.91 mL, 68.2 mmol) followed by NMP (20 mL). The flask was sealed and the reaction was heated at 120° C. for 6 h. The reaction mixture was allowed to cool to room temperature and was partitioned between MTBE (50 mL) and water (50 mL). The layers were separated and the organic layers were washed with brine, dried over anhydrous sodium sulfate, filtered and concentrated under reduced pressure to afford a residue. The

452C. (E)-Methyl 3-(4-((2-hydroxy-2-methylpropyl)(isobutyl)amino)-3-nitrophenyl)pent-2-enoate A pressure tube equipped with Teflon cap, was charged with 452B (2 g, 5.79 mmol), (E)-methyl pent-2-enoate (1.984 g, 17.38 mmol), tetrabutylammonium bromide (0.934 g, 2.90 mmol) and dioxane (20 mL). Argon gas was bubbled through this mixture for 10 min and then dichloro-bis-(tri-o-tolylphosphine)palladium(II) (0.455 g, 0.579 mmol) was added at room temperature. Argon gas was bubbled through the mixture for another 5 min. The tube was crew-capped and heated at 110° C. for 14 h. The reaction mixture was allowed to cool to room temperature, filtered through pad of CELITE®. The CELITE® pad was washed with ethyl acetate (50 mL). The organic layers were washed with water (50 mL) and the aqueous layer was extracted with ethyl acetate (2×50 mL). The combined organic layers were washed with brine, dried over sodium sulfate, filtered and concentrated under reduced pressure to afford the crude residue. The residue was purified via silica gel flash column chromatography using ethyl acetate in pet ether to afford 452C (orange oil, 0.6 g, 1.585 mmol, 27.4% yield). LC-MS Anal. Calc'd. for $C_{20}H_{30}N_2O_5$, 378.215, found [M+H] 379.6, $T_r$=1.19 (Method AA).

452D. Methyl 3-(3-amino-4-((2-hydroxy-2-ethyl-propyl)(isobutyl)amino)phenyl)pentanoate The solution of 452C (1 g, 2.64 mmol) in methanol (10 mL) was charged to a sealable hydrogen flask. The solution was sequentially evacuated and purged with nitrogen gas for 3 times. To this carefully added 10% palladium on carbon (0.562 g, 0.528 mmol) under nitrogen atmosphere. The reaction mixture was stirred under hydrogen atmosphere at room temperature for 12 h. The reaction mixture was filtered through a CELITE® pad and the residue on the pad was thoroughly rinsed with MeOH (3×20 mL). The combined filtrates were concentrated under reduced pressure to afford 452D (brown oil, 0.6 g, 7.712 mmol, 64.8% yield). LC-MS Anal. Calc'd. for $C_{20}H_{34}N_2O_3$, 350.257, found [M+H] 351.8, $T_r$=1.15 min (Method AY).

452E. Methyl 3-(4-((2-hydroxy-2-methylpropyl)(isobutyl)amino)-3-((2-methylbenzo[d] thiazol-6-yl)amino)phenyl)pentanoate A microwave tube equipped with Teflon cap was charged with 452D (100 mg, 0.285 mmol), 6-bromo-2-methylbenzo[d]thiazole (65.1 mg, 0.285 mmol), Xantphos (41.3 mg, 0.071 mmol), $Cs_2CO_3$ (93 mg, 0.285 mmol) and dioxane (5 mL). The resulting mixture was stirred at room temperature while argon gas was bubbled through the mixture for 5 min. Then bis(dibenzylideneacetone)palladium (16.41 mg, 0.029 mmol) was added and the argon gas was bubbled through the mixture for an additional 5 min. The reaction mixture was sealed and heated in microwave at 110° C. for 2 h. The reaction mixture was allowed to cool to room temperature and concentrated under reduced pressure to afford the residue. The residue was reconstituted in a mixture of ethyl acetate (20 mL) and water (20 mL). The organic layer was separated and aqueous layer was extracted with ethyl acetate (2×20 mL). The combined organic layers were washed with water (20 mL), brine (20 mL), dried over anhydrous sodium sulfate, filtered and concentrated under reduced pressure to afford a residue. The residue was purified via flash silica gel column chromatography using ethyl acetate in pet ether as an eluant to afford 452E (brown solid, 80 mg, 0.161 mmol, 56.3% yield). LC-MS Anal. Calc'd. for $C_{28}H_{39}N_3O_3S$, 497.271, found [M+H] 498.2, $T_r$=1.05 (Method AA).

Example 452 3-(4-((2-Hydroxy-2-methylpropyl)(isobutyl)amino)-3-((2-methylbenzo[d] thiazol-6-yl)amino)phenyl)pentanoic acid To a stirred solution of 452E (80 mg, 0.161 mmol) in a mixture of MeOH (2 mL), THF (2 mL) and water (2 mL) was added LiOH (15.40 mg, 0.643 mmol). The resulting mixture was stirred at RT for 4 h. The reaction mixture was concentrated and the aqueous solution was acidified with saturated citric acid solution (pH~4-5). The aqueous layer was diluted with water (5 mL) and extracted with ethyl acetate (2×10 mL). The combined organic layers were washed with water (10 mL), brine (10 mL), dried over anhydrous sodium sulfate, filtered and concentrated under reduced pressure to afford the residue. The residue was purified by preparative LCMS to afford racemic Example 452 (off-white solid, 14.2 mg, 0.029 mmol, 18.26% yield). LC-MS Anal. Calc'd. for $C_{27}H_{37}N_3O_3S$, 483.256, found [M+H] 484.3, $T_r$=2.168 (Method O). $^1$H NMR (400 MHz, DMSO-$d_6$) δ 8.25 (s, 1H), 7.72-7.74 (m, 1H), 7.57-7.58 (m, 1H), 7.10-7.21 (m, 4H), 6.68-6.71 (m, 1H), 4.78 (s, 1H), 3.16-3.17 (m, 2H), 2.79-2.83 (m, 3H), 2.71 (s, 3H), 2.39-2.45 (m, 2H), 1.59-1.61 (m, 1H), 1.40-1.47 (m, 2H), 1.07-1.07 (m, 6H), 0.70-0.76 (m, 9H).

Example 453

Racemate

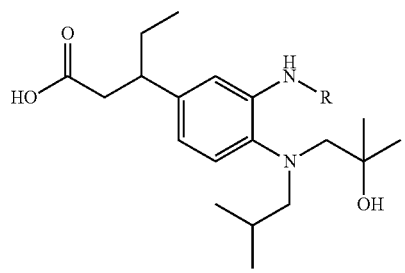

Example 453 was prepared using 452D and 1-bromo-4-chloro benzene following the procedure described for the synthesis of Example 452.

| Ex. No. | Name | R | $T_r$ (min) | [M+H]$^+$ |
|---|---|---|---|---|
| 453 | 3-(3-((4-chlorophenyl)amino)-4-((2-hydroxy-2-methyl-propyl)(isobutyl)amino)phenyl)pentanoic acid | ![structure with 4-chlorophenyl] | 2.336 (Method O) | 447.2 |

Example 455

Enantiomer 1

(S)-3-(3-((2-Ethoxypyrimidin-5-yl)amino)-4-(ethyl(tetrahydro-2H-pyran-4-yl)amino)phenyl)pentanoic acid

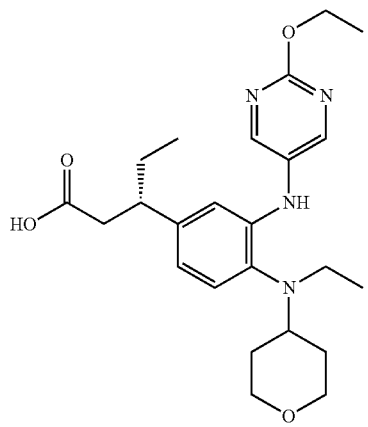 [SMILES: CCOc1ncc(Nc2cc([C@@H](CC)CC(=O)O)ccc2N(CC)C2CCOCC2)cn1]

455A. N-Ethyltetrahydro-2H-pyran-4-amine

To a stirred solution MeOH (100 mL) and THF (50 mL) containing 10 g of powdered and activated 4 Å molecular sieves was added sequentially dihydro-2H-pyran-4(3H)-one (9.22 mL, 100 mmol), 2M ethanamine in THF (49.9 mL, 100 mmol) and the reaction mixture was stirred for 6 h at room temperature. The reaction mixture was then cooled to 0° C., and NaBH$_4$ (11.34 g, 300 mmol) was added portionwise followed by stirring at room temperature for 6 h. The reaction mixture was then quenched with ice cold water (250 mL) and concentrated under reduced pressure to remove the volatiles.

Then the aqueous solution was extracted with ethyl acetate (3×100 mL). The combined organic layers were dried over sodium sulfate, filtered and concentrated under vacuum pressure to afford 455A (colorless liquid, 8 g, 61.9 mmol, 62.0% yield). $^1$H NMR (400 MHz, DMSO-d$_6$) δ 3.79-3.84 (m, 2H), 3.25-3.30 (m, 2H), 2.51-2.60 (m, 3H), 1.71-1.77 (m, 3H), 1.19-1.25 (m, 2H), 0.98-1.11 (m, 3H).

455B. N-(4-Bromo-2-nitrophenyl)-N-ethyltetrahydro-2H-pyran-4-amine

To a stirred solution of 4-bromo-1-fluoro-2-nitrobenzene (12 g, 54.5 mmol) in a sure seal bottle was added 455A (8.46 g, 65.5 mmol) followed by NMP (25 mL). The reaction mixture was sealed and heated at 120° C. for 16 h. The reaction mixture was then cooled to room temperature, diluted with water (200 mL) and extracted with ethyl acetate (2×200 mL). The combined organic layers were combined and washed with brine solution (1×75 mL), dried over sodium sulfate, filtered and concentrated under reduced pressure to give the crude product. The crude material was purified via silica gel flash chromatography gave 455B (pale orange solid, 10 g, 30.4 mmol, 55.7% yield). LCMS Anal. Calc'd. C$_{13}$H$_{17}$BrN$_2$O$_3$, 329.2, found [M+2H] 331.2, T$_r$=2.9 min (Method N).

455C. N-(4-(5,5-Dimethyl-1,3,2-dioxaborinan-2-yl)-2-nitrophenyl)-N-ethyltetrahydro-2H-pyran-4-amine A mixture of 455B (9 g, 27.3 mmol), bis(neopentyl glycolato)diboron (8.03 g, 35.5 mmol) and potassium acetate (8.05 g, 82 mmol) in DMSO (90 mL), at room temperature in a sealable flask, was purged with argon for 20 minutes. Then PdCl$_2$ (dppf).CH$_2$Cl$_2$ Adduct (0.670 g, 0.820 mmol) was added and the flask was sealed and the reaction heated at 80° C. for 6 h. Then the reaction mixture was cooled to room temperature and poured into water (250 mL), extracted with EtOAc (2×150 mL). The combined organic layers were washed with brine (1×150 mL), dried over anhydrous sodium sulfate, filtered and concentrated under reduced pressure. The crude material was purified via silica gel flash chromatography gave 455C (pale orange liquid, 9 g, 24.85 mmol, 91% yield). $^1$H NMR (400 MHz, DMSO-d$_6$) δ 7.88 (s, 1H), 7.78-7.81 (m, 1H), 7.41 (d, J=8.00 Hz, 1H), 3.83-3.86 (m, 2H), 3.76 (s, 4H), 3.19-3.27 (m, 3H), 3.11-3.17 (m, 2H), 1.58-1.63 (m, 4H), 0.96 (s, 6H), 0.88-0.85 (m, 3H).

455D. Methyl (S)-3-(4-(ethyl(tetrahydro-2H-pyran-4-yl)amino)-3-nitrophenyl)pentanoate (Enantiomer 1)

1,4-Dioxane (50 mL) was purged with argon for 10 minutes, then chlorobis(ethylene)rhodium(I)dimer (0.064 g, 0.166 mmol) and R-BINAP (0.151 g, 0.243 mmol) were added followed by purging with argon for 5 minutes. To the above reaction mixture was added 455C (4 g, 11.04 mmol), E-methyl pent-2-enoate (4.11 mL, 33.1 mmol), sodium hydroxide (9.94 mL, 9.94 mmol) and the mixture purged with argon for another 5 minutes. The reaction mixture was heated at 50° C. with stirring for 3 h. The reaction mixture was then cooled to room temperature and quenched with acetic acid (0.569 mL, 9.94 mmol) followed by partitioning between ethyl acetate (125 mL) and water (125 mL). The aqueous layer was extracted with ethyl acetate (100 mL) and the combined organic layers were washed with brine (75 mL), dried over sodium sulfate, filtered and concentrated under reduced pressure to give the crude product. Purification via silica gel flash chromatography gave 455D (pale orange solid, 2.35 g, 6.33 mmol, 57.3%). LC-MS Anal. Calc'd. for C$_{19}$H$_{28}$N$_2$O$_5$, 364.4, found [M+H] 365.2, T$_r$=3.2 min (Method N).

455E. Methyl (S)-3-(3-amino-4-(ethyl(tetrahydro-2H-pyran-4-yl)amino)phenyl)pentanoate A solution of 455D (10.2 g, 28.0 mmol) in ethyl acetate (150 mL) was charged to a sealable hydrogen flask. The flask was sequentially evacuated and purged with nitrogen gas. 10% palladium on carbon (1.02 g, 0.958 mmol) was then added under nitrogen atmosphere. The reaction mixture was stirred under a 40 psi hydrogen atmosphere at room temperature for 4 h. The reaction mixture was then filtered through a CELITE® pad and the residue on the pad was thoroughly rinsed with MeOH (3×15 mL). The combined filtrate was concentrated under reduced pressure. The enantiomeric mixture (90:10) were resolved via preparative SFC (Method AF) to yield 455E Enantiomer 1 (RT=3.39) as a the major product. The fractions were collected and concentrated under reduced pressure to afford 455E (pale red liquid, 6.75 g, 20.2 mmol, 72%). LC-MS Anal. Calc'd. for C$_{19}$H$_{30}$N$_2$O$_3$, 334.4, found [M+H] 335.4, T$_r$=2.9 min (Method N).

455F. Methyl (S)-3-(3-((2-ethoxypyrimidin-5-yl)amino)-4-(ethyl(tetrahydro-2H-pyran-4-yl)amino)phenyl)pentanoate To a stirred solution of 455E (60 mg, 0.179 mmol) in 1,4-dioxane (4 mL) was added 5-bromo-2-ethoxypyrimidine (364 mg, 1.794 mmol) and cesium carbonate (731 mg, 2.242 mmol) and the mixture purged with argon for 10 min. To the above reaction mixture was added 4,5-bis(diphenylphosphino)-9,9-dimethylxanthene (87 mg, 0.149 mmol), bis(dibenzylideneacetone)palladium (43.0 mg, 0.075 mmol) followed by purging with argon for another 10 min. Then the reaction temperature was raised to 110° C. and the mixture stirred for 3 h. The reaction mixture was then cooled to room temperature, concentrated to dryness and diluted with ethyl acetate (15 mL). The organic layer was washed with water (1×10 mL), brine (1×10 mL), dried over $Na_2SO_4$, filtered, concentrated under reduced pressure to afford the crude residue. The crude material was purified by flash silica column chromatography using 0-40% EtOAc in pet ether as an eluent to afford 455F (pale yellow liquid, 40 mg, 0.081 mmol, 45.4% yield). LC-MS Anal. Calc'd. for $C_{25}H_{36}N_4O_4$, 456.5, found [M+H] 457.3, $T_r$=3.9 min (Method N).

Example 455 Enantiomer 1. (S)-3-(3-((2-Ethoxypyrimidin-5-yl)amino)-4-(ethyl(tetrahydro-2H-pyran-4-yl)amino)phenyl)pentanoic acid To a stirred solution of 455F (40 mg, 0.088 mmol) in a mixture of THF (1 mL), MeOH (1 mL) and $H_2O$ (0.5 mL) was added LiOH (16.78 mg, 0.701 mmol). The resulting mixture was stirred at room temperature for 12 h. The reaction mixture was then concentrated and the resulting residue was diluted with water (15 mL), acidified with saturated citric acid solution and extracted with ethyl acetate (2×20 mL). The combined organic layers were dried over sodium sulfate, filtered and concentrated under reduced pressure. The crude material was purified via preparative LC/MS to give Example 455 Enantiomer 1 (pale yellow solid, 25 mg, 0.056 mmol 63.8%). Absolute stereochemistry was assigned based on the expected enantiomer produced in the conjugate addition using (R)-BINAP to prepare 455D. LC-MS Anal. Calc'd. for $C_{24}H_{34}N_4O_4$, 442.5, found [M+H] 443.6, $T_r$=2.11 min. (Method N). $^1$H NMR (400 MHz, $CD_3OD$) δ 8.43 (s, 2H), 7.17 (d, J=8.00 Hz, 1H), 6.84 (d, J=1.20 Hz, 1H), 6.74 (d, J=8.00 Hz, 1H), 4.38-4.43 (m, 2H), 3.90 (dd, J=10.80, 3.00 Hz, 2H), 3.36-3.38 (m, 2H), 3.04-3.09 (m, 3H), 2.86 (s, 1H), 2.57-2.62 (m, 1H), 2.47-2.51 (m, 1H), 1.77-1.80 (m, 2H), 1.67-1.69 (m, 1H), 1.54-1.55 (m, 3H), 1.39-1.43 (m, 3H), 0.91 (t, J=7.20 Hz, 3H), 0.80 (t, J=7.20 Hz, 3H).

Examples 456 to 486

Enantiomer 1

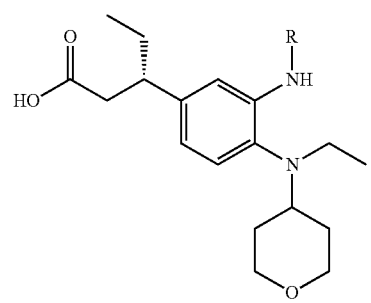

Examples 456 to 486 were prepared using 455E and corresponding aryl halides following the procedure described for the synthesis of Example 455 Enantiomer 1. Absolute stereochemistry was assigned based on the expected enantiomer produced in the conjugate addition using (R)-BINAP to prepare 455D.

| Ex. No. | Name | R | $T_r$ min | Method | (M + H) |
|---|---|---|---|---|---|
| 456 | (S)-3-(3-((4-chlorophenyl)amino)-4-(ethyl(tetrahydro-2H-pyran-4-yl)amino)phenyl)pentanoic acid | 4-chlorophenyl | 1.77 | O | 431.2 |
| 457 | (S)-3-(4-(ethyl(tetrahydro-2H-pyran-4-yl)amino)-3-((5-ethylpyrimidin-2-yl)amino)phenyl)pentanoic acid | 5-ethylpyrimidin-2-yl | 1.30 | R | 427.3 |
| 458 | (S)-3-(3-((4-cyanophenyl)amino)-4-(ethyl(tetrahydro-2H-pyran-4-yl)amino)phenyl)pentanoic acid | 4-cyanophenyl | 1.81 | O | 422.1 |

| Ex. No. | Name | R | T_r min | Method | (M + H) |
|---|---|---|---|---|---|
| 459 | (S)-3-(3-((2-(dimethylamino) pyrimidin-5-yl)amino)-4-(ethyl(tetrahydro-2H-pyran-4-yl)amino)phenyl)pentanoic acid | | 1.78 | O | 442.1 |
| 460 | (S)-3-(3-((5-chloropyridin-2-yl)amino)-4-(ethyl(tetrahydro-2H-pyran-4-yl)amino)phenyl)pentanoic acid | | 1.98 | O | 432.1 |
| 461 | (S)-3-(3-((5-cyanopyridin-2-yl)amino)-4-(ethyl(tetrahydro-2H-pyran-4-yl)amino)phenyl)pentanoic acid | | 1.69 | O | 423.1 |
| 462 | (S)-3-(4-(ethyl(tetrahydro-2H-pyran-4-yl)amino)-3-((5-methoxypyridin-2-yl)amino) phenyl)pentanoic acid | | 1.72 | O | 428.1 |
| 463 | (S)-3-(3-((6-(dimethylamino) pyridine-3-yl)amino)-4-(ethyl(tetrahydro-2H-pyran-4-yl)amino)phenyl)pentanoic acid | | 1.84 | O | 441.1 |
| 464 | (S)-3-(4-(ethyl(tetrahydro-2H-pyran-4-yl)amino)-3-((5-methoxypyrazin-2-yl)amino) phenyl)pentanoic acid | | 1.72 | O | 429.1 |
| 465 | (S)-3-(3-((5-ethoxypyrazin-2-yl)amino)-4-(ethyl(tetrahydro-2H-pyran-4-yl)amino)phenyl) pentanoic acid | | 1.88 | O | 443.1 |
| 466 | (S)-3-(3-((6-ethoxypyridin-3-yl)amino)-4-(ethyl(tetrahydro-2H-pyran-4-yl)amino)phenyl) pentanoic acid | | 1.93 | O | 442.1 |
| 467 | (S)-3-(3-((6-ethoxypyridazin-3-yl)amino)-4-(ethyl (tetrahydro-2H-pyran-4-yl) amino)phenyl)pentanoic acid | | 1.68 | O | 443.1 |

| Ex. No. | Name | R | $T_r$, min | Method | (M + H) |
|---|---|---|---|---|---|
| 468 | (S)-3-(4-(ethyl(tetrahydro-2H-pyran-4-yl)amino)-3-(pyrazolo[1,5-a]pyrimidin-5-ylamino)phenyl)pentanoic acid | 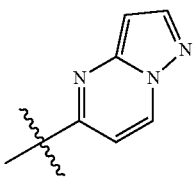 [SMILES: *c1ccn2nccc2n1] | 1.59 | O | 438 |
| 469 | (S)-3-(4-(ethyl(tetrahydro-2H-pyran-4-yl)amino)-3-((6-fluoro-2-methylpyrazolo[1,5-a]pyrimidin-5-yl)amino)phenyl)pentanoic acid | 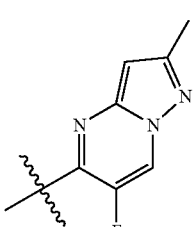 | 1.74 | O | 470 |
| 470 | (S)-3-(4-(ethyl(tetrahydro-2H-pyran-4-yl)amino)-3-((3-fluoro-2-methylpyrazolo[1,5-a]pyridine-5-yl)amino)phenyl)pentanoic acid | 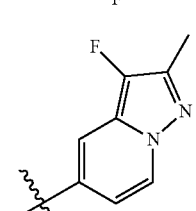 | 1.84 | O | 469 |
| 471 | (S)-3-(3-([1,2,4]triazolo[4,3-a]pyridine-6-ylamino)-4-(ethyl(tetrahydro-2H-pyran-4-yl)amino)phenyl)pentanoic acid | 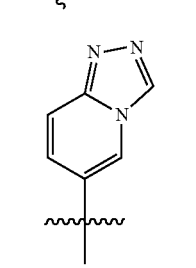 | 1.36 | O | 438 |
| 472 | (S)-3-(4-(ethyl(tetrahydro-2H-pyran-4-yl)amino)-3-(imidazo[1,2-a]pyrazin-3-ylamino)phenyl)pentanoic acid | 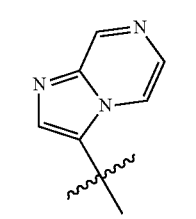 | 1.37 | O | 438 |
| 473 | (S)-3-(4-(ethyl(tetrahydro-2H-pyran-4-yl)amino)-3-((3-fluoro-2-methylpyrazolo[1,5-a]pyrimidin-5-yl)amino)phenyl)pentanoic acid | 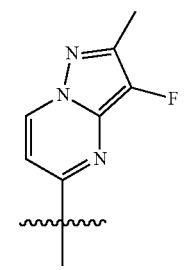 [SMILES: *c1ccn2nc(C)c(F)c2n1] | 1.52 | O | 470 |
| 474 | (S)-3-(3-((4-ethoxyphenyl)amino)-4-(ethyl(tetrahydro-2H-pyran-4-yl)amino)phenyl)pentanoic acid | 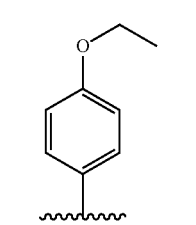 | 1.355 | R | 441.4 |

-continued

| Ex. No. | Name | R | $T_r$, min | Method | (M + H) |
|---|---|---|---|---|---|
| 475 | (S)-3-(4-(ethyl(tetrahydro-2H-pyran-4-yl)amino)-3-((4-(2,2,2-trifluoroethoxy)phenyl)amino)phenyl)pentanoic acid | 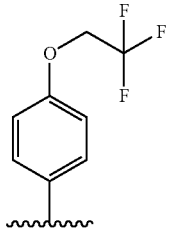 [SMILES: *c1ccc(OCC(F)(F)F)cc1] | 1.979 | O | 495.4 |
| 476 | (S)-3-(3-((4-(cyclopropylmethoxy)phenyl)amino)-4-(ethyl(tetrahydro-2H-pyran-4-yl)amino)phenyl)pentanoic acid | 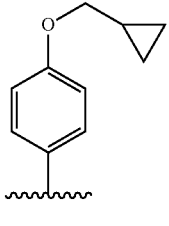 [SMILES: *c1ccc(OCC2CC2)cc1] | 1.501 | R | 467.4 |
| 477 | (S)-3-(4-(ethyl(tetrahydro-2H-pyran-4-yl)amino)-3-((4-ethylphenyl)amino)phenyl)pentanoic acid | 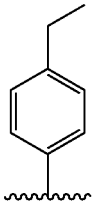 [SMILES: *c1ccc(CC)cc1] | 1.488 | R | 425.4 |
| 478 | (S)-3-(4-(ethyl(tetrahydro-2H-pyran-4-yl)amino)-3-((6-methoxypyridin-3-yl)amino)phenyl)pentanoic acid | 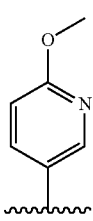 | 1.776 | O | 428.2 |
| 479 | (S)-3-(4-(ethyl(tetrahydro-2H-pyran-4-yl)amino)-3-((2-methoxypyrimidin-5-yl)amino)phenyl)pentanoic acid | 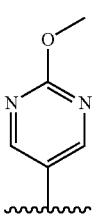 | 1.326 | R | 429.3 |
| 480 | (S)-3-(3-((2-(cyclopropylmethoxy)pyrimidin-5-yl)amino)-4-(ethyl(tetrahydro-2H-pyran-4-yl)amino)phenyl)pentanoic acid | 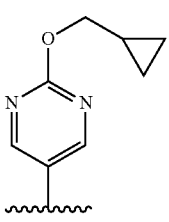 [SMILES: *c1cnc(OCC2CC2)nc1] | 1.661 | R | 469.3 |
| 481 | (S)-3-(3-((4-chloro-3-methoxyphenyl)amino)-4-(ethyl(tetrahydro-2H-pyran-4-yl)amino)phenyl)pentanoic acid | 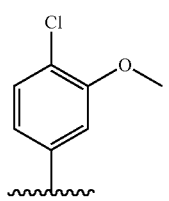 [SMILES: *c1ccc(Cl)c(OC)c1] | 1.706 | R | 461.3 |

-continued

| Ex. No. | Name | R | $T_r$, min | Method | (M + H) |
|---|---|---|---|---|---|
| 482 | (S)-3-(3-((5-ethoxypyridin-2-yl)amino)-4-(ethyl(tetrahydro-2H-pyran-4-yl)amino)phenyl)pentanoic acid | | 1.894 | O | 442.2 |
| 483 | (S)-3-(4-(ethyl(tetrahydro-2H-pyran-4-yl)amino)-3-(imidazo[1,2-a]pyrazin-6-ylamino)phenyl)pentanoic acid | | 1.098 | O | 438.3 |
| 484 | (S)-3-(4-(ethyl(tetrahydro-2H-pyran-4-yl)amino)-3-((2-methylbenzo[d]thiazol-6-yl)amino)phenyl)pentanoic acid | | 1.650 | O | 468.3 |
| 485 | (S)-3-(4-(ethyl(tetrahydro-2H-pyran-4-yl)amino)-3-((4-(ethylsulfonyl)phenyl)amino)phenyl)pentanoic acid | | 1.637 | O | 489.1 |
| 486 | (S)-3-(3-((2,3-dihydrobenzo[b][1,4]dioxin-6-yl)amino)-4-(ethyl(tetrahydro-2H-pyran-4-yl)amino)phenyl)pentanoic acid | | 1.75 | O | 455 |

Example 487

Enantiomer 1 and Enantiomer 2

3-(4-(Ethyl(tetrahydro-2H-pyran-4-yl)amino)-3-(3-(p-tolyl)ureido)phenyl)pentanoic acid

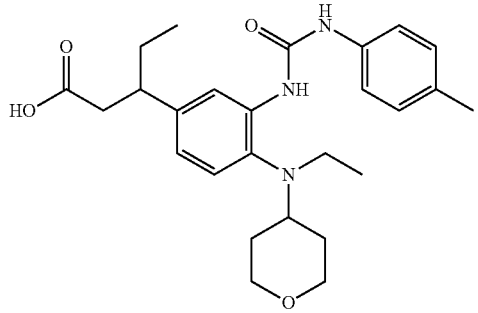 [SMILES: CCC(CC(=O)O)c1ccc(N(CC)C2CCOCC2)c(NC(=O)Nc2ccc(C)cc2)c1]

487A. Methyl 3-(4-(ethyl(tetrahydro-2H-pyran-4-yl)amino)-3-nitrophenyl)pentanoate (Racemate)

1,4-Dioxane (10 mL) was purged with argon for 10 minutes, then chloro(1,5-cyclooctadiene)rhodium(I) dimer (0.116 g, 0.235 mmol) was added and purging continued with argon for 5 minutes. 455C (1.7 g, 4.69 mmol), E-methyl pent-2-enoate (1.53 mL, 14.08 mmol) and sodium hydroxide (4.28 mL, 4.28 mmol) were added and the mixture purged argon for another 5 minutes. The reaction mixture was then heated at 50° C. and stirred for 3 h followed by cooling to room temperature. The reaction was then quenched with acetic acid (0.242 mL, 4.22 mmol) before it was partitioned between ethyl acetate (50 mL) and water (50 mL). Aqueous layer was extracted with ethyl acetate (100 mL) and the combined organic layers were washed with brine (50 mL), dried over sodium sulfate, filtered and concentrated under reduced pressure. Purification via flash chromatography gave 487A (pale orange liquid, 1 g, 2.74 mmol, 58.5%).

487B. Methyl 3-(3-amino-4-(ethyl(tetrahydro-2H-pyran-4-yl)amino)phenyl)pentanoate Compound 487B was prepared using compound 487A following the procedure described for the synthesis of 455E. LC-MS Anal. Calc'd. for $C_{19}H_{30}N_2O_3$, 334.4, found [M+H] 335.2, $T_r$=2.90 min. (Method N).

487C. Methyl 3-(3-(3-(4-chloro-2-fluorophenyl) ureido)-4-(ethyl(tetrahydro-2H-pyran-4-yl)amino) phenyl)pentanoate To a stirred solution of 487B (60 mg, 0.179 mmol) in THF (1.5 mL) was added 1-isocyanato-4-methylbenzene (28.7 mg, 0.215 mmol) under nitrogen. The reaction was stirred at room temperature for 3 h followed by concentration under reduced pressure to give 487C (pale yellow liquid, 63.8 mg, 0.136 mmol, 76%). LC-MS Anal. Calc'd. for $C_{27}H_{37}N_3O_4$, 467.6, found [M+H] 468.2, $T_r$=3.4 min. (Method U).

Example 487 Enantiomer 1 and Enantiomer 2. 3-(4-(Ethyl(tetrahydro-2H-pyran-4-yl)amino)-3-(3-(p-tolyl)ureido)phenyl)pentanoic acid Example 487 was prepared using compound 487C (racemate) following the hydrolysis procedure described for the synthesis of Example 455. LC-MS Anal. Calc'd. for $C_{26}H_{35}N_3O_4$, 453.2, found [M+H] 454.3, $T_r$=2.06 min. (Method N).

Chiral separation of racemate Example 487 gave 487 Enantiomer 1 and 487 Enantiomer 2 (Method BM). Enantiomer 1 $T_r$=2.41 min, Enantiomer 2 $T_r$=3.66 min (Method BM).

Example 487 Enantiomer 1 (absolute stereochemistry not determined). LC-MS Anal. Calc'd. for $C_{26}H_{35}N_3O_4$, 453.2, found [M+H] 454.3, $T_r$=1.54 min. (Method N). $^1$H NMR (400 MHz, DMSO-$d_6$) δ 8.49 (s, 1H), 8.08 (d, J=2.00 Hz, 1H), 7.37 (d, J=8.4 Hz, 2H), 7.13 (d, J=8.0 Hz, 1H), 7.08 (d, J=8.4 Hz, 2H), 6.78 (dd, J=8.0, 2.00 Hz, 1H), 3.81 (d, J=2.80 Hz, 2H), 3.28-3.43 (m, 3H), 3.20-3.26 (m, 3H), 2.97 (d, J=7.20 Hz, 3H), 2.67-2.71 (m, 1H), 2.39-2.41 (m, 1H), 2.24 (s, 3H), 1.64-1.71 (m, 2H), 1.36-1.40 (m, 2H), 0.78 (t, J=7.2 Hz, 3H), 0.69-0.71 (t, J=7.2 Hz, 3H).

Example 487 Enantiomer 2 (absolute stereochemistry not determined). LC-MS Anal. Calc'd. for $C_{26}H_{35}N_3O_4$, 453.2, found [M+H] 454.3, $T_r$=1.54 min. (Method N). $^1$H NMR (400 MHz, DMSO-$d_6$) δ 8.49 (s, 1H), 8.08 (d, J=2.00 Hz, 1H), 7.37 (d, J=8.4 Hz, 2H), 7.13 (d, J=8.0 Hz, 1H), 7.08 (d, J=8.4 Hz, 2H), 6.78 (dd, J=8.0, 2.00 Hz, 1H), 3.81 (d, J=2.80 Hz, 2H), 3.28-3.43 (m, 3H), 3.20-3.26 (m, 3H), 2.97 (d, J=7.20 Hz, 3H), 2.67-2.71 (m, 1H), 2.39-2.41 (m, 1H), 2.24 (s, 3H), 1.64-1.71 (m, 2H), 1.36-1.40 (m, 2H), 0.78 (t, J=7.2 Hz, 3H), 0.69-0.71 (t, J=7.2 Hz, 3H).

Example 488

Enantiomer 1 and Enantiomer 2

3-(4-(Ethyl(tetrahydro-2H-pyran-4-yl)amino)-3-(3-(2-methylpyrimidin-5-yl)ureido)phenyl)pentanoic acid

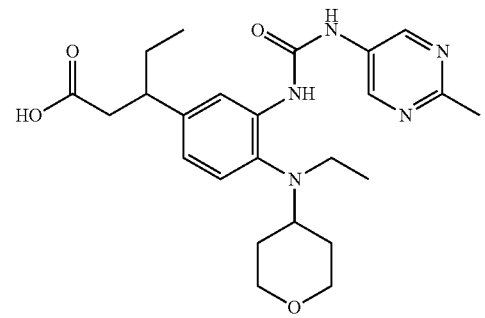 [SMILES: CCC(CC(=O)O)c1ccc(N(CC)C2CCOCC2)c(NC(=O)Nc2cnc(C)nc2)c1]

488A. Methyl 3-(4-(ethyl(tetrahydro-2H-pyran-4-yl) amino)-3-(((4-nitrophenoxy)carbonyl)amino)phenyl) pentanoate To a stirred solution of 487B (120 mg, 0.359 mmol) in THF (6 mL) was added 4-nitrophenyl carbonochloridate (72.3 mg, 0.359 mmol). The reaction was stirred at room temperature for 2 h. The reaction mixture was then concentrated and the residue was partitioned between ethyl acetate (2×50 mL) and water (50 mL). The combined organic layers were dried over sodium sulfate, filtered and concentrated under reduced pressure gave 488A. LC-MS Anal. Calc'd. for $C_{26}H_{33}N_3O_7$ 499.5 found [M+H] 500.6, $T_r$=1.08 min. (Method AA).

488B. Methyl 3-(4-(ethyl(tetrahydro-2H-pyran-4-yl) amino)-3-(3-(2-methylpyrimidin-5-yl)ureido)phenyl) pentanoate To a solution of 488A (140 mg, 0.280 mmol) in THF (6 mL) was added pyridine (0.057 mL, 0.701 mmol) and a catalytic amount of DMAP (3.42 mg, 0.028 mmol). To the above reaction mixture 2-methylpyrimidin-5-amine (36.7 mg, 0.336 mmol) was added and stirred at 60° C. for 4 h. The reaction mixture was concentrated and the residue was portioned between ethyl acetate (2×50 mL) and water (50 mL). The combined organic layers were dried over sodium sulfate, filtered and concentrated under reduced pressure. The residue was purified by flash silica column chromatography using 0-40% EtOAc in pet ether as an eluent to afford 488B (pale yellow liquid, 100 mg, 0.213 mmol, 76% yield). LC-MS Anal. Calc'd. for $C_{25}H_{35}N_5O_4$, 469.5, found [M+H] 470.2, $T_r$=2.59 min (Method N).

Example 488 Enantiomer 1 and Enantiomer 2. 3-(4-(Ethyl(tetrahydro-2H-pyran-4-yl)amino)-3-(3-(2-methylpyrimidin-5-yl)ureido)phenyl)pentanoic acid Example 488 was prepared using compound 488B (racemate) following the hydrolysis procedure described for the synthesis of Example 455. LC-MS Anal. Calc'd. for $C_{24}H_{33}N_5O_4$, 455.5, found [M+H] 456.3, $T_r$=1.16 min. (Method O).

Chiral separation of Example 488 racemate gave Example 488 Enantiomer 1 and Example 488 Enantiomer 2 (Method CN). Enantiomer 1 $T_r$=7.4 min, Enantiomer 2 $T_r$=9.1 min (Method CN).

Example 488 Enantiomer 1 (absolute stereochemistry not determined). LC-MS Anal. Calc'd. for $C_{24}H_{33}N_5O_4$, 455.5, found [M+H] 456.3, $T_r$=1.18 min. (Method O). $^1$H NMR (400 MHz, DMSO-$d_6$) δ 9.86 (s, 1H), 8.82 (s, 2H), 8.17 (s, 1H), 8.09 (d, J=2.00 Hz, 1H), 7.18 (d, J=8.00 Hz, 1H), 6.84 (dd, J=8.00, 2.00 Hz, 1H), 3.83 (t, J=2.80 Hz, 2H), 3.22-3.28 (m, 3H), 2.99-3.01 (m, 3H), 2.96-2.97 (m, 1H), 2.56 (s, 3H), 2.42-2.44 (m, 1H), 1.70-1.73 (m, 2H), 1.41-1.42 (m, 2H), 0.95 (d, J=6.40 Hz, 2H), 0.80 (t, J=7.20 Hz, 3H), 0.72 (t, J=7.20 Hz, 3H).

Example 488 Enantiomer 2 (absolute stereochemistry not determined). LC-MS Anal. Calc'd. for $C_{24}H_{33}N_5O_4$, 455.5, found [M+H] 456.3, $T_r$=1.18 min. (Method O). $^1$H NMR (400 MHz, DMSO-$d_6$) δ 9.86 (s, 1H), 8.82 (s, 2H), 8.17 (s, 1H), 8.09 (d, J=2.00 Hz, 1H), 7.18 (d, J=8.00 Hz, 1H), 6.84 (dd, J=8.00, 2.00 Hz, 1H), 3.83 (t, J=2.80 Hz, 2H), 3.22-3.28 (m, 3H), 2.99-3.01 (m, 3H), 2.96-2.97 (m, 1H), 2.56 (s, 3H), 2.42-2.44 (m, 1H), 1.70-1.73 (m, 2H), 1.41-1.42 (m, 2H), 0.95 (d, J=6.40 Hz, 2H), 0.80 (t, J=7.20 Hz, 3H), 0.72 (t, J=7.20 Hz, 3H).

Examples 489 to 497

Enantiomer 1

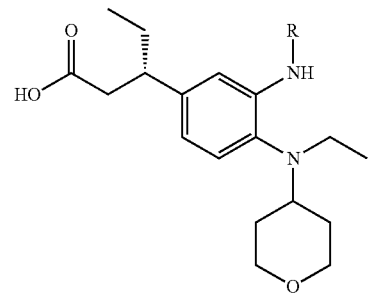

Examples 489 to 495 were prepared using 455E instead of 487B and the corresponding isocyanates following the procedure described for the synthesis of Example 487.

Examples 496 and 497 were prepared by using 455E instead of 487B and the corresponding amines (as in step 488B) following the procedure described for the synthesis of Example 488.

| Ex. No. | Name | R | $T_r$ min | Method | (M + H) |
|---|---|---|---|---|---|
| 489 | (S)-3-(3-(4-chloro-2-fluorophenyl)ureido)-4-(ethyl(tetrahydro-2H-pyran-4-yl)amino)phenyl)pentanoic acid | | 1.653 | O | 492.3 |
| 490 | (S)-3-(4-(ethyl(tetrahydro-2H-pyran-4-yl)amino)-3-(3-(4-fluorophenyl)ureido)phenyl)pentanoic acid | | 1.332 | R | 458.3 |
| 491 | (S)-3-(3-(3-(4-ethoxyphenyl)ureido)-4-pyran-4-yl)amino)phenyl)pentanoic acid | | 1.418 | R | 484.4 |
| 492 | (S)-3-(4-(ethyl(tetrahydro-2H-pyran-4-yl)amino)-3-(3-(4-methoxyphenyl)ureido)phenyl)pentanoic acid | | 1.288 | R | 470.4 |
| 493 | (S)-3-(4-(ethyl(tetrahydro-2H-pyran-4-yl)amino)-3-(3-(2-fluoro-4-methoxyphenyl)ureido)phenyl)pentanoic acid | | 1.411 | O | 488.4 |
| 494 | (S)-3-(3-(3-(4-chlorophenyl)ureido)-4-(ethyl(tetrahydro-2H-pyran-4-yl)amino)phenyl)pentanoic acid | | 1.787 | R | 474.2 |

-continued

| Ex. No. | Name | R | $T_r$, min | Method | (M + H) |
|---|---|---|---|---|---|
| 495 | (S)-3-(3-(3-(6-chloropyridin-3-yl)ureido)-4-(ethyl(tetrahydro-2H-pyran-4-yl)amino)phenyl)pentanoic acid | | 1.649 | O | 475.2 |
| 496 | (S)-3-(3-(3-(2,2-dioxido-1,3-dihydrobenzo[c]thiophen-5-yl)ureido)-4-(ethyl(tetrahydro-2H-pyran-4-yl)amino)phenyl)pentanoic acid | | 1.417 | R | 530.2 |
| 497 | (S)-3-(4-(ethyl(tetrahydro-2H-pyran-4-yl)amino)-3-(3-(5-methylisoxazol-3-yl)ureido)phenyl)pentanoic acid | | 1.260 | R | 445.3 |

Example 498

Enantiomer 2

(R)-3-(3-((2-Ethoxypyrimidin-5-yl)amino)-4-(ethyl(tetrahydro-2H-pyran-4-yl)amino)phenyl)pentanoic acid

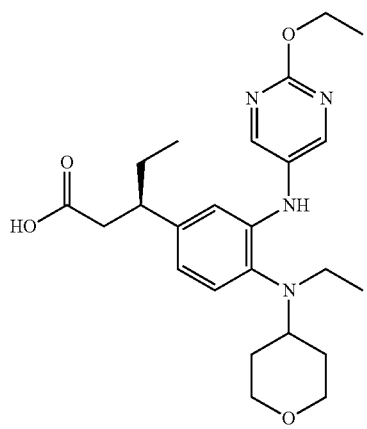 [SMILES: CCOc1ncc(Nc2cc([C@H](CC)CC(=O)O)ccc2N(CC)C2CCOCC2)cn1]

498A. Methyl (R)-3-(4-(ethyl(tetrahydro-2H-pyran-4-yl)amino)-3-nitrophenyl)pentanoate Compound 498A was prepared utilizing S-BINAP and 455C following the procedure described for the synthesis of 455D. LC-MS Anal. Calc'd. for $C_{19}H_{28}N_2O_5$, 364.4, found [M+H] 365.2, $T_r$=3.16 min. (Method N).

498B. Methyl (R)-3-(3-amino-4-(ethyl(tetrahydro-2H-pyran-4-yl)amino)phenyl)pentanoate Compound 498B was prepared using compound 498A following the procedure described for the synthesis of 455E. SFC chiral purity shows 94.7% ee ($T_r$=4.86 min. (Method AF). LC-MS Anal. Calc'd. for $C_{19}H_{30}N_2O_3$, 334.4, found [M+H] 335.2, $T_r$=2.90 min. (Method N).

498C. Methyl (R)-3-(3-((2-ethoxypyrimidin-5-yl)amino)-4-(ethyl(tetrahydro-2H-pyran-4-yl)amino)phenyl)pentanoate Compound 498C was prepared using compound 498B and 5-bromo-2-ethoxy-pyrimidine following the procedure described for the synthesis of 455F. LC-MS Anal. Calc'd. for $C_{25}H_{36}N_4O_4$, 456.5, found [M+H] 457.3, $T_r$=3.9 min (Method N).

Example 498. (R)-3-(3-((2-Ethoxypyrimidin-5-yl)amino)-4-(ethyl(tetrahydro-2H-pyran-4-yl)amino)phenyl)pentanoic acid Example 498 was prepared using compound 498C following the procedure described for the synthesis of Example 455 Enantiomer 1. Absolute stereochemistry of Example 498 was assigned based on the expected enantiomer produced in the conjugate addition using (S)-BINAP to prepare 498A. LC-MS Anal. Calc'd. for $C_{24}H_{34}N_4O_4$ 442.5, found [M+H] 443.6, $T_r$=2.13 min. (Method N). $^1$H NMR (400 MHz, CD$_3$OD) δ 8.43 (s, 2H), 7.17 (d, J=8.00 Hz, 1H), 6.84 (d, J=1.20 Hz, 1H), 6.74 (d, J=8.00 Hz, 1H), 4.38-4.43 (m, 2H), 3.90 (dd, J=10.80, 3.00 Hz, 2H), 3.36-3.38 (m, 2H), 3.04-3.09 (m, 3H), 2.86 (s, 1H), 2.57-2.62 (m, 1H), 2.47-2.51 (m, 1H), 1.77-1.80 (m, 2H), 1.67-1.69 (m, 1H), 1.54-1.55 (m, 3H), 1.39-1.43 (m, 3H), 0.91 (t, J=7.20 Hz, 3H), 0.80 (t, J=7.20 Hz, 3H).

Examples 499 to 525

Enantiomer 2

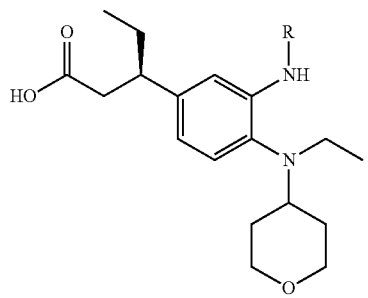

Examples 499 to 525 were prepared using 498B and corresponding aryl halides (as in step 498C) following the procedure described for the synthesis of Example 498 Enantiomer 2.

| Ex. No. | Name | R | $T_r$, min | Method | (M + H) |
|---|---|---|---|---|---|
| 499 | (R)-3-(3-((4-chlorophenyl)amino)-4-(ethyl(tetrahydro-2H-pyran-4-yl)amino)phenyl)pentanoic acid | 4-chlorophenyl | 2.1 | O | 431.2 |
| 500 | (R)-3-(4-(ethyl(tetrahydro-2H-pyran-4-yl)amino)-3-((5-ethylpyrimidin-2-yl)amino)phenyl)pentanoic acid | 5-ethylpyrimidin-2-yl | 1.84 | O | 427.3 |
| 501 | (R)-3-(3-((4-cyanophenyl)amino)-4-(ethyl(tetrahydro-2H-pyran-4-yl)amino)phenyl)pentanoic acid | 4-cyanophenyl | 1.81 | O | 422.1 |
| 502 | (R)-3-(3-((2-(dimethylamino)pyrimidin-5-yl)amino)-4-(ethyl(tetrahydro-2H-pyran-4-yl)amino)phenyl)pentanoic acid | 2-(dimethylamino)pyrimidin-5-yl | 1.79 | O | 442.1 |
| 503 | (R)-3-(3-((5-chloropyridin-2-yl)amino)-4-(ethyl(tetrahydro-2H-pyran-4-yl)amino)phenyl)pentanoic acid | 5-chloropyridin-2-yl | 1.98 | O | 432.1 |
| 504 | (R)-3-(3-((5-cyanpyridin-2-yl)amino)-4-(ethyl(tetrahydro-2H-pyran-4-yl)amino)phenyl)pentanoic acid | 5-cyanopyridin-2-yl | 1.70 | O | 423.1 |

-continued

| Ex. No. | Name | R | T, min | Method | (M + H) |
|---|---|---|---|---|---|
| 505 | (R)-3-(4-(ethyl(tetrahydro-2H-pyran-4-yl)amino)-3-((5-methoxypyridin-2-yl)amino)phenyl)pentanoic acid | | 1.70 | O | 428.1 |
| 506 | (R)-3-(3-((6-(dimethylamino)pyridin-3-yl)amino)-4-(ethyl(tetrahydro-2H-pyran-4-yl)amino)phenyl)pentanoic acid | | 1.81 | O | 441.2 |
| 507 | (R)-3-(4-(ethyl(tetrahydro-2H-pyran-4-yl)amino)-3-((5-methoxypyrazin-2-yl)amino)phenyl)pentanoic acid | | 1.72 | O | 429.1 |
| 508 | (R)-3-(3-((5-ethoxypyrazin-2-yl)amino)-4-(ethyl(tetrahydro-2H-pyran-4-yl)amino)phenyl)pentanoic acid | | 1.87 | O | 443.1 |
| 509 | (R)-3-(3-((6-ethoxypyridin-3-yl)amino)-4-(ethyl(tetrahydro-2H-pyran-4-yl)amino)phenyl)pentanoic acid | | 1.92 | O | 442.1 |
| 510 | (R)-3-(3-((6-ethoxypyridazin-3-yl)amino)-4-(ethyl(tetrahydro-2H-pyran-4-yl)amino)phenyl)pentanoic acid | | 1.69 | O | 443.1 |
| 511 | (R)-3-(4-(ethyl(tetrahydro-2H-pyran-4-yl)amino)-3-(pyrazolo[1,5-a]pyrimidin-5-ylamino)phenyl)pentanoic acid | | 1.48 | O | 438 |
| 512 | (R)-3-(3-([1,2,4]triazolo[4,3-a]pyridin-6-ylamino)-4-(ethyl(tetrahydro-2H-pyran-4-yl)amino)phenyl)pentanoic acid | | 1.15 | O | 438 |

-continued

| Ex. No. | Name | R | T$_r$ min | Method | (M + H) |
|---|---|---|---|---|---|
| 513 | (R)-3-(4-(ethyl(tetrahydro-2H-pyran-4-yl)amino)-3-((3-fluoro-2-methylpyrazolo[1,5-a]pyridin-5-yl)amino)phenyl)pentanoic acid | | 1.85 | O | 469 |
| 514 | (R)-3-((4-ethoxyphenyl)amino)-4-(ethyl(tetrahydro-2H-pyran-4-yl)amino)phenyl)pentanoic acid | | 1.35 | R | 441.4 |
| 515 | (R)-3-(4-(ethyl(tetrahydro-2H-pyran-4-yl)amino)-3-((4-(2,2,2-trifluoroethoxy)phenyl)amino)phenyl)pentanoic acid | | 1.480 | R | 495.4 |
| 516 | (R)-3-(3-((4-(cyclopropylmethoxy)phenyl)amino)-4-(ethyl(tetrahydro-2H-pyran-4-yl)amino)phenyl)pentanoic acid | | 1.483 | R | 467.4 |
| 517 | (R)-3-(4-(ethyl(tetrahydro-2H-pyran-4-yl)amino)-3-((4-ethylphenyl)amino)phenyl)pentanoic acid | | 2.068 | O | 425.4 |
| 518 | (R)-3-(4-(ethyl(tetrahydro-2H-pyran-4-yl)amino)-3-((6-methoxypyridin-3-yl)amino)phenyl)pentanoic acid | | 1.331 | R | 428.2 |
| 519 | (R)-3-(4-(ethyl(tetrahydro-2H-pyran-4-yl)amino)-3-((2-methoxypyrimidin-5-yl)amino)phenyl)pentanoic acid | | 1.294 | O | 429.3 |

-continued

| Ex. No. | Name | R | $T_r$ min | Method | (M + H) |
|---|---|---|---|---|---|
| 520 | (R)-3-(3-((2-(cyclopropylmethoxy)pyrimidin-5-yl)amino)-4-(ethyl(tetrahydro-2H-pyran-4-yl)amino)phenyl)pentanoic acid | 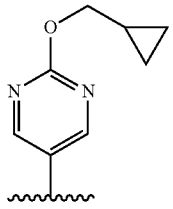 [SMILES: *c1cnc(OCC2CC2)nc1] | 1.867 | O | 469.3 |
| 521 | (R)-3-(3-((4-chloro-3-methoxyphenyl)amino)-4-(ethyl(tetrahydro-2H-pyran-4-yl)amino)phenyl)pentanoic acid | 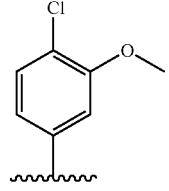 [SMILES: *c1ccc(Cl)c(OC)c1] | 1.668 | O | 461.3 |
| 522 | (R)-3-(3-((5-ethoxypyridin-2-yl)amino)-4-(ethyl(tetrahydro-2H-pyran-4-yl)amino)phenyl)pentanoic acid | 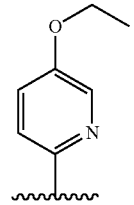 [SMILES: *c1ccc(OCC)cn1] | 1.822 | O | 442.2 |
| 523 | (R)-3-(4-(ethyl(tetrahydro-2H-pyran-4-yl)amino)-3-(imidazo[1,2-a]pyrazin-6-ylamino)phenyl)pentanoic acid | 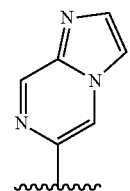 | 1.098 | O | 438.3 |
| 524 | (R)-3-(4-(ethyl(tetrahydro-2H-pyran-4-yl)amino)-3-((2-methylbenzo[d]thiazol-6-yl)amino)phenyl)pentanoic acid | 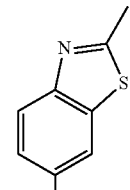 | 1.177 | R | 468.3 |
| 525 | (R)-3-(4-(ethyl(tetrahydro-2H-pyran-4-yl)amino)-3-((4-(ethylsulfonyl)phenyl)amino)phenyl)pentanoic acid | 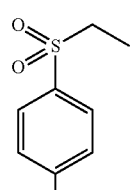 | 1.637 | O | 489.1 |

Examples 526 to 534

Enantiomer 2

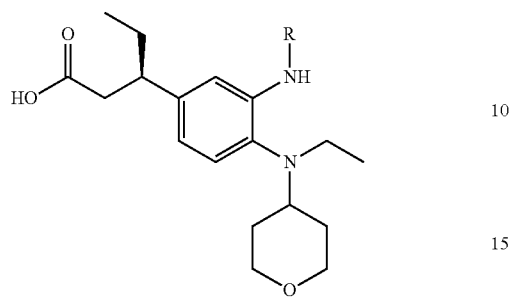

Examples 526 to 532 were prepared using 498B (instead of 487B) and corresponding isocyanates following the procedure described for the synthesis of Example 487.

Examples 533 and 534 were prepared using 498B (instead of 487B) and corresponding amines (as in step 488B) following the procedure described for the synthesis of Example 488.

| Ex. No. | Name | R | $T_r$ min | Method | (M + H) |
|---|---|---|---|---|---|
| 526 | (R)-3-(3-(3-(4-chloro-2-fluorophenyl)ureido)-4-(ethyl(tetrahydro-2H-pyran-4-yl)amino)phenyl) pentanoic acid | | 1.527 | R | 492.3 |
| 527 | (R)-3-(4-(ethyl (tetrahydro-2H-pyran-4-yl)amino)-3-(3-(4-fluorophenyl)ureido) phenyl)pentanoic acid | | 1.473 | O | 458.3 |
| 528 | (R)-3-(3-(3-(4-ethoxyphenyl)ureido)-4-(ethyl(tetrahydro-2H-pyran-4-yl)amino)phenyl) pentanoic acid | | 1.414 | R | 484.4 |
| 529 | (R)-3-(4-(ethyl (tetrahydro-2H-pyran-4-yl)amino)-3-(3-(4-methoxyphenyl)ureido) phenyl)pentanoic acid | | 1.278 | R | 470.4 |
| 530 | (R)-3-(4-(ethyl (tetrahydro-2H-pyran-4-yl)amino)-3-(3-(2-fluoro-4-methoxyphenyl)ureido) phenyl)pentanoic acid | | 1.396 | O | 488.4 |
| 531 | (R)-3-(3-(3-(4-chlorophenyl)ureido)-4-(ethyl(tetrahydro-2H-pyran-4-yl)amino)phenyl) pentanoic acid | | 1.814 | O | 474.2 |

-continued

| Ex. No. | Name | R | $T_r$ min | Method | (M + H) |
|---|---|---|---|---|---|
| 532 | (R)-3-(3-(3-(6-chloropyridin-3-yl)ureido)-4-(ethyl (tetrahydro-2H-pyran-4-yl)amino)phenyl) pentanoic acid | | 1.569 | O | 475.2 |
| 533 | (R)-3-(3-(3-(2,2-dioxido-1,3-dihydrobenzo[c] thiophen-5-yl)ureido)-4-(ethyl(tetrahydro-2H-pyran-4-yl)amino)phenyl) pentanoic acid | | 1.441 | R | 530.2 |
| 534 | (R)-3-(4-(ethyl (tetrahydro-2H-pyran-4-yl)amino)-3-(3-(5-methyl-isoxazol-3-yl)ureido) phenyl) pentanoic acid | | 1.287 | R | 445.3 |

Example 535

Enantiomer 1

(S)-3-(3-((2-Ethoxypyrimidin-5-yl)amino)-4-(propyl (tetrahydro-2H-pyran-4-yl)amino)phenyl)pentanoic acid

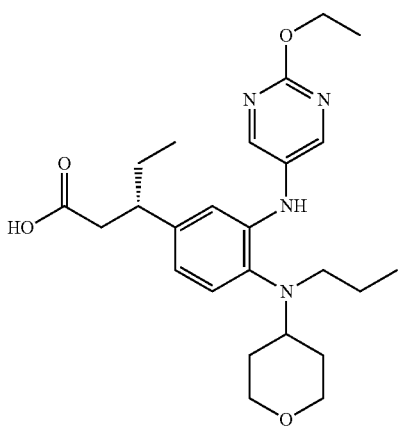 [SMILES: CCCN(c1ccc([C@@H](CC)CC(=O)O)cc1Nc1cnc(OCC)nc1)C1CCOCC1]

535A. N-Propyltetrahydro-2H-pyran-4-amine

To a solution of MeOH (100 mL) and THF (100 mL) containing 10 g of powdered and activated 4 A molecular sieves, was added sequentially propan-1-amine (9.07 mL, 110 mmol), and dihydro-2H-pyran-4(3H)-one (9.22 mL, 100 mmol). Then the reaction mixture was stirred for 6 h at room temperature. The reaction mixture was then cooled to 0° C., NaBH$_4$ (11.34 g, 300 mmol) was then added portionwise and the resulting mixture was stirred at RT for 6 h. The reaction mixture was then quenched with ice cold water (250 mL) and concentrated under reduced pressure. Then the aqueous solution was then extracted with ethyl acetate (2×250 mL). The combined organic layers were dried over sodium sulfate, filtered and concentrated under reduced pressure to afford 535A (pale yellow liquid, (10 g, 69.8 mmol, 69.9% yield). LC-MS Anal. Calc'd. for $C_8H_{17}NO$, 143.2, found [M+H] 144.4, $T_r$=0.46 min. (Method N).

535B. N-(4-Bromo-2-nitrophenyl)-N-propyltetrahydro-2H-pyran-4-amine 535B was prepared utilizing 535A and 5-bromo-2-fluoro-1-nitro benzene following the procedure described for the synthesis of 455B. LC-MS Anal. Calc'd. for $C_{14}H_{19}BrN_2O_3$, 343.2, found [M−H] 344.4, $T_r$=3.34 min. (Method N).

535C. N-(4-(5,5-Dimethyl-1,3,2-dioxaborinan-2-yl)-2-nitrophenyl)-N-propyltetrahydro-2H-pyran-4-amine Compound 535C was prepared utilizing compound 535B following the procedure described for the synthesis of 455C. $^1$H NMR (400 MHz, DMSO-d$_6$) δ 7.88 (d, J=2.00 Hz, 1H), 7.76 (dd, J=10.80, 1.80 Hz, 1H), 7.38 (d, J=11.20 Hz, 1H), 3.99-4.04 (m, 2H), 3.47 (s, 4H), 3.13-3.26 (m, 3H), 3.05-3.09 (m, 2H), 1.56-1.68 (m, 4H), 1.22-1.30 (m, 2H), 0.95 (s, 6H), 0.75-0.80 (m, 3H).

535D. Methyl (S)-3-(3-nitro-4-(propyl(tetrahydro-2H-pyran-4-yl)amino)phenyl)pentanoate 535D was prepared utilizing compound 535C and R-BINAP following the procedure described for the synthesis of 455D. LC-MS Anal. Calc'd. for $C_{20}H_{30}N_2O_5$, 378.4, found [M+H] 379.6, $T_r$=3.92 min. (Method N).

535E. Methyl (S)-3-(3-amino-4-(propyl(tetrahydro-2H-pyran-4-yl)amino)phenyl)pentanoate 535E was prepared utilizing compound 535D following the procedure described for the synthesis of 455E Enantiomer 1. SFC chiral purity shows 100% ee ($T_r$=2.55 Min) (Method AF) of 535E Enantiomer 1. LC-MS Anal. Calc'd. for $C_{20}H_{32}N_2O_3$, 348.4, found [M+H] 349.6, $T_r$=3.92 min. (Method N).

535F. Methyl (S)-3-(3-((2-ethoxypyrimidin-5-yl)amino)-4-(propyl(tetrahydro-2H-pyran-4-yl)amino)phenyl)pentanoate 535F was prepared utilizing compound 535E and 5-bromo-2-ethoxy-pyrimidine following the procedure described for the synthesis of 455F. LC-MS Anal. Calc'd. for $C_{26}H_{38}N_4O_4$, 470.6, found [M+H] 471.2, $T_r$=3.72 min. (Method N).

Example 535 Enantiomer 1. (S)-3-(3-((2-Ethoxypyrimidin-5-yl)amino)-4-(propyl(tetrahydro-2H-pyran-4-yl)amino)phenyl)pentanoic acid Example 535 was prepared utilizing compound 535F following the procedure described for the synthesis of Example 455. LC-MS Anal. Calc'd. for $C_{25}H_{36}N_4O_4$ 456.5, found [M+H] 457.3, $T_r$=1.79 min. (Method O). $^1$H NMR (400 MHz, DMSO-$d_6$) δ 8.41 (s, 2H), 7.24 (s, 1H), 7.12 (d, J=8.00 Hz, 1H), 6.81 (s, 1H), 6.67 (d, J=7.60 Hz, 1H), 4.29 (dd, J=14.00, 7.00 Hz, 2H), 3.81 (d, J=8.00 Hz, 2H), 3.16-3.20 (m, 2H), 2.87-2.91 (m, 3H), 2.76-2.77 (m, 1H), 2.41-2.43 (m, 1H), 1.67 (d, J=12.40 Hz, 2H), 1.58-1.61 (m, 1H), 1.45-1.47 (m, 3H), 1.32 (t, J=7.20 Hz, 3H), 1.21-1.23 (m, 2H), 0.77 (t, J=7.20 Hz, 3H), 0.70 (t, J=7.60 Hz, 3H) (Note: one multiplet of CH is buried under the solvent peak).

Examples 536 to 543

Enantiomer 1

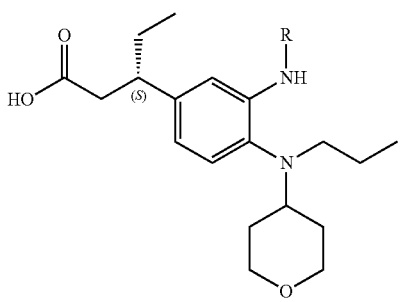

Examples 536 to 543 were prepared using 535E and corresponding aryl halides (as in Step 535F) following the procedure described for the synthesis of Example 535.

| Ex. No. | Name | R | $T_r$ min | Method | (M + H) |
|---|---|---|---|---|---|
| 536 | (S)-3-(3-((4-cyanophenyl)amino)-4-(propyl(tetrahydro-2H-pyran-4-yl)amino)phenyl) pentanoic acid | CN | 1.91 | O | 436.3 |
| 537 | (S)-3-(3-((2-methylbenzo[d]thiazol-6-yl)amino)-4-(propyl(tetrahydro-2H-pyran-4-yl)amino)phenyl) pentanoic acid | | 1.98 | O | 482.3 |
| 538 | (S)-3-(3-((4-fluorophenyl)amino)-4-(propyl(tetrahydro-2H-pyran-4-yl)amino)phenyl) pentanoic acid | F | 2.16 | O | 429.2 |
| 539 | (S)-3-(3-((2,2-difluorobenzo[d][1,3]dioxol-5-yl)amino)-4-(propyl(tetrahydro-2H-pyran-4-yl)amino)phenyl)pentanoic acid | | 2.37 | O | 491.2 |
| 540 | (S)-3-(3-((2-methoxypyrimidin-5-yl)amino)-4-(propyl(tetrahydro-2H-pyran-4-yl)amino)phenyl) pentanoic acid | | 1.7 | O | 443.3 |
| 541 | (S)-3-(3-((4-chlorophenyl)amino)-4-(propyl(tetrahydro-2H-pyran-4-yl)amino)phenyl) pentanoic acid | Cl | 2.39 | O | 445.2 |
| 542 | (S)-3-(3-((6-methoxypyridin-3-yl)amino)-4-(propyl(tetrahydro-2H-pyran-4-yl)amino)phenyl) pentanoic acid | | 1.94 | O | 442.3 |
| 543 | (S)-3-(3-((2-(cyclopropylmethoxy)pyrimidin-5-yl)amino)-4-(propyl(tetrahydro-2H-pyran-4-yl)amino)phenyl)-4-methoxybutanoic acid | | 1.52 | O | 499.4 |

Example 544

Enantiomer 1

(S)-3-(3-(3-(4-Chloro-2-fluorophenyl)ureido)-4-(propyl(tetrahydro-2H-pyran-4-yl)amino)phenyl)pentanoic acid

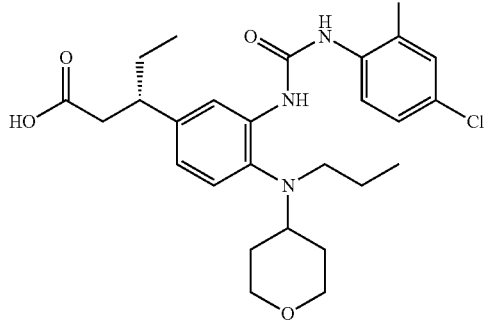

544A. Methyl 3-(3-(3-(4-chloro-2-fluorophenyl)ureido)-4-(propyl(tetrahydro-2H-pyran-4-yl)amino)phenyl)pentanoate 544A was prepared using compound 535E Enantiomer 1 and 4-chloro-2-fluoro-1-isocyanatobenzene following the procedure described for the synthesis of 487C. LC-MS Anal. Calc'd. for $C_{27}H_{35}ClFN_3O_4$, 520.03, found [M+2H] 522.4, $T_r$=1.7 min. (Method AY).

Example 544 Enantiomer 1. 3-(3-(3-(4-Chloro-2-fluorophenyl)ureido)-4-(propyl(tetrahydro-2H-pyran-4-yl)amino)phenyl)pentanoic acid Example 544 Enantiomer 1 was prepared utilizing compound 544A following the procedure described for the synthesis of Example 455 Enantiomer 1. LC-MS Anal. Calc'd. for $C_{26}H_{33}ClFN_3O_4$, 505, found [M+H] 506.2, $T_r$=1.88 Min. $^1$H NMR (400 MHz, MeOD) δ 7.99-8.03 (m, 2H), 7.15-7.25 (m, 3H), 6.89 (dd, J=8.40, 1.80 Hz, 1H), 3.91 (dd, J=11.20, 3.00 Hz, 2H), 3.30-3.38 (m, 2H), 2.92-2.95 (m, 4H), 2.56-2.62 (m, 2H), 1.49-1.78 (m, 6H), 1.25-1.29 (m, 2H), 0.81 (t, J=7.60 Hz, 6H).

Example 545

Enantiomer 1

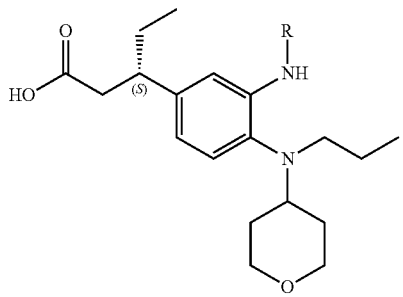

Example 545 was using 535E Enantiomer 1 and corresponding isocyanates following the procedure described for the synthesis of Example 487.

| Ex. No. | Name | R | $T_r$ min | Method | (M + H) |
|---|---|---|---|---|---|
| 545 | (S)-3-(3-(3-(4-cyanophenyl)ureido)-4-(propyl(tetrahydro-2H-pyran-4-yl)amino)phenyl)pentanoic acid | ![R group with 4-cyanophenyl amide] | 1.82 | O | 479.3 |

Example 546

Enantiomer 2

(R)-3-(3-((2-Ethoxypyrimidin-5-yl)amino)-4-(propyl(tetrahydro-2H-pyran-4-yl)amino)phenyl)pentanoic acid

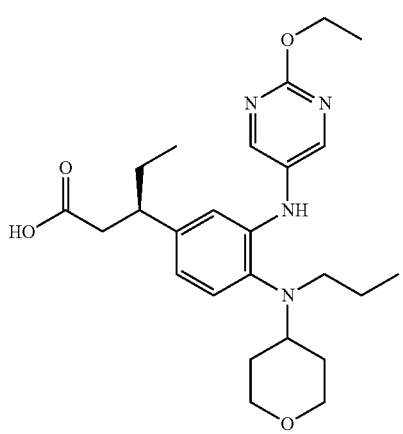 [SMILES: CCCN(c1ccc([C@H](CC)CC(=O)O)cc1Nc1cnc(OCC)nc1)C1CCOCC1]

546A. Methyl 3-(3-nitro-4-(propyl(tetrahydro-2H-pyran-4-yl)amino)phenyl)pentanoate 546A was prepared utilizing 535C and S-BINAP following the procedure described for the synthesis of 455D. LC-MS Anal. Calc'd. for $C_{20}H_{30}N_2O_5$, 378.4, found [M+H] 379.2, $T_r$=3.37 min. (Method N).

546B. Methyl 3-(3-amino-4-(propyl(tetrahydro-2H-pyran-4-yl)amino)phenyl)pentanoate 546B was prepared utilizing compound 546A following the procedure described for the synthesis of 455E Enantiomer 1. SFC chiral purity of 546B Enantiomer 2 shows 93.5% ee ($T_r$=3.59 min. (Method AF). LC-MS Anal. Calc'd. for $C_{20}H_{32}N_2O_3$ 348.4, found [M+H] 349.2, $T_r$=3.92 min. (Method N).

546C. Methyl 3-(3-((2-ethoxypyrimidin-5-yl)amino)-4-(propyl(tetrahydro-2H-pyran-4-yl)amino)phenyl)pentanoate 546C was prepared utilizing compound 546B Enantiomer 2 following the procedure described for the synthesis of 455F. LC-MS Anal. Calc'd. for $C_{26}H_{38}N_4O_4$, 470.6, found [M+H] 471.2, $T_r$=3.72 min. (Method N).

Example 546 Enantiomer 2. 3-(3-((2-Ethoxypyrimidin-5-yl)amino)-4-(propyl(tetrahydro-2H-pyran-4-yl)amino)phenyl)pentanoic acid Example 546 Enantiomer 2 was prepared utilizing compound 546C following the procedure described for the synthesis of Example 455 Enantiomer 1. LC-MS Anal. Calc'd. for $C_{25}H_{36}N_4O_4$, 456.5, found [M+H] 457, $T_r$=1.88 min. (Method O). $^1$H NMR (400 MHz, DMSO-$d_6$) δ 8.41 (s, 2H), 7.24 (s, 1H), 7.12 (d, J=8.00 Hz, 1H), 6.81 (s, 1H), 6.67 (d, J=7.60 Hz, 1H), 4.29 (dd, J=14.00, 7.00 Hz, 2H), 3.81 (d, J=8.00 Hz, 2H), 3.16-3.20 (m, 2H), 2.87-2.91 (m, 3H), 2.76-2.77 (m, 1H), 2.41-2.43 (m, 1H), 1.67 (d, J=12.40 Hz, 2H), 1.58-1.61 (m, 1H), 1.45-1.47 (m, 3H), 1.32 (t, J=7.20 Hz, 3H), 1.21-1.23 (m, 2H), 0.77 (t, J=7.20 Hz, 3H), 0.70 (t, J=7.60 Hz, 3H) (Note: one multiplet of CH is buried under the solvent peak).

Examples 547 to 554

Enantiomer 2

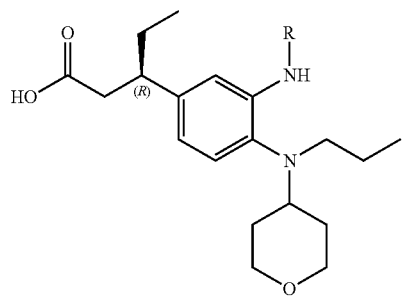

Examples 547 to 554 were prepared using 546B and corresponding aryl halides following the procedure described for the synthesis of Example 546.

| Ex. No. | Name | R | $T_r$ min | Method | (M + H) |
|---|---|---|---|---|---|
| 547 | (R)-3-(3-((4-cyanophenyl)amino)-4-(propyl(tetrahydro-2H-pyran-4-yl)amino)phenyl)pentanoic acid | 4-CN-phenyl | 1.91 | O | 436.3 |
| 548 | (R)-3-(3-((2-methylbenzo[d]thiazol-6-yl)amino)-4-(propyl(tetrahydro-2H-pyran-4-yl)amino)phenyl)pentanoic acid | 2-methylbenzo[d]thiazol-6-yl | 1.98 | O | 482.3 |
| 549 | (R)-3-(3-((4-fluorophenyl)amino)-4-(propyl(tetrahydro-2H-pyran-4-yl)amino)phenyl)pentanoic acid | 4-F-phenyl | 2.16 | O | 429.2 |

-continued

| Ex. No. | Name | R | $T_r$, min | Method | (M + H) |
|---|---|---|---|---|---|
| 550 | (R)-3-(3-((2,2-difluorobenzo[d][1,3]dioxol-5-yl)amino)-4-(propyl(tetrahydro-2H-pyran-4-yl)amino)phenyl)pentanoic acid | *(2,2-difluorobenzo[d][1,3]dioxol-5-yl structure)* | 2.37 | O | 491.2 |
| 551 | (R)-3-(3-((2-methoxypyrimidin-5-yl)amino)-4-(propyl(tetrahydro-2H-pyran-4-yl)amino)phenyl)pentanoic acid | *(2-methoxypyrimidin-5-yl structure)* | 1.7 | O | 443.3 |
| 552 | (R)-3-(3-((4-chlorophenyl)amino)-4-(propyl(tetrahydro-2H-pyran-4-yl)amino)phenyl)pentanoic acid | *(4-chlorophenyl structure)* | 2.39 | O | 445.2 |
| 553 | (R)-3-(3-((6-methoxypyridin-3-yl)amino)-4-(propyl(tetrahydro-2H-pyran-4-yl)amino)phenyl)pentanoic acid | *(6-methoxypyridin-3-yl structure)* | 442.3 | O | 442.3 |
| 554 | (R)-3-(3-((2-(cyclopropylmethoxy)pyrimidin-5-yl)amino)-4-(propyl(tetrahydro-2H-pyran-4-yl)amino)phenyl)pentanoic acid | *(2-(cyclopropylmethoxy)pyrimidin-5-yl structure)* | 2.12 | O | 483.3 |

Example 555

Enantiomer 2

(R)-3-(3-(3-(4-Chloro-2-fluorophenyl)ureido)-4-(propyl(tetrahydro-2H-pyran-4-yl)amino)phenyl)pentanoic acid

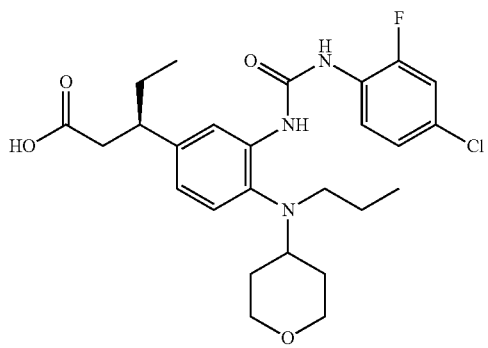 [SMILES: CCCN(c1ccc([C@H](CC)CC(=O)O)cc1NC(=O)Nc1ccc(Cl)cc1F)C1CCOCC1]

555A. Methyl (R)-3-(3-(3-(4-chloro-2-fluorophenyl)ureido)-4-(propyl(tetrahydro-2H-pyran-4-yl)amino)phenyl)pentanoate 555A was prepared using 546B Enantiomer 2 and 4-chloro-2-fluoro-1-isocyanatobenzene following the procedure described for the synthesis of 487C. LC-MS Anal. Calc'd. for $C_{27}H_{35}ClFN_3O_4$, 519.2, found [M+H] 520.4, $T_r$=1.7 min. (Method AY).

Example 555 Enantiomer 2. (R)-3-(3-(3-(4-Chloro-2-fluorophenyl)ureido)-4-(propyl(tetrahydro-2H-pyran-4-yl)amino)phenyl)pentanoic acid Example 555 Enantiomer 2 was prepared utilizing compound 555A following the procedure described for the synthesis of Example 555 Enantiomer 1. LC-MS Anal. Calc'd. for $C_{26}H_{33}ClFN_3O_4$, 505.0, found [M+H] 506.2, $T_r$=2.0 min (Method O). $^1H$ NMR (400 MHz, DMSO-$d_6$) δ 9.53 (s, 1H), 8.80 (s, 1H), 8.12 (t, J=8.80 Hz, 1H), 8.02 (d, J=1.60 Hz, 1H), 7.44 (dd, J=11.20, 2.00 Hz, 1H), 7.15-7.22 (m, 2H), 6.82 (dd, J=8.00, 1.40 Hz, 1H), 3.81-3.83 (m, 2H), 3.17-3.25 (m, 3H), 2.82-2.95 (m, 3H), 2.54-2.56 (m, 1H), 2.43-2.45 (m, 1H), 1.63-1.71 (m, 3H), 1.37-1.41 (m, 3H), 1.16-1.22 (m, 2H), 0.69-0.79 (m, 6H).

Example 556

Enantiomer 2

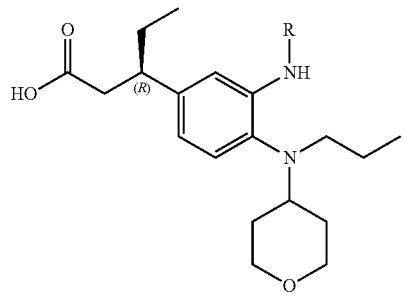

Example 556 was prepared using 546B and corresponding isocyanate following the procedure described for the synthesis of Example 544.

| Ex. No. | Name | R | $T_r$ min | Method | (M + H) |
|---|---|---|---|---|---|
| 556 | (R)-3-(3-(3-(4-cyanophenyl)ureido)-4-(propyl(tetrahydro-2H-pyran-4-yl)amino)phenyl)pentanoic acid | ![R group: -C(=O)-NH-C6H4-CN] | 1.82 | O | 479.3 |

Example 557

Enantiomer 1 and Enantiomer 2

3-(4-(Propyl(tetrahydro-2H-pyran-4-yl)amino)-3-(3-(p-tolyl)ureido)phenyl)pentanoic acid

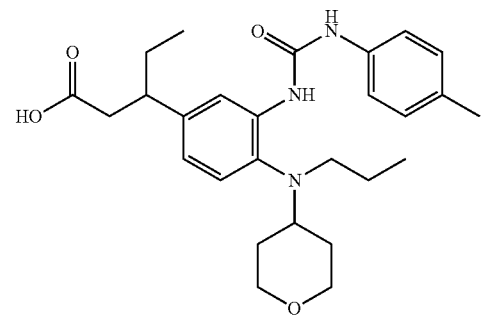 [SMILES: CCCN(c1ccc(C(CC)CC(=O)O)cc1NC(=O)Nc1ccc(C)cc1)C1CCOCC1]

557A. Methyl 3-(3-nitro-4-(propyl(tetrahydro-2H-pyran-4-yl)amino)phenyl)pentanoate (Racemate)

557A was prepared using compound 535C following the procedure described for the synthesis of 487A. LC-MS Anal. Calc'd. for $C_{20}H_{30}N_2O_5$, 378.4, found [M+H] 379.2, $T_r$=3.29 min. (Method N).

557B. Methyl 3-(3-amino-4-(propyl(tetrahydro-2H-pyran-4-yl)amino)phenyl)pentanoate 557B was prepared using compound 557A following the procedure described for the synthesis of 455E. LC-MS Anal. Calc'd. for $C_{20}H_{32}N_2O_3$, 348.4, found [M+H] 349.2, $T_r$=3.18 min. (Method N).

557C. Methyl 3-(4-(propyl(tetrahydro-2H-pyran-4-yl)amino)-3-(3-(p-tolyl)ureido)phenyl)pentanoate 557C was prepared using compound 557B following the procedure described for the synthesis of 487C. LC-MS Anal. Calc'd. for $C_{28}H_{39}N_3O_4$, 481.6, found [M+H] 482.2, $T_r$=3.59 min. (Method N).

Example 557 Enantiomer 1 and Enantiomer 2. 3-(4-(Propyl(tetrahydro-2H-pyran-4-yl)amino)-3-(3-(p-tolyl)ureido)phenyl)pentanoic acid Example 557 was prepared using 557C (racemate) following the procedure described for the synthesis of Example 455. LC-MS Anal. Calc'd. for $C_{27}H_{37}N_3O_4$ 467.6, found [M+H] 468.2, $T_r$=1.65 min. (Method O).

Chiral separation of Example 557 racemate gave Example 557 Enantiomer 1 and Example 557 Enantiomer 2 (Method BM). Enantiomer 1 $T_r$=2.22 min, Enantiomer 2 $T_r$=2.97 min (Method BM).

Example 557 Enantiomer 1. LC-MS Anal. Calc'd. for $C_{27}H_{37}N_3O_4$, 467.6, found [M+H] 468.3, $T_r$=1.62 min. (Method R). $^1$H NMR (400 MHz, DMSO-$d_6$) δ 8.43 (s, 1H), 8.06 (d, J=2.00 Hz, 1H), 7.37 (d, J=8.40 Hz, 2H), 7.07-7.14 (m, 3H), 6.77 (dd, J=8.00, 2.00 Hz, 1H), 3.80-3.84 (m, 2H), 3.17-3.25 (m, 5H), 2.85-2.93 (m, 3H), 2.39-2.41 (m, 1H), 2.24 (s, 3H), 1.68-1.71 (m, 3H), 1.37-1.41 (m, 3H), 1.18-1.20 (m, 2H), 0.71 (t, J=7.60 Hz, 3H), 0.77 (t, J=7.60 Hz, 3H).

Example 557 Enantiomer 2 LC-MS Anal. Calc'd. for $C_{27}H_{37}N_3O_4$, 467.6, found [M+H] 468.3, $T_r$=1.65 min. (Method O). $^1$H NMR (400 MHz, DMSO-$d_6$) δ 8.43 (s, 1H), 8.06 (d, J=2.00 Hz, 1H), 7.37 (d, J=8.40 Hz, 2H), 7.07-7.14 (m, 3H), 6.77 (dd, J=8.00, 2.00 Hz, 1H), 3.80-3.84 (m, 2H), 3.17-3.25 (m, 5H), 2.85-2.93 (m, 3H), 2.39-2.41 (m, 1H), 2.24 (s, 3H), 1.68-1.71 (m, 3H), 1.37-1.41 (m, 3H), 1.18-1.20 (m, 2H), 0.71 (t, J=7.60 Hz, 3H), 0.77 (t, J=7.60 Hz, 3H).

Example 558

Enantiomer 1

(S)-3-(3-((4-Cyanophenyl)amino)-4-(propyl(tetrahydro-2H-pyran-4-yl)amino)phenyl)-4-methoxybutanoic acid

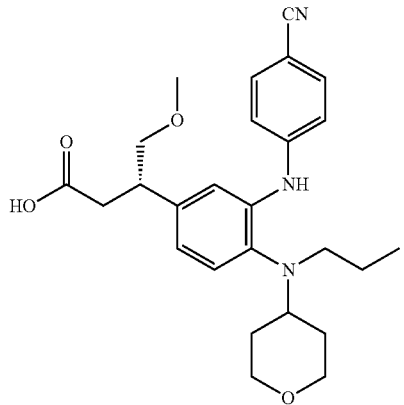 [SMILES: CCCN(c1ccc([C@@H](COC)CC(=O)O)cc1Nc1ccc(C#N)cc1)C1CCOCC1]

558A. Methyl 4-methoxy-(S)-3-(3-nitro-4-(propyl(tetrahydro-2H-pyran-4-yl)amino)phenyl)butanoate 1,4-Dioxane (35 mL) was purged with argon for 10 minutes before chloro(1,5-cyclooctadiene)rhodium(I) dimer (0.059 g, 0.120 mmol) and (R)-BINAP (0.109 g, 0.175 mmol) were added. The reaction was then purged with argon for 5 minutes. To the above reaction mixture 535C (3 g, 7.97 mmol), (E)-methyl 4-methoxybut-2-enoate (1.245 g, 9.57 mmol), sodium hydroxide (7.28 ml, 7.28 mmol) were added respectively and purged argon for another 5 minutes. The reaction mixture was heated at 50° C. and stirred for 3 h before being cooled to room temperature and quenched with acetic acid (0.411 mL, 7.18 mmol) and it was stirred for 5 minutes before it was partitioned between ethyl acetate (125 mL) and water (125 mL). The layers were separated and the aqueous layer was extracted with ethyl acetate (100 mL). The combined organic layers were washed with brine (75 mL), dried over anhydrous sodium sulfate, filtered and concentrated under reduced pressure. Purification via silica gel flash chromatography gave 558A (pale orange solid, 2.3 g, 5.83 mmol, 73.1% yield). LC-MS Anal. Calc'd. for $C_{20}H_{30}N_2O_6$, 394.4, found [M+H] 395.2, $T_r$=2.9 min (Method N).

558B. Methyl (S)-3-(3-amino-4-(propyl(tetrahydro-2H-pyran-4-yl)amino)phenyl)-4-methoxybutanoate 558B was prepared utilizing compound 558A following the procedure described for the synthesis of 455E. SFC chiral purity shows 100% ee ($T_r$=6.39 min). (Method AF). LC-MS Anal. Calc'd. for $C_{20}H_{32}N_2O_4$, 364.4, found [M+H] 365.2, $T_r$=2.76 min. (Method N).

558C. Methyl (S)-3-(3-((4-cyanophenyl)amino)-4-(propyl(tetrahydro-2H-pyran-4-yl)amino)phenyl)-4-methoxybutanoate 558C was prepared utilizing compound 558B and 4-bromobenzonitrile following the procedure described for the synthesis of 455F. LC-MS Anal. Calc'd. for $C_{27}H_{35}N_3O_4$, 465.5, found [M+H] 466.2, $T_r$=3.26 min. (Method N).

Example 558 Enantiomer 1. (S)-3-(3-((4-Cyanophenyl)amino)-4-(propyl(tetrahydro-2H-pyran-4-yl)amino)phenyl)-4-methoxybutanoic acid Example 558 Enantiomer 1 was prepared utilizing 558C following the procedure described for the synthesis of Example 455 Enantiomer 1. LC-MS Anal. Calc'd. for $C_{26}H_{33}N_3O_4$, 451.5, found [M+H] 452.2, $T_r$=1.72 min. (Method O). $^1$H NMR (400 MHz, DMSO-$d_6$) δ 7.87 (s, 1H), 7.57 (d, J=8.80 Hz, 2H), 7.17-7.18 (m, 2H), 7.09-7.11 (m, 2H), 6.94 (dd, J=8.40, 1.80 Hz, 1H), 3.76-3.80 (m, 2H), 3.42-3.47 (m, 2H), 3.24-3.34 (m, 4H), 3.05-3.10 (m, 2H), 2.88-2.91 (m, 3H), 2.64-2.68 (m, 1H), 2.48-2.51 (m, 1H), 1.55-1.58 (m, 2H), 1.47-1.47 (m, 2H), 1.21-1.25 (m, 2H), 0.76 (t, J=7.20 Hz, 3H).

Examples 559 to 565

Enantiomer 1

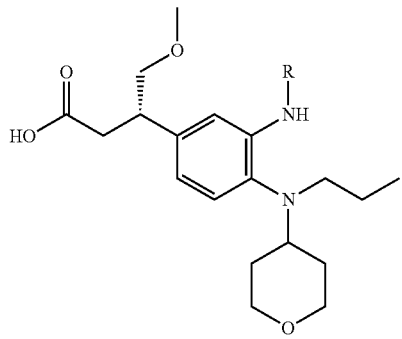

Examples 559 to 565 were prepared using 558 B and the corresponding aryl halides following the procedure described for the synthesis of Example 558.

| Ex. No. | Name | R | $T_r$, min | Method | (M + H) |
|---|---|---|---|---|---|
| 559 | (S)-3-(3-((2-ethoxypyrimidin-5-yl)amino)-4-(propyl(tetrahydro-2H-pyran-4-yl)amino)phenyl)-4-methoxybutanoic acid | ethoxypyrimidinyl | 1.66 | O | 473.3 |
| 560 | 4-methoxy-(S)-3-(3-((2-methylbenzo[d]thiazol-6-yl)amino)-4-(propyl(tetrahydro-2H-pyran-4-yl)amino)phenyl) butanoic acid | 2-methylbenzothiazol-6-yl | 1.75 | O | 498.2 |
| 561 | (S)-3-(3-((2,2-difluorobenzo[d][1,3]dioxol-5-yl)amino)-4-(propyl(tetrahydro-2H-pyran-4-yl)amino)phenyl)-4-methoxybutanoic acid | 2,2-difluorobenzodioxol-5-yl | 2.15 | O | 507.2 |
| 562 | (S)-3-(3-((4-fluorophenyl)amino)-4-(propyl(tetrahydro-2H-pyran-4-yl)amino)phenyl)-4-methoxybutanoic acid | 4-fluorophenyl | 1.93 | O | 445.2 |

-continued

| Ex. No. | Name | R | $T_r$, min | Method | (M + H) |
|---|---|---|---|---|---|
| 563 | (S)-3-(3-((2-(cyclopropylmethoxy)pyrimidin-5-yl)amino)-4-(propyl(tetrahydro-2H-pyran-4-yl)amino)phenyl)-4-methoxybutanoic acid | 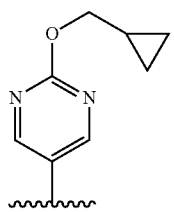 [SMILES: *c1cnc(OCC2CC2)nc1] | 1.52 | O | 499.4 |
| 564 | (S)-3-(3-((4-chlorophenyl)amino)-4-(propyl(tetrahydro-2H-pyran-4-yl)amino)phenyl)-4-methoxybutanoic acid | 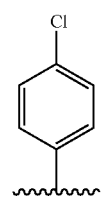 [SMILES: *c1ccc(Cl)cc1] | 1.78 | O | 461.3 |
| 565 | 4-methoxy-(S)-3-(3-((6-methoxypyridin-3-yl)amino)-4-(propyl(tetrahydro-2H-pyran-4-yl)amino)phenyl)butanoic acid | 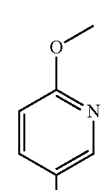 | 1.65 | O | 458.2 |

Example 566

Enantiomer 1

(S)-3-(3-(3-(4-Chloro-2-fluorophenyl)ureido)-4-(propyl(tetrahydro-2H-pyran-4-yl)amino)phenyl)-4-methoxybutanoic acid

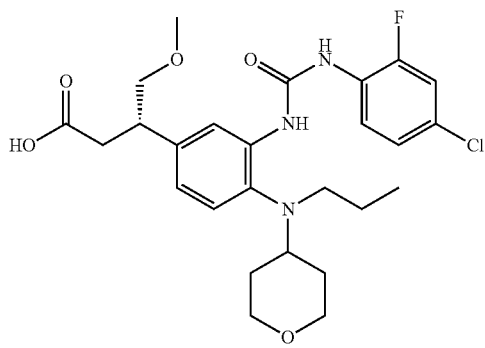 [SMILES: CCCN(c1ccc([C@@H](COC)CC(=O)O)cc1NC(=O)Nc1ccc(Cl)cc1F)C1CCOCC1]

566A. Methyl (S)-3-(3-(3-(4-chloro-2-fluorophenyl)ureido)-4-(propyl(tetrahydro-2H-pyran-4-yl)amino)phenyl)-4-methoxybutanoate 566A was prepared using compound 558B and 4-chloro-2-fluoro-1-isocyanato benzene following the procedure described for the synthesis of 487C. LC-MS Anal. Calc'd. for $C_{27}H_{35}ClFN_3O_5$, 535.2, found [M+H] 536.4, $T_r$=1.61 min. (Method BA).

Example 566 Enantiomer 1. (S)-3-(3-(3-(4-Chloro-2-fluorophenyl)ureido)-4-(propyl(tetrahydro-2H-pyran-4-yl)amino)phenyl)-4-methoxybutanoic acid Example 566 Enantiomer 1 was prepared utilizing compound 566A following the procedure described for the synthesis of Example 486 Enantiomer 1. LC-MS Anal. Calc'd. for $C_{26}H_{33}ClFN_3O_5$, 521.2, found [M+H] 522.2. $T_r$=1.76 Min $^1$H NMR (400 MHz, DMSO-d$_6$) δ 9.54 (s, 1H), 8.78 (s, 1H), 8.12 (t, J=8.80 Hz, 1H), 8.05 (s, 1H), 7.45 (dd, J=11.20, 2.40 Hz, 1H), 7.21-7.23 (m, 1H), 7.16 (d, J=8.00 Hz, 1H), 6.86 (d, J=7.60 Hz, 1H), 3.80-3.83 (m, 2H), 3.17-3.40 (m, 6H), 2.85-2.89 (m, 3H), 2.61-2.67 (m, 1H), 2.43-2.45 (m, 1H), 1.68-1.71 (m, 2H), 1.38-1.41 (m, 2H), 1.18-1.20 (m, 2H), 0.77 (t, J=7.60 Hz, 3H) (2H is buried under the Solvent residual peak).

Example 567

Enantiomer 1

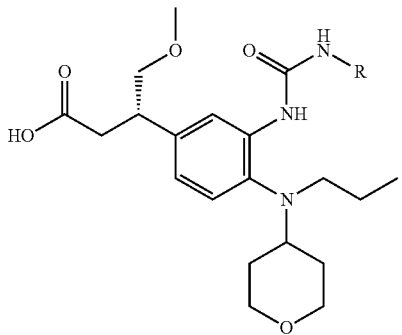

Example 567 was prepared using 558B and corresponding isocyanates following the procedure described for the synthesis of Example 566.

| Ex. No. | Name | R | $T_r$ min | Method | (M + H) |
|---|---|---|---|---|---|
| 567 | (S)-3-(3-(3-(4-cyanophenyl)ureido)-4-(propyl(tetrahydro-2H-pyran-4-yl)amino)phenyl)-4-methoxybutanoic acid | 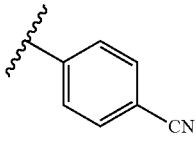 [SMILES: *c1ccc(C#N)cc1] | 1.54 | O | 495.3 |

Example 568

Enantiomer 2

(R)-3-(3-((4-Cyanophenyl)amino)-4-(propyl(tetrahydro-2H-pyran-4-yl)amino)phenyl)-4-methoxybutanoic acid

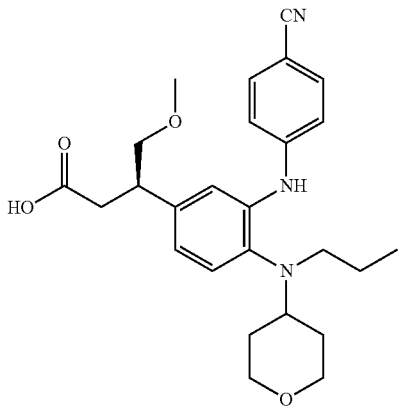 [SMILES: CCCN(c1ccc([C@H](COC)CC(=O)O)cc1Nc1ccc(C#N)cc1)C1CCOCC1]

568A. Methyl 4-methoxy-(R)-3-(3-nitro-4-(propyl(tetrahydro-2H-pyran-4-yl)amino)phenyl)butanoate 568A was prepared utilizing S-BINAP and 535C following the procedure described for the synthesis of 558A. LC-MS Anal. Calc'd. for $C_{20}H_{30}N_2O_6$, 394.4, found [M+H] 395.4, $T_r$=2.81 min. (Method N).

568B. Methyl (R)-3-(3-amino-4-(propyl(tetrahydro-2H-pyran-4-yl)amino)phenyl)-4-methoxybutanoate 568B was prepared using 568A following the procedure described for the synthesis of 558B. Enantiomer 1. SFC chiral purity of 568B Enantiomer 2 shows 100% ee ($T_r$=5.23 min. (Method AF). LC-MS Anal. Calc'd. for $C_{20}H_{32}N_2O_4$, 364.4, found [M+H] 365.2, $T_r$=2.69 min. (Method N).

568C. Methyl (R)-3-(3-((4-cyanophenyl)amino)-4-(propyl(tetrahydro-2H-pyran-4-yl)amino)phenyl)-4-methoxybutanoate 568C was prepared using 568B Enantiomer 2 and 4-bromobenzonitrile following the procedure described for the synthesis of 558C. LC-MS Anal. Calc'd. for $C_{27}H_{35}N_3O_4$, 465.5, found [M+H] 466.2, $T_r$=3.6 min. (Method N).

Example 568 Enantiomer 2. (R)-3-(3-((4-Cyanophenyl)amino)-4-(propyl(tetrahydro-2H-pyran-4-yl)amino)phenyl)-4-methoxybutanoic acid Example 568 Enantiomer 2 was prepared utilizing compound 568C following the procedure described for the synthesis of Example 455 Enantiomer 1. LC-MS Anal. Calc'd. for $C_{26}H_{33}N_3O_4$, 451.2, found [M+H] 452.2, $T_r$=1.72 min (Method O). $^1$H NMR (400 MHz, DMSO-$d_6$) δ 7.87 (s, 1H), 7.57 (d, J=8.80 Hz, 2H), 7.17-7.18 (m, 2H), 7.07-7.09 (m, 2H), 6.94 (dd, J=8.40, 1.80 Hz, 1H), 3.76-3.80 (m, 2H), 3.42-3.47 (m, 2H), 3.24-3.34 (m, 4H), 3.05-3.10 (m, 2H), 2.88-2.91 (m, 3H), 2.64-2.68 (m, 1H), 1.55-1.58 (m, 2H), 1.43-1.48 (m, 2H), 1.21-1.25 (m, 2H), 0.76 (t, J=7.20 Hz, 3H). (1H is buried under solvent peak).

Examples 569 to 575

Enantiomer 2

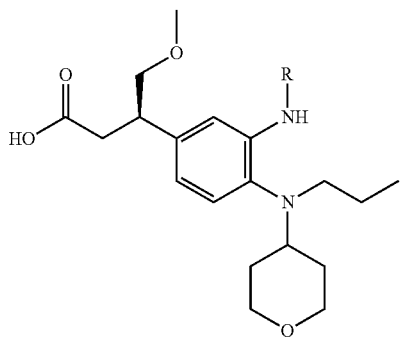

Examples 569 to 575 were prepared using 568B and corresponding aryl halides following the procedure described for the synthesis of Example 568.

| Ex. No. | Name | R | $T_r$ min | Method | (M + H) |
|---|---|---|---|---|---|
| 569 | (R)-3-(3-((2-ethoxypyrimidin-5-yl)amino)-4-(propyl(tetrahydro-2H-pyran-4-yl)amino)phenyl)-4-methoxybutanoic acid | 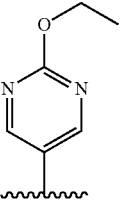 [SMILES: *c1cnc(OCC)nc1] | 1.56 | O | 473.3 |

-continued

| Ex. No. | Name | R | T$_r$, min | Method | (M + H) |
|---|---|---|---|---|---|
| 570 | 4-methoxy-(R)-3-(3-((2-methylbenzo[d]thiazol-6-yl)amino)-4-(propyl(tetrahydro-2H-pyran-4-yl)amino)phenyl)butanoic acid | | 1.75 | O | 498.2 |
| 571 | 3-(3-((2,2-difluorobenzo[d][1,3]dioxol-5-yl)amino)-4-(propyl(tetrahydro-2H-pyran-4-yl)amino)phenyl)-4-methoxybutanoic acid | | 2.04 | O | 507.2 |
| 572 | (R)-3-(3-((4-fluorophenyl)amino)-4-(propyl(tetrahydro-2H-pyran-4-yl)amino)phenyl)-4-methoxybutanoic acid | | 1.82 | O | 445.2 |
| 573 | (R)-3-(3-((2-(cyclopropylmethoxy)pyrimidin-5-yl)amino)-4-(propyl(tetrahydro-2H-pyran-4-yl)amino)phenyl)-4-methoxybutanoic acid | | 1.51 | O | 499.4 |
| 574 | (R)-3-(3-((4-chlorophenyl)amino)-4-(propyl(tetrahydro-2H-pyran-4-yl)amino)phenyl)-4-methoxybutanoic acid | | 1.78 | O | 461.3 |
| 575 | 4-methoxy-(R)-3-(3-((6-methoxypyridin-3-yl)amino)-4-(propyl(tetrahydro-2H-pyran-4-yl)amino)phenyl)butanoic acid | | 1.65 | O | 458.2 |

Example 576

Enantiomer 2

(R)-3-(3-(3-(4-Chloro-2-fluorophenyl)ureido)-4-(propyl(tetrahydro-2H-pyran-4-yl)amino)phenyl)-4-methoxybutanoic acid

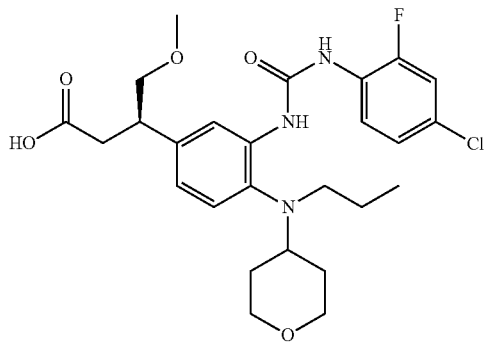 [SMILES: CCCN(c1ccc([C@H](COC)CC(=O)O)cc1NC(=O)Nc1ccc(Cl)cc1F)C1CCOCC1]

Example 577

Enantiomer 2

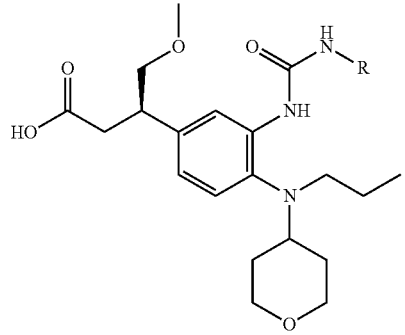

Example 577 was prepared using 568B and corresponding isocyanates following the procedure described for the synthesis of Example 576.

| Ex. No. | Name | R | $T_r$, min | Method | (M + H) |
|---|---|---|---|---|---|
| 577 | (R)-3-(3-(3-(4-cyanophenyl)ureido)-4-(propyl(tetrahydro-2H-pyran-4-yl)amino)phenyl)-4-methoxybutanoic acid | | 1.54 | O | 495.2 |

576A. Methyl (R)-3-(3-(3-(4-chloro-2-fluorophenyl)ureido)-4-(propyl(tetrahydro-2H-pyran-4-yl)amino)phenyl)-4-methoxybutanoate 576A was prepared using compound 568B and 4-chloro-2-fluoro-1-isocyanatobenzene following the procedure described for the synthesis of 487C. LC-MS Anal. Calc'd. for $C_{27}H_{35}ClFN_3O_5$, 535.2, found [M+H] 536.4, $T_r=1.59$ min. (Method BA).

Example 576 Enantiomer 2. (R)-3-(3-(3-(4-Chloro-2-fluorophenyl)ureido)-4-(propyl(tetrahydro-2H-pyran-4-yl)amino)phenyl)-4-methoxybutanoic acid Example 576 Enantiomer 2 was prepared utilizing compound 576A following the procedure described for the synthesis of Example 455 Enantiomer 1. LC-MS Anal. Calc'd. for $C_{26}H_{33}ClFN_3O_5$, 521.2, found [M+H] 522.2. $T_r=1.76$ Min $^1$H NMR 400 MHz, DMSO-$d_6$: δ 9.54 (s, 1H), 8.78 (s, 1H), 8.12 (t, J=8.80 Hz, 1H), 8.05 (s, 1H), 7.45 (dd, J=11.20, 2.40 Hz, 1H), 7.21-7.23 (m, 1H), 7.16 (d, J=8.00 Hz, 1H), 6.86 (d, J=7.60 Hz, 1H), 3.80-3.83 (m, 2H), 3.17-3.40 (m, 6H), 2.85-2.89 (m, 3H), 2.61-2.67 (m, 1H), 2.43-2.45 (m, 1H), 1.68-1.71 (m, 2H), 1.38-1.41 (m, 2H), 1.18-1.20 (m, 2H), 0.77 (t, J=7.60 Hz, 3H) (2H is buried under the Solvent residual peak).

Example 578

Enantiomer 1

3-(3-((2-Ethoxypyrimidin-5-yl)amino)-4-(ethyl(tetrahydro-2H-pyran-4-yl)amino)phenyl)-3-phenylpropanoic acid

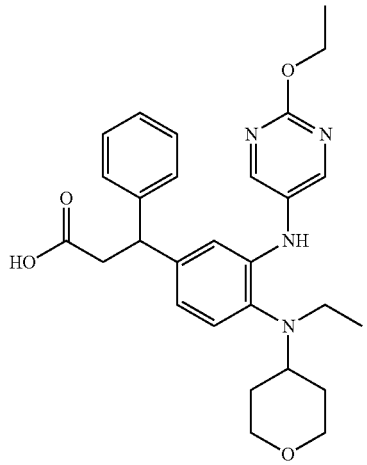 [SMILES: CCOc1ncc(Nc2cc(C(CC(=O)O)c3ccccc3)ccc2N(CC)C2CCOCC2)cn1]

578A. Methyl 3-(4-(ethyl(tetrahydro-2H-pyran-4-yl)amino)-3-nitrophenyl)-3-phenylpropanoate 1,4-Dioxane (20 mL) was purged with argon for 10 minutes, then chlorobis(ethylene)rhodium(I) dimer (0.032 g, 0.083 mmol), (R)-BINAP (0.076 g, 0.121 mmol) was added and purged with argon for 5 minutes. To the above reaction mixture 455C (2 g, 5.52 mmol), methyl cinnamate (1.075 g, 6.63 mmol), sodium hydroxide (5.04 mL, 5.04 mmol) were added respectively and purged argon for another 5 minutes. The reaction mixture was heated at 50° C. and stirred for 3 h. Reaction mixture was cooled to room temperature and quenched with acetic acid (0.284 mL, 4.97 mmol) and it was stirred for 5 minutes before it was partitioned between ethyl acetate (100 mL) and water (100 mL). Aqueous layer was extracted with ethyl acetate (2×75 mL). The combined organic layers were washed with brine (75 mL), dried over anhydrous sodium sulfate, filtered and concentrated under reduced pressure. Purification via silica gel flash chromatography gave 578A (pale orange solid, 0.6 g, 1.396 mmol, 25.3% yield). LC-MS Anal. Calc'd. for $C_{23}H_{28}N_2O_5$, 412.4, found [M+H] 413.2, $T_r$=1.175 min (Method N).

578B. Methyl 3-(3-amino-4-(ethyl(tetrahydro-2H-pyran-4-yl)amino)phenyl)-3-phenylpropanoate 578B was prepared utilizing compound 578A following the procedure described for the synthesis of 455E. SFC chiral purity of 578B Enantiomer 1 shows 100% ee ($T_r$=4.3 min). (Method Z). LC-MS Anal. Calc'd. for $C_{23}H_{30}N_2O_3$, 382.4, found [M+H] 383.1, $T_r$=3.6 min. (Method N).

578C. Methyl 3-(3-((2-ethoxypyrimidin-5-yl)amino)-4-(ethyl(tetrahydro-2H-pyran-4-yl)amino)phenyl)-3-phenylpropanoate 578C was prepared utilizing compound 578B and 5-bromo-2-ethoxypyrimidine following the procedure described for the synthesis of 455F. LC-MS Anal. Calc'd. for $C_{29}H_{36}N_4O_4$, 504.2, found [M+H] 505, $T_r$=3.01 min. (Method N).

Example 578 Enantiomer 1. 3-(3-((2-Ethoxypyrimidin-5-yl)amino)-4-(ethyl(tetrahydro-2H-pyran-4-yl)amino)phenyl)-3-phenylpropanoic acid Example 578 Enantiomer 1 was prepared utilizing compound 578C following the procedure described for the synthesis of Example 455 Enantiomer 1. LC-MS Anal. Calc'd. for $C_{28}H_{34}N_4O_4$, 490.2, found [M+H] 491.4, $T_r$=1.84 min (Method R). $^1$H NMR (400 MHz, DMSO-$d_6$) δ 8.40 (s, 2H), 7.27-7.31 (m, 5H), 7.15-7.17 (m, 3H), 6.73-6.79 (m, 1H), 4.30-4.32 (m, 3H), 3.78-3.80 (m, 2H), 3.19-3.22 (m, 2H), 2.93-2.95 (m, 5H), 1.64-1.67 (m, 2H), 1.41-1.43 (m, 2H), 1.34 (t, J=7.20 Hz, 3H), 0.81 (t, J=10.40 Hz, 3H).

Examples 579 to 583

Enantiomer 1

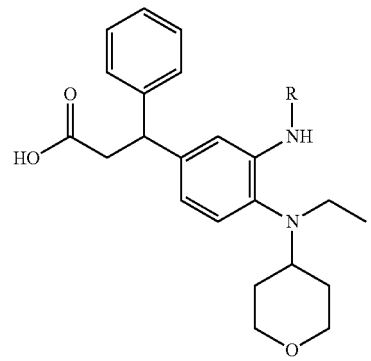

Examples 579 to 583 were prepared using 578B and corresponding aryl halides following the procedure described for the synthesis of Example 578 Enantiomer 1.

| Ex. No. | Name | R | $T_r$ min | Method | (M + H) |
|---|---|---|---|---|---|
| 579 | 3-(4-(ethyl(tetrahydro-2H-pyran-4-yl)amino)-3-((2-methylbenzo[d]thiazol-6-yl)amino)phenyl)-3-phenylpropanoic acid | 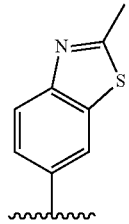 [SMILES: *c1ccc2nc(C)sc2c1] | 1.544 | R | 516.2 |
| 580 | 3-(3-((4-chlorophenyl)amino)-4-(ethyl(tetrahydro-2H-pyran-4-yl)amino)phenyl)-3-phenylpropanoic acid | 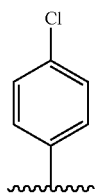 | 2.184 | R | 479.2 |

-continued

| Ex. No. | Name | R | $T_r$ min | Method | (M + H) |
|---|---|---|---|---|---|
| 581 | 3-(3-((4-cyanophenyl)amino)-4-(ethyl(tetrahydro-2H-pyran-4-yl)amino)phenyl)-3-phenylpropanoic acid | 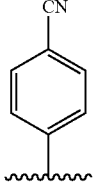 [SMILES: *c1ccc(C#N)cc1] | 1.54 | R | 470.2 |
| 582 | 3-(3-((4-chloro-2-fluorophenyl)amino)-4-(ethyl(tetrahydro-2H-pyran-4-yl)amino)phenyl)-3-phenylpropanoic acid | 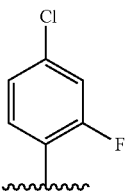 [SMILES: *c1ccc(Cl)cc1F] | 2.052 | R | 479.2 |
| 583 | 3-(3-((4-(difluoromethoxy)phenyl)amino)-4-(ethyl(tetrahydro-2H-pyran-4-yl)amino)phenyl)-3-phenylpropanoic acid | 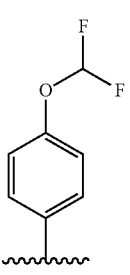 [SMILES: *c1ccc(OC(F)F)cc1] | 2.11 | R | 511.2 |

Example 584

Enantiomer 1

3-(4-(Ethyl(tetrahydro-2H-pyran-4-yl)amino)-3-(3-(p-tolyl)ureido)phenyl)-3-phenylpropanoic acid

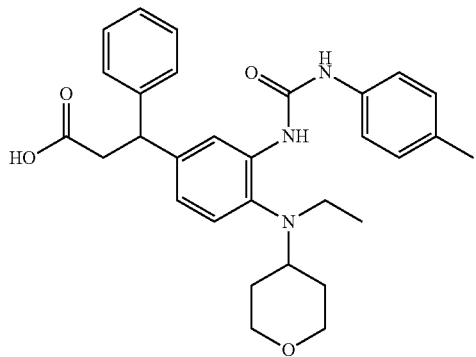 [SMILES: CCN(c1ccc(C(CC(=O)O)c2ccccc2)cc1NC(=O)Nc1ccc(C)cc1)C1CCOCC1]

584A. Methyl 3-(4-(ethyl(tetrahydro-2H-pyran-4-yl)amino)-3-(3-(p-tolyl)ureido)phenyl)-3-phenylpropanoate 584A was prepared using compound 578B and 4-methyl-1-isocyanato benzene following the procedure described for the synthesis of 487C. LC-MS Anal. Calc'd. $C_{31}H_{37}N_3O_4$ for 515.28 found [M+H] 516.3. $T_r$=1.81 min. (Method R).

Example 584 Enantiomer 1. 3-(4-(Ethyl(tetrahydro-2H-pyran-4-yl)amino)-3-(3-(p-tolyl)ureido)phenyl)-3-phenylpropanoic acid Example 584 Enantiomer 1 was prepared utilizing compound 584A following the procedure described for the synthesis of Example 487 Enantiomer 1. LC-MS Anal. Calc'd. $C_{30}H_{35}N_3O_4$ for 501.2, found [M+H] 502.3, $T_r$=2.15 min. (Method R). $^1$H NMR (400 MHz, DMSO-$d_6$) δ 9.54 (s, 1H), 8.85 (s, 1H), 8.19 (s, 1H), 7.35-7.37 (m, 2H), 7.28-7.29 (m, 5H), 7.14-7.17 (m, 4H), 4.34 (s, 1H), 3.79-3.82 (m, 2H), 3.21-3.24 (m, 2H), 2.93-2.95 (m, 5H), 2.25 (s, 3H), 1.67-1.70 (m, 2H), 1.24-1.25 (m, 2H), 0.78 (t, J=6.80 Hz, 3H).

Examples 585 to 587

Enantiomer 1

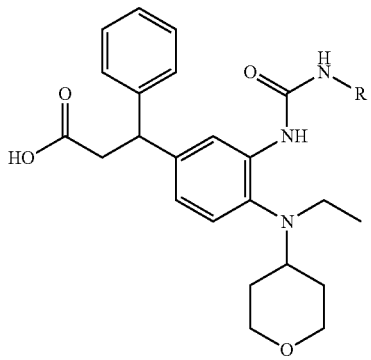

Examples 585 and 586 were prepared by using 578B and corresponding isocyanates following the procedure described for the synthesis of Example 584.

Example 587 were prepared using 578B and corresponding amines following the procedure described for the synthesis of Example 488.

588A. Methyl 3-(4-(ethyl(tetrahydro-2H-pyran-4-yl)amino)-3-nitrophenyl)-3-phenylpropanoate 588A was prepared utilizing S-BINAP and 455C following the procedure described for the synthesis of 578A.

| Ex. No. | Name | R | $T_r$ min | Method | (M + H) |
|---|---|---|---|---|---|
| 585 | 3-(3-(3-(4-chloro-2-fluorophenyl)ureido)-4-(ethyl(tetrahydro-2H-pyran-4-yl)amino)phenyl)-3-phenylpropanoic acid | 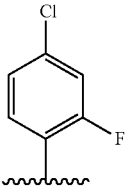 [SMILES: *c1ccc(Cl)cc1F] | 2.29 | O | 540.2 |
| 586 | 3-(4-(ethyl(tetrahydro-2H-pyran-4-yl)amino)-3-(3-(2-fluoro-4-methoxyphenyl)ureido)phenyl)-3-phenylpropanoic acid | 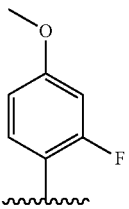 [SMILES: *c1ccc(OC)cc1F] | 2.065 | O | 536.4 |
| 587 | 3-(4-(ethyl(tetrahydro-2H-pyran-4-yl)amino)-3-(3-(5-methylisoxazol-3-yl)ureido)phenyl)-3-phenylpropanoic acid | 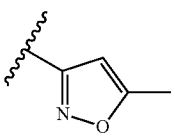 [SMILES: *c1cc(C)on1] | 2.027 | O | 493.4 |

Example 588

Enantiomer 2

3-(3-((2-Ethoxypyrimidin-5-yl)amino)-4-(ethyl(tetrahydro-2H-pyran-4-yl)amino)phenyl)-3-phenylpropanoic acid

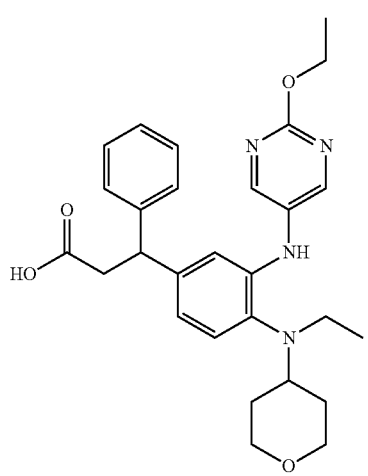 [SMILES: CCOc1ncc(Nc2cc(C(CC(=O)O)c3ccccc3)ccc2N(CC)C2CCOCC2)cn1]

LC-MS Anal. Calc'd. for $C_{23}H_{28}N_2O_5$, 412.4, found [M+H] 413.2, $T_r$=1.174 min (Method N).

588B. Methyl 3-(3-amino-4-(ethyl(tetrahydro-2H-pyran-4-yl)amino)phenyl)-3-phenylpropanoate 588B was prepared utilizing compound 588A following the procedure described for the synthesis of 455E. SFC chiral purity of 588B Enantiomer 2 shows 97.6% ee ($T_r$=4.9 min). (Method Z). LC-MS Anal. Calc'd. for $C_{23}H_{30}N_2O_3$, 382.4, found [M+H] 383.1, $T_r$=3.01 min. (Method N).

588C. Methyl 3-(3-((2-ethoxypyrimidin-5-yl)amino)-4-(ethyl(tetrahydro-2H-pyran-4-yl)amino)phenyl)-3-phenylpropanoate 588C was prepared utilizing compound 588B and 5-bromo-2-ethoxypyrimidine following the procedure described for the synthesis of 455F. LC-MS Anal. Calc'd. for $C_{29}H_{36}N_4O_4$, 504.2, found [M+H] 505, $T_r$=3.01 min. (Method N).

Example 588 Enantiomer 2. 3-(3-((2-Ethoxypyrimidin-5-yl)amino)-4-(ethyl(tetrahydro-2H-pyran-4-yl)amino)phenyl)-3-phenylpropanoic acid Example 588 Enantiomer 2 was prepared utilizing compound 588C following the procedure described for the synthesis of Example 455 Enantiomer 1. LC-MS Anal. Calc'd. for $C_{28}H_{34}N_4O_4$, 490.2, found [M+H] 491.4, $T_r$=1.87 min. (Method R). $^1$H NMR (400 MHz, DMSO-$d_6$) δ 8.40 (s, 2H), 7.27-7.31 (m, 5H), 7.15-7.17 (m, 3H), 6.73-6.79 (m, 1H), 4.30-4.32 (m, 3H), 3.78-3.80 (m, 2H), 3.19-3.22 (m, 2H), 2.93-2.95 (m, 5H), 1.64-1.67 (m, 2H), 1.41-1.43 (m, 2H), 1.31-1.39 (m, 3H), 0.81 (t, J=10.40 Hz, 3H).

Examples 589 to 593

Enantiomer 2

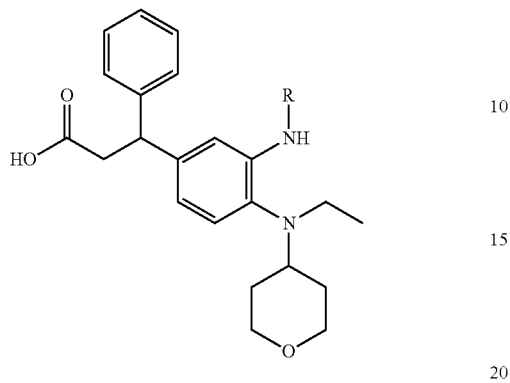

Examples 589 to 593 were prepared using 588B and corresponding aryl halides following the procedure described for the synthesis of Example 588.

| Ex. No. | Name | R | $T_r$ min | Method | (M + H) |
|---|---|---|---|---|---|
| 589 | 3-(4-(ethyl(tetrahydro-2H-pyran-4-yl)amino)-3-((2-methylbenzo[d]thiazol-6-yl)amino)phenyl)-3-phenylpropanoic acid | 2-methylbenzo[d]thiazol-6-yl | 1.895 | R | 516.3 |
| 590 | 3-(3-((4-chlorophenyl)amino)-4-(ethyl(tetrahydro-2H-pyran-4-yl)amino)phenyl)-3-phenylpropanoic acid | 4-chlorophenyl | 2.16 | R | 479.3 |
| 591 | 3-(3-((4-cyanophenyl)amino)-4-(ethyl(tetrahydro-2H-pyran-4-yl)amino)phenyl)-3-phenylpropanoic acid | 4-cyanophenyl | 1.9 | R | 470.3 |
| 592 | 3-(3-((4-chloro-2-fluorophenyl)amino)-4-(ethyl(tetrahydro-2H-pyran-4-yl)amino)phenyl)-3-phenylpropanoic acid | 4-chloro-2-fluorophenyl | 2.41 | R | 497.3 |

| Ex. No. | Name | R | $T_r$ min | Method | (M + H) |
|---|---|---|---|---|---|
| 593 | 3-(3-((4-(difluoromethoxy)phenyl)amino)-4-(ethyl(tetrahydro-2H-pyran-4-yl)amino)phenyl)-3-phenylpropanoic acid | | 2.11 | R | 511.2 |

Example 594

Enantiomer 2

3-(4-(Ethyl(tetrahydro-2H-pyran-4-yl)amino)-3-(3-(p-tolyl)ureido)phenyl)-3-phenylpropanoic acid

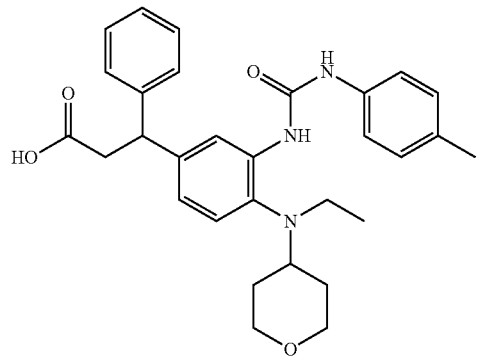 [SMILES: CCN(c1ccc(C(CC(=O)O)c2ccccc2)cc1NC(=O)Nc1ccc(C)cc1)C1CCOCC1]

594A. Methyl 3-(4-(ethyl(tetrahydro-2H-pyran-4-yl)amino)-3-(3-(p-tolyl)ureido)phenyl)-3-phenylpropanoate 594A was prepared using 588B and 4-methyl-1-isocyanatobenzene following the procedure described for the synthesis of 584A. LC-MS Anal. Calc'd. $C_{31}H_{37}N_3O_4$ for 515.28, found [M+H] 516.3, $T_r$=1.81 min. (Method R).

Example 594 Enantiomer 2. 3-(4-(Ethyl(tetrahydro-2H-pyran-4-yl)amino)-3-(3-(p-tolyl)ureido)phenyl)-3-phenylpropanoic acid Example 594 Enantiomer 2 was prepared utilizing compound 594A following the procedure described for the synthesis of Example 455 Enantiomer 1. LC-MS Anal. Calc'd. $C_{30}H_{35}N_3O_4$ for 501.2, found [M+H] 502.3, $T_r$=2.15 min. (Method R). $^1$H NMR (400 MHz, DMSO-$d_6$) δ 9.54 (s, 1H), 8.85 (s, 1H), 8.19 (s, 1H), 7.35-7.37 (m, 2H), 7.28-7.29 (m, 5H), 7.14-7.17 (m, 4H), 4.34 (s, 1H), 3.79-3.82 (m, 2H), 3.21-3.24 (m, 2H), 2.93-2.95 (m, 5H), 2.25 (s, 3H), 1.67-1.70 (m, 2H), 1.24-1.25 (m, 2H), 0.78 (t, J=6.80 Hz, 3H).

Examples 595 to 597

Enantiomer 2

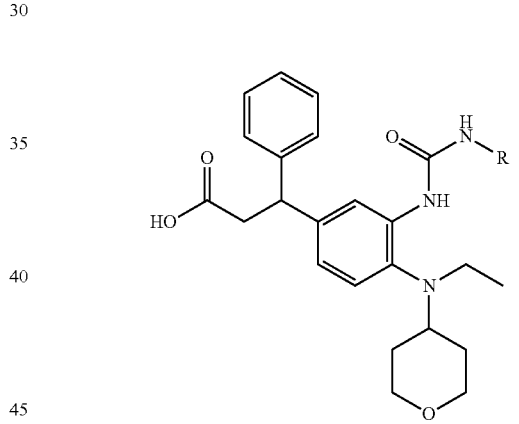

Examples 595 and 596 were prepared using 588B and corresponding isocyanates following the procedure described for the synthesis of Example 487.

Example 597 was prepared using 588B and corresponding amines following the procedure described for the synthesis of Example 488.

| Ex. No. | Name | R | $T_r$ min | Method | (M + H) |
|---|---|---|---|---|---|
| 595 | 3-(3-(3-(4-chloro-2-fluorophenyl)ureido)-4-(ethyl(tetrahydro-2H-pyran-4-yl)amino)phenyl)-3-phenylpropanoic acid | | 1.198 | O | 540.2 |

-continued

| Ex. No. | Name | R | $T_r$ min | Method | (M + H) |
|---|---|---|---|---|---|
| 596 | 3-(4-(ethyl(tetrahydro-2H-pyran-4-yl)amino)-3-(3-(2-fluoro-4-methoxyphenyl)ureido)phenyl)-3-phenylpropanoic acid | | 1.702 | O | 536.3 |
| 597 | 3-(4-(ethyl(tetrahydro-2H-pyran-4-yl)amino)-3-(3-(5-methylisoxazol-3-yl)ureido)phenyl)-3-phenylpropanoic acid | | 1.661 | O | 493.2 |

Example 598

Enantiomer 1

(S)-3-(3-((2-Ethoxypyrimidin-5-yl)amino)-4-(ethyl(tetrahydro-2H-pyran-4-yl)amino)phenyl)-4,4,4-trifluorobutanoic acid

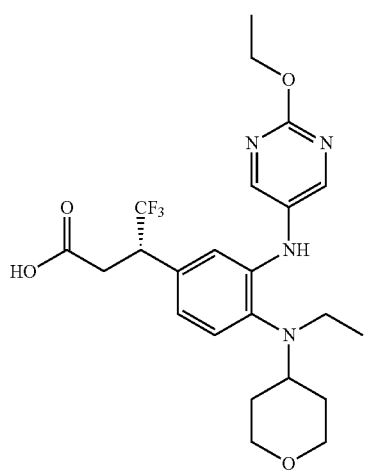

598A. Methyl (S)-3-(4-(ethyl(tetrahydro-2H-pyran-4-yl)amino)-3-nitrophenyl)-4,4,4-trifluorobutanoate 1,4-Dioxane (6 mL) was purged with argon for 10 minutes, then chlorobis (ethylene)rhodium(I) dimer (8.05 mg, 0.021 mmol) and (R)-BINAP (18.91 mg, 0.030 mmol) was added and the mixture purged with argon for another 10 minutes. To the above reaction mixture was added N-(4-(5,5-dimethyl-1,3,2-dioxaborinan-2-yl)-2-nitrophenyl)-N-ethyltetrahydro-2H-pyran-4-amine (500 mg, 1.380 mmol), (E)-methyl 4,4,4-trifluorobut-2-enoate (277 mg, 1.794 mmol) and sodium hydroxide (1.242 mL, 1.242 mmol). The resulting mixture was then purged with argon for 10 minutes. The reaction mixture was heated at 50° C. for 3 h in a sealed tube and then cooled to room temperature followed by quenching with acetic acid (0.071 mL, 1.242 mmol). Stirring was continued for 5 minutes before it was partitioned between ethyl acetate (25 ml) and water (25 mL). The aqueous layer was extracted with ethyl acetate (2×15 mL) and the combined organic layers were washed with brine (25 mL), dried over sodium sulfate, filtered and concentrated under reduced pressure. Purification via silica gel flash chromatography gave 598A (pale orange liquid, (230 mg, 0.596 mmol, 41.2%). LC-MS Anal. Calc'd. for $C_{18}H_{23}F_3N_2O_5$, 404.38, found [M+H] 405.2, $T_r$=3.12 min. (Method N).

598B. Methyl (S)-3-(3-amino-4-(ethyl(tetrahydro-2H-pyran-4-yl)amino)phenyl)-4,4,4-trifluorobutanoate 598B was prepared utilizing compound 598A following the procedure described for the synthesis of 455E. SFC chiral purity of 598B Enantiomer 1 shows 100% ee ($T_r$=1.82 min). (Method AF). LC-MS Anal. Calc'd. for $C_{18}H_{25}F_3N_2O_3$ 374.3 found [M+H] 375.2. $T_r$=3.99 min. (Method N).

598C. Methyl (S)-3-(3-((2-ethoxypyrimidin-5-yl)amino)-4-(ethyl(tetrahydro-2H-pyran-4-yl)amino)phenyl)-4,4,4-trifluorobutanoate 598C was prepared utilizing 598B and 5-bromo-2-ethoxypyrimidine following the procedure described for the synthesis of 455F. LC-MS Anal. Calc'd. for $C_{24}H_{31}F_3N_4O_4$, 496.5, found [M+H] 497.2, $T_r$=1.53 min. (Method T).

Example 598 Enantiomer 1. (S)-3-(3-((2-Ethoxypyrimidin-5-yl)amino)-4-(ethyl(tetrahydro-2H-pyran-4-yl)amino)phenyl)-4,4,4-trifluorobutanoic acid Example 598 Enantiomer 1 was prepared utilizing 598C following the procedure described for the synthesis of Example 455 Enantiomer 1. LC-MS Anal. Calc'd. for $C_{23}H_{29}F_3N_4O_4$, 482.4, found [M+H] 483.1, $T_r$=1.485 min. (Method O). $^1$H NMR (400 MHz, MeOD) δ 8.42 (s, 2H), 7.23 (d, J=8.40 Hz, 1H), 6.95 (s, 1H), 6.88 (d, J=8.00 Hz, 1H), 4.39-4.44 (m, 2H), 3.89-3.90 (m, 2H), 3.85-3.86 (m, 1H), 3.33-3.36 (m, 2H), 3.08-3.11 (m, 3H), 2.91-2.92 (m, 1H), 2.81-2.83 (m, 1H), 1.77-1.80 (m, 2H), 1.54-1.60 (m, 2H), 1.41 (t, J=7.20 Hz, 3H), 0.92 (t, J=7.20 Hz, 3H).

Example 599

Enantiomer 1

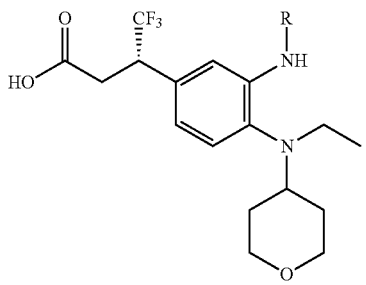

Example 599 was prepared using 598B and corresponding aryl halides (as in step 598C) following the procedure described for the synthesis of Example 598.

| Ex. No. | Name | R | $T_r$ min | Method | (M + H) |
|---|---|---|---|---|---|
| 599 | (S)-3-(4-(ethyl(tetrahydro-2H-pyran-4-yl)amino)-3-((2-methoxypyrimidin-5-yl)amino)phenyl)-4,4,4-trifluorobutanoic acid | 2-methoxypyrimidin-5-yl | 1.42 | O | 468.4 |

Example 600

Enantiomer 2

(R)-3-(3-((2-Ethoxypyrimidin-5-yl)amino)-4-(ethyl(tetrahydro-2H-pyran-4-yl)amino)phenyl)-4,4,4-trifluorobutanoic acid

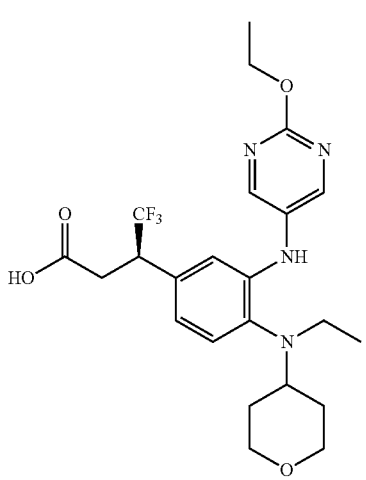

600A. Methyl (R)-3-(4-(ethyl(tetrahydro-2H-pyran-4-yl)amino)-3-nitrophenyl)-4,4,4-trifluorobutanoate 600A was prepared utilizing S-BINAP and 455C following the procedure described for the synthesis of 598A. LC-MS Anal. Calc'd. for $C_{18}H_{23}F_3N_2O_5$ 404.38, found [M+H] 405.2, $T_r$=3.5 min. (Method N).

600B. Methyl (R)-3-(3-amino-4-(ethyl(tetrahydro-2H-pyran-4-yl)amino)phenyl)-4,4,4-trifluorobutanoate 600B was prepared utilizing compound 600A following the procedure described for the synthesis of 455E. SFC chiral purity of 600B shows 100% ee ($T_r$=2.27 min). (Method AF). LC-MS Anal. Calc'd. for $C_{18}H_{25}F_3N_2O_3$, 374.3, found [M+H] 375.2, $T_r$=2.9 min. (Method N).

600C. Methyl (R)-3-(3-((2-ethoxypyrimidin-5-yl)amino)-4-(ethyl(tetrahydro-2H-pyran-4-yl)amino)phenyl)-4,4,4-trifluorobutanoate 600C was prepared utilizing compound 600B and 5-bromo-2-ethoxypyrimidine following the procedure described for the synthesis of 455F. LC-MS Anal. Calc'd. for $C_{24}H_{31}F_3N_4O_4$, 496.5, found [M+H] 497.2, $T_r$=1.53 min. (Method T).

Example 600 Enantiomer 2. (R)-3-(3-((2-Ethoxypyrimidin-5-yl)amino)-4-(ethyl(tetrahydro-2H-pyran-4-yl)amino)phenyl)-4,4,4-trifluorobutanoic acid Example 600 Enantiomer 2 was prepared utilizing compound 600C following the procedure described for the synthesis of Example 455 Enantiomer 1. LC-MS Anal. Calc'd. for $C_{23}H_{29}F_3N_4O_4$, 482.4, found [M+H] 483.1, $T_r$=1.532 min (Method O). $^1$H NMR (400 MHz, MeOD) δ 8.42 (s, 2H), 7.23 (d, J=8.40 Hz, 1H), 6.95 (s, 1H), 6.88 (d, J=8.00 Hz, 1H), 4.39-4.44 (m, 2H), 3.89-3.90 (m, 2H), 3.85-3.86 (m, 1H), 3.33-3.36 (m, 2H), 3.08-3.11 (m, 3H), 2.91-2.92 (m, 1H), 2.81-2.83 (m, 1H), 1.77-1.80 (m, 2H), 1.54-1.60 (m, 2H), 1.41 (t, J=7.20 Hz, 3H), 0.92 (t, J=7.20 Hz, 3H).

Example 601

Enantiomer 2

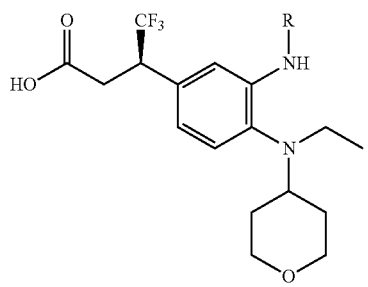

Example 601 was prepared using 600 B and corresponding aryl halides following the procedure described for the synthesis of Example 600.

| Ex. No. | Name | R | $T_r$ min | Method | (M + H) |
|---|---|---|---|---|---|
| 601 | (R)-3-(4-(ethyl(tetrahydro-2H-pyran-4-yl)amino)-3-((2-methoxypyrimidin-5-yl)amino)phenyl)-4,4,4-trifluorobutanoic acid | 2-methoxypyrimidin-5-yl (O-methyl) | 1.43 | O | 469.1 |

Example 602

Diastereomer 1 and Diastereomer 2

3-(3-((4-Cyanophenyl)amino)-4-((2S,6R)-2,6-dimethylmorpholino)phenyl)-4-methoxybutanoic acid

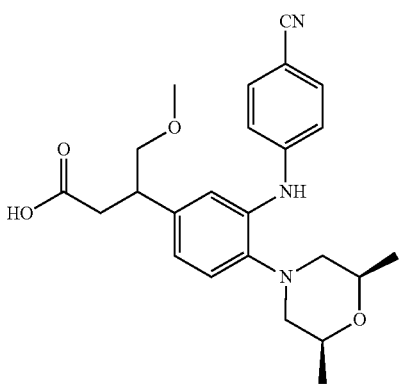 [SMILES: COCC(CC(=O)O)c1ccc(N2C[C@@H](C)O[C@@H](C)C2)c(Nc2ccc(C#N)cc2)c1]

602A. (2S,6R)-4-(4-Bromo-2-nitrophenyl)-2,6-dimethylmorpholine

To a stirred solution of 4-bromo-1-fluoro-2-nitrobenzene (5 g, 22.73 mmol) and (2S,6R)-2,6-dimethylmorpholine (2.62 g, 22.73 mmol) in NMP (10 mL) was added DIPEA (11.91 mL, 68.2 mmol). Then the reaction mixture was stirred at room temperature for 16 h. The reaction mixture was diluted with ethyl acetate (100 mL). The organic layers were then washed sequentially with 10% aq. AcOH solution, 10% $NaHCO_3$ solution, brine, dried over anhydrous sodium sulfate, filtered and concentrated under reduced pressure to give the crude material. Purification via silica gel flash chromatography gave 602A (pale orange solid, 6.2 g, 19.48 mmol, 86% yield). LCMS Anal. Calc'd. $C_{12}H_{15}BrN_2O_3$, 315.1, found [M+2H] 317.0, $T_r$=3.8 min (Method N).

602B. (2S,6R)-4-(4-(5,5-Dimethyl-1,3,2-dioxaborinan-2-yl)-2-nitrophenyl)-2,6-dimethylmorpholine To a stirred solution of 602A (6.2 g, 19.67 mmol) in DMSO (70 mL) was added bis(neopentyl glycolato)diboron (5.78 g, 25.6 mmol) and potassium acetate (5.79 g, 59.0 mmol). The above reaction mixture was purged with argon for 10 minutes. Then $PdCl_2$ (dppf).$CH_2Cl_2$ Adduct (0.482 g, 0.590 mmol) was added and the reaction mixture was purged for another 10 min. The flask was sealed and the reaction mixture heated at 80° C. and stirred for 12 hours. The reaction mixture was cooled to room temperature and then poured into water (100 mL) and extracted with EtOAc (2×75 mL). The combined organic layers were washed with brine, dried over anhydrous sodium sulfate, filtered and concentrated under reduced pressure to give the crude material. Purification via silica gel flash chromatography gave 602B (pale orange liquid, 3 g, 8.62 mmol, 43.8% yield). $^1$H NMR (400 MHz, DMSO-$d_6$) δ 8.18 (d, J=2.00 Hz, 1H), 7.84 (dd, J=10.80, 2.00 Hz, 1H), 7.02 (d, J=11.20 Hz, 1H), 3.82-3.88 (m, 2H), 3.75 (s, 4H), 3.08-3.12 (m, 2H), 2.57-2.64 (m, 2H), 1.20 (d, J=8.40 Hz, 6H), 1.01 (s, 6H).

602C. Methyl 3-(4-((2S,6R)-2,6-dimethylmorpholino)-3-nitrophenyl)-4-methoxybutanoate 602C was prepared utilizing compound 602B following the procedure described for the synthesis of 558A. LC-MS Anal. Calc'd. for $C_{18}H_{26}N_2O_6$, 366.4, found [M+H] 367.2, $T_r$=2.49 min. (Method BE).

602D. Methyl 3-(3-amino-4-((2S,6R)-2,6-dimethylmorpholino)phenyl)-4-methoxybutanoate 602D was prepared utilizing compound 602C following the procedure described for the synthesis of 455E.

Chiral separation of 602D (Method CC) gave Diastereomer 1 and Diastereomer 2.

602D Diastereomer 1 (absolute and relative stereochemistry not determined): SFC chiral purity shows 100% ee ($T_r$=4.87 min). (Method CC). LC-MS Anal. Calc'd. for $C_{18}H_{28}N_2O_4$, 336.4, found [M+H] 337.3, $T_r$=2.8 min. (Method N).

602D Diastereomer 2 (absolute and relative stereochemistry not determined): SFC chiral purity shows 100% ee (T$_r$=6.6 min). (Method CC). LC-MS Anal. Calc'd. for C$_{18}$H$_{28}$N$_2$O$_4$, 336.4, found [M+H] 337.3, T$_r$=2.3 min. (Method N).

602E. Methyl 3-(3-((4-cyanophenyl)amino)-4-((2S, 6R)-2,6-dimethylmorpholino)phenyl)-4-methoxybutanoate 602E was prepared utilizing 602D Diastereomer and 4-bromobenzonitrile following the procedure described for the synthesis of 455F. LC-MS Anal. Calc'd. for C$_{25}$H$_{31}$N$_3$O$_4$, 437.5, found [M+H] 438.2, T$_r$=1.42 min. (Method BA).

Example 602 Diastereomer 1. 3-(3-((4-Cyanophenyl)amino)-4-((2S,6R)-2,6-dimethylmorpholino)phenyl)-4-methoxybutanoic acid (absolute and relative stereochemistry not determined)

Example 602 Diastereomer 1 was prepared utilizing 602E following the procedure described for the synthesis of Example 455 Enantiomer 1. LC-MS Anal. Calc'd. for C$_{24}$H$_{29}$N$_3$O$_4$, 423.5, found [M+H] 424.3, T$_r$=1.28 min (Method O). $^1$H NMR (400 MHz, DMSO-d$_6$) δ 8.18 (s, 1H), 7.51 (d, J=8.80 Hz, 2H), 7.08 (s, 1H), 6.97 (s, 2H), 6.90 (d, J=8.80 Hz, 2H), 3.16-3.21 (m, 6H), 2.97 (d, J=10.80 Hz, 2H), 2.61-2.65 (m, 1H), 2.41-2.45 (m, 1H), 2.20-2.27 (m, 2H), 0.98-1.00 (m, 6H). (One multiplet of CH$_2$ is buried under the Solvent residual peak).

Example 602 Diastereomer 2. 3-(3-((4-Cyanophenyl)amino)-4-((2S,6R)-2,6-dimethylmorpholino)phenyl)-4-methoxybutanoic acid (absolute and relative stereochemistry not determined)

Example 602 Diastereomer 2 was prepared utilizing 602D Diastereomer 2 and 4-bromobenzonitrile following the procedure described for the synthesis of Example 455 Enantiomer 1. LC-MS Anal. Calc'd. for C$_{24}$H$_{29}$N$_3$O$_4$, 423.5, found [M+H] 424.3, T$_r$=1.28 min (Method O). $^1$H NMR (400 MHz, DMSO-d$_6$) δ 8.18 (s, 1H), 7.51 (d, J=8.80 Hz, 2H), 7.08 (s, 1H), 6.97 (s, 2H), 6.90 (d, J=8.80 Hz, 2H), 3.16-3.21 (m, 6H), 2.97 (d, J=10.80 Hz, 2H), 2.61-2.65 (m, 1H), 2.41-2.45 (m, 1H), 2.20-2.27 (m, 2H), 0.98-1.00 (m, 6H). (One multiplet of CH$_2$ is buried under the Solvent residual peak).

Example 603

Diastereomer 1

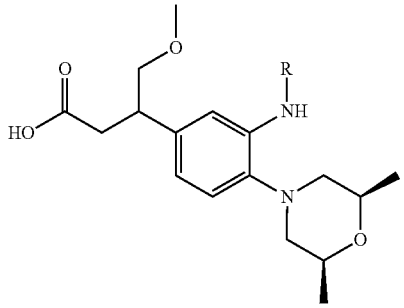

Example 603 was prepared using 602D Diastereomer 1 and corresponding aryl halides following the procedure described for the synthesis of Example 602 Diastereomer 1.

| Ex. No. | Name | R | T$_r$ min | Method | (M + H) |
|---|---|---|---|---|---|
| 603 | 3-(3-((4-chlorophenyl)amino)-4-((2S,6R)-2,6-dimethylmorpholino)phenyl)-4-methoxybutanoic acid | 4-Cl-C$_6$H$_4$- | 1.86 | O | 433.1 |

Example 604

Diastereomer 2

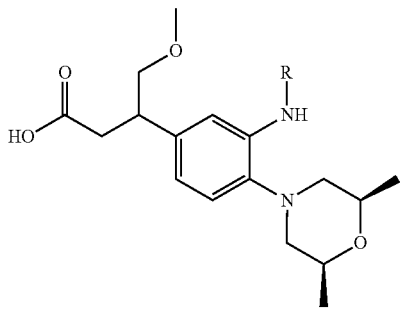

Example 604 were prepared using 602D Diastereomer 2 and corresponding aryl halides following the procedure described for the synthesis of Example 602 Diastereomer 2 (absolute and relative stereochemistry not determined).

| Ex. No. | Name | R | $T_r$ min | Method | (M + H) |
|---|---|---|---|---|---|
| 604 | 3-(3-((4-chlorophenyl)amino)-4-((2S,6R)-2,6-dimethylmorpholino)phenyl)-4-methoxybutanoic acid | 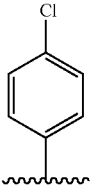 | 1.84 | O | 433.1 |

Example 605

Diastereomer 1 and Diastereomer 2

3-(3-(3-(4-Cyanophenyl)ureido)-4-((2S,6R)-2,6-dimethylmorpholino)phenyl)-4-methoxybutanoic acid

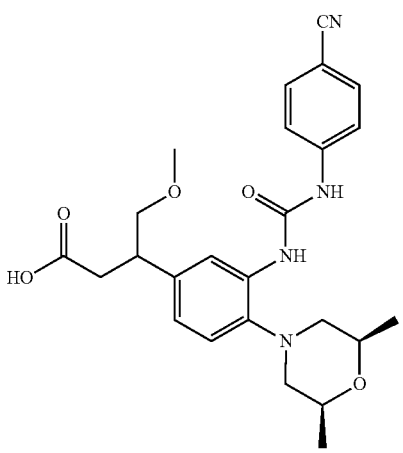 [SMILES: COCC(CC(=O)O)c1ccc(N2C[C@@H](C)O[C@@H](C)C2)c(NC(=O)Nc2ccc(C#N)cc2)c1]

605A. Ethyl 3-(4-((2S,6R)-2,6-dimethylmorpholino)-3-nitrophenyl)-4-methoxybutanoate 605A was prepared using (E)-ethyl 4-methoxybut-2-enoate following the procedure described for the synthesis of 558A. LC-MS Anal. Calc'd. for $C_{19}H_{28}N_2O_6$, 380.4, found [M+H] 381.3, $T_r$=4.089 min. (Method N).

605B. Ethyl 3-(3-amino-4-((2S,6R)-2,6-dimethylmorpholino)phenyl)-4-methoxybutanoate 605B was prepared utilizing 605A following the procedure described for the synthesis of 455E. Chiral separation of 605 B (Method CC) gave 605B Diastereomer 1 and 605B Diastereomer 2.

605B Diastereomer 1 (absolute and relative stereochemistry not determined): SFC chiral purity shows 100% ee ($T_r$=4.89 min). (Method CC). LC-MS Anal. Calc'd. for $C_{19}H_{30}N_2O_4$, 350.4, found [M+H] 351.2, $T_r$=2.66 min. (Method N).

605B Diastereomer 2 (absolute and relative stereochemistry not determined): SFC chiral purity shows 100% ee ($T_r$=6.97 min). (Method CC). LC-MS Anal. Calc'd. for $C_{19}H_{30}N_2O_4$, 350.4, found [M+H] 351.2, $T_r$=2.66 min. (Method N).

605C. Ethyl 3-(3-(3-(4-cyanophenyl)ureido)-4-((2S,6R)-2,6-dimethylmorpholino)phenyl)-4-methoxybutanoate 605C was prepared using 605B Diastereomer 1 and 4-Cyano-1-isocyanatobenzene following the procedure described for the synthesis of 487C. LC-MS Anal. Calc'd. for $C_{27}H_{34}N_4O_5$, 494.2, found [M+2H] 495.3, $T_r$=1.35 min. (Method BA).

Example 605 Diastereomer 1. 3-(3-(3-(4-Cyanophenyl)ureido)-4-((2S,6R)-2,6-dimethylmorpholino)phenyl)-4-methoxybutanoic acid (absolute and relative stereochemistry not determined)

Example 605 Diastereomer 1 was prepared utilizing compound 605C following the procedure described for the synthesis of Example 455 Enantiomer 1. LC-MS Anal. Calc'd. for $C_{25}H_{30}N_4O_5$, 466.5, found [M+H] 467.3, $T_r$=1.314 min (Method O). $^1$H NMR (400 MHz, MeOD) δ 8.05 (d, J=2.00 Hz, 1H), 7.65-7.71 (m, 4H), 7.16 (d, J=8.00 Hz, 1H), 6.97-6.99 (m, 1H), 3.95-3.99 (m, 2H), 3.53-3.57 (m, 2H), 3.33-3.38 (m, 4H), 2.77-2.86 (m, 3H), 2.55-2.61 (m, 1H), 2.42-2.48 (m, 2H), 1.19-1.21 (m, 6H).

Example 605 Diastereomer 2. 3-(3-(3-(4-Cyanophenyl)ureido)-4-((2S,6R)-2,6-dimethylmorpholino)phenyl)-4-methoxybutanoic acid (absolute and relative stereochemistry not determined)

Example 605 Diastereomer 2 was prepared utilizing compound 605B Diastereomer 2 and 4-cyano-1-isocyanatobenzene following the procedure described for the synthesis of Example 605 Diastereomer 1 by. LC-MS Anal. Calc'd. for $C_{25}H_{30}N_4O_5$, 466.5, found [M+H] 467.3, $T_r$=1.314 min. (Method O). $^1$H NMR (400 MHz, MeOD) δ 8.05 (d, J=2.00 Hz, 1H), 7.65-7.71 (m, 4H), 7.16 (d, J=8.00 Hz, 1H), 6.97-6.99 (m, 1H), 3.95-3.99 (m, 2H), 3.53-3.57 (m, 2H), 3.33-3.38 (m, 4H), 2.77-2.86 (m, 3H), 2.55-2.61 (m, 1H), 2.42-2.48 (m, 2H), 1.19-1.21 (m, 6H).

Example 606

Diastereomer 1

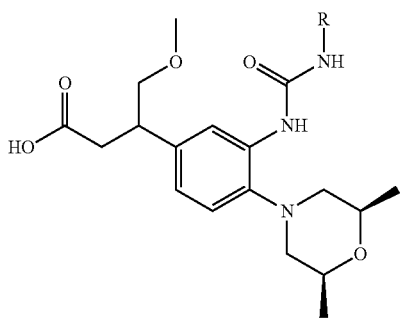

Example 606 was prepared using 605B Diastereomer 1 and corresponding isocyanate following the procedure described for the synthesis of Example 605 Diastereomer 1 (absolute and relative stereochemistry not determined).

| Ex. No. | Name | R | $T_r$ min | Method | (M + H) |
|---|---|---|---|---|---|
| 606 | 3-(3-(3-(4-chloro-2-fluorophenyl)ureido)-4-((2S,6R)-2,6-dimethylmorpholino)phenyl)-4-methoxybutanoic acid | | 1.55 | O | 494.1 |

Example 607

Diastereomer 2

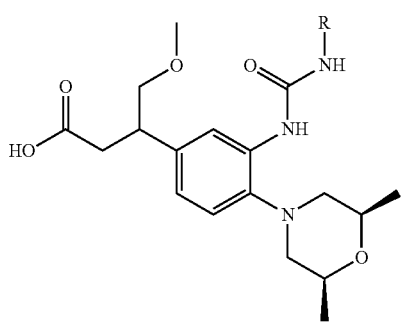

Example 607 was prepared using 605B Diastereomer 2 and corresponding isocyanates following the procedure described for the synthesis of Example 605 Diastereomer 1 (absolute and relative stereochemistry not determined).

| Ex. No. | Name | R | $T_r$ min | Method | (M + H) |
|---|---|---|---|---|---|
| 607 | 3-(3-(3-(4-chloro-2-fluorophenyl)ureido)-4-((2S,6R)-2,6-dimethylmorpholino)phenyl)-4-methoxybutanoic acid | | 1.55 | O | 494.1 |

Example 608

Racemate 3-(4-(Ethyl(tetrahydro-2H-pyran-4-yl)amino)-3-(3-(2-fluoro-4-methoxyphenyl)ureido)phenyl)pentanoic acid

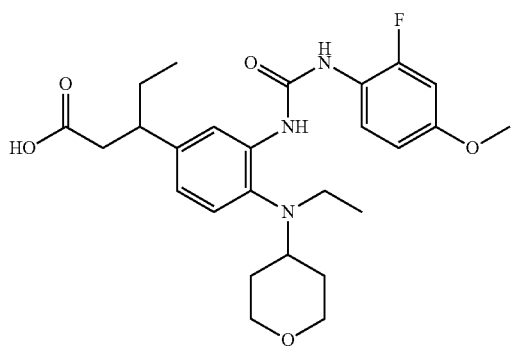 [SMILES: CCC(CC(=O)O)c1ccc(N(CC)C2CCOCC2)c(NC(=O)Nc2ccc(OC)cc2F)c1]

608A. Methyl 3-(4-(ethyl(tetrahydro-2H-pyran-4-yl)amino)-3-(3-(2-fluoro-4-methoxyphenyl)ureido)phenyl)pentanoate 608A was prepared using compound 488A and 2-fluoro-4-methoxyphenyl amine following the procedure described for the synthesis of 488B. LC-MS Anal. Calc'd. for $C_{27}H_{36}FN_3O_5$, 501.5, found [M+H] 502.4, $T_r$=3.56 min (Method N).

Example 608 3-(4-(Ethyl(tetrahydro-2H-pyran-4-yl)amino)-3-(3-(2-fluoro-4-methoxyphenyl)ureido)phenyl)pentanoic acid Example 608 was prepared as a racemate using 608A following the procedure described for the synthesis of Example 455. LC-MS Anal. Calc'd. for $C_{26}H_{34}FN_3O_5$ 487.5, found [M+H] 488.2, $T_r$=1.66 min. (Method O). $^1$H NMR (400 MHz, DMSO-$d_6$) δ 9.11 (s, 1H), 8.67 (s, 1H), 8.03 (d, J=2.00 Hz, 1H), 7.71-7.74 (m, 1H), 7.14 (d, J=8.00 Hz, 1H), 6.90 (dd, J=12.80, 2.80 Hz, 1H), 6.74-6.80 (m, 2H), 3.82 (t, J=2.80 Hz, 2H), 3.76 (s, 3H), 3.19-3.22 (m, 3H), 2.93-2.96 (m, 3H), 2.89-2.91 (m, 1H), 2.42-2.44 (m, 1H), 1.64-1.69 (m, 3H), 1.35-1.38 (m, 3H), 0.77 (t, J=7.20 Hz, 3H), 0.71 (t, J=7.20 Hz, 3H), 9.11 (s, 1H).

Example 609

Racemate 3-(3-(3-(2-Fluoro-4-methoxyphenyl)ureido)-4-(propyl(tetrahydro-2H-pyran-4-yl)amino)phenyl)pentanoic acid

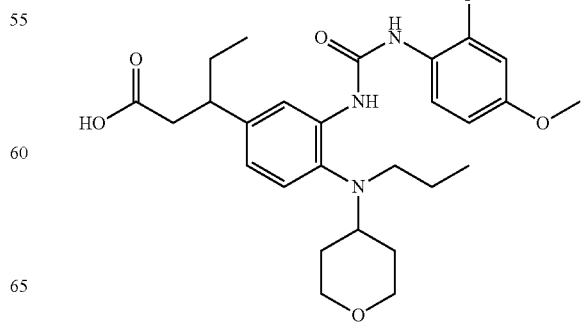

609A. Methyl 3-(3-(((4-nitrophenoxy)carbonyl) amino)-4-(propyl(tetrahydro-2H-pyran-4-yl)amino) phenyl)pentanoate 609A was prepared using compound 557B following the procedure described for the synthesis of 488A. LC-MS Anal. Calc'd. for $C_{27}H_{35}N_3O_7$, 513.5, found [M+H] 514.6, $T_r$=1.54 min (Method DM).

609B. Methyl 3-(3-(3-(2-fluoro-4-methoxyphenyl) ureido)-4-(propyl(tetrahydro-2H-pyran-4-yl)amino) phenyl)pentanoate 609B was prepared using compound 609A following the procedure described for the synthesis of 488B. LC-MS Anal. Calc'd. for $C_{28}H_{38}FN_3O_5$, 515.6, found [M+H] 516.7, $T_r$=1.37 min (Method DM).

Example 609 3-(3-(3-(2-Fluoro-4-methoxyphenyl) ureido)-4-(propyl(tetrahydro-2H-pyran-4-yl)amino) phenyl)pentanoic acid Example 609 was prepared using compound 609B as racemate following the procedure described for the synthesis of Example 455. LC-MS Anal. Calc'd. for $C_{27}H_{36}FN_3O_5$, 501.5, found [M+H] 502.2, $T_r$=1.77 min (Method O). $^1$H NMR (400 MHz, DMSO-$d_6$) δ 9.11 (s, 1H), 8.67 (s, 1H), 8.03 (d, J=2.00 Hz, 1H), 7.71-7.74 (m, 1H), 7.14 (d, J=8.00 Hz, 1H), 6.90 (dd, J=12.80, 2.80 Hz, 1H), 6.74-6.80 (m, 2H), 3.82 (t, J=2.80 Hz, 2H), 3.76 (s, 3H), 3.19-3.22 (m, 4H), 2.84-2.88 (m, 4H), 2.44-2.50 (m, 1H), 1.65-1.71 (m, 2H), 1.42-1.49 (m, 3H), 1.17-1.19 (m, 2H), 0.77 (t, J=7.20 Hz, 3H), 0.71 (t, J=7.20 Hz, 3H).

Example 610

Racemate

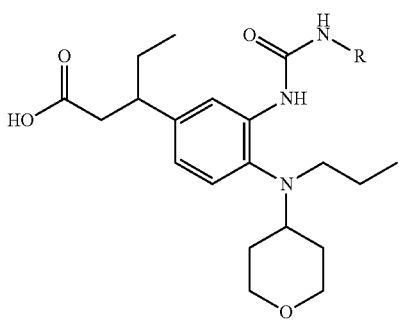

Example 610 was prepared using 609A and corresponding amine following the procedure described for the synthesis of Example 609.

Example 611

Racemate 3-(3-((5-Ethylpyrimidin-2-yl)amino)-4-(propyl(tetrahydro-2H-pyran-4-yl)amino)phenyl)pentanoic acid

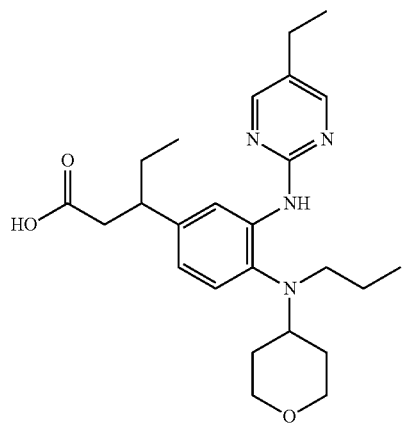 [SMILES: CCCN(c1ccc(C(CC)CC(=O)O)cc1Nc1ncc(CC)cn1)C1CCOCC1]

611A. Methyl 3-(3-((5-ethylpyrimidin-2-yl)amino)-4-(propyl(tetrahydro-2H-pyran-4-yl)amino)phenyl) pentanoate 611A was prepared utilizing compound 557B and 2-bromo-5-ethylpyrimidine following the procedure described for the synthesis of 455F. LC-MS Anal. Calc'd. for $C_{26}H_{38}N_4O_3$, 454.6, found [M+H] 455.6, $T_r$=1.34 min (Method AV).

Example 611 3-(3-((5-Ethylpyrimidin-2-yl)amino)-4-(propyl(tetrahydro-2H-pyran-4-yl)amino)phenyl) pentanoic acid Example 611 was prepared using 611A as racemate following the procedure described for the synthesis of Example 455. LC-MS Anal. Calc'd. for $C_{25}H_{36}N_4O_3$ 440.5, found [M+H] 441.3, $T_r$=1.69 min. (Method O). $^1$H NMR (400 MHz, DMSO-$d_6$) δ 8.69 (s, 1H), 8.40 (t, J=2.00 Hz, 3H), 7.18 (d, J=0.00 Hz, 1H), 6.78 (dd, J=2.00, 8.00 Hz, 1H), 3.79-3.82 (m, 2H), 3.17-3.35 (m, 5H), 2.93-2.97 (m, 5H), 2.41-2.46 (m, 3H), 1.68-1.71 (m, 3H), 1.15-1.19 (m, 5H), 0.80 (t, J=7.60 Hz, 3H), 0.72 (t, J=7.20 Hz, 3H).

| Ex. No. | Name | R | $T_r$ min | Method | (M + H) |
|---|---|---|---|---|---|
| 610 | 3-(3-(3-(2-methylpyrimidin-5-yl)ureido)-4-(propyl(tetrahydro-2H-pyran-4-yl)amino)phenyl)pentanoic acid | | 1.25 | O | 470.2 |

Example 612

Enantiomer 1 and Enantiomer 2

3-(3-((4-Chlorophenyl)amino)-4-(ethyl(tetrahydro-2H-pyran-4-yl)amino)phenyl)butanoic acid

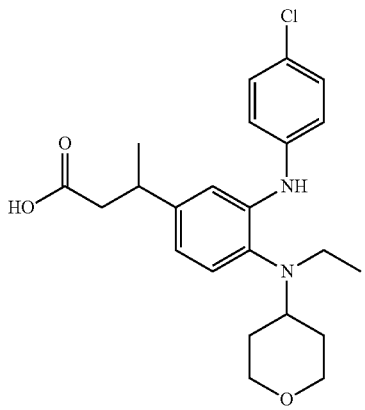 [SMILES: CCN(c1ccc(C(C)CC(=O)O)cc1Nc1ccc(Cl)cc1)C1CCOCC1]

612A. Methyl 3-(4-(ethyl(tetrahydro-2H-pyran-4-yl)amino)-3-nitrophenyl)butanoate In a pressure tube equipped with Teflon cap 455C (5 g, 13.80 mmol), 1,4-dioxane (50 ml) were added followed by sodium hydroxide (12.42 ml, 12.42 mmol). To it argon gas was passed through for 15 mins and then methyl crotonate (4.39 ml, 41.4 mmol) and chloro(1,5-cyclooctadiene)rhodium(I) dimer (0.340 g, 0.690 mmol) were added at room temperature. Argon gas was further passed through it for 5 mins. It was then screw-capped and heated at 50° C. for 2 h. The reaction mixture was cooled to room temperature, quenched with acetic acid (0.790 mL, 13.80 mmol) and was stirred for 5 mins before it was diluted with water (100 mL). The aqueous layers were extracted with ethyl acetate (3×100 mL). The combined organic layers were washed with water (50 mL), brine (50 mL), dried over anhydrous sodium sulfate, filtered and concentrated under reduced pressure to afford the crude material. The crude material was purified by flash silica gel column chromatography to afford 612A (orange oil, 3.5 g, 8.99 mmol, 65.1% yield). LC-MS Anal. Calc'd. for $C_{18}H_{26}N_2O_5$, 350.184, found [M+H] 351.2, $T_r$=2.874 min (Method U).

612B. Methyl 3-(3-amino-4-(ethyl(tetrahydro-2H-pyran-4-yl)amino)phenyl)butanoate The solution of 612A (3 g, 8.56 mmol) in ethyl acetate (30 mL) was charged to a sealable hydrogen flask. The solution was sequentially evacuated and purged with nitrogen gas. To this 10% Pd—C (0.15 g, 0.141 mmol) was added under nitrogen atmosphere. The reaction mixture was stirred under pressurized 40 psi of hydrogen atmosphere at room temperature for 2 h. The reaction mixture was filtered through a CELITE® pad and the residue on the pad was thoroughly rinsed with ethyl acetate (75 mL). The combined filtrate was concentrated under reduced pressure to afford racemate (brown oil, 2.2 g, 6.85 mmol, 80.29%). LC-MS Anal. Calc'd. for $C_{18}H_{28}N_2O_3$ 320.210, found [M+H] 321.2, $T_r$=2.750 min (Method U).

Chiral separation of 612B racemate gave 612B Enantiomer 1 and 612B Enantiomer 2 (Method BM).

612B Enantiomer 1 (brown oil, 881 mg, 2.69 mmol, 31.5%) $T_r$=3.75 min. (Method BM). LC-MS Anal. Calc'd. for $C_{18}H_{28}N_2O_3$, 320.210, found [M+H] 321.4, $T_r$=2.576 min (Method U).

612B Enantiomer 2 (brown oil, 890 mg, 2.75 mmol, 31.5%) $T_r$=7.15 min. (Method BM). LC-MS Anal. Calc'd. for $C_{18}H_{28}N_2O_3$, 320.210, found [M+H] 321.4, $T_r$=2.750 min (Method U).

612C. Methyl 3-(3-((4-chlorophenyl)amino)-4-(ethyl(tetrahydro-2H-pyran-4-yl)amino)phenyl)butanoate The mixture of 612B Enantiomer 1 (40 mg, 0.125 mmol), 1-bromo-4-chlorobenzene (23.90 mg, 0.125 mmol), Xantphos (14.45 mg, 0.025 mmol) and $Cs_2CO_3$ (102 mg, 0.312 mmol) in 1,4-dioxane (2 mL) was stirred for 5 minutes. Argon gas was bubbled through the mixture for 5 mins. Bis(dibenzylideneacetone)palladium (3.59 mg, 6.24 μmol) was added and argon gas was bubbled through the mixture for 5 mins. The reaction mixture was sealed and placed in preheated oil bath at 110° C. for 16 h. The reaction mixture was cooled to room temperature and concentrated under reduced pressure to afford a residue. The residue was reconstituted in a mixture of ethyl acetate (25 mL) and water (15 mL). The organic layer was separated and aqueous layer was extracted with ethyl acetate (2×25 mL). The combined organic layers were washed with water (15 mL), brine (15 mL), dried over anhydrous sodium sulfate, filtered and concentrated under reduced pressure to afford a residue. The residue was purified via flash silica gel column chromatography to afford 612C (yellow oil, 50 mg, 0.075 mmol, 60.4% yield). LC-MS Anal. Calc'd. for $C_{24}H_{31}ClN_2O_3$, 430.202, found [M+H] 431.4, $T_r$=3.934 min (Method U).

Example 612 Enantiomer 1. 3-(3-((4-Chlorophenyl)amino)-4-(ethyl(tetrahydro-2H-pyran-4-1)amino)phenyl)butanoic acid To a stirred solution of 612C (50 mg, 0.116 mmol) in a mixture of THF (0.5 ml), methanol (1 ml) and water (0.25 mL) was added $LiOH.H_2O$ (13.89 mg, 0.580 mmol). The reaction mixture was stirred at room temperature for 3 h. The reaction mixture was concentrated under reduced pressure. The aqueous residue was acidified with saturated citric acid solution to pH~3-4. The aqueous layer was diluted with water (10 mL) and extracted with ethyl acetate (2×10 mL). The combined organic layers were washed with water (10 mL), brine (10 mL), dried over anhydrous sodium sulfate and concentrated under reduced pressure to afford a residue. The residue was purified via preparative LCMS to afford Example 612 Enantiomer 1 (absolute stereochemistry not determined) (pale yellow solid, 5.9 mg, 0.014 mmol, 11.71% yield). LC-MS Anal. Calc'd. for $C_{23}H_{29}ClN_2O_3$, 416.187, found [M+H] 417.2, $T_r$=2.019 min (Method O). $^1H$ NMR (400 MHz, $CD_3OD$) δ 7.23-7.26 (m, 2H), 7.11-7.18 (m, 4H), 6.79-6.82 (m, 1H), 3.88-3.91 (m, 2H), 3.29-3.37 (m, 2H), 3.17-3.19 (m, 1H), 3.02-3.08 (m, 3H), 2.55-2.57 (m, 2H), 1.76-1.79 (m, 2H), 1.42-1.52 (m, 2H), 1.30 (d, J=7.20 Hz, 3H), 0.90 (t, J=7.2 Hz, 3H).

Example 612 Enantiomer 2. 3-(3-((4-Chlorophenyl)amino)-4-(ethyl(tetrahydro-2H-pyran-4-1)amino)phenyl)butanoic acid Example 612 Enantiomer 2 (absolute stereochemistry not determined) was prepared utilizing 612B Enantiomer 2 and 1-bromo-4-chlorobenzene following the procedure described for the synthesis of Example 612 Enantiomer 1. LC-MS Anal. Calc'd. for $C_{23}H_{29}ClN_2O_3$, 416.187, found [M+H] 417.2, $T_r$=2.019 min (Method O). $^1H$ NMR (400 MHz, $CD_3OD$) δ 7.23-7.26 (m, 2H), 7.11-7.18 (m, 4H), 6.79-6.82 (m, 1H), 3.88-3.91 (m, 2H), 3.29-3.37 (m, 2H), 3.17-3.19 (m, 1H), 3.02-3.08 (m, 3H), 2.55-2.57 (m, 2H), 1.76-1.79 (m, 2H), 1.53-1.54 (m, 2H), 1.30 (d, J=6.80 Hz, 3H), 0.90 (t, J=7.2 Hz, 3H).

Examples 613 to 623

Enantiomer 1

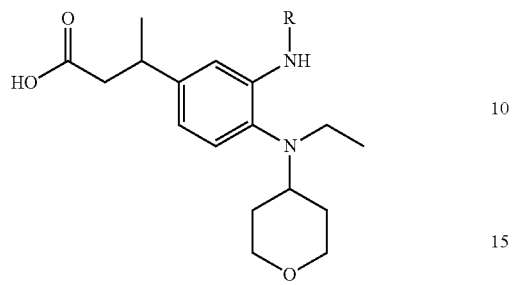

Examples 613 to 623 were prepared using 612B Enantiomer 1 and corresponding halides following the procedure described for the synthesis of Example 612 (absolute stereochemistry not determined).

| Ex. No. | Name | R | $T_R$ (min) Method O | $[M + H]^+$ |
|---|---|---|---|---|
| 613 | 3-(3-((4-cyanophenyl)amino)-4-(ethyl(tetrahydro-2H-pyran-4-yl)amino)phenyl)butanoic acid | 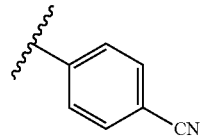 [SMILES: *c1ccc(C#N)cc1] | 1.637 | 408.2 |
| 614 | 3-(3-((2-(cyclopropylmethoxy)pyrimidin-5-yl)amino)-4-(ethyl(tetrahydro-2H-pyran-4-yl)amino)phenyl)butanoic acid | 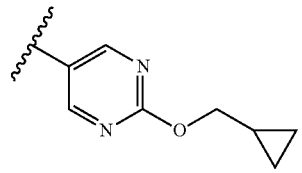 [SMILES: *c1cnc(OCC2CC2)nc1] | 1.703 | 455.3 |
| 615 | 3-(4-(ethyl(tetrahydro-2H-pyran-4-yl)amino)-3-((4-fluorophenyl)amino)phenyl)butanoic acid | 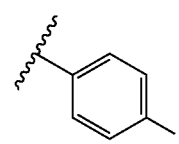 | 1.857 | 401.2 |
| 616 | 3-(3-((2,2-difluorobenzo[d][1,3]dioxol-5-yl)amino)-4-(ethyl(tetrahydro-2H-pyran-4-yl)amino)phenyl)butanoic acid | 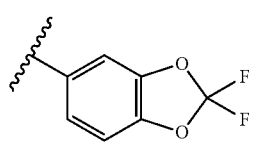 [SMILES: *c1ccc2c(c1)OC(F)(F)O2] | 2.116 | 463.2 |
| 617 | 3-(4-(ethyl(tetrahydro-2H-pyran-4-yl)amino)-3-((2-methylbenzo[d]thiazol-6-yl)amino)phenyl)butanoic acid | 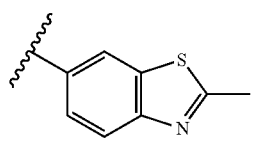 [SMILES: *c1ccc2nc(C)sc2c1] | 1.778 | 454.2 |

-continued

| Ex. No. | Name | R | T$_R$ (min) Method O | [M + H]$^+$ |
|---|---|---|---|---|
| 618 | 3-(3-((5-ethoxypyrazin-2-yl)amino)-4-(ethyl(tetrahydro-2H-pyran-4-yl)amino)phenyl)butanoic acid | | 1.711 | 429.1 |
| 619 | 3-(3-((2-ethoxypyrimidin-5-yl)amino)-4-(ethyl(tetrahydro-2H-pyran-4-yl)amino)phenyl)butanoic acid | | 1.630 | 429.3 |
| 620 | 3-(4-(ethyl(tetrahydro-2H-pyran-4-yl)amino)-3-((2-methoxypyrimidin-5-yl)amino)phenyl)butanoic acid | | 1.393 | 415.2 |
| 621 | 3-(4-(ethyl(tetrahydro-2H-pyran-4-yl)amino)-3-((2-propoxypyrimidin-5-yl)amino)phenyl)butanoic acid | | 1.444 | 443.4 |
| 622 | 3-(4-(ethyl(tetrahydro-2H-pyran-4-yl)amino)-3-((2-isopropoxypyrimidin-5-yl)amino)phenyl)butanoic acid | | 1.419 | 443.4 |
| 623 | 3-(4-(ethyl(tetrahydro-2H-pyran-4-yl)amino)-3-((2-methylpyrimidin-5-yl)amino)phenyl)butanoic acid | | 1.264 | 399.2 |
| 624 | 3-(3-((6-ethoxypyridazin-3-yl)amino)-4-(ethyl(tetrahydro-2H-pyran-4-yl)amino)phenyl)butanoic acid | | 1.561 | 429.1 |

Examples 625 to 636

Enantiomer 2

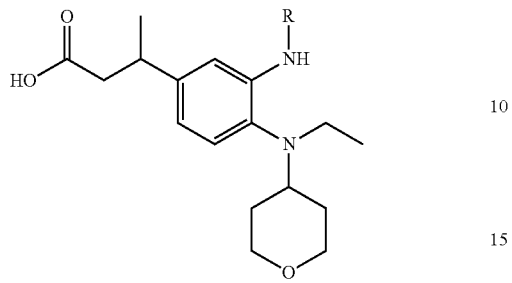

Examples 625 to 636 were prepared using 612B Enantiomer 2 and corresponding halides following the procedure described for the synthesis of Example 612 (absolute stereochemistry not determined).

| Ex. No. | Name | R | $T_R$ (min) Method O | [M + H]$^+$ |
|---|---|---|---|---|
| 625 | 3-(3-((4-cyanophenyl)amino)-4-(ethyl(tetrahydro-2H-pyran-4-yl)amino)phenyl)butanoic acid | | 1.691 | 408.2 |
| 626 | 3-(3-((2-(cyclopropylmethoxy)pyrimidin-5-yl)amino)-4-(ethyl(tetrahydro-2H-pyran-4-yl)amino)phenyl)butanoic acid | | 1.734 | 455.2 |
| 627 | 3-(4-(ethyl(tetrahydro-2H-pyran-4-yl)amino)-3-((4-fluorophenyl)amino)phenyl)butanoic acid | | 1.861 | 401.2 |
| 628 | 3-(3-((2,2-difluorobenzo[d][1,3]dioxol-5-yl)amino)-4-(ethyl(tetrahydro-2H-pyran-4-yl)amino)phenyl)butanoic acid | | 2.119 | 463.2 |
| 629 | 3-(4-(ethyl(tetrahydro-2H-pyran-4-yl)amino)-3-((2-methylbenzo[d]thiazol-6-yl)amino)phenyl)butanoic acid | | 1.780 | 454.2 |
| 630 | 3-(3-((5-ethoxypyrazin-2-yl)amino)-4-(ethyl(tetrahydro-2H-pyran-4-yl)amino)phenyl)butanoic acid | | 3.677 | 429.1 |

| Ex. No. | Name | R | T$_R$ (min) Method O | [M + H]$^+$ |
|---|---|---|---|---|
| 631 | 3-(3-((6-ethoxypyridazin-3-yl)amino)-4-(ethyl(tetrahydro-2H-pyran-4-yl)amino)phenyl)butanoic acid | 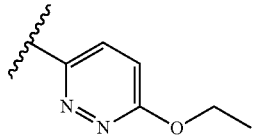 [SMILES: *c1ccc(OCC)nn1] | 1.553 | 429.1 |
| 632 | 3-(3-((2-ethoxypyrimidin-5-yl)amino)-4-(ethyl(tetrahydro-2H-pyran-4-yl)amino)phenyl)butanoic acid | 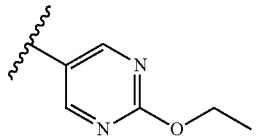 [SMILES: *c1cnc(OCC)nc1] | 1.630 | 429.2 |
| 633 | 3-(4-(ethyl(tetrahydro-2H-pyran-4-yl)amino)-3-((2-methoxypyrimidin-5-yl)amino)phenyl)butanoic acid | 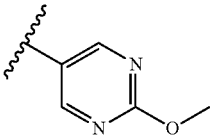 [SMILES: *c1cnc(OC)nc1] | 1.393 | 415.2 |
| 634 | 3-(4-(ethyl(tetrahydro-2H-pyran-4-yl)amino)-3-((2-propoxypyrimidin-5-yl)amino)phenyl)butanoic acid | 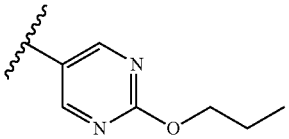 [SMILES: *c1cnc(OCCC)nc1] | 1.432 | 443.3 |
| 635 | 3-(4-(ethyl(tetrahydro-2H-pyran-4-yl)amino)-3-((2-isopropoxypyrimidin-5-yl)amino)phenyl)butanoic acid | 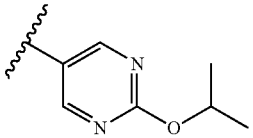 [SMILES: *c1cnc(OC(C)C)nc1] | 1.415 | 443.4 |
| 636 | 3-(4-(ethyl(tetrahydro-2H-pyran-4-yl)amino)-3-((2-methylpyrimidin-5-yl)amino)phenyl)butanoic acid | 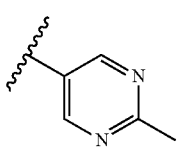 [SMILES: *c1cnc(C)nc1] | 1.259 | 399.2 |

Example 637

Enantiomer 1 and Enantiomer 2

3-(3-(3-(4-Chloro-2-fluorophenyl)ureido)-4-(ethyl (tetrahydro-2H-pyran-4-yl)amino)phenyl)butanoic acid

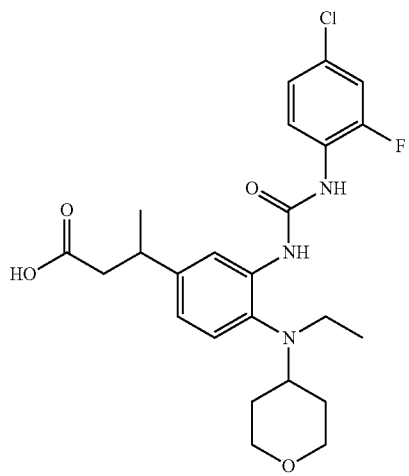 [SMILES: CCN(c1ccc(C(C)CC(=O)O)cc1NC(=O)Nc1ccc(Cl)cc1F)C1CCOCC1]

637A. Methyl 34343-(4-chloro-2-fluorophenyl) ureido)-4-(ethyl(tetrahydro-2H-pyran-4-yl)amino) phenyl)butanoate To a stirred solution of 612B Enantiomer 1 (40 mg, 0.125 mmol) in dichloromethane (4 mL), 4-chloro-2-fluoro-1-isocyanatobenzene (27.8 mg, 0.162 mmol) was added and it was stirred for 12 h. The reaction mass was concentrated under reduced pressure to afford 637A (pale yellow solid, 40 mg, 0.069 mmol, 55.4%). LC-MS Anal. Calc'd. for $C_{25}H_{31}ClFN_3O_4$, 491.199, found [M+H] 492.2, $T_r$=3.479 min (Method U).

Example 637 Enantiomer 1. 3-(3-(3-(4-Chloro-2-fluorophenyl)ureido)-4-(ethyl(tetrahydro-2H-pyran-4-yl)amino)phenyl)butanoic acid To a stirred solution 637A (40 mg, 0.081 mmol) in mixture of THF (0.5 ml), methanol (1 ml) and water (0.25 mL) was added LiOH.H₂O (12.17 mg, 0.508 mmol). The reaction mixture was stirred at room temperature for 3 h. The reaction mixture was concentrated under reduced pressure. The aqueous residue was acidified with saturated citric acid solution to pH~3-4. The aqueous layer was diluted with water (10 mL) and extracted with ethyl acetate (2×10 mL). The combined organic layers were washed with water (10 mL), brine 10 mL), dried over anhydrous sodium sulfate, filtered and concentrated under reduced pressure to afford a residue which was purified via preparative LCMS to afford Example 637 Enantiomer 1 (absolute stereochemistry not determined) (pale yellow solid, 18.6 mg, 0.039 mmol, 38.3% yield). LC-MS Anal. Calc'd. for $C_{24}H_{29}ClFN_3O_4$, 477.183, found [M+H] 478.2, $T_r$=1.757 min (Method O). ¹H NMR (400 MHz, CD₃OD) δ 8.09-8.10 (m, 1H), 8.04-8.07 (m, 1H), 7.24-7.27 (m, 1H), 7.17-7.21 (m, 2H), 6.94-6.96 (m, 1H), 3.91-3.94 (m, 2H), 3.32-3.41 (m, 2H), 3.17-3.30 (m, 1H), 3.04-3.09 (m, 3H), 2.56-2.62 (m, 2H), 1.77-1.80 (m, 2H), 1.53-1.54 (m, 2H), 1.329 (d, J=6.8 Hz, 3H), 0.89 (t, J=7.2 Hz, 3H).

Example 637 Enantiomer 2. 3-(3-(3-(4-Chloro-2-fluorophenyl)ureido)-4-(ethyl(tetrahydro-2H-pyran-4-yl)amino)phenyl)butanoic acid Example 637 Enantiomer 2 (absolute stereochemistry not determined) was synthesized using 612B Enantiomer 2 and 4-chloro-2-fluoro-1-isocyanatobenzene following the procedure described for the synthesis of Example 637 Enantiomer 1. LC-MS Anal. Calc'd. for $C_{24}H_{29}ClFN_3O_4$, 477.183, found [M+H] 478.2, $T_r$=1.760 min (Method O). ¹H NMR (400 MHz, DMSO-d₆) δ 8.10-8.10 (m, 1H), 8.04-8.07 (m, 1H), 7.24-7.27 (m, 1H), 7.17-7.21 (m, 2H), 6.94-6.96 (m, 1H), 3.91-3.94 (m, 2H), 3.32-3.41 (m, 2H), 3.17-3.30 (m, 1H), 3.04-3.09 (m, 3H), 2.56-2.62 (m, 2H), 1.77-1.80 (m, 2H), 1.49-1.51 (m, 2H), 1.329 (d, J=6.8 Hz, 3H), 0.89 (t, J=7.2 Hz, 3H).

Examples 638 and 639

Enantiomer 1

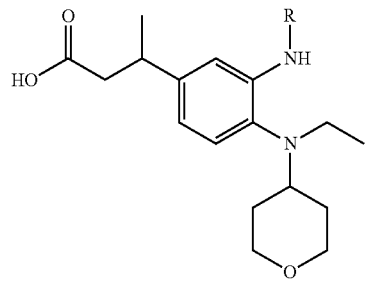

Examples 638 and 639 were prepared using 612B Enantiomer 1 and corresponding isocyanates following the procedure described for the synthesis of Example 637 (absolute stereochemistry not determined).

| Ex. No. | Name | R | $T_R$ (min) Method O | [M + H]⁺ |
|---|---|---|---|---|
| 638 | 3-(4-(ethyl(tetrahydro-2H-pyran-4-yl)amino)-3-(3-(2-fluorophenyl)ureido)phenyl) butanoic acid | ![R group with 2-fluorophenyl urea] | 1.491 | 444.2 |
| 639 | 3-(4-(ethyl(tetrahydro-2H-pyran-4-yl)amino)-3-(3-(p-tolyl)ureido)phenyl)butanoic acid | ![R group with p-tolyl urea] | 1.584 | 440.2 |

Examples 640 and 641

Enantiomer 2

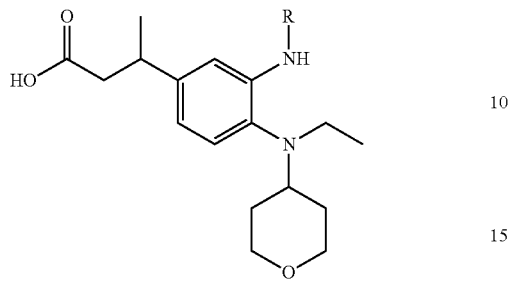

Examples 640 and 641 were prepared following the procedure for Example 637 Enantiomer 1 by using 612B Enantiomer 2 and corresponding isocyanates (absolute stereochemistry not determined).

| Ex. No. | Name | R | $T_R$ (min) Method O | $[M + H]^+$ |
|---|---|---|---|---|
| 640 | 3-(4-(ethyl(tetrahydro-2H-pyran-4-yl)amino)-3-(3-(2-fluorophenyl)ureido)phenyl)butanoic acid | | 1.495 | 444.2 |
| 641 | 3-(4-(ethyl(tetrahydro-2H-pyran-4-yl)amino)-3-(3-(p-tolyl)ureido)phenyl)butanoic acid | | 1.577 | 440.3 |

Examples 642 to 648

Enantiomer 1

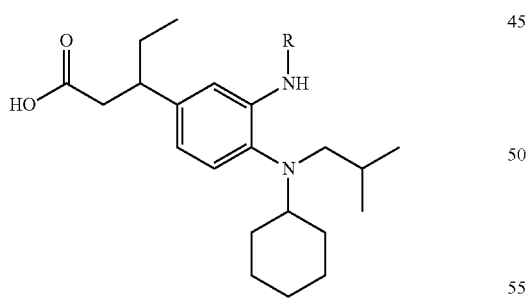

Examples 642 to 648 were prepared using enantiomerically pure 3-(3-amino-4-(cyclohexyl(isobutyl)amino)phenyl)pentanoate. (Racemic 3-(3-amino-4-(cyclohexyl(isobutyl)amino)phenyl)pentanoate 1073D was separated into individual antipodes by preparative chiral SFC on a CHIRALPAK® IC column with 10% acetonitrile/$CO_2$ (first peak, $T_R$=3.51 min on a 250 mm×4.6 mm CHIRALPAK® IC column with 3 g/min acetonitrile/$CO_2$, absolute stereochemistry unknown)) and the corresponding aryl halides following the procedure described for the synthesis of Example 299.

| Ex. No. | Name | R | T_R (min) Method O | [M + H]+ |
|---|---|---|---|---|
| 642 | 3-(3-((4-chloro-3-(difluoromethoxy)phenyl)amino)-4-cyclohexyl(isobutyl)amino)phenyl)pentanoic acid | 3-(difluoromethoxy)-4-chlorophenyl ether | 3.147 | 523.3 |
| 643 | 3-(3-((4-chloro-3-(2,2-difluoroethoxy)phenyl)amino)-4-(cyclohexyl(isobutyl)amino)phenyl)pentanoic acid | 3-(2,2-difluoroethoxy)-4-chlorophenyl | 2.521 | 537.3 |
| 644 | 3-(3-((4-chloro-3-(2,2,2-trifluoroethoxy)phenyl)amino)-4-(cyclohexyl(isobutyl)amino)phenyl)pentanoic acid | 3-(2,2,2-trifluoroethoxy)-4-chlorophenyl | 2.677 | 555.2 |
| 645 | 3-(3-((4-chloro-3-(cyclopropylmethoxy)phenyl)amino)-4-(cyclohexyl(isobutyl)amino)phenyl)pentanoic acid | 3-(cyclopropylmethoxy)-4-chlorophenyl | 3.231 | 527.3 |
| 646 | 3-(3-((4-chloro-3-ethoxyphenyl)amino)-4-(cylcohexyl(isobutyl)amino)phenyl)pentanoic acid | 3-ethoxy-4-chlorophenyl | 3.188 | 501.3 |
| 647 | 3-(4-(cyclohexyl(isobutyl)amino)-3-((2-propoxypyrimidin-5-yl)amino)phenyl)pentanoic acid | 2-propoxypyrimidin-5-yl | 2.894 | 483.3 |
| 648 | 3-(4-(cyclohexyl(isobutyl)amino)-3-((2-isopropoxypyrimidin-5-yl)amino)phenyl)pentanoic acid | 2-isopropoxypyrimidin-5-yl | 2.821 | 483.4 |

Examples 649 to 655

Enantiomer 2

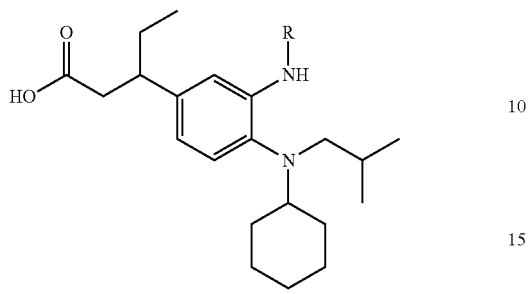

Examples 649 to 655 were prepared using enantiomerically pure 3-(3-amino-4-(cyclohexyl(isobutyl)amino)phenyl)pentanoate (Racemic 3-(3-amino-4-(cyclohexyl(isobutyl)amino)phenyl)pentanoate 1073D was separated into individual antipodes by preparative chiral SFC on a CHIRALPAK® IC column with 10% acetonitrile/$CO_2$ (second peak, $T_R$=4.63 min on a 250 mm×4.6 mm CHIRALPAK® IC column with 3 g/min acetonitrile/$CO_2$, absolute stereochemistry unknown)) and the corresponding aryl halides following the procedure described for the synthesis of Example 299.

| Ex. No. | Name | R | $T_R$ (min) Method O | [M + H]⁺ |
|---|---|---|---|---|
| 649 | 3-(3-((4-chloro-3-(difluoromethoxy)phenyl)amino)-4-cyclohexyl(isobutyl)amino)phenyl)pentanoic acid | | 3.145 | 523.3 |
| 650 | 3-(3-((4-chloro-3-(2,2-difluoroethoxy)phenyl)amino)-4-(cyclohexyl(isobutyl)amino)phenyl)pentanoic acid | | 2.521 | 537.3 |
| 651 | 3-(3-((4-chloro-3-(2,2,2-trifluoroethoxy)phenyl)amino)-4-(cyclohexyl(isobutyl)maino)phenyl)pentanoic acid | | 2.677 | 555.2 |
| 652 | 3-(3-((4-chloro-3-(cyclopropylmethoxy)phenyl)amino)-4-(cyclohexyl(isobutyl)amino)phenyl)pentanoic acid | | 3.231 | 527 |
| 653 | 3-(3-((4-chloro-3-ethoxyphenyl)amino)-4-(cyclohexyl)isobutyl)amino)phenyl)pentanoic acid | | 3.188 | 501.3 |

| Ex. No. | Name | R | $T_R$ (min) Method O | $[M + H]^+$ |
|---|---|---|---|---|
| 654 | 3-(4-(cyclohexyl(isobutyl)amino)-3-((2-propoxypyrimidin-5-yl)amino)phenyl)pentanoic acid | pyrimidine with 2-propoxy | 2.825 | 483.4 |
| 655 | 3-(4-(cyclohexyl(isobutyl)amino)-3-((2-isopropoxypyrimidin-5-yl)amino)phenyl)pentanoic acid | pyrimidine with 2-isopropoxy | 2.821 | 483.3 |

Example 656

Enantiomer 1 and Enantiomer 2

3-(3-((4-Chlorophenyl)amino)-4-((cyclopropylmethyl)(propyl)amino)phenyl)pentanoic acid

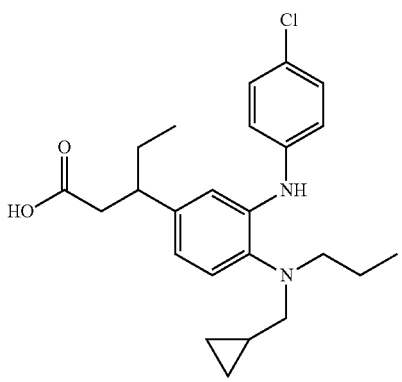 [SMILES: CCCN(CC1CC1)c1ccc(C(CC)CC(=O)O)cc1Nc1ccc(Cl)cc1]

656A. 4-Bromo-N-(cyclopropylmethyl)-2-nitro-N-propylaniline

In a pressure tube equipped with a Teflon cap, 4-bromo-1-fluoro-2-nitrobenzene (7 g, 31.8 mmol) and N-methyl-2-pyrrolidone (20 mL) were added followed by N-(cyclopropylmethyl)propan-1-amine (3.60 g, 31.8 mmol) and DIPEA (16.67 mL, 95 mmol) and the tube was screw-capped and heated to 120° C. for 16 h. The reaction mixture was extracted with diethyl ether (3×50 mL) and water (50 ml). The combined organic layers were washed with brine solution (2×50 mL), dried over sodium sulfate, filtered and concentrated under reduced pressure to get the crude which was purified by flash silica gel column chromatography to afford 656A (brown oil, 8.458 g, 14.31 mmol, 45.0% yield). LC-MS Anal. Calc'd. for $C_{13}H_{17}BrN_2O_2$, 312.047, found [M+2H] 315.2, $T_r$=3.830 min (Method U).

656B. N-(Cyclopropylmethyl)-4-(5,5-dimethyl-1,3,2-dioxaborinan-2-yl)-2-nitro-N-propylaniline The mixture of 656A (2.171 g, 9.61 mmol) and potassium acetate (2.122 g, 21.62 mmol) in 1,4-dioxane (15 mL) was stirred at room temperature. Argon gas was bubbled through the mixture for 5 min. [1,1'-Bis(diphenylphosphino)ferrocene]dichloropalladium (II) (0.176 g, 0.240 mmol) was added and argon gas was bubbled through the mixture for another 5 min. The reaction mixture was heated at 90° C. for 5 h. The reaction mixture was cooled to room temperature and diluted with ethyl acetate (100 mL). The organic layers were washed with water (50 mL), dried over anhydrous sodium sulfate, filtered and concentrated under reduced pressure to afford a residue. The residue was purified via flash silica gel column chromatography to afford 656B (orange oil, 1.117 g, 3.23 mmol, 67.1%). LC-MS Anal. Calc'd. for $C_{18}H_{27}N_2O_4$, 346.206, found [M-68] 279.2, for parent boronic acid, $T_r$=2.715 min (Method U).

656C. Methyl 3-(4-((cyclopropylmethyl)(propyl)amino)-3-nitrophenyl)pentanoate In a pressure tube equipped with Teflon cap, 656B (2 g, 5.78 mmol), 1,4-dioxane (20 mL) and NaOH (5.27 mL, 5.27 mmol) were added. Argon gas was bubbled through the mixture for 10 min and chloro(1,5-cyclooctadiene)rhodium (I) dimer (0.142 g, 0.289 mmol) and methyl 2-pentenoate (1.978 g, 17.33 mmol) were added at room temperature. Argon gas was bubbled through the mixture for another 5 min. The tube was then screw-capped and heated at 50° C. for 2 h. The reaction mixture was cooled to room temperature, quenched with acetic acid (0.331 mL, 5.78 mmol) and was stirred for 5 min before it was diluted with water (50 mL). The aqueous layer was extracted with ethyl acetate (3×50 mL). The combined organic layers were washed with water (50 mL), brine (50 mL), dried over anhydrous sodium sulfate, filtered and concentrated under reduced pressure to afford a residue. The residue was purified via flash silica gel column chromatography to afford 656C (orange liquid, 1.978 g, 5.39 mmol, 74.7% yield). LC-MS Anal. Calc'd. for $C_{19}H_{28}N_2O_4$, 348.205, found [M+H] 349.2, $T_r$=3.616 min (Method U).

656D. Methyl 3-(3-amino-4-((cyclopropylmethyl)(propyl)amino)phenyl)pentanoate The solution 656C in ethyl acetate (50 mL) was charged to a sealable hydrogen flask. The solution was sequentially evacuated and purged with nitrogen gas. To this 10% Pd on carbon (200 mg, 1.879 mmol) was added under nitrogen atmosphere. The reaction mixture was stirred under pressurized 40 psi hydrogen atmosphere at room temperature for 1 h. The reaction mixture was filtered through a CELITE® pad and the residue on the pad was thoroughly rinsed with ethyl acetate (3×25 mL). The combined filtrate was concentrated under reduced pressure to afford 656D racemate (brown oil, 1.3 g, 4.08 mmol, 74.9% yield). LC-MS Anal. Calc'd. for $C_{19}H_{30}N_2O_2$, 318.231, found [M+H] 319.4, $T_r$=3.612 min (Method U).

Chiral separation of 656D racemate gave 656D Enantiomer 1 and 656D Enantiomer 2 (Method DP). 656D Enantiomer 1 (brown oil, 366 mg, 1.149 mmol, 21.08% yield). $T_r$=2.89 mins., 656D Enantiomer 2 (brown oil, 442 mg, 1.388 mmol, 25.5% yield), $T_r$=3.4 min. (Method BJ).

656D Enantiomer 1: LC-MS Anal. Calc'd. for $C_{19}H_{30}N_2O_2$, 318.231, found [M+H] 319.4, $T_r$=3.695 min (Method U).

656D Enantiomer 2: LC-MS Anal. Calc'd. for $C_{19}H_{30}N_2O_2$, 318.231, found [M+H] 319.4, $T_r$=3.688 min (Method U).

656E. Methyl 3-(3-((4-chlorophenyl)amino)-4-((cyclopropylmethyl)(propyl)amino)phenyl)pentanoate The mixture of 656D Enantiomer 1 (50 mg, 0.157 mmol), 1-bromo-4-chlorobenzene (30.1 mg, 0.157 mmol), Xantphos (18.17 mg, 0.031 mmol) and $Cs_2CO_3$ (128 mg, 0.393 mmol) in 1,4-dioxane (2 mL) was stirred at room temperature. Argon gas was bubbled through the mixture for 5 min. Bis(dibenzylideneacetone)palladium (4.51 mg, 7.85 μmol) was added and argon gas was bubbled through the mixture for another 5 mins. The reaction mixture was sealed and placed in preheated oil bath at 110° C. for 16 h. The reaction mixture was cooled to room temperature and concentrated under reduced pressure to afford a residue. The residue was reconstituted in a mixture of ethyl acetate (25 mL) and water (15 mL). The organic layer was separated and aqueous layer was extracted with ethyl acetate (2×25 mL). The combined organic layers were washed with water (15 mL), brine (15 mL), dried over anhydrous sodium sulfate, filtered and concentrated under reduced pressure to afford a residue. The residue was purified via flash silica gel column chromatography to afford 656E (brown mass, 50 mg, 0.117 mmol, 74.2% yield). LC-MS Anal. Calc'd. for $C_{25}H_{33}N_3O_2$, 428.223, found [M+H] 429.4, $T_r$=4.384 min (Method U).

Example 656 Enantiomer 1. 3-(3-((4-Chlorophenyl)amino)-4-((cyclopropylmethyl)(propyl)amino)phenyl)pentanoic acid To a stirred solution of 656 E (50 mg, 0.117 mmol), THF (0.5 ml) and methanol (1 mL) and water (0.25 mL) was added LiOH.H$_2$O (13.96 mg, 0.583 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 656 Enantiomer 1 (absolute stereochemistry not determined, pale yellow solid, 23 mg, 0.055 mmol, 47.6% yield). LC-MS Anal. Calc'd. for $C_{24}H_{31}ClN_2O_2$, 414.207, found [M+H] 415.2, $T_r$=2.716 min (Method O). $^1$H NMR (400 MHz, DMSO-d$_6$) δ 7.39 (s, 1H), 7.26-7.25 (m, 2H), 7.06-7.12 (m, 3H), 7.02-7.02 (m, 1H), 6.73-6.75 (m, 1H), 2.90-2.94 (m, 2H), 2.72-2.82 (m, 1H), 2.67-2.68 (m, 2H), 2.51-2.53 (m, 1H), 2.43-2.45 (m, 1H), 1.61-1.62 (m, 1H), 1.42-1.51 (m, 1H), 1.31-1.33 (m, 3H), 0.78-0.80 (m, 3H), 0.71-0.73 (m, 3H), 0.28-0.31 (m, 2H), −0.06-−0.03 (m, 2H).

Example 656 Enantiomer 2. 3-(3-((4-Chlorophenyl)amino)-4-((cyclopropylmethyl)(propyl)amino)phenyl)pentanoic acid Example 656 Enantiomer 2 was synthesized using 656D Enantiomer 2 and following the procedure described for the synthesis of Example 656 Enantiomer 1 (absolute stereochemistry not determined). LC-MS Anal. Calc'd. for $C_{24}H_{31}ClN_2O_2$, 414.207, found [M+H] 415.2, $T_r$=2.720 min (Method O). $^1$H NMR (400 MHz, DMSO-d$_6$) δ 7.43-7.47 (m, 1H), 7.23-7.25 (m, 3H), 6.98-7.11 (m, 3H), 2.85-3.18 (m, 5H), 1.60-1.65 (m, 2H), 1.48-1.52 (m, 4H), 0.71-0.86 (m, 7H), 0.31-0.33 (m, 2H), −0.05-−0.03 (m, 2H).

Examples 657 to 659

Enantiomer 1

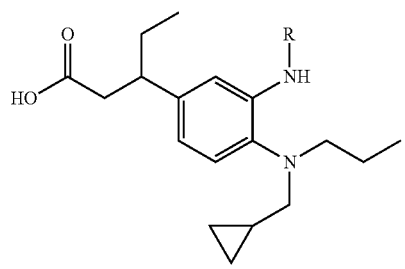

Examples 657 to 659 were prepared using 656D Enantiomer 1 and the corresponding aryl halides following the procedure described for the synthesis of Example 656 (absolute stereochemistry not determined).

| Ex. No. | Name | R | $T_R$ (min) Method O | [M + H]$^+$ |
|---|---|---|---|---|
| 657 | 3-(4-((cyclopropylmethyl)(propyl)amino)-3-((2-ethoxypyrimidin-5-yl)amino)phenyl)pentanoic acid | | 2.273 | 427.3 |

-continued

| Ex. No. | Name | R | $T_R$ (min) Method O | $[M + H]^+$ |
|---|---|---|---|---|
| 658 | 3-(4-((cyclopropylmethyl)(propyl)amino)-3-((2-methylbenzo[d]thiazol-6-yl)amino)phenyl)pentanoic acid | 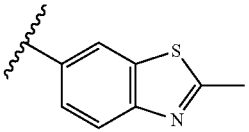 [SMILES: *c1ccc2nc(C)sc2c1] | 2.425 | 452.2 |
| 659 | 3-(4-((cyclopropylmethyl)(propyl)amino)-3-((2,2-difluorobenzo[d][1,3]dioxol-5-yl)amino)phenyl)pentanoic acid | 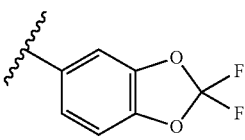 [SMILES: *c1ccc2c(c1)OC(F)(F)O2] | 2.815 | 461.2 |

Examples 660 to 662

Enantiomer 2

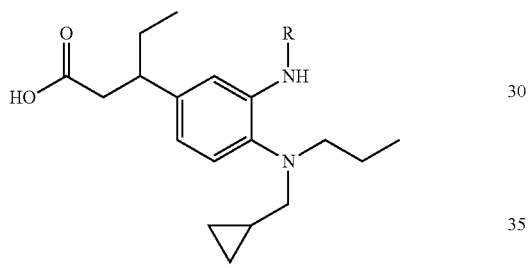

Examples 660 to 662 were prepared using 654D Enantiomer 2 and the corresponding aryl halides following the procedure described for the synthesis of Example 654 (absolute stereochemistry not determined).

| Ex. No. | Name | R | $T_R$ (min) Method O | $[M + H]^+$ |
|---|---|---|---|---|
| 660 | 3-(4-((cyclopropylmethyl)(propyl)amino)-3-((2-ethoxypyrimidin-5-yl)amino)phenyl)pentanoic acid | 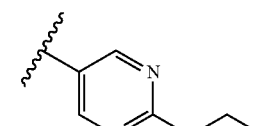 | 2.213 | 427.3 |
| 661 | 3-(4-((cyclopropylmethyl)(propyl)amino)-3-((2-methylbenzo[d]thiazol-6-yl)amino)phenyl)pentanoic acid | 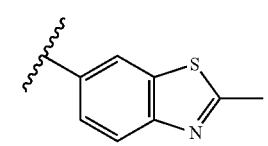 [SMILES: *c1ccc2nc(C)sc2c1] | 2.430 | 452.3 |
| 662 | 3-(4-((cyclopropylmethyl)(propyl)amino)-3-((2,2-difluorobenzo[d][1,3]dioxol-5-yl)amino)phenyl)pentanoic acid | 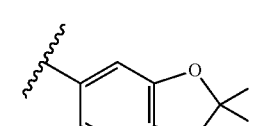 | 2.808 | 461.2 |

Example 666

Diastereomer 1 and Diastereomer 2

3-(4-((1S,4S)-5-Benzyl-2,5-diazabicyclo[2.2.1]heptan-2-yl)-3-(p-tolylamino)phenyl)pentanoic acid

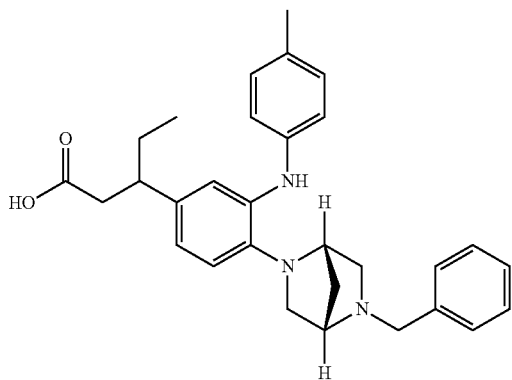 [SMILES: CCC(CC(=O)O)c1ccc(N2C[C@@H]3C[C@H]2CN3Cc2ccccc2)c(Nc2ccc(C)cc2)c1]

666A. (1R,4S)-tert-Butyl 5-benzyl-2,5-diazabicyclo[2.2.1]heptanes-2-carboxylate To a stirred solution of (1R,4S)-tert-butyl 2,5-diazabicyclo[2.2.1]heptanes-2-carboxylate (3 g, 15.13 mmol) in DMF (15 mL), $K_2CO_3$ (5.23 g, 37.8 mmol) was added followed by benzyl bromide (1.980 mL, 16.64 mmol) and stirred at room temperature for 12 h. The reaction mixture was diluted with water (50 mL) and ethyl acetate (50 mL). The organic layer was separated and the aqueous layer was extracted with ethyl acetate (2×50 mL). The combined organic layers were washed with brine solution (100 mL), water (100 mL), dried over sodium sulfate, filtered and concentrated under reduced pressure to afford (1R,4S)-tert-butyl 5-benzyl-2,5-diazabicyclo[2.2.1]heptanes-2-carboxylate (yellow oil, 3 g, 1040 mmol, 68.7%). LC-MS Anal. Calc'd. for $C_{17}H_{24}N_2O_2$, 288.18, found [M+H] 289.2, $T_r$=2.410 min (Method U).

666B. (1S,4R)-2-Benzyl-2,5-diazabicyclo[2.2.1]heptane

To a cooled solution of (1R,4S)-tert-butyl 5-benzyl-2,5-diazabicyclo[2.2.1] heptanes-2-carboxylate (3.0 g, 10.40 mmol) in dioxane (30 mL) at 0° C. HCl in dioxane (4M) (30 mL, 120 mmol) was added and stirred at room temperature for 12 h. The reaction mixture was concentrated under reduced pressure to afford a solid residue. The solid was stirred with the mixture of ethyl acetate (10 mL) and pet ether (90 mL). The solvent decanted and the residue was azeotroped with toluene (3×50 mL) to afford (1S,4R)-2-benzyl-2,5-diazabicyclo[2.2.1]heptane.2HCl (brown solid, 2.7 g, 10.34 mmol, 99%). LC-MS Anal. Calc'd. for $C_{12}H_{16}N_2$, 188.13, found [M+H] 189.2, $T_r$=0.331 min (Method U).

666C. (1S,4S)-2-Benzyl-5-(4-bromo-2-nitrophenyl)-2,5-diazabicyclo[2.2.1]heptanes In a pressure tube equipped with a Teflon cap, 4-bromo-1-fluoro-2-nitrobenzene (1.7 g, 7.73 mmol), N-methyl-2-pyrrolidone (15 mL) was added followed by (1S,4S)-2-benzyl-2,5-diazabicyclo[2.2.1]heptane, 2 HCl (2 g, 7.66 mmol) and DIPEA (5.40 mL, 30.9 mmol) and the tube was screw-capped and heated to 120° C. for 16 h. The reaction mixture was extracted with diethyl ether (3×50 ml) and water (50 ml). The organic layers were washed with brine solution (2×50 mL). The combined organic layers were dried over sodium sulfate, filtered and concentrated under reduced pressure to afford the crude, which was purified by flash silica gel column chromatography to afford 666C (brown oil, 2.6 g, 5.89 mmol, 76%). LC-MS Anal. Calc'd. for $C_{18}H_{18}BrN_3O_2$ 387.058, found [M+2H] 390.2, $T_r$=3.623 min (Method U).

666D. (1S,4S)-2-Benzyl-5-(4-(5,5-dimethyl-1,3,2-dioxaborinan-2-yl)-2-nitrophenyl)-2,5-diazabicyclo[2.2.1]heptanes The mixture of 666C (2 g, 5.15 mmol), 5,5,5',5'-tetramethyl-2,2'-bi(1,3,2-dioxaborinane) (2.327 g, 10.30 mmol), and potassium acetate (2.275 g, 23.18 mmol) in 1,4-dioxane (25 mL) was stirred at room temperature. Argon gas was bubbled through the mixture for 5 min. [1,1'-Bis(diphenylphosphino)ferrocene]dichloropalladium(II) (0.188 g, 0.258 mmol) was added and argon gas was bubbled through the mixture for 5 min. The reaction mixture was heated at 90° C. for 5 h. The reaction mixture was cooled to room temperature and diluted with ethyl acetate (100 mL). The organic layers were washed with water (50 mL), dried over anhydrous sodium sulfate, filtered and concentrated under reduced pressure to afford a residue. The residue was purified via flash silica gel column chromatography to afford 666D (orange oil, 1.216 g, 2.66 mmol, 51.5%). LC-MS Anal. Calc'd. for $C_{23}H_{28}BN_3O_4$, 421.217, found [M-68] 354.2, for parent boronic acid, $T_r$=2.502 min (Method U).

666E. Methyl 3-(4-((1S,4S)-5-benzyl-2,5-diazabicyclo[2.2.1]heptan-2-yl)-3-nitrophenyl)pentanoate In a pressure tube equipped with Teflon cap 666D (1 g, 2.374 mmol), 1,4-dioxane (10 ml) were added followed by sodium hydroxide (2.167 ml, 2.167 mmol). Argon gas was passed through the mixture for 5 mins, then methyl 2-pentenoate (0.813 g, 7.12 mmol) and chloro(1,5-cyclooctadiene)rhodium(I) dimer (0.059 g, 0.120 mmol) was added at room temperature. Argon gas was passed through the mixture for another 5 mins. It was then screw-capped and heated at 50° C. for 2 h. The reaction mixture was cooled to room temperature, quenched with acetic acid (0.136 mL, 2.374 mmol) and was stirred for 5 mins before it was diluted with water (50 mL). The aqueous layer was extracted with ethyl acetate (3×50 mL). The combined organic layers were washed with water (50 mL), brine (50 mL), dried over anhydrous sodium sulfate, filtered and concentrated under reduced pressure to afford the crude. The crude was purified by flash silica gel column chromatography to afford 666E (brown solid, 910 mg, 1.869 mmol, 79% yield). LC-MS Anal. Calc'd. for $C_{24}H_{29}N_3O_4$, 423.505, found [M+H] 424.2, $T_r$=3.265 min (Method U).

666F. Methyl 3-(3-amino-4-((1S,4S)-5-benzyl-2,5-diazabicyclo[2.2.1]heptan-2-yl)phenyl)pentanoate To a solution of 666E (900 mg, 2.125 mmol) in ethanol (7 mL) was added water (0.560 mL) followed by ammonium chloride (501 mg, 9.37 mmol). The mixture was stirred for 5 min, and then treated with zinc (1.389 g, 21.25 mmol) at 0° C. The mixture was stirred at room temperature for 18 h.

The reaction mixture was filtered through CELITE® bed. The CELITE® bed was washed with excess of ethyl acetate and the filtrate so obtained was concentrated under reduced pressure. The residue was extracted with ethyl acetate (3×25 mL) and water (25 mL). The organic layers were dried over sodium sulfate, filtered and evaporated under reduced pressure to afford the crude material, which was purified by flash silica gel column chromatography to afford 666F diastereomeric mixture (brown oil, 300 mg, 0.762 mmol, 71.8%). LC-MS Anal. Calc'd. for $C_{24}H_{31}N_3O_2$, 393.242, found [M+H] 394.2, $T_r$=2.770 mins (Method U).

Chiral separation of 666F diastereomeric mixture (Method DN) gave 666F Diastereomer 1 ($T_r$=10.4 min) and 666F Diastereomer 2 ($T_r$=12.47 min) (Method AQ).

664F Diastereomer 1 (absolute and relative stereochemistry unknown, brown oil, 33 mg, 0.084 mmol, 7.89%), $T_r$=10.4 min (Method DN). LC-MS Anal. Calc'd. for $C_{24}H_{31}N_3O_2$, 279.174, found [M+H] 280.2, $T_r$=1.975 mins (Method U).

664F Diastereomer 2 (absolute and relative stereochemistry unknown, brown oil, 42 mg, 10.05 mmol, 10.05%), $T_r$=12.47 min. (Method DN). LC-MS Anal. Calc'd. for $C_{24}H_{31}N_3O_2$, 279.174, found [M+H] 280.2, $T_r$=1.975 min (Method U).

666G. Methyl 3-(4-((1S,4S)-5-benzyl-2,5-diazabicyclo[2.2.1]heptan-2-yl)-3-(p-tolylamino)phenyl)pentanoate The mixture of 666F Diastereomer 1 (18 mg, 0.046 mmol), 1-bromo-4-methylbenzene (11.73 mg, 0.069 mmol), Xantphos (5.29 mg, 9.15 µmol) and $Cs_2CO_3$ (44.7 mg, 0.137 mmol) in 1,4-dioxane (1 mL) was stirred at room temperature. Argon gas was bubbled through the mixture for 5 mins. Bis(dibenzylideneacetone)palladium (2.63 mg, 4.57 µmol) was added and argon gas was bubbled through the mixture for another 5 min. The reaction mixture was sealed and placed in preheated oil bath at 110° C. for 16 h. The reaction mixture was cooled to room temperature and concentrated under reduced pressure to afford a residue. The residue was reconstituted in a mixture of ethyl acetate (15 mL) and water (10 mL). The organic layer was separated and aqueous layer was extracted with ethyl acetate (2×15 mL). The combined organic layers were washed with water (10 mL), brine (15 mL), dried over anhydrous sodium sulfate, filtered and concentrated under reduced pressure to afford crude 664G, which was taken to next step without further purification.

Example 666 Diastereomer 1. 3-(4-((1S,4S)-5-Benzyl-2,5-diazabicyclo[2.2.1]heptan-2-yl)-3-(p-tolylamino)phenyl)pentanoic acid To a stirred solution of 666G in mixture of THF (0.25 ml), methanol (0.5 ml) and water (0.15 mL) was added $LiOH.H_2O$ (10.95 mg, 0.457 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 666 Diastereomer 1 (absolute and relative stereochemistry not confirmed, pale yellow solid, 8 mg, 0.016 mmol, 35.4% yield). LC-MS Anal. Calc'd. for $C_{34}H_{47}N_3O_2$, 469.27, found [M+H] 470.4, $T_r$=1.549 min (Method O). $^1$H NMR (400 MHz, DMSO-$d_6$) δ 11.90 (s, 1H), 9.40 (s, 1H), 7.55-7.56 (m, 1H), 7.54-7.54 (m, 3H), 6.91-7.46 (m, 4H), 6.78-6.79 (m, 2H), 6.63-6.76 (m, 2H), 4.24-4.39 (m, 4H), 3.19-3.22 (m, 3H), 2.70-2.87 (m, 1H), 2.64-2.42 (m, 2H), 2.20-2.21 (m, 1H), 2.18 (s, 3H), 1.47-1.18 (m, 4H), 0.71 (t, J=7.2, 3H).

Example 666 Diastereomer 2. 3-(4-((1S,4S)-5-Benzyl-2,5-diazabicyclo[2.2.1]heptan-2-yl)-3-(p-tolylamino)phenyl)pentanoic acid Example 666 Diastereomer 2 was synthesized using 666F Diastereomer 2 and 1-bromo-4-methylbenzene following the procedure described for the synthesis of Example 666 Diastereomer 1 (absolute and relative stereochemistry not confirmed, pale yellow solid, 3 mg, 0.006 mmol, 13.2% yield). LC-MS Anal. Calc'd. for $C_{34}H_{47}N_3O_2$, 469.27, found [M+H] 470.4, $T_r$=1.588 min (Method O). $^1$H NMR (400 MHz, DMSO-$d_6$) δ11.93 (s, 1H), 9.40 (s, 1H), 7.53-7.54 (m, 1H), 7.45-7.53 (m, 3H), 6.91-7.44 (m, 4H), 6.78-6.79 (m, 2H), 6.62-6.64 (m, 2H), 4.24-4.39 (m, 4H), 3.47-3.60 (m, 2H), 3.18-3.23 (m, 2H), 2.67-2.67 (m, 1H), 2.36-2.44 (m, 2H), 2.17 (s, 3H), 1.37-1.71 (m, 4H), 0.70 (t, J=7.2, 3H).

Example 667

Diastereomer 1 and Diastereomer 2

3-(4-((1S,4S)-5-Benzyl-2,5-diazabicyclo[2.2.1]heptan-2-yl)-3-(3-(p-tolyl)ureido)phenyl)pentanoic acid

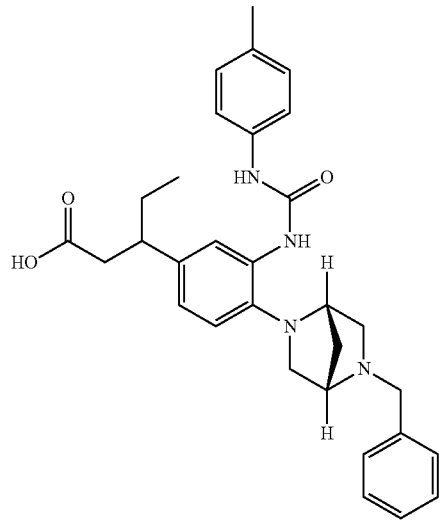 [SMILES: CCC(CC(=O)O)c1ccc(N2C[C@@H]3C[C@H]2CN3Cc2ccccc2)c(NC(=O)Nc2ccc(C)cc2)c1]

667A. Methyl 3-(4-((1S,4S)-5-benzyl-2,5-diazabicyclo[2.2.1]heptan-2-yl)-3-(3-(p-tolyl)ureido)phenyl)pentanoate To a stirred solution of 666F Diastereomer 1 (15 mg, 0.038 mmol) in THF (1 mL), p-tolyl isocyanate (6.09 mg, 0.046 mmol) was added and it was stirred for 1 h. The reaction mass was concentrated under reduced pressure to afford crude 667A, which was taken to next step without further purification.

Example 667 Diastereomer 1. 3-(4-((1S,4S)-5-Benzyl-2,5-diazabicyclo[2.2.1]heptan-2-yl)-3-(3-(p-tolyl)ureido)phenyl)pentanoic acid To a stirred solution of 667A (50 mg, 0.116 mmol) in mixture of THF (0.25 ml), methanol (0.5 ml) and water (0.15 mL) was added LiOH.H$_2$O (9.13 mg, 0.381 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 667 Diastereomer 1 (absolute and relative stereochemistry not confirmed, pale yellow solid, 7 mg, 0.013 mmol, 34.8% yield). LC-MS Anal. Calc'd. for C$_{63}$H$_{77}$N$_7$O$_5$, 512.28, found [M+H] 513.3, T$_r$=1.604 min (Method O). $^1$H NMR (400 MHz, DMSO-d$_6$) δ 11.90 (s, 1H), 9.75 (s, 1H), 9.04 (s, 1H), 7.78-7.80 (m, 1H), 7.58-7.67 (m, 2H), 7.36-7.45 (m, 4H), 7.30-7.34 (m, 2H), 6.82-7.22 (m, 2H), 6.80-6.82 (m, 1H), 4.26-4.35 (m, 4H), 3.60-3.70 (m, 1H), 3.50-3.54 (m, 2H), 3.10-3.20 (m, 1H), 2.78-2.90 (m, 1H), 2.33-2.34 (m, 1H), 2.16-2.33 (m, 4H), 1.24-1.60 (m, 4H), 0.72 (t, J=7.2 Hz, 3H).

Example 667 Diastereomer 2. 3-(4-((1S,4S)-5-Benzyl-2,5-diazabicyclo[2.2.1]heptan-2-yl)-3-(3-(p-tolyl)ureido)phenyl)pentanoic acid Example 667 Diastereomer 2 was synthesized using 666F Diastereomer 2 and p-tolyl isocyanate following the procedure described for the synthesis of Example 667 Diastereomer 1 (absolute and relative stereochemistry not confirmed, pale yellow solid, 9 MG, 0.017 mmol, 45.8% yield). C$_{63}$H$_{77}$N$_7$O$_5$, 512.28, found [M+H] 513.3, T$_r$=1.625 min (Method O). $^1$H NMR (400 MHz CD$_3$OD) δ 11.93 (s, 1H), 9.40 (s, 1H), 7.53-7.54 (m, 1H), 7.45-7.53 (m, 3H), 6.91-7.44 (m, 4H), 6.78-6.79 (m, 2H), 6.62-6.64 (m, 2H), 4.24-4.39 (m, 4H), 3.47-3.60 (m, 2H), 3.18-3.23 (m, 2H), 2.67-2.67 (m, 1H), 2.36-2.44 (m, 2H), 2.17 (s, 3H), 1.37-1.71 (m, 4H), 0.70 (t, J=7.2, 3H).

Example 668

Enantiomer 1 and Enantiomer 2

3-(3-((4-Cyanophenyl)amino)-4-(4-(methoxycarbonyl)piperazin-1-yl)phenyl)pentanoic acid

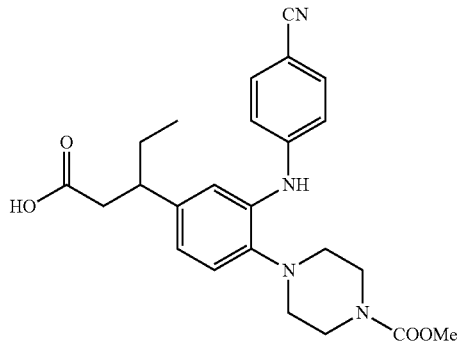 [SMILES: CCC(CC(=O)O)c1ccc(N2CCN(C(=O)OC)CC2)c(Nc2ccc(C#N)cc2)c1]

668A. tert-Butyl 4-(4-(1-methoxy-1-oxopentan-3-yl)-2-nitrophenyl)piperazine-1-carboxylate To a stirred solution of 443B Enantiomer 1 (0.6 g, 2.351 mmol), tert-butyl piperazine-1-carboxylate (0.525 g, 2.82 mmol) in NMP (10 mL) was added DIPEA (1.232 mL, 7.05 mmol) and heated at 120° C. for 6 h. The reaction mixture was allowed to cool to room temperature and partitioned between MTBE (50 mL) and water (50 mL). The layers were separated and the organic layers were washed with brine, dried over anhydrous sodium sulfate, filtered and concentrated under reduced pressure to afford the crude product. The crude material was purified via silica gel flash chromatography to afford 668A Enantiomer 1 (orange oil, 0.6 g, 1.424 mmol, 60.6% yield). LC-MS Anal. Calc'd. for C$_{21}$H$_{31}$N$_3$O$_6$, 421.221, found [M+H] 422.4, T$_r$=3.434 min (Method U).

668B. tert-Butyl 4-(2-amino-4-(1-methoxy-1-oxopentan-3-yl)phenyl) piperazine-1-carboxylate To a stirred solution of 668A Enantiomer 1 (0.6 g, 1.424 mmol) in ethanol (10 mL) and THF (10 mL) was added ammonium chloride in water (5 mL, 7.12 mmol) followed by zinc (0.093 g, 1.424 mmol) and stirred at room temperature for 4 h. The reaction mixture was filtered through a pad of CELITE®. The CELITE® pad washed with THF (50 mL) and the solution was concentrated under reduced pressure. The residue was basified with aqueous saturated sodium bicarbonate solution (pH~8-9) and extracted with ethyl acetate (3×30 mL). The combined organic layers were washed with brine, dried over sodium sulfate, filtered and concentrated under reduced pressure to afford a residue. The residue was purified via silica gel flash chromatography to afford 668B Enantiomer 1 (brown oil, 0.45 g, 1.149 mmol, 81% yield). LC-MS Anal. Calc'd. for C$_{21}$H$_{33}$N$_3$O$_4$, 391.247, found [M+H] 392.4, T$_r$=3.218 min (Method U).

668C. tert-Butyl 4-(2-((4-cyanophenyl)amino)-4-(1-methoxy-1-oxopentan-3-yl)phenyl)piperazine-1-carboxylate The mixture 668B Enantiomer 1 (200 mg, 0.511 mmol), 4-bromobenzonitrile (121 mg, 0.664 mmol), Xantphos (59.1 mg, 0.102 mmol) and Cs$_2$CO$_3$ (416 mg, 1.277 mmol) in 1,4-dioxane (2 mL) was stirred at room temperature. Argon gas was bubbled through the mixture for 5 min. Bis(dibenzylideneacetone)palladium (14.69 mg, 0.026 mmol) was added and argon gas was bubbled through the mixture for another 5 min. The reaction mixture was sealed and placed in a preheated oil bath at 110° C. for 16 h. The reaction mixture was cooled to room temperature and concentrated under reduced pressure to afford a residue. The residue was reconstituted in a mixture of ethyl acetate (25 mL) and water (15 mL). The organic layer was separated and aqueous layer was extracted with ethyl acetate (2×25 mL). The combined organic layers were washed with water (15 mL), brine (15 mL), dried over anhydrous sodium sulfate, filtered and concentrated under reduced pressure to afford a residue. The residue was purified via silica gel flash chromatography to afford 668C Enantiomer 1 (yellow oil, 110 mg, 0.191 mmol, 37.4% yield). LC-MS Anal. Calc'd. for C$_{28}$H$_{36}$N$_4$O$_4$, 492.274, found [M+H] 493.2, T$_r$=3.399 min (Method CP).

668D. Methyl 3-(3-((4-cyanophenyl)amino)-4-(piperazin-1-yl)phenyl)pentanoate

To a stirred solution of 668C Enantiomer 1 (85 mg, 0.173 mmol) in DCM (2.5 ml), trifluoroacetic acid (2 ml, 26.0 mmol) was added and stirred at room temperature for 12 h. The reaction mixture was concentrated under reduced pressure. To the residue saturated sodium bicarbonate solution (25 mL) was added followed by extraction with ethyl acetate (3×25 ml). The organic layers were washed with brine, dried over anhydrous sodium sulfate, filtered, and concentrated under reduced pressure to afford 668D Enantiomer 1 (off-white oil, 60 mg, 0.111 mmol, 64.2% yield). LC-MS Anal. Calc'd. for $C_{23}H_{28}N_4O_2$, 392.221, found [M+H] 393.2, $T_r$=1.623 min (Method U).

668E. Methyl 4-(2-((4-cyanophenyl)amino)-4-(1-methoxy-1-oxopentan-3-yl)phenyl)piperazine-1-carboxylate To a stirred solution of 668D Enantiomer 1 (20 mg, 0.048 mmol) in DCM (2 ml), DIPEA (0.025 ml, 0.145 mmol) was added. The solution was cooled to 0° C., methyl chloroformate (4.57 mg, 0.048 mmol) was added and stirred for 3 h at room temperature.

The reaction mixture was concentrated under reduced pressure to afford 668E (20 mg, 0.042 mmol, 88% yield). LC-MS Anal. Calc'd. for $C_{24}H_{33}N_5O_5$, 450.227, found [M+H] 451.4, $T_r$=2.958 min (Method BD).

Example 668 Enantiomer 1. 3-(3-((4-Cyanophenyl)amino)-4-(4-(methoxycarbonyl)piperazin-1-yl)phenyl)pentanoic acid To a stirred solution of 668E Enantiomer 1 (20 mg, 0.044 mmol) in mixture of THF (0.5 ml), methanol (1 ml) and water (0.25 mL) was added LiOH.H₂O (6.08 mg, 0.254 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 668 Enantiomer 1 (absolute stereochemistry not confirmed, pale yellow solid, 1.9 mg, 4.35 μmol, 9.81% yield). LC-MS Anal. Calc'd. for $C_{24}H_{28}N_4O_4$, 436.211, found [M+H] 437.2, $T_r$=1.607 min (Method O). ¹H NMR (400 MHz, CD₃OD) δ 7.37-7.41 (m, 2H), 7.04-7.04 (m, 1H), 6.90-6.97 (m, 3H), 6.83-6.86 (m, 1H), 3.59 (s, 3H), 3.38-3.40 (m, 4H), 2.74-2.76 (m, 5H), 2.50-2.52 (m, 1H), 2.37-2.43 (m, 1H), 1.60-1.61 (m, 1H), 1.48-1.51 (m, 1H), 0.71 (t, J=7.2 Hz, 3H).

Example 668 Enantiomer 2. 3-(3-((4-Cyanophenyl)amino)-4-(4-(methoxycarbonyl)piperazin-1-yl)phenyl)pentanoic acid Example 668 Enantiomer 2 was synthesized using 443B Enantiomer 2 from 668A and following the procedure described for the synthesis of Example 668 Enantiomer 1 (absolute stereochemistry not confirmed). LC-MS Anal. Calc'd. for $C_{24}H_{28}N_4O_4$ 436.211, found [M+H] 437.2, $T_r$=1.601 min (Method O). ¹H NMR (400 MHz, CD₃OD) δ 7.50-7.53 (m, 2H), 7.16-7.16 (m, 1H), 7.03-7.09 (m, 3H), 6.95-6.98 (m, 1H), 3.71 (s, 3H), 3.51-3.52 (m, 4H), 2.87-2.94 (m, 5H), 2.62-2.94 (m, 1H), 2.49-2.55 (m, 1H), 1.70-1.67 (m, 1H), 1.58-1.64 (m, 1H), 0.83 (t, J=7.4 Hz, 3H).

Example 669

Enantiomer 1

3-(3-((2-Ethoxypyrimidin-5-yl)amino)-4-(4-(methoxycarbonyl)piperazin-1-yl)phenyl)pentanoic acid

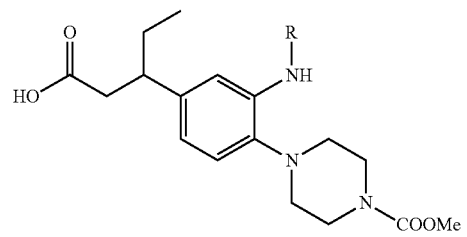

Example 669 Enantiomer 1 was prepared using 443B Enantiomer 1 and corresponding aryl halides following the procedure described for the synthesis of Example 668.

| Ex. No. | Name | R | $T_R$ (min) Method O | [M + H]⁺ |
|---|---|---|---|---|
| 669 | 3-(3-((2-ethoxypyrimidin-5-yl)amino)-4-(4-(methoxycarbonyl)piperazin-1-yl)phenyl)pentanoic acid | pyrimidinyl-OEt | 1.244 | 458.2 |

Example 670

Enantiomer 2

3-(3-((2-Ethoxypyrimidin-5-yl)amino)-4-(4-(methoxycarbonyl)piperazin-1-yl)phenyl)pentanoic acid

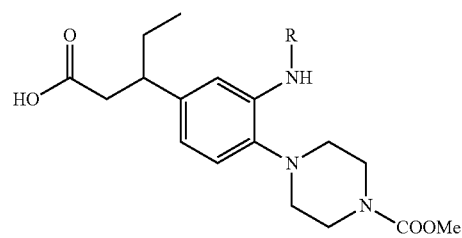

Example 670 Enantiomer 2 was prepared using 443B Enantiomer 2 and corresponding aryl halides following the procedure described for the synthesis of Example 668.

| Ex. No. | Name | R | $T_R$ (min) Method O | $[M + H]^+$ |
|---|---|---|---|---|
| 670 | 3-(3-((2-ethoxypyrimidin-5-yl)amino)-4-(4-(methoxycarbonyl)piperazin-1-yl)phenyl)pentanoic acid | 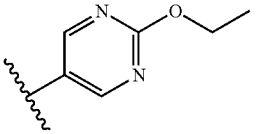 [SMILES: *c1cnc(OCC)nc1] | 1.477 | 458.2 |

Example 671

Enantiomer 1 and Enantiomer 2

3-(3-((4-Cyanophenyl)amino)-4-(piperazin-1-yl)phenyl)pentanoic acid

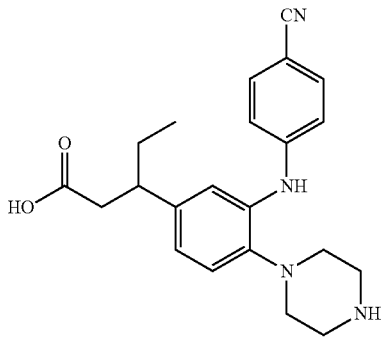 [SMILES: CCC(CC(=O)O)c1ccc(N2CCNCC2)c(Nc2ccc(C#N)cc2)c1]

Example 671 Enantiomer 1. 3-(3-((4-Cyanophenyl)amino)-4-(piperazin-1-yl)phenyl)pentanoic acid To a stirred solution of 668D Enantiomer 1 (20 mg, 0.051 mmol) in mixture of THF (0.5 ml), methanol (1 ml) and water (0.25 mL) was added LiOH.H₂O (6.08 mg, 0.254 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 671 Enantiomer 1 (pale yellow solid, 3.2 mg, 8.46 μmol, 16.59% yield). LC-MS Anal. Calc'd. for $C_{22}H_{26}N_4O_2$, 378.206, found [M+H] 379.2, $T_r$=1.00 min (Method O). ¹H NMR (400 MHz CD₃OD) δ 7.53 (d, J=8.40 Hz, 2H), 7.17-7.18 (m, 1H), 7.11-7.13 (m, 1H), 7.01-7.03 (m, 3H), 3.16-3.37 (m, 8H), δ 2.92-2.95 (m, 1H), 2.62-2.68 (m, 1H), 2.06-2.55 (m, 1H), 1.64-1.75 (m, 1H), 1.31-1.62 (m, 1H), 0.825 (t, J=7.2 Hz, 3H).

Example 671 Enantiomer 2. 3-(3-((4-Cyanophenyl)amino)-4-(piperazin-1-yl)phenyl)pentanoic acid Example 671 Enantiomer 2 was synthesized from compound 668A using compound 443B Enantiomer 2 and following the procedure described for the synthesis of Example 671 Enantiomer 1. LC-MS Anal. Calc'd. for $C_{22}H_{26}N_4O_2$, 378.206, found [M+H] 379.2, $T_r$=1.032 min (Method O). ¹H NMR (400 MHz, CD₃OD) δ 7.53 (d, J=8.80 Hz, 2H), 7.17-7.17 (m, 1H), 7.11-7.13 (m, 1H), 7.01-7.03 (m, 3H), 3.16-3.13 (m, 8H), 2.87-3.00 (m, 1H), 2.63-2.64 (m, 1H), 2.52-2.54 (m, 1H), 1.70-1.77 (m, 1H), 1.56-1.64 (m, 1H), 0.82 (t, J=7.2 Hz, 3H).

Example 672

Enantiomer 1

3-(3-((2-Ethoxypyrimidin-5-yl)amino)-4-(piperazin-1-yl)phenyl)pentanoic acid

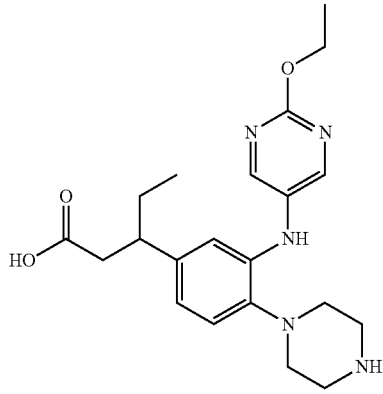 [SMILES: CCOc1ncc(Nc2cc(C(CC)CC(=O)O)ccc2N2CCNCC2)cn1]

672A. tert-Butyl 4-(2-((2-ethoxypyrimidin-5-yl)amino)-4-(1-methoxy-1-oxopentan-3-yl)phenyl)piperazine-1-carboxylate 672A was prepared using 443B Enantiomer 1 and 5-bromo-2-ethoxypyrimidine following the procedure described for the synthesis of 668C Enantiomer 1. LC-MS Anal. Calc'd. for $C_{27}H_{39}N_5O_5$, 513.295, found [M+H] 514.4, $T_r$=3.466 min (Method N). 672B. Methyl 3-(3-((2-ethoxypyrimidin-5-yl)amino)-4-(piperazin-1-yl)phenyl)pentanoate 672B was prepared using 672A following the procedure described for the synthesis of 668D Enantiomer 1. LC-MS Anal. Calc'd. for $C_{22}H_{31}N_5O_3$, 413.2, found [M+H] 414.4, $T_r$=1.354 min (Method CQ).

Example 672. 3-(3-((2-Ethoxypyrimidin-5-yl)amino)-4-(piperazin-1-yl)phenyl)pentanoic acid Example 672 was prepared using 672B following the procedure described for the synthesis of Example 671 Enantiomer 1. LC-MS Anal. Calc'd. for $C_{21}H_{29}N_5O_3$ 399.227, found [M+H] 400.2, $T_r$=0.959 min (Method O). ¹H NMR (400 MHz, CD₃OD) δ 8.33 (s, 2H), 7.08-7.20 (m, 1H), 6.84-6.87 (m, 2H), 4.39-4.44 (m, 2H), 3.32-3.27 (m, 4H), 3.11-3.16 (m, 4H), 2.85-2.89 (m, 1H), 2.44-2.54 (m, 2H), 1.67-1.73 (m, 1H), 1.51-1.58 (m, 1H), 1.38 (t, J=6.8 Hz, 3H) 0.79 (t, J=7.2 Hz, 3H).

Example 673

Enantiomer 2

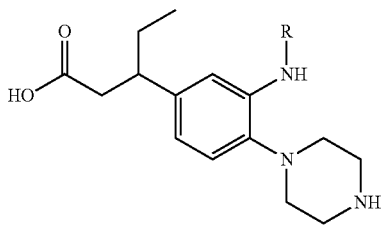

Example 673 were prepared using 443B Enantiomer 2 and 5-bromo-2-ethoxypyrimidine following the procedure described for the synthesis of Example 672.

| Ex. No. | Name | R | $T_R$ (min) Method O | $[M + H]^+$ |
|---|---|---|---|---|
| 673 | 3-(3-((2-ethoxypyrimidin-5-yl)amino)-4-(piperazin-1-yl)phenyl)pentanoic acid | pyrimidine-OEt | 0.948 | 400.2 |

Example 674

Enantiomer 1 and Enantiomer 2

3-(4-(4-(tert-Butoxycarbonyl)piperazin-1-yl)-3-((4-cyanophenyl)amino)phenyl)pentanoic acid

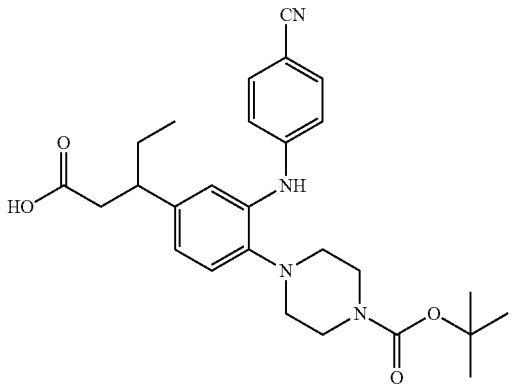 [SMILES: CCC(CC(=O)O)c1ccc(N2CCN(C(=O)OC(C)(C)C)CC2)c(Nc2ccc(C#N)cc2)c1]

Example 674 Enantiomer 1. 3-(4-(4-(tert-Butoxycarbonyl)piperazin-1-yl)-3-((4-cyanophenyl)amino)phenyl)pentanoic acid To a stirred solution of 668C Enantiomer 1 (25 mg, 0.051 mmol) in mixture of THF (0.5 ml), methanol (1 ml) and water (0.25 mL) was added LiOH.H₂O (6.08 mg, 0.254 mmol). The reaction mixture was stirred at room temperature for 3 h. The reaction mixture was concentrated under reduced pressure. The aqueous residue was acidified with saturated solution of citric acid to pH~3-4. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LCMS to afford Example 674 Enantiomer 1 (pale yellow solid, 10.1 mg, 0.020 mmol, 39.1% yield). LC-MS Anal. Calc'd. for $C_{27}H_{34}N_4O_4$, 478.258, found [M+H] 479.2, $T_r$=2.041 min (Method O). ¹H NMR (400 MHz, CD₃OD) δ 7.37-7.41 (m, 2H), 7.04 (d, J=2.00 Hz, 1H), 6.94-6.97 (m, 1H), 6.90-6.92 (m, 2H), 6.83-6.86 (m, 1H), 3.34-3.38 (m, 4H), 2.77-2.85 (m, 1H), 2.72-2.74 (m, 4H), 2.48-2.50 (m, 1H), 2.39-2.42 (m, 1H), 1.57-1.69 (m, 1H), 1.47-1.55 (m, 1H), 1.37 (s, 9H), 0.71 (t, J=7.4 Hz, 3H).

Example 674 Enantiomer 2. -(4-(4-(tert-Butoxycarbonyl)piperazin-1-yl)-3-((4-cyanophenyl)amino)phenyl)pentanoic acid Example 674 Enantiomer 2 was synthesized from compound 668A using 443B Enantiomer 2 following the procedure described for the synthesis Example 674

Enantiomer 1. LC-MS Anal. Calc'd. for $C_{27}H_{34}N_4O_4$, 478.258 found [M+H] 479.2. $T_r$=2.034 min (Method O). ¹H NMR data: 400 MHz, CD₃OD: δ 7.39 (d, J=8.80 Hz, 2H), 7.04-7.05 (m, 1H), 6.91-6.97 (m, 3H), 6.84-6.86 (m, 1H), 3.21-3.34 (m, 4H), 2.72-2.74 (m, 5H), 2.50-2.58 (m, 1H), 2.36-2.40 (m, 1H), 1.60-1.36 (m, 1H), 1.45-1.59 (m, 1H), 1.36 (s, 9H), 0.71 (t, J=7.4 Hz, 3H).

Example 675

Enantiomer 2

3-(4-(4-(tert-Butoxycarbonyl)piperazin-1-yl)-3-((2-ethoxypyrimidin-5-yl)amino)phenyl)pentanoic acid

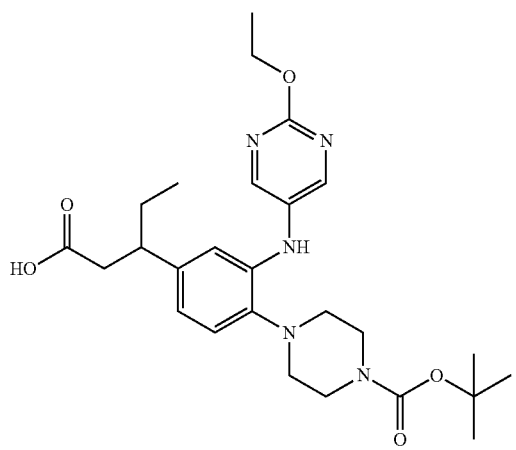 [SMILES: CCOc1ncc(Nc2cc(C(CC)CC(=O)O)ccc2N2CCN(C(=O)OC(C)(C)C)CC2)cn1]

675A. tert-Butyl 4-(2-((2-ethoxypyrimidin-5-yl)amino)-4-(1-methoxy-1-oxopentan-3-yl)phenyl)piperazine-1-carboxylate 675A was prepared using 443B Enantiomer 2 and 5-bromo-2-ethoxypyrimidine following the procedure described for the synthesis of 668C Enantiomer 1. LC-MS Anal. Calc'd. for $C_{27}H_{39}N_5O_5$, 513.295, found [M+H] 514.2, $T_r$=4.28 min (Method CQ).

Example 675. 3-(4-(4-(tert-Butoxycarbonyl)piperazin-1-yl)-3-((2-ethoxypyrimidin-5-yl)amino)phenyl)pentanoic acid Example 675 was prepared using 672B following the procedure described for the synthesis of Example 671 Enantiomer 1. LC-MS Anal. Calc'd. for $C_{21}H_{29}N_5O_3$ 499.3, found [M+H] 500.2, $T_r$=1.931 min (Method O).

Example 676

Enantiomer 1

3-(4-(((Cyclopropylmethyl)(tetrahydro-2H-pyran-4-yl)amino)-3-(3-(p-tolyl)ureido)phenyl)-4-methoxybutanoic acid

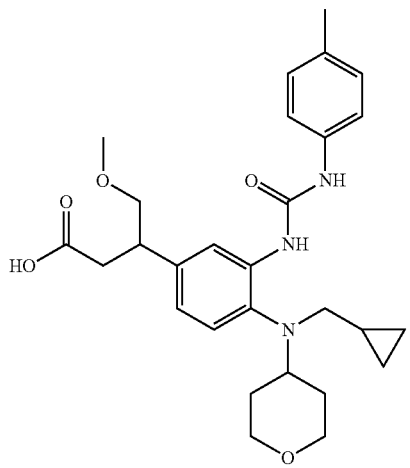 [SMILES: COCC(CC(=O)O)c1ccc(N(CC2CC2)C2CCOCC2)c(NC(=O)Nc2ccc(C)cc2)c1]

676A. N-(Cyclopropylmethyl)tetrahydro-2H-pyran-4-amine

To a stirred solution of cyclopropylmethanamine (6.10 mL, 70.3 mmol) in tetrahydrofuran (30 mL) and MeOH (30 mL) was added dihydro-2H-pyran-4(3H)-one (7.04 g, 70.3 mmol) followed by 4 Å molecular sieves (5 g) at ambient temperature. The reaction was then stirred at room temperature for 18 h. The reaction mixture was cooled to 0° C., and sodium borohydride (7.98 g, 211 mmol) was added portionwise and stirred at room temperature for 2 h. The reaction mixture was under reduced pressure. The resultant semisolid was quenched with 10% $NaHCO_3$ solution. The solids were filtered through pad of CELITE®. The filtrate was extracted with ethyl acetate (2×250 mL). The combined organic layer was washed with brine (2×250 mL) and dried over $Na_2SO_4$, concentrated under reduced pressure to afford 676A (brown oil, 5.2 g, 33.5 mmol, 47.6% yield). LC-MS Anal. Calc'd. for $C_9H_{17}NO$, 155.13, found [M+H] 156.2, $T_r$=1.56 min (Method U).

676B. N-(4-Bromo-2-nitrophenyl)-N-(cyclopropylmethyl)tetrahydro-2H-pyran-4-amine 4-Bromo-1-fluoro-2-nitrobenzene (7.56 g, 34.4 mmol) was added to stirred solution of 676A (8 g, 51.5 mmol) in NMP (50 mL) and allowed to stir at 100° C. for 12 h. The reaction mixture was cooled to room temperature, quenched with water (200 mL) and extracted ethyl acetate (2×200 mL). The separated organic layer was washed with brine solution (100 mL), dried over sodium sulfate concentrated under reduced pressure. The crude sample was purified by flash chromatography (5% ethyl acetate: pet ether; 12 g silica gel column) to afford 676B (yellow solid, 5.1 g, 14.36 mmol, 41.8% yield). LC-MS Anal. Calc'd. for $C_9H_{17}NO$, 354.05, found [M+H] 354.8, $T_r$=2.42 min (Method U).

676C. N-(Cyclopropylmethyl)-N-(4-(5,5-dimethyl-1,3,2-dioxaborinan-2-yl)-2-nitrophenyl)tetrahydro-2H-pyran-4-amine Compound 676B (6.0 g, 16.89 mmol) was dissolved in DMSO (30 mL). To this solution was added bis(neopentyl glycolato)diboron (4.96 g, 21.96 mmol) and potassium acetate (4.97 g, 50.7 mmol). The reaction mixture was purged with nitrogen for 15 minutes. Then to this solution was added [1,1'-bis(diphenylphosphino)ferrocene] dichloropalladium(II) (0.371 g, 0.507 mmol) and the reaction mixture was stirred at 80° C. overnight. Reaction mixture was then cooled to room temperature and quenched with water (50 mL) and then extracted with ethyl acetate (2×100 mL). The separated organic layer was washed with brine (2×50 mL), dried over sodium sulfate and concentrated under reduced pressure. The crude sample was purified by flash chromatography (10% ethyl acetate: pet ether; 40 g silica gel column) to afford 676C (yellow solid, 5.2 g, 13.39 mmol, 79% yield). LC-MS Anal. Calc'd. for $C_{20}H_{29}BN_2O_5$, 388.21, found [M+H] 321.2 (for parent boronic acid) $T_r$=2.16 min (Method U).

676D. Methyl 3-(4-((cyclopropylmethyl)(tetrahydro-2H-pyran-4-yl)amino)-3-nitrophenyl)-4-methoxybutanoate To a nitrogen flushed sealed tube was added dioxane (1 mL) followed by (R)-(+)-2,2'-bis(diphenylphosphino)-1,1'-binaphthyl (0.035 g, 0.057 mmol) and chlorobis(ethylene) rhodium(I) dimer (0.015 g, 0.039 mmol). The reaction mixture was purged with nitrogen for 15 minutes. In a separate flask, a solution of 676C (1.0 g, 2.58 mmol), (E)-methyl 4-methoxybut-2-enoate (1.006 g, 7.73 mmol) and 1N sodium hydroxide (2.318 mL, 2.318 mmol) in dioxane (10 mL) was purged with nitrogen for 15 minutes. The resulting solution was then added to the above reaction mixture in a sealed tube. This reaction mixture was heated to 50° C. and stirred for 1 h. The reaction mixture was cooled to room temperature, quenched with acetic acid (0.133 mL, 2.318 mmol), diluted with water (10 mL) and extracted using ethyl acetate (2×25 mL). The separated organic layer was washed with (30 mL) brine solution, dried over sodium sulfate and concentrated under reduced pressure. The crude sample was purified by flash chromatography (10% ethyl acetate: pet ether; 12 g silica gel column) to afford 676D (colorless oil, 0.8 g, 1.968 mmol, 76% yield). LC-MS Anal. Calc'd. for $C_{21}H_{30}N_2O_6$, 406.21, found [M+H] 407.2. $T_r$=2.80 min (Method U).

676E Enantiomer 1. Methyl 3-(3-amino-4-((cyclopropylmethyl)(tetrahydro-2H-pyran-4-yl)amino)phenyl)-4-methoxybutanoate To a solution of 676D in ethyl acetate (15 mL) was added 10% Pd/C (0.157 g, 0.148 mmol) and the mixture stirred under hydrogen gas atmosphere at 40 psi for 2 h. The reaction mixture was filtered through pad of CELITE® and then washed with ethyl acetate (2×20 mL). The combined filtrate was concentrated under reduced pressure. The crude sample was purified by flash chromatography (15% ethyl acetate: pet ether; 12 g silica gel column) to afford 676E Enantiomer 1 (colorless gummy solid, 0.51 g, 1.355 mmol, 92% yield). LC-MS Anal. Calc'd. for $C_{21}H_{32}N_2O_4$, 376.23, found [M+H] 377.2, $T_r$=2.76 min (Method U). Chiral HPLC $T_r$=9.25 min. (Method BR) and ee=91.48%.

676F. Methyl 3-(4-((cyclopropylmethyl)(tetrahydro-2H-pyran-4-yl)amino)-3-(3-(p-tolyl)ureido)phenyl)-4-methoxybutanoate The compound 676E Enantiomer 1 (0.03 g, 0.080 mmol) was dissolved in DCM (1 mL). To this solution was added 1-isocyanato-4-methylbenzene (10.61 mg, 0.080 mmol) and the mixture stirred at RT for 2 h. The reaction mixture was diluted with water (20 mL), extracted with ethyl acetate (2×10 mL). The separated organic layer were washed with 10% sodium bicarbonate (20 mL) and dried over sodium sulfate and concentrated under reduced pressure to afford 676F (white solid, 0.032 g, 0.063 mmol, 79% yield). LC-MS Anal. Calc'd. for $C_{29}H_{39}N_3O_5$, 509.28, found [M+H] 510.5, $T_r$=3.06 min (Method U).

Example 676. 3-(4-((Cyclopropylmethyl)(tetrahydro-2H-pyran-4-yl)amino)-3-(3-(p-tolyl)ureido)phenyl)-4-methoxybutanoic acid To a solution of 676F (0.04 g, 0.078 mmol) in a mixture of tetrahydrofuran (1 mL), MeOH (0.5 mL) and H₂O (0.5 mL) was added lithium hydroxide (5.64 mg, 0.235 mmol). The resulting mixture was allowed to stir for 12 h at room temperature. The reaction mixture was then concentrated under reduced pressure, diluted with water (5 mL) and acidified (pH~4) with saturated solution of citric acid. The resulting mixture was extracted with ethyl acetate (2×20 mL). The combined organic layer was washed with brine (10 mL), dried over sodium sulfate and concentrated under reduced pressure. The crude material was purified via preparative prep HPLC to afford Example 676 (absolute stereochemistry unknown, off-white solid, 0.036 g, 0.072 mmol, 92% yield). LC-MS Anal. Calc'd. for $C_{28}H_{37}N_3O_5$, 495.27, found [M+H] 496.3, $T_r$=1.52 min (Method R). ¹H NMR (400 MHz, DMSO-d₆) δ 9.38 (s, 1H), 8.54 (s, 1H), 8.10 (d, J=2.0 Hz, 1H), 7.37 (d, J=8.4 Hz, 2H), 7.17 (d, J=8.0 Hz, 1H), 7.09 (d, J=8.4 Hz, 2H), 6.82 (dd, J=2.0, 8.0 Hz, 1H), 3.82 (d, J=11.0 Hz, 2H), 3.25-3.17 (m, 6H), 3.09-3.00 (m, 1H), 2.77 (d, J=6.4 Hz, 2H), 2.68-2.67 (m, 1H), 2.41-2.38 (m, 1H), 2.25 (s, 3H), 1.69 (m, 2H), 1.36 (d, J=13.0 Hz, 2H), 0.61 (s, 1H), 0.21 (d, J=8.0 Hz, 2H), −0.06 (d, J=5.4 Hz, 2H) (Note: 2 protons buried under solvent peak).

Example 677

Enantiomer 2

3-(4-((Cyclopropylmethyl)(tetrahydro-2H-pyran-4-yl)amino)-3-(3-(p-tolyl)ureido)phenyl)-4-methoxybutanoic acid

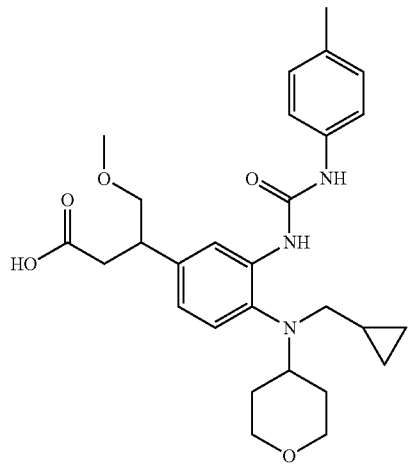 [SMILES: COCC(CC(=O)O)c1ccc(N(CC2CC2)C2CCOCC2)c(NC(=O)Nc2ccc(C)cc2)c1]

677A. Methyl 3-(4-((cyclopropylmethyl)(tetrahydro-2H-pyran-4-yl)amino)-3-nitrophenyl)-4-methoxybutanoate 677A was prepared from 676C and (S)-(−)-2,2'-bis(diphenylphosphino)-1,1'-binaphthyl following the procedure described for the synthesis of 676D. LC-MS Anal. Calc'd. for $C_{21}H_{30}N_2O_6$, 406.2, found 407.2. $T_r$=2.77 min (Method U).

677B Enantiomer 2. Methyl 3-(3-amino-4-((cyclopropylmethyl)(tetrahydro-2H-pyran-4-yl)amino)phenyl)-4-methoxybutanoate 677B Enantiomer 2 was prepared from 677A following the procedure described for the synthesis of 676E. LC-MS Anal. Calc'd. for $C_{21}H_{32}N_2O_4$, 376.2, found [M+H] 377.2. $T_r$=2.76 min (Method U). Chiral HPLC $T_r$=10.66. (Method BR) and ee=90.2%

Example 677. 3-(4-((Cyclopropylmethyl)(tetrahydro-2H-pyran-4-yl)amino)-3-(3-(p-tolyl)ureido)phenyl)-4-methoxybutanoic acid Example 677 was prepared from 677B Enantiomer 2 and 1-isocyanato-4-methylbenzene following the procedure described for the synthesis of Example 676 from 676F (absolute stereochemistry unknown). LC-MS Anal. Calc'd. for $C_{28}H_{37}N_3O_5$ 495.27, found [M+H] 496.3. $T_r$=1.6 min (Method R). ¹H NMR (400 MHz, methanol-d₄) δ 8.06 (d, J=2.0 Hz, 1H), 7.29 (d, J=8.0 Hz, 2H), 7.18 (d, J=8.0 Hz, 1H), 7.12 (d, J=8.4 Hz, 2H), 6.89 (dd, J=8.4, 1.8 Hz, 1H), 3.86 (d, J=8.0 Hz, 2H), 3.57-3.51 (m, 2H), 3.39-3.31 (m, 6H), 3.06-2.97 (m, 1H), 2.81-2.72 (m, 3H), 2.55 (dd, J=15.6, 8.4 Hz, 1H), 2.28 (s, 3H), 1.70 (d, J=12.0 Hz, 1H), 1.38 (d, J=8.0 Hz, 2H), 0.59 (m, 1H), 0.29-0.21 (m, 2H), −0.05--0.14 (m, 2H).

Example 678

Enantiomer 2

3-(3-(3-(4-Chloro-2-fluorophenyl)ureido)-4-((cyclopropylmethyl)(tetrahydro-2H-pyran-4-yl)amino)phenyl)-4-methoxybutanoic acid

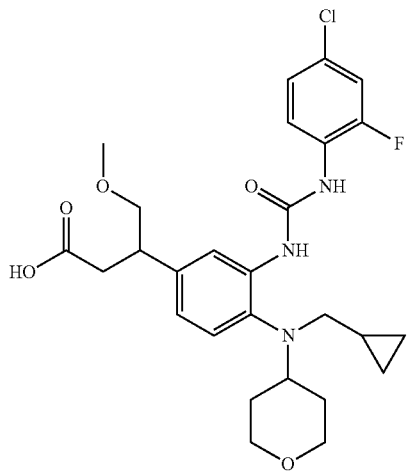 [SMILES: COCC(CC(=O)O)c1ccc(N(CC2CC2)C2CCOCC2)c(NC(=O)Nc2ccc(Cl)cc2F)c1]

Example 678 was prepared from 677B Enantiomer 2 and 4-chloro-2-fluoro-1-isocyanatobenzene following the procedure described for the synthesis of Example 677 (absolute stereochemistry not determined). LC-MS Anal. Calc'd. for $C_{27}H_{33}ClFN_3O_5$, 533.20, found [M+H] 534.2, $T_r$=1.78 min (Method O). $^1$H NMR (400 MHz, methanol-$d_4$) δ 8.01 (t, J=8.6 Hz, 2H), 7.35-7.13 (m, 3H), 7.02 (d, J=5.6 Hz, 1H), 3.93 (d, J=10.4 Hz, 2H), 3.62-3.54 (m, 2H), 3.45-3.34 (m, 5H), 3.16 (m, 1H), 2.85-2.79 (m, 4H), 2.60 (dd, J=16.4, 9.2 Hz, 1H), 1.92-1.69 (m, 2H), 1.53 (m, 2H), 0.70 (m, 1H), 0.33 (m, 2H), −0.01 (m, 2H).

Example 679

Enantiomer 1

3-(3-((4-Chlorophenyl)amino)-4-((cyclopropylmethyl)(tetrahydro-2H-pyran-4-yl)amino)phenyl)-4-methoxybutanoic acid

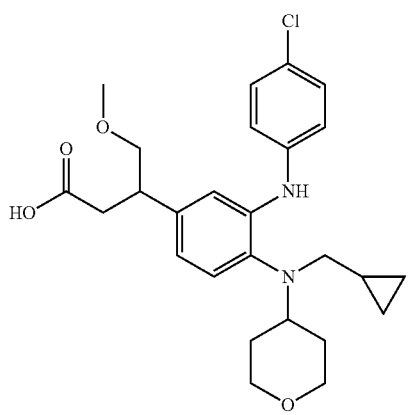 [SMILES: COCC(CC(=O)O)c1ccc(N(CC2CC2)C2CCOCC2)c(Nc2ccc(Cl)cc2)c1]

679A. Methyl 3-(4-((cyclopropylmethyl)(tetrahydro-2H-pyran-4-yl)amino)-3-((2-methylbenzo[d]thiazol-6-yl)amino)phenyl)-4-methoxybutanoate To a degassed solution of 676E Enantiomer 1 (0.05 g, 0.133 mmol), 1-bromo-4-chlorobenzene (0.028 g, 0.146 mmol), $Cs_2CO_3$ (0.130 g, 0.398 mmol) in dioxane (3 ml) was added Xantphos (0.023 g, 0.040 mmol) and bis(dibenzylideneacetone)palladium (7.64 mg, 0.013 mmol). The mixture was then stirred at 110° C. in sealed vessel for 12 h. The reaction mixture was then diluted with water (20 mL), extracted with ethyl acetate (2×10 mL), separated organic layer were washed with brine (20 mL), dried over sodium sulfate and concentrated under reduced pressure. The crude sample was purified by flash chromatography (10% ethyl acetate: pet ether; 4 g silica gel column) to afford 679A (brown oil, 0.030 g, 0.062 mmol, 46.4% yield). LC-MS Anal. Calc'd. for $C_{27}H_{35}ClN_2O_4$, 486.22, found [M+H] 487.2, $T_r$=3.67 min (Method U).

Example 679. 3-(3-((4-Chlorophenyl)amino)-4-((cyclopropylmethyl)(tetrahydro-2H-pyran-4-yl)amino)phenyl)-4-methoxybutanoic acid Example 679 was prepared from 679A following the procedure described for the synthesis of Example 676 from 676F (absolute stereochemistry not determined). LC-MS Anal. Calc'd. for $C_{26}H_{33}ClN_2O_4$, 472.21, found [M+H] 473.2. $T_r$=1.53 min (Method R). $^1$H NMR (400 MHz, DMSO-$d_6$) δ 7.51 (s, 1H), 7.27-7.22 (m, 2H), 7.19-7.08 (m, 4H), 6.76 (dd, J=8.2, 1.8 Hz, 1H), 3.78 (d, J=9.0 Hz, 2H), 3.22-3.14 (m, 6H), 3.05-2.95 (m, 1H), 2.77 (d, J=6.8 Hz, 2H), 2.63 (dd, J=15.4, 6.0 Hz, 1H), 2.42 (dd, J=15.4, 8.6 Hz, 1H), 1.64 (d, J=13.2 Hz, 2H), 1.41-1.29 (m, 2H), 0.63 (s, 1H), 0.25-0.19 (m, 2H), −0.01--0.09 (m, 2H), (2 Protons were buried under solvent peak).

Examples 680 to 688

Enantiomer 1

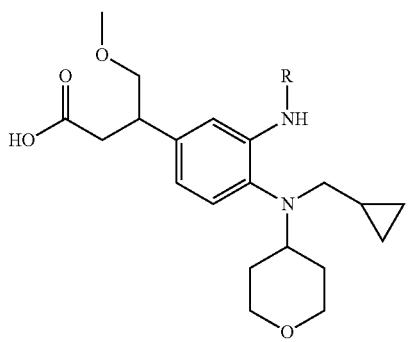

Examples 680 to 688 was prepared from 676E Enantiomer 1 and corresponding aryl halides following the procedure described for the synthesis of Example 679 (absolute stereochemistry not determined).

| Ex. No. | Name | R | $T_r$ min | Method | (M + H) |
|---|---|---|---|---|---|
| 680 | 3-(4-((cyclopropylmethyl) (tetrahydro-2H-pyran-4-yl)amino)-3-((2-methylbenzo[d]thiazol-6-yl)amino)phenyl)-4-methoxybutanoic acid | 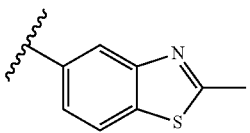 [SMILES: *c1ccc2sc(C)nc2c1] | 1.30 | R | 510.2 |
| 681 | 3-(3-((4-chloro-3-(difluoromethoxy) phenyl)amino)-4-((cyclopropylmethyl) (tetrahydro-2H-pyran-4-yl)amino)phenyl)-4-methoxybutanoic acid | 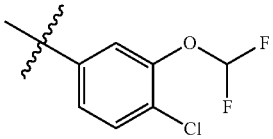 [SMILES: *c1ccc(Cl)c(OC(F)F)c1] | 2.12 | O | 539.2 |
| 682 | 3-(3-((4-chloro-3-(2,2,2-trifluoroethoxy)phenyl) amino)-4-((cyclopropylmethyl) (tetrahydro-2H-pyran-4-yl)amino)phenyl)-4-methoxybutanoic acid | 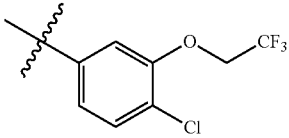 [SMILES: *c1ccc(Cl)c(OCC(F)(F)F)c1] | 2.23 | O | 571.2 |
| 683 | 3-(3-((4-chloro-3-(cyclopropylmethoxy) phenyl)amino)-4-((cyclopropylmethyl) (tetrahydro-2H-pyran-4-yl)amino)phenyl)-4-methoxybutanoic acid | 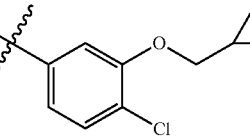 | 1.96 | R | 543.3 |
| 684 | 3-(3-((4-chloro-3-(2,2-difluoroethoxy)phenyl) amino)-4-((cyclopropylmethyl) (tetrahydro-2H-pyran-4-yl)amino)phenyl)-4-methoxybutanoic acid | 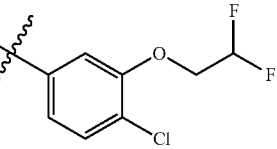 | 1.77 | O | 553.2 |
| 685 | 3-(3-((4-chloro-3-ethoxyphenyl)amino)-4-((cyclopropylmethyl) (tetrahydro-2H-pyran-4-yl)amino)phenyl)-4-methoxybutanoic acid | 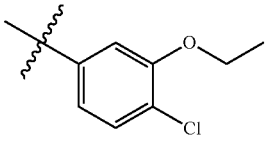 [SMILES: *c1ccc(Cl)c(OCC)c1] | 2.15 | O | 517.2 |
| 686 | 3-(3-((4-cyano-3-methylphenyl)amino)-4-((cyclopropylmethyl) (tetrahydro-2H-pyran-4-yl)amino)phenyl)-4-methoxybutanoic acid | 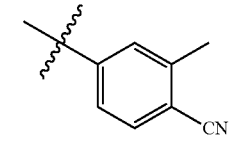 | 1.63 | R | 478.3 |
| 687 | 3-(3-((4-cyanophenyl) amino)-4-((cyclopropylmethyl) (tetrahydro-2H-pyran-4-yl)amino)phenyl)-4-methoxybutanoic acid | 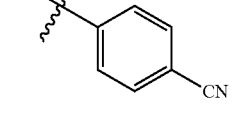 | 1.36 | R | 464.2 |
| 688 | 3-(3-((6-carbamoylpyridin-3-yl) amino)-4-((cyclopropylmethyl) (tetrahydro-2H-pyran-4-yl)amino)phenyl)-4-methoxybutanoic acid | 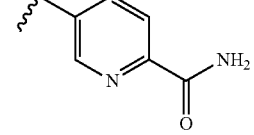 | 1.1 | O | 483 |

443
Examples 689 to 694
Enantiomer 2

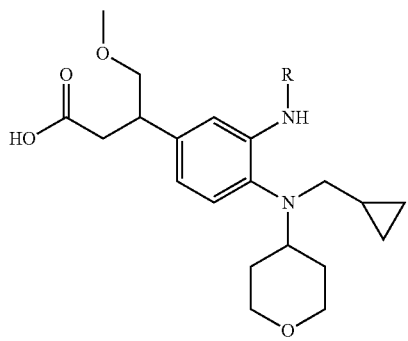

Examples 689 to 694 was prepared from 677B Enantiomer 2 and corresponding aryl halides following the procedure described for the synthesis of Example 679 (absolute stereochemistry not determined).

444
Example 695
Enantiomer 1

3-(4-((Cyclopropylmethyl)(tetrahydro-2H-pyran-4-yl)amino)-3-(3-(p-tolyl)ureido)phenyl)pentanoic acid

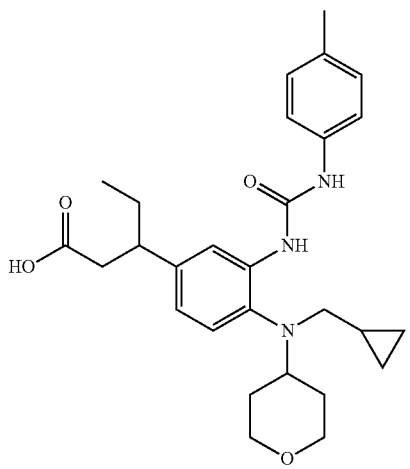 [SMILES: CCC(CC(=O)O)c1ccc(N(CC2CC2)C2CCOCC2)c(NC(=O)Nc2ccc(C)cc2)c1]

| Ex. No. | Name | R | $T_r$, min | Method | (M + H) |
|---|---|---|---|---|---|
| 689 | 3-(4-((cyclopropylmethyl)(tetrahydro-2H-pyran-4-yl)amino)-3-((2-methylbenzo[d]thiazol-6-yl)amino)phenyl)-4-methoxybutanoic acid | 2-methylbenzo[d]thiazol-6-yl | 1.23 | R | 510.3 |
| 690 | 3-(3-((4-chlorophenyl)amino)-4-((cyclopropylmethyl)(tetrahydro-2H-pyran-4-yl)amino)phenyl)-4-methoxybutanoic acid | 4-chlorophenyl | 1.47 | R | 473.2 |
| 691 | 3-(3-((4-cyanophenyl)amino)-4-((cyclopropylmethyl)(tetrahydro-2H-pyran-4-yl)amino)phenyl)-4-methoxybutanoic acid | 4-cyanophenyl | 1.36 | R | 464.3 |
| 692 | 3-(3-((4-cyano-3-methylphenyl)amino)-4-((cyclopropylmethyl)(tetrahydro-2H-pyran-4-yl)amino)phenyl)-4-methoxybutanoic acid | 4-cyano-3-methylphenyl | 1.49 | R | 478.3 |
| 693 | 3-(3-((6-carbamoylpyridin-3-yl)amino)-4-((cyclopropylmethyl)(tetrahydro-2H-pyran-4-yl)amino)phenyl)-4-methoxybutanoic acid | 6-carbamoylpyridin-3-yl | 0.8 | R | 483 |

695A. Methyl 3-(4-(((cyclopropylmethyl)(tetra-hydro-2H-pyran-4-yl)amino)-3-nitrophenyl)pentanoate To a nitrogen flushed sealed tube was added dioxane (05 mL) followed by (R)-(+)-2,2'-bis(diphenylphosphino)-1,1'-binaphthyl (0.046 g, 0.074 mmol) and chlorobis (ethylene) rhodium(I) dimer (0.020 g, 0.050 mmol), purged with nitrogen for 15 minutes. Then in a separate flask, a solution of 676C (1.0 g, 2.58 mmol), methyl 2-pentenoate (0.764 g, 6.70 mmol) and 1N sodium hydroxide (3.01 mL, 3.01 mmol) in dioxane (10 mL) was purged with nitrogen for 15 minutes. This solution was then added to the above reaction mixture in a sealed tube. This reaction mixture was heated to 50° C., stirred for 1 h. The reaction mixture was then cooled to room temperature, quenched with acetic acid (0.173 mL, 3.01 mmol), diluted with water (50 mL) and extracted using ethyl acetate (2×50 mL). The combined organics were washed with (30 mL) brine solution, dried over sodium sulfate and concentrated under reduced pressure. The crude sample was purified by flash chromatography (10% ethyl acetate: pet ether; 12 g silica gel column) to afford 695A (gummy yellow solid, 0.9 g, 2.305 mmol, 68.8% yield). LC-MS Anal. Calc'd. for $C_{21}H_{30}N_2O_5$, 390.21, found [M+H] 391.3, $T_r$=3.93 min (Method U).

695B Enantiomer 1. Methyl 3-(3-amino-4-((cyclopropylmethyl)(tetrahydro-2H-pyran-4-yl)amino)phenyl)pentanoate To a solution of 695A (0.91 g, 2.331 mmol) in ethyl acetate (15 mL) was added Pd/C (0.248 g, 0.233 mmol) and stirred under hydrogen gas atmosphere for 2 h. The reaction mixture was filtered through a pad of CELITE®, followed by rinsing with ethyl acetate (2×20 mL). The combined filtrate was concentrated under reduced pressure. The crude sample was purified by flash chromatography (15% ethyl acetate: pet ether; 12 g silica gel column) to afford 695B Enantiomer 1 (absolute stereochemistry not determined, pale yellow gummy solid, 0.68 g, 1.886 mmol, 81% yield). LC-MS Anal. Calc'd. for $C_{21}H_{32}N_2O_3$, 360.24, found [M+H] 361.2, $T_r$=3.25 min (Method BO). Chiral HPLC $T_r$=6.54 min. (Method CH) and ee=87.14%.

Example 695. 3-(4-((Cyclopropylmethyl)(tetrahydro-2H-pyran-4-yl)amino)-3-(3-(p-tolyl ureido)phenyl)pentanoic acid Example 695 was prepared from 695B Enantiomer 1 and 1-isocyanato-4-methylbenzene following the procedure described for the synthesis of Example 676 (absolute stereochemistry not determined). LC-MS Anal. Calc'd. for $C_{28}H_{37}N_3O_4$ 479.27, found [M+H] 480.3, $T_r$=1.87 min (Method O). $^1$H NMR (400 MHz, methanol-$d_4$) δ 8.06 (d, J=2.0 Hz, 1H), 7.35-7.26 (m, 2H), 7.21-7.07 (m, 3H), 6.85 (dd, J=8.0, 2.2 Hz, 1H), 3.89 (dd, J=11.6, 2.9 Hz, 2H), 3.39-3.33 (m, 2H), 3.09-2.91 (m, 2H), 2.79 (d, J=6.8 Hz, 2H), 2.67-2.51 (m, 2H), 2.31 (s, 3H), 1.81-1.57 (m, 4H), 1.48-1.34 (m, 2H), 0.81 (t, J=7.4 Hz, 3H), 0.69-0.58 (m, 1H), 0.31-0.22 (m, 2H), -0.09 (q, J=4.8 Hz, 2H).

Example 696

Enantiomer 1

3-(3-(3-(4-Chloro-2-fluorophenyl)ureido)-4-((cyclopropylmethyl)(tetrahydro-2H-pyran-4-yl)amino)phenyl)pentanoic acid

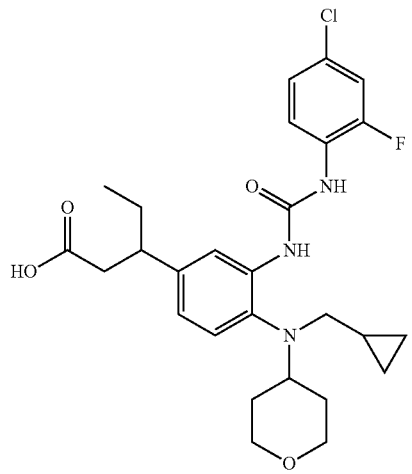 [SMILES: CCC(CC(=O)O)c1ccc(N(CC2CC2)C2CCOCC2)c(NC(=O)Nc2ccc(Cl)cc2F)c1]

Example 696 was prepared from 695B Enantiomer 1 and 4-chloro-2-fluoro-1-isocyanatobenzene following the procedure described for the synthesis of Example 695 (absolute stereochemistry not determined). LC-MS Anal. Calc'd. for $C_{27}H_{33}ClFN_3O_4$, 517.21, found [M+H] 518.2, $T_r$=1.88 min (Method R). $^1$H NMR (400 MHz, methanol-$d_4$) δ 8.07-7.92 (m, 2H), 7.27-7.10 (m, 3H), 6.88 (d, J=8.6 Hz, 1H), 3.95-3.82 (m, 2H), 3.42-3.33 (m, 2H), 3.15-3.04 (m, 1H), 3.00-2.88 (m, 1H), 2.81 (s, 2H), 2.68-2.48 (m, 2H), 1.83-1.67 (m, 3H), 1.67-1.55 (m, 1H), 1.54-1.39 (m, 2H), 0.81 (s, 3H), 0.72-0.57 (m, 1H), 0.31-0.19 (m, 2H), -0.05--0.16 (m, 2H).

Example 697

Enantiomer 1

3-(4-((Cyclopropylmethyl)(tetrahydro-2H-pyran-4-yl)amino)-3-(3-(5-methylisoxazol-3-yl)ureido)phenyl)pentanoic acid

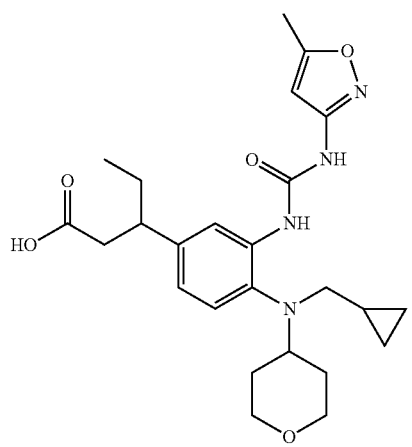 [SMILES: CCC(CC(=O)O)c1ccc(N(CC2CC2)C2CCOCC2)c(NC(=O)Nc2cc(C)on2)c1]

697A. Methyl 3-(4-((cyclopropylmethyl)(tetrahydro-2H-pyran-4-yl)amino)-3-(3-(5-methylisoxazol-3-yl)ureido)phenyl)pentanoate The compound 695B Enantiomer 1 (0.03 g, 0.083 mmol) was dissolved in tetrahydrofuran (1 mL) and to this solution was added 4-nitrophenyl carbonochloridate (0.017 g, 0.083 mmol) and the mixture stirred at room temperature for 2 h. Then triethylamine (0.023 mL, 0.166 mmol) was added followed by 5-methylisoxazol-3-amine (9.80 mg, 0.100 mmol). The resulting mixture was allowed to stir at 70° C. for 12 h. The reaction mixture was then cooled to room temperature and diluted with water (5 mL) and extracted with ethyl acetate (2×10 mL). The combined organics were washed with brine (10 mL), dried over sodium sulfate, filtered and concentrated under reduced pressure to afford 697A (absolute stereochemistry not determined, yellow solid, 0.025 g, 0.052 mmol, 62.0% yield). LC-MS Anal. Calc'd. for $C_{26}H_{36}N_4O_5$, 484.26, found [M+H] 485.5, $T_r$=1.12 min (Method CI).

Example 697. 3-(4-((Cyclopropylmethyl)(tetrahydro-2H-pyran-4-yl)amino)-3-(3-(5-methylisoxazol-3-yl)ureido)phenyl)pentanoic acid Example 697 was prepared from 697A following the procedure described for the synthesis of Example 676 from 676F (absolute stereochemistry not determined). LC-MS Anal. Calc'd. for $C_{25}H_{34}N_4O_5$, 470.25, found [M+H] 471.2. $T_r$=1.75 min (Method R). $^1$H NMR (400 MHz, methanol-$d_4$) δ 8.13 (d, J=2.0 Hz, 1H), 7.24 (d, J=8.2 Hz, 1H), 6.91 (dd, J=8.2, 2.0 Hz, 1H), 6.23 (s, 1H), 3.91 (d, J=9.4 Hz, 2H), 3.41-3.33 (m, 2H), 3.15-3.05 (m, 1H), 2.95 (dd, J=14.6, 6.0 Hz, 1H), 2.84 (d, J=6.8 Hz, 2H), 2.67-2.51 (m, 2H), 2.39 (s, 3H), 1.84-1.70 (m, 3H), 1.68-1.47 (m, 3H), 0.81 (t, J=7.2 Hz, 3H), 0.73-0.61 (m, 1H), 0.26-0.18 (m, 2H), −0.06-−0.13 (m, 2H).

Example 698

Enantiomer 2

Methyl 3-(4-((cyclopropylmethyl)(tetrahydro-2H-pyran-4-yl)amino)-3-(3-(p-tolyl)ureido)phenyl)pentanoate

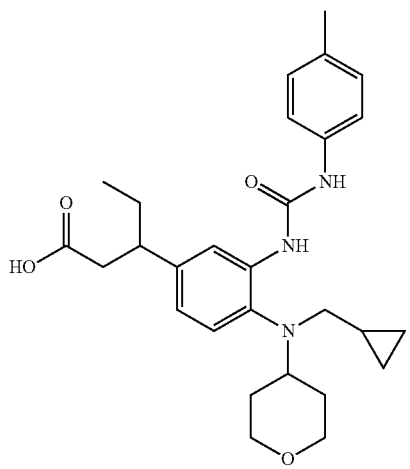 [SMILES: CCC(CC(=O)O)c1ccc(N(CC2CC2)C2CCOCC2)c(NC(=O)Nc2ccc(C)cc2)c1]

698A. Methyl 3-(4-((cyclopropylmethyl)(tetrahydro-2H-pyran-4-yl)amino)-3-(3-(p-tolyl)ureido)phenyl)pentanoate 698A was prepared from 676C and (S)-(−)-2,2'-bis(diphenylphosphino)-1,1'-binaphthyl following the procedure described for the synthesis of 695A. LC-MS Anal. Calc'd. for $C_{21}H_{30}N_2O_5$, 390.21, found 391.3. $T_r$=4 min. (Method U). $^1$H NMR (300 MHz, chloroform-d) δ 7.42 (s, 1H), 7.32-7.28 (m, 2H), 3.97 (d, J=10.8 Hz, 2H), 3.59 (s, 3H), 3.35 (m, 2H), 3.26-3.12 (m, 1H), 3.11-2.97 (m, 1H), 2.90 (d, J=6.6 Hz, 2H), 2.73-2.46 (m, 2H), 1.83-1.60 (m, 6H), 0.83 (t, J=7.4 Hz, 3H), 0.78-0.67 (m, 1H), 0.39-0.28 (m, 2H), −0.07 (q, J=4.8 Hz, 2H).

698B Enantiomer 2. Methyl 3-(3-amino-4-((cyclopropylmethyl)(tetrahydro-2H-pyran-4-yl)amino)phenyl)pentanoate 698B Enantiomer 2 was prepared from 698A following the procedure described for the synthesis of 695B (absolute stereochemistry not determined). LC-MS Anal. Calc'd. for $C_{21}H_{32}N_2O_3$, 360.24, found [M+H] 361.2. $T_r$=3.27 min (Method U). Chiral HPLC $T_r$=9.08 min (Method CH) and ee=86.65%.

698C. Methyl 3-(4-((cyclopropylmethyl)(tetrahydro-2H-pyran-4-yl)amino)-3-(3-(p-tolyl)ureido)phenyl)pentanoate 698C was prepared from 698B Enantiomer 2 following the procedure described for the synthesis of 676F. LC-MS Anal. Calc'd. for $C_{29}H_{39}N_3O_4$, 493.29, found [M+H] 494.5. $T_r$=1.65 min (Method AY).

Example 698. Methyl 3-(4-((cyclopropylmethyl)(tetrahydro-2H-pyran-4-yl)amino)-3-(3-(p-tolyl)ureido)phenyl)pentanoate Example 698 was prepared from 698C following the procedure described for the synthesis of Example 676 from 676F (absolute stereochemistry not determined). LC-MS Anal. Calc'd. for $C_{28}H_{37}N_3O_4$, 479.27, found [M+H] 480.3. $T_r$=1.85 min (Method R). $^1$H NMR (400 MHz, methanol-$d_4$) δ 8.06 (d, J=2.2 Hz, 1H), 7.34-7.29 (m, 2H), 7.19 (d, J=8.2 Hz, 1H), 7.14 (d, J=8.2 Hz, 2H), 6.86 (dd, J=8.2, 2.0 Hz, 1H), 3.89 (d, J=14.4 Hz, 2H), 3.40-3.33 (m, 2H), 3.04 (t, J=11.2 Hz, 1H), 2.99-2.90 (m, 1H), 2.78 (d, J=6.6 Hz, 2H), 2.67-2.50 (m, 3H), 2.33-2.26 (m, 3H), 1.82-1.56 (m, 3H), 1.51-1.33 (m, 3H), 0.81 (t, J=7.2 Hz, 3H), 0.63 (s, 1H), 0.31-0.22 (m, 2H), −0.09 (q, J=4.8 Hz, 2H).

Example 699

Enantiomer 2

3-(3-(3-(4-Chloro-2-fluorophenyl)ureido)-4-((cyclopropylmethyl)(tetrahydro-2H-pyran-4-yl)amino)phenyl)pentanoic acid

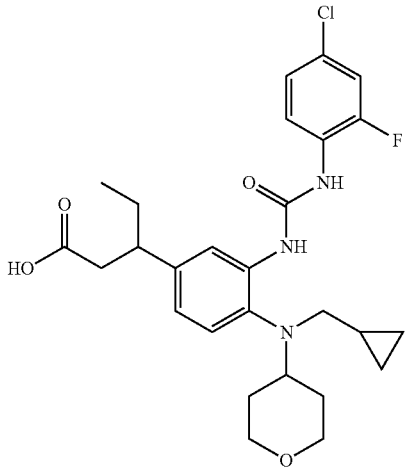 [SMILES: CCC(CC(=O)O)c1ccc(N(CC2CC2)C2CCOCC2)c(NC(=O)Nc2ccc(Cl)cc2F)c1]

Example 699 was prepared from 698B Enantiomer 2 and 4-chloro-2-fluoro-1-isocyanatobenzene following the procedure described for the synthesis of Example 678. LC-MS Anal. Calc'd. for $C_{27}H_{33}ClFN_3O_4$, 517.21, found [M+H] 518.2, $T_r$=2.05 min (Method O). $^1$H NMR (400 MHz, methanol-d$_4$) δ 8.07-7.92 (m, 2H), 7.27-7.10 (m, 3H), 6.88 (d, J=8.6 Hz, 1H), 3.95-3.82 (m, 2H), 3.42-3.33 (m, 2H), 3.15-3.04 (m, 1H), 3.00-2.88 (m, 1H), 2.81 (s, 2H), 2.68-2.48 (m, 2H), 1.83-1.67 (m, 3H), 1.67-1.55 (m, 1H), 1.54-1.39 (m, 2H), 0.81 (s, 3H), 0.72-0.57 (m, 1H), 0.31-0.19 (m, 2H), −0.05--0.16 (m, 2H).

Example 700

Enantiomer 2

3-(4-((Cyclopropylmethyl)(tetrahydro-2H-pyran-4-yl)amino)-3-(3-(5-methylisoxazol-3-yl)ureido)phenyl)pentanoic acid

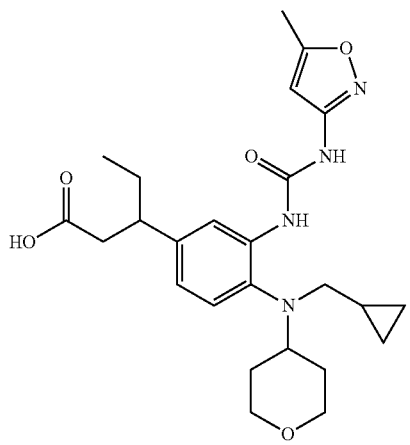 [SMILES: CCC(CC(=O)O)c1ccc(N(CC2CC2)C2CCOCC2)c(NC(=O)Nc2cc(C)on2)c1]

Example 700 was prepared from 698B Enantiomer 2 following the procedure described for the synthesis of Example 697 (absolute stereochemistry not determined). LC-MS Anal. Calc'd. for $C_{25}H_{34}N_4O_{55}$, 470.25, found [M+H] 471.3, $T_r$=1.74 min (Method R). $^1$H NMR (400 MHz, methanol-d$_4$) δ 8.12 (d, J=2.0 Hz, 1H), 7.23 (d, J=8.2 Hz, 1H), 6.92 (dd, J=8.2, 2.0 Hz, 1H), 6.24 (s, 1H), 3.90 (d, J=6.6 Hz, 2H), 3.42-3.33 (m, 2H), 3.15-3.05 (m, 1H), 3.01-2.90 (m, 1H), 2.83 (d, J=6.8 Hz, 2H), 2.68-2.51 (m, 2H), 2.39 (s, 3H), 1.84-1.68 (m, 3H), 1.67-1.45 (m, 3H), 0.81 (t, J=7.2 Hz, 3H), 0.66 (d, J=7.8 Hz, 1H), 0.26-0.18 (m, 2H), −0.09 (q, J=4.8 Hz, 2H).

Example 701

Enantiomer 1

3-(4-((Cyclopropylmethyl)(tetrahydro-2H-pyran-4-yl)amino)-3-((2-methylbenzo[d]thiazol-6-yl)amino)phenyl)pentanoic acid

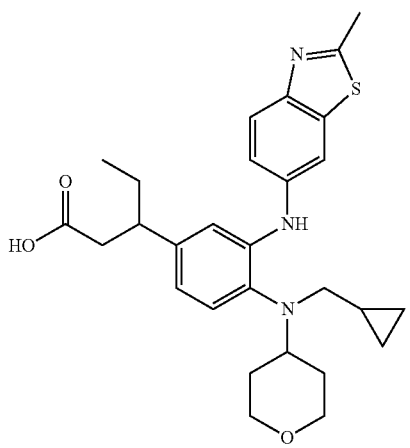 [SMILES: CCC(CC(=O)O)c1ccc(N(CC2CC2)C2CCOCC2)c(Nc2ccc3nc(C)sc3c2)c1]

Example 701 was prepared from 695B Enantiomer 1 and 6-bromo-2-methylbenzo[d]thiazole following the procedure described for the synthesis of Example 679 (absolute stereochemistry not determined). LC-MS Anal. Calc'd. for $C_{28}H_{35}N_3O_3S$, 493.24, found [M+H] 494.3, $T_r$=1.64 min (Method R). $^1$H NMR (400 MHz, methanol-d$_4$) δ 7.75 (d, J=8.8 Hz, 1H), 7.67 (d, J=2.4 Hz, 1H), 7.28-7.16 (m, 3H), 6.77 (dd, J=8.0, 2.0 Hz, 1H), 3.87 (d, J=12.7 Hz, 2H), 3.37-3.33 (m, 2H), 3.12-3.02 (m, 1H), 2.97-2.88 (m, 1H), 2.86 (d, J=6.8 Hz, 2H), 2.77 (s, 3H), 2.68-2.60 (m, 1H), 2.58-2.49 (m, 1H), 1.84-1.65 (m, 3H), 1.65-1.54 (m, 1H), 1.53-1.41 (m, 2H), 0.83 (t, J=7.2 Hz, 3H), 0.71 (m, 1H), 0.31-0.24 (m, 2H), 0.01--0.04 (m, 2H).

Examples 702 to 706

Enantiomer 1

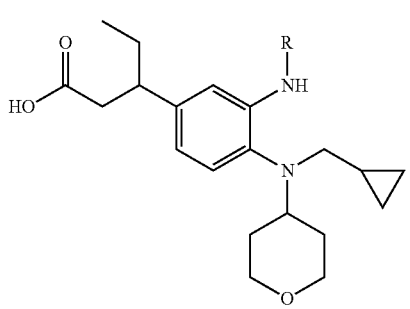

Examples 702 to 706 was prepared from 695B Enantiomer 1 and corresponding aryl halides following the procedure described for the synthesis of Example 679 (absolute stereochemistry not determined).

| Ex. No. | Name | R | $T_r$, min | Method | (M + H) |
|---|---|---|---|---|---|
| 702 | 3-(3-((4-chlorophenyl)amino)-4-((cyclopropylmethyl)(tetrahydro-2H-pyran-4-yl)amino)phenyl)pentanoic acid | | 1.92 | R | 457.2 |
| 703 | 3-(4-((cyclopropylmethyl)(tetrahydro-2H-pyran-4-yl)amino)-3-((2-methoxypyrimidin-5-yl)amino)phenyl)pentanoic acid | | 1.49 | R | 455.3 |
| 704 | 3-(4-((cyclopropylmethyl)(tetrahydro-2H-pyran-4-yl)amino)-3-((2,2-difluorobenzo[d][1,3]dioxol-5-yl)amino)phenyl)pentanoic acid | | 2.01 | R | 503.3 |
| 705 | 3-(4-((cyclopropylmethyl)(tetrahydro-2H-pyran-4-yl)amino)-3-((2-ethoxypyrimidin-5-yl)amino)phenyl)pentanoic acid | | 2.42 | U | 469.4 |
| 706 | 3-(3-((4-cyanophenyl)amino)-4-((cyclopropylmethyl)(tetrahydro-2H-pyran-4-yl)amino)phenyl)pentanoic acid | | 1.54 | R | 448.2 |

Example 707

Enantiomer 2

3-(4-((Cyclopropylmethyl)(tetrahydro-2H-pyran-4-yl)amino)-3-((2-methylbenzo[d]thiazol-6-yl)amino)phenyl)pentanoic acid

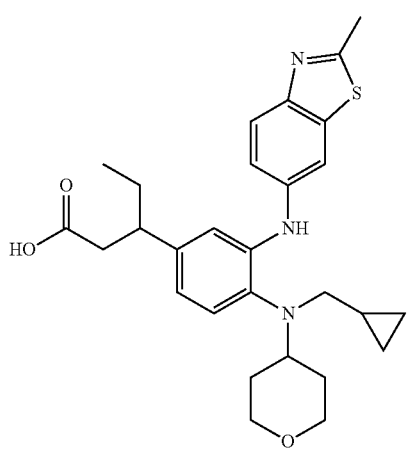 [SMILES: CCC(CC(=O)O)c1ccc(N(CC2CC2)C2CCOCC2)c(Nc2ccc3nc(C)sc3c2)c1]

Example 707 was prepared from 698B Enantiomer 2 following the procedure described for the synthesis of Example 679 (absolute stereochemistry not determined). LC-MS Anal. Calc'd. for $C_{28}H_{35}N_3O_3S$, 493.24, found [M+H] 494.3, $T_r$=1.63 min (Method R). $^1$H NMR (400 MHz, methanol-$d_4$) δ 7.75 (d, J=8.6 Hz, 1H), 7.66 (d, J=2.2 Hz, 1H), 7.28-7.20 (m, 2H), 7.18 (d, J=2.0 Hz, 1H), 6.77 (dd, J=8.0, 2.0 Hz, 1H), 3.88 (d, J=12.2 Hz, 2H), 3.38-3.33 (m, 2H), 3.15-3.00 (m, 1H), 2.97-2.83 (m, 3H), 2.77 (s, 3H), 2.68-2.59 (m, 1H), 2.58-2.46 (m, 1H), 1.84-1.66 (m, 3H), 1.66-1.33 (m, 3H), 0.83 (t, J=7.2 Hz, 3H), 0.76-0.65 (m, 1H), 0.31-0.23 (m, 2H), 0.01--0.05 (m, 2H).

Examples 708 to 712

Enantiomer 2

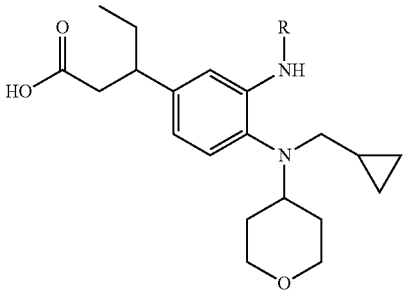

Examples 708 to 712 were prepared from 698B Enantiomer 2 and corresponding aryl halides following the procedure described for the synthesis of Example 679 (absolute stereochemistry not determined).

| Ex. No. | Name | R | $T_r$, min | Method | (M + H) |
|---|---|---|---|---|---|
| 708 | 3-(3-((4-chlorophenyl)amino)-4-((cyclopropylmethyl)(tetrahydro-2H-pyran-4-yl)amino)phenyl)pentanoic acid | | 1.87 | R | 457.2 |
| 709 | 3-(4-((cyclopropylmethyl)(tetrahydro-2H-pyran-4-yl)amino)-3-((2-methoxypyrimidin-5-yl)amino)phenyl)pentanoic acid | | 2.53 | U | 455.2 |
| 710 | 3-(4-((cyclopropylmethyl)(tetrahydro-2H-pyran-4-yl)amino)-3-((2,2-difluorobenzo[d][1,3]dioxol-5-yl)amino)phenyl)pentanoic acid | | 2.0 | R | 503.3 |
| 711 | 3-(4-((cyclopropylmethyl)(tetrahydro-2H-pyran-4-yl)amino)-3-((2-ethoxypyrimidin-5-yl)amino)phenyl)pentanoic acid | | 2.14 | U | 469.4 |
| 712 | 3-(3-((4-cyanophenyl)amino)-4-((cyclopropylmethyl)(tetrahydro-2H-pyran-4-yl)amino)phenyl)pentanoic acid | | 1.53 | R | 448.3 |

Example 713

Enantiomer 1

3-(4-((Cyclopropylmethyl)(isopropyl)amino)-3-((2-methylbenzo[d]thiazol-6-yl)amino)phenyl)pentanoic acid

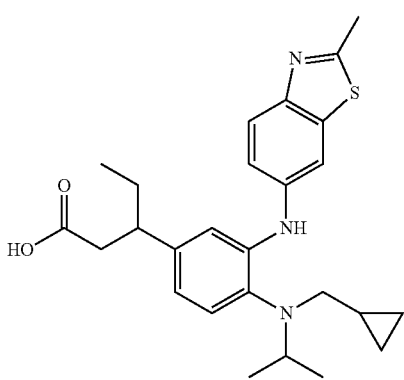 [SMILES: CCC(CC(=O)O)c1ccc(N(CC2CC2)C(C)C)c(Nc2ccc3nc(C)sc3c2)c1]

713A. N-(Cyclopropylmethyl)propan-2-amine

To a stirred solution of cyclopropanecarbaldehyde (8 g, 114 mmol) in tetrahydrofuran (40 mL) and MeOH (40 mL) was added propan-2-amine (6.75 g, 114 mmol) followed by 4 Å molecular sieves (5 g) at ambient temperature. Reaction mixture was stirred at room temperature for 18 h. The reaction mixture was cooled to 0° C., was added sodium borohydride (12.95 g, 342 mmol) portionwise and stirred at room temperature for 2 h. The reaction mixture was concentrated under reduced pressure. The resultant semi-solid was quenched with 10% NaHCO$_3$ solution. The solids were filtered through pad of CELITE®. The filtrate was extracted with ethyl acetate (2×250 mL). The combined organic layer was washed with brine (2×250 mL) and dried over Na$_2$SO$_4$, concentrated under reduced pressure to afford 713A (colorless oil, 6.3 g, 55.7 mmol, 48.8% yield). $^1$H NMR (400 MHz, DMSO-d$_6$) δ5.56 (br. s., 1H), 3.22-3.11 (m, 1H), 2.61-2.52 (m, 2H), 1.10-1.00 (m, 6H), 0.55-0.40 (m, 2H), 0.29-0.11 (m, 2H) (Note: one proton buried under solvent peak).

713B. 4-Bromo-N-(cyclopropylmethyl)-N-isopropyl-2-nitroaniline 713B was prepared from 713A following the procedure described for the synthesis of 676B. LC-MS Anal. Calc'd. for C$_{13}$HrBrN$_2$O$_2$, 312.04, found [M+H] 313.0, T$_r$=3.85 min (Method U).

713C. N-(Cyclopropylmethyl)-4-(5,5-dimethyl-1,3,2-dioxaborinan-2-yl)-N-isopropyl-2-nitroaniline 713C was prepared from 713B following the procedure described for the synthesis of 676C. LC-MS Anal. Calc'd. for C$_{18}$H$_{27}$BN$_2$O$_4$, 346.22, found [M+H] 279.2 (for parent boronic acid), T$_r$=2.64 min (Method U).

713D. Methyl 3-(4-((cyclopropylmethyl)(isopropyl)amino)-3-nitrophenyl)pentanoate 713D was prepared from 713C and (S)-(−)-2,2'-bis(diphenylphosphino)-1,1'-binaphthyl following the procedure described for the synthesis of 695A. LC-MS Anal. Calc'd. for $C_{19}H_{28}N_2O_4$, 348.43, found [M+H] 349.2. $T_r$=3.78 min (Method U).

713E Enantiomer-1. Methyl 3-(3-amino-4-((cyclopropylmethyl)(isopropyl)amino)phenyl)pentanoate 713E Enantiomer 1 was prepared from 713D following the procedure described for the synthesis of 676E. LC-MS Anal. Calc'd. for $C_{19}H_{30}N_2O_2$, 318.45, found [M+H] 319.2. $T_r$=3.75 min (Method U). Chiral HPLC $T_r$=7.52 min. (Method CJ) and ee=86%.

Example 713. 3-(4-((Cyclopropylmethyl)(isopropyl)amino)-3-((2-methylbenzo[d]thiazol-6-yl)amino)phenyl)pentanoic acid Example 713 was prepared from 713E Enantiomer 1 and 6-bromo-2-methylbenzo[d]thiazole following the procedure described for the synthesis of Example 679 (absolute stereochemistry not determined). LC-MS Anal. Calc'd. for $C_{26}H_{33}N_3O_2S$, 451.62, found [M+H] 452.2, $T_r$=1.49 min (Method R). $^1$H NMR (400 MHz, methanol-$d_4$) δ 7.76 (d, J=9.0 Hz, 1H), 7.67 (d, J=2.0 Hz, 1H), 7.29-7.24 (m, 1H), 7.24-7.18 (m, 2H), 6.78 (dd, J=8.0, 2.0 Hz, 1H), 3.25-3.15 (m, 1H), 2.99-2.89 (m, 1H), 2.86 (d, J=7.0 Hz, 2H), 2.79 (s, 3H), 2.69-2.62 (m, 1H), 2.60-2.51 (m, 1H), 1.79-1.69 (m, 1H), 1.67-1.56 (m, 1H), 1.06 (d, J=6.6 Hz, 6H), 0.85 (t, J=7.4 Hz, 3H), 0.71 (d, J=8.0 Hz, 1H), 0.32-0.26 (m, 2H), 0.05--0.01 (m, 2H).

Examples 714 and 715

Enantiomer 1

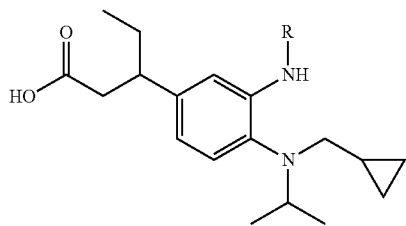

Examples 714 and 715 was prepared from 713E Enantiomer 1 and corresponding aryl halides following the procedure described for the synthesis of Example 679 (absolute stereochemistry not determined).

Example 716

Enantiomer 2

3-(4-((Cyclopropylmethyl)(isopropyl)amino)-3-((2-methylbenzo[d]thiazol-6-yl)amino)phenyl)pentanoic acid

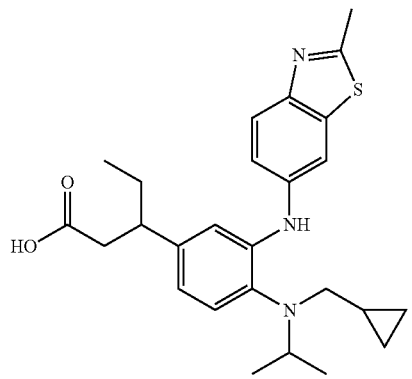 [SMILES: CCC(CC(=O)O)c1ccc(N(CC2CC2)C(C)C)c(Nc2ccc3nc(C)sc3c2)c1]

716A. Methyl 3-(4-((cyclopropylmethyl)(isopropyl)amino)-3-nitrophenyl)pentanoate 716A was prepared from 713C and (R)-(+)-2,2'-bis(diphenylphosphino)-1,1'-binaphthyl following the procedure described for the synthesis of 695A. LC-MS Anal. Calc'd. for $C_{19}H_{28}N_2O_4$, 348.43, found [M+H] 349.2, $T_r$=3.74 min (Method U).

716B Enantiomer 2. Methyl 3-(3-amino-4-((cyclopropylmethyl)(isopropyl)amino)phenyl)pentanoate 716B Enantiomer 2 was prepared from 716A following the procedure described for the synthesis of 676E (absolute stereochemistry not determined). LC-MS Anal. Calc'd. for $C_{19}H_{30}N_2O_2$, 318.45, found [M+H] 319.2, $T_r$=3.74 min (Method U). Chiral HPLC $T_r$=9.07 min. (Method CJ) and ee=86%.

Example 716. 3-(4-((Cyclopropylmethyl)(isopropyl)amino)-3-((2-methylbenzo[d]thiazol-6-yl)amino)phenyl)pentanoic acid Example 716 was prepared from 716B Enantiomer 2 following the procedure described for the synthesis of

| Ex. No. | Name | R | $T_r$ min | Method | (M + H) |
|---|---|---|---|---|---|
| 714 | 3-(3-((4-chlorophenyl)amino)-4-((cyclopropylmethyl)(isopropyl)amino)phenyl)pentanoic acid | *4-chlorophenyl* | 1.72 | R | 415.2 |
| 715 | 3-(4-((cyclopropylmethyl)(isopropyl)amino)-3-((2,2-difluorobenzo[d][1,3]dioxol-5-yl)amino)phenyl)pentanoic acid | *2,2-difluorobenzo[d][1,3]dioxol-5-yl* | 1.87 | R | 461.2 |

Example 679 (absolute stereochemistry not determined). LC-MS Anal. Calc'd. for $C_{26}H_{33}N_3O_2S$, 451.62, found [M+H] 452.3, $T_r$=1.49 min (Method R). $^1$H NMR (400 MHz, methanol-$d_4$) δ 7.73 (d, J=8.4 Hz, 2H), 7.60-7.47 (m, 1H), 7.34 (m, 2H), 7.09 (m, 1H), 3.35 (s, 1H), 3.08-2.93 (m, 1H), 2.76 (s, 3H), 2.73-2.63 (m, 1H), 2.60-2.50 (m, 1H), 1.84-1.70 (m, 1H), 1.67-1.53 (m, 1H), 1.38-1.15 (m, 6H), 0.82 (t, J=7.2 Hz, 6H), 0.41 (m, 2H), 0.14 (s, 2H).

Examples 717 and 718
Enantiomer 2

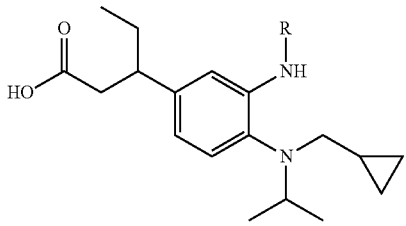

Examples 717 and 718 was prepared from 716B Enantiomer 2 and corresponding aryl halides following the procedure described for the synthesis of Example 679 (absolute stereochemistry not determined).

| Ex. No. | Name | R | $T_r$, min | Method | (M + H) |
|---|---|---|---|---|---|
| 717 | 3-(3-((4-chlorophenyl)amino)-4-((cyclopropylmethyl)(isopropyl)amino)phenyl)pentanoic acid | 4-chlorophenyl | 1.70 | O | 415.2 |
| 718 | 3-(4-((cyclopropylmethyl)(isopropyl)amino)-3-((2-ethoxypyrimidin-5-yl)amino)phenyl)pentanoic acid | 2-ethoxypyrimidin-5-yl | 1.37 | R | 427.3 |

Example 727. 3-(3-((4-Chlorophenyl)amino)-4-(isobutyl(isopropyl)amino)phenyl)pentanoic acid To the crude residue 727A, lithium hydroxide (11.96 mg, 0.499 mmol), methanol (0.5 mL) and water (0.2 mL) were added and the reaction mixture was stirred for 3 h at room temperature. The solvent was removed under reduced pressure. The crude residue was dissolved in DCM (0.5 mL) and treated with 1.5 N HCl to pH~2. The compound was extracted with DCM (10 mL). Reverse phase prep LCMS gave Example 727 (absolute stereochemistry not determined). LC-MS Anal. Calc'd. for $C_{24}H_{33}ClN_2O_2$, 416.99, found [M+H] 417.3, $T_r$=2.545 min (Method O). $^1$H NMR (400 MHz, DMSO-$d_6$) δ 12.00 (s, 1H), 7.20-7.30 (m, 2H), 6.90-7.10 (m, 5H), 6.65-6.75 (m, 1H), 2.32-2.82 (m, 6H), 1.24-1.64 (m, 3H), 0.99 (d, J=5.60 Hz, 6H), 0.81 (d, J=6.80 Hz, 6H), 0.73 (t, J=7.60 Hz, 3H).

Example 727
Enantiomer 1
3-(3-((4-Chlorophenyl)amino)-4-(isobutyl(isopropyl)amino)phenyl)pentanoic acid

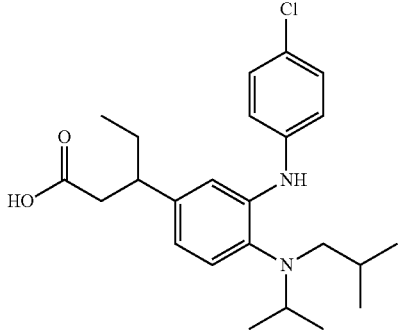 [SMILES: CCC(CC(=O)O)c1ccc(N(CC(C)C)C(C)C)c(Nc2ccc(Cl)cc2)c1]

727A. Methyl 3-(3-((4-chlorophenyl)amino)-4-(isobutyl(isopropyl)amino)phenyl)pentanoate To a vial containing 719E (20 mg, 0.062 mmol), 1-bromo-4-chlorobenzene (17.92 mg, 0.094 mmol) and cesium carbonate (50.8 mg, 0.156 mmol) was added 1,4-dioxane (1 mL). The mixture was purged with nitrogen for about 10 minutes. Then Xantphos (7.22 mg, 0.012 mmol) and bis(dibenzylideneacetone)palladium (3.59 mg, 6.24 μmol) were added and the reaction mixture was heated for 6 h at 110° C. The solvent was removed under reduced pressure to afford 727A. LC-MS Anal. Calc'd. for $C_{25}H_{35}ClN_2O_2$ 431.01, found [M+H] 431.3, $T_r$=3.017 min. (Method DK).

Example 728
Enantiomer 2
3-(3-((4-Chlorophenyl)amino)-4-(isobutyl(isopropyl)amino)phenyl)pentanoic acid

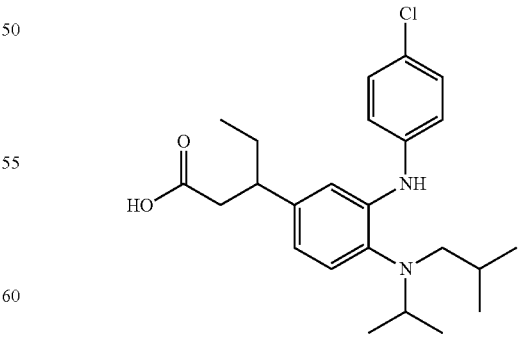

728A. Methyl 3-(4-(isobutyl(isopropyl)amino)-3-nitrophenyl)pentanoate 728A was prepared from 719C and (S)-(−)-2,2'-bis(diphenylphosphino)-1,1'-binaphthyl following the procedure described for the synthesis of 719D. LC-MS Anal. Calc'd. for $C_{19}H_{30}N_2O_4$, 350.453, found [M+H] 351.4. $T_r$=3.905 min (Method U).

728B. Methyl 3-(3-amino-4-(isobutyl(isopropyl)amino)phenyl)pentanoate 728B was prepared from 728A following the procedure described for the synthesis of 719E. LC-MS Anal. Calc'd. for $C_{19}H_{32}N_2O_2$, 320.470, found [M+H] 321.4. $T_r$=3.891 min. Chiral analytical analysis verified and enantiomeric excess (ee) was 100%. $T_r$=16.274 min (Method DA).

Example 728 was prepared from 728B following the procedure described for the synthesis of Example 727 (absolute stereochemistry not determined). LC-MS Anal. Calc'd. for $C_{24}H_{33}ClN_2O_2$, 417.2, found [M+H] 418.3. $T_r$=2.055 min (Method R). $^1$H NMR (400 MHz, DMSO-$d_6$) δ12.00 (s, 1H), 7.20-7.30 (m, 2H), 6.90-7.10 (m, 5H), 6.65-6.75 (m, 1H), 2.32-2.82 (m, 6H), 1.24-1.64 (m, 3H), 0.99 (d, J=5.60 Hz, 6H), 0.81 (d, J=6.80 Hz, 6H), 0.73 (t, J=7.60 Hz, 3H).

Example 729

Enantiomer 1

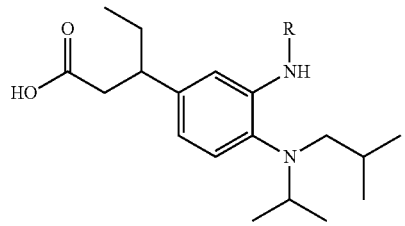

Example 729 was prepared from 719E following the procedure described for the synthesis of Example 727.

| Ex. No. | Name | R | $T_r$ min | Method | (M + H) |
|---|---|---|---|---|---|
| 729 | 3-(4-(isobutyl(isopropyl)amino)-3-((2-methylbenzo[d]thiazol-6-yl)amino)phenyl)pentanoic acid | | 2.247 | O | 454.4 |

Example 730

Enantiomer 2 homochiral, absolute stereochemistry not determined

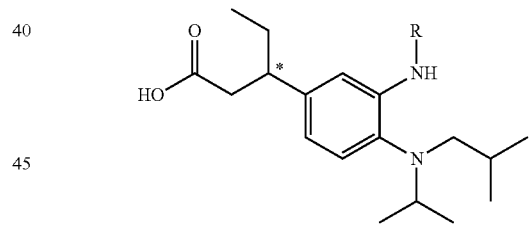

Example 730 was prepared from 728B and corresponding halide following the procedure described for the synthesis of Example 727.

| Ex. No. | Name | R | $T_r$ min | Method | (M + H) |
|---|---|---|---|---|---|
| 730 | 3-(4-(isobutyl(isopropyl)amino)-3-((2-methylbenzo[d]thiazol-6-yl)amino)phenyl)pentanoic acid | | 2.460 | O | 454.3 |

Example 731

3-(3-((4-Cyanophenyl)amino)-4-((2S,6R)-2,6-dimethylmorpholino)phenyl)-3-methylbutanoic acid

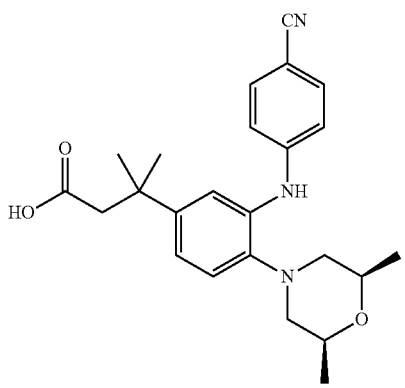 [SMILES: C[C@@H]1CN(c2ccc(C(C)(C)CC(=O)O)cc2Nc2ccc(C#N)cc2)C[C@H](C)O1]

731A. Methyl 3-(4-((2S,6R)-2,6-dimethylmorpholino)-3-nitrophenyl)-3-methylbutanoate To a solution of 1F (0.6 g, 2.351 mmol) and (2S,6R)-2,6-dimethylmorpholine (0.298 g, 2.59 mmol) in N-methyl-2-pyrrolidone (5 mL) was added N,N-diisopropylethylamine (1.232 mL, 7.05 mmol). After stirring at 120° C. for 16 h, the reaction mixture was cooled to RT and diluted with diethyl ether. The organic layer was washed with 10% aq. AcOH solution, 10% NaHCO$_3$ solution, and brine. The combined organics were dried over Na$_2$SO$_4$, filtered, and concentrated under reduced pressure. Purification via flash chromatography gave 731A (orange semi-solid, 0.7 g, 1.998 mmol, 85% yield). LC-MS Anal. Calc'd. for C$_{18}$H$_{26}$N$_2$O$_5$, 350.409, found [M+H] 351.2, T$_r$=3.568 min (Method U).

731B. Methyl 3-(3-amino-4-((2S,6R)-2,6-dimethylmorpholino)phenyl)-3-methylbutanoate The solution of 731A (0.7 g, 1.998 mmol) in ethyl acetate (30 mL) was charged to a sealable Parr hydrogenation flask. The solution was sequentially evacuated and purged with nitrogen gas. To this 10% palladium on carbon (0.106 g, 0.100 mmol) was added under nitrogen atmosphere. The reaction mixture was stirred under hydrogen atmosphere (40 psi). The reaction mixture was stirred at room temperature for 3 hours. The reaction mixture was filtered through a CELITE® pad and the residue on the pad was thoroughly rinsed with MeOH (3×50 mL). The combined filtrate was concentrated under reduced pressure to afford 731B (colorless liquid, 0.6 g, 1.873 mmol, 94% yield). LC-MS Anal. Calc'd. for C$_{18}$H$_{28}$N$_2$O$_3$, 320.427, found [M+H] 321.4. T$_r$=2.969 min (Method U).

731C. 3-(3-((4-Cyanophenyl)amino)-4-((2S,6R)-2,6-dimethylmorpholino)phenyl)-3-methylbutanoic acid The mixture of 731B (25 mg, 0.078 mmol), 4-bromobenzonitrile (18.46 mg, 0.101 mmol), Xantphos (9.03 mg, 0.016 mmol) and cesium carbonate (76 mg, 0.234 mmol) in 1,4-dioxane (1 mL) was stirred at room temperature. Argon gas was bubbled through the mixture for 10 min. Bis(dibenzylideneacetone)palladium (4.49 mg, 7.80 μmol) was added and argon gas was bubbled through the mixture for 5 min. The reaction mixture was sealed and placed in preheated oil bath at 110° C. for 18 hours. The reaction mixture was cooled to room temperature and concentrated under reduced pressure to afford a residue. The residue was reconstituted in a mixture of DCM (50 mL) and water (10 mL). The organic layer was separated and was washed with water (10 mL), brine (10 mL), dried over anhydrous sodium sulfate, filtered, and concentrated under reduced pressure to afford 731C. LC-MS Anal. Calc'd. for C$_{25}$H$_{31}$N$_3$O$_3$, 421.53, found [M+H] 422.2. T$_r$=3.02 min (Method CK).

Example 731. 3-(3-((4-Cyanophenyl)amino)-4-((2S,6R)-2,6-dimethylmorpholino)phenyl)-3-methylbutanoic acid To the crude residue 731C, lithium hydroxide (14.95 mg, 0.624 mmol), and methanol (0.5 mL) were added and the reaction mixture was stirred for 2 h at room temperature. Desired product mass was observed. The solvent was removed. The crude residue was dissolved with DCM (0.5 mL) and treated with 1.5 N HCl until pH is acidic. The compound was extracted with DCM. The organic layer was dried over sodium sulfate, filtered, and concentrated under reduced pressure. The compound was purified by prep HPLC to obtain Example 731. LC-MS Anal. Calc'd. for C$_{24}$H$_{29}$N$_3$O$_3$, 407.51, found [M+H] 408.3. T$_r$=1.599 min (Method O). $^1$H NMR (400 MHz, DMSO-d$_6$) δ11.85 (s, 1H), 8.19 (s, 1H), 7.50 (dd, J=1.60, 7.00 Hz, 2H), 7.18 (dd, J=2.40, Hz, 1H), 7.11 (dd, J=2.40, 8.40 Hz, 1H), 6.96 (d, J=8.40 Hz, 1H), 6.88 (dd, J=2.00, 7.00 Hz, 2H), 3.43-3.47 (m, 2H), 2.99 (d, J=10.80 Hz, 2H), 2.53 (s, 2H), 2.24 (t, J=10.80 Hz, 2H), 1.35 (s, 6H), 0.99 (d, J=6.40 Hz, 6H).

Examples 732 to 736

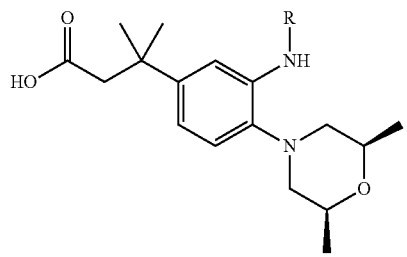

Examples 732 to 736 was prepared from 731B and the corresponding aryl halides following the procedure described for the synthesis of Example 731.

| Ex. No. | Name | R | $T_r$, min | Method | (M + H) |
|---|---|---|---|---|---|
| 732 | 3-(4-((2S,6R)-2,6-dimethylmorpholino)-3-((4-fluorophenyl)amino)phenyl)-3-methylbutanoic acid | 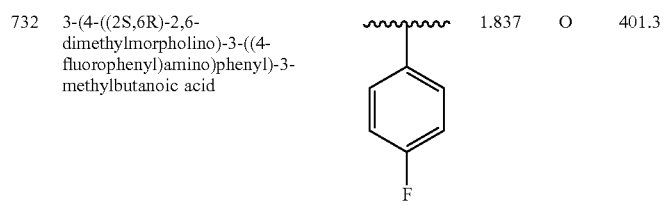 | 1.837 | O | 401.3 |
| 733 | 3-(3-((4-chlorophenyl)amino)-4-((2S,6R)-2,6-dimethylmorpholino)phenyl)-3-methylbutanoic acid | 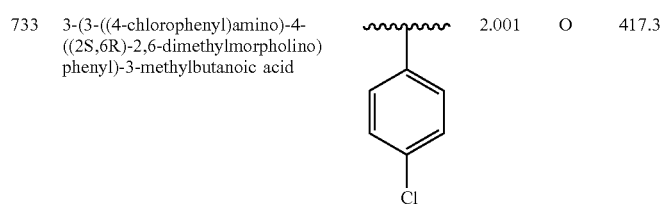 | 2.001 | O | 417.3 |
| 734 | 3-(4-((2S,6R)-2,6-dimethylmorpholino)-3-((4-ethylphenyl)amino)phenyl)-3-methylbutanoic acid | 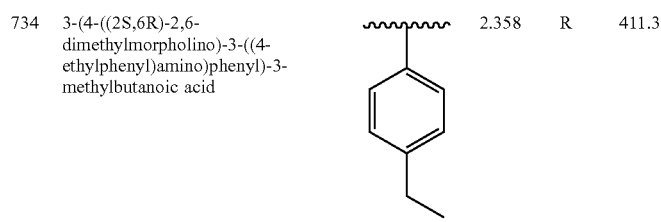 | 2.358 | R | 411.3 |
| 735 | 3-(4-((2S,6R)-2,6-dimethylmorpholino)-3-((2-methoxypyrimidin-5-yl)amino)phenyl)-3-methylbutanoic acid | 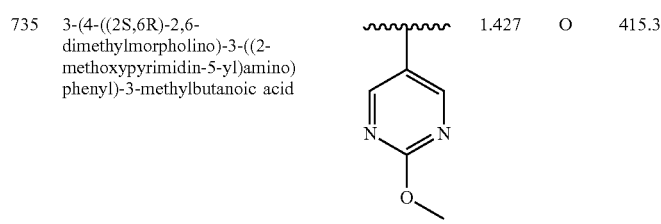 | 1.427 | O | 415.3 |
| 736 | 3-(4-((2S,6R)-2,6-dimethylmorpholino)-3-((2-ethoxypyrimidin-5-yl)amino)phenyl)-3-methylbutanoic acid | 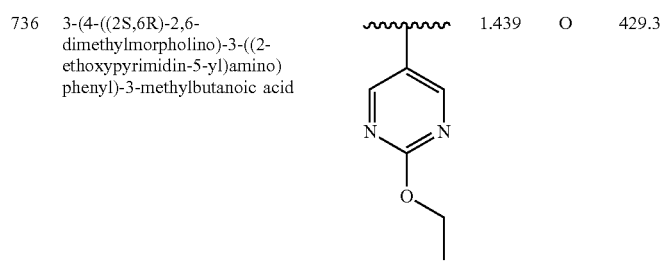 | 1.439 | O | 429.3 |

Example 737

Enantiomer 1

3-(3-((4-Cyanophenyl)amino)-4-((2S,6R)-2,6-dimethylmorpholino)phenyl)butanoic acid (Homochiral, Absolute Stereochemistry not Determined)

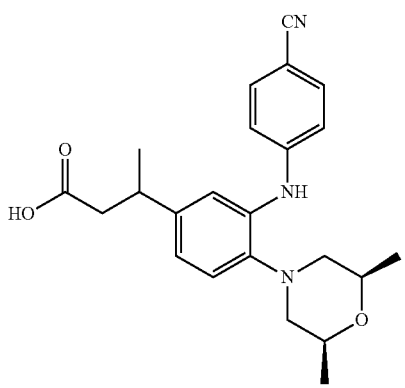 [SMILES: CC(CC(=O)O)c1ccc(N2C[C@@H](C)O[C@@H](C)C2)c(Nc2ccc(C#N)cc2)c1]

737A. 2-(4-Fluoro-3-nitrophenyl)-5,5-dimethyl-1,3,2-dioxaborinane

To a stirred solution of 4-bromo-1-fluoro-2-nitrobenzene (10.0 g, 45.5 mmol), 5,5,5',5'-tetramethyl-2,2'-bi(1,3,2-dioxaborinane) (12.32 g, 54.5 mmol), potassium acetate (13.38 g, 136 mmol) in dry dioxane (100 mL) purged argon for 10 minutes added $PdCl_2$ (dppf).$CH_2Cl_2$ Adduct (1.856 g, 2.273 mmol) and purged argon for 10 minutes. Reaction was sealed and placed in the microwave at 120° C. and heated overnight. Reaction mixture cooled to room temperature, diluted with ethyl acetate (100 mL), and washed with water (50 mL). The organic layer was separated, and the aqueous layer was back extracted with ethyl acetate (2×50 mL). The combined organic layer was dried over sodium sulfate, filtered, and concentrated under reduced pressure. Purification via flash chromatography gave 737A (off-white solid, 9.75 g, 38.5 mmol, 85%). $^1$H NMR (400 MHz, $CDCl_3$) δ 8.46 (dd, J=1.60, 8.00 Hz, 1H), 8.00-8.04 (m, 1H), 7.24 (dd, J=8.40, 10.40 Hz, 1H), 3.78 (s, 4H), 1.03 (s, 6H).

737B. Methyl 3-(4-fluoro-3-nitrophenyl)butanoate

In a sealed tube 737A (10.0 g, 39.5 mmol), (E)-methyl but-2-enoate (3.96 g, 39.5 mmol) and sodium hydroxide (36.1 mL, 36.1 mmol) in 1,4-dioxane (50 mL) was purged with argon for 30 min. To this chloro(1,5-cyclooctadiene)rhodium(I) dimer (0.974 g, 1.976 mmol) was added and purged with argon for 10 min. The reaction mixture was heated at 50° C. for 3 h. Reaction mixture was cooled to room temperature and quenched with acetic acid (2.036 mL, 35.6 mmol) and it was stirred for 5 minutes. The reaction mixture was partitioned between ethyl acetate and water. Aqueous layer was extracted with ethyl acetate. The combined organic layer was washed with brine, dried over anhydrous sodium sulfate, filtered, and concentrated under reduced pressure. Purification via flash chromatography gave 737B (orange solid, 2.3 g, 6.26 mmol, 75% yield). $^1$H NMR (400 MHz, $CDCl_3$) δ 7.91 (dd, J=2.40, 7.20 Hz, 1H), 7.48-7.52 (m, 1H), 7.22 (dd, J=8.40, 10.60 Hz, 1H), 3.63 (s, 3H), 3.37 (q, J=7.20 Hz, 1H), 2.61 (dd, J=7.20, Hz, 2H), 1.33 (dd, J=7.20, Hz, 3H).

737C. Methyl 3-(4-((2S,6R)-2,6-dimethylmorpholino)-3-nitrophenyl)butanoate

To a solution of 737B (2.0 g, 8.29 mmol) and (2S,6R)-2,6-dimethylmorpholine (1.050 g, 9.12 mmol) in N-methyl-2-pyrrolidone (15 mL) was added N,N-diisopropylethylamine (4.34 mL, 24.87 mmol). After stirring at 120° C. for 16 hours, the reaction mixture was cooled to room temperature and diluted with diethyl ether. The organic layer was washed with 10% aq. AcOH solution, 10% $NaHCO_3$ solution, and brine. The combined organics were dried over $Na_2SO_4$, filtered, and concentrated under reduced pressure. Purification via flash chromatography gave 737C (orange solid, 2.3 g, 6.26 mmol, 75% yield). LC-MS Anal. Calc'd. for $C_{17}H_{24}N_2O_5$, 336.383, found [M+H] 337.4. $T_r$=2.969 min (Method BE).

737D. Methyl 3-(3-amino-4-((2S,6R)-2,6-dimethylmorpholino)phenyl)butanoate

The solution of 737C (2.3 g, 6.84 mmol) in ethyl acetate (100 mL) was charged to a sealable Parr hydrogenation flask. The solution was sequentially evacuated and purged with nitrogen gas. To this 10% Pd on carbon (0.364 g, 0.342 mmol) was added under nitrogen atmosphere. The reaction mixture was stirred under hydrogen atmosphere (40 psi). The reaction mixture was stirred at room temperature for 3 hours. The reaction mixture was filtered through a CELITE® pad and the residue on the pad was thoroughly rinsed with MeOH (3×100 mL). The combined filtrate was concentrated under reduced pressure. Purification via flash chromatography gave racemic 737D. LC-MS Anal. Calc'd. for $C_{17}H_{26}N_2O_3$, 306.19, found [M+H] 307.2. $T_r$=2.803 min (Method U).

Chiral separation of racemic 737D gave Enantiomer 1 and Enantiomer 2 (Method DD).

737D Enantiomer 1 (brown semi-solid, 0.85 g, 2.77 mmol, 40.5% yield): $T_r$=2.64 min; (Method DD). LC-MS Anal. Calc'd. for $C_{17}H_{26}N_2O_3$, 306.19, found [M+H] 307.2. $T_r$=2.803 min (Method U). 737D Enantiomer 2 (brown semi-solid, 0.9 g, 2.91 mmol, 42.5% yield): $T_r$=4.53 min (Method DD). LC-MS Anal. Calc'd. for $C_{17}H_{26}N_2O_3$, 306.19, found [M+H] 307.2. $T_r$=2.803 min (Method U).

737E. Methyl 3-(3-((4-cyanophenyl)amino)-4-((2S,6R)-2,6-dimethylmorpholino)phenyl)butanoate To a vial containing 737D Enantiomer 1 (25 mg, 0.082 mmol), sodium tert-butoxide (15.68 mg, 0.163 mmol) and 1-bromo-4-cyanobenzene (18.56 mg; 0.106 mmol) was added, 1,4-dioxane (1 mL). The mixture was degasified with nitrogen for about 15 minutes and then Xantphos (9.44 mg, 0.016 mmol) and bis(dibenzylideneacetone)palladium (4.69 mg, 8.16 μmol) were added to this. The reaction mixture was sealed and heated at 110° C. for 12 hours. The solvent was removed under reduced pressure to obtain 737E. LC-MS Anal. Calc'd. for $C_{24}H_{29}N_3O_3$, 407.51, found [M+H] 408.3. $T_r$=2.981 min. (Method DC).

Example 737 3-(3-((4-Cyanophenyl)amino)-4-((2S,6R)-2,6-dimethylmorpholino)phenyl)butanoic acid To the crude residue 737E, lithium hydroxide (15.63 mg, 0.653 mmol) and methanol (0.5 mL) were added and the reaction mixture was stirred for 2 h at room temperature. The reaction mixture was concentrated under reduced pressure. The aqueous residue so obtained was acidified with 1(N) HCl to pH~2. The aqueous layer was diluted with water (5 mL) and extracted with ethyl acetate (2×20 mL). Combined organic layer was washed with water (10 mL), brine (10 mL), dried over anhydrous sodium sulfate and concentrated under reduced pressure to afford a residue. The residue was purified via preparative LC/MS to afford Example 737 (13 mg, 0.033 mmol, 42.2%). LC-MS Anal. Calc'd. for $C_{23}H_{27}N_3O_3$, 393.48, found [M+H] 394.3. $T_r$=1.833 min (Method O). $^1$H NMR (400 MHz, DMSO-$d_6$) δ12.01 (s, 1H), 8.16 (s, 1H), 7.51 (d, J=8.80 Hz, 2H), 7.08 (s, 1H), 6.89-6.97 (m, 4H), 3.45-3.48 (m, 2H), 2.96-3.13 (m, 3H), 2.21-2.27 (m, 2H), 1.16 (d, J=4.00 Hz, 3H), 0.91 (d, J=8.00 Hz, 6H) (Note: one doublet —CH$_2$ were buried under solvent peak).

Examples 738 to 742

Enantiomer 1 homochiral, absolute stereochemistry was not determined

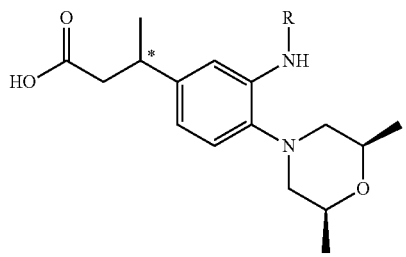

Examples 738 to 742 were prepared from 737D Enantiomer 1 and corresponding aryl halides following the procedure described for the synthesis of Example 737 Enantiomer 1.

| Ex. No. | Name | R | $T_r$ min | Method | (M + H) |
|---|---|---|---|---|---|
| 738 | 3-(4-((2S,6R)-2,6-dimethylmorpholino)-3-((4-fluorophenyl)amino)phenyl)butanoic acid | 4-fluorophenyl | 2.017 | R | 387.3 |
| 739 | 3-(3-((4-chlorophenyl)amino)-4-((2S,6R)-2,6-dimethylmorpholino)phenyl)butanoic acid | 4-chlorophenyl | 1.815 | O | 403.3 |
| 740 | 3-(4-((2S,6R)-2,6-dimethylmorpholino)-3-((4-ethylphenyl)amino)phenyl)butanoic acid | 4-ethylphenyl | 2.275 | R | 397.3 |
| 741 | 3-(4-((2S,6R)-2,6-dimethylmorpholino)-3-((2-methoxypyrimidin-5-yl)amino)phenyl)butanoic acid | 2-methoxypyrimidin-5-yl | 1.160 | O | 401.3 |

| Ex. No. | Name | R | $T_r$ min | Method | (M + H) |
|---|---|---|---|---|---|
| 742 | 3-(4-((2S,6R)-2,6-dimethylmorpholino)-3-((2-ethoxypyrimidin-5-yl)amino)phenyl)butanoic acid | | 1.677 | R | 415.3 |

Example 743

Enantiomer 2 homochiral, absolute stereochemistry not determined 3-(3-((4-Cyanophenyl)amino)-4-((2S,6R)-2,6-dimethylmorpholino)phenyl)butanoic acid

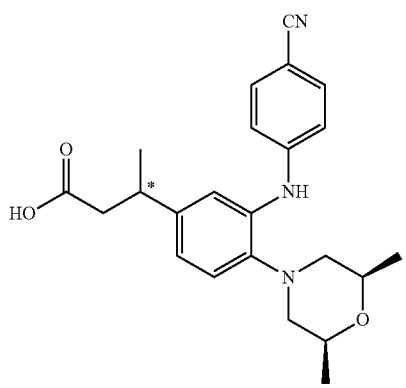 [SMILES: CC(CC(=O)O)c1ccc(N2C[C@@H](C)O[C@@H](C)C2)c(Nc2ccc(C#N)cc2)c1]

Example 743 was prepared from 737D Enantiomer 2 following the procedure described for the synthesis of Example 737. LC-MS Anal. Calc'd. for $C_{23}H_{27}N_3O_3$ 393.48, found [M+H] 394.3. $T_r$=1.476 min (Method O). $^1$H NMR (400 MHz, DMSO-$d_6$) δ12.01 (s, 1H), 8.16 (s, 1H), 7.51 (d, J=8.80 Hz, 2H), 7.08 (s, 1H), 6.89-6.97 (m, 4H), 3.45-3.48 (m, 2H), 2.96-3.13 (m, 3H), 2.21-2.27 (m, 2H), 1.16 (d, J=4.00 Hz, 3H), 0.91 (d, J=8.00 Hz, 6H) (Note: one doublet $CH_2$ was buried under solvent peak).

Examples 744 to 748

Enantiomer 2 homochiral, absolute stereochemistry not determined 3-(3-((4-Cyanophenyl)amino)-4-((2S,6R)-2,6-dimethylmorpholino)phenyl)butanoic acid

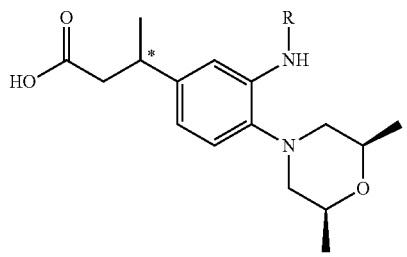

Examples 744 to 748 were prepared from 737D Enantiomer 2 and corresponding halides following the procedure described for the synthesis of Example 737 Enantiomer 1.

| Ex. No. | Name | R | $T_r$ min | Method | (M + H) |
|---|---|---|---|---|---|
| 744 | 3-(4-((2S,6R)-2,6-dimethylmorpholino)-3-((4-fluorophenyl)amino)phenyl)butanoic acid | 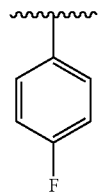 [SMILES: *c1ccc(F)cc1] | 2.079 | O | 387.3 |
| 745 | 3-(3-((4-chlorophenyl)amino)-4-((2S,6R)-2,6-dimethylmorpholino)phenyl)butanoic acid | 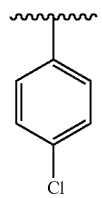 [SMILES: *c1ccc(Cl)cc1] | 1.827 | O | 403.3 |

| Ex. No. | Name | R | $T_r$ min | Method | (M + H) |
|---|---|---|---|---|---|
| 746 | 3-(4-((2S,6R)-2,6-dimethylmorpholino)-3-((4-ethylphenyl)amino)phenyl)butanoic acid | | 1.951 | O | 397.4 |
| 747 | 3-(4-((2S,6R)-2,6-dimethylmorpholino)-3-((2-methoxypyrimidin-5-yl)amino)phenyl)butanoic acid | | 1.201 | O | 401.3 |
| 748 | 3-(4-((2S,6R)-2,6-dimethylmorpholino)-3-((2-ethoxypyrimidin-5-yl)amino)phenyl)butnaoic acid | | 1.317 | O | 415.3 |

Example 749

Enantiomer 1 and Enantiomer 2

Each Homochiral, Absolute Stereochemistry Not Determined

Methyl 3-(3-(3-(4-chloro-2-fluorophenyl)ureido)-4-((2S,6R)-2,6-dimethylmorpholino)phenyl)butanoate

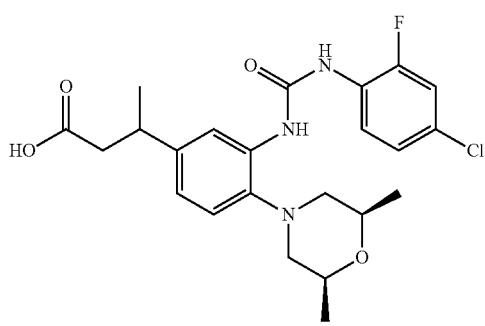 [SMILES: CC(CC(=O)O)c1ccc(N2C[C@@H](C)O[C@@H](C)C2)c(NC(=O)Nc2ccc(Cl)cc2F)c1]

749A. Methyl 3-(3-(3-(4-chloro-2-fluorophenyl)ureido)-4-((2S,6R)-2,6-dimethylmorpholino)phenyl)butanoate To a solution of methyl 737D Enantiomer 1 (0.025 g, 0.082 mmol) in THF (1 mL) was added 4-chloro-2-fluoro-1-isocyanatobenzene (0.017 g, 0.098 mmol) under nitrogen. Then the reaction was stirred for 2 hours at room temperature. Removed volatiles under reduced pressure to afford 749A (0.025 g, 0.050 mmol, 60.9% yield) as crude. LC-MS Anal. Calc'd. for $C_{24}H_{29}ClFN_3O_4$, 477.1, found [M+H] 478.4, $T_r$=1.56 min (Method BA).

Example 749 Enantiomer 1. Methyl 3-(3-(3-(4-chloro-2-fluorophenyl)ureido)-4-((2S,6R)-2,6-dimethylmorpholino)phenyl)butanoate To a solution of 749A (0.025 g, 0.052 mmol) in mixture of THF (1 mL), MeOH (1 mL) and water (1 mL) was added LiOH (5.01 mg, 0.209 mmol) at room temperature and stirred overnight. Volatiles were removed under reduced pressure, and the crude mass was acidified with 1.5N HCl. The aqueous was extracted with DCM and the combined organics were concentrated under reduced pressure. The resulting crude residue was purified via flash chromatography to afford Example 749 Enantiomer 1 (0.018 g, 0.038 mmol, 73.4% yield) as an off-white solid. LC-MS Anal. Calc'd. for $C_{23}H_{27}ClFN_3O_4$, 463.1, found [M+H] 464.2, $T_r$=2.088 min (Method R). $^1$H NMR (400 MHz, DMSO-$d_6$) δ 9.46 (s, 1H), 8.50 (s, 1H), 8.15 (t, J=8.80 Hz, 1H), 7.95 (d, J=2.00 Hz, 1H), 7.45-7.48 (m, 1H), 7.23 (d, J=8.80 Hz, 1H), 7.08 (d, J=8.40 Hz, 1H), 6.87-6.89 (m, 1H), 3.91-3.95 (m, 2H), 3.05-3.11 (m, 1H), 2.79-2.82 (m, 2H), 2.44-2.45 (m, 2H), 2.31-2.41 (m, 2H), 1.19 (d, J=4.00 Hz, 3H), 1.10 (d, J=8.40 Hz, 6H).

Example 749 Enantiomer 2. Methyl 3-(3-(3-(4-chloro-2-fluorophenyl)ureido)-4-((2S,6R)-2,6-dimethylmorpholino)phenyl)butanoate Example 749 Enantiomer 2 was prepared from 737D Enantiomer 2 following the procedure described for the synthesis of Example 749 Enantiomer 1. LC-MS Anal. Calc'd. for $C_{23}H_{27}ClFN_3O_4$, 463.1, found [M+H] 464.2, $T_r$=1.716 min (Method O). $^1$H NMR (400 MHz, DMSO-$d_6$) δ 9.46 (s, 1H), 8.50 (s, 1H), 8.15 (t, J=8.80 Hz, 1H), 7.95 (d, J=2.00 Hz, 1H), 7.45-7.48 (m, 1H), 7.23 (d, J=8.80 Hz, 1H), 7.08 (d, J=8.40 Hz, 1H), 6.87-6.89 (m, 1H), 3.91-3.95 (m, 2H), 3.05-3.11 (m, 1H), 2.79-2.82 (m, 2H), 2.44-2.45 (m, 2H), 2.31-2.41 (m, 2H), 1.19 (d, J=4.00 Hz, 3H), 1.10 (d, J=8.40 Hz, 6H).

Examples 750 and 751

Enantiomer 1 homochiral, absolute stereochemistry was not determined

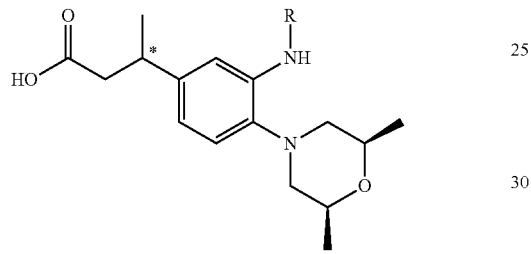

Examples 750 and 751 were prepared from 737D Enantiomer 1 and corresponding isocyanates following the procedures described for Example 749 Enantiomer 1.

Examples 752 and 753

Enantiomer 2 homochiral, absolute stereochemistry not determined

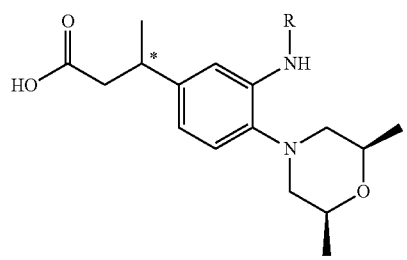

Examples 752 and 753 were prepared using 737D Enantiomer 2 and corresponding isocyanates following the procedures described for Example 749 Enantiomer 1.

| Ex. No. | Name | R | $T_r$ min | Method | (M + H) |
|---|---|---|---|---|---|
| 750 | 3-(3-(3-(4-cyanophenyl)ureido)-4-((2S,6R)-2,6-dimethylmorpholino)phenyl)butanoic acid | 4-cyanophenyl-NHC(O)- | 1.854 | R | 437.2 |
| 751 | 3-(4-((2S,6R)-2,6-dimethylmorpholino)-3-(3-(p-tolyl)ureido)phenyl)butanoic acid | p-tolyl-NHC(O)- | 1.932 | R | 426.2 |

| Ex. No. | Name | R | $T_r$ min | Method | (M + H) |
|---|---|---|---|---|---|
| 752 | 3-(3-(3-(4-cyanophenyl)ureido)-4-((2S,6R)-2,6-dimethylmorpholino)phenyl)butanoic acid | CN-C6H4-NH-C(O)-NH- | 1.853 | R | 437.2 |
| 753 | 3-(4-((2S,6R)-2,6-dimethylmorpholino)-3-(3-(p-tolyl)ureido)phenyl)butanoic acid | p-tolyl-NH-C(O)-NH- | 1.931 | R | 426.2 |

Example 754

Enantiomer 1

3-(4-((2S,6R)-2,6-Dimethylmorpholino)-3-(3-(p-tolyl)ureido)phenyl)pentanoic acid

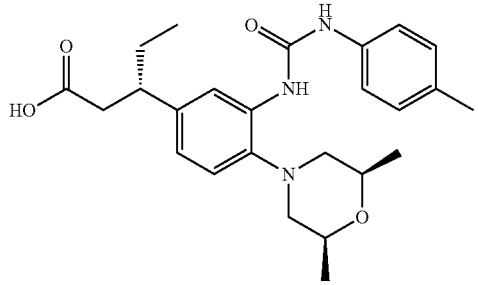 [SMILES: CC[C@@H](CC(=O)O)c1ccc(N2C[C@@H](C)O[C@@H](C)C2)c(NC(=O)Nc2ccc(C)cc2)c1]

754A. (2S,6R)-4-(4-Bromo-2-nitrophenyl)-2,6-dimethylmorpholine

To a solution of 4-bromo-1-fluoro-2-nitrobenzene (3.0 g, 13.64 mmol) and (2R,6S)-2,6-dimethylmorpholine (1.885 g, 16.36 mmol) in NMP (10 mL) was added DIPEA (7.15 mL, 40.9 mmol). After stirring at 80° C. for 16 h, the reaction mixture was cooled to room temperature and diluted with diethyl ether. The organic layer was washed with 10% aq. AcOH solution, 10% NaHCO$_3$ solution, and brine. The combined organics were dried over Na$_2$SO$_4$, filtered, and concentrated under reduced pressure. Purification via flash chromatography gave 754A (orange liquid, 4.1 g, 12.67 mmol, 93% yield). LC-MS Anal. Calc'd. for C$_{12}$H$_{15}$BrN$_2$O$_3$, 315.163, found [M+2] 317.0. $T_r$=3.198 min (Method U).

754B. (2S,6R)-4-(4-(5,5-Dimethyl-1,3,2-dioxaborinan-2-yl)-2-nitrophenyl)-2,6-dimethylmorpholine In a sealed tube, 754A (1.0 g, 3.17 mmol), bis(neopentyl glycolato)diboron (0.946 g, 4.19 mmol) and potassium acetate (0.934 g, 9.52 mmol) in dioxane (10 mL) was purged with argon for 20 min. To this PdCl$_2$ (dppf).CH$_2$Cl$_2$ Adduct (0.078 g, 0.095 mmol) was added and purged with argon for 5 min. The reaction mixture was sealed and heated at 80° C. for 6 hours. The reaction mixture was cooled to room temperature and filtered through a pad of CELITE®. The CELITE® was rinsed with dichloromethane (3×40 mL), and the filtrate was concentrated under reduced pressure to get residue which was diluted with dichloromethane (50 mL) and water (50 mL), DCM layer separated. Aqueous layer was extracted with DCM (2×50 mL). The combined organic layer was washed with brine (50 mL), dried over anhydrous sodium sulfate, filtered, and concentrated under reduced pressure. Purification via flash chromatography gave 754B (yellow liquid, 0.9 g, 2.58 mmol, 81% yield). $^1$H NMR (400 MHz, CDCl$_3$) δ 8.18 (d, J=1.60 Hz, 1H), 7.84 (dd, J=1.60, 8.00 Hz, 1H), 7.03 (d, J=8.40 Hz, 1H), 3.82-3.87 (m, 2H), 3.76 (s, 4H), 3.10 (dd, J=2.00, 9.60 Hz, 2H), 2.61 (dd, J=10.40, 12.20 Hz, 2H), 1.20 (s, 3H), 1.19 (s, 3H), 1.02 (s, 6H).

754C. Methyl 3-(4-((2S,6R)-2,6-dimethylmorpholino)-3-nitrophenyl)pentanoate

In a sealed tube 1,4-dioxane (20 mL) was purged with argon for 15 min. (R)-(+)-2,2'-Bis(diphenylphosphino)-1,1'-binaphthyl (0.035 g, 0.057 mmol) and chlorobis (ethylene) rhodium(I) dimer (0.015 g, 0.039 mmol) was added to the reaction mixture and it was purged with argon for 30 min. To this 754B (0.9 g, 2.58 mmol), (E)-methyl pent-2-enoate (0.354 g, 3.10 mmol) and sodium hydroxide (2.326 mL, 2.326 mmol) was added and the reaction mixture was purged with argon for 10 min. The reaction mixture was heated at 50° C. for 1 h. Reaction mixture was cooled to room temperature and quenched with acetic acid (0.2 mL). It was stirred for 5 minutes before it was partitioned between ethyl acetate (100 mL) and water (50 mL). Aqueous layer was extracted with ethyl acetate (100 mL). The combined organic layer was washed with brine, dried over anhydrous sodium sulfate, filtered, and concentrated under reduced pressure. Purification via flash chromatography gave 754C (yellow liquid, 0.7 g, 1.956 mmol, 76% yield). LC-MS Anal. Calc'd. for C$_{18}$H$_{26}$N$_2$O$_5$, 350.409, found [M+H] 351.2. $T_r$=3.217 min (Method U).

754D. Methyl 3-(3-amino-4-((2S,6R)-2,6-dimethylmorpholino)phenyl)pentanoate

To a stirred solution of 754C (0.7 g, 1.998 mmol) in ethyl acetate (30 mL) was added palladium on carbon (0.106 g, 0.100 mmol). The reaction mixture was stirred at room temperature under H$_2$ atmosphere (40 psi) for 3 hours. The reaction mixture was filtered through a pad of CELITE® and it was washed with methanol (5×100 mL), filtrate was concentrated under reduced pressure. Purification via flash chromatography gave Racemate 754D (0.5 g). LC-MS Anal. Calc'd. for $C_{18}H_{28}N_2O_3$, 320.427, found [M+H] 321.4. $T_r$=2.660 min (Method U).

Chiral separation of Racemate 754D gave Enantiomer 1, $T_r$=3.2 min, and Enantiomer 2, $T_r$=3.8 min (Ratio of Enantiomer 1:Enantiomer 2=86:14) (Method DE).

754D Enantiomer 1 (brown semi-solid, 0.6 g, 1.807 mmol, 90% yield): $T_r$=3.2 min. (Method DE). LC-MS Anal. Calc'd. for $C_{18}H_{28}N_2O_3$, 320.427, found [M+H] 321.4. $T_r$=2.660 min (Method U).

754E. Methyl 3-(4-((2S,6R)-2,6-dimethylmorpholino)-3-(3-(p-tolyl)ureido)phenyl)pentanoate To a solution of 754D Enantiomer 1 (20 mg, 0.062 mmol) in THF (0.5 mL) was added 1-isocyanato-4-methylbenzene (9.14 mg, 0.069 mmol). The mixture was stirred at room temperature for 1 h. The reaction mixture was concentrated under reduced pressure. The resultant solid was washed with hexane (2×3 mL) and dried under vacuum to give 754E (off-white solid, 25 mg, 0.036 mmol, 57.4% yield). LC-MS Anal. Calc'd. for $C_{26}H_{35}N_3O_4$, 453.574, found [M+H] 454.5. $T_r$=4.057 min (Method N).

Example 754 Enantiomer 1. 3-(4-((2S,6R)-2,6-Dimethylmorpholino)-3-(3-(p-tolyl)ureido)phenyl)pentanoic acid To a solution of 754E (25 mg, 0.055 mmol) in THF (1 mL), MeOH (1 mL) and water (1 mL), was added lithium hydroxide (3.96 mg, 0.165 mmol) and was stirred at room temperature for 2 hours. Solvent was concentrated under reduced pressure. The crude pH was adjusted to ~2 with 1.5 (N) HCl solution. The aqueous layer was extracted with EtOAc (2×25 mL). The combined organic layer was dried over anhydrous sodium sulfate, filtered, and concentrated under reduced pressure. Purification via flash chromatography gave Example 754 Enantiomer 1 (off-white solid, 21.3 mg, 0.048 mmol, 87%). LC-MS Anal. Calc'd. for $C_{25}H_{33}N_3O_4$, 439.55, found [M+H] 440.2. $T_r$=2.127 min (Method R). $^1$H NMR (400 MHz, DMSO-$d_6$) δ 9.37 (s, 1H), 8.08 (s, 1H), 7.99 (d, J=2.00 Hz, 1H), 7.37 (d, J=8.40 Hz, 2H), 7.09 (d, J=9.20 Hz, 2H), 7.06 (s, 1H), 6.79 (dd, J=2.00, 8.00 Hz, 1H), 3.89-3.93 (m, 2H), 2.76-2.81 (m, 3H), 2.31-2.49 (m, 3H), 2.25 (s, 3H), 1.60-1.62 (m, 1H), 1.46-1.50 (m, 1H), 1.10 (d, J=6.00 Hz, 6H), 0.72 (t, J=7.20 Hz, 3H) (Note: 1H multiplet CH was buried under solvent peak).

Example 755

Enantiomer 1

3-(3-((4-Chlorophenyl)amino)-4-((2S,6R)-2,6-dimethylmorpholino)phenyl)pentanoic acid

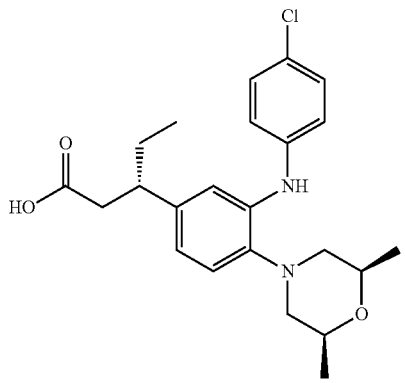 [SMILES: CC[C@@H](CC(=O)O)c1ccc(N2C[C@@H](C)O[C@@H](C)C2)c(Nc2ccc(Cl)cc2)c1]

755A. Methyl 3-(3-((4-chlorophenyl)amino)-4-((2S, 6R)-2,6-dimethylmorpholino)phenyl)pentanoate To a suspension of 754D Enantiomer 1 (30 mg, 0.094 mmol), 1-bromo-4-chlorobenzene (19.72 mg, 0.103 mmol), $Cs_2CO_3$ (92 mg, 0.281 mmol) and Xantphos (10.83 mg, 0.019 mmol) in degassed dioxane (2.0 mL) was added bis(dibenzylideneacetone)palladium (5.38 mg, 9.36 μmol). The mixture was placed in preheated oil bath at 110° C., and stirred for 18 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL) and brine (10 mL), dried over anhydrous sodium sulfate, filtered, and concentrated under reduced pressure to afford 755A (30 mg, 0.070 mmol, 74.4% yield). LC-MS Anal. Calc'd. for $C_{24}H_{31}ClN_2O_3$, 430.968, found [M+H] 431.7. $T_r$=4.5 min (Method N).

Example 755 Enantiomer 1. 3-(3-((4-Chlorophenyl) amino)-4-((2S,6R)-2,6-dimethylmorpholino)phenyl) pentanoic acid A solution of 755A (30 mg, 0.070 mmol) in tetrahydrofuran (0.5 mL) and MeOH (0.5 mL) was treated with lithium hydroxide (5.00 mg, 0.209 mmol) in water (0.5 mL) and the reaction was stirred at room temperature for 4 hours. The reaction mixture was concentrated under reduced pressure. The aqueous residue so obtained was acidified with aqueous citric acid to pH~2. The aqueous layer was diluted with water (10 mL) and extracted with ethyl acetate (2×10 mL). Combined organic layer was washed with water (10 mL) and brine (10 mL), dried over anhydrous sodium sulfate, filtered, and concentrated under reduced pressure to afford a residue. The residue was purified via preparative LCMS to afford Example 755 Enantiomer 1 (off-white solid, 14.6 mg, 0.035 mmol, 50.3%). LC-MS Anal. Calc'd. for $C_{23}H_{29}ClN_2O_3$, 416.941, found [M+H] 417.2. $T_r$=2.540 min (Method R). $^1$H NMR (400 MHz, DMSO-$d_6$) δ 7.36 (s, 1H), 7.18-7.21 (m, 2H), 6.94-6.99 (m, 4H), 6.76-6.78 (m, 1H), 3.59-3.63 (m, 2H), 2.94 (d, J=10.80 Hz, 2H), 2.70-2.80 (m, 1H), 2.50-2.55 (m, 1H), 2.36-2.42 (m, 1H), 2.22-2.28 (m, 2H), 1.46-1.60 (m, 2H), 1.02 (d, J=6.00 Hz, 6H), 0.72 (t, J=7.60 Hz, 3H).

Examples 756 to 759

Enantiomer 1

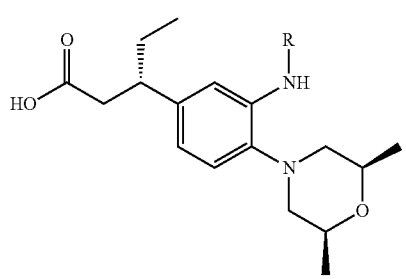

Examples 756 to 759 were prepared from 754D Enantiomer 1 and corresponding aryl halides following the procedure described for the synthesis of Example 754 Enantiomer 1.

| Ex. No. Name | R | $T_r$, min | Method | (M + H) |
|---|---|---|---|---|
| 756 3-(4-((2S,6R)-2,6-dimethylmorpholino)-3-((2-ethoxypyrimidin-5-yl)amino)phenyl)pentanoic acid | 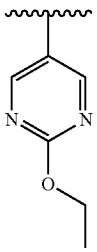 | 2.021 | R | 429.3 |
| 757 3-(4-((2S,6R)-2,6-dimethymorpholino)-3-((2-methylbenzo[d]thiazol-6-yl)amino)phenyl)pentanoic acid | 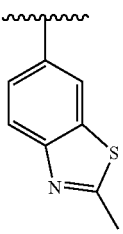 [SMILES: *c1ccc2nc(C)sc2c1] | 1.917 | R | 454.2 |
| 758 3-(3-((2,2-difluorobenzo[d][1,3]dioxol-5-yl)amino)-4-((2S,6R)-2,6-dimethylmorpholino)phenyl)pentanoic acid | 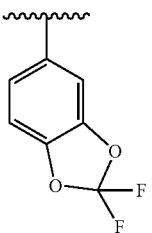 [SMILES: *c1ccc2c(c1)OC(F)(F)O2] | 2.196 | O | 463.2 |
| 759 3-(4-((2S,6R)-2,6-dimethymorpholino)-3-((4-fluorophenyl)amino)phenyl)pentanoic acid | 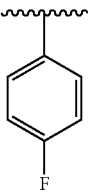 | 2.015 | O | 401.2 |

Example 760

Enantiomer 2

3-(4-((2S,6R)-2,6-Dimethylmorpholino)-3-(3-(p-tolyl)ureido)phenyl)pentanoic acid

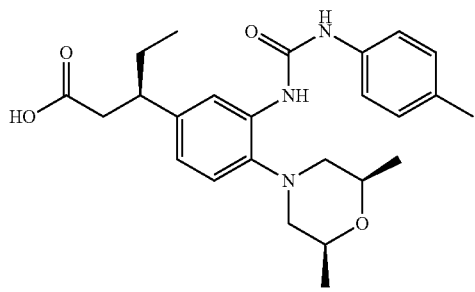 [SMILES: CC[C@H](CC(=O)O)c1ccc(N2C[C@@H](C)O[C@@H](C)C2)c(NC(=O)Nc2ccc(C)cc2)c1]

760A. Methyl 3-(4-((2S,6R)-2,6-dimethylmorpholino)-3-nitrophenyl)pentanoate 760A was prepared from 754B and (S)-(−)-2,2'-bis(diphenylphosphino)-1,1'-binaphthyl following the procedure described for the synthesis of 754C. LC-MS Anal. Calc'd. for $C_{18}H_{26}N_2O_5$, 350.409, found [M+H] 351.2, $T_r$=3.183 min (Method U).

760B. Methyl 3-(3-amino-4-((2S,6R)-2,6-dimethylmorpholino)phenyl)pentanoate 760B was prepared from 760A following the procedure described for the synthesis of 754D. LC-MS Anal. Calc'd. for $C_{18}H_{28}N_2O_3$, 320.427, found [M+H] 321.2. $T_r$=2.681 min (Method U).

Chiral separation of 760B (enantiomeric mixture) gave Enantiomer 1, $T_r$=3.2 min, and Enantiomer 2, $T_r$=3.8 min (Ratio of Enantiomer 1:Enantiomer 2=12:87) (Method DE).

760B Enantiomer 2 (brown semi-solid, 0.4 g, 1.230 mmol, 71.8% yield) $T_r$=2.58 min. (Method DE). LC-MS Anal. Calc'd. for $C_{18}H_{28}N_2O_3$, 320.427, found [M+H] 321.2, $T_r$=2.681 min (Method U).

Example 760. 3-(4-((2S,6R)-2,6-Dimethylmorpholino)-3-(3-(p-tolyl)ureido)phenyl)pentanoic acid Example 760 was prepared following the same procedure for Example 749 by using 760B Enantiomer 2 and 1-isocyanato-4-methylbenzene. LC-MS Anal. Calc'd. for $C_{25}H_{33}N_3O_4$, 439.55, found [M+H] 440.3. $T_r$=2.123 min (Method R). $^1$H NMR (400 MHz, DMSO-$d_6$) δ 9.37 (s, 1H), 8.08 (s, 1H), 7.99 (d, J=2.00 Hz, 1H), 7.37 (d, J=8.40 Hz, 2H), 7.09 (d, J=9.20 Hz, 2H), 7.06 (s, 1H), 6.79 (dd, J=2.00, 8.00 Hz, 1H), 3.89-3.93 (m, 2H), 2.76-2.81 (m, 3H), 2.31-2.49 (m, 3H), 2.25 (s, 3H), 1.60-1.62 (m, 1H), 1.46-1.50 (m, 1H), 1.10 (d, J=6.00 Hz, 6H), 0.72 (t, J=7.20 Hz, 3H) (Note: one multiplet CH was buried under solvent peak).

Example 761

Enantiomer 2

3-(3-((4-Chlorophenyl)amino)-4-((2S,6R)-2,6-dimethylmorpholino)phenyl)pentanoic acid

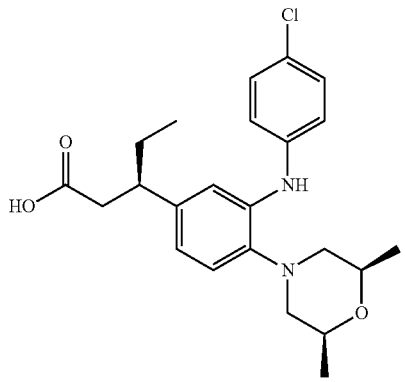 [SMILES: CC[C@H](CC(=O)O)c1ccc(N2C[C@@H](C)O[C@@H](C)C2)c(Nc2ccc(Cl)cc2)c1]

Example 761 was prepared following the same procedure for Example 755 by utilizing 760B Enantiomer 2 and 1-bromo-4-chlorobenzene. LC-MS Anal. Calc'd. for $C_{23}H_{29}ClN_2O_3$, 416.941, found [M+H] 417.2. $T_r$=2.540 min (Method R). $^1$H NMR (400 MHz, DMSO-$d_6$) δ 7.36 (s, 1H), 7.18-7.21 (m, 2H), 6.94-6.99 (m, 4H), 6.76-6.78 (m, 1H), 3.59-3.63 (m, 2H), 2.94 (d, J=10.80 Hz, 2H), 2.70-2.80 (m, 1H), 2.50-2.55 (m, 1H), 2.36-2.42 (m, 1H), 2.22-2.28 (m, 2H), 1.46-1.60 (m, 2H), 1.02 (d, J=6.00 Hz, 6H), 0.72 (t, J=7.60 Hz, 3H).

Examples 762 to 766

Enantiomer 2

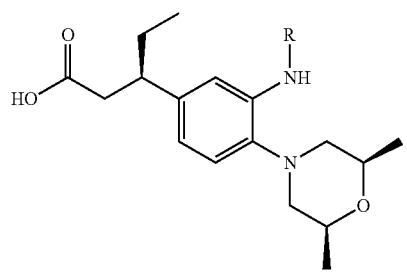

Examples 762 to 766 were prepared from 760B Enantiomer 2 and corresponding halides following the procedure described for the synthesis of Example 761.

| Ex. No. | Name | R | $T_r$ min | Method | (M + H) |
|---|---|---|---|---|---|
| 762 | 3-(4-((2S,6R)-2,6-dimethylmorpholino)-3-((2-ethoxypyrimidin-5-yl)amino)phenyl)pentanoic acid | 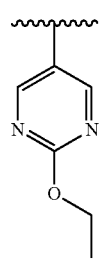 | 2.027 | R | 429.2 |
| 763 | 3-(4-((2S,6R)-2,6-dimethylmorpholino)-3-((2-methylbenzo[d]thiazol-6-yl)amino)phenyl)pentanoic acid | 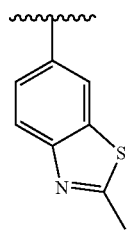 [SMILES: *c1ccc2nc(C)sc2c1] | 2.218 | R | 454.1 |

-continued

| Ex. No. Name | R | T$_r$ min | Method | (M + H) |
|---|---|---|---|---|
| 764 3-(3-((4-cyanophenyl)amino)-4-((2S,6R)-2,6-dimethylmorpholino)phenyl)pentanoic acid | 4-cyanophenyl | 2.257 | R | 408.2 |
| 765 3-(3-((2,2-difluorobenzo[d][1,3]dioxol-5-yl)amino)-4-((2S,6R)-2,6-dimethylmorpholino)phenyl)pentanoic acid | 2,2-difluorobenzo[d][1,3]dioxol-5-yl | 2.668 | R | 463.2 |
| 766 3-(4-((2S,6R)-2,6-dimethylmorpholino)-3-((4-fluorophenyl)amino)phenyl)pentanoic acid | 4-fluorophenyl | 2.05 | O | 401.2 |

Example 767

Diastereomer 2

3-(4-((S)-2-(2-Hydroxypropan-2-yl)pyrrolidin-1-yl)-3-(3-(p-tolyl)ureido)phenyl)pentanoic acid

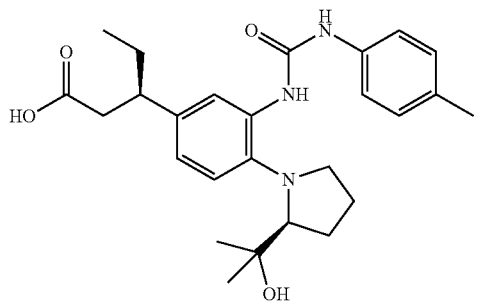 [SMILES: CC[C@H](CC(=O)O)c1ccc(N2CCC[C@H]2C(C)(C)O)c(NC(=O)Nc2ccc(C)cc2)c1]

767A. (S)-1-Benzyl 2-methyl pyrrolidine-1,2-dicarboxylate

To a solution of (S)-1-((benzyloxy)carbonyl)pyrrolidine-2-carboxylic acid (10 g, 40.1 mmol) in MeOH (80 mL) was added concentrated H$_2$SO$_4$ (20 ml, 375 mmol) over 10 min at RT. An exothermic reaction resulted. The resulting solution was stirred at RT for 16 h. The reaction mixture was poured onto 300 g of crushed ice. The mixture was extracted with Et$_2$O (2×200 ml). The combined organic layers were dried over K$_2$CO$_3$ and concentrated on a rotary evaporator to give 767A (clear syrup, 6.0 g, 22.79 mmol, 56.8% yield). $^1$H NMR (400 MHz, CDCl$_3$) δ 7.26-7.36 (m, 5H), 5.03-5.20 (m, 2H), 4.33-4.41 (m, 1H), 3.75 (s, 3H), 3.49-3.64 (m, 2H), 2.20-2.24 (m, 1H), 1.88-2.04 (m, 3H).

767B. (S)-Benzyl 2-(2-hydroxypropan-2-yl)pyrrolidine-1-carboxylate

To a rapidly stirring solution of 767A (1.0 g, 3.80 mmol) in dry THF (6.0 mL) cooled to −20° C. was added dropwise methylmagnesium bromide (3.80 mL, 11.39 mmol). After stirring at −20° C. for 0.5 h, the cooling bath was changed to one of ice water and stirring continued for a further 1 h. The reaction was quenched by slowly pouring into a saturated NH$_4$Cl solution containing some ice and after separation of the organic layer, the aqueous phase was extracted with ether (4×100 mL). The combined organic layer was dried over Na$_2$SO$_4$, filtered, concentrated to get 767B (clear oil, 0.8 g, 3.04 mmol, 80% yield). LC-MS Anal. Calc'd. for C$_{15}$H$_{21}$NO$_3$, 263.332, found [M+H] 264.2. T$_r$=2.129 min (Method U).

767C. (S)-2-(Pyrrolidin-2-yl)propan-2-ol 767C was prepared from 767B following the procedure described for the synthesis of 737C. $^1$H NMR (400 MHz, CDCl$_3$) δ 2.91-3.07 (m, 4H), 1.61-1.79 (m, 4H), 1.18 (s, 3H), 1.13 (s, 3H).

767D. (S)-2-(1-(4-Bromo-2-nitrophenyl)pyrrolidin-2-yl)propan-2-ol

To a solution of 4-bromo-1-fluoro-2-nitrobenzene (5.0 g, 22.73 mmol) and 767C (2.94 g, 22.73 mmol) in N-methyl-2-pyrrolidone (25 mL) was added N,N-diisopropylethylamine (11.91 mL, 68.2 mmol). After stirring at 150° C. for 18 hours, the reaction mixture was cooled to room temperature and diluted with diethyl ether. The organic layer was washed with 10% aq. AcOH solution, 10% NaHCO$_3$ solution, and brine. The combined organics were dried over Na$_2$SO$_4$, filtered, and concentrated under reduced pressure to afford a residue. The residue was purified via flash silica gel column chromatography (0-100% ethyl acetate in pet ether as eluent) to afford 767D (orange liquid, 7.0 g, 21.26 mmol, 94% yield). LC-MS Anal. Calc'd. for C$_{13}$H$_{17}$BrN$_2$O$_3$ 329.190, found [M+2] 331.2. T$_r$=2.688 min (Method U).

767E. (S)-2-(1-(4-(5,5-Dimethyl-1,3,2-dioxaborinan-2-yl)-2-nitrophenyl)pyrrolidin-2-yl)propan-2-ol In a sealed tube 767D (1.0 g, 3.04 mmol), bis(neopentyl glycolato)diboron (0.906 g, 4.01 mmol) and potassium acetate (0.894 g, 9.11 mmol) in dioxane (10 mL) purged with argon for 20 min. To this PdCl$_2$ (dppf).CH$_2$Cl$_2$ Adduct (0.074 g, 0.091 mmol) was added and purged with argon for 5 min. The reaction mixture was sealed and heated at 80° C. for 6 h. Reaction mixture was cooled to room temperature and it was filtered through a pad of CELITE® and rinsed with dichloromethane (3×40 mL), filtrate was concentrated under reduced pressure. The resulting residue was diluted with dichloromethane (50 mL) and water (50 mL). DCM layer separated. Aqueous layer was extracted with DCM (2×50 mL). The combined organic layer was washed with brine (50 mL), dried over anhydrous sodium sulfate, concentrated under reduced pressure to get crude compound. The crude compound was purified (silica gel; using 0-100% ethyl acetate in pet ether as mobile phase) to get 767E (gummy liquid, 1.0 g, 2.65 mmol, 87% yield). LC-MS Anal. Calc'd. for C$_{18}$H$_{27}$BN$_2$O$_5$, 362.228, found [M+H] 363.2. T$_r$=1.574 min (Method T).

767F. Methyl 3-(4-((S)-2-(2-hydroxypropan-2-yl)pyrrolidin-1-yl)-3-nitrophenyl)pentanoate (Diastereomeric Mixture)

In a sealed tube 1,4-dioxane (20 mL) was purged with argon for 15 min. (S)-(−)-2,2'-Bis(diphenylphosphino)-1,1'-binaphthyl (0.038 g, 0.061 mmol) and chlorobis (ethylene) rhodium(I) dimer (0.016 g, 0.041 mmol) was added to the reaction mixture and it was purged with argon for 30 min. To this 767E (1.0 g, 2.76 mmol), (E)-methyl pent-2-enoate (0.378 g, 3.31 mmol) and sodium hydroxide (2.485 mL, 2.485 mmol) were added and the reaction mixture was purged with argon for 10 min. The reaction mixture was heated at 50° C. for 1 h. The reaction mixture was cooled to room temperature and quenched with acetic acid (0.2 mL) and it was stirred for 5 minutes before it was partitioned between ethyl acetate (100 mL) and water (50 mL). The aqueous layer was extracted with ethyl acetate (100 mL). The combined organic layer was washed with brine (50 mL), dried over anhydrous sodium sulfate, filtered, and concentrated under reduced pressure to get the residue. The residue was purified via flash silica gel column chromatography (conditions: 0-100% ethyl acetate in pet ether or gradient of ethyl acetate in pet ether) to afford 767F as a diastereomeric mixture (yellow liquid, 0.65 g, 1.730 mmol, 62.7% yield). LC-MS Anal. Calc'd. for C$_{19}$H$_{28}$N$_2$O$_5$, 364.436, found [M+H] 365.2, T$_r$=2.816 min (Method U).

767G. Methyl 3-(3-amino-4-((S)-2-(2-hydroxypropan-2-yl)pyrrolidin-1-yl)phenyl)pentanoate To a stirred solution of 767F (0.65 g, 1.784 mmol) in ethyl acetate (20 mL) was added palladium on carbon (0.095 g, 0.089 mmol). The reaction mixture was stirred at room temperature under H$_2$ atmosphere (40 psi) for 3 hours. The reaction mixture was filtered through a pad of CELITE® and it was washed with methanol (5×100 mL), filtrate was concentrated under reduced pressure to get crude compound. The residue was purified via flash silica gel column chromatography (conditions: 0-100% ethyl acetate in pet ether or gradient of ethyl acetate in pet ether) to afford Diastereomeric mixture 767G (brown solid). LC-MS Anal. Calc'd. for C$_{19}$H$_{30}$N$_2$O$_3$, 334.453, found [M+H] 335.2, T$_r$=2.651 min (Method U).

Chiral separation of Diastereomeric mixture 767G gave Diastereomer 1 and Diastereomer 2 (Ratio of Diastereomer 1:Diastereomer 2=13:87 (Method DH). Diastereomer 1, T$_r$=6.59 min, Diastereomer 2, T$_r$=11.26 min (Method DH).

767G Diastereomer 2 (brown semi-solid, 0.5 g, 1.425 mmol, 80% yield) T$_r$=11.97 min (Method DG). LC-MS Anal. Calc'd. for C$_{19}$H$_{30}$N$_2$O$_3$, 334.453, found [M+H] 335.2, T$_r$=2.651 min (Method U).

767H. Methyl 3-(4-((S)-2-(2-hydroxypropan-2-yl)pyrrolidin-1-yl)-3-(3-(p-tolyl)ureido)phenyl)pentanoate To a solution of 767G Diastereomer 2 (0.03 g, 0.090 mmol) in THF (0.5 mL) was added 1-isocyanato-4-methylbenzene (0.013 g, 0.099 mmol) at 0° C., the mixture was stirred at room temperature for 1 hour. The reaction mixture was concentrated to get the crude product. The resultant solid was washed with hexane (2×10 mL) and dried under vacuum to get 767H (off-white solid, 0.03 g, 0.055 mmol, 60.8% yield). LC-MS Anal. Calc'd. for C$_{27}$H$_{37}$N$_3$O$_4$, 467.60, found [M+H] 468.6. T$_r$=1.16 min (Method DO).

Example 767. 3-(4-((S)-2-(2-Hydroxypropan-2-yl)pyrrolidin-1-yl)-3-(3-(p-tolyl) ureido)phenyl)pentanoic acid To a stirred solution of 767H (0.03 g, 0.064 mmol) in a mixture of tetrahydrofuran (0.5 mL), MeOH (0.5 mL) and water (0.5 mL), was added lithium hydroxide (4.61 mg, 0.192 mmol). The reaction mixture was stirred at room temperature for 3 hours. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL) and brine (5.0 mL), dried over anhydrous sodium sulfate, filtered, and concentrated under reduced pressure to afford a residue. The residue was purified via preparative LC/MS to afford Example 767 (0.019 g, 0.041 mmol, 64.6% yield). LC-MS Anal. Calc'd. for C$_{26}$H$_{35}$N$_3$O$_4$, 453.574, found [M+H] 454.3. T$_r$=1.680 min (Method O). $^1$H NMR (400 MHz, DMSO-d$_6$) δ 9.60 (s, 1H), 8.61 (s, 1H), 7.94 (s, 1H), 7.42 (d, J=8.40 Hz, 2H), 7.13 (d, J=8.00 Hz, 1H), 7.07 (d, J=8.40 Hz, 2H), 6.71 (d, J=6.80 Hz, 1H), 4.35 (s, 1H), 3.55-3.59 (m, 2H), 2.75-2.90 (m, 1H), 2.25 (s, 3H), 2.33-2.43 (m, 2H), 1.96-1.99 (m, 2H), 1.75-1.78 (m, 1H), 1.64-1.66 (m, 3H), 1.41-1.43 (m, 1H), 0.93 (s, 3H), 0.85 (s, 3H), 0.68 (t, J=7.2 Hz, 3H).

Example 768

Diastereomer 2

3-(4-((S)-2-(2-Hydroxypropan-2-yl)pyrrolidin-1-yl)-3-((2-methylbenzo[d]thiazol-6-yl)amino)phenyl)pentanoic acid

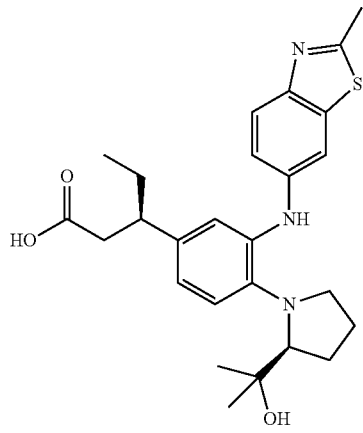 [SMILES: CC[C@H](CC(=O)O)c1ccc(N2CCC[C@H]2C(C)(C)O)c(Nc2ccc3nc(C)sc3c2)c1]

Example 768 was prepared following the procedure for Example 755 by using 767G Diastereomer 2 and 6-bromo-2-methylbenzo[d]thiazole. LC-MS Anal. Calc'd. for $C_{26}H_{33}N_3O_3S$, 467.62, found [M+H] 468.2. $T_r$=1.783 min (Method O). $^1$H NMR (400 MHz, DMSO-d$_6$) δ 7.74 (d, J=8.78 Hz, 1H) 7.66 (s, 1H) 7.57 (d, J=2.20 Hz, 1H) 7.22 (dd, J=8.78, 2.26 Hz, 1H) 7.09-7.17 (m, 1H) 6.94-7.07 (m, 1H) 6.66 (dd, J=8.28, 1.88 Hz, 1H) 4.16 (s, 1H) 3.65 (t, J=7.00 Hz, 1H) 2.71 (m, 1H) 2.66 (s, 3H) 2.25-2.40 (m, 4H) 1.89-1.98 (q, J=6.82 Hz, 2H) 1.53-1.84 (m, 3H) 1.35-1.51 (m, 1H) 0.96 (s, 3H) 0.88 (s, 3H) 0.56-0.78 (t, J=7.2 Hz, 3H).

Example 769

Diastereomer 1

3-(4-((S)-2-(2-Hydroxypropan-2-yl)pyrrolidin-1-yl)-3-(3-(p-tolyl)ureido)phenyl)pentanoic acid

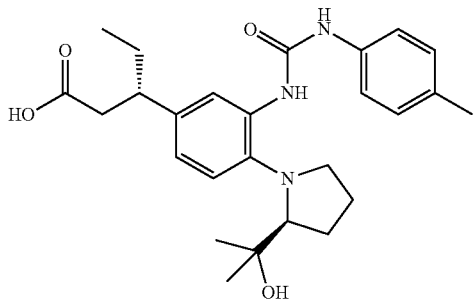 [SMILES: CC[C@@H](CC(=O)O)c1ccc(N2CCC[C@H]2C(C)(C)O)c(NC(=O)Nc2ccc(C)cc2)c1]

769A. Methyl 3-(4-((S)-2-(2-hydroxypropan-2-yl)pyrrolidin-1-yl)-3-nitrophenyl)pentanoate (Diastereomeric Mixture)

769A was prepared from 767E and (R)-(+)-2,2'-bis(diphenylphosphine)-1,1'-binaphthyl following the procedure described for the synthesis of 767F. LC-MS Anal. Calc'd. for $C_{19}H_{28}N_2O_5$, 364.436, found [M+H] 365.2, $T_r$=2.896 min (Method U).

769B. Methyl 3-(3-amino-4-((S)-2-(2-hydroxypropan-2-yl)pyrrolidin-1-yl)phenyl)pentanoate To a stirred solution of 769A (0.88 g, 2.415 mmol) in ethyl acetate (27 mL) was added palladium on carbon (0.128 g, 0.121 mmol). The reaction mixture was stirred at room temperature under H$_2$ atmosphere (40 psi) for 3 hours. The reaction mixture was filtered through a pad of CELITE® and it was washed with methanol (5×100 mL), filtrate was concentrated under reduced pressure to get crude compound. The residue was purified via flash silica gel column chromatography (conditions: 0-100% ethyl acetate in pet ether or gradient of ethyl acetate in pet ether) to afford Diastereomeric mixture 769B (brown solid).

Chiral separation of Diastereomeric mixture 769B gave Diastereomer 1 and Diastereomer 2 (Ratio of Diastereomer 1:Diastereomer 2=82:18, Method DH). Diastereomer 1, $T_r$=6.47 min, Diastereomer 2, $T_r$=11.86 min (Method DH)

769B Diastereomer 1 (brown semi-solid, 0.65 g, 1.846 mmol, 76% yield) $T_r$=6.62 min (Method DG). LC-MS Anal. Calc'd. for $C_{19}H_{30}N_2O_3$, 334.453, found [M+H] 335.2, $T_r$=2.636 min (Method U).

769C. Methyl 3-(4-((S)-2-(2-hydroxypropan-2-yl)pyrrolidin-1-yl)-3-(3-(p-tolyl)ureido)phenyl)pentanoate To a solution of 769B Diastereomer 1 (0.03 g, 0.090 mmol) in THF (0.5 mL) was added 1-isocyanato-4-methylbenzene (0.013 g, 0.099 mmol) at 0° C., the mixture was stirred at room temperature for 1 hour. The reaction mixture was concentrated to get the crude product. The resultant solid was washed with hexane (2×10 mL) and dried under vacuum to get 769C (off-white solid, 0.03 g, 0.057 mmol, 63.7% yield). LC-MS Anal. Calc'd. for $C_{27}H_{37}N_3O_4$, 467.60, found [M+H] 468.6. $T_r$=1.16 min (Method DO).

Example 769. 3-(4-((S)-2-(2-Hydroxypropan-2-yl)pyrrolidin-1-yl)-3-(3-(p-tolyl)ureido)phenyl)pentanoic acid To a stirred solution of 769C (0.03 g, 0.064 mmol) in mixture tetrahydrofuran (0.5 mL), MeOH (0.5 mL) and water (0.5 mL), was added lithium hydroxide (4.61 mg, 0.192 mmol). The reaction mixture was stirred at room temperature for 3 h. The reaction mixture was concentrated under reduced pressure. The aqueous residue so obtained was acidified with solid citric acid to pH~3.5. The aqueous layer was diluted with water (5 mL) and extracted with ethyl acetate (2×5.0 mL). Combined organic layer was washed with water (5.0 mL), brine (5.0 mL), dried over anhydrous sodium sulfate and concentrated under reduced pressure to afford a residue. The residue was purified via preparative LC/MS to afford Example 769 (0.001 g, 0.0021 mmol, 3.4% yield). LC-MS Anal. Calc'd. for $C_{26}H_{35}N_3O_4$, 453.574, found [M+H] 454.3. $T_r$=1.617 min (Method R). $^1$H NMR (400 MHz, DMSO-d$_6$) δ 9.60 (s, 1H), 8.61 (s, 1H), 7.94 (s, 1H), 7.42 (d, J=8.40 Hz, 2H), 7.13 (d, J=8.00 Hz, 1H), 7.07 (d, J=8.40 Hz, 2H), 6.71 (d, J=6.80 Hz, 1H), 4.35 (s, 1H), 3.55-3.59 (m, 2H), 2.75-2.90 (m, 1H), 2.25 (s, 3H), 2.33-2.43 (m, 2H), 1.96-1.99 (m, 2H), 1.75-1.78 (m, 1H), 1.64-1.66 (m, 3H), 1.41-1.42 (m, 1H), 0.93 (s, 3H), 0.85 (s, 3H), 0.68 (t, J=7.2 Hz, 3H).

Example 770

Diastereomer 1

3-(4-((S)-2-(2-Hydroxypropan-2-yl)pyrrolidin-1-yl)-3-((2-methylbenzo[d]thiazol-6-yl)amino)phenyl)pentanoic acid

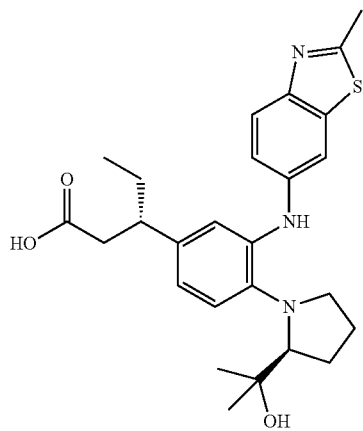 [SMILES: CC[C@@H](CC(=O)O)c1ccc(N2CCC[C@H]2C(C)(C)O)c(Nc2ccc3nc(C)sc3c2)c1]

Example 770 was prepared from 769B Diastereomer 1 and 6-bromo-2-methylbenzo[d]thiazole following the procedure described for the synthesis of Example 768. LC-MS Anal. Calc'd. for $C_{26}H_{33}N_3O_3S$, 467.62, found [M+H] 468.2. $T_r$=1.791 min (Method O). $^1$H NMR (400 MHz, DMSO-$d_6$) δ 7.74 (d, J=8.78 Hz, 1H) 7.65 (s, 1H) 7.58 (d, J=2.13 Hz, 1H) 7.22 (dd, J=8.78, 2.20 Hz, 1H) 7.13 (d, J=8.34 Hz, 1H) 7.01 (d, J=1.82 Hz, 1H) 6.64 (dd, J=8.22, 1.82 Hz, 1H) 4.17 (s, 1H) 3.65 (t, J=6.84 Hz, 1H) 2.71 (m, 1H) 2.66 (s, 3H) 2.20-2.42 (m, 4H) 1.93 (q, J=6.82 Hz, 2H) 1.71-1.83 (m, 1H) 1.53-1.69 (m, 2H) 1.29-1.45 (m, 1H) 0.96 (s, 3H) 0.85 (s, 3H) 0.70 (t, J=7.2 Hz, 3H).

Example 771

Diastereomer 3

3-(3-((4-Cyanophenyl)amino)-4-((R)-2-(2-hydroxypropan-2-yl)pyrrolidin-1-yl)phenyl)pentanoic acid

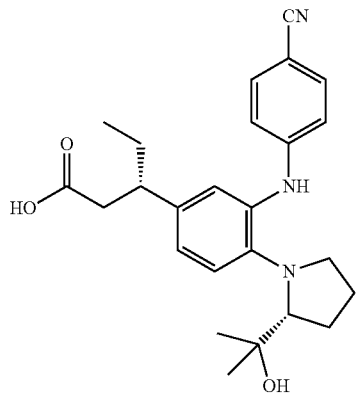 [SMILES: CC[C@@H](CC(=O)O)c1ccc(N2CCC[C@@H]2C(C)(C)O)c(Nc2ccc(C#N)cc2)c1]

771A. 2-(4-Fluorophenyl)-5,5-dimethyl-1,3,2-dioxaborinane

In a sealed tube 1-bromo-4-fluorobenzene (10 g, 57.1 mmol), bis(neopentyl glycolato)diboron (19.36 g, 86 mmol) and potassium acetate (16.82 g, 171 mmol) in toluene (100 mL) purged with argon for 20 min. To this $PdCl_2$(dppf).$CH_2Cl_2$ Adduct (1.400 g, 1.714 mmol) was added and purged with argon for 5 min. The reaction mixture was heated at 80° C. for 2 hours. Reaction mixture was cooled to room temperature and it was filtered through a pad of CELITE® and rinsed with dichloromethane (3×40 mL), filtrate was concentrated under reduced pressure to get residue which was diluted with dichloromethane (50 mL) and water (50 mL), DCM layer separated. Aqueous layer was extracted with DCM (2×50 mL). The combined organic layer was washed with brine (50 mL), dried over anhydrous sodium sulfate, filtered, and concentrated under reduced pressure. Purification via flash chromatography gave 771A (10 g, 48.1 mmol, 84% yield). $^1$H NMR (300 MHz, CDCl$_3$) δ 7.78 (q, J=6.60 Hz, 2H), 7.03 (t, J=9.00 Hz, 2H), 3.76 (s, 4H), 1.02 (s, 6H).

771B. Methyl 3-(4-fluorophenyl)pentanoate

In a sealed tube 1,4-dioxane (20 mL) was purged with argon for 15 min. (R)-(+)-2,2'-Bis(diphenylphosphino)-1,1'-binaphthyl (0.066 g, 0.106 mmol) and chlorobis (ethylene) rhodium(I) dimer (0.028 g, 0.072 mmol) was added to the reaction mixture and it was purged with argon for 30 min. To this 771A (1.0 g, 4.81 mmol), sodium hydroxide (4.33 mL, 4.33 mmol) and (E) methyl pent-2-enoate (4.33 mL, 4.33 mmol) was added and the reaction mixture was purged with argon for 10 min. The reaction mixture was heated at 50° C. for 18 h. Reaction mixture was cooled to room temperature and quenched with acetic acid (0.2 mL) and it was stirred for 5 minutes before it was partitioned between ethyl acetate and water. Aqueous layer was extracted with ethyl acetate (2×100 mL). The combined organic layer was washed with brine (50 mL), dried over anhydrous sodium sulfate, concentrated under reduced pressure to afford a residue. Purification via flash chromatography gave 771B (colorless liquid, 0.8 g, 3.81 mmol, 79% yield). $^1$H NMR (300 MHz, CDCl$_3$) δ 7.11-7.16 (m, 2H), 6.94-7.10 (m, 2H), 3.57 (s, 3H), 2.94-3.04 (m, 1H), 2.49-2.65 (m, 2H), 1.61-1.74 (m, 2H), 0.78 (t, J=7.50 Hz, 3H).

771C. Methyl 3-(4-fluoro-3-nitrophenyl)pentanoate

To stirred conc. $H_2SO_4$ (30 mL, 563 mmol) at 3° C. was added 771B (0.6 g, 2.85 mmol) followed by potassium nitrate (0.346 g, 3.42 mmol) in two approximately equal portions about four minutes apart. The reaction was slowly poured into crushed ice/water and extracted with ethyl acetate (200 mL). The extract was concentrated under reduced pressure to afford a residue. Purification via flash chromatography gave 771C (0.4 g, 1.567 mmol, 54.9% yield). $^1$H NMR (400 MHz, CDCl$_3$) δ 7.88 (q, J=2.40 Hz, 1H), 7.45-7.48 (m, 1H), 7.20-7.26 (m, 1H), 3.57 (s, 3H), 3.08-3.12 (m, 1H), 2.67-2.73 (m, 1H), 2.53-2.59 (m, 1H), 1.58-1.79 (m, 2H), 0.82 (t, J=7.50 Hz, 3H).

771D. Methyl 3-(4-((R)-2-(2-hydroxypropan-2-yl)pyrrolidin-1-yl)-3-nitrophenyl)pentanoate 771D was prepared from (R)-2-(pyrrolidin-2-yl)propan-2-ol and 771C following the procedure described for the synthesis of 767D. LC-MS Anal. Calc'd. for $C_{19}H_{28}N_2O_5$, 364.436, found [M+H] 365.2. $T_r$=2.886 min (Method U).

771E. Methyl 3-(3-amino-4-((R)-2-(2-hydroxypropan-2-yl)pyrrolidin-1-yl)phenyl)pentanoate To a stirred solution of 771D (0.5 g, 1.372 mmol) in ethyl acetate (25 mL) was added palladium on carbon (0.073 g, 0.069 mmol). The reaction mixture was stirred at room temperature under $H_2$ atmosphere (40 psi) for 3 hours. The reaction mixture was filtered through a pad of CELITE® and it was washed with methanol (5×100 mL), filtrate was concentrated under reduced pressure to get crude compound. The residue was purified via flash silica gel column chromatography (conditions: 0-100% ethyl acetate in pet ether or gradient of ethyl acetate in pet ether) to afford Diastereomeric mixture 771E (0.5 g, brown solid). LC-MS Anal. Calc'd. for $C_{19}H_{30}N_2O_3$, 334.453, found [M+H] 335.2, $T_r$=2.636 min (Method U).

Chiral separation of Diastereomeric mixture 771E gave Diastereomer 1 and Diastereomer 2 (Ratio of Diastereomer 1:Diastereomer 2=93:07, Method DI). Diastereomer 1, $T_r$=6.22 min, Diastereomer 2, $T_r$=10.16 min (Method DI)

771E Diastereomer 1 (brown semi-solid, 0.4 g, 1.110 mmol, 81% yield). LC-MS Anal. Calc'd. for $C_{19}H_{30}N_2O_3$, 334.453, found [M+H] 335.2, $T_r$=2.636 min (Method U).

771F. Methyl 3-(3-((4-cyanophenyl)amino)-4-((R)-2-(2-hydroxypropan-2-yl)pyrrolidin-1-yl)phenyl)pentanoate The mixture of 771E Diastereomer 1 (50 mg, 0.149 mmol), 4-bromobenzonitrile (29.9 mg, 0.164 mmol), Xantphos (17.30 mg, 0.030 mmol) and $Cs_2CO_3$ (146 mg, 0.448 mmol) in 1,4-dioxane (2.0 mL) was stirred at room temperature. Argon gas was bubbled through the mixture for 5 min. Bis(dibenzylideneacetone)palladium (8.60 mg, 0.015 mmol) was added and argon gas was bubbled through the mixture for another 5 min. The reaction mixture was sealed and placed in preheated oil bath at 110° C. for 12 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL) and brine (10 mL), dried over anhydrous sodium sulfate, filtered, and concentrated under reduced pressure to afford 771F (pale yellow solid, 50 mg, 0.115 mmol, 77% yield). LC-MS Anal. Calc'd. for $C_{26}H_{33}N_3O_3$, 435.559, found [M+H] 436.3, $T_r$=0.80 min. (Method AA).

Example 771. 3-(3-((4-Cyanophenyl)amino)-4-((R)-2-(2-hydroxypropan-2-yl)pyrrolidin-1-yl)phenyl)pentanoic acid To a stirred solution of 771F (50 mg, 0.115 mmol) in mixture tetrahydrofuran (1.0 mL), MeOH (1.0 mL) and water (1.0 mL), was added lithium hydroxide (8.25 mg, 0.344 mmol). The reaction mixture was stirred at room temperature for 3 h. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL) and brine (5.0 mL), dried over anhydrous sodium sulfate, filtered, and concentrated under reduced pressure to afford a residue. The residue was purified via preparative LCMS to afford Example 771 (off-white solid, 16.7 mg, 0.038 mmol, 33.5%). LC-MS Anal. Calc'd. for $C_{25}H_{31}N_3O_3$, 421.532, found [M+H] 422.2. $T_r$=1.548 min (Method R). $^1$H NMR (400 MHz, DMSO-$d_6$) δ12.00 (s, 1H), 8.10 (s, 1H), 7.54 (d, J=8.80 Hz, 2H), 7.19 (d, J=8.40 Hz, 1H), 6.98-7.02 (m, 3H), 6.82 (dd, J=2.00, 8.40 Hz, 1H), 4.10 (s, 1H), 3.78 (q, J=Hz, 1H), 2.75-2.85 (m, 1H), 2.55-2.55 (m, 1H), 2.40-2.43 (m, 1H), 1.86-1.90 (m, 2H), 1.50-1.71 (m, 4H), 0.96 (s, 3H), 0.86 (s, 3H), 0.72 (t, J=7.20 Hz, 3H) (Note: a multiplet —$CH_2$ were buried under solvent peak).

Examples 772 and 773

Diastereomer 3

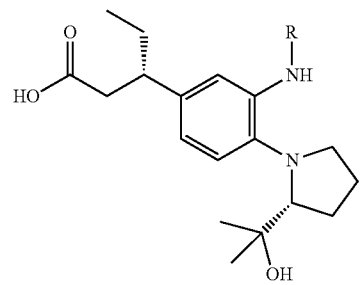

Examples 772 and 773 was prepared from 771E Diastereomer 1 and the corresponding halides following the procedure described for the synthesis of Example 771.

| Ex. No. | Name | R | $T_r$, min | Method | (M + H) |
| --- | --- | --- | --- | --- | --- |
| 772 | 3-(3-((4-fluorophenyl)amino)-4-((R)-2-(2-hydroxypropan-2-yl)pyrrolidin-1-yl)phenyl)pentanoic acid | 4-fluorophenyl | 1.621 | R | 415.2 |

| Ex. No. | Name | R | $T_r$, min | Method | (M + H) |
|---|---|---|---|---|---|
| 773 | 3-(3-((4-chlorophenyl)amino)-4-((R)-2-(2-hydroxypropan-2-yl)pyrrolidin-1-yl)phenyl)pentanoic acid | 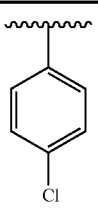 | 1.768 | R | 431.2 |

Example 774

Diastereomer 4

3-(4-((R)-2-(2-Hydroxypropan-2-yl)pyrrolidin-1-yl)-3-(3-(p-tolyl)ureido)phenyl)pentanoic acid

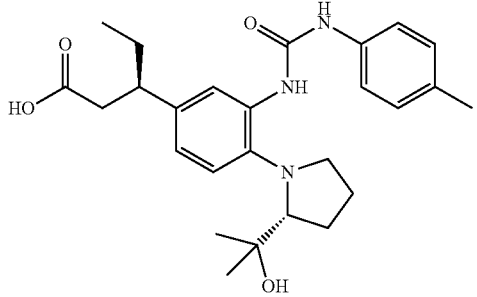 [SMILES: CC[C@H](CC(=O)O)c1ccc(N2CCC[C@@H]2C(C)(C)O)c(NC(=O)Nc2ccc(C)cc2)c1]

774A. Methyl 3-(4-fluorophenyl)pentanoate 774A was prepared following the procedure for 771B by utilizing (S)-(−)-2,2'-bis(diphenylphosphino)-1,1'-binaphthyl and 771A. $^1$H NMR (300 MHz, CDCl$_3$) δ 7.11-7.16 (m, 2H), 6.94-7.10 (m, 2H), 3.57 (s, 3H), 2.94-3.04 (m, 1H), 2.49-2.65 (m, 2H), 1.61-1.74 (m, 2H), 0.78 (t, J=7.50 Hz, 3H).

774B. Methyl 3-(4-fluoro-3-nitrophenyl)pentanoate 774B was prepared following the procedure for 771C by utilizing 774A. $^1$H NMR (400 MHz, CDCl$_3$) δ 7.88 (q, J=2.40 Hz, 1H), 7.45-7.48 (m, 1H), 7.20-7.26 (m, 1H), 3.57 (s, 3H), 3.08-3.12 (m, 1H), 2.67-2.73 (m, 1H), 2.53-2.59 (m, 1H), 1.58-1.79 (m, 2H), 0.82 (t, J=7.50 Hz, 3H).

774C. Methyl 3-(4-((R)-2-(2-hydroxypropan-2-yl)pyrrolidin-1-yl)-3-nitrophenyl)pentanoate 774C was prepared from (R)-2-(pyrrolidin-2-yl)propan-2-ol and 774B following the procedure described for the synthesis of 771D. LC-MS Anal. Calc'd. for C$_{19}$H$_{28}$N$_2$O$_5$, 364.436, found [M+H] 365.2. $T_r$=2.886 min (Method U).

774D. Methyl 3-(3-amino-4-((R)-2-(2-hydroxypropan-2-yl)pyrrolidin-1-yl)phenyl)pentanoate To a stirred solution of 774C (0.7 g, 1.921 mmol) in ethyl acetate (35 mL) was added palladium on carbon (0.102 g, 0.096 mmol). The reaction mixture was stirred at room temperature under H$_2$ atmosphere (40 psi) for 3 hours. The progress of the reaction was monitored by TLC. The complete consumption of starting material was observed. The reaction mixture was filtered through a pad of CELITE® and it was washed with methanol (5×100 mL), filtrate was concentrated under reduced pressure to get crude compound. The residue was purified via flash silica gel column chromatography (conditions: 0-100% ethyl acetate in pet ether or gradient of ethyl acetate in pet ether) to afford Diastereomeric mixture 774D (brown solid).

Chiral separation of Diastereomeric mixture 774D gave Diastereomer 1 and Diastereomer 2 (Ratio of Diastereomer 1:Diastereomer 2=09:91, Method DI). Diastereomer 1, $T_r$=6.2 min, Diastereomer 2, $T_r$=9.66 min (Method DI).

774D Diastereomer 2 (brown semi-solid, 0.6 g, 1.794 mmol, 62% yield). LC-MS Anal. Calc'd. for C$_{19}$H$_{30}$N$_2$O$_3$, 334.453, found [M+H] 335.2. $T_r$=2.636 min (Method U).

774E. Methyl 3-(4-((R)-2-(2-hydroxypropan-2-yl)pyrrolidin-1-yl)-3-(3-(p-tolyl)ureido)phenyl)pentanoate To a solution of 774D Diastereomer 2 (0.02 g, 0.060 mmol) in THF (0.5 mL) was added 1-isocyanato-4-methylbenzene (0.013 g, 0.087 mmol) at 0° C., the mixture was stirred at room temperature for 1 hour. The reaction mixture was concentrated to get the crude product. The resultant solid was washed with hexane (2×10 mL) and dried under vacuum to get 774E (off-white solid, 0.02 g, 0.034 mmol, 79% yield). LC-MS Anal. Calc'd. for C$_{27}$H$_{37}$N$_3$O$_4$, 467.60, found [M+H] 468.6. $T_r$=1.53 min (Method AY).

Example 774. 3-(4-((R)-2-(2-Hydroxypropan-2-yl)pyrrolidin-1-yl)-3-(3-(p-tolyl)ureido)phenyl)pentanoic acid To a stirred solution of 774E (0.02 g, 0.043 mmol) in a mixture of tetrahydrofuran (0.5 mL), MeOH (0.5 mL) and water (0.5 mL), was added lithium hydroxide (3.07 mg, 0.128 mmol). The reaction mixture was stirred at room temperature for 3 hours. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL) and brine (5.0 mL), dried over anhydrous sodium sulfate, filtered, and concentrated under reduced pressure to afford a residue. The residue was purified via preparative LC/MS to afford Example 774 (0.0186 g, 0.041 mmol, 96% yield). LC-MS Anal. Calc'd. for C$_{26}$H$_{35}$N$_3$O$_4$, 453.574, found [M+H] 454.3, $T_r$=1.675 min (Method R). $^1$H NMR (400 MHz, DMSO-d$_6$) δ$^1$H NMR: 400 MHz, DMSO-d$_6$: δ 9.20 (s, 1H), 8.29 (s, 1H), 8.01 (s, 1H), 7.37 (d, J=8.00 Hz, 1H), 7.20 (d, J=8.40 Hz, 1H), 7.10 (d, J=8.40 Hz, 1H), 6.76 (dd, J=2.00, 8.00 Hz, 1H), 3.94 (s, 1H), 2.79-2.89 (m, 1H), 2.42-2.44 (m, 1H), 2.25 (s, 3H), 1.70-2.10 (m, 4H), 1.35-1.70 (m, 2H), 0.93 (s, 3H), 0.86 (s, 3H), 0.71 (t, J=7.60 Hz, 3H) (Note: two multiplet CH$_2$ were buried under solvent peak).

Examples 775 to 779

Diastereomer 4

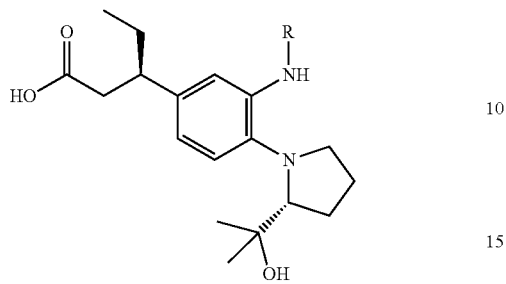

Examples 775 to 779 were prepared from 774D Diastereomer 2 and the corresponding isocyanates following the procedure described for the synthesis of Example 774.

| Ex. No. | Name | R | $T_r$, min | Method | (M + H) |
|---|---|---|---|---|---|
| 775 | 3-(3-(3-(4-fluorophenyl)ureido)-4-((R)-2-(2-hydroxypropan-2-yl)pyrrolidin-1-yl)phenyl)pentanoic acid | 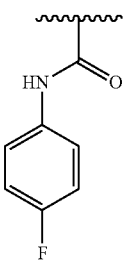 [SMILES: *C(=O)Nc1ccc(F)cc1] | 1.605 | R | 458.2 |
| 776 | 3-(3-(3-(4-chloro-2-fluorophenyl)ureido)-4-((R)-2-(2-hydroxypropan-2-yl)pyrrolidin-1-yl)phenyl)pentanoic acid | 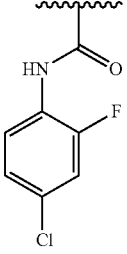 [SMILES: *C(=O)Nc1ccc(Cl)cc1F] | 1.833 | R | 492.2 |
| 777 | 3-(4-((R)-2-(2-hydroxypropan-2-yl)pyrrolidin-1-yl)-3-(3-(4-methoxyphenyl)ureido)phenyl)pentanoic acid | 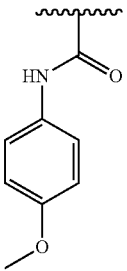 [SMILES: *C(=O)Nc1ccc(OC)cc1] | 1.534 | R | 470.2 |

| Ex. No. | Name | R | $T_r$, min | Method | (M + H) |
|---|---|---|---|---|---|
| 778 | 3-(3-(3-(4-ethoxyphenyl)ureido)-4-((R)-2-(2-hydroxypropan-2-yl)pyrrolidin-1-yl)phenyl)pentanoic acid | ![structure with HN-C(=O)-phenyl-OEt] | 1.666 | R | 484.3 |
| 779 | 3-(4-((R)-2-(2-hydroxypropan-2-yl)pyrrolidin-1-yl)-3-(3-(p-tolyl)ureido)phenyl)pentanoic acid | ![structure with C(=O)-NH-phenyl-Me] | 1.640 | O | 454.2 |

Example 780

Diastereomer 4

3-(3-((4-Chlorophenyl)amino)-4-((R)-2-(2-hydroxy-propan-2-yl)pyrrolidin-1-yl)phenyl)pentanoic acid

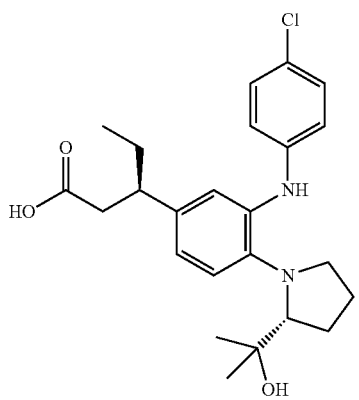 [SMILES: CC[C@H](CC(=O)O)c1ccc(N2CCC[C@@H]2C(C)(C)O)c(Nc2ccc(Cl)cc2)c1]

780A. Methyl 3-(3-((4-chlorophenyl)amino)-4-((R)-2-(2-hydroxypropan-2-yl)pyrrolidin-1-yl)phenyl)pentanoate The mixture of 774D Diastereomer 2 (30 mg, 0.090 mmol), 1-bromo-4-chlorobenzene (18.89 mg, 0.099 mmol), Xantphos (10.38 mg, 0.018 mmol) and $Cs_2CO_3$ (88 mg, 0.269 mmol) in 1,4-dioxane (2.0 mL) was stirred at room temperature. Argon gas was bubbled through the mixture for 5 min. Bis(dibenzylideneacetone)palladium (5.16 mg, 8.97 µmol) was added and argon gas was bubbled through the mixture for another 5 min. The reaction mixture was sealed and placed in preheated oil bath at 110° C. for 12 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). The combined organic layer was washed with water (10 mL) and brine (10 mL), dried over anhydrous sodium sulfate, filtered, and concentrated under reduced pressure to afford 780A (pale yellow solid, 30 mg, 0.067 mmol, 75% yield). LC-MS Anal. Calc'd. for $C_{25}H_{33}ClN_2O_3$, 444.994, found [M+H] 445.6. $T_r$=1.78 min. (Method AY).

Example 780. 3-(3-((4-Chlorophenyl)amino)-4-((R)-2-(2-hydroxypropan-2-yl)pyrrolidin-1-yl)phenyl) pentanoic acid To a stirred solution of 780A (20 mg, 0.045 mmol) in mixture tetrahydrofuran (0.5 mL), MeOH (0.5 mL) and water (0.5 mL), was added lithium hydroxide (3.23 mg, 0.135 mmol). The reaction mixture was stirred at room temperature for 3 hours. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). The combined organic layer was washed with water (5.0 mL), brine (5.0 mL), dried over anhydrous sodium sulfate and concentrated under reduced pressure to afford a residue. The residue was purified via preparative LCMS to afford Example 780 (off-white solid, 8.3 mg, 0.018 mmol, 41.1%). LC-MS Anal. Calc'd. for $C_{24}H_{31}ClN_2O_3$, 430.968, found [M+H] 431.2, $T_r$=2.010 min (Method O). $^1$H NMR (400 MHz, DMSO-$d_6$) δ 7.56 (s, 1H), 7.24 (d, J=2.00 Hz, 1H), 7.23 (d, J=2.00 Hz, 1H), 7.14 (d, J=8.40 Hz, 1H), 7.05 (d, J=2.00 Hz, 1H), 7.07 (d, J=2.00 Hz, 1H), 6.95 (d, J=2.00 Hz, 1H), 6.67 (dd, J=2.00, 8.00 Hz, 1H), 4.18 (s, 1H), 3.66 (t, J=Hz, 1H), 2.70-2.85 (m, 1H), 2.41-2.43 (m, 1H), 1.90-1.94 (m, 2H), 1.46-1.66 (m, 4H), 0.96 (s, 3H), 0.86 (s, 3H), 0.72 (t, J=7.60 Hz, 3H) (Note: one multiplet —$CH_2$ and one —CH were buried under solvent peak).

Examples 781 to 784

Diastereomer 4

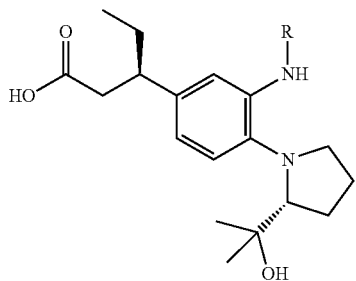

Examples 781 to 784 was prepared following the procedure for Example 780 by using 774D Diastereomer 2 and the corresponding halide.

Example 785

Diastereomer 1

3-(4-((S)-2-(2-Fluoropropan-2-yl)pyrrolidin-1-yl)-3-(3-(p-tolyl)ureido)phenyl)pentanoic acid

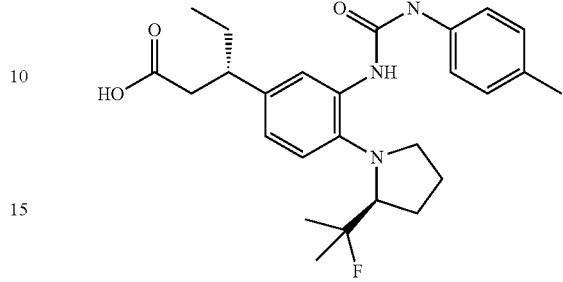

785A. (S)-1-(4-Bromo-2-nitrophenyl)-2-(2-fluoropropan-2-yl)pyrrolidine

A 50 mL round-bottomed flask was charged with 767D (3.5 g, 10.63 mmol) and DCM (175 mL). The solution was

| Ex. No. | Name | R | $T_r$ min | Method | (M + H) |
|---|---|---|---|---|---|
| 781 | 3-(3-((2,2-difluorobenzo[d][1,3]dioxol-5-yl)amino)-4-((R)-2-(2-hydroxypropan-2-yl)pyrrolidin-1-yl)phenyl)pentanoic acid | ![benzodioxole-F2] | 2.107 | R | 477.2 |
| 782 | 3-(3-((4-cyanophenyl)amino)-4-((R)-2-(2-hydroxypropan-2-yl)pyrrolidin-1-yl)phenyl)pentanoic acid | ![4-CN-phenyl] | 1.679 | O | 422.2 |
| 783 | 3-(3-((4-chlorophenyl)amino)-4-((R)-2-(2-hydroxypropan-2-yl)pyrrolidin-1-yl)phenyl)pentanoic acid | ![4-CN-phenyl] | 1.991 | O | 431.2 |
| 784 | 3-(3-((4-fluorophenyl)amino)-4-((R)-2-(2-hydroxypropan-2-yl)pyrrolidin-1-yl)phenyl)pentanoic acid | ![4-F-phenyl] | 1.829 | O | 415.2 | cooled to 0° C. and DAST (2.81 mL, 21.26 mmol) was added over a period of 2 min. The reaction was gradually warmed to room temperature over a period of 6.5 hours. The reaction mixture was quenched with sat. aq. NaHCO$_3$ (18 mL). The layers were separated and the aqueous phase was back-extracted with CH$_2$Cl$_2$ (3×20 mL). The combined organic phases were dried (Na$_2$SO$_4$) and concentrated under reduced pressure. The residue was purified via flash silica gel column chromatography (conditions: 0-100% ethyl acetate in pet ether or gradient of ethyl acetate in pet ether) to afford 785A (orange liquid, 2.8 g, 8.20 mmol, 77% yield). LC-MS Anal. Calc'd. for C$_{13}$H$_{16}$BrFN$_2$O$_2$, 331.181, found [M+2] 333.0. T$_r$=3.318 min (Method U).

785B. (S)-1-(4-(5,5-Dimethyl-1,3,2-dioxaborinan-2-yl)-2-nitrophenyl)-2-(2-fluoropropan-2-yl)pyrrolidine In a sealed tube 785A (1.0 g, 3.02 mmol), bis(neopentyl glycolato)diboron (0.900 g, 3.99 mmol) and potassium acetate (0.889 g, 9.06 mmol) in dioxane (10 mL) purged with argon for 20 min. To this PdCl$_2$ (dppf).CH$_2$Cl$_2$ Adduct (0.074 g, 0.091 mmol) was added and purged with argon for 5 min. The reaction mixture was heated at 80° C. for 6 hours. Reaction mixture was cooled to room temperature and it was filtered through a pad of CELITE® and rinsed with dichloromethane (3×40 mL), filtrate was concentrated under reduced pressure to get residue which was diluted with dichloromethane (50 mL) and water (50 mL), DCM layer separated. Aqueous layer was extracted with DCM (2×50 mL). The combined organic layer was washed with brine (50 mL), dried over anhydrous sodium sulfate, filtered, and concentrated under reduced pressure. The residue was purified via flash silica gel column chromatography (conditions: 0-100% ethyl acetate in pet ether or gradient of ethyl acetate in pet ether) to afford 785B (gummy liquid, 0.36 g, 0.988 mmol, 32.7% yield). $^1$H NMR (400 MHz, CDCl$_3$) δ 8.20 (s, 1H), 7.69 (dd, J=1.60, 8.80 Hz, 1H), 7.27 (dd, J=4.80, 7.80 Hz, 1H), 4.40-4.43 (m, 1H), 3.74 (s, 4H), 3.46-3.52 (m, 1H), 2.72-2.77 (m, 1H), 2.18-2.19 (m, 1H), 1.91-1.93 (m, 1H), 1.70-1.71 (m, 2H), 1.39 (s, 3H), 1.34 (s, 3H), 1.00 (s, 6H).

785C. Methyl 3-(4-((S)-2-(2-fluoropropan-2-yl)pyrrolidin-1-yl)-3-nitrophenyl)pentanoate In a pressure tube equipped with Teflon cap, 785B (0.85 g, 2.334 mmol) and 1,4-dioxane (15.0 mL) were added followed by (E)-methyl pent-2-enoate (0.266 g, 2.334 mmol), (R)-(+)-2,2'-bis(diphenylphosphino)-1,1'-binaphthyl (0.032 g, 0.051 mmol) and 1M solution of sodium hydroxide (2.100 mL, 2.100 mmol). Argon gas was bubbled through the mixture for 10 min and chlorobis(ethylene)rhodium(I) dimer (0.014 g, 0.035 mmol) was added at room temperature. Argon gas was bubbled through the mixture for 5 min. The tube was then screw-capped and heated at 50° C. for 3 h. The reaction mixture was cooled to room temperature, quenched with acetic acid (0.2 mL) and was stirred for 5 minutes before it was diluted with water (10 mL). The aqueous layer was extracted with ethyl acetate (3×20 mL). The combined organic layer was washed with water (20 mL) and brine (20 mL), dried over anhydrous sodium sulfate, filtered, and concentrated under reduced pressure to afford a residue. The residue was purified via flash silica gel column chromatography (conditions: 0-100% ethyl acetate in pet ether or gradient of ethyl acetate in pet ether) to afford 785C (yellow liquid, 0.45 g, 1.201 mmol, 51.5% yield). LC-MS Anal. Calc'd. for C$_{19}$H$_{27}$FN$_2$O$_4$, 366.427, found [M+H] 367.2. T$_r$=3.395 min (Method U).

785D. 3-(3-Amino-4-((S)-2-(2-fluoropropan-2-yl)pyrrolidin-1-yl)phenyl)pentanoate The solution of 785C (0.45 g, 1.228 mmol) in ethyl acetate (15 mL) was charged to a sealable Parr hydrogenation flask. The solution was sequentially evacuated and purged with nitrogen gas. To this 10% palladium on carbon (0.065 g, 0.061 mmol) was added under nitrogen atmosphere. The reaction mixture was stirred under hydrogen atmosphere (40 psi) at room temperature for 3 hours. The reaction mixture was filtered through a CELITE® pad and the residue on the pad was thoroughly rinsed with MeOH (3×20 mL). The combined filtrate was concentrated under reduced pressure. The crude mixture was purified by ISCO 12 g silica gel chromatography by using 0-50% EtOAc/hexane as eluent). Pure fractions were collected and concentrated under reduced pressure to afford 785D (Diastereomeric mixture). LC-MS Anal. Calc'd. C$_{19}$H$_{29}$FN$_2$O$_2$ for 336.444, found [M+H] 363.4, T$_r$=4.002 min (Method N).

Chiral separation of diastereomeric mixture 785D (Method DJ) gave Diastereomer 1, T$_r$=3.71 min (Method DJ), Diastereomer 2, T$_r$=4.36 min (Method DJ). (Ratio of Diastereomer 1:Diastereomer 2=82:18 (Method DJ)).

785D Diastereomer 1 (brown semi-solid, 0.13 g, 0.383 mmol, 31.1% yield). T$_r$=3.94 min (Method DJ). LC-MS Anal. Calc'd. C$_{19}$H$_{29}$FN$_2$O$_2$ [M+H] 363.4, T$_r$=4.002 min (Method N).

785E. Methyl 3-(4-((S)-2-(2-fluoropropan-2-yl)pyrrolidin-1-yl)-3-(3-(p-tolyl)ureido)phenyl)pentanoate To a solution of 785D Diastereomer 1 (0.015 g, 0.045 mmol) in THF (0.5 mL) was added 1-isocyanato-4-methylbenzene (0.065 g, 0.049 mmol) at 0° C., the mixture was stirred at room temperature for 1 hour. The reaction mixture was concentrated to get the crude product. The resultant solid was washed with hexane (2×10 mL) and dried under vacuum to get 785E. LC-MS Anal. Calc'd. for C$_{27}$H$_{37}$N$_3$O$_4$, 467.6, found [M+H] 468.6. T$_r$=1.53 min (Method AY).

Example 785. 3-(4-((S)-2-(2-Fluoropropan-2-yl)pyrrolidin-1-yl)-3-(3-(p-tolyl)ureido)phenyl)pentanoic acid To a stirred solution of 785E crude in mixture tetrahydrofuran (0.5 mL), MeOH (0.5 mL) and water (0.5 mL), was added lithium hydroxide (8.54 mg, 0.375 mmol). The reaction mixture was stirred at room temperature for 3 hours. The reaction mixture was concentrated under reduced pressure. The aqueous residue so obtained was acidified with solid citric acid to pH~3.5. The aqueous layer was diluted with water (5 mL) and extracted with ethyl acetate (2×5.0 mL). Combined organic layer was washed with water (5.0 mL), brine (5.0 mL), dried over anhydrous sodium sulfate and concentrated under reduced pressure to afford a residue. The residue was purified via preparative LCMS to afford Example 785. LC-MS Anal. Calc'd. for C$_{26}$H$_{34}$FN$_3$O$_3$, 455.57, found [M+H] 456.3. T$_r$=2.268 min (Method R). $^1$H NMR (400 MHz, DMSO-d$_6$) δ11.90 (s, 1H), 9.39 (s, 1H), 8.04 (s, 1H), 8.00 (s, 1H), 7.37 (d, J=8.40 Hz, 2H), 7.24 (d, J=8.40 Hz, 1H), 7.11 (d, J=8.00 Hz, 2H), 6.77 (dd, J=2.00, 8.40 Hz, 1H), 3.65-3.80 (m, 1H), 3.32-3.36 (m, 1H), 2.75-2.90 (m, 1H), 2.50-2.70 (m, 3H), 2.34 (s, 3H), 1.40-1.90 (m, 6H), 1.13-1.26 (m, 6H), 0.73 (t, J=7.20 Hz, 3H).

Examples 786 and 787

Diastereomer 1

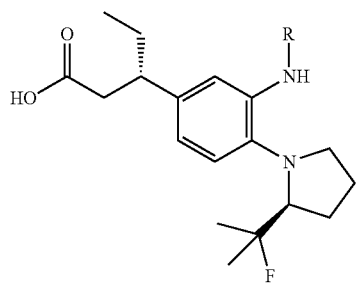

Examples 786 and 787 were prepared following the procedure for Example 785 by using 785D Diastereomer 1 and the corresponding isocyanates.

and concentrated under reduced pressure to afford 788A. LC-MS Anal. Calc'd. for $C_{25}H_{32}ClFN_2O_2$, 446.99, found [M+H] 447.3. $T_r$=2.636 min. (Method CZ).

| Ex. No. | Name | R | $T_r$, min | Method | (M + H) |
|---|---|---|---|---|---|
| 786 | 3-(3-(4-chloro-2-fluorophenyl)ureido)-4-((S)-2-(2-fluoropropan-2-yl)pyrrolidin-1-yl)phenyl) pentanoic acid | | 2.444 | R | 494.2 |
| 787 | 3-(3-(2-fluoro-4-methoxyphenyl)ureido)-4-((S)-2-(2-fluoropropan-2-yl)pyrrolidin-1-yl)phenyl) pentanoic acid | | 2.164 | R | 490.2 |

Example 788

Diastereomer 1

3-(3-((4-Chlorophenyl)amino)-4-((S)-2-(2-fluoropropan-2-yl)pyrrolidin-1-yl)phenyl)pentanoic acid

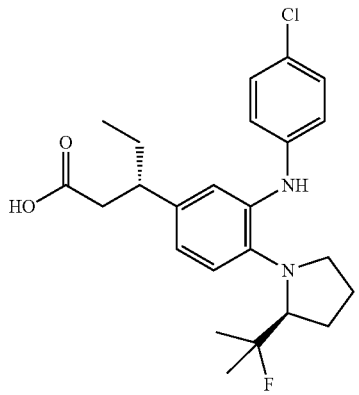 [SMILES: CC[C@@H](CC(=O)O)c1ccc(N2CCC[C@H]2C(C)(C)F)c(Nc2ccc(Cl)cc2)c1]

788A. Methyl 3-(3-((4-chlorophenyl)amino)-4-((S)-2-(2-fluoropropan-2-yl)pyrrolidin-1-yl)phenyl)pentanoate The mixture of 785D Diastereomer 1 (20 mg, 0.059 mmol), 1-bromo-4-chlorobenzene (13.66 mg, 0.071 mmol), Xantphos (6.88 mg, 0.012 mmol) and $Cs_2CO_3$ (38.7 mg, 0.119 mmol) in 1,4-dioxane (2.0 mL) was stirred at room temperature. Argon gas was bubbled through the mixture for 5 min. Bis(dibenzylideneacetone)palladium (3.42 mg, 5.94 μmol) was added and argon gas was bubbled through the mixture for another 5 min. The reaction mixture was sealed and placed in preheated oil bath at 110° C. for 12 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). The combined organic layer was washed with water (10 mL), brine (10 mL), dried over anhydrous sodium sulfate Example 788. 3-(3-((4-Chlorophenyl)amino)-4-((S)-2-(2-fluoropropan-2-yl)pyrrolidin-1-yl)phenyl)pentanoic acid To a stirred solution of 788A crude in mixture tetrahydrofuran (0.5 mL), MeOH (0.5 mL) and water (0.5 mL), was added lithium hydroxide (11.39 mg, 0.476 mmol). The reaction mixture was stirred at room temperature for 3 h. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL), brine (5.0 mL), dried over anhydrous sodium sulfate and concentrated under reduced pressure to afford a residue. The residue was purified via preparative LCMS to afford Example 788. LC-MS Anal. Calc'd. for $C_{24}H_{30}ClFN_2O_2$, 432.96, found [M+H] 433.2. $T_r$=2.517 min (Method O). $^1$H NMR (400 MHz, DMSO-$d_6$: δ 12.00 (s, 1H), 7.20-7.26 (m, 4H), 7.18 (dd, J=2.40, 5.40 Hz, 1H), 6.93-6.96 (m, 2H), 6.74 (dd, J=2.00, 8.40 Hz, 1H), 3.80-3.90 (m, 1H), 2.32-2.73 (m, 2H), 1.40-1.77 (m, 8H), 1.11-1.23 (m, 7H), 0.71 (t, J=7.60 Hz, 3H).

Examples 789 and 790

Diastereomer 1

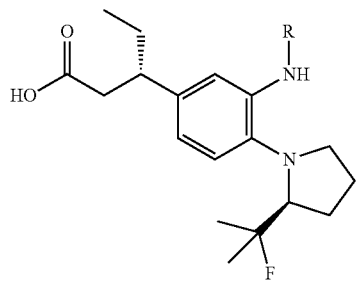

Examples 789 and 790 were prepared from 785D Diastereomer 1 and the corresponding halides following the procedure described for the synthesis of Example 788.

| Ex. No. | Name | R | $T_r$, min | Method | (M + H) |
|---|---|---|---|---|---|
| 789 | 3-(4-((S)-2-(2-fluoropropan-2-yl)pyrrolidin-1-yl)-3-((2-methylbenzo[d]thiazol-6-yl)amino)phenyl)pentanoic acid | | 2.191 | R | 470.2 |
| 790 | 3-(3-((2,2-difluorobenzo[d][1,3]dioxol-5-yl)amino)-4-((S)-2-(2-fluoropropan-2-yl)pyrrolidin-1-yl)phenyl)pentanoic acid | | 2.739 | R | 479.2 |

Example 791

Diastereomer 2

3-(3-(3-(4-Chloro-2-fluorophenyl)ureido)-4-((S)-2-(2-fluoropropan-2-yl)pyrrolidin-1-yl)phenyl)pentanoic acid

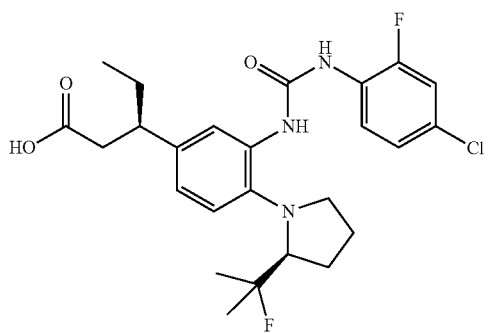 [SMILES: CC[C@H](CC(=O)O)c1ccc(N2CCC[C@H]2C(C)(C)F)c(NC(=O)Nc2ccc(Cl)cc2F)c1]

791A. Methyl 3-(4-((S)-2-(2-fluoropropan-2-yl)pyrrolidin-1-yl)-3-nitrophenyl)pentanoate 791A was prepared from 785B and (S)-(−)-2,2'-bis(diphenylphosphino)-1,1'-binaphthyl following the procedure described for the synthesis of 785C. LC-MS Anal. Calc'd. for $C_{19}H_{27}FN_2O_4$, 366.427, found [M+H] 367.2. $T_r$=2.816 min (Method N).

791B. 3-(3-Amino-4-((S)-2-(2-fluoropropan-2-yl)pyrrolidin-1-yl)phenyl)pentanoate 791B was prepared from 791A following the procedure described for the synthesis of 785D. LC-MS Anal. Calc'd. for $C_{19}H_{29}FN_2O_2$, 336.444, found [M+H] 337.2. $T_r$=3.290 min (Method N). Chiral analytical analysis verified and diastereomeric excess (de) was 85.1%, $T_r$=4.32 min (Method DJ).

Example 791. 3-(3-(3-(4-Chloro-2-fluorophenyl)ureido)-4-((S)-2-(2-fluoropropan-2-yl)pyrrolidin-1-yl)phenyl)pentanoic acid Example 791 was prepared from 791B and the corresponding isocyanate following the procedure described for the synthesis of Example 785. LC-MS Anal. Calc'd. for $C_{25}H_{30}ClF_2N_3O_3$, 493.97, found [M+H] 494.2. $T_r$=2.080 min (Method O). $^1$H NMR (400 MHz, DMSO-$d_6$) δ12.10 (s, 1H), 9.51 (s, 1H), 8.40 (s, 1H), 8.20 (dd, J=8.80, 62.60 Hz, 1H), 7.89 (d, J=2.00 Hz, 1H), 7.47 (dd, J=2.40, 11.20 Hz, 1H), 7.24 (dd, J=5.60, 8.40 Hz, 2H), 6.81 (dd, J=2.00, 8.40 Hz, 1H), 3.70-3.80 (m, 1H), 3.30-3.90 (m, 4H), 2.10-2.20 (m, 1H), 1.40-1.86 (m, 6H), 1.14-1.24 (m, 6H), 0.72 (t, J=7.20 Hz, 3H).

Examples 792 and 793

Diastereomer 2

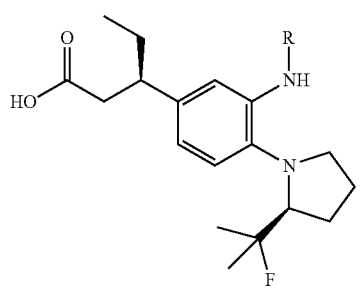

Examples 792 and 793 were prepared from 791B and the corresponding isocyanates following the procedure described for the synthesis of Example 785.

| Ex. No. | Name | R | $T_r$ min | Method | (M + H) |
|---|---|---|---|---|---|
| 792 | 3-(4-((S)-2-(2-fluoropropan-2-yl)pyrrolidin-1-yl)-3-(3-(p-tolyl)ureido)phenyl)pentanoic acid | 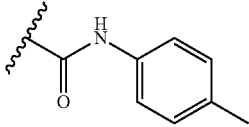 | 1.954 | O | 456.2 |
| 793 | 3-(3-(3-(2-fluoro-4-methoxyphenyl)ureido)-4-((S)-2-(2-fluoropropan-2-yl)pyrrolidin-1-yl)phenyl)pentanoic acid | 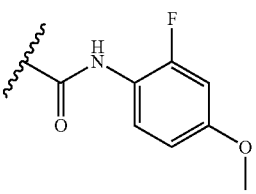 [SMILES: *C(=O)Nc1ccc(OC)cc1F] | 2.170 | R | 490.3 |

Examples 794 to 796

Diastereomer 2

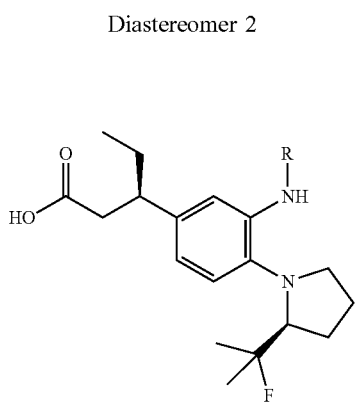

Examples 794 to 796 were prepared from 791B and corresponding halides following the procedure described for the synthesis of Example 788.

| Ex. No. | Name | R | $T_r$ min | Method | (M + H) |
|---|---|---|---|---|---|
| 794 | 3-4-((S)-2-(2-fluoropropan-2-yl)pyrrolidin-1-yl)-3-((2-methylbenzo[d]thiazol-6-yl)amino)phenyl)pentanoic acid | 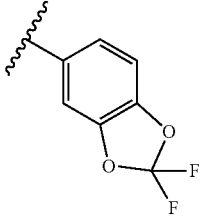 | 2.191 | O | 470.2 |
| 795 | 3-(3-((4-chlorophenyl)amino)-4-((S)-2-(2-fluoropropan-2-yl)pyrrolidin-1-yl)phenyl)pentanoic acid | 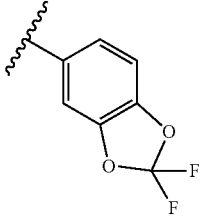 | 2.636 | R | 433.2 |

-continued

| Ex. No. | Name | R | $T_r$ min | Method | (M + H) |
|---|---|---|---|---|---|
| 796 | 3-(3-((2,2-difluorobenzo[d][1,3]dioxol-5-yl)amino)-4-((S)-2-(2-fluoropropan-2-yl)pyrrolidin-1-yl)phenyl)pentanoic acid | 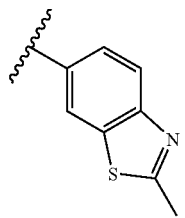 [SMILES: *c1ccc2nc(C)sc2c1] | 2.734 | R | 479.2 |

Example 797

Diastereomer 1 homochiral, absolute stereochemistry not determined 3-(3-((4-Cyanophenyl)amino)-4-((S)-2-(2-hydroxypropan-2-yl)pyrrolidin-1-yl)phenyl)butanoic acid

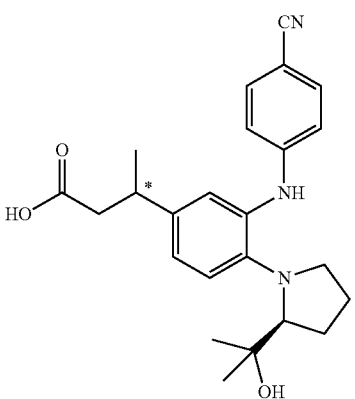 [SMILES: CC(CC(=O)O)c1ccc(N2CCC[C@H]2C(C)(C)O)c(Nc2ccc(C#N)cc2)c1]

797A. Methyl 3-(4-((S)-2-(2-hydroxypropan-2-yl)pyrrolidin-1-yl)-3-nitrophenyl)butanoate To a solution of 737B (2.0 g, 8.29 mmol) and (S)-2-(pyrrolidin-2-yl)propan-2-ol (1.285 g, 9.95 mmol) in N-methyl-2-pyrrolidone (15 mL) was added N,N-diisopropylethylamine (4.34 mL, 24.87 mmol). After stirring at 120° C. for 16 hours, the reaction mixture was cooled to room temperature and diluted with diethyl ether. The organic layer was washed with 10% aq. AcOH solution, 10% $NaHCO_3$ solution, brine, dried over $Na_2SO_4$ and was concentrated under reduced pressure to afford a residue. The residue was purified via flash silica gel column chromatography (0-100% ethyl acetate in pet ether as eluent) to afford 797A (orange solid, 2.65 g, 7.38 mmol, 89% yield). LC-MS Anal. Calc'd. for $C_{18}H_{26}N_2O_5$, 350.409, found [M+H] 351.2. $T_r$=2.826 min (Method U).

797B. Methyl 3-(3-amino-4-((S)-2-(2-hydroxypropan-2-yl)pyrrolidin-1-yl)phenyl)butanoate The solution of 797A (2.65 g, 7.56 mmol) in ethyl acetate (100 mL) was charged to a sealable Parr hydrogenation flask. The solution was sequentially evacuated and purged with nitrogen gas. To this 10% palladium on carbon (0.402 g, 0.378 mmol) was added under nitrogen atmosphere. The reaction mixture was stirred under hydrogen atmosphere (40 psi) at room temperature for 3 hours. The reaction mixture was filtered through a CELITE® pad and the residue on the pad was thoroughly rinsed with MeOH (3×20 mL). The combined filtrate was concentrated under reduced pressure. The crude mixture was purified by silica gel chromatography (0-50% EtOAc/hexane as eluent) and concentrated under reduced pressure to afford 797B (Diastereomeric mixture).

Chiral separation of diastereomeric mixture 797B (Method CK) gave Diastereomer 1, $T_r$=3.41 min (Method CK), Diastereomer 2, $T_r$=9.68 min (Method CK).

797B Diastereomer 1 (brown semi-solid, 0.85 g, 2.65 mmol, 35.1% yield): LC-MS Anal. Calc'd. $C_{18}H_{28}N_2O_3$ [M+H] 321.2, $T_r$=2.477 min (Method U).

797B Diastereomer 2 (brown semi-solid, 0.9 g, 2.75 mmol, 36.4% yield): LC-MS Anal. Calc'd. $C_{18}H_{28}N_2O_3$ [M+H] 321.2, $T_r$=2.477 min (Method U).

797C. Methyl 3-(3-((4-cyanophenyl)amino)-2-(2-hydroxypropan-2-yl)pyrrolidin-1-yl)phenyl)butanoate The mixture of 797B Diastereomer 1 (20 mg, 0.062 mmol), 4-bromobenzonitrile (14.77 mg; 0.081 mmol), Xantphos (7.22 mg, 0.012 mmol) and cesium carbonate (61.0 mg, 0.187 mmol in dioxane (1.0 mL) was stirred at room temperature. Argon gas was bubbled through the mixture for 10 min. Bis(dibenzylideneacetone)palladium (3.59 mg, 6.24 µmol) was added and argon gas was bubbled through the mixture for 5 min. The reaction mixture was sealed and placed in preheated oil bath at 110° C. for 18 hours. The reaction mixture was cooled to room temperature and concentrated under reduced pressure to afford a residue. The residue was reconstituted in a mixture of DCM (50 mL) and water (10 mL). The organic layer was separated and was washed with water (10 mL) and brine (10 mL), dried over anhydrous sodium sulfate, filtered, and concentrated under reduced pressure to afford a residue of 797C (13 mg, 0.0319 mmol, 67.15%). LC-MS Anal. Calc'd. $C_{25}H_{31}N_3O_3$ [M+H] 422.2, $T_r$=2.86 min (Method DC).

Example 797. 3-(3-((4-Cyanophenyl)amino)-2-(2-hydroxypropan-2-yl)pyrrolidin-1-yl)phenyl)butanoic acid To a stirred solution of above residue 797C in mixture of THF (1.0 mL), MeOH (1.0 mL) and water (0.5 mL), was added lithium hydroxide (11.96 mg, 0.499 mmol. The reaction mixture was stirred at room temperature for 12 hours. The reaction mixture was concentrated under reduced pressure. The aqueous residue so obtained was acidified with 1(N) HCl to pH~2. The aqueous layer was diluted with water (5 mL) and extracted with ethyl acetate (2×20 mL). Combined organic layer was washed with water (10 mL) and brine (10 mL), dried over anhydrous sodium sulfate and concentrated under reduced pressure to afford a residue. The residue was purified via preparative LC/MS to afford Example 797. LC-MS Anal. Calc'd. for $C_{24}H_{29}N_3O_3$, 407.51, found [M+H] 408.3. $T_r$=1.374 min (Method O). $^1$H NMR (400 MHz, DMSO-$d_6$) δ 8.09 (s, 1H), 7.56 (d, J=8.80 Hz, 2H), 7.21 (d, J=3.60 Hz, 1H), 7.09 (d, J=2.80 Hz, 1H), 7.02 (d, J=8.80 Hz, 2H), 6.88 (d, J=8.00 Hz, 1H), 3.93 (q, J=6.80 Hz, 1H), 3.31-3.33 (m, 1H), 3.06 (m, 1H), 1.50-1.93 (m, 4H), 1.19 (d, J=6.80 Hz, 3H), 0.99 (s, 3H), 0.88 (s, 3H) (Note: 4 protons were buried under solvent peak).

Examples 798 to 801

Diastereomer 1 homochiral, absolute stereochemistry unknown

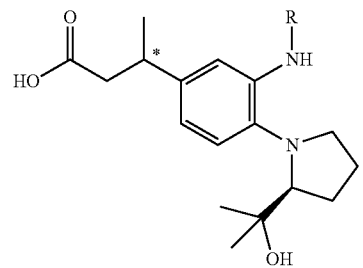

Examples 798 to 801 were prepared from 797B Diastereomer 1 and the corresponding halides following the procedure described for the synthesis of Example 797.

| Ex. No. | Name | R | $T_r$ min | Method | (M + H) |
|---|---|---|---|---|---|
| 798 | 3-(3-((4-fluorophenyl)amino)-4-((S)-2-(2-hydroxypropan-2-yl)pyrrolidin-1-yl)phenyl)butanoic acid | ![F-phenyl] | 1.468 | O | 401.3 |
| 799 | 3-(3-((4-chlorophenyl)amino)-4-((S)-2-(2-hydroxypropan-2-yl)pyrrolidin-1-yl)phenyl)butanoic acid | ![Cl-phenyl] | 1.345 | R | 417.3 |

-continued

| Ex. No. | Name | R | $T_r$, min | Method | (M + H) |
|---|---|---|---|---|---|
| 800 | 3-(3-((2-ethoxy-pyrimidin-5-yl)amino)-4-((S)-2-(2-hydroxy-propan-2-yl)pyrrolidin-1-yl)phenyl)butanoic acid | | 1.078 | R | 429.3 |
| 801 | 3-(4-((S)-2-(2-hydroxypropan-2-yl)pyrrolidin-1-yl)-3-((2-methoxy-pyrimidin-5-yl)amino)phenyl)butanoic acid | | 0.962 | R | 415.3 |

Example 802

Diastereomer 2 homochiral, absolute diastereochemistry not determined 3-(3-((4-Cyanophenyl)amino)-2-(2-hydroxypropan-2-yl)pyrrolidin-1-yl)phenyl)butanoic acid

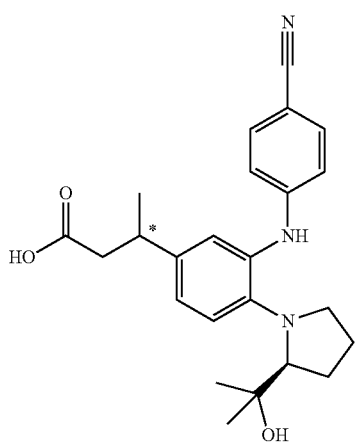 [SMILES: CC(CC(=O)O)c1ccc(N2CCC[C@H]2C(C)(C)O)c(Nc2ccc(C#N)cc2)c1]

Example 802 was prepared from 797B Diastereomer 2 and 4-bromobenzonitrile following the procedure described for the synthesis of Example 797. LC-MS Anal. Calc'd. for $C_{24}H_{29}N_3O_3$, 407.51, found [M+H] 408.3, $T_r$=1.451 min (Method O). $^1$H NMR (400 MHz, DMSO-$d_6$) δ 8.09 (s, 1H), 7.56 (d, J=8.80 Hz, 2H), 7.21 (d, J=3.60 Hz, 1H), 7.09 (d, J=2.80 Hz, 1H), 7.02 (d, J=8.80 Hz, 2H), 6.88 (d, J=8.00 Hz, 1H), 3.93 (q, J=6.80 Hz, 1H), 3.31-3.33 (m, 1H), 3.06 (m, 1H), 1.50-1.93 (m, 4H), 1.19 (d, J=6.80 Hz, 3H), 0.99 (s, 3H), 0.88 (s, 3H) (Note: 4H multiplet CH were buried under solvent peak).

Examples 803 to 806

Diastereomer 2

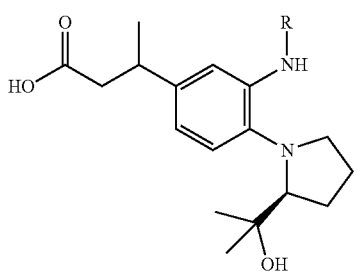

Examples 803 to 806 were prepared from 797B Diastereomer 2 and the corresponding halides following the procedure described for the synthesis of Example 797.

| Ex. No. | Name | R | $T_r$, min | Method | (M + H) |
|---|---|---|---|---|---|
| 803 | 3-(3-((4-fluorophenyl)amino)-4-((S)-2-(2-hydroxypropan-2-yl)pyrrolidin-1-yl)phenyl)butanoic acid | | 1.218 | R | 401.3 |
| 804 | 3-(3-((4-chlorophenyl)amino)-4-((S)-2-(2-hydroxypropan-2-yl)pyrrolidin-1-yl)phenyl)butanoic acid | | 1.344 | R | 417.3 |
| 805 | 3-(4-((S)-2-(2-hydroxypropan-2-yl)pyrrolidin-1-yl)-3-((2-methoxypyrimidin-5-yl)amino)phenyl)butanoic acid | | 0.960 | R | 415.3 |
| 806 | 3-(3-((2-ethoxy-pyrimidin-5-yl)amino)-4-((S)-2-(2-hydroxy-propan-2-yl)pyrrolidin-1-yl)phenyl)butanoic acid | | 1.077 | R | 429.3 |

Example 807

(S)-3-(3-((4-Fluorophenyl)amino)-4-(2-(2-hydroxypropan-2-yl)pyrrolidin-1-yl)phenyl)-3-methylbutanoic acid

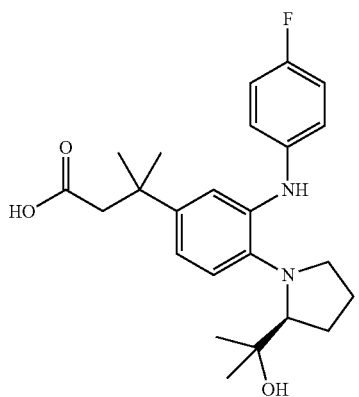 [SMILES: CC(C)(CC(=O)O)c1ccc(N2CCC[C@H]2C(C)(C)O)c(Nc2ccc(F)cc2)c1]

807A. (S)-Methyl 3-(4-(2-(2-hydroxypropan-2-yl)pyrrolidin-1-yl)-3-nitrophenyl)-3-methylbutanoate To a solution of 1F (0.65 g, 2.55 mmol) and (S)-2-(pyrrolidin-2-yl)propan-2-ol (0.395 g, 3.06 mmol) in N-methyl-2-pyrrolidine (8.0 mL) was added N,N-diisopropylethylamine (1.334 mL, 7.64 mmol). After stirring at 120° C. for 16 hours, the reaction mixture was cooled to room temperature and diluted with diethyl ether, the organic layer was washed with 10% aq. AcOH solution, 10% $NaHCO_3$ solution and brine. The combined organics were dried over $Na_2SO_4$ and concentrated. The crude product was chromatographed on silica gel (eluting with EtOAc/hexane) to afford 807A (orange solid, 0.8 g, 2.037 mmol, 80% yield). LC-MS Anal. Calc'd. for $C_{19}H_{28}N_2O_5$, 364.436, found [M+H] 365.2, $T_r$=2.977 min (Method U).

807B. (S)-Methyl 3-(3-amino-4-(2-(2-hydroxypropan-2-yl)pyrrolidin-1-yl)phenyl)-3-methylbutanoate The solution of methyl 807A (0.8 g, 2.195 mmol) in ethyl acetate (40 mL) was charged to a sealable Parr hydrogenation flask. The solution was sequentially evacuated and purged with nitrogen gas. To this 10% palladium on carbon (0.117 g, 0.110 mmol) was added under nitrogen atmosphere. The reaction mixture was stirred under hydrogen atmosphere (40 psi) at room temperature for 16 hours. The reaction mixture was filtered through a CELITE® pad and the residue on the pad was thoroughly rinsed with MeOH (3×20 mL). The combined filtrate was concentrated under reduced pressure to afford 807B (brown solid, 0.6 g, 1.633 mmol, 74.4% yield). LC-MS Anal. Calc'd. for $C_{19}H_{30}N_2O_3$, 334.453, found [M+H] 335.2, $T_r$=3.014 min (Method N).

807C. (S)-Methyl 3-(3-((4-fluorophenyl)amino)-4-(2-(2-hydroxypropan-2-yl)pyrrolidin-1-yl)phenyl)-3-methylbutanoate To a suspension of 807B (50 mg, 0.149 mmol), 1-bromo-4-fluorobenzene (28.8 mg, 0.164 mmol), $Cs_2CO_3$ (146 mg, 0.448 mmol) and Xantphos (17.30 mg, 0.030 mmol) in degassed dioxane (2.0 mL) was added bis(dibenzylideneacetone)palladium (8.60 mg, 0.015 mmol). The mixture was placed in preheated oil bath at 110° C., and stirred it for 18 hours. The reaction mixture was cooled to room temperature diluted with methanol (10 ml), filtered through CELITE® pad. The filtrate was concentrated under reduced pressure to afford 807C (50 mg, 0.117 mmol, 78% yield). LC-MS Anal. Calc'd. for $C_{25}H_{33}FN_2O_3$, 428.540, found [M+H] 429.6, $T_r$=0.77 min (Method AA).

Example 807. (S)-3-(3-((4-Fluorophenyl)amino)-4-(2-(2-hydroxypropan-2-yl)pyrrolidin-1-yl)phenyl)-3-methylbutanoic acid A solution of 807C (50 mg, 0.117 mmol) in tetrahydrofuran (1.0 mL) and MeOH (1.0 mL) was treated with lithium hydroxide (8.38 mg, 0.350 mmol) in water (1.000 mL) and the reaction was stirred at room temperature for 4 hours. The reaction mixture was concentrated under reduced pressure. The aqueous residue so obtained was acidified with solid citric acid to pH~3.5. The aqueous layer was diluted with water (5 mL) and extracted with ethyl acetate (2×5.0 mL). Combined organic layer was washed with water (5.0 mL) and brine (5.0 mL), dried over anhydrous sodium sulfate, filtered, and concentrated under reduced pressure to afford a residue. The residue was purified via preparative LC/MS to afford Example 807 (6.7 mg, 0.015 mmol, 13.02% yield). LC-MS Anal. Calc'd. for $C_{24}H_{31}FN_2O_3$, 414.513, found [M+H] 415.2, $T_r$=1.548 min (Method T). $^1$H NMR (400 MHz, DMSO-$d_6$) δ11.90 (s, 1H), 7.05-7.22 (m, 6H), 6.79 (dd, J=1.60, 8.40 Hz, 1H), 4.17 (s, 1H), 3.64 (t, J=Hz, 1H), 2.45-2.50 (m, 2H), 1.63-2.08 (m, 6H), 1.32 (s, 3H), 1.30 (s, 3H), 0.96 (s, 3H), 0.88 (s, 3H) (Note: one multiplet —CH was buried under solvent peak).

Examples 808 and 809

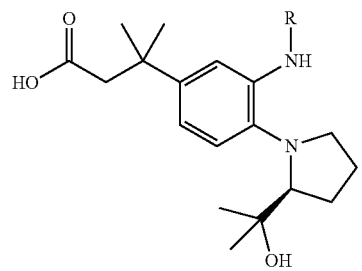

Examples 808 and 809 were prepared from 807B and corresponding halides following the procedure described for the synthesis of Example 807.

| Ex. No. | Name | R | $T_r$ min | Method | (M + H) |
|---|---|---|---|---|---|
| 808 | (S)-3-(3-((4-chlorophenyl)amino)-4-(2-(2-hydroxypropan-2-yl)pyrrolidin-1-yl)phenyl)-3-methylbutanoic acid | ![4-chlorophenyl] | 1.728 | R | 431.2 |

-continued

| Ex. No. | Name | R | $T_r$ min | Method | (M + H) |
|---|---|---|---|---|---|
| 809 | (S)-3-(3-((4-cyanophenyl)amino)-4-(2-(2-hydroxypropan-2-yl)pyrrolidin-1-yl)phenyl)-3-methylbutanoic acid | (4-cyanophenyl) | 1.521 | R | 422.2 |

Example 810

Diastereomer 1

3-(3-(3-(4-Ethoxyphenyl)ureido)-4-((S)-2-(2-hydroxypropan-2-yl)pyrrolidin-1-yl)phenyl)pentanoic acid

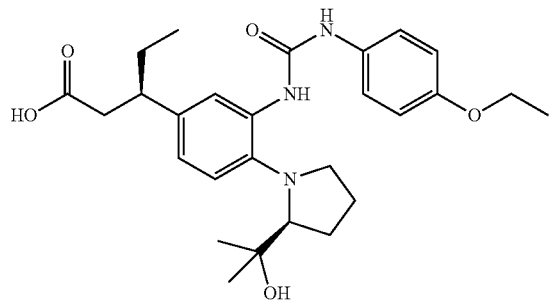 [SMILES: CCOc1ccc(NC(=O)Nc2cc([C@H](CC)CC(=O)O)ccc2N2CCC[C@H]2C(C)(C)O)cc1]

810A. 2-(4-Fluorophenyl)-5,5-dimethyl-1,3,2-dioxaborinane

In a sealed tube 1-bromo-4-fluorobenzene (10 g, 57.1 mmol), bis(neopentyl glycolato)diboron (19.36 g, 86 mmol) and potassium acetate (16.82 g, 171 mmol) in toluene (100 mL) purged with argon for 20 min. To this $PdCl_2$ (dppf).$CH_2Cl_2$ Adduct (1.400 g, 1.714 mmol) was added and purged with argon for 5 min. The reaction mixture was heated at 80° C. for 2 hours. Reaction mixture was cooled to room temperature and it was filtered through a pad of CELITE® and rinsed with dichloromethane (3×40 mL), filtrate was concentrated under reduced pressure to get residue which was diluted with dichloromethane (50 mL) and water (50 mL), DCM layer separated. Aqueous layer was extracted with DCM (2×50 mL). The combined organic layer was washed with brine (50 mL), dried over anhydrous sodium sulfate, concentrated under reduced pressure. Purification via flash chromatography gave 810A (off-white solid, 10 g, 48.1 mmol, 84% yield). $^1$H NMR (300 MHz, CDCl$_3$) δ 7.78 (q, J=6.60 Hz, 2H), 7.03 (t, J=9.00 Hz, 2H), 3.76 (s, 4H), 1.02 (s, 6H).

810B. Methyl 3-(4-fluorophenyl)pentanoate

In a sealed tube 1,4-dioxane (60 mL) was purged with argon for 15 min. (S)-(−)-2,2'-Bis(diphenylphosphino)-1,1'-binaphthyl (0.230 g, 0.370 mmol) and chlorobis(ethylene)rhodium(I) dimer (0.098 g, 0.252 mmol) was added to the reaction mixture and it was purged with argon for 30 min. To this 810A (3.5 g, 16.82 mmol), (E)-methyl pent-2-enoate (2.304 g, 20.19 mmol) and sodium hydroxide (15.14 mL, 15.14 mmol) was added and the reaction mixture was purged with argon for 10 min. The reaction mixture was heated at 50° C. for 18 hours. Reaction mixture was cooled to room temperature and quenched with acetic acid (0.2 mL) and it was stirred for 5 minutes before it was partitioned between ethyl acetate and water. Aqueous layer was extracted with ethyl acetate (2×200 mL). The combined organic layer was washed with brine (50 mL), dried over anhydrous sodium sulfate, concentrated under reduced pressure to afford a residue. Purification via flash chromatography gave 810B (colorless liquid, 3.5 g, 16.65 mmol, 99% yield). $^1$H NMR (300 MHz, CDCl$_3$) δ 7.11-7.16 (m, 2H), 6.94-7.10 (m, 2H), 3.57 (s, 3H), 2.94-3.04 (m, 1H), 2.49-2.65 (m, 2H), 1.61-1.74 (m, 2H), 0.78 (t, J=7.50 Hz, 3H).

810C. Methyl 3-(4-fluoro-3-nitrophenyl)pentanoate

To stirred conc. $H_2SO_4$ (90 mL, 1688 mmol) at 3° C. was added 810B (3.5 g, 16.65 mmol) followed by potassium nitrate (2.020 g, 19.98 mmol) in two approximately equal portions about four minutes apart. The reaction was slowly poured into crushed ice/water and extracted with ethyl acetate (200 mL). The extract was concentrated under reduced pressure to afford a residue. Purification via flash chromatography gave 810C (yellow liquid, 3.0 g, 11.75 mmol, 70.6% yield). $^1$H NMR (400 MHz, CDCl$_3$) δ 7.88 (q, J=2.40 Hz, 1H), 7.45-7.48 (m, 1H), 7.20-7.26 (m, 1H), 3.57 (s, 3H), 3.08-3.12 (m, 1H), 2.67-2.73 (m, 1H), 2.53-2.59 (m, 1H), 1.58-1.79 (m, 2H), 0.82 (t, J=7.50 Hz, 3H).

810D. Methyl 3-(4-((S)-2-(2-hydroxypropan-2-yl)pyrrolidin-1-yl)-3-nitrophenyl)pentanoate To a solution of 810C (1.5 g, 5.88 mmol) in NMP (10 mL) was added DIPEA (3.08 mL, 17.63 mmol), followed by (S)-2-(pyrrolidin-2-yl)propan-2-ol (0.911 g, 7.05 mmol). Reaction mixture was heated to 120° C. and was stirred overnight. LCMS indicated completion of reaction. The reaction mixture was cooled to room temperature and diluted with diethyl ether. The organic layer was washed with 10% aq. AcOH solution, 10% NaHCO$_3$ solution and brine. The combined organics were dried over Na$_2$SO$_4$ and concentrated under reduced pressure to afford a residue. Purification via flash chromatography gave 810D (orange liquid, 1.5 g, 4.07 mmol, 69.2% yield). LC-MS Anal. Calc'd. $C_{19}H_{28}N_2O_5$ [M+H] 365.2, $T_r$=2.994 min (Method U).

810E. Methyl 3-(3-amino-4-((S)-2-(2-hydroxypropan-2-yl)pyrrolidin-1-yl)phenyl)pentanoate The solution of 810D (1.5 g, 4.12 mmol)) in ethyl acetate (60.0 mL) was charged to a sealable Parr hydrogenation flask. The solution was sequentially evacuated and purged with nitrogen gas. To this 10% palladium on carbon (0.219 g, 0.206 mmol) was added under nitrogen atmosphere. The reaction mixture was stirred under hydrogen atmosphere (40 psi) at room temperature for 3 hours. The reaction mixture was filtered through a CELITE® pad and the residue on the pad was thoroughly rinsed with MeOH (3×50 mL). The combined filtrate was concentrated under reduced pressure. Purification via flash chromatography gave 810E (Diastereomeric mixture). LC-MS Anal. Calc'd. $C_{19}H_{30}N_2O_3$ [M+H] 335.2, $T_r$=2.735 min (Method U).

Chiral separation of diastereomeric mixture 810E (Method DH) gave Diastereomer 1 $T_r$=6.49 min (Method CM), Diastereomer 2 $T_r$=11.67 min (Method DH).

810E Diastereomer 1 (brown semi-solid, 0.6 g, 1.794 mmol, 43.6% yield): LC-MS Anal. Calc'd. $C_{19}H_{30}N_2O_3$ [M+H] 335.2, $T_r$=2.735 min (Method U).

810E Diastereomer 2 (brown semi-solid, 0.7 g, 2.072 mmol, 50.3% yield): LC-MS Anal. Calc'd. $C_{19}H_{30}N_2O_3$ [M+H] 335.2, $T_r$=2.735 min (Method U).

810F. Methyl 34343-(4-ethoxyphenyl)ureido)-4-((S)-2-(2-hydroxypropan-2-yl)pyrrolidin-1-yl)phenyl)pentanoate To a solution of 810E Diastereomer 1 (15 mg, 0.045 mmol) in THF (0.5 mL) was added 1-ethoxy-4-isocyanato-benzene (8.05 mg, 0.049 mmol). The mixture was stirred at room temperature for 1 hour. The reaction mixture was concentrated. The resultant solid was washed with hexane (2×3 mL) and dried under vacuum to get 810F. LC-MS Anal. Calc'd. for $C_{28}H_{39}N_3O_5$, 497.63, found [M+H] 498.4. $T_r$=2.287 min (Method CZ).

Example 810. 3-(3-(3-(4-Ethoxyphenyl)ureido)-4-((S)-2-(2-hydroxypropan-2-yl)pyrrolidin-1-yl)phenyl)pentanoic acid To a stirred solution of 810F crude in mixture tetrahydrofuran (0.5 mL), MeOH (0.5 mL) and water (0.5 mL), was added lithium hydroxide (8.59 mg, 0.165 mmol). The reaction mixture was stirred at room temperature for 3 h. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL) and brine (5.0 mL), dried over anhydrous sodium sulfate, filtered, and concentrated under reduced pressure to afford a residue. The residue was purified via preparative LCMS to afford Example 810 (14 mg, 0.028 mmol, 96.5%). LC-MS Anal. Calc'd. for $C_{27}H_{37}N_3O_5$, 483.60, found [M+H] 484.3. $T_r$=1.603 min (Method R). $^1$H NMR (400 MHz, DMSO-$d_6$) δ 9.10 (s, 1H), 8.20 (s, 1H), 7.98 (s, 1H), 7.38 (d, J=2.00 Hz, 2H), 7.21-7.38 (m, 2H), 6.86-7.37 (m, 4H), 3.97-4.05 (m, 2H), 2.80-2.90 (m, 2H), 2.30-2.57 (m, 2H), 1.31-2.08 (m, 8H), 1.22-1.40 (m, 3H), 0.74 (s, 3H), 0.72 (s, 3H), 0.70 (t, J=7.20 Hz, 3H).

Examples 811 to 815

Diastereomer 1

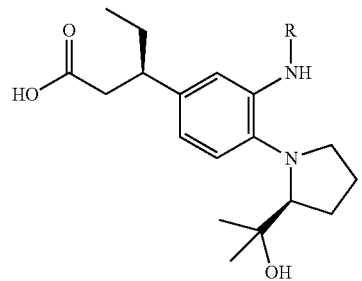

Examples 811 to 814 was prepared from 810E Diastereomer 1 and corresponding isocyanates following the procedure described for the synthesis of Example 810.

Example 815 was prepared from 810E Diastereomer 1 and corresponding amine following the procedure described for the synthesis of Example 767.

| Ex. No. | Name | R | $T_r$ min | Method | (M + H) |
|---|---|---|---|---|---|
| 811 | 3-(4-((S)-2-(2-hydroxypropan-2-yl)pyrrolidin-1-yl)-3-(3-(4-methoxyphenyl)ureido)phenyl)pentanoic acid | *structure* | 1.474 | R | 470.3 |
| 812 | 3-(3-(3-(4-chloro-2-fluorophenyl)ureido)-4-((S)-2-(2-hydroxypropan-2-yl)pyrrolidin-1-yl)phenyl)pentanoic acid | *structure* | 1.750 | R | 492.1 |
| 813 | 3-(3-(3-(4-fluorophenyl)ureido)-4-((S)-2-(2-hydroxypropan-2-yl)pyrrolidin-1-yl)phenyl)pentanoic acid | *structure* | 1.575 | O | 458.3 |
| 814 | 3-(3-(3-(2-fluoro-4-methoxyphenyl)ureido)-4-((S)-2-(2-hydroxypropan-2-yl)pyrrolidin-1-yl)phenyl)pentanoic acid | *structure* | 1.531 | O | 488.3 |

-continued

| Ex. No. | Name | R | $T_r$, min | Method | (M + H) |
|---|---|---|---|---|---|
| 815 | 3-(4-((S)-2-(2-hydroxypropan-2-yl)pyrrolidin-1-yl)-3-(3-(5-methylisoxazol-3-yl)ureido)phenyl)pentanoic acid | | 1.438 | O | 445.3 |

Example 816

Diastereomer 1

3-(3-((4-Ethoxyphenyl)amino)-4-((S)-2-(2-hydroxy-propan-2-yl)pyrrolidin-1-yl)phenyl)pentanoic acid

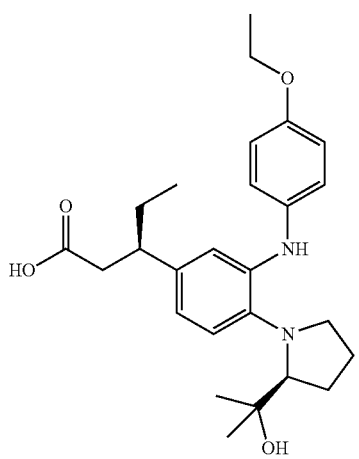 [SMILES: CCOc1ccc(Nc2cc([C@H](CC)CC(=O)O)ccc2N2CCC[C@H]2C(C)(C)O)cc1]

816A. Methyl 3-(3-((4-ethoxyphenyl)amino)-4-((S)-2-(2-hydroxypropan-2-yl)pyrrolidin-1-yl)phenyl)pentanoate The mixture of 810E Diastereomer 1 (20 mg, 0.060 mmol), 1-bromo-4-ethoxybenzene (15.63 mg, 0.103 mmol), Xantphos (6.92 mg, 0.012 mmol) and $Cs_2CO_3$ (58.5 mg, 0.179 mmol) in 1,4-dioxane (2.0 mL) was stirred at room temperature. Argon gas was bubbled through the mixture for 5 min. Bis(dibenzylideneacetone)palladium (3.44 mg, 5.98 μmol) was added and argon gas was bubbled through the mixture for another 5 min. The reaction mixture was sealed and placed in preheated oil bath at 110° C. for 12 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). The combined organic layer was washed with water (10 mL) and brine (10 mL), dried over anhydrous sodium sulfate, filtered, and concentrated under reduced pressure to afford 816A. LC-MS Anal. Calc'd. for $C_{27}H_{38}N_2O_4$, 454.60, found [M+H] 455.4. $T_r$=2.201 min. (Method CZ).

Example 816 3-(3-((4-Ethoxyphenyl)amino)-4-((S)-2-(2-hydroxypropan-2-yl)pyrrolidin-1-yl)phenyl)pentanoic acid To a stirred solution of 816A (crude mixture) tetrahydrofuran (0.5 mL), MeOH (0.5 mL) and water (0.5 mL), was added lithium hydroxide (11.46 mg, 0.478 mmol). The reaction mixture was stirred at room temperature for 3 hours. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). The combined organic layer was washed with water (5.0 mL) and brine (5.0 mL), dried over anhydrous sodium sulfate, filtered, and concentrated under reduced pressure to afford a residue. The residue was purified via preparative LCMS to afford Example 816. LC-MS Anal. Calc'd. for $C_{26}H_{36}N_2O_4$ 440.58, found [M+H] 441.3, $T_r$=1.593 min. (Method R). $^1$H NMR (400 MHz, DMSO-$d_6$) δ12.00 (s, 1H), 7.21 (s, 1H), 7.04 (d, J=8.40 Hz, 2H), 6.87 (d, J=0.80 Hz, 2H), 6.81-6.86 (m, 2H), 4.00 (m, 2H), 3.45-3.47 (m, 2H), 2.33-2.74 (m, 6H), 1.83-2.08 (m, 4H), 1.30-1.57 (m, 2H), 1.24 (t, J=4.80 Hz, 3H), 0.98 (s, 3H), 0.89 (s, 3H), 0.70 (t, J=7.20 Hz, 3H).

Examples 817 to 829

Diastereomer 1

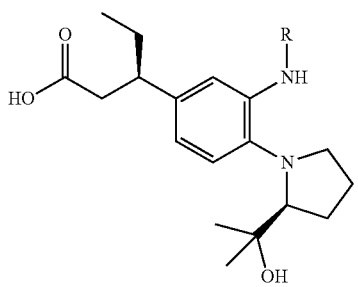

Examples 817 to 829 were prepared from 810E Diastereomer 1 and corresponding halides following the procedure described for the synthesis of Example 816.

| Ex. No. | Name | R | T$_r$, min | Method | (M + H) |
|---|---|---|---|---|---|
| 817 | 3-(4-((S)-2-(2-hydroxypropan-2-yl)pyrrolidin-1-yl)-3-((2-morpholinopyrimidin-4-yl)amino)phenyl) pentanoic acid | | 1.480 | O | 484.3 |
| 818 | 3-(3-((4-(cyclopropylmethoxy)phenyl)amino)-4-((S)-2-(2-hydroxypropan-2-yl)pyrrolidin-1-yl)phenyl) pentanoic acid | | 2.066 | O | 467.3 |
| 819 | 3-(3-((4-ethylphenyl)amino)-4-((S)-2-(2-hydroxypropan-2-yl)pyrrolidin-1-yl)phenyl) pentanoic acid | | 2.097 | O | 425.3 |
| 820 | 3-(3-((4-chlorophenyl)amino)-4-((S)-2-(2-hydroxypropan-2-yl)pyrrolidin-1-yl)phenyl) pentanoic acid | | 1.638 | R | 431.2 |
| 821 | 3-(3-((2,2-difluorobenzo[d][1,3]dioxol-5-yl)amino)-4-((S)-2-(2-hydroxypropan-2-yl)pyrrolidin-1-yl)phenyl) pentanoic acid | | 2.076 | O | 477.2 |
| 822 | 3-(3-((2-(cyclopropylmethoxy)pyrimidin-5-yl)amino)-4-((S)-2-(2-hydroxypropan-2-yl)pyrrolidin-1-yl)phenyl) pentanoic acid | | 1.654 | O | 469.3 |
| 823 | 3-(3-((2-ethoxypyrimidin-5-yl)amino)-4-((S)-2-(2-hydroxypropan-2-yl)pyrrolidin-1-yl)phenyl) pentanoic acid | | 1.418 | R | 443.3 |

-continued

| Ex. No. | Name | R | $T_r$ min | Method | (M + H) |
|---|---|---|---|---|---|
| 824 | 3-(4-((S)-2-(2-hydroxypropan-2-yl)pyrrolidin-1-yl)-3-((2-methoxypyrimidin-5-yl)amino)phenyl)pentanoic acid | 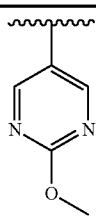 | 1.390 | R | 429.2 |
| 825 | 3-(3-((4-cyanophenyl)amino)-4-((S)-2-(2-hydroxypropan-2-yl)pyrrolidin-1-yl)phenyl)pentanoic acid | 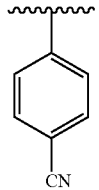 [SMILES: *c1ccc(C#N)cc1] | 1.253 | R | 422.3 |

Examples 826 to 831

Diastereomer 2

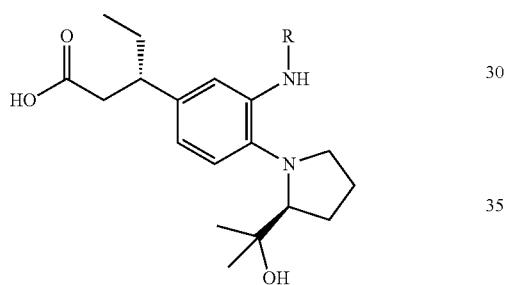

Examples 826 to 831 were prepared from 810E Diastereomer 2 and corresponding isocyanates following the procedure described for the synthesis of Example 810.

| Ex. No. | Name | R | $T_r$ min | Method | (M + H) |
|---|---|---|---|---|---|
| 826 | 3-(3-(3-(4-ethoxyphenyl)ureido)-4-((S)-2-(2-hydroxypropan-2-yl)pyrrolidin-1-yl)phenyl)pentanoic acid | 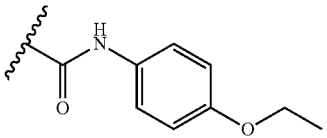 [SMILES: *C(=O)Nc1ccc(OCC)cc1] | 1.445 | R | 484.3 |
| 827 | 3-(4-((S)-2-(2-hydroxypropan-2-yl)pyrrolidin-1-yl)-3-(3-(4-methoxyphenyl)ureido)phenyl)pentanoic acid | 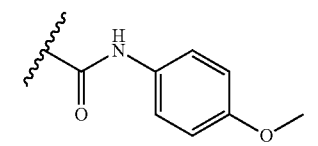 [SMILES: *C(=O)Nc1ccc(OC)cc1] | 1.310 | R | 470.3 |
| 828 | 3-(3-(3-(4-chloro-2-fluorophenyl)ureido)-4-((S)-2-(2-hydroxypropan-2-yl)pyrrolidin-1-yl)phenyl)pentanoic acid | 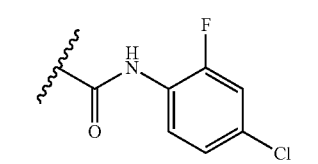 [SMILES: *C(=O)Nc1ccc(Cl)cc1F] | 1.593 | R | 492.2 |

| Ex. No. | Name | R | $T_r$ min | Method | (M + H) |
|---|---|---|---|---|---|
| 829 | 3-(3-(3-(4-fluorophenyl)ureido)-4-((S)-2-(2-hydroxypropan-2-yl)pyrrolidin-1-yl)phenyl)pentanoic acid | | 1.449 | O | 458.3 |
| 830 | 3-(3-(3-(2-fluoro-4-methoxyphenyl)ureido)-4-((S)-2-(2-hydroxypropan-2-yl)pyrrolidin-1-yl)phenyl)pentanoic acid | | 1.420 | O | 488.3 |
| 831 | 3-(4-((S)-2-(2-hydroxypropan-2-yl)pyrrolidin-1-yl)-3-(3-(5-methylisoxazol-3-yl)ureido)phenyl)pentanoic acid | | 1.331 | O | 445.3 |

Examples 832 to 841

Diastereomer 2

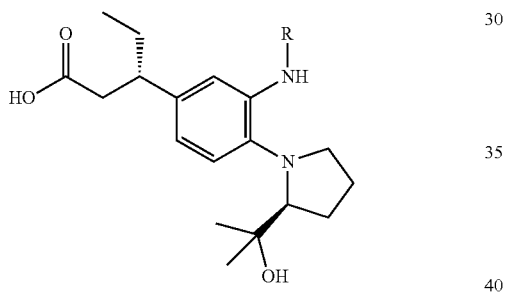

Examples 832 to 841 were prepared from 810E Diastereomer 2 and corresponding halides following the procedure described for the synthesis of Example 816.

| Ex. No. | Name | R | $T_r$ min | Method | (M + H) |
|---|---|---|---|---|---|
| 832 | 3-(4-((S)-2-(2-hydroxypropan-2-yl)pyrrolidin-1-yl)-3-((2-morpholinopyrimidin-4-yl)amino)phenyl)pentanoic acid | | 1.400 | O | 484.3 |
| 833 | 3-(3-((4-ethoxyphenyl)amino)-4-((S)-2-(2-hydroxypropan-2-yl)pyrrolidin-1-yl)phenyl)pentanoic acid | | 1.831 | O | 441.3 |

-continued

| Ex. No. | Name | R | T$_r$ min | Method | (M + H) |
|---|---|---|---|---|---|
| 834 | 3-(3-((4-(cyclopropylmethoxy) phenyl)amino)-4-((S)-2-(2-hydroxypropan-2-yl)pyrrolidin-1-yl)phenyl)pentanoic acid | | 1.568 | R | 467.3 |
| 835 | 3-(3-((4-ethylphenyl)amino)-4-((S)-2-(2-hydroxypropan-2-yl)pyrrolidin-1-yl)phenyl) pentanoic acid | | 1.563 | R | 425.3 |
| 836 | 3-(3-((4-chlorophenyl)amino)-4-(S)-2-(2-hydroxypropan-2-yl)pyrrolidin-1-yl)phenyl) pentanoic acid | | 1.911 | O | 431.2 |
| 837 | 3-(3-((2,2-difluorobenzo[d][1,3]dioxol-5-yl)amino)-4-((S)-2-(2-hydroxypropan-2-yl)pyrrolidin-1-yl)phenyl) pentanoic acid | | 2.018 | O | 477.2 |
| 838 | 3-(3-((2-(cyclopropylmethoxy) pyrimidin-5-yl)amino)-4-((S)-2-(2-hydroxypropan-2-yl)pyrrolidin-1-yl)phenyl)pentanoic acid | | 1.631 | O | 469.3 |
| 839 | 3-(3-((2-ethoxypyrimidin-5-yl)amino)-4-((S)-2-(2-hydroxypropan-2-yl) pyrrolidin-1-yl)phenyl) pentanoic acid | | 1.191 | R | 443.3 |
| 840 | 3-(3-((4-fluorophenyl)amino)-4-((S)-2-(2-hydroxypropan-2-yl)pyrrolidin-1-yl)phenyl) pentanoic acid | | 1.320 | R | 415.3 |
| 841 | 3-(4-((S)-2-(2-hydroxypropan-2-yl)pyrrolidin-1-yl)-3-((2-methoxypyrimidin-5-yl)amino) phenyl)pentanoic acid | | 1.236 | O | 429.3 |

Example 842

Diastereomer 4

3-(3-((2-(Cyclopropylmethoxy)pyrimidin-5-yl)amino)-4-((R)-2-(2-hydroxypropan-2-yl)pyrrolidin-1-yl)phenyl)pentanoic acid

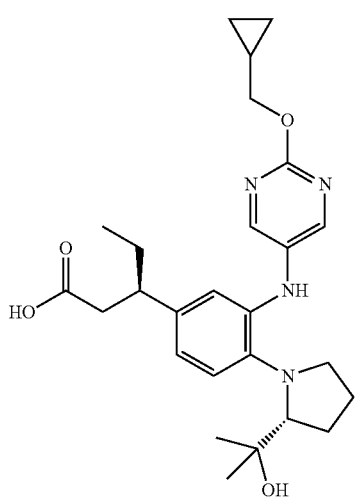 [SMILES: CC[C@H](CC(=O)O)c1ccc(N2CCC[C@@H]2C(C)(C)O)c(Nc2cnc(OCC3CC3)nc2)c1]

842A. Methyl 3-(3-((2-(cyclopropylmethoxy)pyrimidin-5-yl)amino)-4-((R)-2-(2-hydroxypropan-2-yl)pyrrolidin-1-yl)phenyl)pentanoate The mixture of 774D Diastereomer 2 (30 mg, 0.090 mmol), 5-bromo-2-(cyclopropylmethoxy)pyrimidine (22.60 mg, 0.099 mmol), Xantphos (10.38 mg, 0.018 mmol) and $Cs_2CO_3$ (88 mg, 0.269 mmol) in 1,4-dioxane (2.0 mL) was stirred at room temperature. Argon gas was bubbled through the mixture for 5 min. Bis(dibenzylideneacetone)palladium (5.16 mg, 8.97 µmol) was added and argon gas was bubbled through the mixture for another 5 min. The reaction mixture was sealed and placed in preheated oil bath at 110° C. for 12 hours. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). The combined organic layer was washed with water (10 mL) and brine (10 mL), dried over anhydrous sodium sulfate, filtered, and concentrated under reduced pressure to afford 842A (yellow solid, 30 mg, 0.062 mmol, 69.3% yield). LC-MS Anal. Calc'd. for $C_{27}H_{38}N_4O_4$, 482.615, found [M+H] 483.6, $T_r$=1.60 min. (Method AY).

Example 842. 3-(3-((2-(Cyclopropylmethoxy)pyrimidin-5-yl)amino)-4-((R)-2-(2-hydroxypropan-2-yl)pyrrolidin-1-yl)phenyl)pentanoic acid To a stirred solution of 842A (0.02 g, 0.041 mmol) in mixture tetrahydrofuran (0.5 mL), MeOH (0.5 mL) and water (0.5 mL), was added lithium hydroxide (3.07 mg, 0.128 mmol). The reaction mixture was stirred at room temperature for 3 hours. The reaction mixture was concentrated under reduced pressure. The aqueous residue so obtained was acidified with solid citric acid to pH~6.5. The aqueous layer was diluted with water (5 mL) and extracted with ethyl acetate (2×5.0 mL). Combined organic layer was washed with water (5.0 mL), brine (5.0 mL), dried over anhydrous sodium sulfate and concentrated under reduced pressure to afford a residue. The residue was purified via preparative LC/MS to afford Example 842 (0.005 g, 0.010 mmol, 25% yield). LC-MS Anal. Calc'd. for $C_{26}H_{36}N_4O_4$, 468.588, found [M+H] 469.3, $T_r$=1.708 min (Method O). $^1$H NMR (400 MHz, DMSO-$d_6$) δ$^1$H NMR (400 MHz, DMSO-$d_6$) δ 8.38 (s, 2H), 7.49 (s, 1H), 7.14 (d, J=8.40 Hz, 1H), 6.75 (d, J=1.60 Hz, 1H), 6.61 (dd, J=1.60, 8.00 Hz, 1H), 4.09 (d, J=7.20 Hz, 2H), 3.50-3.60 (m, 1H), 3.15-3.20 (m, 1H), 2.70-2.80 (m, 1H), 2.50-2.60 (m, 3H), 2.35-2.45 (m, 1H), 1.92-1.96 (m, 2H), 1.35-1.90 (m, 4H), 1.23-1.25 (m, 1H), 0.65 (s, 3H), 0.85 (s, 3H), 0.69 (t, J=7.60 Hz, 3H), 0.54-0.57 (m, 2H), 0.33-0.35 (m, 2H).

Example 843

Enantiomer 1

3-(5-((4-Cyanophenyl)amino)-4-(ethyl(tetrahydro-2H-pyran-4-yl)amino)-2-fluorophenyl)-4-methoxybutanoic acid

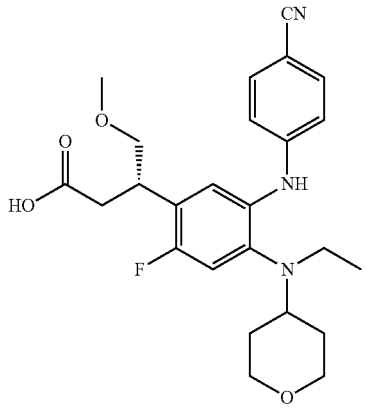 [SMILES: CCN(c1cc(F)c([C@@H](COC)CC(=O)O)cc1Nc1ccc(C#N)cc1)C1CCOCC1]

843A. N-Ethyltetrahydro-2H-pyran-4-amine

To a stirred suspension of 4 A powdered molecular sieves and dihydro-2H-pyran-4(3H)-one (27.8 mL, 300 mmol) in MeOH (100 mL) and tetrahydrofuran (50 mL) was added 2M ethanamine in tetrahydrofuran (150 mL, 300 mmol) dropwise. The above reaction mixture was stirred overnight at room temperature. Reaction mixture was cooled to 0-5° C., then sodium borohydride (22.67 g, 599 mmol) was added portionwise for 20 min and stirred for 6 hours at room temperature. Reaction mixture was quenched with 10% $NaHCO_3$ solution (300 mL) and concentrated under reduced pressure to remove the volatiles. The above reaction mixture was diluted with ethyl acetate (300 mL) filtered through CELITE® bed and washed with ethyl acetate (100 mL). The aqueous layer was separated and extracted with ethyl acetate (2×150 mL). The combined organic layer was dried over sodium sulfate, filtered, and concentrated completely under reduced pressure to get crude 843A (yellow liquid, 26 g, 199 mmol, 66.5% yield) and taken for next step without further purification. LC-MS Anal. Calc'd. for $C_7H_{15}NO$, 129.11, found [M+H] 130.12. $T_r$=0.359 min (Method U).

843B. N-(4-Bromo-5-fluoro-2-nitrophenyl)-N-ethyl-tetrahydro-2H-pyran-4-amine To a stirred solution of 1-bromo-2,4-difluoro-5-nitrobenzene (8.0 g, 33.6 mmol) in N-methyl-2-pyrrolidone (32 mL) was added 843A (4.34 g, 33.6 mmol) and diethylisopropylethylamine (17.61 mL, 101 mmol). The reaction mixture was stirred at 110° C. overnight. Reaction mixture was cooled to room temperature. The reaction was then diluted with ethyl acetate (300 mL) and washed with 10% brine solution (4×75 mL). The aqueous layer was back extracted with ethyl acetate (100 mL). The combined organic layer was dried over sodium sulfate, filtered, and concentrated under reduced pressure. Purification via flash chromatography gave 843B (orange solid, 6.5 g, 18.35 mmol, 54.6% yield). LC-MS Anal. Calc'd. for $C_{13}H_{16}BrFN_2O_3$, 347.18, found [M+H] 348.18, $T_r$=3.42 min (Method U).

843C. N-(4-(5,5-Dimethyl-1,3,2-dioxaborinan-2-yl)-5-fluoro-2-nitrophenyl)-N-ethyltetrahydro-2H-pyran-4-amine To a stirred solution of 843B (4.0 g, 11.52 mmol) in dioxane (80 mL) was added 5,5,5',5'-tetramethyl-2,2'-bi(1,3,2-dioxaborinane) (5.21 g, 23.04 mmol. Then reaction mixture was purged for 10 min with argon. Then was added potassium acetate (5.09 g, 51.8 mmol) and 1,1'-bis(diphenylphosphino)ferrocene-palladium(II) dichloride dichloromethane complex (0.283 g, 0.346 mmol). The reaction mixture was sealed and stirred at 80° C. for 5 hours. Reaction mixture was cooled to room temperature, diluted with ethyl acetate (300 mL) and washed with 10% brine solution (3×100 mL). The organic layer was dried over sodium sulfate, filtered, and concentrated under reduced pressure to afford 843C (brown liquid, 4.3 g, 8.48 mmol, 73.6% yield). LC-MS Anal. Calc'd. for $C_{18}H_{26}BFN_2O_5$, 380.21, found (M+H) 381.21. $T_r$=2.17 min (Method U).

843D. Methyl 4-methoxybut-2-enoate

To a stirred solution of methyl 4-bromobut-2-enoate (13.12 mL, 112 mmol) in methanol (100 mL) was added silver oxide (20.71 g, 89 mmol) and stirred overnight at room temperature. Then reaction mixture was diluted with dichloromethane (150 mL) and filtered. The filter cake was washed with dichloromethane (100 mL), concentrated under reduced pressure. Purification via flash chromatography gave 843D (yellow liquid, 8 g, 61.5 mmol, 55.0% yield) as yellow liquid. $^1$H NMR (400 MHz, DMSO-$d_6$) δ 6.86-6.94 (m, 1H), 5.96-6.03 (m, 1H), 4.07-4.09 (m, 2H), 3.67 (s, 3H), 3.31 (d, J=11.60 Hz, 3H).

843E. Methyl 3-(4-(ethyl(tetrahydro-2H-pyran-4-yl)amino)-2-fluoro-5-nitrophenyl)-4-methoxybutanoate To a stirred solution of 843C (2.15 g, 5.65 mmol) in dioxane (6 mL) was added 843D (2.208 g, 16.96 mmol), 1N sodium hydroxide (5.09 mL, 5.09 mmol) and (R)-(+)-2,2'-bis(diphenylphosphino)-1,1'-binaphthyl (0.176 g, 0.283 mmol). Then the reaction mixture was purged with argon for 10 min and was added chlorobis(ethylene)rhodium(I) dimer (0.066 g, 0.170 mmol). The above reaction mixture was sealed and stirred for 45 min at 50° C. Reaction mixture was cooled to room temperature, diluted with ethyl acetate (100 mL) and washed with 10% brine solution (4×20 mL). The organic layer was dried over sodium sulfate and concentrated completely under reduced pressure to get crude. Purification via flash chromatography gave 843E (orange liquid, 360 mg, 0.813 mmol, 14.38% yield). LC-MS Anal. Calc'd. for $C_{19}H_{27}FN_2O_6$, 398.18, found [M+H] 399.18. $T_r$=2.78 min (Method U).

843F. Methyl 3-(5-amino-4-(ethyl(tetrahydro-2H-pyran-4-yl)amino)-2-fluorophenyl)-4-methoxybutanoate To a stirred solution of 843E (360 mg, 0.904 mmol) in ethyl acetate (4 mL) was added 10% Pd/C (120 mg, 0.113 mmol) and stirred under hydrogen gas bladder pressure overnight at room temperature. The reaction mixture was diluted with ethyl acetate (100 mL) and filtered through CELITE® bed filter. The CELITE® bed filter was washed with ethyl acetate (50 mL). The combined filtrate was concentrated under reduced pressure to afford 843F Enantiomeric mixture. LC-MS Anal. Calc'd. for $C_{19}H_{29}FN_2O_4$, 368.18, found (M+H) 369.18. $T_r$=2.44 min (Method U).

Chiral separation of 843F Enantiomer mixture (97:3) gave Enantiomer 1, $T_r$=7.72 min and Enantiomer 2 $T_r$=7.04 min (Method CO).

843F Enantiomer 1 (brown liquid, 320 mg, 0.799 mmol, 88% yield): LC-MS Anal. Calc'd. for $C_{19}H_{29}FN_2O_4$, 368.18, found [M+H] 369.18. $T_r$=2.44 min (Method U).

843G. Methyl 3-(5-((4-cyanophenyl)amino)-4-(ethyl(tetrahydro-2H-pyran-4-yl)amino)-2-fluorophenyl)-4-methoxybutanoate To a stirred solution of 843F Enantiomer 1 (50 mg, 0.136 mmol) in dioxane (1 mL) was added 4-bromobenzonitrile (29.6 mg, 0.163 mmol) in dioxane (1 mL) and cesium carbonate (66.3 mg, 0.204 mmol). Reaction mixture was purged with nitrogen for 5 min then was added Xantphos (7.85 mg, 0.014 mmol) and bis(dibenzylideneacetone)palladium (3.90 mg, 6.79 μmol). The reaction mixture was sealed and stirred at 110° C. overnight. Reaction mixture was cooled to room temperature, diluted with ethyl acetate (5 mL) and washed with 10% brine solution (2×5 mL). The organic layer was dried over $Na_2SO_4$, filtered, and concentrated under reduced pressure to afford 843G (brown pasty mass, 50 mg, 0.079 mmol, 58.1% yield). LC-MS Anal. Calc'd. for $C_{26}H_{32}FN_3O_4$, 469.54, found [M+H] 470.54, $T_r$=3.07 min (Method U).

Example 843. 3-(5-((4-Cyanophenyl)amino)-4-(ethyl(tetrahydro-2H-pyran-4-yl)amino)-2-fluorophenyl)-4-methoxybutanoic acid To a stirred solution of 843G (50 mg, 0.106 mmol) in MeOH (1 mL) and tetrahydrofuran (2 mL) was added lithium hydroxide (10.20 mg, 0.426 mmol) and stirred overnight at room temperature. Reaction mixture was concentrated under reduced pressure and diluted with water (5 mL), and acidified (pH~4) with solid citric acid. The aqueous layer was extracted with ethyl acetate (10 mL). The organic layer was dried over sodium sulfate and concentrated completely under reduced pressure. The crude residue was purified by preparative HPLC to obtain Example 843 (11.6 mg, 0.024 mmol, 22.72% yield). LC-MS Anal. Calc'd. for $C_{25}H_{30}FN_3O_4$, 455.22, found [M+H] 456.22. $T_r$=1.30 min (Method O). $^1$H NMR (400 MHz, DMSO-$d_6$) δ 7.93 (s, 1H), 7.51 (d, J=8.80 Hz, 2H), 7.16 (d, J=8.00 Hz, 1H), 6.98 (d, J=12.40 Hz, 1H), 6.90 (d, J=8.40 Hz, 2H), 3.76 (d, J=10.80 Hz, 2H), 3.22 (s, 3H), 2.97-3.02 (m, 5H), 2.62-2.67

(m, 2H), 1.42-1.51 (m, 4H), 0.84 (t, J=7.20 Hz, 3H) (Note: 3H buried under water peak).

Example 844

Enantiomer 1

3-(5-((4-Chlorophenyl)amino)-4-(ethyl(tetrahydro-2H-pyran-4-yl)amino)-2-fluorophenyl)-4-methoxybutanoic acid

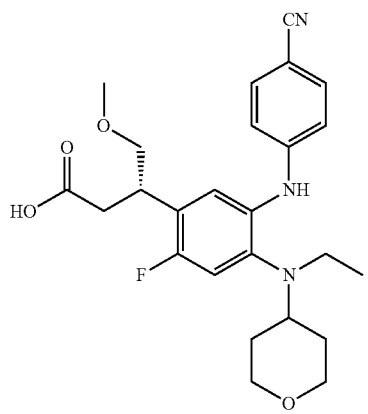 [SMILES: CCN(c1cc(F)c([C@@H](COC)CC(=O)O)cc1Nc1ccc(C#N)cc1)C1CCOCC1]

844A. Methyl 3-(5-((4-chlorophenyl)amino)-4-(ethyl(tetrahydro-2H-pyran-4-yl)amino)-2-fluorophenyl)-4-methoxybutanoate 844A was prepared from 843F Enantiomer 1 and 1-bromo-4-chlorobenzene following the procedure described for the synthesis of 843G. LC-MS Anal. Calc'd. for $C_{25}H_{32}ClFN_2O_4$, 478.20, found (M+H) 479.20, $T_r$=3.57 min (Method U).

Example 844. 3-(5-((4-chlorophenyl)amino)-4-(ethyl(tetrahydro-2H-pyran-4-yl)amino)-2-fluorophenyl)-4-methoxybutanoic acid To a stirred solution of 844A (30 mg, 0.063 mmol) in MeOH (1 mL) and tetrahydrofuran (2 mL) was added lithium hydroxide (6.00 mg, 0.251 mmol) in water (1 mL) and stirred overnight at room temperature. Reaction mixture was concentrated completely and diluted with water (5 mL), and acidified (pH~4) with solid citric acid. The aqueous layer was extracted with ethyl acetate (10 mL). The organic layer was dried over sodium sulfate, filtered, and concentrated completely under reduced pressure to get crude. The crude compound was purified by preparative HPLC to obtain Example 844 (9.5 mg, 0.020 mmol, 19.37% yield). LC-MS Anal. Calc'd. for $C_{25}H_{30}FN_3O_4$, 473.21, found (M+H) 474.21, $T_r$=1.64 min (Method O). $^1H$ NMR (400 MHz, DMSO-$d_6$) δ 7.18-7.22 (m, 3H), 7.10 (d, J=8.00 Hz, 1H), 6.97-7.00 (m, 3H), 3.77-3.79 (m, 2H), 3.22 (s, 3H), 3.07-3.12 (m, 3H), 2.94-2.99 (m, 2H), 2.61-2.67 (m, 2H), 1.56-1.59 (m, 2H), 1.42-1.44 (m, 2H), 0.82 (t, J=6.80 Hz, 3H) (Note: 1H buried under DMSO and 2H buried under water peak).

Examples 845 to 847

Enantiomer 1

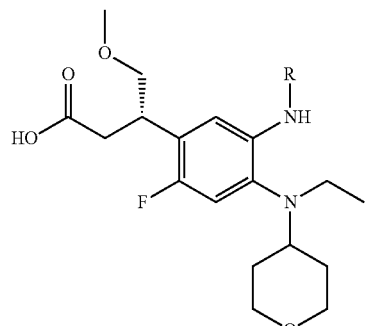

Examples 845 to 847 were prepared from 843F Enantiomer 1 and corresponding aryl halides following the procedure described for the synthesis of Example 843.

| Ex. No. | Name | R | $T_r$ min | Method | (M+H) |
|---|---|---|---|---|---|
| 845 | 3-(5-((4-chlorophenyl)amino)-4-(ethyl(tetrahydro-2H-pyran-4-yl)amino)-2-fluorophenyl)-4-methoxybutanoic acid | 4-CN, 3-Me phenyl | 1.66 | O | 470 |
| 846 | 3-(5-((4-cyano-3-fluorophenyl)amino)-4-(ethyl(tetrahydro-2H-pyran-4-yl)amino)-2-fluorophenyl)-4-methoxybutanoic acid | 4-CN, 3-F phenyl | 1.64 | R | 474 |
| 847 | 3-(5-((4-cyano-2-fluorophenyl)amino)-4-(ethyl(tetrahydro-2H-pyran-4-yl)amino)-2-fluorophenyl)-4-methoxybutanoic acid | 4-CN, 2-F phenyl | 1.41 | O | 474 |

Example 848

Enantiomer 1

3-(5-(3-(4-Chloro-2-fluorophenyl)ureido)-4-(ethyl(tetrahydro-2H-pyran-4-yl)amino)-2-fluorophenyl)-4-methoxybutanoic acid

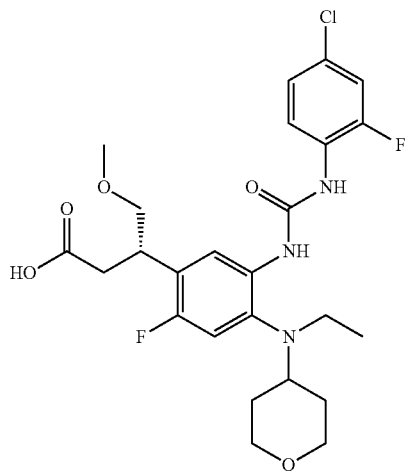 [SMILES: CCN(c1cc(F)c([C@@H](COC)CC(=O)O)cc1NC(=O)Nc1ccc(Cl)cc1F)C1CCOCC1]

848A. Methyl 3-(5-(3-(4-chloro-2-fluorophenyl)ureido)-4-(ethyl(tetrahydro-2H-pyran-4-yl)amino)-2-fluorophenyl)-4-methoxybutanoate To a stirred solution of 843F Enantiomer 1 (30 mg, 0.081 mmol) in tetrahydrofuran (4 mL) was added 4-chloro-2-fluoro-1-isocyanatobenzene (16.76 mg, 0.098 mmol). The resulting mixture was stirred at room temperature overnight. The reaction mass was diluted with ethyl acetate (10 mL) and washed with brine solution (2×10 mL). The organic layer was dried over sodium sulfate and concentrated under reduced pressure to get 848A (30 mg, 0.055 mmol, 68.18% yield). LC-MS Anal. Calc'd. for $C_{25}H_{30}ClF_2N_3O_5$, 539.2, found (M+H) 540.2. $T_r$=3.23 min (Method O).

Example 848. 3-(5-(3-(4-Chloro-2-fluorophenyl)ureido)-4-(ethyl(tetrahydro-2H-pyran-4-yl)amino)-2-fluorophenyl)-4-methoxybutanoic acid To a stirred solution of 848A (30 mg, 0.056 mmol) in MeOH (1 mL) and tetrahydrofuran (2 mL) was added lithium hydroxide (5.32 mg, 0.222 mmol) in water (1 mL). The resulting mixture was stirred overnight at room temperature. Reaction mixture was concentrated completely, diluted with water (5 mL), and acidified (pH~4) with solid citric acid. The aqueous layer was extracted with ethyl acetate (10 mL). The organic layer was dried over sodium sulfate, filtered, and concentrated completely under reduced pressure to get crude. The crude compound was purified by preparative HPLC to obtain Example 848 (16.1 mg, 0.030 mmol, 54.5% yield). LC-MS Anal. Calc'd. for $C_{25}H_{30}FN_3O_4$, 525.18, found (M+H) 526.2, $T_r$=1.67 min (Method O). $^1$H NMR (400 MHz, DMSO-$d_6$) δ 9.50 (s, 1H), 8.73 (s, 1H), 8.08-8.17 (m, 2H), 7.43-7.46 (m, 1H), 7.22 (d, J=8.80 Hz, 1H), 7.06 (d, J=11.60 Hz, 1H), 3.82-3.84 (m, 2H), 3.22 (s, 3H), 2.95-2.99 (m, 3H), 2.61-2.67 (m, 3H), 2.41-2.43 (m, 1H), 1.69-1.71 (m, 2H), 1.36-1.44 (m, 2H), 0.81 (t, J=6.80 Hz, 3H) (Note: 3H buried under the moisture peak).

Example 849

Enantiomer 1

3-(5-(3-(4-Cyanophenyl)ureido)-4-(ethyl(tetrahydro-2H-pyran-4-yl)amino)-2-fluorophenyl)-4-methoxybutanoic acid

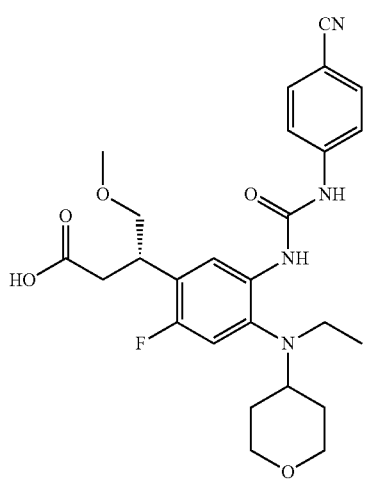 [SMILES: CCN(c1cc(F)c([C@@H](COC)CC(=O)O)cc1NC(=O)Nc1ccc(C#N)cc1)C1CCOCC1]

849A. Methyl 3-(5-(3-(4-cyanophenyl)ureido)-4-(ethyl(tetrahydro-2H-pyran-4-yl)amino)-2-fluorophenyl)-4-methoxybutanoate 849A was prepared from 843F Enantiomer 1 and 4-isocyanatobenzonitrile following the procedure described for the synthesis of 848A.

849. 3-(5-(3-(4-Chloro-2-fluorophenyl)ureido)-4-(ethyl(tetrahydro-2H-pyran-4-yl)amino)-2-fluorophenyl)-4-methoxybutanoic acid To a stirred solution of 849A (35 mg, 0.068 mmol) in MeOH (1 mL) and tetrahydrofuran (2 mL) was added lithium hydroxide (6.54 mg, 0.273 mmol). The resulting mixture was stirred overnight at room temperature. Reaction mixture was concentrated completely, diluted with water (5 mL), and acidified (pH~4) with solid citric acid. The aqueous layer was extracted with ethyl acetate (10 mL). The organic layer was dried over sodium sulfate and concentrated completely under reduced pressure. The crude compound was purified by preparative HPLC to obtain Example 849 (16.1 mg, 0.030 mmol, 54.5% yield). LC-MS Anal. Calc'd. for $C_{26}H_{31}FN_4O_5$, 498.22, found (M+H) 499.22. $T_r$=1.19 min (Method O). $^1$H NMR (400 MHz, DMSO-$d_6$) δ10.10 (s, 1H), 8.13 (d, J=8.00 Hz, 1H), 7.66-7.74 (m, 4H), 7.10 (d, J=11.60 Hz, 1H), 3.81-3.83 (m, 1H), 3.44-3.45 (m, 2H), 3.17-3.26 (m, 5H), 2.96-3.01 (m, 3H), 2.63-2.69 (m, 1H), 2.47-2.51 (m, 1H), 1.69-1.72 (m, 2H), 1.37-1.41 (m, 2H), 0.80 (t, J=6.80 Hz, 3H) (Note: 3H buried under moisture peak).

Example 850

Enantiomer 2

3-(5-((4-Cyanophenyl)amino)-4-(ethyl(tetrahydro-2H-pyran-4-yl)amino)-2-fluorophenyl)-4-methoxybutanoic acid

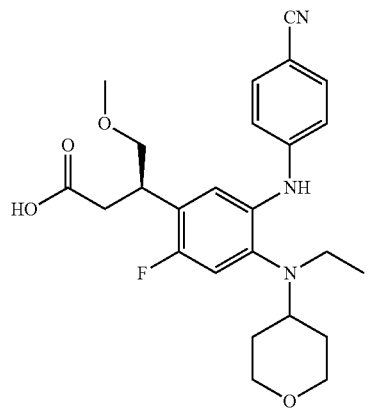 [SMILES: CCN(c1cc(F)c([C@H](COC)CC(=O)O)cc1Nc1ccc(C#N)cc1)C1CCOCC1]

850A. Methyl 3-(4-(ethyl(tetrahydro-2H-pyran-4-yl)amino)-2-fluoro-5-nitrophenyl)-4-methoxybutanoate To a stirred solution of 843C (2.15 g, 5.65 mmol) in dioxane (6 mL) was added 843D (2.208 g, 16.96 mmol), 1N sodium hydroxide (5.09 mL, 5.09 mmol) and (S)-(−)-2,2'-bis(diphenylphosphino)-1,1'-binaphthyl (0.176 g, 0.283 mmol), then the reaction mixture was purged for 10 min with argon then was added chlorobis(ethylene)rhodium(I) dimer (0.066 g, 0.170 mmol). The above reaction mixture was sealed and stirred for 45 min at 50° C. Reaction mixture was diluted with ethyl acetate (200 mL) and washed with 10% brine solution (4×75 mL). The organic layer was dried over sodium sulfate and concentrated completely under reduced pressure to get crude. The crude obtained was purified by silica gel flash column chromatography to afford 850A (orange liquid, 400 mg, 0.914 mmol, 16.16% yield). LC-MS Anal. Calc'd. for $C_{19}H_{29}FN_2O_4$, 398.18, found (M+H) 399.18. $T_r$=3.09 min (Method U).

850B. Methyl 3-(5-amino-4-(ethyl(tetrahydro-2H-pyran-4-yl)amino)-2-fluorophenyl)-4-methoxybutanoate 850B (Enantiomeric mixture) was prepared from 850A following the procedure described for the synthesis of 843F. LC-MS Anal. Calc'd. for $C_{19}H_{29}FN_2O_4$, 368.21, found (M+H) 369.12. $T_r$=3.12 min (Method U).

Chiral separation of 850B Enantiomer mixture (20:80) gave Enantiomer 1 $T_r$=7.79 min and Enantiomer 2 $T_r$=7.11 min (Method CO).

850B Enantiomer 2: LC-MS Anal. Calc'd. for $C_{19}H_{29}FN_2O_4$, 368.21, found (M+H) 369.12, $T_r$=2.57 min (Method U).

850C. Methyl 3-(5-((4-cyanophenyl)amino)-4-(ethyl(tetrahydro-2H-pyran-4-yl)amino)-2-fluorophenyl)-4-methoxybutanoate 850C was prepared from 850B Enantiomer 2 following the procedure described for the synthesis of 843G. LC-MS Anal. Calc'd. for $C_{26}H_{32}FN_3O_4$, 469.23, found (M+H) 470.23. $T_r$=3.12 min (Method CP).

Example 850

3-(5-((4-Cyanophenyl)amino)-4-(ethyl(tetrahydro-2H-pyran-4-yl)amino)-2-fluorophenyl)-4-methoxybutanoic acid Example 850 was prepared from 850C following the procedure described for the synthesis of Example 843. LC-MS Anal. Calc'd. for $C_{25}H_{30}FN_3O_4$, 455.22, found (M+H) 456.22, $T_r$=1.32 min (Method O). $^1$H NMR (400 MHz, DMSO-$d_6$) δ 7.95 (s, 1H), 7.51 (d, J=8.80 Hz, 2H), 7.17 (d, J=8.00 Hz, 1H), 6.99 (d, J=12.40 Hz, 1H), 6.90 (d, J=8.80 Hz, 2H), 3.77 (d, J=10.80 Hz, 2H), 3.47-3.55 (m, 2H), 3.23 (s, 3H), 2.97-3.05 (m, 6H), 2.63-2.69 (m, 1H), 2.53-2.55 (m, 1H), 1.45-1.52 (m, 4H), 0.85 (t, J=7.20 Hz, 3H).

Examples 851 to 854

Enantiomer 2

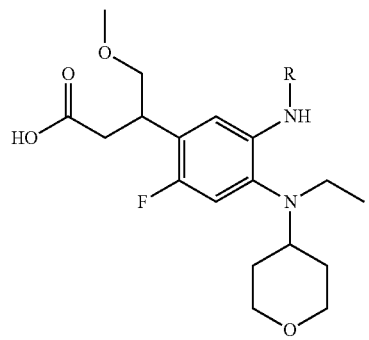

Example 851 was prepared from 850B Enantiomer 2 and corresponding aryl halide following the procedure described for the synthesis of Example 844.

Examples 852 to 854 were prepared from 850B Enantiomer 2 and corresponding aryl halides following the procedure described for the synthesis of Example 843.

| Ex. No. | Name | R | $T_r$ min | Method | (M + H) |
|---|---|---|---|---|---|
| 851 | 3-(5-((4-chlorophenyl)amino)-4-(ethyl(tetrahydro-2H-pyran-4-yl)amino)-2-fluorophenyl)-4-methoxybutanoic acid | 4-Cl-phenyl | 1.89 | O | 465 |
| 852 | 3-(5-((4-chlorophenyl)amino)-4-(ethyl(tetrahydro-2H-pyran-4-yl)amino)-2-fluorophenyl)-4-methoxybutanoic acid | 3-methyl-4-CN-phenyl | 1.67 | O | 470 |

-continued

| Ex. No. Name | R | $T_r$ min | Method | (M + H) |
|---|---|---|---|---|
| 853 3-(5-((4-cyano-3-fluorophenyl)amino)-4-(ethyl(tetrahydro-2H-pyran-4-yl)amino)-2-fluorophenyl)-4-methoxybutanoic acid | ![structure with F and CN] | 1.62 | O | 474 |
| 854 3-(5-((4-cyano-2-fluorophenyl)amino)-4-(ethyl(tetrahydro-2H-pyran-4-yl)amino)-2-fluorophenyl)-4-methoxybutanoic acid | ![structure with F and CN] | 1.75 | O | 474 |

Example 855

Enantiomer 2

3-(5-((4-Cyanophenyl)amino)-4-(ethyl(tetrahydro-2H-pyran-4-yl)amino)-2-fluorophenyl)-4-methoxybutanoic acid

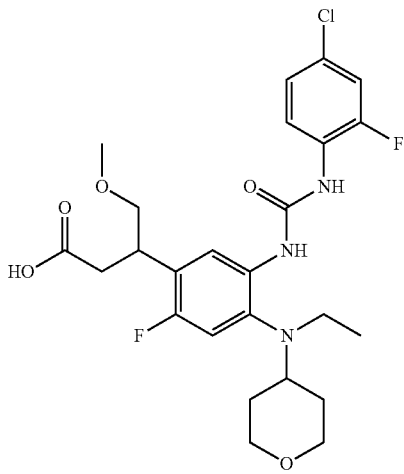

855A. Methyl 3-(5-(3-(4-chloro-2-fluorophenyl)ureido)-4-(ethyl(tetrahydro-2H-pyran-4-yl)amino)-2-fluorophenyl)-4-methoxybutanoate 855A was prepared from 850B Enantiomer 2 and 4-chloro-2-fluoro-1-isocyanatobenzene following the procedure described for the synthesis of 848A. LC-MS Anal. Calc'd. for $C_{25}H_{30}ClF_2N_3O_5$, 539.2, found (M+H) 540.2, $T_r$=3.23 min (Method U).

Example 855. 3-(5-(3-(4-Chloro-2-fluorophenyl)ureido)-4-(ethyl(tetrahydro-2H-pyran-4-yl)amino)-2-fluorophenyl)-4-methoxybutanoic acid Example 855 was prepared from 855A following the procedure described for the synthesis of Example 848. LC-MS Anal. Calc'd. for $C_{25}H_{30}FN_3O_4$, 525.18, found (M+H) 526.2, $T_r$=1.41 min (Method O). $^1$H NMR (400 MHz, DMSO-$d_6$) δ10.10 (s, 1H), 8.13 (d, J=8.00 Hz, 1H), 7.66-7.74 (m, 4H), 7.10 (d, J=11.60 Hz, 1H), 3.81-3.83 (m, 1H), 3.44-3.45 (m, 2H), 3.17-3.26 (m, 5H), 2.96-3.01 (m, 3H), 2.63-2.69 (m, 1H), 2.47-2.51 (m, 1H), 1.69-1.72 (m, 2H), 1.37-1.41 (m, 2H), 0.80 (t, J=6.80 Hz, 3H) (Note: 3H buried under moisture peak).

Example 856

Enantiomer 1

3-(5-((4-Chlorophenyl)amino)-4-(ethyl(tetrahydro-2H-pyran-4-yl)amino)-2-fluorophenyl)pentanoic acid

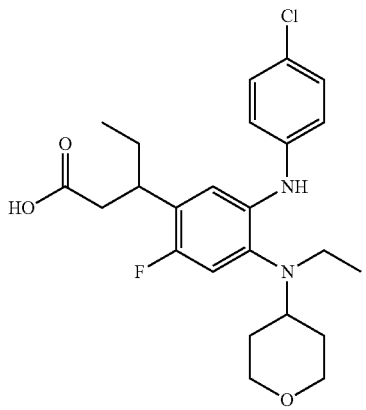 [SMILES: CCC(CC(=O)O)c1cc(Nc2ccc(Cl)cc2)c(N(CC)C2CCOCC2)cc1F]

856A. Methyl 3-(4-(ethyl(tetrahydro-2H-pyran-4-yl)amino)-2-fluoro-5-nitrophenyl)pentanoate 856A was prepared from 843C, (E)-methyl pent-2-enoate and (R)-(+)-2,2'-bis(diphenylphosphino)-1,1'-binaphthyl following the procedure described for the synthesis of 843E. LC-MS Anal. Calc'd. for $C_{19}H_{27}FN_2O_5$, 382.19, found (M+H) 383.19, $T_r$=2.78 min (Method U).

856B. Methyl 3-(5-amino-4-(ethyl(tetrahydro-2H-pyran-4-yl)amino)-2-fluorophenyl)pentanoate 856B was prepared from 856A following the procedure described for the synthesis of 843F. LC-MS Anal. Calc'd. for $C_{19}H_{29}FN_2O_3$, 352.21, found (M+H) 353.19, $T_r$=2.78 min (Method U). 856B, $T_r$=2.72 (Method BJ) and (ee, 94.74%).

856C. Methyl 3-(5-((4-chlorophenyl)amino)-4-(ethyl(tetrahydro-2H-pyran-4-yl)amino)-2-fluorophenyl)pentanoate 856C was prepared from 856B and 1-bromo-4-chlorobenzene following the procedure described for the synthesis of 843G. LC-MS Anal. Calc'd. for $C_{25}H_{32}ClFN_2O_3$, 462.20, found (M+H) 463.20, $T_r$=4.13 min (Method U).

Example 856. 3-(5-((4-Chlorophenyl)amino)-4-(ethyl(tetrahydro-2H-pyran-4-yl)amino)-2-fluorophenyl)pentanoic acid Example 856 was prepared from 856C following the procedure described for the synthesis of Example 844 from 844A. LC-MS Anal. Calc'd. for $C_{24}H_{30}ClFN_2O_3$, 448.19, found (M+H) 449.19, $T_r=1.92$ min (Method O). $^1$H NMR (400 MHz, DMSO-$d_6$) δ 7.19-7.25 (m, 3H), 6.98-7.05 (m, 4H), 3.77-3.80 (m, 2H), 3.08-3.18 (m, 3H), 2.97-3.00 (m, 3H), 2.59-2.61 (m, 1H), 1.41-1.64 (m, 6H), 0.82 (t, J=7.20 Hz, 3H), 0.76 (t, J=7.20 Hz, 3H) (Note: 1H buried under solvent peak).

Examples 857 to 860

Enantiomer 1

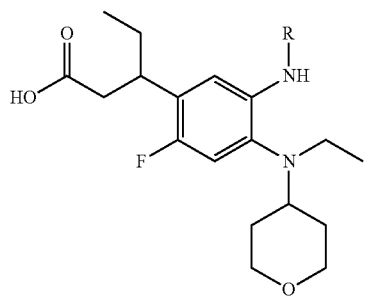

Example 857 was prepared from 856B and corresponding aryl halides following the procedure described for the synthesis of Example 843.

Examples 858 to 860 were prepared from 856B and corresponding aryl halides following the procedure described for the synthesis of Example 844.

| Ex. No. | Name | R | $T_r$ min | Method | (M+H) |
|---|---|---|---|---|---|
| 857 | 3-(5-((5-cyanopyridin-2-yl)amino)-4-(ethyl(tetrahydro-2H-pyran-4-yl)amino)-2-fluorophenyl)pentanoic acid | | 1.69 | O | 441 |
| 858 | 3-(5-((2-(cyclopropylmethoxy)pyrimidin-5-yl)amino)-4-(ethyl(tetrahydro-2H-pyran-4-yl)amino)-2-fluorophenyl)pentanoic acid | | 1.68 | O | 487 |
| 859 | 3-(4-(ethyl(tetrahydro-2H-pyran-4-yl)amino)-2-fluoro-5-((2-methoxypyrimidin-5-yl)amino)phenyl)pentanoic acid | | 1.33 | O | 447 |
| 860 | 3-(5-((2-ethoxypyrimidin-5-yl)amino)-4-(ethyl(tetrahydro-2H-pyran-4-yl)amino)-2-fluorophenyl)pentanoic acid | | 1.46 | O | 461 |

Example 861

Enantiomer 2

3-(5-((4-Chlorophenyl)amino)-4-(ethyl(tetrahydro-2H-pyran-4-yl)amino)-2-fluorophenyl)pentanoic acid

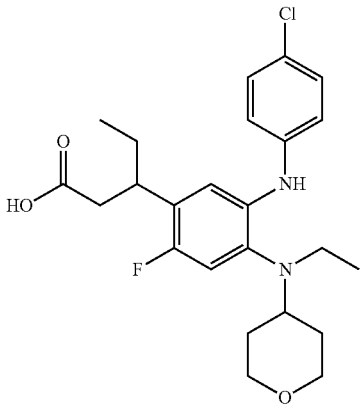 [SMILES: CCC(CC(=O)O)c1cc(Nc2ccc(Cl)cc2)c(N(CC)C2CCOCC2)cc1F]

861A. Methyl 3-(4-(ethyl(tetrahydro-2H-pyran-4-yl)amino)-2-fluoro-5-nitrophenyl)pentanoate 861A was prepared from 843C, (E)-methyl pent-2-enoate) and (S)-(−)-2,2'-bis(diphenylphosphino)-1,1'-binaphthyl following the procedure described for the synthesis of 850A. LC-MS Anal. Calc'd. for $C_{19}H_{27}FN_2O_5$, 382.19, found (M+H) 383.19, $T_r=3.12$ min (Method U).

861B. Methyl 3-(5-amino-4-(ethyl(tetrahydro-2H-pyran-4-yl)amino)-2-fluorophenyl)pentanoate 861B was prepared from 861A following the procedure described for the synthesis of 843F. LC-MS Anal. Calc'd. for $C_{19}H_{29}FN_2O_3$, 352.21, found (M+H) 353.19, $T_r=2.67$ min (Method CQ). Chiral purity; ee=94.12%, $T_r=3.3$ min. (Method BJ).

861C. Methyl 3-(5-((4-chlorophenyl)amino)-4-(ethyl(tetrahydro-2H-pyran-4-yl)amino)-2-fluorophenyl)pentanoate 861C was prepared from 861B following the procedure described for the synthesis of 843G. LC-MS Anal. Calc'd. for $C_{25}H_{32}ClFN_2O_3$, 462.20, found (M+H) 463.20, $T_r=4.18$ min (Method U).

Example 861

3-(5-((4-Chlorophenyl)amino)-4-(ethyl(tetrahydro-2H-pyran-4-yl)amino)-2-fluorophenyl)pentanoic acid Example 861 was prepared from 861C following the procedure described for the synthesis of Example 844 from 844A. LC-MS Anal. Calc'd. for $C_{24}H_{30}ClFN_2O_3$, 448.19, found (M+H) 449.19, $T_r$=1.92 min (Method O). $^1$H NMR (400 MHz, DMSO-$d_6$) δ 7.18-7.24 (m, 3H), 6.95-6.99 (m, 4H), 3.78-3.81 (m, 2H), 3.05-3.17 (m, 6H), 2.53-2.59 (m, 1H), 1.43-1.64 (m, 6H), 0.83 (t, J=7.20 Hz, 3H), 0.75 (t, J=7.20 Hz, 3H) (Note: 1H buried under solvent peak).

Examples 862 to 865

Enantiomer 2

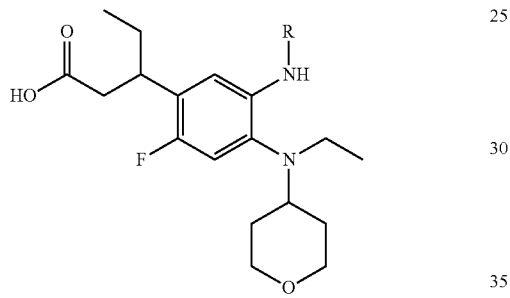

Example 862 was prepared from Intermediate 861B and corresponding aryl halides following the procedure described for the synthesis of Example 843.

Examples 863 to 865 was prepared from 861B and corresponding aryl halides following the procedure described for the synthesis of Example 844.

| Ex. No. | Name | R | $T_r$ min | Method | (M+H) |
|---|---|---|---|---|---|
| 862 | 3-(5-((5-cyanopyridin-2-yl)amino)-4-(ethyl(tetrahydro-2H-pyran-4-yl)amino)-2-fluorophenyl)pentanoic acid | [pyridine with CN] | 1.42 | O | 441 |
| 863 | 3-(5-((2-(cyclopropylmethoxy)pyrimidin-5-yl)amino)-4-(ethyl(tetrahydro-2H-pyran-4-yl)amino)-2-fluorophenyl)pentanoic acid | [pyrimidine with OCH2-cyclopropyl] | 1.63 | O | 487 |
| 864 | 3-(4-(ethyl(tetrahydro-2H-pyran-4-yl)amino)-2-fluoro-5-((2-methoxypyrimidin-5-yl)amino)phenyl)pentanoic acid | [pyrimidine with OMe] | 1.33 | O | 447 |
| 865 | 3-(5-((2-ethoxypyrimidin-5-yl)amino)-4-(ethyl(tetrahydro-2H-pyran-4-yl)amino)-2-fluorophenyl)pentanoic acid | [pyrimidine with OEt] | 1.46 | O | 461 |

Example 866

Enantiomer 1

3-(3-((4-Cyanophenyl)amino)-4-(methyl(tetrahydro-2H-pyran-4-yl)amino)phenyl)pentanoic acid

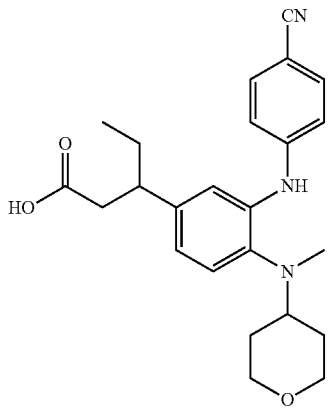 [SMILES: CCC(CC(=O)O)c1ccc(N(C)C2CCOCC2)c(Nc2ccc(C#N)cc2)c1]

866A. N-Methyltetrahydro-2H-pyran-4-amine

To a stirred suspension of 4 Å powdered molecular sieves and dihydro-2H-pyran-4(3H)-one (27.8 mL, 300 mmol) in ethanol (300 mL), tetrahydrofuran (150 mL) was added methanamine (180 mL, 360 mmol) dropwise and stirred overnight at room temperature. Reaction mixture was cooled to 0-5° C., then was added sodium borohydride (22.67 g, 599 mmol) lot wise for 20 min and stirred for 6 h at room temperature. Reaction mixture was quenched with 10% solution of NaHCO$_3$ (300 mL) and concentrated under reduced pressure to remove the volatiles. The above reaction mixture was diluted with ethyl acetate (300 mL) and filtered through CELITE® bed filter. The CELITE® bed was washed with ethyl acetate (100 mL). The aqueous layer was separated and extracted with ethyl acetate (2×100 mL). The combined organic layer was dried over sodium sulfate and concentrated under reduced pressure to get crude 866A (25 g, 211 mmol, 70.3% yield) as yellow liquid and taken for next step without further purification. LC-MS Anal. Calc'd. for $C_6H_{13}NO$, 115.10, found (M+H) 116.10. $T_r$=0.36 min (Method U).

866B. N-(4-Bromo-2-nitrophenyl)-N-methyltetrahydro-2H-pyran-4-amine 866B was prepared from 866A following the procedure described for the synthesis of 843B. LC-MS Anal. Calc'd. for $C_{12}H_{15}BrN_2O_3$, 314.02, found (M+H) 315.02, $T_r$=2.91 min (Method U).

866C. N-(4-(5,5-Dimethyl-1,3,2-dioxaborinan-2-yl)-2-nitrophenyl)-N-methyltetrahydro-2H-pyran-4-amine 866C was prepared from 866B following the procedure described for the synthesis of 843C. LC-MS Anal. Calc'd. for $C_{17}H_{25}BN_2O_5$, 348.18, found (M+H) 313.18 (for parent boronic acid), $T_r$=1.98 min (Method U).

866D. Methyl 3-(4-(methyl(tetrahydro-2H-pyran-4-yl)amino)-3-nitrophenyl)pentanoate 866D was prepared from 866C, (E)-methyl pent-2-enoate) and (S)-(−)-2,2'-bis(diphenylphosphino)-1,1'-binaphthyl following the procedure described for the synthesis of 850A. LC-MS Anal. Calc'd. for $C_{18}H_{26}N_2O_5$, 350.18, found (M+H) 351.18, $T_r$=2.97 min (Method U).

866E. Methyl 3-(3-amino-4-(methyl(tetrahydro-2H-pyran-4-yl)amino)phenyl)pentanoate 866E Enantiomer mixture was prepared from Intermediate 866D following the procedure described for the synthesis of 843F. LC-MS Anal. Calc'd. for $C_{18}H_{28}N_2O_3$, 320.21, found (M+H) 321.21, $T_r$=2.89 min (Method U).

Chiral separation of 866E Enantiomer mixture (88:12) gave Enantiomer 1 $T_r$=3.72 min and Enantiomer 2 $T_r$=2.96 min (Method CR).

866E Enantiomer 1: LC-MS Anal. Calc'd. for $C_{18}H_{28}N_2O_3$, 320.21, found (M+H) 321.21, $T_r$=2.89 min (Method U).

866F. Methyl 3-(3-((4-cyanophenyl)amino)-4-(methyl(tetrahydro-2H-pyran-4-yl)amino)phenyl)pentanoate 866F was prepared from 866E Enantiomer 1 following the procedure described for the synthesis of 843G. LC-MS Anal. Calc'd. for $C_{25}H_{31}N_3O_3$, 421.23, found (M+H) 422.23, $T_r$=3.20 min (Method U).

Example 866. 3-(3-((4-Cyanophenyl)amino)-4-(methyl(tetrahydro-2H-pyran-4-yl)amino)phenyl)pentanoic acid Example 866 was prepared from 866F following the procedure described for the synthesis of Example 843. LC-MS Anal. Calc'd. for $C_{24}H_{29}N_3O_3$, 407.22, found (M+H) 408.22, $T_r$=1.62 min (Method O). $^1$H NMR (400 MHz, DMSO-$d_6$) δ 8.11 (s, 1H), 7.54 (d, J=8.80 Hz, 2H), 7.22-7.26 (m, 1H), 7.10-7.13 (m, 1H), 6.92-7.01 (m, 3H), 3.79-3.82 (m, 2H), 3.02-3.08 (m, 3H), 2.84-2.87 (m, 1H), 2.68 (s, 3H), 2.55-2.60 (m, 1H), 2.42-2.48 (m, 1H), 1.52-1.67 (m, 6H), 0.74 (t, J=7.60 Hz, 3H).

Example 867

Enantiomer 1

3-(3-((4-Chlorophenyl)amino)-4-(methyl(tetrahydro-2H-pyran-4-yl)amino)phenyl)pentanoic acid

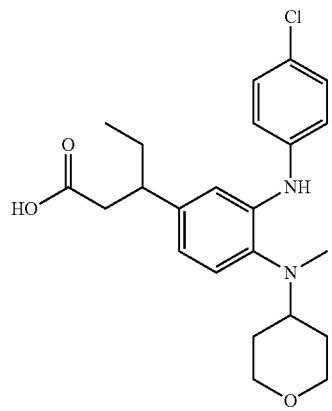 [SMILES: CCC(CC(=O)O)c1ccc(N(C)C2CCOCC2)c(Nc2ccc(Cl)cc2)c1]

To a stirred solution of 866E Enantiomer 1 (40 mg, 0.125 mmol) in dioxane (1 mL) was added 1-bromo-4-chlorobenzene (28.7 mg, 0.150 mmol) in dioxane (1 mL) and sodium tert-butoxide (36.0 mg, 0.375 mmol). Reaction mixture was purged with nitrogen for 5 min then was added Xantphos (36.1 mg, 0.062 mmol), bis(dibenzylideneacetone) palladium (7.18 mg, 0.012 mmol), which was sealed and stirred at 110° C. overnight. Reaction mixture was concentrated completely under reduced pressure and diluted with water (5 mL), acidified (pH~4) with solid citric acid. The aqueous layer was extracted with ethyl acetate (10 mL). The organic layer was dried over sodium sulfate, concentrated completely under reduced pressure to get crude. The crude compound was purified by preparative HPLC to obtain Example 867 (39.8 mg, 0.094 mmol, 74.9% yield). LC-MS Anal. Calc'd. for $C_{23}H_{29}ClN_2O_3$, 416.18, found (M+H) 417.18, $T_r$=1.62 min (Method O). $^1$H NMR (400 MHz, DMSO-$d_6$) δ 7.44 (br s, 1H), 7.17-7.24 (m, 3H), 7.02-7.04 (m, 3H), 6.81-6.82 (m, 1H), 3.80-3.82 (m, 2H), 3.09-3.18 (m, 3H), 2.80-2.83 (m, 1H), 2.63 (s, 3H), 2.54-2.58 (m, 1H), 2.34-2.45 (m, 1H), 1.45-1.63 (m, 6H), 0.73 (t, J=7.20 Hz, 3H).

Examples 868 and 869

Enantiomer 1

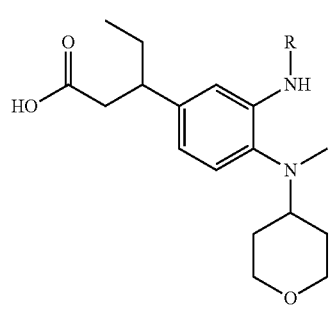

Examples 868 and 869 were prepared from 866E Enantiomer 1 and corresponding aryl halides following the procedure described for the synthesis of Example 844.

| Ex. No. | Name | R | $T_r$ min | Method | (M+H) |
|---|---|---|---|---|---|
| 868 | 3-(3-((2-methoxy-pyrimidin-5-yl)amino)-4-(methyl(tetrahydro-2H-pyran-4-yl)amino)phenyl)pentanoic acid | | 1.36 | O | 415 |
| 869 | 3-(3-((2-ethoxy-pyrimidin-5-yl)amino)-4-(methyl(tetrahydro-2H-pyran-4-yl)amino)phenyl)pentanoic acid | | 1.5 | O | 429 |

Example 870

Enantiomer 2

3-(3-((4-Cyanophenyl)amino)-4-(methyl(tetrahydro-2H-pyran-4-yl)amino)phenyl)pentanoic acid

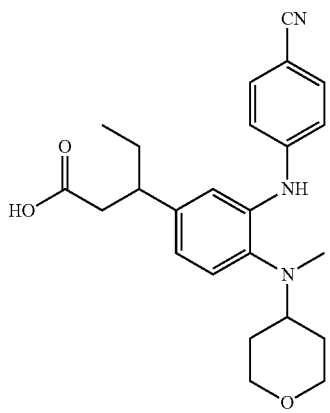 [SMILES: CCC(CC(=O)O)c1ccc(N(C)C2CCOCC2)c(Nc2ccc(C#N)cc2)c1]

870A. Methyl 3-(4-(methyl(tetrahydro-2H-pyran-4-yl)amino)-3-nitrophenyl)pentanoate 870A was prepared from 866 C, (E)-methyl pent-2-enoate) and (R)-(+)-2,2'-bis(diphenylphosphino)-1,1'-binaphthyl following the procedure described for the synthesis of 843E. LC-MS Anal. Calc'd. for $C_{18}H_{26}N_2O_5$, 380.19, found (M+H) 313.18 (for parent boronic acid), $T_r$=1.98 min (Method U).

870B. Methyl 3-(3-amino-4-(methyl(tetrahydro-2H-pyran-4-yl)amino)phenyl)pentanoate 870B was prepared from 870A following the procedure described for the synthesis of 843F. LC-MS Anal. Calc'd. for $C_{18}H_{28}N_2O_3$, 320.21, found (M+H) 321.21, $T_r$=3.77 min (Method U). Chiral 870B Enantiomer 2 $T_r$=2.88 min (Method CR) and ee=99%.

870C. Methyl 3-(3-((4-cyanophenyl)amino)-4-(methyl(tetrahydro-2H-pyran-4-yl)amino)phenyl)pentanoate 870C was prepared from 870B Enantiomer 2 following the procedure described for the synthesis of 843G. LC-MS Anal. Calc'd. for $C_{25}H_{31}N_3O_3$, 421.23, found (M+H) 422.23, $T_r$=3.20 min (Method U).

Example 870. 3-(3-((4-Cyanophenyl)amino)-4-(methyl(tetrahydro-2H-pyran-4-yl)amino) phenyl) pentanoic acid Example 870 was prepared from 870C following the procedure described for the synthesis of Example 843. LC-MS Anal. Calc'd. for $C_{24}H_{29}N_3O_3$, 407.22, found (M+H) 408.22, $T_r$=1.35 min (Method R). $^1$H NMR (400 MHz, DMSO-$d_6$) δ 8.06 (s, 1H), 7.52 (d, J=11.60 Hz, 2H), 7.07-7.14 (m, 2H), 6.96 (d, J=8.80 Hz, 3H), 3.77-3.79 (m, 2H), 2.99-3.04 (m, 3H), 2.82-2.85 (m, 1H), 2.53-2.60 (m, 4H), 2.40-2.46 (m, 1H), 1.45-1.64 (m, 6H), 0.70-0.78 (m, 3H).

Examples 871 and 872

Enantiomer 2

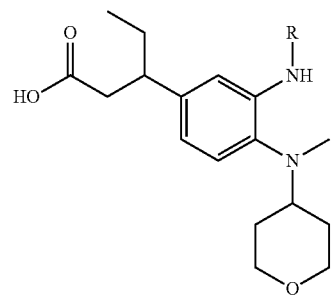

Examples 871 and 872 were prepared from 870B Enantiomer 2 and corresponding aryl halides following the procedure described for the synthesis of Example 844.

| Ex. No. | Name | R | $T_r$ min | Method | (M+H) |
|---|---|---|---|---|---|
| 871 | 3-(3-((2-methoxy-pyrimidin-5-yl)amino)-4-(methyl(tetrahydro-2H-pyran-4-yl)amino)phenyl)pentanoic acid | | 1.41 | O | 415 |
| 872 | 3-(3-((2-ethoxy-pyrimidin-5-yl)amino)-4-(methyl(tetrahydro-2H-pyran-4-yl)amino)phenyl)pentanoic acid | | 1.55 | O | 429 |

Example 873

Enantiomer 1

3-(3-((4-Cyanophenyl)amino)-4-(methyl(tetrahydro-2H-pyran-4-yl)amino)phenyl)-4-methoxybutanoic acid

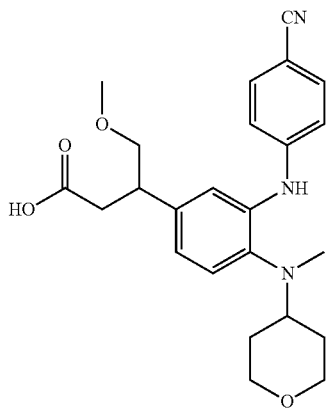 [SMILES: COCC(CC(=O)O)c1ccc(N(C)C2CCOCC2)c(Nc2ccc(C#N)cc2)c1]

873A. (E)-Ethyl 4-methoxybut-2-enoate

To a solution of ethyl but-2-ynoate (70 g, 624 mmol) in dry toluene (350 mL) then was added methanol (30.3 mL, 749 mmol), triphenylphosphine (8.19 g, 31.2 mmol), catalytic amount of acetic acid (7.15 mL, 125 mmol) was added at room temperature, and the reaction mixture allowed to stir for 10 minutes. Reaction heated to 110° C. and maintained for 20 h. Above reaction mixture was cooled to room temperature, then added water (50 mL) and extracted with ethyl acetate (3×50 mL). The combined organic layer was dried over sodium sulfate and concentrated to give yellow oil. Above oil was purified via flash silica gel column chromatography using gradient elution from hexane to 15% ethyl acetate in hexane. The fractions of product collected separately concentrated under reduced pressure to get 873A (35 g, 243 mmol, 38.9% yield) as light yellow liquid. $^1$H NMR (400 MHz, DMSO-$d_6$) δ6.84-6.91 (m, 1H), 5.94-5.99 (m, 1H), 4.07-4.15 (m, 4H), 3.29 (s, 3H), 1.22 (t, J=3.20 Hz, 3H).

873B. Ethyl 4-methoxy-3-(4-(methyl(tetrahydro-2H-pyran-4-yl)amino)-3-nitrophenyl)butanoate 873B was prepared from 866C, (s)-(−)-2,2'-bis(diphenylphosphino)-1,1'-binaphthyl and 873A following the procedure described for the synthesis of 850A. LC-MS Anal. Calc'd. for $C_{19}H_{28}N_2O_6$, 380.19, found (M+H) 381.19, $T_r$=3.83 min (Method U).

873C. Ethyl 3-(3-amino-4-(methyl(tetrahydro-2H-pyran-4-yl)amino)phenyl)-4-methoxybutanoate 873C was prepared from 873B following the procedure described for the synthesis of 843F. LC-MS Anal. Calc'd. for $C_{19}H_{30}N_2O_4$, 350.22, found (M+H) 351.22, $T_r$=1.88 min (Method BB).

Chiral separation of enantiomeric mixture 873C (96:4) gave Enantiomer 1 $T_r$=5.0 min and Enantiomer 2 $T_r$=6.0 min (Method BH).

873C Enantiomer 1, LC-MS Anal. Calc'd. for $C_{19}H_{30}N_2O_4$, 350.22, found (M+H) 351.22, $T_r$=1.88 min (Method BB).

873D. Ethyl 3-(3-((4-cyanophenyl)amino)-4-(methyl(tetrahydro-2H-pyran-4-yl)amino)phenyl)-4-methoxybutanoate 873D was prepared from 873C Enantiomer 1 and 4-chlorobenzonitrile following the procedure described for the synthesis of 843G. LC-MS Anal. Calc'd. for $C_{26}H_{33}N_3O_4$, 451.10, found (M+H) 452.10, $T_r$=1.99 min (Method CS).

Example 873. 3-(3-((4-Cyanophenyl)amino)-4-(methyl(tetrahydro-2H-pyran-4-yl)amino)phenyl)-4-methoxybutanoic acid Example 873 was prepared from 873D following the procedure described for the synthesis of Example 843. LC-MS Anal. Calc'd. for $C_{24}H_{29}N_3O_4$, 423.10, found (M+H) 424.10, $T_r$=1.52 min (Method O). $^1$H NMR (400 MHz, DMSO-$d_6$) δ 8.20 (s, 1H), 7.50-7.60 (m, 2H), 6.90-7.20 (m, 5H), 3.75-3.85 (m, 2H), 3.35-3.46 (m, 2H), 3.18-3.25 (m, 4H), 2.94-3.05 (m, 3H), 2.56-2.69 (m, 4H), 2.40-2.43 (m, 1H), 1.40-1.60 (m, 4H).

Examples 874 to 878

Enantiomer 1

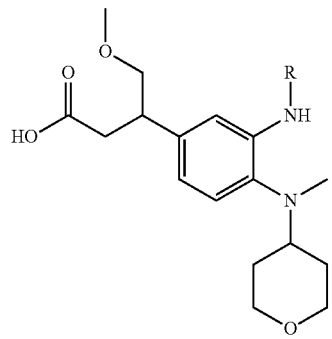

Examples 874 to 876 were prepared from 873C Enantiomer 1 and corresponding aryl halides following the procedure described for the synthesis of Example 843.

Examples 877 and 878 were prepared from 873C Enantiomer 1 and corresponding aryl halides following the procedure described for the synthesis of Example 844.

| Ex. No. | Name | R | $T_r$, min | Method | (M + H) |
|---|---|---|---|---|---|
| 874 | 3-(3-((5-cyanopyridin-2-yl)amino)-4-(methyl(tetrahydro-2H-pyran-4-yl)amino)phenyl)-4-methoxybutanoic acid | | 1.24 | O | 425 |
| 875 | 3-(3-((4-cyano-3-fluorophenyl)amino)-4-(methyl(tetrahydro-2H-pyran-4-yl)amino)phenyl)-4-methoxybutanoic acid | | 1.45 | O | 442 |
| 876 | 3-(3-((4-cyano-2-fluorophenyl)amino)-4-(methyl(tetrahydro-2H-pyran-4-yl)amino)phenyl)-4-methoxybutanoic acid | | 1.50 | O | 442 |
| 877 | 3-(3-((4-chlorophenyl)amino)-4-(methyl(tetrahydro-2H-pyran-4-yl)amino)phenyl)-4-methoxybutanoic acid | | 1.66 | O | 433 |
| 878 | 3-(3-((2-ethoxypyrimidin-5-yl)amino)-4-(methyl(tetrahydro-2H-pyran-4-yl)amino)phenyl)-4-methoxybutanoic acid | | 1.26 | O | 445 |

Example 879

Enantiomer 1

3-(3-(3-(4-Chloro-2-fluorophenyl)ureido)-4-(methyl(tetrahydro-2H-pyran-4-yl)amino)phenyl)-4-methoxybutanoic acid

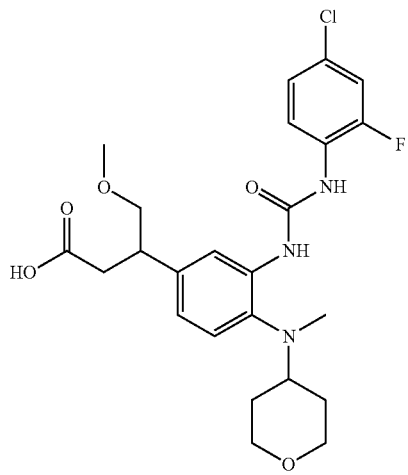 [SMILES: COCC(CC(=O)O)c1ccc(N(C)C2CCOCC2)c(NC(=O)Nc2ccc(Cl)cc2F)c1]

Example 879 was prepared from 873C Enantiomer 1 and 4-chloro-2-fluoro-1-isocyanatobenzene following the procedure described for the synthesis of Example 848. LC-MS Anal. Calc'd. for $C_{24}H_{29}N_3O_5$, 423.10, found (M+H) 424.10, $T_r$=1.52 min (Method O). $^1$H NMR (400 MHz, DMSO-$d_6$) δ 9.52 (s, 1H), 8.80 (s, 1H), 8.13-8.18 (m, 1H), 8.04 (s, 1H), 7.43-7.47 (m, 1H), 7.17-7.24 (m, 2H), 6.80-6.90 (m, 1H), 3.82-3.86 (m, 2H), 3.34-3.43 (m, 2H), 3.16-3.29 (m, 6H), 2.80-2.93 (m, 1H), 2.51-2.67 (m, 4H), 2.33-2.46 (m, 1H), 1.66-1.69 (m, 2H), 1.40-1.52 (m, 2H).

Example 880

Enantiomer 2

3-(3-((4-Cyanophenyl)amino)-4-(methyl(tetrahydro-2H-pyran-4-yl)amino)phenyl)-4-methoxybutanoic acid

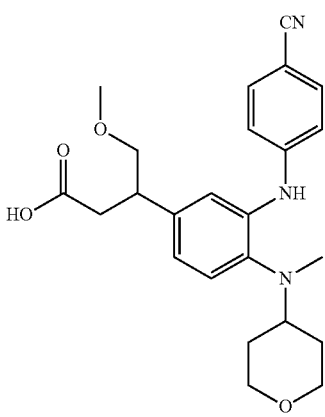 [SMILES: COCC(CC(=O)O)c1ccc(N(C)C2CCOCC2)c(Nc2ccc(C#N)cc2)c1]

880A. Ethyl 4-methoxy-3-(4-(methyl(tetrahydro-2H-pyran-4-yl)amino)-3-nitrophenyl)butanoate 880A was prepared from 866C, 873A and (R)-(+)-2,2'-bis(diphenylphosphino)-1,1'-binaphthyl following the procedure described for the synthesis of 843E. LC-MS Anal. Calc'd. for $C_{19}H_{28}N_2O_6$, 380.19, found (M+H) 381.19, $T_r$=2.76 min (Method U).

880B. Ethyl 3-(3-amino-4-(methyl(tetrahydro-2H-pyran-4-yl)amino)phenyl)-4-methoxybutanoate 880B Enantiomer mixture was prepared following the procedure for 843F by utilizing Intermediate 880B. LC-MS Anal. Calc'd. for $C_{19}H_{30}N_2O_4$, 350.22, found (M+H) 351.22, $T_r$=1.73 min (Method BB).

Chiral separation of 880B Enantiomer mixture (4:96) gave Enantiomer 1, $T_r$=5.0 min and Enantiomer 2, $T_r$=6.0 min (Method BH).

880B Enantiomer 2. LC-MS Anal. Calc'd. for $C_{19}H_{30}N_2O_4$, 350.22, found (M+H) 351.22, $T_r$=1.73 min (Method BB).

880C. Ethyl 3-(3-((4-cyanophenyl)amino)-4-(methyl(tetrahydro-2H-pyran-4-yl)amino) phenyl)-4-methoxybutanoate 880C was prepared from 880B Enantiomer 2 following the procedure described for the synthesis of 843G. LC-MS Anal. Calc'd. for $C_{26}H_{33}N_3O_4$, 451.10, found (M+H) 452.10, $T_r$=1.99 min (Method CS).

Example 880. 3-(3-((4-Cyanophenyl)amino)-4-(methyl(tetrahydro-2H-pyran-4-yl)amino)phenyl)-4-methoxybutanoic acid Example 880 was prepared from 880C following the procedure described for the synthesis of Example 843. LC-MS Anal. Calc'd. for $C_{24}H_{29}N_3O_4$, 423.10, found (M+H) 424.10, $T_r$=1.29 min (Method O). $^1$H NMR (400 MHz, DMSO-$d_6$) δ 8.20 (s, 1H), 7.50-7.60 (m, 2H), 6.90-7.20 (m, 5H), 3.75-3.85 (m, 2H), 3.35-3.46 (m, 2H), 3.18-3.25 (m, 4H), 2.94-3.05 (m, 3H), 2.56-2.69 (m, 4H), 2.40-2.43 (m, 1H), 1.40-1.60 (m, 4H).

Examples 881 to 885

Enantiomer 2

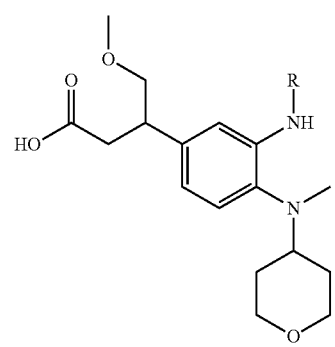

Examples 881 to 883 was prepared from 880B Enantiomer 2 and corresponding aryl halides following the procedure described for the synthesis of Example 843.

Examples 884 and 885 were prepared from 880B Enantiomer 2 and corresponding aryl halides following the procedure described for the synthesis of Example 884.

| Ex. No. | Name | R | $T_r$ min | Method | (M + H) |
|---|---|---|---|---|---|
| 881 | 3-(3-((5-cyanopyridin-2-yl)amino)-4-(methyl(tetrahydro-2H-pyran-4-yl)amino)phenyl)-4-methoxybutanoic acid | pyridin-2-yl with 5-CN | 1.16 | O | 425 |
| 882 | 3-(3-((4-cyano-3-fluorophenyl)amino)-4-(methyl(tetrahydro-2H-pyran-4-yl)amino)phenyl)-4-methoxybutanoic acid | phenyl with 3-F, 4-CN | 1.43 | O | 442 |
| 883 | 3-(3-((4-cyano-2-fluorophenyl)amino)-4-(methyl(tetrahydro-2H-pyran-4-yl)amino)phenyl)-4-methoxybutanoic acid | phenyl with 2-F, 4-CN | 1.48 | O | 442 |
| 884 | 3-(3-((4-chlorophenyl)amino)-4-(methyl(tetrahydro-2H-pyran-4-yl)amino)phenyl)-4-methoxybutanoic acid | phenyl with 4-Cl | 1.56 | O | 433 |

| Ex. No. | Name | R | T$_r$ min | Method | (M + H) |
|---|---|---|---|---|---|
| 885 | 3-(3-((2-ethoxypyrimidin-5-yl)amino)-4-(methyl(tetrahydro-2H-pyran-4-yl)amino)phenyl)-4-methoxybutanoic acid | 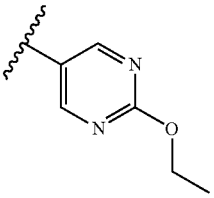 [SMILES: *c1cnc(OCC)nc1] | 1.25 | O | 445 |

Example 886

Enantiomer 2

3-(3-(3-(4-Chloro-2-fluorophenyl)ureido)-4-(methyl(tetrahydro-2H-pyran-4-yl)amino)phenyl)-4-methoxybutanoic acid

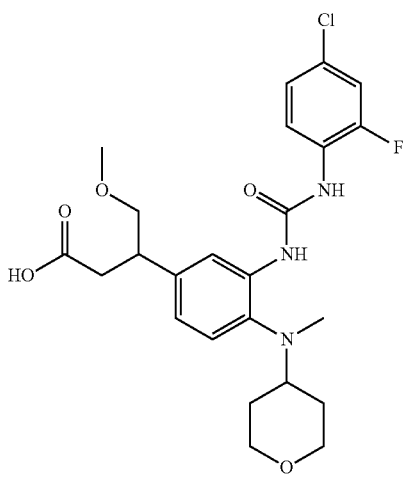 [SMILES: COCC(CC(=O)O)c1ccc(N(C)C2CCOCC2)c(NC(=O)Nc2ccc(Cl)cc2F)c1]

Example 886 was prepared from 880B Enantiomer 2 and 4-chloro-2-fluoro-1-isocyanatobenzene following the procedure described for the synthesis of Example 848. LC-MS Anal. Calc'd. for $C_{24}H_{29}N_3O_5$, 423.10, found (M+H) 424.10, T$_r$=1.41 min (Method O). $^1$H NMR (400 MHz, DMSO-d$_6$) δ 9.52 (s, 1H), 8.80 (s, 1H), 8.13-8.18 (m, 1H), 8.04 (s, 1H), 7.43-7.47 (m, 1H), 7.17-7.24 (m, 2H), 6.80-6.90 (m, 1H), 3.82-3.86 (m, 2H), 3.34-3.43 (m, 2H), 3.16-3.29 (m, 6H), 2.80-2.93 (m, 1H), 2.51-2.67 (m, 4H), 2.33-2.46 (m, 1H), 1.66-1.69 (m, 2H), 1.40-1.52 (m, 2H).

Example 887

Diastereomer 1

3-(3-((4-Cyanophenyl)amino)-4-((R)-3-isopropylmorpholino)phenyl)pentanoic acid

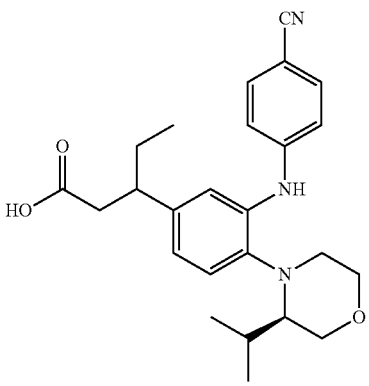 [SMILES: CCC(CC(=O)O)c1ccc(N2CCOC[C@H]2C(C)C)c(Nc2ccc(C#N)cc2)c1]

887A. (R)-4-(4-Bromo-2-nitrophenyl)-3-isopropylmorpholine 887A was prepared from (R)-3-isopropylmorpholine following the procedure described for the synthesis of 74C. LC-MS Anal. Calc'd. for $C_{13}H_{17}BrN_2O_3$, 328.04, found (M+H) 331.04, T$_r$=3.35 min (Method U).

887B. (R)-4-(4-(5,5-Dimethyl-1,3,2-dioxaborinan-2-yl)-2-nitrophenyl)-3-isopropylmorpholine 887B was prepared from 887A following the procedure described for the synthesis of 74D. LC-MS Anal. Calc'd. for $C_{18}H_{27}BN_2O_5$, 362.20, found (M+H) 295.14 for parent boronic acid mass), T$_r$=1.92 min (Method U).

887C. Methyl 3-(4-((R)-3-isopropylmorpholino)-3-nitrophenyl)pentanoate 887C was prepared from 887B and (R)-(+)-2,2'-bis(diphenylphosphino)-1,1'-binaphthyl following the procedure described for the synthesis of 74E. LC-MS Anal. Calc'd. for $C_{19}H_{28}N_2O_5$, 364.20, found (M+H) 365.20, T$_r$=3.19 min (Method U).

887D. Methyl 3-(3-amino-4-((R)-3-isopropylmorpholino)phenyl)pentanoate 887D (Diastereomer mixture) was prepared from 887C following the procedure described for the synthesis of 74F.

LC-MS Anal. Calc'd. for $C_{19}H_{30}N_2O_3$, 334.22, found (M+H) 335.22, $T_r$=3.01 min (Method U).

Chiral separation of diastereomer mixture (88:12) 887D gave Diastereomer 1 $T_r$=2.8 min, Diastereomer 2 $T_r$=3.5 min (Method CT).

887D Diastereomer 1: LC-MS Anal. Calc'd. for $C_{19}H_{30}N_2O_3$, 334.2, found (M+H) 335.2 $T_r$=3.01 min (Method U).

887E. Methyl 3-(3-((4-cyanophenyl)amino)-4-((R)-3-isopropylmorpholino)phenyl)pentanoate 887E was prepared from 887D Diastereomer 1 and 4-bromobenzonitrile following the procedure described for the synthesis of 78A. LC-MS Anal. Calc'd. for $C_{26}H_{33}N_3O_3$, 435.25, found (M+H) 436.25, $T_r$=3.64 min (Method U).

Example 887. 3-(3-((4-Cyanophenyl)amino)-4-((R)-3-isopropylmorpholino)phenyl)pentanoic acid Example 887 was prepared from 887E following the procedure described for the synthesis of Example 83. LC-MS Anal. Calc'd. for $C_{25}H_{31}N_3O_3$, 421.23, found (M+H) 422.23, $T_r$=1.98 min (Method O). $^1$H NMR (400 MHz, DMSO-$d_6$) δ12.00 (br s, 1H), 8.01 (s, 1H), 7.55-7.59 (m, 2H), 7.16 (d, J=8.40 Hz, 1H), 7.09-7.11 (m, 3H), 6.89-6.91 (m, 1H), 3.62-3.69 (m, 3H), 3.47-3.52 (m, 1H), 3.10-3.30 (m, 1H), 2.80-2.86 (m, 2H), 2.68-2.72 (m, 1H), 2.54-2.56 (m, 1H), 2.45-2.51 (m, 1H), 1.75-1.82 (m, 1H), 1.59-1.67 (m, 1H), 1.48-1.53 (m, 1H), 0.70-0.75 (m, 6H), 0.64 (d, J=6.80 Hz, 3H).

Examples 888 to 894

Diastereomer 1

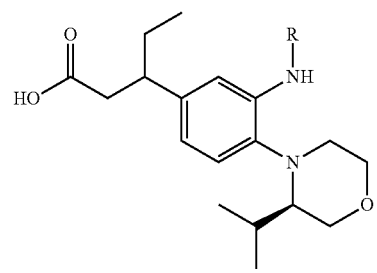

Examples 888 to 890 were prepared from 887D Diastereomer 1 and corresponding aryl halides following the procedure described for the synthesis of Example 84.

Examples 891 to 894 were prepared from 887D Diastereomer 1 and corresponding aryl halides following the procedure described for the synthesis of Example 78.

| Ex. No. | Name | R | $T_r$ min | Method | (M + H) |
|---|---|---|---|---|---|
| 888 | 3-(3-((4-chlorophenyl)amino)-4-((R)-3-isopropylmorpholino)phenyl)pentanoic acid | 4-chlorophenyl | 2.18 | O | 431 |
| 889 | 3-(3-((4-fluorophenyl)amino)-4-((R)-3-isopropylmorpholino)phenyl)pentanoic acid | 4-fluorophenyl | 1.9 | O | 415 |
| 890 | 3-(3-((4-ethylphenyl)amino)-4-((R)-3-isopropylmorpholino)phenyl)pentanoic acid | 4-ethylphenyl | 2.30 | O | 425 |
| 891 | 3-(3-((2-ethoxypyrimidin-5-yl)amino)-4-((R)-3-isopropylmorpholino)phenyl)pentanoic acid | 2-ethoxypyrimidin-5-yl | 1.71 | O | 443 |
| 892 | 3-(4-((R)-3-isopropylmorpholino)-3-((2-methylbenzo[d]thiazol-6-yl)amino)phenyl)pentanoic acid | 2-methylbenzo[d]thiazol-6-yl | 1.85 | O | 468 |

-continued

| Ex. No. | Name | R | $T_r$, min | Method | (M + H) |
|---|---|---|---|---|---|
| 893 | 3-(3-((2,2-difluorobenzo[d][1,3]dioxol-5-yl)amino)-4-((R)-3-isopropylmorpholino)phenyl)pentanoic acid | | 2.20 | O | 477 |
| 894 | 3-(3-((4-ethoxyphenyl)amino)-4-((R)-3-isopropylmorpholino)phenyl)pentanoic acid | | 2.06 | O | 441 |

Example 895

Diastereomer 1

3-(4-((R)-3-Isopropylmorpholino)-3-(3-(p-tolyl)ureido)phenyl)pentanoic acid

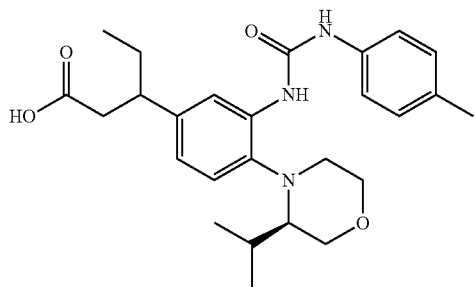 [SMILES: CCC(CC(=O)O)c1ccc(N2CCOC[C@H]2C(C)C)c(NC(=O)Nc2ccc(C)cc2)c1]

895A. Methyl 3-(4-((R)-3-isopropylmorpholino)-3-(3-(p-tolyl)ureido)phenyl)pentanoate 895A was prepared from 887D Diastereomer 1 and p-tolyl isocyanate following the procedure described for the synthesis of 74G. LC-MS Anal. Calc'd. for $C_{27}H_{37}N_3O_4$, 467.27, found (M+H) 468.27, $T_r$=3.45 min (Method U).

Example 895. 3-(4-((R)-3-Isopropylmorpholino)-3-(3-(p-tolyl)ureido)phenyl)pentanoic acid Example 895 was prepared from 895A following the procedure described for the synthesis of Example 74. LC-MS Anal. Calc'd. for $C_{26}H_{35}N_3O_4$, 453.26, found (M+H) 454.26, $T_r$=1.81 min (Method O). $^1$H NMR (400 MHz, DMSO-$d_6$) δ 9.46 (s, 1H), 8.38 (s, 1H), 8.10 (s, 1H), 7.36 (d, J=8.00 Hz, 2H), 7.09-7.16 (m, 3H), 6.78-6.80 (m, 1H), 3.70-3.88 (m, 4H), 2.99-3.01 (m, 1H), 2.78-2.86 (m, 1H), 2.62-2.64 (m, 2H), 2.41-2.43 (m, 1H), 2.24 (s, 3H), 1.42-1.62 (m, 3H), 0.79 (d, J=7.20 Hz, 3H), 0.67-0.73 (m, 6H) (Note: 1H buried under solvent peak).

Examples 896 and 897

Diastereomer 1

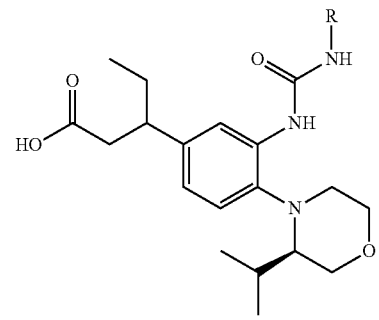

Examples 896 and 897 were prepared from 887D Diastereomer 1 and corresponding isocyanates following the procedure described for the synthesis of Example 74.

| Ex. No. | Name | R | $T_r$, min | Method | (M + H) |
|---|---|---|---|---|---|
| 896 | 3-(3-(3-(4-chloro-2-fluorophenyl)ureido)-4-((R)-3-isopropylmorpholino)phenyl)pentanoic acid | | 1.99 | O | 492 |
| 897 | 3-(3-(3-(2-fluoro-4-methoxyphenyl)ureido)-4-((R)-3-isopropylmorpholino)phenyl)pentanoic acid | | 1.61 | O | 488 |

Example 898

Diastereomer 1

3-(4-((R)-3-Isopropylmorpholino)-3-(3-(5-methyl-isoxazol-3-yl)ureido)phenyl)pentanoic acid

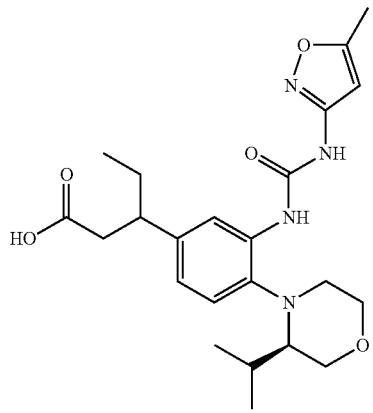 [SMILES: CCC(CC(=O)O)c1ccc(N2CCOC[C@H]2C(C)C)c(NC(=O)Nc2cc(C)on2)c1]

898A. Methyl 3-(4-((R)-3-isopropylmorpholino)-3-(3-(5-methylisoxazol-3-yl)ureido)phenyl)pentanoate 898A was prepared from 887D Diastereomer 1 following the procedure described for the synthesis of 77A. LC-MS Anal. Calc'd. for $C_{24}H_{34}N_4O_5$, 458.25, found (M+H) 459.25, $T_r$=3.20 min (Method U).

Example 898. 3-(4-((R)-3-Isopropylmorpholino)-3-(3-(5-methylisoxazol-3-yl)ureido)phenyl)pentanoic acid Example 898 was prepared from 898A following the procedure described for the synthesis of Example 77. LC-MS Anal. Calc'd. for $C_{23}H_{32}N_4O_5$, 444.23, found (M+H) 445.23, $T_r$=1.54 min (Method O). $^1$H NMR (400 MHz, DMSO-$d_6$) δ 10.35 (s, 1H), 9.50 (s, 1H), 8.15 (s, 1H), 7.21 (d, J=8.40 Hz, 1H), 6.86 (dd, J=2.00, 8.00 Hz, 1H), 6.38 (s, 1H), 3.87-3.89 (m, 2H), 3.72 (d, J=10.40 Hz, 1H), 3.56-3.59 (m, 2H), 3.04 (d, J=10.40 Hz, 1H), 2.79-2.84 (m, 1H), 2.62-2.65 (m, 1H), 2.51-2.54 (m, 1H), 2.43-2.46 (m, 1H), 2.37 (d, J=0.80 Hz, 3H), 1.48-1.59 (m, 3H), 0.80 (d, J=7.20 Hz, 3H), 0.72 (t, J=7.60 Hz, 3H), 0.66 (d, J=7.20 Hz, 3H).

Example 899

Diastereomer 2

3-(3-((4-Cyanophenyl)amino)-4-((R)-3-isopropyl-morpholino)phenyl)pentanoic acid

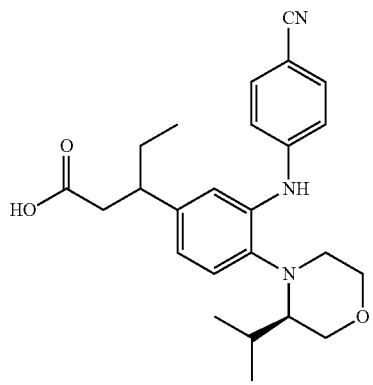 [SMILES: CCC(CC(=O)O)c1ccc(N2CCOC[C@H]2C(C)C)c(Nc2ccc(C#N)cc2)c1]

899A. Methyl 3-(4-((R)-3-isopropylmorpholino)-3-nitrophenyl)pentanoate 899A was prepared from 887B and (S)-(−)-2,2'-bis(diphenylphosphino)-1,1'-binaphthyl following the procedure described for the synthesis of 74E. LC-MS Anal. Calc'd. for $C_{19}H_{28}N_2O_5$, 364.20, found (M+H) 365.20, $T_r$=3.19 min (Method U).

899B. Methyl 3-(3-amino-4-((R)-3-isopropylmorpholino)phenyl)pentanoate 899B (Diastereomer mixture) was prepared from 899A following the procedure described for the synthesis of 74F. LC-MS Anal. Calc'd. for $C_{19}H_{30}N_2O_3$, 334.22, found (M+H) 335.22, $T_r$=3.01 min (Method U).

Chiral separation of 899B Diastereomer mixture (12:88) gave Diastereomer 1 $T_r$=2.8 min, Diastereomer 2 $T_r$=3.5 min (Method CT).

899B Diastereomer 2: LC-MS Anal. Calc'd. for $C_{19}H_{30}N_2O_3$, 334.2, found (M+H) 335.2 $T_r$=3.01 min (Method U).

899C. Methyl 3-(3-((4-cyanophenyl)amino)-4-((R)-3-isopropylmorpholino)phenyl)pentanoate 899C was prepared from 899B Diastereomer 2 and 4-bromobenzonitrile following the procedure described for the synthesis of 78A. LC-MS Anal. Calc'd. for $C_{26}H_{33}N_3O_3$, 435.25, found (M+H) 436.25, $T_r$=3.78 min (Method U).

Example 899. 3-(3-((4-Cyanophenyl)amino)-4-((R)-3-isopropylmorpholino)phenyl)pentanoic acid Example 899 was prepared from 899C following the procedure described for the synthesis of Example 83. LC-MS Anal. Calc'd. for $C_{25}H_{31}N_3O_3$, 421.23, found (M+H) 422.23, $T_r$=1.89 min (Method O). $^1$H NMR (400 MHz, DMSO-$d_6$) δ 8.00 (s, 1H), 7.55-7.59 (m, 2H), 7.16 (d, J=8.40 Hz, 1H), 7.10 (d, J=8.80 Hz, 3H), 6.89-6.91 (m, 1H), 3.63-3.69 (m, 3H), 3.49-3.52 (m, 1H), 3.01-3.03 (m, 1H), 2.84-2.86 (m, 2H), 2.68-2.73 (m, 1H), 2.54-2.60 (m, 1H), 2.41-2.50 (m, 1H), 2.78-1.80 (m, 1H), 1.61-1.66 (m, 1H), 1.46-1.53 (m, 1H), 0.71-0.75 (m, 6H), 0.64 (d, J=7.20 Hz, 3H).

Examples 900 to 906

Diastereomer 2

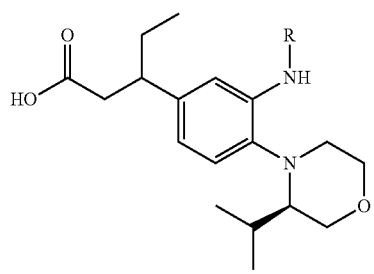

Examples 900 to 902 were prepared from 899B Diastereomer 2 and corresponding aryl halides following the procedure described for the synthesis of Example 84.

Examples 903 to 906 were prepared from 898B Diastereomer 2 and corresponding aryl halides following the procedure described for the synthesis of Example 78.

| Ex. No. | Name | R | $T_r$ min | Method | (M + H) |
|---|---|---|---|---|---|
| 900 | 3-(3-((4-chlorophenyl)amino)-4-((R)-3-isopropylmorpholino)phenyl)pentanoic acid | | 2.18 | O | 431 |
| 901 | 3-(3-((4-fluorophenyl)amino)-4-((R)-3-isopropylmorpholino)phenyl)pentanoic acid | | 2.02 | O | 415 |
| 902 | 3-(3-((4-ethylphenyl)amino)-4-((R)-3-isopropylmorpholino)phenyl)pentanoic acid | | 2.29 | O | 425 |
| 903 | 3-(3-((2-ethoxypyrimidin-5-yl)amino)-4-((R)-3-isopropylmorpholino)phenyl)pentanoic acid | | 1.64 | O | 443 |
| 904 | 3-(3-((2,2-difluorobenzo[d][1,3]dioxol-5-yl)amino)-4-((R)-3-isopropylmorpholino)phenyl)pentanoic acid | | 2.25 | O | 477 |
| 905 | 3-(3-((2-(cyclopropylmethoxy)pyrimidin-5-yl)amino)-4-((R)-3-isopropylmorpholino)phenyl)pentanoic acid | | 1.94 | O | 469 |
| 906 | 3-(4-((R)-3-isopropylmorpholino)-3-((2-methoxypyrimidin-5-yl)amino)phenyl)pentanoic acid | | 1.64 | O | 429 |

Example 907

Diastereomer 2

3-(4-((R)-3-Isopropylmorpholino)-3-(3-(p-tolyl)ureido)phenyl)pentanoic acid

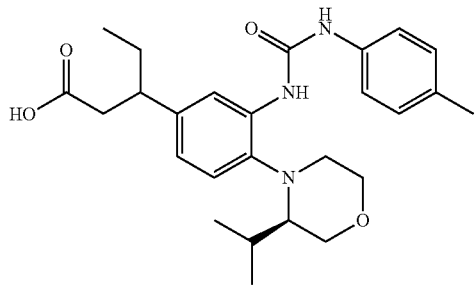 [SMILES: CCC(CC(=O)O)c1ccc(N2CCOC[C@H]2C(C)C)c(NC(=O)Nc2ccc(C)cc2)c1]

907A. Methyl 3-(4-((R)-3-isopropylmorpholino)-3-(3-(p-tolyl)ureido)phenyl)pentanoate 907A was prepared from 899B Diastereomer 2 and p-tolyl isocyanate following the procedure described for the synthesis of 74G. LC-MS Anal. Calc'd. for $C_{27}H_{37}N_3O_4$, 467.27, found (M+H) 468.27, $T_r$=3.45 min (Method U).

Example 907. 3-(4-((R)-3-Isopropylmorpholino)-3-(3-(p-tolyl)ureido)phenyl)pentanoic acid Example 907 was prepared from 907A following the procedure described for the synthesis of Example 74. LC-MS Anal. Calc'd. for $C_{26}H_{35}N_3O_4$, 453.26, found (M+H) 454.26, $T_r$=1.82 min (Method O). $^1$H NMR (400 MHz, DMSO-$d_6$) δ 9.43 (s, 1H), 8.37 (s, 1H), 8.11 (s, 1H), 7.38 (d, J=8.40 Hz, 2H), 7.10-7.17 (m, 3H), 6.78-6.81 (m, 1H), 3.53-3.89 (m, 4H), 3.01-3.32 (m, 1H), 2.80-2.88 (m, 1H), 2.62-2.69 (m, 2H), 2.40-2.49 (m, 1H), 2.26 (s, 3H), 1.42-1.63 (m, 3H), 0.81 (d, J=7.20 Hz, 3H), 0.69-0.74 (m, 6H) (Note: 1H buried under solvent peak).

Example 908

Diastereomer 2

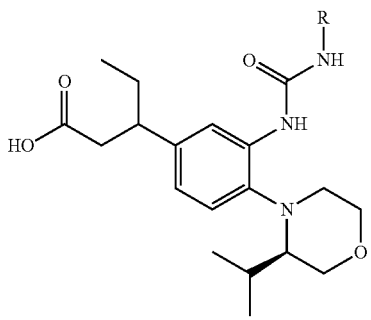

Example 908 was prepared from 899B Diastereomer 2 and corresponding isocyanates following the procedure described for the synthesis of Example 74.

| Ex. No. | Name | R | $T_r$ min | Method | (M + H) |
|---|---|---|---|---|---|
| 908 | 3-(3-(3-(4-chloro-2-fluorophenyl)ureido)-4-((R)-3-isopropylmorpholino)phenyl) pentanoic acid | | 1.94 | O | 492 |

Example 909

Diastereomer 1

3-(3-((4-Cyanophenyl)amino)-4-((R)-3-isopropylmorpholino)phenyl)-4-methoxybutanoic acid

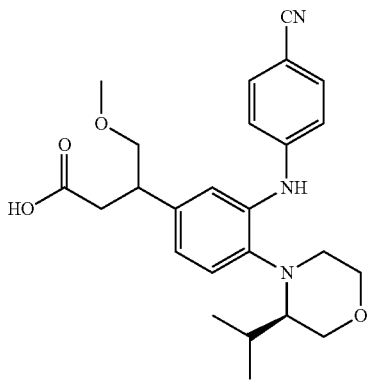

909A. Methyl 3-(4-((R)-3-isopropylmorpholino)-3-nitrophenyl)-4-methoxybutanoate 909A was prepared from 887B, Intermediate 843D and (R)-(+)-2,2'-bis(diphenylphosphino)-1,1'-binaphthyl following the procedure described for the synthesis of 74E. LC-MS Anal. Calc'd. for $C_{19}H_{28}N_2O_6$, 380.19, found (M+H) 381.19, $T_r$=2.95 min (Method U).

909B. Methyl 3-(3-amino-4-((R)-3-isopropylmorpholino)phenyl)-4-methoxybutanoate Example 909B (diastereomeric mixture) was prepared from 909A following the procedure described for the synthesis of 74F. LC-MS Anal. Calc'd. for $C_{19}H_{30}N_2O_4$, 350.22, found (M+H) 351.22, $T_r$=2.61 min (Method U).

Chiral separation of diastereomeric mixture (97:3) 909 B yielded 909B Diastereomer 1 $T_r$=3.11 Min, 909B Diastereomer 2 $T_r$=4.05 min (Method CT).

909B Diastereomer 1: LC-MS Anal. Calc'd. for $C_{19}H_{30}N_2O_3$, 350.22, found 351.22, $T_r$=2.61 min (Method U).

909C. Methyl 3-(3-((4-cyanophenyl)amino)-4-((R)-3-isopropylmorpholino)phenyl)-4-methoxybutanoate 909C was prepared from 909B Diastereomer 1 following the procedure described for the synthesis of 78A. LC-MS Anal. Calc'd. for $C_{26}H_{33}N_3O_4$, 451.24, found (M+H) 452.24, $T_r$=3.37 min (Method U).

Example 909. 3-(3-((4-Cyanophenyl)amino)-4-((R)-3-isopropylmorpholino)phenyl)-4-methoxybutanoic acid Example 909 was prepared from 909C following the procedure described for the synthesis of Example 83. LC-MS Anal. Calc'd. for $C_{25}H_{31}N_3O_4$, 437.23, found (M+H) 438.23, $T_r$=1.38 min (Method U). $^1$H NMR (400 MHz, DMSO-$d_6$) δ 8.00 (s, 1H), 7.58 (d, J=8.80 Hz, 2H), 7.12-7.18 (m, 4H), 6.93-6.95 (m, 1H), 3.65-3.69 (m, 3H), 3.49-3.52 (m, 2H), 3.17-3.23 (m, 4H), 3.00-3.50 (m, 1H), 2.81-2.83 (m, 1H), 2.65-2.69 (m, 2H), 2.48-2.51 (m, 1H), 1.76-1.80 (m, 1H), 0.74 (d, J=7.20 Hz, 3H), 0.65 (d, J=6.80 Hz, 3H) (Note: 1H buried under solvent peak).

Example 910

Diastereomer 1

3-(3-((4-Chlorophenyl)amino)-4-((R)-3-isopropylmorpholino)phenyl)-4-methoxybutanoic acid

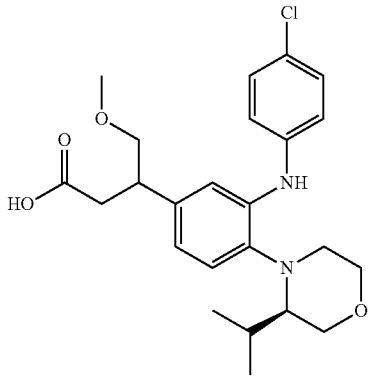 [SMILES: COCC(CC(=O)O)c1ccc(N2CCOC[C@H]2C(C)C)c(Nc2ccc(C#N)cc2)c1]

Example 910 was prepared from 909B Diastereomer 1 and 1-bromo-4-chlorobenzene following the procedure described for the synthesis of Example 84. LC-MS Anal. Calc'd. for $C_{24}H_{31}ClN_2O_4$, 446.19, found (M+H) 447.19, $T_r$=1.95 min (Method U). $^1$H NMR (400 MHz, DMSO-$d_6$) δ 7.44 (s, 1H), 7.25-7.28 (m, 2H), 7.09-7.17 (m, 4H), 6.75-6.77 (m, 1H), 3.77-3.82 (m, 1H), 3.68-3.72 (m, 2H), 3.38-3.52 (m, 3H), 3.17-3.21 (m, 4H), 3.01-3.06 (m, 1H), 2.55-2.72 (m, 3H), 2.42-2.50 (m, 1H), 1.70-1.72 (m, 1H), 0.78 (d, J=7.20 Hz, 3H), 0.66 (d, J=6.80 Hz, 3H).

Example 911

Diastereomer 1

3-(3-(3-(4-Cyanophenyl)ureido)-4-((R)-3-isopropyl-morpholino)phenyl)-4-methoxybutanoic acid

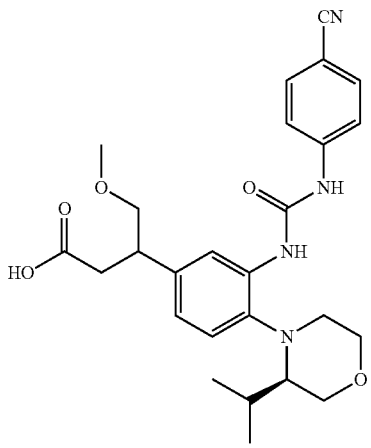 [SMILES: COCC(CC(=O)O)c1ccc(N2CCOC[C@H]2C(C)C)c(NC(=O)Nc2ccc(C#N)cc2)c1]

911A. Methyl 3-(3-(3-(4-cyanophenyl)ureido)-4-((R)-3-isopropylmorpholino)phenyl)-4-methoxybutanoate 911A was prepared from 909B Diastereomer 1 and 4-isocyanatobenzonitrile following the procedure described for the synthesis of 74G. LC-MS Anal. Calc'd. for $C_{27}H_{34}N_4O_5$, 494.25, found (M+H) 495.25, $T_r$=2.93 min (Method U).

Example 911. 3-(3-(3-(4-Cyanophenyl)ureido)-4-((R)-3-isopropylmorpholino)phenyl)-4-methoxybutanoic acid Example 911 was prepared from 911A following the procedure described for the synthesis of Example 83. LC-MS Anal. Calc'd. for $C_{26}H_{32}N_4O_5$, 480.23, found (M+H) 481.23, $T_r$=1.21 min (Method O). $^1$H NMR (400 MHz, DMSO-$d_6$) δ10.12 (s, 1H), 8.55 (s, 1H), 8.12 (d, J=2.00 Hz, 1H), 7.69-7.76 (m, 4H), 7.21 (d, J=8.40 Hz, 1H), 6.90 (dd, J=2.00, 8.20 Hz, 1H), 3.72-3.91 (m, 3H), 3.51-3.59 (m, 2H), 3.20-3.24 (m, 4H), 3.03-3.05 (m, 1H), 2.63-2.68 (m, 3H), 2.42-2.45 (m, 1H), 1.59-1.63 (m, 1H), 0.81 (d, J=7.20 Hz, 3H), 0.70 (d, J=7.20 Hz, 3H) (Note: 1H buried under solvent peak).

Example 912

Diastereomer 2

3-(3-((4-Cyanophenyl)amino)-4-((R)-3-isopropyl-morpholino)phenyl)-4-methoxybutanoic acid

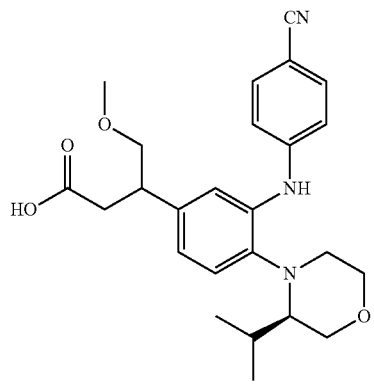 [SMILES: COCC(CC(=O)O)c1ccc(N2CCOC[C@H]2C(C)C)c(Nc2ccc(C#N)cc2)c1]

912A. Methyl 3-(4-((R)-3-isopropylmorpholino)-3-nitrophenyl)-4-methoxybutanoate 912A was prepared from 887B, 843D and (S)-(−)-2,2'-bis(diphenylphosphino)-1,1'-binaphthyl following the procedure described for the synthesis of 74E. LC-MS Anal. Calc'd. for $C_{19}H_{28}N_2O_6$, 380.19, found (M+H) 381.19, $T_r$=2.96 min (Method U).

912B. Methyl 3-(3-amino-4-((R)-3-isopropylmorpholino)phenyl)-4-methoxybutanoate 912B was prepared from 912A following the procedure described for the synthesis of 74F. LC-MS Anal. Calc'd. for $C_{19}H_{30}N_2O_4$, 350.22, found (M+H) 351.22, $T_r$=2.61 min (Method U).

Chiral separation of 912B diastereomer mixture (5:95) gave Diastereomer 1 $T_r$=3.11 min, Diastereomer 2 $T_r$=4.01 min (Method CT).

912B Diastereomer 2: LC-MS Anal. Calc'd. for $C_{19}H_{30}N_2O_3$, 350.22, found (M+H) 351.22, $T_r$=2.61 min (Method U).

912C. Methyl 3-(3-((4-cyanophenyl)amino)-4-((R)-3-isopropylmorpholino)phenyl)-4-methoxybutanoate 912C was prepared from 912B Diastereomer 2 following the procedure described for the synthesis of 78A. LC-MS Anal. Calc'd. for $C_{26}H_{33}N_3O_4$, 451.24, found (M+H) 452.24, $T_r$=3.37 min (Method U).

Example 912. 3-(3-((4-Cyanophenyl)amino)-4-((R)-3-isopropylmorpholino)phenyl)-4-methoxybutanoic acid Example 912 was prepared from 912C following the procedure described for the synthesis of Example 83. LC-MS Anal. Calc'd. for $C_{25}H_{31}N_3O_4$, 437.23, found (M+H) 438.23, $T_r$=1.38 min (Method U). $^1$H NMR (400 MHz, DMSO-$d_6$) δ 8.00 (s, 1H), 7.58 (d, J=8.80 Hz, 2H), 7.12-7.18 (m, 4H), 6.93-6.95 (m, 1H), 3.65-3.69 (m, 3H), 3.49-3.52 (m, 2H), 3.17-3.23 (m, 4H), 3.00-3.50 (m, 1H), 2.81-2.83 (m, 1H), 2.65-2.69 (m, 2H), 2.48-2.51 (m, 1H), 1.76-1.80 (m, 1H), 0.74 (d, J=7.20 Hz, 3H), 0.65 (d, J=6.80 Hz, 3H) (Note: 1H buried under solvent peak).

Example 913

Diastereomer 2

3-(3-((4-Chlorophenyl)amino)-4-((R)-3-isopropyl-morpholino)phenyl)-4-methoxybutanoic acid

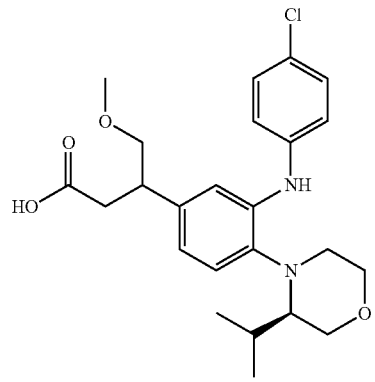 [SMILES: COCC(CC(=O)O)c1ccc(N2CCOC[C@H]2C(C)C)c(Nc2ccc(Cl)cc2)c1]

Example 913 was prepared from 912B Diastereomer 2 and 1-bromo-4-chlorobenzene following the procedure described for the synthesis of Example 84. LC-MS Anal. Calc'd. for $C_{24}H_{31}ClN_2O_4$, 446.19, found (M+H) 447.19, $T_r$=1.95 min (Method U). $^1$H NMR (400 MHz, DMSO-$d_6$) δ 7.44 (s, 1H), 7.25-7.28 (m, 2H), 7.09-7.17 (m, 4H), 6.75-6.77 (m, 1H), 3.77-3.82 (m, 1H), 3.68-3.72 (m, 2H), 3.38-3.52 (m, 3H), 3.17-3.21 (m, 4H), 3.01-3.06 (m, 1H), 2.55-2.72 (m, 3H), 2.42-2.50 (m, 1H), 1.70-1.72 (m, 1H), 0.78 (d, J=7.20 Hz, 3H), 0.66 (d, J=6.80 Hz, 3H).

Example 914

Diastereomer 2

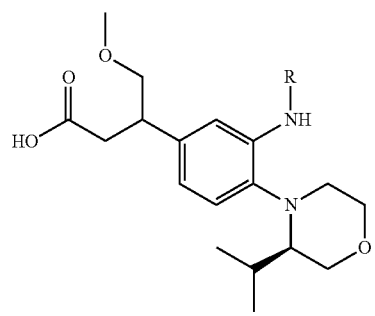

Example 914 was prepared from 912B Diastereomer 2 and corresponding aryl halide following the procedure described for the synthesis of Example 78.

Example 915

Diastereomer 2

3-(3-(3-(4-Cyanophenyl)ureido)-4-((R)-3-isopropyl-morpholino)phenyl)-4-methoxybutanoic acid

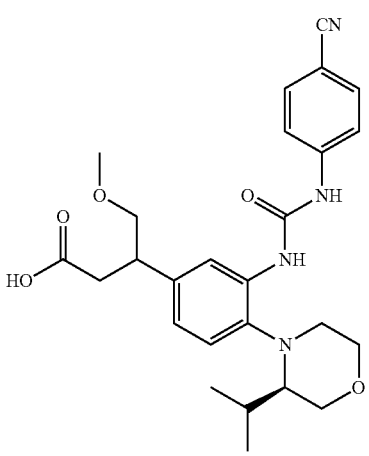 [SMILES: COCC(CC(=O)O)c1ccc(N2CCOC[C@H]2C(C)C)c(NC(=O)Nc2ccc(C#N)cc2)c1]

915A. Methyl 3-(3-(3-(4-cyanophenyl)ureido)-4-((R)-3-isopropylmorpholino)phenyl)-4-methoxybu-tanoate 915A was prepared from 912B Diastereomer 2 and 4-iso-cyanatobenzonitrile following the procedure described for the synthesis of 74G. LC-MS Anal. Calc'd. for $C_{27}H_{34}N_4O_5$, 494.25, found (M+H) 495.25, $T_r$=3.05 min (Method U).

Example 915. 3-(3-(3-(4-Cyanophenyl)ureido)-4-((R)-3-isopropylmorpholino)phenyl)-4-methoxybu-tanoic acid Example 915 was prepared from 915A following the procedure described for the synthesis of Example 83. LC-MS Anal. Calc'd. for $C_{26}H_{32}N_4O_5$, 480.23, found (M+H) 481.23, $T_r$=1.21 min (Method O). $^1$H NMR (400 MHz, DMSO-$d_6$) δ 10.13 (s, 1H), 8.56 (s, 1H), 8.13 (d, J=2.00 Hz, 1H), 7.70-7.77 (m, 4H), 7.22 (d, J=8.00 Hz, 1H), 6.91-6.93 (m, 1H), 3.74-3.93 (m, 3H), 3.51-3.58 (m, 2H), 3.18-3.26 (m, 4H), 3.04-3.06 (m, 1H), 2.64-2.69 (m, 2H), 2.45-2.50 (m, 1H), 1.55-1.65 (m, 1H), 0.82 (d, J=7.20 Hz, 3H), 0.71 (d, J=7.20 Hz, 3H) (Note: 2H buried under solvent peak).

| Ex. No. | Name | R | $T_r$, min | Method | (M + H) |
|---|---|---|---|---|---|
| 914 | 3-(3-((2-ethoxypyrimidin-5-yl)amino)-4-((R)-3-isopropylmorpholino)phenyl)-4-methoxybutanoic acid | (2-ethoxypyrimidin-5-yl) | 1.49 | O | 459 |

Example 916

Enantiomer 1

3-(3-((4-Cyanophenyl)amino)-4-(ethyl(tetrahydro-2H-pyran-4-yl)amino)-5-fluorophenyl)-4-methoxybutanoic acid

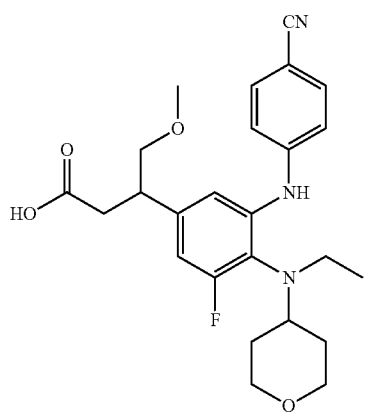 [SMILES: CCN(c1c(F)cc(C(COC)CC(=O)O)cc1Nc1ccc(C#N)cc1)C1CCOCC1]

916A. Methyl 3-(4-(ethyl(tetrahydro-2H-pyran-4-yl)amino)-3-fluoro-5-nitrophenyl)-4-methoxybut-2-enoate 916A was prepared from 133A and 843D following the procedure described for the synthesis of 133B. LC-MS Anal. Calc'd. for $C_{19}H_{25}FN_2O_6$, 396.17, found (M+H) 397.17, $T_r$=3.17 min (Method U).

916B. Methyl 3-(3-amino-4-(ethyl(tetrahydro-2H-pyran-4-yl)amino)-5-fluorophenyl)-4-methoxybutanoate 916B was prepared from 916A following the procedure described for the synthesis of 133C. LC-MS Anal. Calc'd. for $C_{19}H_{29}FN_2O_4$, 368.21, found (M+H) 369.21, $T_r$=2.65 min (Method U).

Chiral separation of Racemate 916B gave Enantiomer 1, $T_r$=11.56 min and Enantiomer 2, $T_r$=16.43 min (Method BZ).

916B Enantiomer 1, LC-MS Anal. Calc'd. for $C_{19}H_{29}FN_2O_4$, 368.21, found (M+H) 369.21, $T_r$=2.69 min (Method U).

916B Enantiomer 2, LC-MS Anal. Calc'd. for $C_{19}H_{29}FN_2O_4$, 368.21, found (M+H) 369.21, $T_r$=2.68 min (Method U).

916C. Methyl 3-(3-((4-cyanophenyl)amino)-4-(ethyl(tetrahydro-2H-pyran-4-yl)amino)-5-fluorophenyl)-4-methoxybutanoate 916C was prepared from 916B Enantiomer 1 and 4-bromobenzonitrile following the procedure described for the synthesis of 83A. LC-MS Anal. Calc'd. for $C_{26}H_{32}FN_3O_4$, 469.23, found (M+H) 470.23, $T_r$=3.4 min (Method U).

Example 916. 3-(3-((4-Cyanophenyl)amino)-4-(ethyl(tetrahydro-2H-pyran-4-yl)amino)-5-fluorophenyl)-4-methoxybutanoic acid Example 916 was prepared from 916C following the procedure described for the synthesis of Example 83. LC-MS Anal. Calc'd. for $C_{25}H_{30}FN_3O_4$, 455.22, found (M+H) 456.22, $T_r$=1.84 min (Method O). $^1$H NMR (400 MHz, DMSO-$d_6$) δ 400 MHz, DMSO-$d_6$: δ 7.99 (s, 1H), 7.63 (d, J=8.80 Hz, 2H), 7.28 (d, J=8.80 Hz, 2H), 7.05 (s, 1H), 6.73 (d, J=12.80 Hz, 1H), 3.77-3.80 (m, 2H), 3.42-3.49 (m, 2H), 3.21-3.27 (m, 5H), 3.00-3.15 (m, 3H), 2.60-2.65 (m, 1H), 2.44-2.46 (m, 1H), 1.55-1.68 (m, 2H), 1.32-1.40 (m, 2H), 0.82 (t, J=7.20 Hz, 3H) (Note: 1H buried under solvent peak).

Example 917

Enantiomer 1

3-(3-(3-(4-Chloro-2-fluorophenyl)ureido)-4-(ethyl(tetrahydro-2H-pyran-4-yl)amino)-5-fluorophenyl)-4-methoxybutanoic acid

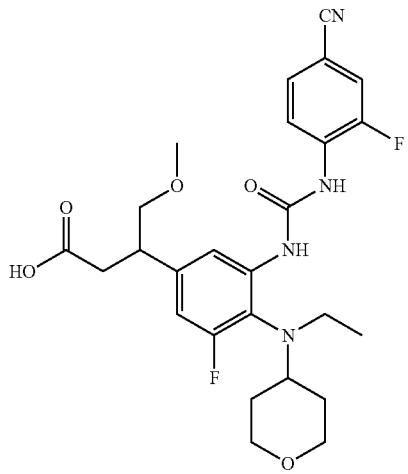 [SMILES: CCN(c1c(F)cc(C(COC)CC(=O)O)cc1NC(=O)Nc1ccc(C#N)cc1F)C1CCOCC1]

917A. Methyl 3-(3-(3-(4-chloro-2-fluorophenyl)ureido)-4-(ethyl(tetrahydro-2H-pyran-4-yl)amino)-5-fluorophenyl)-4-methoxybutanoate 917A was prepared from 916B Enantiomer 1 and 4-chloro-2-fluoro-1-isocyanatobenzene following the procedure described for the synthesis of 74G. LC-MS Anal. Calc'd. for $C_{26}H_{32}ClF_2N_3O_5$, 539.20, found (M+H) 540.20, $T_r$=3.48 min (Method U).

Example 917. 3-(3-(3-(4-Chloro-2-fluorophenyl)ureido)-4-(ethyl(tetrahydro-2H-pyran-4-yl)amino)-5-fluorophenyl)-4-methoxybutanoic acid Example 917 was prepared from 917A following the procedure described for the synthesis of Example 74. LC-MS Anal. Calc'd. for $C_{25}H_{30}ClF_2N_3O_5$, 525.18, found (M+H) 526.18, $T_r$=1.70 min (Method O). $^1$H NMR (400 MHz, DMSO-$d_6$) δ 9.62 (s, 1H), 8.89 (s, 1H), 8.08-8.12 (m, 1H), 7.95 (s, 1H), 7.44-7.48 (m, 1H), 7.22-7.24 (m, 1H), 6.70-6.74 (m, 1H), 3.62-3.80 (m, 2H), 3.20-3.27 (m, 5H), 3.03-3.12 (m, 2H), 2.61-2.65 (m, 1H), 2.41-2.49 (m, 1H), 1.94-2.30 (m, 1H), 1.41-1.58 (m, 4H), 0.83 (t, J=7.20 Hz, 3H) (Note: 2H buried under moisture peak and 1H buried under solvent peak).

Example 918

Enantiomer 2

3-(3-((4-Cyanophenyl)amino)-4-(ethyl(tetrahydro-2H-pyran-4-yl)amino)-5-fluorophenyl)-4-methoxybutanoic acid

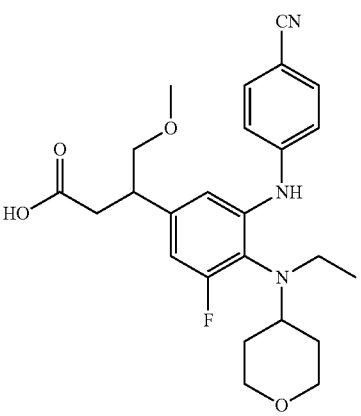 [SMILES: CCN(c1c(F)cc(C(COC)CC(=O)O)cc1Nc1ccc(C#N)cc1)C1CCOCC1]

918A. Methyl 3-(3-((4-cyanophenyl)amino)-4-(ethyl(tetrahydro-2H-pyran-4-yl)amino)-5-fluorophenyl)-4-methoxybutanoate 918A was prepared from 916B Enantiomer 2 and 4-bromobenzonitrile following the procedure described for the synthesis of 83A. LC-MS Anal. Calc'd. for $C_{26}H_{32}FN_3O_4$, 469.23, found (M+H) 470.23, $T_r$=3.36 min (Method U).

Example 918. 3-(3-((4-Cyanophenyl)amino)-4-(ethyl(tetrahydro-2H-pyran-4-yl)amino)-5-fluorophenyl)-4-methoxybutanoic acid Example 918 was prepared from 918A following the procedure described for the synthesis of Example 83. LC-MS Anal. Calc'd. for $C_{25}H_{30}FN_3O_4$, 455.22, found (M+H) 456.22, $T_r$=1.42 min (Method O). $^1$H NMR (400 MHz, DMSO-$d_6$) δ 7.99 (s, 1H), 7.63 (d, J=8.80 Hz, 2H), 7.28 (d, J=8.80 Hz, 2H), 7.05 (s, 1H), 6.73 (d, J=12.80 Hz, 1H), 3.77-3.80 (m, 2H), 3.42-3.49 (m, 2H), 3.21-3.27 (m, 5H), 3.00-3.15 (m, 3H), 2.60-2.65 (m, 1H), 2.44-2.46 (m, 1H), 1.55-1.68 (m, 2H), 1.32-1.40 (m, 2H), 0.82 (t, J=7.20 Hz, 3H) (Note: 1H buried under solvent peak).

Example 919

Enantiomer 2

3-(3-(3-(4-Chloro-2-fluorophenyl)ureido)-4-(ethyl(tetrahydro-2H-pyran-4-yl)amino)-5-fluorophenyl)-4-methoxybutanoic acid

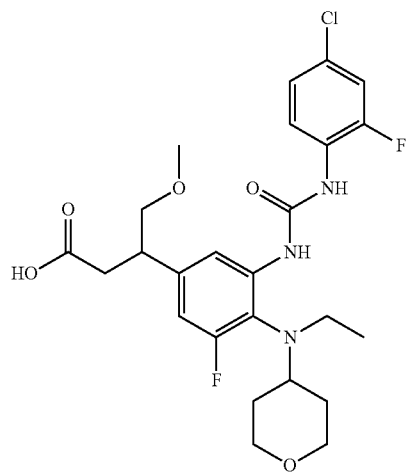 [SMILES: CCN(c1c(F)cc(C(COC)CC(=O)O)cc1NC(=O)Nc1ccc(Cl)cc1F)C1CCOCC1]

919A. Methyl 3-(3-(3-(4-chloro-2-fluorophenyl)ureido)-4-(ethyl(tetrahydro-2H-pyran-4-yl)amino)-5-fluorophenyl)-4-methoxybutanoate 919A was prepared from 916B Enantiomer 2 and 4-chloro-2-fluoro-1-isocyanatobenzene following the procedure described for the synthesis of 74G. LC-MS Anal. Calc'd. for $C_{26}H_{32}ClF_2N_3O_5$, 539.20, found (M+H) 540.20, $T_r$=3.49 min (Method U).

Example 919. 3-(3-(3-(4-Chloro-2-fluorophenyl)ureido)-4-(ethyl(tetrahydro-2H-pyran-4-yl)amino)-5-fluorophenyl)-4-methoxybutanoic acid Example 919 was prepared from 919A following the procedure described for the synthesis of 74. LC-MS Anal. Calc'd. for $C_{25}H_{30}ClF_2N_3O_5$, 525.18, found (M+H) 526.18, $T_r$=1.48 min (Method O). $^1$H NMR (400 MHz, DMSO-$d_6$) δ 9.63 (s, 1H), 8.89 (s, 1H), 8.09-8.13 (m, 1H), 7.96 (s, 1H), 7.44-7.48 (m, 1H), 7.21-7.24 (m, 1H), 6.70-6.74 (m, 1H), 3.72-3.90 (m, 2H), 3.40-3.51 (m, 3H), 3.17-3.26 (m, 4H), 3.04-3.14 (m, 4H), 2.61-2.67 (m, 1H), 2.41-2.50 (m, 1H), 1.95-2.04 (m, 1H), 1.18-1.58 (m, 3H), 0.84 (t, J=7.20 Hz, 3H).

Example 920

Enantiomer 1

3-(3-((4-Chlorophenyl)amino)-4-(diisobutylamino)-5-fluorophenyl)-4-methoxybutanoic acid

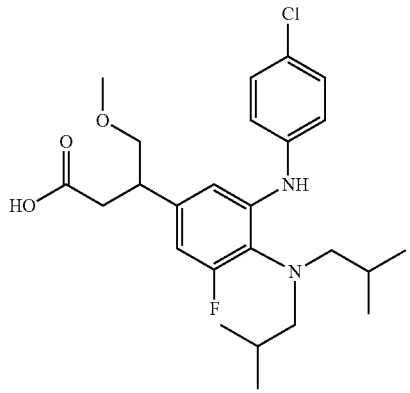 [SMILES: COCC(CC(=O)O)c1cc(F)c(N(CC(C)C)CC(C)C)c(Nc2ccc(Cl)cc2)c1]

920A. Methyl 3-(4-(diisobutylamino)-3-fluoro-5-nitrophenyl)-4-methoxybutanoate 920A was prepared from 95B and 843D following the procedure described for the synthesis of 95C. LC-MS Anal. Calc'd. for $C_{20}H_{31}FN_2O_5$, 398.22, found (M+H) 399.22, $T_r$=3.93 min (Method U).

920B. Methyl 3-(3-amino-4-(diisobutylamino)-5-fluorophenyl)-4-methoxybutanoate 920B was prepared from 920A following the procedure described for the synthesis of 95D. LC-MS Anal. Calc'd. for $C_{20}H_{33}FN_2O_3$, 368.24, found (M+H) 369.24, $T_r$=3.88 min (Method U).

Chiral separation of Racemate 920 B gave Enantiomer 1, $T_r$=1.95 min and Enantiomer 2, $T_r$=2.46 min (Method CV).

920B Enantiomer 1: LC-MS Anal. Calc'd. for $C_{20}H_{33}FN_2O_3$, 368.24, found (M+H) 369.24, $T_r$=3.88 min (Method U).

920B Enantiomer 2: LC-MS Anal. Calc'd. for $C_{20}H_{33}FN_2O_3$, 368.24, found (M+H) 369.24, $T_r$=3.88 min (Method U).

920C. Methyl 3-(3-((4-chlorophenyl)amino)-4-(diisobutylamino)-5-fluorophenyl)-4-methoxybutanoate 920C was prepared from 920B Enantiomer 1 following the procedure described for the synthesis of 95E. LC-MS Anal. Calc'd. for $C_{26}H_{36}ClFN_2O_3$, 478.24, found (M+H) 479.24, $T_r$=4.68 min (Method U).

Example 920. 3-(3-((4-Chlorophenyl)amino)-4-(diisobutylamino)-5-fluorophenyl)-4-methoxybutanoic acid Example 920 was prepared from 920C following the procedure described for the synthesis of Example 95. LC-MS Anal. Calc'd. for $C_{25}H_{34}ClFN_2O_3$, 464.22, found (M+H) 465.22, $T_r$=2.62 min (Method O). $^1$H NMR (400 MHz, DMSO-$d_6$) δ 7.42 (s, 1H), 7.33 (d, J=8.80 Hz, 2H), 7.13 (d, J=8.80 Hz, 2H), 6.91 (s, 1H), 6.58 (d, J=13.20 Hz, 1H), 3.16-3.21 (m, 6H), 2.57-2.69 (m, 5H), 2.39-2.45 (m, 1H), 1.56-1.63 (m, 2H), 0.85 (d, J=6.40 Hz, 12H).

Example 921

Enantiomer 2

3-(3-((4-Chlorophenyl)amino)-4-(diisobutylamino)-5-fluorophenyl)-4-methoxybutanoic acid

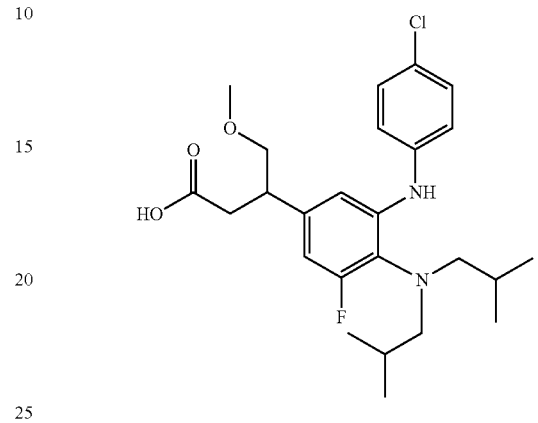

921A. Methyl 3-(3-((4-chlorophenyl)amino)-4-(diisobutylamino)-5-fluorophenyl)-4-methoxybutanoate 921A was prepared from 920B Enantiomer 2 following the procedure described for the synthesis of 920C. LC-MS Anal. Calc'd. for $C_{26}H_{36}ClFN_2O_3$, 478.24, found (M+H) 479.24, $T_r$=4.50 min (Method U).

Example 921. 3-(3-((4-Chlorophenyl)amino)-4-(diisobutylamino)-5-fluorophenyl)-4-methoxybutanoic acid Example 921 was prepared from 921A following the procedure described for the synthesis of Example 920. LC-MS Anal. Calc'd. for $C_{25}H_{34}ClFN_2O_3$, 464.22, found (M+H) 465.22, $T_r$=2.63 min (Method O). $^1$H NMR (400 MHz, DMSO-$d_6$) δ 7.42 (s, 1H), 7.33 (d, J=8.80 Hz, 2H), 7.13 (d, J=8.40 Hz, 2H), 6.91 (s, 1H), 6.58 (d, J=13.60 Hz, 1H), 3.13-3.21 (m, 6H), 2.57-2.69 (m, 5H), 2.39-2.45 (m, 1H), 1.55-1.64 (m, 2H), 0.85 (d, J=6.40 Hz, 12H).

Examples 922 to 925

Enantiomer 1

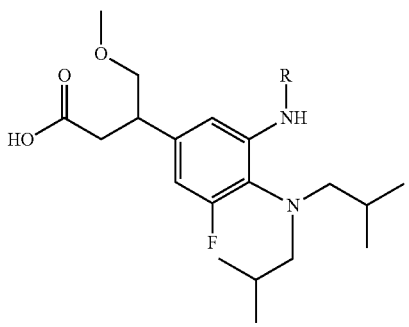

Examples 922 to 925 were prepared from 920B Enantiomer 1 and corresponding aryl halide following the procedure described for the synthesis of Example 920.

| Ex. No. | Name | R | $T_r$, min | Method | (M + H) |
|---|---|---|---|---|---|
| 922 | 3-(4-(diisobutylamino)-3-((4-ethylphenyl)amino)-5-fluorophenyl)-4-methoxybutanoic acid | | 2.74 | O | 459 |
| 923 | 3-(4-(diisobutylamino)-3-((4-ethoxyphenyl)amino)-5-fluorophenyl)-4-methoxybutanoic acid | | 2.65 | O | 475 |
| 924 | 3-(3-((2,2-difluorobenzo[d][1,3]dioxol-5-yl)amino)-4-(diisobutylamino)-5-fluorophenyl)-4-methoxybutanoic acid | | 2.68 | O | 511 |
| 925 | 3-(4-(diisobutylamino)-3-fluoro-5-((2-methylbenzo[d]thiazol-6-yl)amino)phenyl)-4-methoxybutanoic acid | | 2.36 | O | 502 |

Examples 926 to 928

Enantiomer 2

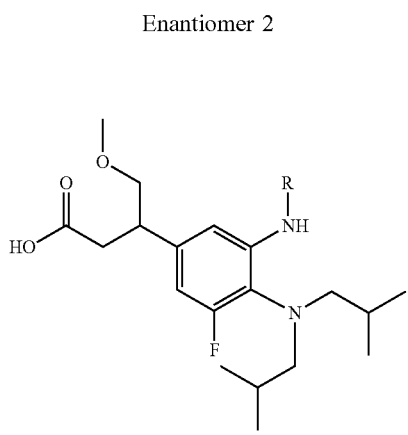

Example 928

Enantiomer 1 and Enantiomer 2

3-(3-((4-Cyanophenyl)amino)-4-((tetrahydro-2H-pyran-4-yl)amino)phenyl)-4-methoxybutanoic acid

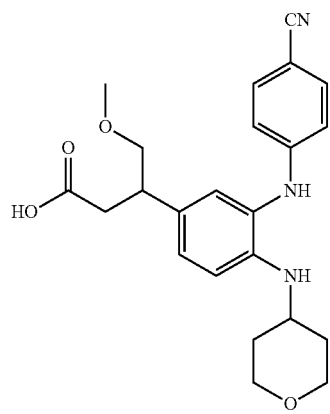 [SMILES: COCC(CC(=O)O)c1ccc(NC2CCOCC2)c(Nc2ccc(C#N)cc2)c1]

Examples 926 to 928 were prepared from 920B Enantiomer 2 and corresponding aryl halide following the procedure described for the synthesis of Example 921.

| Ex. No. | Name | R | $T_r$, min | Method | (M + H) |
|---|---|---|---|---|---|
| 926 | 3-(4-(diisobutylamino)-3-((4-ethylphenyl)amino)-5-fluorophenyl)-4-methoxybutanoic acid. | | 2.83 | O | 459 |
| 927 | 3-(3-((2,2-difluorobenzo[d][1,3]dioxol-5-yl)amino)-4-(diisobutylamino)-5-fluorophenyl)-4-methoxybutanoic acid. | | 2.76 | O | 511 |

928A. Ethyl 4-methoxy-3-(3-nitro-4-((tetrahydro-2H-pyran-4-yl)amino)phenyl)butanoate To a stirred of Racemate 694A (500 mg, 1.753 mmol) in N-methyl-2-pyrrolidone (10 mL) was added tetrahydro-2H-pyran-4-amine, 01 HCl (241 mg, 1.753 mmol) and diethyl-isopropylethylamine (0.918 mL, 5.26 mmol). The reaction mixture was stirred at 110° C. overnight. Reaction mixture was cooled to room temperature and diluted with ethyl acetate (30 mL), washed with 10% brine solution (4×15 mL). The aqueous layer was back extracted with ethyl acetate (10 mL). The combined organic layer was dried over sodium sulfate and concentrated under reduced pressure to get crude. The crude obtained was Purification via flash chromatography gave 928A (orange liquid, 500 mg, 1.310 mmol, 74.7% yield). LC-MS Anal. Calc'd. for $C_{18}H_{26}N_2O_6$, 366.17, found (M+H) 367.17, $T_r$=2.68 min (Method U).

928B. Ethyl 3-(3-amino-4-((tetrahydro-2H-pyran-4-yl)amino)phenyl)-4-methoxybutanoate 928B was prepared from 928A following the procedure described for the synthesis of 694B. LC-MS Anal. Calc'd. for $C_{18}H_{28}N_2O_4$, 336.20, found (M+H) 337.20, $T_r$=1.07 min (Method BB).

928C. Ethyl 3-(3-((4-cyanophenyl)amino)-4-((tetrahydro-2H-pyran-4-yl)amino)phenyl)-4-methoxybutanoate To a stirred solution of 928B (90 mg, 0.268 mmol) in dioxane (1 mL) was added 4-bromobenzonitrile (39.0 mg, 0.214 mmol) in dioxane (1 mL) and cesium carbonate (131 mg, 0.401 mmol). Reaction mixture was purged with nitrogen for 5 min then was added Xantphos (15.48 mg, 0.027 mmol) and bis(dibenzylideneacetone)palladium (4.61 mg, 8.03 μmol). The reaction mixture was sealed and stirred at 110° C. overnight. Reaction mixture was cooled to room temperature and diluted with ethyl acetate (5 mL), washed with 10% brine solution (2×5 mL). The organic layer was dried over $Na_2SO_4$ and concentrated under reduced pressure to get crude; purification via flash chromatography gave Racemate 928C (brown pasty wax, 30 mg, 0.069 mmol, 25.6% yield). LC-MS Anal. Calc'd. for $C_{25}H_{31}N_3O_4$, 437.23, found (M+H) 438.23, $T_r$=2.15 min (Method BB).

Example 928. 3-(3-((4-Cyanophenyl)amino)-4-((tetrahydro-2H-pyran-4-yl)amino)phenyl)-4-methoxybutanoic acid Racemate Example 928 was prepared from 928C following the procedure described for the synthesis of Example 694. LC-MS Anal. Calc'd. for $C_{23}H_{27}N_3O_4$, 409.20, found (M+H) 410.20, $T_r$=1.08 min (Method BB).

Chiral separation of racemate Example 928 gave Enantiomer 1, $T_r$=2.64 min and Enantiomer 2, $T_r$=3.74 min (Method BS).

Example 928 Enantiomer 1: LC-MS Anal. Calc'd. for $C_{23}H_{27}N_3O_4$, 409.20, found (M+H) 410.20, $T_r$=1.186 min (Method O). $^1$H NMR (400 MHz, DMSO-$d_6$) δ 8.00 (s, 1H), 7.48-7.53 (m, 2H), 6.94-6.97 (m, 2H), 6.69-6.73 (m, 3H), 4.39-4.42 (m, 1H), 3.80-3.83 (m, 2H), 3.38-3.42 (m, 5H), 3.21 (s, 3H), 3.08-3.18 (m, 1H), 2.61 (dd, J=5.60, 15.60 Hz, 1H), 2.39 (dd, J=9.20, 15.40 Hz, 1H), 1.84-1.86 (m, 2H), 1.32-1.34 (m, 2H).

Example 928 Enantiomer 2: LC-MS Anal. Calc'd. for $C_{23}H_{27}N_3O_4$, 409.20, found (M+H) 410.20, $T_r$=1.189 min (Method O). $^1$H NMR (400 MHz, DMSO-$d_6$) δ 7.99 (s, 1H), 7.47-7.50 (m, 2H), 6.93-6.96 (m, 2H), 6.69-6.73 (m, 3H), 4.39-4.42 (m, 1H), 3.80-3.82 (m, 2H), 3.38-3.41 (m, 5H), 3.20 (s, 3H), 3.09-3.18 (m, 1H), 2.58-2.62 (m, 1H), 2.37-2.41 (m, 1H), 1.83-1.85 (m, 2H), 1.30-1.39 (m, 2H).

Example 929

Diastereomer 1

3-(3-((4-Cyanophenyl)amino)-4-((S)-3-isopropylmorpholino)phenyl)-4-methoxybutanoic acid

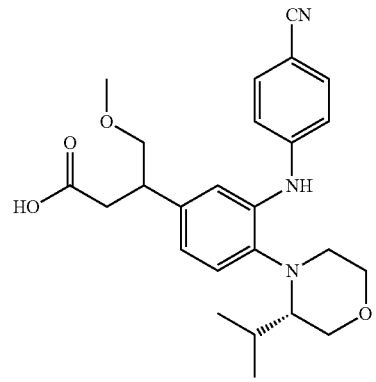

929A. Methyl 3-(4-((S)-3-isopropylmorpholino)-3-nitrophenyl)-4-methoxybutanoate 929A was prepared from 74D, (R)-(+)-2,2'-bis(diphenylphosphino)-1,1'-binaphthyl and (E)-methyl 4-methoxybut-2-enoate following the procedure described for the synthesis of 74E. LC-MS Anal. Calc'd. for $C_{19}H_{28}N_2O_6$, 380.19, found [M+H] 381.2 $T_r$=3.59 min (Method CQ).

929B. Methyl 3-(3-amino-4-((S)-3-isopropylmorpholino)phenyl)-4-methoxybutanoate 929B (Diastereomer mixture) was prepared from 929A following the procedure described for the synthesis of 74F. LC-MS Anal. Calc'd. for $C_{19}H_{30}N_2O_4$, 350.2, found [M+H] 351.2. $T_r$=2.49 min (Method U).

Chiral separation of 929B diastereomer mixture (96:4) gave Diastereomer 1 $T_r$=6.92 min, Diastereomer 2 $T_r$=5.63 min (Method CY).

929B Diastereomer 1: LC-MS Anal. Calc'd. for $C_{19}H_{30}N_2O_4$, 350.2, found [M+H] 351.2 $T_r$=2.54 min (Method U).

929C. Methyl 3-(3-((4-cyanophenyl)amino)-4-((S)-3-isopropylmorpholino)phenyl)-4-methoxybutanoate 929C was prepared from 929B Diastereomer 1 following the procedure described for the synthesis of 78A. LC-MS Anal. Calc'd. for $C_{26}H_{33}N_3O_4$, 451.24, found (M+H) 452.24, $T_r$=3.86 min (Method U).

Example 929: 3-(3-((4-Cyanophenyl)amino)-4-((S)-3-isopropylmorpholino)phenyl)-4-methoxybutanoic acid Example 929 was prepared from 929C following the procedure described for the synthesis of Example 83. LC-MS Anal. Calc'd. for $C_{25}H_{31}N_3O_4$, 437.23, found (M+H) 438.23, $T_r$=1.38 min (Method U). $^1$H NMR (400 MHz, DMSO-$d_6$) δ 7.97 (s, 1H), 7.57 (d, J=8.80 Hz, 2H), 7.11-7.18 (m, 4H), 6.92-6.95 (m, 1H), 3.64-3.68 (m, 3H), 3.44-3.51 (m, 2H), 3.17-3.24 (m, 5H), 3.03-3.04 (m, 1H), 2.80-2.83 (m, 1H), 2.62-2.68 (m, 2H), 2.46-2.50 (m, 1H), 1.73-1.79 (m, 1H), 0.73 (d, J=6.80 Hz, 3H), 0.63 (d, J=6.80 Hz, 3H).

Example 930

Diastereomer 1

3-(3-((4-Chlorophenyl)amino)-4-((S)-3-isopropyl-morpholino)phenyl)-4-methoxybutanoic acid

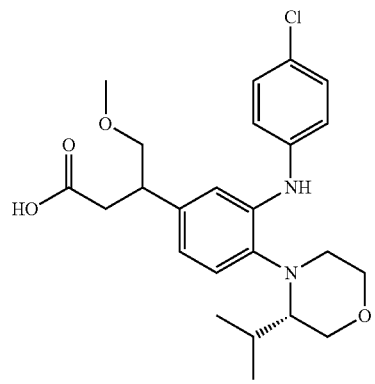 [SMILES: COCC(CC(=O)O)c1ccc(N2CCOC[C@@H]2C(C)C)c(Nc2ccc(Cl)cc2)c1]

Example 930 was prepared from 929B Diastereomer 1 and 1-bromo-4-chlorobenzene following the procedure described for the synthesis of Example 84. LC-MS Anal. Calc'd. for $C_{24}H_{31}ClN_2O_4$, 446.19, found (M+H) 447.19, $T_r$=1.94 min (Method U). $^1$H NMR (400 MHz, DMSO-$d_6$) δ 7.45 (s, 1H), 7.26-7.29 (m, 2H), 7.13-7.18 (m, 3H), 7.09-7.10 (m, 1H), 6.76-6.78 (m, 1H), 3.78-3.81 (m, 1H), 3.69-3.72 (m, 2H), 3.49-3.52 (m, 1H), 3.18-3.22 (m, 5H), 3.03-3.05 (m, 1H), 2.60-2.71 (m, 3H), 2.51-2.55 (m, 1H), 2.41-2.47 (m, 1H), 1.70-1.73 (m, 1H), 0.79 (d, J=6.80 Hz, 3H), 0.67 (d, J=6.80 Hz, 3H).

Example 931

Diastereomer 1

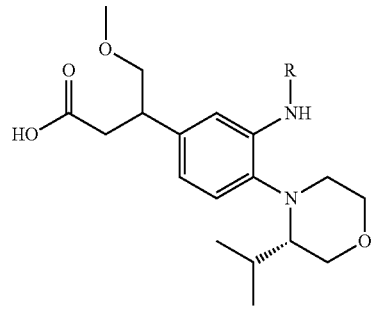

Example 931 was prepared from 929B Diastereomer 1 and corresponding aryl halide following the procedure described for the synthesis of Example 78.

Example 932

Diastereomer 1

3-(3-(3-(4-Cyanophenyl)ureido)-4-((S)-3-isopropyl-morpholino)phenyl)-4-methoxybutanoic acid

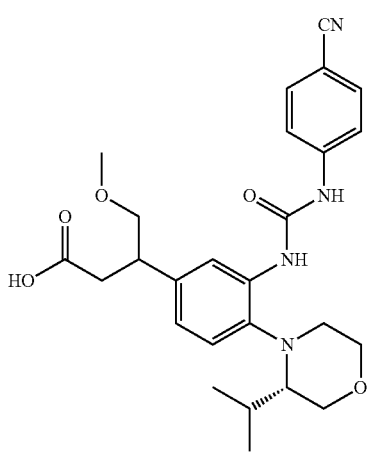 [SMILES: COCC(CC(=O)O)c1ccc(N2CCOC[C@@H]2C(C)C)c(NC(=O)Nc2ccc(C#N)cc2)c1]

932A. Methyl 3-(3-(3-(4-cyanophenyl)ureido)-4-((S)-3-isopropylmorpholino)phenyl)-4-methoxybutanoate

932A was prepared from 929B Diastereomer 1 and 4-isocyanatobenzonitrile following the procedure described for the synthesis of 74G. LC-MS Anal. Calc'd. for $C_{27}H_{34}N_4O_5$, 494.25, found (M+H) 495.25, $T_r$=3.53 min (Method U).

Example 932. 3-(3-(3-(4-Cyanophenyl)ureido)-4-((S)-3-isopropylmorpholino)phenyl)-4-methoxybutanoic acid

Example 932 was prepared from 932A following the procedure described for the synthesis of Example 83. LC-MS Anal. Calc'd. for $C_{26}H_{32}N_4O_5$, 480.23, found (M+H) 481.23, $T_r$=1.62 min (Method O). $^1$H NMR (400 MHz, DMSO-$d_6$) δ10.11 (s, 1H), 8.55 (s, 1H), 8.13 (d, J=2.00 Hz, 1H), 7.70-7.76 (m, 4H), 7.22 (d, J=8.40 Hz, 1H), 6.91 (dd, J=1.60, 8.20 Hz, 1H), 3.72-3.95 (m, 3H), 3.54-3.60 (m, 2H), 3.17-3.26 (m, 4H), 3.02-3.08 (m, 1H), 2.64-2.69 (m, 3H), 2.45-2.51 (m, 1H), 1.60-1.62 (m, 1H), 0.82 (d, J=7.20 Hz, 3H), 0.71 (d, J=6.80 Hz, 3H) (Note: 1H buried under solvent peak).

| Ex. No. | Name | R | $T_r$ min | Method | (M + H) |
|---|---|---|---|---|---|
| 931 | 3-(3-((2-ethoxypyrimidin-5-yl)amino)-4-((S)-3-isopropylmorpholino)phenyl)-4-methoxybutanoic acid | 2-ethoxypyrimidin-5-yl | 1.51 | O | 459 |

Example 933

3-(3-((4-Cyanophenyl)amino)-4-((S)-3-isopropyl-morpholino)phenyl)-4-methoxybutanoic acid (Diastereomer 2)

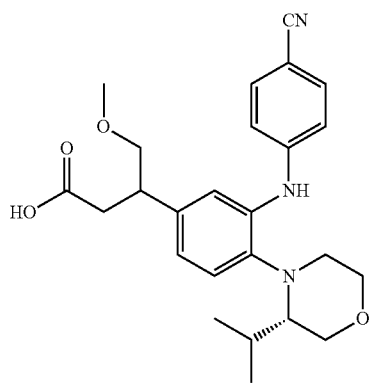 [SMILES: COCC(CC(=O)O)c1ccc(N2CCOC[C@@H]2C(C)C)c(Nc2ccc(C#N)cc2)c1]

933A. Methyl 3-(4-((S)-3-isopropylmorpholino)-3-nitrophenyl)-4-methoxybutanoate 933A was prepared from 74D, (S)-(−)-2,2'-bis(diphenylphosphino)-1,1'-binaphthyl and (E)-methyl 4-methoxybut-2-enoate following the procedure described for the synthesis of 74E. LC-MS Anal. Calc'd. for $C_{19}H_{28}N_2O_6$, 380.19, found [M+H] 381.2. $T_r$=2.68 min (Method CQ).

933B. Methyl 3-(3-amino-4-((S)-3-isopropylmorpholino)phenyl)-4-methoxybutanoate 933B (Diastereomer mixture) was prepared from 933A following the procedure described for the synthesis of 74F. LC-MS Anal. Calc'd. for $C_{19}H_{30}N_2O_4$, 350.2, found [M+H] 351.2, $T_r$=2.49 min (Method U).

Chiral separation of 933B diastereomer mixture (3:97) gave Diastereomer 1 $T_r$=6.92 min, Diastereomer 2 $T_r$=5.63 min (Method CY).

933B Diastereomer 2: LC-MS Anal. Calc'd. for $C_{19}H_{30}N_2O_4$, 350.2, found [M+H] 351.2, $T_r$=3.06 min (Method U).

933C. Methyl 3-(3-((4-cyanophenyl)amino)-4-((S)-3-isopropylmorpholino)phenyl)-4-methoxybutanoate 933C was prepared from 933B Diastereomer 2 following the procedure described for the synthesis of 78A. LC-MS Anal. Calc'd. for $C_{26}H_{33}N_3O_4$, 451.24, found (M+H) 452.24, $T_r$=3.33 min (Method U).

Example 933. 3-(3-((4-Cyanophenyl)amino)-4-((S)-3-isopropylmorpholino)phenyl)-4-methoxybutanoic acid Example 933 was prepared from 933C following the procedure described for the synthesis of Example 83. LC-MS Anal. Calc'd. for $C_{25}H_{31}N_3O_4$, 437.23, found (M+H) 438.23, $T_r$=1.58 min (Method U). $^1$H NMR (400 MHz, DMSO-d$_6$) δ 7.97 (s, 1H), 7.57 (d, J=8.80 Hz, 2H), 7.11-7.18 (m, 4H), 6.92-6.95 (m, 1H), 3.64-3.68 (m, 3H), 3.44-3.51 (m, 2H), 3.17-3.24 (m, 5H), 3.03-3.04 (m, 1H), 2.80-2.83 (m, 1H), 2.62-2.68 (m, 2H), 2.46-2.50 (m, 1H), 1.73-1.79 (m, 1H), 0.73 (d, J=6.80 Hz, 3H), 0.63 (d, J=6.80 Hz, 3H).

Example 934

Diastereomer 2

3-(3-((4-Chlorophenyl)amino)-4-((S)-3-isopropyl-morpholino)phenyl)-4-methoxybutanoic acid

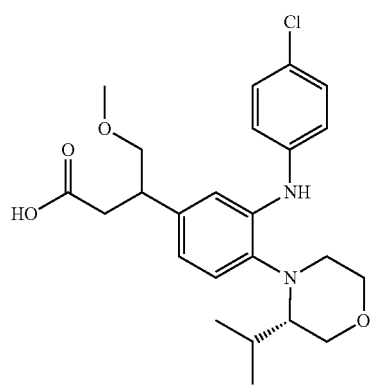

Example 934 was prepared from 933B Diastereomer 2 and 1-bromo-4-chlorobenzene following the procedure described for the synthesis of Example 84. LC-MS Anal. Calc'd. for $C_{24}H_{31}ClN_2O_4$, 446.19, found (M+H) 447.19, $T_r$=1.95 min (Method U). $^1$H NMR (400 MHz, DMSO-d$_6$) δ 7.45 (s, 1H), 7.26-7.29 (m, 2H), 7.13-7.18 (m, 3H), 7.09-7.10 (m, 1H), 6.76-6.78 (m, 1H), 3.78-3.81 (m, 1H), 3.69-3.72 (m, 2H), 3.49-3.52 (m, 1H), 3.18-3.22 (m, 5H), 3.03-3.05 (m, 1H), 2.60-2.71 (m, 3H), 2.51-2.55 (m, 1H), 2.41-2.47 (m, 1H), 1.70-1.73 (m, 1H), 0.79 (d, J=6.80 Hz, 3H), 0.67 (d, J=6.80 Hz, 3H).

Example 935

Diastereomer 2

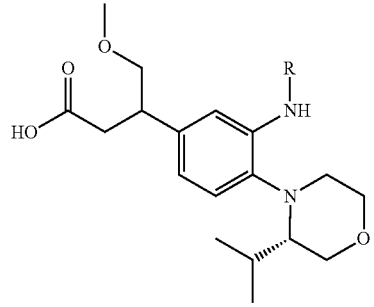

Example 935 was prepared from 933B Diastereomer 2 and corresponding aryl halide following the procedure described for the synthesis of Example 78.

| Ex. No. | Name | R | $T_r$, min | Method | (M + H) |
|---|---|---|---|---|---|
| 935 | 3-(3-((2-ethoxypyrimidin-5-yl)amino)-4-((S)-3-isopropylmorpholino)phenyl)-4-methoxybutanoic acid | | 1.49 | O | 459 |

Example 936

Diastereomer 2

3-(3-(3-(4-Cyanophenyl)ureido)-4-((S)-3-isopropyl-morpholino)phenyl)-4-methoxybutanoic acid

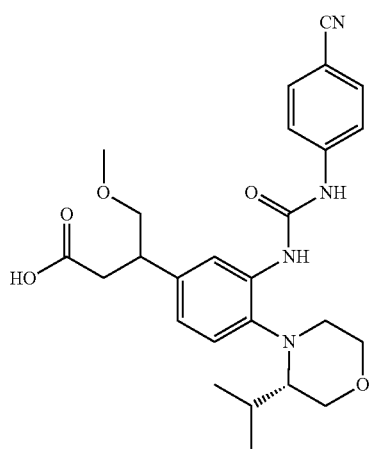 [SMILES: COCC(CC(=O)O)c1ccc(N2CCOC[C@@H]2C(C)C)c(NC(=O)Nc2ccc(C#N)cc2)c1]

936A. Methyl 3-(3-(3-(4-cyanophenyl)ureido)-4-((S)-3-isopropylmorpholino)phenyl)-4-methoxybutanoate 936A was prepared from 933B Diastereomer 2 and 4-isocyanatobenzonitrile following the procedure described for the synthesis of 74G. LC-MS Anal. Calc'd. for $C_{27}H_{34}N_4O_5$, 494.25, found (M+H) 495.25, $T_r$=3.53 min (Method U).

Example 936. 3-(3-(3-(4-Cyanophenyl)ureido)-4-((S)-3-isopropylmorpholino)phenyl)-4-methoxybutanoic acid Example 936 was prepared from 936A following the procedure described for the synthesis of Example 83. LC-MS Anal. Calc'd. for $C_{26}H_{32}N_4O_5$, 480.23, found (M+H) 481.23, $T_r$=1.62 min (Method O). $^1$H NMR (400 MHz, DMSO-$d_6$) δ10.08 (s, 1H), 8.53 (s, 1H), 8.12 (d, J=2.00 Hz, 1H), 7.69-7.75 (m, 4H), 7.21 (d, J=8.40 Hz, 1H), 6.90 (d, J=10.40 Hz, 1H), 3.72-3.98 (m, 3H), 3.52-3.60 (m, 1H), 3.23-3.27 (m, 4H), 3.02-3.08 (m, 1H), 2.64-2.69 (m, 3H), 2.42-2.47 (m, 1H), 1.60-1.62 (m, 1H), 0.82 (d, J=7.20 Hz, 3H), 0.71 (d, J=6.80 Hz, 3H) (Note: 2H buried under solvent peak).

Example 937

Enantiomer 2

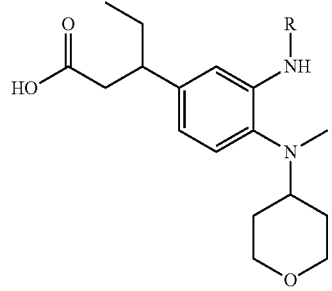

Example 937 was prepared from 870B Enantiomer 2 and corresponding aryl halide following the procedure described for the synthesis of Example 867.

| Ex. No. | Name | R | $T_r$, min | Method | (M + H) |
|---|---|---|---|---|---|
| 937 | 3-(3-((4-chlorophenyl)amino)-4-(methyl(tetrahydro-2H-pyran-4-yl)amino)phenyl) pentanoic acid | | 2.04 | O | 417 |

Example 938

Diastereomer 1

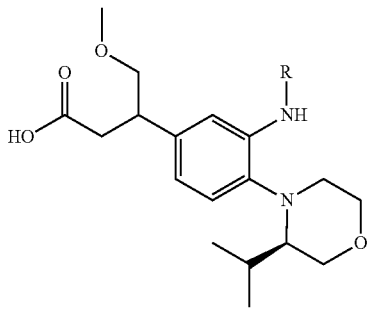

Example 938 was prepared from 909B Diastereomer 1 and corresponding aryl halide following the procedure described for the synthesis of Example 78.

| Ex. No. | Name | R | T$_r$, min | Method | (M + H) |
|---|---|---|---|---|---|
| 938 | 3-(3-((2-ethoxypyrimidin-5-yl)amino)-4-((R)-3-isopropylmorpholino)phenyl)-4-methoxybutanoic acid | (2-ethoxypyrimidin-5-yl) | 1.48 | O | 459 |

Example 939

Enantiomer 1

3-(4-((1-Benzylpiperidin-4-yl)(ethyl)amino)-3-((2-ethoxypyrimidin-5-yl)amino)phenyl)pentanoic acid

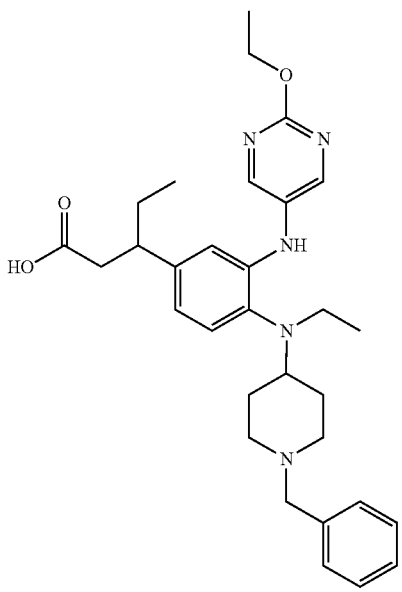 [SMILES: CCOc1ncc(Nc2cc(C(CC)CC(=O)O)ccc2N(CC)C2CCN(Cc3ccccc3)CC2)cn1]

939A. 1-Benzyl-N-ethylpiperidin-4-amine

To a stirred solution MeOH (60 mL) and THF (15 mL) containing 15 g of powdered and activated 4 Å molecular sieves at room temperature was added sequentially 1-benzyl-piperidin-4-one (6 g, 31.7 mmol), 2M solution of ethanamine in THF (15.9 mL, 31.7 mmol) and the reaction mixture was stirred for 6 h. The reaction mixture was cooled to 0° C., added NaBH$_4$ (2.39 g, 63.4 mmol) portionwise and stirred at room temperature for 6 h. The reaction mixture was quenched with ice cold water (250 mL) and concentrated under reduced pressure. Then the aqueous solution was extracted with ethyl acetate (3×100 mL). The combined organic layer was dried over sodium sulfate, filtered and concentrated under reduced pressure gave 939A (colorless liquid, (light brown oil, 5.65 g, 25.9 mmol, 82.0% yield). $^1$H NMR (400 MHz, CDCl$_3$) δ 7.29-7.21 (m, 5H), 3.48 (s, 2H), 2.86-2.82 (m, 2H), 2.69-2.62 (m, 2H), 2.49-2.42 (m, 1H), 2.16-1.99 (m, 4H), 1.96-1.82 (m, 2H), 1.12-1.07 (m, 3H).

939B. 2-(4-Fluorophenyl)-5,5-dimethyl-1,3,2-dioxaborinane

A mixture of 1-bromo-4-fluoro benzene (20 g, 114 mmol), bis(neopentyl glycolato)diboron (31.0 g, 137 mmol) and potassium acetate (33.6 g, 343 mmol) in toluene (200 mL), at room temperature in a sealable flask, was purged with argon for 20 minutes before PdCl$_2$ (dppf).CH$_2$Cl$_2$ Adduct (2.8 g, 3.43 mmol) was added, the flask was sealed and the reaction heated at 80° C. for 2 h. The reaction mixture was cooled to RT and poured into water, extracted with EtOAc (2×150 mL). The combined organic layers were washed with brine, dried over anhydrous sodium sulfate, filtered and concentrated under reduced pressure. The crude sample was purified via silica gel flash chromatography to afford 939B (white solid, 21 g, 96 mmol, 84% yield). $^1$H NMR (400 MHz, DMSO-d$_6$) δ 7.73 (dd, J=8 Hz, 6.6 Hz, 2H), 7.16 (dd, J=10 Hz, 8.8 Hz, 2H), 3.75 (s, 4H), 0.95 (s, 6H).

939C. Methyl 3-(4-fluorophenyl)pentanoate

To a stirring and argon bubbling solution of 939B (5 g, 24.03 mmol) and (E)-methyl pent-2-enoate (4.1 g, 36.1 mmol) in 1,4-dioxane (100 mL) was added 1M sodium hydroxide (21.94 mL, 21.94 mmol) and (R)-BINAP (0.329 g, 0.529 mmol), bubbling continued, then chlorobis(ethylene)rhodium(I) dimer (0.093 g, 0.024 mmol) was added and bubbled argon for another 5 minutes. The reaction mixture was heated at 50° C. for 16 h in sealed tube. Reaction mixture was cooled to room temperature and quenched with acetic acid (1.238 mL, 21.63 mmol) and it was stirred for 5 minutes before partitioned between ethyl acetate (250 ml) and water (100 mL). Aqueous layer was extracted with ethyl acetate (2×100 mL). The combined organic layers were washed with brine, dried over anhydrous sodium sulfate, filtered and concentrated under reduced pressure to afford the crude material. The crude sample was purified via silica gel flash chromatography to afford 939C (pale yellow oil, 4.1 g, 17.55 mmol, 73% yield). $^1$H NMR (400 MHz, DMSO-$d_6$) δ 7.26-7.23 (m, 2H), 7.12-7.08 (m, 2H), 3.57 (s, 3H), 2.92-2.90 (m, 1H), 2.72-2.2.69 (dd, J=15.4 Hz, 8 Hz, 1H), 2.68-2.50 (m, 1H), 1.66-1.51 (m, 2H), 0.70 (t, J=7.4 Hz, 3H).

939D. Methyl 3-(4-fluoro-3-nitrophenyl)pentanoate

To a stirred solution of methyl 3-(4-fluorophenyl)pentanoate (5 g, 23.78 mmol) in $H_2SO_4$ (80 mL, 1501 mmol) under cooled condition, was added potassium nitrate (2.89 g, 28.5 mmol). Then the reaction was stirred for 20 min at room temperature. The reaction mixture was poured into crushed ice, extracted with EtOAc (2×100 mL). The combined organic layers were dried over anhydrous sodium sulfate, filtered and concentrated under reduced pressure to afford the crude material. The crude sample was purified via silica gel flash chromatography to afford 939D (yellow liquid, 4 g, 14.89 mmol, 62.6% yield). $^1$H NMR (400 MHz, DMSO-$d_6$) δ 8.00 (dd, J=7.2 Hz, 2.4 Hz, 1H), 7.72-7.68 (m, 1H), 7.54-7.49 (dd, J=11.2 Hz, 8.8 Hz, 1H), 3.50 (s, 3H), 3.07-3.04 (m, 1H), 2.79-2.73 (m, 1H), 2.69-2.63 (m, 1H), 1.70-1.56 (m, 2H), 0.72 (t, J=7.6 Hz, 3H).

939E. Methyl 3-(4-((1-benzylpiperidin-4-yl)(ethyl) amino)-3-nitrophenyl)pentanoate The mixture of 939D (0.49 g, 1.92 mmol), 939A (0.35 g, 1.60 mmol) and DIPEA (0.56 mL, 3.2 mmol) was stirred and heated at 160° C. for 16 h without solvent. The reaction mixture was cooled to RT and poured into water (50 mL) extracted with EtOAc (3×50 mL). The combined organic layers were washed with brine, dried over anhydrous sodium sulfate, filtered and concentrated under reduced pressure to afford the crude material. The crude sample purified via Neutral Alumina flash chromatography to afford 939E (orange oil, 0.385 g, 0.535 mmol, 33% yield). LC-MS Analysis Calc'd. for $C_{26}H_{35}BrN_3O_4$, 453.263, found [M+H] 454.2, $T_r$=3.874 min (Method U).

939F. Methyl 3-(3-amino-4-((1-benzylpiperidin-4-yl) (ethyl)amino)phenyl)pentanoate To a stirred solution of 939E (0.335 g, 0.739 mmol) in ethanol (10 mL), THF (5 ml) was added water (2.5 mL) followed by ammonium chloride (593 mg, 11.08 mmol). The mixture was stirred for 5 min, and then treated with zinc (724 mg, 11.08 mmol) at 0° C. The mixture was stirred at room temperature for 4 h. The reaction mixture was concentrated under reduced pressure to afford the residue. The residue was diluted with ethyl acetate (30 mL), washed with water (30 mL), brine (30 mL), dried over sodium sulfate, filtered and concentrated to afford the crude residue. The residue was purified by SFC to afford 939F Enantiomer 1 (brown oil, 210 mg, 0.495 mmol, 67% yield). LC-MS Anal. Calc'd. for $C_{26}H_{37}N_3O_2$, 423.289, found [M+H] 424.4, $T_r$=3.133 min (Method U).
Chiral LC purity (92:8) shows 939F Enantiomer 1 $T_r$=13.54 min 939F Enantiomer 2 $T_r$=14.48 min (Method DQ), which was taken to next step without further purification.

939G. Methyl 3-(4-((1-benzylpiperidin-4-yl)(ethyl) amino)-3-((2-ethoxypyrimidin-5-yl)amino)phenyl) pentanoate To the mixture of 939F Enantiomer 1 (30 mg, 0.07 mmol), 5-bromo-2-ethoxypyridine (21.5 mg, 0.106 mmol), Xant-phos (8.2 mg, 0.014 mmol), cesium carbonate (69.2 mg, 0.212 mmol) in 1,4-dioxane (5 mL), argon gas was bubbled for 5 minutes. Then the bis(dibenzylideneacetone)palladium (4.07 mg, 7.08 μmol) was added and the argon gas was bubbled through the mixture for 5 minutes. The reaction mixture was sealed and heated in sealed tube at 110° C. for 6 h. The reaction mixture was allowed to cool to room temperature and concentrated under reduced pressure to afford the residue. The residue was reconstituted in a mixture of ethyl acetate (20 mL) and water (20 mL). The organic layers were separated and the aqueous layers were extracted with ethyl acetate (2×20 mL). The combined organic layers were washed with water (20 mL), brine (20 mL), dried over anhydrous sodium sulfate, filtered and concentrated under reduced pressure to afford crude 939G Enantiomer 1, taken to next step without further purification (light brown solid, 35 mg, 0.017 mmol, 23.55% yield). LC-MS Anal. Calc'd. for $C_{23}H_{43}N_5O_3$, 545.337, found [M+H] 546.4, $T_r$=3.073 min (Method U).

Example 939 Enantiomer 1. 3-(4-((1-Benzylpiperidin-4-yl)(ethyl)amino)-3-((2-ethoxypyrimidin-5-yl) amino)phenyl)pentanoic acid To a stirred solution of 939G Enantiomer 1 (40 mg, 0.073 mmol) in a mixture of MeOH (2 mL), THF (2 mL) and water (2 mL), LiOH (14.04 mg, 0.586 mmol) was added and stirred at room temperature for 4 h. The reaction mixture was concentrated and the aqueous solution was acidified with saturated citric acid solution (pH~4-5). The aqueous layer was diluted with water (5 mL) and extracted with ethyl acetate (2×10 mL). The combined organic layers were washed with water (10 mL), brine (10 mL), dried over anhydrous sodium sulfate, filtered and concentrated under reduced pressure to afford the residue. The residue was purified by preparative LCMS to afford Example 939 Enantiomer 1 (off-white solid, 8.4 mg, 0.016, 21.3% yield). LC-MS Anal. Calc'd. for $C_{31}H_{41}N_5O_3$, 531.321, found [M+H] 532.3, $T_r$=1.785 min (Method O). $^1$H NMR (400 MHz, DMSO-$d_6$) δ 8.41 (s, 2H), 7.30-7.21 (m, 6H), 7.08 (d, J=8.4 Hz, 1H), 6.82 (s, 1H), 6.66 (dd, J=8 Hz, 1.6 Hz, 1H), 4.32-4.26 (m, 2H), 3.37 (s, 2H), 3.17 (s, 1H), 2.99-2.94 (m, 3H), 2.78-2.73 (m, 5H), 2.51-2.39 (m, 2H), 1.70 (d, J=10.4 Hz, 2H), 1.71-1.43 (m, 4H), 1.32 (t, J=7.2 Hz, 3H), 0.81 (t, J=7.2 Hz, 3H), 0.69 (t, J=7.2 Hz, 3H).

Example 940

Enantiomer 1

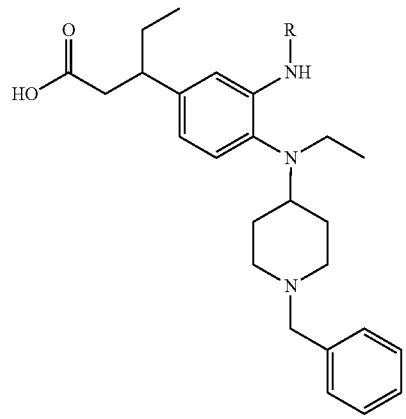

Example 940 was prepared using 939F Enantiomer 1 and the corresponding aryl bromides following the procedure described for the synthesis of Example 939.

| Ex. No. | Name | R | $T_r$ (min) (Method O) | $[M + H]^+$ |
|---|---|---|---|---|
| 940 | 3-(4-((1-benzyl-piperidin-4-yl)(ethyl)amino)-3-((4-cyano-phenyl)amino)phenyl)pentanoic acid | 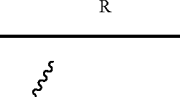 | 1.730 | 511.4 |

Example 943

Enantiomer 2

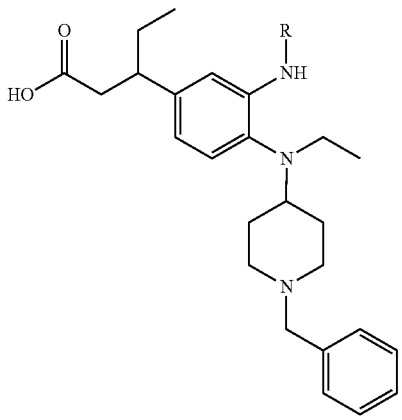

Example 943 Enantiomer 2 were prepared using 942D Enantiomer 2 and the corresponding aryl bromides following the procedure described for the synthesis of Example 939.

| Ex. No. | Name | R | $T_r$ (min) (Method O) | $[M + H]^+$ |
|---|---|---|---|---|
| 943 | 3-(4-((1-benzyl-piperidin-4-yl)(ethyl)amino)-3-((4-cyano-phenyl)amino)phenyl)pentanoic acid | 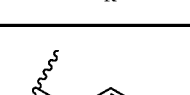 | 1.731 | 511.4 |

Example 945

Diastereomer 1 and Diastereomer 2

3-(3-((2-Ethoxypyrimidin-5-yl)amino)-4-(ethyl(tetrahydrofuran-3-yl)amino)phenyl)pentanoic acid

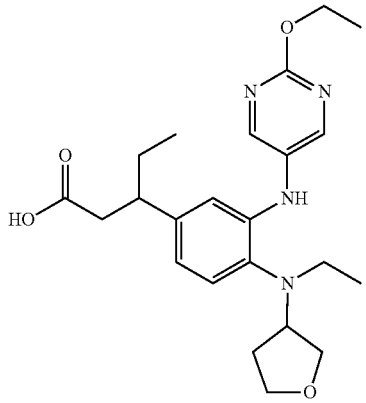 [SMILES: CCOc1ncc(Nc2cc(C(CC)CC(=O)O)ccc2N(CC)C2CCOC2)cn1]

945A. N-Ethyltetrahydrofuran-3-amine

To a stirred solution MeOH (60 mL) and THF (15 mL) containing 14 g of powdered and activated 4 Å molecular sieves at room temperature was added sequentially dihydrofuran-3(2H)-one (6 g, 69.7 mmol), 2M solution of ethanamine in THF (34.8 mL, 69.7 mmol) and the reaction mixture was stirred for 16 h. The reaction mixture was cooled to 0° C., added NaBH₄ (5.27 g, 139 mmol) portionwise and stirred at room temperature for 2 h. The reaction mixture was quenched with ice cold water (250 mL) and concentrated under reduced pressure. Then the aqueous solution was extracted with ethyl acetate (3×100 mL). The combined organic layers were dried over sodium sulfate, filtered and concentrated under reduced pressure gave 945A (light brown oil, 6.7 g, 58.2 mmol, 83.0% yield). $^1$H NMR (400 MHz, CDCl₃) δ 3.99-3.89 (m, 2H), 3.83-3.69 (m, 2H), 3.57-3.53 (m, 1H), 3.4 (br s, 1H), 2.84-2.79 (m, 1H), 2.26-2.20 (m, 1H), 2.00-1.85 (m, 1H), 1.80-1.60 (m, 1H), 1.32-1.21 (m, 3H).

945B. Methyl 3-(4-(ethyl(tetrahydrofuran-3-yl)amino)-3-nitrophenyl)pentanoate

The mixture of 939D (0.931 g, 3.65 mmol), 945A (0.35 g, 3.04 mmol) and DIPEA (1.06 mL, 6.08 mmol) was stirred and heated at 160° C. for 16 h without solvent. The reaction mixture was cooled to RT and poured into water (50 mL) extracted with EtOAc (3×50 mL). The combined organic layers were washed with brine, dried over anhydrous sodium sulfate, filtered and concentrated under reduced pressure to afford the crude material. The crude sample purified via Neutral Alumina flash chromatography to afford 945B (orange oil, 0.485 g, 1.066 mmol, 35% yield). LC-MS Analysis Calc'd. for $C_{18}H_{26}N_2O_5$, 350.184, found [M+H] 351.2, $T_r$=2.940 min (Method DR).

945C. Methyl 3-(3-amino-4-(ethyl(tetrahydrofuran-3-yl)amino)phenyl)pentanoate

To a stirred solution of 945B (0.375 g, 1.07 mmol) in ethanol (10 mL) was carefully added Pd/C (0.114 g, 0.107 mmol). The flask was sequentially evacuated then purged with nitrogen before being pressurized to atmospheric pressure of hydrogen for 3 h. The reaction mixture was filtered through CELITE® bed, washed with ethanol (30 ml) and the filtrate was concentrated under reduced pressure to get 945C Diastereomeric mixture. LC-MS Anal. Calc'd. for $C_{18}H_{28}N_2O_3$, 320.210, found [M+H] 321.2, $T_r$=3.024 min (Method N).

Purification and chiral separation of 945C Diastereomeric mixture gave 945C Diastereomer 1 and 945C Diastereomer 2 as single Diastereomers. Diastereomer 1 $T_r$=3.09 min and Enantiomer 2 $T_r$=3.48 min (Method DS).

945C Diastereomer 1. (0.13 g, 0.812 mmol, 75.8% yield). LC-MS Anal. Calc'd. for $C_{18}H_{28}N_2O_3$, 320.2, found [M+H] 321.2, $T_r$=2.671 min (Method N).

945C Diastereomer 2. (0.125 g, 0.780 mmol, 73% yield). LC-MS Anal. Calc'd. for $C_{18}H_{28}N_2O_3$, 320.2, found [M+H] 321.2, $T_r$=2.510 min (Method N).

945D. Methyl 3-(3-((2-ethoxypyrimidin-5-yl)amino)-4-(ethyl(tetrahydrofuran-3-yl)amino)phenyl)pentanoate To the mixture of 945C Diastereomer 1 (30 mg, 0.094 mmol), 5-bromo-2-ethoxypyridine (28.5 mg, 0.140 mmol), Xantphos (10.8 mg, 0.019 mmol), cesium carbonate (92 mg, 0.281 mmol) in 1,4-dioxane (3 mL), argon gas was bubbled for 5 minutes. Then the bis(dibenzylideneacetone)palladium (5.38 mg, 9.36 µmol) was added and the argon gas was bubbled through the mixture for 5 minutes. The reaction mixture was sealed and heated in sealed tube at 110° C. for 6 h. The reaction mixture was allowed to cool to room temperature and concentrated under reduced pressure to afford the residue. The residue was reconstituted in a mixture of ethyl acetate (20 mL) and water (20 mL). The organic layers were separated and the aqueous layers were extracted with ethyl acetate (2×20 mL). The combined organic layers were washed with water (20 mL), brine (20 mL), dried over anhydrous sodium sulfate, filtered and concentrated under reduced pressure to afford crude, which was purified via flash chromatography to afford the 945D Diastereomer 1 (light brown solid, 34 mg, 0.069 mmol, 73.7% yield). LC-MS Anal. Calc'd. for $C_{24}H_{34}N_4O_4$, 442.258, found [M+H] 443.4, $T_r$=3.027 min (Method BD).

Example 945 Diastereomer 1. 3-(3-((2-Ethoxypyrimidin-5-yl)amino)-4-(ethyl(tetrahydrofuran-3-yl)amino)phenyl)pentanoic acid To a stirred solution of 945D Diastereomer 1 (32 mg, 0.065 mmol) in a mixture of MeOH (2 mL), THF (2 mL) and water (2 mL), LiOH (12.47 mg, 0.521 mmol) was added and stirred at room temperature for 4 h. The reaction mixture was concentrated and the aqueous solution was acidified with saturated citric acid solution (pH~4-5). The aqueous layer was diluted with water (5 mL) and extracted with ethyl acetate (2×10 mL). The combined organic layers were washed with water (10 mL), brine (10 mL), dried over anhydrous sodium sulfate, filtered and concentrated under reduced pressure to afford the residue. The residue was purified by preparative LCMS to afford Example 945 Diastereomer 1 (off-white solid, 3 mg, 6.93 µmol, 10.65% yield). LC-MS Anal. Calc'd. for $C_{23}H_{32}N_4O_4$, 428.242, found [M+H] 429.3, $T_r$=1.604 min (Method O). $^1$H NMR (400 MHz, DMSO-d$_6$) δ 8.41 (s, 2H), 7.34 (s, 1H), 7.15 (d, J=8 Hz, 1H), 6.79 (s, 1H), 6.66 (d, J=8 Hz, 1H), 4.32-4.26 (m, 2H), 3.77-3.72 (m, 2H), 3.68-3.59 (m, 3H), 2.90-2.86 (m, 2H), 2.76 (m, 1H), 2.41-2.39 (m, 1H), 1.87 (m, 1H), 1.75 (m, 1H), 1.58 (m, 1H), 1.45 (m, 1H), 1.32 (t, J=7.2 Hz, 3H), 0.80 (t, J=7 Hz, 3H), 0.70 (t, J=7.2 Hz, 3H).

Example 945 Diastereomer 2. 3-(3-((2-Ethoxypyrimidin-5-yl)amino)-4-(ethyl(tetrahydrofuran-3-yl)amino)phenyl)pentanoic acid Example 945 Diastereomer 2 was synthesized using 945C Diastereomer 2 and 5-bromo-2-ethoxypyrimidine following the procedure described for the synthesis of Example 945 Diastereomer 1 (off-white solid, 8 mg, 0.018, 33.4% yield). LC-MS Anal. Calc'd. for $C_{23}H_{32}N_4O_4$, 428.242, found [M+H] 429.3, $T_r$=1.610 min (Method O). $^1$H NMR (400 MHz, DMSO-d$_6$) δ 8.41 (s, 2H), 7.34 (s, 1H), 7.15 (d, J=8 Hz, 1H), 6.79 (s, 1H), 6.66 (d, J=8 Hz, 1H), 4.32-4.26 (m, 2H), 3.77-3.72 (m, 2H), 3.68-3.59 (m, 3H), 2.90-2.86 (m, 2H), 2.76 (m, 1H), 2.41-2.39 (m, 1H), 1.87 (m, 1H), 1.75 (m, 1H), 1.58 (m, 1H), 1.45 (m, 1H), 1.32 (t, J=7.2 Hz, 3H), 0.80 (t, J=7 Hz, 3H), 0.70 (t, J=7.2 Hz, 3H).

Example 946

Diastereomer 1 and Diastereomer 2

3-(3-(3-(4-Chloro-2-fluorophenyl)ureido)-4-(ethyl(tetrahydrofuran-3-yl)amino)phenyl)pentanoic acid

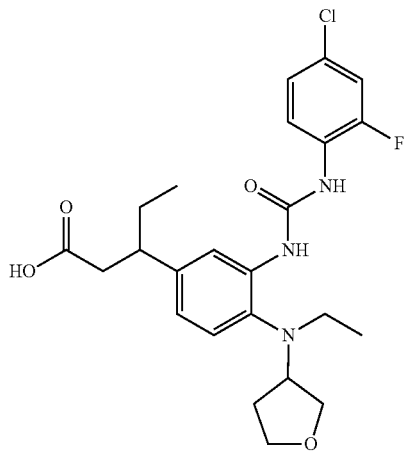 [SMILES: CCC(CC(=O)O)c1ccc(N(CC)C2CCOC2)c(NC(=O)Nc2ccc(Cl)cc2F)c1]

946A. Methyl 3-(3-(3-(4-chloro-2-fluorophenyl)ureido)-4-(ethyl(tetrahydrofuran-3-yl)amino)phenyl)pentanoate To a stirred solution of 945C Diastereomer 1 (25 mg, 0.078 mmol) in DCM (3 mL), was added 4-chloro-2-fluoro-1-isocyanatobenzene (13.38 mg, 0.078 mmol) at room temperature. The reaction mixture was stirred at room temperature for 4 h. The solvent was removed under reduced pressure to afford 946A. The crude material was taken to next step without further purification (off-white solid, 25 mg, 0.022 mmol, 28.9% yield). LC-MS Anal. Calc'd. for $C_{25}H_{31}ClFN_3O_4$, 491.199, found [M+H] 492.2, $T_r$=3.519 min (Method CQ).

Example 946 Diastereomer 1. 3-(3-(3-(4-Chloro-2-fluorophenyl)ureido)-4-(ethyl(tetrahydrofuran-3-yl)amino)phenyl)pentanoic acid To a stirred solution of 946A (11 mg, 0.023 mmol) in MeOH (5 mL), water (5 mL) and THF (5 mL), LiOH (4.28 mg, 0.179 mmol) was added and stirred at room temperature for 4 h. The reaction mixture was concentrated and the aqueous solution was acidified with saturated citric acid solution (pH~4-5). The aqueous solution was extracted with ethyl acetate (3×20 mL). The combined organic layers were dried over sodium sulfate, filtered and concentrated to afford brown colored residue. The residue was purified via preparative LC-MS to afford Example 946 Diastereomer 1 (off-white solid, 2.5 mg, 5.04 μmol, 22.5% yield). LC-MS Anal. Calc'd. for $C_{24}H_{29}ClFN_3O_4$ 477.183, found [M+H] 478.2, $T_r$=1.866 min (Method O). $^1$H NMR (400 MHz, DMSO-$d_6$) δ 9.56 (s, 1H), 8.85 (s, 1H), 8.14 (t, J=9 Hz, 1H), 7.46 (dd, J=2.4 Hz, 1H), 7.21-7.19 (m, 2H), 6.83 (dd, J=8 Hz, 1.6 Hz, 1H), 3.78-3.71 (m, 4H), 3.66-3.62 (m, 2H), 2.90-2.87 (m, 2H), 2.51-2.42 (m, 2H), 1.88-1.86 (m, 1H), 1.69-1.62 (m, 2H), 1.50-1.48 (m, 1H), 0.79 (t, J=7 Hz, 3H), 0.71 (t, J=7.2 Hz, 3H).

Example 946 Diastereomer 2. 3-(3-(3-(4-Chloro-2-fluorophenyl)ureido)-4-(ethyl(tetrahydrofuran-3-yl)amino)phenyl)pentanoic acid Example 946 Diastereomer 2 was synthesized using 945C Diastereomer 2 and 4-chloro-2-fluoro-1-isocyanatobenzene following the procedure described for the synthesis of Example 946 Diastereomer 1 (off-white solid, 16.1 mg, 0.033 mmol, 78% yield). LC-MS Anal. Calc'd. for $C_{24}H_{29}ClFN_3O_4$, 477.183, found [M+H] 478.2, $T_r$=1.856 min (Method O). $^1$H NMR (400 MHz, DMSO-$d_6$) δ 9.56 (s, 1H), 8.85 (s, 1H), 8.14 (t, J=9 Hz, 1H), 7.46 (dd, J=2.4 Hz, 1H), 7.21-7.19 (m, 2H), 6.83 (dd, J=8 Hz, 1.6 Hz, 1H), 3.78-3.71 (m, 4H), 3.66-3.62 (m, 2H), 2.90-2.87 (m, 2H), 2.51-2.42 (m, 2H), 1.88-1.86 (m, 1H), 1.69-1.62 (m, 2H), 1.50-1.48 (m, 1H), 0.79 (t, J=7 Hz, 3H), 0.71 (t, J=7.2 Hz, 3H).

Example 947

Diastereomer 3 and Diastereomer 4

3-(3-((2-Ethoxypyrimidin-5-yl)amino)-4-(ethyl(tetrahydrofuran-3-yl)amino)phenyl)pentanoic acid

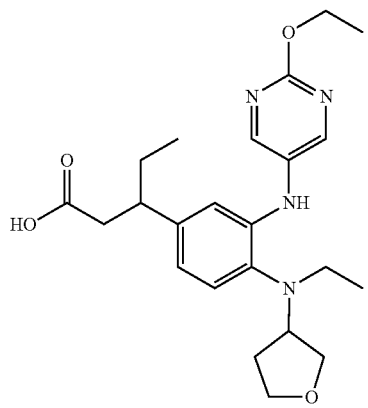 [SMILES: CCOc1ncc(Nc2cc(C(CC)CC(=O)O)ccc2N(CC)C2CCOC2)cn1]

947A. Methyl 3-(4-(ethyl(tetrahydrofuran-3-yl)amino)-3-nitrophenyl)pentanoate 947A was synthesized using 942B and 945A following the procedure described for the synthesis of 945B (orange oil, 0.780 g, 1.994 mmol, 65.6% yield). LC-MS Analysis Calc'd. for $C_{18}H_{26}N_2O_5$, 350.184, found [M+H] 351.2, $T_r$=3.239 min (Method N).

947B. Methyl 3-(3-amino-4-(ethyl(tetrahydrofuran-3-yl)amino)phenyl)pentanoate

947B Diastereomeric mixture was synthesized using 947A following the procedure described for the synthesis of 945C Diastereomeric mixture. LC-MS Anal. Calc'd. for $C_{18}H_{28}N_2O_3$, 320.210, found [M+H] 321.4, $T_r$=2.794 min (Method N).

Purification and chiral separation of 947B Diastereomeric mixture gave 947B Diastereomer 3 and 947B Diastereomer 4 as single Diastereomers. Diastereomer 3 $T_r$=2.86 min and Diastereomer 4 $T_r$=4.14 min (Method CR).

947B Diastereomer 3. (0.220 g, 0.673 mmol, 62.8% yield). LC-MS Anal. Calc'd. for $C_{18}H_{28}N_2O_3$, 320.210, found [M+H] 321.2, $T_r$=2.799 min (Method N).

947B Diastereomer 4. (0.235 g, 0.660 mmol, 61.6% yield). LC-MS Anal. Calc'd. for $C_{18}H_{28}N_2O_3$, 320.210, found [M+H] 321.2, $T_r$=2.796 min (Method N).

947C. Methyl 3-(3-((2-ethoxypyrimidin-5-yl)amino)-4-(ethyl(tetrahydrofuran-3-yl)amino)phenyl)pentanoate 947C Diastereomer 3 was synthesized using 947B Diastereomer 3 and 5-bromo-2-ethoxypyrimidine following the procedure described for the synthesis of 945D Diastereomer 1 (light brown solid, 35 mg, 0.075 mmol, 85% yield). LC-MS Anal. Calc'd. for $C_{24}H_{34}N_4O_4$, 442.258, found [M+H] 443.4, $T_r$=3.029 min (Method BD).

Example 947 Diastereomer 3. 3-(3-((2-Ethoxypyrimidin-5-yl)amino)-4-(ethyl(tetrahydrofuran-3-yl)amino)phenyl)pentanoic acid Example 947 Diastereomer 3 was synthesized using 947C Diastereomer 3 following the procedure described for the synthesis of Example 945 Diastereomer 1 (off-white solid, 5 mg, 0.012 mmol, 17.94% yield). LC-MS Anal. Calc'd. for $C_{23}H_{32}N_4O_4$, 428.242, found [M+H] 429.2, $T_r$=1.609 min (Method O). $^1$H NMR (400 MHz, DMSO-$d_6$) δ 8.41 (s, 2H), 7.34 (s, 1H), 7.15 (d, J=8 Hz, 1H), 6.79 (s, 1H), 6.66 (d, J=8 Hz, 1H), 4.32-4.26 (m, 2H), 3.77-3.72 (m, 2H), 3.68-3.59 (m, 3H), 2.90-2.86 (m, 2H), 2.76 (m, 1H), 2.41-2.39 (m, 1H), 1.87 (m, 1H), 1.75 (m, 1H), 1.58 (m, 1H), 1.45 (m, 1H), 1.32 (t, J=7.2 Hz, 3H), 0.80 (t, J=7 Hz, 3H), 0.70 (t, J=7.2 Hz, 3H).

Example 947

Diastereomer 4. 3-(3-((2-Ethoxypyrimidin-5-yl)amino)-4-(ethyl(tetrahydrofuran-3-yl)amino)phenyl)pentanoic acid Example 947 Diastereomer 4 was synthesized using 947B Diastereomer 4 and 5-bromo-2-ethoxypyrimidine following the procedure described for the synthesis of Example 945 Diastereomer 1 (off-white solid, 2.3 mg, 5.23 μmol, 7.88% yield). LC-MS Anal. Calc'd. for $C_{23}H_{32}N_4O_4$, 428.242, found [M+H] 429.2, $T_r$=1.615 (Method O). $^1$H NMR (400 MHz, DMSO-$d_6$) δ 8.41 (s, 2H), 7.34 (s, 1H), 7.15 (d, J=8 Hz, 1H), 6.79 (s, 1H), 6.66 (d, J=8 Hz, 1H), 4.32-4.26 (m, 2H), 3.77-3.72 (m, 2H), 3.68-3.59 (m, 3H), 2.90-2.86 (m, 2H), 2.76 (m, 1H), 2.41-2.39 (m, 1H), 1.87 (m, 1H), 1.75 (m, 1H), 1.58 (m, 1H), 1.45 (m, 1H), 1.32 (t, J=7.2 Hz, 3H), 0.80 (t, J=7 Hz, 3H), 0.70 (t, J=7.2 Hz, 3H).

Example 948

Diastereomer 3 and Diastereomer 4

3-(3-(3-(4-Chloro-2-fluorophenyl)ureido)-4-(ethyl (tetrahydrofuran-3-yl)amino)phenyl)pentanoic acid

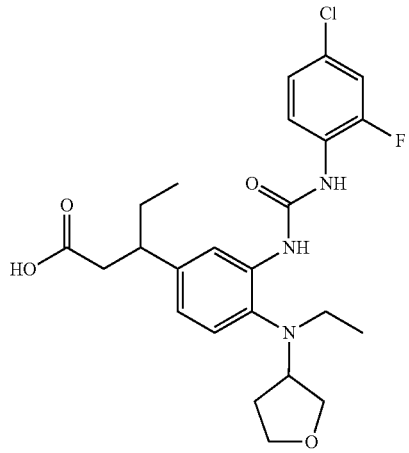

948A. Methyl 3-(3-(3-(4-chloro-2-fluorophenyl) ureido)-4-(ethyl(tetrahydrofuran-3-yl)amino)phenyl) pentanoate 948A was synthesized using 947B Diastereomer 3 and 4-chloro-2-fluoro-1-isocyanatobenzene following the procedure described for the synthesis of 946A (off-white solid, 34 mg, 0.061 mmol, 78% yield). LC-MS Anal. Calc'd. for $C_{25}H_{31}ClFN_3O_4$, 491.199, found [M+H] 492.2, $T_r$=3.521 min (Method CQ).

Example 948 Diastereomer 3. 3-(3-(3-(4-Chloro-2-fluorophenyl)ureido)-4-(ethyl(tetrahydrofuran-3-yl) amino)phenyl)pentanoic acid Example 948 Diastereomer 3 was synthesized using 948A following the procedure described for the synthesis of Example 946 Diastereomer 1 (off-white solid, 22.6 mg, 0.047 mmol, 87% yield). LC-MS Anal. Calc'd. for $C_{24}H_{29}ClFN_3O_4$ 477.183, found [M+H] 478.2, $T_r$=1.858 min (Method O). $^1$H NMR (400 MHz, DMSO-d$_6$) δ 9.56 (s, 1H), 8.85 (s, 1H), 8.14 (t, J=9 Hz, 1H), 7.46 (dd, J=2.4 Hz, 1H), 7.21-7.19 (m, 2H), 6.83 (dd, J=8 Hz, 1.6 Hz, 1H), 3.78-3.71 (m, 4H), 3.66-3.62 (m, 2H), 2.90-2.87 (m, 2H), 2.51-2.42 (m, 2H), 1.88-1.86 (m, 1H), 1.69-1.62 (m, 2H), 1.50-1.48 (m, 1H), 0.79 (t, J=7 Hz, 3H), 0.71 (t, J=7.2 Hz, 3H).

Example 948 Diastereomer 4. 3-(3-(3-(4-Chloro-2-fluorophenyl)ureido)-4-(ethyl(tetrahydrofuran-3-yl) amino)phenyl)pentanoic acid Example 948 Diastereomer 4 was synthesized using 947B Diastereomer 4 and 4-chloro-2-fluoro-1-isocyanatobenzene following the procedure described for the synthesis of Example 946 Diastereomer 1 (off-white solid, 15.8 mg, 0.033 mmol, 69.7% yield). LC-MS Anal. Calc'd. for $C_{24}H_{29}ClFN_3O_4$, 477.183, found [M+H] 478.2, $T_r$=1.857 min (Method O). $^1$H NMR (400 MHz, DMSO-d$_6$) δ 9.56 (s, 1H), 8.85 (s, 1H), 8.14 (t, J=9 Hz, 1H), 7.46 (dd, J=2.4 Hz, 1H), 7.21-7.19 (m, 2H), 6.83 (dd, J=8 Hz, 1.6 Hz, 1H), 3.78-3.71 (m, 4H), 3.66-3.62 (m, 2H), 2.90-2.87 (m, 2H), 2.51-2.42 (m, 2H), 1.88-1.86 (m, 1H), 1.69-1.62 (m, 2H), 1.50-1.48 (m, 1H), 0.79 (t, J=7 Hz, 3H), 0.71 (t, J=7.2 Hz, 3H).

Example 949

(+/−)-3-(4-(Diisobutylamino)-3-(2-(p-tolyl)acetamido)phenyl)pentanoic acid

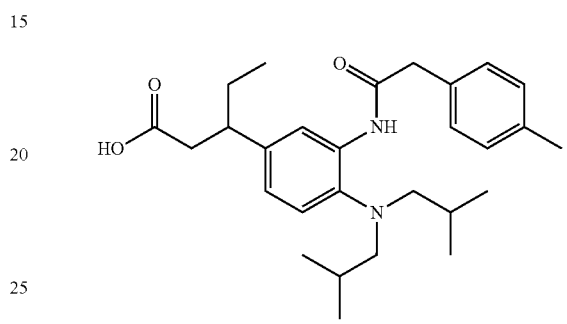

949A. (+/−)-Methyl 3-(4-(diisobutylamino)-3-nitrophenyl)pentanoate

To a homogeneous mixture of 4-(5,5-dimethyl-1,3,2-dioxaborinan-2-yl)-N,N-diisobutyl-2-nitroaniline (WO 14/150677; 2.00 g, 5.52 mmol) in anhydrous dioxane (12 mL), in a sealable tube at rt, was added (E)-methyl pent-2-enoate (1.89 g, 16.56 mmol) followed by NaOH (aq) (1M solution, 5 mL, 5.00 mmol). The resulting mixture was sequentially evacuated then purged with nitrogen, for a total of three cycles, before chloro(1,5-cyclooctadiene)rhodium (I) dimer (0.14 g, 0.28 mmol) was added. The resulting mixture was again sequentially evacuated then purged with nitrogen, for a total of three cycles, before the tube was capped and the reaction warmed to 50° C. for 17 hours. After cooling to room temperature, the reaction mixture was treated with acetic acid (0.32 mL, 5.52 mmol) and stirred for 5 minutes before being partitioned between EtOAc and water. The layers were separated and the aqueous layer was extracted again with EtOAc. The organic extracts were combined, washed twice with water then once with brine before being concentrated in vacuo to afford an oil which was purified on an Isco CombiFlash System: REDISEP® normal phase silica flash column (80 g), detection wavelength=254 nm, run time=40 min, flow rate=60 mL/min. Mobile Phase: (5 min at 100% hexane then 20 min gradient from 0-25% EtOAc in hexane). Concentration of the appropriate fractions afforded (+/−)-methyl 3-(4-(diisobutylamino)-3-nitrophenyl)pentanoate (1.27 g, 63% yield) as an orange oil. $^1$H NMR (400 MHz, chloroform-d) δ 7.50 (d, J=2.2 Hz, 1H), 7.20 (dd, J=8.7, 2.3 Hz, 1H), 7.05 (d, J=8.7 Hz, 1H), 3.59 (s, 3H), 3.01-2.92 (m, 1H), 2.88 (d, J=7.2 Hz, 4H), 2.66-2.48 (m, 2H), 1.92-1.82 (m, 2H), 1.73-1.51 (m, 2H), 0.84-0.78 (m, 15H). MS(ES): m/z=365 [M+H]$^+$, $T_r$=1.23 min (Method A).

949B. (+/−)-Methyl 3-(3-amino-4-(diisobutylamino) phenyl)pentanoate

To a sealable hydrogen stirring flask, charged with (+/−)-methyl 3-(4-(diisobutylamino)-3-nitrophenyl)pentanoate (1.22 g, 3.35 mmol) and 10% Pd—C (0.23 g, 0.22 mmol) and under flow of nitrogen, was carefully added EtOAc (14 mL). The resulting mixture was sequentially evacuated then purged with nitrogen before the flask was pressured to 40 psi of hydrogen and stirred at ambient temperature for 4 hours. The reaction mixture was filtered through a pad of CELITE® which was then thoroughly rinsed with EtOAc. The combined filtrates were concentrated in vacuo to afford (+/−)-methyl 3-(3-amino-4-(diisobutylamino)phenyl)pentanoate as a gold-brown oil (1.05 g, 94% yield), which was used without further purification. $^1$H NMR (400 MHz, chloroform-d) δ 6.96 (d, J=7.9 Hz, 1H), 6.54-6.48 (m, 2H), 4.08 (br. s., 2H), 3.59 (s, 3H), 2.90-2.82 (m, 1H), 2.58-2.53 (m, 6H), 1.79-1.61 (m, 4H), 0.89 (d, J=6.6 Hz, 12H), 0.78 (t, J=7.3 Hz, 3H). MS(ES): m/z=335 [M+H]$^+$, T$_r$=0.91 min (Method A).

949C. (+/−)-Methyl 3-(4-(diisobutylamino)-3-(2-(p-tolyl)acetamido)phenyl)pentanoate To a homogeneous mixture of (+/−)-methyl 3-(3-amino-4-(diisobutylamino)phenyl)pentanoate (50 mg, 0.15 mmol) in anhydrous THF (2 mL), at room temperature in a sealable vial, was added 2-(p-tolyl)-acetic acid (26.9 mg, 0.18 mmol) followed by BOP (79.0 mg, 0.18 mmol) and TEA (0.10 mL, 0.72 mmol). The vial was capped and the mixture was stirred at ambient temperature for 87 hours. The reaction mixture was quenched with water then thoroughly extracted with Et$_2$O. The organic layers were combined and washed with brine then concentrated in vacuo to afford (+/−)-methyl 3-(4-(diisobutylamino)-3-(2-(p-tolyl)acetamido)phenyl) pentanoate as an oil (70 mg) which was used without further purification. MS(ES): m/z=467 [M+H]$^+$, T$_r$=1.23 min (Method A).

Example 949 (+/−)-3-(4-(Diisobutylamino)-3-(2-(p-tolyl)acetamido)phenyl)pentanoic acid To a mixture of (+/−)-methyl 3-(4-(diisobutylamino)-3-(2-(p-tolyl)acetamido)phenyl)pentanoate (0.07 g, 0.15 mmol) in anhydrous THF (0.5 mL) and MeOH (0.2 mL), at room temperature in a sealable vial, was added NaOH (aq) (1M solution, 0.75 mL, 0.75 mmol). The vial was capped and the mixture was stirred at ambient temperature for 24 hours before being warmed to 50° C. After 3 hours, LiOH (aq) (1M solution, 0.8 mL, 0.80 mmol) was added and stirring was continued at 50° C. After 17 hours, the reaction was cooled to room temperature then treated with acetic acid (until pH 5-6 on BDH pH 0-14 test strips). The mixture was then partitioned between EtOAc and brine. The layers were separated and the aqueous layer was extracted once more with EtOAc. The organic extracts were combined and concentrated in vacuo to afford a residue which was diluted with DMF then purified by preparative RP HPLC (MeCN/H$_2$O gradient+0.1% TFA) afford Example 949 53 mg; 78% yield. $^1$H NMR (500 MHz, DMSO-d$_6$) δ 8.72 (s, 1H), 8.12 (s, 1H), 7.27-7.09 (m, 5H), 6.87 (d, J=7.9 Hz, 1H), 3.64 (s, 2H), 2.85-2.75 (m, 1H), 2.55-2.33 (m, ~6H (integration distorted by solvent peak)), 2.28 (s, 3H), 1.65-1.37 (m, 4H), 0.76 (d, J=6.4 Hz, 12H), 0.68 (t, J=7.2 Hz, 3H). MS(ES): m/z=453 [M+H]$^+$, HPLC T$_r$: 2.31 min (Method C).

Example 950

(+/−)-3-(3-(2-(4-Cyanophenyl)acetamido)-4-(diisobutylamino)phenyl)pentanoic acid

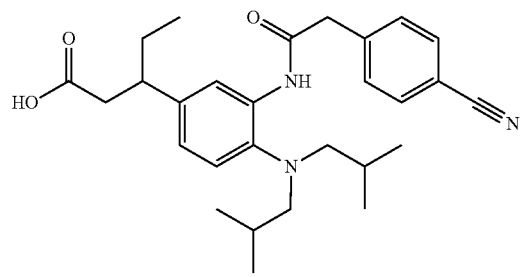 [SMILES: CCC(CC(=O)O)c1ccc(N(CC(C)C)CC(C)C)c(NC(=O)Cc2ccc(C#N)cc2)c1]

950A. (+/−)-Methyl 3-(3-(2-(4-cyanophenyl)acetamido)-4-(diisobutylamino)phenyl)pentanoate To a homogeneous mixture of (+/−)-methyl 3-(3-amino-4-(diisobutylamino)phenyl)pentanoate (50 mg, 0.15 mmol) in anhydrous THF (2 mL), at room temperature in a sealable vial, was added 2-(4-cyanophenyl)acetic acid (28.9 mg, 0.18 mmol) followed by BOP (79 mg, 0.18 mmol) and TEA (0.1 mL, 0.72 mmol). The vial was capped and the mixture was stirred at ambient temperature for 87 hours. The reaction mixture was quenched with water then thoroughly extracted with Et$_2$O. The organic layers were combined and washed with brine then concentrated in vacuo to afford (+/−)-methyl 3-(3-(2-(4-cyanophenyl)acetamido)-4-(diisobutylamino) phenyl)pentanoate as an oil (78 mg) which was used without further purification. MS(ES): m/z=478 [M+H]$^+$, T$_r$=1.15 min (Method A).

Example 950. 3-(3-(2-(4-Cyanophenyl)acetamido)-4-(diisobutylamino)phenyl)pentanoic acid To a mixture of (+/−)-methyl 3-(3-(2-(4-cyanophenyl) acetamido)-4-(diisobutylamino)phenyl)pentanoate (0.07 g, 0.15 mmol) in anhydrous THF (0.5 mL) and MeOH (0.2 mL), at room temperature in a sealable vial, was added NaOH (aq) (1M solution, 0.75 mL, 0.75 mmol). The vial was capped and the mixture was stirred at ambient temperature for 24 hours before being warmed to 50° C. After 3 hours, LiOH (aq) (1M solution, 0.8 mL, 0.80 mmol) was added and stirring was continued at 50° C. After 17 hours, the reaction was cooled to room temperature then treated with acetic acid (until pH 5-6 on BDH pH 0-14 test strips). The mixture was then partitioned between EtOAc and brine. The layers were separated and the aqueous layer was extracted once more with EtOAc. The organic extracts were combined and concentrated in vacuo to afford a residue which was diluted with DMF then purified by preparative RP HPLC (MeCN/H$_2$O gradient+10-mM NH$_4$OAc) to afford Example 950 (23 mg; 33% yield). $^1$H NMR (500 MHz, DMSO-d$_6$) δ 8.85 (s, 1H), 8.05 (s, 1H), 7.82 (d, J=7.9 Hz, 2H), 7.53 (d, J=7.7 Hz, 2H), 7.20 (d, J=8.2 Hz, 1H), 6.90 (d, J=8.1 Hz, 1H), 3.85 (s, 2H), 2.86-2.75 (m, 1H), 2.56-2.34 (m, 6H (integration distorted by solvent peak)), 1.68-1.39

(m, 4H), 0.80 (d, J=6.5 Hz, 12H), 0.68 (t, J=7.2 Hz, 3H). MS(ES): m/z=464 [M+H]⁺, HPLC T$_r$: 2.10 min (Method C).

Example 951

(+/−)-3-(4-(Cyclohexyl(isobutyl)amino)-2-fluoro-5-(3-(p-tolyl)ureido)phenyl)pentanoic acid

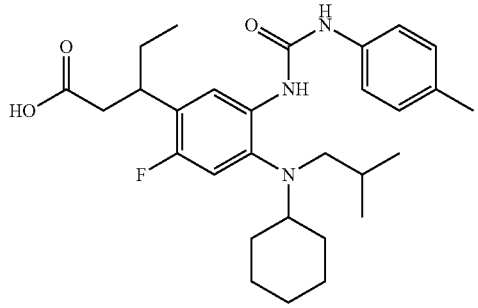 [SMILES: CCC(CC(=O)O)c1cc(NC(=O)Nc2ccc(C)cc2)c(N(CC(C)C)C2CCCCC2)cc1F]

951A. 4-Bromo-N-cyclohexyl-5-fluoro-N-isobutyl-2-nitroaniline

To a homogeneous mixture of 5-bromo-2,4-difluoronitrobenzene (2.0 g, 8.40 mmol) in anhydrous NMP (8 mL), at room temperature under nitrogen, was added DIPEA (4.40 mL, 25.20 mmol) followed by N-isobutyl-cyclohexanamine (1.44 g, 9.24 mmol). The mixture was stirred at 110° C. for 23 hours, then cooled to room temperature, before being diluted with Et$_2$O then washed twice with 1N HCl (aq). The organic layer was washed with a saturated aqueous NaHCO$_3$ solution, then brine, before being dried (Na$_2$SO$_4$), filtered and concentrated in vacuo to afford an oil which was purified on an Isco CombiFlash System Purified REDISEP® normal phase silica flash column (80 g), detection wavelength=254 nm, run time=35 min. Mobile Phase: (5 min at 100% hexane then 20 min gradient from 0-25% EtOAc in hexane). Concentration of the appropriate fractions afforded 4-bromo-N-cyclohexyl-5-fluoro-N-isobutyl-2-nitroaniline (2.71 g, 86% yield) as a red-orange solid. ¹H NMR (400 MHz, DMSO-d$_6$) δ 8.14 (d, J=7.5 Hz, 1H), 7.41 (d, J=11.4 Hz, 1H), 2.90 (d, J=7.3 Hz, 2H), 2.87-2.77 (m, 1H), 1.73-1.61 (m, 4H), 1.59-1.35 (m, 4H), 1.14-1.00 (m, 3H), 0.83 (d, J=6.6 Hz, 6H). MS(ES): m/z=373 [M+H]⁺, T$_r$=1.32 min (Method A).

951B. N-Cyclohexyl-4-(5,5-dimethyl-1,3,2-dioxaborinan-2-yl)-5-fluoro-N-isobutyl-2-nitroaniline A mixture of 4-bromo-N-cyclohexyl-5-fluoro-N-isobutyl-2-nitroaniline (1.50 g, 4.02 mmol), 5,5,5',5'-tetramethyl-2,2'-bi(1,3,2-dioxaborinane) (1.21 g, 5.34 mmol) and potassium acetate (1.18 g, 12.06 mmol) in DMSO (6.70 ml), at room temperature in a sealable flask, was purged with argon for 20 minutes before PdCl$_2$ (dppf).CH$_2$Cl$_2$ Adduct (0.097 g, 0.13 mmol) was added, the flask was sealed and the reaction heated at 80° C. for 6 hours. The cooled reaction mixture was filtered to remove any solids, which were then rinsed with DCM, before combined filtrate was purified on Isco CombiFlash System: REDISEP® normal phase silica flash column (120 g), detection wavelength=254 nm, run time=45 min, flow rate=85 mL/min. Mobile Phase: (10 min at 100% hexane then 30 min gradient from 0-50% EtOAc in hexane). Concentration of the appropriate fractions afforded N-cyclohexyl-4-(5,5-dimethyl-1,3,2-dioxaborinan-2-yl)-5-fluoro-N-isobutyl-2-nitroaniline (0.80 g, 49% yield) as an oil. ¹H NMR (400 MHz, chloroform-d) δ 8.13 (d, J=6.7 Hz, 1H), 6.65 (d, J=12.3 Hz, 1H), 3.76 (s, 4H), 2.97-2.89 (m, 1H), 2.88 (d, J=7.2 Hz, 2H), 1.84-1.73 (m, 6H), 1.62-1.54 (m, 3H), 1.42-1.36 (m, 2H), 1.02 (s, 6H), 0.88 (d, J=6.6 Hz, 6H). Expected product appears as corresponding boronic acid under acidic MS conditions: MS(ES): m/z=339 [M+H]⁺, T$_r$=1.10 min (Method A).

951C. (+/−)-Methyl 3-(4-(cyclohexyl(isobutyl) amino)-2-fluoro-5-nitrophenyl)pentanoate To a homogeneous mixture of N-cyclohexyl-4-(5,5-dimethyl-1,3,2-dioxaborinan-2-yl)-5-fluoro-N-isobutyl-2-nitroaniline (802 mg, 1.97 mmol) in anhydrous dioxane (5 mL), in a sealable tube at room temperature, was added methyl 2-pentenoate (676 mg, 5.92 mmol) followed by NaOH (aq) (1M solution, 1.8 mL, 1.80 mmol). The resulting mixture was sequentially evacuated then purged with nitrogen for a total of three cycles before chloro(1,5-cyclooctadiene)rhodium(I) dimer (48.7 mg, 0.10 mmol) was added. The resulting mixture was again sequentially evacuated then purged with nitrogen for a total of three cycles, before the tube was capped and the reaction warmed to 50° C. for 6 hours. After cooling to room temperature, the reaction was quenched with acetic acid (0.10 mL, 1.78 mmol) and stirred for 5 minutes before being partitioned between EtOAc and water. The layers were separated and the aqueous layer was extracted again with EtOAc. The organic extracts were combined, washed twice with water then once with brine before being concentrated in vacuo to afford an oil which was purified on an Isco CombiFlash System Purified REDISEP® normal phase silica flash column (40 g), detection wavelength=254 nm, run time=40 min, flow rate=40 mL/min. Mobile Phase: (5 min at 100% hexane then 25 min gradient from 0-25% EtOAc in hexane). Concentration of the appropriate fractions afforded (+/−)-methyl 3-(4-(cyclohexyl(isobutyl)amino)-2-fluoro-5-nitrophenyl)pentanoate (164 mg, 20% yield) as an oil. ¹H NMR (400 MHz, chloroform-d) δ 7.59 (d, J=7.9 Hz, 1H), 6.76 (d, J=12.8 Hz, 1H), 3.62 (s, 3H), 3.30-3.21 (m, 1H), 2.92-2.79 (m, 3H), 2.70-2.55 (m, 2H), 1.86-1.81 (m, 2H), 1.78-1.58 (m, 6H), 1.45-1.35 (m, 2H), 1.27-1.14 (m, 2H), 1.10-1.01 (m, 1H), 0.91-0.80 (m, 9H). MS(ES): m/z=409 [M+H]⁺, T$_r$=1.29 min (Method A).

951D. (+/−)-Methyl 3-(5-amino-4-(cyclohexyl (isobutyl)amino)-2-fluorophenyl)pentanoate To a sealable hydrogen stirring flask, charged with methyl 3-(4-(cyclohexyl(isobutyl)amino)-2-fluoro-5-nitrophenyl) pentanoate (164 mg, 0.40 mmol) and 10% Pd—C (25 mg, 0.02 mmol) was carefully added EtOAc (2 mL). The flask was sequentially evacuated then purged with nitrogen before being pressurized to 40 psi of hydrogen. After 2 hours of stirring at ambient temperature, the reaction mixture was filtered through a pad of CELITE® which was then thoroughly rinsed with DCM. The combined filtrates were concentrated in vacuo to afford an oil which was purified on Isco CombiFlash System: REDISEP® normal phase silica flash column (24 g), detection wavelength=254 nm, run time=40 min, flow rate=35 mL/min. Mobile Phase: (5 min at 100% hexane then 20 min gradient from 0-50% EtOAc in hexane). Concentration of the appropriate fractions afforded (+/−)-methyl 3-(5-amino-4-(cyclohexyl(isobutyl)amino)-2- fluorophenyl)pentanoate (57 mg, 37% yield) as an oil. MS(ES): m/z=379 [M+14]⁺, T$_r$=0.98 min (Method A).

Example 951 (+/−)-3-(4-(Cyclohexyl(isobutyl)amino)-2-fluoro-5-(3-(p-tolyl)-ureido)phenyl)pentanoic acid To a homogeneous mixture of (+/−)-methyl 3-(5-amino-4-(cyclohexyl(isobutyl)amino)-2-fluoro-phenyl)pentanoate (28 mg, 0.07 mmol) in THF (2 mL), at room temperature in a sealable vial, was added 1-isocyanato-4-methylbenzene (12 mg, 0.09 mmol). The resulting mixture was stirred at ambient temperature for 22 hours before 1-isocyanato-4-methylbenzene (12 mg, 0.09 mmol) was added and stirring continued for another 96 hours. The reaction was then treated with MeOH (0.5 mL), followed by addition of LiOH (aq) (1M solution, 0.5 mL, 0.50 mmol). After 6 hours, the reaction was treated with acetic acid (until pH 5-6 on BDH pH 0-14 test strips). The mixture was then partitioned between EtOAc and brine. The layers were separated and the aqueous layer was extracted once more with EtOAc. The organic extracts were combined and concentrated in vacuo to afford a residue (43 mg) which was diluted with DMF then purified by preparative RP HPLC (MeCN/H$_2$O gradient+10-mM NH$_4$OAc) to afford Example 951 (30 mg, 81% yield). $^1$H NMR (500 MHz, DMSO-d$_6$) δ 9.37 (s, 1H), 7.88 (d, J=7.8 Hz, 1H), 7.77 (s, 1H), 7.34 (d, J=7.9 Hz, 2H), 7.09 (d, J=8.0 Hz, 2H), 6.97 (d, J=11.7 Hz, 1H), 3.22-3.09 (m, 1H), 2.75-2.71 (m, 1H), 2.60-2.54 (m, 3H (integration distorted by solvent peak)), 2.24 (s, 3H), 1.92-1.80 (m, 3H), 1.72-1.59 (m, 3H), 1.55-1.43 (m, 2H), 1.36-0.96 (m, 6H), 0.81 (d, J=6.3 Hz, 6H), 0.74 (t, J=7.2 Hz, 3H). MS(ES): m/z=498 [M+H]⁺, T$_r$=2.35 min (Method C).

Example 952

(+/−)-3-(4-(Cyclohexyl(isobutyl)amino)-5-(3-(4-ethoxyphenyl)ureido)-2-fluorophenyl)pentanoic acid

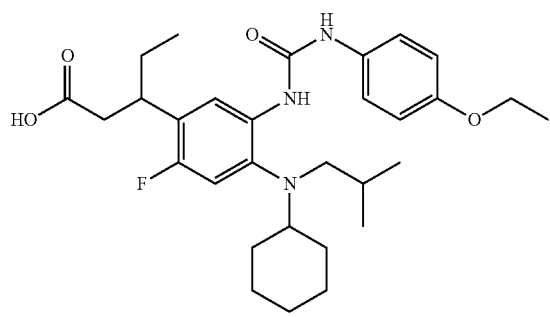 [SMILES: CCOc1ccc(NC(=O)Nc2cc(C(CC)CC(=O)O)c(F)cc2N(CC(C)C)C2CCCCC2)cc1]

Example 952 (38 mg, 98% yield) was prepared following a procedure analogous to that for the synthesis of Example 951, except that 1-ethoxy-4-isocyanatobenzene (16 mg, 0.098 mmol) was used instead of 1-isocyanato-4-methylbenzene. $^1$H NMR (500 MHz, DMSO-d$_6$) δ 9.24 (br. s., 1H), 7.88 (d, J=8.1 Hz, 1H), 7.72 (s, 1H), 7.32 (d, J=8.7 Hz, 2H), 6.96 (d, J=11.8 Hz, 1H), 6.85 (d, J=8.8 Hz, 2H), 3.97 (q, J=7.0 Hz, 2H), 3.21-3.08 (m, 1H), 2.80-2.71 (m, 1H), 2.59-2.43 (m, 5H (integration distorted by solvent peak)), 1.85-1.74 (m, 2H), 1.72-1.56 (m, 3H), 1.55-1.40 (m, 2H), 1.30 (t, J=6.9 Hz, 3H), 1.24-0.90 (m, 5H), 0.80 (d, J=6.4 Hz, 6H), 0.73 (t, J=7.2 Hz, 3H). MS(ES): m/z=528 [M+H]⁺, HPLC T$_r$: 2.30 min (Method C).

Example 953

Enantiomer 1

3-(4-(Diisobutylamino)-3-(2-(p-tolyl)acetamido)phenyl)butanoic acid

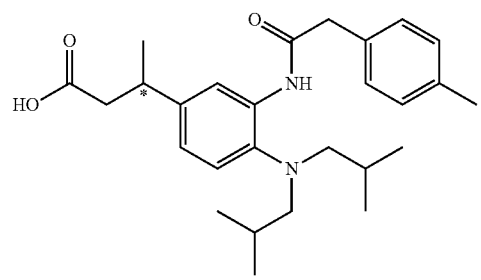 [SMILES: Cc1ccc(CC(=O)Nc2cc(C(C)CC(=O)O)ccc2N(CC(C)C)CC(C)C)cc1]

953A. Methyl 3-(3-amino-4-(diisobutylamino)phenyl)butanoate (Enantiomer 1 and Enantiomer 2)

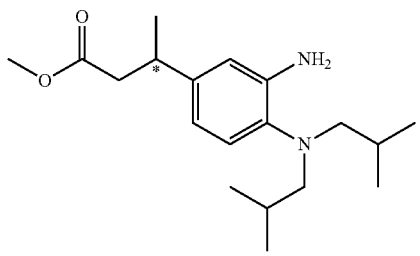 [SMILES: COC(=O)CC(C)c1ccc(N(CC(C)C)CC(C)C)c(N)c1]

Chiral separation of the racemic methyl 3-(3-amino-4-(diisobutylamino)phenyl)butanoate (prepared according to WO 2014/150646, Example 3C). (Waters SFC-100, Column: AD 25×3 cm ID, 5 µm, Flow rate: 120 mL/min, Mobile Phase: 90/10 CO2/MeOH) afforded Enantiomer 1 T$_r$=2.65 min. as 953A1 and Enantiomer 2 T$_r$=3.5 min. as 953A2 (homochiral, stereochemistry unknown, absolute stereochemistry was not determined) LCMS: M+H=321.2 (T$_r$=2.9 min), (Method B).

953B. Methyl-3-(4-(diisobutylamino)-3-(2-(p-tolyl)acetamido)phenyl)butanoic acid

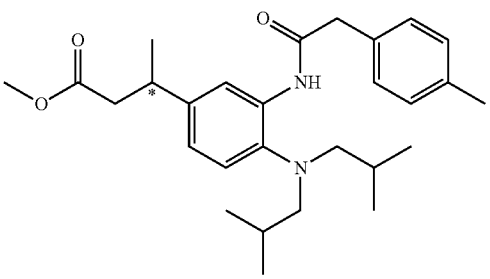

To a solution of preparation 953A1 (20 mg, 0.062 mmol) in DMF (2 mL) at RT was added 2-(p-tolyl)acetic acid (18.74 mg, 0.125 mmol), EDC (23.93 mg, 0.125 mmol), 1-hydroxybenzotriazole (16.87 mg, 0.125 mmol) and Hunig's base (0.033 mL, 0.187 mmol). The reaction was stirred at RT for 16 h. The reaction was diluted with MeOH and purified with prep HPLC (PHENOMENEX® Luna, 5μ, 30×100 mm), 40 mL/min flow rate with gradient of 20% B-100% B over 10 minutes, hold at 100% B for 5 min. (A: 0.1% TFA in water/MeOH (90:10), B: 0.1% TFA in water/MeOH (10:90) monitoring at 254 nm to afford preparation 953B (10 mg, 36% yield). LC-MS: M+H=453.2 (T$_r$=1.2 min) (Method A).

Example 953. 3-(4-(Diisobutylamino)-3-(2-(p-tolyl) acetamido)phenyl)butanoic acid To above ester was added MeOH (0.5 mL), THF (0.5 mL) followed by 1.5 M LiOH aqueous solution (1 mL, 1.500 mmol). The reaction was stirred at RT for 3 h. LC-MS indicated that the product formed. 1N HCl was added to adjusted pH 5. The aqueous phase was then extracted with EtOAc (3×) and the combined organic phase was washed with brine, dried with Na$_2$SO$_4$ and concentrated. The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-95% B over 15 minutes, then a 8-minute hold at 100% B; Flow: 20 mL/min. Fractions containing the desired product were combined and dried via centrifugal evaporation to give Example 953 (9.2 mg, 0.021 mmol, 33% yield). Anal. Calc'd. for C$_{26}$H$_{37}$N$_3$O$_3$, 438.28, found [M+H] 439.2 HPLC: T$_r$=2.354 min. (Method B). 1H NMR (500 MHz, DMSO-d$_6$) δ 8.73 (br. s., 1H), 8.15 (s, 1H), 7.23-7.10 (m, 5H), 6.92 (d, J=7.3 Hz, 1H), 3.64 (s, 1H), 3.11-2.96 (m, 1H), 2.55-2.37 (m, 5H), 2.27 (s, 3H), 1.50 (dt, J=13.3, 6.6 Hz, 2H), 1.16 (d, J=6.9 Hz, 3H), 0.76 (d, J=6.6 Hz, 12H).

Example 954

Enantiomer 2

3-(4-(Diisobutylamino)-3-(2-(p-tolyl)acetamido) phenyl)butanoic acid

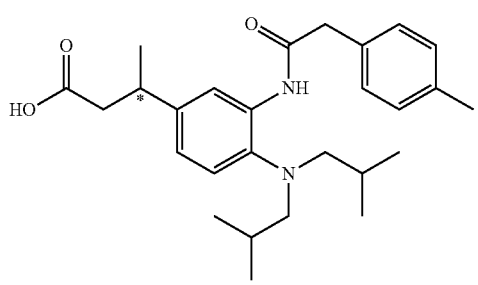

Example 954 was prepared following the procedure for Example 953 using preparation 953A2 as the starting material. Anal. Calc'd. for C$_{26}$H$_{37}$N$_3$O$_3$, 438.28, found [M+H] 439.2. $^1$H NMR (500 MHz, DMSO-d$_6$) δ 8.73 (br. s., 1H), 8.15 (s, 1H), 7.23-7.10 (m, 5H), 6.92 (d, J=7.3 Hz, 1H), 3.64 (s, 1H), 3.11-2.96 (m, 1H), 2.55-2.37 (m, 5H), 2.27 (s, 3H), 1.50 (dt, J=13.3, 6.6 Hz, 2H), 1.16 (d, J=6.9 Hz, 3H), 0.76 (d, J=6.6 Hz, 12H). LC-MS: M+H=453.2 (T$_r$=1.2 min) (Method A).

Example 955

(+/−)-3-(4-(Cyclohexyl(isobutyl)amino)-2-fluoro-5-(3-(p-tolyl)ureido)phenyl)butanoic acid

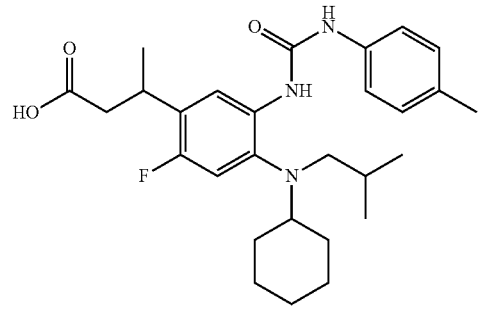 [SMILES: Cc1ccc(NC(=O)Nc2cc(C(C)CC(=O)O)c(F)cc2N(CC(C)C)C2CCCCC2)cc1]

955A. 1-(5-Bromo-2-(cyclohexyl(isobutyl)amino)-4-fluorophenyl)-3-(p-tolyl)urea

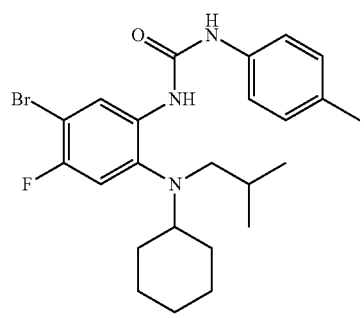 [SMILES: Cc1ccc(NC(=O)Nc2cc(Br)c(F)cc2N(CC(C)C)C2CCCCC2)cc1]

To a solution of 4-bromo-N1-cyclohexyl-5-fluoro-N1-isobutylbenzene-1,2-diamine (prepared following the procedures in Example 951A and 951D) (2.32 g, 6.76 mmol) in THF (50 mL) at RT was added 4-nitrophenyl carbonochloridate (1.561 g, 7.43 mmol). The reaction was stirred at RT for 2 h. Then p-toluidine (1.086 g, 10.14 mmol) was added followed by triethylamine (1.884 mL, 13.52 mmol). The reaction was stirred at 50° C. for 1 h and then cooled to RT. The mixture was diluted with EtOAc and then it was washed with 1N NaOH (2×) (nitrophenol was removed), 1N HCl (2×) (Et$_3$N and excess p-toluidine were removed), saturated NaHCO$_3$, brine and dried over MgSO$_4$, filtered and concentrated to give a crude material. This crude material was dissolved in CH$_2$C$_2$. Insoluble material was removed by filtration. The filtration was purified with ISCO 220 g column, 150 mL/min. 0-30% EtOAc/hexane in 40 min. The desired product was eluted with 10% EtOAc/hexane. Combined fractions containing the product and concentrated to give 1-(5-bromo-2-(cyclohexyl(isobutyl)amino)-4-fluorophenyl)-3-(p-tolyl)urea (2.6 g, 5.40 mmol, 80% yield) as white solid. $^1$H NMR (400 MHz, DMSO-d$_6$) δ 9.46 (s, 1H), 8.27 (d, J=7.7 Hz, 1H), 7.85 (s, 1H), 7.41-7.30 (m, J=8.6 Hz, 2H), 7.27 (d, J=10.3 Hz, 1H), 7.15-6.95 (m, J=8.4 Hz, 2H), 2.78 (d, J=6.6 Hz, 2H), 2.60-2.51 (m, 1H), 2.24 (s, 3H), 1.85

(d, J=11.2 Hz, 2H), 1.68 (d, J=12.1 Hz, 2H), 1.50 (d, J=10.8 Hz, 1H), 1.42-1.28 (m, 1H), 1.28-1.14 (m, 2H), 1.14-0.90 (m, 3H), 0.81 (d, J=6.6 Hz, 6H) Anal. Calc'd. for $C_{24}H_{31}BrFN_3O$, 475.16, found [M+H] 476.3, 478.3.

955B. Methyl 3-(4-(cyclohexyl(isobutyl)amino)-2-fluoro-5-(3-O-tolyl)ureido)phenyl)but-2-enoate

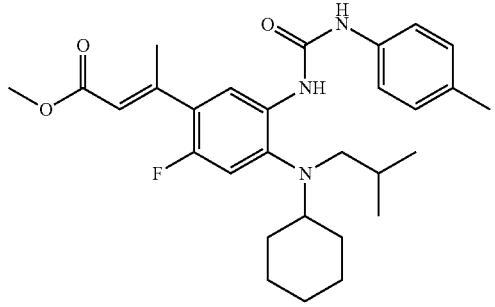

To a solution of 1-(5-bromo-2-(cyclohexyl(isobutyl)amino)-4-fluorophenyl)-3-(p-tolyl)urea (50 mg, 0.105 mmol) in DMF (2 mL) at RT was added (E)-methyl but-2-enoate (21.01 mg, 0.210 mmol), tetrabutylammonium bromide (6.77 mg, 0.021 mmol) and triethyl amine (0.029 mL, 0.210 mmol). The mixture was purged with $N_2$ for 5 min. Then dichlorobis(tri-o-tolylphosphine)palladium(II) (8.25 mg, 10.49 µmol) was added. The mixture was sealed and stirred at 110° C. overnight. The mixture was diluted with MeOH and filtered through 0.24 µM membrane. The filtrate was purified with prep HPLC (PHENOMENEX® Luna, 5µ, 30×100 mm), 40 mL/min flow rate with gradient of 20% B-100% B over 10 minutes, hold at 100% B for 5 min. (A: 0.1% TFA in water/MeOH (90:10), B: 0.1% TFA in water/MeOH (10:90) monitoring at 254 nm. methyl 3-(4-(cyclohexyl(isobutyl)amino)-2-fluoro-5-(3-(p-tolyl)ureido)phenyl)but-2-enoate (18 mg, 0.035 mmol, 32.9% yield) was obtained as clear sticky liquid. Anal. Calc'd. for $C_{29}H_{38}FN_3O_3$, 495.29, found [M+H] 496.2.

Example 955 (+/−)-3-(4-(Cyclohexyl(isobutyl)amino)-2-fluoro-5-(3-(p-tolyl)ureido)phenyl)butanoic acid

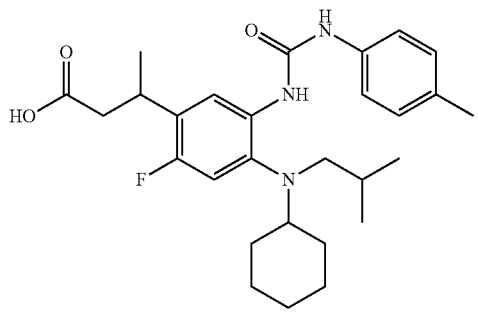 [SMILES: Cc1ccc(NC(=O)Nc2cc(C(C)CC(=O)O)c(F)cc2N(CC(C)C)C2CCCCC2)cc1]

To a solution of methyl 3-(4-(cyclohexyl(isobutyl)amino)-2-fluoro-5-(3-(p-tolyl)ureido)phenyl)but-2-enoate (18 mg, 0.036 mmol) in MeOH (2 mL) at RT was added 10% Pd/C (15 mg, 0.036 mmol). The reaction was evacuated with vacuum and filled with $H_2$ (repeated 3×). Then it was stirred under Hz balloon for 16 h. The mixture was evacuated with vacuum and filled with $N_2$. Filtered through 0.24 µm membrane to remove the solid. The filtrate was concentrated to give methyl 3-(4-(cyclohexyl(isobutyl)amino)-2-fluoro-5-(3-(p-tolyl)ureido)phenyl)butanoate (18 mg, 0.036 mmol) which was used without any purification. To above ester (18 mg, 0.036 mmol) in MeOH (2 mL) at RT was added 1N NaOH (0.5 mL, 0.500 mmol). The reaction was stirred at RT for 3 h. The pH was adjusted to 6 with 1N HCl. The crude material was purified via preparative LC/MS with the following conditions: Column: Waters XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-100% B over 10 minutes, then a 5-minute hold at 100% B; Flow: 20 mL/min. Fractions containing the desired product were combined and dried via centrifugal evaporation. Example 955 (14.7 mg, 0.030 mmol, 84%) was obtained. $^1$H NMR (500 MHz, DMSO-$d_6$) δ 9.38 (s, 1H), 7.88 (d, J=8.2 Hz, 1H), 7.74 (s, 1H), 7.38-7.28 (m, 2H), 7.13-7.03 (m, 2H), 6.98 (d, J=11.9 Hz, 1H), 3.39-3.28 (m, 1H), 2.73 (br. s., 2H), 2.55 (s, 3H), 2.24 (m, 2H), 1.83 (br. s., 2H), 1.67 (d, J=11.6 Hz, 2H), 1.50 (d, J=10.6 Hz, 1H), 1.31 (dt, J=13.0, 6.4 Hz, 1H), 1.24-1.16 (m, 4H), 1.12-0.94 (m, 2H), 0.81 (d, J=6.6 Hz, 6H). MS: Anal. Calc'd. for $C_{28}H_{38}BFN_3O_3$, 483.29, found [M+H] 484.25, HPLC $T_r$=2.08 min (Method B).

Example 956

Enantiomer 1

3-(4-(Cyclohexyl(isobutyl)amino)-2-fluoro-5-(3-(p-tolyl)ureido)phenyl)butanoic acid

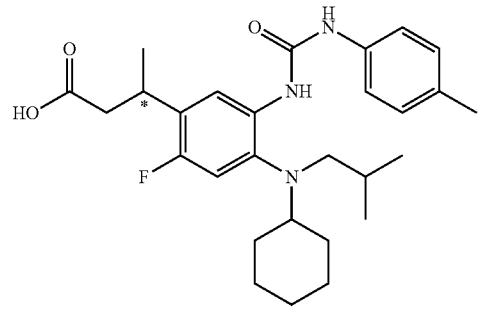 [SMILES: Cc1ccc(NC(=O)Nc2cc(C(C)CC(=O)O)c(F)cc2N(CC(C)C)C2CCCCC2)cc1]

Example 956 was the first eluent peak prepared from Example 955 (3.9 mg, 8.06 µmol) by using the following conditions: UV visualization at 220 nm; Column: Chiral AD-H 25×3 cm ID, 5 µm; Flow rate: 85 mL/min, Mobile Phase: 85/15, $CO_2$/MeOH $T_r$=10.48 min. Example 956 (1.5 mg, 3.1 µmol, 38%) was obtained. $^1$H NMR (500 MHz, DMSO-$d_6$) δ 9.38 (s, 1H), 7.88 (d, J=8.2 Hz, 1H), 7.74 (s, 1H), 7.38-7.28 (m, 2H), 7.13-7.03 (m, 2H), 6.98 (d, J=11.9 Hz, 1H), 3.39-3.28 (m, 1H), 2.73 (br. s., 2H), 2.55 (s, 3H), 2.24 (m, 2H), 1.83 (br. s., 2H), 1.67 (d, J=11.6 Hz, 2H), 1.50 (d, J=10.6 Hz, 1H), 1.31 (dt, J=13.0, 6.4 Hz, 1H), 1.24-1.16 (m, 4H), 1.12-0.94 (m, 2H), 0.81 (d, J=6.6 Hz, 6H) MS: Anal. Calc'd. for $C_{28}H_{38}BFN_3O_3$, 483.29, found [M+H] 484.25, HPLC $T_r$=2.098 min. Method B

Example 957

Enantiomer 2

3-(4-(Cyclohexyl(isobutyl)amino)-2-fluoro-5-(3-(p-tolyl)ureido)phenyl)butanoic acid

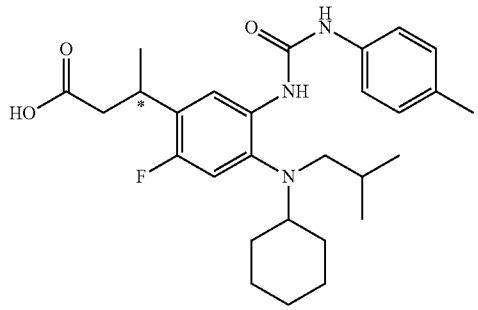 [SMILES: Cc1ccc(NC(=O)Nc2cc(C(C)CC(=O)O)c(F)cc2N(CC(C)C)C2CCCCC2)cc1]

Example 957 was the second eluent peak prepared from Example 955 (3.9 mg, 8.06 μmol) by using the following conditions: UV visualization at 220 nm; Column: Chiral AD-H 25×3 cm ID, 5 μm; Flow rate: 85 mL/min, Mobile Phase: 85/15, CO$_2$/MeOH T$_r$=12.06 min. Example 957 (1.7 mg, 3.5 μmol, 43%) was obtained. $^1$H NMR (500 MHz, DMSO-d$_6$) δ 9.38 (s, 1H), 7.88 (d, J=8.2 Hz, 1H), 7.74 (s, 1H), 7.38-7.28 (m, 2H), 7.13-7.03 (m, 2H), 6.98 (d, J=11.9 Hz, 1H), 3.39-3.28 (m, 1H), 2.73 (br. s., 2H), 2.55 (s, 3H), 2.24 (m, 2H), 1.83 (br. s., 2H), 1.67 (d, J=11.6 Hz, 2H), 1.50 (d, J=10.6 Hz, 1H), 1.31 (dt, J=13.0, 6.4 Hz, 1H), 1.24-1.16 (m, 4H), 1.12-0.94 (m, 2H), 0.81 (d, J=6.6 Hz, 6H) MS: Anal. Calc'd. for C$_{28}$H$_{38}$BFN$_3$O$_3$, 483.29, found [M+H] 484.25, HPLC T$_r$=2.098 min. Method B.

Example 958

Enantiomer 1

3-(4-(Isobutyl(tetrahydro-2H-pyran-4-yl)amino)-3-(3-(p-tolyl)ureido)phenyl)butanoic acid

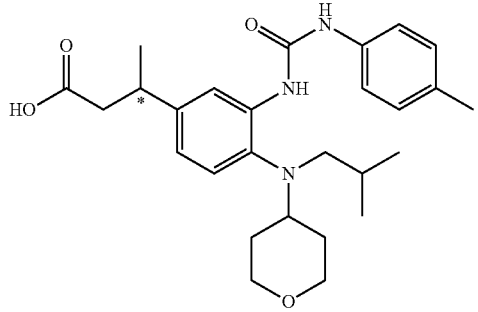 [SMILES: Cc1ccc(NC(=O)Nc2cc(C(C)CC(=O)O)ccc2N(CC(C)C)C2CCOCC2)cc1]

958A. N-(Tetrahydro-2H-pyran-4-yl)isobutyramide

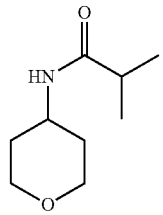

To a suspension of tetrahydro-2H-pyran-4-amine (10g, 99 mmol) in THF (100 mL) at 0° C. was added triethylamine (16.54 mL, 119 mmol). To this mixture was added isobutyryl chloride (10.36 mL, 99 mmol) dropwise. It became a slurry. The reaction was stirred at RT for 16 h. Filtered to remove the solid. Rinsed the solid with THF. The solid contained most Et$_3$N HCl salt. The filtrate contained the desired product with small amount of Et$_3$N HCl salt by LC-MS. The filtrate was concentrated to dryness and then it was dissolved in minimum amount of CH$_2$Cl$_2$ and purified with ISCO 220 g column, 150 mL/min. 0-100% EtOAc/CH$_2$Cl$_2$ in 35 min. The desired product was eluted with 35% EtOAc/CH$_2$Cl$_2$. Combined fractions containing desired product. After concentration, N-(tetrahydro-2H-pyran-4-yl)isobutyramide (9.0 g, 52 mol, 52%) was obtained. $^1$H NMR (400 MHz, chloroform-d) δ 5.33 (br. s., 1H), 4.06-3.90 (m, 3H), 3.50 (td, J=11.7, 2.2 Hz, 2H), 2.33 (dt, J=13.8, 6.9 Hz, 1H), 1.97-1.85 (m, 2H), 1.52-1.38 (m, 2H), 1.22-1.12 (m, 6H) Anal. Calc'd. for C$_9$H$_{17}$NO$_2$, 171.126, found [M+H] 172.1.

958B. N-Isobutyltetrahydro-2H-pyran-4-amine

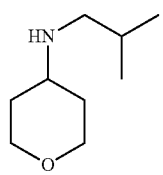

To a solution of N-(tetrahydro-2H-pyran-4-yl)isobutyramide (9 g, 52.6 mmol) in THF (100 mL) cooled to 0° C. was added BH$_3$-Me$_2$S in Et$_2$O (21.02 mL, 105 mmol) slowly. The reaction was stirred at RT for 3 days. Then it was cooled to 0° C. in an ice bath. Methanol was slowly added dropwise until evolution of gas ceased. The material was concentrated to remove the solvent. The crude material was taken up in MeOH (150 mL) and stirred at RT for 2 days and heated at 80° C. for 5 h to break up the borane complex. The reaction was allowed to cool to rt. The solvent was evaporated to give N-isobutyltetrahydro-2H-pyran-4-amine (8.0 g, 40.7 mmol, 77%). $^1$H NMR (400 MHz, chloroform-d) δ 4.05-3.94 (m, 2H), 3.42 (td, J=11.7, 2.2 Hz, 2H), 2.71-2.59 (m, 1H), 2.46 (d, J=6.8 Hz, 2H), 1.90-1.79 (m, 2H), 1.78-1.63 (m, 1H), 1.49-1.29 (m, 2H), 0.98-0.89 (m, 6H) MS: Anal. Calc'd. for C$_9$H$_{19}$NO, 157.141, found [M+H] 158.1.

958C. N-(4-Bromo-2-nitrophenyl)-N-isobutyltetrahydro-2H-pyran-4-amine

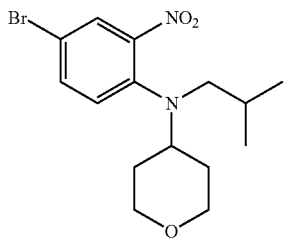 [SMILES: CC(C)CN(c1ccc(Br)cc1[N+](=O)[O-])C1CCOCC1]

To a solution of 4-bromo-1-fluoro-2-nitrobenzene (0.979 g, 4.45 mmol) in NMP (5 mL) at RT was added N-isobutyltetrahydro-2H-pyran-4-amine (0.7 g, 4.45 mmol). The reaction was sealed and heated at 125° C. for 16 h. The reaction was cooed to RT. The mixture was diluted with EtOAc and water. The organic layer was separated and washed with water (2×), brine, dried over MgSO$_4$, filtered and concentrated to give the crude product. This crude material was purified with ISCO 80 g, 60 mL/min. 0-15% EtOAc/hexane in 30 min. The desired product was eluted with 10% EtOAc/hexane. N-(4-Bromo-2-nitrophenyl)-N-isobutyltetrahydro-2H-pyran-4-amine (970 mg, 2.69 mmol, 60.4% yield) was obtained as an orange liquid. $^1$H NMR (400 MHz, chloroform-d) δ 7.83 (d, J=2.4 Hz, 1H), 7.53 (dd, J=8.9, 2.4 Hz, 1H), 7.13 (d, J=8.8 Hz, 1H), 4.00 (dd, J=11.5, 4.5 Hz, 2H), 3.33 (td, J=11.7, 2.3 Hz, 2H), 3.12 (tt, J=11.4, 4.2 Hz, 1H), 2.87 (d, J=7.2 Hz, 2H), 1.88-1.66 (m, 4H), 1.65-1.57 (m, 1H), 0.94-0.78 (m, 6H) MS: Anal. Calc'd. for C$_{15}$H$_{21}$BrN$_2$O$_3$, 356.074, found M+H=356.9, 358.9.

958D. (E)-Methyl 3-(4-(isobutyl(tetrahydro-2H-pyran-4-yl)amino)-3-nitrophenyl)but-2-enoate

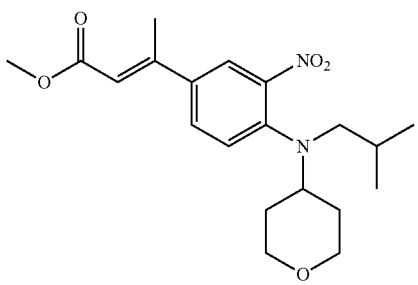 [SMILES: COC(=O)/C=C(\C)c1ccc(N(CC(C)C)C2CCOCC2)c([N+](=O)[O-])c1]

To a solution of N-(4-bromo-2-nitrophenyl)-N-isobutyltetrahydro-2H-pyran-4-amine (300 mg, 0.840 mmol) in DMF (10 mL) was added (E)-methyl but-2-enoate (0.178 mL, 1.680 mmol), tetrabutylammonium bromide (54.1 mg, 0.168 mmol), triethylamine (0.234 mL, 1.680 mmol) and dichlorobis(tri-o-tolylphosphine)palladium(II) (66.0 mg, 0.084 mmol). The mixture was purged with N$_2$ for 10 min. Then it was sealed and heated at 110° C. overnight. After cooled to RT, the mixture was filtered through CELITE® and diluted with water and EtOAc. The organic layer was separated and washed with brine, dried over MgSO$_4$, filtered and concentrated to give a crude material. This crude material was purified with ISCO 40 g column, 40 mL/min, 0-40% EtOAc/hexane in 30 min. The desired product was eluted with 20% EtOAc/hexane to give (E)-methyl 3-(4-(isobutyl(tetrahydro-2H-pyran-4-yl)amino)-3-nitrophenyl)but-2-enoate (180 mg, 0.474 mmol, 56.4% yield). $^1$H NMR (400 MHz, chloroform-d) δ 7.85 (d, J=2.4 Hz, 1H), 7.56 (dd, J=8.7, 2.3 Hz, 1H), 7.19 (d, J=8.8 Hz, 1H), 6.17 (q, J=1.2 Hz, 1H), 4.01 (dd, J=11.4, 4.4 Hz, 2H), 3.78 (s, 3H), 3.34 (td, J=11.7, 2.2 Hz, 2H), 3.24-3.08 (m, 1H), 2.94 (d, J=7.2 Hz, 2H), 2.58 (d, J=1.2 Hz, 3H), 1.91-1.62 (m, 6H), 0.91 (d, J=6.6 Hz, 6H) MS: Anal. Calc'd. for C$_{20}$H$_{28}$N$_2$O$_5$, 376.200, found [M+H] 377.4.

958E. Methyl 3-(3-amino-4-(isobutyl(tetrahydro-2H-pyran-4-yl)amino)phenyl)butanoate

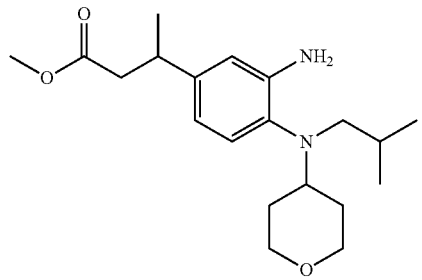 [SMILES: COC(=O)CC(C)c1ccc(N(CC(C)C)C2CCOCC2)c(N)c1]

To a solution of (E)-methyl 3-(4-(isobutyl(tetrahydro-2H-pyran-4-yl)amino)-3-nitrophenyl)but-2-enoate (800 mg, 2.125 mmol) in MeOH (100 mL) at RT was added 10% Pd/C (225 mg, 0.213 mmol). The reaction was evacuated with vacuum and filled with H$_2$ (repeated 3×). Then it was stirred under H$_2$ for 5 h. The reaction was evacuated with vacuum and filled with N$_2$. The mixture was filtered through 0.45 μM membrane. The filtrate was concentrated to give methyl 3-(3-amino-4-(isobutyl(tetrahydro-2H-pyran-4-yl)amino)phenyl)butanoate (740 mg, 2.017 mmol, 95% yield) MS: Anal. Calc'd. for C$_{20}$H$_{32}$N$_2$O$_3$, 348.241, found [M+H] 349.5.

958F1. Methyl 3-(3-amino-4-(isobutyl(tetrahydro-2H-pyran-4-yl)amino)phenyl)butanoate

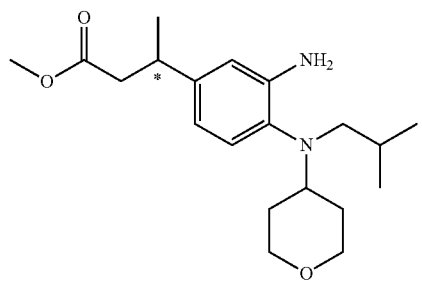 [SMILES: COC(=O)CC(C)c1ccc(N(CC(C)C)C2CCOCC2)c(N)c1]

Example 958F1 was the first eluent peak (T$_r$=3.9 min.) prepared from Example 958E (680 mg, 1.95 mmol) by using the following conditions: UV visualization at 220 nm; Column: Chiral AD-H 25×3 cm ID, 5 μm; Flow rate: 85 mL/min, Mobile Phase: 85/15, CO$_2$/MeOH methyl 3-(3-amino-4-(isobutyl(tetrahydro-2H-pyran-4-yl)amino)phenyl) butanoate (280 mg, 0.8 mmol, 41% yield) was obtained. $^1$H NMR (400 MHz, chloroform-d) δ 6.99 (d, J=8.1 Hz, 1H), 6.62 (d, J=2.1 Hz, 1H), 6.56 (dd, J=8.1, 2.1 Hz, 1H), 4.06 (s, 2H), 4.03-3.90 (m, 2H), 3.66 (s, 3H), 3.34 (br. s., 2H), 3.21-3.11 (m, 1H), 2.87 (br. s., 2H), 2.62 (dd, J=15.0, 6.2 Hz, 1H), 2.49 (dd, J=15.0, 8.9 Hz, 1H), 1.72 (br. s., 4H), 1.53-1.37 (m, 1H), 1.28 (d, J=6.8 Hz, 3H), 0.86 (d, J=6.6 Hz, 6H) M+H=349.1 MS: Anal. Calc'd. for $C_{20}H_{32}N_2O_3$, 348.241, found [M+H] 349.5 HPLC: $T_r$=1.13 min. Method A. Absolute stereochemistry was not determined.

958F2. Methyl 3-(3-amino-4-(isobutyl(tetrahydro-2H-pyran-4-yl)amino)phenyl)butanoate

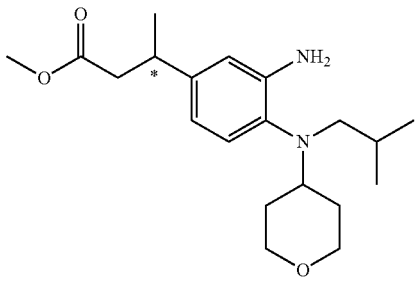 [SMILES: COC(=O)CC(C)c1ccc(N(CC(C)C)C2CCOCC2)c(N)c1]

Example 958F2 was the second eluent peak ($T_r$=4.6 min.) prepared from Example 954E (680 mg, 1.95 mmol) by using the following conditions: UV visualization at 220 nm; Column: Chiral AD-H 25×3 cm ID, 5 μm; Flow rate: 85 mL/min, Mobile Phase: 85/15, $CO_2$/MeOH methyl 3-(3-amino-4-(isobutyl(tetrahydro-2H-pyran-4-yl)amino)phenyl) butanoate (280 mg, 0.8 mmol, 41% yield) was obtained. $^1$H NMR (400 MHz, chloroform-d) δ 6.99 (d, J=8.1 Hz, 1H), 6.62 (d, J=2.1 Hz, 1H), 6.56 (dd, J=8.1, 2.1 Hz, 1H), 4.06 (s, 2H), 4.03-3.90 (m, 2H), 3.66 (s, 3H), 3.34 (br. s., 2H), 3.21-3.11 (m, 1H), 2.87 (br. s., 2H), 2.62 (dd, J=15.0, 6.2 Hz, 1H), 2.49 (dd, J=15.0, 8.9 Hz, 1H), 1.72 (br. s., 4H), 1.53-1.37 (m, 1H), 1.28 (d, J=6.8 Hz, 3H), 0.86 (d, J=6.6 Hz, 6H) M+H=349.1 MS: Anal. Calc'd. for $C_{20}H_{32}N_2O_3$, 348.241, found [M+H] 349.5 HPLC: $T_r$=1.13 min. Method A. Absolute stereochemistry was not determined.

Example 958. 3-(4-(Isobutyl(tetrahydro-2H-pyran-4-yl)amino)-3-(3-(p-tolyl)ureido)phenyl)butanoic acid To a solution of 958F1 (10 mg, 0.029 mmol) in THF (0.5 mL) at RT was added 1-isocyanato-4-methylbenzene (7.64 mg, 0.057 mmol). The reaction was stirred at RT for 1 h. To the above reaction was added MeOH (0.2 mL), followed by 1N NaOH (0.5 mL, 0.500 mmol). The reaction was stirred at RT for 3 h. The pH was adjusted to 5 with concentrated HCl. The mixture was diluted with DMF and filtered through a 0.45 μM membrane. The filtrate was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 20 minutes, then a 5-minute hold at 100% B; Flow: 20 mL/min. Fractions containing the desired product were combined and dried via centrifugal evaporation to afford Example 958 (4.8 mg, 10.1 μmol, 35% yield). $^1$H NMR (500 MHz, DMSO-$d_6$) δ 9.46 (s, 1H), 8.19 (s, 1H), 8.04 (br. s., 1H), 7.95 (s, 1H), 7.36 (d, J=8.1 Hz, 2H), 7.27 (s, 1H), 7.19-7.14 (m, 1H), 7.12-6.98 (m, 2H), 6.84 (d, J=7.9 Hz, 1H), 3.83 (d, J=9.1 Hz, 2H), 3.56 (br. s., 2H), 3.19 (t, J=11.4 Hz, 2H), 3.12-3.00 (m, 1H), 2.81 (br. s., 1H), 2.55 (s, 3H), 2.25 (s, 3H), 1.70 (br. s., 2H), 1.54-1.37 (m, 1H), 1.34-1.11 (m, 4H), 0.84-0.71 (m, 6H) MS: Anal. Calc'd. for $C_{27}H_{37}N_3O_4$, 467.278, found [M+H] 468.3. $T_r$=1.677 min. Method B.

Examples 959 to 961

These compounds (homochiral, stereochemistry unknown) were obtained following the procedures in Example 958 using 958F1 and the corresponding isocyanate.

| Ex. No. | Name | R | $T_r$ (min) Method B | [M + H]⁺ |
|---|---|---|---|---|
| 959 | 3-(4-(isobutyl(tetrahydro-2H-pyran-4-yl)amino)-3-(3-(4-phenoxyphenyl)ureido)phenyl) butanoic acid | 4-phenoxyphenyl | 1.94 | 466.0 |
| 960 | 3-(3-(3-(4-ethoxyphenyl)ureido)-4-(isobutyl(tetrahydro-2H-pyran-4-yl)amino)phenyl)butanoic acid | 4-ethoxyphenyl | 1.71 | 498.0 |
| 961 | 3-(4-(isobutyl(tetrahydro-2H-pyran-4-yl)amino)-3-(3-(pyrimidin-5-yl)ureido)phenyl) butanoic acid | pyrimidin-5-yl | 1.28 | 456.5 |

Examples 962 to 965

These compounds (homochiral, stereochemistry unknown) were obtained following the procedures in Example 958 using 958F2 and the corresponding isocyanate.

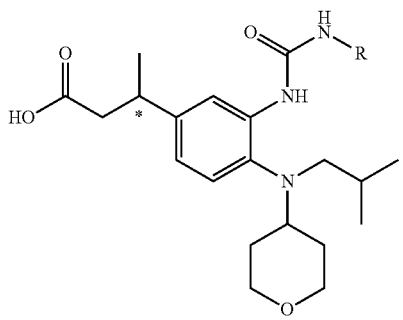

| Ex. No. | Name | R | T_r (min) Method B | [M + H]+ |
|---|---|---|---|---|
| 962 | 3-(4-(isobutyl(tetrahydro-2H-pyran-4-yl)amino)-3-(3-(4-phenoxyphenyl)ureido)phenyl)butanoic acid | | 1.94 | 466.0 |
| 963 | 3-(3-(3-(4-ethoxyphenyl)ureido)-4-(isobutyl(tetrahydro-2H-pyran-4-yl)amino)phenyl)butanoic acid | | 1.71 | 498.0 |
| 964 | 3-(4-(isobutyl(tetrahydro-2H-pyran-4-yl)amino)-3-(3-(pyrimidin-5-yl)ureido)phenyl)butanoic acid | | 1.28 | 456.5 |
| 965 | 3-(4-(isobutyl(tetrahydro-2H-pyran-4-yl)amino)-3-(3-(p-tolyl)ureido)phenyl)butanoic acid | | 1.70 | 468.0 |

Example 966

Enantiomer 1

3-(4-(Isobutyl(tetrahydro-2H-pyran-4-yl)amino)-3-(2-(p-tolyl)acetamido)phenyl)butanoic acid

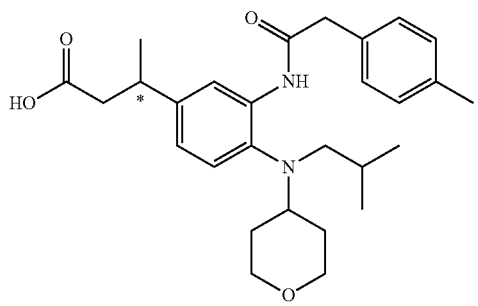

Example 966 was obtained following the procedures in Example 953 using 958F1. MS: Anal. Calc'd. for $C_{28}H_{38}N_2O_4$, 466.283, found [M+H] 467.3 $^1$H NMR (500 MHz, DMSO-$d_6$) δ 8.63 (s, 1H), 8.25 (s, 1H), 7.28-7.07 (m, 5H), 6.91 (d, J=6.8 Hz, 1H), 3.73 (br. s., 1H), 3.15-2.95 (m, 3H), 2.61 (br. s., 2H), 2.46-2.35 (m, 2H), 2.29 (s, 3H), 1.23 (br. s., 1H), 1.21-1.03 (m, 7H), 0.68 (d, J=6.6 Hz, 6H) HPLC T_r=1.82 min. Method A.

Example 967

Enantiomer 2

3-(4-(Isobutyl(tetrahydro-2H-pyran-4-yl)amino)-3-(2-(p-tolyl)acetamido)phenyl)butanoic acid

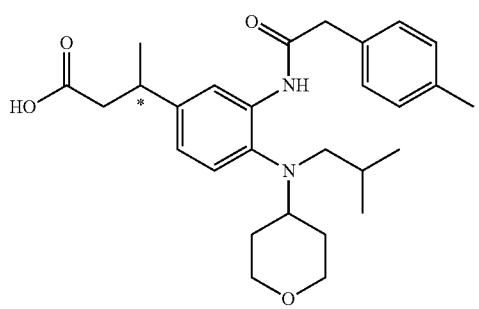 [SMILES: Cc1ccc(CC(=O)Nc2cc(C(C)CC(=O)O)ccc2N(CC(C)C)C2CCOCC2)cc1]

Example 967 was obtained following the procedures in Example 954 using 958F2. MS: Anal. Calc'd. for $C_{28}H_{38}N_2O_4$, 466.283, found [M+H] 467.3. $^1$H NMR (500 MHz, DMSO-$d_6$) δ 8.63 (s, 1H), 8.25 (s, 1H), 7.28-7.07 (m, 5H), 6.91 (d, J=6.8 Hz, 1H), 3.73 (br. s., 1H), 3.15-2.95 (m, 3H), 2.61 (br. s., 2H), 2.46-2.35 (m, 2H), 2.29 (s, 3H), 1.23 (br. s., 1H), 1.21-1.03 (m, 7H), 0.68 (d, J=6.6 Hz, 6H) HPLC $T_r$=1.82 min. Method A.

Example 968

Enantiomer 1

3-(3-(Benzo[d]oxazol-2-ylamino)-4-(isobutyl(tetrahydro-2H-pyran-4-yl)amino)phenyl)butanoic acid

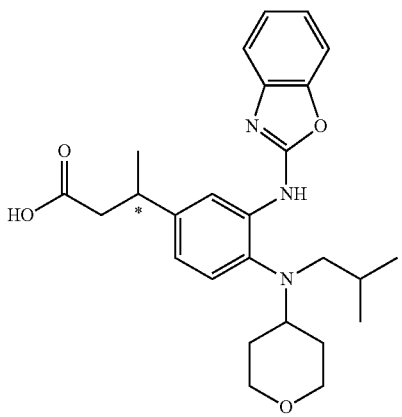 [SMILES: CC(C)CN(c1ccc(C(C)CC(=O)O)cc1Nc1nc2ccccc2o1)C1CCOCC1]

To 958F1 (10 mg, 0.029 mmol) in a 2 dram vial was added 2-chlorobenzo[d] oxazole (6.55 µl, 0.057 mmol), followed by 2,6-lutidine (0.1 mL, 0.029 mmol). The reaction was stirred at 140° C. for 4 h. After cooling to RT, the reaction mixture was diluted with EtOAc and 1N HCl. The organic layer was separated and washed with water and brine, dried over MgSO$_4$, filtered and concentrated to give the crude product. This crude material was purified with ISCO 4 g column, 18 mL/min. 0-15% EtOAc/hexane in 25 min. The desire product was eluted with 10% EtOAc/hexane. The combined fractions containing the product were concentrated to give methyl 3-(3-(benzo[d]oxazol-2-ylamino)-4-(isobutyl(tetrahydro-2H-pyran-4-yl)amino)phenyl) butanoate (3 mg, 6.38 µmol, 22.23% yield) was obtained as an off-white solid. MS: Anal. Calc'd. for $C_{27}H_{35}N_3O_4$, 465.263, found [M+H] 466.0. To methyl 3-(3-(benzo[d] oxazol-2-ylamino)-4-(isobutyl(tetrahydro-2H-pyran-4-yl) amino)phenyl)butanoate (3 mg, 6.44 µmol) in a 1 dram vial was added MeOH (0.2 mL), followed by 1N NaOH (0.5 mL, 0.500 mmol). The reaction was stirred at RT for 3 h. pH was adjusted to 5 with concentrated HCl. The mixture was diluted with DMF and filtered through 0.45 µM membrane. The filtrate was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 12 minutes, then a 4-minute hold at 100% B; Flow: 20 mL/min. Fractions containing the desired product were combined and dried via centrifugal evaporation. Example 968 (2.7 mg, 5.7 µmol, 89% yield) was obtained. $^1$H NMR (500 MHz, DMSO-$d_6$) δ 8.22 (br. s., 1H), 7.53 (d, J=7.3 Hz, 2H), 7.32-7.21 (m, 2H), 7.21-7.13 (m, 1H), 6.98 (d, J=7.4 Hz, 1H), 3.82 (d, J=10.7 Hz, 2H), 3.25-3.11 (m, 3H), 2.91 (br. s., 1H), 2.84-2.68 (m, 2H), 2.55 (m., 2H), 2.50-2.37 (m, 2H), 1.69 (d, J=11.3 Hz, 2H), 1.48 (d, J=11.4 Hz, 2H), 1.34 (br. s., 1H), 1.25 (d, J=4.8 Hz, 3H), 0.84 (d, J=4.6 Hz, 6H) MS: Anal. Calc'd. for $C_{26}H_{33}N_3O_4$, 451.247, found [M+H] 452.3 HPLC $T_r$=1.698 min and Method B.

Example 969

Enantiomer 2

3-(3-(Benzo[d]oxazol-2-ylamino)-4-(isobutyl(tetrahydro-2H-pyran-4-yl)amino)phenyl)butanoic acid

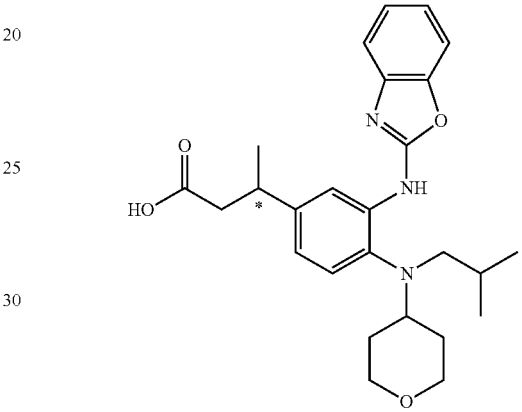

Example 969 was obtained following the procedures in Example 968 using 958F2. $^1$H NMR (500 MHz, DMSO-$d_6$) δ 8.22 (br. s., 1H), 7.53 (d, J=7.3 Hz, 2H), 7.32-7.21 (m, 2H), 7.21-7.13 (m, 1H), 6.98 (d, J=7.4 Hz, 1H), 3.82 (d, J=10.7 Hz, 2H), 3.25-3.11 (m, 3H), 2.91 (br. s., 1H), 2.84-2.68 (m, 2H), 2.55 (m., 2H), 2.50-2.37 (m, 2H), 1.69 (d, J=11.3 Hz, 2H), 1.48 (d, J=11.4 Hz, 2H), 1.34 (br. s., 1H), 1.25 (d, J=4.8 Hz, 3H), 0.84 (d, J=4.6 Hz, 6H) MS: Anal. Calc'd. for $C_{26}H_{33}N_3O_4$, 451.247, found [M+H] 452.3. HPLC $T_r$=1.698 min Method B.

Example 970

(+/−)-3-(4-(Diisobutylamino)-3-fluoro-5-(3-(p-tolyl) ureido)phenyl)pentanoic acid, TFA

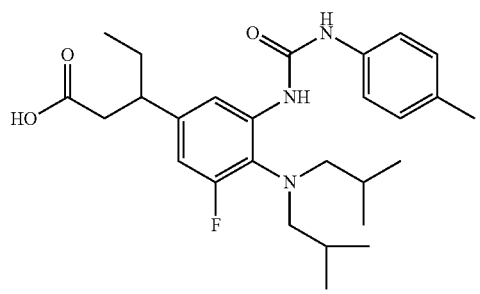 [SMILES: CCC(CC(=O)O)c1cc(F)c(N(CC(C)C)CC(C)C)c(NC(=O)Nc2ccc(C)cc2)c1]

970A.
4-Bromo-2-fluoro-N,N-diisobutyl-6-nitroaniline

A solution of 5-bromo-1,2-difluoro-3-nitrobenzene (1 g, 4.20 mmol) and diisobutylamine (1.629 g, 12.61 mmol) was placed under nitrogen and heated at 130° C. for 2 h. The reaction was diluted with ether and washed with 5% HOAc then brine. The org. phase was dried, stripped, and chromatographed on silica gel (EtOAc-hexane) to afford 4-bromo-2-fluoro-N,N-diisobutyl-6-nitroaniline (1.28 g, 83% yield) as an orange oil. MS(ES): m/z=347 [M+H]$^+$, T$_r$=1.34 min (Method A).

970B. 4-(5,5-Dimethyl-1,3,2-dioxaborinan-2-yl)-2-fluoro-N,N-diisobutyl-6-nitroaniline A solution of 5,5,5',5'-tetramethyl-2,2'-bi(1,3,2-dioxaborinane) (1.015 g, 4.49 mmol) and 4-bromo-2-fluoro-N,N-diisobutyl-6-nitroaniline (1.2 g, 3.46 mmol) and potassium acetate (1.018 g, 10.37 mmol) in degassed DMSO (4.94 ml) was treated with 1,1'-bis(diphenylphosphino)ferrocenedichloro palladium(II) dichloromethane complex (0.126 g, 0.173 mmol). This dark solution was placed under nitrogen and heated to 80° C. for 2 h then cooled to RT. The reaction was purified by flash chromatography (EtOAc-hexane). Concentration of the appropriate fractions afforded 4-(5,5-dimethyl-1,3,2-dioxaborinan-2-yl)-2-fluoro-N,N-diisobutyl-6-nitroaniline (1.23 g, 89% yield) as an orange oil. MS(ES): m/z=313 [M+H]$^+$ for parent boronic acid. T$_r$=1.11 min (Method A).

970C. (+/−)-Methyl 3-(4-(diisobutylamino)-3-fluoro-5-nitrophenyl)pentanoate

A reaction vial was charged with 4-(5,5-dimethyl-1,3,2-dioxaborinan-2-yl)-2-fluoro-N,N-diisobutyl-6-nitroaniline (1.2 g, 3.16 mmol). The SM was dissolved in dioxane (10 mL), and (E)-methyl pent-2-enoate (1.081 g, 9.47 mmol) was added followed by 1M aq. sodium hydroxide (2.84 mL, 2.84 mmol). The sample was degassed by freezing under vacuum then thawing under nitrogen twice. The reaction was charged with chloro(1,5-cyclooctadiene)rhodium(I) dimer (0.078 g, 0.158 mmol), and the freeze/thaw purge cycle was repeated. The reaction was stirred 4.5 h at 50° C., treated with acetic acid (0.361 mL, 6.31 mmol) then applied to a flash column and eluted with 5-15% EtOAc-hexane. Concentration of the appropriate fractions afforded (+/−)-methyl 3-(4-(diisobutylamino)-3-fluoro-5-nitrophenyl)pentanoate (0.81 g, 64% yield) as an orange oil. MS(ES): m/z=383 [M+H]$^+$. T$_r$=1.29 min (Method A).

970D. (+/−)-Methyl 3-(3-amino-4-(diisobutylamino)-5-fluorophenyl)pentanoate

In a small Parr bottle, a solution of (+/−)-methyl 3-(4-(diisobutylamino)-3-fluoro-5-nitrophenyl)pentanoate (0.6 g, 1.569 mmol) in ethyl acetate (12 mL) was placed under nitrogen and treated with 10% palladium on carbon (0.334 g, 0.314 mmol). This mixture was hydrogenated at 40 psi for 2 h then diluted with dichloromethane and filtered with the aid of a little MgSO$_4$. The filtrate was concentrated under reduced pressure to afford (+/−)-methyl 3-(3-amino-4-(diisobutylamino)-5-fluorophenyl)pentanoate (0.55 g, 94% yield) as a light brown oil. MS(ES): m/z=353 [M+H]$^+$. T$_r$=1.22 min (Method A).

Example 970. (+/−)-3-(4-(Diisobutylamino)-3-fluoro-5-(3-(p-tolyl)ureido)phenyl)pentanoic acid, TFA A solution of (+/−)-methyl 3-(3-amino-4-(diisobutylamino)-5-fluorophenyl)pentanoate (0.05 g, 0.142 mmol) in THF (0.5 mL) was treated with 1-isocyanato-4-methylbenzene (0.023 g, 0.170 mmol) and stirred 1 h. at RT. LCMS indicates that the reaction is complete, so it was treated with 0.01 mL of N,N-dimethylethylenediamine to quench excess isocyanate. The reaction was then treated with lithium hydroxide (0.027 g, 1.135 mmol) in 0.2 mL of water. Methanol, ~0.5 mL was added to give a single phase, and the solution was warmed to 60° C. for 1.5 h. The reaction was then cooled to RT and quenched with 0.1 mL of glacial HOAc. The sample was diluted to 2 mL with MeOH and purified by prep HPLC. Concentration of the appropriate fractions afforded (+/−)-3-(4-(diisobutylamino)-3-fluoro-5-(3-(p-tolyl)ureido)phenyl)pentanoic acid, TFA (0.057 g, 65% yield). $^1$H NMR (400 MHz, DMSO-d$_6$) δ 9.47 (s, 1H), 8.16 (s, 1H), 7.81 (s, 1H), 7.36 (d, J=8.0 Hz, 2H), 7.09 (d, J=8.2 Hz, 2H), 6.63 (d, J=13.2 Hz, 1H), 2.70-2.85 (m, 5H), 2.39-2.57 (m, ~2H (integration distorted by solvent peak)), 1.43-1.66 (m, 4H), 0.83 (d, J=5.1 Hz, 12H), 0.71 (t, J=7.2 Hz, 3H). MS(ES): m/z=472 [M+H]$^+$. T$_r$=1.19 min (Method A).

Example 971

(+/−)-3-(3-(3-(5-(tert-Butyl)isoxazol-3-yl)ureido)-4-(diisobutylamino)-5-fluorophenyl)pentanoic acid, TFA

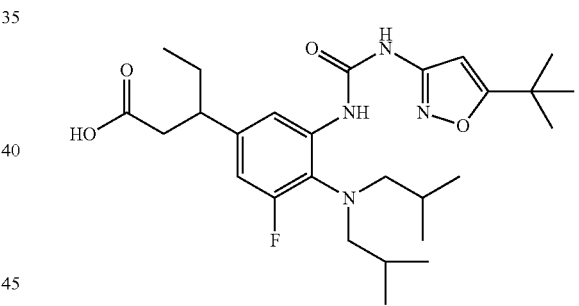

A solution of Preparation 970D (0.018 g, 0.051 mmol) and phenyl (5-(tert-butyl)isoxazol-3-yl)carbamate (0.016 g, 0.061 mmol) in THF (0.5 mL) was treated with triethylamine (0.011 mL, 0.082 mmol). The reaction was stirred 1 h at 60° C. then cooled to RT. The reaction was treated with lithium hydroxide (7.34 mg, 0.306 mmol) in 0.3 mL of water. Methanol, 0.5 mL was added to give a single phase, and the reaction was stirred 1 h at 50° C. The reaction was cooled to ambient temperature, quenched with 0.1 mL of glacial HOAc, diluted to 2 mL with DMF, and purified by prep HPLC (acetonitrile-water gradient, 10 mM NH$_4$OAc). Concentration of the appropriate fractions afforded (+/−)-3-(3-(3-(5-(tert-butyl)isoxazol-3-yl)ureido)-4-(diisobutylamino)-5-fluorophenyl)pentanoic acid, TFA (0.02 g, 60% yield). $^1$H NMR (400 MHz, DMSO-d$_6$) δ10.65 (s, 1H), 8.66 (s, 1H), 7.82 (s, 1H), 6.70 (d, J=13.1 Hz, 1H), 6.49 (s, 1H), 2.69-2.85 (m, 5H), 2.39-2.58 (m, ~2H (integration distorted by solvent peak)), 1.41-1.66 (m, 4H), 1.30 (s, 9H), 0.83 (d, J=5.2 Hz, 12H), 0.71 (t, J=7.2 Hz, 3H). MS(ES): m/z=505 [M+H]$^+$. T$_r$=2.41 min (Method B).

Example 972

(+/−)-3-(3-(2-(4-Chloro-2-fluorophenyl)acetamido)-4-(diisobutylamino)-5-fluorophenyl)pentanoic acid

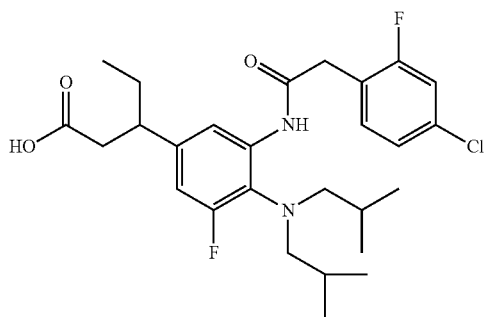 [SMILES: CCC(CC(=O)O)c1cc(F)c(N(CC(C)C)CC(C)C)c(NC(=O)Cc2ccc(Cl)cc2F)c1]

A solution of Preparation 970D (0.05 g, 0.142 mmol) and 2-(4-chloro-2-fluorophenyl)acetic acid (0.032 g, 0.170 mmol) and triethylamine (0.032 mL, 0.227 mmol) in THF (0.5 mL) was treated with BOP (0.075 g, 0.170 mmol). The reaction was stirred 1 h at RT then treated with lithium hydroxide (0.020 g, 0.851 mmol) in 0.3 mL of water. Methanol, 0.5 mL was added to give a single phase, and the reaction was stirred 2 h at 60° C. The reaction was cooled to ambient temperature, quenched with 0.1 mL of glacial HOAc, diluted to 2 mL with MeOH, and purified by prep HPLC (acetonitrile-water gradient, 10 mM NH$_4$OAc). Concentration of the appropriate fractions afforded (+/−)-3-(3-(2-(4-chloro-2-fluorophenyl)acetamido)-4-(diisobutylamino)-5-fluorophenyl)pentanoic acid (0.02 g, 60% yield). $^1$H NMR (400 MHz, DMSO-d$_6$) δ 8.95 (s, 1H), 7.96 (s, 1H), 7.41-7.47 (m, 2H), 7.31 (d, J=8.0 Hz, 1H), 6.79 (d, J=13.3 Hz, 1H), 3.79 (s, 2H), 2.37-2.84 (m, ~7H (integration distorted by solvent peak)), 1.41-1.63 (m, 4H), 0.82 (d, J=5.9 Hz, 12H), 0.68 (t, J=7.2 Hz, 3H). MS(ES): m/z=509 [M+H]$^+$. T$_r$=2.41 min (Method B).

Examples 973 to 978

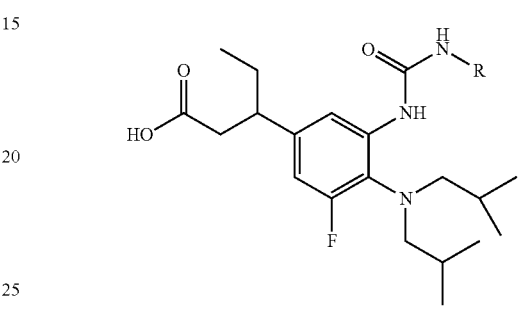

EXAMPLES 973 to 978 were prepared from Intermediate 970D using the procedures outlined above and the appropriate electrophiles (isocyanates for 973 to 977 and phenyl carbamate for 978).

| Ex. No. | Name | R | T$_r$ (min) Method C | [M + H]$^+$ |
|---|---|---|---|---|
| 973 | (+/−)-3-(3-(3-(4-butylphenyl)ureido)-4-(diisobutylamino)-5-fluorophenyl)pentanoic acid | 4-butylphenyl | 2.50 | 514 |
| 974 | (+/−)-3-(4-(diisobutylamino)-3-fluoro-5-(3-(3-fluoro-4-methylphenyl)ureido)phenyl)pentanoic acid | 3-fluoro-4-methylphenyl | 2.29 | 490 |
| 975 | (+/−)-3-(3-(3-(2-chlorophenyl)ureido)-4-(diisobutylamino)-5-fluorophenyl)pentanoic acid | 2-chlorophenyl | 2.32 | 492 |
| 976 | (+/−)-3-(4-(diisobutylamino)-3-fluoro-5-(3-(2-fluoro-5-(trifluoromethyl)phenyl)ureido)phenyl)pentanoic acid | 2-fluoro-5-(trifluoromethyl)phenyl | 2.42 | 544 |
| 977 | (+/−)-3-(3-(3-(4-chloro-2-fluorophenyl)ureido)-4-(diisobutylamino)-5-fluorophenyl)pentanoic acid | 4-chloro-2-fluorophenyl | 2.36 | 510 |

-continued

| Ex. No. | Name | R | T$_r$ (min) Method C | [M + H]$^+$ |
|---|---|---|---|---|
| 978 | (+/−)-3-(3-(3-(3-chloro-4-cyanophenyl)ureido)-4-(diisobutylamino)-5-fluorophenyl)pentanoic acid | 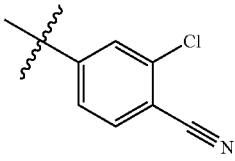 [SMILES: *c1ccc(C#N)c(Cl)c1] | 2.22 | 517 |

Example 979

(+/−)-3-(4-(Diisobutylamino)-3-fluoro-5-(2-(p-tolyl)acetamido)phenyl)pentanoic acid, TFA

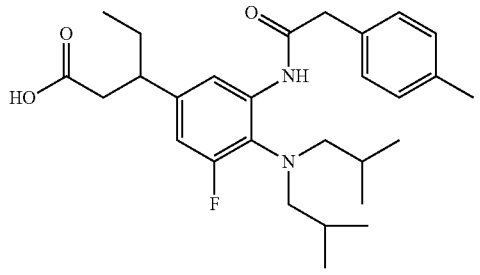 [SMILES: CCC(CC(=O)O)c1cc(F)c(N(CC(C)C)CC(C)C)c(NC(=O)Cc2ccc(C)cc2)c1]

Example 979. (+/−)-3-(4-(Diisobutylamino)-3-fluoro-5-(2-(p-tolyl)acetamido)phenyl)pentanoic acid A solution of Preparation 970D (0.05 g, 0.142 mmol) and 2-(p-tolyl)acetic acid (0.026 g, 0.170 mmol) and triethylamine (0.032 mL, 0.227 mmol) in THF (0.5 mL) was treated with BOP (0.075 g, 0.170 mmol). The reaction was stirred ON at RT then treated with lithium hydroxide (0.020 g, 0.851 mmol) in 0.3 mL of water. Methanol, 0.5 mL was added to give a single phase, and the reaction was stirred 1 h at 50° C. The reaction was cooled to ambient temperature, quenched with 0.1 mL of glacial HOAc, diluted to 2 mL with DMF, and purified by prep HPLC (acetonitrile-water gradient, 10 mM NH$_4$OAc). Concentration of the appropriate fractions afforded (+/−)-3-(4-(diisobutylamino)-3-fluoro-5-(2-(p-tolyl)acetamido)phenyl)pentanoic acid (0.048 g, 58% yield). MS(ES): m/z=471 [M+H]$^+$. T$_r$=2.44 min (Method B).

Example 980

Enantiomer 1 and Enantiomer 2

Example 980 Enantiomer 1: 3-(4-(Diisobutylamino)-3-fluoro-5-(2-(p-tolyl)acetamido)phenyl)pentanoic acid

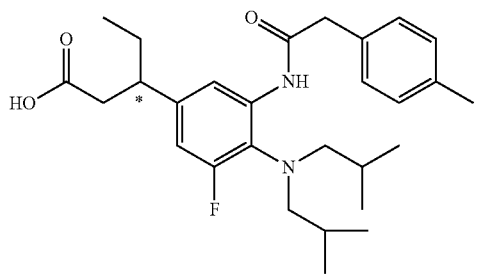

Example 980 Enantiomer 2: 3-(4-(Diisobutylamino)-3-fluoro-5-(2-(p-tolyl)acetamido)phenyl)pentanoic acid

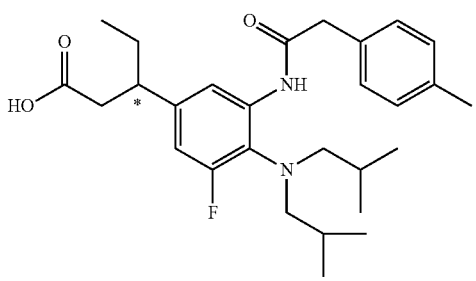 [SMILES: CCC(CC(=O)O)c1cc(F)c(N(CC(C)C)CC(C)C)c(NC(=O)Cc2ccc(C)cc2)c1]

Example 980 Enantiomer 1 and Enantiomer 2: Chiral separation of the racemic Example 979 (Berger SFC MGII, Column: WHELK-O1®) Komosil 25×3 cm ID, 5 μm, Flow rate: 85.0 mL/min, Mobile Phase: 90/10 CO$_2$/MeOH) gave Enantiomer 1 T$_r$=12.5 min (Berger SFC, Column: WHELK-O1®) Komosil 250×4.6 mm ID, 5 μm, Flow rate: 2.0 mL/min, Mobile Phase: 90/10 CO$_2$/MeOH) and Enantiomer 2 T$_r$=13.4 min (Berger SFC, Column: WHELK-O1®) Komosil 250×4.6 mm ID, 5 μm, Flow rate: 2.0 mL/min, Mobile Phase: 90/10 CO$_2$/MeOH) Absolute stereochemistry was not determined.

Example 980 Enantiomer 1: $^1$H NMR (400 MHz, DMSO-d$_6$) δ 8.81 (s, 1H), 8.02 (s, 1H), 7.20 (d, J=7.7 Hz, 2H), 7.17 (d, J=7.6 Hz, 2H), 6.77 (d, J=13.3 Hz, 1H), 3.68 (s, 2H), 2.79-2.86 (m, 1H), 2.37-2.69 (m, ~6H (integration distorted by solvent peak)), 2.29 (s, 3H), 1.41-1.65 (m, 4H), 0.77 (br. s, 12H), 0.69 (t, J=7.2 Hz, 3H). MS(ES): m/z=471 [M+H]$^+$. T$_r$=2.48 min (Method B).

Example 980 Enantiomer 2: $^1$H NMR (400 MHz, DMSO-d$_6$) δ 8.81 (s, 1H), 8.02 (s, 1H), 7.20 (d, J=7.7 Hz, 2H), 7.17 (d, J=7.6 Hz, 2H), 6.77 (d, J=13.3 Hz, 1H), 3.68 (s, 2H), 2.79-2.86 (m, 1H), 2.37-2.69 (m, ~6H (integration distorted by solvent peak)), 2.29 (s, 3H), 1.41-1.65 (m, 4H), 0.77 (br. s, 12H), 0.69 (t, J=7.2 Hz, 3H). MS(ES): m/z=471 [M+H]$^+$. T$_r$=2.48 min (Method B).

Example 981

Enantiomer 1 and Enantiomer 2

Example 981 Enantiomer 1: 3-(3-(3-(4-Chloro-2-fluorophenyl)ureido)-4-(diisobutylamino)-5-fluorophenyl)pentanoic

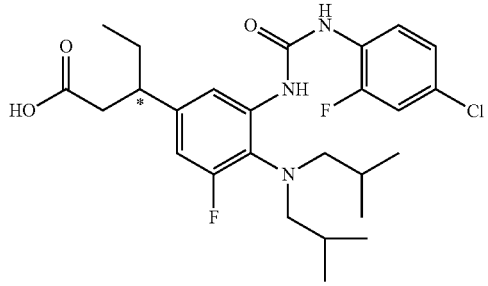 [SMILES: CCC(CC(=O)O)c1cc(F)c(N(CC(C)C)CC(C)C)c(NC(=O)Nc2ccc(Cl)cc2F)c1]

Example 981 Enantiomer 2: 3-(3-(3-(4-Chloro-2-fluorophenyl)ureido)-4-(diisobutylamino)-5-fluorophenyl)pentanoic acid

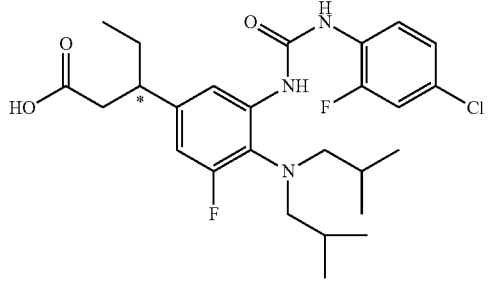 [SMILES: CCC(CC(=O)O)c1cc(F)c(N(CC(C)C)CC(C)C)c(NC(=O)Nc2ccc(Cl)cc2F)c1]

Example 981 Enantiomer 1 and Enantiomer 2: Chiral separation of the racemic Example 977 (Waters SFC-100, Column: OD-H 25×3 cm ID, 5 μm, Flow rate: 100 mL/min, Mobile Phase: 90/10 $CO_2$/MeOH) gave Enantiomer 1 $T_r$=5.99 min (Aurora SFC, Column: OD-H 250×4.6 mm ID, 5 μm, Flow rate: 2.0 mL/min, Mobile Phase: 90/10 $CO_2$/MeOH) and Enantiomer 2 $T_r$=7.06 min (Aurora SFC, Column: OD-H 250×4.6 mm ID, 5 μm, Flow rate: 2.0 mL/min, Mobile Phase: 90/10 $CO_2$/MeOH) Absolute stereochemistry was not determined.

Example 981 Enantiomer 1: $^1$H NMR (400 MHz, DMSO-$d_6$) δ 9.62 (s, 1H), 8.48 (s, 1H), J=8.7 Hz, 1H), 7.75 (s, 1H), 7.47 (d, J=10.9 Hz, 1H), 7.23 (d, J=8.6 Hz, 1H), 6.65 (d, J=13.2 Hz, 1H), 2.69-2.84 (m, 5H), 2.29-2.47 (m, 2H), 1.39-1.68 (m, 4H), 0.83 (d, J=5.9 Hz, 12H), J=6.8 Hz, 3H). MS(ES): m/z=510 [M+H]+. $T_r$=2.36 min (Method B).

Example 981 Enantiomer 2: $^1$H NMR (400 MHz, DMSO-$d_6$) δ 9.62 (s, 1H), 8.48 (s, 1H), 8.03 (t, J=8.7 Hz, 1H), 7.75 (s, 1H), 7.47 (d, J=10.9 Hz, 1H), 7.23 (d, J=8.6 Hz, 1H), 6.65 (d, J=13.2 Hz, 1H), 2.69-2.84 (m, 5H), 2.29-2.47 (m, 2H), 1.39-1.68 (m, 4H), 0.83 (d, J=5.9 Hz, 12H), J=6.8 Hz, 3H). MS(ES): m/z=510 [M+H]+. $T_r$=2.35 min (Method B).

Example 982

Enantiomer 1 and Enantiomer 2

Example 982 Enantiomer 1: 3-(4-(Diisobutylamino)-3-fluoro-5-(3-(3-fluoro-4-methylphenyl)ureido)phenyl)pentanoic acid

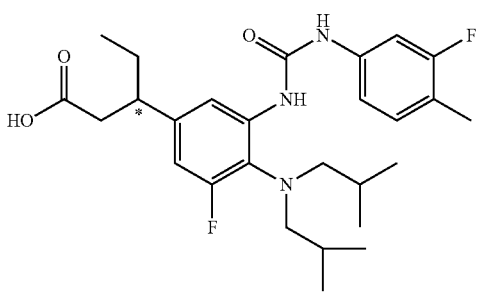 [SMILES: CCC(CC(=O)O)c1cc(F)c(N(CC(C)C)CC(C)C)c(NC(=O)Nc2ccc(C)c(F)c2)c1]

Example 982 Enantiomer 2: 3-(4-(Diisobutylamino)-3-fluoro-5-(3-(3-fluoro-4-methylphenyl)ureido)phenyl)pentanoic acid

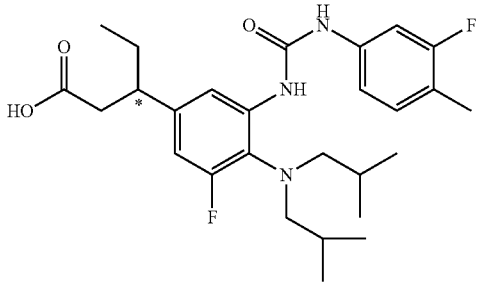

Example 982 Enantiomer 1 and Enantiomer 2: Chiral separation of the racemic Example 974 (Berger SFC MGII, Column: OD-H 25×3 cm ID, 5 μm, Flow rate: 85 mL/min, Mobile Phase: 90/10 $CO_2$/MeOH) gave Enantiomer 1 $T_r$=6.07 min (Aurora SFC, Column: OD-H 250×4.6 mm ID, 5 μm, Flow rate: 2.0 mL/min, Mobile Phase: 90/10 $CO_2$/MeOH) and Enantiomer 2 $T_r$=6.97 min (Aurora SFC, Column: OD-H 250×4.6 mm ID, 5 nm, Flow rate: 2.0 mL/min, Mobile Phase: 90/10 $CO_2$/MeOH) Absolute stereochemistry was not determined.

Example 982 Enantiomer 1: $^1$H NMR (400 MHz, DMSO-$d_6$) δ 9.71 (s, 1H), 8.21 (s, 1H), 7.81 (s, 1H), 7.45 (d, J=12.5 Hz, 1H), 8.03 (t, J=8.6 Hz, 1H), 7.07 (d, J=8.3 Hz, 1H), 6.66 (d, J=13.1 Hz, 1H), 2.71-2.86 (m, 5H), 2.40-2.58 (m, ~2H (integration distorted by solvent)), 2.17 (s, 3H), 1.42-1.66 (m, 4H), 0.84 (d, J=5.9 Hz, 12H), 0.71 (t, J=7.2 Hz, 3H). MS(ES): m/z=490 [M+H]+. $T_r$=2.27 min (Method B).

Example 982 Enantiomer 2: $^1$H NMR (400 MHz, DMSO-$d_6$) δ 9.71 (s, 1H), 8.21 (s, 1H), 7.81 (s, 1H), 7.45 (d, J=12.5 Hz, 1H), 8.03 (t, J=8.6 Hz, 1H), 7.07 (d, J=8.3 Hz, 1H), 6.66 (d, J=13.1 Hz, 1H), 2.71-2.86 (m, 5H), 2.40-2.58 (m, ~2H (integration distorted by solvent)), 2.17 (s, 3H), 1.42-1.66 (m, 4H), 0.84 (d, J=5.9 Hz, 12H), 0.71 (t, J=7.2 Hz, 3H). MS(ES): m/z=490 [M+H]+. $T_r$=2.27 min (Method B).

Example 983

(+/−)-3-(4-(Cyclohexyl(isobutyl)amino)-3-(3-(2-fluorophenyl)ureido)phenyl)-4-methoxybutanoic acid

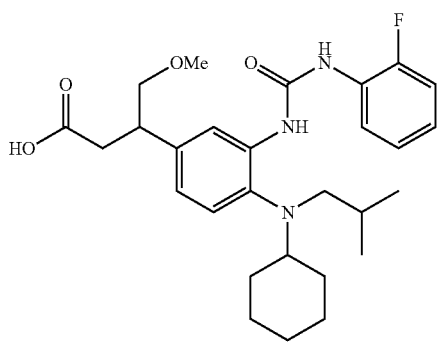 [SMILES: COCC(CC(=O)O)c1ccc(N(CC(C)C)C2CCCCC2)c(NC(=O)Nc2ccccc2F)c1]

Preparation 983A: (E) and (Z)-Methyl 3-(4-(cyclohexyl(isobutyl)amino)-3-nitrophenyl)-4-methoxybut-2-enoate

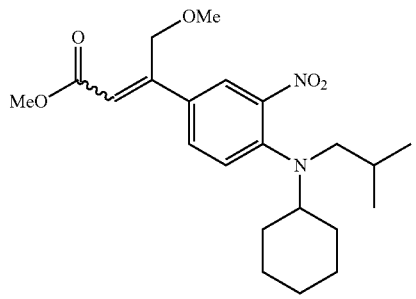 [SMILES: COCC(=CC(=O)OC)c1ccc(N(CC(C)C)C2CCCCC2)c([N+](=O)[O-])c1]

To a stirred solution of 4-bromo-N-cyclohexyl-N-isobutyl-2-nitroaniline (Balog, A. et al., "Preparation of Aromatic Urea Derivatives as IDO Inhibitors", WO 2014/150646, A1 (Sep. 25, 2014), the disclosure of which is incorporated by reference in its entirety, (0.300 g, 0.844 mmol) in N-methyl-2-pyrrolidinone (3.01 ml) was added methyl 4-methoxybut-2-enoate (0.221 ml, 1.689 mmol), palladium(II) acetate (9.48 mg, 0.042 mmol), potassium acetate (0.249 g, 2.53 mmol) and tetrabutylammonium chloride (0.050 g, 0.169 mmol). The reaction was heated at 150° C. for 1 h in a BIOTAGE® microwave. The reaction was quenched with water and diluted with EtOAc. The layers were separated. The aqueous phase was extracted with EtOAc (2×). The organic phases were combined, washed with water, dried over Na$_2$SO$_4$, filtered, and concentrated to afford an orange residue. The crude material was dissolved in a minimal amount of hexanes and chromatographed. Purification of the crude material by silica gel chromatography using an ISCO machine (40 g column, 40 mL/min, 0-20% EtOAc in hexanes over 13 min, T$_r$=7.5, 10.5 min) gave Preparation 983A (E-isomer: 0.174 g, 0.430 mmol, 51% yield; (Z)-isomer: 0.069 g, 0.171 mmol, 20% yield) as orange residue. ESI MS (M+H)$^+$=405.2.

Preparation 983B: (E)-Methyl 3-(3-amino-4-(cyclohexyl(isobutyl)amino)phenyl)-4-methoxybut-2-enoate

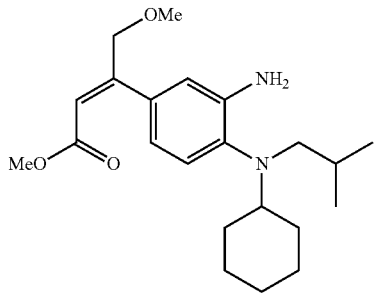 [SMILES: COC/C(=C/C(=O)OC)c1ccc(N(CC(C)C)C2CCCCC2)c(N)c1]

To a solution of ammonium chloride (0.138 g, 2.58 mmol) in water (0.269 mL) was added EtOH (0.7 mL). The reaction vessel was cooled to 0° C., then charged with zinc flake 325 mesh (0.232 g, 3.55 mmol). The mixture was treated with Preparation 983A (E-isomer: 0.1741 g, 0.430 mmol) in EtOH (1.7 mL). The reaction mixture was allowed to warm to rt and stirred for 1 h. The reaction was filtered through CELITE® and the filter cake was washed with CH$_2$C$_2$. The filtrate was concentrated to afford an orange residue. The crude material was dissolved in a minimal amount of hexanes and chromatographed. Purification of the crude material by silica gel chromatography using an ISCO machine (40 g column, 40 mL/min, 0-20% EtOAc in hexanes over 20 min, T$_r$=15.5 min) gave Preparation 983B (92.5 mg, 0.247 mmol, 57.4% yield) as an orange residue. ESI MS (M+H)$^+$=375.5.

Preparation 983C: (E)-Methyl 3-(3-(3-(4-chloro-2-fluorophenyl)ureido)-4-(cyclohexyl(isobutyl)amino)phenyl)-4-methoxybut-2-enoate

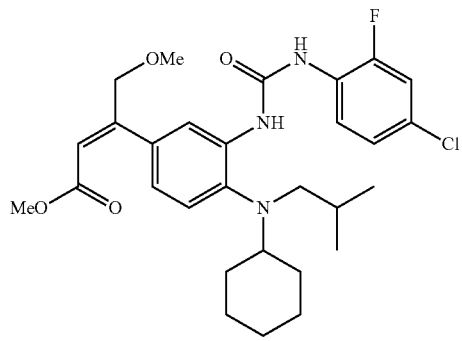 [SMILES: COC/C(=C/C(=O)OC)c1ccc(N(CC(C)C)C2CCCCC2)c(NC(=O)Nc2ccc(Cl)cc2F)c1]

To a solution of Preparation 983B (25.2 mg, 0.067 mmol) in THF (336 µl) was added 4-chloro-2-fluoro-1-isocyanatobenzene (17.05 µl, 0.135 mmol) at rt. After 2.5 h, the reaction was quenched with water and diluted with EtOAc. Layers were separated. The aqueous phase was extracted with EtOAc (2×). The organic phases were combined, dried over Na$_2$SO$_4$, filtered, and concentrated. The crude material was further dried under high vacuum to afford Preparation 983C as a brown residue. ESI MS (M+H)$^+$=532.5.

Example 983

To a solution of Preparation 983C (13.1 mg, 0.024 mmol) in MeOH (0.2 mL) and CH$_2$Cl$_2$ (0.1 mL) was added Pd/C (4 mg, 3.76 µmol). The reaction was placed under a H₂ balloon. After 1.5 h, the reaction was filtered through CELITE® and the filter cake was washed with CH₂C₂. The filtrate was concentrated to afford a yellow residue. The crude material was re-dissolved in THF (120 µl) and MeOH (0.15 mL), then LiOH (1M, 240 µl, 0.240 mmol) was added. The reaction was heated at 70° C. for 2 h. The reaction was adjusted to pH 6 with 1N HCl (0.22 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 4-minute hold at 75% B; Flow: 20 mL/min. Fractions containing the desired product were combined and dried via centrifugal evaporation to give the racemic title compound (5.7 mg, 47%). ESI MS (M+H)⁺=500.3. HPLC Peak T$_r$=1.88 minutes. Purity=98%. HPLC conditions: C. ¹H NMR (500 MHz, DMSO-d₆) δ 9.39 (s, 1H), 8.17 (s, 1H), 7.95 (t, J=7.9 Hz, 1H), 7.83 (s, 1H), 7.31-7.12 (m, 2H), 7.12-6.77 (m, 3H), 3.22 (s 3H), 2.84-2.58 (m, 3H), 2.55 (s, 5H), 2.41 (dd, J=15.7, 8.3 Hz, 1H), 1.90-1.62 (m, 4H), 1.57-1.27 (m, 2H), 1.27-0.93 (m, 5H), 0.81 (d, J=6.3 Hz, 6H)

Example 984

(+/−)-3-(3-(3-(4-Chloro-2-fluorophenyl)ureido)-4-(cyclohexyl(isobutyl)amino)phenyl)-4-methoxybutanoic acid

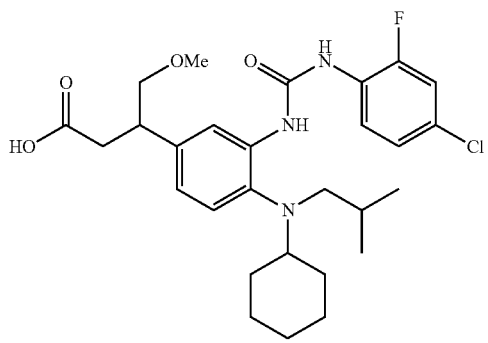 [SMILES: COCC(CC(=O)O)c1ccc(N(CC(C)C)C2CCCCC2)c(NC(=O)Nc2ccc(Cl)cc2F)c1]

To a solution of Preparation 983C (13.1 mg, 0.024 mmol) in MeOH (0.2 mL) and CH₂Cl₂ (0.1 mL) was added Pd/C (4 mg, 3.76 µmol). The reaction was placed under a H₂ balloon. The reaction was filtered through CELITE® and the filter cake was washed with CH₂C₂. The filtrate was concentrated to afford a yellow residue. The crude material was re-dissolved in THF (120 µl) and MeOH (0.15 mL), then LiOH (1M, 240 µl, 0.240 mmol) was added. The reaction was heated at 70° C. for 2 h. The reaction was adjusted to pH 6 with 1N HCl (0.22 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 4-minute hold at 75% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 20 minutes, then a 5-minute hold at 100% B; Flow: 20 mL/min. Fractions containing the desired product were combined and dried via centrifugal evaporation to afford the racemic title compound (2.2 mg, 17%). ESI MS (M+H)⁺=534.3. HPLC Peak T$_r$=2.04 minutes. Purity=99%. HPLC conditions: C. ¹H NMR (500 MHz, DMSO-d₆) δ 9.53 (s, 1H), 8.22 (s, 1H), 8.02 (t, J=8.8 Hz, 1H), 7.81 (s, 1H), 7.46 (d, J=11.0 Hz, 1H), 7.24 (d, J=9.6 Hz, 1H), 7.09 (d, J=8.1 Hz, 1H), 6.86 (d, J=7.9 Hz, 1H), 3.44 (br. s., 2H), 3.22 (s, 3H), 2.76 (br. s., 1H), 2.70-2.60 (m, 1H), 2.55 (s, 8H), 2.47-2.38 (m, 1H), 1.95-1.62 (m, 3H), 1.56-1.47 (m, 1H), 1.39-0.92 (m, 7H), 0.82 (d, J=6.5 Hz, 6H)

Example 985

Enantiomer 1 and Enantiomer 2

Example 985 Enantiomer 1: 3-(3-(3-(4-Chloro-2-fluorophenyl)ureido)-4-(cyclohexyl(isobutyl)amino)phenyl)-4-methoxybutanoic acid

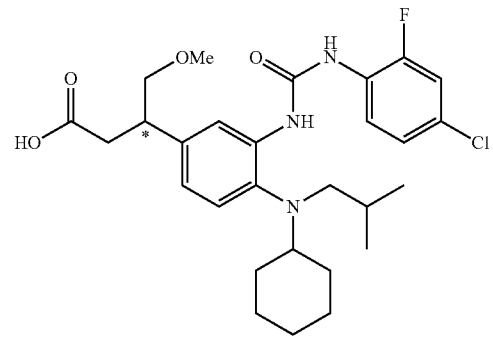 [SMILES: COCC(CC(=O)O)c1ccc(N(CC(C)C)C2CCCCC2)c(NC(=O)Nc2ccc(Cl)cc2F)c1]

Example 985 Enantiomer 2: 3-(3-(3-(4-Chloro-2-fluorophenyl)ureido)-4-(cyclohexyl(isobutyl)amino)phenyl)-4-methoxybutanoic acid

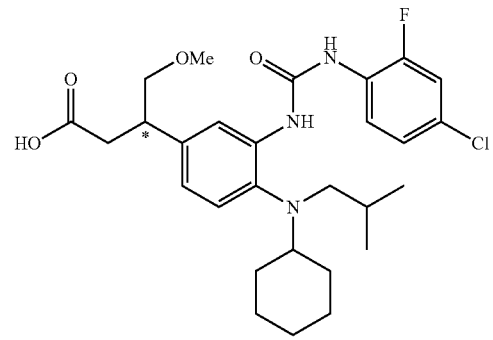 [SMILES: COCC(CC(=O)O)c1ccc(N(CC(C)C)C2CCCCC2)c(NC(=O)Nc2ccc(Cl)cc2F)c1]

Approximately 25 mg of racemic Example 984 was resolved. The racemic material was purified via preparative SFC with the following conditions: Column: Chiral OZ, 25×3 cm ID, 5-μm particles; Mobile Phase A: 85/15 $CO_2$/MeOH with 0.1% DEA+FA; Detector Wavelength: 220 nm; Flow: 85 mL/min. The fractions ("Peak-1" $T_r$=10.751 and "Peak-2" $T_r$=12.876; analytical conditions: Column: Chiral OZ, 250×4.6 mm ID, 5-μm particles; Mobile Phase A: 85/15 $CO_2$/MeOH; Flow: 2.0 mL/min) were collected in MeOH. The stereoisomeric purity of each fraction was estimated to be greater than 99.0% based on the prep-SFC chromatograms. Each enantiomer was further purified via preparative LC/MS with the following conditions: First eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford:

Example 985 Enantiomer 1: 11.1 mg, 18% of the first eluting enantiomer. ESI MS $(M+H)^+$=534.2. HPLC Peak $T_r$=2.176 minutes. Purity=98%. HPLC conditions: C. $^1$H NMR (500 MHz, DMSO-$d_6$) δ 9.53 (s, 1H), 8.23 (s, 1H), 8.03 (t, J=8.2 Hz, 1H), 7.82 (s, 1H), 7.47 (d, J=11.0 Hz, 1H), 7.24 (d, J=8.1 Hz, 1H), 7.09 (d, J=8.1 Hz, 1H), 6.86 (d, J=8.2 Hz, 1H), 3.23 (s, 3H), 2.89 (d, J=7.2 Hz, 1H), 2.76 (br. s., 1H), 2.70-2.60 (m, 1H), 2.55 (s, 3H), 2.43 (dd, J=15.9, 8.5 Hz, 1H), 1.95-1.63 (m, 4H), 1.51 (d, J=11.2 Hz, 1H), 1.38-1.27 (m, 1H), 1.27-0.94 (m, 7H), 0.82 (d, J=6.3 Hz, 6H). Absolute stereochemistry not determined.

Second eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford:

Example 985 Enantiomer 2: 11 mg, 18% of the second eluting enantiomer. ESI MS $(M+H)^+$=534.3. HPLC Peak $T_r$=2.244 minutes. Purity=95%. HPLC conditions: C. $^1$H NMR (500 MHz, DMSO-$d_6$) δ 9.53 (s, 1H), 8.23 (s, 1H), 8.03 (t, J=8.2 Hz, 1H), 7.82 (s, 1H), 7.47 (d, J=11.0 Hz, 1H), 7.24 (d, J=8.1 Hz, 1H), 7.09 (d, J=8.1 Hz, 1H), 6.86 (d, J=8.2 Hz, 1H), 3.23 (s, 3H), 2.89 (d, J=7.2 Hz, 1H), 2.76 (br. s., 1H), 2.70-2.60 (m, 1H), 2.55 (s, 3H), 2.43 (dd, J=15.9, 8.5 Hz, 1H), 1.95-1.63 (m, 4H), 1.51 (d, J=11.2 Hz, 1H), 1.38-1.27 (m, 1H), 1.27-0.94 (m, 7H), 0.82 (d, J=6.3 Hz, 6H) Absolute stereochemistry was not determined.

Example 986

(+/−)-3-(4-(Cyclohexyl(isobutyl)amino)-3-(3-(5-methylisoxazol-3-yl)ureido)phenyl)-4-methoxybutanoic acid

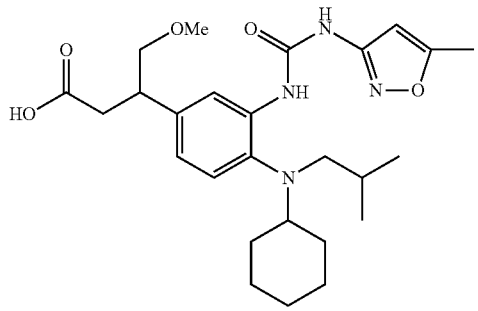 [SMILES: COCC(CC(=O)O)c1ccc(N(CC(C)C)C2CCCCC2)c(NC(=O)Nc2cc(C)on2)c1]

Preparation 986A: (+/−)-Methyl 3-(3-amino-4-(cyclohexyl(isobutyl)amino)phenyl)-4-methoxybutanoate

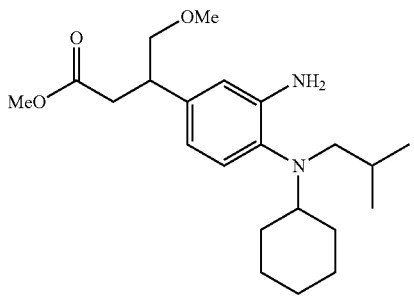 [SMILES: COCC(CC(=O)OC)c1ccc(N(CC(C)C)C2CCCCC2)c(N)c1]

To a solution of Preparation 983A (E-isomer: 0.901 g, 2.227 mmol) in MeOH (11.14 ml) was added Pd/C (0.237 g, 0.223 mmol). The reaction was placed under a $H_2$ balloon and allowed to stir at rt. After 2.5 h, the reaction was filtered through CELITE® and the filter cake was washed with $CH_2C_2$. The filtrate was concentrated to afford Preparation 986A as a dark orange residue. ESI MS $(M+H)^+$=377.5.

Example 986B:(+/−)-Methyl 3-(4-(cyclohexyl (isobutyl)amino)-3-(3-(5-methylisoxazol-3-yl) ureido)phenyl)-4-methoxybutanoic acid

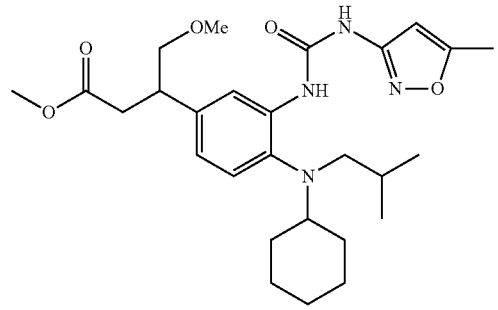

To a solution of Preparation 986A (0.320 g, 0.850 mmol) in THF (4.25 ml) at rt was added 4-nitrophenyl carbonochloridate (0.180 g, 0.892 mmol). The mixture was stirred at rt for 3 h. To this reaction were added 5-methylisoxazol-3-amine (0.250 g, 2.55 mmol) and triethylamine (0.355 ml, 2.55 mmol). The reaction was heated at 50° C. overnight. The reaction was diluted with water and extracted with EtOAc. The layers were separated. The aqueous phase was extracted with EtOAc (3×). The organic phases were combined, dried over $Na_2SO_4$, filtered, and concentrated to afford an orange residue. The crude material was dissolved in a minimal amount of $CH_2Cl_2$ and chromatographed. Purification of the crude material by silica gel chromatography using an ISCO machine (40 g column, 40 mL/min, 0-80% EtOAc in hexanes over 22 min, $T_r$=13 min) gave the racemic title compound (0.146 g, 0.277 mmol, 32.6% yield) as an off-white solid. ESI MS $(M+H)^+$=501.6. HPLC Peak $T_r$=1.03 minutes. Purity>95%. HPLC conditions: D.

Example 986

Preparation 986B (13.5 mg, 0.027 mmol) was dissolved in THF (136 μl) and MeOH (0.15 mL), then LiOH (1M, 273 μl, 0.273 mmol) was added. The reaction was heated at 70° C. for 2.5 h, then allowed to cool to rt. The reaction was adjusted to pH 6 with 1N HCl (0.3 mL), then diluted with EtOAc. The layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 4-minute hold at 75% B; Flow: 20 mL/min. Fractions containing the desired product were combined and dried via centrifugal evaporation. The material was further purified via preparative LC/MS with the following conditions: Column: Waters XBridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 4-minute hold at 70% B; Flow: 20 mL/min. Fractions containing the desired product were combined and dried via centrifugal evaporation to afford the racemic title compound (1.2 mg, 9%). ESI MS $(M+H)^+$=487.3. HPLC Peak $T_r$=1.84 minutes. Purity=98%. HPLC conditions: C. $^1$H NMR (500 MHz, DMSO-$d_6$) δ10.41 (br. s., 1H), 8.84-8.71 (m, 1H), 7.98 (s, 1H), 7.27 (s, 1H), 7.19-7.11 (m, 2H), 7.06 (s, 1H), 6.88 (d, J=7.2 Hz, 1H), 6.44 (br. s., 1H), 3.52-3.36 (m, 1H), 3.29-3.12 (m, 3H), 2.82-2.71 (m, 1H), 2.65 (dd, J=15.8, 6.0 Hz, 1H), 2.55 (s, 3H), 2.36 (s, 3H), 1.95-1.59 (m, 4H), 1.51 (d, J=10.4 Hz, 1H), 1.32-1.15 (m, 3H), 1.15-0.93 (m, 3H), 0.80 (d, J=6.2 Hz, 6H).

Example 987

Enantiomer 1 and Enantiomer 2

Example 987 Enantiomer 1: 3-(4-(Cyclohexyl (isobutyl)amino)-3-(3-(5-methylisoxazol-3-yl) ureido) phenyl)-4-methoxybutanoic acid

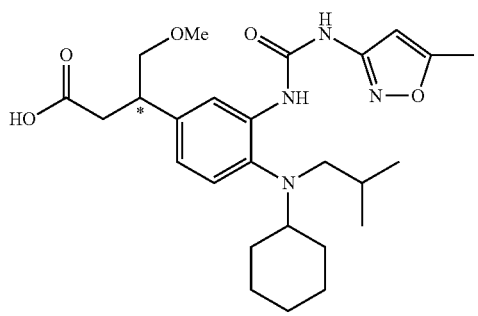 [SMILES: COCC(CC(=O)O)c1ccc(N(CC(C)C)C2CCCCC2)c(NC(=O)Nc2cc(C)on2)c1]

Example 987 Enantiomer 2: 3-(4-(Cyclohexyl (isobutyl)amino)-3-(3-(5-methylisoxazol-3-yl) ureido) phenyl)-4-methoxybutanoic acid

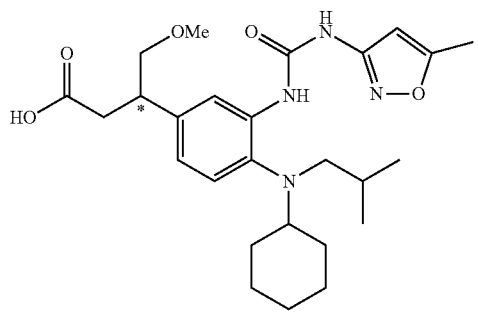 [SMILES: COCC(CC(=O)O)c1ccc(N(CC(C)C)C2CCCCC2)c(NC(=O)Nc2cc(C)on2)c1]

Approximately 13 mg of racemic Example 986 were resolved via preparative SFC with the following conditions: Column: Whelk-O R,R KROMASIL®, 25×3 cm ID, 5-μm particles; Mobile Phase A: 90/10 $CO_2$/MeOH with 0.1% DEA+FA; Detector Wavelength: 220 nm; Flow: 85 mL/min. The fractions ("Peak-1" $T_r$=13.604 and "Peak-2" $T_r$=14.095; analytical conditions: Column: Whelk-O R,R KROMASIL®, 250×4.6 mm ID, 5-μm particles; Mobile Phase A: 90/10 $CO_2$/MeOH with 0.1% DEA+FA; Flow: 2.0 mL/min) were collected in MeOH w/0.1% DEA and 0.1% formic acid. The stereoisomeric purity of each fraction was estimated to be greater than 90.0% based on the prep-SFC chromatograms. Each enantiomer was further purified via preparative LC/MS with the following conditions: First eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation to afford:

Enantiomer 1: 3.9 mg, 7.4% of the first eluting enantiomer. ESI MS $(M+H)^+$=487.2. HPLC Peak $T_r$=1.814 minutes. Purity=97%. HPLC conditions: C. $^1$H NMR (500 MHz, DMSO-$d_6$) δ10.38 (br. s., 1H), 8.72 (br. s., 1H), 7.95 (s, 1H), 7.09 (d, J=8.2 Hz, 1H), 6.83 (d, J=7.7 Hz, 1H), 6.41 (br. s., 1H), 3.19 (s, 2H), 2.71 (d, J=11.9 Hz, 1H), 2.60 (dd, J=15.6, 5.8 Hz, 1H), 2.47 (br. s., 8H), 2.39 (dd, J=15.8, 8.3 Hz, 1H), 2.32 (s, 3H), 1.84 (d, J=10.0 Hz, 2H), 1.69-1.42 (m, 3H), 1.32-1.12 (m, 4H), 1.12-0.91 (m, 3H), 0.77 (d, J=6.1 Hz, 6H). Absolute stereochemistry was not determined.

Second eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation to afford:

Enantiomer 2: 4.9 mg, 9.3% of the second eluting enantiomer. ESI MS $(M+H)^+$=487.1. HPLC Peak $T_r$=1.815 minutes. Purity=97%. HPLC conditions: C. $^1$H NMR (500 MHz, DMSO-$d_6$) δ10.38 (br. s., 1H), 8.72 (br. s., 1H), 7.95 (s, 1H), 7.09 (d, J=8.2 Hz, 1H), 6.83 (d, J=7.7 Hz, 1H), 6.41 (br. s., 1H), 3.19 (s, 2H), 2.71 (d, J=11.9 Hz, 1H), 2.60 (dd, J=15.6, 5.8 Hz, 1H), 2.47 (br. s., 8H), 2.39 (dd, J=15.8, 8.3 Hz, 1H), 2.32 (s, 3H), 1.84 (d, J=10.0 Hz, 2H), 1.69-1.42 (m, 3H), 1.32-1.12 (m, 4H), 1.12-0.91 (m, 3H), 0.77 (d, J=6.1 Hz, 6H). Absolute stereochemistry was not determined.

Example 988

(+/−)-3-(4-(Cyclohexyl(isobutyl)amino)-3-(3-(p-tolyl)ureido)phenyl)-4-methoxybutanoic acid

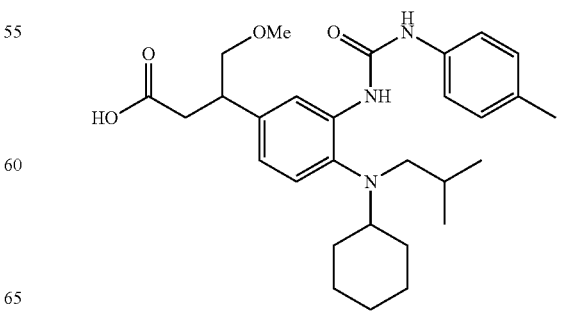

Preparation 988A: (E)-3-(4-(Cyclohexyl(isobutyl)amino)-3-(3-(p-tolyl)ureido)phenyl)-4-methoxybut-2-enoic acid

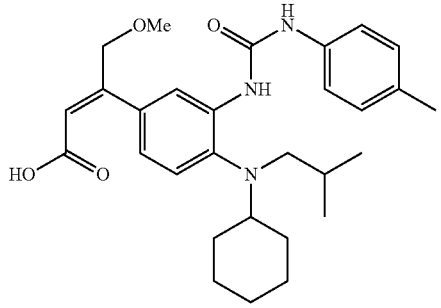 [SMILES: COC/C(=C/C(=O)O)c1ccc(N(CC(C)C)C2CCCCC2)c(NC(=O)Nc2ccc(C)cc2)c1]

To a solution of Preparation 983B (21.8 mg, 0.058 mmol) in THF (291 μl) was added 1-isocyanato-4-methylbenzene (14.65 μl, 0.116 mmol) at rt. After 2.5 h, MeOH (0.15 mL) and a 1M solution of lithium hydroxide (582 μl, 0.582 mmol) were added. The reaction was heated at 70° C. for 2 h. The reaction was adjusted to pH 6 with 1N HCl (0.6 mL), then diluted with EtOAc. The layers were separated. The aqueous phase was extracted with EtOAc (2×). The organic phases were combined, dried over $Na_2SO_4$, filtered, and concentrated to afford a brown residue. Approx. 40% of total crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-85% B over 20 minutes, then a 5-minute hold at 100% B; Flow: 20 mL/min. Fractions containing the desired product were combined and dried via centrifugal evaporation to afford Preparation 40A (6.4 mg, 22%). ESI MS $(M+H)^+=494.5$.

Example 988

To a solution of Preparation 988A (13.1 mg, 0.027 mmol) in MeOH (0.3 mL) was added Pd/C (4 mg, 3.76 μmol). The reaction was placed under a $H_2$ balloon and allowed to stir at rt. After 4 h, the reaction was filtered through CELITE® and the filter cake was washed with $CH_2C_2$. The filtrate was concentrated to afford a yellow residue. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford the racemic title compound (2.9 mg, 22%). ESI MS $(M+H)^+=496.2$. HPLC Peak $T_r=1.93$ minutes. Purity=98%. HPLC conditions: C. $^1$H NMR (500 MHz, DMSO-$d_6$) δ 9.40 (s, 1H), 7.97 (d, J=7.7 Hz, 2H), 7.37 (d, J=8.2 Hz, 2H), 7.10 (d, J=8.2 Hz, 3H), 6.82 (d, J=7.5 Hz, 1H), 3.29-3.15 (m, 3H), 2.74 (s, 1H), 2.63 (dd, J=15.7, 5.9 Hz, 1H), 2.55 (s, 2H), 2.42 (dd, J=15.7, 8.3 Hz, 1H), 2.26 (s, 3H), 1.92-1.63 (m, 4H), 1.52 (d, J=11.3 Hz, 1H), 1.35-1.14 (m, 3H), 1.14-0.94 (m, 3H), 0.82 (d, J=6.2 Hz, 6H).

Example 989

Enantiomer 1 and Enantiomer 2

Example 989 Enantiomer 1: 3-(4-(Cyclohexyl(isobutyl)amino)-3-(3-(p-tolyl)ureido)phenyl)-4-methoxybutanoic acid

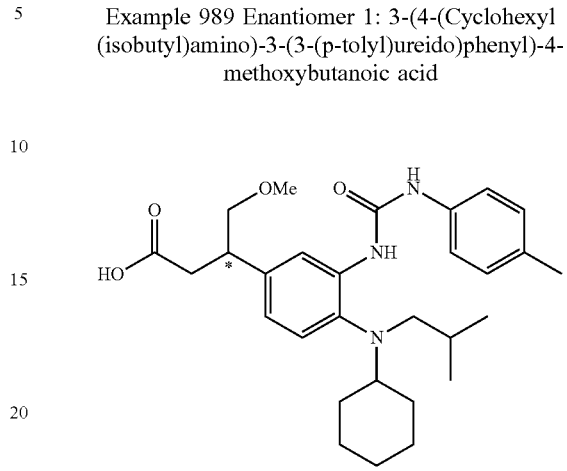

Example 989 Enantiomer 2: 3-(4-(Cyclohexyl(isobutyl)amino)-3-(3-(p-tolyl)ureido)phenyl)-4-methoxybutanoic acid

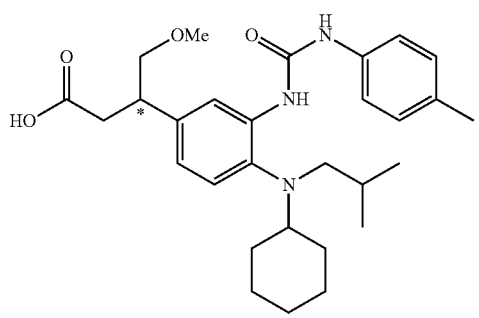 [SMILES: COCC(CC(=O)O)c1ccc(N(CC(C)C)C2CCCCC2)c(NC(=O)Nc2ccc(C)cc2)c1]

Approximately 23 mg of Example 40 was resolved. The racemic material was purified via preparative SFC with the following conditions: Column: Chiral IC, 25×3 cm ID, 5-μm particles; Mobile Phase A: 87/13 $CO_2$/MeOH; Detector Wavelength: 220 nm; Flow: 85 mL/min. The fractions ("Peak-1" $T_r=6.756$ and "Peak-2" $T_r=7.162$; analytical conditions: Column: Chiral IC, 250×4.6 mm ID, 5-μm particles; Mobile Phase A: 85/15 $CO_2$/MeOH; Flow: 2.0 mL/min) were collected in MeOH. The stereoisomeric purity of each fraction was estimated to be greater than 95.0% based on the prep-SFC chromatograms. Each enantiomer was further purified via preparative LC/MS with the following conditions: First eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 3-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-80% B over 20 minutes, then a 5-minute hold at 100% B; Flow: 20 mL/min. Fractions containing the desired product were combined and dried via centrifugal evaporation to afford:

Enantiomer 1: 7.5 mg, 12% of the first eluting enantiomer. ESI MS $(M+H)^+$=496.4. HPLC Peak $T_r$=2.142 minutes. Purity=99%. HPLC conditions: C. $^1$H NMR (500 MHz, DMSO-$d_6$) δ 9.40 (s, 1H), 7.97 (d, J=8.4 Hz, 2H), 7.37 (d, J=8.2 Hz, 2H), 7.10 (d, J=8.2 Hz, 3H), 6.82 (d, J=7.9 Hz, 1H), 3.23 (s, 3H), 2.75 (d, J=11.9 Hz, 1H), 2.64 (dd, J=15.7, 6.1 Hz, 1H), 2.55 (s, 5H), 2.43 (dd, J=15.6, 8.2 Hz, 1H), 2.25 (s, 3H), 1.92-1.64 (m, 4H), 1.51 (d, J=11.1 Hz, 1H), 1.33-1.15 (m, 3H), 1.15-0.95 (m, 3H), 0.84-0.84 (m, 1H), 0.82 (d, J=6.3 Hz, 6H). Absolute stereochemistry was not determined.

Second eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 3-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-80% B over 20 minutes, then a 5-minute hold at 100% B; Flow: 20 mL/min. Fractions containing the desired product were combined and dried via centrifugal evaporation to afford:

Enantiomer 2: 8.3 mg, 13% of the second eluting enantiomer. ESI MS $(M+H)^+$=496.3. HPLC Peak $T_r$=2.142 minutes. Purity=99%. $^1$H NMR (500 MHz, DMSO-$d_6$) δ 9.40 (s, 1H), 7.97 (d, J=8.4 Hz, 2H), 7.37 (d, J=8.2 Hz, 2H), 7.10 (d, J=8.2 Hz, 3H), 6.82 (d, J=7.9 Hz, 1H), 3.23 (s, 3H), 2.75 (d, J=11.9 Hz, 1H), 2.64 (dd, J=15.7, 6.1 Hz, 1H), 2.55 (s, 5H), 2.43 (dd, J=15.6, 8.2 Hz, 1H), 2.25 (s, 3H), 1.92-1.64 (m, 4H), 1.51 (d, J=11.1 Hz, 1H), 1.33-1.15 (m, 3H), 1.15-0.95 (m, 3H), 0.84-0.84 (m, 1H), 0.82 (d, J=6.3 Hz, 6H). Absolute stereochemistry was not determined.

Example 990 (+/−)-3-(4-(Cyclohexyl(isobutyl) amino)-3-(3-(pyrimidin-5-yl)ureido)phenyl)-4-methoxybutanoic acid

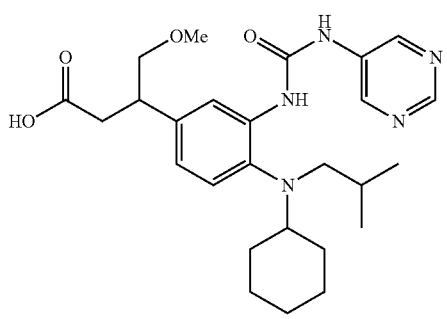 [SMILES: COCC(CC(=O)O)c1ccc(N(CC(C)C)C2CCCCC2)c(NC(=O)Nc2cncnc2)c1]

Preparation 990A. (E)-Methyl 3-(4-(cyclohexyl (isobutyl)amino)-3-(3-(pyrimidin-5-yl)ureido)phenyl)-4-methoxybut-2-enoate

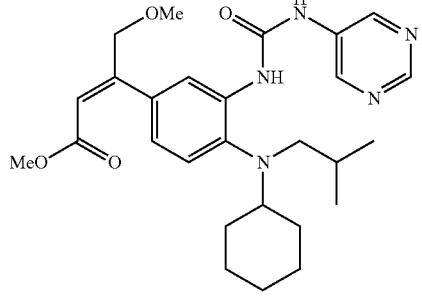

To a solution of Preparation 983B (22.8 mg, 0.061 mmol) in THF (304 μl) at rt was added 4-nitrophenyl carbonochloridate (12.88 mg, 0.064 mmol). The mixture was stirred at rt for 3 h. To this reaction were added pyrimidin-5-amine (17.37 mg, 0.183 mmol) and triethylamine (25.5 μl, 0.183 mmol). The reaction was heated at 50° C. overnight. The reaction was quenched with water and diluted with EtOAc. The layers were separated. The aqueous phase was extracted with EtOAc (3×). The organic phases were combined, dried over $Na_2SO_4$, filtered, and concentrated to afford a brown residue. The crude material was further dried under high vacuum, then dissolved in a minimal amount of $CH_2Cl_2$ and purified by ISCO chromatography to afford Preparation 990A. ESI MS $(M+H)^+$=496.5.

Example 990

To a solution of Preparation 990A (13.7 mg, 0.028 mmol) in MeOH (0.2 mL) and $CH_2Cl_2$ (0.1 mL) was added Pd/C (4 mg, 3.76 μmol). The reaction was placed under a $H_2$ balloon. The reaction was filtered through CELITE® and the filter cake was washed with $CH_2C_2$. The filtrate was concentrated to afford a yellow residue. The crude material was re-dissolved in THF (138 μl) and MeOH (0.15 mL), then LiOH (276 μl, 0.276 mmol) was added. The reaction was heated at 70° C. for 1.25 h. The reaction was adjusted to pH 6 with 1N HCl (0.3 mL), then diluted with EtOAc. The layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 minutes, then a 5-minute hold at 100% B; Flow: 20 mL/min. Fractions containing the desired product were combined and dried via centrifugal evaporation to afford Example 990 (3.7 mg, 27%). ESI MS $(M+H)^+$=484.3. HPLC Peak $T_r$=1.53 minutes. Purity=97%. HPLC conditions: C. $^1$H NMR (500 MHz, DMSO-$d_6$) δ 9.99 (s, 1H), 8.94 (s, 2H), 8.83 (s, 1H), 8.25 (s, 1H), 7.97 (br. s., 1H), 7.15 (d, J=8.2 Hz, 1H), 6.89 (d, J=7.9 Hz, 1H), 3.23 (s, 3H), 2.86-2.60 (m, 3H), 2.55 (s, 4H), 2.44 (dd, J=15.7, 8.4 Hz, 1H), 1.96-1.87 (m, 2H), 1.70 (d, J=12.5 Hz, 2H), 1.52 (d, J=12.3 Hz, 1H), 1.35-1.17 (m, 3H), 1.17-0.94 (m, 3H), 0.83 (d, J=6.4 Hz, 6H).

Example 991

Enantiomer 1 and Enantiomer 2

Example 991 Enantiomer 1: 3-(4-(Cyclohexyl (isobutyl)amino)-3-(3-(pyrimidin-5-yl)ureido)phenyl)-4-methoxybutanoic acid

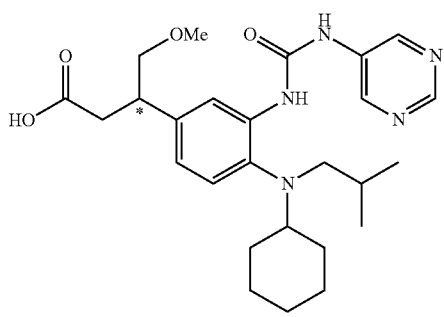 [SMILES: COCC(CC(=O)O)c1ccc(N(CC(C)C)C2CCCCC2)c(NC(=O)Nc2cncnc2)c1]

Example 991 Enantiomer 2: 3-(4-(Cyclohexyl (isobutyl)amino)-3-(3-(pyrimidin-5-yl)ureido)phenyl)-4-methoxybutanoic acid

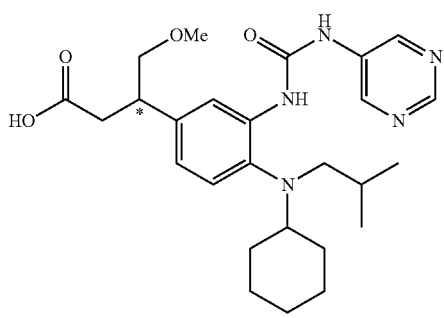 [SMILES: COCC(CC(=O)O)c1ccc(N(CC(C)C)C2CCCCC2)c(NC(=O)Nc2cncnc2)c1]

Approximately 13 mg of Example 990 was resolved. The racemic material was purified via preparative SFC with the following conditions: Column: Chiral IC, 25×3 cm ID, 5-μm particles; Mobile Phase A: 85/15 CO$_2$/MeOH; Detector Wavelength: 220 nm; Flow: 85 mL/min. The fractions ("Peak-1" T$_r$=6.901 and "Peak-2" T$_r$=7.271; analytical conditions: Column: Chiral IC, 250×4.6 mm ID, 5-μm particles; Mobile Phase A: 85/15 CO$_2$/MeOH; Flow: 2.0 mL/min) were collected in MeOH. The stereoisomeric purity of each fraction was estimated to be greater than 90.0% based on the prep-SFC chromatograms. Each enantiomer was further purified via preparative LC/MS with the following conditions: First eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to afford:

Enantiomer 1: 3.6 mg, 7% of the first eluting enantiomer. ESI MS (M+H)$^+$=484.4. HPLC Peak T$_r$=1.581 minutes. Purity=98%. HPLC conditions: C. $^1$H NMR (500 MHz, DMSO-d$_6$) δ10.03 (s, 1H), 8.95 (s, 2H), 8.82 (s, 1H), 8.26 (s, 1H), 7.97 (s, 1H), 7.15 (d, J=8.1 Hz, 1H), 6.88 (d, J=8.1 Hz, 1H), 3.23 (s, 2H), 2.94-2.73 (m, 2H), 2.64 (dd, J=15.9, 6.1 Hz, 1H), 2.55 (s, 5H), 2.44 (dd, J=15.9, 8.6 Hz, 1H), 1.92 (d, J=10.7 Hz, 2H), 1.70 (d, J=11.2 Hz, 2H), 1.52 (d, J=11.0 Hz, 1H), 1.35-1.17 (m, 3H), 1.17-1.06 (m, 4H), 1.01 (t, J=12.2 Hz, 1H), 0.83 (d, J=6.2 Hz, 6H). Absolute stereochemistry was not determined.

Second eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to afford:

Enantiomer 2: 4.8 mg, 10% of the second eluting enantiomer. ESI MS (M+H)$^+$=484.3. HPLC Peak T$_r$=1.582 minutes. Purity=98%. HPLC conditions: C. $^1$H NMR (500 MHz, DMSO-d$_6$) δ10.03 (s, 1H), 8.95 (s, 2H), 8.82 (s, 1H), 8.26 (s, 1H), 7.97 (s, 1H), 7.15 (d, J=8.1 Hz, 1H), 6.88 (d, J=8.1 Hz, 1H), 3.23 (s, 2H), 2.94-2.73 (m, 2H), 2.64 (dd, J=15.9, 6.1 Hz, 1H), 2.55 (s, 5H), 2.44 (dd, J=15.9, 8.6 Hz, 1H), 1.92 (d, J=10.7 Hz, 2H), 1.70 (d, J=11.2 Hz, 2H), 1.52 (d, J=11.0 Hz, 1H), 1.35-1.17 (m, 3H), 1.17-1.06 (m, 4H), 1.01 (t, J=12.2 Hz, 1H), 0.83 (d, J=6.2 Hz, 6H). Absolute stereochemistry was not determined.

Example 992

(+/−)-3-(4-(Diisobutylamino)-3-(3-(p-tolyl)ureido) phenyl)-4-methoxybutanoic acid

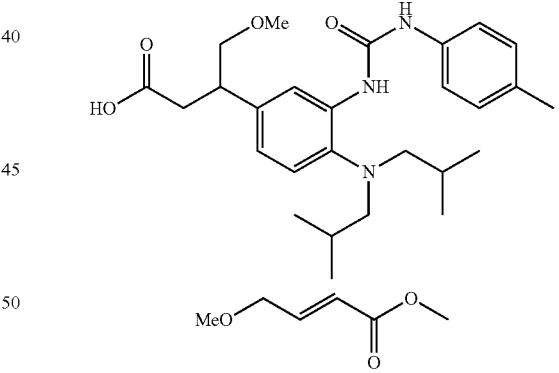

Preparation 992A. Methyl 4-methoxybut-2-enoate

To MeOH (2 mL) was added (E)-methyl 4-bromobut-2-enoate (4.00 mL, 33.5 mmol) and silver oxide (6.21 g, 26.8 mmol). The mixture was sonicated for 16 hours. The mixture was filtered and concentrated. The crude material was purified by ISCO (EtOAc/Hex 0-10%). Fractions containing product were concentrated to yield 992A (4 g, 30.7 mmol, 92% yield) as a clear oil. $^1$H NMR (400 MHz, chloroform-d) δ 6.95 (dt, J=15.8, 4.3 Hz, 1H), 6.07 (dt, J=15.8, 2.0 Hz, 1H), 4.09 (dd, J=4.3, 2.0 Hz, 2H), 3.75 (s, 3H), 3.43-3.35 (m, 3H).

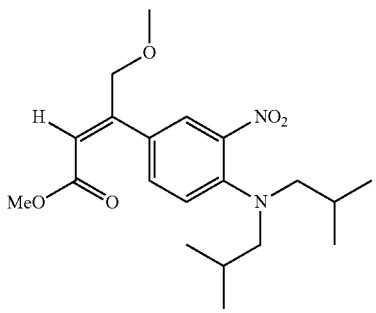 [SMILES: COC/C(=C/C(=O)OC)c1ccc(N(CC(C)C)CC(C)C)c([N+](=O)[O-])c1]

Preparation 992B. (E)-Methyl 3-(4-(diisobutylamino)-3-nitrophenyl)-4-methoxybut-2-enoate To a stirred solution of 4-bromo-N,N-diisobutyl-2-nitroaniline (1.4 g, 4.25 mmol) in N-methyl-2-pyrrolidinone (5 mL) at room temperature were added 44A (1.107 g, 8.50 mmol) and potassium acetate (1.252 g, 12.76 mmol). After degassing with $N_2$ for 10 min, palladium(II) acetate (0.076 g, 0.340 mmol) was added. The reaction mixture was heated at 150° C. in the microwave for 1 hour. After cooling to rt, the reaction mixture was quenched with water and extracted twice with ethyl acetate. The combined organic layers were dried over sodium sulfate and concentrated under reduced pressure. The crude product was purified by ISCO (eluting with cyclohexane-ethyl acetate from 0 to 30%). Fractions containing product were concentrated to yield 992B (950 mg, 2.5 mmol, 59% yield) as a yellow oil. LC-MS Anal. Calc'd. for $C_{20}H_{30}N_2O_5$, 378.21, found [M+H] 379.08. $T_r$=1.18 min. (Method C). $^1$H NMR (500 MHz, chloroform-d) δ 7.99 (d, J=2.4 Hz, 1H), 7.58 (dd, J=8.9, 2.4 Hz, 1H), 7.04 (d, J=8.9 Hz, 1H), 6.22 (s, 1H), 3.75 (s, 3H), 3.66 (s, 3H), 3.23 (d, J=0.5 Hz, 2H), 2.90 (d, J=7.3 Hz, 4H), 1.89 (dt, J=13.5, 6.8 Hz, 2H), 0.83 (d, J=6.6 Hz, 12H).

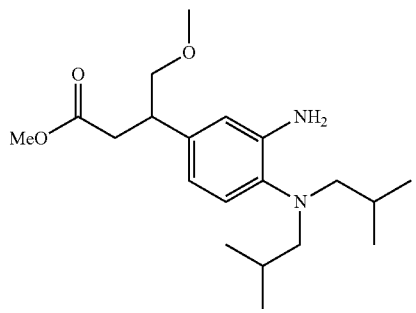 [SMILES: COCC(CC(=O)OC)c1ccc(N(CC(C)C)CC(C)C)c(N)c1]

Preparation 992C. Methyl 3-(3-amino-4-(diisobutylamino)phenyl)-4-methoxybutanoate To a solution of 992B (300 mg, 0.793 mmol) in MeOH (5 mL) was added 10% Pd—C (8.44 mg, 7.93 μmol). After stirring at room temperature for 2 hours, the mixture was filtered. The filtrate was concentrated to yield Preparation 992C (250 mg, 0.713 mmol, 90% yield) as a yellow oil. LC-MS Anal. Calc'd. for $C_{20}H_{34}N_2O_3$, 350.26, found [M+H] 351.08. $T_r$=0.85 min. (Method C). $^1$H NMR (400 MHz, chloroform-d) δ 6.97 (d, J=8.1 Hz, 1H), 6.67-6.36 (m, 2H), 4.23-4.05 (m, 1H), 3.69 (d, J=7.0 Hz, 1H), 3.61 (s, 3H), 3.55-3.49 (m, 1H), 3.47-3.38 (m, 1H), 3.32 (s, 3H), 2.76 (dd, J=15.4, 7.1 Hz, 1H), 2.62-2.48 (m, 4H), 1.81-1.60 (m, 2H), 0.94-0.84 (m, 12H).

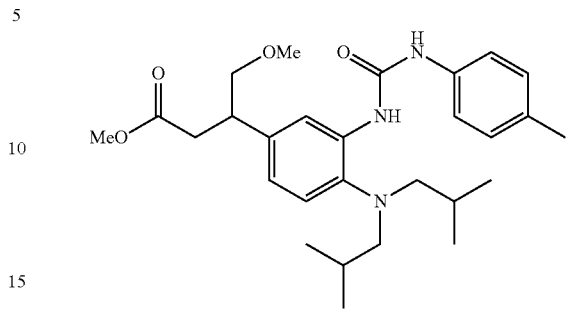

Preparation 992D. Methyl 3-(4-(diisobutylamino)-3-(3-(p-tolyl)ureido)phenyl)-4-methoxybutanoate To a solution of 992C (60 mg, 0.171 mmol) in THF (5 mL) was added 1-isocyanato-4-methylbenzene (43.1 μl, 0.342 mmol). After the mixture was stirred at room temperature for 16 hours, 20% of the reaction mixture was taken out and purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-95% B over 15 minutes, then a 8-minute hold at 100% B; Flow: 20 mL/min. Fractions containing the desired product were combined and dried via centrifugal evaporation to afford Preparation 992D as a racemic mixture (8 mg, 0.010 mmol, 30% yield). LC-MS Anal. Calc'd. for $C_{28}H_{41}N_3O_4$, 483.31, found [M+H] 484.32. $T_r$=0.85 min. (Method A). $^1$H NMR (500 MHz, DMSO-$d_6$) δ 9.34 (s, 1H), 7.84 (s, 2H), 7.35 (d, J=8.1 Hz, 2H), 7.16-7.07 (m, 3H), 6.82 (d, J=8.1 Hz, 1H), 3.50 (s, 3H), 3.45-3.37 (m, 1H), 3.22 (s, 4H), 2.71 (dd, J=15.6, 6.2 Hz, 1H), 2.62 (d, J=6.7 Hz, 4H), 2.57-2.52 (m, 2H), 2.24 (s, 3H), 1.61 (dt, J=13.0, 6.5 Hz, 2H), 0.83 (d, J=6.4 Hz, 12H).

Example 992

To the remaining 80% of reaction mixture of 49D, NaOH (1M, 1712 μl, 1.712 mmol) was added. The mixture was heated at 50° C. for 1 hour. The reaction mixture was neutralized with HCl to pH~4, filtered and the crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-95% B over 15 minutes, then a 8-minute hold at 100% B; Flow: 20 mL/min. Fractions containing the desired product were combined and dried via centrifugal evaporation to afford the title compound as a racemic mixture (33 mg, 0.07 mmol, 41% yield). LC-MS Anal. Calc'd. for $C_{27}H_{39}N_3O_4$, 469.29, found [M+H] 470.08. $T_r$=0.93 min (Method A). $^1$H NMR (500 MHz, DMSO-$d_6$) δ 9.34 (s, 1H), 7.82 (br. s., 2H), 7.33 (d, J=8.3 Hz, 2H), 7.26 (s, 1H), 7.16 (s, 1H), 6.83 (d, J=7.0 Hz, 1H), 3.60-3.48 (m, 1H), 3.43-3.35 (m, 1H), 3.20 (s, 3H), 3.19-3.12 (m, 1H), 2.68-2.61 (m, 1H), 2.60 (d, J=6.9 Hz, 4H), 2.42 (dd, J=15.8, 8.6 Hz, 1H), 2.31-2.15 (m, 3H), 1.60 (dt, J=13.2, 6.6 Hz, 2H), 0.82 (d, J=6.6 Hz, 12H).

Example 993

Enantiomer 1 and Enantiomer 2

3-(4-(Diisobutylamino)-3-(3-(p-tolyl)ureido)phenyl)-4-methoxybutanoic acid

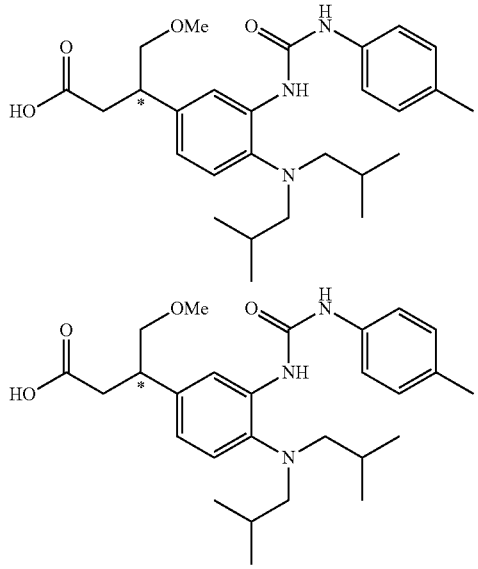

Approximately 33 mg of racemic Example 44 was resolved. The racemic material was purified via preparative SFC with the following conditions: Column: Chiral IC 25×3 cm ID, 5-μm particles; Mobile Phase A: 87/13 $CO_2$/MeOH with 0.1% DEA+FA; Detector Wavelength: 220 nm; Flow: 85 mL/min. The fractions ("Peak-1" $T_r$=19.242 and "Peak-2" $T_r$=20.604; analytical conditions: Column: Chiral IC 250×4.6 mm ID, 5-μm particles; Mobile Phase A: 90/10 $CO_2$/MeOH with 0.1% DEA+FA; Flow: 2.0 mL/min) were collected in MeOH w/0.1% DEA and 0.1% formic acid. The stereoisomeric purity of each fraction was estimated to be greater than 90.0% based on the prep-SFC chromatograms. Each enantiomer was further purified via preparative LC/MS with the following conditions: First eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation to afford Example 993 Enantiomer 1 (10.2 mg, 0.02 mmol, 31% yield). $^1$H NMR (500 MHz, DMSO-$d_6$) δ 9.33 (s, 1H), 7.84 (d, J=11.7 Hz, 2H), 7.35 (d, J=8.2 Hz, 2H), 7.20-7.03 (m, 3H), 6.83 (d, J=8.0 Hz, 1H), 3.55-3.34 (m, 1H), 3.22 (s, 3H), 2.69-2.57 (m, 6H), 2.42 (dd, J=15.8, 8.5 Hz, 2H), 2.24 (s, 3H), 1.62 (dt, J=13.2, 6.6 Hz, 2H), 0.84 (d, J=6.5 Hz, 12H). LC-MS Anal. Calc'd. for $C_{27}H_{39}N_3O_4$ 469.29, found [M+H] 470.29. $T_r$=1.93 min (Method B). HPLC Peak $T_r$=20.604 minute (Method E).

Second eluting enantiomer: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation to afford Example 993 Enantiomer 2 (9.5 mg, 0.02 mmol, 29% yield). $^1$H NMR (500 MHz, DMSO-$d_6$) δ 9.44-9.14 (m, 1H), 7.96-7.73 (m, 2H), 7.50-7.26 (m, 2H), 7.18-7.03 (m, 3H), 6.84 (d, J=8.3 Hz, 1H), 3.43 (br. s., 1H), 3.28-3.04 (m, 3H), 2.69-2.57 (m, 6H), 2.47-2.34 (m, 2H), 2.30-2.12 (m, 3H), 1.62 (d, J=6.5 Hz, 2H), 0.90-0.75 (m, 12H). LC-MS Anal. Calc'd. for $C_{27}H_{39}N_3O_4$, 469.29, found [M+H] 470.29. $T_r$=1.74 min (Method B). HPLC Peak $T_r$=19.242 minute (Method E).

Example 994

(+/−)-3-(3-(3-(4-Chloro-2-fluorophenyl)ureido)-4-(diisobutylamino)phenyl)-4-methoxybutanoic acid

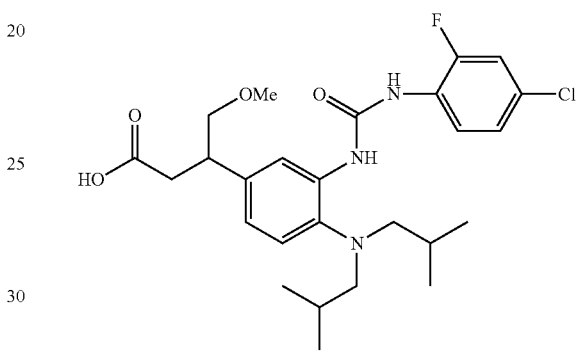

Example 994 was obtained following the procedure in Example 44 using 4-chloro-2-fluoro-1-isocyanatobenzene. LC-MS Anal. Calc'd. for $C_{26}H_{35}ClFN_3O_4$ 507.23, found [M+H] 508.08. $T_r$=0.98 min (Method A). $^1$H NMR (500 MHz, DMSO-$d_6$) δ 9.44 (s, 1H), 8.11 (s, 1H), 8.05 (t, J=8.8 Hz, 1H), 7.73 (s, 1H), 7.49-7.41 (m, 1H), 7.25-7.19 (m, 1H), 7.13-7.08 (m, 1H), 6.87 (d, J=7.9 Hz, 1H), 3.90 (m, 2H), 3.49-3.32 (m, 1H), 3.21 (s, 3H), 3.19-3.12 (m, 1H), 2.67-2.59 (m, 4H), 2.42 (dd, J=15.8, 8.5 Hz, 1H), 1.64 (dt, J=13.2, 6.6 Hz, 2H), 0.92-0.77 (m, 12H).

Example 995

Enantiomer 1 and Enantiomer 2

3-(3-(3-(4-Chloro-2-fluorophenyl)ureido)-4-(diisobutylamino) phenyl)-4-methoxybutanoic acid

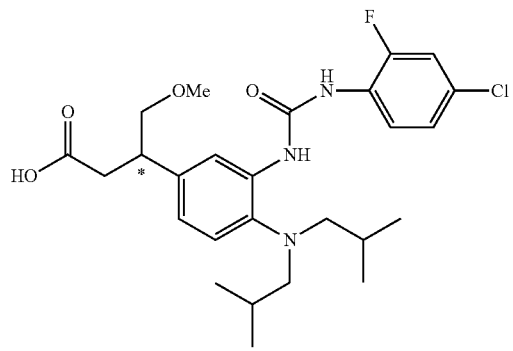 [SMILES: COCC(CC(=O)O)c1ccc(N(CC(C)C)CC(C)C)c(NC(=O)Nc2ccc(Cl)cc2F)c1]

-continued

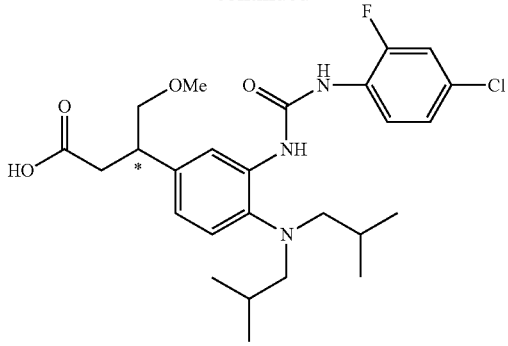

Chiral separation was obtained following the procedure in Example 993.

Enantiomer 1: $^1$H NMR (500 MHz, DMSO-$d_6$) δ 9.44 (br. s., 1H), 8.31 (br. s., 1H), 8.11 (s, 1H), 8.05 (t, J=8.8 Hz, 1H), 7.73 (br. s., 1H), 7.45 (d, J=10.4 Hz, 1H), 7.22 (d, J=8.4 Hz, 1H), 7.10 (d, J=8.2 Hz, 1H), 6.87 (d, J=7.7 Hz, 1H), 3.39 (d, J=7.3 Hz, 1H), 3.21 (s, 3H), 2.87 (d, J=7.2 Hz, 2H), 2.70-2.55 (m, 5H), 2.40 (dd, J=15.9, 8.6 Hz, 1H), 1.76-1.53 (m, 2H), 0.83 (d, J=6.4 Hz, 12H). LC-MS Anal. Calc'd. for $C_{26}H_{35}ClFN_3O_4$, 507.23, found [M+H] 508.23. $T_r$=2.10 min (Method B). HPLC Peak $T_r$=11.123 minute (Method E).

Enantiomer 2: $^1$H NMR (500 MHz, DMSO-$d_6$) δ 9.44 (s, 1H), 8.29 (br. s., 1H), 8.10 (s, 1H), 8.04 (t, J=8.8 Hz, 1H), 7.73 (s, 1H), 7.45 (d, J=11.0 Hz, 1H), 7.22 (d, J=8.8 Hz, 1H), 7.10 (d, J=8.2 Hz, 1H), 6.87 (d, J=7.9 Hz, 1H), 3.51-3.32 (m, 1H), 3.25-3.10 (m, 3H), 2.88 (q, J=7.2 Hz, 2H), 2.69-2.57 (m, 5H), 2.40 (dd, J=15.7, 8.5 Hz, 1H), 1.64 (dt, J=13.1, 6.6 Hz, 2H), 0.83 (d, J=6.5 Hz, 12H). LC-MS Anal. Calc'd. for $C_{26}H_{35}ClFN_3O_4$, 507.23, found [M+H] 508.23. $T_r$=1.89 min (Method B). HPLC Peak $T_r$=9.923 minute (Method E).

Example 996

(+/−)-3-(4-(Diisobutylamino)-3-(3-(pyrimidin-5-yl)ureido)phenyl)-4-methoxybutanoic acid

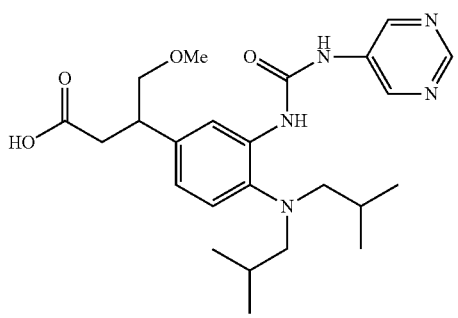

To a solution of 992C (80 mg, 0.228 mmol) in THF (1141 µl) was added 4-nitrophenyl carbonochloridate (55.2 mg, 0.274 mmol). After stirring at room temperature for 2 hours, pyrimidin-5-amine (65.1 mg, 0.685 mmol) and TEA (95 µl, 0.685 mmol) were added. The mixture was heated to 50° C. overnight. The reaction mixture was diluted with MeOH, followed by sodium hydroxide (1M, 1826 µl, 1.826 mmol) and heated to 50° C. for 1 h. The mixture was neutralized to pH-4, filtered and purified via preparative LC/MS with the following conditions: Column: Waters XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-95% B over 15 minutes, then a 8-minute hold at 100% B; Flow: 20 mL/min. Fractions containing the desired product were combined and dried via centrifugal evaporation to afford Example 48 (80 mg, 0.18 mmol, 77% yield). LC-MS Anal. Calc'd. for $C_{24}H_{35}N_5O_4$, 457.27, found [M+H] 458.20. $T_r$=0.79 min. (Method A). $^1$H NMR (500 MHz, DMSO-$d_6$) δ 9.90 (s, 1H), 8.91 (s, 2H), 8.80 (s, 1H), 8.09 (s, 1H), 7.83 (s, 1H), 7.16 (d, J=8.2 Hz, 1H), 6.89 (d, J=7.2 Hz, 1H), 3.61-3.49 (m, 1H), 3.40 (t, J=6.7 Hz, 1H), 3.20 (s, 3H), 2.89 (d, J=7.2 Hz, 1H), 2.68-2.58 (m, 4H), 2.41 (dd, J=15.7, 8.6 Hz, 1H), 1.61 (dt, J=13.2, 6.6 Hz, 2H), 1.14 (t, J=7.2 Hz, 1H), 0.84 (d, J=6.6 Hz, 12H).

EXAMPLE 997

Enantiomer 1 and Enantiomer 2

3-(4-(Diisobutylamino)-3-(3-(pyrimidin-5-yl)ureido)phenyl)-4-methoxybutanoic acid

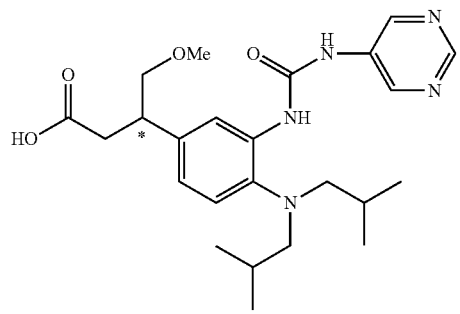 [SMILES: COCC(CC(=O)O)c1ccc(N(CC(C)C)CC(C)C)c(NC(=O)Nc2cncnc2)c1]

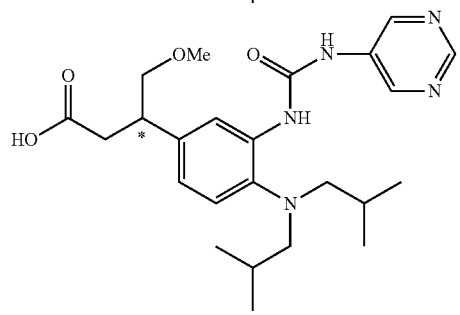

Chiral separation was obtained following the procedure in Example 993.

Enantiomer 1: $^1$H NMR (500 MHz, DMSO-$d_6$) δ 9.86 (s, 1H), 8.92 (s, 2H), 8.81 (s, 1H), 8.08 (s, 1H), 7.86 (s, 1H), 7.16 (d, J=8.2 Hz, 1H), 6.89 (d, J=8.1 Hz, 1H), 3.48-3.31 (m, 1H), 3.21 (s, 3H), 2.78-2.58 (m, 6H), 2.45 (d, J=8.7 Hz, 2H), 1.76-1.44 (m, 2H), 0.85 (d, J=6.6 Hz, 12H). LC-MS Anal. Calc'd. for $C_{24}H_{35}N_5O_4$, 457.27, found [M+H] 458.27. $T_r$=1.53 min. (Method B). HPLC Peak $T_r$=6.823 minute (Method E).

Enantiomer 2: $^1$H NMR (500 MHz, DMSO-$d_6$) δ 9.87 (s, 1H), 8.92 (s, 2H), 8.81 (s, 1H), 8.09 (s, 1H), 7.86 (s, 1H), 7.16 (d, J=8.2 Hz, 1H), 6.89 (d, J=8.0 Hz, 1H), 3.62-3.29 (m, 1H), 3.21 (s, 3H), 2.64 (d, J=7.0 Hz, 6H), 2.44 (d, J=8.7 Hz, 2H), 1.75-1.43 (m, 2H), 0.85 (d, J=6.5 Hz, 12H) LC-MS Anal. Calc'd. for $C_{24}H_{35}N_5O_4$, 457.27, found [M+H] 458.27. $T_r$=1.53 min. (Method B). HPLC Peak $T_r$=5.920 minute (Method E).

Example 998

(+/−)-3-(4-(Diisobutylamino)-3-(3-(5-methylisoxazol-3-yl)ureido)phenyl)-4-methoxybutanoic acid

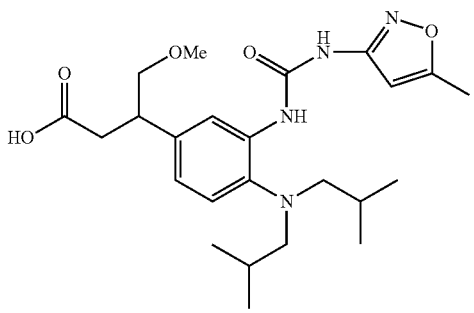 [SMILES: COCC(CC(=O)O)c1ccc(N(CC(C)C)CC(C)C)c(NC(=O)Nc2cc(C)on2)c1]

Example 998 was obtained following the procedure in Example 996 using 5-methylisoxazol-3-amine. LC-MS Anal. Calc'd. for $C_{24}H_{36}N_4O_5$, 460.27, found [M+H] 461.20. $T_r$=0.78 min (Method A). $^1$H NMR (500 MHz, DMSO-$d_6$) δ10.34 (br. S., 1H), 8.54 (br. S., 1H), 7.85 (br. S., 1H), 7.14 (d, J=8.1 Hz, 1H), 6.87 (d, J=7.2 Hz, 1H), 6.42 (s, 1H), 3.48 (br. S., 1H), 3.39 (d, J=6.3 Hz, 1H), 3.20 (s, 3H), 3.20-3.15 (m, 1H), 2.61 (d, J=6.6 Hz, 4H), 2.40 (dd, J=15.7, 8.9 Hz, 1H), 2.34 (s, 3H), 1.68-1.49 (m, 2H), 0.81 (d, J=6.4 Hz, 12H).

Example 999

Enantiomer 1 and Enantiomer 2

3-(4-(Diisobutylamino)-3-(3-(5-methylisoxazol-3-yl)ureido)phenyl)-4-methoxybutanoic acid

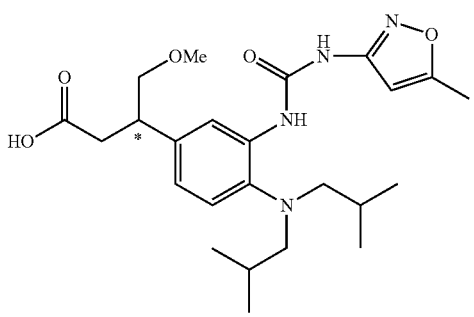

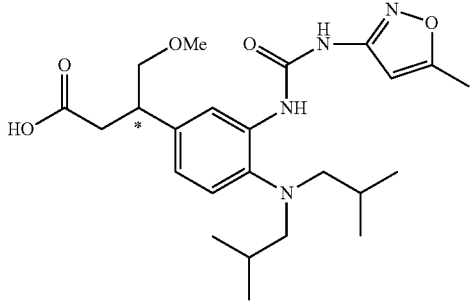

Chiral separation was obtained following the procedure in Example 993.

Enantiomer 1: $^1$H NMR (500 MHz, DMSO-$d_6$) δ 8.13 (s, 1H), 7.84 (s, 1H), 7.16 (d, J=8.2 Hz, 1H), 6.90 (d, J=7.0 Hz, 1H), 5.98 (s, 1H), 3.41 (br. s., 1H), 3.21 (s, 3H), 3.16 (d, J=5.1 Hz, 1H), 2.68-2.55 (m, 5H), 2.42 (dd, J=15.8, 8.6 Hz, 2H), 2.16 (s, 3H), 1.59 (dt, J=13.1, 6.5 Hz, 2H), 0.83 (d, J=6.5 Hz, 12H); LC-MS Anal. Calc'd. for $C_{24}H_{36}N_4O_5$, 460.27, found [M+H] 461.27. $T_r$=1.66 min (Method B). HPLC Peak $T_r$=7.750 minute (Method E).

Enantiomer 2: $^1$H NMR (500 MHz, DMSO-$d_6$) δ 8.13 (s, 1H), 7.83 (s, 1H), 7.16 (d, J=8.3 Hz, 1H), 6.90 (d, J=8.3 Hz, 1H), 5.98 (s, 1H), 3.42 (br. s., 1H), 3.21 (s, 3H), 3.16 (d, J=5.0 Hz, 1H), 2.68-2.55 (m, 5H), 2.42 (dd, J=15.7, 8.5 Hz, 2H), 2.16 (s, 3H), 1.71-1.45 (m, 2H), 0.83 (d, J=6.6 Hz, 12H). LC-MS Anal. Calc'd. for $C_{24}H_{36}N_4O_5$, 460.27, found [M+H] 461.27. $T_r$=1.66 min (Method B). HPLC Peak $T_r$=6.189 minute (Method E).

Example 1000

(+/−)-3-(3-(3-(4-Chloro-2-fluorophenyl)ureido)-4-(diisobutylamino)phenyl)-4-(dimethylamino)butanoic acid

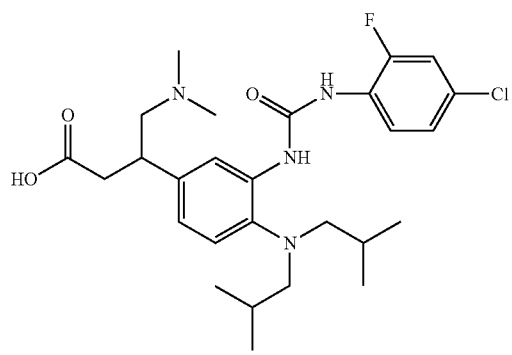

Preparation 1000A. (E)-Methyl 4-(dimethylamino)but-2-enoate

A solution of dimethylamine (25.1 mL, 50.3 mmol) was added dropwise to a solution of (E)-methyl 4-bromobut-2-enoate (2.000 mL, 16.76 mmol) in THF (10 mL) at 0° C. under $N_2$. The reaction mixture was stirred at room temperature overnight, then concentrated and purified by ISCO (0-5% MeOH/DCM). Fractions containing the product were concentrated to yield 1000A (1.800 g, 12.57 mmol, 75% yield) as a brown oil. $^1$H NMR (400 MHz, chloroform-d) δ 6.95 (dt, J=15.7, 6.2 Hz, 1H), 5.98 (dt, J=15.7, 1.7 Hz, 1H), 3.77-3.72 (m, 3H), 3.07 (dd, J=6.2, 1.6 Hz, 2H), 2.26-2.22 (m, 6H).

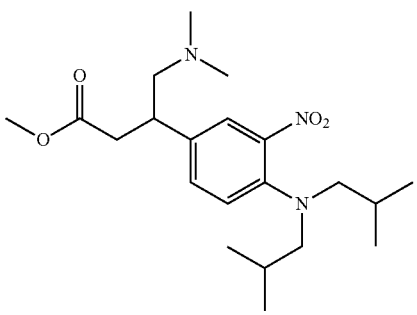 [SMILES: COC(=O)CC(CN(C)C)c1ccc(N(CC(C)C)CC(C)C)c([N+](=O)[O-])c1]

Preparation 1000B. Methyl 3-(4-(diisobutylamino)-3-nitrophenyl)-4-(dimethylamino)butanoate A reaction vial was charged with 4-(5,5-dimethyl-1,3,2-dioxaborinan-2-yl)-N,N-diisobutyl-2-nitroaniline (500 mg, 1.38 mmol) and 52A (398 mg, 2.76 mmol). The materials were dissolved in dioxane (6 mL). Sodium hydroxide (1M, 2.070 mL, 2.070 mmol) (1 M) was added and nitrogen was bubbled through for 20 minutes. Chloro(1,5-cyclooctadiene)rhodium(I) dimer (34.0 mg, 0.069 mmol) was then added, and the vial was sealed and warmed at 50° C. overnight. The reaction was quenched with acetic acid (0.119 mL, 2.070 mmol). The reaction mixture was concentrated and purified by ISCO column (0-30% EtOAc/hexane). Fractions containing product were concentrated to give 1000B (20 mg, 0.051 mmol, 3.68% yield) as an orange oil. LC-MS Anal. Calc'd. for $C_{21}H_{35}N_3O_4$, 393.26, found [M+H] 394.08. $T_r$=0.86 min (Method A). $^1$H NMR (400 MHz, chloroform-d) δ 7.53 (d, J=2.2 Hz, 1H), 7.22 (dd, J=8.7, 2.4 Hz, 1H), 7.05 (d, J=8.7 Hz, 1H), 3.58 (s, 3H), 3.27 (s, 1H), 2.88 (d, J=7.2 Hz, 4H), 2.83 (dd, J=15.5, 6.0 Hz, 1H), 2.52-2.33 (m, 3H), 2.23 (s, 6H), 2.01-1.74 (m, 2H), 0.82 (d, J=6.6 Hz, 12H).

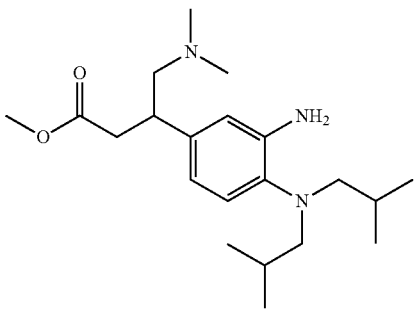 [SMILES: COC(=O)CC(CN(C)C)c1ccc(N(CC(C)C)CC(C)C)c(N)c1]

Preparation 1000C. (+/−)-Methyl 3-(3-amino-4-(diisobutylamino)phenyl)-4-(dimethylamino)butanoate Preparation 1000C was obtained following the procedure for Example 992C using 52B. LC-MS Anal. Calc'd. for $C_{21}H_{37}N_3O_2$, 363.29, found [M+H] 364.30. $T_r$=0.71 min (Method A). $^1$H NMR (400 MHz, chloroform-d) δ 6.96 (d, J=7.9 Hz, 1H), 6.64-6.29 (m, 2H), 4.08 (s, 2H), 3.57 (s, 3H), 3.26-3.10 (m, 1H), 2.77 (dd, J=15.3, 6.5 Hz, 1H), 2.59-2.53 (m, 3H), 2.51-2.39 (m, 2H), 2.37-2.28 (m, 1H), 2.27-2.14 (m, 6H), 1.72 (dt, J=13.5, 6.8 Hz, 3H), 0.98-0.78 (m, 12H).

Example 1000

Example 1000 was obtained following the procedure in Example 44 using 52C and 4-chloro-2-fluoro-1-isocyanatobenzene. LC-MS Anal. Calc'd. for $C_{27}H_{38}ClFN_4O_3$, 520.26, found [M+H] 521.60. $T_r$=0.87 min (Method A). $^1$H NMR (500 MHz, DMSO-$d_6$) δ 9.44 (s, 1H), 9.57-9.25 (m, 1H), 8.11 (s, 1H), 8.02 (t, J=8.8 Hz, 1H), 7.69 (s, 1H), 7.44 (dd, J=10.9, 2.1 Hz, 1H), 7.22 (d, J=8.9 Hz, 1H), 7.11 (d, J=8.2 Hz, 1H), 6.86 (d, J=8.2 Hz, 1H), 3.51 (br. s., 1H), 3.16 (br. s., 1H), 2.81-2.72 (m, 2H), 2.66-2.59 (m, 4H), 2.35 (br. s., 6H), 1.90 (s, 1H), 1.62 (dt, J=13.3, 6.6 Hz, 2H), 0.82 (d, J=6.6 Hz, 12H).

Example 1001

(+/−)-3-(4-(Disobutylamino)-3-(3-(pyrimidin-5-yl)ureido)phenyl)-4-(dimethylamino)butanoic acid

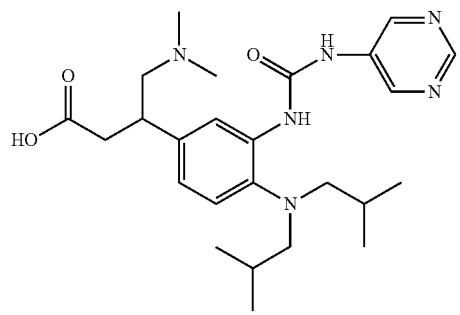 [SMILES: CC(C)CN(CC(C)C)c1ccc(C(CC(=O)O)CN(C)C)cc1NC(=O)Nc1cncnc1]

Example 1001 was obtained following the procedure for Example 44D using 52C and pyrimidin-5-amine. LC-MS Anal. Calc'd. for $C_{25}H_{38}N_6O_3$, 470.30, found [M+H] 471.60. $T_r$=0.68 min. (Method A). $^1$H NMR (500 MHz, DMSO-$d_6$) δ 9.90 (s, 1H), 8.91 (s, 2H), 8.81 (s, 1H), 8.09 (s, 1H), 7.82 (s, 1H), 7.17 (d, J=8.2 Hz, 1H), 6.88 (d, J=7.4 Hz, 1H), 3.59-3.43 (m, 1H), 3.18 (br. s., 1H), 2.81-2.71 (m, 2H), 2.63 (d, J=6.8 Hz, 4H), 2.35 (s, 7H), 1.60 (dt, J=13.1, 6.6 Hz, 2H), 0.84 (d, J=6.5 Hz, 12H).

Example 1002

(+/−)-3-(3-(3-(4-Chloro-2-fluorophenyl)ureido)-4-(cyclohexyl(isobutyl)amino)phenyl)-4-((2,2-difluorocyclopropyl)methoxy)butanoic acid

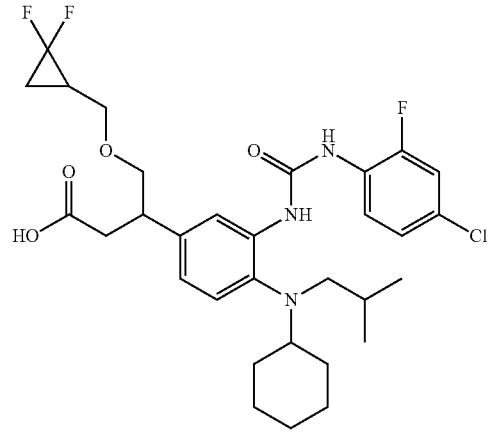

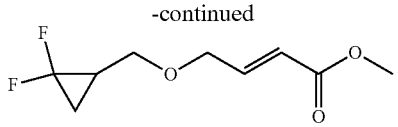

Preparation 1002A. (E)-Methyl 4-((2,2-difluorocyclopropyl)methoxy)but-2-enoate Preparation 1002A was obtained following the procedure for 44A using (2,2-difluorocyclopropyl) methanol. $^1$H NMR (400 MHz, chloroform-d) δ 6.95 (dt, J=15.7, 4.4 Hz, 1H), 6.09 (dt, J=15.8, 2.0 Hz, 1H), 4.31-4.03 (m, 2H), 3.68-3.57 (m, 1H), 3.55-3.41 (m, 1H), 2.02-1.78 (m, 1H), 1.57-1.38 (m, 1H), 1.26-1.06 (m, 1H).

Example 1002

Example 1002 was obtained following the procedure for Example 992 using 1002A. LC-MS Anal. Calc'd. for $C_{31}H_{39}ClF_3N_3O_4$, 609.26, found [M+H] 610.08. $T_r$=1.03 min (Method B). $^1$H NMR (500 MHz, DMSO-$d_6$) δ 9.52 (s, 1H), 8.23 (s, 1H), 8.03 (t, J=8.8 Hz, 1H), 7.83 (s, 1H), 7.46 (d, J=9.4 Hz, 1H), 7.22 (d, J=8.8 Hz, 1H), 7.09 (d, J=8.1 Hz, 1H), 6.87 (d, J=7.8 Hz, 1H), 3.90 (s, 1H), 3.49 (br. s., 1H), 3.20 (br. s., 1H), 2.75 (br. s., 1H), 2.65 (d, J=16.0 Hz, 1H), 2.48-2.37 (m, 4H), 1.98-1.80 (m, 4H), 1.67 (d, J=11.5 Hz, 2H), 1.57-1.45 (m, 2H), 1.38-1.26 (m, 1H), 1.25-1.13 (m, 3H), 1.13-0.89 (m, 3H), 0.81 (d, J=6.3 Hz, 6H).

Example 1003

(+/−)-3-(4-(Cyclohexyl(isobutyl)amino)-3-(3-(p-tolyl)ureido)phenyl)-5-methoxypentanoic acid

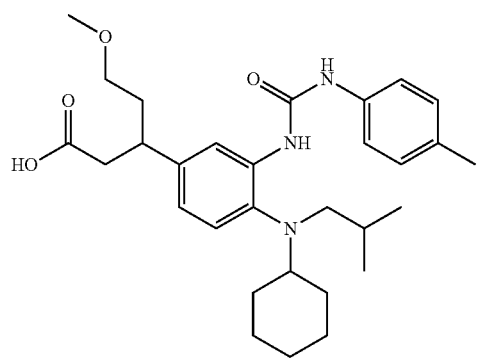 [SMILES: COCCC(CC(=O)O)c1ccc(N(CC(C)C)C2CCCCC2)c(NC(=O)Nc2ccc(C)cc2)c1]

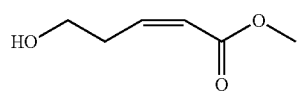

Preparation 1003A. (Z)-Methyl 5-hydroxypent-2-enoate 5,6-Dihydro-2H-pyran-2-one (1.756 mL, 20.39 mmol) was dissolved in 10 mL of water. Potassium hydroxide (1.373 g, 24.46 mmol) was added and the reaction mixture stirred at ambient temperature for 5 h. The solvent was removed in vacuo to yield a colorless glassy solid, which was dissolved in 20 mL of dimethyl formamide. Iodomethane (2.54 mL, 40.8 mmol) was then added resulting in an exotherm to 40° C. The reaction mixture was stirred at room temperature for 10 hours and partitioned between 150 mL of ethyl acetate/diethyl ether in a 20/80 ratio and ice water. The aqueous layer was separated and re-extracted with 100 mL of diethyl ether. The organic layers were combined, dried ($Na_2SO_4$), filtered and stripped of all solvent to yield 1003A (1.327 g, 10.19 mmol, 50% yield). $^1$H NMR (400 MHz, chloroform-d) δ 6.98 (dt, J=15.7, 7.1 Hz, 1H), 5.94 (dt, J=15.7, 1.5 Hz, 1H), 3.83-3.76 (m, 2H), 3.75-3.72 (m, 3H), 2.63-2.39 (m, 2H).

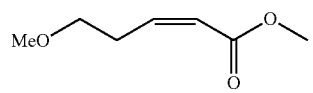

Preparation 1003B. (Z)-Methyl 5-methoxypent-2-enoate 1003B was obtained following the procedure in Example 992A using 1003A and methyl iodide. $^1$H NMR (400 MHz, chloroform-d) δ 6.97 (dt, J=15.7, 6.9 Hz, 1H), 5.90 (dt, J=15.8, 1.6 Hz, 1H), 3.78-3.68 (m, 3H), 3.50 (t, J=6.4 Hz, 2H), 3.38-3.29 (m, 3H), 2.48 (qd, J=6.6, 1.6 Hz, 2H).

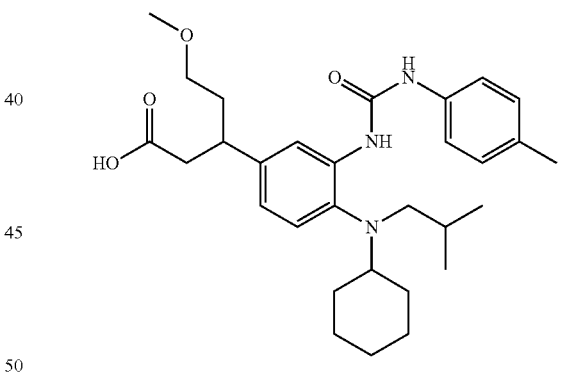

Example 1003

Example 1003 was obtained following the procedure in Example 992 using 1003B. LC-MS Anal. Calc'd. for $C_{30}H_{43}N_3O_4$, 509.32, found [M+H] 510.70. $T_r$=0.95 min. (Method A). $^1$H NMR (500 MHz, DMSO-$d_6$) δ 9.39 (s, 1H), 8.02 (s, 1H), 7.93 (s, 1H), 7.35 (d, J=8.2 Hz, 2H), 7.09 (d, J=7.9 Hz, 3H), 6.77 (d, J=6.9 Hz, 1H), 3.52-3.27 (m, 1H), 3.15 (s, 3H), 3.11 (d, J=7.1 Hz, 1H), 3.03 (d, J=7.1 Hz, 1H), 2.75 (br. s., 2H), 2.48-2.36 (m, 2H), 2.24 (s, 3H), 1.86 (d, J=7.0 Hz, 2H), 1.67 (d, J=9.0 Hz, 3H), 1.50 (d, J=12.1 Hz, 1H), 1.39-0.90 (m, 7H), 0.80 (d, J=6.1 Hz, 6H).

Example 1004

(+/−)-3-(3-(3-(4-Chloro-2-fluorophenyl)ureido)-4-(isobutyl((1R,4R)-4-methoxycyclohexyl)amino)phenyl)-4-methoxybutanoic acid

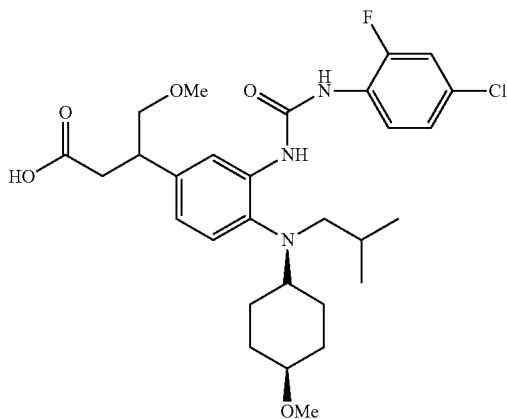

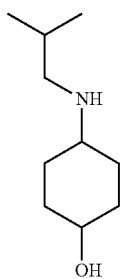

Preparation 1004A. 4-(Isobutylamino)cyclohexanol

A solution of 4-hydroxycyclohexanone (3.5 g, 30.7 mmol) and 2-methylpropan-1-amine (3.35 ml, 33.7 mmol) in MeOH (61.3 ml) was heated at 40° C. for 1 hour, then allowed to cool to room temperature. Sodium borohydride (1.740 g, 46.0 mmol) was added slowly. The reaction was allowed to stir at room temperature overnight. The solvent was evaporated and the crude material was taken up in EtOAc and H$_2$O. Layers were separated. The aqueous phase was extracted with EtOAc (2×). The combined organic phases were dried over Na$_2$SO$_4$, filtered, and concentrated to afford 1004A (4.0 g, 23.35 mmol, 76% yield) as a colorless oil. $^1$H NMR (400 MHz, chloroform-d) δ 5.30 (s, 1H), 3.87 (br. s., 1H), 3.61 (br. s., 1H), 2.50 (d, J=3.8 Hz, 1H), 2.41 (dd, J=6.7, 2.0 Hz, 2H), 2.07-1.87 (m, 2H), 1.80-1.66 (m, 2H), 1.67-1.50 (m, 3H), 1.39-1.22 (m, 1H), 1.22-1.05 (m, 1H), 0.96-0.85 (m, 6H).

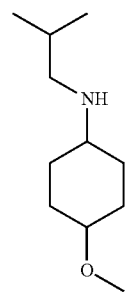

Preparation 1004B. N-isobutyl-4-methoxycyclohexanamine

To a solution of 1004A (0.5 g, 2.92 mmol) in DCM (5.84 ml) was added TEA (0.814 ml, 5.84 mmol) and di-tert-butyl dicarbonate (0.765 g, 3.50 mmol). The mixture was stirred at rt overnight. The mixture was diluted with DCM, washed with water, brine, dried over Na$_2$SO$_4$ and concentrated to yield a yellow oil, which was dissolved in THF (1474 μl), then Ag$_2$O (768 mg, 3.3 mmol) and iodomethane (210 μl, 3.3 mmol) were added. The mixture was heated at 50° C. overnight. The mixture was filtered. The filtrate was concentrated, then treated with 4M HCl (737 μl, 2.95 mmol) in dioxane. After 2 h, the mixture was concentrated and the resultant residue dissolved in EtOAc, washed with sodium bicarbonate solution, water, brine, dried over Na$_2$SO$_4$ and concentrated to yield 1004B (300 mg, 1.62 mmol, 73.2% yield) as a light yellow oil. $^1$H NMR (400 MHz, chloroform-d) δ 3.89-3.67 (m, 1H), 3.42-3.26 (m, 3H), 3.19-3.01 (m, 1H), 2.54-2.38 (m, 2H), 2.10-1.84 (m, 3H), 1.77-1.62 (m, 2H), 1.58-1.39 (m, 2H), 1.28-1.14 (m, 2H), 0.98-0.84 (m, 6H).

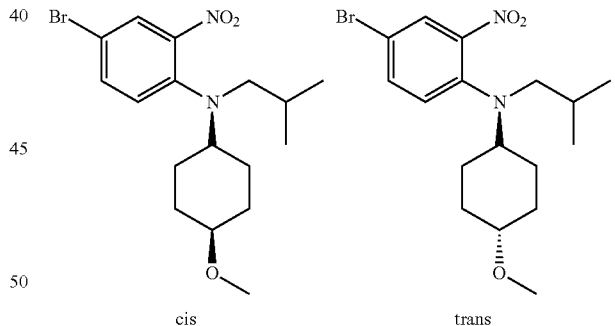

cis         trans

Preparation 1004C. 4-Bromo-N-isobutyl-N-((1R,4R)-4-methoxycyclohexyl)-2-nitroaniline To a stirred, cooled (0° C.) solution of 4-bromo-1-fluoro-2-nitrobenzene (200 mg, 0.90 mmol) in NMP (1 ml) was added TEA (0.25 ml, 1.80 mmol) and 1004B (300 mg, 1.35 mmol). The mixture was heated at 140° C. for 4 hours. The mixture was cooled to room temperature and diluted with EtOAc, washed with water twice, brine, dried over Na$_2$SO$_4$ and concentrated. The crude material was purified by ISCO (EtOAc/hexane 0-50% gradient). Fractions containing the product were concentrated to yield 56C-cis (135 mg, 0.35 mmol, 33%) and 56C-trans (75 mg, 0.20 mmol, 18%).

Preparation 1004C-cis: $^1$H NMR (400 MHz, chloroform-d) δ 7.79 (d, J=2.4 Hz, 1H), 7.46 (dd, J=8.9, 2.4 Hz, 1H), 7.05 (d, J=8.9 Hz, 1H), 3.35 (t, J=2.8 Hz, 1H), 3.32-3.28 (m, 3H), 2.91-2.83 (m, 2H), 2.05-1.93 (m, 2H), 1.80-1.68 (m, 2H), 1.63-1.55 (m, 2H), 1.37-1.25 (m, 2H), 1.37-1.21 (m, 2H), 0.92-0.77 (m, 6H).

Preparation 1004C-trans: $^1$H NMR (400 MHz, chloroform-d) δ 7.79 (d, J=2.4 Hz, 1H), 7.49 (dd, J=8.9, 2.4 Hz, 1H), 7.07 (d, J=8.9 Hz, 1H), 3.31 (s, 3H), 3.05 (s, 1H), 2.92 (s, 1H), 2.80 (d, J=7.2 Hz, 2H), 2.08 (d, J=12.6 Hz, 2H), 1.85 (d, J=12.7 Hz, 2H), 1.57 (d, J=6.7 Hz, 1H), 1.46 (dd, J=11.9, 3.2 Hz, 2H), 1.27-1.13 (m, 2H), 0.84 (d, J=6.6 Hz, 6H).

Example 1004

Example 1004 was obtained following the procedure in Example 992 using 1004C-cis. LC-MS Anal. Calc'd. for $C_{29}H_{39}ClFN_3O_5$, 563.26, found [M+H] 564.08. $T_r$=0.75 min. (Method A). $^1$H NMR (500 MHz, DMSO-$d_6$) δ 9.55 (s, 1H), 8.24 (s, 1H), 8.02 (br. s., 1H), 7.82 (br. s., 1H), 7.45 (d, J=10.8 Hz, 1H), 7.24 (br. s., 1H), 7.22 (br. s., 1H), 7.14 (s, 1H), 7.09 (d, J=8.2 Hz, 1H), 7.03 (s, 1H), 6.86 (d, J=7.0 Hz, 1H), 3.39 (br. s., 1H), 3.26 (br. s., 1H), 3.21 (s, 3H), 3.20 (br. s., 1H), 3.14 (s, 3H), 2.74 (br. s., 2H), 2.61-2.66 (m, 2H), 2.42 (dd, J=15.8, 8.5 Hz, 1H), 1.85 (d, J=13.2 Hz, 2H), 1.59 (br. s., 2H), 1.48 (d, J=12.5 Hz, 2H), 1.29 (d, J=7.2 Hz, 1H), 1.21 (d, J=13.3 Hz, 2H), 0.86 (d, J=6.6 Hz, 1H), 0.80 (d, J=6.2 Hz, 6H).

Example 1005

(+/−)-Methyl 3-(4-(isobutyl((1R,4R)-4-methoxycyclohexyl)amino)-3-(3-(p-tolyl)ureido)phenyl)-4-methoxybutanoate

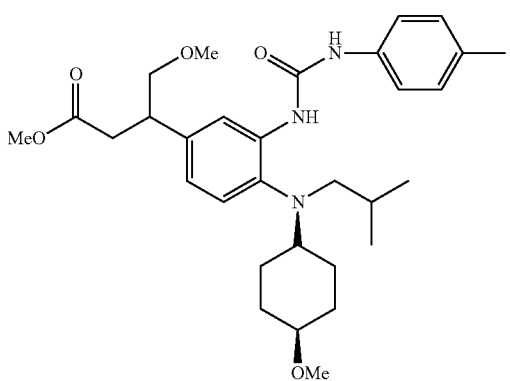

Example 1005 was obtained following the procedure in Example 992 using 1004C-cis. LC-MS Anal. Calc'd. for $C_{29}H_{39}ClFN_3O_5$, 563.26, found [M+H] 564.08. min. (Method A). $^1$H NMR (500 MHz, DMSO-$d_6$) δ 9.43 (s, 1H), 8.03-7.94 (m, 2H), 7.36 (d, J=8.2 Hz, 2H), 7.24 (br. s., 1H), 7.14 (br. s., 1H), 7.12-7.06 (m, 3H), 7.04 (br. s., 1H), 6.81 (d, J=7.7 Hz, 1H), 3.50 (s, 3H), 3.48-3.36 (m, 1H), 3.26 (br. s., 1H), 3.22 (s, 3H), 3.20 (br. s., 1H), 3.14 (s, 3H), 2.82-2.64 (m, 2H), 2.24 (s, 3H), 1.85 (d, J=13.7 Hz, 2H), 1.60 (br. s., 2H), 1.47 (d, J=12.7 Hz, 2H), 1.35-1.11 (m, 3H), 0.86 (d, J=6.5 Hz, 1H), 0.80 (d, J=6.1 Hz, 6H).

Example 1006

(+/−)-3-(3-(3-(4-Chloro-2-fluorophenyl)ureido)-4-(isobutyl((1r,4r)-4-methoxycyclohexyl)amino)phenyl)-4-methoxybutanoic acid

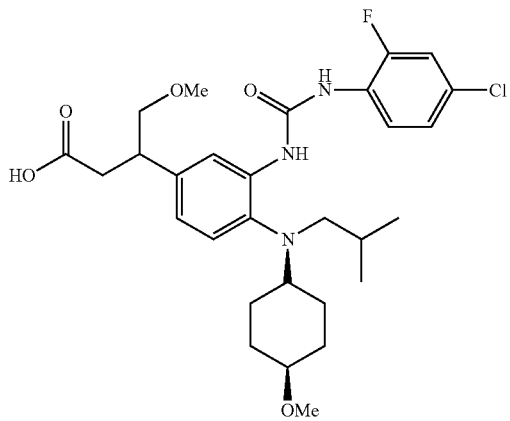

Example 1006 was obtained following the procedure in Example 992 using 1004C-cis. LC-MS Anal. Calc'd. for $C_{29}H_{39}ClFN_3O_5$, 563.26, found [M+H] 564.26. $T_r$=1.90 min (Method B). $^1$H NMR (500 MHz, DMSO-$d_6$) δ 9.55 (s, 1H), 8.24 (s, 1H), 8.02 (br. s., 1H), 7.82 (br. s., 1H), 7.45 (d, J=10.8 Hz, 1H), 7.24 (br. s., 1H), 7.22 (br. s., 1H), 7.14 (s, 1H), 7.09 (d, J=8.2 Hz, 1H), 7.03 (s, 1H), 6.86 (d, J=7.0 Hz, 1H), 3.39 (br. s., 1H), 3.26 (br. s., 1H), 3.21 (s, 3H), 3.20 (br. s., 1H), 3.14 (s, 3H), 2.74 (br. s., 2H), 2.61-2.66 (m, 2H), 2.42 (dd, J=15.8, 8.5 Hz, 1H), 1.85 (d, J=13.2 Hz, 2H), 1.59 (br. s., 2H), 1.48 (d, J=12.5 Hz, 2H), 1.29 (d, J=7.2 Hz, 1H), 1.21 (d, J=13.3 Hz, 2H), 0.86 (d, J=6.6 Hz, 1H), 0.80 (d, J=6.2 Hz, 6H).

Example 1007

Enantiomer 1 and Enantiomer 2

Example 1007 Enantiomer 1: 3-(4-(tert-Butyl(methyl)amino)-3-(2-(p-tolyl)acetamido)phenyl)-4-methylpentanoic acid

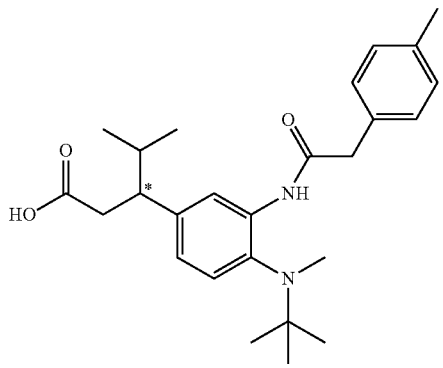 [SMILES: Cc1ccc(CC(=O)Nc2cc(C(CC(=O)O)C(C)C)ccc2N(C)C(C)(C)C)cc1]

Example 1007 Enantiomer 2: 3-(4-(tert-Butyl (methyl)amino)-3-(2-(p-tolyl)acetamido)phenyl)-4-methylpentanoic acid

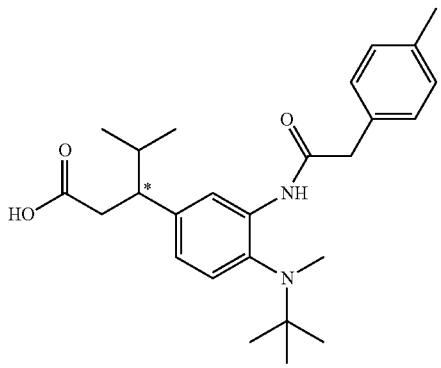 [SMILES: Cc1ccc(CC(=O)Nc2cc(C(CC(=O)O)C(C)C)ccc2N(C)C(C)(C)C)cc1]

1007A.
4-(tert-Butyl(methyl)amino)-3-nitrobenzaldehyde

A reaction vial was charged with 4-fluoro-3-nitrobenzaldehyde (0.98 g, 5.80 mmol) in NMP (2 mL). N,2-dimethylpropan-2-amine (2.084 ml, 17.39 mmol) was added and the reaction warmed to 60° C. overnight. The reaction turned bright orange. The cooled reaction was poured into water (ca. 100 mL) and stirred for a few hours. The water was decanted off and replaced with ca. 10 mL of fresh water. The material remained an orange oil and did not solidify. The material was transferred to a separatory funnel and extracted with ether. The organic layer was washed with brine and dried over magnesium sulfate. Filtration and evaporation provided 4-(tert-butyl(methyl)amino)-3-nitrobenzaldehyde (1.19 g, 5.04 mmol, 87% yield) as an orange oil that gradually solidified. MS(ES): m/z=237 [M+H]$^+$. $T_r$=0.96 min (Method A). $^1$H NMR (400 MHz, chloroform-d) δ 9.91 (s, 1H), 8.18 (d, J=2.1 Hz, 1H), 7.89 (dd, J=8.7, 2.1 Hz, 1H), 7.46 (d, J=8.6 Hz, 1H), 2.80 (s, 3H), 1.38 (s, 9H).

1007B. (E)-Methyl 3-(4-(tert-butyl(methyl)amino)-3-nitrophenyl)acrylate

A reaction vial was charged with 4-(tert-butyl(methyl)amino)-3-nitrobenzaldehyde (458 mg, 1.938 mmol) in dry toluene (2 mL). Methyl (triphenylphosphoranylidene)acetate (713 mg, 2.132 mmol) was added and the vial was subjected to three cycles of vacuum/nitrogen purge. The reaction was then warmed to 50° C. overnight. The cooled reaction was applied to a flash silica gel column and eluted with 40% ether in hexanes. Evaporation of the appropriate fractions provided (E)-methyl 3-(4-(tert-butyl(methyl)amino)-3-nitrophenyl)acrylate (473 mg, 1.618 mmol, 83% yield) as an orange oil. Isolated material is mostly the trans isomer by NMR. MS(ES): m/z=293 [M+H]$^+$. $T_r$=1.04 min (Method A). $^1$H NMR (400 MHz, chloroform-d) δ 7.73 (d, J=2.1 Hz, 1H), 7.64 (d, J=16.0 Hz, 1H), 7.57 (dd, J=8.6, 2.1 Hz, 1H), 7.43 (d, J=8.4 Hz, 1H), 6.42 (d, J=16.0 Hz, 1H), 3.84 (s, 3H), 2.74 (s, 3H), 1.22 (s, 9H).

1007C. Methyl 3-(4-(tert-butyl(methyl)amino)-3-nitrophenyl)-4-methylpent-4-enoate A vial was charged with (E)-methyl 3-(4-(tert-butyl(methyl)amino)-3-nitrophenyl)acrylate (473 mg, 1.618 mmol) and 4,4,5,5-tetramethyl-2-(prop-1-en-2-yl)-1,3,2-dioxaborolane (912 µl, 4.85 mmol). The materials were dissolved in dioxane (10 mL). A solution of sodium hydroxide (1 M, 3236 µl, 3.24 mmol) was added and reaction subjected to three cycles of vacuum/argon. Chloro(1,5-cyclooctadiene)rhodium(I) dimer (39.9 mg, 0.081 mmol) was then added and the flask was purged twice more. After warming to 50° C., the reaction was stirred overnight. The cooled reaction was quenched with acetic acid (185 µl, 3.24 mmol). The quenched reaction was applied to a flash silica gel column and eluted with 30% ether in hexanes. Evaporation of the appropriate fractions gave methyl 3-(4-(tert-butyl (methyl)amino)-3-nitrophenyl)-4-methylpent-4-enoate (241 mg, 0.721 mmol, 44.5% yield) as an orange oil. MS(ES): m/z=335 [M+H]$^+$. $T_r$=1.04 min (Method A). $^1$H NMR (400 MHz, chloroform-d) δ 7.41-7.37 (m, 1H), 7.36 (d, J=2.1 Hz, 1H), 7.34-7.30 (m, 1H), 4.96 (s, 1H), 4.94 (d, J=0.7 Hz, 1H), 3.83 (t, J=7.8 Hz, 1H), 3.65 (s, 3H), 2.92-2.83 (m, 1H), 1.65 (s, 3H), 1.56 (s, 3H), 1.12 (s, 9H) Second CH next to the ester is obscured by the DMSO peak.

1007D. Methyl 3-(3-amino-4-(tert-butyl(methyl) amino)phenyl)-4-methylpentanoate

A Parr bottle was charged with methyl 3-(4-(tert-butyl (methyl)amino)-3-nitrophenyl)-4-methylpent-4-enoate (241 mg, 0.721 mmol) in ethyl acetate (ca. 7 mL). 10% Pd/C (47 mg) was added and the bottle pressurized with hydrogen (30 psi). After hydrogenating overnight, the reaction was filtered and evaporated to give the crude product. This material was used directly in the next reaction. MS(ES): m/z=307 [M+H]$^+$. $T_r$=0.72 min (Method A).

1007E. (+/−)-3-(4-(tert-Butyl(methyl)amino)-3-(2-(p-tolyl)acetamido)phenyl)-4-methylpentanoic acid A reaction vial was charged with methyl 3-(3-amino-4-(tert-butyl(methyl)amino)phenyl)-4-methylpentanoate (44.1 mg, 0.144 mmol) in THF (1 mL). 2-(p-Tolyl)acetic acid (28.1 mg, 0.187 mmol) was added, followed by triethylamine (0.060 mL, 0.432 mmol) and BOP (83 mg, 0.187 mmol). The reaction was then stirred for 4 days. Methanol (0.3 mL) and a solution of sodium hydroxide (1 M, 720 µl, 0.720 mmol) were added and stirring continued for an additional day. The reaction was neutralized with acetic acid (41.2 µl, 0.720 mmol) and concentrated under a stream of nitrogen. The material was redissolved in DMF (1.5 mL) and purified by RP-HPLC. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 18 minutes, then a 5-minute hold at 100% B; Flow: 20 mL/min. Fractions containing the desired product were combined and dried via centrifugal evaporation. MS(ES): m/z=425 [M+H]$^+$. $T_r$=0.83 min (Method A).

Example 1007 Enantiomer 1 and Enantiomer 2: Chiral separation of the racemic Example 1007E was performed under the following conditions: (Berger SFC MGII, Column: Lux Cellular2 25×3 cm ID, 5 µm, Flow rate: 85.0 mL/min, Mobile Phase: 85/15 CO$_2$/MeOH) to give Enantiomer 1 (15.9 mg) and Enantiomer 2 (16.2 mg). Absolute stereochemistry was not determined.

Enantiomer 1: MS(ES): m/z=425 [M+H]$^+$. $T_r$=1.53 min LCMS conditions were as follows: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. $^1$H NMR (500 MHz, DMSO-$d_6$) δ 9.02 (s, 1H), 8.21 (br s, 1H), 7.33-7.25 (m, 2H), 7.21 (br d, J=7.7 Hz, 2H), 7.16 (br d, J=8.1 Hz, 1H), 6.80 (br d, J=7.9 Hz, 1H), 3.79-3.60 (m, 2H), 2.73-2.67 (m, 1H), 2.42 (br s, 1H), 2.34 (s, 3H), 2.30 (s, 3H), 1.81-1.67 (m, 1H), 0.87 (br d, J=6.6 Hz, 3H), 0.80 (s, 9H), 0.67 (br d, J=6.6 Hz, 3H).

Enantiomer 2: MS(ES): m/z=425 [M+H]$^+$. $T_r$=2.30 min Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. $^1$H NMR (500 MHz, DMSO-$d_6$) δ 9.02 (s, 1H), 8.21 (br s, 1H), 7.33-7.25 (m, 2H), 7.21 (br d, J=7.7 Hz, 2H), 7.16 (br d, J=8.0 Hz, 1H), 6.80 (br d, J=7.7 Hz, 1H), 3.79-3.59 (m, 2H), 2.70 (br s, 1H), 2.42 (br d, J=9.8 Hz, 1H), 2.34 (s, 3H), 2.30 (s, 3H), 1.79-1.69 (m, 1H), 0.87 (br d, J=6.6 Hz, 3H), 0.80 (s, 9H), 0.67 (br d, J=6.6 Hz, 3H).

Example 1008

Enantiomer 1 and Enantiomer 2

Example 1008 Enantiomer 1: 3-(3-(Benzo[d]oxazol-2-ylamino)-4-(tert-butyl(methyl)amino)phenyl)-4-methylpentanoic acid

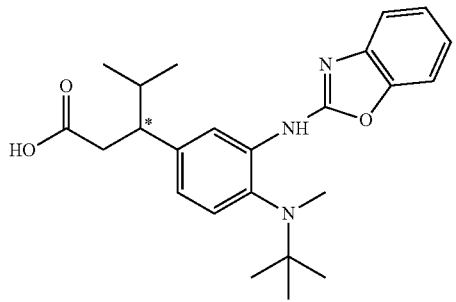 [SMILES: CC(C)C(CC(=O)O)c1ccc(N(C)C(C)(C)C)c(Nc2nc3ccccc3o2)c1]

Example 1008 Enantiomer 2: 3-(3-(Benzo[d]oxazol-2-ylamino)-4-(tert-butyl(methyl)amino)phenyl)-4-methylpentanoic acid

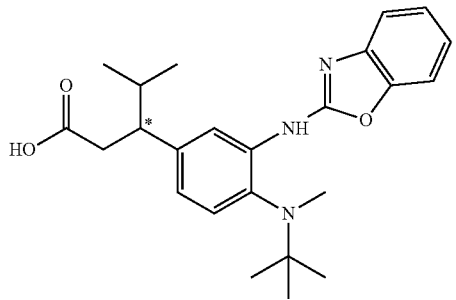 [SMILES: CC(C)C(CC(=O)O)c1ccc(N(C)C(C)(C)C)c(Nc2nc3ccccc3o2)c1]

1008A. Methyl 3-(3-(benzo[d]oxazol-2-ylamino)-4-(tert-butyl(methyl)amino)phenyl)-4-methylpentanoate A reaction vial was charged with methyl 3-(3-amino-4-(tert-butyl(methyl)amino)phenyl)-4-methylpentanoate (113 mg, 0.369 mmol) (Intermediate 59D) in 2,6-lutidine (0.4 mL, 3.43 mmol). 2-Chlorobenzo[d]oxazole (0.063 mL, 0.553 mmol) was added and the reaction degassed with three cycles of vacuum/nitrogen purge. The reaction was then heated to 140° C. for 1.5 hours. The cooled reaction was diluted with methanol and purified by RP-HPLC (PHENOMENEX® Axia C18 5μ, 30×100 mm, methanol-water gradient+0.1% TFA). Evaporation of the product containing fractions followed by azeotroping with ethanol gave the product methyl 3-(3-(benzo[d]oxazol-2-ylamino)-4-(tert-butyl(methyl)amino)phenyl)-4-methylpentanoate (38 mg, 0.090 mmol, 24%). MS(ES): m/z=424 [M+H]$^+$. $T_r$=0.92 min (Method A). $^1$H NMR (400 MHz, chloroform-d) δ 7.73 (s, 1H), 7.38-7.27 (m, 2H), 7.26-7.18 (m, 2H), 7.17-7.08 (m, 1H), 6.97 (br d, J=8.3 Hz, 1H), 3.58 (s, 3H), 3.17 (s, 3H), 3.06-2.94 (m, 1H), 2.92-2.82 (m, 1H), 2.71-2.60 (m, 1H), 1.94 (dq, J=13.8, 6.8 Hz, 1H), 1.45 (s, 9H), 1.01 (d, J=6.6 Hz, 3H), 0.84 (d, J=6.7 Hz, 3H).

1008B. (+/−)-3-(3-(Benzo[d]oxazol-2-ylamino)-4-(tert-butyl(methyl)amino)phenyl)-4-methylpentanoic acid Methyl 3-(3-(benzo[d]oxazol-2-ylamino)-4-(tert-butyl(methyl)amino)phenyl)-4-methylpentanoate (38 mg, 0.090 mmol) was dissolved in THF (0.5 mL) and methanol (0.2 mL). A solution of sodium hydroxide (1 M, 292 μl, 0.292 mmol) was added and stirring continued overnight. The cooled reaction was quenched with acetic acid (16.69 μl, 0.292 mmol) and concentrated under a stream of nitrogen. The residue was diluted with DMF (1.6 mL) and purified under the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 15 minutes, then a 3-minute hold at 100% B; Flow: 20 mL/min. Fractions containing the desired product were combined and dried via centrifugal evaporation to give (+/−)-3-(3-(benzo[d]oxazol-2-ylamino)-4-(tert-butyl(methyl)amino)phenyl)-4-methylpentanoic acid. This material was taken directly into the chiral resolution. MS(ES): m/z=410 [M+H]$^+$. $T_r$=0.82 min (Method A).

Example 1008 Enantiomer 1 and Enantiomer 2: Chiral separation of the racemic Example 1008B was performed under the following conditions: (Berger SFC MGM, Column: Lux Cellular2 25×3 cm ID, 5 μm, Flow rate: 85.0 mL/min, Mobile Phase: 90/10 CO$_2$/MeOH) to give Enantiomer 1 (7.7 mg) and Enantiomer 2 (7.8 mg). Absolute stereochemistry was not determined.

Enantiomer 1: MS(ES): m/z=410 [M+H]$^+$. $T_r$=2.28 min LCMS (Method C). $^1$H NMR (500 MHz, DMSO-$d_6$) δ 8.18 (br s, 1H), 7.51 (br d, J=7.7 Hz, 2H), 7.31 (br d, J=7.9 Hz, 1H), 7.24 (br t, J=7.7 Hz, 1H), 7.20-7.07 (m, 1H), 6.87 (br d, J=7.7 Hz, 1H), 2.81 (br s, 1H), 2.74 (br dd, J=15.2, 4.8 Hz, 1H), 2.62 (s, 3H), 1.83 (br d, J=6.5 Hz, 1H), 1.11 (s, 9H), 0.93 (br d, J=6.4 Hz, 3H), 0.74 (br d, J=5.9 Hz, 3H).

Enantiomer 2: MS(ES): m/z=410 [M+F1]$^+$. $T_r$=2.30 min (Method C). $^1$H NMR (500 MHz, DMSO-$d_6$) δ 8.18 (br s, 1H), 7.51 (br d, J=7.6 Hz, 2H), 7.31 (br d, J=8.1 Hz, 1H), 7.24 (br t, J=7.6 Hz, 1H), 7.19-7.08 (m, 1H), 6.87 (br d, J=7.8 Hz, 1H), 2.82 (br s, 1H), 2.75 (br d, J=14.6 Hz, 1H), 2.62 (s, 3H), 1.83 (br d, J=6.8 Hz, 1H), 1.10 (s, 9H), 0.93 (br d, J=6.2 Hz, 3H), 0.74 (br d, J=5.4 Hz, 3H).

Example 1009

(+/−)3-(4-(Diisobutylamino)-3-(3-(4-(trifluoromethoxy)phenyl)ureido)phenyl)-3-phenylpropanoic acid

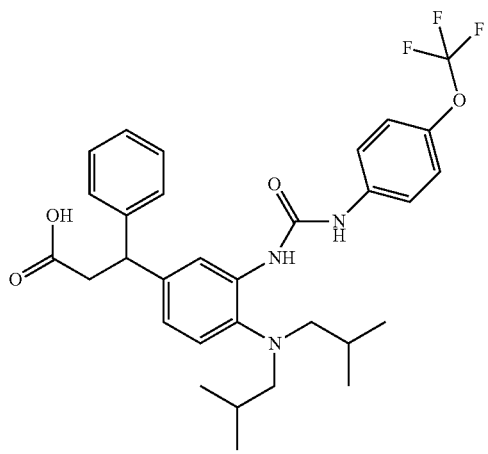 [SMILES: CC(C)CN(CC(C)C)c1ccc(C(CC(=O)O)c2ccccc2)cc1NC(=O)Nc1ccc(OC(F)(F)F)cc1]

1009A. 4-(Diisobutylamino)-3-nitrobenzaldehyde

A reaction vial was charged with 4-fluoro-3-nitrobenzaldehyde (673 mg, 3.98 mmol) in DMF (4 mL). Nitrogen was bubbled through the solution for 10 minutes. Diisobutylamine (2085 μl, 11.94 mmol) was added and the vial sealed and warmed to 90° C. The vial was stirred overnight. The cooled reaction was treated with water (8 mL). After stirring, a solid precipitated. The solid was filtered and rinsed with water. The material was then dissolved in ethyl acetate, dried over magnesium sulfate, filtered and evaporated. This process gave 4-(diisobutylamino)-3-nitrobenzaldehyde (1.06 g, 3.81 mmol, 96% yield) as an orange solid. MS(ES): m/z=320 [M+CH$_3$CN+H]$^+$. T$_r$=1.10 min (Method A). $^1$H NMR (400 MHz, chloroform-d) δ 9.82 (s, 1H), 8.25 (d, J=2.1 Hz, 1H), 7.88 (dd, J=8.9, 2.1 Hz, 1H), 7.17 (d, J=8.9 Hz, 1H), 3.07 (d, J=7.3 Hz, 4H), 2.06-1.92 (m, 2H), 0.88 (d, J=6.6 Hz, 12H).

1009B. (E)-Ethyl 3-(4-(diisobutylamino)-3-nitrophenyl)acrylate

A reaction vial was charged with 4-(diisobutylamino)-3-nitrobenzaldehyde (498 mg, 1.789 mmol) in dry toluene (4 mL). Ethyl 2-(triphenylphosphoranylidene)acetate (748 mg, 2.147 mmol) was added and the reaction was evacuated and a nitrogen atmosphere introduced. The vial was warmed to 90° C. for an hour. The cooled reaction was applied to a 40 g Isco silica gel column and eluted with 0-50% ethyl acetate in hexanes. Evaporation of the product containing fractions gave (E)-ethyl 3-(4-(diisobutylamino)-3-nitrophenyl)acrylate (550 mg, 1.578 mmol, 88% yield) as an orange oil. MS(ES): m/z=349 [M+H]$^+$. T$_r$=1.22 min (Method A). $^1$H NMR (400 MHz, DMSO-d$_6$) δ 8.06 (d, J=2.2 Hz, 1H), 7.84 (dd, J=8.9, 2.2 Hz, 1H), 7.60 (d, J=15.9 Hz, 1H), 7.34 (d, J=8.9 Hz, 1H), 6.54 (d, J=16.0 Hz, 1H), 4.18 (q, J=7.1 Hz, 2H), 3.00 (d, J=7.2 Hz, 4H), 1.87 (m, 2H), 1.26 (t, J=7.1 Hz, 3H), 0.79 (d, J=6.6 Hz, 12H).

1009C. Ethyl 3-(4-(diisobutylamino)-3-nitrophenyl)-3-phenylpropanoate

A reaction vial was charged with (E)-ethyl 3-(4-(diisobutylamino)-3-nitrophenyl)acrylate (97.8 mg, 0.281 mmol) and phenylboronic acid (103 mg, 0.842 mmol). The materials were dissolved in dioxane (2 mL) and a solution of sodium hydroxide (1 M, 140 IA, 0.140 mmol) was added. Nitrogen was bubbled through the solution for 20 minutes. Chloro(1,5-cyclooctadiene)rhodium(I) dimer (6.92 mg, 0.014 mmol) was then added and the vial was sealed. The reaction was warmed to 50° C. and stirred overnight. The cooled reaction was quenched with acetic acid (8.03 μl, 0.140 mmol) and applied to a 24 g Isco silica gel column. The column was eluted with 0 to 50% ethyl acetate in hexanes. Evaporation of the product containing fractions gave ethyl 3-(4-(diisobutylamino)-3-nitrophenyl)-3-phenylpropanoate (103 mg, 0.241 mmol, 86%) as an orange oil. MS(ES): m/z=427 [M+H]$^+$. T$_r$=1.26 min (Method A). $^1$H NMR (400 MHz, chloroform-d) δ 7.60 (d, J=2.3 Hz, 1H), 7.37-7.22 (m, 6H), 7.04 (d, J=8.7 Hz, 1H), 4.50 (t, J=8.1 Hz, 1H), 4.11-4.01 (m, 2H), 3.03 (d, J=8.1 Hz, 2H), 2.89 (d, J=7.2 Hz, 4H), 1.88 (m, 2H), 1.13 (t, J=7.2 Hz, 3H), 0.83 (d, J=6.6 Hz, 12H).

1009D. Ethyl 3-(3-amino-4-(diisobutylamino)phenyl)-3-phenylpropanoate

Ethyl 3-(4-(diisobutylamino)-3-nitrophenyl)-3-phenylpropanoate (103 mg, 0.241 mmol) was dissolved in ethanol (5 mL) under nitrogen. Water (0.5 mL) and ammonium chloride (129 mg, 2.415 mmol) were added to the vigorously stirred reaction. The reaction was initiated with the addition of zinc (158 mg, 2.415 mmol). After stirring for 0.5 hours, the reaction was filtered and rinsed with methylene chloride. The liquid was transferred to a separatory funnel where it was washed with water and brine. Drying over magnesium sulfate filtration and evaporation then provided the crude product. This material was applied to a 24 g Isco silica gel column and eluted with 0-100% ethyl acetate in hexanes. Evaporation of the product containing fractions gave ethyl 3-(3-amino-4-(diisobutylamino)phenyl)-3-phenylpropanoate (36 mg, 0.091 mmol, 38%) as a viscous oil. MS(ES): m/z=397 [M+H]$^+$. T$_r$=1.01 min (Method A).

1009. (+/−)3-(4-(Diisobutylamino)-3-(3-(4-(trifluoromethoxy)phenyl)ureido)phenyl)-3-phenylpropanoic acid Ethyl 3-(3-amino-4-(diisobutylamino)phenyl)-3-phenylpropanoate (18 mg, 0.045 mmol) was dissolved in THF (1 mL). 1-Isocyanato-4-methylbenzene (6.87 μl, 0.054 mmol) was added and stirring continued for 2 days. A solution of lithium hydroxide (1 M, 75 μL) was added and the reaction warmed to 50° C. As little reaction was evident by LCMS, more lithium hydroxide (75 μL) was added and some methanol to help with solubility. Heating was continued until LCMS showed good conversion to product. The cooled reaction was quenched with acetic acid (8.59 μl, 0.150 mmol). The solvent was evaporated and the residue diluted with DMF. The crude material was purified by RP-HPLC under the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 18 minutes, then a 5-minute hold at 100% B; Flow: 20 mL/min. Fractions containing the desired product were combined and dried via centrifugal evaporation to give (+/−)3-(4-(diisobutylamino)-3-(3-(4-(trifluoromethoxy)phenyl)ureido)phenyl)-3-phenylpropanoic acid (15.7 mg, 0.031 mmol, 69%). MS(ES): m/z=502 [M+H]$^+$. T$_r$=2.34 min (Method C). $^1$H NMR (500 MHz, DMSO-d$_6$) δ 9.33 (s, 1H), 7.92 (s, 1H), 7.82 (s, 1H), 7.35 (d, J=8.1 Hz, 2H), 7.32-7.25 (m, 4H), 7.17 (t, J=6.4 Hz, 1H), 7.14-7.06 (m, 3H), 6.91 (d, J=6.4 Hz, 1H), 4.33 (t, J=7.9 Hz, 1H), 2.96 (d, J=7.1 Hz, 2H), 2.60 (d, J=6.7 Hz, 4H), 2.25 (s, 3H), 1.60 (m, 2H), 0.83 (d, J=6.4 Hz, 12H).

Example 1010

(+/−)-3-(4-(Diisobutylamino)-3-(2-p-tolyl)acetamido)phenyl)-4-methylpentanoic acid

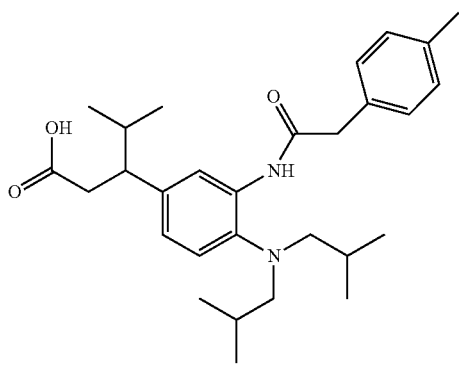 [SMILES: Cc1ccc(CC(=O)Nc2cc(C(CC(=O)O)C(C)C)ccc2N(CC(C)C)CC(C)C)cc1]

1010A. Ethyl 3-(4-(diisobutylamino)-3-nitrophenyl)-4-methylpent-4-enoate

A reaction vial was charged with (E)-ethyl 3-(4-(diisobutylamino)-3-nitrophenyl)acrylate (249 mg, 0.715 mmol) (Example 1009B) and 4,4,5,5-tetramethyl-2-(prop-1-en-2-yl)-1,3,2-dioxaborolane (403 µl, 2.144 mmol). The materials were dissolved in dioxane (6 mL). A solution of sodium hydroxide (1 M, 1072 µl, 1.072 mmol) was added and nitrogen was bubbled through the reaction for 20 minutes. Chloro(1,5-cyclooctadiene)rhodium(I) dimer (17.62 mg, 0.036 mmol) was then added and the vial was sealed. The vial was warmed to 50° C. and stirred overnight. The cooled reaction was quenched with acetic acid (61.4 µl, 1.072 mmol) and the applied to a flash silica gel column. The column was eluted with 15% ether in hexanes. As only partial purification was achieved, the material repurified as above to give ethyl 3-(4-(diisobutylamino)-3-nitrophenyl)-4-methylpent-4-enoate (176 mg, 0.451 mmol, 63.1% yield) as an orange oil. $^1$H NMR (400 MHz, DMSO-d$_6$) δ 7.53 (d, J=2.1 Hz, 1H), 7.38-7.33 (m, 1H), 7.32-7.27 (m, 1H), 4.91 (s, 1H), 4.85 (s, 1H), 3.98 (q, J=7.1 Hz, 2H), 3.69 (t, J=8.0 Hz, 1H), 2.90-2.83 (m, 4H), 2.84-2.79 (m, 1H), 2.77 (d, J=8.4 Hz, 1H), 1.89-1.74 (m, 2H), 1.05 (t, J=7.1 Hz, 3H), 0.78 (d, J=6.6 Hz, 12H).

1010B. Ethyl 3-(3-amino-4-(diisobutylamino)phenyl)-4-methylpentanoate

A Parr bottle was charged with ethyl 3-(4-(diisobutylamino)-3-nitrophenyl)-4-methylpent-4-enoate (176 mg, 0.451 mmol) in ethyl acetate (6 mL). 10% Pd/C (28 mg) was added and the bottle pressurized to 40 psi hydrogen. After 4.5 hours, the reaction was filtered through a pad of magnesium sulfate and evaporated. Purification on a 24 g Isco silica gel column, eluting with 0-50% ethyl acetate in hexanes, gave ethyl 3-(3-amino-4-(diisobutylamino)phenyl)-4-methylpentanoate (94.2 mg, 0.260 mmol, 57.7% yield) as a pink oil. MS(ES): m/z=363 [M+H]$^+$. T$_r$=0.95 min (Method A).

Example 1010

Ethyl 3-(3-amino-4-(diisobutylamino)phenyl)-4-methylpentanoate (28.6 mg, 0.079 mmol) was dissolved in THF (0.5 mL). 2-(p-Tolyl)acetic acid (14.22 mg, 0.095 mmol), triethylamine (33.0 µl, 0.237 mmol), and BOP (41.9 mg, 0.095 mmol) were added and stirring continued overnight. A solution of sodium hydroxide (1 M, 150 µL) was added along with some methanol to solubilize. The reaction was warmed to 50° C. After ca. 4 hours, another 0.15 mL of sodium hydroxide was added and stirring continued for another day. The cooled reaction was quenched with acetic acid (17.2 µl, 0.300 mmol) and evaporated. The residue was dissolved in DMF (2 mL) and passed through a syringe filter. The material was then purified by RP-HPLC as follows: Column: Waters XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-100% B over 20 minutes, then a 5-minute hold at 100% B; Flow: 20 mL/min. Fractions containing the desired product were combined and dried via centrifugal evaporation to give (+/−)-3-(4-(diisobutylamino)-3-(2-(p-tolyl)acetamido)phenyl)-4-methylpentanoic acid (17.5 mg, 0.037 mmol, 47%). MS(ES): m/z=467 [M+H]$^+$. T$_r$=2.53 min (Method C). $^1$H NMR (500 MHz, DMSO-d$_6$) δ 8.72 (br s, 1H), 8.09 (br s, 1H), 7.33-7.08 (m, 5H), 6.85 (br d, J=6.4 Hz, 1H), 2.70-2.62 (m, 1H), 2.41 (br dd, J=15.1, 10.1 Hz, 1H), 2.28 (s, 3H), 1.84-1.67 (m, 1H), 1.58-1.39 (m, 2H), 0.85 (br d, J=6.4 Hz, 3H), 0.76 (br d, J=6.7 Hz, 12H), 0.67 (br d, J=6.4 Hz, 3H) (N—CH$_2$ was irradiated in the water suppression).

Example 1011

3-(3-(3-(4-Cyano-2-fluorophenyl)ureido)-4-(cyclohexyl(isobutyl)amino)phenyl)-2-methoxypropanoic acid (racemic)

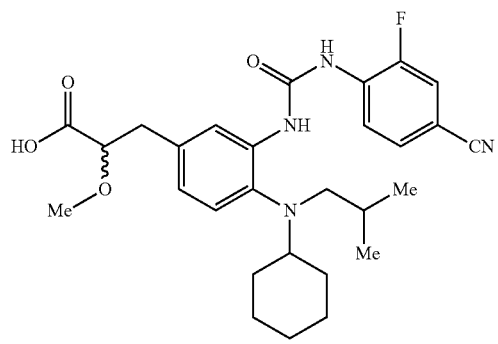 [SMILES: COC(Cc1ccc(N(CC(C)C)C2CCCCC2)c(NC(=O)Nc2ccc(C#N)cc2F)c1)C(=O)O]

1011A. N-Cyclohexylisobutyramide

Cyclohexanamine (1.262 mL, 11.01 mmol) and triethylamine (1.673 mL, 12.01 mmol) were dissolved in THF (10 mL) and cooled to 0° C. over an ice bath. Isobutyryl chloride (1.048 mL, 10.00 mmol) was added dropwise over 2 minutes (slurry forms immediately). The reaction was allowed to stir 30 minutes at 0° C. before warming to room temperature. After stirring another 30 minutes at room temperature, the reaction was then diluted with 1:1 hexanes-ether (200 mL) and washed with aq 1N HCl (50 mL) followed by sat'd aq. NaHCO$_3$ (50 mL). The organics were combined, dried with MgSO$_4$, filtered, and concentrated in vacuo to give Intermediate 1011A (white solid, 1.55 g, 8.70 mmol, 87% yield). $^1$H NMR (400 MHz, chloroform-d) δ 5.24 (br. s., 1H), 3.70-3.81 (m, 1H), 2.28 (spt, J=6.9 Hz, 1H), 1.90 (dd, J=12.5, 3.6 Hz, 2H), 1.70 (dt, J=13.5, 3.6 Hz, 2H), 1.58-1.65 (m, 1H), 1.30-1.43 (m, 2H), 1.15-1.22 (m, 1H), 1.14 (d, J=6.8 Hz, 6H), 1.04-1.12 (m, 2H)

1011B. N-Isobutylcyclohexanamine

Intermediate 1011A (18.71 g, 111 mmol) was dissolved in THF (221 ml) and cooled to 0° C. with an ice bath. Lithium aluminum hydride (5.45 g, 144 mmol) was added slowly to the solution at 0° C. After the addition was complete, the flask was equipped with a reflux condenser and heated to reflux (70° C.) for 24 hours. After 24 hours, the reaction was cooled to 0° C. and diluted with EtOAc (220 mL). The reaction was then quenched with the Fieser method (5.45 mL water then 10.9 mL 1N NaOH, then 16.5 mL water) (Caution: addition of water causes exotherm and bubbling) and after stirring for one hour the slurry was dried with sodium sulfate, filtered over packed CELITE®, and concentrated in vacuo to afford Intermediate 1011B (clear oil, 16.59 g, 101 mmol, 92% yield). $^1$H NMR (400 MHz, chloroform-d) δ 2.42 (d, J=6.7 Hz, 2H), 2.32-2.40 (m, 1H), 1.82-1.91 (m, 2H), 1.65-1.75 (m, 3H), 1.55-1.65 (m, 1H), 0.98-1.31 (m, 6H), 0.89 (d, J=6.6 Hz, 6H)

1011C. 4-(Cyclohexyl(isobutyl)amino)-3-nitrobenzaldehyde

A mixture of 4-fluoro-3-nitrobenzaldehyde (2 g, 11.83 mmol), Intermediate 1011B (3.67 g, 23.65 mmol), and DIPEA (4.13 ml, 23.65 mmol) was heated at 100° C. for 3 h in a pressure release vial, then allowed to cool to rt. The crude reaction was directly purified via flash column chromatography on silica gel to give 1011C (3.49 g, 11.47 mmol, 97% yield) as a thick, orange foam. LC-MS Anal. Calc'd. for C$_{17}$H$_{24}$N$_2$O$_3$ 304.18, found [M+H] 379.5. T$_r$=1.18 min (Method A).

1011D. Ethyl 3-(4-(cyclohexyl(isobutyl)amino)-3-nitrophenyl)-3-hydroxy-2-methoxypropanoate LHMDS (0.385 g, 2.300 mmol) was added to dry THF (8.21 ml) at −78° C. and placed under nitrogen atmosphere. Methyl 2-methoxyacetate (0.195 ml, 1.971 mmol) was added and after 15 minutes, Intermediate 1011C (500 mg, 1.643 mmol) (as a solution in 3 mL dry THF) was added dropwise. Reaction stirred at −78° C. for 1.5 hours before quenching with ammonium chloride at −78° C. and allowing to warm to room temperature. The reaction was extracted with EtOAc and the combined organics were dried sodium sulfate, filtered and concentrate in vacuo to give crude 1011D (705 mg, 1.726 mmol, 105% yield) (some HMDS still present). LC-MS Anal. Calc'd. for C$_{21}$H$_{32}$N$_2$O$_6$ 408.23, found [M+H] 409.5. T$_r$=1.13 min (Method A).

1011E. Ethyl 3-(4-(cyclohexyl(isobutyl)amino)-3-nitrophenyl)-2-methoxyacrylate

Intermediate 1011D (0.700 g, 1.714 mmol) was added to dry DCM (3.43 ml) at room temperature and placed under nitrogen atmosphere. TEA (0.311 ml, 2.228 mmol) and mesyl-Cl (0.160 ml, 2.056 mmol) were added. After 1 hour, THF (3.43 ml) and DBU (0.775 ml, 5.14 mmol) were added and the reaction stirred at room temperature overnight. After 16 hours, the reaction was concentrated in vacuo and purified via silica gel flash column chromatography to give Intermediate 1011E (610 mg, 1.562 mmol, 91% yield). LC-MS Anal. Calc'd. for C$_{21}$H$_{30}$N$_2$O$_5$, 390.22, found [M+H] 391.5. T$_r$=1.29 min (Method A).

1011F. Ethyl 3-(3-amino-4-(cyclohexyl(isobutyl) amino)phenyl)-2-methoxy acrylate Intermediate 1011E (475 mg, 1.216 mmol) was taken up in EtOAc (6082 μl) in a Parr vessel and palladium hydroxide (12.95 mg, 0.122 mmol) was added. The reaction was placed in a Parr shaker at 50 PSI hydrogen. After 16 hours, the reaction was filtered over CELITE® and concentrated in vacuo to give methyl Intermediate 1011F (367 mg, 1.018 mmol, 84% yield). LC-MS Anal. Calc'd. for C$_{21}$H$_{32}$N$_2$O$_3$, 360.24, found [M+H] 361.1. T$_r$=0.93 min (Method A).

1011G. Ethyl 3-(3-amino-4-(cyclohexyl(isobutyl) amino)phenyl)-2-methoxypropanoate Intermediate 63F (367 mg, 1.018 mmol) was taken up in MeOH (10.200 ml) and added to magnesium (495 mg, 20.36 mmol) in MeOH (10.200 ml) and stirred at room temperature (slight exotherm sometimes brings reaction to reflux on addition of substrate to magnesium/MeOH). After 1 hour, the reaction was carefully quenched with ammonium chloride (sat'd aq) and extracted with EtOAc. The combined organics were dried with sodium sulfate, filtered, and concentrated in vacuo to give crude Intermediate 1011G (365 mg, 1.007 mmol, 99% yield). LC-MS Anal. Calc'd. for C$_{21}$H$_{34}$N$_2$O$_3$ 362.26, found [M+H] 363.4. T$_r$=0.93 min (Method A).

Example 1011

Intermediate 1011G (73 mg, 0.201 mmol) was taken up in THF and phenyl (4-cyano-2-fluorophenyl)carbamate (103 mg, 0.403 mmol) was added along with triethylamine (84 μl, 0.604 mmol). The reaction was heated to 60° C. for 2 hours. After 2 hours, water (1 mL), MeOH (0.3 mL) and lithium hydroxide (48.2 mg, 2.014 mmol) were added and after 1 hour, the reaction was concentrated in vacuo, acidified with 1N HCl and extracted with EtOAc. Combined organic extracts were dried sodium sulfate, filtered and concentrated in vacuo. The crude residue was purified via preparative HPLC to give Example 1011 (25 mg, 24%). LC-MS Anal. Calc'd. for C$_{28}$H$_{35}$FN$_4$O$_4$, 510.26, found [M+H] 511.5. T$_r$=0.92 min (Method A). $^1$H NMR (500 MHz, DMSO-d$_6$) δ: 8.43 (s, 1H), 8.38 (t, J=8.4 Hz, 1H), 7.86 (d, J=10.3 Hz, 1H), 7.77 (s, 1H), 7.62 (d, J=8.5 Hz, 1H), 7.07 (d, J=8.2 Hz, 1H), 6.87 (d, J=7.7 Hz, 1H), 3.86 (dd, J=8.1, 4.2 Hz, 1H), 2.86-2.92 (m, 1H), 2.71-2.79 (m, 2H), 2.54 (s, 3H), 1.84-1.91 (m, 2H), 1.67 (d, J=11.7 Hz, 2H), 1.49 (d, J=11.4 Hz, 1H), 1.29-1.40 (m, 1H), 0.91-1.27 (m, 8H), 0.81 (d, J=6.5 Hz, 6H)

Example 1012

3-(3-(3-(4-Chloro-2-fluorophenyl)ureido)-4-(cyclohexyl(isobutyl)amino)phenyl)-2-methoxypropanoic acid

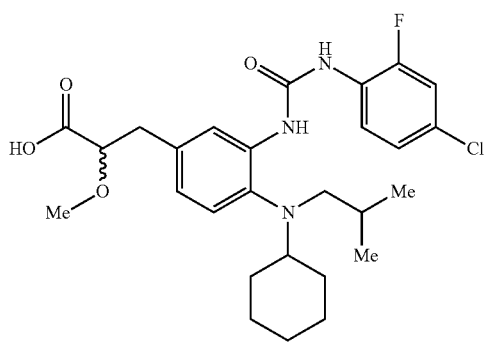 [SMILES: COC(Cc1ccc(N(CC(C)C)C2CCCCC2)c(NC(=O)Nc2ccc(Cl)cc2F)c1)C(=O)O]

Example 1012 was made from Intermediate 1011G and phenyl (4-chloro-2-fluorophenyl)carbamate followed the procedure in Example 1011. LC-MS Anal. Calc'd. for $C_{27}H_{35}ClFN_3O_4$, 519.23, found [M+H] 520.4. $T_r$=0.99 min (Method A). $^1$H NMR (500 MHz, DMSO-$d_6$) δ: 9.52 (s, 1H), 8.23 (s, 1H), 8.04 (t, J=8.8 Hz, 1H), 7.80 (s, 1H), 7.46 (dd, J=10.9, 1.9 Hz, 1H), 7.22 (d, J=8.8 Hz, 1H), 7.06 (d, J=8.2 Hz, 1H), 6.83 (d, J=8.0 Hz, 1H), 3.85 (dd, J=7.8, 4.0 Hz, 1H), 2.85-2.91 (m, 1H), 2.71-2.78 (m, 2H), 2.54 (s, 3H), 1.87 (d, J=10.9 Hz, 2H), 1.67 (d, J=11.3 Hz, 2H), 1.50 (d, J=11.4 Hz, 1H), 1.33 (dt, J=13.1, 6.6 Hz, 1H), 0.90-1.25 (m, 8H), 0.81 (d, J=6.5 Hz, 6H).

Examples 1013 to 1017

These compounds (homochiral, stereochemistry unknown) were obtained following the procedures in Example 958 using 958F1 and the corresponding isocyanate.

| Ex. No. | Name | R | $T_r$ (min) Method B | [M + H]$^+$ |
|---|---|---|---|---|
| 1013 | 3-(3-(3-(4-cyanophenyl)ureido)-4-(isobutyl(tetrahydro-2H-pyran-4-yl)amino)phenyl)butanoic acid | 4-CN-C6H4- | 1.62 | 479.1 |
| 1014 | 3-(3-(3-(4-chloro-2-fluorophenyl)ureido)-4-(isobutyl(tetrahydro-2H-pyran-4-yl)amino)phenyl)butanoic acid | 4-Cl-2-F-C6H3- | 1.80 | 506.3 |
| 1015 | 3-(3-(3-(4-chlorophenyl)ureido)-4-(isobutyl(tetrahydro-2H-pyran-4-yl)amino)phenyl)butanoic acid | 4-Cl-C6H4- | 1.80 | 488.2 |
| 1016 | 3-(3-(3-(4-ethoxy-2-fluorophenyl)ureido)-4-(isobutyl(tetrahydro-2H-pyran-4-yl)amino)phenyl)butanoic acid | 4-OEt-2-F-C6H3- | 1.73 | 516.4 |
| 1017 | 3-(4-(isobutyl(tetrahydro-2H-pyran-4-yl)amino)-3-(3-(4-(trifluoromethoxy)phenyl)ureido)phenyl)butanoic acid | 4-OCF3-C6H4- | 1.90 | 538.1 |

Examples 1018 to 1022

These compounds (homochiral, stereochemistry unknown) were obtained following the procedures in Example 958 using 958F2 and the corresponding isocyanate.

| Ex. No. | Name | R | T$_r$ (min) Method B | [M + H]$^+$ |
|---|---|---|---|---|
| 1018 | 3-(3-(3-(4-cyanophenyl)ureido)-4-(isobutyl(tetrahydro-2H-pyran-4-yl)amino)phenyl)butanoic acid | | 1.62 | 479.1 |
| 1019 | 3-(3-(3-(4-chloro-2-fluorophenyl)ureido)-4-(isobutyl(tetrahydro-2H-pyran-4-yl)amino)phenyl)butanoic acid | | 1.80 | 506.3 |
| 1020 | 3-(3-(3-(4-chlorophenyl)ureido)-4-(isobutyl(tetrahydro-2H-pyran-4-yl)amino)phenyl)butanoic acid | | 1.80 | 488.2 |
| 1021 | 3-(3-(3-(4-ethoxy-2-fluorophenyl)ureido)-4-(isobutyl(tetrahydro-2H-pyran-4-yl)amino)phenyl)butanoic acid | | 1.73 | 516.4 |
| 1022 | 3-(4-(isobutyl(tetrahydro-2H-pyran-4-yl)amino)-3-(3-(4-(trifluoromethoxy)phenyl)ureido)phenyl)butanoic acid | | 1.90 | 538.1 |

Examples 1023 to 1025

These compounds (homochiral, stereochemistry unknown) were obtained following the procedures in Example 956 using the corresponding isocyanate.

| Ex. No. | Name | R | T$_r$ (min) Method B | [M + H]$^+$ |
|---|---|---|---|---|
| 1023 | 3-(4-(cyclohexyl(isobutyl)amino)-2-fluoro-5-(3-(4-(trifluoromethoxy)phenyl)ureido)phenyl)butanoic acid | | 2.32 | 554.1 |
| 1024 | 3-(5-(3-(4-chloro-2-fluorophenyl)ureido)-4-(cyclohexyl(isobutyl)amino)-2-fluorophenyl)butanoic acid | | 2.28 | 522.0 |

| Ex. No. | Name | R | T_r (min) Method B | [M + H]+ |
|---|---|---|---|---|
| 1025 | 3-(4-(cyclohexyl(isobutyl) amino)-5-(3-(4-ethoxyphenyl) ureido)-2-fluorophenyl)butanoic acid | 4-ethoxyphenyl | 2.19 | 514.1 |

Examples 1026 to 1028

These compounds (homochiral, stereochemistry unknown) were obtained following the procedures in Example 957 using the corresponding isocyanate.

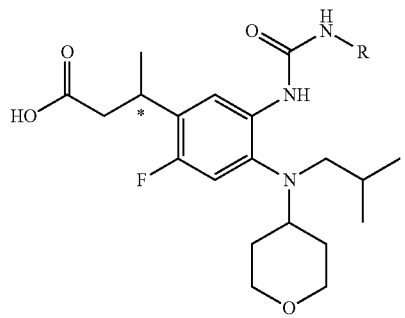

| Ex. No. | Name | R | T_r (min) Method B | [M + H]+ |
|---|---|---|---|---|
| 1026 | 3-(4-(cyclohexyl(isobutyl)amino)-2-fluoro-5-(3-(4-(trifluoromethoxy)phenyl)ureido)phenyl)butanoic acid | 4-OCF3-phenyl | 2.32 | 554.1 |
| 1027 | 3-(5-(3-(4-chloro-2-fluorophenyl) ureido)-4-(cyclohexyl(isobutyl) amino)-2-fluorophenyl)butanoic acid | 2-fluoro-4-chlorophenyl | 2.28 | 522.0 |
| 1028 | 3-(4-(cyclohexyl(isobutyl)amino)-5-(3-(4-ethoxyphenyl)ureido)-2-fluorophenyl)butanoic acid | 4-ethoxyphenyl | 2.19 | 514.1 |

Examples 1029 to 1049

1029A. Methyl 3-(3-amino-4-(isobutyl(tetrahydro-2H-pyran-4-yl)amino)phenyl)pentanoate

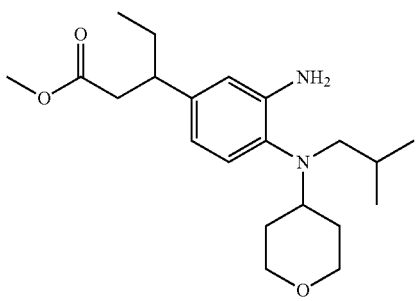 [SMILES: CCC(CC(=O)OC)c1ccc(N(CC(C)C)C2CCOCC2)c(N)c1]

Example 1029A was prepared according Example 958 using the E-methylpent-2-enoate.

1029B. Methyl 3-(3-amino-4-(isobutyl(tetrahydro-2H-pyran-4-yl)amino)phenyl)pentanoate

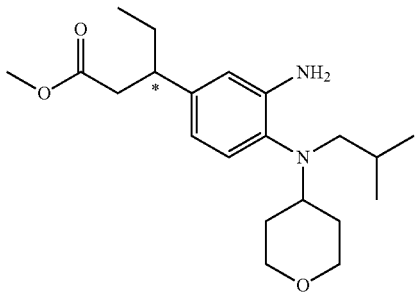 [SMILES: CCC(CC(=O)OC)c1ccc(N(CC(C)C)C2CCOCC2)c(N)c1]

Example 1029B was the first eluent peak ($T_r$=7.12 min.) prepared from Example 17A (850 mg, 2.35 mmol) by using the following conditions: UV visualization at 220 nm; Column: Chiral IC-25×3 cm ID, 5 μm; Flow rate: 100 mL/min, Mobile Phase: 93/7, $CO_2$/MeOH methyl 3-(3-amino-4-(isobutyl(tetrahydro-2H-pyran-4-yl)amino)phenyl) butanoate (265 mg, 0.71 mmol, 30% yield) was obtained. $^1$H NMR (400 MHz, chloroform-d) δ 6.98 (d, J=8.1 Hz, 1H), 6.57 (d, J=2.0 Hz, 1H), 6.52 (dd, J=8.1, 2.0 Hz, 1H), 4.05 (s, 2H), 3.99 (dt, J=11.4, 2.7 Hz, 2H), 3.61 (s, 3H), 3.34 (t, J=12.3 Hz, 2H), 2.98-2.76 (m, 3H), 2.65-2.45 (m, 2H), 1.79-1.53 (m, 7H), 1.47 (dt, J=13.4, 6.7 Hz, 1H), 0.91-0.76 (m, 9H) MS: [M+H] 364.3 HPLC: $T_r$=0.88 min. Method A. Absolute stereochemistry was not determined.

1029C. Methyl 3-(3-amino-4-(isobutyl(tetrahydro-2H-pyran-4-yl)amino)phenyl)pentanoate

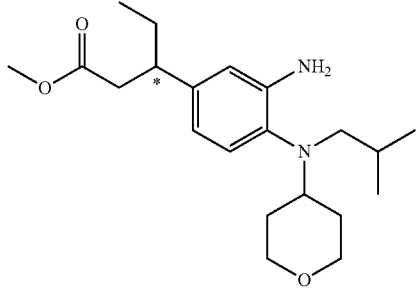 [SMILES: CCC(CC(=O)OC)c1ccc(N(CC(C)C)C2CCOCC2)c(N)c1]

Example 1029C was the second eluent peak ($T_r$=7.90 min.) prepared from Example 1029A (850 mg, 2.35 mmol) by using the following conditions: UV visualization at 220 nm; Column: Chiral IC-25×3 cm ID, 5 μm; Flow rate: 100 mL/min, Mobile Phase: 93/7, $CO_2$/MeOH methyl 3-(3-amino-4-(isobutyl(tetrahydro-2H-pyran-4-yl)amino)phenyl) butanoate (275 mg, 0.736 mmol, 31% yield) was obtained. $^1$H NMR (400 MHz, chloroform-d) δ 6.98 (d, J=8.1 Hz, 1H), 6.57 (d, J=2.0 Hz, 1H), 6.52 (dd, J=8.1, 2.0 Hz, 1H), 4.05 (s, 2H), 3.99 (dt, J=11.4, 2.7 Hz, 2H), 3.61 (s, 3H), 3.34 (t, J=12.3 Hz, 2H), 2.98-2.76 (m, 3H), 2.65-2.45 (m, 2H), 1.79-1.53 (m, 7H), 1.47 (dt, J=13.4, 6.7 Hz, 1H), 0.91-0.76 (m, 9H). MS: [M+H] 364.3 HPLC: $T_r$=0.88 min. Method A. Absolute stereochemistry was not determined.

These compounds (homochiral, stereochemistry unknown) were obtained following the procedures in Example 958 using 1029B and corresponding isocyanate.

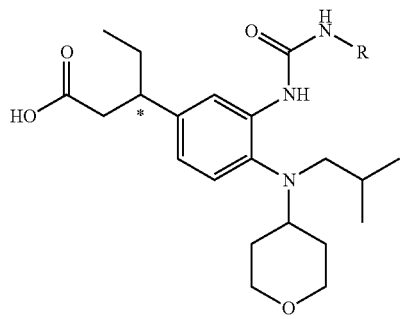

| Ex. No. | Name | R | $T_r$ (min) Method B | [M + H]$^+$ |
|---|---|---|---|---|
| 1029 | 3-(4-(isobutyl(tetrahydro-2H-pyran-4-yl)amino)-3-(3-(p-tolyl)ureido)phenyl)pentanoic acid | ![p-tolyl] | 1.79 | 482.1 |

-continued

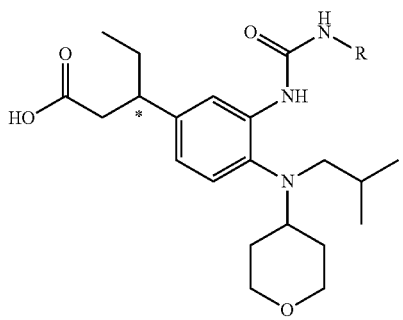

| Ex. No. | Name | R | T$_r$ (min) Method B | [M + H]$^+$ |
|---|---|---|---|---|
| 1030 | 3-(4-(isobutyl(tetrahydro-2H-pyran-4-yl)amino)-3-(3-(4-(trifluoromethoxy)phenyl)ureido)phenyl)pentanoic acid | 2-F, 4-OCF$_3$ phenyl | 2.00 | 552.4 |
| 1031 | 3-(3-(3-(4-chloro-2-fluorophenyl)ureido)-4-(isobutyl(tetrahydro-2H-pyran-4-yl)amino)phenyl)pentanoic acid | 2-F, 4-Cl phenyl | 1.91 | 520.4 |
| 1032 | 3-(4-(isobutyl(tetrahydro-2H-pyran-4-yl)amino)-3-(3-(4-(trifluoromethyl)phenyl)ureido)phenyl)pentanoic acid | 4-CF$_3$ phenyl | 2.00 | 536.4 |
| 1033 | 3-(3-(3-(4-chlorophenyl)ureido)-4-(isobutyl(tetrahydro-2H-pyran-4-yl)amino)phenyl)pentanoic acid | 4-Cl phenyl | 1.88 | 502.4 |
| 1034 | 3-(3-(3-(4-ethoxy-2-fluorophenyl)ureido)-4-(isobutyl(tetrahydro-2H-pyran-4-yl)amino)phenyl)pentanoic acid | 2-F, 4-OEt phenyl | 1.84 | 530.1 |
| 1035 | 3-(3-(3-(6-ethoxypyridin-3-yl)ureido)-4-(isobutyl(tetrahydro-2H-pyran-4-yl)amino)phenyl)pentanoic acid | 6-ethoxypyridin-3-yl | 1.63 | 513.2 |
| 1036 | 3-(4-(isobutyl(tetrahydro-2H-pyran-4-yl)amino)-3-(3-(2-methoxypyrimidin-5-yl)ureido)phenyl)pentanoic acid | 2-methoxypyrimidin-5-yl | 1.46 | 500.4 |

-continued

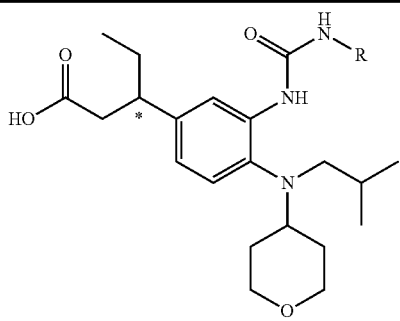

| Ex. No. | Name | R | T_r (min) Method B | [M + H]+ |
|---|---|---|---|---|
| 1037 | 3-(3-(3-(4-ethoxyphenyl)ureido)-4-(isobutyl(tetrahydro-2H-pyran-4-yl)amino)phenyl)pentanoic acid | | 1.80 | 512.3 |
| 1038 | 3-(3-(3-(4-cyanophenyl)ureido)-4-(isobutyl(tetrahydro-2H-pyran-4-yl)amino)phenyl)pentanoic acid | | 1.73 | 493.1 |

These compounds (homochiral, stereochemistry unknown) were obtained following the procedures in Example 958 using 1029C and corresponding isocyanate.

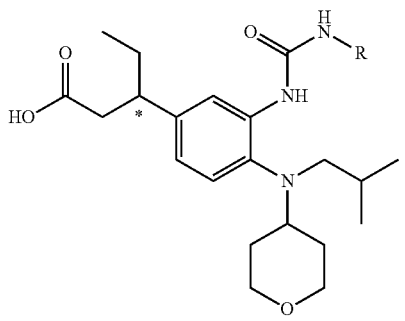

| Ex. No. | Name | R | T_r (min) Method B | [M + H]+ |
|---|---|---|---|---|
| 1039 | 3-(4-(isobutyl(tetrahydro-2H-pyran-4-yl)amino)-3-(3-(p-tolyl)ureido)phenyl)pentanoic acid | | 1.79 | 482.1 |
| 1040 | 3-(4-(isobutyl(tetrahydro-2H-pyran-4-yl)amino)-3-(3-(4-(trifluoromethoxy)phenyl)ureido)phenyl)pentanoic acid | | 2.00 | 552.4 |

-continued

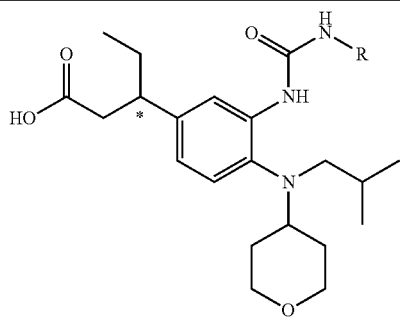

| Ex. No. | Name | R | T_r (min) Method B | [M + H]+ |
|---|---|---|---|---|
| 1041 | 3-(3-(3-(4-chloro-2-fluorophenyl)ureido)-4-(isobutyl(tetrahydro-2H-pyran-4-yl)amino)phenyl)pentanoic acid | 2-F, 4-Cl phenyl | 1.91 | 520.4 |
| 1042 | 3-(4-(isobutyl(tetrahydro-2H-pyran-4-yl)amino)-3-(3-(4-(trifluoromethyl)phenyl)ureido)phenyl)pentanoic acid | 4-CF3 phenyl | 2.00 | 536.4 |
| 1043 | 3-(3-(3-(4-chlorophenyl)ureido)-4-(isobutyl(tetrahydro-2H-pyran-4-yl)amino)phenyl)pentanoic acid | 4-Cl phenyl | 1.88 | 502.4 |
| 1044 | 3-(3-(3-(4-ethoxy-2-fluorophenyl)ureido)-4-(isobutyl(tetrahydro-2H-pyran-4-yl)amino)phenyl)pentanoic acid | 2-F, 4-OEt phenyl | 1.84 | 530.1 |
| 1045 | 3-(3-(3-(4-ethoxyphenyl)ureido)-4-(isobutyl(tetrahydro-2H-pyran-4-yl)amino)phenyl)pentanoic acid | 4-OEt phenyl | 1.80 | 512.3 |
| 1046 | 3-(4-(isobutyl(tetrahydro-2H-pyran-4-yl)amino)-3-(3-(2-methoxypyrimidin-5-yl)ureido)phenyl)pentanoic acid | 2-methoxypyrimidin-5-yl | 1.46 | 500.4 |
| 1047 | 3-(3-(3-(4-cyanophenyl)ureido)-4-(isobutyl(tetrahydro-2H-pyran-4-yl)amino)phenyl)pentanoic acid | 4-CN phenyl | 1.73 | 493.1 |
| 1048 | 3-(4-(isobutyl(tetrahydro-2H-pyran-4-yl)amino)-3-(3-(3-methylisoxazol-5-yl)ureido)phenyl)pentanoic acid | 3-methylisoxazol-5-yl | 1.66 | 473.3 |

-continued

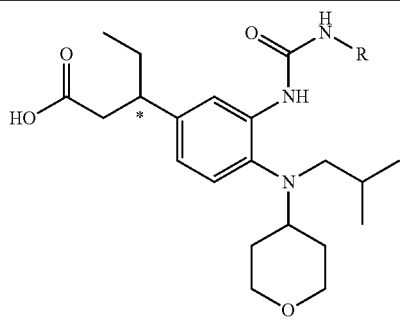

| Ex. No. | Name | R | T_r (min) Method B | [M + H]+ |
|---|---|---|---|---|
| 1049 | 3-(3-(3-(6-ethoxypyridin-3-yl)ureido)-4-(isobutyl(tetrahydro-2H-pyran-4-yl)amino)phenyl) pentanoic acid | | 1.63 | 513.2 |

Example 1050

Enantiomer 1 and Enantiomer 2

Example 1050 Enantiomer 1: 6,6,6-Trifluoro-3-(4-(isobutyl(tetrahydro-2H-pyran-4-yl)amino)-3-(3-(p-tolyl)ureido)phenyl)hexanoic acid

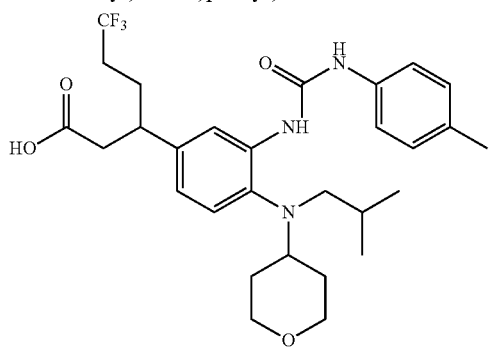

Example 1050 Enantiomer 2: 6,6,6-Trifluoro-3-(4-(isobutyl(tetrahydro-2H-pyran-4-yl)amino)-3-(3-(p-tolyl)ureido)phenyl)hexanoic acid

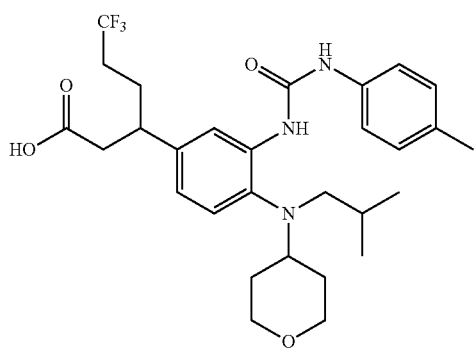 [SMILES: Cc1ccc(NC(=O)Nc2cc(C(CCC(F)(F)F)CC(=O)O)ccc2N(CC(C)C)C2CCOCC2)cc1]

1050A. (+/−) Ethyl 3-(3-amino-4-(isobutyl(tetrahydro-2H-pyran-4-yl)amino)phenyl)-6,6,6-trifluorohexanoate Example 1050A was prepared according to Example 958 using the E-ethyl 6,6,6-trifluorohex-2-enoate.

Example 1050B Enantiomer 1 and Enantiomer 2. Ethyl 3-(3-amino-4-(isobutyl(tetrahydro-2H-pyran-4-yl)amino)phenyl)-6,6,6-trifluorohexanoate

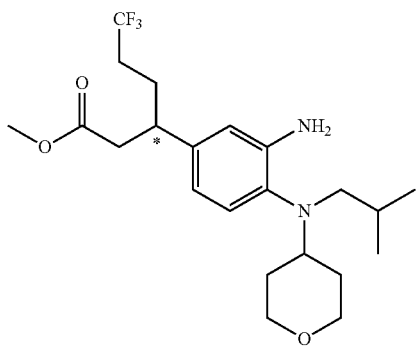 [SMILES: COC(=O)CC(CCC(F)(F)F)c1ccc(N(CC(C)C)C2CCOCC2)c(N)c1]

Example 1050B Enantiomer 1 was the first eluent peak (T_r=12.6 min.) prepared from Example 39A (380 mg, 0.855 mmol) by using the following conditions: UV visualization at 220 nm; Column: Chiral Lux2 25×3 cm ID, 5 µm; Flow rate: 85 mL/min, Mobile Phase: 95/5, $CO_2$/MeOH ethyl 3-(3-amino-4-(isobutyl(tetrahydro-2H-pyran-4-yl)amino) phenyl)-6,6,6-trifluorohexanoate (100 mg, 0.22 mmol, 26% yield) was obtained. $^1$H NMR (400 MHz, chloroform-d) δ 7.00 (d, J=8.1 Hz, 1H), 6.56 (d, J=2.1 Hz, 1H), 6.51 (dd, J=8.1, 2.1 Hz, 1H), 4.15-4.04 (m, 3H), 4.04-3.85 (m, 2H), 3.52 (s, 1H), 3.33 (d, J=14.2 Hz, 2H), 3.00 (d, J=7.3 Hz, 1H), 2.87 (br. s., 1H), 2.64-2.49 (m, 2H), 2.02-1.88 (m, 3H), 1.79 (dd, J=10.6, 2.9 Hz, 2H), 1.72 (br. s., 3H), 1.58 (br. s., 3H), 1.53-1.38 (m, 1H), 1.17 (t, J=7.2 Hz, 3H), 0.86 (d, J=6.6 Hz, 6H) MS: [M+H] 445.6 HPLC: $T_r$=0.90 min. Method A. Absolute stereochemistry was not determined.

1050B Enantiomer 2 was the second eluent peak ($T_r$=14.4 min.) prepared from Example 1050A (380 mg, 0.855 mmol) by using the following conditions: UV visualization at 220 nm; Column: Chiral Lux2 25×3 cm ID, 5 μm; Flow rate: 85 mL/min, Mobile Phase: 95/5, $CO_2$/MeOH ethyl 3-(3-amino-4-(isobutyl(tetrahydro-2H-pyran-4-yl)amino)phenyl)-6,6,6-trifluorohexanoate (100 mg, 0.22 mmol, 26% yield) was obtained. $^1$H NMR (400 MHz, chloroform-d) δ 7.00 (d, J=8.1 Hz, 1H), 6.56 (d, J=2.1 Hz, 1H), 6.51 (dd, J=8.1, 2.1 Hz, 1H), 4.15-4.04 (m, 3H), 4.04-3.85 (m, 2H), 3.52 (s, 1H), 3.33 (d, J=14.2 Hz, 2H), 3.00 (d, J=7.3 Hz, 1H), 2.87 (br. s., 1H), 2.64-2.49 (m, 2H), 2.02-1.88 (m, 3H), 1.79 (dd, J=10.6, 2.9 Hz, 2H), 1.72 (br. s., 3H), 1.58 (br. s., 3H), 1.53-1.38 (m, 1H), 1.17 (t, J=7.2 Hz, 3H), 0.86 (d, J=6.6 Hz, 6H) MS: [M+H] 445.6 HPLC: $T_r$=0.90 min. Method A. Absolute stereochemistry was not determined.

Example 1050 Enantiomer 1

To a solution of 1050B Enantiomer 1 (14 mg, 0.031 mmol) in THF (0.2 mL) at RT was added 1-isocyanato-4-methylbenzene (8.39 mg, 0.063 mmol). The reaction was stirred at RT for 2 h. To above reaction was added MeOH (0.2 mL), followed by 1N NaOH (0.5 mL, 0.500 mmol). The reaction was stirred at RT for 3 h. pH was adjusted to 5 with concentrated HCl. The mixture was diluted with DMF and filtered through 0.45 μM membrane. The filtrate was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 8.3 mg (0.015 mmol, 46%) $^1$H NMR (500 MHz, DMSO-$d_6$) δ 9.47 (s, 1H), 8.23 (s, 1H), 8.02 (s, 1H), 7.39-7.31 (m, J=8.2 Hz, 2H), 7.24-7.13 (m, 1H), 7.13-7.03 (m, 2H), 6.85 (d, J=7.2 Hz, 1H), 3.83 (d, J=9.0 Hz, 2H), 3.20 (t, J=12.0 Hz, 2H), 3.00 (br. s., 1H), 2.83 (br. s., 1H), 2.75 (d, J=19.0 Hz, 2H), 2.62 (dd, J=15.6, 6.7 Hz, 1H), 2.24 (s, 3H), 2.20-2.07 (m, 1H), 2.00-1.76 (m, 2H), 1.70 (d, J=10.1 Hz, 3H), 1.50-1.35 (m, 2H), 1.35-1.20 (m, 1H), 0.80 (d, J=5.9 Hz, 6H) MS: [M+H] 550.1 HPLC: $T_r$=1.976 min. Method B. Absolute stereochemistry was not determined.

Example 1050 Enantiomer 2

To a solution of 1050B Enantiomer 2 (14 mg, 0.031 mmol) in THF (0.2 mL) at RT was added 1-isocyanato-4-methylbenzene (8.39 mg, 0.063 mmol). The reaction was stirred at RT for 2H. To above reaction was added MeOH (0.2 mL), followed by 1N NaOH (0.5 mL, 0.500 mmol). The reaction was stirred at RT for 3 h. pH was adjusted to 5 with concentrated HCl. The mixture was diluted with DMF and filtered through 0.45 μM membrane. The filtrate was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 11.3 mg (0.020 mmol, 59%) $^1$H NMR (500 MHz, DMSO-$d_6$) δ 9.47 (s, 1H), 8.23 (s, 1H), 8.02 (s, 1H), 7.39-7.31 (m, J=8.2 Hz, 2H), 7.24-7.13 (m, 1H), 7.13-7.03 (m, 2H), 6.85 (d, J=7.2 Hz, 1H), 3.83 (d, J=9.0 Hz, 2H), 3.20 (t, J=12.0 Hz, 2H), 3.00 (br. s., 1H), 2.83 (br. s., 1H), 2.75 (d, J=19.0 Hz, 2H), 2.62 (dd, J=15.6, 6.7 Hz, 1H), 2.24 (s, 3H), 2.20-2.07 (m, 1H), 2.00-1.76 (m, 2H), 1.70 (d, J=10.1 Hz, 3H), 1.50-1.35 (m, 2H), 1.35-1.20 (m, 1H), 0.80 (d, J=5.9 Hz, 6H) MS: [M+H] 550.1 HPLC: $T_r$=1.976 min. Method B. Absolute stereochemistry was not determined.

Examples 1052 to 1055

These compounds (homochiral, absolute stereochemistry unknown) were obtained following the procedures in Example 1050 Enantiomer 1 using 1050B Enantiomer 1 and corresponding isocyanate.

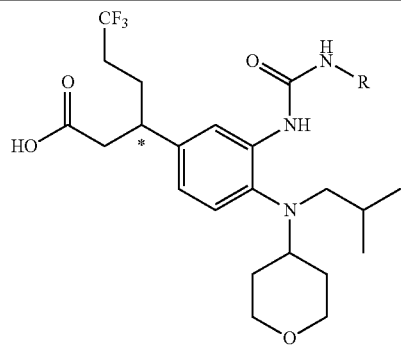

| Ex. No. | Name | R | $T_r$ (min) Method B | [M + H]$^+$ |
|---|---|---|---|---|
| 1052 | 3-(3-(3-(4-chloro-2-fluorophenyl)ureido)-4-(isobutyl(tetrahydro-2H-pyran-4-yl)amino)phenyl)-6,6,6-trifluorohexanoic acid | (2-fluoro-4-chlorophenyl) | 2.08 | 588.3 |

-continued

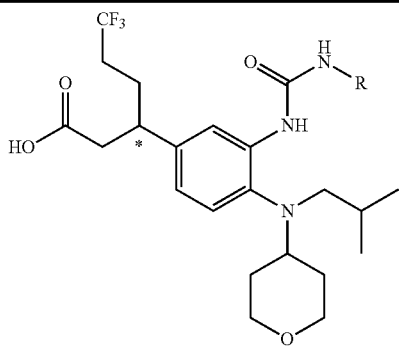

| Ex. No. | Name | R | $T_r$ (min) Method B | $[M + H]^+$ |
|---|---|---|---|---|
| 1053 | 3-(3-(3-(4-chlorophenyl)ureido)-4-(isobutyl(tetrahydro-2H-pyran-4-yl)amino)phenyl)-6,6,6-trifluorohexanoic acid | 4-Cl-C6H4 | 2.03 | 570.1 |
| 1054 | 3-(3-(3-(4-cyanophenyl)ureido)-4-(isobutyl(tetrahydro-2H-pyran-4-yl)amino)phenyl)-6,6,6-trifluorohexanoic acid | 4-CN-C6H4 | 1.89 | 561.3 |
| 1055 | 3-(3-(3-(4-ethoxyphenyl)ureido)-4-(isobutyl(tetrahydro-2H-pyran-4-yl)amino)phenyl)-6,6,6-trifluorohexanoic acid | 4-EtO-C6H4 | 1.97 | 580.3 |

Examples 1057 to 1060

These compounds (homochiral, absolute stereochemistry unknown) were obtained following the procedures in Example 1050 Enantiomer 2 using 1050B enantiomer 2 and corresponding isocyanate.

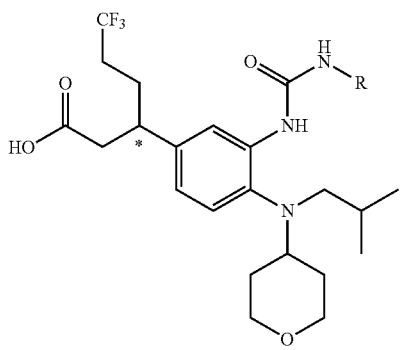

| Ex. No. | Name | R | $T_r$ (min) Method B | $[M + H]^+$ |
|---|---|---|---|---|
| 1057 | 3-(3-(3-(4-chloro-2-fluorophenyl)ureido)-4-(isobutyl(tetrahydro-2H-pyran-4-yl)amino)phenyl)-6,6,6-trifluorohexanoic acid | 2-F-4-Cl-C6H3 | 2.08 | 588.3 |

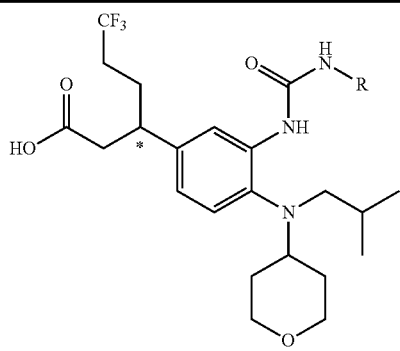

| Ex. No. | Name | R | T$_r$ (min) Method B | [M + H]$^+$ |
|---|---|---|---|---|
| 1058 | 3-(3-(3-(4-chlorophenyl)ureido)-4-(isobutyl(tetrahydro-2H-pyran-4-yl)amino)phenyl)-6,6,6-trifluorohexanoic acid | 4-Cl-C$_6$H$_4$- | 2.03 | 570.1 |
| 1059 | 3-(3-(3-(4-cyanophenyl)ureido)-4-(isobutyl(tetrahydro-2H-pyran-4-yl)amino)phenyl)-6,6,6-trifluorohexanoic acid | 4-CN-C$_6$H$_4$- | 1.89 | 561.3 |
| 1060 | 3-(3-(3-(4-ethoxyphenyl)ureido)-4-(isobutyl(tetrahydro-2H-pyran-4-yl)amino)phenyl)-6,6,6-trifluorohexanoic acid | 4-EtO-C$_6$H$_4$- | 1.97 | 580.3 |

Examples 1061 and 1062

These compounds (homochiral, absolute stereochemistry unknown) were obtained following the procedures in Example 953 using 1050B Enantiomer 1 and corresponding acid.

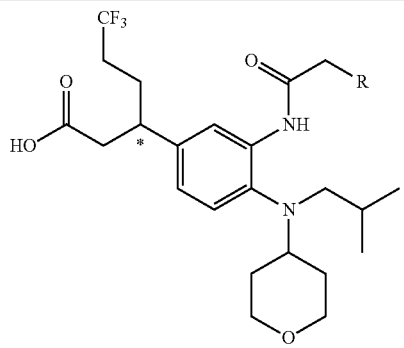

| Ex. No. | Name | R | T$_r$ (min) Method B | [M + H]$^+$ |
|---|---|---|---|---|
| 1061 | 6,6,6-trifluoro-3-(4-(isobutyl(tetrahydro-2H-pyran-4-yl)amino)-3-(2-(p-tolyl)acetamido)phenyl)hexanoic acid | 4-Me-C$_6$H$_4$- | 2.23 | 549.2 |

-continued

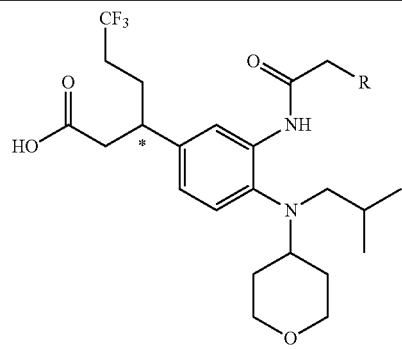

| Ex. No. | Name | R | T$_r$ (min) Method B | [M + H]$^+$ |
|---|---|---|---|---|
| 1062 | 3-(3-(2-(4-chloro-2-fluorophenyl)acetamido)-4-(isobutyl(tetrahydro-2H-pyran-4-yl)amino)phenyl)-6,6,6-trifluorohexanoic acid | *4-chloro-2-fluorophenyl* | 2.32 | 587.5 |

Examples 1063 and 1064

These compounds (homochiral, absolute stereochemistry unknown) were obtained following the procedures in Example 953 using 1050B Enantiomer 2 and corresponding acid.

Examples 1065 to 1068

These compounds (homochiral, stereochemistry unknown) were obtained following the procedures in Example 953 using 1029B and corresponding acid.

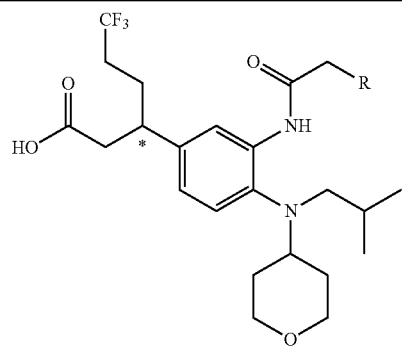

| Ex. No. | Name | R | T$_r$ (min) Method B | [M + H]$^+$ |
|---|---|---|---|---|
| 1063 | 6,6,6-trifluoro-3-(4-(isobutyl(tetrahydro-2H-pyran-4-yl)amino)-3-(2-(p-tolyl)acetamido)phenyl)hexanoic acid | *p-tolyl* | 2.23 | 549.2 |
| 1064 | 3-(3-(2-(4-chloro-2-fluorophenyl)acetamido)-4-(isobutyl(tetrahydro-2H-pyran-4-yl)amino)phenyl)-6,6,6-trifluorohexanoic acid | *4-chloro-2-fluorophenyl* | 2.32 | 587.5 |

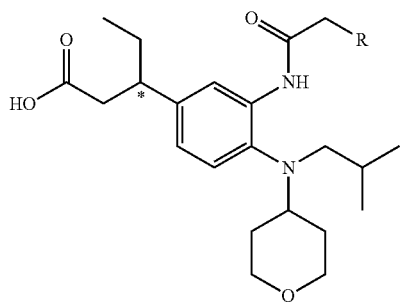

| Ex. No. | Name | R | T_r (min) Method B | [M + H]+ |
|---|---|---|---|---|
| 1065 | 3-(4-(isobutyl(tetrahydro-2H-pyran-4-yl)amino)-3-(2-(p-tolyl)acetamido)phenyl)pentanoic acid | | 2.09 | 481.1 |
| 1066 | 3-(4-(isobutyl(tetrahydro-2H-pyran-4-yl)amino)-3-(2-(5-methylisoxazol-3-yl)acetamido)phenyl)pentanoic acid | | 1.74 | 472.1 |
| 1067 | 3-(3-(2-(4-ethoxyphenyl)acetamido)-4-(isobutyl(tetrahydro-2H-pyran-4-yl)amino)phenyl)pentanoic acid | | 2.06 | 511.2 |
| 1068 | 3-(3-(2-(4-chloro-2-fluorophenyl)acetamido)-4-(isobutyl(tetrahydro-2H-pyran-4-yl)amino)phenyl)pentanoic acid | | 1.84 | 530.1 |

Examples 1069 to 1072

These compounds (homochiral, stereochemistry unknown) were obtained following the procedures in Example 953 using 1029C and corresponding acid.

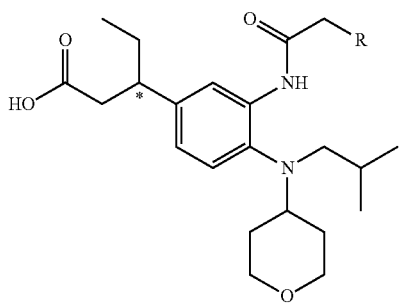

| Ex. No. | Name | R | T_r (min) Method B | [M + H]+ |
|---|---|---|---|---|
| 1069 | 3-(4-(isobutyl(tetrahydro-2H-pyran-4-yl)amino)-3-(2-(p-tolyl)acetamido)phenyl)pentanoic acid | | 2.09 | 481.1 |

-continued

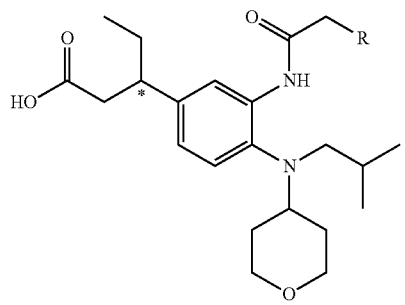

| Ex. No. | Name | R | $T_r$ (min) Method B | $[M + H]^+$ |
|---|---|---|---|---|
| 1070 | 3-(4-(isobutyl(tetrahydro-2H-pyran-4-yl)amino)-3-(2-(5-methylisoxazol-3-yl)acetamido)phenyl)pentanoic acid | 5-methylisoxazol-3-yl | 1.74 | 472.1 |
| 1071 | 3-(3-(2-(4-ethoxyphenyl)acetamido)-4-(isobutyl(tetrahydro-2H-pyran-4-yl)amino)phenyl)pentanoic acid | 4-ethoxyphenyl | 2.06 | 511.2 |
| 1072 | 3-(3-(2-(4-chloro-2-fluorophenyl)acetamido)-4-(isobutyl(tetrahydro-2H-pyran-4-yl)amino)phenyl)pentanoic acid | 4-chloro-2-fluorophenyl | 1.84 | 530.1 |

Example 1073

3-(4-(Cyclohexyl(isobutyl)amino)-3-(4-ethoxybenzamido)phenyl)pentanoic acid (racemic)

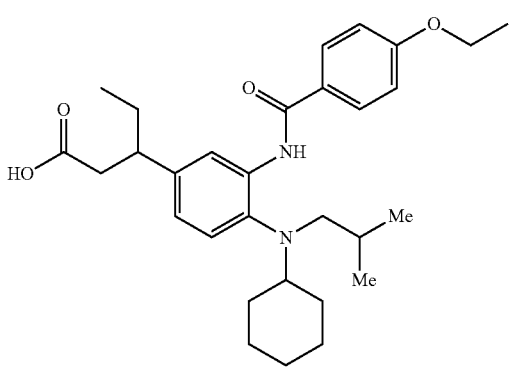 [SMILES: CCOc1ccc(C(=O)Nc2cc(C(CC)CC(=O)O)ccc2N(CC(C)C)C2CCCCC2)cc1]

1073A.
4-Bromo-N-cyclohexyl-N-isobutyl-2-nitroaniline

To a solution of 4-bromo-1-fluoro-2-nitrobenzene (3 g, 13.64 mmol) and Intermediate 1011A (3.60 g, 23.18 mmol) was added Hunig's base (3.10 ml, 17.73 mmol). The solution was placed under a nitrogen atmosphere, sealed and heated at 115° C. for 12 h. Crude mixture purified directly via flash column chromatography (80 g, 65 mL/min, 0-20% EtOAc in hexanes with just straight hexanes for first 5 minutes) to give Intermediate 1073A (3.63 g, 74.9% yield). LC-MS Anal. Calc'd. for $C_{16}H_{23}BrN_2O_2$, 354.10, found [M+H] 355.3. $T_r$=1.35 min (Method A).

1073B. N-Cyclohexyl-4-(5,5-dimethyl-1,3,2-dioxaborinan-2-yl)-N-isobutyl-2-nitroaniline A solution of 5,5,5',5'-tetramethyl-2,2'-bi(1,3,2-dioxaborinane) (413 mg, 1.830 mmol) and Intermediate 1073A (500 mg, 1.407 mmol) and potassium acetate (414 mg, 4.22 mmol) in degassed DMSO (2011 µl) was treated with 1,1'-bis(diphenylphosphino)ferrocenedichloro palladium(II) dichloromethane complex (51.5 mg, 0.070 mmol). This dark solution was placed under nitrogen and heated to 80° C. for 2 h then cooled to RT. LCMS shows conversion to peak with M+1 of boronic acid (boronic ester degrades on column). The reaction was purified by flash chromatography (80 g, 60 mL/min, 0-50% EtOAc). Concentration of the appropriate fractions afforded Intermediate 1073B (472 mg, 86% yield) as an orange oil. LC-MS Anal. Calc'd. for $C_{21}H_{33}BN_2O_4$, 388.25, found [M+H] 320.3 (corresponding to M+1 of boronic acid) $T_r$=1.10 min (Method A).

1073C. Methyl 3-(4-(cyclohexyl(isobutyl)amino)-3-nitrophenyl)pentanoate

A reaction vial was charged with Intermediate 1073B (472 mg, 1.216 mmol). This material was dissolved in dioxane (10 mL). (E)-Methyl pent-2-enoate (416 mg, 3.65 mmol) was added followed by NaOH (1094 μl, 1.094 mmol). The sample was degassed by bubbling vigorously with nitrogen gas for 10 minutes. Chloro(1,5-cyclooctadiene)rhodium(I) dimer (30.0 mg, 0.061 mmol) was added and again the reaction was bubbled with nitrogen gas to purge oxygen. The reaction was stirred 4.5 hours at 50° C. The reaction was then treated with acetic acid (139 μl, 2.431 mmol), concentrated in vacuo, and then purified directly with flash column chromatography. Concentration of the appropriate fractions afforded Intermediate 1073C (415 mg, 87% yield) as an orange oil. LC-MS Anal. Calc'd. for $C_{22}H_{34}N_2O_4$, 390.52, found [M+H] 391.1. $T_r$=1.27 min (Method A).

1073D. Methyl 3-(3-amino-4-(cyclohexyl(isobutyl)amino)phenyl)pentanoate

Intermediate 1073C (415 mg, 1.063 mmol) taken up in MeOH (10.600 ml) in a Parr bottle. The solution was vacated and flushed with nitrogen gas several times before the addition of Pd/C (10% by wt.) (113 mg, 106 mmol) followed by reacting in Parr shaker for 4 hours at 50 PSI. Reaction was then filtered over CELITE® and concentrated in vacuo to give Intermediate 1073D (325 mg, 85% yield). LC-MS Anal. Calc'd. for $C_{22}H_{36}N_2O_2$, 360.53, found [M+H] 361.5. $T_r$=0.88 min (Method A).

Example 1073 3-(4-(Cyclohexyl(isobutyl)amino)-3-(4-ethoxybenzamido)phenyl)pentanoic acid (racemic)

Intermediate 1073D (35 mg, 0.097 mmol) was dissolved in DMF (485 μl). 4-Ethoxybenzoic acid (22.58 mg, 0.136 mmol) was added followed by triethylamine (40.6 μl, 0.291 mmol) and BOP (51.5 mg, 0.116 mmol). The reaction was allowed to stir at 50° C. overnight. The reaction was diluted with water (0.5 mL) and methanol (0.25 mL) and LiOH (23.25 mg, 0.971 mmol) was added. Reaction stirred 1 hour at room temperature. After 1 hour, the reaction was diluted with 1N HCl and extracted with EtOAc three times. The combined organics were washed with water twice, and then ½ saturated aq. NaCl solution followed by sat. NaHCO₃ solution. The organics were dried with sodium sulfate, filtered, and concentrated in vacuo to give crude product. The crude residue was purified via preparative HPLC to give Example 1073 (11.6 mg, 0.023 mmol, 24.16% yield). LC-MS Anal. Calc'd. for $C_{30}H_{42}N_2O_4$, 494.31, found [M+H] 495.6. $T_r$=1.10 min (Method A). $^1$H NMR (500 MHz, DMSO-d$_6$) δ: 9.56 (s, 1H), 8.25 (s, 1H), 7.80 (d, J=8.7 Hz, 2H), 7.25 (d, J=8.2 Hz, 1H), 7.10 (d, J=8.7 Hz, 2H), 6.92 (d, J=8.0 Hz, 1H), 4.11 (q, J=7.0 Hz, 2H), 2.77-2.92 (m, 3H), 2.50 (m, 3H), 1.76 (d, J=11.0 Hz, 2H), 1.59-1.72 (m, 3H), 1.44-1.59 (m, 2H), 1.35 (t, J=6.9 Hz, 3H), 1.19-1.32 (m, 4H), 1.08 (q, J=12.4 Hz, 2H), 0.99 (t, J=12.5 Hz, 1H), 0.80 (d, J=6.6 Hz, 6H), 0.73 (t, J=7.2 Hz, 3H).

Example 1074 3-(4-(Cyclohexyl(isobutyl)amino)-3-(4-phenoxybenzamido)phenyl)pentanoic acid (racemic)

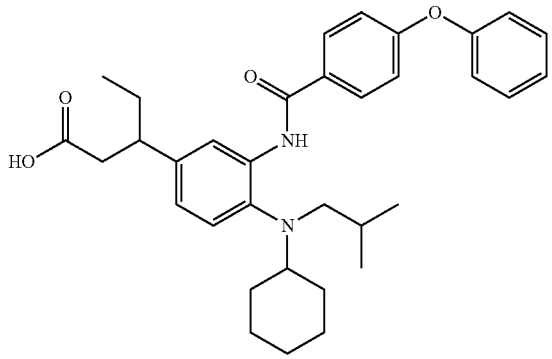 [SMILES: CCC(CC(=O)O)c1ccc(N(CC(C)C)C2CCCCC2)c(NC(=O)c2ccc(Oc3ccccc3)cc2)c1]

Example 1074 was made from Intermediate 1073D and 4-phenoxybenzoic acid following the procedure in Example 1073. LC-MS Anal. Calc'd. for $C_{34}H_{42}N_2O_5$ 542.31, found [M+H] 543.5. $T_r$=1.18 min (Method A). $^1$H NMR (500 MHz, DMSO-d$_6$) δ: 9.60 (s, 1H), 8.24 (s, 1H), 7.87 (d, J=8.7 Hz, 2H), 7.47 (t, J=7.9 Hz, 2H), 7.22-7.28 (m, 2H), 7.14 (dd, J=8.4, 2.9 Hz, 4H), 6.94 (d, J=6.8 Hz, 1H), 2.76-2.91 (m, 3H), 2.50 (m, 3H), 1.75 (d, J=11.0 Hz, 2H), 1.59-1.70 (m, 3H), 1.42-1.59 (m, 2H), 1.17-1.36 (m, 3H), 1.08 (q, J=12.5 Hz, 2H), 0.98 (t, J=12.4 Hz, 1H), 0.79 (d, J=6.6 Hz, 6H), 0.73 (t, J=7.3 Hz, 3H).

Example 1075 3-(4-(Cyclohexyl(isobutyl)amino)-3-(2,2-difluoro-2-(p-tolyl)acetamido)phenyl)pentanoic acid (racemic)

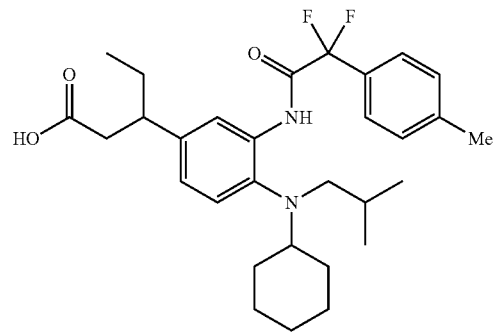 [SMILES: CCC(CC(=O)O)c1ccc(N(CC(C)C)C2CCCCC2)c(NC(=O)C(F)(F)c2ccc(C)cc2)c1]

Example 1075 was made from Intermediate 1073D and 2,2-difluoro-2-(p-tolyl)acetic acid following the procedure in Example 1073. LC-MS Anal. Calc'd. for $C_{30}H_{40}F_2N_2O_3$, 514.30, found [M+H] 515.6. $T_r$=1.32 min (Method A). $^1$H NMR (500 MHz, DMSO-d$_6$) δ: 9.81 (s, 1H), 8.07 (s, 1H), 7.51 (d, J=8.1 Hz, 2H), 7.38 (d, J=7.9 Hz, 2H), 7.30 (d, J=8.2 Hz, 1H), 7.01 (d, J=7.0 Hz, 1H), 2.73-2.90 (m, 2H), 2.50 (m, 6H), 1.57-1.75 (m, 5H), 1.39-1.54 (m, 2H), 1.12-1.25 (m, 4H), 1.07 (q, J=12.4 Hz, 2H), 0.98 (t, J=12.3 Hz, 1H), 0.77 (d, J=6.6 Hz, 6H), 0.69 (t, J=7.3 Hz, 3H).

Example 1075 Enantiomer 1 and Enantiomer 2

Chiral separation of the racemic sample (Method F) gave Enantiomer 1 $T_r$=7.17 min (Method G) and Enantiomer 2 $T_r$=7.68 min (Method Y) Absolute stereochemistry was not determined.

Example 1075 Enantiomer 1: LC-MS Anal. Calc'd. for $C_{30}H_{40}F_2N_2O_3$ 514.30, found [M+H] 515.5. $T_r$=2.691 min (Method B). $^1$H NMR (500 MHz, DMSO-d$_6$) δ: 9.81 (s, 1H), 8.07 (s, 1H), 7.51 (d, J=8.1 Hz, 2H), 7.38 (d, J=7.9 Hz, 2H), 7.30 (d, J=8.2 Hz, 1H), 7.01 (d, J=7.0 Hz, 1H), 2.73-2.90 (m, 2H), 2.50 (m, 6H), 1.57-1.75 (m, 5H), 1.39-1.54 (m, 2H), 1.12-1.25 (m, 4H), 1.07 (q, J=12.4 Hz, 2H), 0.98 (t, J=12.3 Hz, 1H), 0.77 (d, J=6.6 Hz, 6H), 0.69 (t, J=7.3 Hz, 3H)

Example 1075 Enantiomer 2: LC-MS Anal. Calc'd. for $C_{30}H_{40}F_2N_2O_3$ 514.30, found [M+H] 515.4. $T_r$=2.682 min (Method B). $^1$H NMR (500 MHz, DMSO-d$_6$) δ: 9.81 (s, 1H), 8.07 (s, 1H), 7.51 (d, J=8.1 Hz, 2H), 7.38 (d, J=7.9 Hz, 2H), 7.30 (d, J=8.2 Hz, 1H), 7.01 (d, J=7.0 Hz, 1H), 2.73-2.90 (m, 2H), 2.50 (m, 6H), 1.57-1.75 (m, 5H), 1.39-1.54 (m, 2H), 1.12-1.25 (m, 4H), 1.07 (q, J=12.4 Hz, 2H), 0.98 (t, J=12.3 Hz, 1H), 0.77 (d, J=6.6 Hz, 6H), 0.69 (t, J=7.3 Hz, 3H).

Example 1076

3-(3-((2-Ethoxypyrimidin-5-yl)amino)-4-(ethyl(tetrahydro-2H-pyran-4-yl)amino)phenyl)-N-(methylsulfonyl)pentanamide (Homochiral)

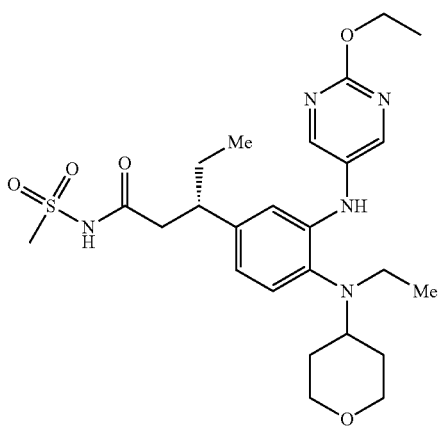 [SMILES: CCOc1ncc(Nc2cc([C@@H](CC)CC(=O)NS(C)(=O)=O)ccc2N(CC)C2CCOCC2)cn1]

Example 455 (40 mg, 0.090 mmol) was dissolved in THF (452 μl) and CDI (21.98 mg, 0.136 mmol) was added. The mixture was heated to reflux for 1 hour. After 1 hour, the resulting solution was added to a solution of methanesulfonamide (12.90 mg, 0.136 mmol) in THF (452 μl) and then DBU (21.80 μl, 0.145 mmol) was added. The reaction was allowed to stir at room temperature. After 3 hours, another portion of methanesulfonamide and DBU was added. After stirring an additional 16 hours, the reaction was diluted with EtOAc. Organics were washed with 1N HCl, concentrated in vacuo, dissolved in DMF, filtered and purified via HPLC to give Example 1076 (18.9 mg, 34 mmol, 38% yield). LC-MS Anal. Calc'd. for $C_{25}H_{37}N_5O_5S$, 519.25, found [M+H] 520.3. $T_r$=0.69 min (Method A). $^1$H NMR (500 MHz, DMSO-d$_6$) δ: 8.43 (s, 2H), 7.34 (s, 1H), 7.11 (d, J=8.0 Hz, 1H), 6.78 (s, 1H), 6.65 (d, J=8.0 Hz, 1H), 4.30 (q, J=7.0 Hz, 2H), 3.80 (d, J=9.7 Hz, 2H), 3.41 (br. s., 1H), 3.20 (t, J=11.5 Hz, 2H), 3.02 (s, 3H), 2.90-3.00 (m, 2H), 2.76-2.87 (m, 1H), 2.52-2.59 (m, 2H), 2.40-2.49 (m, 1H), 1.66 (d, J=11.4 Hz, 2H), 1.51-1.62 (m, 1H), 1.35-1.51 (m, 3H), 1.32 (t, J=7.0 Hz, 3H), 0.81 (t, J=6.9 Hz, 3H), 0.70 (t, J=7.2 Hz, 3H)

Example 1077

3-(3-((4-Cyanophenyl)amino)-4-(ethyl(tetrahydro-2H-pyran-4-yl)amino)phenyl)-4-methoxy-N-(methylsulfonyl)butanamide (Homochiral)

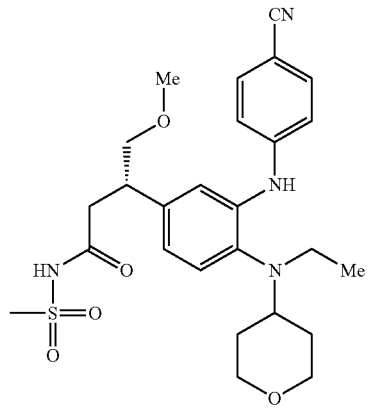 [SMILES: CCN(c1ccc([C@@H](COC)CC(=O)NS(C)(=O)=O)cc1Nc1ccc(C#N)cc1)C1CCOCC1]

Example 1077 was synthesized following the same procedure used to make Example 1076 except Example 349 was used as starting material. LC-MS Anal. Calc'd. for $C_{26}H_{34}N_4O_5S$, 514.23, found [M+H] 515.3. $T_r$=0.64 min (Method A). $^1$H NMR (500 MHz, DMSO-d$_6$) δ: 7.95 (s, 1H), 7.56 (d, J=8.6 Hz, 2H), 7.16 (d, J=7.1 Hz, 1H), 7.07-7.14 (m, 2H), 6.91 (d, J=8.2 Hz, 1H), 3.76 (d, J=8.8 Hz, 2H), 3.41-3.51 (m, 1H), 3.23 (s, 2H), 3.01-3.12 (m, 5H), 2.90-3.01 (m, 4H), 2.89 (s, 1H), 2.73 (s, 1H), 2.67 (dd, J=15.4, 6.7 Hz, 1H), 2.51-2.59 (m, 3H), 1.55 (d, J=11.3 Hz, 2H), 1.35-1.49 (m, 2H), 0.81 (t, J=6.9 Hz, 3H)

Example 1078

3-(3-((2-Ethoxypyrimidin-5-yl)amino)-4-(ethyl(tetrahydro-2H-pyran-4-yl)amino)phenyl)-N-(methylsulfonyl)pentanamide (Homochiral)

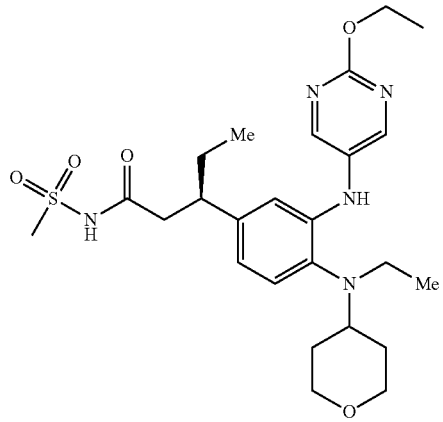 [SMILES: CCOc1ncc(Nc2cc([C@H](CC)CC(=O)NS(C)(=O)=O)ccc2N(CC)C2CCOCC2)cn1]

Example 1078 was synthesized following the same procedure used to make Example 1076 except Example 498 was used as starting material. LC-MS Anal. Calc'd. for $C_{25}H_{37}N_5O_5S$, 519.25, found [M+H] 520.3. $T_r$=0.69 min (Method A). $^1$H NMR (500 MHz, DMSO-d$_6$) δ: 8.43 (s, 2H), 7.34 (s, 1H), 7.11 (d, J=8.0 Hz, 1H), 6.78 (s, 1H), 6.65 (d, J=8.0 Hz, 1H), 4.30 (q, J=7.0 Hz, 2H), 3.80 (d, J=9.7 Hz, 2H), 3.41 (br. s., 1H), 3.20 (t, J=11.5 Hz, 2H), 3.02 (s, 3H), 2.90-3.00 (m, 2H), 2.76-2.87 (m, 1H), 2.52-2.59 (m, 2H), 2.40-2.49 (m, 1H), 1.66 (d, J=11.4 Hz, 2H), 1.51-1.62 (m, 1H), 1.35-1.51 (m, 3H), 1.32 (t, J=7.0 Hz, 3H), 0.81 (t, J=6.9 Hz, 3H), 0.70 (t, J=7.2 Hz, 3H).

Example 1079

(+/−)-3-(4-(Cyclohexyl(isopentyl)amino)-3-(2-(p-tolyl)acetamido)phenyl)pentanoic acid

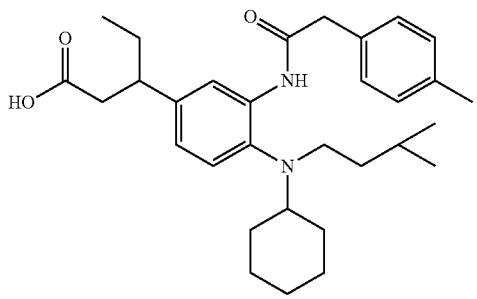 [SMILES: CCC(CC(=O)O)c1ccc(N(CCC(C)C)C2CCCCC2)c(NC(=O)Cc2ccc(C)cc2)c1]

1079A. N-Isopentylcyclohexanamine

A stirred, cooled (−10° C.) solution of cyclohexanamine (5.45 g, 55.0 mmol) and triethylamine (8.36 ml, 60.0 mmol) in THF (30 ml) was treated with 3-methylbutanoyl chloride (6.10 ml, 50 mmol) over 5 min. Additional THF, ~20 mL was introduced to make stirring easier, and the mixture was warmed to RT. The reaction was quenched with water, diluted with 1:1 EtOAc-hexane, and washed twice with 10% aq. HOAc. The org. phase was then washed twice with sat. aq. sodium bicarbonate, dried, and stripped to afford a white solid. This material was dissolved in 40 mL of THF and placed under nitrogen. The solution was treated with lithium aluminum hydride (2.85 g, 75 mmol), carefully brought to reflux, and stirred for two days. The reaction was cooled to RT and stirred two days longer. The reaction was then cooled to 0° C. and carefully quenched by the method of Fieser. A significant amount (~80 mL) of THF was added during the quench to assist with stirring. After stirring briefly at RT, MgSO$_4$ was added, and stirring was continued for 1 h longer. The resulting slurry was filtered (ether rinse), and the filtrate was concentrated under reduced pressure to afford N-isopentylcyclohexanamine (6.7 g, 79% yield) as a colorless oil. MS(ES): m/z=170 [M+H]$^+$, T$_r$=1.34 min (Method A).

1079B. 4-Bromo-N-cyclohexyl-N-isopentyl-2-nitroaniline

A solution of 4-bromo-1-fluoro-2-nitrobenzene (1.5 g, 6.82 mmol) and N-isopentylcyclohexanamine (2.309 g, 13.64 mmol) in NMP (2 mL) was treated with DIEA (1.429 mL, 8.18 mmol) and placed under nitrogen. This solution was heated at 125° C. for 3 h then cooled to RT. The reaction was diluted with 1:1 EtOAc-hexane and washed with 5% aq. HOAc then sat. aq. sodium bicarbonate. The org. phase was dried and stripped to afford an orange oil. Purification by ISCO chromatography afforded 4-bromo-N-cyclohexyl-N-isopentyl-2-nitroaniline (2.03 g, 81% yield) as an orange oil.

$^1$H NMR (400 MHz, DMSO-d$_6$) δ 7.97 (d, J=2.4 Hz, 1H), 7.69 (dd, J=8.8, 2.6 Hz, 1H), 7.37 (d, J=8.8 Hz, H), 3.06 (t, J=7.4 Hz, 2H), 2.79-2.88 (m, 1H), 1.03-1.75 (m, 13H), 0.81 (d, J=6.6 Hz, 6H).

1079C. N-Cyclohexyl-4-(5,5-dimethyl-1,3,2-dioxaborinan-2-yl)-N-isopentyl-2-nitroaniline A suspension of 4-bromo-N-cyclohexyl-N-isopentyl-2-nitroaniline (1.9 g, 5.14 mmol) and 5,5,5',5'-tetramethyl-2,2'-bi(1,3,2-dioxaborinane) (1.395 g, 6.17 mmol) and potassium acetate (1.515 g, 15.43 mmol) in degassed DMSO (10 mL) was treated with PdCl$_2$ (dppf).CH$_2$Cl$_2$ Adduct (0.126 g, 0.154 mmol) and placed under nitrogen. This mixture was heated to 85° C. for 2 h then cooled and purified by flash chromatography. Concentration of the appropriate fractions afforded N-cyclohexyl-4-(5,5-dimethyl-1,3,2-dioxaborinan-2-yl)-N-isopentyl-2-nitroaniline (1.89 g, 92% yield) as an orange oil. MS(ES): m/z=335 [M+H]$^+$ for parent boronic acid. T$_r$=1.13 min (Method A).

1079D. (+/−)-Methyl 3-(4-(cyclohexyl(isopentyl)amino)-3-nitrophenyl)pentanoate

A solution of N-cyclohexyl-4-(5,5-dimethyl-1,3,2-dioxaborinan-2-yl)-N-isopentyl-2-nitroaniline (0.805 g, 2 mmol) and (E)-methyl pent-2-enoate (0.685 g, 6.00 mmol) in degassed dioxane (6 mL) was charged with aq. sodium hydroxide (1.900 mL, 1.900 mmol) followed by chloro(1,5-cyclooctadiene)rhodium(I) dimer (0.039 g, 0.080 mmol). This solution was placed under nitrogen and warmed to 50° C. for 3 h. The reaction was cooled to RT and stirred ON. The reaction was neutralized with 0.25 mL of glacial HOAc and applied to a silica gel column which had been equilibrated with 5% EtOAc-hexane. The product was eluted with a gradient of up to 15% EtOAc-hexane. Concentration of the appropriate fractions afforded methyl 3-(4-(cyclohexyl(isopentyl)amino)-3-nitrophenyl)pentanoate (0.65 g, 80% yield) as an orange oil. MS(ES): m/z=405 [M+H]$^+$. T$_r$=1.28 min (Method A).

1079E. (+/−)-Methyl 3-(3-amino-4-(cyclohexyl(isopentyl)amino)phenyl)pentanoate

A solution of methyl 3-(4-(cyclohexyl(isopentyl)amino)-3-nitrophenyl)pentanoate (0.405 g, 1 mmol) in ethyl acetate (15 mL) was placed under nitrogen and treated with palladium on carbon (0.213 g, 0.200 mmol). This mixture was hydrogenated at 50 psi for 2 h then treated with MgSO$_4$, filtered, and concentrated under a stream of nitrogen to afford methyl 3-(3-amino-4-(cyclohexyl(isopentyl)amino)phenyl)pentanoate (0.35 g, 94% yield) as a colorless oil. MS(ES): m/z=375 [M+H]$^+$. T$_r$=0.94 min (Method A).

Example 1079 (+/−)-3-(4-(Cyclohexyl(isopentyl)amino)-3-(2-(p-tolyl)acetamido)phenyl)pentanoic acid A solution of methyl 3-(3-amino-4-(cyclohexyl(isopentyl)amino)phenyl)pentanoate (0.056 g, 0.15 mmol) and N-methylmorpholine (0.033 mL, 0.3 mmol) in THF (0.3 mL) was treated with 2-(p-tolyl)acetic acid (0.027 g, 0.180 mmol) followed by BOP (0.08 g, 0.18 mmol). This solution was stirred 1 h at RT then treated with lithium hydroxide (0.018 g, 0.750 mmol) in 0.3 mL of water. Methanol, ~0.3 mL was added to give a single phase, and the resulting solution was stirred 1 h at 50° C. Most of the solvent was removed under a stream of THF, and the reaction was treated with 0.1 mL of glacial HOAc, dissolved in DMF, and purified by prep HPLC. Concentration of the appropriate fractions afforded (+/−)-3-(4-(cyclohexyl(isopentyl)amino)-3-(2-(p-tolyl)acetamido)phenyl)pentanoic acid (0.049 g, 66% yield). $^1$H NMR (400 MHz, DMSO-$d_6$) δ 8.80 (s, 1H), 8.20 (d, J=1.4 Hz, 1H), 7.26 (d, J=7.8 Hz, 2H), 7.21 (d, J=7.8 Hz, 2H), 7.10 (d, J=8.1 Hz, 1H), 6.85 (dd, J=8.1, 1.5 Hz, 1H), 2.78-2.85 (m, 1H), 2.67 (t, J=7.6 Hz, 2H), 2.49-2.56 (m, integration distorted by solvent peak), 2.36-2.44 (m, 3H), 2.32 (s, 3H), 0.78-1.65 (m, 15H), 0.75 (d, J=6.7 Hz, 6H), 0.69 (t, J=7.3 Hz, 3H). MS(ES): m/z=493 [M+H]$^+$. $T_r$=2.60 min (Method B).

Example 1080

(+/−)-3-(4-(Cyclohexyl(isobutyl)amino)-3-fluoro-5-(2-(p-tolyl)acetamido)phenyl)pentanoic acid

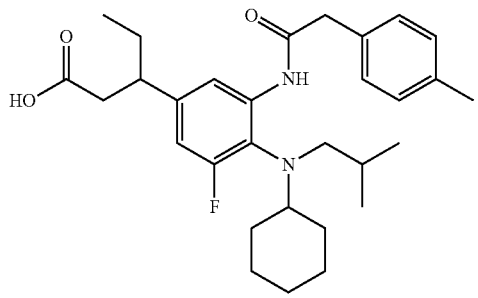 [SMILES: CCC(CC(=O)O)c1cc(F)c(N(CC(C)C)C2CCCCC2)c(NC(=O)Cc2ccc(C)cc2)c1]

1080A. 4-Bromo-N-cyclohexyl-2-fluoro-N-isobutyl-6-nitroaniline

A solution of 5-bromo-1,2-difluoro-3-nitrobenzene (0.5 g, 2.101 mmol) and N-isobutylcyclohexanamine (0.979 g, 6.30 mmol) was placed under nitrogen and heated at 130° C. for 2.5 h. The reaction was then cooled to RT and purified by flash chromatography. Concentration of the appropriate fractions afforded 4-bromo-N-cyclohexyl-2-fluoro-N-isobutyl-6-nitroaniline (0.56 g, 71% yield) as an orange oil. MS(ES): m/z=373 [M+H]$^+$. $T_r$=1.39 min (Method A).

1080B. N-Cyclohexyl-4-(5,5-dimethyl-1,3,2-dioxaborinan-2-yl)-2-fluoro-N-isobutyl-6-nitroaniline A solution of 5,5,5',5'-tetramethyl-2,2'-bi(1,3,2-dioxaborinane) (0.385 g, 1.707 mmol) and 4-bromo-N-cyclohexyl-2-fluoro-N-isobutyl-6-nitroaniline (0.49 g, 1.313 mmol) and potassium acetate (0.387 g, 3.94 mmol) in degassed DMSO (1.875 ml) was treated with 1,1'-bis(diphenylphosphino)ferrocenedichloro palladium(II) dichloromethane complex (0.048 g, 0.066 mmol). This dark solution was placed under nitrogen and heated to 80° C. for 1 h then cooled to RT and purified by flash chromatography. Concentration of the appropriate fractions afforded N-cyclohexyl-4-(5,5-dimethyl-1,3,2-dioxaborinan-2-yl)-2-fluoro-N-isobutyl-6-nitroaniline (0.48 g, 90% yield) as an orange oil. MS(ES): m/z=339 [M+H]$^+$ for parent boronic acid. $T_r$=1.17 min (Method A).

1080C. (+/−)-Methyl 3-(4-(cyclohexyl(isobutyl)amino)-3-fluoro-5-nitrophenyl)pentanoate A reaction vial was charged with N-cyclohexyl-4-(5,5-dimethyl-1,3,2-dioxaborinan-2-yl)- 2-fluoro-N-isobutyl-6-nitroaniline (0.46 g, 1.132 mmol). The SM was dissolved in dioxane (10 mL), and (E)-methyl pent-2-enoate (0.517 g, 4.53 mmol) was added followed by sodium hydroxide (1.02 ml, 1.02 mmol). The sample was degassed by freezing under vacuum then thawing under nitrogen twice. This mixture was treated with chloro(1,5-cyclooctadiene)rhodium(I) dimer (0.039 g, 0.079 mmol) and the freeze/thaw purge cycle was repeated. The reaction was stirred 2.5 h at 50° C., after which time LCMS indicates that no SM remained. The reaction was treated with acetic acid (0.130 ml, 2.264 mmol) then applied to a flash column and eluted with 5-15% EtOAc-hexane. Concentration of the appropriate fractions afforded (+/−)-methyl 3-(4-(cyclohexyl(isobutyl)amino)-3-fluoro-5-nitrophenyl)pentanoate (0.34 g, 74% yield) as an orange oil. MS(ES): m/z=410 [M+H]$^+$. $T_r$=1.34 min (Method A).

1080D. (+/−)-Methyl 3-(3-amino-4-(cyclohexyl(isobutyl)amino)-5-fluorophenyl)pentanoate A rapidly-stirred solution of methyl 3-(4-(cyclohexyl(isobutyl)amino)-3-fluoro-5-nitrophenyl)pentanoate (0.33 g, 0.808 mmol) in ethanol (6 mL)-THF (2 mL) was treated simultaneously with zinc (0.528 g, 8.08 mmol) and a solution of ammonium chloride (0.432 g, 8.08 mmol) in 1 mL of water. This mixture was stirred 30 min. at RT then diluted with dichloromethane and treated with ~3 g of MgSO$_4$. The resulting slurry was filtered, and the filtrate was concentrated under a stream of nitrogen. NMR and LCMS indicate that this material is mostly the under-reduced hydroxylamine derivative of the desired aniline. It was taken up in 10 mL of EtOAc and transferred into a small Parr vessel. This vessel was charged with 0.16 g of 10% Pd/C and hydrogenated at ~45 psi for 3 h. LCMS indicates that very little additional reduction is occurring, so the mixture was treated with a little MgSO$_4$, filtered, and concentrated. The residue was re-subjected to the original dissolving metal reduction conditions in EtOH (no THF) and worked up as before. LCMS now shows that reduction to the desired aniline is complete. Flash chromatography (EtOAc-hexanes) afforded methyl 3-(3-amino-4-(cyclohexyl(isobutyl)amino)-5-fluorophenyl)pentanoate (0.162 g, 53% yield) as a colorless oil. MS(ES): m/z=379 [M+H]$^+$. $T_r$=1.21 min (Method A).

Example 1080 (+/−)-3-(4-(Cyclohexyl(isobutyl)amino)-3-fluoro-5-(2-(p-tolyl)acetamido)phenyl)pentanoic acid A solution of methyl 3-(3-amino-4-(cyclohexyl(isobutyl)amino)-5-fluorophenyl)pentanoate (0.05 g, 0.132 mmol) and 2-(p-tolyl)acetic acid (0.026 g, 0.172 mmol) and triethylamine (0.033 mL, 0.238 mmol) in THF (0.5 mL) was treated with BOP (0.076 g, 0.172 mmol). The reaction was stirred 1 h at RT. The reaction was then treated with lithium hydroxide (0.025 g, 1.057 mmol) in 0.3 mL of water. Methanol, 0.5 mL was added to give a single phase, and the reaction was stirred 1 h at 50° C. The reaction was cooled to ambient temperature, quenched with 0.1 mL of glacial HOAc, diluted to 2 mL with DMF, and purified by prep HPLC. Concentration of the appropriate fractions afforded (+/−)-3-(4-(cyclohexyl(isobutyl)amino)-3-fluoro-5-(2-(p-tolyl)acetamido)phenyl)pentanoic acid (0.050 g, 76% yield). $^1$H NMR (400 MHz, DMSO-$d_6$) δ 8.70 (s, 1H), 8.10 (s, 1H), 7.25 (d, J=7.9 Hz, 2H), 7.21 (d, J=7.8 Hz, 2H), 6.74 (d, J=12.9 Hz, 1H), 2.39-2.85 (m, integration distorted by solvent peak), 2.31 (s, 3H), 1.41-1.73 (m, 7H), 0.90-1.20 (m, 6H), 0.66-0.75 (m, 9H). MS(ES): m/z=497 [M+H]$^+$. T$_r$=2.67 min (Method B).

Further compounds of the invention I (Table 1) were prepared as shown in Scheme 12. Accordingly, amines JM Intermediate 1 were coupled with phenylacetic acids R$_4$CH$_2$CO$_2$H using BOP and Et$_3$N in THF. The resulting esters were saponified in situ with aqueous LiOH, and the products were purified by prep HPLC. The procedure followed was that used for the conversion of 1079E into Example 1079. The Examples in this table are all racemic.

Scheme 12

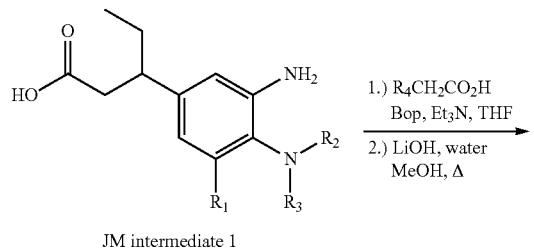

JM intermediate 1

TABLE 1

TABLE 1-continued

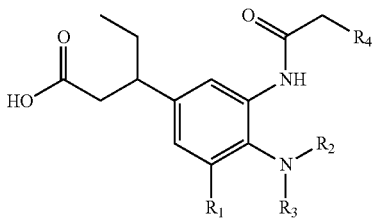

| Ex. No. | R$_1$ | R$_2$ | R$_3$ | R$_4$ | m/z | T$_R$ (min, Method B) |
|---|---|---|---|---|---|---|
| 1081 | F | isobutyl | isobutyl | 4-Cl, 2-F-phenyl | 509 | 2.41 |
| 1082 | F | isobutyl | isobutyl | 2,4-diF-phenyl | 493 | 2.41 |
| 1083 | F | isobutyl | isobutyl | 2-F, 4-Me-phenyl | 489 | 2.51 |
| 1084 | H | isobutyl | cyclohexyl | 4-Me-phenyl | 479 | 2.62 |
| 1085 | H | isobutyl | cyclohexyl | 2-F, 4-Cl-phenyl | 517 | 2.53 |
| 1086 | H | isobutyl | cyclohexyl | 4-CN-phenyl | 490 | 2.26 |
| 1087 | H | isobutyl | cyclohexyl | 2,5-diF-phenyl | 501 | 2.44 |
| 1088 | H | isopentyl | cyclohexyl | 2-F, 4-Cl-phenyl | 531 | 2.75 |
| 1089 | H | isopentyl | cyclohexyl | 4-F-phenyl | 497 | 2.45 |

Further compounds of the invention I (Table 2) were prepared as shown in Scheme 13. Accordingly, amine JM Intermediate 1 was coupled with isocyanates $R_4NCO$ in THF, and upon complete reaction any excess isocyanate was quenched with N,N-dimethylethylenediamine. The resulting esters were saponified in situ with aqueous LiOH, and the products were purified by prep HPLC. The procedure followed was that used for the conversion of Example 970D into Example 970. The Examples in this table are all racemic.

Scheme 13

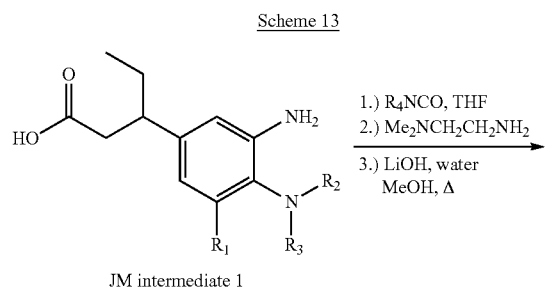

JM intermediate 1

1.) $R_4NCO$, THF
2.) $Me_2NCH_2CH_2NH_2$
3.) LiOH, water MeOH, Δ

I

TABLE 2

| Ex. No. | $R_1$ | $R_2$ | $R_3$ | $R_4$ | m/z | $T_R$ (min, Method B) |
|---|---|---|---|---|---|---|
| 1090 | F | isobutyl | cyclohexyl | (2-F, 4-Cl phenyl) | 526 | 2.47 |
| 1091 | F | isobutyl | cyclohexyl | (4-methylphenyl) | 498 | 2.43 |

Racemic compounds of the invention I could be resolved into their component enantiomers E1 and E2 by chiral SFC as shown in Scheme 14. Table 3 lists these examples along with the preparative conditions under which they were resolved and the analytical conditions under which they were characterized. In all cases, E1 and E2 are homochiral with undetermined absolute stereochemistry.

Scheme 14

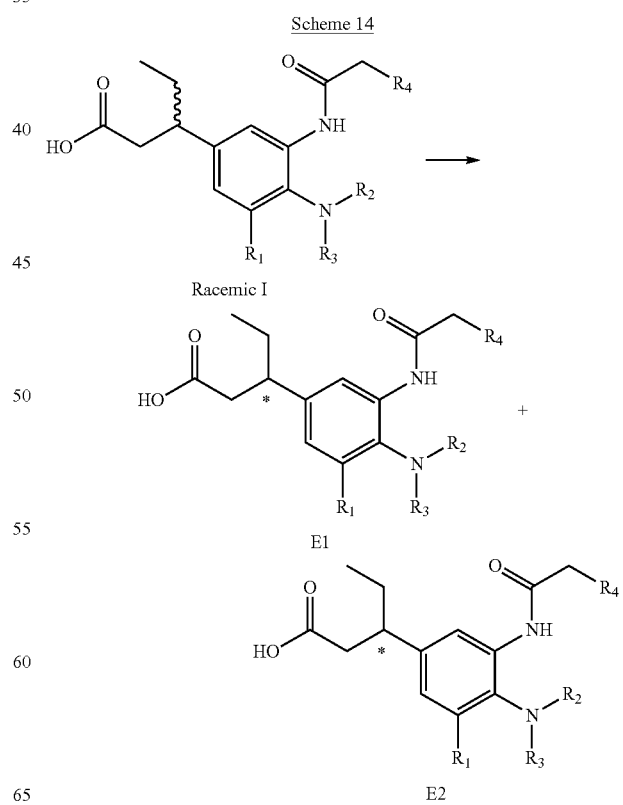

Racemic I

E1

E2

TABLE 3

| Ex. No. | R$_1$ | R$_2$ | R$_3$ | R$_4$ | m/z | Prep/Anal. Method | Anal. T$_R$ |
|---|---|---|---|---|---|---|---|
| 1092E1 | F | isobutyl | isobutyl | 2-F,4-Cl-phenyl | 509 | H/DU | 7.30 |
| 1092E2 | F | isobutyl | isobutyl | 2-F,4-Cl-phenyl | 509 | H/DU | 8.30 |
| 1093E1 | F | isobutyl | isobutyl | 2,4-diF-phenyl | 493 | I/DV | 5.2 |
| 1093E2 | F | isobutyl | isobutyl | 2,4-diF-phenyl | 493 | I/DV | 5.9 |
| 1094E1 | F | isobutyl | isobutyl | 2-F,4-Me-phenyl | 489 | J/DV | 7.77 |
| 1094E2 | F | isobutyl | isobutyl | 2-F,4-Me-phenyl | 489 | J/DV | 8.02 |
| 1095E1 | H | isobutyl | cyclohexyl | 4-Me-phenyl | 479 | K/DW | 11.2 |
| 1095E2 | H | isobutyl | cyclohexyl | 4-Me-phenyl | 479 | K/DW | 12.4 |
| 1096E1 | H | isobutyl | cyclohexyl | 2-F,4-Cl-phenyl | 517 | K/DW | 10.4 |
| 1096E2 | H | isobutyl | cyclohexyl | 2-F,4-Cl-phenyl | 517 | K/DW | 11.2 |

TABLE 3-continued
| Ex. No. | R₁ | R₂ | R₃ | R₄ | m/z | Prep/Anal. Method | Anal. T$_R$ |
|---|---|---|---|---|---|---|---|
| 1097E1 | H | isobutyl | cyclohexyl | 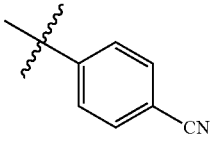 [SMILES: *c1ccc(C#N)cc1] | 490 | K/DW | 17.1 |
| 1097E2 | H | isobutyl | cyclohexyl | 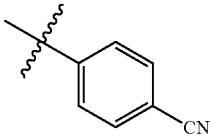 | 490 | K/DW | 18.0 |
| 1098E1 | H | isobutyl | cyclohexyl | 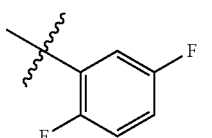 | 501 | K/DW | 7.55 |
| 1098E2 | H | isobutyl | cyclohexyl | 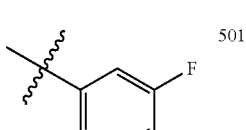 | 501 | K/DW | 8.12 |
| 1099E1 | H | isopentyl | cyclohexyl | 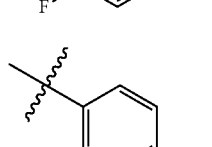 | 493 | L/DY | 7.36 |
| 1099E2 | H | isopentyl | cyclohexyl | 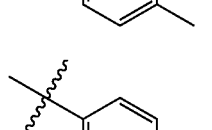 | 493 | L/DY | 7.89 |
| 1100E1 | H | isopentyl | cyclohexyl | 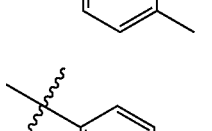 | 497 | M/DX | 12.7 |
| 1100E2 | H | isopentyl | cyclohexyl | 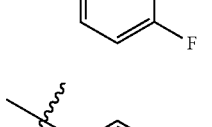 | 497 | M/DX | 13.7 |
| 1101E1 | F | isobutyl | cyclohexyl | 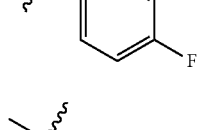 | 497 | K/DW | 7.17 |
| 1101E2 | F | isobutyl | cyclohexyl | 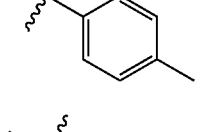 | 497 | K/DW | 7.74 |

Additional racemic compounds of the invention I could be resolved into their component enantiomers E1 and E2 by chiral SFC as shown in Scheme 15. Table 4 lists examples along with the preparative conditions under which they were resolved and the analytical conditions under which they were characterized. In this case, E1 and E2 are homochiral with undetermined absolute stereochemistry.

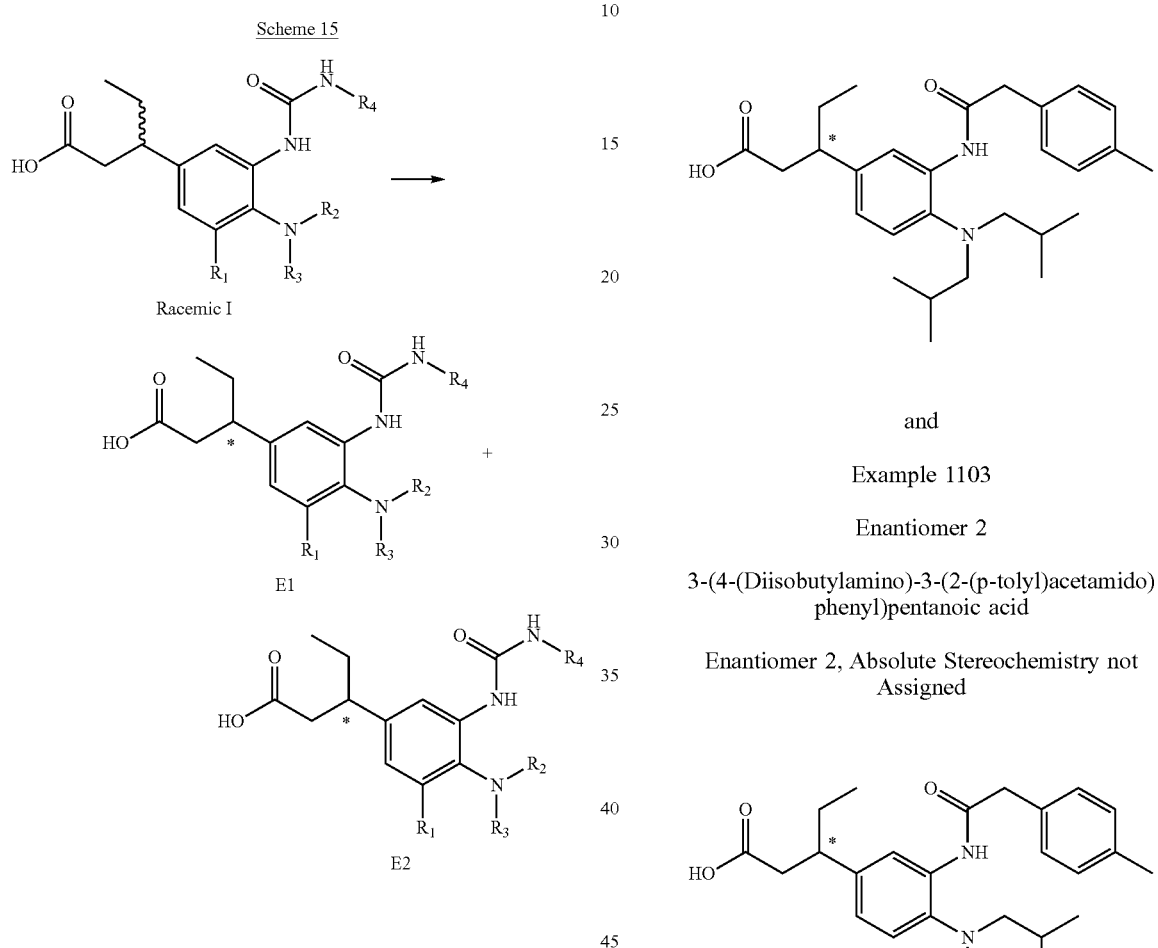

Example 1103

Enantiomer 1

3-(4-(Diisobutylamino)-3-(2-(p-tolyl)acetamido)phenyl)pentanoic acid

Enantiomer 1, Absolute Stereochemistry not Assigned and

Example 1103

Enantiomer 2

3-(4-(Diisobutylamino)-3-(2-(p-tolyl)acetamido)phenyl)pentanoic acid

Enantiomer 2, Absolute Stereochemistry not Assigned

Racemic Example 949, (±)-3-(4-(diisobutylamino)-3-(2-(p-tolyl)acetamido)phenyl)pentanoic acid (52 mg), was purified by chiral SFC (90/10 $CO_2$/MeOH mobile phase, WHELK-O1® (R,R), KROMASIL® 25×3 cm, 5 μm column, 85 ml/min, detector wavelength=220 nm). Concentration of the appropriate (earlier eluting) fractions afforded Example 1103 Enantiomer 1 (18.3 mg) assigned as 3-(4-(diisobutylamino)-3-(2-(p-tolyl)acetamido)phenyl)pentanoic acid (Enantiomer 1). $^1$H NMR (500 MHz, DMSO-$d_6$) δ 8.72 (s, 1H), 8.12 (s, 1H), 7.21-7.12 (m, 5H), 6.87 (d, J=7.8 Hz, 1H), 3.64 (s, 2H), 2.85-2.75 (m, 1H), 2.57-2.47 (m, ~5H (integration distorted by solvent peak)), 2.43-2.35 (m, 1H), 2.27 (s, 3H), 1.65-1.55 (m, 1H), 1.55-1.40 (m, 3H), 0.76 (d, J=6.6 Hz, 12H), 0.68 (t, J=7.2 Hz, 3H). MS(ES): m/z=453 [M+H]$^+$. $T_r$=2.39 min (Method C). Concentration of the later eluting fractions afforded Example 1103 Enantiomer 2 (24.2 mg) assigned as 3-(4-(diisobutylamino)-3-(2-(p-tolyl)

TABLE 4

| Ex. No. | $R_1$ | $R_2$ | $R_3$ | $R_4$ | m/z | Prep/Anal. Method | Anal. $T_R$ |
|---|---|---|---|---|---|---|---|
| 1102E1 | F | iso-butyl | cyclo-hexyl | *p-tolyl* | 498 | DT/DZ | 9.4 |
| 1102E2 | F | iso-butyl | cyclo-hexyl | *p-tolyl* | 498 | DT/DZ | 11.2 | acetamido)phenyl)pentanoic acid (Enantiomer 2). $^1$H NMR (500 MHz, DMSO-d$_6$) δ 8.72 (s, 1H), 8.11 (s, 1H), 7.21-7.12 (m, 5H), 6.87 (d, J=8.1 Hz, 1H), 3.64 (s, 2H), 2.84-2.75 (m, 1H), 2.61-2.47 (m, ~5H (integration distorted by solvent peak)), 2.43-2.35 (m, 1H), 2.27 (s, 3H), 1.65-1.55 (m, 1H), 1.54-1.39 (m, 3H), 0.75 (d, J=6.5 Hz, 12H), 0.67 (t, J=7.2 Hz, 3H). MS(ES): m/z=453 [M+H]$^+$. T$_r$=2.41 min (Method C).

Example 1104

3-(3-(2-(4-Cyanophenyl)acetamido)-4-(diisobutylamino)phenyl)pentanoic acid

Enantiomer 1, Absolute Stereochemistry not Assigned

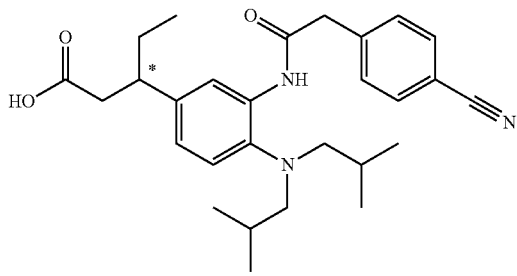 [SMILES: CCC(CC(=O)O)c1ccc(N(CC(C)C)CC(C)C)c(NC(=O)Cc2ccc(C#N)cc2)c1]

and

Example 1105

3-(3-(2-(4-Cyanophenyl)acetamido)-4-(diisobutylamino)phenyl)pentanoic acid

Enantiomer 2, Absolute Stereochemistry not Assigned

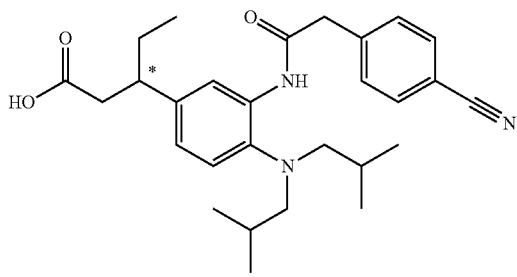 [SMILES: CCC(CC(=O)O)c1ccc(N(CC(C)C)CC(C)C)c(NC(=O)Cc2ccc(C#N)cc2)c1]

Racemic Example 950, (±)-3-(3-(2-(4-cyanophenyl)acetamido)-4-(diisobutylamino)phenyl)pentanoic acid (20 mg), was purified by chiral SFC (85/15 CO$_2$/MeOH mobile phase, Chiral AD-H 25×3 cm, 5 µm column, 85 ml/min, detector wavelength=220 nm). Concentration of the appropriate (earlier eluting) fractions afforded Example 1104 (8.7 mg) assigned as 3-(3-(2-(4-cyanophenyl)acetamido)-4-(diisobutylamino)phenyl)pentanoic acid (Enantiomer 1). $^1$H NMR (500 MHz, DMSO-d$_6$) δ 8.85 (s, 1H), 8.04 (s, 1H), 7.82 (d, J=8.1 Hz, 2H), 7.53 (d, J=8.0 Hz, 2H), 7.20 (d, J=8.2 Hz, 1H), 6.90 (d, J=8.1 Hz, 1H), 3.85 (s, 2H), 2.84-2.75 (m, 1H), 2.58-2.51 (m, ~5H (integration distorted by solvent peak)), 2.43-2.35 (m, 1H), 1.65-1.50 (m, 3H), 1.49-1.39 (m, 1H), 0.79 (d, J=6.5 Hz, 12H), 0.67 (t, J=7.3 Hz, 3H). MS(ES): m/z=464 [M+H]$^+$. T$_r$=2.19 min (Method C). Concentration of the later eluting fractions afforded Example 1105 (8.3 mg) assigned 3-(3-(2-(4-cyanophenyl)acetamido)-4-(diisobutylamino) phenyl)pentanoic acid (Enantiomer 2). $^1$H NMR (500 MHz, DMSO-d$_6$) δ 8.85 (s, 1H), 8.05 (s, 1H), 7.82 (d, J=8.1 Hz, 2H), 7.53 (d, J=8.0 Hz, 2H), 7.20 (d, J=8.2 Hz, 1H), 6.90 (d, J=6.9 Hz, 1H), 3.85 (s, 2H), 2.84-2.76 (m, 1H), 2.58-2.51 (m, ~5H (integration distorted by solvent peak)), 2.43-2.34 (m, 1H), 1.64-1.50 (m, 3H), 1.50-1.40 (m, 1H), 0.80 (d, J=6.6 Hz, 12H), 0.68 (t, J=7.3 Hz, 3H). MS(ES): m/z=464 [M+H]$^+$. T$_r$=2.19 min (Method C).

Example 1106

3-(4-(Cyclohexyl(isobutyl)amino)-2-fluoro-5-(3-(p-tolyl)ureido)phenyl)pentanoic acid Enantiomer 1, Absolute Stereochemistry not Assigned

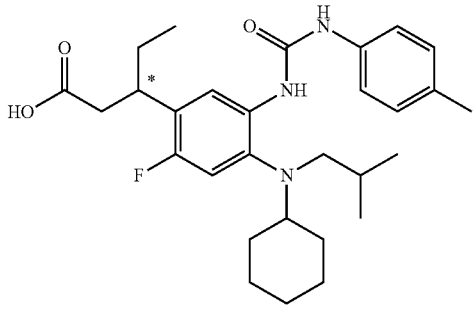 [SMILES: CCC(CC(=O)O)c1cc(NC(=O)Nc2ccc(C)cc2)c(N(CC(C)C)C2CCCCC2)cc1F]

and

Example 1107

3-(4-(Cyclohexyl(isobutyl)amino)-2-fluoro-5-(3-(p-tolyl)ureido)phenyl)pentanoic acid Enantiomer 2, Absolute Stereochemistry not Assigned

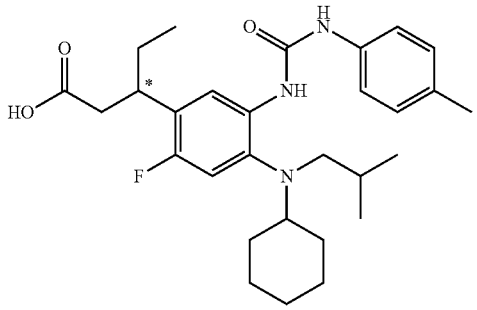 [SMILES: CCC(CC(=O)O)c1cc(NC(=O)Nc2ccc(C)cc2)c(N(CC(C)C)C2CCCCC2)cc1F]

Racemic Example 951, (±)-3-(4-(cyclohexyl(isobutyl)amino)-2-fluoro-5-(3-(p-tolyl)ureido)phenyl)pentanoic acid (29 mg), was purified by chiral SFC (80/20 CO$_2$/MeOH mobile phase, Chiral AD-H 25×3 cm, 5 µm column, 100 ml/min, detector wavelength=220 nm). Concentration of the appropriate (earlier eluting) fractions afforded Example 1106 (10.9 mg) assigned as 3-(4-(cyclohexyl(isobutyl) amino)-2-fluoro-5-(3-(p-tolyl)ureido)phenyl)pentanoic acid (Enantiomer 1). $^1$H NMR (500 MHz, DMSO-$d_6$) δ 9.38 (s, 1H), 7.88 (d, J=8.0 Hz, 1H), 7.77 (s, 1H), 7.35 (d, J=8.2 Hz, 2H), 7.09 (d, J=8.1 Hz, 2H), 6.97 (d, J=11.8 Hz, 1H), 3.20-3.11 (m, 1H), 2.77-2.72 (m, 1H), 2.58-2.54 (m, 3H (integration distorted by solvent peak)), 2.24 (s, 3H), 1.92-1.80 (m, 2H), 1.71-1.59 (m, 3H), 1.53-1.44 (m, 2H), 1.35-1.17 (m, 5H), 1.09-1.00 (m, 2H), 0.82 (d, J=6.4 Hz, 6H), 0.73 (t, J=7.2 Hz, 3H). MS(ES): m/z=498 [M+H]$^+$. $T_r$=2.36 min (Method C). Concentration of the later eluting fractions afforded Example 1107 (10.4 mg) assigned as 3-(4-(cyclohexyl(isobutyl)amino)-2-fluoro-5-(3-(p-tolyl)ureido)phenyl)pentanoic acid (Enantiomer 2). $^1$H NMR (500 MHz, DMSO-$d_6$) δ 9.39 (s, 1H), 7.87 (d, J=8.1 Hz, 1H), 7.78 (s, 1H), 7.35 (d, J=8.0 Hz, 2H), 7.08 (d, J=7.9 Hz, 2H), 6.96 (d, J=11.8 Hz, 1H), 3.21-3.10 (m, 1H), 2.76-2.73 (m, 1H), 2.57-2.54 (m, 3H (integration distorted by solvent peak)), 2.24 (s, 3H), 1.90-1.80 (m, 2H), 1.72-1.60 (m, 3H), 1.54-1.42 (m, 2H), 1.39-1.15 (m, 5H), 1.10-1.00 (m, 2H), 0.82 (d, J=6.3 Hz, 6H), 0.73 (t, J=7.0 Hz, 3H). MS(ES): m/z=498 [M+H]$^+$. $T_r$=2.36 min (Method C).

Example 1108

3-(4-(Cyclohexyl(isobutyl)amino)-5-(3-(4-ethoxyphenyl)ureido)-2-fluorophenyl)pentanoic acid Enantiomer 1, Absolute Stereochemistry not Assigned

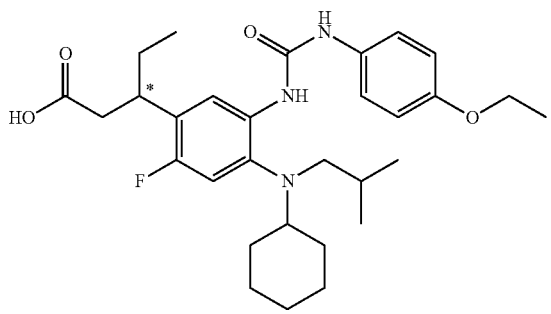 [SMILES: CCOc1ccc(NC(=O)Nc2cc(C(CC)CC(=O)O)c(F)cc2N(CC(C)C)C2CCCCC2)cc1]

and

Example 1109

3-(4-(Cyclohexyl(isobutyl)amino)-5-(3-(4-ethoxyphenyl)ureido)-2-fluorophenyl)pentanoic acid Enantiomer 2, Absolute Stereochemistry not Assigned

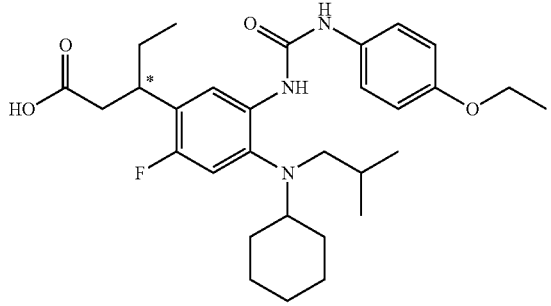 [SMILES: CCOc1ccc(NC(=O)Nc2cc(C(CC)CC(=O)O)c(F)cc2N(CC(C)C)C2CCCCC2)cc1]

Racemic Example 952, (±)-3-(4-(cyclohexyl(isobutyl) amino)-5-(3-(4-ethoxyphenyl)ureido)-2-fluorophenyl)pentanoic acid (37 mg), was purified by chiral SFC (80/20 $CO_2$/MeOH mobile phase, Chiral AD 25×3 cm, 5 μm column, 85 ml/min, detector wavelength=220 nm). Concentration of the appropriate (earlier eluting) fractions afforded Example 1108 (13.4 mg) assigned as 3-(4-(cyclohexyl (isobutyl)amino)-5-(3-(4-ethoxyphenyl)ureido)-2-fluorophenyl)pentanoic acid (Enantiomer 1). $^1$H NMR (500 MHz, DMSO-$d_6$) δ 9.24 (s, 1H), 7.89 (d, J=8.2 Hz, 1H), 7.72 (s, 1H), 7.32 (d, J=8.8 Hz, 2H), 6.96 (d, J=11.9 Hz, 1H), 6.85 (d, J=8.8 Hz, 2H), 3.97 (q, J=6.9 Hz, 2H), 3.25-3.08 (m, 1H), 2.76-2.70 (m, 1H), 2.60-2.50 (m, 5H (integration distorted by solvent peak)), 1.86-1.74 (m, 2H), 1.72-1.58 (m, 3H), 1.57-1.42 (m, 2H), 1.30 (t, J=6.9 Hz, 3H), 1.22-0.99 (m, 5H), 0.80 (d, J=6.5 Hz, 6H), 0.73 (t, J=7.2 Hz, 3H). MS(ES): m/z=528 [M+H]$^+$. $T_r$=2.38 min (Method C). Concentration of the later eluting fractions afforded Example 1109 (13.6 mg) assigned as 3-(4-(cyclohexyl(isobutyl)amino)-5-(3-(4-ethoxyphenyl)ureido)-2-fluorophenyl)pentanoic acid (Enantiomer 2). $^1$H NMR (500 MHz, DMSO-$d_6$) δ 9.24 (s, 1H), 7.89 (d, J=8.2 Hz, 1H), 7.72 (s, 1H), 7.32 (d, J=8.7 Hz, 2H), 6.96 (d, J=11.9 Hz, 1H), 6.85 (d, J=8.8 Hz, 2H), 3.97 (q, J=6.9 Hz, 2H), 3.20-3.08 (m, 1H), 2.74-2.72 (m, 1H), 2.60-2.50 (m, 5H, (integration distorted by solvent peak)), 1.85-1.74 (m, 2H), 1.73-1.58 (m, 3H), 1.54-1.43 (m, 2H), 1.30 (t, J=6.9 Hz, 3H), 1.23-0.98 (m, 5H), 0.80 (d, J=6.4 Hz, 6H), 0.73 (t, J=7.2 Hz, 3H). MS(ES): m/z=528 [M+H]$^+$. $T_r$=2.28 min (Method C).

Example 1110

(±)-3-(5-(3-(Benzo[d][1,3]dioxol-5-yl)ureido)-4-(cyclohexyl(isobutyl)amino)-2-fluorophenyl)pentanoic acid

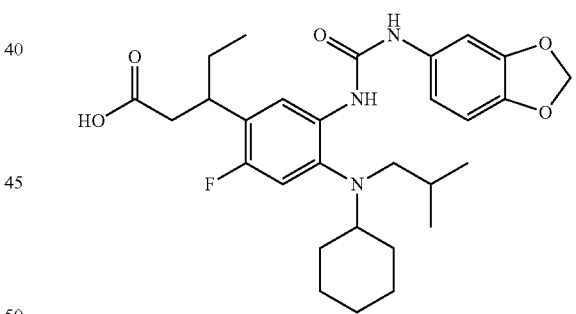

To a homogeneous mixture of (+/−)-methyl 3-(5-amino-4-(cyclohexyl(isobutyl)amino)-2-fluoro-phenyl)pentanoate (compound 951D, 45 mg, 0.12 mmol) in THF (1 mL), at room temperature in a sealable vial, was added 5-isocyanatobenzo[d][1,3]dioxole (33 mg, 0.20 mmol). The resulting mixture was stirred at ambient temperature for 16 hours before MeOH (0.5 mL) was added to the reaction vial followed by LiOH (aq) (1M solution, 0.5 mL, 0.50 mmol). After 6.5 hours, the reaction was treated with acetic acid (0.03 mL, 0.52 mmol). The mixture was then diluted with DMSO then purified by preparative RP HPLC (MeCN/$H_2O$ gradient+10-mM $NH_4OAc$) to afford Example 1110 (46 mg, 73% yield). $^1$H NMR (500 MHz, DMSO-$d_6$) δ 9.32 (s, 1H), 7.86 (d, J=8.2 Hz, 1H), 7.74 (s, 1H), 7.16 (s, 1H), 6.96 (d, J=11.8 Hz, 1H), 6.83 (d, J=8.2 Hz, 1H), 6.75 (dd, J=8.4, 1.7 Hz, 1H), 5.96 (s, 2H), 3.21-3.08 (m, 1H), 2.82-2.61 (m, 2H), 2.60-2.54 (m, 2H), 1.84-1.75 (m, 2H), 1.72-1.58 (m, 3H), 1.54-1.43 (m, 2H), 1.35-0.92 (m, 7H), 0.80 (d, J=6.6 Hz, 6H), 0.73 (t, J=7.3 Hz, 3H). MS(ES): m/z=528 [M+H]+, T$_r$=2.18 min (Method C).

Example 1111

3-(5-(3-(Benzo[d][1,3]dioxol-5-yl)ureido)-4-(cyclohexyl(isobutyl)amino)-2-fluorophenyl)pentanoic acid Enantiomer 1, Absolute Stereochemistry not Assigned

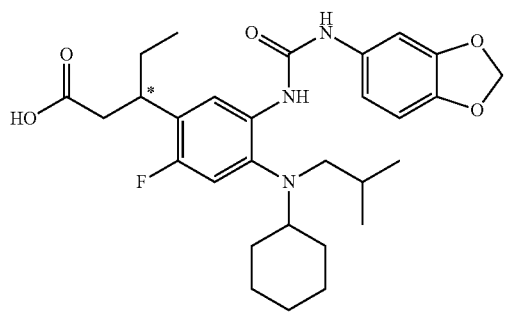 [SMILES: CCC(CC(=O)O)c1cc(NC(=O)Nc2ccc3c(c2)OCO3)c(N(CC(C)C)C2CCCCC2)cc1F]

and

Example 1112

3-(5-(3-(Benzo[d][1,3]dioxol-5-yl)ureido)-4-(cyclohexyl(isobutyl)amino)-2-fluorophenyl)pentanoic acid Enantiomer 2, Absolute Stereochemistry not Assigned

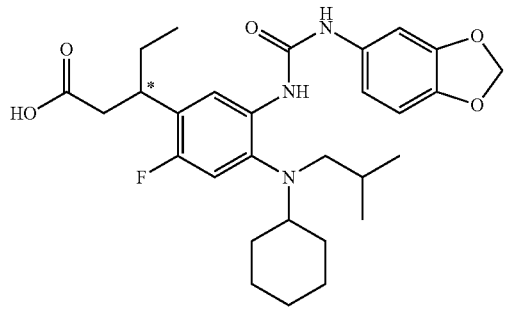 [SMILES: CCC(CC(=O)O)c1cc(NC(=O)Nc2ccc3c(c2)OCO3)c(N(CC(C)C)C2CCCCC2)cc1F]

Racemic mixture Example 1110, (±)-3-(5-(3-(benzo[d][1,3]dioxol-5-yl)ureido)-4-(cyclohexyl(isobutyl)amino)-2-fluorophenyl)pentanoic acid (45 mg), was purified by chiral SFC (80/20 CO$_2$/[1:1 MeOH:ACN] mobile phase, Chiral AD-H 25×3 cm, 5 μm column, 85 ml/min, detector wavelength=220 nm). Concentration of the appropriate (earlier eluting) fractions afforded Example 1111 (11.4 mg) assigned as 3-(5-(3-(benzo[d][1,3]dioxol-5-yl)ureido)-4-(cyclohexyl(isobutyl)amino)-2-fluorophenyl)pentanoic acid (Enantiomer 1). $^1$H NMR (500 MHz, DMSO-d$_6$) δ 9.32 (s, 1H), 7.87 (d, J=8.1 Hz, 1H), 7.74 (s, 1H), 7.17 (s, 1H), 6.97 (d, J=11.9 Hz, 1H), 6.88-6.81 (m, 1H), 6.79-6.68 (m, 1H), 5.96 (s, 2H), 3.19-3.10 (m, 1H), 2.80-2.63 (m, 2H), 2.60-2.50 (m, 2H (integration distorted by solvent peak)), 1.85-1.78 (m, 2H), 1.72-1.60 (m, 3H), 1.54-1.43 (m, 2H), 1.34-1.14 (m, 4H), 1.12-0.96 (m, 3H), 0.80 (d, J=6.6 Hz, 6H), 0.73 (t, J=7.3 Hz, 3H). MS(ES): m/z=528 [M+H]+. T$_r$=2.16 min (Method C). Concentration of the later eluting fractions afforded Example 1112 (14.2 mg) assigned as 3-(5-(3-(benzo[d][1,3]dioxol-5-yl)ureido)-4-(cyclohexyl(isobutyl)amino)-2-fluorophenyl)pentanoic acid (Enantiomer 2). $^1$H NMR (500 MHz, DMSO-d$_6$) δ 9.33 (s, 1H), 7.86 (d, J=8.1 Hz, 1H), 7.74 (s, 1H), 7.17 (s, 1H), 6.96 (d, J=11.9 Hz, 1H), 6.88-6.80 (m, 1H), 6.80-6.72 (m, 1H), 5.96 (s, 2H), 3.21-3.08 (m, 1H), 2.79-2.67 (m, 2H), 2.58-2.54 (m, 2H (integration distorted by solvent peak)), 1.85-1.76 (m, 2H), 1.71-1.60 (m, 3H), 1.55-1.43 (m, 2H), 1.36-1.13 (m, 4H), 1.13-0.96 (m, 3H), 0.80 (d, J=6.6 Hz, 6H), 0.73 (t, J=7.2 Hz, 3H). MS(ES): m/z=528 [M+H]+. T$_r$=2.16 min (Method C).

Example 1113

(±)-3-(4-(Cyclohexyl(isobutyl)amino)-2-fluoro-5-(3-(3-methylisoxazol-5-yl)ureido)phenyl)pentanoic acid

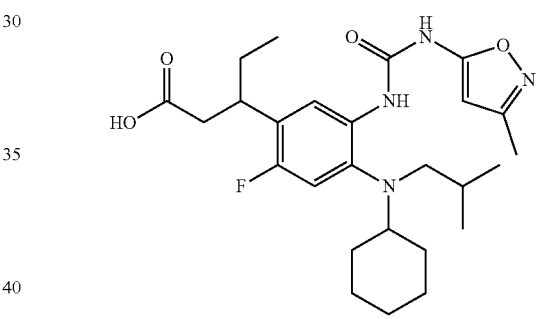

To a homogeneous mixture of (+/−)-methyl 3-(5-amino-4-(cyclohexyl(isobutyl)amino)-2-fluoro-phenyl)pentanoate (compound 951D, 45 mg, 0.12 mmol) in THF (1 mL), at room temperature in a sealable vial, was added 4-nitrophenyl carbonochloridate (34 mg, 0.17 mmol). The resulting mixture was stirred at ambient temperature for 40 minutes before 3-methylisoxazol-5-amine (35 mg, 0.35 mmol) and TEA (0.10 mL, 0.72 mmol) were added. The mixture was then stirred at 50° C. for 13 hours, then at room temperature for two hours, before MeOH (0.5 mL) was added to the reaction vial followed by LiOH (aq) (1M solution, 0.5 mL, 0.50 mmol). After 6.5 hours, the reaction was treated with NaOH (aq) (2M solution, 0.2 mL, 0.4 mmol) and stirred for 20 hours before being treated with acetic acid (0.06 mL, 1.05 mmol). The mixture was diluted with DMSO then purified by preparative RP HPLC (MeCN/H$_2$O gradient+10-mM NH$_4$OAc) to afford Example 1113 (23.9 mg, 41% yield). $^1$H NMR (500 MHz, DMSO-d$_6$) δ 8.14 (s, 1H), 7.89 (d, J=8.1 Hz, 1H), 7.03 (d, J=11.7 Hz, 1H), 5.98 (s, 1H), 3.23-3.10 (m, 1H), 2.83-2.69 (m, 2H), 2.59-2.52 (m, 4H (integration distorted by solvent peak)), 2.16 (s, 3H), 1.91-1.82 (m, 2H), 1.73-1.60 (m, 3H), 1.55-1.43 (m, 2H), 1.33-1.16 (m, 3H), 1.13-0.97 (m, 3H), 0.81 (d, J=6.6 Hz, 6H), 0.73 (t, J=7.3 Hz, 3H). MS(ES): m/z=489 [M+H]+, T$_r$=2.04 min (Method C).

Example 1114

3-(4-(Cyclohexyl(isobutyl)amino)-2-fluoro-5-(3-(3-methylisoxazol-5-yl)ureido)phenyl)pentanoic acid Enantiomer 1, Absolute Stereochemistry not Assigned

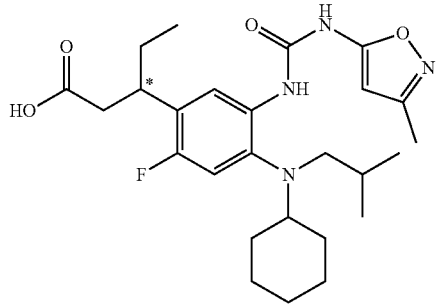 [SMILES: CCC(CC(=O)O)c1cc(NC(=O)Nc2cc(C)no2)c(N(CC(C)C)C2CCCCC2)cc1F]

and

Example 1115

3-(4-(Cyclohexyl(isobutyl)amino)-2-fluoro-5-(3-(3-methylisoxazol-5-yl)ureido)phenyl)pentanoic acid Enantiomer 2, Absolute Stereochemistry not Assigned

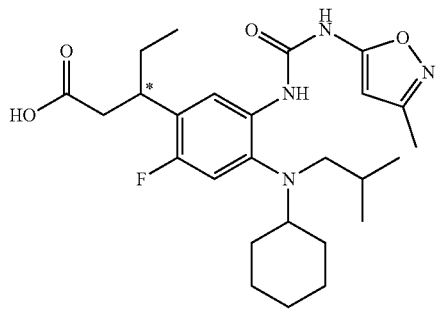 [SMILES: CCC(CC(=O)O)c1cc(NC(=O)Nc2cc(C)no2)c(N(CC(C)C)C2CCCCC2)cc1F]

Racemic mixture Example 1113, (±)-3-(4-(cyclohexyl(isobutyl)amino)-2-fluoro-5-(3-(3-methylisoxazol-5-yl)ureido)phenyl)pentanoic acid (23 mg), was purified by chiral SFC (90/10 CO$_2$/MeOH w/0.1% formic acid and 0.1% diethylamine mobile phase, Chiral AD-H 25×3 cm, 5 μm column, 85 ml/min, detector wavelength=220 nm). Concentration of the appropriate (earlier eluting) fractions afforded Example 1114 (8.7 mg) assigned as 3-(4-(cyclohexyl(isobutyl)amino)-2-fluoro-5-(3-(3-methylisoxazol-5-yl)ureido)phenyl)pentanoic acid (Enantiomer 1). $^1$H NMR (500 MHz, DMSO-d$_6$) δ 8.14 (s, 1H), 7.88 (d, J=8.0 Hz, 1H), 7.03 (d, J=11.8 Hz, 1H), 5.98 (s, 1H), 3.20-3.11 (m, 1H), 2.80-2.70 (m, 2H), 2.59-2.54 (m, 4H (integration distorted by solvent peak)), 2.16 (s, 3H), 1.92-1.81 (m, 2H), 1.73-1.59 (m, 3H), 1.55-1.43 (m, 2H), 1.32-1.17 (m, 3H), 1.11-0.95 (m, 3H), 0.81 (d, J=6.6 Hz, 6H), 0.73 (t, J=7.2 Hz, 3H). MS(ES): m/z=489 [M+H]$^+$. T$_r$=2.03 min (Method C). Concentration of the later eluting fractions afforded Example 1115 (12.4 mg) assigned as 3-(4-(cyclohexyl(isobutyl)amino)-2-fluoro-5-(3-(3-methylisoxazol-5-yl)ureido)phenyl)pentanoic acid (Enantiomer 2). $^1$H NMR (500 MHz, DMSO-d$_6$) δ 8.14 (s, 1H), 7.88 (d, J=8.1 Hz, 1H), 7.03 (d, J=11.7 Hz, 1H), 5.98 (s, 1H), 3.22-3.10 (m, 1H), 2.81-2.71 (m, 2H), 2.60-2.54 (m, 4H (integration distorted by solvent peak)), 2.16 (s, 3H), 1.91-1.82 (m, 2H), 1.72-1.59 (m, 3H), 1.55-1.44 (m, 2H), 1.32-1.17 (m, 3H), 1.12-0.97 (m, 3H), 0.81 (d, J=6.6 Hz, 6H), 0.73 (t, J=7.2 Hz, 3H). MS(ES): m/z=489 [M+H]$^+$. T$_r$=2.03 min (Method C).

Example 1116

(±)-3-(4-(Cyclohexyl(isobutyl)amino)-5-(3-(4-ethoxy-2-fluorophenyl)ureido)-2-fluorophenyl)pentanoic acid

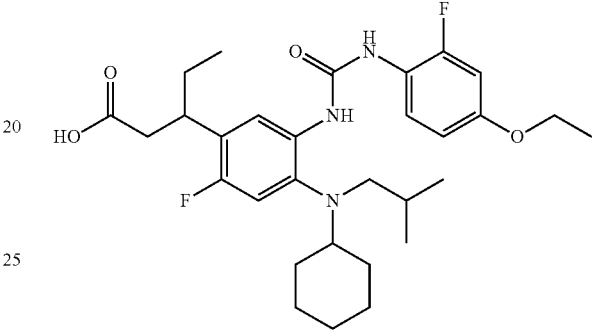

Example 1116 (20.5 mg, 31% yield) was prepared following a procedure analogous to that for the synthesis of Example 1113, except that 4-ethoxy-2-fluoroaniline, HCl (68 mg, 0.35 mmol) was used instead of 3-methylisoxazol-5-amine and the amount of TEA (0.15 mL, 1.08 mmol) used was increased. $^1$H NMR (500 MHz, DMSO-d$_6$) δ 8.99 (br. s., 1H), 7.90-7.74 (m, 2H), 7.64-7.55 (m, 1H), 6.94 (d, J=11.9 Hz, 1H), 6.89-6.82 (m, 1H), 6.74-6.69 (m, 1H), 4.00 (q, J=6.9 Hz, 2H), 3.21-3.09 (m, 1H), 2.79-2.66 (m, 2H), 2.50-2.40 (m, 3H (integration distorted by solvent peak)), 1.83-1.70 (m, 2H), 1.70-1.56 (m, 3H), 1.54-1.38 (m, 2H), 1.35-1.25 (m, 4H), 1.24-1.13 (m, 2H), 1.12-0.92 (m, 3H), 0.79 (d, J=6.6 Hz, 6H), 0.72 (t, J=7.3 Hz, 3H). MS(ES): m/z=546 [M+H]$^+$. T$_r$=2.36 min (Method C).

Example 1117

3-(4-(Cyclohexyl(isobutyl)amino)-5-(3-(4-ethoxy-2-fluorophenyl)ureido)-2-fluorophenyl)pentanoic acid Enantiomer 1, Absolute Stereochemistry not Assigned

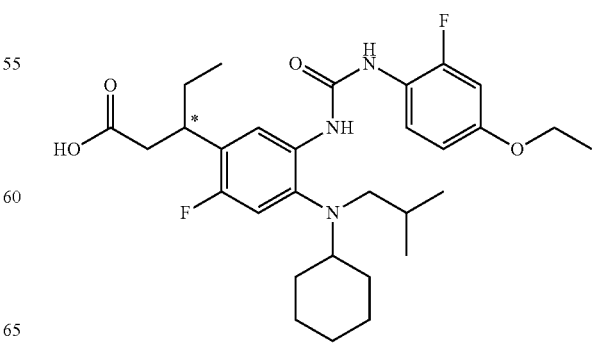

Example 1118

3-(4-(Cyclohexyl(isobutyl)amino)-5-(3-(4-ethoxy-2-fluorophenyl)ureido)-2-fluorophenyl)pentanoic acid Enantiomer 2, Absolute Stereochemistry not Assigned

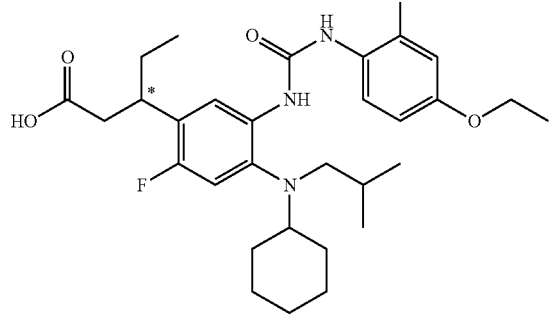

Racemic mixture Example 1116, (±)-3-(4-(cyclohexyl(isobutyl)amino)-5-(3-(4-ethoxy-2-fluorophenyl)ureido)-2-fluorophenyl)pentanoic acid (20 mg), was purified by chiral SFC (85/15 $CO_2$/MeOH mobile phase, Chiral AD-H 25×3 cm, 5 μm column, 85 ml/min, detector wavelength=220 nm). Concentration of the appropriate (earlier eluting) fractions afforded Example 1117 (9.0 mg) assigned as 3-(4-(cyclohexyl(isobutyl)amino)-5-(3-(4-ethoxy-2-fluorophenyl)ureido)-2-fluorophenyl)pentanoic acid (Enantiomer 1). $^1$H NMR (500 MHz, DMSO-$d_6$) δ 9.00 (br. s., 1H), 7.90-7.76 (m, 2H), 7.64-7.55 (m, 1H), 6.94 (d, J=11.9 Hz, 1H), 6.87 (dd, J=12.6, 2.5 Hz, 1H), 6.78-6.68 (m, 1H), 4.05-3.96 (m, 2H), 3.20-3.09 (m, 1H), 2.76-2.66 (m, 2H), 2.49-2.39 (m, 3H (integration distorted by solvent peak)), 1.82-1.72 (m, 2H), 1.71-1.58 (m, 3H), 1.54-1.40 (m, 2H), 1.35-1.27 (m, 4H), 1.25-1.17 (m, 2H), 1.08-0.95 (m, 3H), 0.80 (d, J=6.6 Hz, 6H), 0.72 (t, J=7.2 Hz, 3H). MS(ES): m/z=546 [M+H]$^+$. $T_r$=2.31 min (Method C). Concentration of the later eluting fractions afforded Example 1118 (8.6 mg) assigned as 3-(4-(cyclohexyl(isobutyl)amino)-5-(3-(4-ethoxy-2-fluorophenyl)ureido)-2-fluorophenyl)pentanoic acid (Enantiomer 2). $^1$H NMR (500 MHz, DMSO-$d_6$) δ 9.00 (br. s., 1H), 7.92-7.75 (m, 2H), 7.66-7.57 (m, 1H), 6.95 (d, J=11.9 Hz, 1H), 6.87 (dd, J=12.6, 2.5 Hz, 1H), 6.79-6.69 (m, 1H), 4.01 (q, J=6.9 Hz, 2H), 3.20-3.07 (m, 1H), 2.82-2.62 (m, 2H), 2.50-2.38 (m, 3H (integration distorted by solvent peak)), 1.83-1.72 (m, 2H), 1.71-1.58 (m, 3H), 1.56-1.41 (m, 2H), 1.34-1.28 (m, 4H), 1.23-1.17 (m, 2H), 1.12-0.97 (m, 3H), 0.80 (d, J=6.5 Hz, 6H), 0.73 (t, J=7.2 Hz, 3H). MS(ES): m/z=546 [M+H]$^+$. $T_r$=2.31 min (Method C).

Example 1119

(±)-3-(4-(Cyclohexyl(isobutyl)amino)-2-fluoro-5-(3-(2-fluoro-4-methylphenyl)ureido)phenyl)pentanoic acid

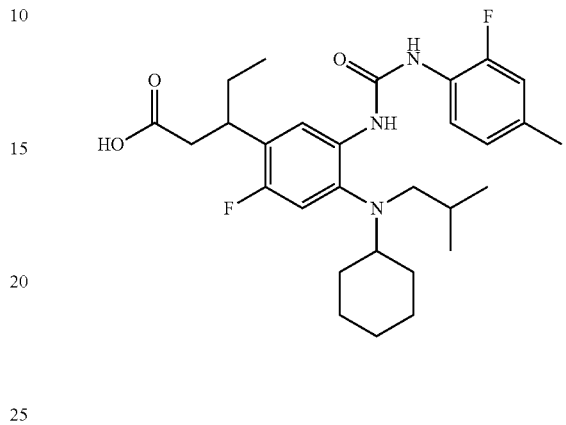

Example 1119 (31.8 mg, 52% yield) was prepared following a procedure analogous to that for the synthesis of Example 1116, except that 2-fluoro-4-methylaniline (44 mg, 0.35 mmol) was used instead of 3-methylisoxazol-5-amine. $^1$H NMR (500 MHz, DMSO-$d_6$) δ 9.19 (s, 1H), 7.93 (s, 1H), 7.81-7.69 (m, 2H), 7.05 (d, J=11.9 Hz, 1H), 6.99-6.88 (m, 2H), 3.20-3.09 (m, 1H), 2.82-2.66 (m, 2H), 2.58-2.51 (m, 3H (integration distorted by solvent peak)), 2.26 (s, 3H), 1.86-1.75 (m, 2H), 1.71-1.57 (m, 3H), 1.54-1.41 (m, 2H), 1.39-1.28 (m, 1H), 1.26-1.15 (m, 2H), 1.12-0.95 (m, 3H), 0.81 (d, J=6.6 Hz, 6H), 0.73 (t, J=7.3 Hz, 3H). MS(ES): m/z=516 [M+H]$^+$. $T_r$=2.37 min (Method C).

Example 1120

3-(4-(Cyclohexyl(isobutyl)amino)-2-fluoro-5-(3-(2-fluoro-4-methylphenyl)ureido)phenyl)pentanoic acid Enantiomer 1, Absolute Stereochemistry not Assigned

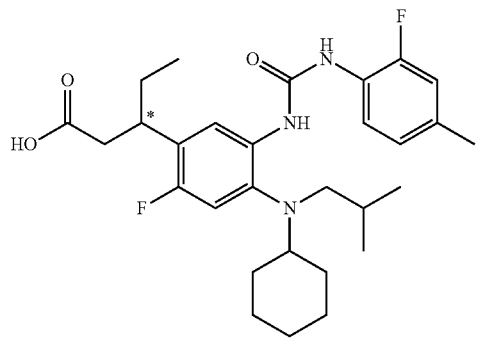 [SMILES: CCC(CC(=O)O)c1cc(NC(=O)Nc2ccc(C)cc2F)c(N(CC(C)C)C2CCCCC2)cc1F]

Example 1121

3-(4-(Cyclohexyl(isobutyl)amino)-2-fluoro-5-(3-(2-fluoro-4-methylphenyl)ureido)phenyl)pentanoic acid Enantiomer 2, Absolute Stereochemistry not Assigned

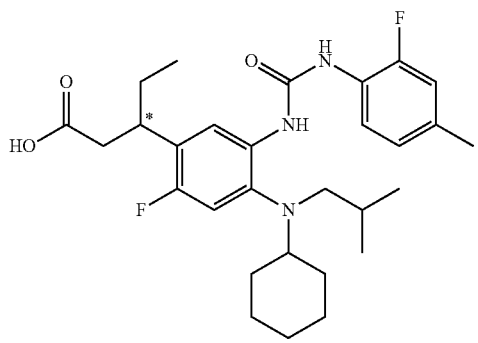 [SMILES: CCC(CC(=O)O)c1cc(NC(=O)Nc2ccc(C)cc2F)c(N(CC(C)C)C2CCCCC2)cc1F]

Racemic mixture Example 1119, (±)-3-(4-(cyclohexyl(isobutyl)amino)-2-fluoro-5-(3-(2-fluoro-4-methylphenyl)ureido)phenyl)pentanoic acid (31 mg), was purified by chiral SFC (85/15 $CO_2$/MeOH mobile phase, Chiral AD-H 25×3 cm, 5 μm column, 85 ml/min, detector wavelength=220 nm). Concentration of the appropriate (earlier eluting) fractions afforded Example 1120 (12.6 mg) assigned as 3-(4-(cyclohexyl(isobutyl)amino)-2-fluoro-5-(3-(2-fluoro-4-methylphenyl)ureido)phenyl)pentanoic acid (Enantiomer 1). $^1$H NMR (500 MHz, DMSO-$d_6$) δ 9.18 (s, 1H), 7.91 (s, 1H), 7.76-7.67 (m, 2H), 7.05 (d, J=11.9 Hz, 1H), 6.99-6.86 (m, 2H), 3.21-3.05 (m, 1H), 2.77-2.64 (m, 2H), 2.59-2.54 (m, 3H (integration distorted by solvent peak)), 2.25 (s, 3H), 1.83-1.72 (m, 2H), 1.69-1.57 (m, 3H), 1.52-1.42 (m, 2H), 1.36-1.25 (m, 1H), 1.24-1.13 (m, 2H), 1.10-0.93 (m, 3H), 0.79 (d, J=6.5 Hz, 6H), 0.72 (t, J=7.3 Hz, 3H). MS(ES): m/z=516 [M+H]$^+$. $T_r$=2.42 min (Method C). Concentration of the later eluting fractions afforded Example 1121 (13.5 mg) assigned as 3-(4-(cyclohexyl(isobutyl)amino)-2-fluoro-5-(3-(2-fluoro-4-methylphenyl)ureido)phenyl)pentanoic acid (Enantiomer 2). $^1$H NMR (500 MHz, DMSO-$d_6$) δ 9.18 (s, 1H), 7.91 (s, 1H), 7.76-7.63 (m, 2H), 7.05 (d, J=12.1 Hz, 1H), 6.98-6.87 (m, 2H), 3.19-3.07 (m, 1H), 2.78-2.66 (m, 2H), 2.59-2.54 (m, 3H (integration distorted by solvent peak)), 2.25 (s, 3H), 1.83-1.71 (m, 2H), 1.70-1.57 (m, 3H), 1.54-1.40 (m, 2H), 1.35-1.25 (m, 1H), 1.23-1.13 (m, 2H), 1.11-0.91 (m, 3H), 0.79 (d, J=6.6 Hz, 6H), 0.72 (t, J=7.3 Hz, 3H). MS(ES): m/z=516 [M+H]$^+$. $T_r$=2.39 min (Method C).

Example 1122

(±)-3-(4-(Cyclohexyl(isobutyl)amino)-2-fluoro-5-(3-(pyrimidin-5-yl)ureido)phenyl)pentanoic acid

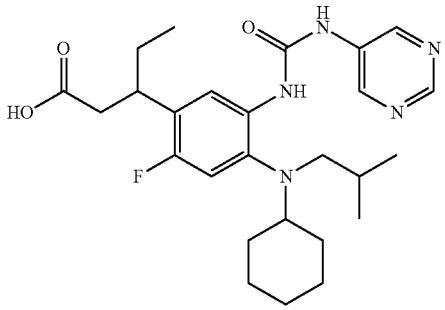 [SMILES: CCC(CC(=O)O)c1cc(NC(=O)Nc2cncnc2)c(N(CC(C)C)C2CCCCC2)cc1F]

Example 1122 (26.0 mg, 45% yield) was prepared following a procedure analogous to that for the synthesis of Example 1116, except that pyrimidin-5-amine (34 mg, 0.35 mmol) was used instead of 3-methylisoxazol-5-amine. $^1$H NMR (500 MHz, DMSO-$d_6$) δ 9.94 (s, 1H), 8.91 (s, 2H), 8.81 (s, 1H), 8.05 (s, 1H), 7.88 (d, J=8.1 Hz, 1H), 7.07-6.98 (m, 1H), 3.20-3.11 (m, 1H), 2.83-2.72 (m, 2H), 2.61-2.54 (m, 3H), 1.93-1.85 (m, 2H), 1.73-1.59 (m, 3H), 1.55-1.45 (m, 2H), 1.37-1.17 (m, 3H), 1.15-0.93 (m, 3H), 0.82 (d, J=6.5 Hz, 6H), 0.74 (t, J=7.3 Hz, 3H). MS(ES): m/z=486 [M+H]$^+$. $T_r$=1.86 min (Method C).

Example 1123

3-(4-(Cyclohexyl(isobutyl)amino)-2-fluoro-5-(3-(pyrimidin-5-yl)ureido)phenyl)pentanoic acid Enantiomer 1, Absolute Stereochemistry not Assigned

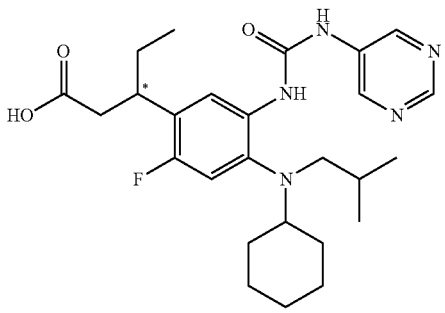 [SMILES: CCC(CC(=O)O)c1cc(NC(=O)Nc2cncnc2)c(N(CC(C)C)C2CCCCC2)cc1F]

Example 1124

3-(4-(Cyclohexyl(isobutyl)amino)-2-fluoro-5-(3-(pyrimidin-5-yl)ureido)phenyl)pentanoic acid Enantiomer 2, Absolute Stereochemistry not Assigned

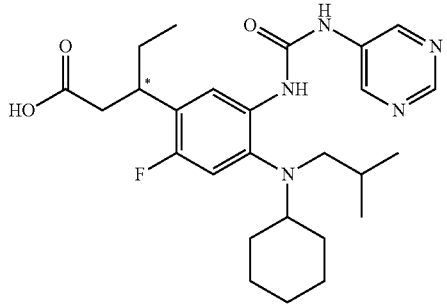 [SMILES: CCC(CC(=O)O)c1cc(NC(=O)Nc2cncnc2)c(N(CC(C)C)C2CCCCC2)cc1F]

Racemic mixture Example 1122, (±)-3-(4-(cyclohexyl(isobutyl)amino)-2-fluoro-5-(3-(pyrimidin-5-yl)ureido)phenyl)pentanoic acid (25 mg), was purified by chiral SFC (88/12 CO$_2$/[1:1 MeOH:ACN] mobile phase, Chiral IC 25×3 cm, 5 μm column, 100 ml/min, detector wavelength=220 nm). Concentration of the appropriate (earlier eluting) fractions afforded Example 1123 (4.3 mg) assigned as 3-(4-(cyclohexyl(isobutyl)amino)-2-fluoro-5-(3-(pyrimidin-5-yl)ureido)phenyl)pentanoic acid (Enantiomer 1). $^1$H NMR (500 MHz, DMSO-d$_6$) δ10.04 (s, 1H), 8.92 (s, 2H), 8.81 (s, 1H), 8.09 (s, 1H), 7.87 (d, J=8.1 Hz, 1H), 7.01 (d, J=11.8 Hz, 1H), 3.21-3.10 (m, 1H), 2.83-2.73 (m, 2H), 2.62-2.54 (m, 3H), 1.90-1.88 (m, 2H), 1.72-1.64 (m, 3H), 1.53-1.46 (m, 2H), 1.35-1.20 (m, 3H), 1.14-0.98 (m, 3H), 0.82 (d, J=6.6 Hz, 6H), 0.73 (t, J=7.3 Hz, 3H). MS(ES): m/z=486 [M+H]$^+$. T$_r$=1.84 min (Method C). Concentration of the later eluting fractions afforded Example 1124 (6.7 mg) assigned as 3-(4-(cyclohexyl(isobutyl)amino)-2-fluoro-5-(3-(pyrimidin-5-yl)ureido) phenyl)pentanoic acid (Enantiomer 2). $^1$H NMR (500 MHz, DMSO-d$_6$) δ 9.94 (s, 1H), 8.91 (s, 2H), 8.81 (s, 1H), 8.05 (s, 1H), 7.88 (d, J=8.1 Hz, 1H), 7.02 (d, J=11.8 Hz, 1H), 3.24-3.09 (m, 1H), 2.85-2.71 (m, 2H), 2.61-2.54 (m, 3H), 1.95-1.83 (m, 2H), 1.74-1.61 (m, 3H), 1.57-1.44 (m, 2H), 1.34-1.21 (m, 3H), 1.12-0.94 (m, 3H), 0.82 (d, J=6.6 Hz, 6H), 0.73 (t, J=7.3 Hz, 3H). MS(ES): m/z=486 [M+H]$^+$. T$_r$=1.86 min (Method C).

Example 1125

(±)-3-(4-(Cyclohexyl(isobutyl)amino)-2-fluoro-5-(3-(2-methylpyrimidin-5-yl)ureido)phenyl)pentanoic acid

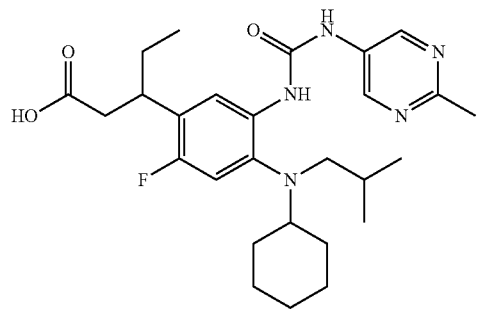 [SMILES: CCC(CC(=O)O)c1cc(NC(=O)Nc2cnc(C)nc2)c(N(CC(C)C)C2CCCCC2)cc1F]

Example 1125 (37.6 mg, 63% yield) was prepared following a procedure analogous to that for the synthesis of Example 1116, except that 2-methylpyrimidin-5-amine (13 mg, 0.12 mmol) was used instead of 3-methylisoxazol-5-amine. $^1$H NMR (500 MHz, DMSO-d$_6$) δ 9.84 (s, 1H), 8.78 (s, 2H), 7.99 (s, 1H), 7.85 (d, J=8.1 Hz, 1H), 7.00 (d, J=11.8 Hz, 1H), 3.20-3.09 (m, 1H), 2.81-2.71 (m, 2H), 2.60-2.52 (m, 6H), 1.91-1.82 (m, 2H), 1.72-1.59 (m, 3H), 1.53-1.43 (m, 2H), 1.35-1.16 (m, 3H), 1.12-0.91 (m, 3H), 0.81 (d, J=6.5 Hz, 6H), 0.72 (t, J=7.3 Hz, 3H). MS(ES): m/z=500 [M+H]$^+$. T$_r$=1.88 min (Method C).

Example 1126

3-(4-(Cyclohexyl(isobutyl)amino)-2-fluoro-5-(3-(2-methylpyrimidin-5-yl)ureido)phenyl)pentanoic acid Enantiomer 1, Absolute Stereochemistry not Assigned

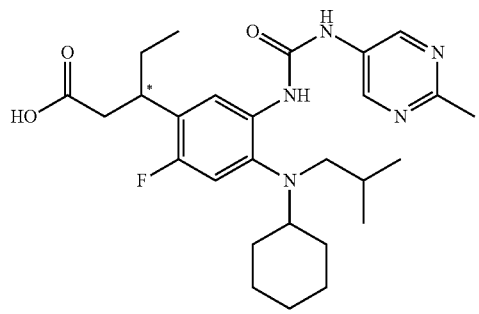 [SMILES: CCC(CC(=O)O)c1cc(NC(=O)Nc2cnc(C)nc2)c(N(CC(C)C)C2CCCCC2)cc1F]

and

Example 1127

3-(4-(Cyclohexyl(isobutyl)amino)-2-fluoro-5-(3-(2-methylpyrimidin-5-yl)ureido)phenyl)pentanoic acid Enantiomer 2, Absolute Stereochemistry not Assigned

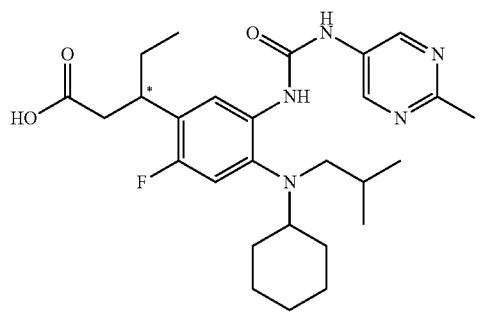 [SMILES: CCC(CC(=O)O)c1cc(NC(=O)Nc2cnc(C)nc2)c(N(CC(C)C)C2CCCCC2)cc1F]

Racemic mixture Example 1125, (±)-3-(4-(cyclohexyl(isobutyl)amino)-2-fluoro-5-(3-(2-methylpyrimidin-5-yl)ureido)phenyl)pentanoic acid (37 mg), was purified by chiral SFC (85/15 CO$_2$/[1:1 MeOH:ACN] mobile phase, Chiral IC 25×3 cm, 5 μm column, 100 ml/min, detector wavelength=220 nm). Concentration of the appropriate (earlier eluting) fractions afforded Example 1126 (11.7 mg) assigned as 3-(4-(cyclohexyl(isobutyl)amino)-2-fluoro-5-(3-(2-methylpyrimidin-5-yl)ureido)phenyl)pentanoic acid (Enantiomer 1). $^1$H NMR (500 MHz, DMSO-$d_6$) δ 9.80 (s, 1H), 8.79 (s, 2H), 8.00 (s, 1H), 7.88 (d, J=8.1 Hz, 1H), 7.02 (d, J=11.8 Hz, 1H), 3.23-3.08 (m, 1H), 2.85-2.70 (m, 2H), 2.56-2.54 (m, 6H), 1.92-1.85 (m, 2H), 1.72-1.61 (m, 3H), 1.54-1.45 (m, 2H), 1.36-1.17 (m, 3H), 1.15-0.95 (m, 3H), 0.82 (d, J=6.6 Hz, 6H), 0.73 (t, J=7.3 Hz, 3H). MS(ES): m/z=500 [M+H]$^+$. $T_r$=1.87 min (Method C). Concentration of the later eluting fractions afforded Example 1127 (9.4 mg) assigned as 3-(4-(cyclohexyl(isobutyl)amino)-2-fluoro-5-(3-(2-methylpyrimidin-5-yl)ureido)phenyl)pentanoic acid (Enantiomer 2). $^1$H NMR (500 MHz, DMSO-$d_6$) δ 9.80 (s, 1H), 8.79 (s, 2H), 8.00 (s, 1H), 7.88 (d, J=8.1 Hz, 1H), 7.02 (d, J=11.8 Hz, 1H), 3.22-3.07 (m, 1H), 2.83-2.72 (m, 2H), 2.56-2.54 (m, 6H), 1.91-1.86 (m, 2H), 1.72-1.60 (m, 3H), 1.55-1.44 (m, 2H), 1.36-1.18 (m, 3H), 1.14-0.97 (m, 3H), 0.82 (d, J=6.6 Hz, 6H), 0.73 (t, J=7.3 Hz, 3H). MS(ES): m/z=500 [M+H]$^+$. $T_r$=1.87 min (Method C).

Example 1128

(±)-3-(4-(Diisobutylamino)-2-fluoro-5-(3-(p-tolyl)ureido)phenyl)pentanoic acid

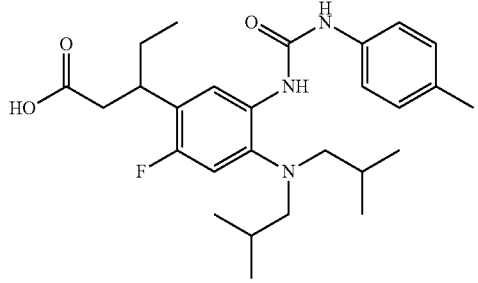 [SMILES: CCC(CC(=O)O)c1cc(NC(=O)Nc2ccc(C)cc2)c(N(CC(C)C)CC(C)C)cc1F]

1128A. 4-Bromo-5-fluoro-N,N-diisobutyl-2-nitroaniline

To a homogeneous mixture of 5-bromo-2,4-difluoronitrobenzene (2.0 g, 8.40 mmol) in anhydrous NMP (8 mL), at room temperature under nitrogen, was added DIPEA (4.40 mL, 25.20 mmol) followed by diisobutylamine (1.61 mL, 9.24 mmol). The mixture was stirred at 110° C. for 23 hours, then cooled to room temperature, before being diluted with Et$_2$O then washed twice with 1N HCl (aq). The organic layer was washed with a saturated aqueous NaHCO$_3$ solution, then brine, before being dried (Na$_2$SO$_4$), filtered and concentrated in vacuo to afford an oil which was purified on an Isco CombiFlash System Purified: REDISEP® normal phase silica flash column (80 g), detection wavelength=254 nm, run time=35 min. Mobile Phase: (5 min at 100% hexane then 20 min gradient from 0-25% EtOAc in hexane). Concentration of the appropriate fractions afforded 4-bromo-5-fluoro-N,N-diisobutyl-2-nitroaniline (2.78 g, 95% yield) as an orange solid. $^1$H NMR (400 MHz, CDCl$_3$) δ 8.00 (d, J=7.5 Hz, 1H), 6.82 (d, J=11.2 Hz, 1H), 2.91 (d, J=7.3 Hz, 4H), 1.96-1.86 (m, 2H), 0.84 (d, J=6.6 Hz, 12H). MS(ES): m/z=347 [M+H]$^+$, $T_r$=1.26 min (Method A).

1128B. 4-(5,5-Dimethyl-1,3,2-dioxaborinan-2-yl)-5-fluoro-N,N-diisobutyl-2-nitroaniline A mixture of 4-bromo-5-fluoro-N,N-diisobutyl-2-nitroaniline (1.50 g, 4.32 mmol), 5,5,5',5'-tetramethyl-2,2'-bi(1,3,2-dioxaborinane) (1.30 g, 5.75 mmol) and potassium acetate (1.27 g, 12.98 mmol) in DMSO (7.20 ml), at room temperature in a sealable flask, was purged with argon for 20 minutes before PdCl$_2$ (dppf).CH$_2$Cl$_2$ Adduct (0.10 g, 0.14 mmol) was added, the flask was sealed and the reaction heated at 80° C. for 6 hours. The cooled reaction mixture was filtered to remove any solids, which were then rinsed with EtOAc, before combined filtrate was purified on Isco CombiFlash System: REDISEP® normal phase silica flash column (220 g), detection wavelength=254 nm, run time=40 min, flow rate=150 mL/min. Mobile Phase: (10 min at 100% hexane then 30 min gradient from 0-50% EtOAc in hexane). Concentration of the appropriate fractions afforded 4-(5,5-dimethyl-1,3,2-dioxaborinan-2-yl)-5-fluoro-N,N-diisobutyl-2-nitroaniline (0.53 g, 32% yield) as an oil. $^1$H NMR (400 MHz, chloroform-d) δ 8.18 (d, J=6.8 Hz, 1H), 6.63 (d, J=12.6 Hz, 1H), 3.76 (s, 4H), 2.94 (d, J=7.3 Hz, 4H), 1.97-1.91 (m, 2H), 1.02 (s, 6H), 0.83 (d, J=6.6 Hz, 12H). Expected product appears as corresponding boronic acid under acidic MS conditions: MS(ES): m/z=313 [M+H]$^+$, $T_r$=1.02 min (Method A).

1128C. (±)-Methyl 3-(4-(diisobutylamino)-2-fluoro-5-nitrophenyl)pentanoate

To a homogeneous mixture of 4-(5,5-dimethyl-1,3,2-dioxaborinan-2-yl)-5-fluoro-N,N-diisobutyl-2-nitroaniline (531 mg, 1.40 mmol) in anhydrous dioxane (5 mL), in a sealable tube at room temperature, was added methyl 2-pentenoate (478 mg, 4.20 mmol) followed by NaOH (aq) (1M solution, 1.3 mL, 1.30 mmol). The resulting mixture was sequentially evacuated then purged with nitrogen for a total of three cycles before chloro(1,5-cyclooctadiene)rhodium(I) dimer (34.4 mg, 0.07 mmol) was added. The resulting mixture was again sequentially evacuated then purged with nitrogen for a total of three cycles, before the tube was capped and the reaction warmed to 50° C. for 6 hours. After cooling to room temperature, the reaction was quenched with acetic acid (0.08 mL, 1.36 mmol) and stirred for 5 minutes before being partitioned between EtOAc and water. The layers were separated and the aqueous layer was extracted again with EtOAc. The organic extracts were combined, washed twice with water then once with brine before being concentrated in vacuo to afford an oil which was purified on an Isco CombiFlash System: REDISEP® normal phase silica flash column (40 g), detection wavelength=254 nm, run time=40 min, flow rate=40 mL/min. Mobile Phase: (10 min at 100% hexane then 20 min gradient from 0-25% EtOAc in hexane). Concentration of the appropriate fractions afforded methyl 3-(4-(diisobutylamino)-2-fluoro-5-nitrophenyl)pentanoate (75.3 mg, 14% yield) as an oil. MS(ES): m/z=383 [M+H]$^+$, $T_r$=1.23 min (Method A).

1128D. (±)-Methyl 3-(5-amino-4-(diisobutylamino)-2-fluorophenyl)pentanoate

To a sealable hydrogen stirring flask, charged with methyl 3-(4-(diisobutylamino)-2-fluoro-5-nitrophenyl)pentanoate (75.3 mg, 0.20 mmol) and 10% Pd—C (21 mg, 0.02 mmol) was carefully added EtOAc (2 mL). The flask was sequentially evacuated then purged with nitrogen before being pressurized to 40 psi of hydrogen. After 2 hours of stirring at ambient temperature, the reaction mixture was filtered through a pad of CELITE® which was then thoroughly rinsed with DCM. The combined filtrates were concentrated in vacuo to afford an oil which was resubjected to the original conditions of the reaction, except using 10% Pd—C (42 mg, 0.04 mmol). The flask was sequentially evacuated then purged with nitrogen before being pressurized to 40 psi of hydrogen. After 4 hours of stirring at ambient temperature, the reaction mixture was filtered through a pad of CELITE® which was then thoroughly rinsed with EtOAc. The combined filtrates were concentrated in vacuo to afford (±)-methyl 3-(5-amino-4-(diisobutylamino)-2-fluorophenyl)pentanoate (59.3 mg, 85% yield) as an amber residue which was used without further purification. MS(ES): m/z=353 [M+H]$^+$, T$_r$=1.04 min (Method A).

Example 1128 (±)-3-(4-(Diisobutylamino)-2-fluoro-5-(3-(p-tolyl)ureido)phenyl)pentanoic acid To a homogeneous mixture of (±)-methyl 3-(5-amino-4-(diisobutylamino)-2-fluorophenyl)pentanoate (59.3 mg, 0.17 mmol) in THF (1 mL), at room temperature in a sealable vial, was added 1-isocyanato-4-methylbenzene (23 mg, 0.17 mmol). The resulting mixture was stirred at ambient temperature for 22 hours before 1-isocyanato-4-methylbenzene (12 mg, 0.09 mmol) was added and stirring continued for another 4 hours. The reaction was then treated with MeOH (0.5 mL), followed by addition of LiOH (aq) (1M solution, 0.5 mL, 0.50 mmol). After 15 hours, the reaction was treated with acetic acid (until pH 5-6 on BDH pH 0-14 test strips). The mixture was then partitioned between EtOAc and brine. The layers were separated and the aqueous layer was extracted once more with EtOAc. The organic extracts were combined and concentrated in vacuo to afford a residue which was diluted with DMF then purified by preparative RP HPLC (MeCN/H$_2$O gradient+ 10-mM NH$_4$OAc) to afford Example 1128 (59.3 mg, 75% yield). $^1$H NMR (500 MHz, DMSO-d$_6$) δ 9.30 (s, 1H), 7.81-7.74 (m, 1H), 7.65 (s, 1H), 7.34 (d, J=7.0 Hz, 2H), 7.08 (d, J=6.6 Hz, 2H), 6.99 (d, J=11.4 Hz, 1H), 3.19-3.08 (m, 1H), 2.70-2.60 (m, 4H), 2.61-2.52 (m, 2H), 2.24 (s, 3H), 1.71-1.56 (m, 3H), 1.55-1.40 (m, 1H), 0.87-0.78 (m, 12H), 0.76-0.69 (m, 3H). MS(ES): m/z=472 [M+H]$^+$, T$_r$=2.29 min (Method C).

Example 1129

3-(4-(Diisobutylamino)-2-fluoro-5-(3-(p-tolyl)ureido)phenyl)pentanoic acid

Enantiomer 1, Absolute Stereochemistry not Assigned

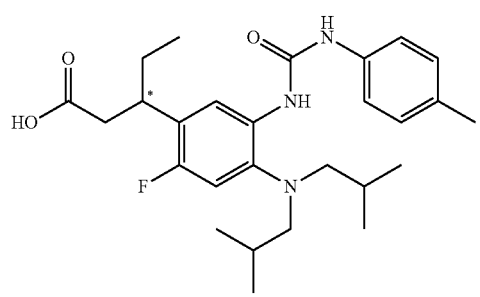 [SMILES: CCC(CC(=O)O)c1cc(NC(=O)Nc2ccc(C)cc2)c(N(CC(C)C)CC(C)C)cc1F]

and

Example 1130

3-(4-(Diisobutylamino)-2-fluoro-5-(3-(p-tolyl)ureido)phenyl)pentanoic acid

Enantiomer 2, Absolute Stereochemistry not Assigned

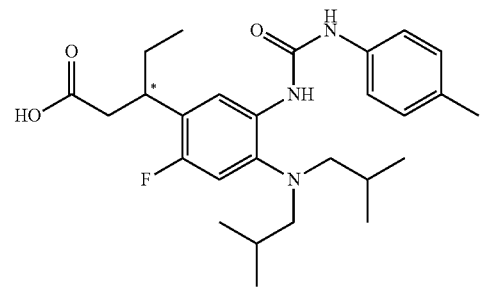 [SMILES: CCC(CC(=O)O)c1cc(NC(=O)Nc2ccc(C)cc2)c(N(CC(C)C)CC(C)C)cc1F]

Racemic mixture Example 1128, (±)-3-(4-(diisobutylamino)-2-fluoro-5-(3-(p-tolyl)ureido)phenyl)pentanoic acid (55 mg), was purified by chiral SFC (85/15 CO$_2$/MeOH mobile phase, Chiral AD-H 25×3 cm, 5 μm column, 85 ml/min, detector wavelength=220 nm). Concentration of the appropriate (earlier eluting) fractions afforded Example 1129 (23.2 mg) assigned as 3-(4-(diisobutylamino)-2-fluoro-5-(3-(p-tolyl)ureido)phenyl)pentanoic acid (Enantiomer 1). $^1$H NMR (500 MHz, DMSO-d$_6$) δ 9.30 (s, 1H), 7.78 (d, J=8.1 Hz, 1H), 7.65 (s, 1H), 7.33 (d, J=8.3 Hz, 2H), 7.08 (d, J=8.2 Hz, 2H), 6.99 (d, J=11.9 Hz, 1H), 3.21-3.07 (m, 1H), 2.67-2.60 (m, 4H), 2.60-2.52 (m, 2H), 2.23 (s, 3H), 1.70-1.59 (m, 3H), 1.54-1.43 (m, 1H), 0.86-0.80 (m, 12H), 0.72 (t, J=7.3 Hz, 3H). MS(ES): m/z=472 [M+H]$^+$. T$_r$=2.31 min (Method C). Concentration of the later eluting fractions afforded Example 1130 (23.8 mg) assigned as 3-(4-(diisobutylamino)-2-fluoro-5-(3-(p-tolyl)ureido)phenyl)pentanoic acid (Enantiomer 2). $^1$H NMR (500 MHz, DMSO-d$_6$) δ 9.30 (s, 1H), 7.77 (d, J=8.1 Hz, 1H), 7.65 (s, 1H), 7.33 (d, J=8.3 Hz, 2H), 7.08 (d, J=8.2 Hz, 2H), 6.98 (d, J=11.9 Hz, 1H), 3.21-3.07 (m, 1H), 2.69-2.59 (m, 4H), 2.59-2.52 (m, 2H), 2.23 (s, 3H), 1.70-1.56 (m, 3H), 1.55-1.41 (m, 1H), 0.88-0.77 (m, 12H), 0.72 (t, J=7.3 Hz, 3H). MS(ES): m/z=472 [M+H]$^+$. T$_r$=2.31 min (Method C).

Example 1131

(±)-3-(4-(Diisobutylamino)-5-(3-(4-ethoxyphenyl)ureido)-2-fluorophenyl)pentanoic acid

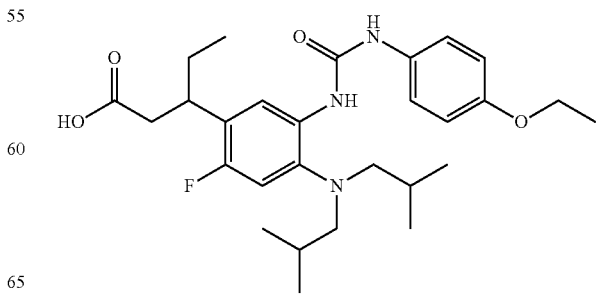

To a homogeneous mixture of (±)-methyl 3-(5-amino-4-(diisobutylamino)-2-fluorophenyl)pentanoate (1128D, 25.4 mg, 0.07 mmol) in THF (1 mL), at room temperature in a sealable vial, was added 1-ethoxy-4-isocyanatobenzene (18 mg, 0.11 mmol). The resulting mixture was stirred at ambient temperature for 18 hours before being treated with MeOH (0.5 mL), then LiOH (aq) (1M solution, 1.0 mL, 1.00 mmol). After 20 hours, the reaction was treated with acetic acid (0.06 mL, 1.05 mmol). The mixture was then diluted with DMSO then purified by preparative RP HPLC (MeCN/$H_2O$ gradient+10-mM $NH_4OAc$) to afford Example 1131 (26.6 mg, 72% yield). $^1$H NMR (500 MHz, DMSO-$d_6$) δ 9.20 (s, 1H), 7.80 (d, J=8.1 Hz, 1H), 7.63 (s, 1H), 7.33 (d, J=8.8 Hz, 2H), 6.99 (d, J=11.9 Hz, 1H), 6.85 (d, J=8.7 Hz, 2H), 3.97 (q, J=6.9 Hz, 2H), 3.18-3.10 (m, 1H), 2.70-2.58 (m, 4H), 2.56-2.54 (m, 2H), 1.69-1.59 (m, 3H), 1.53-1.42 (m, 1H), 1.30 (t, J=6.9 Hz, 3H), 0.83 (d, J=3.6 Hz, 12H), 0.72 (t, J=7.1 Hz, 3H). MS(ES): m/z=502 [M+H]$^+$, T$_r$=2.18 min (Method C).

Example 1132

3-(4-(Diisobutylamino)-5-(3-(4-ethoxyphenyl)ureido)-2-fluorophenyl)pentanoic acid Enantiomer 1, Absolute Stereochemistry not Assigned

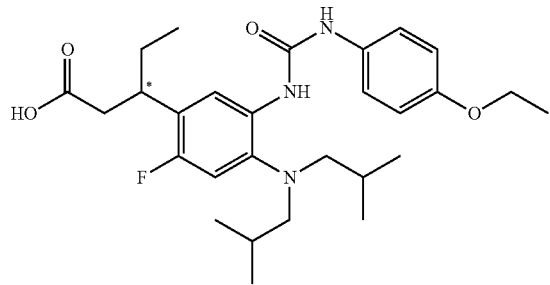 [SMILES: CCOc1ccc(NC(=O)Nc2cc(C(CC)CC(=O)O)c(F)cc2N(CC(C)C)CC(C)C)cc1]

and

Example 1133

3-(4-(Diisobutylamino)-5-(3-(4-ethoxyphenyl)ureido)-2-fluorophenyl)pentanoic acid Enantiomer 2, Absolute Stereochemistry not Assigned

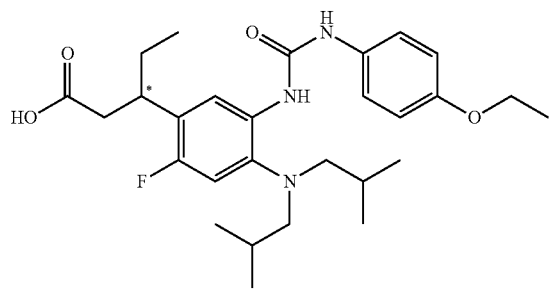 [SMILES: CCOc1ccc(NC(=O)Nc2cc(C(CC)CC(=O)O)c(F)cc2N(CC(C)C)CC(C)C)cc1]

Racemic mixture Example 1131, (±)-3-(4-(diisobutylamino)-5-(3-(4-ethoxyphenyl)ureido)-2-fluorophenyl)pentanoic acid (26 mg), was purified by chiral SFC (85/15 $CO_2$/MeOH mobile phase, Chiral AD 25×3 cm, 5 μm column, 85 ml/min, detector wavelength=220 nm). Concentration of the appropriate (earlier eluting) fractions afforded Example 1132 (10.7 mg) assigned as 3-(4-(diisobutylamino)-5-(3-(4-ethoxyphenyl)ureido)-2-fluorophenyl)pentanoic acid (Enantiomer 1). $^1$H NMR (500 MHz, DMSO-$d_6$) δ 9.19 (s, 1H), 7.80 (d, J=8.2 Hz, 1H), 7.62 (s, 1H), 7.33 (d, J=8.8 Hz, 2H), 6.99 (d, J=11.9 Hz, 1H), 6.85 (d, J=8.9 Hz, 2H), 3.97 (q, J=6.9 Hz, 2H), 3.20-3.09 (m, 1H), 2.68-2.59 (m, 4H), 2.58-2.54 (m, 2H), 1.70-1.58 (m, 3H), 1.54-1.43 (m, 1H), 1.30 (t, J=6.9 Hz, 3H), 0.87-0.78 (m, 12H), 0.73 (t, J=7.3 Hz, 3H). MS(ES): m/z=502 [M+H]$^+$. T$_r$=2.18 min (Method C). Concentration of the later eluting fractions afforded Example 1133 (11.0 mg) assigned as 3-(4-(diisobutylamino)-5-(3-(4-ethoxyphenyl)ureido)-2-fluorophenyl)pentanoic acid (Enantiomer 2). $^1$H NMR (500 MHz, DMSO-$d_6$) δ 9.19 (s, 1H), 7.80 (d, J=8.1 Hz, 1H), 7.62 (s, 1H), 7.33 (d, J=8.8 Hz, 2H), 6.99 (d, J=11.9 Hz, 1H), 6.85 (d, J=8.9 Hz, 2H), 3.97 (q, J=7.0 Hz, 2H), 3.19-3.09 (m, 1H), 2.68-2.59 (m, 4H), 2.59-2.53 (m, 2H), 1.70-1.58 (m, 3H), 1.54-1.42 (m, 1H), 1.30 (t, J=6.9 Hz, 3H), 0.87-0.77 (m, 12H), 0.73 (t, J=7.3 Hz, 3H). MS(ES): m/z=502 [M+H]$^+$. T$_r$=2.18 min (Method C).

Example 1134

(±)-3-(5-(3-(Benzo[d][1,3]dioxol-5-yl)ureido)-4-(diisobutylamino)-2-fluorophenyl)pentanoic acid

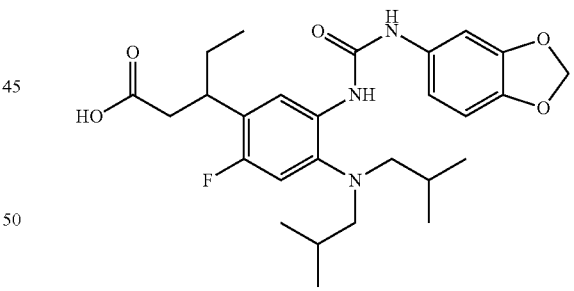

Example 1134 (27.9 mg, 77% yield) was prepared following a procedure analogous to that for the synthesis of Example 1131, except that 5-isocyanato-benzo[d][1,3]dioxole (18 mg, 0.11 mmol) was used instead of 1-ethoxy-4-isocyanatobenzene. $^1$H NMR (500 MHz, DMSO-$d_6$) δ 9.28 (s, 1H), 7.78 (d, J=8.1 Hz, 1H), 7.64 (s, 1H), 7.21-7.16 (m, 1H), 6.99 (d, J=11.9 Hz, 1H), 6.86-6.80 (m, 1H), 6.79-6.73 (m, 1H), 5.96 (s, 2H), 3.19-3.09 (m, 1H), 2.69-2.59 (m, 4H), 2.57-2.52 (m, 2H), 1.69-1.59 (m, 3H), 1.53-1.42 (m, 1H), 0.85-0.80 (m, 12H), 0.72 (t, J=7.3 Hz, 3H). MS(ES): m/z=502 [M+H]$^+$. T$_r$=2.06 min (Method C).

Example 1135

3-(5-(3-(Benzo[d][1,3]dioxol-5-yl)ureido)-4-(diisobutylamino)-2-fluorophenyl)pentanoic acid Enantiomer 1, Absolute Stereochemistry not Assigned

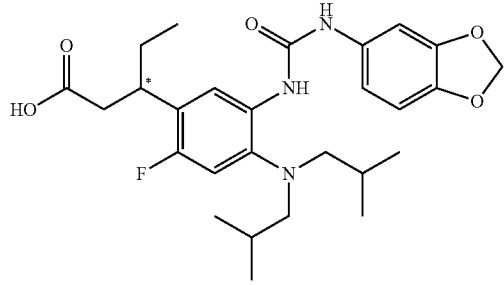 [SMILES: CCC(CC(=O)O)c1cc(NC(=O)Nc2ccc3c(c2)OCO3)c(N(CC(C)C)CC(C)C)cc1F]

and

Example 1136

3-(5-(3-(Benzo[d][1,3]dioxol-5-yl)ureido)-4-(diisobutylamino)-2-fluorophenyl)pentanoic acid Enantiomer 2, Absolute Stereochemistry not Assigned

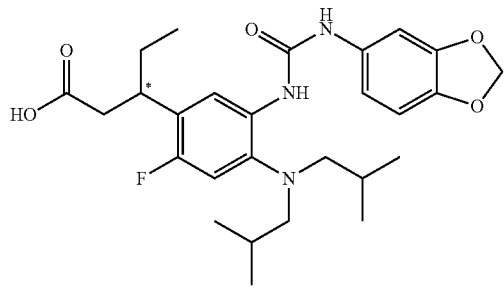 [SMILES: CCC(CC(=O)O)c1cc(NC(=O)Nc2ccc3c(c2)OCO3)c(N(CC(C)C)CC(C)C)cc1F]

Racemic mixture Example 1134, (±)-3-(5-(3-(benzo[d][1,3]dioxol-5-yl)ureido)-4-(diisobutylamino)-2-fluorophenyl)pentanoic acid (27 mg), was purified by chiral SFC (80/20 CO$_2$/MeOH mobile phase, Chiral AD-H 25×3 cm, 5 µm column, 100 ml/min, detector wavelength=220 nm). Concentration of the appropriate (earlier eluting) fractions afforded Example 1135 (10.8 mg) assigned as 3-(5-(3-(benzo[d][1,3]dioxol-5-yl)ureido)-4-(diisobutylamino)-2-fluorophenyl)pentanoic acid (Enantiomer 1). $^1$H NMR (500 MHz, DMSO-d$_6$) δ 9.28 (s, 1H), 7.77 (d, J=8.1 Hz, 1H), 7.63 (s, 1H), 7.18 (d, J=1.6 Hz, 1H), 6.99 (d, J=11.9 Hz, 1H), 6.86-6.80 (m, 1H), 6.75 (dd, J=8.3, 1.7 Hz, 1H), 5.96 (s, 2H), 3.21-3.05 (m, 1H), 2.68-2.60 (m, 4H), 2.58-2.53 (m, 2H), 1.70-1.59 (m, 3H), 1.54-1.42 (m, 1H), 0.87-0.78 (m, 12H), 0.72 (t, J=7.3 Hz, 3H). MS(ES): m/z=502 [M+H]$^+$. T$_r$=2.05 min (Method C). Concentration of the later eluting fractions afforded Example 1136 (10.9 mg) assigned as 3-(5-(3-(benzo[d][1,3]dioxol-5-yl)ureido)-4-(diisobutylamino)-2-fluorophenyl)pentanoic acid (Enantiomer 2). $^1$H NMR (500 MHz, DMSO-d$_6$) δ 9.28 (s, 1H), 7.76 (d, J=8.2 Hz, 1H), 7.63 (s, 1H), 7.17 (d, J=1.8 Hz, 1H), 6.98 (d, J=11.9 Hz, 1H), 6.87-6.80 (m, 1H), 6.75 (dd, J=8.4, 1.8 Hz, 1H), 5.95 (s, 2H), 3.19-3.09 (m, 1H), 2.67-2.59 (m, 4H), 2.58-2.52 (m, 2H), 1.69-1.56 (m, 3H), 1.53-1.40 (m, 1H), 0.86-0.77 (m, 12H), 0.72 (t, J=7.3 Hz, 3H). MS(ES): m/z=502 [M+H]$^+$. T$_r$=2.05 min (Method C).

Example 1137

(±)-3-(4-(Diisobutylamino)-5-(3-(4-ethoxy-2-fluorophenyl)ureido)-2-fluorophenyl)pentanoic acid

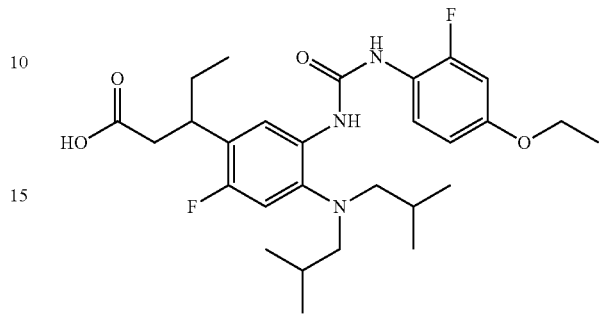

To a homogeneous mixture of (±)-methyl 3-(5-amino-4-(diisobutylamino)-2-fluorophenyl)pentanoate (compound 1128D, 25.4 mg, 0.07 mmol) in THF (1 mL), at room temperature in a sealable vial, was added 4-nitrophenyl carbonochloridate (25 mg, 0.12 mmol). The resulting mixture was stirred at ambient temperature for one hour before 4-ethoxy-2-fluoroaniline, HCl (41 mg, 0.22 mmol) and TEA (0.10 mL, 0.72 mmol) were added. The mixture was then stirred at 50° C. for 16 hours then at room temperature for two hours before MeOH (0.5 mL) was added to the reaction vial followed by LiOH (aq) (1M solution, 0.5 mL, 0.50 mmol). After 1.5 hours, the reaction was treated with LiOH (aq) (1M solution, 0.5 mL, 0.50 mmol) and stirred for 20 hours before being treated with acetic acid (0.06 mL, 1.05 mmol). The mixture was diluted with DMSO then purified by preparative RP HPLC (MeCN/H$_2$O gradient+10-mM NH$_4$OAc) to afford Example 1137 (22.6 mg, 60% yield). $^1$H NMR (500 MHz, DMSO-d$_6$) δ 8.97 (s, 1H), 7.80 (s, 1H), 7.75-7.63 (m, 2H), 6.96 (d, J=11.9 Hz, 1H), 6.86 (dd, J=12.7, 2.5 Hz, 1H), 6.76-6.66 (m, 1H), 4.00 (q, J=6.9 Hz, 2H), 3.19-3.06 (m, 1H), 2.72-2.58 (m, 4H), 2.54-2.51 (m, 2H), 1.71-1.59 (m, 3H), 1.54-1.40 (m, 1H), 1.31 (t, J=6.9 Hz, 3H), 0.89-0.76 (m, 12H), 0.72 (t, J=7.3 Hz, 3H). MS(ES): m/z=520 [M+H]$^+$, T$_r$=2.25 min (Method C).

Example 1138

3-(4-(Diisobutylamino)-5-(3-(4-ethoxy-2-fluorophenyl)ureido)-2-fluorophenyl)pentanoic acid Enantiomer 1, Absolute Stereochemistry not Assigned

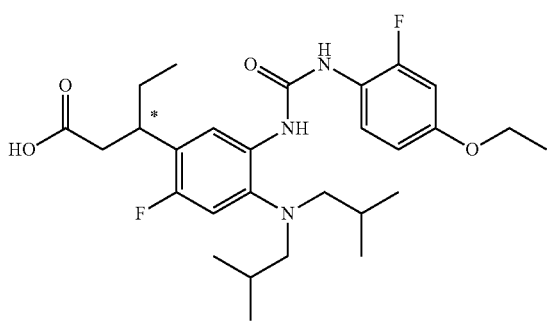 [SMILES: CCOc1ccc(NC(=O)Nc2cc(C(CC)CC(=O)O)c(F)cc2N(CC(C)C)CC(C)C)c(F)c1]

Example 1139

3-(4-(Diisobutylamino)-5-(3-(4-ethoxy-2-fluorophenyl)ureido)-2-fluorophenyl)pentanoic acid Enantiomer 2, Absolute Stereochemistry not Assigned

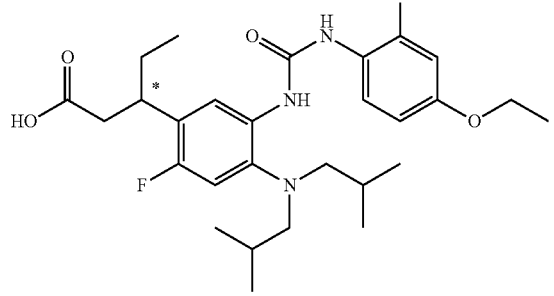

Racemic mixture Example 1137, (±)-3-(4-(diisobutylamino)-5-(3-(4-ethoxy-2-fluorophenyl)ureido)-2-fluorophenyl)pentanoic acid (22 mg), was purified by chiral SFC (85/15 $CO_2$/MeOH mobile phase, Chiral AD-H 25×3 cm, 5 μm column, 100 ml/min, detector wavelength=220 nm). Concentration of the appropriate (earlier eluting) fractions afforded Example 1138 (9.1 mg) assigned as 3-(4-(diisobutylamino)-5-(3-(4-ethoxy-2-fluorophenyl)ureido)-2-fluorophenyl)pentanoic acid (Enantiomer 1). $^1$H NMR (500 MHz, DMSO-$d_6$) δ 8.97 (s, 1H), 7.80 (s, 1H), 7.75-7.63 (m, 2H), 6.97 (d, J=11.9 Hz, 1H), 6.86 (dd, J=12.8, 2.6 Hz, 1H), 6.75-6.69 (m, 1H), 4.00 (q, J=7.0 Hz, 2H), 3.22-3.06 (m, 1H), 2.69-2.60 (m, 4H), 2.58-2.53 (m, 2H), 1.70-1.58 (m, 3H), 1.52-1.41 (m, 1H), 1.31 (t, J=6.9 Hz, 3H), 0.85-0.79 (m, 12H), 0.72 (t, J=7.3 Hz, 3H). MS(ES): m/z=520 [M+H]$^+$. $T_r$=2.24 min (Method C). Concentration of the later eluting fractions afforded Example 1139 (7.6 mg) assigned as 3-(4-(diisobutylamino)-5-(3-(4-ethoxy-2-fluorophenyl)ureido)-2-fluorophenyl)pentanoic acid (Enantiomer 2). $^1$H NMR (500 MHz, DMSO-$d_6$) δ 8.97 (s, 1H), 7.80 (s, 1H), 7.75-7.63 (m, 2H), 6.97 (d, J=11.9 Hz, 1H), 6.86 (dd, J=12.7, 2.6 Hz, 1H), 6.75-6.69 (m, 1H), 4.00 (q, J=7.0 Hz, 2H), 3.19-3.09 (m, 1H), 2.70-2.60 (m, 4H), 2.57-2.53 (m, 2H), 1.70-1.58 (m, 3H), 1.52-1.42 (m, 1H), 1.31 (t, J=6.9 Hz, 3H), 0.86-0.78 (m, 12H), 0.72 (t, J=7.3 Hz, 3H). MS(ES): m/z=520 [M+H]$^+$. $T_r$=2.28 min (Method C).

Example 1140

(±)-3-(4-(Diisobutylamino)-2-fluoro-5-(3-(2-methoxypyrimidin-5-yl)ureido)phenyl)pentanoic acid

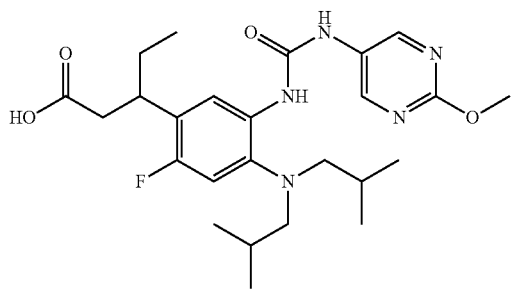 [SMILES: CCC(CC(=O)O)c1cc(NC(=O)Nc2cnc(OC)nc2)c(N(CC(C)C)CC(C)C)cc1F]

Example 1140 (25.7 mg, 73% yield) was prepared following a procedure analogous to that for the synthesis of Example 1137, except that 2-methoxypyrimidin-5-amine (27.1 mg, 0.22 mmol) was used instead of 4-ethoxy-2-fluoroaniline, HCl. $^1$H NMR (500 MHz, DMSO-$d_6$) δ 9.55 (s, 1H), 8.66 (s, 2H), 7.85 (s, 1H), 7.80 (d, J=8.1 Hz, 1H), 7.03 (d, J=11.9 Hz, 1H), 3.88 (s, 3H), 3.20-3.08 (m, 1H), 2.75-2.61 (m, 4H), 2.58-2.54 (m, 2H), 1.71-1.59 (m, 3H), 1.54-1.41 (m, 1H), 0.89-0.80 (m, 12H), 0.72 (t, J=7.3 Hz, 3H). MS(ES): m/z=490 [M+H]$^+$. $T_r$=1.82 min (Method C).

Example 1141

3-(4-(Diisobutylamino)-2-fluoro-5-(3-(2-methoxypyrimidin-5-yl)ureido)phenyl)pentanoic acid Enantiomer 1, Absolute Stereochemistry not Assigned

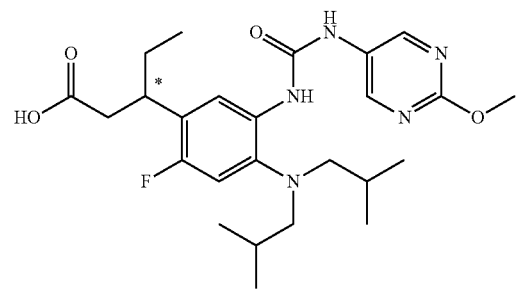 [SMILES: CCC(CC(=O)O)c1cc(NC(=O)Nc2cnc(OC)nc2)c(N(CC(C)C)CC(C)C)cc1F]

and

Example 1142

3-(4-(Diisobutylamino)-2-fluoro-5-(3-(2-methoxypyrimidin-5-yl)ureido)phenyl)pentanoic acid Enantiomer 2, Absolute Stereochemistry not Assigned

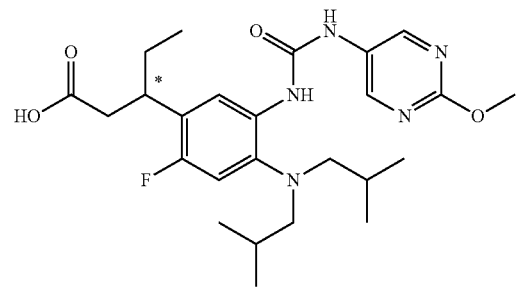 [SMILES: CCC(CC(=O)O)c1cc(NC(=O)Nc2cnc(OC)nc2)c(N(CC(C)C)CC(C)C)cc1F]

Racemic mixture Example 1140, (±)-3-(4-(diisobutylamino)-2-fluoro-5-(3-(2-methoxypyrimidin-5-yl)ureido)phenyl)pentanoic acid (25 mg), was purified by chiral SFC (90/10 $CO_2$/MeOH mobile phase, Chiral AD-H 25×3 cm, 5 μm column, 100 ml/min, detector wavelength=220 nm). Concentration of the appropriate (earlier eluting) fractions afforded Example 1141 (8.8 mg) assigned as 3-(4-(diisobutylamino)-2-fluoro-5-(3-(2-methoxypyrimidin-5-yl)ureido)phenyl)pentanoic acid (Enantiomer 1). $^1$H NMR (500 MHz, DMSO-$d_6$) δ 9.55 (s, 1H), 8.64 (s, 2H), 7.84 (s, 1H), 7.78 (d, J=8.0 Hz, 1H), 7.02 (d, J=11.9 Hz, 1H), 3.87 (s, 3H), 3.18-3.08 (m, 1H), 2.70-2.59 (m, 4H), 2.57-2.54 (m, 2H), 1.70-1.56 (m, 3H), 1.53-1.40 (m, 1H), 0.86-0.80 (m, 12H), 0.71 (t, J=7.3 Hz, 3H). MS(ES): m/z=490 [M+H]$^+$. T$_r$=1.81 min (Method C). Concentration of the later eluting fractions afforded Example 1142 (9.3 mg) assigned as 3-(4-(diisobutylamino)-2-fluoro-5-(3-(2-methoxypyrimidin-5-yl)ureido)phenyl)pentanoic acid (Enantiomer 2). $^1$H NMR (500 MHz, DMSO-d$_6$) δ 9.55 (s, 1H), 8.64 (s, 2H), 7.83 (s, 1H), 7.77 (d, J=7.9 Hz, 1H), 7.02 (d, J=11.9 Hz, 1H), 3.87 (s, 3H), 3.20-3.07 (m, 1H), 2.70-2.60 (m, 4H), 2.58-2.54 (m, 2H), 1.70-1.57 (m, 3H), 1.54-1.40 (m, 1H), 0.87-0.77 (m, 12H), 0.71 (t, J=7.1 Hz, 3H). MS(ES): m/z=490 [M+H]$^+$. T$_r$=1.81 min (Method C).

Example 1143

(±)-3-(4-((R)-2-(Methoxymethyl)pyrrolidin-1-yl)-3-(2-(p-tolyl)acetamido)phenyl)pentanoic acid

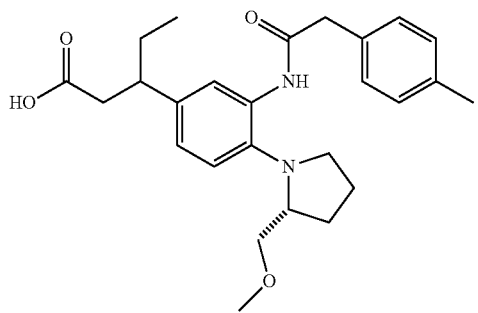 [SMILES: CCC(CC(=O)O)c1ccc(N2CCC[C@@H]2COC)c(NC(=O)Cc2ccc(C)cc2)c1]

1143A. (R)-1-(4-Bromo-2-nitrophenyl)-2-(methoxymethyl)pyrrolidine

To a homogeneous mixture of 4-bromo-1-fluoro-2-nitrobenzene (0.35 mL, 2.88 mmol) in anhydrous NMP (0.2 mL), at room temperature in a sealable vial, was added (R)-2-(methoxymethyl)pyrrolidine followed by TEA (0.44 mL, 3.16 mmol). The vial was sealed and the mixture was stirred at 100° C. for 17.5 hours, then cooled to room temperature. The crude reaction mixture was purified on an Isco CombiFlash System: REDISEP® normal phase silica flash column (24 g), detection wavelength=254 nm, run time=30 min. Mobile Phase: (5 min at 100% hexane then 20 min gradient from 0-50% EtOAc in hexane). Concentration of the appropriate fractions afforded (R)-1-(4-bromo-2-nitrophenyl)-2-(methoxymethyl)pyrrolidine (0.91 g, 100% yield) as an orange oil. NMR (400 MHz, CDCl$_3$) δ 7.89 (d, J=2.4 Hz, 1H), 7.43 (dd, J=9.2, 2.4 Hz, 1H), 7.01 (d, J=9.3 Hz, 1H), 4.04 (dd, J=7.0, 4.3 Hz, 1H), 3.53-3.43 (m, 2H), 3.31-3.25 (m, 4H), 2.77-2.67 (m, 1H), 2.35-2.23 (m, 1H), 2.03-1.94 (m, 1H), 1.91-1.71 (m, 2H). MS(ES): m/z=315 [M+H]$^+$, T$_r$=1.07 min (Method A).

1143B. (R)-1-(4-(5,5-Dimethyl-1,3,2-dioxaborinan-2-yl)-2-nitrophenyl)-2-(methoxymethyl)pyrrolidine A mixture of (R)-1-(4-bromo-2-nitrophenyl)-2-(methoxymethyl)pyrrolidine (0.66 g, 2.09 mmol), 5,5,5',5'-tetramethyl-2,2'-bi(1,3,2-dioxaborinane) (0.63 g, 2.79 mmol) and potassium acetate (0.62 g, 6.28 mmol) in DMSO (4 ml), at room temperature in a sealable flask, was purged with argon for 20 minutes before PdCl$_2$ (dppf).CH$_2$Cl$_2$ Adduct (0.08 g, 0.11 mmol) was added, the flask was sealed and the reaction heated at 80° C. for 2 hours. The cooled reaction mixture was partitioned between EtOAc and water, the layers were separated and the aqueous layer was extracted twice more with EtOAc. These organic extracts were combined with the original organic layer and were washed with brine, dried (MgSO$_4$), filtered and concentrated in vacuo to afford an oil which was purified on an Isco CombiFlash System: REDISEP® normal phase silica flash column (40 g), detection wavelength=254 nm, run time=40 min. Mobile Phase: (5 min at 100% hexane then 30 min gradient from 0-100% EtOAc in hexane). Concentration of the appropriate fractions afforded (R)-1-(4-(5,5-dimethyl-1,3,2-dioxaborinan-2-yl)-2-nitrophenyl)-2-(methoxymethyl)pyrrolidine (0.73 g, 100% yield) as a gold-orange oil. $^1$H NMR (400 MHz, CDCl$_3$) δ 8.17 (d, J=1.6 Hz, 1H), 7.73 (dd, J=8.6, 1.6 Hz, 1H), 7.02 (d, J=8.7 Hz, 1H), 4.11-4.05 (m, 1H), 3.74 (s, 4H), 3.58 (dd, J=9.8, 3.7 Hz, 1H), 3.49 (d, J=6.1 Hz, 1H), 3.30 (s, 3H), 3.27 (dd, J=9.7, 6.5 Hz, 1H), 2.82-2.73 (m, 1H), 2.36-2.23 (m, 1H), 2.03-1.68 (m, 3H), 1.01 (s, 6H). Expected product appears as corresponding boronic acid under acidic MS conditions: MS(ES): m/z=281 [M+H]$^+$, T$_r$=0.77 min (Method A).

1143C. Methyl 3-(4-((R)-2-(methoxymethyl)pyrrolidin-1-yl)-3-nitrophenyl)pentanoate (Mixture of Diastereomers)

To a homogeneous mixture of (R)-1-(4-(5,5-dimethyl-1,3,2-dioxaborinan-2-yl)-2-nitrophenyl)-2-(methoxymethyl)pyrrolidine (0.73 g, 2.09 mmol) in anhydrous dioxane (4 ml), in a sealable tube at ambient temperature, was added (E)-methyl pent-2-enoate (0.72 g, 6.28 mmol) followed by NaOH (aq) (1M solution, 1.9 ml, 1.90 mmol). The resulting mixture sequentially evacuated then purged with nitrogen for a total of three cycles before chloro(1,5-cyclooctadiene)rhodium(I) dimer (0.052 g, 0.11 mmol) was added. The resulting mixture was again sequentially evacuated then purged with nitrogen for a total of three cycles, before the tube was capped and the reaction warmed to 50° C. After 18 hours, the reaction was cooled to room temperature, then quenched with acetic acid (0.12 ml, 2.09 mmol) and stirred for 5 minutes before being partitioned between EtOAc and water. The layers were separated and the aqueous layer was extracted again with EtOAc. The organic extracts were combined, washed twice with water then once with brine before being concentrated in vacuo to afford an oil. The crude product was purified on an Isco CombiFlash System: REDISEP® normal phase silica flash column (40 g), detection wavelength=254 nm, run time=25 min, flow rate=40 mL/min. Mobile Phase: (5 min at 100% hexane then 15 min gradient from 0-100% EtOAc in hexane). Concentration of the appropriate fractions afforded the title compound as a mixture of diastereomers (0.56 g, 76% yield) as an orange oil. $^1$H NMR (400 MHz, CDCl$_3$) δ 7.57 (d, J=2.2 Hz, 1H), 7.21 (dd, J=8.7, 2.2 Hz, 1H), 7.03 (d, J=8.8 Hz, 1H), 4.03 (dd, J=7.4, 3.7 Hz, 1H), 3.61 (s, 3H), 3.59-3.53 (m, 1H), 3.53-3.44 (m, 1H), 3.30 (s, 3H), 3.28-3.20 (m, 1H), 3.02-2.91 (m, 1H), 2.75-2.68 (m, 1H), 2.67-2.59 (m, 1H), 2.57-2.48 (m, 1H), 2.34-2.25 (m, 1H), 2.01-1.92 (m, 1H), 1.86-1.76 (m, 1H), 1.72-1.64 (m, 1H), 1.62-1.51 (m, 2H), 0.84-0.78 (m, 3H). MS(ES): m/z=351 [M+H]$^+$, T$_r$=1.04 min (Method A).

1143D. Methyl 3-(3-amino-4-((R)-2-(methoxymethyl)pyrrolidin-1-yl)phenyl)pentanoate (Mixture of Diastereomers)

To a sealable hydrogen stirring flask, charged with the diastereomeric mixture methyl 3-(4-((R)-2-(methoxymethyl)-pyrrolidin-1-yl)-3-nitrophenyl)pentanoate (1143C, 0.56 g, 1.59 mmol) and 10% palladium on carbon (0.17 g, 0.16 mmol) and under a flow of nitrogen, was carefully added EtOAc (10 mL). The resulting mixture was sequentially evacuated then purged with nitrogen before the flask was pressured to 40 psi of hydrogen and stirred at ambient temperature. After three hours, the flask was sequentially evacuated then purged with nitrogen three times before the reaction mixture was filtered through a pad of CELITE® which was then thoroughly rinsed with EtOAc. The combined filtrates were concentrated in vacuo to afford the title compound as a mixture of diastereomers (445.6 mg, 87% yield) which was used without further purification. $^1$H NMR (400 MHz, CDCl$_3$) δ 7.00 (d, J=7.8 Hz, 1H), 6.57-6.50 (m, 2H), 4.12 (br. s., 2H), 3.60 (s, 3H), 3.55-3.45 (m, 1H), 3.40-3.33 (m, 1H), 3.31-3.27 (m, 1H), 3.26 (s, 3H), 3.15-3.07 (m, 1H), 2.90-2.82 (m, 1H), 2.79-2.71 (m, 1H), 2.59-2.52 (m, 2H), 2.14 (s, 1H), 1.95-1.84 (m, 2H), 1.83-1.73 (m, 1H), 1.68-1.58 (m, 1H), 1.58-1.52 (m, 1H), 0.79 (t, J=7.3 Hz, 3H). MS(ES): m/z=321 [M+H]$^+$, T$_r$=0.68 min (Method A).

Example 1143 3-(4-((R)-2-(Methoxymethyl)pyrrolidin-1-yl)-3-(2-(p-tolyl)acetamido)phenyl)pentanoic acid (Mixture of Diastereomers)

To the diastereomeric mixture of methyl 3-(3-amino-4-((R)-2-(methoxymethyl)pyrrolidin-1-yl)phenyl)pentanoate (1143D, 0.05 g, 0.15 mmol) in anhydrous THF (1.0 mL), at ambient temperature in a sealable vial, was added 2-(p-tolyl) acetic acid (0.03 g, 0.19 mmol) followed by BOP (0.08 g, 0.19 mmol) and TEA (0.1 mL, 0.72 mmol). The vial was capped and the mixture was stirred at ambient temperature for 42 hours before MeOH (0.5 mL) then NaOH (aq) (1M solution, 0.8 mL, 0.80 mmol) were added. The mixture was stirred at ambient temperature for 18 hours before being treated with acetic acid (until pH 5-6 on BDH pH 0-14 test strips). The mixture was partitioned between EtOAc and brine. The layers were separated and the aqueous layer was extracted once more with EtOAc. The organic extracts were combined and concentrated in vacuo to afford a residue which was diluted with DMF then purified by preparative RP HPLC (MeCN/H$_2$O gradient+10-mM NH$_4$OAc) to afford Example 1143 (53 mg; 77% yield). $^1$H NMR (500 MHz, DMSO-d$_6$) δ 8.82 (s, 1H), 7.99 (s, 1H), 7.28-7.24 (m, 2H), 7.22-7.19 (m, 2H), 7.13 (d, J=8.2 Hz, 1H), 6.85 (d, J=7.2 Hz, 1H), 3.65 (s, 2H), 3.45-3.33 (m, 1H), 3.07 (s, 3H), 2.91-2.62 (m, 4H), 2.58-2.52 (m, 1H), 2.40-2.36 (m, 1H), 2.31 (s, 3H), 2.00-1.91 (m, 1H), 1.77-1.68 (m, 1H), 1.65-1.55 (m, 2H), 1.50-1.40 (m, 2H), 1.24-1.21 (m, 1H), 0.69 (t, J=7.2 Hz, 3H). MS(ES): m/z=439 [M+H]$^+$. T$_r$=1.86 min (Method C).

Example 1144

3-(4-((R)-2-(Methoxymethyl)pyrrolidin-1-yl)-3-(2-(p-tolyl)acetamido)phenyl)pentanoic acid Enantiomer 1, Absolute Stereochemistry not Assigned

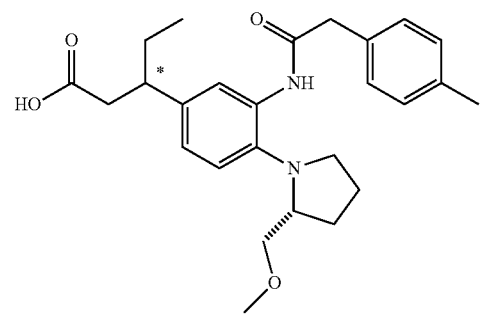 [SMILES: CCC(CC(=O)O)c1ccc(N2CCC[C@@H]2COC)c(NC(=O)Cc2ccc(C)cc2)c1]

and

Example 1145

3-(4-((R)-2-(Methoxymethyl)pyrrolidin-1-yl)-3-(2-(p-tolyl)acetamido)phenyl)pentanoic acid Enantiomer 2, Absolute Stereochemistry not Assigned

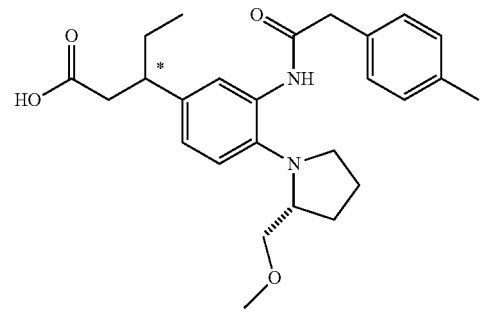 [SMILES: CCC(CC(=O)O)c1ccc(N2CCC[C@@H]2COC)c(NC(=O)Cc2ccc(C)cc2)c1]

Diastereomeric mixture Example 1143, 3-(4-((R)-2-(methoxymethyl)pyrrolidin-1-yl)-3-(2-(p-tolyl)acetamido) phenyl)pentanoic acid (35 mg), was purified by chiral SFC (85/15 CO$_2$/IPA mobile phase, Chiral AS 25×3 cm, 5 μm column, 85 ml/min, detector wavelength=220 nm). Concentration of the appropriate (earlier eluting) fractions afforded Example 1144 (17.6 mg) assigned as 3-(4-((R)-2-(methoxymethyl)pyrrolidin-1-yl)-3-(2-(p-tolyl)acetamido) phenyl)pentanoic acid (Enantiomer 1). $^1$H NMR (500 MHz, DMSO-d$_6$) δ 8.81 (s, 1H), 8.00 (s, 1H), 7.29-7.24 (m, 2H), 7.24-7.18 (m, 2H), 7.13 (d, J=8.2 Hz, 1H), 6.85 (d, J=8.0 Hz, 1H), 3.66 (s, 2H), 3.54-3.24 (m, 1H), 3.07 (s, 3H), 2.93-2.66 (m, 4H), 2.60-2.55 (m, 1H), 2.42-2.35 (m, 1H), 2.31 (s, 3H), 2.01-1.91 (m, 1H), 1.78-1.67 (m, 1H), 1.67-1.55 (m, 2H), 1.51-1.39 (m, 2H), 1.27-1.20 (m, 1H), 0.69 (t, J=7.3 Hz, 3H). MS(ES): m/z=439 [M+H]$^+$. T$_r$=1.75 min (Method C). Concentration of the later eluting fractions afforded Example 1145 (17.2 mg) assigned as 3-(4-((R)-2-

(methoxymethyl)pyrrolidin-1-yl)-3-(2-O-tolyl)acetamido) phenyl)pentanoic acid (Enantiomer 2). $^1$H NMR (500 MHz, DMSO-$d_6$) δ 8.81 (s, 1H), 7.99 (s, 1H), 7.30-7.24 (m, 2H), 7.24-7.18 (m, 2H), 7.13 (d, J=8.1 Hz, 1H), 6.85 (d, J=8.0 Hz, 1H), 3.66 (s, 2H), 3.52-3.24 (m, 1H), 3.07 (s, 3H), 2.91-2.67 (m, 4H), 2.58-2.55 (m, 1H), 2.40-2.33 (m, 1H), 2.31 (s, 3H), 2.01-1.91 (m, 1H), 1.78-1.69 (m, 1H), 1.65-1.57 (m, 2H), 1.49-1.40 (m, 2H), 1.26-1.19 (m, 1H), 0.69 (t, J=7.3 Hz, 3H). MS(ES): m/z=439 [M+H]$^+$. $T_r$=1.75 min (Method C).

Example 1146

Enantiomer 1 and Enantiomer 2

Example 1146 Enantiomer 1: 3-(4-(tert-Butyl (methyl)amino)-3-(2-(p-tolyl)acetamido)phenyl)-4-methylpentanoic acid

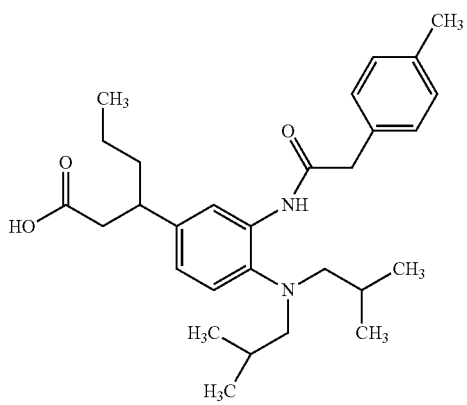 [SMILES: CCCC(CC(=O)O)c1ccc(N(CC(C)C)CC(C)C)c(NC(=O)Cc2ccc(C)cc2)c1]

Example 1146 Enantiomer 2: 3-(4-(tert-Butyl (methyl)amino)-3-(2-(p-tolyl)acetamido)phenyl)-4-methylpentanoic acid

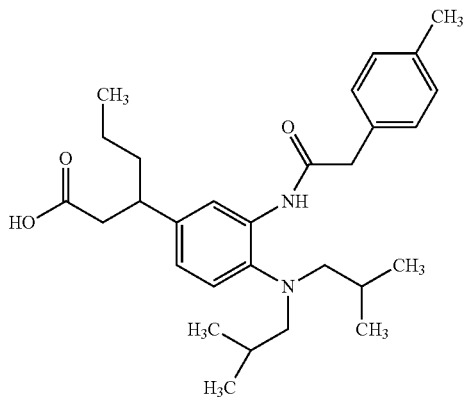 [SMILES: CCCC(CC(=O)O)c1ccc(N(CC(C)C)CC(C)C)c(NC(=O)Cc2ccc(C)cc2)c1]

1146A (+/−)-Methyl 3-(4-(diisobutylamino)-3-nitrophenyl)hexanoate

A reaction vial was charged with 4-(5,5-dimethyl-1,3,2-dioxaborinan-2-yl)-N,N-diisobutyl-2-nitroaniline (337 mg, 0.930 mmol) (WO 14/150677). This material was dissolved in dry dioxane (3 mL). (E)-Methyl hex-2-enoate (358 mg, 2.79 mmol) and sodium hydroxide (1 N solution, 837 µl, 0.837 mmol) were then added. The vial was subjected to three cycles of vacuum/nitrogen purge. Chloro(1,5-cyclooctadiene)rhodium(I) dimer (22.93 mg, 0.047 mmol) was added and vacuum/nitrogen purge repeated. The reaction was then warmed to 50° C. and allowed to stir overnight. The cooled reaction was then quenched with acetic acid (47.9 µl, 0.837 mmol) and applied to a flash silica gel column. The column was eluted with 25% ether in hexanes. The chromatography achieved only partial separation. The material was further purified on an 80 g Isco silica gel column eluting with 0-25% ethyl acetate in hexanes. Evaporation of the appropriate fractions gave methyl 3-(4-(diisobutylamino)-3-nitrophenyl)hexanoate (226 mg, 0.597 mmol, 64.2% yield) as an orange oil. $^1$H NMR (400 MHz, DMSO-$d_6$) δ7.53 (d, J=2.1 Hz, 1H), 7.41-7.32 (m, 1H), 7.30-7.25 (m, 1H), 3.49 (s, 3H), 3.07-2.94 (m, 1H), 2.84 (d, J=7.2 Hz, 4H), 2.67 (dd, J=15.4, 6.6 Hz, 1H), 2.61-2.53 (m, 1H), 1.78 (dquin, J=13.4, 6.7 Hz, 2H), 1.62-1.45 (m, 2H), 1.21-1.00 (m, 2H), 0.82 (t, J=7.2 Hz, 3H), 0.78 (d, J=6.5 Hz, 12H).

1146B. (+/−)-Methyl 3-(3-amino-4-(diisobutylamino)phenyl)hexanoate

A Parr bottle was charged with methyl 3-(4-(diisobutylamino)-3-nitrophenyl)hexanoate (226 mg, 0.597 mmol) in ethyl acetate (15 mL). 10% Pd/C (77 mg) was added and the bottle pressured to 43 psi hydrogen. After 2 hours of reaction, analysis by LCMS showed good conversion to the desired product. The reaction was passed through a syringe filter and evaporated. This diamine darkens rapidly with exposure to air and was consequently rapidly subjected to acylation without further characterization.

1146C (+/−)-3-(4-(tert-Butyl(methyl)amino)-3-(2-(p-tolyl)acetamido)phenyl)-4-methylpentanoic acid A reaction vial was charged with methyl 3-(3-amino-4-(diisobutylamino)phenyl)hexanoate (42 mg, 0.121 mmol) in THF (1 mL). 2-(p-Tolyl)acetic acid (21.72 mg, 0.145 mmol) was added followed by triethylamine (50 µL, 0.362 mmol) and BOP (64 mg, 0.145 mmol). The reaction was stirred for two days when methanol (0.3 mL) was added. A 1 N solution of sodium hydroxide (724 µl, 0.724 mmol) was added. The reaction was then stirred overnight. The reaction was neutralized with acetic acid (41.4 µl, 0.724 mmol). The reaction was concentrated under a stream of nitrogen and the redissolved in DMF (1.7 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 7-minute hold at 100% B; Flow: 20 mL/min. Fractions containing the desired product were combined and dried via centrifugal evaporation to give (+/−)-3-(4-(tert-butyl(methyl)amino)-3-(2-(p-tolyl)acetamido)phenyl)-4-methylpentanoic acid. This material was taken directly into the chiral resolution.

Example 1146 Enantiomer 1 and Enantiomer 2

Chiral separation of the racemic Example 1146C was performed under the following conditions: (Berger SFC MGII, Column: AS 25×3 cm ID, 5 µm, Flow rate: 85.0 mL/min, Mobile Phase: 92/8 CO$_2$/MeOH) to give Enantiomer 1 (14.9 mg) and Enantiomer 2 (15.5 mg).

Example 1146 Enantiomer 1: MS(ES): m/z=467 [M+H]+. T$_r$=2.39 min LCMS (Method C). $^1$H NMR (500 MHz, DMSO-d$_6$) δ 8.74 (s, 1H), 8.13 (s, 1H), 7.27-7.09 (m, 5H), 6.88 (br d, J=7.8 Hz, 1H), 3.65 (s, 2H), 2.90 (br d, J=7.0 Hz, 1H), 2.49 (br d, J=7.0 Hz, 4H), 2.44-2.33 (m, 1H), 2.28 (s, 3H), 1.62-1.38 (m, 4H), 1.17-0.99 (m, 2H), 0.84-0.72 (m, 15H) (likely a peak obscured under DMSO).

Example 1146 Enantiomer 2: MS(ES): m/z=467 [M+H]+. T$_r$=2.39 min (Method C). $^1$H NMR (500 MHz, DMSO-d$_6$) δ 8.74 (s, 1H), 8.13 (s, 1H), 7.40-7.08 (m, 5H), 6.88 (br d, J=7.9 Hz, 1H), 3.65 (s, 2H), 3.05-2.81 (m, 1H), 2.49 (br d, J=7.0 Hz, 4H), 2.43-2.35 (m, 1H), 2.28 (s, 3H), 1.61-1.39 (m, 4H), 1.16-0.99 (m, 2H), 0.87-0.72 (m, 15H) (likely a peak obscured under DMSO).

TABLE 1

The following compounds were obtained by the procedures described in Example 1004, utilizing Preparation 1004C-trans or Preparation 1004C-cis.

| Ex. No. | Structure and Name | T$_r$ (Min) | [M + H]+ | Stereochemistry |
|---|---|---|---|---|
| 1147 | 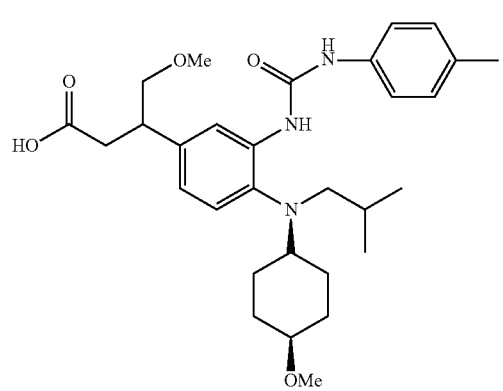<br>3-(4-(isobutyl((1r,4r)-4-methoxycyclohexyl)amino)-3-(3-(p-tolyl)ureido)phenyl)-4-methoxybutanoic acid | 1.832 B | 526.25 | racemate |
| 1148 | 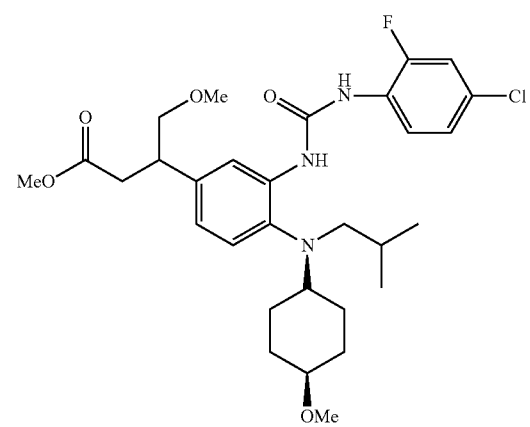<br>methyl 3-(3-(3-(4-chloro-2-fluorophenyl)ureido)-4-(isobutyl ((1r,4r)-4-methoxycyclohexyl) amino)phenyl)-4-methoxybutanoate | 2.542 B | 578.20 | racemate |

TABLE 1-continued

The following compounds were obtained by the procedures described in Example 1004, utilizing Preparation 1004C-trans or Preparation 1004C-cis.

| Ex. No. | Structure and Name | T$_r$ (Min) | [M + H]$^+$ | Stereochemistry |
|---|---|---|---|---|
| 1149 | 3-(3-(3-(4-chloro-2-fluorophenyl)ureido)-4-(isobutyl((1s,4s)-4-methoxycyclohexyl)amino)phenyl)-4-methoxybutanoic acid | 1.852 B | 564.25 | racemate |
| 1150 | 3-(3-(3-(4-chloro-2-fluorophenyl)ureido)-4-(isobutyl((1r,4r)-4-methoxycyclohexyl)amino)phenyl)-4-methoxybutanoic acid | 1.914 B | 564.20 | racemate |
| 1151 | methyl 3-(3-(3-(4-chloro-2-fluorophenyl)ureido)-4-(isobutyl((1s,4s)-4-methoxycyclohexyl)amino)phenyl)-4-methoxybutanoate | 2.523 B | 578.25 | racemate |

Example 1152

3-(4-(Cyclohexyl(isobutyl)amino)-3-fluoro-5-(3-(2-fluoro-4-methoxyphenyl)ureido)phenyl)-4-methoxybutanoic acid

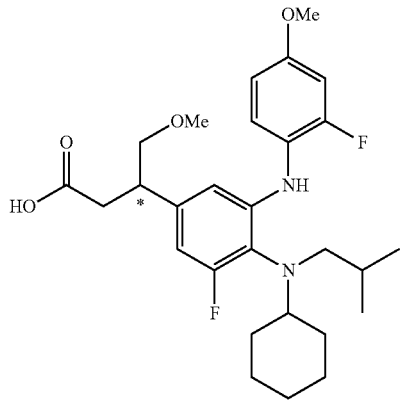 [SMILES: COCC(CC(=O)O)c1cc(F)c(N(CC(C)C)C2CCCCC2)c(Nc2ccc(OC)cc2F)c1]

1152A Enantiomers 1 and Enantiomer 2

Chiral separation of compound 986A (+/−methyl 3-(3-amino-4-(cyclohexyl(isobutyl)amino)-5-fluorophenyl)-4-methoxybutanoate) was done by SFC preparative chromatography by the following method: ($CO_2$/MeOH w 0.1% $NH_4OH$ (90/10) Mobile Phase, Lux Cellulose-4 (3×25 cm 5 µm) column, 160 ml/min, detector wavelength=220 nm) to provide:

1152A Enantiomer 1: $T_r$=2.27 min (homochiral, absolute stereochemistry was not determined), LCMS: M+H=395.7 ($T_r$=1.23 min) (Method A).

1152A Enantiomer 2: $T_r$=2.52 min. (homochiral, absolute stereochemistry was not determined), LCMS: M+H=395.7 ($T_r$=1.23 Min) (Method A).

TABLE 1

The following compounds were prepared by the method described for the preparation of Example 951 using 1152A Enantiomer 1 or Enantiomer 2 as noted in the Table 1 below (absolute stereochemistry unknown).

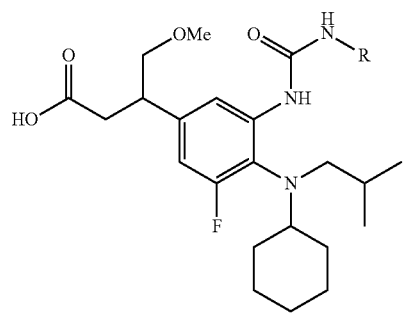

| Ex. No. | Name | R | $T_r$ (min) | $[M + H]^+$ | Stereo-chemistry | 1152 Enantiomer Used |
|---|---|---|---|---|---|---|
| 1152 | 3-(4-(cyclohexyl(isobutyl)amino)-3-fluoro-5-(3-(2-fluoro-4-methoxyphenyl)ureido)phenyl)-4-methoxybutanoic acid | 3-F, 4-OMe phenyl | 2.011 B | 548.29 | homochiral | 2 |
| 1153 | 3-(4-(cyclohexyl(isobutyl)amino)-3-(3-(4-ethoxyphenyl)ureido)-5-fluorophenyl)-4-methoxybutanoic acid | 4-OEt phenyl | 2.087 B | 544.30 | homochiral | 1 |
| 1154 | 3-(4-(cyclohexyl(isobutyl)amino)-3-fluoro-5-(3-(4-(trifluoromethoxy)phenyl)ureido)phenyl)-4-methoxybutanoic acid | 4-$OCF_3$ phenyl | 2.242 B | 584.25 | homochiral | 1 |
| 1155 | 3-(4-(cyclohexyl(isobutyl)amino)-3-fluoro-5-(3-(p-tolyl)ureido)phenyl)-4-methoxybutanoic acid | p-tolyl | 2.133 B | 514.25 | homochiral | 1 |

TABLE 1-continued

The following compounds were prepared by the method described for the preparation of Example 951 using 1152A Enantiomer 1 or Enantiomer 2 as noted in the Table 1 below (absolute stereochemistry unknown).

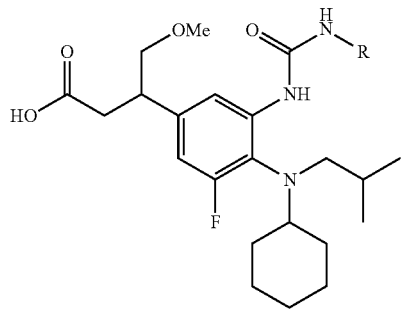

| Ex. No. | Name | R | T$_r$ (min) | [M + H]$^+$ | Stereo-chemistry | 1152 Enantiomer Used |
|---|---|---|---|---|---|---|
| 1156 | 3-(3-(3-(4-chloro-2-fluorophenyl)ureido)-4-(cyclohexyl(isobutyl)amino)-5-fluorophenyl)-4-methoxybutanoic acid | 2-F, 4-Cl phenyl | 2.187 B | 552.20 | homochiral | 1 |
| 1157 | 3-(4-(cyclohexyl(isobutyl)amino)-3-(3-(4-ethoxy-2-fluorophenyl)ureido)-5-fluorophenyl)-4-methoxybutanoic acid | 2-F, 4-OEt phenyl | 2.162 B | 562.30 | homochiral | 1 |
| 1158 | 3-(4-(cyclohexyl(isobutyl)amino)-3-fluoro-5-(3-(5-methylisoxazol-3-yl)ureido)phenyl)-4-methoxybutanoic acid | 5-methylisoxazol-3-yl | 2.411 B | 505.28 | homochiral | 1 |
| 1159 | 3-(4-(cyclohexyl(isobutyl)amino)-3-fluoro-5-(3-(2-fluoro-4-methoxyphenyl)ureido)phenyl)-4-methoxybutanoic acid | 3-F, 4-OMe phenyl | 2.040 B | 549.20 | homochiral | 1 |
| 1160 | 3-(4-(cyclohexyl(isobutyl)amino)-3-(3-(4-ethoxyphenyl)ureido)-5-fluorophenyl)-4-methoxybutanoic acid | 4-OEt phenyl | 2.172 B | 544.32 | homochiral | 2 |
| 1161 | 3-(4-(cyclohexyl(isobutyl)amino)-3-fluoro-5-(3-(p-tolyl)ureido)phenyl)-4-methoxybutanoic acid | 4-methylphenyl | 2.186 B | 514.31 | homochiral | 2 |
| 1162 | 3-(3-(3-(4-chlorophenyl)ureido)-4-(cyclohexyl(isobutyl)amino)-5-fluorophenyl)-4-methoxybutanoic acid | 4-Cl phenyl | 2.145 B | 534.25 | homochiral | 1 |

TABLE 1-continued

The following compounds were prepared by the method described for the preparation of Example 951 using 1152A Enantiomer 1 or Enantiomer 2 as noted in the Table 1 below (absolute stereochemistry unknown).

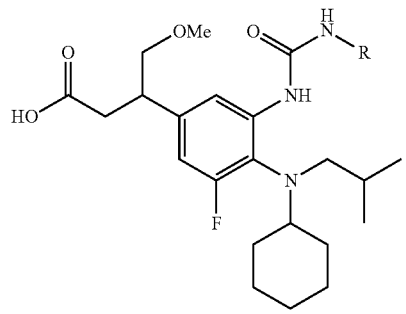

| Ex. No. | Name | R | $T_r$ (min) | $[M + H]^+$ | Stereo-chemistry | 1152 Enantiomer Used |
|---|---|---|---|---|---|---|
| 1163 | 3-(4-(cyclohexyl (isobutyl)amino)-3-fluoro-5-(3-(4-(trifluoromethoxy) phenyl)ureido) phenyl)-4-methoxybutanoic acid | 4-OCF₃-phenyl | 2.343 B | 584.27 | homochiral | 2 |
| 1164 | 3-(3-(3-(4-chloro-2-fluorophenyl)ureido)-4-(cyclohexyl (isobutyl)amino)-5-fluorophenyl)-4-methoxybutanoic acid | 2-F-4-Cl-phenyl | 2.248 B | 552.24 | homochiral | 2 |
| 1165 | 3-(4-(cyclohexyl (isobutyl)amino)-3-(3-(4-ethoxy-2-fluorophenyl)ureido)-5-fluorophenyl)-4-methoxybutanoic acid | 2-F-4-OEt-phenyl | 2.124 B | 562.31 | homochiral | 2 |
| 1166 | 3-(3-(3-(4-chlorophenyl)ureido)-4-(cyclohexyl (isobutyl)amino)-5-fluorophenyl)-4-methoxybutanoic acid | 4-Cl-phenyl | 2.546 B | 534.25 | homochiral | 2 |
| 1167 | 3-(4-(cyclohexyl (isobutyl)amino)-3-fluoro-5-(3-(5-methylisoxazol-3-yl)ureido)phenyl)-4-methoxybutanoic acid | 5-methylisoxazol-3-yl | 1.953 B | 505.25 | homochiral | 2 |

TABLE 2

The following compounds were prepared by the method described for the preparation of Example 950 using 1152A Enantiomer 1 or Enantiomer 2 as noted in the Table 2 below (absolute stereochemistry unknown).

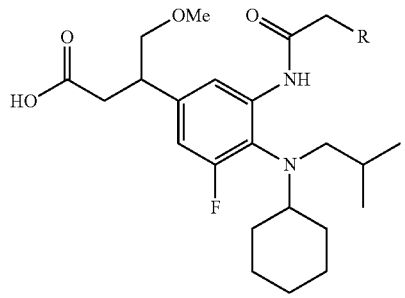

| Ex. No. | Name | R | $T_r$ (min) | $[M + H]^+$ | Stereo-chemistry | 1152 Enantiomer Used |
|---|---|---|---|---|---|---|
| 1168 | 3-(4-(cyclohexyl (isobutyl)amino)-3-(2-(4-ethoxyphenyl) acetamido)-5-fluorophenyl)-4-methoxybutanoic acid | 4-OEt-phenyl | 2.254 B | 543.30 | homochiral | 1 |
| 1169 | 3-(4-(cyclohexyl (isobutyl)amino)-3-fluoro-5-(2-(5-methylisoxazol-3-yl) acetamido)phenyl)-4-methoxybutanoic acid | 5-methylisoxazol-3-yl | 1.950 B | 504.29 | homochiral | 1 |
| 1170 | 3-(4-(cyclohexyl (isobutyl)amino)-3-fluoro-5-(2-(p-tolyl) acetamido)phenyl)-4-methoxybutanoic acid | p-tolyl | 2.324 B | 513.30 | homochiral | 1 |
| 1171 | 3-(4-(cyclohexyl (isobutyl)amino)-3-fluoro-5-(3-(5-methylisoxazol-3-yl)ureido)phenyl)-4-methoxybutanoic acid | 5-methylisoxazol-3-yl | 1.952 B | 505.28 | homochiral | 2 |
| 1172 | 3-(3-(2-(4-chloro-2-fluorophenyl) acetamido)-4-(cyclohexyl(isobutyl) amino)-5-fluorophenyl)-4-methoxybutanoic acid | 4-Cl-2-F-phenyl | 2.354 B | 551.25 | homochiral | 2 |
| 1173 | 3-(4-(cyclohexyl (isobutyl)amino)-3-(2-(4-ethoxyphenyl) acetamido)-5-fluorophenyl)-4-methoxybutanoic acid | 4-OEt-phenyl | 2.261 B | 543.30 | homochiral | 2 |
| 1174 | 3-(4-(cyclohexyl (isobutyl)amino)-3-fluoro-5-(2-(p-tolyl) acetamido)phenyl)-4-methoxybutanoic acid | p-tolyl | 2.332 B | 513.30 | homochiral | 2 |
| 1175 | 3-(3-(2-(4-chloro-2-fluorophenyl) acetamido)-4-(cyclohexyl(isobutyl) amino)-5-fluorophenyl)-4-methoxybutanoic acid | 4-Cl-2-F-phenyl | 2.354 B | 551.25 | homochiral | 1 |

Example 1176

3-(4-(Diisobutylamino)-3-fluoro-5-(3-(2-fluoro-4-methoxyphenyl)ureido)phenyl)-4-methoxybutanoic acid

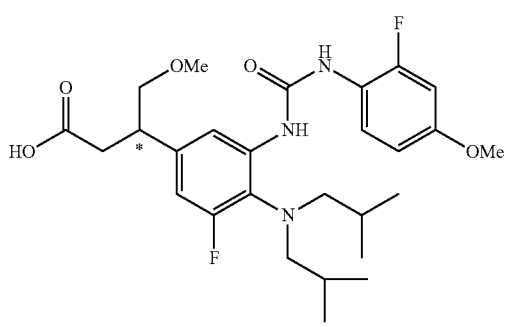 [SMILES: COCC(CC(=O)O)c1cc(F)c(N(CC(C)C)CC(C)C)c(NC(=O)Nc2ccc(OC)cc2F)c1]

1176A. 4-Bromo-2-fluoro-N,N-diisobutyl-6-nitroaniline

A neat solution of 5-bromo-1,2-difluoro-3-nitrobenzene (1.5190 g, 6.38 mmol) and diisobutylamine (3.33 ml, 19.15 mmol) was heated at 130° C. for 1 h in a sealed tube.

The reaction was diluted with ether and washed with 5% AcOH. The aqueous phase was extracted with ether (3x). The combined organic phases were dried over $Na_2SO_4$, filtered, and concentrated to afford 1176A (2.22 g, 6.07 mmol, 95% yield) as a red-orange oil. ESI MS $(M+H)^+=347.2$.

1176B. 4-(5,5-Dimethyl-1,3,2-dioxaborinan-2-yl)-2-fluoro-N,N-diisobutyl-6-nitroaniline A suspension of potassium acetate (1.882 g, 19.18 mmol), 5,5,5',5'-tetramethyl-2,2'-bi(1,3,2-dioxaborinane) (1.877 g, 8.31 mmol), and 4-bromo-2-fluoro-N,N-diisobutyl-6-nitroaniline (2.22 g, 6.39 mmol) in DMSO (9.57 ml) was degassed with $N_2$ for 10 min, then treated with $PdCl_2$ (dppf) (0.140 g, 0.192 mmol). The reaction was sparged with $N_2$ for an additional 10 min. The reaction was heated at 80° C. overnight, then allowed to cool to rt. The reaction was quenched with $H_2O$ and diluted with EtOAc. Layers were separated. The aqueous phase was extracted with EtOAc (3x). The combined organic phases were washed with water (1x), dried over $Na_2SO_4$, filtered, and concentrated to afford a black residue. The crude material was dissolved in a minimal amount of $CH_2Cl_2$ and chromatographed. Purification of the crude material by silica gel chromatography using an ISCO machine (80 g column, 60 mL/min, 0-20% EtOAc in hexanes over 20 min, $T_r=10$ min) gave 1176B (1.358 g, 3.57 mmol, 55.9% yield) as an orange residue. ESI MS $(M+H)^+=313.1$ (boronic acid).

1176C. Methyl 3-(4-(diisobutylamino)-3-fluoro-5-nitrophenyl)-4-methoxybutanoate To a solution of 4-(5,5-dimethyl-1,3,2-dioxaborinan-2-yl)-2-fluoro-N,N-diisobutyl-6-nitroaniline (0.561 g, 1.475 mmol) in dioxane (7.38 ml) was added (E)-methyl 4-methoxybut-2-enoate (0.580 ml, 4.43 mmol) followed by sodium hydroxide (1.328 ml, 1.328 mmol). The reaction was evacuated and back-filled with nitrogen once. To this solution was added chloro(1,5-cyclooctadiene)rhodium(I) dimer (0.036 g, 0.074 mmol) and the resultant solution was evacuated and back-filled with nitrogen 3 times. The reaction was heated at 50° C. for 2.5 h (start at 2:50 pm). The reaction was quenched with acetic acid (0.076 ml, 1.328 mmol) and partitioned between EtOAc and water. Layers were separated. The aqueous phase was extracted with EtOAc (3x). The combined organic phases were dried over $Na_2SO_4$, filtered, and concentrated to afford a brown residue. The crude material was combined with another lot and dissolved in a minimal amount of $CH_2Cl_2$ and chromatographed. Purification of the crude material by silica gel chromatography using an ISCO machine (80 g column, 60 mL/min, 0-20% EtOAc in hexanes over 22 min, $T_r=13$ min) gave 1176C (0.327 g, 0.780 mmol, 52.9% yield) as an orange residue. ESI MS $(M+H)^+=399.4$.

1176D Enantiomer 1 and Enantiomer 2. Methyl 3-(3-amino-4-(diisobutylamino)-5-fluorophenyl)-4-methoxybutanoate (absolute stereochemistry not determined)

To a solution of methyl 3-(4-(diisobutylamino)-3-fluoro-5-nitrophenyl)-4-methoxybutanoate (0.753 g, 1.890 mmol) in ethyl acetate (9.45 ml) was added Pd/C (0.201 g, 0.189 mmol). The reaction was placed under a $H_2$ balloon and allowed to stir at rt for 2 h. The reaction was filtered through CELITE® and the filter cake was washed with EtOAc. The filtrate was concentrated to afford an orange residue. Approx. 623 mg of racemic material was resolved. The racemic material was purified via preparative SFC with the following conditions: Column: Lux Cellulose-4, 25x3 cm ID, 5-µm particles; Mobile Phase A: 87/13 $CO_2$/IPA with 0.1% $NH_4OH$; Detector Wavelength: 220 nm; Flow: 85 mL/min. The fractions ("Peak-1" $T_r=1.83$ min, and "Peak-2" $T_r=2.39$ min; analytical conditions: Column: Lux Cellulose-4, 25x0.46 cm ID, 5-µm particles; Mobile Phase A: 85/15 $CO_2$/IPA with 0.1% $NH_4OH$) were collected in IPA. The stereoisomeric purity of each fraction was estimated to be greater than 99.6% based on the prep-SFC chromatograms.

Enantiomer 1: 266 mg, 38% of the first eluting enantiomer. ESI MS $(M+H)^+=369.3$.

Enantiomer 2: 259 mg, 37% of the second eluting enantiomer. ESI MS $(M+H)^+=369.3$.

Example 1176 3-(4-(Diisobutylamino)-3-fluoro-5-(3-(2-fluoro-4-methoxyphenyl)ureido)phenyl)-4-methoxybutanoic acid To a solution of 1176D Enantiomer 1 (15.4 mg, 0.042 mmol) in THF (209 µl) at rt was added 4-nitrophenyl carbonochloridate (8.85 mg, 0.044 mmol). After 3 h, 2-fluoro-4-methoxyaniline (17.70 mg, 0.125 mmol) and triethylamine (17.48 µl, 0.125 mmol) were added. The reaction was heated at 50° C. overnight. To this reaction were added MeOH (0.15 mL) and a 1 M solution of lithium hydroxide (418 µl, 0.418 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2x). The organic phases were combined, dried over $Na_2SO_4$, filtered, and concentrated to afford a brown residue. The crude material was purified via preparative LC/MS with the following conditions: Column: XBridge C18, 19x200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 3-minute hold at 100% B; Flow: 20 mL/min. Fractions containing the desired product were combined and dried via centrifugal evaporation to afford Example 1176 (17.7 mg, 81%). ESI MS (M+H)⁺=522.4. HPLC Peak T$_r$=1.964 min. Purity=100%. HPLC conditions: C. Absolute stereochemistry not determined.

Example 1177

3-(4-(Diisobutylamino)-3-fluoro-5-(2-(p-tolyl)acetamido)phenyl)-4-methoxybutanoic acid

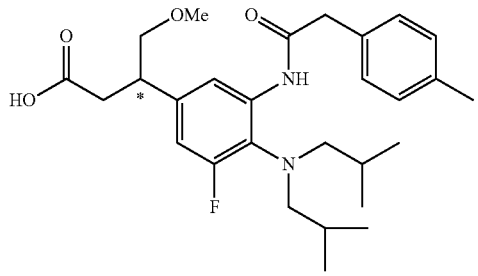

To a solution of 1176D Enantiomer 1 (17.4 mg, 0.047 mmol) in THF (337 µL) at rt was added 2-(p-tolyl)acetic acid (21.27 mg, 0.142 mmol), followed by 1-(3-dimethylaminopropyl)-3-ethylcarbodiimide hydrochloride (27.2 mg, 0.142 mmol), 4-hydroxybenzotriazole (19.14 mg, 0.142 mmol) and Hunig's base (33.0 µl, 0.189 mmol). The reaction was stirred at rt for 16 h. To this reaction were added MeOH (135 µl) and lithium hydroxide (472 µl, 0.472 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1177 (3.4 mg, 14%). ESI MS (M+H)⁺=487.4. HPLC Peak T$_r$=2.278 min. Purity=96%. HPLC conditions: C. Absolute stereochemistry not determined.

Example 1178

3-(4-(Diisobutylamino)-3-(3-(4-ethoxy-2-fluorophenyl)ureido)-5-fluorophenyl)-4-methoxybutanoic acid

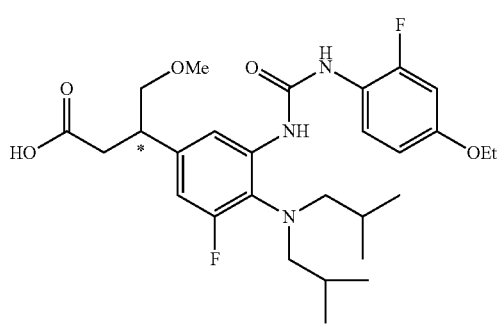 [SMILES: CCOc1ccc(NC(=O)Nc2cc(C(COC)CC(=O)O)cc(F)c2N(CC(C)C)CC(C)C)c(F)c1]

To a solution of 1176D Enantiomer 1 (15.7 mg, 0.043 mmol) in THF (213 µL) at rt was added 4-nitrophenyl carbonochloridate (9.02 mg, 0.045 mmol). After 3 h, 4-ethoxy-2-fluoroaniline, HCl (24.49 mg, 0.128 mmol) and triethylamine (23.75 µl, 0.170 mmol) were added. The reaction was heated at 50° C. overnight. To this reaction were added MeOH (0.15 mL) and a 1 M solution of lithium hydroxide (426 µl, 0.426 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 3-minute hold at 100% B; Flow: 20 mL/min. Fractions containing the desired product were combined and dried via centrifugal evaporation to afford Example 1178 (15.1 mg, 64%). ESI MS (M+H)⁺=536.4. HPLC Peak T$_r$=2.082 min. Purity=97%. HPLC conditions: C. Absolute stereochemistry not determined.

Example 1179

3-(4-(Diisobutylamino)-3-(3-(4-ethoxyphenyl)ureido)-5-fluorophenyl)-4-methoxybutanoic acid

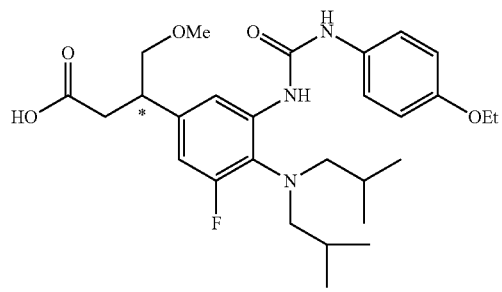 [SMILES: CCOc1ccc(NC(=O)Nc2cc(C(COC)CC(=O)O)cc(F)c2N(CC(C)C)CC(C)C)cc1]

To a solution of 1176D Enantiomer 1 (15.5 mg, 0.042 mmol) in THF (210 µl) at rt was added 4-nitrophenyl carbonochloridate (8.90 mg, 0.044 mmol). After 3 h, 4-ethoxyaniline (16.25 µl, 0.126 mmol) and triethylamine (17.59 µl, 0.126 mmol) were added. The reaction was heated at 50° C. overnight. To this reaction were added MeOH (0.15 mL) and a 1 M solution of lithium hydroxide (421 µL, 0.421 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 20 minutes, then a 5-minute hold at 100% B; Flow: 20 mL/min. Fractions containing the desired product were combined and dried via centrifugal evaporation to afford Example 1179 (14.6 mg, 66%). ESI MS (M+H)⁺=518.4. HPLC Peak $T_r$=2.154 min. Purity=99%. HPLC conditions: C. Absolute stereochemistry not determined.

Example 1180

3-(3-(2-(4-Chloro-2-fluorophenyl)acetamido)-4-(diisobutylamino)-5-fluorophenyl)-4-methoxybutanoic acid

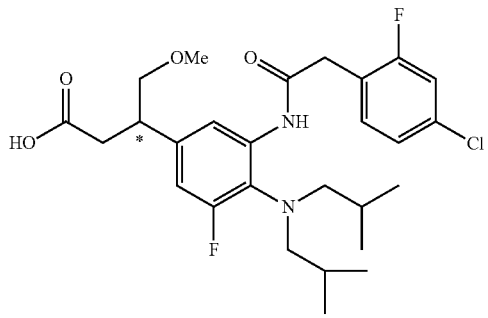 [SMILES: COCC(CC(=O)O)c1cc(F)c(N(CC(C)C)CC(C)C)c(NC(=O)Cc2ccc(Cl)cc2F)c1]

To a solution of 1176D Enantiomer 1 (18.5 mg, 0.050 mmol) in THF (359 μl) at rt was added 2-(4-chloro-2-fluorophenyl)acetic acid (28.4 mg, 0.151 mmol), followed by 1-(3-dimethylaminopropyl)-3-ethylcarbodiimide hydrochloride (28.9 mg, 0.151 mmol), 4-hydroxybenzotriazole (20.35 mg, 0.151 mmol) and Hunig's base (35.1 μL, 0.201 mmol). The reaction was stirred at rt for 16 h. To this reaction was added MeOH (143 μl) and lithium hydroxide (502 μl, 0.502 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 3-minute hold at 100% B; Flow: 20 mL/min. Fractions containing the desired product were combined and dried via centrifugal evaporation to afford Example 1180 (14.4 mg, 54%). ESI MS (M+H)$^+$=525.3. HPLC Peak $T_r$=2.323 min. Purity=99%. HPLC conditions: C. Absolute stereochemistry not determined.

Example 1181

3-(4-(Diisobutylamino)-3-(2-(4-ethoxyphenyl)acetamido)-5-fluorophenyl)-4-methoxybutanoic acid

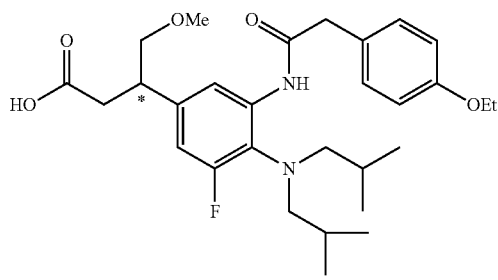 [SMILES: CCOc1ccc(CC(=O)Nc2cc(C(COC)CC(=O)O)cc(F)c2N(CC(C)C)CC(C)C)cc1]

To a solution of 1176D Enantiomer 1 (17.6 mg, 0.048 mmol) in THF (341 μL) at rt was added 2-(4-ethoxyphenyl)acetic acid (25.8 mg, 0.143 mmol), followed by 1-(3-dimethylaminopropyl)-3-ethylcarbodiimide hydrochloride (27.5 mg, 0.143 mmol), 4-hydroxybenzotriazole (19.36 mg, 0.143 mmol) and Hunig's base (33.4 μL, 0.191 mmol). The reaction was stirred at rt for 16 h. To this reaction was added MeOH (136 μl) and lithium hydroxide (478 μl, 0.478 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1181 (4.4 mg, 18%). ESI MS (M+H)$^+$=517.4. HPLC Peak $T_r$=2.230 min. Purity=99%. HPLC conditions: C. Absolute stereochemistry not determined.

Example 1182

3-(3-(3-(4-Chloro-2-fluorophenyl)ureido)-4-(diisobutylamino)-5-fluorophenyl)-4-methoxybutanoic acid

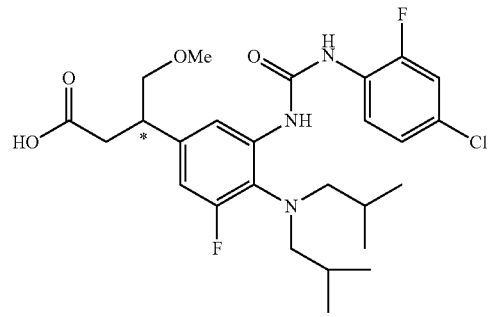

To a solution of 1176D Enantiomer 2 (15.4 mg, 0.042 mmol) in THF (209 μl) was added 4-chloro-2-fluoro-1-isocyanatobenzene (10.59 μl, 0.084 mmol) at rt. After 2.5 h, MeOH (0.15 mL) and a 1M solution of lithium hydroxide (418 μl, 0.418 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 3-minute hold at 100% B; Flow: 20 mL/min. Fractions containing the desired product were combined and dried via centrifugal evaporation to afford Example 1182 (14.5 mg, 66%). ESI MS (M+H)⁺=526.3. HPLC Peak $T_r$=2.149 min. Purity=100%. HPLC conditions: C. Absolute stereochemistry not determined.

Example 1183

3-(4-(Diisobutylamino)-3-fluoro-5-(3-(pyrimidin-5-yl)ureido)phenyl)-4-methoxybutanoic acid

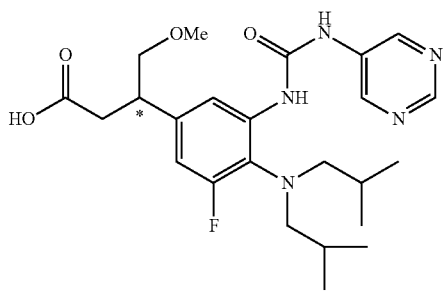 [SMILES: COCC(CC(=O)O)c1cc(F)c(N(CC(C)C)CC(C)C)c(NC(=O)Nc2cncnc2)c1]

To a solution of 1176D Enantiomer 2 (19.9 mg, 0.054 mmol) in THF (270 µl) at rt was added 4-nitrophenyl carbonochloridate (11.43 mg, 0.057 mmol). After 3 h, pyrimidin-5-amine (15.41 mg, 0.162 mmol) and triethylamine (22.58 µl, 0.162 mmol) were added. The reaction was heated at 50° C. overnight. To this reaction were added MeOH (0.15 mL) and a 1 M solution of lithium hydroxide (540 µl, 0.540 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation to afford Example 1183 (17.0 mg, 64%). ESI MS (M+H)⁺=476.3. HPLC Peak $T_r$=1.573 min. Purity=96%. HPLC conditions: C. Absolute stereochemistry not determined.

Example 1184

3-(4-(Diisobutylamino)-3-fluoro-5-(3-(5-methylisoxazol-3-yl)ureido)phenyl)-4-methoxybutanoic acid

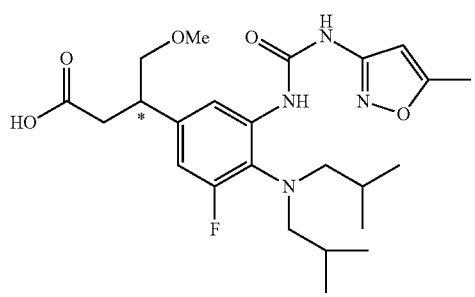 [SMILES: COCC(CC(=O)O)c1cc(F)c(N(CC(C)C)CC(C)C)c(NC(=O)Nc2cc(C)on2)c1]

To a solution of 1176D Enantiomer 2 (21.0 mg, 0.057 mmol) in THF (285 µl) at rt was added 4-nitrophenyl carbonochloridate (12.06 mg, 0.060 mmol). The mixture was stirred at rt for 3 h. To this reaction were added 5-methylisoxazol-3-amine (16.77 mg, 0.171 mmol) and triethylamine (23.83 µl, 0.171 mmol). The reaction was heated at 50° C. overnight. To this reaction were added MeOH (0.15 mL) and a 1 M solution of lithium hydroxide (570 µl, 0.570 mmol). The reaction was heated at 70° C. for 2 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 3-minute hold at 100% B; Flow: 20 mL/min. Fractions containing the desired product were combined and dried via centrifugal evaporation to afford Example 1184 (16.6 mg, 58%). ESI MS (M+H)⁺=479.3. HPLC Peak $T_r$=1.861 min. Purity=96%. HPLC conditions: C. Absolute stereochemistry not determined.

Example 1185

3-(4-(Diisobutylamino)-3-(3-(4-ethoxyphenyl)ureido)-5-fluorophenyl)-4-methoxybutanoic acid

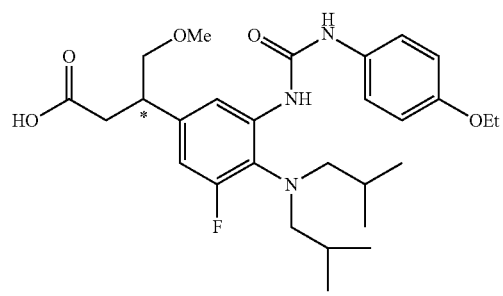 [SMILES: CCOc1ccc(NC(=O)Nc2cc(C(COC)CC(=O)O)cc(F)c2N(CC(C)C)CC(C)C)cc1]

To a solution of 1176D Enantiomer 2 (16.3 mg, 0.044 mmol) in THF (221 µl) at rt was added 4-nitrophenyl carbonochloridate (9.36 mg, 0.046 mmol). After 1.5 h, 4-ethoxyaniline (17.09 µl, 0.133 mmol) and triethylamine (18.50 µl, 0.133 mmol) were added. The reaction was heated at 50° C. overnight. To this reaction were added MeOH (0.15 mL) and a 1 M solution of lithium hydroxide (442 µl, 0.442 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1185 (14.2 mg, 61%). ESI MS (M+H)⁺=518.4. HPLC Peak $T_r$=2.039 min. Purity=99%. HPLC conditions: C. Absolute stereochemistry not determined.

Example 1186

3-(4-(Diisobutylamino)-3-fluoro-5-(3-(p-tolyl)ureido)phenyl)-4-methoxybutanoic acid

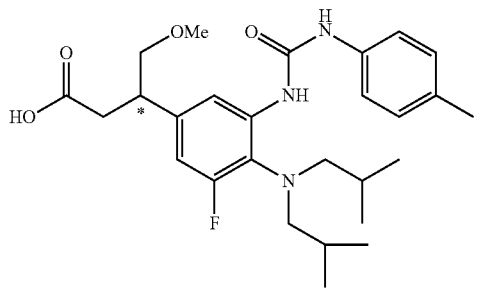 [SMILES: COCC(CC(=O)O)c1cc(F)c(N(CC(C)C)CC(C)C)c(NC(=O)Nc2ccc(C)cc2)c1]

To a solution of 1176D Enantiomer 2 (16.6 mg, 0.045 mmol) in THF (225 μl) was added 1-isocyanato-4-methylbenzene (11.34 μl, 0.090 mmol) at rt. After 2.5 h, MeOH (0.15 mL) and a 1M solution of lithium hydroxide (450 μl, 0.450 mmol) were added. The reaction was heated at 70° C. for 2 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 45-90% B over 20 minutes, then a 10-minute hold at 100% B; Flow: 20 mL/min. Fractions containing the desired product were combined and dried via centrifugal evaporation to afford Example 1186 (14.3 mg, 63%). ESI MS (M+H)$^+$=488.4. HPLC Peak T$_r$=2.040 min. Purity=96%. HPLC conditions: C. Absolute stereochemistry not determined.

Example 1187

3-(3-(2-(4-Chloro-2-fluorophenyl)acetamido)-4-(diisobutylamino)-5-fluorophenyl)-4-methoxybutanoic acid

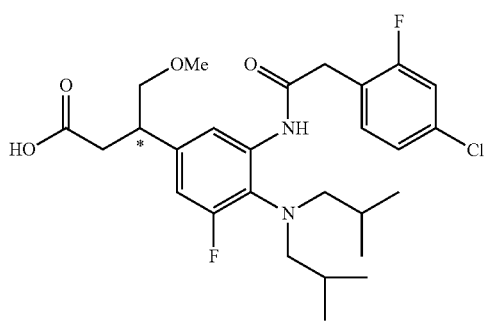 [SMILES: COCC(CC(=O)O)c1cc(F)c(N(CC(C)C)CC(C)C)c(NC(=O)Cc2ccc(Cl)cc2F)c1]

To a solution of 1176D Enantiomer 2 (16.9 mg, 0.046 mmol) in THF (328 μl) at rt was added 2-(4-chloro-2-fluorophenyl)acetic acid (25.9 mg, 0.138 mmol), followed by 1-(3-dimethylaminopropyl)-3-ethylcarbodiimide hydrochloride (26.4 mg, 0.138 mmol), 4-hydroxybenzotriazole (18.59 mg, 0.138 mmol) and Hunig's base (32.0 μl, 0.183 mmol). The reaction was stirred at rt for 16 h. To this reaction were added MeOH (131 μl) and lithium hydroxide (459 μl, 0.459 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to afford Example 1187 (13.1 mg, 54%). ESI MS (M+H)$^+$=525.0. HPLC Peak T$_r$=2.307 min. Purity=99%. HPLC conditions: C. Absolute stereochemistry not determined.

Example 1188

3-(4-(Diisobutylamino)-3-fluoro-5-(3-(5-methylisoxazol-3-yl)ureido)phenyl)-4-methoxybutanoic acid

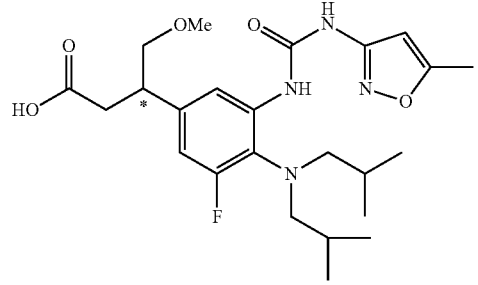 [SMILES: COCC(CC(=O)O)c1cc(F)c(N(CC(C)C)CC(C)C)c(NC(=O)Nc2cc(C)on2)c1]

To a solution of 1176D Enantiomer 1 (20.9 mg, 0.057 mmol) in THF (284 μl) at rt was added 4-nitrophenyl carbonochloridate (12.00 mg, 0.060 mmol). The mixture was stirred at rt for 3 h. To this reaction were added 5-methylisoxazol-3-amine (16.69 mg, 0.170 mmol) and triethylamine (23.72 μl, 0.170 mmol). The reaction was heated at 50° C. overnight. To this reaction were added MeOH (0.15 mL) and a 1 M solution of lithium hydroxide (567 μl, 0.567 mmol). The reaction was heated at 70° C. for 2 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-80% B over 20 minutes, then a 10-minute hold at 100% B; Flow: 20 mL/min. Fractions containing the desired product were combined and dried via centrifugal evaporation to afford Example 1188 (14.6 mg, 52%). ESI MS (M+H)$^+$=479.1. HPLC Peak T$_r$=1.831 min. Purity=96%. HPLC conditions: C. Absolute stereochemistry not determined.

Example 1189

3-(4-(Diisobutylamino)-3-fluoro-5-(3-(2-fluoro-4-methoxyphenyl)ureido)phenyl)-4-methoxybutanoic acid

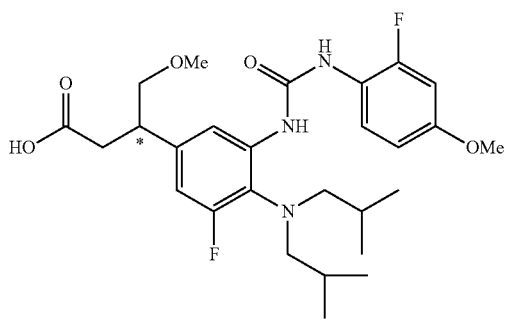 [SMILES: COCC(CC(=O)O)c1cc(F)c(N(CC(C)C)CC(C)C)c(NC(=O)Nc2ccc(OC)cc2F)c1]

To a solution of 1176D Enantiomer 2 (17.3 mg, 0.047 mmol) in THF (235 μl) at rt was added 4-nitrophenyl carbonochloridate (9.94 mg, 0.049 mmol). After 3 h, 2-fluoro-4-methoxyaniline (19.88 mg, 0.141 mmol) and triethylamine (26.2 μl, 0.188 mmol) were added. The reaction was heated at 50° C. overnight. To this reaction were added MeOH (0.15 mL) and a 1 M solution of lithium hydroxide (469 μl, 0.469 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to afford Example 1189 (21.8 mg, 88%). ESI MS (M+H)$^+$=522.4. HPLC Peak T$_r$=1.916 min. Purity=99%. HPLC conditions: C. Absolute stereochemistry not determined.

Example 1190

3-(4-(Diisobutylamino)-3-fluoro-5-(2-(p-tolyl)acetamido)phenyl)-4-methoxybutanoic acid

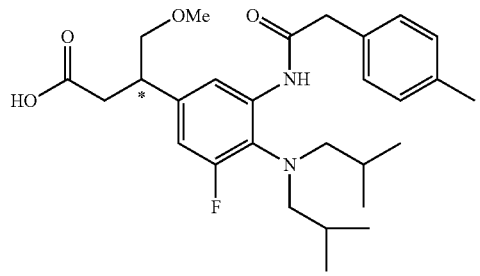 [SMILES: COCC(CC(=O)O)c1cc(F)c(N(CC(C)C)CC(C)C)c(NC(=O)Cc2ccc(C)cc2)c1]

To a solution of 1176D Enantiomer 2 (19.7 mg, 0.053 mmol) in THF (382 μl) at rt was added 2-(p-tolyl)acetic acid (24.09 mg, 0.160 mmol), followed by 1-(3-dimethylaminopropyl)-3-ethylcarbodiimide hydrochloride (30.7 mg, 0.160 mmol), 4-hydroxybenzotriazole (21.67 mg, 0.160 mmol) and Hunig's base (37.3 μl, 0.214 mmol). The reaction was stirred at rt for 16 h. To this reaction was added MeOH (153 μl) and lithium hydroxide (535 μl, 0.535 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to afford Example 1190 (8.6 mg, 32%). ESI MS (M+H)$^+$=487.1. HPLC Peak T$_r$=2.256 min. Purity=98%. HPLC conditions: C. Absolute stereochemistry not determined.

Example 1191

3-(4-(Diisobutylamino)-3-(3-(4-ethoxy-2-fluorophenyl)ureido)-5-fluorophenyl)-4-methoxybutanoic acid

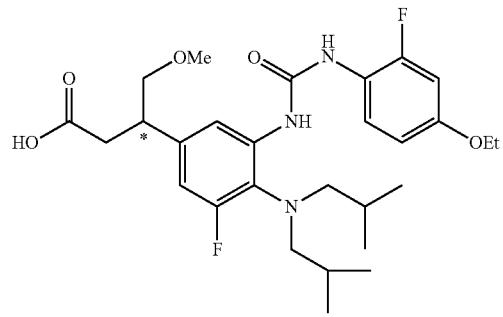 [SMILES: CCOc1ccc(NC(=O)Nc2cc(C(COC)CC(=O)O)cc(F)c2N(CC(C)C)CC(C)C)c(F)c1]

To a solution of 1176D Enantiomer 2 (16.0 mg, 0.043 mmol) in THF (217 μl) at rt was added 4-nitrophenyl carbonochloridate (9.19 mg, 0.046 mmol). After 3 h, 4-ethoxy-2-fluoroaniline, HCl (24.96 mg, 0.130 mmol) and triethylamine (24.21 µl, 0.174 mmol) were added. The reaction was heated at 50° C. overnight. To this reaction were added MeOH (0.15 mL) and a 1 M solution of lithium hydroxide (434 µl, 0.434 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1191 (17.7 mg, 75%). ESI MS $(M+H)^+=536.1$. HPLC Peak $T_r=2.066$ min. Purity=99%. HPLC conditions: C. Absolute stereochemistry not determined.

Example 1192

3-(4-(Diisobutylamino)-3-fluoro-5-(3-(4-(trifluoromethoxy)phenyl)ureido)phenyl)-4-methoxybutanoic acid

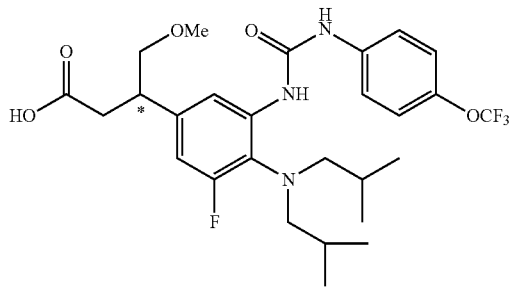 [SMILES: COCC(CC(=O)O)c1cc(F)c(N(CC(C)C)CC(C)C)c(NC(=O)Nc2ccc(OC(F)(F)F)cc2)c1]

To a solution of 1176D Enantiomer 2 (17.5 mg, 0.047 mmol) in THF (237 µl) was added 1-isocyanato-4-(trifluoromethoxy)benzene (14.33 µl, 0.095 mmol) at rt. After 2.5 h, MeOH (0.15 mL) and a 1M solution of lithium hydroxide (475 µl, 0.475 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1192 (21.2 mg, 78%). ESI MS $(M+H)^+=558.1$. HPLC Peak $T_r=2.184$ min. Purity=98%. HPLC conditions: C. Absolute stereochemistry not determined.

Example 1193

3-(4-(Diisobutylamino)-3-(2-(4-ethoxyphenyl)acetamido)-5-fluorophenyl)-4-methoxybutanoic acid

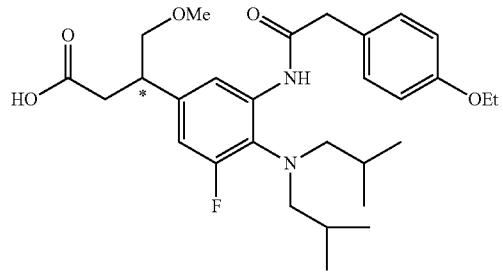 [SMILES: CCOc1ccc(CC(=O)Nc2cc(C(COC)CC(=O)O)cc(F)c2N(CC(C)C)CC(C)C)cc1]

To a solution of 1176D Enantiomer 2 (18.1 mg, 0.049 mmol) in THF (351 µl) at rt was added 2-(4-ethoxyphenyl)acetic acid (26.6 mg, 0.147 mmol), followed by 1-(3-dimethylaminopropyl)-3-ethylcarbodiimide hydrochloride (28.2 mg, 0.147 mmol), 4-hydroxybenzotriazole (19.91 mg, 0.147 mmol) and Hunig's base (42.9 µl, 0.246 mmol). The reaction was stirred at rt for 16 h. To this reaction were added MeOH (140 µl) and lithium hydroxide (491 µl, 0.491 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to afford Example 1193 (3.5 mg, 13%). ESI MS $(M+H)^+=517.1$. HPLC Peak $T_r=2.216$ min. Purity=97%. HPLC conditions: C. Absolute stereochemistry not determined.

Example 1194

3-(4-(Diisobutylamino)-3-fluoro-5-(3-(p-tolyl)ureido)phenyl)-4-methoxybutanoic acid

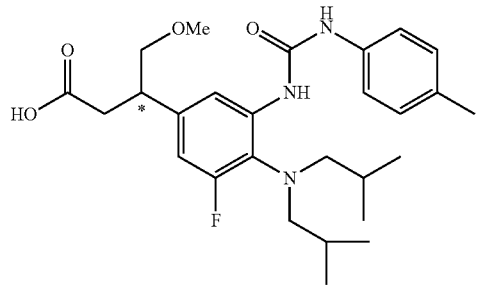 [SMILES: COCC(CC(=O)O)c1cc(F)c(N(CC(C)C)CC(C)C)c(NC(=O)Nc2ccc(C)cc2)c1]

To a solution of 1176D Enantiomer 1 (15.9 mg, 0.043 mmol) in THF (216 µl) was added 1-isocyanato-4-methylbenzene (10.86 µl, 0.086 mmol) at rt. After 2.5 h, MeOH (0.15 mL) and a 1M solution of lithium hydroxide (431 µl, 0.431 mmol) were added. The reaction was heated at 70° C. for 2 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 3-minute hold at 100% B; Flow: 20 mL/min. Fractions containing the desired product were combined and dried via centrifugal evaporation to afford Example 1194 (15.3 mg, 72%). ESI MS (M+H)$^+$=488.4. HPLC Peak T$_r$=2.067 min. Purity=99%. HPLC conditions: C. Absolute stereochemistry not determined.

Example 1195

3-(3-(3-(4-Chloro-2-fluorophenyl)ureido)-4-(diisobutylamino)-5-fluorophenyl)-4-methoxybutanoic acid

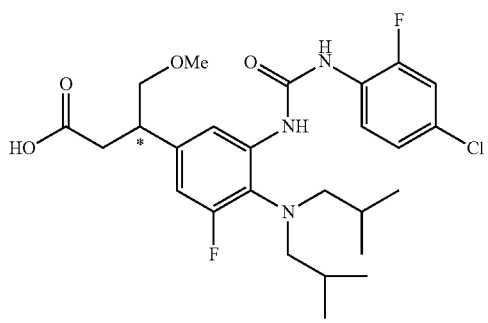 [SMILES: COCC(CC(=O)O)c1cc(F)c(N(CC(C)C)CC(C)C)c(NC(=O)Nc2ccc(Cl)cc2F)c1]

To a solution of 1176D Enantiomer 1 (15.2 mg, 0.041 mmol) in THF (206 µl) was added 4-chloro-2-fluoro-1-isocyanatobenzene (10.45 µl, 0.082 mmol) at rt (start at 3:20 pm). After 2.5 h, LC-MS showed desired product and no SM left. To this reaction were added MeOH (0.15 mL) and a 1M solution of lithium hydroxide (412 µl, 0.412 mmol). The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Example 1195 (12.9 mg, 59%). ESI MS (M+H)$^+$=526.3. HPLC Peak T$_r$=2.149 min. Purity=99%. HPLC conditions: C. Absolute stereochemistry not determined.

Example 1196

3-(4-(Diisobutylamino)-3-fluoro-5-(3-(pyrimidin-5-yl)ureido)phenyl)-4-methoxybutanoic acid

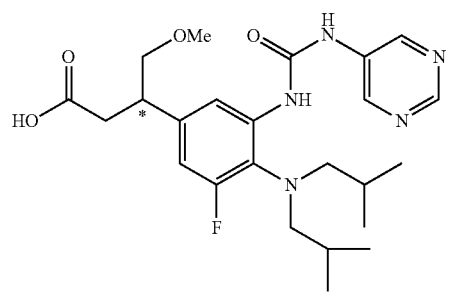 [SMILES: COCC(CC(=O)O)c1cc(F)c(N(CC(C)C)CC(C)C)c(NC(=O)Nc2cncnc2)c1]

To a solution of 1176D Enantiomer 1 (19.0 mg, 0.052 mmol) in THF (258 µl) at rt was added 4-nitrophenyl carbonochloridate (10.91 mg, 0.054 mmol). After 3 h, pyrimidin-5-amine (14.71 mg, 0.155 mmol) and triethylamine (21.56 µl, 0.155 mmol) were added. The reaction was heated at 50° C. overnight. To this reaction were added MeOH (0.15 mL) and a 1 M solution of lithium hydroxide (516 µl, 0.516 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation to afford Example 1196 (15.5 mg, 63%). ESI MS (M+H)$^+$=476.3. HPLC Peak T$_r$=1.573 min. Purity=100%. HPLC conditions: C. Absolute stereochemistry not determined.

Example 1197

3-(4-(Diisobutylamino)-3-fluoro-5-(3-(4-(trifluoromethoxy)phenyl)ureido)phenyl)-4-methoxybutanoic acid

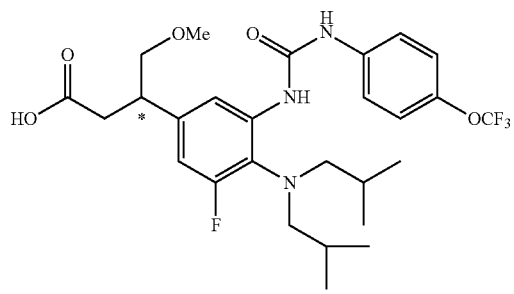 [SMILES: COCC(CC(=O)O)c1cc(F)c(N(CC(C)C)CC(C)C)c(NC(=O)Nc2ccc(OC(F)(F)F)cc2)c1]

To a solution of 1176D Enantiomer 1 (16.1 mg, 0.044 mmol) in THF (218 µl) was added 1-isocyanato-4-(trifluoromethoxy)benzene (13.19 µl, 0.087 mmol) at rt. After 2.5 h, MeOH (0.15 mL) and a 1M solution of lithium hydroxide (437 µl, 0.437 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 5-minute hold at 100% B; Flow: 20 mL/min. Fractions containing the desired product were combined and dried via centrifugal evaporation to afford Example 1197 (16.4 mg, 65%). ESI MS $(M+H)^+=558.4$. HPLC Peak $T_r=2.198$ min. Purity=96%. HPLC conditions: C. Absolute stereochemistry not determined.

Example 1198

(+/−)-3-(3-(3-(4-Chloro-2-fluorophenyl)ureido)-4-(isobutyl(tetrahydro-2H-pyran-4-yl)amino)phenyl)-3-cyclopropylpropanoic acid

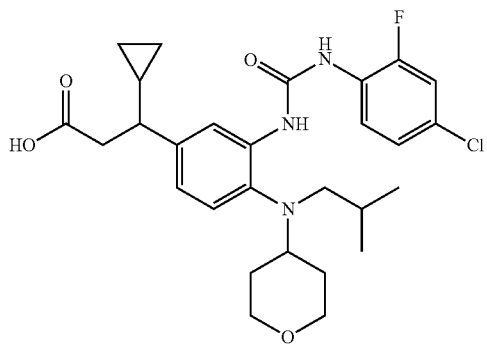 [SMILES: CC(C)CN(c1ccc(C(CC(=O)O)C2CC2)cc1NC(=O)Nc1ccc(Cl)cc1F)C1CCOCC1]

1198A. N-(4-(5,5-Dimethyl-1,3,2-dioxaborinan-2-yl)-2-nitrophenyl)-N-isobutyltetrahydro-2H-pyran-4-amine A suspension of potassium acetate (0.685 g, 6.98 mmol), 5,5,5',5'-tetramethyl-2,2'-bi(1,3,2-dioxaborinane) (0.683 g, 3.02 mmol), and N-(4-bromo-2-nitrophenyl)-N-isobutyltetrahydro-2H-pyran-4-amine (Preparation 958C) (0.831 g, 2.326 mmol) in DMSO (3.48 ml) was degassed with $N_2$ for 10 min, then treated with $PdCl_2$ (dppf) (0.051 g, 0.070 mmol). The reaction was sparged with $N_2$ for an additional 10 min. The reaction was heated at 80° C. overnight, then allowed to cool to rt. The reaction was quenched with $H_2O$ and diluted with EtOAc. Layers were separated. The aqueous phase was extracted with EtOAc (3×). The combined organic phases were washed with water (1×), dried over $Na_2SO_4$, filtered, and concentrated to afford a black residue. The crude material was dissolved in a minimal amount of $CH_2Cl_2$ and chromatographed. Purification of the crude material by silica gel chromatography using an ISCO machine (80 g column, 40 mL/min, 0-20% EtOAc in hexanes over 20 min, $T_r=17$ min) gave 1198A (0.464 g, 1.129 mmol, 48.6% yield) as an orange residue. ESI MS $(M+H)^+=323.1$ (boronic acid).

1198B. Ethyl 3-cyclopropyl-3-(4-(isobutyl(tetrahydro-2H-pyran-4-yl)amino)-3-nitrophenyl)propanoate To a solution of 23A (0.544 g, 1.394 mmol) in dioxane (6.97 ml) was added (E)-ethyl 3-cyclopropylacrylate (0.610 ml, 4.18 mmol) followed by sodium hydroxide (1.254 ml, 1.254 mmol). The reaction was evacuated and back-filled with nitrogen once. To this solution was added chloro(1,5-cyclooctadiene)rhodium(I) dimer (0.034 g, 0.070 mmol) and the resultant solution was evacuated and back-filled with nitrogen 3 times.

The reaction was heated at 50° C. for 2.5 h. The reaction was quenched with acetic acid (0.072 ml, 1.254 mmol) and partitioned between EtOAc and water. Layers were separated. The aqueous phase was extracted with EtOAc (3×). The combined organic phases were dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (80 g column, 60 mL/min, 0-15% EtOAc in hexanes over 22 min) gave 1198B (0.366 g, 0.874 mmol, 62.7% yield) as an orange residue. ESI MS $(M+H)^+=419.4$.

1198C. Ethyl 3-(3-amino-4-(isobutyl(tetrahydro-2H-pyran-4-yl)amino)phenyl)-3-cyclopropylpropanoate To a solution of 1198B (0.366 g, 0.874 mmol) in MeOH (4.37 ml) was added Pd/C (0.093 g, 0.087 mmol). The reaction was placed under a $H_2$ balloon and allowed to stir at rt. After 50 min, the reaction was filtered through CELITE® and the filter cake was washed with $CH_2C_2$. The filtrate was concentrated to afford 1198C as a brown residue. ESI MS $(M+H)^+=389.3$.

Example 1198 (+/−)-3-(3-(3-(4-Chloro-2-fluorophenyl)ureido)-4-(isobutyl(tetrahydro-2H-pyran-4-yl)amino)phenyl)-3-cyclopropylpropanoic acid To a solution of 1198C (47.5 mg, 0.122 mmol) in THF (611 µl) was added 4-chloro-2-fluoro-1-isocyanatobenzene (31.0 µl, 0.245 mmol) at rt. After 2.5 h, MeOH (0.15 mL) and a 1M solution of lithium hydroxide (1223 µl, 1.223 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 minutes, then a 5-minute hold at 100% B; Flow: 20 mL/min. Fractions containing the desired product were combined and dried via centrifugal evaporation to afford Example 1198 (41.0 mg, 62%). ESI MS $(M+H)^+=532.1$. HPLC Peak $T_r=1.910$ min. Purity=99%. HPLC conditions: C.

Example 1199

Enantiomer 1 and Enantiomer 2

Example 1199 Enantiomer 1: 3-(3-(3-(4-Chloro-2-fluorophenyl)ureido)-4-(isobutyl(tetrahydro-2H-pyran-4-yl)amino)phenyl)-3-cyclopropylpropanoic acid

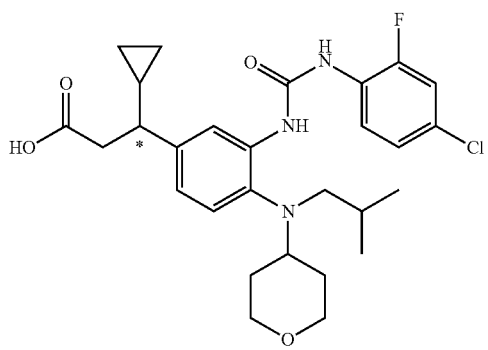 [SMILES: CC(C)CN(c1ccc(C(CC(=O)O)C2CC2)cc1NC(=O)Nc1ccc(Cl)cc1F)C1CCOCC1]

Example 1199 Enantiomer 2: 3-(3-(3-(4-Chloro-2-fluorophenyl)ureido)-4-(isobutyl(tetrahydro-2H-pyran-4-yl)amino)phenyl)-3-cyclopropylpropanoic acid

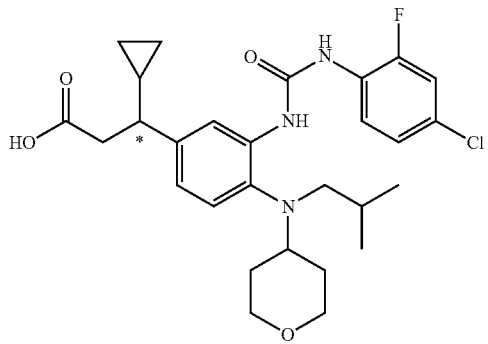 [SMILES: CC(C)CN(c1ccc(C(CC(=O)O)C2CC2)cc1NC(=O)Nc1ccc(Cl)cc1F)C1CCOCC1]

Approximately 41 mg of Example 1198 was resolved. The racemic material was purified via preparative SFC with the following conditions: Column: ID, 25×3 cm ID, 5-μm particles; Mobile Phase A: 98/2 CO$_2$/MeOH; Detector Wavelength: 220 nm; Flow: 85 mL/min. The fractions ("Peak-1" T$_r$=10.6 min, and "Peak-2" T$_r$=11.382 min; analytical conditions: Column: ID, 250×4.6 mm ID, 5-μm particles; Mobile Phase A: 90/10 CO$_2$/MeOH; Flow: 2.0 mL/min) were collected in MeOH. The stereoisomeric purity of each fraction was estimated to be greater than 90.0% based on the prep-SFC chromatograms. Each enantiomer was further purified via preparative LC/MS with the following conditions: First eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 minutes, then a 5-minute hold at 100% B; Flow: 20 mL/min. Fractions containing the desired product were combined and dried via centrifugal evaporation to afford:

Example 1199 Enantiomer 1: 10.8 mg, 16% of the first eluting enantiomer. ESI MS (M+H)$^+$=532.1. HPLC Peak T$_r$=1.965 min. Purity=95%. HPLC conditions: C. Absolute stereochemistry not determined.

Second eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 minutes, then a 5-minute hold at 100% B; Flow: 20 mL/min. Fractions containing the desired product were combined and dried via centrifugal evaporation to afford:

Example 1199 Enantiomer 2: 18.0 mg, 27% of the second eluting enantiomer.

ESI MS (M+H)$^+$=532.1. HPLC Peak T$_r$=1.965 min. Purity=96%. HPLC conditions: C. Absolute stereochemistry not determined.

Example 1200

(+/−)-3-Cyclopropyl-3-(4-(isobutyl(tetrahydro-2H-pyran-4-yl)amino)-3-(3-(5-methylisoxazol-3-yl)ureido)phenyl)propanoic acid

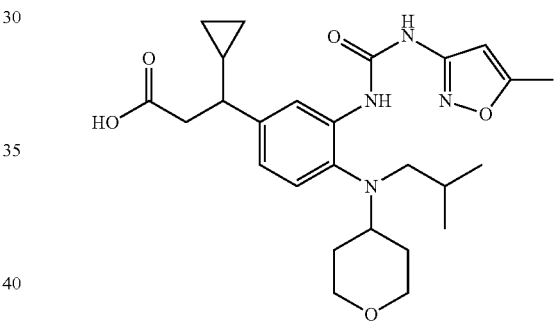

To a solution of 1198C (62.9 mg, 0.162 mmol) in THF (809 μl) at rt was added 4-nitrophenyl carbonochloridate (34.3 mg, 0.170 mmol). The mixture was stirred at rt for 3 h. To this reaction were added 5-methylisoxazol-3-amine (47.6 mg, 0.486 mmol) and triethylamine (67.7 μl, 0.486 mmol). The reaction was heated at 50° C. overnight. To this reaction were added MeOH (0.15 mL) and a 1 M solution of lithium hydroxide (1619 μl, 1.619 mmol). The reaction was heated at 70° C. for 2 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation to afford Example 1200 (27.1 mg, 34%). ESI MS (M+H)$^+$=485.4. HPLC Peak T$_r$=1.655 min. Purity=99%. HPLC conditions: C.

Example 1201

Enantiomer 1 and Enantiomer 2

Example 1201 Enantiomer 1: 3-Cyclopropyl-3-(4-(isobutyl(tetrahydro-2H-pyran-4-yl)amino)-3-(3-(5-methylisoxazol-3-yl)ureido)phenyl)propanoic acid

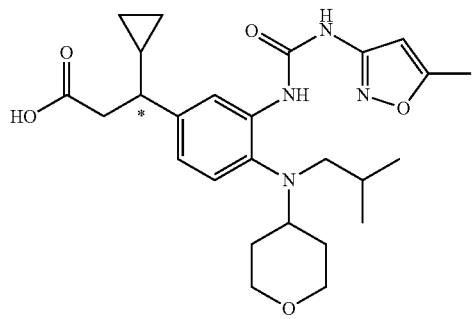 [SMILES: Cc1cc(NC(=O)Nc2cc(C(CC(=O)O)C3CC3)ccc2N(CC(C)C)C2CCOCC2)no1]

Example 1201 Enantiomer 2: 3-Cyclopropyl-3-(4-(isobutyl(tetrahydro-2H-pyran-4-yl)amino)-3-(3-(5-methylisoxazol-3-yl)ureido)phenyl)propanoic acid

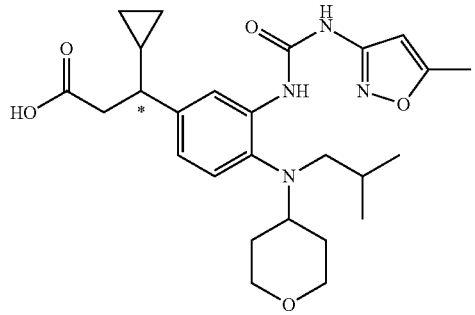 [SMILES: Cc1cc(NC(=O)Nc2cc(C(CC(=O)O)C3CC3)ccc2N(CC(C)C)C2CCOCC2)no1]

Approximately 27 mg of Example 1200 was resolved. The racemic material was purified via preparative SFC with the following conditions: Column: AD, 25×3 cm ID, 5-μm particles; Mobile Phase A: 90/10 CO$_2$/MeOH; Detector Wavelength: 220 nm; Flow: 85 mL/min. The fractions ("Peak-1" T$_r$=23.673 min, and "Peak-2" T$_r$=25.623 min; analytical conditions: Column: AD, 250×4.6 mm ID, 5-μm particles; Mobile Phase A: 90/10 CO$_2$/MeOH; Flow: 2.0 mL/min) were collected in MeOH. The stereoisomeric purity of each fraction was estimated to be greater than 99.3% (Peak-1) and 95.3% (Peak-2) based on the prep-SFC chromatograms. Each enantiomer was further purified via preparative LC/MS with the following conditions: First eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation to afford:

Example 1201 Enantiomer 1: 7.8 mg, 10% of the first eluting enantiomer. ESI MS (M+H)$^+$=485.1. HPLC Peak T$_r$=1.660 min. Purity=100%. HPLC conditions: C. Absolute stereochemistry not determined.

Second eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation to afford:

Example 1201 Enantiomer 2: 9.1 mg, 11% of the second eluting enantiomer. ESI MS (M+H)$^+$=485.1. HPLC Peak T$_r$=1.658 min. Purity=96%. HPLC conditions: C. Absolute stereochemistry not determined.

Example 1202

(+/−)-3-Cyclopropyl-3-(4-(isobutyl(tetrahydro-2H-pyran-4-yl)amino)-3-(3-(p-tolyl)ureido)phenyl)propanoic acid

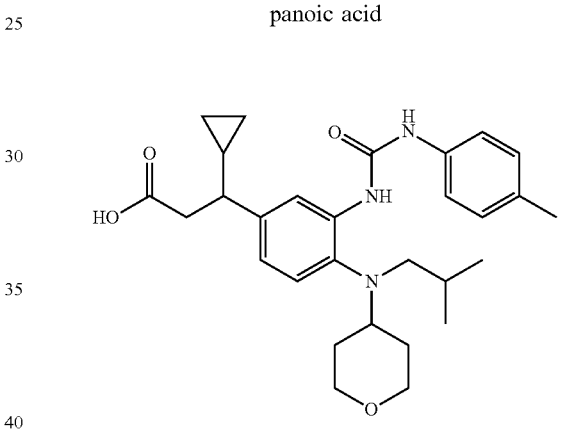

To a solution of 1198C (0.0541 g, 0.139 mmol) in THF (0.696 ml) was added 1-isocyanato-4-methylbenzene (0.035 ml, 0.278 mmol) at rt. After 2.5 h, MeOH (0.30 mL) and a 1M solution of lithium hydroxide (1.392 ml, 1.392 mmol) were added. The reaction was heated at 50° C. for 4 h. The reaction was adjusted to pH 6 with 1N HCl (1.1 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford Example 1202 (34.1 mg, 49%). ESI MS (M+H)$^+$=494.1. HPLC Peak T$_r$=1.865 min. Purity=98%. HPLC conditions: C.

Example 1203

Enantiomer 1 and Enantiomer 2

Example 1203 Enantiomer 1: 3-Cyclopropyl-3-(4-(isobutyl(tetrahydro-2H-pyran-4-yl)amino)-3-(3-(p-tolyl)ureido)phenyl)propanoic acid

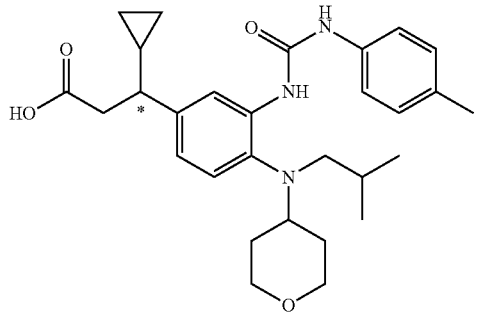 [SMILES: Cc1ccc(NC(=O)Nc2cc(C(CC(=O)O)C3CC3)ccc2N(CC(C)C)C2CCOCC2)cc1]

Example 1203 Enantiomer 2: 3-Cyclopropyl-3-(4-(isobutyl(tetrahydro-2H-pyran-4-yl)amino)-3-(3-(p-tolyl)ureido)phenyl)propanoic acid

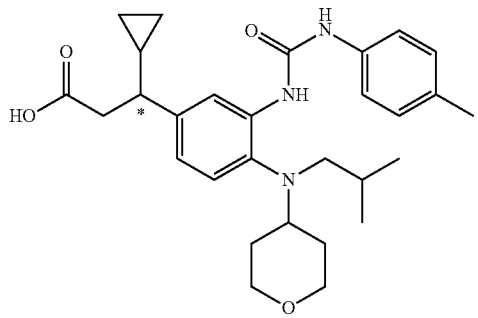 [SMILES: Cc1ccc(NC(=O)Nc2cc(C(CC(=O)O)C3CC3)ccc2N(CC(C)C)C2CCOCC2)cc1]

Approximately 34 mg of Example 1202 was resolved. The racemic material was purified via preparative SFC with the following conditions: Column: AD-H, 25×3 cm ID, 5-µm particles; Mobile Phase A: 80/20 CO$_2$/MeOH; Detector Wavelength: 220 nm; Flow: 85 mL/min. The fractions ("Peak-1" T$_r$=4.863 min, and "Peak-2" T$_r$=5.422 min; analytical conditions: Column: AD, 250×4.6 mm ID, 5-µm particles; Mobile Phase A: 75/25 CO$_2$/MeOH; Flow: 2.0 mL/min) were collected in MeOH. The stereoisomeric purity of each fraction was estimated to be greater than 95.0% based on the prep-SFC chromatograms. Each enantiomer was further purified via preparative LC/MS with the following conditions: First eluting enantiomer: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford:

Example 1203 Enantiomer 1: 12.8 mg, 19% of the first eluting enantiomer. ESI MS (M+H)$^+$=494.4. HPLC Peak T$_r$=1.877 min. Purity=100%. HPLC conditions: C. Absolute stereochemistry not determined.

Second eluting enantiomer: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford:

Example 1203 Enantiomer 2: 13.0 mg, 19% of the second eluting enantiomer. ESI MS (M+H)$^+$=494.4. HPLC Peak T$_r$=1.877 min. Purity=100%. HPLC conditions: C. Absolute stereochemistry not determined.

Example 1204

(+/−)-3-Cyclopropyl-3-(3-(3-(4-ethoxyphenyl)ureido)-4-(isobutyl(tetrahydro-2H-pyran-4-yl)amino)phenyl)propanoic acid

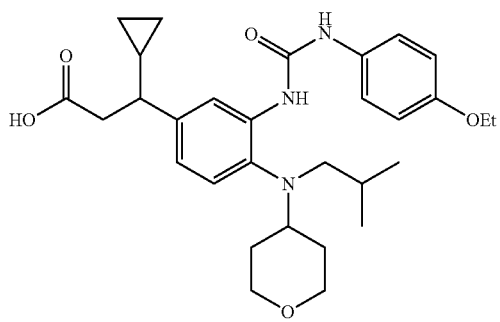 [SMILES: CCOc1ccc(NC(=O)Nc2cc(C(CC(=O)O)C3CC3)ccc2N(CC(C)C)C2CCOCC2)cc1]

To a solution of 1198C (54.1 mg, 0.139 mmol) in THF (696 µl) at rt was added 4-nitrophenyl carbonochloridate (29.5 mg, 0.146 mmol). After stirring for 2 h, 4-ethoxyaniline (53.8 µl, 0.418 mmol) and triethylamine (58.2 µl, 0.418 mmol). The reaction was heated at 50° C. overnight (start at 3:15 pm). To this reaction were added MeOH (0.15 mL) and a 1 M solution of lithium hydroxide (1392 µl, 1.392 mmol). The reaction was heated at 50° C. for 1 h. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 18 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 30×150 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 20 minutes, then a 2-minute hold at 100% B; Flow: 40 mL/min. Fractions containing the desired product were combined and dried via centrifugal evaporation to afford Example 1204 (26.7 mg, 35%). ESI MS (M+H)$^+$=524.4. HPLC Peak T$_r$=1.790 min. Purity=96%. HPLC conditions: C.

Example 1205 Enantiomer 1 and Enantiomer 2

Example 1205 Enantiomer 1: 3-Cyclopropyl-3-(3-(3-(4-ethoxyphenyl)ureido)-4-(isobutyl(tetrahydro-2H-pyran-4-yl)amino)phenyl)propanoic acid

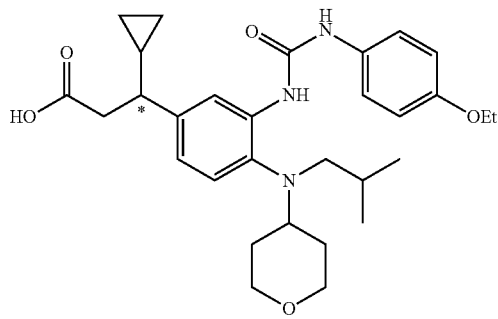 [SMILES: CCOc1ccc(NC(=O)Nc2cc(C(CC(=O)O)C3CC3)ccc2N(CC(C)C)C2CCOCC2)cc1]

Example 1205 Enantiomer 2: 3-Cyclopropyl-3-(3-(3-(4-ethoxyphenyl)ureido)-4-(isobutyl(tetrahydro-2H-pyran-4-yl)amino)phenyl)propanoic acid

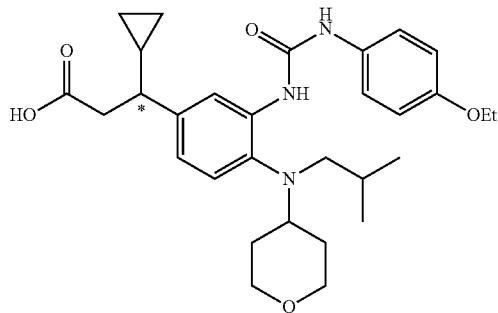 [SMILES: CCOc1ccc(NC(=O)Nc2cc(C(CC(=O)O)C3CC3)ccc2N(CC(C)C)C2CCOCC2)cc1]

Approximately 26 mg Example 1204 was resolved. The racemic material was purified via preparative SFC with the following conditions: Column: AD, 25×3 cm ID, 5-μm particles; Mobile Phase A: 85/15 CO$_2$/MeOH; Detector Wavelength: 220 nm; Flow: 85 mL/min. The fractions ("Peak-1" T$_r$=8.728 min, and "Peak-2" T$_r$=9.510 min; analytical conditions: Column: AD, 250×4.6 mm ID, 5-μm particles; Mobile Phase A: 85/15 CO$_2$/MeOH; Flow: 2.0 mL/min) were collected in MeOH. The stereoisomeric purity of each fraction was estimated to be greater than 98.0% based on the prep-SFC chromatograms. Each enantiomer was further purified via preparative LC/MS with the following conditions: First eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 18 minutes, then a 5-minute hold at 100% B; Flow: 20 mL/min. Fractions containing the desired product were combined and dried via centrifugal evaporation to afford:

Example 1205 Enantiomer 1: 9.8 mg, 13% of the first eluting enantiomer. ESI MS (M+H)$^+$=524.5. HPLC Peak T$_r$=1.939 min. Purity=93%. HPLC conditions: C. Absolute stereochemistry not determined.

Second eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 18 minutes, then a 5-minute hold at 100% B; Flow: 20 mL/min. Fractions containing the desired product were combined and dried via centrifugal evaporation to afford:

Example 1205 Enantiomer 2: 12.3 mg, 17% of the second eluting enantiomer. ESI MS (M+H)$^+$=524.1. HPLC Peak T$_r$=1.941 min. Purity=98%. HPLC conditions: C. Absolute stereochemistry not determined.

Example 1206

(+/−)-3-Cyclopropyl-3-(4-(isobutyl(tetrahydro-2H-pyran-4-yl)amino)-3-(3-(pyrimidin-5-yl)ureido)phenyl)propanoic acid

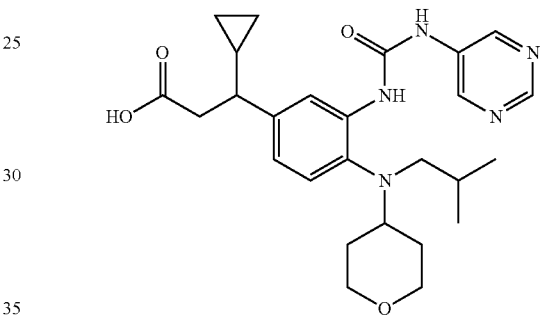

To a solution of 1198C (59.9 mg, 0.154 mmol) in THF (771 μl) at rt was added 4-nitrophenyl carbonochloridate (32.6 mg, 0.162 mmol). After 3 h, reaction checked by LC-MS and showed all carbamate and no SM left. To this reaction were added pyrimidin-5-amine (44.0 mg, 0.462 mmol) and triethylamine (64.5 μl, 0.462 mmol). The reaction was heated at 50° C. overnight. To this reaction were added MeOH (0.15 mL) and a 1 M solution of lithium hydroxide (1542 μl, 1.542 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation to afford Example 1206 (21.5 mg, 27%). ESI MS (M+H)$^+$=482.4. HPLC Peak T$_r$=1.380 min. Purity=94%. HPLC conditions: C.

Example 1207

Enantiomer 1 and Enantiomer 2

Example 1207 Enantiomer 1: 3-Cyclopropyl-3-(4-(isobutyl(tetrahydro-2H-pyran-4-yl)amino)-3-(3-(pyrimidin-5-yl)ureido)phenyl)propanoic acid

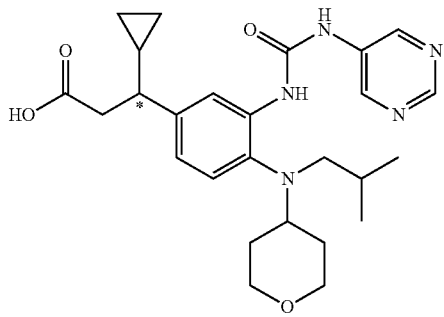 [SMILES: CC(C)CN(c1ccc(C(CC(=O)O)C2CC2)cc1NC(=O)Nc1cncnc1)C1CCOCC1]

Example 1207 Enantiomer 2: 3-Cyclopropyl-3-(4-(isobutyl(tetrahydro-2H-pyran-4-yl)amino)-3-(3-(pyrimidin-5-yl)ureido)phenyl)propanoic acid

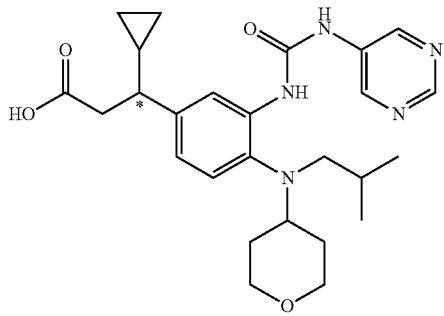 [SMILES: CC(C)CN(c1ccc(C(CC(=O)O)C2CC2)cc1NC(=O)Nc1cncnc1)C1CCOCC1]

Approximately 21 mg Example 1206 was resolved. The racemic material was purified via preparative SFC with the following conditions: Column: PHENOMENEX® Lux Cellulose-4, 25×3 cm ID, 5-μm particles; Mobile Phase A: 70/30 $CO_2$/MeOH; Detector Wavelength: 220 nm; Flow: 100 mL/min. The fractions ("Peak-1" $T_r$=5.436 min, and "Peak-2" $T_r$=6.943 min; analytical conditions: Column: PHENOMENEX® Lux-4, 250×4.6 mm ID, 5-μm particles; Mobile Phase A: 70/30 $CO_2$/MeOH; Flow: 2.0 mL/min) were collected in MeOH. The stereoisomeric purity of each fraction was estimated to be greater than 99.0% based on the prep-SFC chromatograms. Each enantiomer was further purified via preparative LC/MS with the following conditions: First eluting enantiomer Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation to afford:

Example 1207 Enantiomer 1: 7.5 mg, 10% of the first eluting enantiomer. ESI MS (M+H)$^+$=482.4. HPLC Peak $T_r$=1.406 min. Purity=96%. HPLC conditions: C. Absolute stereochemistry not determined.

Second eluting enantiomer: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation to afford:

Example 1207 Enantiomer 2: 7.5 mg, 10% of the second eluting enantiomer. ESI MS (M+H)$^+$=482.4. HPLC Peak $T_r$=1.407 min. Purity=98%. HPLC conditions: C. Absolute stereochemistry not determined.

Example 1208

(+/−)-3-Cyclopropyl-3-(4-(isobutyl(tetrahydro-2H-pyran-4-yl)amino)-3-(2-(p-tolyl)acetamido)phenyl)propanoic acid

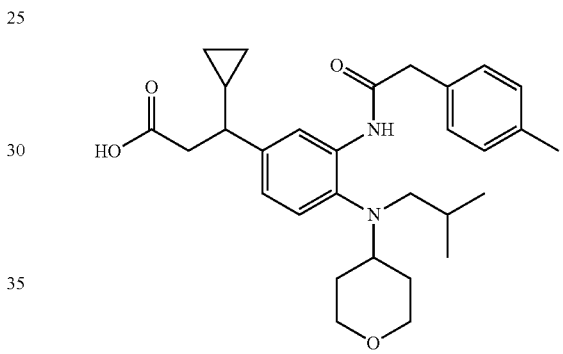

To a solution of 1198C (42.3 mg, 0.109 mmol) in THF (778 μl) at rt was added 2-(p-tolyl)acetic acid (49.0 mg, 0.327 mmol), followed by 1-(3-dimethylaminopropyl)-3-ethylcarbodiimide hydrochloride (62.6 mg, 0.327 mmol), 4-hydroxybenzotriazole (44.1 mg, 0.327 mmol) and Hunig's base (76 μl, 0.435 mmol). The reaction was stirred at rt for 16 h. To this reaction were added MeOH (311 μl) and lithium hydroxide (1089 μl, 1.089 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 minutes, then a 5-minute hold at 100% B; Flow: 20 mL/min. Fractions containing the desired product were combined and dried via centrifugal evaporation to afford Example 1208 (23.2 mg, 42%). ESI MS (M+H)$^+$=493.4. HPLC Peak $T_r$=1.955 min. Purity=98%. HPLC conditions: C.

Example 1209

3-(4-(Isobutyl(tetrahydro-2H-pyran-4-yl)amino)-3-(3-(p-tolyl)ureido)phenyl)-4-methoxybutanoic acid

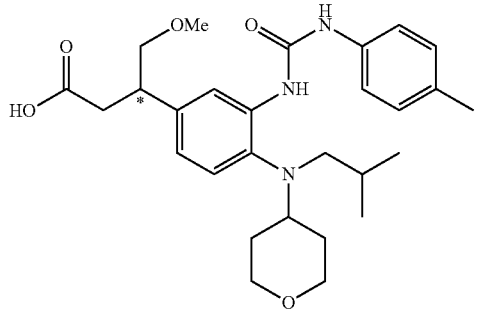 [SMILES: COCC(CC(=O)O)c1ccc(N(CC(C)C)C2CCOCC2)c(NC(=O)Nc2ccc(C)cc2)c1]

1209A. N-Isobutyl-N-(2-nitro-4-(4,4,5,5-tetramethyl-1,3,2-dioxaborolan-2-yl)phenyl)tetrahydro-2H-pyran-4-amine To a solution of N-(4-bromo-2-nitrophenyl)-N-isobutyltetrahydro-2H-pyran-4-amine (Preparation 958C) (800 mg, 2.239 mmol) in DMSO (20 mL) were added 4,4,4',4',5,5,5',5'-octamethyl-2,2'-bi(1,3,2-dioxaborolane) (853 mg, 3.36 mmol) and potassium acetate (440 mg, 4.48 mmol). After the mixture was degassed with $N_2$ for 10 min, $PdCl_2$ (dppf) (82 mg, 0.112 mmol) was added. The mixture was heated at 80° C. overnight. The mixture was partitioned between EtOAc and water. The organic phase was concentrated and purified by ISCO chromatography. Fractions containing the desired product were concentrated to yield 1209A (810 mg, 2.003 mmol, 89% yield) as a brown oil. ESI MS $(M+H)^+=323.1$ (boronic acid).

1209B. Methyl 3-(4-(isobutyl(tetrahydro-2H-pyran-4-yl)amino)-3-nitrophenyl)-4-methoxybutanoate To a solution of 1209A (800 mg, 1.979 mmol) in dioxane (9893 µl) was added (E)-methyl 4-methoxybut-2-enoate (773 mg, 5.94 mmol) followed by sodium hydroxide (1781 µl, 1.781 mmol). The reaction was evacuated and back-filled with nitrogen once. To this solution was added chloro(1,5-cyclooctadiene)rhodium(I) dimer (48.8 mg, 0.099 mmol) and the resultant solution was evacuated and back-filled with nitrogen 3 times. The reaction was heated at 50° C. for 2.5 h. The reaction was quenched with acetic acid (102 µl, 1.781 mmol) and partitioned between EtOAc and water. Layers were separated. The aqueous phase was extracted with EtOAc (3×). The combined organic phases were dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (40 g column, 40 mL/min, 0-5% EtOAc in hexanes over 14 min) gave 1209B (802 mg, 1.963 mmol, 99% yield) as an orange residue. ESI MS $(M+H)^+=409.4$.

1209C Enantiomer 1 and Enantiomer 2. Methyl 3-(3-amino-4-(isobutyl(tetrahydro-2H-pyran-4-yl)amino)phenyl)-4-methoxybutanoate (absolute stereochemistry not determined)

A solution of 1209B (800 mg, 1.958 mmol) in ethyl acetate (5 mL) was hydrogenated with a $H_2$ balloon for 4 h. The reaction mixture was filtered and the filtrate was concentrated to yield methyl 3-(3-amino-4-(isobutyl(tetrahydro-2H-pyran-4-yl)amino)phenyl)-4-methoxybutanoate (741 mg, 1.958 mmol, 100% yield) as a yellow oil. Approx. 741 mg of racemic material was resolved. The racemic material was purified via preparative SFC with the following conditions: Column: Lux Cellulose-4, 25×3 cm ID, 5-µm particles; Mobile Phase A: 87/13 $CO_2$/IPA with 0.1% $NH_4OH$; Detector Wavelength: 220 nm; Flow: 170 mL/min. The fractions ("Peak-1" $T_r=9.61$ min, and "Peak-2" $T_r=10.75$ min; analytical conditions: Column: Lux Cellulose-4, 25×0.46 cm ID, 5-µm particles; Mobile Phase A: 87/13 $CO_2$/IPA with 0.1% $NH_4OH$) were collected in IPA. The stereoisomeric purity of each fraction was estimated to be greater than 99.9% (Peak-1) and 96.8% (Peak-2) based on the prep-SFC chromatograms.

Enantiomer 1: 266 mg, 38% of the first eluting enantiomer. ESI MS $(M+H)^+=379.4$.

Enantiomer 2: 259 mg, 37% of the first eluting enantiomer. ESI MS $(M+H)^+=379.4$.

Example 1209 3-(4-(Isobutyl(tetrahydro-2H-pyran-4-yl)amino)-3-(3-(p-tolyl)ureido)phenyl)-4-methoxybutanoic acid To a solution of 1209C Enantiomer 1 (19.1 mg, 0.050 mmol) in THF (252 µl) was added 1-isocyanato-4-methylbenzene (12.70 µl, 0.101 mmol) at rt. After 2.5 h, MeOH (0.15 mL) and a 1M solution of lithium hydroxide (505 µl, 0.505 mmol) were added. The reaction was heated at 70° C. for 2 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation to afford Example 1209 (12.0 mg, 47%). ESI MS $(M+H)^+=498.4$. HPLC Peak $T_r=1.611$ min. Purity=99%. HPLC conditions: C. Absolute stereochemistry not determined.

Example 1210

3-(3-(3-(4-Chloro-2-fluorophenyl)ureido)-4-(isobutyl(tetrahydro-2H-pyran-4-yl)amino)phenyl)-4-methoxybutanoic acid

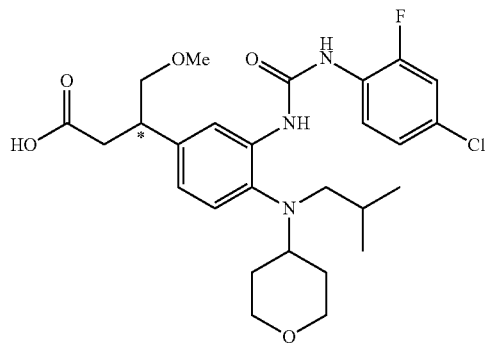 [SMILES: COCC(CC(=O)O)c1ccc(N(CC(C)C)C2CCOCC2)c(NC(=O)Nc2ccc(Cl)cc2F)c1]

To a solution of 1209C Enantiomer 1 (15.2 mg, 0.040 mmol) in THF (201 µl) was added 4-chloro-2-fluoro-1-isocyanatobenzene (10.18 µl, 0.080 mmol) at rt. After 2.5 h, MeOH (0.15 mL) and a 1M solution of lithium hydroxide (402 µl, 0.402 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-75% B over 20 minutes, then a 5-minute hold at 100% B; Flow: 20 mL/min. Fractions containing the desired product were combined and dried via centrifugal evaporation to afford Example 1210 (9.9 mg, 44%). ESI MS (M+H)$^+$=536.4. HPLC Peak T$_r$=1.698 min. Purity=96%. HPLC conditions: C. Absolute stereochemistry not determined.

Example 1211

3-(4-(Isobutyl(tetrahydro-2H-pyran-4-yl)amino)-3-(3-(4-(trifluoromethoxy)phenyl)ureido)phenyl)-4-methoxybutanoic acid

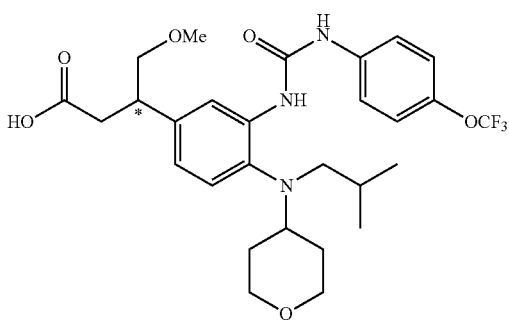 [SMILES: COCC(CC(=O)O)c1ccc(N(CC(C)C)C2CCOCC2)c(NC(=O)Nc2ccc(OC(F)(F)F)cc2)c1]

To a solution of 1209C Enantiomer 1 (15.3 mg, 0.040 mmol) in THF (202 µl) was added 1-isocyanato-4-(trifluoromethoxy)benzene (12.20 µl, 0.081 mmol) at rt (start at 4:30 pm). After 2.5 h, MeOH (0.15 mL) and a 1M solution of lithium hydroxide (404 µl, 0.404 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-80% B over 20 minutes, then a 5-minute hold at 100% B; Flow: 20 mL/min. Fractions containing the desired product were combined and dried via centrifugal evaporation to afford Example 1211 (12.0 mg, 52%). ESI MS (M+H)$^+$=568.5. HPLC Peak T$_r$=1.795 min. Purity=100%. HPLC conditions: C. Absolute stereochemistry not determined.

Example 1212

3-(3-(3-(4-Ethoxyphenyl)ureido)-4-(isobutyl(tetrahydro-2H-pyran-4-yl)amino)phenyl)-4-methoxybutanoic acid

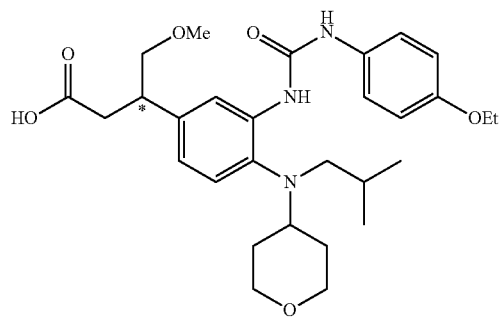 [SMILES: CCOc1ccc(NC(=O)Nc2cc(C(COC)CC(=O)O)ccc2N(CC(C)C)C2CCOCC2)cc1]

To a solution of 1209C Enantiomer 1 (15.3 mg, 0.040 mmol) in THF (202 µl) at rt was added 4-nitrophenyl carbonochloridate (8.56 mg, 0.042 mmol). After 1.5 h, 4-ethoxyaniline (15.62 µl, 0.121 mmol) and triethylamine (16.90 µl, 0.121 mmol) were added. The reaction was heated at 50° C. overnight. To this reaction were added MeOH (0.15 mL) and a 1 M solution of lithium hydroxide (404 µl, 0.404 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 4-minute hold at 100% B; Flow: 20 mL/min. Fractions containing the desired product were combined and dried via centrifugal evaporation to afford Example 1212 (11.0 mg, 52%). ESI MS (M+H)$^+$=528.5. HPLC Peak T$_r$=1.594 min. Purity=100%. HPLC conditions: C. Absolute stereochemistry not determined.

Example 1213

3-(4-(Isobutyl(tetrahydro-2H-pyran-4-yl)amino)-3-(3-(5-methylisoxazol-3-yl)ureido)phenyl)-4-methoxybutanoic acid

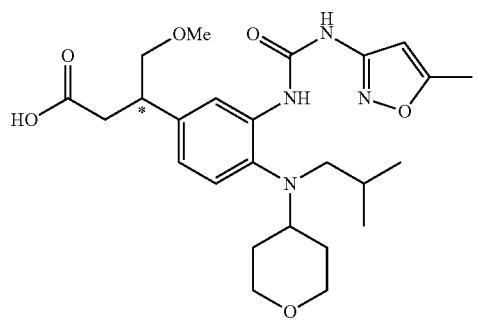 [SMILES: COCC(CC(=O)O)c1ccc(N(CC(C)C)C2CCOCC2)c(NC(=O)Nc2cc(C)on2)c1]

To a solution of 1209C Enantiomer 1 (19.1 mg, 0.050 mmol) in THF (252 μl) at rt was added 4-nitrophenyl carbonochloridate (10.68 mg, 0.053 mmol). The mixture was stirred at rt for 3 h. To this reaction were added 5-methylisoxazol-3-amine (14.85 mg, 0.151 mmol) and triethylamine (21.10 μl, 0.151 mmol). The reaction was heated at 50° C. overnight. To this reaction were added MeOH (0.15 mL) and a 1 M solution of lithium hydroxide (505 μl, 0.505 mmol). The reaction was heated at 70° C. for 2 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 4-minute hold at 100% B; Flow: 20 mL/min. Fractions containing the desired product were combined and dried via centrifugal evaporation to afford Example 1213 (7.9 mg, 31%). ESI MS (M+H)$^+$=489.1. HPLC Peak T$_r$=1.417 min. Purity=98%. HPLC conditions: C. Absolute stereochemistry not determined.

Example 1214

3-(3-(3-(2-Fluoro-4-methoxyphenyl)ureido)-4-(isobutyl(tetrahydro-2H-pyran-4-yl)amino)phenyl)-4-methoxybutanoic acid

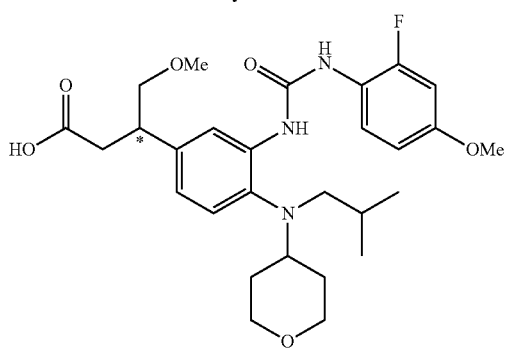

To a solution of 1209C Enantiomer 1 (14.1 mg, 0.037 mmol) in THF (186 μl) at rt was added 4-nitrophenyl carbonochloridate (7.88 mg, 0.039 mmol). After 3 h, 2-fluoro-4-methoxyaniline (15.77 mg, 0.112 mmol) and triethylamine (20.77 μl, 0.149 mmol) were added. The reaction was heated at 50° C. overnight. To this reaction were added MeOH (0.15 mL) and a 1 M solution of lithium hydroxide (373 μl, 0.373 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 4-minute hold at 100% B; Flow: 20 mL/min. Fractions containing the desired product were combined and dried via centrifugal evaporation to afford Example 1214 (17.1 mg, 84%). ESI MS (M+H)$^+$=532.1. HPLC Peak T$_r$=1.505 min. Purity=97%. HPLC conditions: C. Absolute stereochemistry not determined.

Example 1215

3-(3-(3-(4-Ethoxy-2-fluorophenyl)ureido)-4-(isobutyl(tetrahydro-2H-pyran-4-yl)amino)phenyl)-4-methoxybutanoic acid

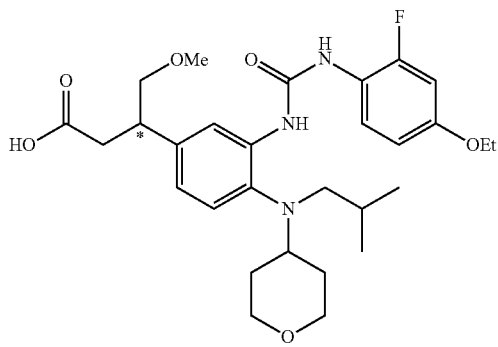 [SMILES: CCOc1ccc(NC(=O)Nc2cc(C(COC)CC(=O)O)ccc2N(CC(C)C)C2CCOCC2)c(F)c1]

To a solution of 1209C Enantiomer 1 (15.6 mg, 0.041 mmol) in THF (206 μl) at rt was added 4-nitrophenyl carbonochloridate (8.72 mg, 0.043 mmol). After 3 h, reaction 4-ethoxy-2-fluoroaniline, HCl (23.69 mg, 0.124 mmol) and triethylamine (22.98 μl, 0.165 mmol) were added. The reaction was heated at 50° C. overnight. To this reaction were added MeOH (0.15 mL) and a 1 M solution of lithium hydroxide (412 μl, 0.412 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 20 minutes, then a 5-minute hold at 100% B; Flow: 20 mL/min. Fractions containing the desired product were combined and dried via centrifugal evaporation to afford Example 1215 (11.5 mg, 49%). ESI MS (M+H)$^+$=546.5. HPLC Peak T$_r$=1.630 min. Purity=95%. HPLC conditions: C. Absolute stereochemistry not determined.

Example 1216

3-(4-(Isobutyl(tetrahydro-2H-pyran-4-yl)amino)-3-(3-(p-tolyl)ureido)phenyl)-4-methoxybutanoic acid

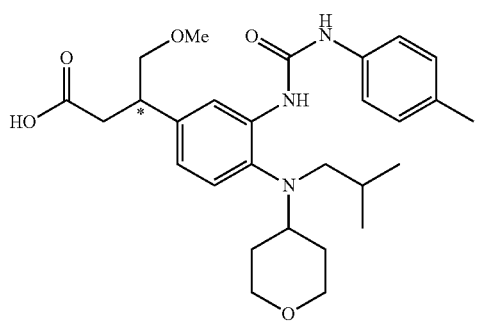 [SMILES: COCC(CC(=O)O)c1ccc(N(CC(C)C)C2CCOCC2)c(NC(=O)Nc2ccc(C)cc2)c1]

To a solution of 1209C Enantiomer 2 (19.4 mg, 0.051 mmol) in THF (256 μl) was added 1-isocyanato-4-methylbenzene (12.90 μl, 0.103 mmol) at rt. After 2.5 h, MeOH (0.15 mL) and a 1M solution of lithium hydroxide (513 μl, 0.513 mmol) were added. The reaction was heated at 70° C. for 2 h. The reaction was adjusted to pH 6 with 1N HCl (0.5 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 4-minute hold at 100% B; Flow: 20 mL/min. Fractions containing the desired product were combined and dried via centrifugal evaporation to afford Example 1216 (16.0 mg, 62%). ESI MS (M+H)⁺=498.2. HPLC Peak T$_r$=1.612 min. Purity=98%. HPLC conditions: C. Absolute stereochemistry not determined.

Example 1217

3-(3-(3-(4-Chloro-2-fluorophenyl)ureido)-4-(isobutyl(tetrahydro-2H-pyran-4-yl)amino)phenyl)-4-methoxybutanoic acid

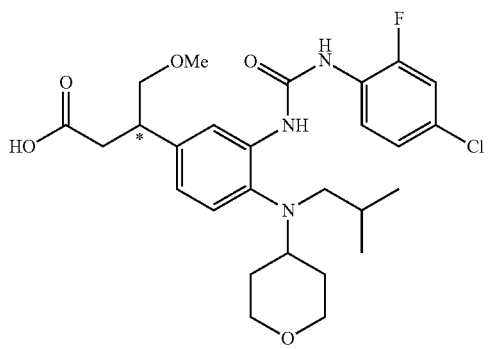 [SMILES: COCC(CC(=O)O)c1ccc(N(CC(C)C)C2CCOCC2)c(NC(=O)Nc2ccc(Cl)cc2F)c1]

To a solution of 1209C Enantiomer 2 (15.1 mg, 0.040 mmol) in THF (199 μl) was added 4-chloro-2-fluoro-1-isocyanatobenzene (10.11 μl, 0.080 mmol) at rt. After 2.5 h, MeOH (0.15 mL) and a 1M solution of lithium hydroxide (399 μl, 0.399 mmol) were added. The reaction was heated at 70° C. for 1 h. The reaction was adjusted to pH 6 with 1N HCl (0.4 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Example 1217 (13.3 mg, 62%). ESI MS (M+H)⁺=536.1. HPLC Peak T$_r$=1.693 min. Purity=99%. HPLC conditions: C. Absolute stereochemistry not determined.

Example 1218

3-(4-(Isobutyl(tetrahydro-2H-pyran-4-yl)amino)-3-(3-(4-(trifluoromethoxy)phenyl)ureido)phenyl)-4-methoxybutanoic acid

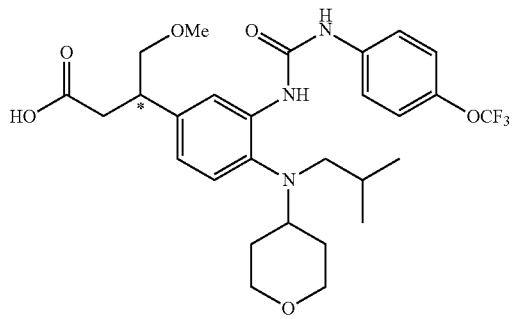 [SMILES: COCC(CC(=O)O)c1ccc(N(CC(C)C)C2CCOCC2)c(NC(=O)Nc2ccc(OC(F)(F)F)cc2)c1]

To a solution of 1209C Enantiomer 2 (18.6 mg, 0.049 mmol) in THF (246 μl) was added 1-isocyanato-4-(trifluoromethoxy)benzene (14.83 μl, 0.098 mmol) at rt. After 2.5 h, MeOH (0.15 mL) and a 1M solution of lithium hydroxide (491 μl, 0.491 mmol) were added. The reaction was heated at 70° C. for 1 h. The reaction was adjusted to pH 6 with 1N HCl (0.5 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 4-minute hold at 100% B; Flow: 20 mL/min. Fractions containing the desired product were combined and dried via centrifugal evaporation to afford Example 1218 (15.8 mg, 56%). ESI MS (M+H)⁺=568.2. HPLC Peak T$_r$=1.795 min. Purity=99%. HPLC conditions: C. Absolute stereochemistry not determined.

Example 1219

3-(3-(3-(4-Ethoxyphenyl)ureido)-4-(isobutyl(tetrahydro-2H-pyran-4-yl)amino)phenyl)-4-methoxybutanoic acid

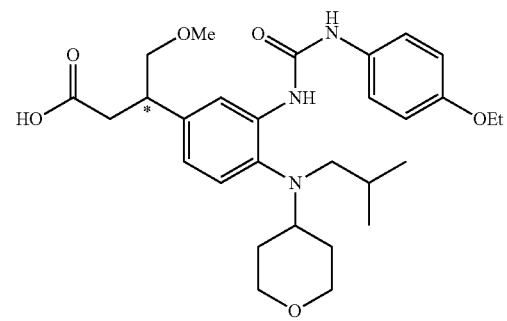 [SMILES: CCOc1ccc(NC(=O)Nc2cc(C(COC)CC(=O)O)ccc2N(CC(C)C)C2CCOCC2)cc1]

To a solution of 1209C Enantiomer 2 (15.4 mg, 0.041 mmol) in THF (203 μl) at rt was added 4-nitrophenyl carbonochloridate (8.61 mg, 0.043 mmol). After 1.5 h, 4-ethoxyaniline (15.72 µl, 0.122 mmol) and triethylamine (17.01 µl, 0.122 mmol) were added. The reaction was heated at 50° C. overnight. To this reaction were added MeOH (0.15 mL) and a 1 M solution of lithium hydroxide (407 µl, 0.407 mmol). The reaction was heated at 50° C. for 1 h. The reaction was adjusted to pH 6 with 1N HCl (0.4 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 20 minutes, then a 5-minute hold at 100% B; Flow: 20 mL/min. Fractions containing the desired product were combined and dried via centrifugal evaporation to afford Example 1219 (10.4 mg, 48%). ESI MS (M+H)$^+$=528.5. HPLC Peak T$_r$=1.593 min. Purity=99%. HPLC conditions: C. Absolute stereochemistry not determined.

Example 1220

3-(4-(Isobutyl(tetrahydro-2H-pyran-4-yl)amino)-3-(3-(5-methy s oxazol-3-yl)ureido)phenyl)-4-methoxybutanoic acid

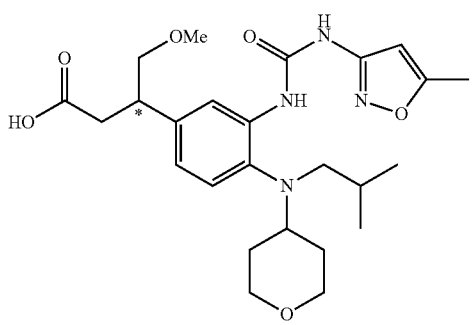

To a solution of 1209C Enantiomer 2 (22.9 mg, 0.061 mmol) in THF (303 µl) at rt was added 4-nitrophenyl carbonochloridate (12.80 mg, 0.064 mmol). The mixture was stirred at rt for 3 h. To this reaction were added 5-methylisoxazol-3-amine (17.81 mg, 0.182 mmol) and triethylamine (25.3 µl, 0.182 mmol). The reaction was heated at 50° C. overnight. After 2.5 h, MeOH (0.15 mL) and a 1 M solution of lithium hydroxide (605 µl, 0.605 mmol) were added. The reaction was heated at 70° C. for 2 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to afford Example 1220 (6.9 mg, 23%). ESI MS (M+H)$^+$=489.4. HPLC Peak T$_r$=1.416 min. Purity=99%. HPLC conditions: C. Absolute stereochemistry not determined.

Example 1221

3-(3-(3-(2-Fluoro-4-methoxyphenyl)ureido)-4-(isobutyl(tetrahydro-2H-pyran-4-yl)amino)phenyl)-4-methoxybutanoic

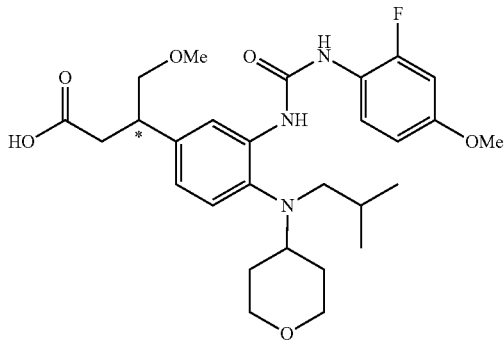 [SMILES: COCC(CC(=O)O)c1ccc(N(CC(C)C)C2CCOCC2)c(NC(=O)Nc2ccc(OC)cc2F)c1]

To a solution of 1209C Enantiomer 2 (13.5 mg, 0.036 mmol) in THF (178 µl) at rt was added 4-nitrophenyl carbonochloridate (7.55 mg, 0.037 mmol). After 3 h, 2-fluoro-4-methoxyaniline (15.10 mg, 0.107 mmol) and triethylamine (19.88 µl, 0.143 mmol) were added. The reaction was heated at 50° C. overnight. To this reaction were added MeOH (0.15 mL) and a 1 M solution of lithium hydroxide (357 µl, 0.357 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×150 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to afford Example 1221 (13.1 mg, 69%). ESI MS (M+H)$^+$=532.1. HPLC Peak T$_r$=1.507 min. Purity=100%. HPLC conditions: C. Absolute stereochemistry not determined.

Example 1222

3-(3-(3-(4-Ethoxy-2-fluorophenyl)ureido)-4-(isobutyl(tetrahydro-2H-pyran-4-yl)amino)phenyl)-4-methoxybutanoic acid

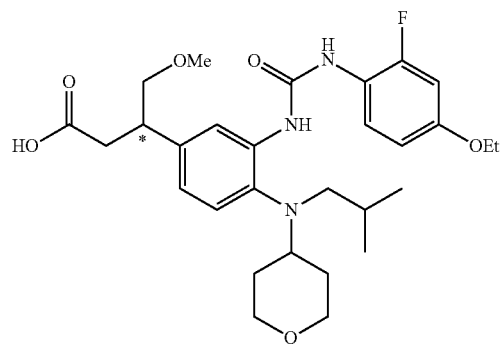 [SMILES: CCOc1ccc(NC(=O)Nc2cc(C(COC)CC(=O)O)ccc2N(CC(C)C)C2CCOCC2)c(F)c1]

To a solution of 1209C Enantiomer 2 (21.1 mg, 0.056 mmol) in THF (279 μl) at rt was added 4-nitrophenyl carbonochloridate (11.80 mg, 0.059 mmol). After 3 h, 4-ethoxy-2-fluoroaniline, HCl (32.0 mg, 0.167 mmol) and triethylamine (31.1 μl, 0.223 mmol) were added. The reaction was heated at 50° C. overnight. To this reaction were added MeOH (0.15 mL) and a 1 M solution of lithium hydroxide (557 μl, 0.557 mmol). The reaction was heated at 50° C. for 1 h. The reaction was adjusted to pH 6 with 1N HCl (0.5 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation to afford Example 1222 (19.6 mg, 64%). ESI MS (M+H)$^+$=546.2. HPLC Peak T$_r$=1.628 min. Purity=99%. HPLC conditions: C. Absolute stereochemistry not determined.

Example 1223

(+/−)-Methyl 3-(4-(cyclohexyl(isobutyl)amino)-3-(3-(p-tolyl)ureido)phenyl)-4-methoxybutanoate

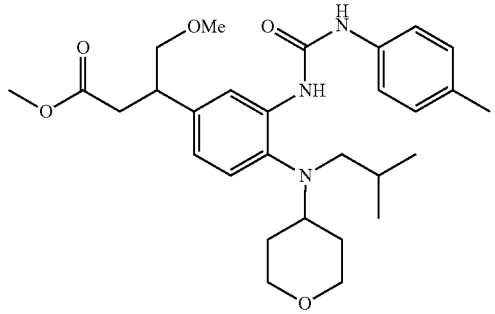

To a solution of (+/−)-methyl 3-(3-amino-4-(cyclohexyl (isobutyl)amino)phenyl)-4-methoxybutanoate (986A) (0.315 g, 0.837 mmol) in THF (4.18 ml) was added 1-isocyanato-4-methylbenzene (0.211 ml, 1.673 mmol) at rt. After 2.5 h, additional isocyanate was added (0.1 mL). The reaction was diluted with water and extracted with EtOAc. Layers were separated. The aqueous phase was extracted with EtOAc (3×). The organic phases were combined, dried over Na$_2$SO$_4$, filtered, and concentrated to afford an orange residue. The crude material was dissolved in a minimal amount of CH$_2$Cl$_2$ and chromatographed. Purification of the crude material by silica gel chromatography using an ISCO machine (40 g column, 40 mL/min, 0-50% EtOAc in hexanes over 25 min, T$_r$=16 min) gave Example 1223 (0.390 g, 0.765 mmol, 91% yield) as an orange solid. ESI MS (M+H)$^+$=510.6. HPLC Peak T$_r$=1.02 min. Purity=100%. HPLC conditions: A.

Example 1224

(+/−)-Methyl 3-(4-(cyclohexyl(isobutyl)amino)-3-(3-(5-methylisoxazol-3-yl)ureido)phenyl)-4-methoxybutanoate

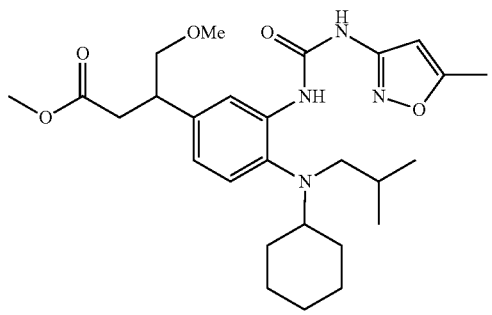

To a solution of (+/−)-methyl 3-(3-amino-4-(cyclohexyl (isobutyl)amino)phenyl)-4-methoxybutanoate (986A) (0.320 g, 0.850 mmol) in THF (4.25 ml) at rt was added 4-nitrophenyl carbonochloridate (0.180 g, 0.892 mmol). The mixture was stirred at rt for 3 h. To this reaction were added 5-methylisoxazol-3-amine (0.250 g, 2.55 mmol) and triethylamine (0.355 ml, 2.55 mmol). The reaction was heated at 50° C. overnight. The reaction was diluted with water and extracted with EtOAc. Layers were separated. The aqueous phase was extracted with EtOAc (3×). The organic phases were combined, dried over Na$_2$SO$_4$, filtered, and concentrated to afford an orange residue. The crude material was dissolved in a minimal amount of CH$_2$Cl$_2$ and chromatographed. Purification of the crude material by silica gel chromatography using an ISCO machine (40 g column, 40 mL/min, 0-80% EtOAc in hexanes over 22 min, T$_r$=13 min) gave Example 1224 (0.146 g, 0.277 mmol, 32.6% yield) as an off-white solid. ESI MS (M+H)$^+$=501.6. HPLC Peak T$_r$=1.03 min. Purity=100%. HPLC conditions: A.

Example 1225

Enantiomer 1 and Enantiomer 2

Example 1225 Enantiomer 1: 3-(4-(Cyclohexyl (isobutyl)amino)-3-(3-(2-fluorophenyl)ureido)phenyl)-4-methoxybutanoic acid

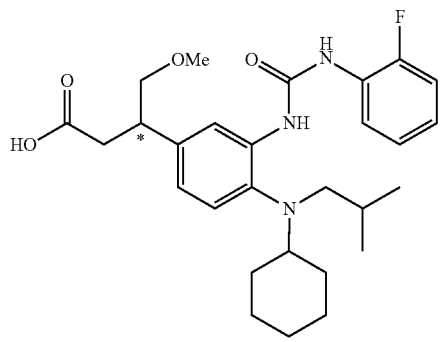 [SMILES: COCC(CC(=O)O)c1ccc(N(CC(C)C)C2CCCCC2)c(NC(=O)Nc2ccccc2F)c1]

Example 1225 Enantiomer 2: 3-(4-(Cyclohexyl(isobutyl)amino)-3-(3-(2-fluorophenyl)ureido)phenyl)-4-methoxybutanoic acid

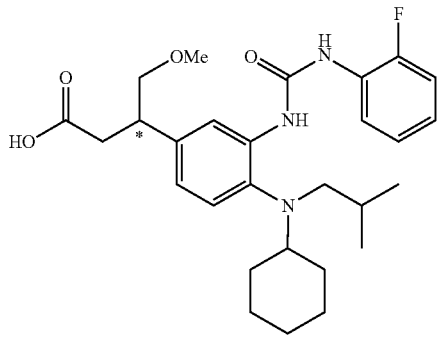 [SMILES: COCC(CC(=O)O)c1ccc(N(CC(C)C)C2CCCCC2)c(NC(=O)Nc2ccccc2F)c1]

Approximately 45 mg of Example 1124 was resolved. The racemic material was purified via preparative SFC with the following conditions: Column: IC, 25×3 cm ID, 5-μm particles; Mobile Phase A: 90/10 $CO_2$/MeOH; Detector Wavelength: 220 nm; Flow: 85 mL/min. The fractions ("Peak-1" $T_r$=16.490 min, and "Peak-2" $T_r$=18.051 min; analytical conditions: Column: IC, 250×4.6 mm ID, 5-μm particles; Mobile Phase A: 90/10 $CO_2$/MeOH; Flow: 2.0 mL/min) were collected in MeOH. The stereoisomeric purity of each fraction was estimated to be greater than 95.0% based on the prep-SFC chromatograms. Each enantiomer was further purified via preparative LC/MS with the following conditions: First eluting enantiomer: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 20 minutes, then a 5-minute hold at 100% B; Flow: 20 mL/min. Fractions containing the desired product were combined and dried via centrifugal evaporation to afford:

Example 1225 Enantiomer 1: 6.7 mg, 8% of the first eluting enantiomer. ESI MS (M+H)$^+$=500.0. HPLC Peak $T_r$=2.089 min. Purity=97%. HPLC conditions: C. Absolute stereochemistry not determined.

Second eluting enantiomer: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 20 minutes, then a 5-minute hold at 100% B; Flow: 20 mL/min. Fractions containing the desired product were combined and dried via centrifugal evaporation to afford:

Example 1225 Enantiomer 2: 10.5 mg, 13% of the second eluting enantiomer. ESI MS (M+H)$^+$=500.2. HPLC Peak $T_r$=2.087 min. Purity=97%. HPLC conditions: C. Absolute stereochemistry not determined.

Example 1226

(+/−)-3-(4-(Cyclohexyl(isobutyl)amino)-3-(2-(p-tolyl)acetamido)phenyl)-4-methoxybutanoic acid

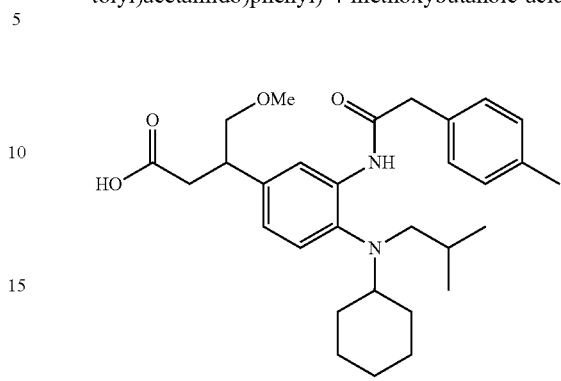

To a solution of 986A (19.6 mg, 0.052 mmol) in THF (372 μl) at rt was added 2-(p-tolyl)acetic acid (23.45 mg, 0.156 mmol), followed by 1-(3-dimethylaminopropyl)-3-ethylcarbodiimide hydrochloride (29.9 mg, 0.156 mmol), 4-hydroxybenzotriazole (21.10 mg, 0.156 mmol) and Hunig's base (36.4 μl, 0.208 mmol). The reaction was stirred at rt for 16 h. To this reaction were added MeOH (149 μl) and lithium hydroxide (521 μl, 0.521 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 12 minutes, then a 4-minute hold at 100% B; Flow: 20 mL/min. Fractions containing the desired product were combined and dried via centrifugal evaporation to afford Example 1226 (12.9 mg, 49%). ESI MS (M+H)$^+$=495.4. HPLC Peak $T_r$=2.261 min. Purity=97%. HPLC conditions: C.

Example 1227

(+/−)-3-(4-(Cyclohexyl(isobutyl)amino)-3-(3-(4-ethoxyphenyl)ureido)phenyl)-4-methoxybutanoic acid

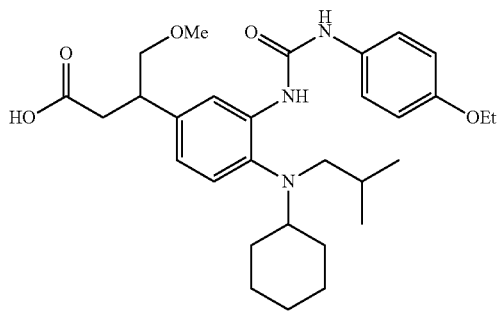 [SMILES: CCOc1ccc(NC(=O)Nc2cc(C(COC)CC(=O)O)ccc2N(CC(C)C)C2CCCCC2)cc1]

To a solution of 986A (19.6 mg, 0.052 mmol) in THF (260 µl) at rt was added 4-nitrophenyl carbonochloridate (11.02 mg, 0.055 mmol). After stirring for 2 h, 4-ethoxyaniline (20.11 µl, 0.156 mmol) and triethylamine (21.77 µl, 0.156 mmol). The reaction was heated at 50° C. overnight. To this reaction were added MeOH (0.15 mL) and a 1 M solution of lithium hydroxide (521 µl, 0.521 mmol). The reaction was heated at 50° C. for 1 h. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 4-minute hold at 100% B; Flow: 20 mL/min. Fractions containing the desired product were combined and dried via centrifugal evaporation to afford Example 1227 (18.4 mg, 67%). ESI MS (M+H)$^+$=526.3. HPLC Peak T$_r$=2.135 min. Purity=99%. HPLC conditions: C.

Example 1228

(+/−)-3-(4-(Cyclohexyl(isobutyl)amino)-3-(2-(4-ethoxyphenyl)acetamido)phenyl)-4-methoxybutanoic acid

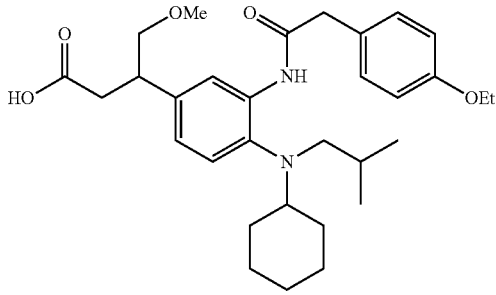 [SMILES: CCOc1ccc(CC(=O)Nc2cc(C(COC)CC(=O)O)ccc2N(CC(C)C)C2CCCCC2)cc1]

To a solution of 986A (20 mg, 0.053 mmol) in THF (0.5 mL) at rt was added 2-(4-ethoxyphenyl)acetic acid (28.7 mg, 0.159 mmol), followed by 1-(3-dimethylaminopropyl)-3-ethylcarbodiimide hydrochloride (30.5 mg, 0.159 mmol), 4-hydroxybenzotriazole (21.53 mg, 0.159 mmol) and Hunig's base (37.1 µl, 0.212 mmol). The reaction was stirred at rt for 16 h. To this reaction was added MeOH (152 µl) and lithium hydroxide (531 µl, 0.531 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 13 minutes, then a 4-minute hold at 100% B; Flow: 20 mL/min. Fractions containing the desired product were combined and dried via centrifugal evaporation to Example 1228 (10.9 mg, 38%). ESI MS (M+H)$^+$=525.5. HPLC Peak T$_r$=2.187 min. Purity=97%. HPLC conditions: C.

Example 1229

(+/−)-3-(3-(2-(4-Chloro-2-fluorophenyl)acetamido)-4-(cyclohexyl(isobutyl)amino)phenyl)-4-methoxybutanoic acid

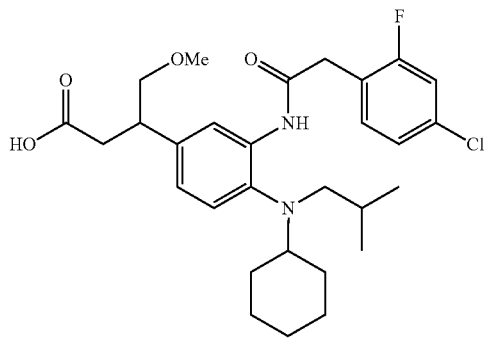

To a solution of 986A (24.1 mg, 0.064 mmol) in THF (0.5 mL) at rt was added 2-(4-chloro-2-fluorophenyl)acetic acid (36.2 mg, 0.192 mmol), followed by 1-(3-dimethylaminopropyl)-3-ethylcarbodiimide hydrochloride (36.8 mg, 0.192 mmol), 4-hydroxybenzotriazole (25.9 mg, 0.192 mmol) and Hunig's base (44.7 µl, 0.256 mmol). The reaction was stirred at rt for 16 h. To this reaction was added MeOH (183 µl) and lithium hydroxide (640 µl, 0.640 mmol). The reaction was heated at 50° C. for 2 h, then allowed to cool to rt. The reaction was adjusted to pH 6 with 1N HCl (0.6 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-100% B over 13 minutes, then a 4-minute hold at 100% B; Flow: 20 mL/min. Fractions containing the desired product were combined and dried via centrifugal evaporation to afford Example 1229 (22.8 mg, 66%). ESI MS (M+H)$^+$=533.0. HPLC Peak T$_r$=2.399 min. Purity=98%. HPLC conditions: C.

Example 1230

(+/−)-3-(4-(Cyclohexyl(isobutyl)amino)-3-(2-(2-fluorophenyl)acetamido)phenyl)-4-methoxybutanoic acid

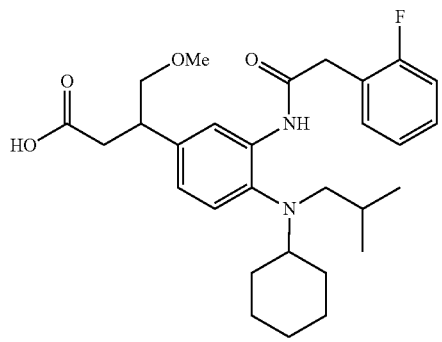 [SMILES: COCC(CC(=O)O)c1ccc(N(CC(C)C)C2CCCCC2)c(NC(=O)Cc2ccccc2F)c1]

To a solution of 986A (19.4 mg, 0.052 mmol) in THF (0.5 mL) at rt was added 2-(2-fluorophenyl)acetic acid (23.82 mg, 0.155 mmol), followed by 1-(3-dimethylaminopropyl)-3-ethylcarbodiimide hydrochloride (29.6 mg, 0.155 mmol), 4-hydroxybenzotriazole (20.89 mg, 0.155 mmol) and Hunig's base (36.0 µl, 0.206 mmol). The reaction was stirred at rt for 16 h. To this reaction was added MeOH (147 µl) and lithium hydroxide (515 µl, 0.515 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 12 minutes, then a 4-minute hold at 100% B; Flow: 20 mL/min. Fractions containing the desired product were combined and dried via centrifugal evaporation to afford Example 1230 (15.0 mg, 56%). ESI MS (M+H)$^+$=499.4. HPLC Peak T$_r$=2.142 min. Purity=96%. HPLC conditions: C.

Example 1231

3-(4-(Cyclohexyl(isobutyl)amino)-3-(3-(4-ethoxyphenyl)ureido)phenyl)-4-methoxybutanoic acid

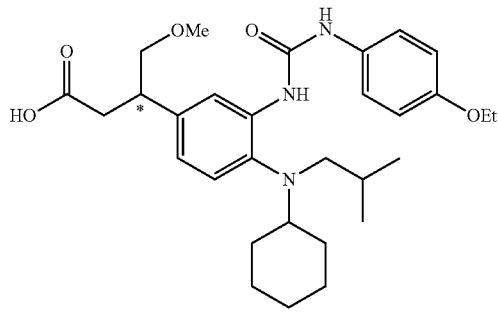 [SMILES: CCOc1ccc(NC(=O)Nc2cc(C(COC)CC(=O)O)ccc2N(CC(C)C)C2CCCCC2)cc1]

1231A Enantiomer 1 and Enantiomer 2. Methyl 3-(3-amino-4-(cyclohexyl(isobutyl)amino)phenyl)-4-methoxybutanoate (absolute stereochemistry not determined)

Approx. 1.81 g of racemic 986A was resolved. The racemic material was purified via preparative SFC with the following conditions: Column: Lux Cellulose-4, 25×3 cm ID, 5-µm particles; Mobile Phase A: 90/10 CO$_2$/MeOH with 0.1% DEA; Detector Wavelength: 220 nm; Flow: 250 mL/min. The fractions ("Peak-1" T$_r$=6.44 min, and "Peak-2" T$_r$=7.61 min) were collected in MeOH. After separation by SFC, each enantiomer was chromatographed by ISCO to remove diethylamine used during chiral separation. Samples were dissolved in a minimal amount of CH$_2$Cl$_2$ and chromatographed. Purification of the crude material by silica gel chromatography using an ISCO machine (40 g column, 40 mL/min, 0-25% EtOAc in hexanes over 16 min, T$_r$=11.5 min) gave Enantiomer 1 (0.320 g, 0.850 mmol, 15.77% yield) and Enantiomer 2 (0.247 g, 0.656 mmol, 12.17% yield) as brown residues.

Enantiomer 1: 320 mg, 16% of the first eluting enantiomer. ESI MS (M+H)$^+$=377.5.

Enantiomer 2: 247 mg, 12% of the second eluting enantiomer. ESI MS (M+H)$^+$=377.5.

example 1231. 3-(4-(Cyclohexyl(isobutyl)amino)-3-(3-(4-ethoxyphenyl)ureido)phenyl)-4-methoxybutanoic acid To a solution of 1231A Enantiomer 1 (16.0 mg, 0.042 mmol) in THF (212 µl) at rt was added 4-nitrophenyl carbonochloridate (8.99 mg, 0.045 mmol). After 3 h, 4-ethoxyaniline (16.42 µl, 0.127 mmol) and triethylamine (17.77 µl, 0.127 mmol) were added. The reaction was heated at 50° C. overnight. To this reaction were added MeOH (0.15 mL) and a 1 M solution of lithium hydroxide (425 µl, 0.425 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation to afford Example 1231 (14.4 mg, 63%). ESI MS (M+H)$^+$=526.4. HPLC Peak T$_r$=2.049 min. Purity=98%. HPLC conditions: C. Absolute stereochemistry not determined.

Example 1232

3-(4-(Cyclohexyl(isobutyl)amino)-3-(3-(4-ethoxy-2-fluorophenyl)ureido)phenyl)-4-methoxybutanoic acid

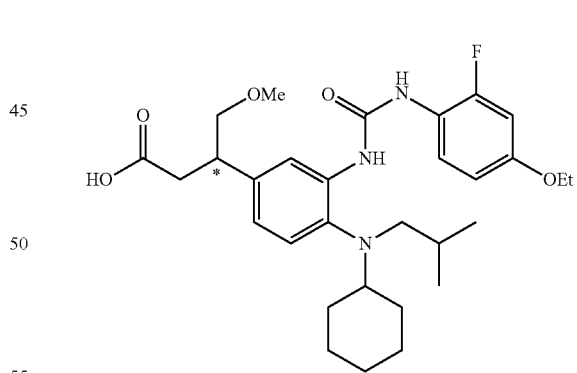

To a solution of 1231A Enantiomer 1 (15.2 mg, 0.040 mmol) in THF (202 µl) at rt was added 4-nitrophenyl carbonochloridate (8.54 mg, 0.042 mmol). After 3 h, 4-ethoxy-2-fluoroaniline, HCl (23.21 mg, 0.121 mmol) and triethylamine (22.51 µl, 0.161 mmol) were added. The reaction was heated at 50° C. overnight. To this reaction were added MeOH (0.15 mL) and a 1 M solution of lithium hydroxide (404 µl, 0.404 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×).

The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation to afford Example 1232 (12.5 mg, 55%). ESI MS (M+H)⁺=544.4. HPLC Peak T$_r$=2.078 min. Purity=96%. HPLC conditions: C. Absolute stereochemistry not determined.

Example 1233

3-(4-(Cyclohexyl(isobutyl)amino)-3-(3-(2-fluoro-4-methoxyphenyl)ureido)phenyl)-4-methoxybutanoic acid

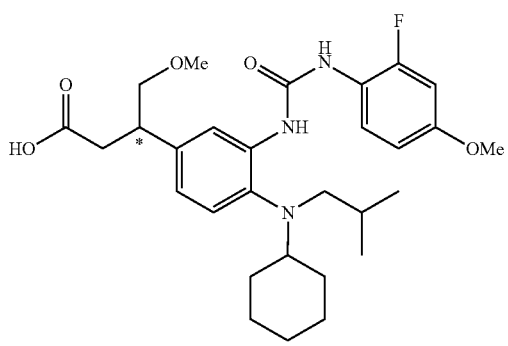 [SMILES: COCC(CC(=O)O)c1ccc(N(CC(C)C)C2CCCCC2)c(NC(=O)Nc2ccc(OC)cc2F)c1]

To a solution of 1231A Enantiomer 1 (15.4 mg, 0.041 mmol) in THF (204 μl) at rt was added 4-nitrophenyl carbonochloridate (8.66 mg, 0.043 mmol). After 3 h, 2-fluoro-4-methoxyaniline (17.32 mg, 0.123 mmol) and triethylamine (17.10 μl, 0.123 mmol) were added. The reaction was heated at 50° C. overnight. To this reaction were added MeOH (0.15 mL) and a 1 M solution of lithium hydroxide (409 μl, 0.409 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-75% B over 20 minutes, then a 4-minute hold at 100% B; Flow: 20 mL/min. Fractions containing the desired product were combined and dried via centrifugal evaporation to afford Example 1233 (16.0 mg, 74%). ESI MS (M+H)⁺=530.0. HPLC Peak T$_r$=2.071 min. Purity=100%. HPLC conditions: C. Absolute stereochemistry not determined.

Example 1234

3-(4-(Cyclohexyl(isobutyl)amino)-3-(2-(5-methylisoxazol-3-yl)acetamido)phenyl)-4-methoxybutanoic acid

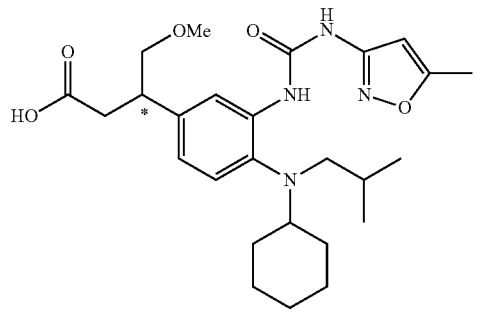 [SMILES: COCC(CC(=O)O)c1ccc(N(CC(C)C)C2CCCCC2)c(NC(=O)Nc2cc(C)on2)c1]

To a solution of 1231A Enantiomer 1 (30.5 mg, 0.081 mmol) in THF (579 μl) at rt was added 2-(5-methylisoxazol-3-yl)acetic acid, HCl (43.2 mg, 0.243 mmol), followed by 1-(3-dimethylaminopropyl)-3-ethylcarbodiimide hydrochloride (46.6 mg, 0.243 mmol), 4-hydroxybenzotriazole (32.8 mg, 0.243 mmol) and Hunig's base (56.6 μl, 0.324 mmol). The reaction was stirred at rt for 16 h. To this reaction was added MeOH (231 μl) and lithium hydroxide (810 μl, 0.810 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na₂SO₄, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation to afford Example 1234 (21.5 mg, 54%). ESI MS (M+H)⁺=486.1. HPLC Peak T$_r$=2.057 min. Purity=98%. HPLC conditions: C. Absolute stereochemistry not determined.

Example 1235

3-(4-(Cyclohexyl(isobutyl)amino)-3-(3-(4-ethoxyphenyl)ureido)phenyl)-4-methoxybutanoic acid

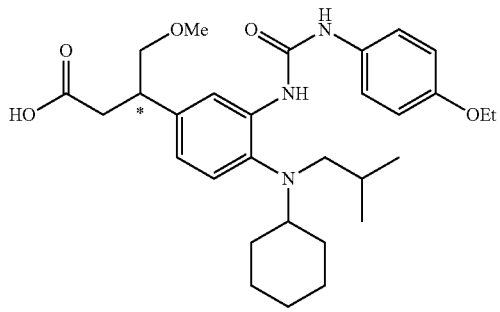 [SMILES: CCOc1ccc(NC(=O)Nc2cc(C(COC)CC(=O)O)ccc2N(CC(C)C)C2CCCCC2)cc1]

To a solution of 1231A Enantiomer 1 (18.8 mg, 0.050 mmol) in THF (250 μl) at rt was added 4-nitrophenyl carbonochloridate (10.57 mg, 0.052 mmol). After 3 h, 4-ethoxyaniline (19.29 μl, 0.150 mmol) and triethylamine (20.88 μl, 0.150 mmol) were added. The reaction was heated at 50° C. overnight. To this reaction were added MeOH (0.15 mL) and a 1 M solution of lithium hydroxide (499 μl, 0.499 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 4-minute hold at 100% B; Flow: 20 mL/min. Fractions containing the desired product were combined and dried via centrifugal evaporation to afford Example 1235 (19.3 mg, 73%). ESI MS (M+H)$^+$=526.1. HPLC Peak $T_r$=2.104 min. Purity=99%. HPLC conditions: C. Absolute stereochemistry not determined.

Example 1236

3-(4-(Cyclohexyl(isobutyl)amino)-3-(3-(4-ethoxy-2-fluorophenyl)ureido)phenyl)-4-methoxybutanoic acid

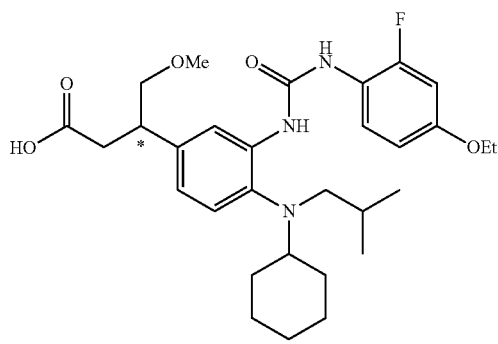 [SMILES: CCOc1ccc(NC(=O)Nc2cc(C(COC)CC(=O)O)ccc2N(CC(C)C)C2CCCCC2)c(F)c1]

To a solution of 1231A Enantiomer 2 (16.0 mg, 0.042 mmol) in THF (212 μl) at rt was added 4-nitrophenyl carbonochloridate (8.99 mg, 0.045 mmol). After 3 h, 4-ethoxy-2-fluoroaniline, HCl (24.43 mg, 0.127 mmol) and triethylamine (23.69 μl, 0.170 mmol) were added. The reaction was heated at 50° C. overnight. To this reaction were added MeOH (0.15 mL) and a 1 M solution of lithium hydroxide (425 μl, 0.425 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 4-minute hold at 100% B; Flow: 20 mL/min. Fractions containing the desired product were combined and dried via centrifugal evaporation to afford Example 1236 (15.1 mg, 63%). ESI MS (M+H)$^+$=544.1. HPLC Peak $T_r$=2.134 min. Purity=96%. HPLC conditions: C. Absolute stereochemistry not determined.

Example 1237

3-(4-(Cyclohexyl(isobutyl)amino)-3-(2-(p-tolyl)acetamido)phenyl)-4-methoxybutanoic acid

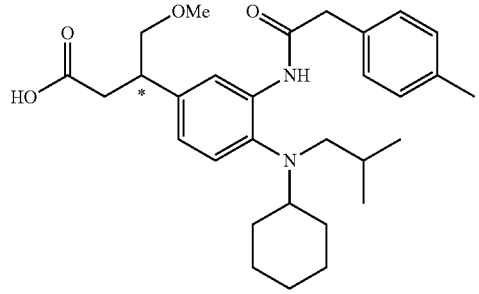 [SMILES: COCC(CC(=O)O)c1ccc(N(CC(C)C)C2CCCCC2)c(NC(=O)Cc2ccc(C)cc2)c1]

To a solution of 1231A Enantiomer 1 (15.2 mg, 0.040 mmol) in THF (288 μl) at rt was added 2-(p-tolyl)acetic acid (18.19 mg, 0.121 mmol), followed by 1-(3-dimethylaminopropyl)-3-ethylcarbodiimide hydrochloride (23.22 mg, 0.121 mmol), 4-hydroxybenzotriazole (16.36 mg, 0.121 mmol) and Hunig's base (28.2 μl, 0.161 mmol). The reaction was stirred at rt for 16 h. To this reaction was added MeOH (115 μl) and lithium hydroxide (404 μl, 0.404 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 20 minutes, then a 5-minute hold at 100% B; Flow: 20 mL/min. Fractions containing the desired product were combined and dried via centrifugal evaporation to afford Example 1237 (10.2 mg, 51%). ESI MS (M+H)$^+$=495.1. HPLC Peak $T_r$=2.340 min. Purity=99%. HPLC conditions: C. Absolute stereochemistry not determined.

Example 1238

3-(4-(Cyclohexyl(isobutyl)amino)-3-(2-(5-methylisoxazol-3-yl)acetamido)phenyl)-4-methoxybutanoic acid

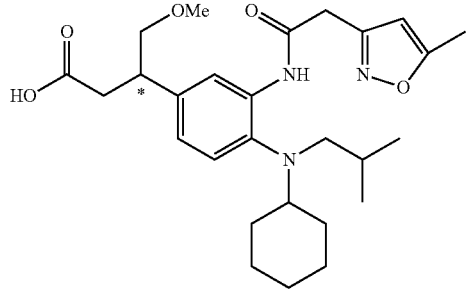 [SMILES: COCC(CC(=O)O)c1ccc(N(CC(C)C)C2CCCCC2)c(NC(=O)Cc2cc(C)on2)c1]

To a solution of 1231A Enantiomer 2 (28.5 mg, 0.076 mmol) in THF (541 µl) at rt was added 2-(5-methylisoxazol-3-yl)acetic acid, HCl (40.3 mg, 0.227 mmol), followed by 1-(3-dimethylaminopropyl)-3-ethylcarbodiimide hydrochloride (43.5 mg, 0.227 mmol), 4-hydroxybenzotriazole (30.7 mg, 0.227 mmol) and Hunig's base (52.9 µl, 0.303 mmol). The reaction was stirred at rt for 16 h. To this reaction was added MeOH (216 µl) and lithium hydroxide (757 µl, 0.757 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 5-minute hold at 100% B; Flow: 20 mL/min. Fractions containing the desired product were combined and dried via centrifugal evaporation to afford Example 1238 (20.4 mg, 54%). ESI MS $(M+H)^+$=486.1. HPLC Peak $T_r$=1.944 min. Purity=98%. HPLC conditions: C. Absolute stereochemistry not determined.

Example 1239

3-(4-(Cyclohexyl(isobutyl)amino)-3-(3-(2-fluoro-4-methoxyphenyl)ureido)phenyl)-4-methoxybutanoic acid

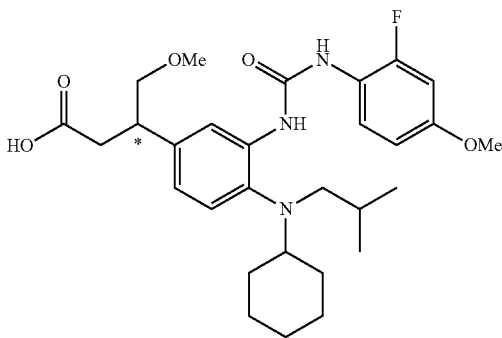 [SMILES: COCC(CC(=O)O)c1ccc(N(CC(C)C)C2CCCCC2)c(NC(=O)Nc2ccc(OC)cc2F)c1]

To a solution of 1231A Enantiomer 2 (16.6 mg, 0.044 mmol) in THF (220 µl) at rt was added 4-nitrophenyl carbonochloridate (9.33 mg, 0.046 mmol). After 3 h, 2-fluoro-4-methoxyaniline (18.67 mg, 0.132 mmol) and triethylamine (18.43 µl, 0.132 mmol) were added. The reaction was heated at 50° C. overnight. To this reaction were added MeOH (0.15 mL) and a 1 M solution of lithium hydroxide (441 µl, 0.441 mmol). The reaction was heated at 50° C. for 1 h. The reaction was adjusted to pH 6 with 1N HCl (0.3 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Example 1239 (16.0 mg, 68%). ESI MS $(M+H)^+$=530.4. HPLC Peak $T_r$=1.976 min. Purity=99%. HPLC conditions: C. Absolute stereochemistry not determined.

Example 1240

3-(4-(Cyclohexyl(isobutyl)amino)-3-(2-(p-tolyl)acetamido)phenyl)-4-methoxybutanoic acid

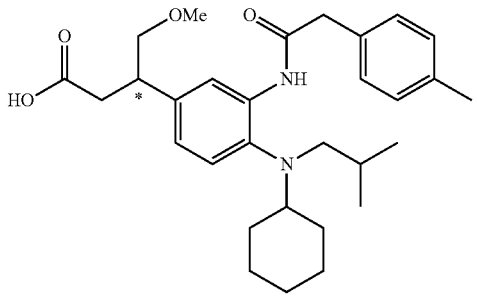 [SMILES: COCC(CC(=O)O)c1ccc(N(CC(C)C)C2CCCCC2)c(NC(=O)Cc2ccc(C)cc2)c1]

To a solution of 1231A Enantiomer 2 (23.4 mg, 0.062 mmol) in THF (444 µl) at rt was added 2-(p-tolyl)acetic acid (28.0 mg, 0.186 mmol), followed by 1-(3-dimethylaminopropyl)-3-ethylcarbodiimide hydrochloride (35.7 mg, 0.186 mmol), 4-hydroxybenzotriazole (25.2 mg, 0.186 mmol) and Hunig's base (43.4 µl, 0.249 mmol). The reaction was stirred at rt for 16 h. To this reaction was added MeOH (178 µl) and lithium hydroxide (621 µl, 0.621 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-95% B over 20 minutes, then a 8-minute hold at 100% B; Flow: 20 mL/min. Fractions containing the desired product were combined and dried via centrifugal evaporation to afford Example 1240 (18.0 mg, 59%). ESI MS $(M+H)^+$=495.5. HPLC Peak $T_r$=2.275 min. Purity=100%. HPLC conditions: C. Absolute stereochemistry not determined.

Example 1241

3-(4-(Cyclohexyl(isobutyl)amino)-3-(2-(4-ethoxyphenyl)acetamido)phenyl)-4-methoxybutanoic acid

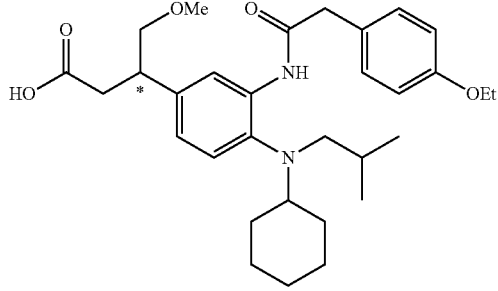 [SMILES: CCOc1ccc(CC(=O)Nc2cc(C(COC)CC(=O)O)ccc2N(CC(C)C)C2CCCCC2)cc1]

To a solution of 1231A Enantiomer 2 (21.1 mg, 0.056 mmol) in THF (400 μl) at rt was added 2-(4-ethoxyphenyl)acetic acid (30.3 mg, 0.168 mmol), followed by 1-(3-dimethylaminopropyl)-3-ethylcarbodiimide hydrochloride (32.2 mg, 0.168 mmol), 4-hydroxybenzotriazole (22.72 mg, 0.168 mmol) and Hunig's base (39.1 μl, 0.224 mmol). The reaction was stirred at rt for 16 h. To this reaction was added MeOH (160 μl) and lithium hydroxide (560 μl, 0.560 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-95% B over 18 minutes, then a 5-minute hold at 100% B; Flow: 20 mL/min. Fractions containing the desired product were combined and dried via centrifugal evaporation to afford Example 1241 (14.4 mg, 48%). ESI MS $(M+H)^+$=525.5. HPLC Peak $T_r$=2.229 min. Purity=98%. HPLC conditions: C. Absolute stereochemistry not determined.

Example 1242

3-(4-(Cyclohexyl(isobutyl)amino)-3-(2-(4-ethoxyphenyl)acetamido)phenyl)-4-methoxybutanoic acid

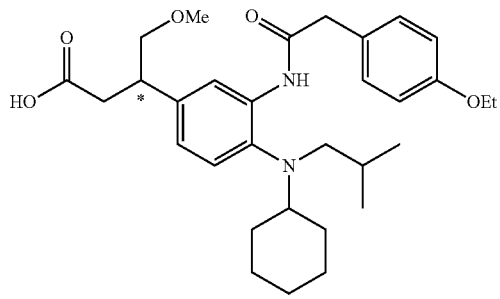

To a solution of 1231A Enantiomer 1 (15.1 mg, 0.040 mmol) in THF (286 μl) at rt was added 2-(4-ethoxyphenyl)acetic acid (21.68 mg, 0.120 mmol), followed by 1-(3-dimethylaminopropyl)-3-ethylcarbodiimide hydrochloride (23.06 mg, 0.120 mmol), 4-hydroxybenzotriazole (16.26 mg, 0.120 mmol) and Hunig's base (28.0 μl, 0.160 mmol). The reaction was stirred at rt for 16 h. To this reaction was added MeOH (115 μl) and lithium hydroxide (401 μl, 0.401 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 17 minutes, then a 5-minute hold at 100% B; Flow: 20 mL/min. Fractions containing the desired product were combined and dried via centrifugal evaporation to afford Example 1242 (10.6 mg, 50%). ESI MS $(M+H)^+$=525.2. HPLC Peak $T_r$=2.206 min. Purity=99%. HPLC conditions: C. Absolute stereochemistry not determined.

Example 1243

3-(4-(Cyclohexyl(isobutyl)amino)-3-(3-(4-(trifluoromethoxy)phenyl)ureido)phenyl)-4-methoxybutanoic acid

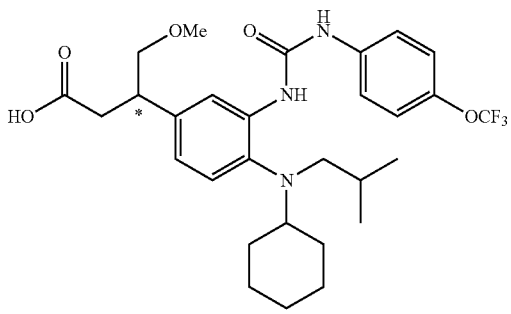 [SMILES: COCC(CC(=O)O)c1ccc(N(CC(C)C)C2CCCCC2)c(NC(=O)Nc2ccc(OC(F)(F)F)cc2)c1]

To a solution of 1231A Enantiomer 1 (18.4 mg, 0.049 mmol) in THF (244 μl) was added 1-isocyanato-4-(trifluoromethoxy)benzene (14.75 μl, 0.098 mmol) at rt (start at 12:25 pm). After 2.5 h, MeOH (0.15 mL) and a 1M solution of lithium hydroxide (489 μl, 0.489 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-100% B over 17 minutes, then a 3-minute hold at 100% B; Flow: 20 mL/min. Fractions containing the desired product were combined and dried via centrifugal evaporation to afford Example 1243 (16.3 mg, 58%). ESI MS $(M+H)^+$=566.1. HPLC Peak $T_r$=2.263 min. Purity=99%. HPLC conditions: C. Absolute stereochemistry not determined.

Example 1244

3-(4-(Cyclohexyl(isobutyl)amino)-3-(3-(4-(trifluoromethoxy)phenyl)ureido)phenyl)-4-methoxybutanoic acid

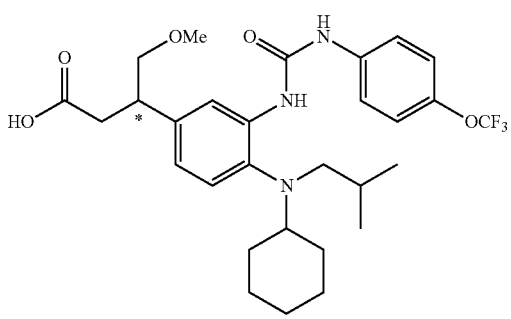 [SMILES: COCC(CC(=O)O)c1ccc(N(CC(C)C)C2CCCCC2)c(NC(=O)Nc2ccc(OC(F)(F)F)cc2)c1]

To a solution of 1231A Enantiomer 2 (17.8 mg, 0.047 mmol) in THF (236 µl) was added 1-isocyanato-4-(trifluoromethoxy)benzene (14.27 µl, 0.095 mmol) at rt (start at 12:25 pm). After 2.5 h, MeOH (0.15 mL) and a 1M solution of lithium hydroxide (473 µl, 0.473 mmol) were added. The reaction was heated at 70° C. for 1 h. The reaction was adjusted to pH 6 with 1N HCl (0.6 mL), then diluted with EtOAc. Layers were separated. The aqueous phase was extracted with EtOAc (2×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 10-minute hold at 100% B; Flow: 20 mL/min. Fractions containing the desired product were combined and dried via centrifugal evaporation to afford Example 1244 (16.2 mg, 59%). ESI MS (M+H)$^+$=566.4. HPLC Peak T$_r$=2.217 min. Purity=97%. HPLC conditions: C. Absolute stereochemistry not determined.

Example 1245

3-(3-(2-(4-Chloro-2-fluorophenyl)acetamido)-4-(cyclohexyl(isobutyl)amino)phenyl)-4-methoxybutanoic acid

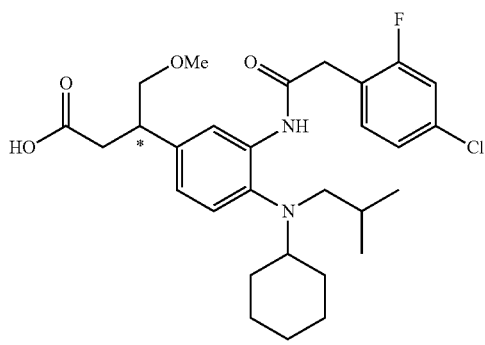 [SMILES: COCC(CC(=O)O)c1ccc(N(CC(C)C)C2CCCCC2)c(NC(=O)Cc2ccc(Cl)cc2F)c1]

To a solution of 1231A Enantiomer 1 (16.9 mg, 0.045 mmol) in THF (321 µl) at rt was added 2-(4-chloro-2-fluorophenyl)acetic acid (25.4 mg, 0.135 mmol), followed by 1-(3-dimethylaminopropyl)-3-ethylcarbodiimide hydrochloride (25.8 mg, 0.135 mmol), 4-hydroxybenzotriazole (18.19 mg, 0.135 mmol) and Hunig's base (31.4 µl, 0.180 mmol). The reaction was stirred at rt for 16 h. To this reaction was added MeOH (128 µl) and lithium hydroxide (449 µl, 0.449 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-95% B over 20 minutes, then a 5-minute hold at 100% B; Flow: 20 mL/min. Fractions containing the desired product were combined and dried via centrifugal evaporation to afford Example 1245 (17.6 mg, 74%). ESI MS (M+H)$^+$=533.0. HPLC Peak T$_r$=2.338 min. Purity=100%. HPLC conditions: C. Absolute stereochemistry not determined.

Example 1246

3-(3-(2-(4-Chloro-2-fluorophenyl)acetamido)-4-(cyclohexyl(isobutyl)amino)phenyl)-4-methoxybutanoic acid

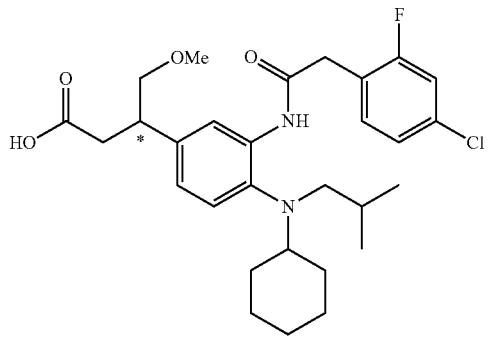 [SMILES: COCC(CC(=O)O)c1ccc(N(CC(C)C)C2CCCCC2)c(NC(=O)Cc2ccc(Cl)cc2F)c1]

To a solution of 1231A Enantiomer 2 (17.2 mg, 0.046 mmol) in THF (326 µl) at rt was added 2-(4-chloro-2-fluorophenyl)acetic acid (25.8 mg, 0.137 mmol), followed by 1-(3-dimethylaminopropyl)-3-ethylcarbodiimide hydrochloride (26.3 mg, 0.137 mmol), 4-hydroxybenzotriazole (18.52 mg, 0.137 mmol) and Hunig's base (31.9 µl, 0.183 mmol). The reaction was stirred at rt for 16 h. To this reaction was added MeOH (131 µl) and lithium hydroxide (457 µl, 0.457 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 8-minute hold at 100% B; Flow: 20 mL/min. Fractions containing the desired product were combined and dried via centrifugal evaporation to afford Example 1246 (17.0 mg, 70%). ESI MS (M+H)$^+$=533.0. HPLC Peak T$_r$=2.339 min. Purity=100%. HPLC conditions: C. Absolute stereochemistry not determined.

Example 1247 3-(4-(Cyclohexyl(isobutyl)amino)-3-(2-(p-tolyl)acetamido)phenyl)-3-cyclopropylpropanoic acid

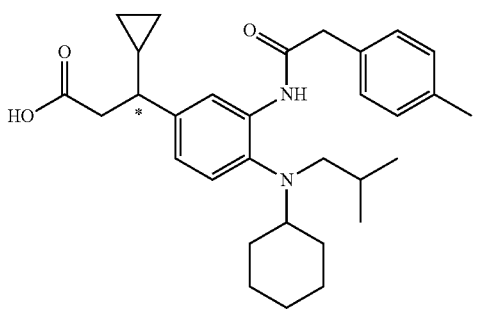 [SMILES: Cc1ccc(CC(=O)Nc2cc(C(CC(=O)O)C3CC3)ccc2N(CC(C)C)C2CCCCC2)cc1]

1247A. N-Cyclohexyl-4-(5,5-dimethyl-1,3,2-dioxaborinan-2-yl)-N-isobutyl-2-nitroaniline A suspension of potassium acetate (0.525 g, 5.35 mmol), 5,5,5',5'-tetramethyl-2,2'-bi(1,3,2-dioxaborinane) (0.524 g, 2.320 mmol), and 4-bromo-N-cyclohexyl-N-isobutyl-2-nitroaniline (Balog, A. et al., "Preparation of Aromatic Urea Derivatives as IDO Inhibitors", WO 2014/150646 A1 (Sep. 25, 2014)), the disclosure of which is incorporated by reference herein, (0.634 g, 1.785 mmol) in DMSO (2.67 ml) was degassed with $N_2$ for 10 min, then treated with $PdCl_2$(dppf) (0.039 g, 0.054 mmol). The reaction was sparged with $N_2$ for an additional 10 min. The reaction was heated at 80° C. overnight, then allowed to cool to rt. The reaction was quenched with $H_2O$ and diluted with EtOAc. Layers were separated. The aqueous phase was extracted with EtOAc (3×). The combined organic phases were washed with water (1×), dried over $Na_2SO_4$, filtered, and concentrated to afford a black residue. The crude material was dissolved in a minimal amount of $CH_2Cl_2$ and chromatographed. Purification of the crude material by silica gel chromatography using an ISCO machine (40 g column, 40 mL/min, 0-25% EtOAc in hexanes over 17 min, $T_r$=6.5 min) gave 1247A (608.6 mg, 1.411 mmol, 79% yield) as an orange residue. ESI MS $(M+H)^+$=321.3 (boronic acid).

1247B. Enantiomer 1 and Enantiomer 2: Ethyl 3-(4-(cyclohexyl(isobutyl)amino)-3-nitrophenyl)-3-cyclopropylpropanoate Absolute Stereochemistry not Determined To a solution of 1247A (0.6086 g, 1.567 mmol) in Dioxane (7.84 ml) was added (E)-ethyl 3-cyclopropylacrylate (0.686 ml, 4.70 mmol) followed by sodium hydroxide (1.411 ml, 1.411 mmol). The reaction was evacuated and back-filled with nitrogen once. To this solution was added chloro(1,5-cyclooctadiene)rhodium(I) dimer (0.039 g, 0.078 mmol) and the resultant solution was evacuated and back-filled with nitrogen 3 times. The reaction was heated at 50° C. for 2.5 h. The reaction was quenched with acetic acid (0.081 ml, 1.411 mmol) and partitioned between EtOAc and water. Layers were separated. The aqueous phase was extracted with EtOAc (3×). The combined organic phases were dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (40 g column, 40 mL/min, 0-5% EtOAc in hexanes over 14 min) gave 1247B (0.143 g, 0.343 mmol, 21.90% yield) as an orange residue. Approx. 389 mg of racemic material was resolved. The racemic material was purified via preparative SFC with the following conditions: Column: Chiralcel OD-H, 25×3 cm ID, 5-μm particles; Mobile Phase A: 93/7 $CO_2$/IPA; Detector Wavelength: 220 nm; Flow: 340 mL/min. The fractions ("Peak-1" $T_r$=3.45 min, and "Peak-2" $T_r$=3.76 min) were collected in IPA. The stereoisomeric purity of each fraction was estimated to be greater than 99.8% (PK-1) and 98.3 (PK-2) based on the prep-SFC chromatograms. Enantiomer 1: 143 mg, 22% of the first eluting enantiomer. ESI MS $(M+H)^+$=417.1. Enantiomer 2: 117 mg, 18% of the second eluting enantiomer. ESI MS $(M+H)^+$=417.1.

1247C. Ethyl 3-(3-amino-4-(cyclohexyl(isobutyl)amino)phenyl)-3-cyclopropylpropanoate To a solution of 1247B Enantiomer 1 (0.143 g, 0.343 mmol) in MeOH (1.716 ml) was added Pd/C (0.037 g, 0.034 mmol). The reaction was placed under a $H_2$ balloon and allowed to stir at rt. After 50 min, the reaction was filtered through CELITE® and the filter cake was washed with $CH_2C_2$. The filtrate was concentrated to afford 1247C as an orange residue. ESI MS $(M+H)^+$=387.3.

1247D. Ethyl 3-(3-amino-4-(cyclohexyl(isobutyl)amino)phenyl)-3-cyclopropylpropanoate To a solution of 1247B Enantiomer 2 (0.117 g, 0.281 mmol) in MeOH (1.404 ml) was added Pd/C (0.030 g, 0.028 mmol). The reaction was placed under a $H_2$ balloon and allowed to stir at rt. After 50 min, the reaction was filtered through CELITE® and the filter cake was washed with $CH_2C_2$. The filtrate was concentrated to afford 1247D as an orange residue. ESI MS $(M+H)^+$=387.2.

Example 1247. 3-(4-(Cyclohexyl(isobutyl)amino)-3-(2-(p-tolyl)acetamido)phenyl)-3-cyclopropylpropanoic acid To a solution of 1247D (15.3 mg, 0.040 mmol) in THF (283 μl) at rt was added 2-(p-tolyl)acetic acid (17.83 mg, 0.119 mmol), followed by 1-(3-dimethylaminopropyl)-3-ethylcarbodiimide hydrochloride (22.76 mg, 0.119 mmol), 4-hydroxybenzotriazole (16.04 mg, 0.119 mmol) and Hunig's base (27.7 μl, 0.158 mmol). The reaction was stirred at rt for 16 h. To this reaction was added MeOH (113 μl) and lithium hydroxide (396 μl, 0.396 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Example 1247 (9.0 mg, 46%). ESI MS $(M+H)^+$=491.1. HPLC Peak $T_r$=2.561 min. Purity=99%. HPLC conditions: C. Absolute stereochemistry not determined.

Example 1248

3-(4-(Cyclohexyl(isobutyl)amino)-3-(2-(4-ethoxyphenyl)acetamido)phenyl)-3-cyclopropylpropanoic acid

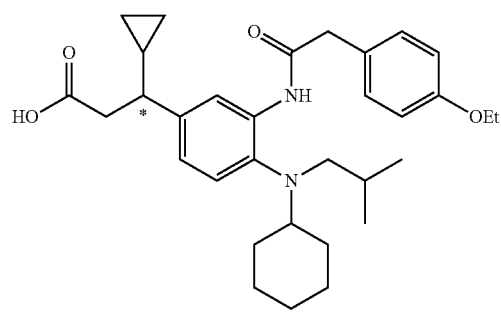 [SMILES: CCOc1ccc(CC(=O)Nc2cc(C(CC(=O)O)C3CC3)ccc2N(CC(C)C)C2CCCCC2)cc1]

To a solution of 1247D (15.1 mg, 0.039 mmol) in THF (279 μl) at rt was added 2-(4-ethoxyphenyl)acetic acid (21.12 mg, 0.117 mmol), followed by 1-(3-dimethylaminopropyl)-3-ethylcarbodiimide hydrochloride (22.46 mg, 0.117 mmol), 4-hydroxybenzotriazole (15.83 mg, 0.117 mmol) and Hunig's base (27.3 μl, 0.156 mmol). The reaction was stirred at rt for 16 h. To this reaction was added MeOH (112 μl) and lithium hydroxide (391 μl, 0.391 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Example 1248 (6.5 mg, 32%). ESI MS (M+H)$^+$=521.1. HPLC Peak T$_r$=2.480 min. Purity=99%. HPLC conditions: C. Absolute stereochemistry not determined.

Example 1249

3-(4-(Cyclohexyl(isobutyl)amino)-3-(2-(p-tolyl)acetamido)phenyl)-3-cyclopropylpropanoic acid

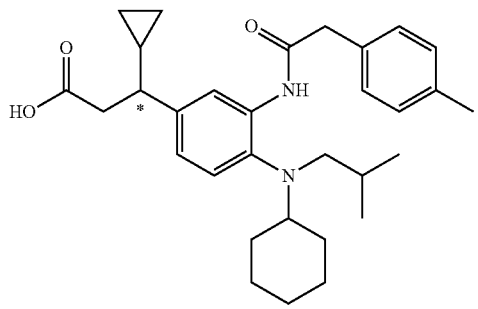 [SMILES: Cc1ccc(CC(=O)Nc2cc(C(CC(=O)O)C3CC3)ccc2N(CC(C)C)C2CCCCC2)cc1]

To a solution of 1247C (15.7 mg, 0.041 mmol) in THF (290 μl) at rt was added 2-(p-tolyl)acetic acid (18.30 mg, 0.122 mmol), followed by 1-(3-dimethylaminopropyl)-3-ethylcarbodiimide hydrochloride (23.36 mg, 0.122 mmol), 4-hydroxybenzotriazole (16.46 mg, 0.122 mmol) and Hunig's base (28.4 μl, 0.162 mmol). The reaction was stirred at rt for 16 h. To this reaction was added MeOH (116 μl) and lithium hydroxide (406 μl, 0.406 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 15 minutes, then a 4-minute hold at 100% B; Flow: 20 mL/min. Fractions containing the desired product were combined and dried via centrifugal evaporation to afford Example 1249 (8.9 mg, 44%). ESI MS (M+H)$^+$=491.4. HPLC Peak T$_r$=2.497 min. Purity=98%. HPLC conditions: C. Absolute stereochemistry not determined.

Example 1250

3-(4-(Cyclohexyl(isobutyl)amino)-3-(2-(4-ethoxyphenyl)acetamido)phenyl)-3-cyclopropylpropanoic acid

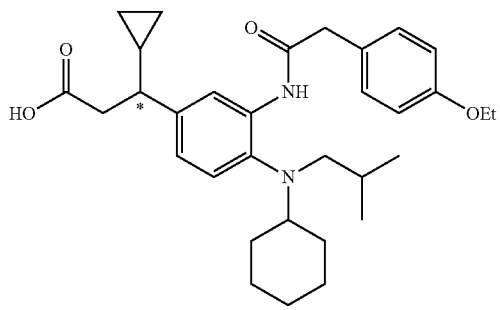 [SMILES: CCOc1ccc(CC(=O)Nc2cc(C(CC(=O)O)C3CC3)ccc2N(CC(C)C)C2CCCCC2)cc1]

To a solution of 1247C (15.4 mg, 0.040 mmol) in THF (285 μl) at rt was added 2-(4-ethoxyphenyl)acetic acid (21.54 mg, 0.120 mmol), followed by 1-(3-dimethylaminopropyl)-3-ethylcarbodiimide hydrochloride (22.91 mg, 0.120 mmol), 4-hydroxybenzotriazole (16.15 mg, 0.120 mmol) and Hunig's base (27.8 μl, 0.159 mmol). The reaction was stirred at rt for 16 h. To this reaction was added MeOH (114 μl) and lithium hydroxide (398 μl, 0.398 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over Na$_2$SO$_4$, filtered, and concentrated to afford a brown residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 15 minutes, then a 4-minute hold at 100% B; Flow: 20 mL/min. Fractions containing the desired product were combined and dried via centrifugal evaporation to afford Example 1250 (6.9 mg, 31%). ESI MS (M+H)$^+$=521.5. HPLC Peak T$_r$=2.416 min. Purity=94%. HPLC conditions: C. Absolute stereochemistry not determined.

Example 1251

3-(4-(Cyclohexyl(isobutyl)amino)-3-(2-(5-methylisoxazol-3-yl)acetamido)phenyl)-3-cyclopropylpropanoic acid

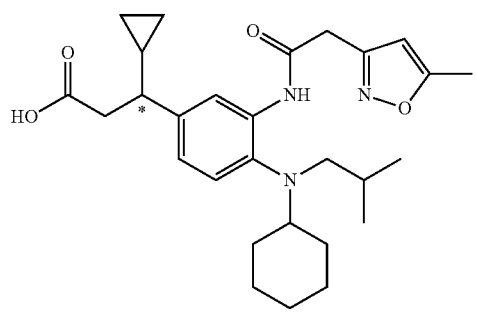 [SMILES: Cc1cc(CC(=O)Nc2cc(C(CC(=O)O)C3CC3)ccc2N(CC(C)C)C2CCCCC2)no1]

To a solution of 1247C (22.7 mg, 0.059 mmol) in THF (419 µl) at rt was added 2-(5-methylisoxazol-3-yl)acetic acid, HCl (31.3 mg, 0.176 mmol), followed by 1-(3-dimethylaminopropyl)-3-ethylcarbodiimide hydrochloride (33.8 mg, 0.176 mmol), 4-hydroxybenzotriazole (23.80 mg, 0.176 mmol) and Hunig's base (41.0 µl, 0.235 mmol). The reaction was stirred at rt for 16 h. To this reaction was added MeOH (168 µl) and lithium hydroxide (587 µl, 0.587 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation to afford Example 1251 (11.0 mg, 37%). ESI MS $(M+H)^+$=482.4. HPLC Peak $T_r$=2.114 min. Purity=95%. HPLC conditions: C. Absolute stereochemistry not determined.

Example 1252

3-(4-(Cyclohexyl(isobutyl)amino)-3-(2-(5-methylisoxazol-3-yl)acetamido)phenyl)-3-cyclopropylpropanoic acid

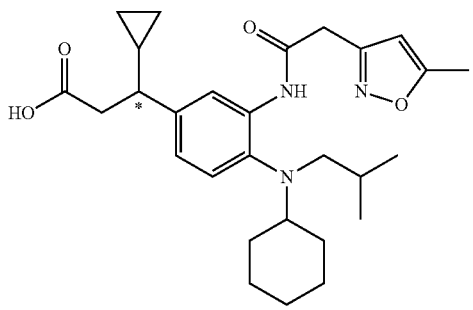 [SMILES: Cc1cc(CC(=O)Nc2cc(C(CC(=O)O)C3CC3)ccc2N(CC(C)C)C2CCCCC2)no1]

To a solution of 1247D (22.8 mg, 0.059 mmol) in THF (421 µl) at rt was added 2-(5-methylisoxazol-3-yl)acetic acid, HCl (31.4 mg, 0.177 mmol), followed by 1-(3-dimethylaminopropyl)-3-ethylcarbodiimide hydrochloride (33.9 mg, 0.177 mmol), 4-hydroxybenzotriazole (23.91 mg, 0.177 mmol) and Hunig's base (41.2 µl, 0.236 mmol). The reaction was stirred at rt for 16 h. To this reaction was added MeOH (169 µl) and lithium hydroxide (590 µl, 0.590 mmol). The reaction was heated at 50° C. for 2 h, then allowed to cool to rt. The reaction was adjusted to pH 6 with 1N HCl (0.5 mL), then diluted with EtOAc. Layers were separated. The aqueous phase was extracted with EtOAc (3×). The organic phases were combined, dried over $Na_2SO_4$, filtered, and concentrated to afford a brown residue. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation to afford Example 1252 (6.3 mg, 21%). ESI MS $(M+H)^+$=482.4. HPLC Peak $T_r$=2.115 min. Purity=95%. HPLC conditions: C. Absolute stereochemistry not determined.

Example 1253

Enantiomer 1 and Enantiomer 2

3-(3-((4-Chlorophenyl)amino)-4-(3-(4-fluorophenyl)-3-hydroxyazetidin-1-yl)phenyl)pentanoic acid

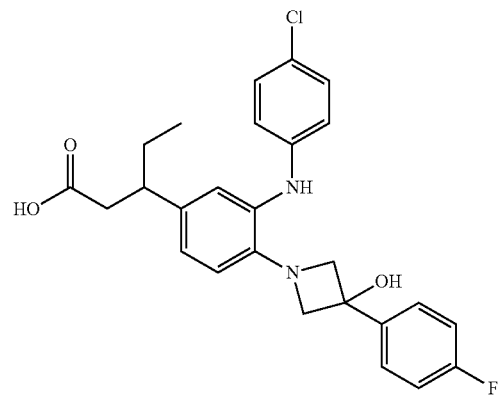 [SMILES: CCC(CC(=O)O)c1ccc(N2CC(O)(c3ccc(F)cc3)C2)c(Nc2ccc(Cl)cc2)c1]

1253A. Benzyl 3-(4-fluorophenyl)-3-hydroxyazetidine-1-carboxylate

To a solution of benzyl 3-oxoazetidine-1-carboxylate (2.5 g, 12.18 mmol) in THF (50 mL) was cooled to 0° C. and added 1M (4-fluorophenyl) magnesium bromide in THF (36.5 mL, 36.5 mmol). The reaction mixture was stirred for 1 h at 0° C. Then reaction mixture was quenched with saturated aqueous ammonium chloride solution (100 mL), extracted with EtOAc (2×100 mL). The combined organic layers were dried over anhydrous sodium sulfate, filtered and concentrated under reduced pressure. The crude sample was purified via silica gel flash chromatography to afford 1253A (white solid, 2 g, 6.31 mmol, 51.8% yield). $^1$H NMR (400 MHz, DMSO-$d_6$) δ 7.55-7.52 (m, 2H), 7.39-7.34 (m, 5H), 7.119-7.17 (m, 2H), 6.45 (s, 1H), 5.09 (s, 2H), 4.13-4.12 (m, 4H).

1253B. 3-(4-Fluorophenyl)azetidin-3-ol

The solution of 1253A (1 g, 3.32 mmol) in MeOH (10 mL) was sequentially evacuated and purged with nitrogen for three times, then added 10% palladium on carbon (0.177 g, 0.166 mmol). The reaction mixture pressurized to 40 psi of hydrogen atmosphere and stirred for 3 h. The reaction mixture was filtered through CELITE® pad, rinsed the pad with methanol and the filtrate was concentrated under reduced pressure. The crude material was triturated with diethyl ether to afford 1253B (white solid, 0.3 g, 1.705 mmol, 51.4% yield) as. LC-MS Anal. Calc'd. for $C_9H_{10}FNO$, 167.1, found [M+H] 168.0, $T_r$=0.54 min (Method AA).

1253C. Methyl 3-(4-(3-(4-fluorophenyl)-3-hydroxyazetidin-1-yl)-3-nitrophenyl)pentanoate 443B (1 g, 3.92 mmol), 1253B (0.982 g, 5.88 mmol) in NMP (5 mL) was taken in a pressure vial, and heated to 130° C. for 3 h. The reaction mixture was cooled to room temperature and poured into water (100 mL). The aqueous solution was extracted with EtOAc (2×100 mL). The combined organic layers were washed with brine solution (100 mL), dried over anhydrous sodium sulfate, filtered and concentrated under reduced pressure. The crude sample was purified via silica gel flash chromatography to afford 1253C (red color oil, 1.1 g, 2.71 mmol, 69.1% yield). LC-MS Anal. Calc'd. for $C_{12}H_{23}FN_2O_5$, 402.2, found [M+H] 403.1, $T_r$=1.42 min (Method BA).

1253D. Methyl 3-(3-amino-4-(3-(4-fluorophenyl)-3-hydroxyazetidin-1-yl)phenyl)pentanoate The solution of 1253C (0.5 g, 1.242 mmol) in ethyl acetate (10 mL) was sequentially evacuated and purged with nitrogen for three times, then added 10% palladium on carbon (0.066 g, 0.062 mmol). The reaction mixture was pressurized to 40 psi of hydrogen atmosphere and stirred for 3 h. The reaction mixture was filtered through CELITE® pad, rinsed pad with methanol and the filtrate was concentrated under reduced pressure to afford 1253D racemate (brown oil, 0.3 g, 0.806 mmol, 64.8% yield).

Chiral separation of 1253D racemate gave 1253D Enantiomer 1 and 1253D Enantiomer 2 as single enantiomers (Method CL). Enantiomer 1 $T_r$=5.58 min and Enantiomer 2 $T_r$=6.47 min 1253D Enantiomer 1. LC-MS Anal. Calc'd. for $C_{21}H_{25}FN_2O_3$, 372.2, found [M+H] 373.2, $T_r$=1.28 min (Method BA) (brown oil, 0.15 g, 0.403 mmol, 32.4% yield).

1253D Enantiomer 2. LC-MS Anal. Calc'd. for $C_{21}H_{25}FN_2O_3$, 372.2, found [M+H] 373.2, $T_r$=1.27 min (Method BA) (brown oil, 0.15 g, 0.403 mmol, 32.4% yield).

1253E. Methyl 3-(3-((4-chlorophenyl)amino)-4-(3-(4-fluorophenyl)-3-hydroxyazetidin-1-yl)phenyl)pentanoate To a solution of 1253D Enantiomer 1 (0.05 g, 0.134 mmol) in 1,4-dioxane (2 mL) argon was purged for 5 min and 1-bromo-4-chlorobenzene (0.031 g, 0.161 mmol), 4,5-bis(diphenylphosphino)-9,9-dimethylxanthene (0.016 g, 0.027 mmol), cesium carbonate (0.109 g, 0.336 mmol) were added followed by the addition of bis(dibenzylideneacetone) palladium (7.72 mg, 0.013 mmol). Reaction mixture bubbled with argon for 5 minutes. Then the reaction mixture heated at 110° C. for 16 h in a sealed vial. Then the reaction mixture was poured into water (25 mL) and extracted with EtOAc (2×25 mL). The combined organic layers were dried over anhydrous sodium sulfate, filtered and concentrated under reduced pressure to afford the crude 1253E (pale yellow oil, 0.05 g, 0.088 mmol, 65.5% yield). LC-MS Anal. Calc'd. for $C_{27}H_{28}ClFN_2O_3$, 482.2, found [M+H] 483.2, $T_r$=1.63 min (Method AA).

Example 1253 Enantiomer 1. 3-(3-((4-Chlorophenyl)amino)-4-(3-(4-fluorophenyl)-3-hydroxyazetidin-1-yl)phenyl)pentanoic acid To a solution of 1253E (0.05 g, 0.104 mmol) in a mixture of THF (1 mL), MeOH (1 mL) and water (1 mL) was added LiOH.H₂O (9.92 mg, 0.414 mmol) at room temperature and stirred for 16 h. Removed the volatiles and the crude was acidified with saturated citric acid solution. The aqueous solution was extracted with DCM (2×10 mL). The combined organic layers were washed with brine solution (25 mL), dried over anhydrous sodium sulfate, filtered and concentrated under reduced pressure. The crude material was purified via preparative HPLC to afford Example 1253 Enantiomer 1 (off-white solid, 0.01 g, 0.021 mmol, 20.39% yield). LC-MS Analysis Calc'd. for $C_{26}H_{26}ClFN_2O_3$, 468.2, found [M+H] 469.2, $T_r$=2.082 min (Method O). ¹H NMR (400 MHz, DMSO-d₆) δ 7.51 (s, 1H), 7.48-7.45 (m, 2H), 7.13-7.04 (m, 4H), 6.93-6.91 (m, 1H), 6.86 (d, J=1.60 Hz, 1H), 6.58-6.55 (m, 3H), 6.03 (s, 1H), 3.85 (q, J=7.6 Hz, 4H), 2.23-2.20 (m, 1H), 2.41-2.33 (m, 2H), 1.62-1.47 (m, 2H), 0.73 (t, J=7.2 Hz, 3H).

Example 1253 Enantiomer 2. 3-(3-((4-Chlorophenyl)amino)-4-(3-(4-fluorophenyl)-3-hydroxyazetidin-1-yl)phenyl)pentanoic acid Example 1253 Enantiomer 2 was prepared using 1253D Enantiomer 2 and 1-bromo-4-chlorobenzene following procedure described for the synthesis of Example 1253 Enantiomer 1. LC-MS Analysis Calc'd. for $C_{26}H_{26}ClFN_2O_3$, 468.2, found [M+H] 469.2, $T_r$=2.076 min (Method O). ¹H (400 MHz, DMSO-d₆) δ 7.51 (s, 1H), 7.48-7.45 (m, 2H), 7.13-7.04 (m, 4H), 6.93-6.91 (m, 1H), 6.86 (d, J=1.60 Hz, 1H), 6.58-6.55 (m, 3H), 6.03 (s, 1H), 3.85 (q, J=7.60 Hz, 4H), 2.23-2.20 (m, 1H), 2.41-2.33 (m, 2H), 1.62-1.47 (m, 2H), 0.73 (t, J=7.20 Hz, 3H).

Example 1254

Enantiomer 1

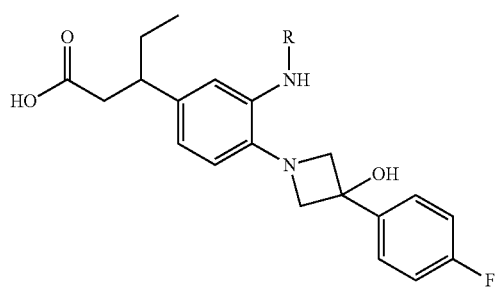

Example 1254 Enantiomer 1 were prepared using 1253D Enantiomer 1 and 4-bromo benzonitrile following the procedure described for the synthesis of Example 1253 Enantiomer 1.

| Ex. No. | Name | R | $T_r$, min | Method | (M + H) |
|---|---|---|---|---|---|
| 1254 | 3-(3-((4-cyanophenyl)amino)-4-(3-(4-fluorophenyl)-3-hydroxyazetidin-1-yl)phenyl)pentanoic acid | 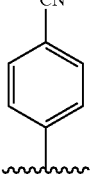 | 1.738 | O | 460.2 |

Examples 1255 and 1256

Enantiomer 2

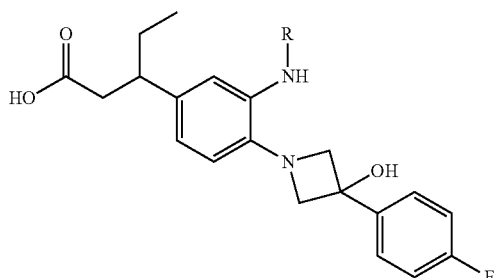

Examples 1255 and 1256 were prepared using 1253D Enantiomer 2 and corresponding halides following the procedure described for the synthesis of Example 1253 Enantiomer 1.

Example 1257

Enantiomer 1 and Enantiomer 2

3-(3-((4-Chlorophenyl)amino)-4-((2-methoxyethyl)(tetrahydro-2H-pyran-4-yl)amino)phenyl)pentanoic acid

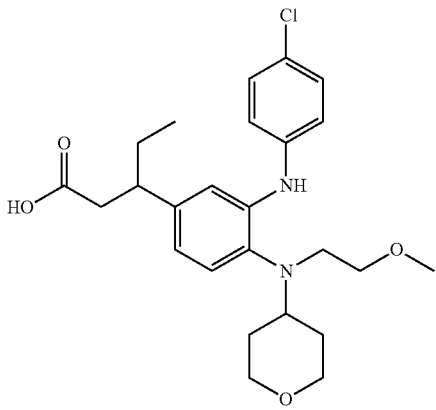

| Ex. No. | Name | R | $T_r$, min | Method | (M + H) |
|---|---|---|---|---|---|
| 1255 | 3-(3-((4-cyanophenyl)amino)-4-(3-(4-fluorophenyl)-3-hydroxyazetidin-1-yl)phenyl)pentanoic acid | 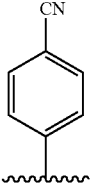 [SMILES: *c1ccc(C#N)cc1] | 1.720 | O | 460.2 |
| 1256 | 3-(3-((2-ethoxypyrimidin-5-yl)amino)-4-(3-(4-fluorophenyl)-3-hydroxyazetidin-1-yl)phenyl)pentanoic acid | 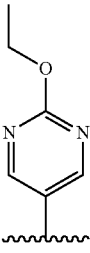 | 1.588 | O | 481.2 |

1257A. Methyl 3-(4-((2-methoxyethyl)(tetrahydro-2H-pyran-4-yl)amino)-3-nitrophenyl)pentanoate 1257A was prepared using 256C and (E)-methyl pent-2-enoate following the procedure described for the synthesis of 33D. LC-MS Anal. Calc'd. for $C_{20}H_{30}N_2O_6$, 394.2, found [M+H] 395.5, $T_r$=1.38 min (Method AY).

1257B. Methyl 3-(3-amino-4-((2-methoxyethyl)(tetrahydro-2H-pyran-4-yl)amino)phenyl)pentanoate 1257B was prepared using 1257A following the procedure described for the synthesis of 33E. LC-MS Anal. Calc'd. for $C_{20}H_{32}N_2O_4$, 364.2, found [M+H] 365.5, $T_r$=1.32 min (Method AY).

Chiral separation of 1257B racemate (Method BU) gave 1257B Enantiomer 1 and 1257B Enantiomer 2 as single enantiomers. Enantiomer 1, $T_r$=5.6 min (Method BU) and Enantiomer 2, $T_r$=6.81 min (Method BU).

1257B Enantiomer 1: LC-MS Anal. Calc'd. for $C_{20}H_{32}N_2O_4$, 364.2, found [M+H] 365.2, $T_r$=2.59 min (Method U).

1257B Enantiomer 2: LC-MS Anal. Calc'd. for $C_{20}H_{32}N_2O_4$, 364.2, found [M+H] 365.2, $T_r$=2.58 min (Method U).

1257C. Methyl 3-(3-((4-chlorophenyl)amino)-4-((2-methoxyethyl)(tetrahydro-2H-pyran-4-yl)amino)phenyl)pentanoate 1257C was prepared using 1257B Enantiomer 1 and 1-chloro-4-bromobenzene following the procedure described for the synthesis of 33F. LC-MS Anal. Calc'd. for $C_{26}H_{35}ClN_2O_4$, 474.2, found [M+H] 475.4, $T_r$=1.76 min (Method AY).

Example 1257 Enantiomer 1. 3-(3-((4-Chlorophenyl)amino)-4-((2-methoxyethyl)(tetrahydro-2H-pyran-4-yl)amino)phenyl)pentanoic acid Example 1257 Enantiomer 1 was prepared using 1257C following the procedure described for the synthesis of Example 41 Enantiomer 1. LC-MS Anal. Calc'd. for $C_{25}H_{33}ClN_2O_4$, 460.2, found [M+H] 461.2, $T_r$=1.96 min (Method O). $^1$H NMR (400 MHz, DMSO-$d_6$) δ 7.54 (s, 1H) 7.28 (m, 2H) 7.19 (m, 1H) 7.06-7.09 (m, 3H) 6.74 (m, 1H) 3.79 (m, 2H) 3.08-3.19 (m, 9H) 2.95-3.03 (m, 1H) 2.76-2.89 (m, 1H) 2.58 (m, 1H) 2.46 (m, 1H) 1.59-1.72 (m, 3H) 1.45-1.55 (m, 1H) 1.28-1.41 (m, 2H) 0.74 (t, J=7.2 Hz, 3H).

Example 1257 Enantiomer 2. 3-(3-((4-Chlorophenyl)amino)-4-((2-methoxyethyl)(tetrahydro-2H-pyran-4-yl)amino)phenyl)pentanoic acid Example 1257 Enantiomer 2 was prepared using 1257B Enantiomer 2 and 1-bromo-4-chlorobenzene following the procedure described for the synthesis of Example 1257 Enantiomer 1. LC-MS Anal. Calc'd. for $C_{25}H_{33}ClN_2O_4$, 460.2, found [M+H] 461.2, $T_r$=1.98 Min (Method O). $^1$H NMR (400 MHz, DMSO-$d_6$) δ 7.53 (s, 1H) 7.24-7.31 (m, 2H) 7.19 (m, 1H) 7.02-7.12 (m, 3H) 6.58-6.79 (m, 1H) 3.78 (m, 2H) 3.09-3.22 (m, 9H) 2.95-3.03 (m, 1H) 2.76-2.88 (m, 1H) 2.58 (m, 1H) 2.46 (m, 1H) 1.59-1.72 (m, 3H) 1.45-1.55 (m, 1H) 1.28-1.41 (m, 2H) 0.74 (t, J=7.2 Hz, 3H).

Examples 1258 to 1260

Enantiomer 1

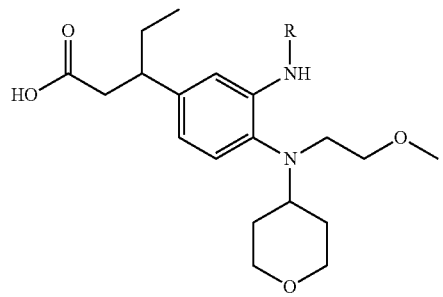

Examples 1258 to 1260 were prepared using 1257B Enantiomer 1 and corresponding halides following the procedure described for the synthesis of Example 1257 Enantiomer 1.

| Ex. No. | Name | R | $T_r$ (min) (Method O) | [M + H]$^+$ |
|---|---|---|---|---|
| 1258 | 3-(3-((4-cyanophenyl)amino)-4-((2-methoxyethyl)(tetrahydro-2H-pyran-4-yl)amino)phenyl)pentanoic acid | CN-C6H4- | 1.64 | 452.2 |
| 1259 | 3-(4-((2-methoxyethyl)(tetrahydro-2H-pyran-4-yl)amino)-3-((2-methoxypyrimidin-5-yl)amino)phenyl)pentanoic acid | 2-methoxypyrimidin-5-yl | 1.38 | 459.2 |

-continued

| Ex. No. | Name | R | $T_r$ (min) (Method O) | $[M + H]^+$ |
|---|---|---|---|---|
| 1260 | 3-(3-((2-ethoxypyrimidin-5-yl)amino)-4-((2-methoxyethyl)(tetrahydro-2H-pyran-4-yl)amino)phenyl)pentanoic acid | 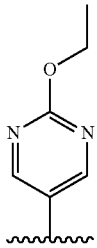 [SMILES: *c1cnc(OCC)nc1] | 1.51 | 473.3 |

Examples 1261 to 1263

Enantiomer 2

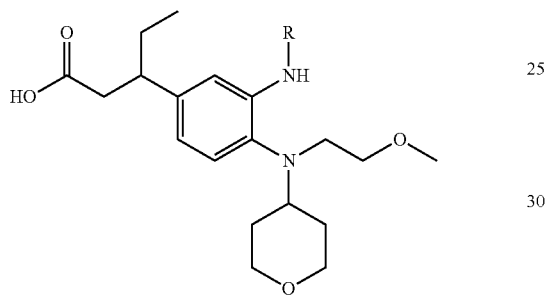

Examples 1261 to 1263 were prepared using 1257B Enantiomer 2 and corresponding halides following the procedure described for the synthesis of Example 1257 Enantiomer 1.

| Ex. No. | Name | R | $T_r$ (min) (Method O) | $[M + H]^+$ |
|---|---|---|---|---|
| 1261 | 3-(3-((4-cyanophenyl)amino)-4-((2-methoxyethyl)(tetrahydro-2H-pyran-4-yl)amino)phenyl)pentanoic acid | 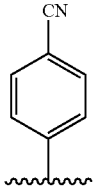 | 1.66 | 452.2 |
| 1262 | 3-(4-((2-methoxyethyl)(tetrahydro-2H-pyran-4-yl)amino)-3-((2-methoxypyrimidin-5-yl)amino)phenyl)pentanoic acid | 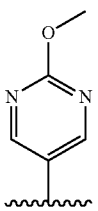 | 1.38 | 459.2 |

| Ex. No. | Name | R | $T_r$ (min) (Method O) | [M + H]+ |
|---|---|---|---|---|
| 1263 | 3-(3-((2-ethoxypyrimidin-5-yl)amino)-4-((2-methoxyethyl)(tetrahydro-2H-pyran-4-yl)amino)phenyl)pentanoic acid | 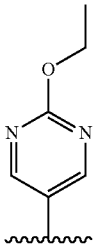 [SMILES: *c1cnc(OCC)nc1] | 1.51 | 473.3 |

Example 1264

Enantiomer 1 and Enantiomer 2

3-(4-((2-Methoxyethyl)(tetrahydro-2H-pyran-4-yl)amino)-3-(3-(p-tolyl)ureido)phenyl)pentanoic acid

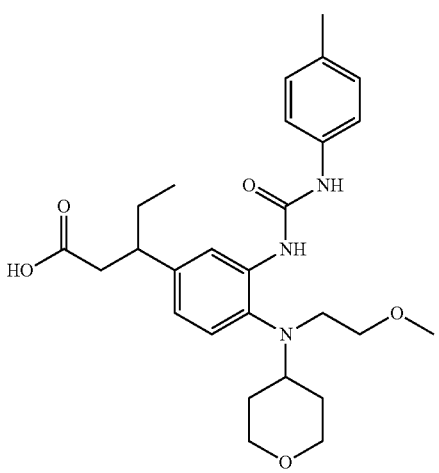 [SMILES: CCC(CC(=O)O)c1ccc(N(CCOC)C2CCOCC2)c(NC(=O)Nc2ccc(C)cc2)c1]

1264A. Methyl 3-(4-((2-methoxyethyl)(tetrahydro-2H-pyran-4-yl)amino)-3-(3-(p-tolyl)ureido)phenyl)pentanoate 1264A was prepared using 1257B Enantiomer 1 and 4-methyl-1-isocyanato benzene following the procedure described for the synthesis of 18A. LC-MS Anal. Calc'd. for $C_{28}H_{39}N_3O_5$, 497.2, found [M+H] 498.5, $T_r$=1.52 min (Method AY).

Example 1264 Enantiomer 1. 3-(4-((2-Methoxyethyl)(tetrahydro-2H-pyran-4-yl)amino)-3-(3-(p-tolyl)ureido)phenyl)pentanoic acid To a stirred solution of 1264A (0.035 g, 0.070 mmol) in mixture of THF (0.5 mL), methanol (0.5 mL) and water (0.1 mL) was added LiOH.H$_2$O (0.012 g, 0.281 mmol). The reaction mixture was stirred at 50° C. for 12 h. The reaction mixture was concentrated under reduced pressure. The aqueous residue was acidified with aqueous citric acid solution. The aqueous layer was diluted with water (10 mL) and extracted with ethyl acetate (2×10 mL). The combined organic layers were washed with water (10 mL), brine (10 mL), dried over anhydrous sodium sulfate, filtered and concentrated under reduced pressure to afford a residue. The residue was purified via preparative LC/MS to afford Example 1264 Enantiomer 1 (15.1 mg, 0.031 mmol, 44% yield). LC-MS Anal. Calc'd. for $C_{27}H_{37}N_3O_5$, 483.3, found [M+H] 484.3, $T_r$=1.63 min (Method O). $^1$H NMR (400 MHz, DMSO-d$_6$) δ 9.36 (s, 1H) 8.42 (s, 1H) 8.07 (m, 1H) 7.38 (m, 2H) 7.18 (m, 1H) 7.09 (m, 2H) 6.64-6.87 (m, 1H) 3.83 (m, 2H) 3.49 (m, 6H) 3.25 (s, 3H) 3.10 (m, 1H) 2.77-2.89 (m, 1H) 2.49-2.57 (m, 2H) 2.25 (s, 3H) 1.58-1.76 (m, 4H) 1.46-1.55 (m, 2H) 0.74 (t, J=7.6 Hz, 3H).

Example 1264 Enantiomer 2. 3-(4-((2-Methoxyethyl)(tetrahydro-2H-pyran-4-yl)amino)-3-(3-(p-tolyl)ureido)phenyl)pentanoic acid Example 1264 Enantiomer 2 was prepared using 1257B Enantiomer 2 and 4-methyl-1-isocycnatobenzene following the procedure described for the synthesis of Example 1264 Enantiomer 1. LC-MS Anal. Calc'd. for $C_{27}H_{37}N_3O_5$, 483.3, found [M+H] 484.3, $T_r$=1.63 min (Method O). $^1$H NMR (400 MHz, DMSO-d$_6$) δ 9.35 (s, 1H) 8.41 (s, 1H) 7.98-8.19 (m, 1H) 7.31-7.46 (m, 2H) 7.19 (m, 1H) 7.05-7.13 (m, 2H) 6.65-6.85 (m, 1H) 3.83 (m, 2H) 3.49 (m, 6H) 3.25 (s, 3H) 3.10 (m, 1H) 2.77-2.89 (m, 1H) 2.49-2.57 (m, 2H) 2.25 (s, 3H) 1.58-1.76 (m, 4H) 1.46-1.55 (m, 2H) 0.74 (t, J=7.6 Hz, 3H).

Example 1265

Enantiomer 1

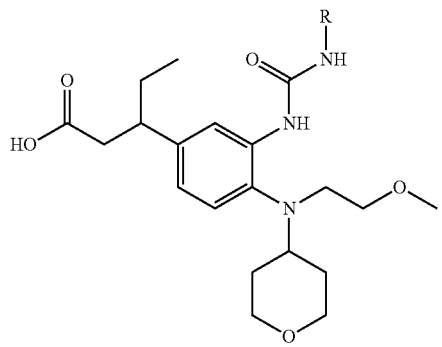

Example 1265 was prepared using 1257B Enantiomer 1 and corresponding isocyanate following the procedure described for the synthesis of Example 1264 Enantiomer 1.

| Ex. No. | Name | R | T_r (min) (Method O) | [M + H]+ |
|---|---|---|---|---|
| 1265 | 3-(3-(3-(4-chloro-2-fluorophenyl)ureido)-4-((2-methoxyethyl)(tetrahydro-2H-pyran-4-yl)amino)phenyl)pentanoic acid | (4-chloro-2-fluorophenyl) | 1.76 | 522.2 |

Example 1266

Enantiomer 2

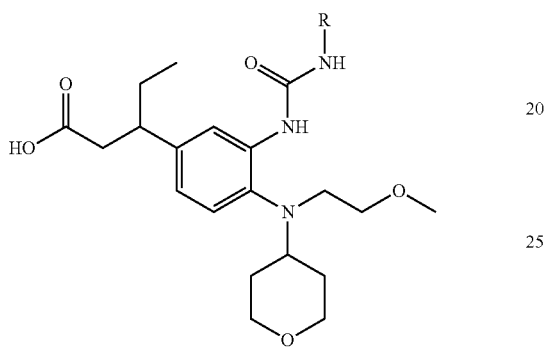

Example 1266 was prepared using 1257B Enantiomer 2 and corresponding isocyanate following the procedure described for the synthesis of Example 1264 Enantiomer 1.

| Ex. No. | Name | R | T_r (min) (Method O) | [M + H]+ |
|---|---|---|---|---|
| 1266 | 3-(3-(3-(4-chloro-2-fluorophenyl)ureido)-4-((2-methoxyethyl)(tetrahydro-2H-pyran-4-yl)amino)phenyl)pentanoic acid | (4-chloro-2-fluorophenyl) | 1.76 | 522.2 |

Example 1267

Enantiomer 1 and Enantiomer 2

(S)-3-(3-(3-(4-Chloro-2-fluorophenyl)ureido)-4-(ethyl(tetrahydro-2H-pyran-4-yl)amino)phenyl)-4,4,4-trifluorobutanoic acid

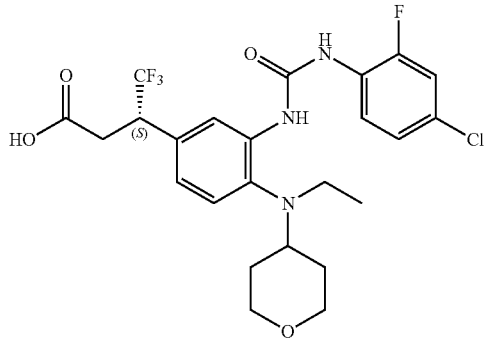

1267A. (S)-Methyl 3-(3-(3-(4-chloro-2-fluorophenyl)ureido)-4-(ethyl(tetrahydro-2H-pyran-4-yl)amino)phenyl)-4,4,4-trifluorobutanoate 1267A was prepared using 598B and 4-chloro-2-fluoro-1-isocyanatobenzene following the procedure described for the synthesis of Example 422. LC-MS Anal. Calc'd. for $C_{25}H_{28}ClF_4N_3O_4$ 545.2 found [M+H] 546.2, $T_r$=1.58 min (Method BA).

Example 1267 Enantiomer 1. (S)-3-(3-(3-(4-Chloro-2-fluorophenyl)ureido)-4-(ethyl(tetrahydro-2H-pyran-4-yl)amino)phenyl)-4,4,4-trifluorobutanoic acid Example 1267 Enantiomer 1 was prepared using 1267A following the procedure described for the synthesis of Example 422 Enantiomer 1. LC-MS Anal. Calc'd. for $C_{24}H_{26}ClF_4N_3O_4$, 531.2, found [M+H] 532.1, $T_r$=1.73 min (Method O). $^1$H NMR (400 MHz, MeOD) δ 8.28 (s, 1H), 8.07 (t, J=8.40 Hz, 1H), 7.24-7.30 (m, 2H), 7.17-7.20 (m, 1H), 7.06 (d, J=8.40 Hz, 1H), 3.93 (d, J=9.60 Hz, 3H), 3.37-3.42 (m, 3H), 3.06-3.11 (m, 3H), 2.92-2.95 (m, 1H), 1.79 (d, J=10.80 Hz, 2H), 1.54 (d, J=12.40 Hz, 2H), 0.88 (t, J=7.20 Hz, 3H).

Examples 1268 and 1269

Enantiomer 1

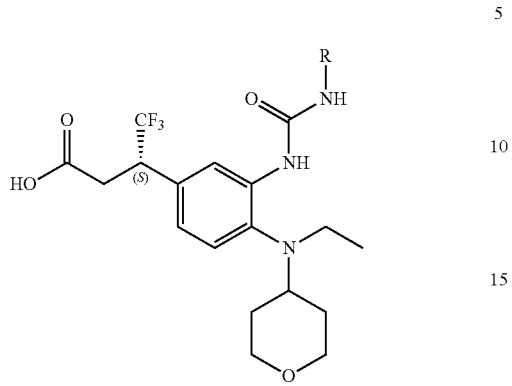

EXAMPLES 1268 and 1269 were prepared using 598B Enantiomer 1 and corresponding isocyanates following the procedure described for the synthesis of Example 422.

| Ex. No. | Name | R | $T_r$, min | Method | (M + H) |
|---|---|---|---|---|---|
| 1268 | (S)-3-(3-(3-(4-cyanophenyl)ureido)-4-(ethyl(tetrahydro-2H-pyran-4-yl)amino)phenyl)-4,4,4-trifluorobutanoic acid | 4-cyanophenyl | 1.52 | O | 505.2 |
| 1269 | (S)-3-(4-(ethyl(tetrahydro-2H-pyran-4-yl)amino)-3-(3-(p-tolyl)ureido)phenyl)-4,4,4-trifluorobutanoic acid | p-tolyl | 1.61 | O | 494.2 |

Example 1270

Enantiomer 2

(R)-3-(3-(3-(4-Chloro-2-fluorophenyl)ureido)-4-(ethyl(tetrahydro-2H-pyran-4-yl)amino)phenyl)-4,4,4-trifluorobutanoic acid

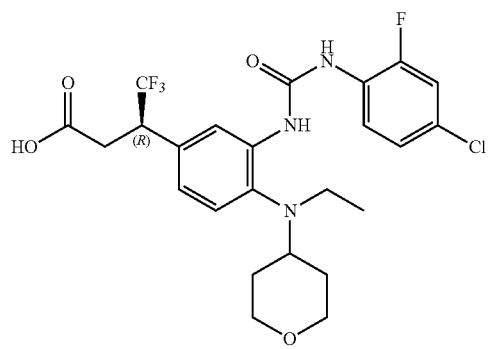

Example 1270 Enantiomer 2. (R)-3-(3-(3-(4-Chloro-2-fluorophenyl)ureido)-4-(ethyl(tetrahydro-2H-pyran-4-yl)amino)phenyl)-4,4,4-trifluorobutanoic acid Example 1270 Enantiomer 2 was prepared using 600B and 4-chloro-3-fluoro-1-isocyanatobenzene following the procedure described for the synthesis of Example 422. LC-MS Anal. Calc'd. for $C_{24}H_{26}ClF_4N_3O_4$, 531.2, found [M+H] 532.2, $T_r$=1.75 min (Method O). $^1$H NMR (400 MHz, MeOD) δ 8.28 (s, 1H), 8.07 (t, J=8.40 Hz, 1H), 7.24-7.30 (m, 2H), 7.17-7.20 (m, 1H), 7.06 (d, J=8.40 Hz, 1H), 3.93 (d, J=9.60 Hz, 3H), 3.37-3.42 (m, 3H), 3.06-3.11 (m, 3H), 2.92-2.95 (m, 1H), 1.79 (d, J=10.80 Hz, 2H), 1.54 (d, J=12.40 Hz, 2H), 0.88 (t, J=7.20 Hz, 3H).

Examples 1271 and 1272

Enantiomer 1

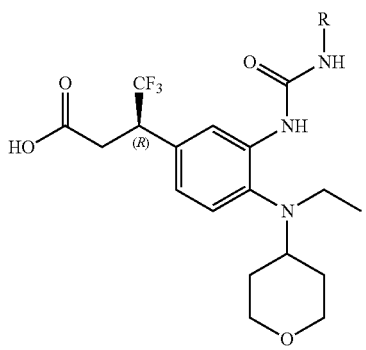

Examples 1271 and 1272 was prepared using 600B Enantiomer 2 and corresponding isocyanates following the procedure described for the synthesis Example 422.

| Ex. No. | Name | R | $T_r$, min | Method | (M + H) |
|---|---|---|---|---|---|
| 1271 | (R)-3-(3-(3-(4-cyanophenyl) ureido)-4-(ethyl(tetrahydro-2H-pyran-4-yl)amino) phenyl)-4,4,4-trifluorobutanoic acid | 4-cyanophenyl group | 1.52 | O | 505.2 |
| 1272 | (R)-3-(4-(ethyl(tetrahydro-2H-pyran-4-yl)amino)-3-(3-(p-tolyl)ureido)phenyl)-4,4,4-trifluorobutanoic acid | p-tolyl group | 1.63 | O | 494.2 |

Example 1281

Diastereomer 1

(3S)-3-(3-((4-Cyanophenyl)amino)-4-(3-ethylmorpholino)phenyl)-4-methoxybutanoic acid

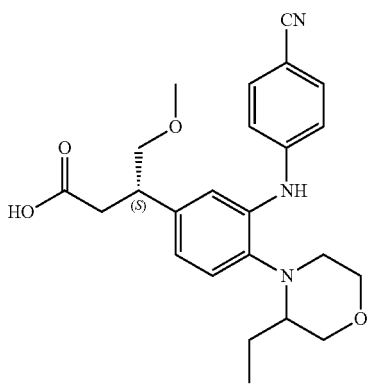

1281A. 5-Ethylmorpholin-3-one 1281A was prepared using 2-aminobutan-1-ol following procedure described for the synthesis of 74A. LC-MS Anal. Calc'd. for $C_6H_{11}NO_2$, 129.2, found [M+H] 130.2, $T_r$=0.43 min (Method DT).

1281B. 3-Ethylmorpholine 1281B was prepared using 1281A following procedure described for the synthesis of 74B. LC-MS Anal. Calc'd. for $C_6H_{13}NO$, 115.2, found [M+H] 116.2, $T_r$=0.4 min (Method U).

1281C. 4-(4-Bromo-2-nitrophenyl)-3-ethylmorpholine 1281C was prepared using 1281B and 4-bromo-2-fluoro-1-nitrobenzene following procedure described for the synthesis of 74C. LC-MS Anal. Calc'd. for $C_{12}H_{15}BrN_2O_3$, 314.2, found [M+H] 315.2, $T_r$=3.16 min (Method U).

1281D. 5-Bromo-2-(3-ethylmorpholino)aniline

To a solution of 1281C (3 g, 9.52 mmol) in AcOH (45 mL) was added iron (2.66 g, 47.6 mmol) and stirred at room temperature for 2 h. The reaction mixture was concentrated under reduced pressure, dissolved in ethyl acetate (100 mL) and filtered through CELITE® bed. The filtrate was concentrated under reduced pressure to afford Racemate 1281D. LC-MS Anal. Calc'd. for $C_{12}H_{17}BrN_2O$, 284.05, found [M+H] 285.2, $T_r$=2.85 min (Method U).

Chiral separation of 1281D racemate yielded 1281D Enantiomer 1 $T_r$=2.7 min, 1281D Enantiomer 2 $T_r$=6.0 min (Method DU).

1281D Enantiomer 1: Brown gummy, 1.45 g, 4.98 mmol, 39.4% yield. LC-MS Anal. Calc'd. for $C_{12}H_{17}BrN_2O$, 284.05, found [M+H] 285.2, $T_r$=1.94 min (Method BB).

1281D Enantiomer 2: Brown gummy, 1.45 g, 4.98 mmol, 39.4% yield. LC-MS Anal. Calc'd. for $C_{12}H_{17}BrN_2O$, 284.05, found [M+H] 285.2, $T_r$=1.95 min (Method BB).

1281E. 5-(5,5-Dimethyl-1,3,2-dioxaborinan-2-yl)-2-(3-ethylmorpholino)aniline 1281D Enantiomer 1 (1.45 g, 5.08 mmol) was dissolved in 1,4-dioxane (30 ml), added bis(neopentyl glycolato)diboron (1.723 g, 7.63 mmol) and potassium acetate (1.497 g, 15.25 mmol). The reaction mixture was purged with nitrogen for 15 minutes. Then added 1,1'-bis(diphenylphosphino)ferrocene-palladium(ii)dichloride dichloromethane complex (0.125 g, 0.153 mmol) and the reaction mixture was stirred at 90° C. for 16 h. The reaction mixture was cooled to room temperature and diluted with ethyl acetate (50 mL), washed with brine solution (2×50 mL). The organic layers were dried over sodium sulfate, filtered and concentrated under reduced pressure to get the crude, which was purified by silica gel flash chromatography to afford 1281E (brown solid, 1.4 g, 4.00 mmol, 79% yield). LC-MS Anal. Calc'd. for $C_{17}H_{27}BN_2O_3$, 318.2, found [M+H] 251.2 (parent boronic acid), $T_r$=0.918 min (Method BB).

1281F. (3S)-Methyl 3-(3-amino-4-(3-ethylmorpholino)phenyl)-4-methoxybutanoate 1281F Diastereomer mixture was prepared using 1281E and (R)-(+)-2,2'-bis(diphenylphosphino)-1,1'-binaphthyl following procedure described for the synthesis of 74E. LC-MS Anal. Calc'd. for $C_{18}H_{28}N_2O_4$, 336.2, found [M+H] 337.2, $T_r$=1.76 min (Method BB).

Chiral separation of 1281F Diastereomer mixture (746:26) yielded 1281F Diastereomer 1 $T_r$=4.32 min, 1281F Diastereomer 2 $T_r$=5.0 min (Method DV).

1281F Diastereomer 1: LC-MS Anal. Calc'd. for $C_{18}H_{28}N_2O_4$, 336.2, found [M+H] 337.2, $T_r$=1.76 min (Method BB).

Example 1281

Diastereomer 1. (3S)-3-(3-((4-Cyanophenyl)amino)-4-(3-ethylmorpholino)phenyl)-4-methoxybutanoic acid

Example 1281 Diastereomer 1 was prepared using 1281F Diastereomer 1 and 4-bromobenzonitrile, following the procedure described for the synthesis of Example 83. LC-MS Anal. Calc'd. for $C_{24}H_{29}N_3O_4$, 423.2, found [M+H] 424.3, $T_r$=1.87 min (Method R). $^1$H NMR (400 MHz, DMSO-$d_6$) δ11.97 (s, 1H), 8.06 (s, 1H), 7.55 (d, J=8.80 Hz, 2H), 7.15 (s, 1H), 7.10 (d, J=8.40 Hz, 1H), 7.04 (d, J=8.80 Hz, 2H), 6.96 (dd, J=2.00, 8.00 Hz, 1H), 3.61-3.66 (m, 3H), 3.40-3.46 (m, 3H), 3.27 (s, 3H), 3.22-3.25 (m, 1H), 2.92-2.94 (m, 2H), 2.63-2.68 (m, 2H), 2.42-2.45 (m, 1H), 1.18-1.22 (m, 2H), 0.64 (t, J=7.60 Hz, 3H).

Examples 1282 to 1286

Diastereomer 1

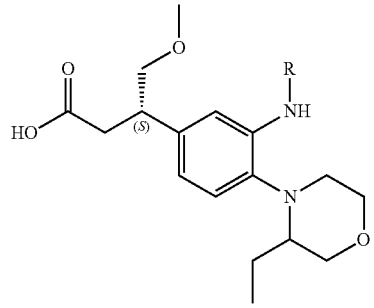

Examples 1282 and 1283 were prepared using 1281F Diastereomer 1 and corresponding aryl halides following the procedure described for the synthesis of Example 83.

Example 1284 and 1285 were prepared using from 1281F Diastereomer 1 and corresponding aryl halides following the procedure described for the synthesis of Example 78.

Example 1286 was prepared using 1281F Diastereomer 1 and corresponding aryl halides following the procedure described for the synthesis of Example 84.

| Ex. No. | Name | R | $T_r$, min | Method | (M + H) |
|---|---|---|---|---|---|
| 1282 | (3S)-3-(3-((4-cyano-3-fluorophenyl)amino)-4-(3-ethylmorpholino)phenyl)-4-methoxybutanoic acid | 3-F, 4-CN phenyl | 1.97 | R | 442.2 |
| 1283 | (3S)-3-(3-((5-cyanopyridin-2-yl)amino)-4-(3-ethylmorpholino)phenyl)-4-methoxybutanoic acid | 5-CN pyridin-2-yl | 1.35 | O | 425.2 |
| 1284 | (3S)-3-(4-(3-ethylmorpholino)-3-((2-methoxypyrimidin-5-yl)amino)phenyl)-4-methoxybutanoic acid | 2-OMe pyrimidin-5-yl | 1.61 | R | 431.2 |
| 1285 | (3S)-3-(3-((2-ethoxypyrimidin-5-yl)amino)-4-(3-ethylmorpholino)phenyl)-4-methoxybutanoic acid | 2-OEt pyrimidin-5-yl | 1.77 | R | 445.2 |
| 1286 | (3S)-3-(3-((4-chlorophenyl)amino)-4-(3-ethylmorpholino)phenyl)-4-methoxybutanoic acid | 4-Cl phenyl | 1.85 | O | 433.1 |

Example 1287

Diastereomer 2

(3R)-3-(3-((4-Cyanophenyl)amino)-4-(3-ethylmorpholino)phenyl)-4-methoxybutanoic acid

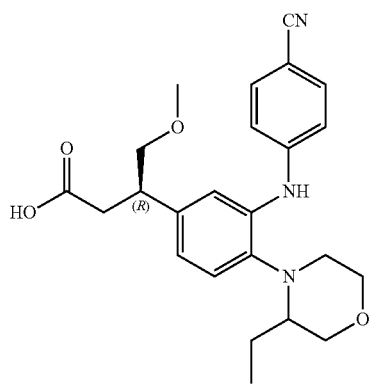

1287A. (3R)-Methyl 3-(3-amino-4-(3-ethylmorpholino)phenyl)-4-methoxybutanoate 1287A Diastereomer mixture was prepared using 1281E and (S)-(−)-2,2'-bis(diphenylphosphino)-1,1'-binaphthyl following the procedure described for the synthesis of 74E. LC-MS Anal. Calc'd. for $C_{18}H_{28}N_2O_4$, 336.2, found [M+H] 337.2, $T_r$=1.76 min (Method BB).

Chiral separation of 1287A diastereomer mixture (22:78) yielded 1287A Diastereomer 1 $T_r$=4.32 min, 1287A Diastereomer 2 $T_r$=5.0 min (Method DV).

1287A Diastereomer 2: LC-MS Anal. Calc'd. for $C_{18}H_{28}N_2O_4$, 336.2, found [M+H] 337.2, $T_r$=1.56 min (Method BB).

Example 1287 Diastereomer 2. (3R)-3-(3-((4-Cyanophenyl)amino)-4-(3-ethylmorpholino)phenyl)-4-methoxybutanoic acid Example 1287 Diastereomer 2 was prepared using 1287A Diastereomer 2 and 4-bromobenzonitrile, following the procedure described for the synthesis of Example 83. LC-MS Anal. Calc'd. for $C_{24}H_{29}N_3O_4$, 423.2, found [M+H] 424.3, $T_r$=1.59 min (Method R). $^1$H NMR (400 MHz, DMSO-$d_6$) δ11.97 (s, 1H), 8.06 (s, 1H), 7.55 (d, J=8.80 Hz, 2H), 7.15 (s, 1H), 7.10 (d, J=8.40 Hz, 1H), 7.04 (d, J=8.80 Hz, 2H), 6.96 (dd, J=2.00, 8.00 Hz, 1H), 3.61-3.66 (m, 3H), 3.40-3.46 (m, 3H), 3.27 (s, 3H), 3.22-3.25 (m, 1H), 2.92-2.94 (m, 2H), 2.63-2.68 (m, 2H), 2.42-2.45 (m, 1H), 1.18-1.22 (m, 2H), 0.64 (t, J=7.60 Hz, 3H).

Examples 1288 to 1294

Diastereomer 2

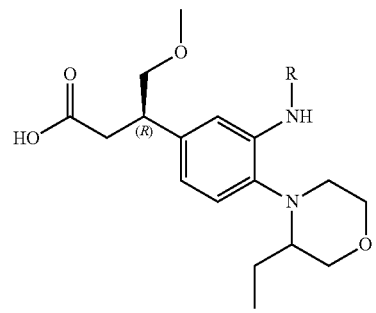

Examples 1288 and 1289 were prepared from 1287A Diastereomer 2 and corresponding aryl halides following the procedure described for the synthesis of Example 83.

Example 1290 and 1291 were prepared from 1287A Diastereomer 2 and corresponding aryl halides following the procedure described for the synthesis of Example 78.

Examples 1292 to 1294 were prepared from 1287A Diastereomer 2 and corresponding aryl halides following the procedure described for the synthesis of Example 84.

| Ex. No. | Name | R | $T_r$ min | Method | (M + H) |
|---|---|---|---|---|---|
| 1288 | (3R)-3-(3-((4-cyano-3-fluorophenyl)amino)-4-(3-ethylmorpholino)phenyl)-4-methoxybutanoic acid | 3-F,4-CN-phenyl | 1.69 | R | 442.2 |
| 1289 | (3R)-3-(3-((5-cyanopyridin-2-yl)amino)-4-(3-ethylmorpholino)phenyl)-4-methoxybutanoic acid | 5-CN-pyridin-2-yl | 1.08 | O | 425.3 |
| 1290 | (3R)-3-(4-(3-ethylmorpholino)-3-((2-methoxypyrimidin-5-yl)amino)phenyl)-4-methoxybutanoic acid | 2-methoxypyrimidin-5-yl | 0.97 | O | 431.3 |

-continued

| Ex. No. | Name | R | $T_r$ min | Method | (M + H) |
|---|---|---|---|---|---|
| 1291 | (3R)-3-(3-((2-ethoxypyrimidin-5-yl)amino)-4-(3-ethylmorpholino)phenyl)-4-methoxybutanoic acid | 2-ethoxypyrimidin-5-yl | 1.10 | O | 445.3 |
| 1292 | (3R)-3-(3-((4-chlorophenyl)amino)-4-(3-ethylmorpholino)phenyl)-4-methoxybutanoic acid | 4-chlorophenyl | 1.92 | R | 433.2 |
| 1293 | (3R)-3-(4-(3-ethylmorpholino)-3-((4-fluorophenyl)amino)phenyl)-4-methoxybutanoic acid | 4-fluorophenyl | 1.39 | O | 417.2 |
| 1294 | (3R)-3-(4-(3-ethylmorpholino)-3-((5-fluoropyridin-2-yl)amino)phenyl)-4-methoxybutanoic acid | 5-fluoropyridin-2-yl | 1.16 | R | 418.3 |

Example 1295

Diastereomer 3

(3S)-3-(3-((4-Cyanophenyl)amino)-4-(3-ethylmorpholino)phenyl)-4-methoxybutanoic acid

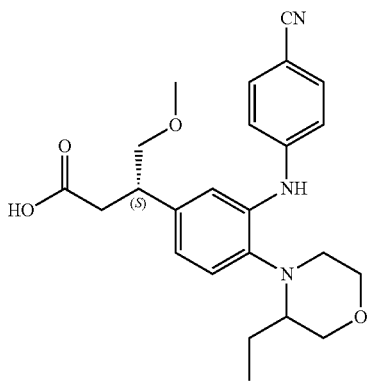

1295A. 5-(5,5-Dimethyl-1,3,2-dioxaborinan-2-yl)-2-(3-ethylmorpholino)aniline 1295A was prepared using 1281D Enantiomer 2 following procedure described for the synthesis of 1281E. LC-MS Anal. Calc'd. for $C_{17}H_{27}BN_2O_3$, 318.2, found [M+H] 251.2 (parent boronic acid), $T_r$=0.81 min (Method BB).

1295B. (3S)-Methyl 3-(3-amino-4-(3-ethylmorpholino)phenyl)-4-methoxybutanoate

1295B Diastereomer mixture was prepared using 1295A and (R)-(+)-2,2'-bis(diphenylphosphino)-1,1'-binaphthyl following procedure described for the synthesis of 74E. LC-MS Anal. Calc'd. for $C_{18}H_{28}N_2O_4$, 336.2, found [M+H] 337.2, $T_r$=1.76 min (Method BB).

Chiral separation of 1295B diastereomer mixture (77:23) yielded 1295B Diastereomer 3 $T_r$=4.7 Min, 1295B Diastereomer 4 $T_r$=6.3 min (Method BK).

1295B Diastereomer 3: LC-MS Anal. Calc'd. for $C_{18}H_{28}N_2O_4$, 336.2, found [M+H] 337.2, $T_r$=1.67 min (Method BB).

Example 1295 Diastereomer 3. (3S)-3-(3-((4-Cyanophenyl)amino)-4-(3-ethylmorpholino)phenyl)-4-methoxybutanoic acid Example 1295 Diastereomer 3 was prepared using 1295B Diastereomer 3 and 4-bromobenzonitrile, following the procedure described for the synthesis of Example 83. LC-MS Anal. Calc'd. for $C_{24}H_{29}N_3O_4$, 423.2, found [M+H] 424.3, $T_r$=1.27 min (Method O). $^1$H NMR (400 MHz, DMSO-$d_6$) δ11.96 (s, 1H), 8.06 (s, 1H), 7.55 (d, J=8.80 Hz, 2H), 7.15 (s, 1H), 7.10 (d, J=8.40 Hz, 1H), 7.04 (d, J=8.80 Hz, 2H), 6.96 (dd, J=2.00, 8.00 Hz, 1H), 3.61-3.66 (m, 3H), 3.40-3.46 (m, 3H), 3.24-3.23 (m, 4H), 2.92-2.94 (m, 2H), 2.63-2.68 (m, 2H), 2.42-2.45 (m, 1H), 1.18-1.22 (m, 2H), 0.64 (t, J=7.20 Hz, 3H).

Examples 1296 to 1302

Diastereomer 3

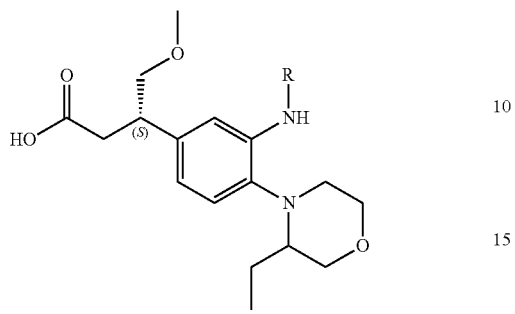

Examples 1296 and 1297 were prepared using 1295B Diastereomer 3 and corresponding aryl halides following the procedure described for the synthesis of Example 83.

Examples 1298 and 1299 were prepared using 1295B Diastereomer 3 and corresponding aryl halides following the procedure described for the synthesis of Example 78.

Examples 1300 to 1302 were prepared from 1295B Diastereomer 3 and corresponding aryl halides following the procedure described for the synthesis of Example 84.

| Ex. No. | Name | R | $T_r$ min | Method | (M + H) |
|---|---|---|---|---|---|
| 1296 | (3S)-3-(3-((4-cyano-3-fluorophenyl)amino)-4-(3-ethylmorpholino)phenyl)-4-methoxybutanoic acid | 3-F, 4-CN phenyl | 1.34 | O | 442.3 |
| 1297 | (3S)-3-(3-((5-cyanopyridin-2-yl)amino)-4-(3-ethylmorpholino)phenyl)-4-methoxybutanoic acid | 5-CN pyridin-2-yl | 1.08 | O | 425.2 |
| 1298 | (3S)-3-(4-(3-ethylmorpholino)-3-((2-methoxypyrimidin-5-yl)amino)phenyl)-4-methoxybutanoic acid | 2-OMe pyrimidin-5-yl | 1.02 | O | 431.3 |
| 1299 | (3S)-3-(3-((2-ethoxypyrimidin-5-yl)amino)-4-(3-ethylmorpholino)phenyl)-4-methoxybutanoic acid | 2-OEt pyrimidin-5-yl | 1.14 | O | 445.3 |
| 1300 | (3S)-3-(3-((4-chlorophenyl)amino)-4-(3-ethylmorpholino)phenyl)-4-methoxybutanoic acid | 4-Cl phenyl | 1.57 | O | 433.2 |

-continued

| Ex. No. | Name | R | $T_r$ min | Method | (M + H) |
|---|---|---|---|---|---|
| 1301 | (3S)-3-(4-(3-ethylmorpholino)-3-((4-fluorophenyl)amino)phenyl)-4-methoxybutanoic acid | | 1.44 | O | 417.3 |
| 1302 | (3S)-3-(4-(3-ethylmorpholino)-3-((5-fluoropyridin-2-yl)amino)phenyl)-4-methoxybutanoic acid | | 1.21 | O | 418.3 |

Example 1303

Diastereomer 4

(3R)-3-(3-((4-Cyanophenyl)amino)-4-(3-ethylmorpholino)phenyl)-4-methoxybutanoic acid

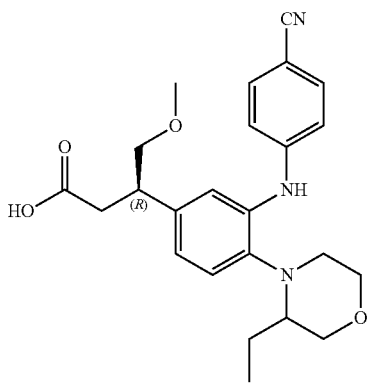

1303A. (3R)-Methyl 3-(3-amino-4-(3-ethylmorpholino) phenyl)-4-methoxybutanoate

1303A Diastereomer mixture was prepared using 1295A and (S)-(−)-2, 2′-bis(diphenylphosphino)-1,1′-binaphthyl following procedure described for the synthesis of 74E. LC-MS Anal. Calc'd. for $C_{18}H_{28}N_2O_4$, 336.2, found [M+H] 337.2, $T_r$=1.76 min (Method BB).

Chiral separation of 1303A diastereomer mixture (23:77) yielded 1303A Diastereomer 3 $T_r$=5.1 Min, 1303A Diastereomer 4 $T_r$=7.4 min (Method BK).

1303A Diastereomer 4: LC-MS Anal. Calc'd. for $C_{18}H_{28}N_2O_4$, 336.2, found [M+H] 337.2, $T_r$=1.76 min (Method BB).

Example 1303 Diastereomer 4. (3R)-3-(3-((4-Cyanophenyl)amino)-4-(3-ethylmorpholino)phenyl)-4-methoxybutanoic acid Example 1303 Diastereomer 4 was prepared using 1303A Diastereomer 4 and 4-bromobenzonitrile, following the procedure described for the synthesis of Example 83. LC-MS Anal. Calc'd. for $C_{24}H_{29}N_3O_4$, 423.2, found [M+H] 424.3, $T_r$=1.27 min (Method O). $^1$H NMR (400 MHz, DMSO-d$_6$) δ11.96 (s, 1H), 8.06 (s, 1H), 7.55 (d, J=8.80 Hz, 2H), 7.15 (s, 1H), 7.10 (d, J=8.40 Hz, 1H), 7.04 (d, J=8.80 Hz, 2H), 6.96 (dd, J=2.00, 8.00 Hz, 1H), 3.61-3.66 (m, 3H), 3.40-3.46 (m, 3H), 3.24-3.23 (m, 4H), 2.92-2.94 (m, 2H), 2.63-2.68 (m, 2H), 2.42-2.45 (m, 1H), 1.18-1.22 (m, 2H), 0.64 (t, J=7.20 Hz, 3H).

Examples 1304 to 1310

Diastereomer 4

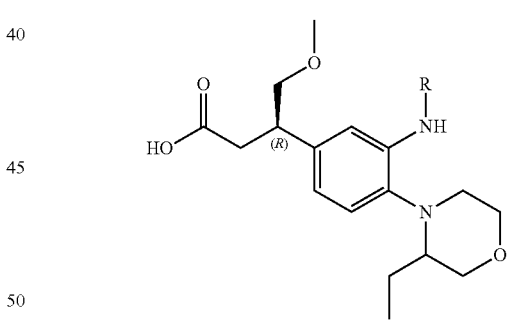

Examples 1304 and 1305 were prepared from 1303A Diastereomer 4 and corresponding aryl halides following the procedure described for the synthesis of Example 83.

Examples 1306 and 1307 were prepared from 1303A Diastereomer 4 and corresponding aryl halides following the procedure described for the synthesis of Example 78.

Examples 1308 to 1310 were prepared from 1303A Diastereomer 4 and corresponding aryl halides following the procedure described for the synthesis of Example 84.

| Ex. No. | Name | R | $T_r$, min | Method | (M + H) |
|---|---|---|---|---|---|
| 1304 | (3R)-3-(3-((4-cyano-3-fluorophenyl)amino)-4-(3-ethylmorpholino)phenyl)-4-methoxybutanoic acid | 3-F, 4-CN phenyl | 1.28 | O | 442.3 |
| 1305 | (3R)-3-(3-((5-cyanopyridin-2-yl)amino)-4-(3-ethylmorpholino)phenyl)-4-methoxybutanoic acid | 5-CN pyridin-2-yl | 1.08 | O | 425.3 |
| 1306 | (3R)-3-(4-(3-ethylmorpholino)-3-((2-methoxypyrimidin-5-yl)amino)phenyl)-4-methoxybutanoic acid | 2-OMe pyrimidin-5-yl | 0.92 | O | 431.3 |
| 1307 | (3R)-3-(3-((2-ethoxypyrimidin-5-yl)amino)-4-(3-ethylmorpholino)phenyl)-4-methoxybutanoic acid | 2-OEt pyrimidin-5-yl | 1.09 | O | 445.3 |
| 1308 | (3R)-3-(3-((4-chlorophenyl)amino)-4-(3-ethylmorpholino)phenyl)-4-methoxybutanoic acid | 4-Cl phenyl | 1.62 | O | 433.2 |
| 1309 | (3R)-3-(4-(3-ethylmorpholino)-3-((4-fluorophenyl)amino)phenyl)-4-methoxybutanoic acid | 4-F phenyl | 1.47 | O | 417.3 |
| 1310 | (3R)-3-(4-(3-ethylmorpholino)-3-((5-fluoropyridin-2-yl)amino)phenyl)-4-methoxubutanoic acid | 5-F pyridin-2-yl | 1.21 | O | 418.2 |

Example 1311

Diastereomer 1 and Diastereomer 2

3-(3-((4-Chlorophenyl)amino)-4-(2-methylmorpholino)phenyl)-4-methoxybutanoic acid

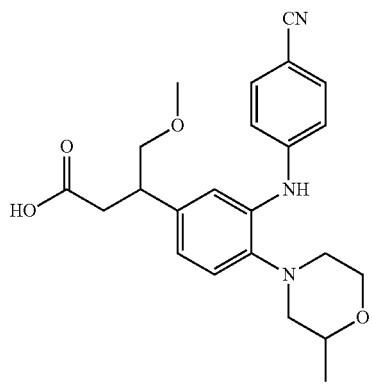 [SMILES: COCC(CC(=O)O)c1ccc(N2CCOC(C)C2)c(Nc2ccc(C#N)cc2)c1]

1311A. Ethyl 3-(4-fluoro-3-nitrophenyl)-4-methoxybutanoate 1311A was prepared using the 737A and (E)-ethyl 4-methoxybut-2-enoate following the procedure described for the synthesis of 41B. LC-MS Anal. Calc'd. for $C_{13}H_{16}FNO_5$, 285.1, found [M+H] 286.0, $T_r$=2.645 (Method U).

1311B. Ethyl 4-methoxy-3-(4-(2-methylmorpholino)-3-nitrophenyl)butanoate 1311B was prepared using the 1311A and 2-methylmorpholine following the procedure described for the synthesis of 41C. LC-MS Anal. Calc'd. for $C_{18}H_{26}N_2O_6$, 366.2, found [M+H] 367.2, $T_r$=2.168 (Method U).

1311C. Ethyl 3-(3-amino-4-(2-methylmorpholino)phenyl)-4-methoxybutanoate 1311C was prepared using the 1311B following the procedure described for the synthesis of 41D. LC-MS Anal. Calc'd. for $C_{18}H_{28}N_2O_4$, 336.2, found [M+H] 337.2, $T_r$=2.314 (Method U).

Chiral separation of 1311C diastereomeric mixture (four compounds) gave the Mixture A, $T_r$=3.67 min (Method DZ) and Mixture B, $T_r$=4.61 min (Method DZ) as mixture of two compounds. Mixture A (brown solid, 1.0 g). Mixture B (brown solid, 1.1 g).

Chiral separation of Mixture A gave 1311C Diastereomer 1 $T_r$=2.58 min (Method DY) and 1311C Diastereomer 2 $T_r$=2.17 min (Method DY) as single diastereomers.

1311C Diastereomer 1 LC-MS Anal. Calc'd. for $C_{18}H_{28}N_2O_4$, 336.2, found [M+H] 337.2, $T_r$=2.365 (Method U).

1311C Diastereomer 2 LC-MS Anal. Calc'd. for $C_{18}H_{28}N_2O_4$, 336.2, found [M+H] 337.2, $T_r$=2.365 (Method U).

Chiral separation of Mixture B gave 1311C Diastereomer 3 $T_r$=3.01 min (Method BF) and 1311C Diastereomer 4 $T_r$=3.82 min (Method BF) as single diastereomers 1311C Diastereomer 3 LC-MS Anal. Calc'd. for $C_{18}H_{28}N_2O_4$, 336.2, found [M+H] 337.2, $T_r$=1.569 (Method U).

1311C Diastereomer 4 LC-MS Anal. Calc'd. for $C_{18}H_{28}N_2O_4$, 336.2, found [M+H] 337.2, $T_r$=1.566 (Method U).

1311D. Ethyl 3-(3-((4-chlorophenyl)amino)-4-(2-methylmorpholino)phenyl)-4-methoxybutanoate To the mixture of 1311C Diastereomer 1 (50 mg, 0.149 mmol), 1-bromo-4-chlorobenzene (31.3 mg, 0.163 mmol)), Xantphos (17.2 mg, 0.030 mmol), $Cs_2CO_3$ (145 mg, 0.446 mmol) in 1,4-dioxane (2 mL), argon gas was bubbled for 5 minutes. Then the bis(dibenzylideneacetone)palladium (8.55 mg, 0.015 mmol) was added and the argon gas was bubbled through the mixture for 5 minutes. The reaction mixture was sealed, stirred and heated at 120° C. for 6 h. The reaction mixture was allowed to cool to room temperature and concentrated under reduced pressure to afford the residue. The residue was reconstituted in a mixture of ethyl acetate (20 mL) and water (20 mL). The organic layers were separated and the aqueous layers were extracted with ethyl acetate (2×20 mL). The combined organic layers were washed with water (20 mL), brine (20 mL), dried over anhydrous sodium sulfate, filtered and concentrated under reduced pressure to afford a residue. The residue was purified via flash silica gel column chromatography using ethyl acetate in pet ether as an eluant to afford 1311D (brown solid, 50 mg, 0.064 mmol, 43.1% yield). LC-MS Anal. Calc'd. for $C_{24}H_{31}ClN_2O_4$, 446.2, found [M+H] 447.5, $T_r$=1.67 (Method BA).

Example 1311 Diastereomer 1. 3-(3-((4-Chlorophenyl)amino)-4-(2-methylmorpholino)phenyl)-4-methoxybutanoic acid To a stirred solution of 1311D (50 mg, 0.112 mmol) in a mixture of MeOH (2 mL), THF (2 mL) and water (2 mL), LiOH (8.04 mg, 0.336 mmol) was added and stirred at room temperature for 4 h. The reaction mixture was concentrated and the aqueous solution was acidified with saturated citric acid solution (pH~4-5). The aqueous layer was diluted with water (5 mL) and extracted with ethyl acetate (2×10 mL). The combined organic layers were washed with water (10 mL), brine (10 mL), dried over anhydrous sodium sulfate, filtered and concentrated under reduced pressure to afford the residue. The residue was purified by preparative LCMS to afford Example 1311 Diastereomer 1 (off-white solid, 23 mg, 0.055, 49.1% yield). LC-MS Anal. Calc'd. for $C_{22}H_{27}ClN_2O_4$, 418.2, found [M+H] 419.1, $T_r$=2.134 (Method R). $^1H$ NMR (400 MHz, DMSO-$d_6$) δ 7.36 (s, 1H), 7.19-7.22 (m, 2H), 7.05 (d, J=1.60 Hz, 1H), 6.95-7.02 (m, 3H), 6.82 (dd, J=2.00, 8.00 Hz, 1H), 3.73-3.76 (m, 1H), 3.56-3.59 (m, 2H), 3.21 (s, 3H), 3.10-3.19 (m, 3H), 2.87-2.96 (m, 2H), 2.61-2.65 (m, 2H), 2.34-2.50 (m, 2H), 1.03 (d, J=6.40 Hz, 3H).

Example 1311 Diastereomer 2. 3-(3-((4-Chlorophenyl)amino)-4-(2-methylmorpholino)phenyl)-4-methoxybutanoic acid Example 1311 Diastereomer 2 was synthesized using 1311C Diastereomer 2 and 1-bromo-4-chlorobenzene following the procedure described for the synthesis of Example 1311 Diastereomer 1. LC-MS Anal. Calc'd. for $C_{22}H_{27}ClN_2O_4$, 418.2, found [M+H] 419.1, $T_r$=2.135 (Method R). $^1H$ NMR (400 MHz, DMSO-$d_6$) δ 7.32 (s, 1H), 7.19 (d, J=8.80 Hz, 2H), 6.94-7.02 (m, 4H), 6.80 (dd, J=2.00, 8.20 Hz, 1H), 3.71-3.74 (m, 4H), 3.19 (s, 3H), 3.13-3.16 (m, 2H), 2.85-2.90 (m, 2H), 2.58-2.63 (m, 2H), 2.32-2.43 (m, 2H), 1.02 (d, J=6.40 Hz, 3H).

Example 1312

Diastereomer 1

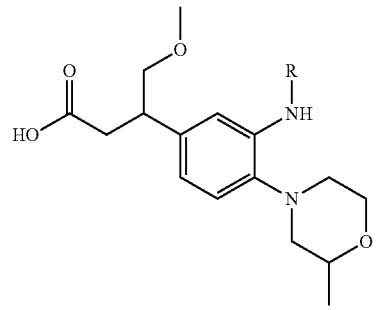

Example 1312 was prepared using 1311C Diastereomer 1 and corresponding aryl halides following the procedure described for the synthesis of Example 1311.

| Ex. No. | Name | R | $T_r$ min | Method | (M + H) |
|---|---|---|---|---|---|
| 1312 | 3-(3-((4-cyanophenyl)amino)-4-(2-methylmorpholino)phenyl)-4-methoxybutanoic acid | 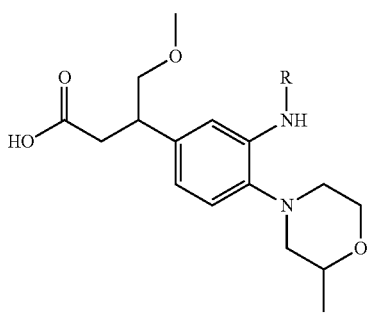 | 1.795 | R | 410.2 |

Example 1313

Diastereomer 2

Example 1313 was prepared using 1311C Diastereomer 2 and corresponding aryl halides following the procedure described for the synthesis of Example 1311.

| Ex. No. | Name | R | $T_r$ min | Method | (M + H) |
|---|---|---|---|---|---|
| 1313 | 3-(3-((4-cyanophenyl)amino)-4-(2-methylmorpholino)phenyl)-4-methoxybutanoic acid | 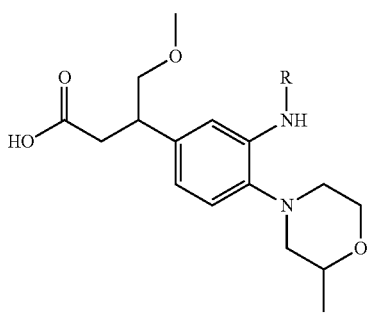 | 1.797 | R | 410.2 |

Example 1314

Diastereomer 1 and Diastereomer 2

3-(3-(3-(4-Chloro-2-fluorophenyl)ureido)-4-(2-methylmorpholino)phenyl)-4-methoxybutanoic acid

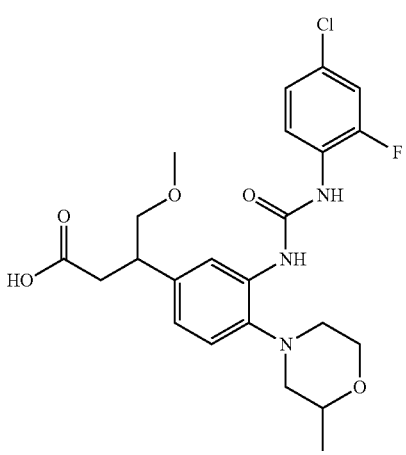

Example 1314 Diastereomer 1 was prepared utilizing 1311C Diastereomer 1 and 4-chloro-2-fluoro-1-isocyanatobenzene following the procedure described for the synthesis of Example 422 Enantiomer 1. LC-MS Anal. Calc'd. for $C_{23}H_{27}ClFN_3O_5$ 479.2, found [M+H] 480.1, $T_r$=1.934 min (Method R). $^1$H NMR (400 MHz, DMSO-$d_6$) δ12.02 (s, 1H), 9.47 (s, 1H), 8.48 (s, 1H), 8.14 (t, J=8.80 Hz, 1H), 7.92 (s, 1H), 7.45 (dd, J=2.00, 11.20 Hz, 1H), 7.23 (d, J=8.80 Hz, 1H), 7.08 (d, J=8.40 Hz, 1H), 7.38 (d, J=408.40 Hz, 1H), 3.86-3.90 (m, 1H), 3.84 (s, 3H), 3.16-3.21 (m, 4H), 2.63-2.84 (m, 5H), 2.38-2.45 (m, 2H), 1.10 (d, J=6.40 Hz, 3H).

Example 1314 Diastereomer 2. 3-(3-(3-(4-Chloro-2-fluorophenyl)ureido)-4-(2-methylmorpholino)phenyl)-4-methoxybutanoic acid Example 1314 Diastereomer 2 was prepared utilizing 1311C Diastereomer 2 and 4-chloro-2-fluoro-1-isocyanatobenzene following the procedure described for the synthesis of Example 422 Enantiomer 1. LC-MS Anal. Calc'd. for $C_{23}H_{27}ClFN_3O_5$ 479.2, found [M+H] 480.1, $T_r$=1.934 min (Method R). $^1$H NMR (400 MHz, DMSO-$d_6$) δ11.86 (s, 1H), 9.47 (s, 1H), 8.48 (s, 1H), 8.15 (t, J=8.80 Hz, 1H), 7.92 (s, 1H), 7.45 (dd, J=1.60, 11.00 Hz, 1H), 7.22 (d, J=8.40 Hz, 1H), 7.08 (d, J=8.40 Hz, 1H), 7.38 (d, J=408.40 Hz, 1H), 3.86-3.90 (m, 1H), 3.84 (s, 3H), 3.17-3.23 (m, 4H), 2.61-2.84 (m, 5H), 2.42-2.45 (m, 2H), 1.10 (d, J=6.40 Hz, 3H).

Example 1315

Enantiomer 1 and Enantiomer 2

3-(3-((4-Chlorophenyl)amino)-4-(2,2-dimethylmorpholino)phenyl)-4-methoxybutanoic acid

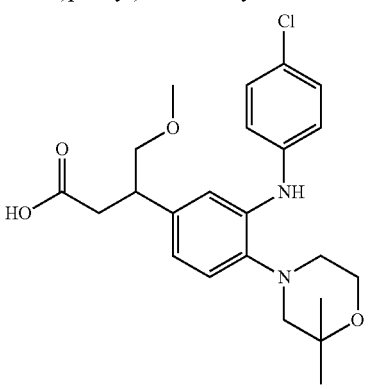

1315A. 2-(Benzyl(2-methylallyl)amino)ethanol

3-Chloro-2-methylprop-1-ene (7.19 g, 79 mmol) was added to a mixture of 2-(benzylamino)ethanol (10.0 g, 66.1 mmol) and potassium carbonate (13.71 g, 99 mmol) in water (60 mL). The mixture was heated and stirred at 60° C. for 17 h. The reaction mixture was cooled to room temperature extracted with tert-butyl methyl ether (2×50 ml). The organic layers were dried over sodium sulfate, filtered, and concentrated under reduced pressure to give 1315A (colorless liquid, 11.5 g, 55.1 mmol, 83% yield). LC-MS Anal. Calc'd. for $C_{13}H_{19}NO$, 205.2, found [M+H] 206.2, $T_r$=2.671 min (Method U).

1315B. 4-Benzyl-2-(iodomethyl)-2-methylmorpholine

Iodine (14.28 g, 56.3 mmol) was added to a biphasic mixture of 1315A (10.5 g, 51.1 mmol) in tert-butyl methyl ether (125 mL) and 1 M sodium bicarbonate (51.1 mL, 51.1 mmol). The reaction mixture was stirred for 18 h at room temperature. The reaction mixture was quenched with 1M $Na_2S_2O_3$ (200 mL), and was extracted with additional tert-butyl methyl ether (2×200 mL). The organic layers were separated, washed with 1M $Na_2S_2O_3$ (100 mL), 1M $NaHCO_3$ (100 mL), dried over sodium sulfate, filtered, and concentrated under reduced pressure to afford 1315B (golden oil, 14.5 g, 43.0 mmol, 84% yield). LC-MS Anal. Calc'd. for $C_{13}H_{18}INO$, 331.0, found [M+H] 332.2, $T_r$=3.459 min (Method U).

1315C. 4-Benzyl-2,2-dimethylmorpholine $NaBH_4$ (2.485 g, 65.7 mmol) was added to a solution of 1315B (14.5 g, 43.8 mmol) DMSO (75 mL) and then the reaction mixture was stirred and heated at 100° C., for 4.5 h. The reaction mixture was quenched with 5M HCl (50 ml) and stirred for 15 minutes. Then added 5M NaOH (50 mL) and 1M $Na_2S_2O_3$ (100 mL) stirred the mixture for 6 h. The mixture diluted with water (100 mL) and extracted with tert-butyl methyl ether (2×250 mL). The organic layers were separated, washed with water (4×100 dried over anhydrous sodium sulfate, filtered and concentrated under reduced pressure to afford the crude, which was purified by flash silica gel column chromatography to afford 1317C (colorless liquid, 5.0 g, 24.36 mmol, 55.6% yield). LC-MS Anal. Calc'd. for $C_{13}H_{19}NO$, 205.2, found [M+H] 206.2, $T_r$=2.641 min (Method U).

1315D. 2,2-Dimethylmorpholine, HCl 1315C (2.5 g, 12.18 mmol) dissolved in DCM (25 mL), followed by addition of 1-chloroethyl chloroformate (2.61 g, 18.27 mmol). The reaction mixture was stirred at room temperature for 4 h. The reaction mixture was concentrated under reduced pressure to afford the residue. The residue dissolved in MeOH (25 mL), heated at 60° C. and stirred for 2 h. The solvents were evaporated and the residue was dissolved in water (10 mL) and washed with tert-butyl methyl ether (25 mL). The aqueous layer concentrated under reduced pressure to afford the residue, dried at 80° C., under vacuum to give 1315D (white solid, 1.5 g, 9.89 mmol, 81% yield). $^1$H NMR (400 MHz, DMSO-$d_6$) δ 9.51 (s, 2H), 3.74-3.82 (m, 2H), 2.91-2.95 (m, 4H), 1.25 (s, 6H).

1315E. Ethyl 3-(4-(2,2-dimethylmorpholino)-3-nitrophenyl)-4-methoxybutanoate 1315E was prepared using the 1315D and 1311A following the procedure described for the synthesis of 41C. LC-MS Anal. Calc'd. for $C_{19}H_{28}N_2O_6$, 380.2, found [M+H] 381.2, $T_r$=2.093 (Method U).

1315F. Ethyl 3-(3-amino-4-(2,2-dimethylmorpholino)phenyl)-4-methoxybutanoate 1315F was prepared using the 1315E racemate following the procedure described for the synthesis of 452D. LC-MS Anal. Calc'd. for $C_{19}H_{30}N_2O_4$, 350.2, found [M+H] 351.2, $T_r$=1.909 (Method U).

Chiral separation of 1315E racemate gave the 1315E Enantiomer 1, $T_r$=7.77 min (Method BU) and 1315E Enantiomer 2, $T_r$=11.42 min (Method BU) as single enantiomers.

1315F Enantiomer 1 (brown solid, 0.3 g, 0.856 mmol, 36.2%). LC-MS Anal. Calc'd. for $C_{19}H_{30}N_2O_4$, 350.2, found [M+H] 351.2, $T_r$=1.909 (Method U).

1315F Enantiomer 2 (brown solid, 0.35 g, 0.993 mmol, 42.0%). LC-MS Anal. Calc'd. for $C_{19}H_{30}N_2O_4$, 350.2, found [M+H] 351.2, $T_r$=1.909 (Method U).

1315G. Ethyl 3-(3-((4-chlorophenyl)amino)-4-(2,2-dimethylmorpholino)phenyl)-4-methoxybutanoate 1315G was prepared using the 1315F Enantiomer 1 and 4-bromo-1-chlorobenzene following the procedure described for the synthesis of 1311D. LC-MS Anal. Calc'd. for $C_{25}H_{33}ClN_2O_4$, 460.2, found [M+H] 461.2, $T_r$=1.74 (Method AY).

Example 1315 Enantiomer 1. 3-(3-((4-Chlorophenyl)amino)-4-(2,2-dimethylmorpholino)phenyl)-4-methoxybutanoic acid Example 1315 Enantiomer 1 was prepared using the 1315G following the procedure described for the synthesis of Example 1311. LC-MS Anal. Calc'd. for $C_{23}H_{29}ClN_2O_4$, 432.2, found [M+H] 433.1, $T_r$=2.228 (Method R). $^1$H NMR (400 MHz, DMSO-$d_6$) δ 7.22 (s, 1H), 7.19 (d, J=5.60 Hz, 2H), 7.08 (d, J=1.60 Hz, 1H), 6.96-6.99 (m, 3H), 6.85 (dd, J=2.00, 8.20 Hz, 1H), 3.68-3.70 (m, 3H), 3.15-3.27 (m, 5H), 2.77 (d, J=2.00 Hz, 2H), 2.40-2.68 (m, 4H), 1.17 (s, 6H).

Example 1315 Enantiomer 2. 3-(3-((4-Chlorophenyl)amino)-4-(2,2-dimethylmorpholino)phenyl)-4-methoxybutanoic acid Example 1315 Enantiomer 2 was prepared using the 1315F Enantiomer 2 and 4-bromo-1-chlorobenzene following the procedure described for the synthesis of Example 1311. LC-MS Anal. Calc'd. for $C_{23}H_{29}ClN_2O_4$, 432.2, found [M+H] 433.0, $T_r$=1.739 (Method O). $^1$H NMR (400 MHz, DMSO-$d_6$) δ 7.22 (s, 1H), 7.19 (d, J=5.60 Hz, 2H), 7.07 (d, J=1.60 Hz, 1H), 6.96-6.99 (m, 3H), 6.85 (dd, J=2.00, 8.20 Hz, 1H), 3.68-3.70 (m, 3H), 3.20 (s, 3H), 3.15-3.18 (m, 2H), 2.76-2.78 (m, 2H), 2.55-2.60 (m, 4H), 1.17 (s, 6H).

Example 1316

Enantiomer 1

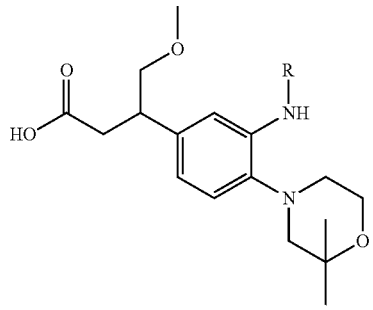

Example 1316 was prepared using 1315F Enantiomer 1 and corresponding aryl bromide following the procedure described for the synthesis of Example 1315

| Ex. No. | Name | R | $T_r$ min | Method | (M + H) |
|---|---|---|---|---|---|
| 1316 | 3-(3-((4-cyanophenyl)amino)-4-(2,2-dimethylmorpholino)phenyl)-4-methoxybutanoic acid |  | 1.008 | R | 424.1 |

Example 1317

Enantiomer 2

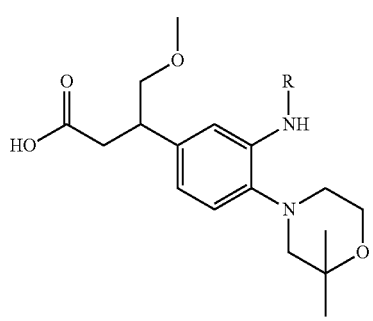

Example 1317 was prepared using 1315F Enantiomer 2 and corresponding aryl bromides following the procedure described for the synthesis of Example 1315.

| Ex. No. | Name | R | $T_r$ min | Method | (M + H) |
|---|---|---|---|---|---|
| 1317 | 3-(3-((4-cyanophenyl)amino)-4-(2,2-dimethylmorpholino)phenyl)-4-methoxybutanoic acid |  | 1.405 | O | 424.1 |

Example 1318

Enantiomer 1 and Enantiomer 2

3-(3-(3-(4-Chloro-2-fluorophenyl)ureido)-4-(2,2-dimethylmorpholino)phenyl)-4-methoxybutanoic acid

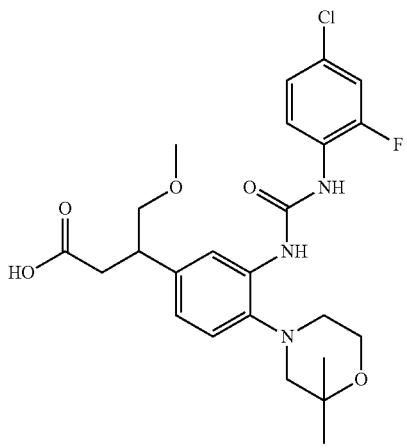

Example 1318 Enantiomer 1. 3-(3-(3-(4-Chloro-2-fluorophenyl)ureido)-4-(2,2-dimethylmorpholino)phenyl)-4-methoxybutanoic acid Example 1318 Enantiomer 1 was prepared utilizing 1315F Enantiomer 1 and 4-chloro-2-fluoro-1-isocyanatobenzene following the procedure described for the synthesis of Example 422 Enantiomer 1. LC-MS Anal. Calc'd. for $C_{24}H_{29}ClFN_3O_5$, 493.2, found [M+H] 494.0, $T_r$=1.507 min (Method O). $^1$H NMR (400 MHz, DMSO-$d_6$) δ 9.35 (s, 1H), 8.15 (s, 1H), 8.08 (t, J=8.80 Hz, 1H), 7.71 (d, J=1.60 Hz, 1H), 7.46 (dd, J=2.00, 11.00 Hz, 1H), 7.23 (d, J=8.80 Hz, 1H), 7.05 (d, J=8.40 Hz, 1H), 6.92 (dd, J=1.20, 8.20 Hz, 1H), 3.82 (s, 3H), 3.18-3.24 (m, 5H), 2.58-2.71 (m, 5H), 2.39-2.45 (m, 1H), 1.28 (s, 6H).

Example 1318 Enantiomer 2. 3-(3-(3-(4-Chloro-2-fluorophenyl)ureido)-4-(2,2-dimethylmorpholino)phenyl)-4-methoxybutanoic acid Example 1318 was prepared utilizing 1315F Enantiomer 2 and 4-chloro-2-fluoro-1-isocyanatobenzene following the procedure described for the synthesis of Example 422 Enantiomer 1. LC-MS Anal. Calc'd. for $C_{24}H_{29}ClFN_3O_5$, 493.2, found [M+H] 494.0, $T_r$=1.504 min (Method O). $^1$H NMR (400 MHz, DMSO-$d_6$) δ 9.35 (s, 1H), 8.15 (s, 1H), 8.08 (t, J=8.80 Hz, 1H), 7.71 (d, J=1.60 Hz, 1H), 7.46 (dd, J=2.00, 11.00 Hz, 1H), 7.23 (d, J=8.80 Hz, 1H), 7.05 (d, J=8.40 Hz, 1H), 6.92 (dd, J=1.20, 8.20 Hz, 1H), 3.82 (s, 3H), 3.18-3.24 (m, 5H), 2.58-2.71 (m, 5H), 2.39-2.45 (m, 1H), 1.28 (s, 6H).

Example 1319

Enantiomer 1 and Enantiomer 2

3-(3-((4-Chlorophenyl)amino)-4-(2,2-dimethylmorpholino)phenyl)pentanoic acid

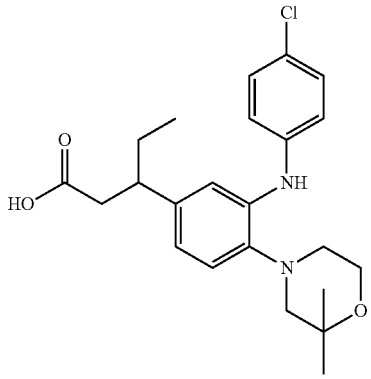

1319A. Methyl 3-(4-fluoro-3-nitrophenyl)pentanoate 1319A was prepared using the 737A and (E)-methyl pent-2-enoate following the procedure described for the synthesis of 41B. $^1$H NMR (400 MHz, CDCl$_3$) δ 7.90 (t, J=2.40 Hz, 1H), 7.47-7.51 (m, 1H), 7.22-7.28 (m, 1H), 3.60 (s, 3H), 3.10-3.73 (m, 1H), 2.55-2.73 (m, 2H), 1.57-1.80 (m, 2H), 0.02 (t, J=3.20 Hz, 3H).

1319B. Methyl 3-(4-(2,2-dimethylmorpholino)-3-nitrophenyl)pentanoate 1319B was prepared using the 1319A and 1315D following the procedure described for the synthesis of 41C. LC-MS Anal. Calc'd. for $C_{18}H_{26}N_2O_5$, 350.2, found [M+H] 351.2, $T_r$=2.194 (Method U).

1319C. Methyl 3-(3-amino-4-(2,2-dimethylmorpholino)phenyl)pentanoate 1319C was prepared using the 1319B following the procedure described for the synthesis of 41D. LC-MS Anal. Calc'd. for $C_{18}H_{28}N_2O_3$, 320.2, found [M+H] 321.2, $T_r$=2.465 (Method U).
Chiral separation of 1319C racemate gave the 1319C Enantiomer 1, $T_r$=3.76 min (Method CR) and 1319C Enantiomer 2, $T_r$=4.73 min (Method CR) as single enantiomers.
1319C Enantiomer 1 (brown solid, 0.34 g, 1.061 mmol, 37.2%). LC-MS Anal. Calc'd. for $C_{18}H_{28}N_2O_3$, 320.2, found [M+H] 321.2, $T_r$=2.465 (Method U).

1319C Enantiomer 2 (brown solid, 0.48 g, 1.498 mmol, 52.5%). LC-MS Anal. Calc'd. for $C_{18}H_{28}N_2O_3$, 320.2, found [M+H] 321.2, $T_r$=2.465 (Method U).

1319D. Methyl 3-(3-((4-chlorophenyl)amino)-4-(2, 2-dimethylmorpholino)phenyl)pentanoate 1319D was prepared using the 1319C Enantiomer 1 and 4-bromo-1-chlorobenzene following the procedure described for the synthesis of 1311D. LC-MS Anal. Calc'd. for $C_{24}H_{31}ClN_2O_3$, 430.2, found [M+H] 431.5, $T_r$=1.84 (Method AY).

Example 1319 Enantiomer 1. 3-(3-((4-Chlorophenyl)amino)-4-(2,2-dimethylmorpholino)phenyl)pentanoic acid Example 1319 Enantiomer 1 was prepared using the 1319D following the procedure described for the synthesis of Example 1311. LC-MS Anal. Calc'd. for $C_{23}H_{29}ClN_2O_3$, 416.941, found [M+H] 417.2, $T_r$=2.313 (Method R). $^1$H NMR (400 MHz, DMSO-$d_6$) δ 7.17-7.22 (m, 3H), 6.95-7.01 (m, 4H), 6.81 (dd, J=2.00, 8.00 Hz, 1H), 3.68 (t, J=5.20 Hz, 3H), 2.76-2.78 (m, 3H), 2.34-2.57 (m, 3H), 1.46-1.59 (m, 2H), 1.17 (s, 6H), 0.71 (t, J=7.20 Hz, 3H).

Example 1319 Enantiomer 2. 3-(3-((4-Chlorophenyl)amino)-4-(2,2-dimethylmorpholino)phenyl)pentanoic acid Example 1319 Enantiomer 2 was prepared using the 1319C Enantiomer 2 and 4-bromo-1-chlorobenzene following the procedure described for the synthesis of Example 1319. LC-MS Anal. Calc'd. for $C_{23}H_{29}ClN_2O_3$, 416.941, found [M+H] 417.2, $T_r$=2.289 (Method R). $^1$H NMR (400 MHz, DMSO-$d_6$) δ 7.18-7.22 (m, 3H), 6.95-7.01 (m, 4H), 6.81 (dd, J=2.00, 8.00 Hz, 1H), 3.68 (t, J=5.20 Hz, 3H), 2.76-2.78 (m, 3H), 2.57 (s, 2H 2.33-2.40 (m, 1H), 1.46-1.61 (m, 2H), 1.17 (s, 6H), 0.71 (t, J=7.20 Hz, 3H).

Example 1320

Enantiomer 1

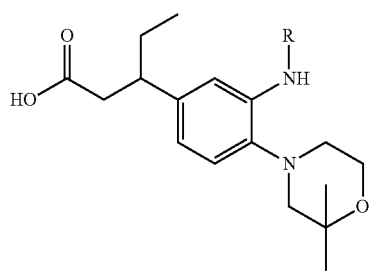

Example 1320 was prepared using 1319C Enantiomer 1 and corresponding aryl halides following the procedure described for the synthesis of Example 1319 Enantiomer 1.

| Ex. No. | Name | R | $T_r$, min | Method | (M + H) |
|---|---|---|---|---|---|
| 1320 | 3-(3-((4-cyanophenyl)amino)-4-(2,2-dimethylmorpholino)phenyl)pentanoic acid | ![R group with 4-cyanophenyl] | 1.968 | R | 408.3 |

Example 1321

Enantiomer 2

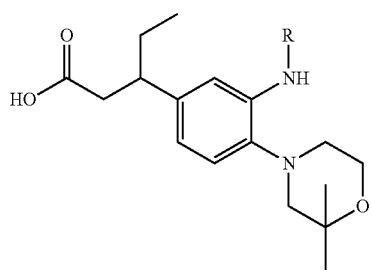

Example 1321 was prepared using 1319C Enantiomer 2 and corresponding aryl halides following the procedure described for the synthesis of Example 1319 Enantiomer 1.

| Ex. No. | Name | R | $T_r$, min | Method | (M + H) |
|---|---|---|---|---|---|
| 1321 | 3-(3-((4-cyanophenyl)amino)-4-(2,2-dimethylmorpholino)phenyl)pentanoic acid | ![R group with 4-cyanophenyl] | 1.939 | R | 408.3 |

Example 1322

Enantiomer 1 and Enantiomer 2

3-(3-(3-(4-Chloro-2-fluorophenyl)ureido)-4-(2,2-dimethylmorpholino)phenyl)pentanoic acid

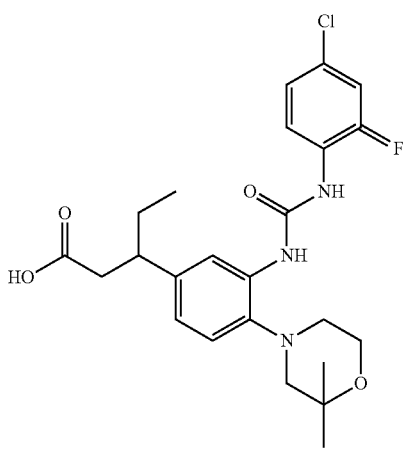

Example 1322 Enantiomer 1. 3-(3-(3-(4-Chloro-2-fluorophenyl)ureido)-4-(2,2-dimethylmorpholino)phenyl)pentanoic acid Example 1322 Enantiomer 1 was prepared utilizing 1319C Enantiomer 1 and 4-chloro-2-fluoro-1-isocyanatobenzene following the procedure described for the synthesis of Example 422 Enantiomer 1. LC-MS Anal. Calc'd. for $C_{24}H_{29}ClFN_3O_4$, 477.2, found [M+H] 478.2, $T_r$=2.005 min (Method R). $^1$H NMR (400 MHz, DMSO-$d_6$) δ 9.34 (s, 1H), 8.15 (s, 1H), 8.08 (t, J=6.60 Hz, 1H), 7.68 (d, J=1.50 Hz, 1H), 7.46 (dd, J=1.80, 8.10 Hz, 1H), 7.23 (d, J=6.60 Hz, 1H), 7.05 (d, J=6.00 Hz, 1H), 6.87 (dd, J=1.50, 6.30 Hz, 1H), 3.82 (t, J=3.90 Hz, 3H), 2.75-2.85 (m, 1H), 2.67-2.71 (m, 2H), 2.53-2.55 (m, 2H), 2.37-2.43 (m, 1H), 1.40-1.70 (m, 2H), 1.28 (s, 6H), 0.72 (t, J=7.4 Hz, 3H).

Example 1322 Enantiomer 2. 3-(3-(3-(4-Chloro-2-fluorophenyl)ureido)-4-(2,2-dimethylmorpholino)phenyl)pentanoic acid Example 1322 Enantiomer 2 was prepared utilizing 1319C Enantiomer 2 and 4-chloro-2-fluoro-1-isocyanatobenzene following the procedure described for the synthesis of Example 422 Enantiomer 1. LC-MS Anal. Calc'd. for $C_{24}H_{29}ClFN_3O_4$, 477.956, found [M+H] 478.2, $T_r$=2.005 min (Method R). $^1$H NMR (400 MHz, DMSO-$d_6$) δ 9.35 (s, 1H), 8.16 (s, 1H), 8.08 (t, J=6.60 Hz, 1H), 7.68 (d, J=1.50 Hz, 1H), 7.46 (dd, J=1.80, 8.10 Hz, 1H), 7.23 (d, J=6.60 Hz, 1H), 7.05 (d, J=6.00 Hz, 1H), 6.87 (dd, J=1.50, 6.30 Hz, 1H), 3.81-3.83 (m, 3H), 2.75-2.85 (m, 1H), 2.68-2.72 (m, 2H), 2.53-2.58 (m, 2H), 2.35-2.41 (m, 1H), 1.47-1.62 (m, 2H), 1.28 (s, 6H), 0.72 (t, J=7.2 Hz, 3H).

Example 1325

(S)-N-(2-(3-((2-Ethoxypyrimidin-5-yl)amino)-4-(ethyl(tetrahydro-2H-pyran-4-yl)amino)phenyl)butyl)ethanesulfonamide

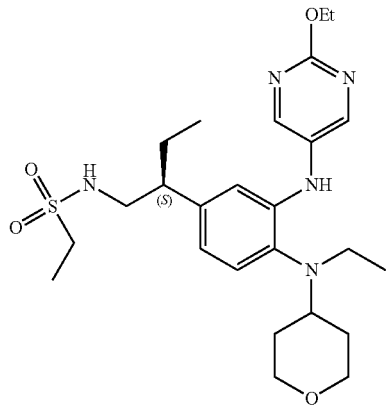

1325A. (S)-Benzyl (2-(3-((2-ethoxypyrimidin-5-yl)amino)-4-(ethyl(tetrahydro-2H-pyran-4-yl)amino)phenyl)butyl)carbamate

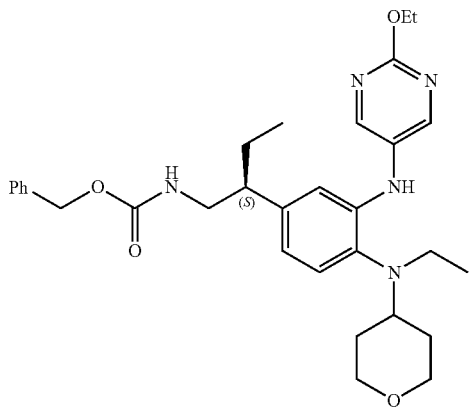

Diphenyl phosphorazidate (0.485 g, 1.763 mmol) and TEA (0.283 mL, 2.034 mmol) were added to a solution of Example 498 (0.6 g, 1.356 mmol) in dry toluene (5 mL). The resulting mixture was stirred at 108° C. under nitrogen atmosphere for 1 h. After adding phenyl methanol (0.733 g, 6.78 mmol). The reaction mixture was stirred at 110° C. for another 3 h. Then the reaction mixture quenched with water (10 mL), diluted with ethyl acetate (50 mL), washed with brine solution (3×50 mL), dried over anhydrous sodium sulfate, filtered and evaporated under reduced pressure to afford the residue, which was purified via Preparative LCMS to afford 1325A (light yellow solid, 0.6 g, 1.096 mmol, 81% yield). LC-MS Anal. Calc'd. for $C_{31}H_{41}N_5O_4$, 547.3, found [M+H] 548.3, $T_r$=2.673 min (Method O). $^1$H NMR (400 MHz, CD$_3$OD) δ 8.46 (s, 2H), 7.28-7.35 (m, 5H), 7.17-7.19 (m, 1H), 6.72-6.83 (m, 2H), 5.02-5.03 (m, 2H), 4.40-4.42 (m, 2H), 3.89-3.93 (m, 2H), 3.29-3.39 (m, 2H), 3.06-3.18 (m, 5H), 2.59-2.62 (m, 1H), 1.80-1.83 (m, 2H), 1.53-1.57 (m, 4H), 1.42 (t, J=6.80 Hz, 3H), 0.93 (t, J=7.20 Hz, 3H), 0.82 (t, J=7.60 Hz, 3H).

1325B. (S)-4-(1-Aminobutan-2-yl)-N2-(2-ethoxypyrimidin-5-yl)-N1-ethyl-N1-(tetrahydro-2H-pyran-4-yl)benzene-1,2-diamine

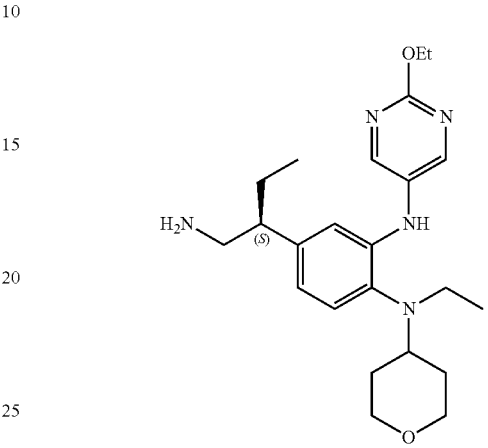

To a stirred solution of 1325A (0.55 g, 1.004 mmol) in ethyl acetate (10 mL) was added palladium on carbon (0.117 g, 0.055 mmol) and the suspension was hydrogenated under 15 psi pressure at room temperature for 12 h. The suspension was filtered through a pad of CELITE® and the filter cake was rinsed with ethyl acetate (30 mL). The combined filtrate was concentrated under reduced pressure to afford the light yellow residue. The residue was purified via Preparative LCMS to afford 1325B (light yellow solid, 0.25 g, 0.605 mmol, 60.2% yield). LC-MS Anal. Calc'd. for $C_{23}H_{35}N_5O_2$, 413.3, found [M+H] 414.3, $T_r$=1.574 min (Method O). $^1$H NMR (400 MHz, CD$_3$OD) δ 8.45 (s, 2H), 7.25-7.27 (m, 1H), 6.76-6.83 (m, 2H), 4.40-4.42 (m, 2H), 3.90-3.93 (m, 2H), 3.30-3.36 (m, 2H), 3.08-3.15 (m, 5H), 2.63-2.66 (m, 1H), 1.70-1.80 (m, 3H), 1.55-1.58 (m, 3H), 1.41 (t, J=7.20 Hz, 3H), 0.94 (t, J=7.20 Hz, 3H), 0.81 (t, J=7.20 Hz, 3H).

Example 1325

A solution of ethanesulfonyl chloride (11.19 mg, 0.087 mmol) in dichloromethane (1 mL) was slowly added to a solution of 1325B (30 mg, 0.073 mmol) in dichloromethane (5 mL) and pyridine (0.029 mL, 0.363 mmol) at 0° C. The resulting mixture was stirred at room temperature for 4 h. The solvent was concentrated under reduced pressure to afford brown colored residue. The residue was purified by preparative LCMS to afford Example 1325 (off-white solid, 2.5 mg, 4.80 μmol, 6.61% yield). LC-MS Anal. Calc'd. for $C_{25}H_{39}N_5O_4S_2$, 505.3, found [M+H] 506.3, $T_r$=2.248 min (Method O). $^1$H NMR (400 MHz, CD$_3$OD) δ 8.46 (s, 2H), 7.21-7.23 (m, 1H), 6.76-6.85 (m, 2H), 4.40-4.45 (m, 2H), 3.91-3.94 (m, 2H), 3.33-3.38 (m, 3H), 3.21-3.24 (m, 2H), 3.09-3.11 (m, 2H), 2.81-2.85 (m, 2H), 2.52-2.56 (m, 1H), 1.80-1.84 (m, 3H), 1.52-1.59 (m, 3H), 1.43 (t, J=6.80 Hz, 3H), 1.18 (t, J=7.20 Hz, 3H), 0.94 (t, J=7.20 Hz, 3H), 0.81 (t, J=7.60 Hz, 3H).

Examples 1326 to 1331

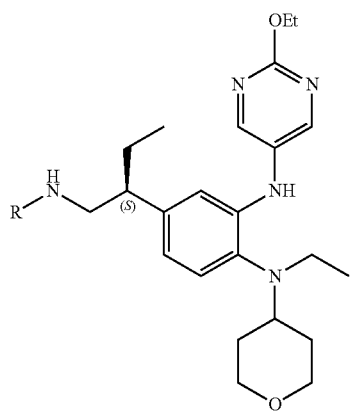

Examples 1326 to 1331 were prepared using the Example 1325B and corresponding sulfonyl chlorides following the procedure described for the synthesis of Example 1325.

Example 1332

(R)-3-(3-((2-Ethoxypyrimidin-5-yl)amino)-4-(ethyl(tetrahydro-2H-pyran-4-yl)amino)phenyl)pentanamide

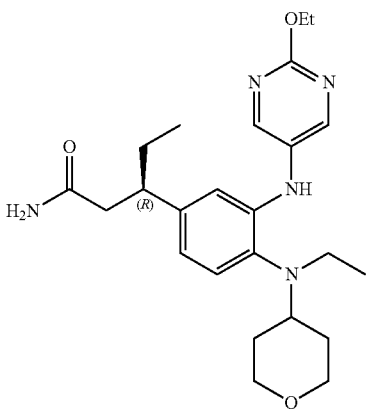

| Ex. No. | Name | R | $T_r$ (min) (Method O) | $[M + H]^+$ |
|---|---|---|---|---|
| 1326 | (S)-N-(2-(3-((2-ethoxypyrimidin-5-yl)amino)-4-(ethyl(tetrahydro-2H-pyran-4-yl)amino)phenyl)butyl)methanesulfonamide | | 2.126 | 492.2 |
| 1327 | (S)-N-(2-(3-((2-ethoxypyrimidin-5-yl)amino)-4-(ethyl(tetrahydro-2H-pyran-4-yl)amino)phenyl)butyl)-3,3,3-trifluoropropane-1-sulfonamide | | 2.507 | 574.3 |
| 1328 | (S)-N-(2-(3-((2-ethoxypyrimidin-5-yl)amino)-4-(ethyl(tetrahydro-2H-pyran-4-yl)amino)phenyl)butyl)-3,5-dimethylisoxazole-4-sulfonamide | | 2.467 | 573.3 |
| 1329 | (S)-N-(2-(3-((2-ethoxypyrimidin-5-yl)amino)-4-(ethyl(tetrahydro-2H-pyran-4-yl)amino)phenyl)butyl)-1,1,1-trifluoromethanesulfonamide | | 2.612 | 546.2 |
| 1330 | (S)-N-(2-(3-((2-ethoxypyrimidin-5-yl)amino)-4-(ethyl(tetrahydro-2H-pyran-4-yl)amino)phenyl)butyl)tetrahydrothiophene-3-sulfonamide 1,1-dioxide | | 2.137 | 596.3 |
| 1331 | (S)-N-(2-(3-((2-ethoxypyrimidin-5-yl)amino)-4-(ethyl(tetrahydro-2H-pyran-4-yl)amino)phenyl)butyl)-2-methylpropane-1-sulfonamide | | 2.485 | 534.3 |

To a stirred solution of Example 498 (500 mg, 1.130 mmol) in DCM (10 mL) and DMF (0.5 mL), was added SOCl₂ (0.124 mL, 1.695 mmol) dropwise at 0° C. for 5 min. The reaction was allowed to warm to room temperature, and then heated at 60° C. for 1.5 h. Then the reaction mixture was allowed to cool to room temperature and concentrated under reduced pressure to afford brown colored residue. The residue was diluted with THF (15 mL), ammonium hydroxide (5 mL, 128 mmol) was added at 0° C. dropwise and stirred for 30 minutes. This suspension was reconstituted in ethyl acetate (15 mL), washed with water (10 mL), aqueous saturated NaHCO₃ solution (20 mL), brine (20 mL), dried over sodium sulfate, filtered and concentrated under reduced pressure to afford the brown colored residue. The residue was purified by preparative LCMS to afford Example 1332 (light yellow solid, 420 mg, 0.951 mmol, 84% yield). LC-MS Anal. Calc'd. for $C_{24}H_{35}N_5O_3$, 441.3, found [M+H] 442.2, $T_r$=1.904 min (Method O). ¹H NMR (400 MHz, CD₃OD) δ 8.43 (s, 2H), 7.16-7.18 (m, 1H), 6.74-6.84 (m, 2H), 4.39-4.43 (m, 2H), 3.89-3.92 (m, 2H), 3.31-3.39 (m, 2H), 3.04-3.09 (m, 3H), 2.85-2.88 (m, 1H), 2.38-2.48 (m, 2H), 1.77-1.81 (m, 2H), 1.42-1.55 (m, 4H), 1.41 (t, J=7.20 Hz, 3H), 0.90 (t, J=6.80 Hz, 3H), 0.79 (t, J=7.20 Hz, 3H).

Example 1333

(R)-3-(3-((2-Ethoxypyrimidin-5-yl)amino)-4-(ethyl(tetrahydro-2H-pyran-4-yl)amino)phenyl)pentanenitrile

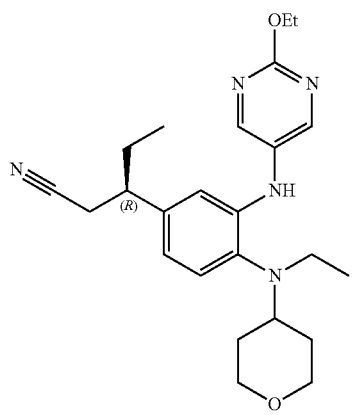

Example 1332 (350 mg, 0.674 mmol) was dissolved in DMF (3 mL), and 2, 4, 6-trichloro-1, 3, 5-triazine (149 mg, 0.808 mmol) was added at 0° C., under nitrogen atmosphere. The reaction mixture was allowed to warm to room temperature and stirred for 2 h. Then water (10 mL) was added and extracted with ethyl acetate (2×20 mL). The organic layers were washed with water (3×10 mL), dried over sodium sulfate, filtered and concentrated under reduced pressure to afford the residue. The residue was purified via preparative LCMS to afford Example 1333 (light yellow solid, 175 mg, 0.413 mmol, 61.3% yield). LC-MS Anal. Calc'd. for $C_{24}H_{33}N_5O_2$, 423.3, found [M+H] 424.2, $T_r$=2.351 min (Method O). ¹H NMR (400 MHz, CD₃OD) δ 8.45 (s, 2H), 7.21-7.23 (m, 1H), 6.88 (d, J=2.00 Hz, 1H), 6.77-6.80 (m, 1H), 4.38-4.43 (m, 2H), 3.90-3.93 (m, 2H), 3.31-3.39 (m, 2H), 3.06-3.11 (m, 3H), 2.68-2.77 (m, 3H), 1.70-1.82 (m, 2H), 1.53-1.57 (m, 4H), 1.41 (t, J=7.20 Hz, 3H), 0.92 (t, J=7.20 Hz, 3H), 0.84 (t, J=7.60 Hz, 3H).

Example 1335

(R)-N2-(2-Ethoxypyrimidin-5-yl)-N1-ethyl-4-(1-(oxazol-5-yl)butan-2-yl)-N1-(tetrahydro-2H-pyran-4-yl)benzene-1,2-diamine

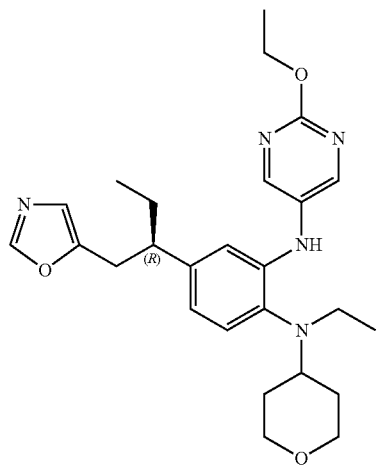

To a stirred solution of 498B (0.6 g, 1.794 mmol) in acetonitrile (20 mL) was added BOC₂O (0.833 mL, 3.59 mmol) and heated to reflux for 16 h. Then the reaction mixture was cooled to room temperature, diluted with ethyl acetate (50 mL) and washed with brine solution (2×30 mL). The organic layers were dried over sodium sulfate, filtered and concentrated under reduced pressure to get the crude, which was purified by silica gel flash chromatography (24 g silica gel column; 10% ethyl acetate:hexane) to afford 1335A (colorless gummy mass, 0.75 g, 1.709 mmol, 95% yield). LC-MS Anal. Calc'd. for $C_{24}H_{38}N_2O_5$, 434.2, found [M+H] 435.2, $T_r$=4.09 min (Method U).

1335B. (R)-tert-Butyl (2-(ethyl(tetrahydro-2H-pyran-4-yl)amino)-5-(1-hydroxypentan-3-yl)phenyl)carbamate To a stirred solution of 1335A (1 g, 2.301 mmol) in THF (3 mL) at 0° C. was added 1M lithium aluminum hydride in THF (4.60 mL, 4.60 mmol) dropwise over 5 min. Then the reaction mixture warmed to room temperature and stirred for 1 h. Reaction mixture was then cooled to 0° C., quenched with saturated sodium sulfate solution (10 mL) and extracted with ethyl acetate (2×25 mL). The combined organic layers were dried over sodium sulfate, filtered and concentrated under reduced pressure to afford 1335B (colorless gummy, 0.9 g, 2.147 mmol, 93% yield). LC-MS Anal. Calc'd. for $C_{23}H_{38}N_2O_4$, 406.2, found [M+H] 407.2, $T_r$=3.46 min (Method U).

1335C. (R)-tert-Butyl (2-(ethyl(tetrahydro-2H-pyran-4-yl)amino)-5-(1-oxopentan-3-yl)phenyl)carbamate To a stirred solution of 1335B (800 mg, 1.968 mmol) in DCM (15 mL) was added Dess-Martin periodinane (1252 mg, 2.95 mmol) and stirred at room temperature for 2 h. Then the reaction mixture was diluted with DCM (50 mL) and washed with sodium bicarbonate solution (2×25 mL) followed by brine solution (2×25 mL). The organic layers were dried over sodium sulfate, filtered and concentrated under reduced pressure to get the crude, which was purified by silica gel flash chromatography to afford 1335C (brown gummy, 0.6 g, 1.083 mmol, 55.0% yield). LC-MS Anal. Calc'd. for $C_{23}H_{36}N_2O_4$, 404.2, found [M+H] 405.2, $T_r$=4.05 min (Method BB).

1335D. (R)-tert-Butyl (2-(ethyl(tetrahydro-2H-pyran-4-yl)amino)-5-(1-(oxazol-5-yl)butan-2-yl)phenyl)carbamate To a stirred solution of 1335C (100 mg, 0.247 mmol) in MeOH (1 mL) was added $K_2CO_3$ (102 mg, 0.742 mmol) followed by toluenesulfonylmethyl isocyanide (57.9 mg, 0.297 mmol) and heated to 80° C. for 2 h. Then the reaction mixture was cooled to room temperature, diluted with ethyl acetate (25 mL) and washed with brine solution (2×15 mL). The organic layers were dried over sodium sulfate, filtered and concentrated under reduced pressure to get the crude, which was purified by silica gel flash chromatography to afford 1335D (brown gummy, 30 mg, 0.041 mmol, 16.42% yield). LC-MS Anal. Calc'd. for $C_{25}H_{37}N_3O_4$, 443.2, found [M+H] 444.2, $T_r$=1.7 min (Method AY).

1335E. (R)-N1-Ethyl-4-(1-(oxazol-5-yl)butan-2-yl)-N1-(tetrahydro-2H-pyran-4-yl)benzene-1,2-diamine To a stirred solution of 1335D (25 mg, 0.056 mmol) in 1,4-dioxane (1 mL) was added 4M HCl in dioxane (0.5 mL, 2.000 mmol) and stirred at room temperature for 2 h. Reaction mixture was concentrated under reduced pressure to get the crude, which was basified (pH~12) with sodium bicarbonate (10%) solution and extracted with ethyl acetate (2×25 mL). The combined organic layers were dried over sodium sulfate, filtered and concentrated under reduced pressure to afford 1335E (brown gummy, 22 mg, 0.039 mmol, 69.3% yield). LC-MS Anal. Calc'd. for $C_{20}H_{29}N_3O_2$, 343.2, found [M+H] 344.2, $T_r$=1.38 min (Method AY).

Example 1335 (R)-N2-(2-Ethoxypyrimidin-5-yl)-N1-ethyl-4-(1-(oxazol-5-yl)butan-2-yl)-N1-(tetrahydro-2H-pyran-4-yl)benzene-1,2-diamine Example 1335 was prepared from 1335E and 5-bromo-2-ethoxypyrimidine, following the procedure described for the synthesis of 455F. LC-MS Anal. Calc'd. for $C_{26}H_{35}N_5O_3$, 465.2, found [M+H] 466.2, $T_r$=2.49 min (Method O). $^1H$ NMR (400 MHz, DMSO-$d_6$) δ 8.37 (s, 2H), 8.11 (s, 1H), 7.29 (s, 1H), 7.10 (d, J=8.00 Hz, 1H), 6.77 (s, 1H), 6.62-6.64 (m, 2H), 4.30 (q, J=7.20 Hz, 2H), 3.80 (d, J=8.80 Hz, 2H), 3.16-3.21 (m, 3H), 2.92-2.99 (m, 4H), 2.83-2.89 (m, 1H), 1.58-1.65 (m, 2H), 1.36-1.52 (m, 4H), 1.32 (t, J=6.80 Hz, 3H), 0.81 (t, J=7.20 Hz, 3H), 0.72 (t, J=7.20 Hz, 3H).

Example 1336

Diastereomer 1 and Diastereomer 2

(4R)-4-(3-((2-Ethoxypyrimidin-5-yl)amino)-4-(ethyl(tetrahydro-2H-pyran-4-yl)amino)phenyl)-1,1,1-trifluorohexan-2-ol

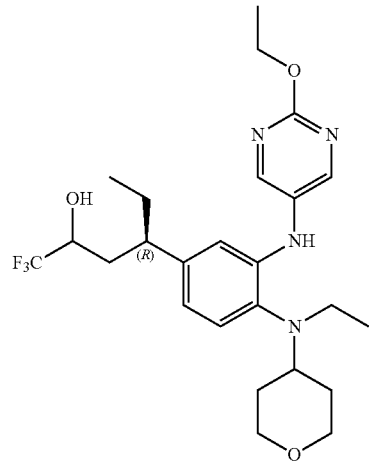

1336A. (4R)-tert-Butyl (2-(ethyl(tetrahydro-2H-pyran-4-yl)amino)-5-(6,6,6-trifluoro-5-hydroxy-hexan-3-yl)phenyl)carbamate To a solution of 1335C (0.1 g, 0.247 mmol) in THF (3 mL) was added (trifluoromethyl)trimethylsilane (0.059 mL, 0.371 mmol) at 0° C. followed by tetrabutylammonium fluoride in THF (0.025 mL, 0.025 mmol) and slowly warmed to room temperature and stirred for 2 h. Then the reaction mixture was quenched with 5 mL of 1.5 N HCl, stirred for 30 minutes and extracted with ethyl acetate (2×25 mL). The combined organic layers were dried over sodium sulfate, filtered and concentrated under reduced pressure to afford 1336A (brown gummy mass, 130 mg, 0.211 mmol, 85% yield). LC-MS Anal. Calc'd. for $C_{24}H_{37}F_3N_2O_4$, 474.2, found [M+H] 475.2, $T_r$=3.09 min (Method BB).

1336B. (4R)-4-(3-Amino-4-(ethyl(tetrahydro-2H-pyran-4-yl)amino)phenyl)-1,1,1-trifluorohexan-2-ol 1336B was prepared using 1336A following the procedure described for the synthesis of 1335E. LC-MS Anal. Calc'd. for $C_{19}H_{29}F_3N_2O_2$, 374.2, found [M+H] 375.2, $T_r$=3.19 min (Method BB).

Example 1336 Diastereomer 1 and Example 1336 Diastereomer 2. (4R)-4-(3-((2-Ethoxypyrimidin-5-yl)amino)-4-(ethyl(tetrahydro-2H-pyran-4-yl)amino)phenyl)-1,1,1-trifluorohexan-2-ol Example 1336 diastereomer mixture was prepared from 1336B and 5-bromo-2-ethoxypyrimidine, following the procedure described for the synthesis of 455F and diastereomers were separated by prep HPLC.

Chiral separation of 1336 Diastereomeric mixture (Method EA) gave 1336 Diastereomer 1, $T_r$=23.6 min (Method EA) and 1347D Enantiomer 2, $T_r$=24.9 min (Method EA).

Example 1336 Diastereomer 1: LC-MS Anal. Calc'd. for $C_{25}H_{35}F_3N_4O_3$ 496.2, found [M+H] 497.2, $T_r$=1.70 min (Method R). $^1$H NMR (400 MHz, DMSO-d$_6$) δ 8.43 (s, 2H), 7.34 (s, 1H), 7.14 (d, J=8.00 Hz, 1H), 6.80 (s, 1H), 6.68 (d, J=7.60 Hz, 1H), 6.09 (d, J=6.40 Hz, 1H), 4.30 (q, J=7.20 Hz, 2H), 3.91 (s, 1H), 3.82 (d, J=9.20 Hz, 2H), 3.22 (t, J=11.60 Hz, 2H), 2.98-3.02 (m, 3H), 2.52-2.55 (m, 1H), 1.81-1.83 (m, 1H), 1.67-1.70 (m, 4H), 1.41-1.44 (m, 3H), 1.32 (t, J=7.20 Hz, 3H), 0.84 (t, J=7.20 Hz, 3H), 0.68 (t, J=7.60 Hz, 3H).

Example 1336 Diastereomer 2: LC-MS Anal. Calc'd. for $C_{25}H_{35}F_3N_4O_3$ 496.2, found [M+H] 497.2, $T_r$=1.75 min (Method R). $^1$H NMR (400 MHz, DMSO-d$_6$) δ 8.40 (s, 2H), 7.35 (s, 1H), 7.22 (s, 1H), 6.84 (s, 1H), 6.71 (s, 1H), 6.01 (s, 1H), 4.29 (q, J=6.80 Hz, 2H), 3.83 (d, J=9.20 Hz, 2H), 3.20-3.26 (m, 2H), 3.01-3.11 (m, 3H), 2.54-2.58 (m, 1H), 1.69-1.76 (m, 5H), 1.48-1.52 (m, 3H), 1.32 (t, J=7.20 Hz, 3H), 0.84 (t, J=6.80 Hz, 3H), 0.72 (t, J=7.60 Hz, 3H).

Example 1337

(R)-4-(1-(1,2,4-Oxadiazol-5-yl)butan-2-yl)-N2-(2-ethoxypyrimidin-5-yl)-N1-ethyl-N1-(tetrahydro-2H-pyran-4-yl)benzene-1,2-diamine

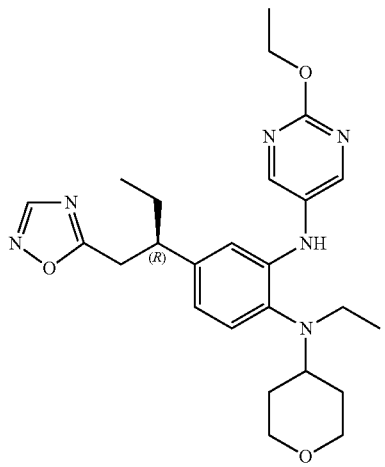

1337A. (R)-N-((Dimethylamino)methylene)-3-(3-((2-ethoxypyrimidin-5-yl)amino)-4-(ethyl(tetrahydro-2H-pyran-4-yl)amino)phenyl)pentanamide To a stirred solution of Example 1332 (100 mg, 0.226 mmol) in THF (1 mL) was added DMF-DMA (0.061 mL, 0.453 mmol) and heated to 90° C. for 2 h. Then the reaction mixture was cooled to room temperature and concentrated under reduced pressure to afford 1337A (brown gummy, 90 mg, 0.167 mmol, 73.6% yield). LC-MS Anal. Calc'd. for $C_{27}H_{40}N_6O_3$, 496.3, found [M+H] 497.2, $T_r$=2.49 min (Method BB).

Example 1337 (R)-4-(1-(1,2,4-Oxadiazol-5-yl)butan-2-yl)-N2-(2-ethoxypyrimidin-5-yl)-N1-ethyl-N1-(tetrahydro-2H-pyran-4-yl)benzene-1,2-diamine To a stirred solution of 1337A (45 mg, 0.091 mmol) in ethanol (1 mL) was added hydroxylamine hydrochloride (12.59 mg, 0.181 mmol) and heated to 90° C. for 4 h. Then the reaction mixture was cooled to room temperature and concentrated under reduced pressure to get the crude, which was purified by prep HPLC to afford Example 1337 (8.3 mg, 0.017 mmol, 19.04% yield). LC-MS Anal. Calc'd. for $C_{25}H_{34}N_6O_3$, 466.2, found [M+H] 467.2, $T_r$=2.24 min (Method O). $^1$H NMR (400 MHz, DMSO-d$_6$) δ 8.77 (s, 1H), 8.38 (s, 2H), 7.30 (s, 1H), 7.09 (d, J=8.00 Hz, 1H), 6.81 (s, 1H), 6.67 (d, J=8.00 Hz, 1H), 4.31 (q, J=7.20 Hz, 2H), 3.80 (d, J=8.80 Hz, 2H), 3.14-3.30 (m, 4H), 2.95-2.97 (m, 4H), 1.58-1.66 (m, 4H), 1.41-1.43 (m, 2H), 1.33 (t, J=6.80 Hz, 3H), 0.72-0.81 (m, 6H).

Example 1338

(R)-4-(1-(4H-1,2,4-Triazol-3-yl)butan-2-yl)-N2-(2-ethoxypyrimidin-5-yl)-N1-ethyl-N1-(tetrahydro-2H-pyran-4-yl)benzene-1,2-diamine

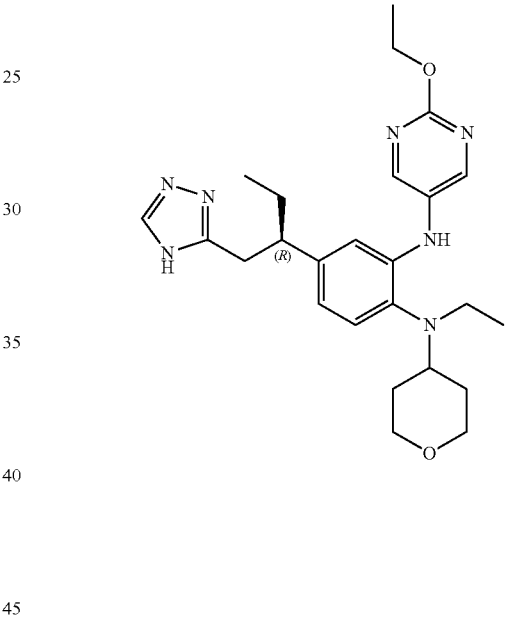

To a stirred solution of 1337A (50 mg, 0.101 mmol) in AcOH (0.5 mL) was added hydrazine hydrate (9.87 μl, 0.201 mmol) and heated to 90° C. for 2 h. Then the reaction mixture was cooled to room temperature, concentrated under reduced pressure to afford the residue. The residue was dissolved in DCM (25 mL) and washed with 10% sodium bicarbonate solution (2×25 mL) followed by brine solution (2×25 mL). The organic layers were dried over sodium sulfate, filtered and concentrated under reduced pressure to get the crude, which was purified by preparative HPLC to afford Example 1338 (14.5 mg, 0.031 mmol, 30.6% yield).). LC-MS Anal. Calc'd. for $C_{25}H_{35}N_7O_2$, 465.2, found [M+H] 466.2, $T_r$=1.91 min (Method O). $^1$H NMR (400 MHz, DMSO-d$_6$) δ 8.38 (s, 2H), 7.92 (s, 1H), 7.28 (s, 1H), 7.08 (d, J=8.00 Hz, 1H), 6.76 (s, 1H), 6.65 (d, J=8.00 Hz, 1H), 4.31 (q, J=7.20 Hz, 2H), 3.80 (d, J=8.80 Hz, 2H), 3.17-3.23 (m, 4H), 2.88-2.93 (m, 4H), 1.58-1.67 (m, 2H), 1.42-1.52 (m, 2H), 1.38-1.41 (m, 2H), 1.31-1.36 (m, 3H), 0.80 (t, J=7.20 Hz, 3H), 0.69 (t, J=7.60 Hz, 3H).

Example 1339

(R)-4-(1-(1H-Tetrazol-5-yl)butan-2-yl)-N2-(2-ethoxypyrimidin-5-yl)-N1-ethyl-N1-(tetrahydro-2H-pyran-4-yl)benzene-1,2-diamine

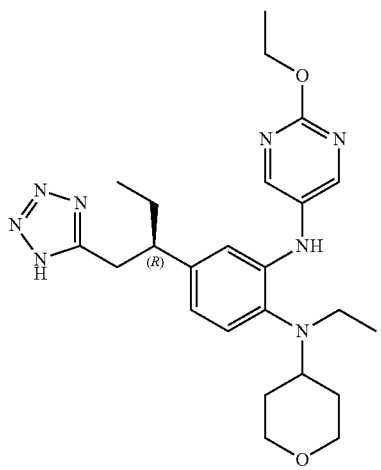

To a stirred solution of Example 1333 (80 mg, 0.189 mmol) in DME (1 mL) was added trimethyl silyl azide (0.100 mL, 0.756 mmol) followed by dibutyltin oxide (11.75 mg, 0.047 mmol) then the tube was sealed and heated to 110° C. for 16 h. Then the reaction mixture was cooled to room temperature and concentrated under reduced pressure to get the crude, which was purified by preparative HPLC to afford Example 1339 (29 mg, 0.062 mmol, 32.6% yield). LC-MS Anal. Calc'd. for $C_{24}H_{34}N_8O_2$ 466.2, found [M+H] 467.3, $T_r$=1.62 min (Method O). $^1$H NMR (400 MHz, DMSO-$d_6$) δ 8.94 (s, 2H), 7.30 (s, 1H), 7.07 (d, J=8.00 Hz, 1H), 6.77 (s, 1H), 6.61 (d, J=7.20 Hz, 1H), 4.32 (q, J=6.80 Hz, 2H), 3.80 (d, J=8.40 Hz, 2H), 3.07-3.21 (m, 4H), 2.85-2.96 (m, 4H), 1.58-1.66 (m, 4H), 1.24-1.44 (m, 5H), 0.79 (t, J=7.20 Hz, 3H), 0.72 (t, J=7.20 Hz, 3H).

Example 1340

(R)-N-(2-(3-((4-Cyanophenyl)amino)-4-(ethyl(tetrahydro-2H-pyran-4-yl)amino)phenyl)-3-methoxypropyl)-3,5-dimethylisoxazole-4-sulfonamide

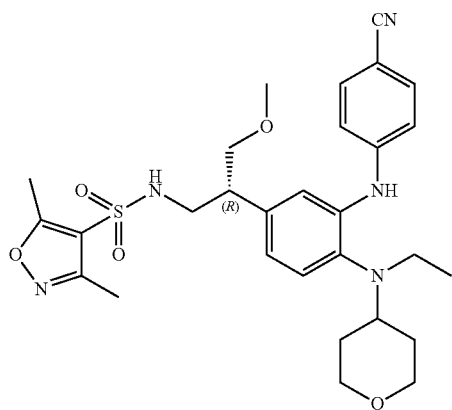

1340A. (R)-2-(Trimethylsilyl)ethyl (2-(3-((4-cyanophenyl)amino)-4-(ethyl(tetrahydro-2H-pyran-4-yl)amino)phenyl)-3-methoxypropyl)carbamate To a stirred solution of 3-(3-((4-cyanophenyl)amino)-4-(ethyl(tetrahydro-2H-pyran-4-yl)amino)phenyl)-4-methoxybutanoic acid (Example 349 Enantiomer 1) (500 mg, 1.143 mmol) in toluene (8 mL), diphenylphosphoryl azide (0.370 mL, 1.714 mmol) and TEA (0.271 mL, 1.943 mmol) were added followed by 2-(trimethylsilyl)ethanol (0.819. mL, 5.71 mmol) and the mixture was heated at 115° C. for 12 h. The reaction mixture quenched with water (1 mL), diluted with ethyl acetate (50 mL), washed with saturated brine solution (3×50 mL), dried over anhydrous sodium sulfate, filtered and then concentrated under reduced pressure to afford the crude, which was purified by flash silica gel column chromatography to afford 1340A (pale yellow oil, 800 mg, 1.447 mmol, 90%). LC-MS Anal. Calc'd. for $C_{30}H_{44}N_4O_4Si$, 552.3, found [M+H] 553.2, $T_r$=3.939 min (Method U).

1340B. (R)-4-((5-(1-Amino-3-methoxypropan-2-yl)-2-(ethyl(tetrahydro-2H-pyran-4-yl)amino)phenyl)amino)benzonitrile To a stirred solution of 1340A (400 mg, 0.724 mmol) in THF (5 mL), TBAF (2.171 mL, 2.171 mmol) was added and it was stirred at room temperature for 12 h. Then the reaction mixture was quenched with saturated ammonium chloride solution (50 mL), followed by water (100 mL) and extracted with ethyl acetate (3×100 mL). The organic layers were dried over sodium sulfate, filtered and concentrated under reduced pressure to afford the product (pale yellow oil, 290 mg, 0.710 mmol, 98%). LC-MS Anal. Calc'd. for $C_{24}H_{32}N_4O_2$, 408.3, found [M+H] 409.2, $T_r$=1.928 min (Method U).

Example 1340

(R)-N-(2-(3-((4-Cyanophenyl)amino)-4-(ethyl(tetrahydro-2H-pyran-4-yl)amino)phenyl)-3-methoxypropyl)-3,5-dimethylisoxazole-4-sulfonamide To a stirred solution of 1340B (40 mg, 0.098 mmol) in DCM (1 mL) and pyridine (1 mL) was added the 3,5-dimethylisoxazole sulfonyl chloride (57.5 mg, 0.294 mmol), and stirred at room temperature for 12 h. The reaction mixture was concentrated under reduced pressure to afford the residue, which was purified by preparative LCMS to afford Example 1340. (Pale yellow solid, 0.23 mg, 0.385 μmol, 0.393% yield). LC-MS Anal. Calc'd. for $C_{29}H_{37}N_5O_5S$, 567.252, found [M+H] 568.3, $T_r$=2.355 min (Method O). $^1$H NMR (400 MHz, CD$_3$OD) δ 7.56 (d, J=8.2 Hz, 2H), 7.19-7.24 (m, 4H), 6.84 (dd, J=2.00, 8.2 Hz, 1H), 3.88-3.91 (m, 2H), 3.54-3.56 (m, 2H), 3.33-3.39 (m, 3H), 3.18-3.25 (m, 2H), 3.01-3.09 (m, 6H), 2.58 (s, 3H), 2.25 (s, 3H), 1.73-1.75 (m, 2H), 1.55-1.58 (m, 2H), 0.93 (t, J=7.20 Hz, 3H).

Examples 1341 to 1344

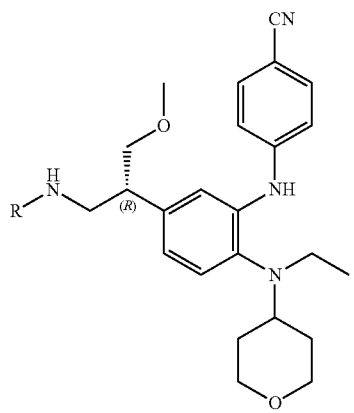

Examples 1341 to 1344 were prepared using 1340B and corresponding sulphonyl halides following the procedure described for the synthesis of Example 1340.

| Ex. No. | Name | R | $T_r$ (min) Method | $[M + H]^+$ |
|---|---|---|---|---|
| 1341 | (R)-N-(2-(3-((4-cyanophenyl)amino)-4-(ethyl(tetrahydro-2H-pyran-4-yl)amino)phenyl)-3-methoxypropyl) methanesulfonamide | | 2.048 O | 487.2 |
| 1342 | (R)-N-(2-(3-((4-cyanophenyl)amino)-4-(ethyl(tetrahydro-2H-pyran-4-yl)amino)phenyl)-3-methoxypropyl)-1,1,1-trifluoromethanesulfonamide | | 1.689 R | 541.2 |
| 1343 | N-((2-(3-((4-cyanophenyl)amino)-4-(ethyl(tetrahydro-2H-pyran-4-yl)amino)phenyl)-3-methoxypropyl) carbamoyl)benzenesulfonamide | | 1.868 O | 592.3 |
| 1344 | N-(2-(3-((4-cyanophenyl)amino)-4-(ethyl(tetrahydro-2H-pyran-4-yl)amino)phenyl)-3-methoxypropyl) cyclopropanesulfonamide | | 2.185 O | 513.2 |

Example 1345

Enantiomer 1

(S)-4-(3-((2-Ethoxypyrimidin-5-yl)amino)-4-(ethyl(tetrahydro-2H-pyran-4-yl)amino)phenyl)-2-methyl-hexan-2-ol

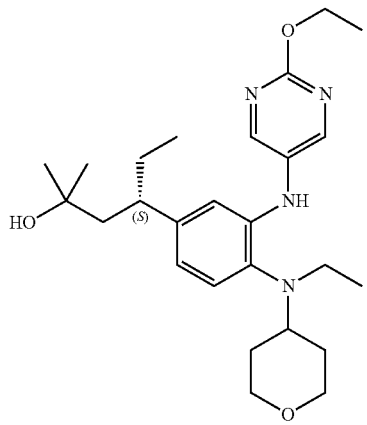

1345A. (S)-Methyl 3-(3-((tert-butoxycarbonyl) amino)-4-(ethyl(tetrahydro-2H-pyran-4-yl)amino) phenyl)pentanoate To a stirred solution of 455E (0.500 g, 1.495 mmol), in acetonitrile (15 mL), BOC$_2$O (0.382 mL, 1.644 mmol) was added at room temperature. Then the reaction mixture heated to 80° C., and stirred for 16 h. Then the reaction mixture was cooled to room temperature and concentrated under reduced pressure to get the crude, which was purified via silica gel flash chromatography to afford 1345A (light yellow liquid, 0.35 g, 0.805 mmol, 54% yield). LC-MS Anal. Calc'd. for $C_{24}H_{38}N_2O_5$, 434.3, found [M+H] 435.2. $T_r$=3.06 min (Method BB).

1345B. (S)-tert-Butyl(2-(ethyl(tetrahydro-2H-pyran-4-yl)amino)-5-(5-hydroxy-5-methylhexan-3-yl)phenyl)carbamate To a stirred solution of 1345A (0.300 g, 0.690 mmol) in THF (2.0 mL) was added methyl magnesium chloride (2.071 mL, 2.071 mmol) at 0° C. by dropwise over 5 min. Then the reaction mixture allowed to warm to room temperature, and stirred for 1 h. The reaction mixture was quenched with saturated aqueous NH$_4$Cl solution (5 mL) and extracted with ethyl acetate (2×10 mL). The combined organic layers were washed with brine (5 mL), dried over anhydrous sodium sulfate, filtered and concentrated under reduced pressure to afford 1345B (off-white semi-solid, 0.285 g, 0.656 mmol, 95% yield). LC-MS Anal. Calc'd. for $C_{25}H_{42}N_2O_4$, 434.3, found [M+H] 435.4, $T_r$=2.55 min (Method BB).

1345C. (S)-N1-Ethyl-4-(5-methyl-5-((trimethylsilyl)oxy)hexan-3-yl)-N1-(tetrahydro-2H-pyran-4-yl)benzene-1,2-diamine To a stirred solution of 1345B (0.200 g, 0.460 mmol) in dry DCM (3.0 mL), 2,6-lutidine (0.161 mL, 1.381 mmol), TMS-OTf (0.249 mL, 1.381 mmol) was added at 0° C. under nitrogen atmosphere. The reaction mixture was stirred at room temperature for 30 minutes. Then the reaction mixture was diluted with ethyl acetate (15 mL) and washed with saturated sodium bicarbonate solution (10 mL). The organic layer was separated and the aqueous layer was extracted with ethyl acetate (2×10 mL). The combined organic layers were dried over anhydrous Na$_2$SO$_4$, filtered and concentrated under reduced pressure to give the crude residue. The residue was purified via silica gel flash chromatography (ethyl acetate in pet ether as eluant) to afford 1345C (brown semi-solid, 0.085 g, 0.209 mmol, 45.4% yield). LC-MS Anal. Calc'd. for $C_{23}H_{42}N_2O_2Si$, 406.3, found [M+H] 407.4, $T_r$=3.26 min (Method BB).

1345D. (S)-N2-(2-Ethoxypyrimidin-5-yl)-N1-ethyl-4-(5-methyl-5-((trimethylsilyl)oxy)hexan-3-yl)-N1-(tetrahydro-2H-pyran-4-yl)benzene-1,2-diamine The mixture of 1345C (100 mg, 0.246 mmol), 5-bromo-2-ethoxypyrimidine (0.060 g, 0.295 mmol), cesium carbonate (0.120 g, 0.369 mmol) in dry dioxane (2.0 mL) was purged with argon for 15 minutes. Then 4,5-bis(diphenylphosphino)-9,9-dimethylxanthene (0.014 g, 0.025 mmol), bis(dibenzylideneacetone)palladium (7.07 mg, 0.012 mmol) was added, followed by purged with argon for 10 minutes. The reaction mixture was sealed and stirred on preheated oil bath at 110° C. for 3 h. The reaction mixture was cooled to room temperature and concentrated under reduced pressure to afford a residue. The residue was diluted with ethyl acetate (2×15 mL), washed with water (1×5 mL) and brine (5 mL). The combined organic layers were dried over Na$_2$SO$_4$, filtered and concentrated under reduced to give the crude residue. The residue was purified via silica gel flash chromatography (ethyl acetate in pet ether as eluant) to afford 1345D (brown semi-solid, 0.080 g, 0.151 mmol, 62% yield). LC-MS Anal. Calc'd. $C_{29}H_{48}N_4O_3Si$ for 528.4, found [M+H] 457.3 for parent desilylated product mass, $T_r$=0.99 min (Method BC).

Example 1345 Enantiomer 1. (S)-4-(3-((2-Ethoxypyrimidin-5-yl)amino)-4-(ethyl(tetrahydro-2H-pyran-4-yl)amino)phenyl)-2-methylhexan-2-ol To a stirred solution of 1345D (0.075 g, 0.142 mmol) in dry THF (1.0 mL), TBAF (0.425 mL, 0.425 mmol) was added at 0° C. under nitrogen atmosphere. Reaction was stirred at room temperature for 1 h. Then the reaction mixture was concentrated under reduced pressure to get the crude residue. The crude material was diluted with ethyl acetate (10 mL), washed with water (5 mL). The organic layer separated and the aqueous layer extracted with ethyl acetate (2×10 mL). The combined organic layers were dried over anhydrous Na$_2$SO$_4$, filtered and concentrated under reduced pressure to give the crude product. The crude material was purified via preparative LCMS to afford Example 1345 (off-white solid, 30.5 mg 0.065 mmol, 46.2%). LC-MS Anal. Calc'd. for $C_{26}H_{40}N_4O_3$, 456.3, found [M+H] 457.3, $T_r$=2.45 min (Method O). $^1$H NMR (400 MHz, DMSO-d$_6$) δ 8.40 (s, 2H), 7.29 (s, 1H), 7.10 (d, J=7.6 Hz, 1H), 6.79 (s, 1H), 6.67 (d, J=8.0 Hz, 1H), 4.32-4.26 (m, 2H), 3.90 (br s, 1H), 3.79-3.65 (m, 2H), 3.21-3.15 (m, 2H), 3.10-2.90 (m, 4H), 1.80-1.60 (m, 4H), 1.50-1.40 (m, 3H), 1.35-1.30 (m, 3H), 0.93-0.90 (m, 6H), 0.81 (t, J=7.20 Hz, 3H), 0.67 (t, J=7.20 Hz, 3H).

Example 1346

(R)-3-(3-((2-Ethoxypyrimidin-5-yl)amino)-4-(ethyl(tetrahydro-2H-pyran-4-yl)amino)phenyl)-N-(oxazol-2-yl)pentanamide

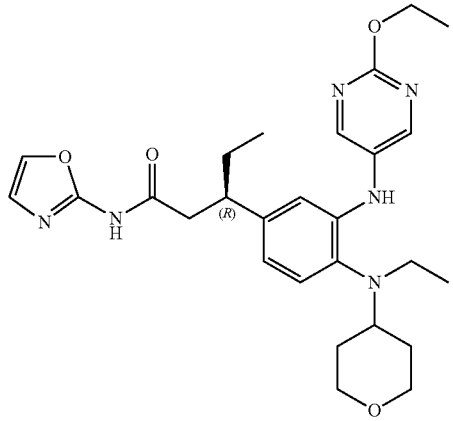

To a stirred solution of Example 498 (0.070 g, 0.158 mmol) in dry DMF (1.0 mL), was added the oxazol-2-amine (0.020 g, 0.237 mmol), HATU (0.090 g, 0.237 mmol) followed by TEA (0.066 mL, 0.475 mmol) at room temperature. Reaction mixture was heated to 80° C. and stirred for 20 h. Then the reaction mixture diluted with ethyl acetate (10 mL) and washed with water (5 mL). The organic layer was separated and the aqueous layer was extracted with ethyl acetate (2×10 mL). The combined organic layers were dried over anhydrous Na$_2$SO$_4$, filtered and evaporated under reduced pressure to give the crude residue. The crude material was purified via preparative LCMS to afford Example 1346 (off-white solid, 14.3 mg 0.026 mmol, 16.7%). LC-MS Anal. Calc'd. for C$_{27}$H$_{36}$N$_6$O$_4$, 508.3, found [M+H] 509.3, T$_r$=2.05 min (Method O). $^1$H NMR (400 MHz, DMSO-d$_6$) δ10.98 (s, 1H), 8.43 (s, 2H), 7.77 (d, J=8.0 Hz, 1H), 7.31 (s, 1H), 7.11 (d, J=8.0 Hz, 1H), 7.02 (m, 1H), 6.81 (s, 1H), 6.67-6.65 (m, 1H), 4.32-4.26 (m, 2H), 3.85-3.70 (m, 2H), 3.21-3.15 (m, 2H), 3.10-2.90 (m, 4H), 2.55-2.40 (m, 2H), 1.60-1.50 (m, 3H), 1.45-1.30 (m, 3H), 1.29-1.20 (m, 3H), 0.82 (t, J=7.20 Hz, 3H), 0.67 (t, J=7.20 Hz, 3H).

Example 1347

Mixture of diastereomers 4-(3-((2-Ethoxypyrimidin-5-yl)amino)-4-(4-phenylpiperidin-1-yl)phenyl)-1,1,1-trifluorohexan-2-ol

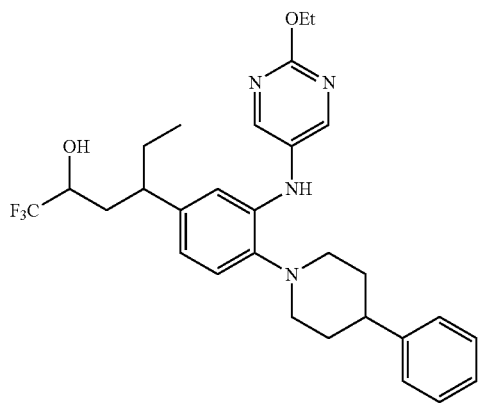 [SMILES: CCOc1ncc(Nc2cc(C(CC)CC(O)C(F)(F)F)ccc2N2CCC(c3ccccc3)CC2)cn1]

1347A.
1-(4-Bromo-2-nitrophenyl)-4-phenylpiperidine

In a round bottom flask containing 4-bromo-1-fluoro-2-nitrobenzene (3.0 g, 13.64 mmol), 4-phenylpiperidine (2.64 g, 16.36 mmol) in NMP (30 mL) was added DIPEA (7.15 mL, 40.9 mmol). The reaction mixture was heated at 135° C. for 2 h. The reaction mixture was cooled to room temperature and quenched with water (50 mL). The aqueous layer was extracted with ethyl acetate (3×50 mL). The combined organic layers were washed with brine (50 mL), dried over anhydrous sodium sulfate, filtered and concentrated under reduced pressure to get the crude material, which was purified via silica gel flash chromatography to afford 1347A (orange solid, 4.5 g, 12.46 mmol, 91% yield). LC-MS Anal. Calc'd. for C$_{17}$H$_{17}$BrN$_2$O$_2$, 360.1, found [M+H] 361.2, T$_r$=2.82 min (Method BB).

1347B. 1-(4-(5,5-Dimethyl-1,3,2-dioxaborinan-2-yl)-2-nitrophenyl)-4-phenylpiperidine To a stirred solution of 1347A (4.8 g, 13.29 mmol), bis(neopentyl glycolato)diboron (4.50 g, 19.93 mmol), potassium acetate (3.91 g, 39.9 mmol) in dry DMSO (50 mL) was purged with argon for 10 min. To this PdCl$_2$ (dppf).CH$_2$Cl$_2$ Adduct (0.543 g, 0.664 mmol) was added and purged with argon for another 5 min. Then the reaction mixture was heated at 80° C. for 3 h. The reaction mixture was cooled to room temperature and quenched with water (50 mL). The aqueous layer was extracted with ethyl acetate (3×50 mL). The combined organic layers were washed with brine (50 mL), dried over anhydrous sodium sulfate, filtered and concentrated under reduced pressure to get the crude material, which was purified via silica gel flash chromatography to afford 1347B (orange solid, 4.5 g, 11.41 mmol, 86% yield). LC-MS Anal. Calc'd. for C$_{22}$H$_{27}$BN$_2$O$_4$, 394.2, found [M+H] 327.2 for parent boronic acid, T$_r$=2.30 min. (Method BB).

1347C. Methyl 3-(3-nitro-4-(4-phenylpiperidin-1-yl)phenyl)pentanoate

In a sealable tube 1347B (3.0 g, 7.61 mmol), (E)-methyl pent-2-enoate (2.83 mL, 22.83 mmol), and 1M sodium hydroxide solution (6.85 mL, 6.85 mmol) in 1,4-dioxane (30.0 mL) was purged with argon for 10 min. Then chloro(1,5-cyclooctadiene)rhodium(I) dimer (0.044 g, 0.114 mmol) was added and purged with argon for another 10 min. Then the reaction mixture was heated at 50° C. for 2 h. Reaction mixture was cooled to room temperature and quenched with acetic acid (0.392 mL, 6.85 mmol) and it was stirred for another 5 minutes. Reaction mixture was partitioned between ethyl acetate (50 mL) and water (20 mL). The aqueous layer was extracted with ethyl acetate (2×25 mL). The combined organic layers were washed with brine, dried over anhydrous sodium sulfate, filtered and concentrated under reduced pressure to get the crude material, which was purified via silica gel flash chromatography to afford the Racemate 1347C (light yellow liquid, 4.0 g, 10.09 mmol, 100% yield). LC-MS Anal. Calc'd. for C$_{23}$H$_{28}$N$_2$O$_4$, 396.2, found [M+H] 397.2, T$_r$=3.23 min (Method BB).

1347D. Methyl 3-(3-amino-4-(4-phenylpiperidin-1-yl)phenyl)pentanoate

To a sealable hydrogen stirring flask, 1347C (4.0 g, 10.09 mmol), 10% Pd/C (0.400 g, 0.376 mmol) charged with dry ethyl acetate (60.0 mL) under flow of nitrogen. The resulting mixture was sequentially evacuated then purged with nitrogen for three times, before the flask was pressurized to 40 psi of hydrogen atmosphere and stirred at room temperature for 4 h. The reaction mixture was filtered through a pad of CELITE® which was then thoroughly rinsed with ethyl acetate (10 mL). The combined filtrates were concentrated under reduced pressure to afford orange semi-solid, purified via silica gel flash chromatography to afford Racemate 1347D (light yellow solid, 3.7 g, 4.6 mmol, 90% yield). LC-MS Anal. Calc'd. for C$_{23}$H$_{30}$N$_2$O$_2$, 366.2, found [M+H] 367.2, T$_r$=4.02 min (Method BB).

Chiral separation of 1347D racemate (Method CK) gave 1347D Enantiomer 1, T$_r$=5.65 min (Method CK) and 1347D Enantiomer 2, T$_r$=6.84 min (Method CK).

1347D Enantiomer 1: (light yellow solid, 1.0 g, 2.73 mmol, 54.1% yield). LC-MS Anal. Calc'd. for C$_{23}$H$_{30}$N$_2$O$_2$, 366.2, found [M+H] 367.4, T$_r$=2.75 min (Method BB).

1347D Enantiomer 2: (light yellow solid, 0.7 g, 1.91 mmol, 38% yield). LC-MS Anal. Calc'd. for C$_{23}$H$_{30}$N$_2$O$_2$, 366.2, found [M+H] 367.4, T$_r$=2.74 min (Method BB).

1347E. Methyl 3-(3-((tert-butoxycarbonyl)amino)-4-(4-phenylpiperidin-1-yl)phenyl)pentanoate To a stirred solution of 1347D Enantiomer 1 (1.0 g, 2.73 mmol), in acetonitrile (20 mL), BOC₂O (0.697 mL, 3.00 mmol) was added at room temperature. Reaction mixture was heated to 80° C. and stirred for 16 h. Then the reaction mixture was cooled to room temperature and concentrated under reduced pressure to get the crude material, which was purified via silica gel flash chromatography to afford 1347E (off-white solid, 1.05 g, 2.25 mmol, 82% yield). LC-MS Anal. Calc'd. for $C_{28}H_{38}N_2O_4$, 466.3, found [M+H] 467.2, $T_r$=3.64 min (Method BB).

1347F. tert-Butyl (5-(1-hydroxypentan-3-yl)-2-(4-phenylpiperidin-1-yl)phenyl)carbamate To a stirred solution 1347E (0.700 g, 1.500 mmol) in dry THF (3.0 mL), 1M lithium aluminium hydride (2.250 mL, 2.250 mmol) in THF solution was added at 0° C. and stirred at room temperature for 1 h. Then the reaction was quenched with ice cold water (5 mL), and diluted with ethyl acetate (10 mL). The organic layer was separated and the aqueous layer was extracted with ethyl acetate (2×10 mL). The combined organic layers were washed with brine, dried over anhydrous sodium sulfate, filtered and concentrated under reduced pressure to afford 1347F (off-white semi-solid, 0.625 g, 1.42 mmol, 95% yield). LC-MS Anal. Calc'd. for $C_{27}H_{38}N_2O_3$, 438.2, found [M+H] 439.2, $T_r$=4.29 min (Method U).

1347G. tert-Butyl (5-(1-oxopentan-3-yl)-2-(4-phenylpiperidin-1-yl)phenyl)carbamate To a stirred solution of 1347F (0.620 g, 1.414 mmol) in dry DCM (12.0 mL) Dess-Martin periodinane (0.899 g, 2.12 mmol) was added at 0° C. and stirred at room temperature for 1 h. Then the reaction mixtures was diluted with DCM (30 mL) and washed with saturated sodium per sulfate (10 mL) and saturated sodium bicarbonate (20 mL) solution. The organic layer was separated and the aqueous layer was extracted with DCM (2×30 mL). The combined organic layers were washed with brine, dried over anhydrous sodium sulfate, filtered and concentrated under reduced pressure to afford the crude material, which was purified via silica gel flash chromatography to afford 1347G (off-white solid, 0.455 g, 1.042 mmol, 73% yield)). LC-MS Anal. Calc'd. for $C_{27}H_{36}N_2O_3$ 436.3 found [M+H] 437.2, $T_r$=3.55 min (Method BB).

1347H. tert-Butyl (2-(4-phenylpiperidin-1-yl)-5-(6,6,6-trifluoro-5-hydroxyhexan-3-yl)phenyl)carbamate (Diastereomeric Mixture)

To a stirred solution of 1347G (0.300 g, 0.687 mmol) in dry THF (3.0 mL), tetrabutylammonium fluoride (0.069 mL, 0.069 mmol) was added and stirred for 5 minutes at room temperature. To this (trifluoromethyl)trimethylsilane (0.165 mL, 1.065 mmol) was added, and stirred for 2 h at room temperature. To this reaction mixture HCl (1.5N, 3 mL) was added and stirred for 1 h at room temperature. Then the solution was diluted with DCM (10 mL). The organic layer was separated and the aqueous layer was extracted with DCM (2×10 mL). The combined organic layers were washed with brine, dried over anhydrous sodium sulfate, filtered and concentrated under reduced pressure to afford the crude material, which was purified via silica gel flash chromatography to afford 1347H (0.285 g, 0.296 mmol, 82% yield). LC-MS Anal. Calc'd. for $C_{28}H_{37}F_3N_2O_3$ 506.3, found [M+H] 507.2, $T_r$=1.50 min (Method BA).

1347I. 4-(3-Amino-4-(4-phenylpiperidin-1-yl)phenyl)-1,1,1-trifluorohexan-2-ol (Diastereomeric Mixture)

To a stirred solution of 1347H (0.280 g, 0.553 mmol) in dry dioxane (1.5 mL), 4M HCl in dioxane (0.207 mL, 0.829 mmol) was added at 0° C., and stirred at room temperature for 3 h. The reaction mixture was added to the ice cold saturated sodium bicarbonate solution (10 mL). The aqueous layer was extracted with ethyl acetate (2×10 mL). The combined organic layers were washed with brine, dried over anhydrous sodium sulfate, filtered and concentrated under reduced pressure to afford the crude material, which was purified via silica gel flash chromatography to afford 1347I (0.165 g, 0.406 mmol, 74% yield) LC-MS Anal. Calc'd. for $C_{23}H_{29}F_3N_2O$, 406.2, found [M+H] 407.3, $T_r$=1.28 min (Method BA).

Example 1347 Diastereomer 1 and Diastereomer 2.

4-(3-((2-Ethoxypyrimidin-5-yl)amino)-4-(4-phenylpiperidin-1-yl)phenyl)-1,1,1-trifluorohexan-2-ol (Diastereomeric Mixture)

To a solution of 1347I (0.070 g, 0.172 mmol) in 1,4-dioxane (15 mL) were added 5-bromo-2-ethoxypyrimidine (0.042 g, 0.207 mmol), cesium carbonate (0.084 g, 0.258 mmol) in a sealed tube. Then argon was purged for 10 min, followed by the addition of 4,5-bis(diphenylphosphino)-9,9-dimethylxanthene (9.96 mg, 0.017 mmol), and bis(dibenzylideneacetone)palladium (4.95 mg, 8.61 µmol). Argon was again purged for another 5 min. The reaction mixture was heated to 110° C. for 3 h. The reaction mixture was allowed to cool to room temperature and concentrated under reduced pressure to afford brown colored residue. The residue was purified via silica gel flash chromatography by using ethyl acetate in pet ether (0-30%) as an eluent to afford Example 1347 Diastereomeric mixture (brown semi-solid, 70 mg, 3.40 mmol, 79% yield). LC-MS Anal. Calc'd. for $C_{29}H_{35}F_3N_4O_2$, 528.3, found [M+H] 529.4, $T_r$=4.32 min (Method N). ¹H NMR (400 MHz, DMSO-d₆) δ 8.24 (s, 2H), 7.44 (s, 1H), 7.30-7.28 (m, 2H), 7.26-7.16 (m, 3H), 7.02 (d, J=8.0 Hz, 1H), 6.80 (d, J=1.6 Hz, 1H), 6.74 (dd, J=8.0, 1.6 Hz, 1H), 6.09 (d, J=7.2 Hz, 1H), 4.30 (q, J=7.2 Hz, 2H), 3.20-3.16 (m, 2H), 2.68-2.55 (m, 5H), 1.74-1.68 (m, 4H), 1.59-1.54 (m, 4H), 1.33 (t, J=7.20 Hz, 3H), 0.75 (t, J=7.20 Hz, 3H).

Example 1348

Diastereomer 3 and Diastereomer 4

4-(3-((2-Ethoxypyrimidin-5-yl)amino)-4-(4-phenylpiperidin-1-yl)phenyl)-1,1,1-trifluorohexan-2-ol

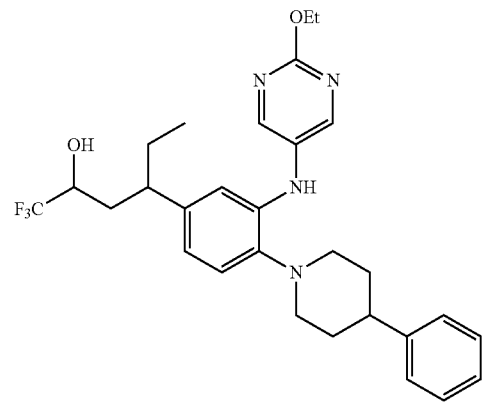 [SMILES: CCOc1ncc(Nc2cc(C(CC)CC(O)C(F)(F)F)ccc2N2CCC(c3ccccc3)CC2)cn1]

Example 1348 was prepared from 1347D Enantiomer 2 following the procedure described for the synthesis of Example 1347 diastereomeric mixture.

Example 1348 Diastereomer 3: (Off-white solid, 9.5 mg 0.018 mmol, 20.67% yield). LC-MS Anal. Calc'd. for $C_{29}H_{35}F_3N_4O_2$, 528.27, found [M+H] 529.3, $T_r$=2.98 min. (Method O). $^1$H NMR (400 MHz, DMSO-$d_6$) δ 8.23 (s, 2H), 7.42 (s, 1H), 7.30-7.28 (m, 2H), 7.27-7.16 (m, 3H), 7.02 (d, J=8.0 Hz, 1H), 6.80 (d, J=1.6 Hz, 1H), 6.74 (dd, J=8.0, 1.6 Hz, 1H), 6.09 (d, J=7.2 Hz, 1H), 4.30 (q, J=7.2 Hz, 2H), 3.20-3.17 (m, 2H), 2.68-2.55 (m, 5H), 1.74-1.62 (m, 4H), 1.58-1.53 (m, 4H), 1.33 (t, J=6.80 Hz, 3H), 0.72 (t, J=7.20 Hz, 3H).

Example 1348 Diastereomer 4: (Off-white solid, 3.5 mg 0.0063 mmol, 7.3% yield). LC-MS Anal. Calc'd. for $C_{29}H_{35}F_3N_4O_2$, 528.27, found [M+H] 529.3, $T_r$=3.01 min. (Method O). $^1$H NMR (400 MHz, DMSO-$d_6$) δ 8.25 (s, 2H), 7.41 (s, 1H), 7.30-7.28 (m, 2H), 7.27-7.17 (m, 3H), 7.04 (d, J=8.0 Hz, 1H), 6.80 (d, J=1.6 Hz, 1H), 6.74 (dd, J=8.0, 1.6 Hz, 1H), 6.10 (br. s, 1H), 4.29 (q, J=7.2 Hz, 2H), 3.21-3.18 (m, 2H), 2.68-2.55 (m, 4H), 1.82-1.79 (m, 4H), 1.74-1.45 (m, 4H), 1.32 (t, J=6.80 Hz, 3H), 0.72 (t, J=7.20 Hz, 3H).

Example 1349

Enantiomer 2

4-(3-((2-Ethoxypyrimidin-5-yl)amino)-4-(4-phenylpiperidin-1-yl)phenyl)-2-methylhexan-2-ol

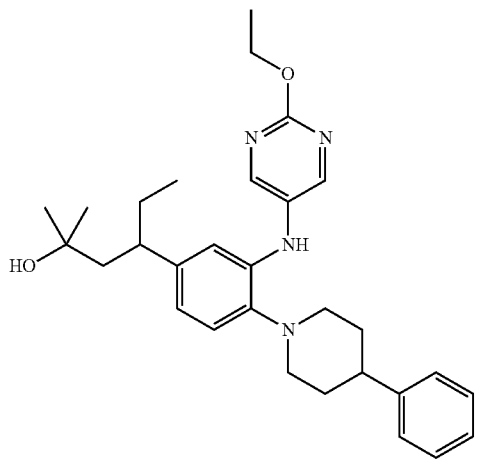 [SMILES: CCOc1ncc(Nc2cc(C(CC)CC(C)(C)O)ccc2N2CCC(c3ccccc3)CC2)cn1]

1349A. Methyl 3-(3-((tert-butoxycarbonyl)amino)-4-(4-phenylpiperidin-1-yl)phenyl)pentanoate To a stirred solution of 1347D Enantiomer 2 (0.7 g, 1.91 mmol), in acetonitrile (15 mL), BOC$_2$O (0.488 mL, 2.101 mmol) was added at room temperature. Reaction mixture was heated to 80° C. and stirred for 16 h. Then the reaction mixture was cooled to room temperature and concentrated under reduced pressure to get the crude material, which was purified via silica gel flash chromatography to afford 1349A (off-white solid, 0.75 g, 1.607 mmol, 84% yield). LC-MS Anal. Calc'd. for $C_{28}H_{38}N_2O_4$, 466.3, found [M+H] 467.2, $T_r$=3.64 min (Method BB).

1349B. tert-Butyl (5-(5-hydroxy-5-methylhexan-3-yl)-2-(4-phenylpiperidin-1-yl)phenyl)carbamate To a stirred solution of 1349A (0.150 g, 0.321 mmol) in dry THF (2.0 mL) was added methyl magnesium chloride (0.32 mL, 0.964 mmol) dropwise over 5 min at 0° C. Then the reaction mixture was stirred at room temperature for 1 h. Reaction mixture was quenched with saturated aqueous NH$_4$Cl solution (2.5 mL) and extracted with ethyl acetate (2×10 mL). The combined organic layers were washed with brine (5 mL), dried over anhydrous sodium sulfate, filtered and concentrated under reduced pressure to afford 1349B (off-white semi-solid, 0.130 g, 0.279 mmol, 87% yield). LC-MS Anal. Calc'd. for $C_{29}H_{42}N_2O_3$, 466.3, found [M+H] 467.2, $T_r$=2.09 min (Method N).

1349C. 5-(5-Methyl-5-((trimethylsilyl)oxy)hexan-3-yl)-2-(4-phenylpiperidin-1-yl)aniline To a stirred solution of 1349B (0.125 g, 0.268 mmol) in dry DCM (3.0 mL), 2, 6-lutidine (0.094 mL, 0.804 mmol), TMS-OTf (0.145 mL, 0.84 mmol) was added at 0° C. under nitrogen atmosphere. Reaction mixture was stirred at room temperature for 30 minutes. Then the reaction mixture was diluted with ethyl acetate (15 mL) and washed with saturated sodium bicarbonate solution (10 mL). The organic layer was separated and the aqueous layer was extracted with ethyl acetate (2×10 mL). The combined organic layers were dried over anhydrous Na$_2$SO$_4$, filtered and concentrated under reduced pressure to give the crude residue, which was purified via silica gel flash chromatography (ethyl acetate in pet ether as eluent) to afford 1349C (brown semi-solid, 0.090 g, 0.205 mmol, 77% yield). LC-MS Anal. Calc'd. $C_{27}H_{42}N_2OSi$ for 438.3 found [M+H] 439.4, $T_r$=3.67 min (Method BB).

1349D. 2-Ethoxy-N-(5-(5-methyl-5-((trimethylsilyl)oxy)hexan-3-yl)-2-(4-phenylpiperidin-1-yl)phenyl)pyrimidin-5-amine The mixture of 1349C (0.090 g, 0.205 mmol), 5-bromo-2-ethoxypyrimidine (0.050 g, 0.246 mmol), cesium carbonate (0.100 g, 0.308 mmol) in dry dioxane (2.0 mL) was purged with argon for 15 minutes, then 4,5-bis(diphenylphosphino)-9,9-dimethylxanthene (0.012 g, 0.021 mmol), bis(dibenzylideneacetone)palladium (5.90 mg, 0.0102 mmol) was added and purged with argon for another 10 minutes. The reaction mixture was sealed and stirred on preheated oil bath at 110° C. for 3 h. The reaction mixture was cooled to room temperature and concentrated under reduced pressure to afford a residue. The residue was diluted with ethyl acetate (15 mL), washed with water (1×5 mL) and brine (5 mL). The combined organic layers were dried over anhydrous sodium sulfate, filtered and concentrated under reduced to get the crude residue, which was purified via silica gel flash chromatography (ethyl acetate in pet ether as eluent) to afford 1349D (brown semi-solid, 0.075 g, 0.134 mmol, 65% yield). LC-MS Anal. Calc'd. $C_{33}H_{48}N_4O_2Si$ for 560.4, found [M+H] 561.2, $T_r$=4.26 min (Method BB).

Example 1349 4-(3-((2-Ethoxypyrimidin-5-yl)amino)-4-(4-phenylpiperidin-1-yl)phenyl)-2-methylhexan-2-ol To a stirred solution of 1349D (0.070 g, 0.125 mmol) in dry THF (1.0 mL), TBAF (0.374 mL, 0.374 mmol) was added at 0° C. under nitrogen atmosphere. Reaction mixture was stirred at room temperature for 1 h. Then the reaction mixture was concentrated under reduced pressure to get the crude residue. The residue was diluted with ethyl acetate (10 mL), washed with water (5 mL). The organic layer was separated and the aqueous layer was extracted with ethyl acetate (2×10 mL). The combined organic layers were dried over anhydrous $Na_2SO_4$, filtered and concentrated under reduced pressure to give the crude product, which was purified via preparative LCMS to afford Example 1349 (off-white solid, 30.0 mg 0.060 mmol, 48.2%). LC-MS Anal. Calc'd. for $C_{30}H_{40}N_4O_2$, 488.3, found [M+H] 489.3, $T_r$=2.94 min. (Method O). $^1$H NMR (400 MHz, DMSO-$d_6$) δ 8.22 (s, 2H), 7.39 (s, 1H), 7.29-7.27 (m, 2H), 7.19-7.16 (m, 3H), 6.97 (d, J=8.0 Hz, 1H), 6.80-6.70 (s, 2H), 4.32-4.26 (m, 2H), 3.17-3.15 (m, 2H), 2.60-2.55 (m, 2H), 2.50-2.40 (m, 3H), 1.75-1.50 (m, 7H), 1.45-1.31 (m, 4H), 0.96 (m, 6H), 0.69 (t, J=7.20 Hz, 3H).

Example 1350

Enantiomer 1 and Enantiomer 2

3-(3-((4-Cyanophenyl)amino)-4-(4-phenylpiperidin-1-yl)phenyl)-4-methoxybutanoic acid

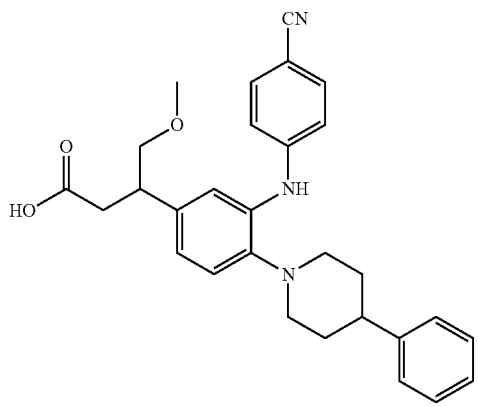 [SMILES: COCC(CC(=O)O)c1ccc(N2CCC(c3ccccc3)CC2)c(Nc2ccc(C#N)cc2)c1]

1350A. Ethyl 4-methoxy-3-(3-nitro-4-(4-phenylpiperidin-1-yl)phenyl)butanoate 1350A was prepared using 1347B and 256D following the procedure described for the synthesis of 33D. LC-MS Anal. Calc'd. for $C_{24}H_{30}N_2O_5$, 426.2, found [M+H] 427.2, $T_r$=2.73 min. (Method BB).

1350B. Ethyl 3-(3-amino-4-(4-phenylpiperidin-1-yl)phenyl)-4-methoxybutanoate 1350B was prepared using 1350A following the procedure described for the synthesis of 33E. LC-MS Anal. Calc'd. for $C_{24}H_{32}N_2O_3$, 396.2, found [M+H] 397.1, $T_r$=1.66 min. (Method AY).

Chiral separation of 1350B racemate (Method CL) gave 1350B Enantiomer 1 and 1350B Enantiomer 2 as single enantiomers. Enantiomer 1, $T_r$=5.1 min (Method CL) and Enantiomer 2, $T_r$=6.01 min (Method CL).

1350B Enantiomer 1: $C_{24}H_{32}N_2O_3$, 396.2, found [M+H] 397.4, $T_r$=2.65 min. (Method BB).

1350B Enantiomer 2: $C_{24}H_{32}N_2O_3$, 396.2, found [M+H] 397.4, $T_r$=3.91 min. (Method BB).

1350C. Ethyl 3-(3-((4-cyanophenyl)amino)-4-(4-phenylpiperidin-1-yl)phenyl)-4-methoxybutanoate 1350C was prepared using 1350B Enantiomer 1 and 4-bromobenzonitrile following the procedure described for the synthesis of 33F. LC-MS Anal. Calc'd. for $C_{31}H_{35}N_3O_3$, 497.2, found [M+H] 498.2, $T_r$=4.28 min (Method U).

Example 1350 Enantiomer 1. 3-(3-((4-Cyanophenyl)amino)-4-(4-phenylpiperidin-1-yl)phenyl)-4-methoxybutanoic acid Example 1350 Enantiomer 1 was prepared using 1350C following the procedure described for the synthesis of Example 41 Enantiomer 1. LC-MS Anal. Calc'd. for $C_{29}H_{31}N_3O_3$, 469.2, found [M+H] 470.2, $T_r$=2.07 min (Method O). $^1$H NMR (400 MHz, DMSO-$d_6$) δ 8.12 (s, 1H), 7.53-7.55 (m, 2H), 7.30 (m, 2H), 7.27 (m, 3H), 7.11 (s, 1H), 6.97-7.05 (m, 4H), 3.89 (s, 2H), 3.16-3.25 (m, 7H), 2.62-2.68 (m, 4H), 1.62-1.72 (m 4H).

Example 1350 Enantiomer 2. 3-(3-((4-Cyanophenyl)amino)-4-(4-phenylpiperidin-1-yl)phenyl)-4-methoxybutanoic acid Example 1350 Enantiomer 2 was prepared using 1350B Enantiomer 2 and 4-bromobenzonitrile following the procedure described for the synthesis of Example 1350 Enantiomer 1. LC-MS Anal. Calc'd. for $C_{29}H_{31}N_3O_3$, 469.2, found [M+H] 470.2, $T_r$=2.07 min (Method O). $^1$H NMR (400 MHz, DMSO-$d_6$) δ 8.13 (s, 1H), 7.53-7.55 (m, 2H), 7.30 (m, 2H), 7.28 (m, 3H), 7.11 (s, 2H), 6.98-7.06 (m, 3H), 3.89 (s, 2H), 3.16-3.22 (m, 7H), 2.62-2.68 (m, 4H), 1.63-1.69 (m, 4H).

Examples 1351 to 1353

Enantiomer 1

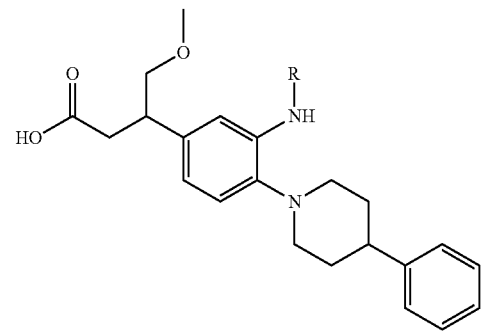

Examples 1351 to 1353 were prepared using 1350B Enantiomer 1 and corresponding aryl halides following the procedure described for the synthesis of Example 1350 Enantiomer 1.

| Ex. No. | Name | R | T$_r$ (min) (Method O) | [M + H]$^+$ |
|---|---|---|---|---|
| 1351 | 3-(3-((2-ethoxypyrimidin-5-yl)amino)-4-(4-phenylpiperidin-1-yl)phenyl)-4-methoxybutanoic acid | | 1.939 | 491.3 |
| 1352 | 3-(3-((4-chlorophenyl)amino)-4-(4-phenylpiperidin-1-yl)phenyl)-4-methoxybutanoic acid | | 2.46 | 479.2 |
| 1353 | 4-methoxy-3-(3-((2-methoxypyrimidin-5-yl)amino)-4-(4-phenylpiperidin-1-yl)phenyl) butanoic acid | | 1.82 | 477.2 |
| 1354 | 3-(3-((2-ethoxypyrimidin-5-yl)amino)-4-(4-phenylpiperidin-1-yl)phenyl)-4-methoxybutanoic acid | | 1.946 | 491.2 |
| 1355 | 3-(3-((4-chlorophenyl)amino)-4-(4-phenylpiperidin-1-yl)phenyl)-4-methoxybutanoic acid | | 2.45 | 479.2 |
| 1356 | 4-methoxy-3-(3-((2-methoxypyrimidin-5-yl)amino)-4-(4-phenylpiperidin-1-yl)phenyl)butanoic acid | | 1.842 | 477.2 |

Examples 1354 to 1356

Enantiomer 2

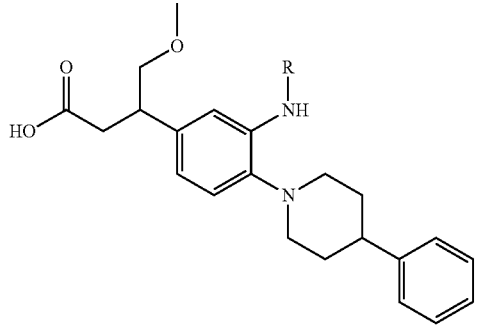

EXAMPLES 1354 to 1356 were prepared using 1350B Enantiomer 2 and corresponding aryl halides following the procedure described for the synthesis of Example 1350 Enantiomer 1.

Example 1357

Enantiomer 1 and Enantiomer 2

3-(3-(3-(4-Chloro-2-fluorophenyl)ureido)-4-(4-phenylpiperidin-1-yl)phenyl)-4-methoxybutanoic acid

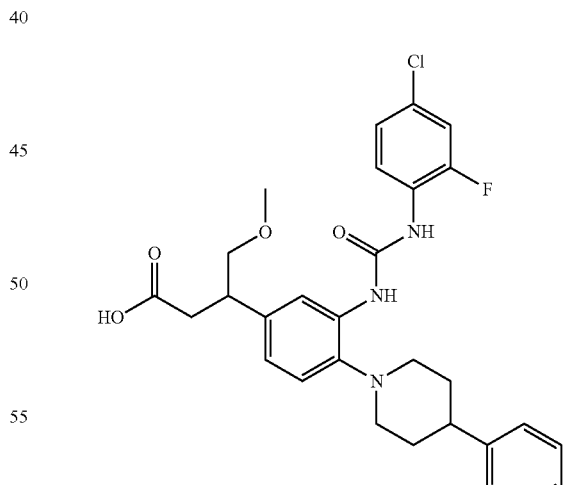

1357A. Ethyl 3-(3-(3-(4-chloro-2-fluorophenyl)ureido)-4-(4-phenylpiperidin-1-yl)phenyl)-4-methoxybutanoate 1357A was prepared using 1350B Enantiomer 1 and 4-chloro-2-fluoro-1-isocyanatobenzene following the procedure described for the synthesis of 18A. LC-MS Anal. Calc'd. for $C_{31}H_{35}ClFN_3O_4$, 567.2, found [M+H] 568.2, $T_r$=1.80 min (Method AY).

Example 1357 Enantiomer 1. 3-(3-(3-(4-Chloro-2-fluorophenyl)ureido)-4-(4-phenylpiperidin-1-yl)phenyl)-4-methoxybutanoic acid Example 1357 Enantiomer 1 was prepared using 1357A following the procedure described for the synthesis of Example 41 Enantiomer 1. LC-MS Anal. Calc'd. for $C_{29}H_{31}ClFN_3O_4$, 539.2, found [M+H] 540.2, $T_r$=2.16 min (Method O). $^1$H NMR (400 MHz, DMSO-$d_6$) δ 9.49 (s, 1H), 8.46 (s, 1H), 8.13-8.17 (m, 1H), 7.89 (m, 1H), 7.47 (m, 1H), 7.31-7.36 (m, 4H), 7.19-7.23 (m, 2H), 7.11 (m, 1H), 6.90 (m, 1H), 3.89 (s, 2H), 3.39-3.42 (m, 2H), 3.22 (s, 3H), 3.07 (m, 2H), 2.62-2.74 (m, 4H), 2.01-2.04 (m, 2H), 1.85 (m, 2H).

Example 1357 Enantiomer 2. 3-(3-(3-(4-Chloro-2-fluorophenyl)ureido)-4-(4-phenylpiperidin-1-yl)phenyl)-4-methoxybutanoic acid Example 1357 Enantiomer 2 was prepared using 1350B Enantiomer 2 and 4-chloro-2-fluoro-1-isocyanatobenzene following the procedure described for the synthesis of Example 1357 Enantiomer 1. LC-MS Anal. Calc'd. for $C_{29}H_{31}ClFN_3O_4$, 539.2, found [M+H] 540.2, $T_r$=2.15 min. (Method O). $^1$H NMR (400 MHz, DMSO-$d_6$) δ 9.49 (s, 1H), 8.46 (s, 1H), 8.12-8.17 (m, 1H), 7.89 (m, 1H), 7.46 (m, 1H), 7.31-7.34 (m, 4H), 7.21-7.23 (m, 2H), 7.11 (m, 1H), 6.90 (m, 1H), 3.89 (s, 2H), 3.37-3.42 (m, 2H), 3.22 (m, 3H), 3.06 (m, 2H), 2.62-2.77 (m, 4H), 2.01-2.06 (m, 2H), 1.85-1.87 (m, 2H).

Example 1358

Enantiomer-1

(S)-3-(4-(2H-Benzo[b][1,4]oxazin-4(3H)-yl)-3-((4-cyanophenyl)amino)phenyl)-4-methoxybutanoic acid

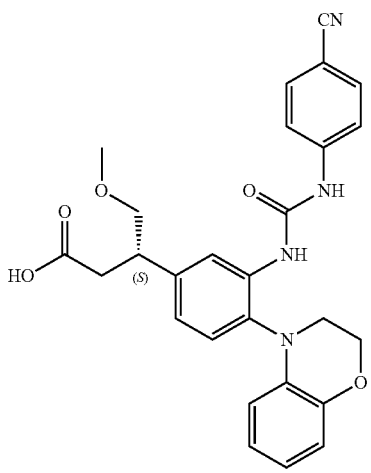

1358A. 4-(4-Bromo-2-nitrophenyl)-3,4-dihydro-2H-benzo[b][1,4]oxazine

To a stirred solution of 3,4-dihydro-2H-benzo[b][1,4]oxazine (1.6 g, 11.84 mmol) in THF (2 mL) was added potassium tert-butoxide (2.66 g, 23.68 mmol) at 0° C. and stirred at room temperature for 30 minutes. Then added 4-bromo-1-fluoro-2-nitrobenzene (2.60 g, 11.84 mmol) in THF (1 mL) and stirred at 0° C. for 1 h. Reaction mixture was quenched with ice water (10 mL) and extracted with ethyl acetate (2×25 mL). The combined organic layers were dried over sodium sulfate and concentrated under reduced pressure to get the crude, purified by silica gel flash chromatography to afford 1358A (brown gummy, 0.95 g, 2.154 mmol, 18.20% yield). LC-MS Anal. Calc'd. for $C_{14}H_{11}BrN_2O_3$, 334.00, found [M+H] 335.2, $T_r$=2.43 min (Method BB).

1358B. 4-(4-(5,5-Dimethyl-1,3,2-dioxaborinan-2-yl)-2-nitrophenyl)-3,4-dihydro-2H-benzo[b][1,4]oxazine 1358B was prepared using 1358A following the procedure described for the synthesis of 74D. LC-MS Anal. Calc'd. for $C_{19}H_{21}BN_2O_5$, 365.2, found [M+H] 301.2 (parent boronic acid), $T_r$=2.17 min (Method BB).

1358C. (S)-Methyl 3-(4-(2H-benzo[b][1,4]oxazin-4(3H)-yl)-3-nitrophenyl)-4-methoxybutanoate 1358C was prepared using 1358B and (R)-(+)-2,2'-bis(diphenylphosphino)-1,1'-binaphthyl following the procedure described for the synthesis of 74E. LC-MS Anal. Calc'd. for $C_{20}H_{22}N_2O_6$, 386.2, found [M+H] 387.2, $T_r$=3.01 min (Method U).

1358D. (S)-Methyl 3-(3-amino-4-(2H-benzo[b][1,4]oxazin-4(3H)-yl)phenyl)-4-methoxybutanoate 1358D enantiomeric mixture was prepared from 1358C following the procedure described for the synthesis of 74F. LC-MS Anal. Calc'd. for $C_{20}H_{24}N_2O_4$, 356.2, found [M+H] 357.2, $T_r$=2.1 min (Method BB).

Chiral separation of 1358D enantiomeric mixture (97:2) yielded 1358D Enantiomer 1 $T_r$=4.13 min, 1358D Enantiomer 2 $T_r$=7.34 min (Method DW).

1358D Enantiomer 1: LC-MS Anal. Calc'd. for $C_{20}H_{24}N_2O_4$, 356.17, found [M+H] 357.2, $T_r$=2.11 min (Method BB).

Example 1358 (S)-3-(4-(2H-Benzo[b][1,4]oxazin-4(3H)-yl)-3-((4-cyanophenyl)amino)phenyl)-4-methoxybutanoic acid Example 1358 was prepared using 1358D Enantiomer 1 and 4-bromobenzonitrile following the procedure described for the synthesis of Example 843. LC-MS Anal. Calc'd. for $C_{26}H_{25}N_3O_4$, 443.2, found [M+H] 444.18, $T_r$=1.596 min (Method O). $^1$H NMR (400 MHz, DMSO-$d_6$): δ 8.31 (s, 1H), 7.50 (d, J=8.00 Hz, 2H), 7.22-7.27 (m, 2H), 6.99-7.05 (m, 3H), 6.73-6.74 (m, 1H), 6.58-6.61 (m, 2H), 6.31-6.33 (m, 1H), 4.19-4.21 (m, 2H), 3.45-3.55 (m, 4H), 3.25-3.30 (m, 4H), 2.66-2.71 (m, 1H), 2.51-2.54 (m, 1H).

Example 1359

Enantiomer-2

(R)-3-(4-(2H-Benzo[b][1,4]oxazin-4(3H)-yl)-3-((4-cyanophenyl)amino)phenyl)-4-methoxybutanoic acid

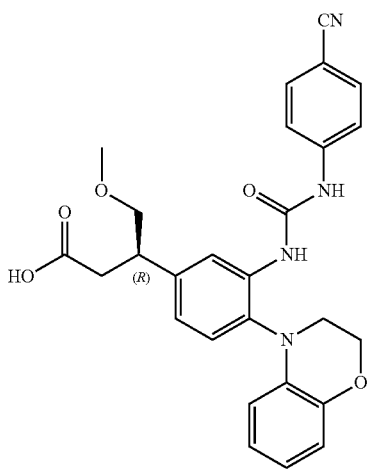

1359A. (R)-Methyl 3-(4-(2H-benzo[b][1,4]oxazin-4(3H)-yl)-3-nitrophenyl)-4-methoxybutanoate 1359A was prepared using 1358B and (S)-(−)-2,2'-bis(diphenylphosphino)-1,1'-binaphthyl following the procedure described for the synthesis of 74E. LC-MS Anal. Calc'd. for $C_{20}H_{22}N_2O_6$, 386.2, found [M+H] 387.2, $T_r$=2.16 min (Method BB).

1359B. (R)-Methyl 3-(3-amino-4-(2H-benzo[b][1,4]oxazin-4(3H)-yl)phenyl)-4-methoxybutanoate 1359B enantiomeric mixture was prepared using 1359A following the procedure described for the synthesis of 74F. LC-MS Anal. Calc'd. for $C_{20}H_{24}N_2O_4$, 356.2, found [M+H] 357.2, $T_r$=2.12 min (Method BB).

Chiral separation of 1359B enantiomeric mixture (4:95) yielded 1359B Enantiomer 1 $T_r$=4.13 Min, 1359B Enantiomer 2 $T_r$=7.34 min (Method DW).

1359B Enantiomer 2: LC-MS Anal. Calc'd. for $C_{20}H_{24}N_2O_4$, 356.2, found [M+H] 357.2, $T_r$=2.11 min (Method BB).

Example 1359 (R)-3-(4-(2H-Benzo[b][1,4]oxazin-4(3H)-yl)-3-((4-cyanophenyl)amino)phenyl)-4-methoxybutanoic acid Example 1359 was prepared using 1359B Enantiomer 2 and 4-bromobenzonitrile following the procedure described for the synthesis of Example 843. LC-MS Anal. Calc'd. for $C_{26}H_{25}N_3O_4$, 443.2, found [M+H] 444.18, $T_r$=1.594 min (Method O). $^1$H NMR (400 MHz, DMSO-$d_6$) δ 8.31 (s, 1H), 7.50 (d, J=8.80 Hz, 2H), 7.05-7.27 (m, 2H), 6.99-7.03 (m, 3H), 6.72-6.75 (m, 1H), 6.58-6.61 (m, 2H), 6.31-6.33 (m, 1H), 4.19-4.21 (m, 2H), 3.44-3.50 (m, 4H), 3.25-3.30 (m, 4H), 2.65-2.71 (m, 1H) (Note: 1H is buried under the solvent peak)

Example 1360

(S)-3-(3-((2-Ethoxypyrimidin-5-yl)amino)-4-(3-(4-fluorophenyl)-8-azabicyclo[3.2.1]octan-8-yl)phenyl)pentanoic acid (Endo Isomer)

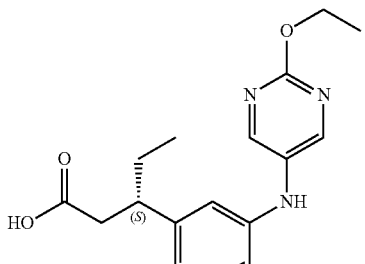

1360A. tert-Butyl 3-(((trifluoromethyl)sulfonyl)oxy)-8-azabicyclo[3.2.1]oct-3-ene-8-carboxylate To a stirred solution of tert-butyl 3-oxo-8-azabicyclo[3.2.1]octane-8-carboxylate (1.0 g, 4.44 mmol) in tetrahydrofuran (10 mL) at −78° C. was added LDA (3.33 mL, 6.66 mmol) and stirred at that temperature for 30 min. Then N,N-bis(trifluoromethylsulfonyl)aniline (1.586 g, 4.44 mmol) in tetrahydrofuran (5 mL) was added and stirred for 1 h. The reaction mixture was warmed to room temperature and stirred for 2 h. Reaction mixture was quenched with saturated ammonium chloride solution (10 mL) and extracted with ethyl acetate (2×100 mL). The organic layer was washed with brine solution (50 mL), dried over sodium sulfate, filtered and concentrated under reduced pressure to get the crude, which was purified by silica gel flash chromatography to afford 1360A (brown oil, 1 g, 2.80 mmol, 63.0% yield). LC-MS Anal. Calc'd. for $C_{13}H_{18}F_3NO_5S$, 357.1, found [M+H] 358.08, $T_r$=2.41 min (Method BB).

1360B. tert-Butyl 3-(4-fluorophenyl)-8-azabicyclo[3.2.1]oct-2-ene-8-carboxylate To a stirred solution of 1360A (1.6 g, 4.48 mmol) in dimethoxyethane (0.5 mL) and water (0.5 mL) was added 4-fluorophenylboronic acid (0.522 g, 3.73 mmol), sodium carbonate (0.593 g, 5.60 mmol) and tetrakis(triphenylphosphine)palladium(0) (0.431 g, 0.373 mmol) at room temperature. The reaction mixture was purged with $N_2$ for 15 min and stirred at 100° C. for 4 h. Reaction mixture was diluted with water (100 mL) and extracted with ethyl acetate (2×50 mL), dried over sodium sulfate, filtered and concentrated under reduced pressure to get crude, which was purified by silica gel flash chromatography to afford 1360B (colorless liquid, 1.0 g, 3.19 mmol, 85% yield). LC-MS Anal. Calc'd. for $C_{18}H_{22}FNO_2$, 303.2, found [M+H] 248 for parent carbamic acid, $T_r$=3.44 min (Method BB).

1360C. 3-(4-Fluorophenyl)-8-azabicyclo[3.2.1]oct-2-ene.HCl

To a stirred solution of 1360B (1 g, 3.30 mmol) in dioxane (2 mL) was added 4M HCl in dioxane (4 mL, 16.00 mmol)

and stirred at room temperature for 16 h. Reaction mixture was concentrated under reduced pressure to get the crude, which was triturated with ethyl acetate (5 mL) to afford 1360C (white solid, 0.58 g, 2.395 mmol, 72.7% yield). LC-MS Anal. Calc'd. for $C_{13}H_{14}FN$, 203.1, found [M+H] 204.1, $T_r$=1.12 min (Method BB).

1360D. 3-(4-Fluorophenyl)-8-azabicyclo[3.2.1]octane.HCl

To a stirred solution of 1360B (480 mg, 2.002 mmol) in MeOH (15 mL) was added Pd/C (150 mg, 0.070 mmol) and stirred under 15 psi pressure of hydrogen at room temperature for 16 h. Reaction mixture was diluted with ethyl acetate (10 mL) and filtered through CELITE® bed, the CELITE® bed was washed with ethyl acetate (10 mL). The combined filtrate was concentrated under reduced pressure to afford 1360D (white solid, 350 mg, 1.404 mmol, 70.1% yield). LC-MS Anal. Calc'd. for $C_{13}H_{16}FN$, 205.1, found [M+H] 206.1, $T_r$=1.11 min (Method BB). $^1$H 2D NOESY confirms the 1360D as endo isomer.

1360E. 8-(4-Bromo-2-nitrophenyl)-3-(4-fluorophenyl)-8-azabicyclo[3.2.1]octane 1360E was prepared using 1360D and 4-bromo-1-fluoro-2-nitrobenzene following the procedure described for the synthesis of 843B. LC-MS Anal. Calc'd. for $C_{19}H_{18}BrFN_2O_2$, 404.1, found [M+H] 405.05, $T_r$=2.93 min (Method U).

1360F. 8-(4-(5,5-Dimethyl-1,3,2-dioxaborinan-2-yl)-2-nitrophenyl)-3-(4-fluorophenyl)-8-azabicyclo[3.2.1]octane 1360F was prepared using 1360E following the procedure described for the synthesis of 843C. LC-MS Anal. Calc'd. for $C_{24}H_{28}BFN_2O_4$, 438.2, found [M+H] 371.3 for parent boronic acid, $T_r$=2.43 min (Method BB).

1360G. (S)-Methyl 3-(4-(3-(4-fluorophenyl)-8-azabicyclo[3.2.1]octan-8-yl)-3-nitrophenyl)pentanoate 1360G was prepared using 1360F, (E)-methyl pent-2-enoate and (R)-(+)-2,2'-bis(diphenylphosphino)-1,1'-binaphthyl following the procedure described for the synthesis of 843E. LC-MS Anal. Calc'd. for $C_{25}H_{29}FN_2O_4$, 440.2, found [M+H] 441.2, $T_r$=3.33 min (Method BB).

1360H. (S)-Methyl 3-(3-amino-4-(3-(4-fluorophenyl)-8-azabicyclo[3.2.1]octan-8-yl)phenyl)pentanoate 1360H was prepared using 1360G following the procedure described for the synthesis of 843F. LC-MS Anal. Calc'd. for $C_{25}H_{31}FN_2O_2$, 410.23, found [M+H] 411.23, $T_r$=2.85 min (Method BB).

Chiral separation of 1360H enantiomeric mixture (95:5) yielded 1360H Enantiomer 1 $T_r$=2.77 Min, 1360H Enantiomer 2 $T_r$=3.08 min (Method DZ).

1360H Enantiomer 1: LC-MS Anal. Calc'd. for $C_{25}H_{31}FN_2O_2$, 410.2, found [M+H] 411.2, $T_r$=4.07 min (Method U).

1360I. (S)-Methyl 3-(3-((2-ethoxypyrimidin-5-yl)amino)-4-(3-(4-fluorophenyl)-8-azabicyclo[3.2.1]octan-8-yl)phenyl)pentanoate 1360I was prepared using 1360H Enantiomer 1 and 5-bromo-2-ethoxypyrimidine following the procedure described for the synthesis of 843G. LC-MS Anal. Calc'd. for $C_{31}H_{37}FN_4O_3$, 532.28, found [M+H] 533.28, $T_r$=1.31 min (Method BB).

Example 1360 (S)-3-(3-((2-Ethoxypyrimidin-5-yl)amino)-4-(3-(4-fluorophenyl)-8-azabicyclo[3.2.1]octan-8-yl)phenyl)pentanoic acid (Endo Isomer)

Example 1360 was prepared using 1360I following the procedure described for the synthesis of Example 843. LC-MS Anal. Calc'd. for $C_{30}H_{35}FN_4O_3$, 518.3, found [M+H] 519.3, $T_r$=2.34 min (Method O). $^1$H NMR (400 MHz, DMSO-$d_6$) δ 8.12 (s, 2H), 7.29-7.31 (m, 1H), 7.15-7.19 (m, 2H), 7.03-7.08 (m, 2H), 6.83-6.85 (m, 2H), 6.74-6.77 (m, 1H), 4.26 (q, J=7.20 Hz, 2H), 3.90-3.99 (m, 2H), 2.50-2.59 (m, 1H), 2.62-2.68 (m, 1H), 2.72-2.78 (m, 1H), 2.60-2.68 (m, 1H), 2.38-2.42 (m, 1H), 2.22-2.25 (m, 1H), 1.81-1.83 (m, 2H), 1.52-1.60 (m, 3H), 1.37-1.46 (m, 3H), 1.30 (t, J=7.20 Hz, 3H), 0.71 (t, J=7.60 Hz, 3H).

Example 1361

Enantiomer 1

(S)-3-(4-(Ethyl(tetrahydro-2H-pyran-4-yl)amino)-3-((2-methylpyrimidin-5-yl)amino)phenyl)pentanoic acid

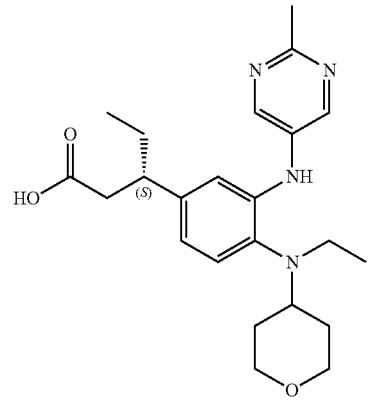

Example 1361 was prepared using 455E and 5-bromo-2-methylpyrimidine following the procedure described for the synthesis of Example 84. LC-MS Anal. Calc'd. for $C_{23}H_{32}N_4O_3$, 412.2, found [M+H] 413.3, $T_r$=1.430 min (Method O). $^1$H NMR (400 MHz, DMSO-$d_6$): δ 8.51 (s, 2H), 7.51 (s, 1H), 7.14 (d, J=8.00 Hz, 1H), 7.01 (d, J=1.60 Hz, 1H), 6.76 (dd, J=1.60, 8.00 Hz, 1H), 3.78-3.81 (m, 2H), 3.17-3.21 (m, 5H), 2.95-3.02 (m, 3H), 2.80-2.83 (m, 1H), 2.39-2.50 (m, 1H), 1.40-1.52 (m, 3H), 1.59-1.65 (m, 3H), 0.81 (t, J=7.20 Hz, 3H), 0.72 (t, J=7.20 Hz, 3H) (Note: 1H buried under solvent peak).

Example 1362

Enantiomer 1

(S)-3-(4-(Ethyl(tetrahydro-2H-pyran-4-yl)amino)-3-((2-ethylpyrimidin-5-yl)amino)phenyl)pentanoic acid

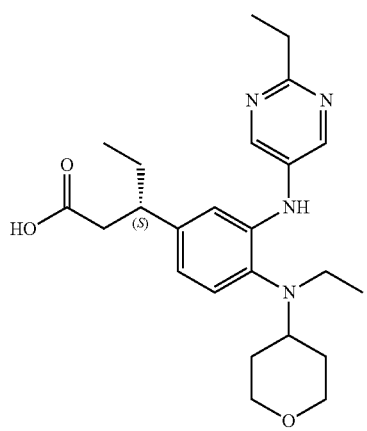

Example 1362 was prepared using 455E and 5-bromo-2-ethylpyrimidine following the procedure described for the synthesis of Example 84. LC-MS Anal. Calc'd. for $C_{24}H_{34}N_4O_3$, 426.3, found [M+H] 427.3, $T_r$=1.57 min (Method O). $^1$H NMR (400 MHz, DMSO-$d_6$): δ 8.54 (s, 2H), 7.51 (s, 1H), 7.14 (d, J=8.00 Hz, 1H), 7.03 (d, J=1.60 Hz, 1H), 6.76 (dd, J=1.60, 8.00 Hz, 1H), 3.79-3.81 (m, 2H), 3.19-3.31 (m, 2H), 2.95-3.00 (m, 3H), 2.77-2.83 (m, 3H), 2.51-2.52 (m, 1H), 2.40-2.46 (m, 1H), 1.62-1.66 (m, 3H), 1.42-1.53 (m, 3H), 1.25 (t, J=7.60 Hz, 3H), 0.81 (t, J=7.20 Hz, 3H), 0.72 (t, J=7.20 Hz, 3H).

Example 1363

Enantiomer 2

(R)-3-(4-(Ethyl(tetrahydro-2H-pyran-4-yl)amino)-3-((2-methylpyrimidin-5-yl)amino)phenyl)pentanoic acid

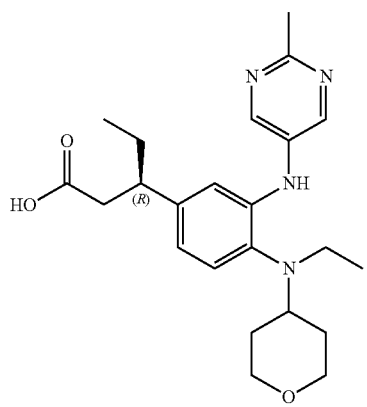

Example 1363 was prepared from 498B and 5-bromo-2-methylpyrimidine following the procedure described for the synthesis of Example 84. LC-MS Anal. Calc'd. for $C_{23}H_{32}N_4O_3$, 412.2, found [M+H] 413.2, $T_r$=1.436 min (Method O). $^1$H NMR (400 MHz, DMSO-$d_6$): δ 8.51 (s, 2H), 7.51 (s, 1H), 7.14 (d, J=8.00 Hz, 1H), 7.01 (d, J=1.60 Hz, 1H), 6.76 (dd, J=1.60, 8.00 Hz, 1H), 3.78-3.81 (m, 2H), 3.17-3.21 (m, 5H), 2.95-3.00 (m, 3H), 2.79-2.83 (m, 1H), 2.40-2.50 (m, 1H), 1.40-1.52 (m, 3H), 1.62-1.65 (m, 3H), 0.81 (t, J=7.20 Hz, 3H), 0.72 (t, J=7.20 Hz, 3H) (Note: 1H buried under solvent peak).

Example 1364

Enantiomer 2

(R)-3-(4-(Ethyl(tetrahydro-2H-pyran-4-yl)amino)-3-((2-ethylpyrimidin-5-yl)amino)phenyl)pentanoic acid

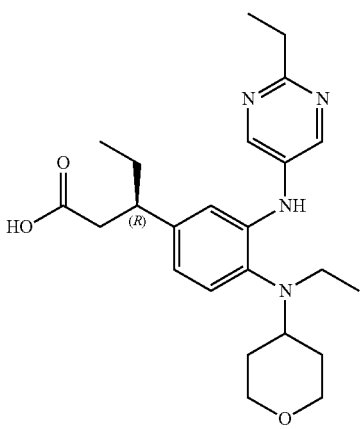

Example 1364 was prepared from 498B and 5-bromo-2-ethylpyrimidine following the procedure described for the synthesis of Example 84. LC-MS Anal. Calc'd. for $C_{24}H_{34}N_4O_3$, 426.3, found [M+H] 427.2, $T_r$=1.573 min (Method O). $^1$H NMR (400 MHz, DMSO-$d_6$): δ 8.54 (s, 2H), 7.51 (s, 1H), 7.13 (d, J=8.00 Hz, 1H), 7.02 (d, J=1.60 Hz, 1H), 6.75 (dd, J=1.60, 8.00 Hz, 1H), 3.79-3.81 (m, 2H), 3.16-3.21 (m, 2H), 2.95-3.00 (m, 3H), 2.77-2.83 (m, 3H), 2.38-2.52 (m, 1H), 1.60-1.68 (m, 3H), 1.38-1.50 (m, 3H), 1.25 (t, J=7.60 Hz, 3H), 0.81 (t, J=6.80 Hz, 3H), 0.71 (t, J=7.20 Hz, 3H) (Note: 1H buried under solvent peak).

Example 1365

Enantiomer 1 and Enantiomer 2

3-(3-((2-Ethoxypyrimidin-5-yl)amino)-4-(3-fluoro-3-(4-fluorophenyl)azetidin-1-yl)phenyl)pentanoic acid

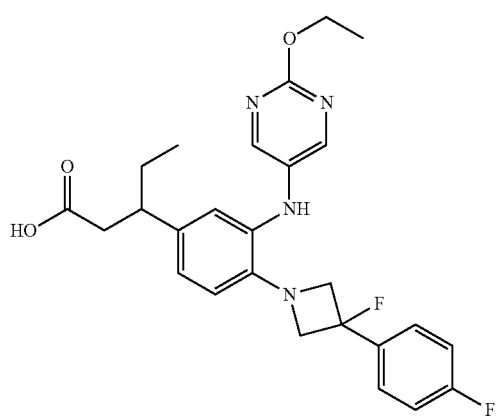 [SMILES: CCOc1ncc(Nc2cc(C(CC)CC(=O)O)ccc2N2CC(F)(c3ccc(F)cc3)C2)cn1]

1365A. Methyl 3-(4-(3-fluoro-3-(4-fluorophenyl)azetidin-1-yl)-3-nitrophenyl)pentanoate To a solution of 1253C (0.05 g, 0.124 mmol) in DCM (2 mL) was added DAST (0.033 mL, 0.248 mmol) at 0° C. under nitrogen. Then the reaction mixture was warmed to room temperature and stirred for 16 h. The reaction mixture was cooled to 0° C. and quenched with NaHCO$_3$ solution (25 mL), extracted with DCM (2×25 mL). The combined organic layers were dried over anhydrous sodium sulfate, filtered and concentrated under reduced pressure. The crude sample was purified via silica gel flash chromatography to afford 1365A (pale yellow oil, 0.045 g, 0.106 mmol, 85% yield). LC-MS Analysis Calc'd. for C$_{21}$H$_{22}$F$_2$N$_2$O$_4$, 404.1, found [M+H] 405.1, T$_r$=1.58 min (Method BA).

1365B. Methyl 3-(3-amino-4-(3-fluoro-3-(4-fluorophenyl)azetidin-1-yl)phenyl)pentanoate The solution of 1365A (0.045 g, 0.111 mmol) in ethyl acetate (5 mL) was sequentially evacuated and purged with nitrogen for three times, then added 10% palladium on carbon (5.92 mg, 5.56 µmol). The reaction mixture was pressurized to 40 psi of hydrogen atmosphere and stirred for 2 h. The reaction mixture was filtered through CELITE® pad, rinsed the pad with MeOH and the filtrate was concentrated under reduced pressure to afford 1365B (pale yellow oil, 0.035 g, 0.084 mmol, 76% yield). LC-MS Analysis Calc'd. for C$_{21}$H$_{24}$F$_2$N$_2$O$_2$, 374.4, found [M+H] 375.1, T$_r$=1.51 min (Method BA).

1365C. Methyl 3-(3-((2-ethoxypyrimidin-5-yl)amino)-4-(3-fluoro-3-(4-fluorophenyl)azetidin-1-yl)phenyl)pentanoate The solution of 1365B in 1,4-dioxane (2 mL) degassed with argon, was added 5-bromo-2-ethoxypyrimidine (0.023 g, 0.112 mmol), 4,5-bis(diphenylphosphino)-9,9-dimethylxanthene (10.82 mg, 0.019 mmol), cesium carbonate (0.076 g, 0.234 mmol) followed by the addition of bis(dibenzylideneacetone)palladium (5.37 mg, 9.35 µmol). Then the reaction temperature was stirred at 110° C. for 16 h in a sealed tube. Then the reaction mixture was poured into water (25 mL) and extracted with EtOAc (2×25 mL). The combined organic layers were dried over anhydrous sodium sulfate, filtered and concentrated under reduced pressure. The crude sample was purified via silica gel flash chromatography to afford 1365C (pale yellow oil, 0.04 g, 0.073 mmol, 78% yield). LC-MS Analysis Calc'd. for C$_{27}$H$_{30}$F$_2$N$_4$O$_3$, 496.2, found [M+H] 497.4, T$_r$=1.51 min (Method BA).

Example 1365 Enantiomer 1 and Enantiomer 2. 3-(3-((2-Ethoxypyrimidin-5-yl)amino)-4-(3-fluoro-3-(4-fluorophenyl)azetidin-1-yl)phenyl)pentanoic acid To a solution of 1365C (0.04 g, 0.081 mmol) in mixture of THF (1 mL), MeOH (1 mL) and water (1 mL) was added LiOH.H$_2$O (7.72 mg, 0.322 mmol) at room temperature and stirred for 16 h. The volatile solvents were evaporated under reduced pressure. The aqueous solution was acidified with citric acid solution, extracted with EtOAc (2×15 mL). The combined organic layers were dried over anhydrous sodium sulfate, filtered and concentrated under reduced pressure to afford the racemate.

Chiral separation of Racemate 1365 yielded Example 1365 Enantiomer 1 T$_r$=6.79 min, Example 1365 Enantiomer 2 T$_r$=9.07 min (Method DB).

Example 1365 Enantiomer 1 (0.007 g, 0.014 mmol, 17.1% yield). LC-MS Anal. Calc'd. for C$_{26}$H$_{28}$F$_2$N$_4$O$_3$, 482.2, found [M+H] 483.2, T$_r$=1.17 min (Method BA). $^1$H NMR (DMSO-d$_6$) δ 7.96 (s, 2H), 7.46-7.42 (m, 2H), 7.39 (s, 1H), 7.21-7.17 (m, 2H), 6.86-6.83 (m, 2H), 6.64 (d, J=8.00 Hz, 1H), 4.23 (q, J=7.20 Hz, 2H), 4.11-4.03 (m, 4H), 2.78-2.75 (m, 1H), 2.11-2.08 (m, 2H), 1.68-1.66 (m, 1H), 1.30 (t, J=6.80 Hz, 3H), 1.20-1.15 (m, 1H), 0.66 (t, J=7.60 Hz, 3H).

Example 1365 Enantiomer 2 (0.007 g, 0.014 mmol, 17.1% yield). LC-MS Anal. Calc'd. for C$_{26}$H$_{28}$F$_2$N$_4$O$_3$, 482.2, found [M+H] 483.2, T$_r$=1.17 min (Method BA). $^1$H NMR (DMSO-d$_6$) δ 7.96 (s, 2H), 7.46-7.42 (m, 2H), 7.38 (s, 1H), 7.23-7.18 (m, 2H), 6.86-6.83 (m, 2H), 6.64 (d, J=8.00 Hz, 1H), 4.24 (q, J=6.80 Hz, 2H), 4.14-4.07 (m, 4H), 2.78-2.75 (m, 1H), 2.11-2.02 (m, 2H), 1.68-1.66 (m, 1H), 1.30 (t, J=6.80 Hz, 3H), 1.20-1.15 (m, 1H), 0.66 (t, J=7.60 Hz, 3H).

Example 1366

(S)-1-(2-(3-((2-Ethoxypyrimidin-5-yl)amino)-4-(ethyl(tetrahydro-2H-pyran-4-yl)amino)phenyl)butyl)-3-ethylurea

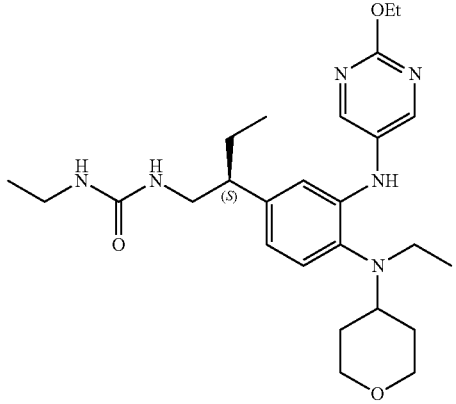

To a stirred solution of Example 1324 (30 mg, 0.073 mmol) in DCM (3 mL), was added isocyanatoethane (7.73 mg, 0.109 mmol) at room temperature. The reaction mixture was stirred at room temperature for 4 h. The solvent was removed under vacuum to afford the residue. The residue was purified by Preparative LCMS to afford Example 1366. (Off-white solid, 11.0 mg, 0.023 mmol, 31.3% yield). LC-MS Analysis Calc'd for C$_{26}$H$_{40}$N$_6$O$_3$, 484.316, found [M+H] 485.3, T$_r$=2.048 min (Method O). $^1$H NMR (400 MHz, DMSO-d$_6$) δ 8.45 (s, 2H), 7.20 (d, J=8.2 Hz, 1H), 6.83 (d, J=1.6 Hz, 1H), 6.75 (dd, J=1.6, 8.2 Hz, 1H), 4.40-4.45 (m, 2H), 3.91-3.94 (m, 2H), 3.33-3.41 (m, 3H), 3.07-3.12 (m, 6H), 2.55-2.58 (m, 1H), 1.80-1.83 (m, 2H), 1.55-1.71 (m, 4H), 1.43 (t, J=7.20 Hz, 3H), 1.05 (t, J=7.20 Hz, 3H), 0.94 (t, J=7.20 Hz, 3H), 0.82 (t, J=7.20 Hz, 3H).

Example 1367

(S)-N-((2-(3-((2-Ethoxypyrimidin-5-yl)amino)-4-(ethyl(tetrahydro-2H-pyran-4-yl)amino)phenyl)butyl)carbamoyl)benzene sulfonamide

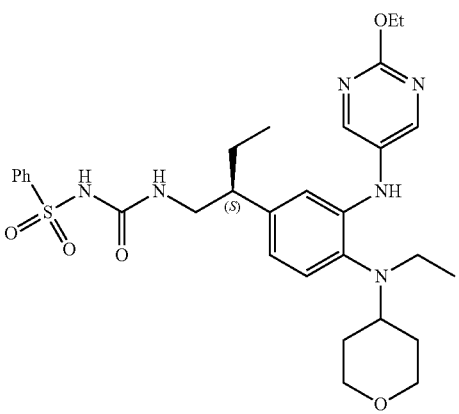

To a stirred solution of Example 1324 (10 mg, 0.023 mmol) in DCM (3 mL), was added benzenesulfonyl isocyanate (5.32 mg, 0.029 mmol) at room temperature. The reaction mixture was stirred at room temperature for 4 h. The solvent was removed under vacuum to afford the residue. The residue was purified by preparative LCMS to afford Example 1367 (off-white solid, 1.7 mg, 2.85 μmol, 11.78% yield). LC-MS Analysis Calc'd for $C_{30}H_{40}N_6O_5S$, 596.278, found [M+H] 597.3, $T_r$=1.757 min (Method O). $^1$H NMR (400 MHz, CD$_3$OD) δ 8.46 (s, 2H), 7.84-7.84 (m, 2H), 7.64-7.68 (m, 1H), 7.54-7.58 (m, 2H), 7.21 (d, J=8.0 Hz, 1H), 6.80 (d, J=2.0 Hz, 1H), 6.69 (dd, J=2.0, 8.0 Hz, 1H), 4.43 (q, J=7.20 Hz, 2H), 3.90-3.93 (m, 2H), 3.32-3.37 (m, 2H), 3.07-3.17 (m, 5H), 2.49-2.53 (m, 1H), 1.81-1.84 (m, 2H), 1.54-1.60 (m, 4H), 1.43 (t, J=7.20 Hz, 3H), 0.94 (t, J=7.20 Hz, 3H), 0.78 (t, J=7.20 Hz, 3H).

Example 1368

Enantiomer 2

(R)-4-(3-((2-Ethoxypyrimidin-5-yl)amino)-4-(ethyl(tetrahydro-2H-pyran-4-yl)amino)phenyl)-2-methyl-hexan-2-ol

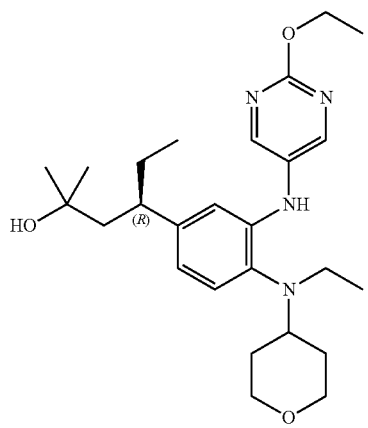

Example 1368 Enantiomer 2 was prepared using compound 498B following the procedure described for the synthesis of Example 1345 Enantiomer 1. LC-MS Anal. Calc'd. for $C_{26}H_{40}N_4O_3$, 456.3, found [M+H] 457.3, $T_r$=2.45 min (Method O). $^1$H NMR (400 MHz, DMSO-d$_6$) δ 8.40 (s, 2H), 7.31 (s, 1H), 7.11 (d, J=7.6 Hz, 1H), 6.80 (s, 1H), 6.68 (d, J=8.0 Hz, 1H), 4.30-4.27 (m, 2H), 3.90 (br s, 1H), 3.79-3.65 (m, 2H), 3.21-3.15 (m, 2H), 3.10-2.90 (m, 4H), 1.80-1.60 (m, 4H), 1.50-1.40 (m, 3H), 1.35-1.30 (m, 3H), 0.93-0.90 (m, 6H), 0.81 (t, J=7.20 Hz, 3H), 0.67 (t, J=7.20 Hz, 3H)

Examples 1369 to 1374

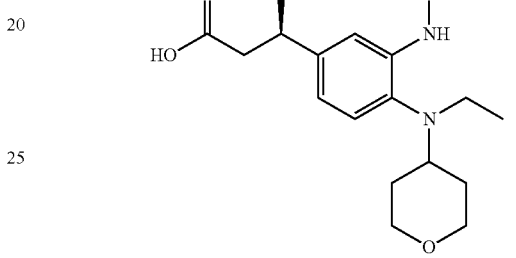

Examples 1369 to 1374 were prepared using (R)-methyl 3-(3-amino-4-(ethyl(tetrahydro-2H-pyran-4-yl)amino)phenyl)pentanoate (compound 498B) and corresponding aryl halides following the procedure described for the synthesis of Example 498 Enantiomer 2.

| Ex. No. | Name | R | $T_r$ min | Method | (M + H) |
|---|---|---|---|---|---|
| 1369 | (R)-3-(4-(ethyl(tetrahydro-2H-pyran-4-yl)amino)-3-(pyrimidin-5-ylamino)phenyl)pentanoic acid | pyrimidin-5-yl | 0.58 | A | 399.3 |
| 1371 | (R)-3-(3-((2-cyclopropylpyrimidin-5-yl)amino)-4-(ethyl(tetrahydro-2H-pyran-4-yl)amino)phenyl)pentanoic acid | 2-cyclopropylpyrimidin-5-yl | 0.68 | A | 439.2 |
| 1372 | (R)-3-(4-(ethyl(tetrahydro-2H-pyran-4-yl)amino)-3-((2-(trifluoromethyl)pyrimidin-5-yl)amino)phenyl)pentanoic acid | 2-(trifluoromethyl)pyrimidin-5-yl | 0.74 | A | 467.2 |

| Ex. No. | Name | R | T$_r$ min | Method | (M + H) |
|---|---|---|---|---|---|
| 1374 | (R)-3-(4-(ethyl(tetrahydro-2H-pyran-4-yl)amino)-3-((5-methoxypyrimidin-2-yl)amino)phenyl)pentanoic acid | (5-methoxypyrimidin-2-yl) | 0.67 | A | 429.3 |

Example 1376

(+/−)-3-(6-(Diisobutylamino)-5-((2-ethoxypyrimidin-5-yl)amino)pyridin-3-yl)pentanoic acid

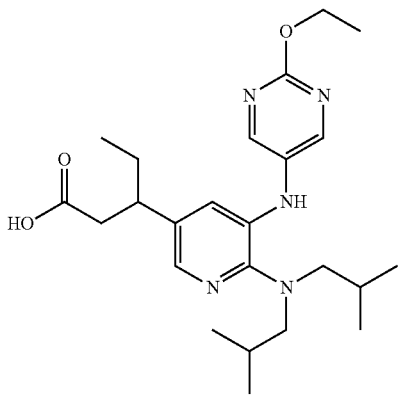 [SMILES: CCOc1ncc(Nc2cc(C(CC)CC(=O)O)cnc2N(CC(C)C)CC(C)C)cn1]

1376A. 5-Bromo-N,N-diisobutyl-3-nitropyridin-2-amine

A solution of 5-bromo-2-chloro-3-nitropyridine (2.2 g, 9.27 mmol) in DMF (1 mL) was treated with diisobutylamine (3.59 g, 27.8 mmol) and warmed to 120° C. for 20 min. The reaction was transferred into water and extracted with 1:1 ether-hexanes. The org. ext. was washed with brine, dried, and stripped to afford 5-bromo-N,N-diisobutyl-3-nitropyridin-2-amine (3.1 g, 99% yield) as an orange oil. MS(ES): m/z=330 [M+I-1]$^+$. T$_r$=1.27 min. (Method A).

1376B. 5-(5,5-Dimethyl-1,3,2-dioxaborinan-2-yl)-N,N-diisobutyl-3-nitropyridin-2-amine A solution of 5-bromo-N,N-diisobutyl-3-nitropyridin-2-amine (1.321 g, 4 mmol) and 5,5,5',5'-tetramethyl-2,2'-bi(1,3,2-dioxaborinane) (1.175 g, 5.20 mmol) in DMSO (6.67 ml) was degassed by purging with nitrogen briefly. It was then treated with potassium acetate (1.178 g, 12.00 mmol) and 1,1'-bis(diphenylphosphino)ferrocenepalladium(II) dichloride dichloromethane complex (0.098 g, 0.120 mmol), placed under nitrogen, and heated to 80° C. for 3 h. The reaction was cooled and purified by flash chromatography (gradient elution with 5-20% EtOAc-hexanes). Concentration of the appropriate fractions afforded 5-(5,5-dimethyl-1,3,2-dioxaborinan-2-yl)-N,N-diisobutyl-3-nitropyridin-2-amine (1.33 g, 87% yield) as a viscous orange oil. MS(ES): m/z=296 [M+H]$^+$ for parent boronic acid. T$_r$=1.01 min. (Method A).

1376C. (+/−)-Methyl 3-(6-(diisobutylamino)-5-((2-ethoxypyrimidin-5-yl)amino)pyridin-3-yl)pentanoate A suspension of 5-(5,5-dimethyl-1,3,2-dioxaborinan-2-yl)-N,N-diisobutyl-3-nitropyridin-2-amine (0.56 g, 1.542 mmol) in dry dioxane (6 mL) was treated with (E)-methyl pent-2-enoate (0.528 g, 4.62 mmol) followed by sodium hydroxide (1387 µl, 1.387 mmol). The vial was subjected to two cycles of vacuum/nitrogen purge. Chloro (1,5-cyclooctadiene)rhodium(I) dimer (0.038 g, 0.077 mmol) was added and the vacuum/nitrogen purge was repeated. This mixture was warmed to 50° C. for 2 h then quenched with acetic acid (80 µl, 1.397 mmol). Most of the dioxane was removed under a stream of nitrogen, and the mixture was purified by flash chromatography (5-20% EtOAc-hexane). Concentration of the appropriate fractions afforded (+/−)-methyl 3-(6-(diisobutylamino)-5-nitropyridin-3-yl)pentanoate (0.32 g, 0.876 mmol, 56.8% yield) as an orange oil. MS(ES): m/z=366 [M+H]$^+$. T$_r$=1.21 min. (Method A).

1376D. (+/−)-Methyl 3-(5-amino-6-(diisobutylamino)pyridin-3-yl)pentanoate

A solution of methyl 3-(6-(diisobutylamino)-5-nitropyridin-3-yl)pentanoate (0.31 g, 0.848 mmol) in ethanol (8 mL)-THF (2 mL) was treated simultaneously with zinc (0.555 g, 8.48 mmol) and ammonium chloride (0.454 g, 8.48 mmol) in water (2 mL) with vigorous stirring. The reaction was stirred 20 min. at RT, diluted with dichloromethane and treated with ~4 g of magnesium sulfate. This mixture was stirred for 2-3 min. then filtered, stripped and quickly chromatographed on silica gel (10-20% EtOAc-hexane). Concentration of the appropriate fractions afforded (+/−)-3-(5-amino-6-(diisobutylamino)pyridin-3-yl)pentanoate (0.13 g, 46%) as an oil. MS(ES): m/z=336 [M+H]$^+$ for parent boronic acid. T$_r$=0.77 min. (Method A).

1376E. (+/−)-Methyl 3-(6-(diisobutylamino)-5-((2-ethoxypyrimidin-5-yl)amino)pyridin-3-yl)pentanoate A suspension of methyl 3-(5-amino-6-(diisobutylamino)pyridin-3-yl)pentanoate (0.063 g, 0.188 mmol), 5-bromo-2-ethoxypyrimidine (0.042 g, 0.207 mmol), cesium carbonate (0.184 g, 0.563 mmol), and Xantphos (0.022 g, 0.038 mmol) in degassed dioxane was placed under nitrogen and treated with bis(dibenzylideneacetone)palladium (10.80 mg, 0.019 mmol). This mixture was heated at 110° C. The reaction was cooled to RT and purified by flash chromatography (10-30% EtOAc-hexane). Concentration of the appropriate fractions afforded methyl 3-(6-(diisobutylamino)-5-((2-ethoxypyrimidin-5-yl)amino)pyridin-3-yl)pentanoate (0.06 g, 69.8% yield) as a yellow oil. MS(ES): m/z=458 [M+H]$^+$. T$_r$=0.86 min. (Method A).

Example 1376 (+/−)-3-(6-(Diisobutylamino)-5-((2-ethoxypyrimidin-5-yl)amino)pyridin-3-yl)pentanoic acid A solution of methyl 3-(6-(diisobutylamino)-5-((2-ethoxypyrimidin-5-yl)amino)pyridin-3-yl)pentanoate (0.059 g, 0.129 mmol) in THF (1 mL) was treated with aq. sodium hydroxide (0.516 mL, 0.516 mmol). Methanol, ~1 mL, was added to give a single phase, and the reaction was stirred 3 h at RT. The reaction was brought to pH-5 with dilute aq. HOAc and ext. twice with dichloromethane. The comb. org. ext. dried, stripped, and purified by prep HPLC. MS(ES): m/z=444 [M+H]$^+$. T$_r$=0.80 min. (Method A). $^1$H NMR (400 MHz, CDCl$_3$) δ 2.63-2.72 (m, 6H), 2.41-2.50 (m, 1H), 2.13-2.20 (m, 2H), 1.45-1.52 (m, 2H), 1.09 (t, J=7.2 Hz, 3H).

Example 1377

(+/−)3-(6-(Ethyl(tetrahydro-2H-pyran-4-yl)amino)-5-(3-(p-tolyl)ureido)pyridin-3-yl)pentanoic acid

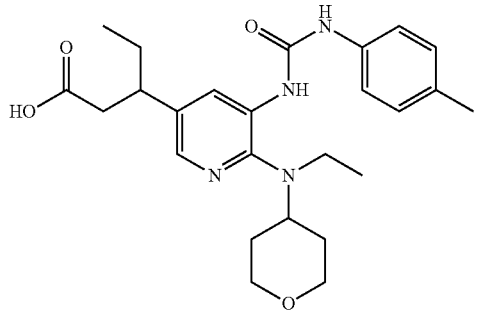 [SMILES: CCC(CC(=O)O)c1cnc(N(CC)C2CCOCC2)c(NC(=O)Nc2ccc(C)cc2)c1]

1377A. 5-Bromo-N,N-diisobutyl-3-nitropyridin-2-amine

A solution of 5-bromo-2-fluoro-3-nitropyridine (1.326 g, 6 mmol) and DIEA (1.572 mL, 9.00 mmol) in NMP (1 mL) was treated with N-ethyltetrahydro-2H-pyran-4-amine (1.008 g, 7.80 mmol) and heated to 100° C. After 2 h, LCMS indicated a complete reaction, so it was cooled to RT and quenched with 10% aq. HOAc. The resulting mixture was stirred briefly, diluted with water and ext. twice with dichloromethane. The comb. org. ext. were dried and stripped to afford a dark oil. This material was run through a quick silica gel column (EtAOc-hexane). Concentration of the appropriate fractions afforded 5-bromo-N-ethyl-3-nitro-N-(tetrahydro-2H-pyran-4-yl)pyridin-2-amine (1.9 g, 96% yield) as an orange oil. MS(ES): m/z=330 [M+H]$^+$. T$_r$=1.03 min. (Method A).

1377B. 5-(5,5-Dimethyl-1,3,2-dioxaborinan-2-yl)-N-ethyl-3-nitro-N-(tetrahydro-2H-pyran-4-yl)pyridin-2-amine A solution of 5-bromo-N-ethyl-3-nitro-N-(tetrahydro-2H-pyran-4-yl)pyridin-2-amine (1.8 g, 5.45 mmol) and 5,5,5',5'-tetramethyl-2,2'-bi(1,3,2-dioxaborinane) (1.601 g, 7.09 mmol) in DMSO (9.09 ml) was degassed by freeze-thaw under vacuum. It was then treated with potassium acetate (1.605 g, 16.35 mmol) and 1,1'-bis(diphenylphosphino)ferrocenepalladium(II) dichloride dichloromethane complex (0.134 g, 0.164 mmol), placed under nitrogen, and heated to 80° C. for 2 h. The reaction was cooled and purified by flash chromatography (gradient elution with 5-20% EtOAc-hexanes). Concentration of the appropriate fractions afforded 5-(5,5-dimethyl-1,3,2-dioxaborinan-2-yl)-N-ethyl-3-nitro-N-(tetrahydro-2H-pyran-4-yl)pyridin-2-amine (1.86 g, 94% yield) as an orange oil which solidified upon standing to a yellow solid, mp 121-126° C. MS(ES): m/z=296 [M+H]$^+$ for parent boronic acid. T$_r$=0.74 min. (Method A).

1377C. (+/−)-Methyl 3-(6-(ethyl(tetrahydro-2H-pyran-4-yl)amino)-5-nitropyridin-3-yl)pentanoate A suspension of 5-(5,5-dimethyl-1,3,2-dioxaborinan-2-yl)-N-ethyl-3-nitro-N-(tetrahydro-2H-pyran-4-yl)pyridin-2-amine (0.84 g, 2.313 mmol) in dioxane (1 mL) was treated with (E)-methyl pent-2-enoate (0.792 g, 6.94 mmol) followed by sodium hydroxide (2081 μl, 2.081 mmol). The vial was subjected to two cycles of vacuum/nitrogen purge. Chloro(1,5-cyclooctadiene)rhodium(I) dimer (0.057 g, 0.116 mmol) was added, and the vacuum/nitrogen purge was repeated. The reaction was warmed to 50° C. The reaction was stirred 2 h then cooled, quenched with acetic acid (80 μl, 1.397 mmol), and applied to a flash silica gel column. The column was eluted with 10-25% ether in hexanes. Concentration of the appropriate fractions afforded (+/−)-methyl 3-(6-(ethyl(tetrahydro-2H-pyran-4-yl)amino)-5-nitropyridin-3-yl)pentanoate (0.49 g, 1.341 mmol, 58.0% yield) as an orange oil. MS(ES): m/z=366 [M+H]$^+$. T$_r$=1.01 min. (Method A).

1377D. (+/−)-Methyl 3-(5-amino-6-(ethyl(tetrahydro-2H-pyran-4-yl)amino)pyridin-3-yl)pentanoate A solution of methyl 3-(6-(ethyl(tetrahydro-2H-pyran-4-yl)amino)-5-nitropyridin-3-yl)pentanoate (0.48 g, 1.314 mmol) in ethyl acetate (15 mL) was placed under nitrogen and charged with palladium on carbon (0.140 g, 0.131 mmol). The mixture was hydrogenated at 45 psi initial pressure for 1.5 h on a Parr shaker. The reaction was diluted with dichloromethane, some MgSO$_4$ was added, and the mixture was filtered. The resulting solution was concentrated under reduced pressure to afford (+/−)-methyl 3-(5-amino-6-(ethyl(tetrahydro-2H-pyran-4-yl)amino)pyridin-3-yl)pentanoate (0.44 g, 100% yield) as a dark oil. MS(ES): m/z=336 [M+H]$^+$ for parent boronic acid. T$_r$=0.63 min. (Method A).

Example 1377 (+/−)-3-(6-(Ethyl(tetrahydro-2H-pyran-4-yl)amino)-5-(3-(p-tolyl)ureido)pyridin-3-yl)pentanoic acid The title compound was prepared from (+/−)-methyl 3-(5-amino-6-(ethyl(tetrahydro-2H-pyran-4-yl)amino)pyridin-3-yl)pentanoate using the procedure for the conversion of 1375D to Example 1375. MS(ES): m/z=455 [M+H]$^+$. T$_r$=0.80 min. (Method A). $^1$H NMR (500 MHz, DMSO-d$_6$) δ 9.54 (s, 1H), 8.38 (s, 1H), 8.36 (s, 1H), 7.88 (d, J=1.4 Hz, 1H), 7.37 (d, J=8.2 Hz, 2H), 7.10 (d, J=8.1 Hz, 2H), 3.78-3.84 (m, 2H), 3.04-3.27 (m, 5H), 2.83-2.90 (m, 1H), 2.41-2.63 (m, integration distorted by overlapping solvent peak), 2.25 (s, 3H), 1.40-1.70 (m, 6H), 0.70-0.78 (m, 6H).

Further compounds of the invention I (Table 3) were prepared as shown in Scheme 16. Accordingly, amines JM Intermediate 1 (prepared as described in Example 1376) were coupled with aryl bromides R$_4$Br. The resulting esters were isolated, saponified with aqueous LiOH, and the products were purified by prep HPLC. The procedure followed was that used for the conversion of 1375D into Example 1376. The Examples in this table are all racemic.

Racemic compounds of the invention I could be resolved into their component Enantiomers E1 and E2 by chiral SFC as shown in Scheme 17. Table 4 lists these Examples along with the preparative conditions under which they were resolved and the analytical conditions under which they were characterized. In all cases, E1 and E2 are homochiral with undetermined absolute stereochemistry.

Scheme 16

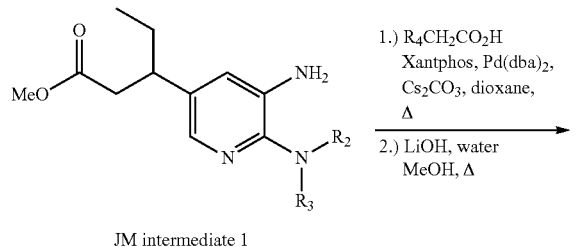

JM intermediate 1

1.) $R_4CH_2CO_2H$
    Xantphos, $Pd(dba)_2$,
    $Cs_2CO_3$, dioxane,
    Δ
2.) LiOH, water
    MeOH, Δ

Scheme 17

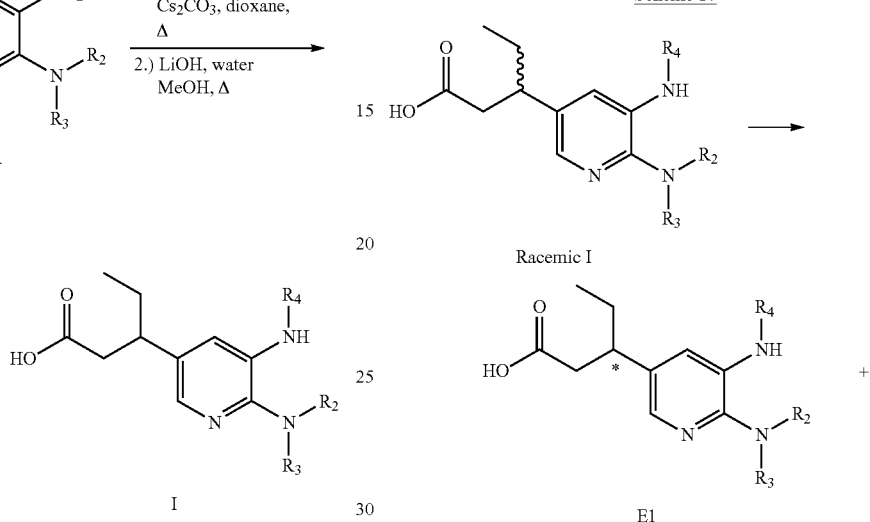

TABLE 3

| Ex. No. | $R_2$ | $R_3$ | $R_4$ | m/z | $T_r$ (min, Method A) |
|---|---|---|---|---|---|
| 1378 | ethyl | tetrahydropyran-4-yl | (2-ethoxypyrimidin-5-yl) | 444 | 0.68 |
| 1379 | ethyl | tetrahydropyran-4-yl | (4-cyanophenyl) | 423 | 0.71 |
| 1380 | ethyl | tetrahydropyran-4-yl | (4-chlorophenyl) | 432 | 0.80 |

-continued

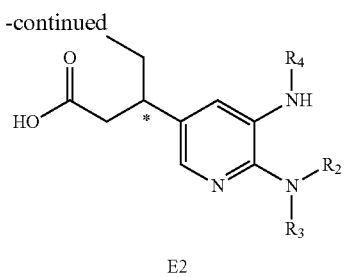

E2

TABLE 4

| Ex. No. | R₂ | R₃ | R₄ | m/z | T_r |
|---|---|---|---|---|---|
| 1383 | isobutyl | isobutyl | 2-ethoxypyrimidin-5-yl | 444 | 1.76 |
| 1384 | isobutyl | isobutyl | 2-ethoxypyrimidin-5-yl | | |
| 1387 | ethyl | tetrahydro-pyran-4-yl | 2-ethoxypyrimidin-5-yl | | |
| 1388 | ethyl | tetrahydro-pyran-4-yl | 2-ethoxypyrimidin-5-yl | | |
| 1389 | ethyl | tetrahydro-pyran-4-yl | 4-cyanophenyl | | |
| 1390 | ethyl | tetrahydro-pyran-4-yl | 4-cyanophenyl | | |
| 1391 | ethyl | tetrahydro-pyran-4-yl | 4-chlorophenyl | 432 | 1.65 |
| 1392 | ethyl | tetrahydro-pyran-4-yl | 4-chlorophenyl | 432 | 1.64 |

Evaluation of Biological Activity

Exemplary compounds were tested for inhibition of IDO activity. Experimental procedures and results are provided below.

Example 1393

Assessment of Human IDO-1 Inhibitory Activity in HEK Cells

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Compounds with an $IC_{50}$ greater than 50 nM are shown with (*), compounds with an $IC_{50}$ less than 50 nM are shown with () and those with an $IC_{50}$ less than 5 nM are shown with (*) (Table 5).

Example 1394

Assessment of Human IDO-1 Inhibitory Activity in Hela Cells

HeLa cells were seeded at 20,000 cells per 30 µL per well with RPMI/phenol red free media containing 10% FBS in a 384-well tissue culture plate (black with clear bottoms). 50 nL of compound was added to cells and incubated at 37° C. for one hour. 20 µL of the recombinant human Interferon-gamma (R&D System, Cat. #285-IF, at final concentration of 10 ng/ml) or recombinant murine Interferon-gamma (PEPROTECH® Inc., Cat. #315-05, final concentration of 5 ng/ml) was added to activate IDO signaling. The cells were incubated for 18 hours in 37° C. incubator with 5% $CO_2$.

Compound treatment was stopped by adding 5 µl trichloroacetic acid to a final concentration of 3%. Subsequently, the cell plate was further incubated at 50° C. for 30 minute. An equal volume supernatant (20 µL) and 2% (w/v) Ehrlich reagent (4-dimethylaminobenzaldehyde) in glacial acetic acid were mixed in a new clear bottom 384-well plate. This plate was incubated at room temperature for 30 minutes. Absorbance at 490 nm was measured on Envision plate reader.

Compound IC$_{50}$ values were calculated using counts from unstimulated (no INF-gamma treatment) wells as 100% inhibition. INF-gamma treatment without compound treatment as 0% inhibition.

Compounds with an IC$_{50}$ greater than 50 nM are shown with (*), compounds with an IC$_{50}$ less than 50 nM are shown with () and those with an IC$_{50}$ less than 5 nM are shown with (*) (Table 6).

TABLE 5

In Vitro Potency in the HEK Human IDO-1 Cellular Assay

| Example No. | HEK Human IDO-1 IC$_{50}$ (nM) |
|---|---|
| 1 | *** |
| 2 | *** |
| 3 | * |
| 5 | ** |
| 9 | * |
| 10 | * |
| 11 | ** |
| 37 | *** |
| 50 | * |
| 51 | * |
| 52 | * |
| 53 | *** |
| 54 | ** |
| 55 | * |
| 56 | ** |
| 59 E1 | *** |
| 59 E2 | *** |
| 60 E1 | *** |
| 69 | *** |
| 70 | *** |
| 71 | ** |
| 72 | *** |
| 73 D1 | *** |
| 73 D2 | *** |
| 73 D3 | ** |
| 73 D4 | *** |
| 74 | * |
| 75 | ** |
| 76 | * |
| 77 | * |
| 78 | ** |
| 79 | * |
| 80 | * |
| 81 | ** |
| 82 | ** |
| 83 | ** |
| 84 | ** |
| 85 | * |
| 86 | ** |
| 87 | * |
| 88 | * |
| 89 | *** |
| 90 | ** |
| 91 | ** |
| 92 | *** |
| 93 | ** |
| 94 | ** |
| 95 | * |
| 96 | ** |
| 97 | ** |
| 98 | * |
| 99 | *** |
| 100 | *** |
| 101 | *** |
| 102 | *** |
| 103 | *** |
| 104 | *** |
| 105 | * |
| 106 | ** |
| 107 | *** |
| 111 | * |
| 112 | ** |
| 113 | ** |
| 114 | * |

TABLE 5-continued

In Vitro Potency in the HEK Human IDO-1 Cellular Assay

| Example No. | HEK Human IDO-1 IC$_{50}$ (nM) |
|---|---|
| 115 | *** |
| 116 | *** |
| 117 | *** |
| 118 | ** |
| 119 | *** |
| 120 | *** |
| 121 | * |
| 122 | ** |
| 123 | *** |
| 127 | * |
| 128 | * |
| 129 | ** |
| 130 | * |
| 131 | ** |
| 132 | * |
| 146 | * |
| 147 | ** |
| 148 | ** |
| 159 | ** |
| 160 | *** |
| 161 | *** |
| 162 | ** |
| 163 | ** |
| 164 | ** |
| 163 | *** |
| 166 | * |
| 167 | ** |
| 191 | * |
| 192 | * |
| 193 | *** |
| 194 | ** |
| 195 | *** |
| 196 | *** |
| 197 | * |
| 198 | *** |
| 199 | *** |
| 200 | ** |
| 201 | ** |
| 202 | * |
| 203 | *** |
| 204 | *** |
| 205 | ** |
| 206 | ** |
| 207 | * |
| 208 | * |
| 209 | * |
| 210 | * |
| 211 | * |
| 212 | * |
| 213 | * |
| 214 | ** |
| 215 | *** |
| 216 | * |
| 217 | * |
| 218 | * |
| 219 | *** |
| 220 | *** |
| 225 | *** |
| 226 | *** |
| 227 | *** |
| 228 | *** |
| 229 | ** |
| 230 | ** |
| 231 | *** |
| 236 | ** |
| 237 | *** |
| 238 | *** |
| 239 | ** |
| 240 | ** |
| 241 | ** |
| 242 | *** |
| 266 | * |
| 270 | * |
| 271 | *** |
| 272 | *** |

TABLE 5-continued

In Vitro Potency in the HEK Human IDO-1 Cellular Assay

| Example No. | HEK Human IDO-1 IC$_{50}$ (nM) |
|---|---|
| 273 | ** |
| 274 | ** |
| 279 | *** |
| 280 | * |
| 281 | ** |
| 282 | *** |
| 283 | *** |
| 284 | *** |
| 285 | *** |
| 286 | * |
| 287 | *** |
| 288 | ** |
| 289 | *** |
| 290 | *** |
| 299 | *** |
| 300 | ** |
| 301 | ** |
| 302 | *** |
| 303 | *** |
| 304 | *** |
| 305 | *** |
| 306 | *** |
| 307 | ** |
| 308 | *** |
| 309 | *** |
| 310 | *** |
| 311 | *** |
| 312 | *** |
| 313 | *** |
| 314 | *** |
| 315 | * |
| 316 | ** |
| 317 | ** |
| 336 | ** |
| 337 | *** |
| 338 | ** |
| 350 | ** |
| 351 | ** |
| 373 | *** |
| 374 | *** |
| 375 | *** |
| 376 | *** |
| 377 | ** |
| 378 | ** |
| 379 | * |
| 387 | ** |
| 416 | * |
| 424 | * |
| 425 | * |
| 426 | * |
| 427 | * |
| 428 | * |
| 429 | * |
| 432 | * |
| 433 | * |
| 434 | ** |
| 435 | * |
| 436 | * |
| 437 | * |
| 438 | * |
| 439 | * |
| 440 | * |
| 445 | *** |
| 446 | ** |
| 447 | ** |
| 452 | * |
| 453 | *** |
| 455 | ** |
| 456 | *** |
| 457 | ** |
| 458 | *** |
| 468 | * |
| 469 | * |
| 470 | ** |
| 471 | * |

TABLE 5-continued

In Vitro Potency in the HEK Human IDO-1 Cellular Assay

| Example No. | HEK Human IDO-1 IC$_{50}$ (nM) |
|---|---|
| 472 | * |
| 473 | * |
| 474 | *** |
| 475 | *** |
| 476 | *** |
| 477 | *** |
| 478 | *** |
| 479 | *** |
| 480 | *** |
| 481 | *** |
| 482 | *** |
| 483 | * |
| 484 | *** |
| 485 | ** |
| 486 | * |
| 487 E1 | *** |
| 487 E2 | *** |
| 488 E1 | * |
| 488 E2 | * |
| 489 | *** |
| 490 | ** |
| 491 | ** |
| 492 | ** |
| 493 | * |
| 494 | * |
| 495 | * |
| 496 | * |
| 497 | * |
| 498 | *** |
| 499 | *** |
| 500 | * |
| 501 | *** |
| 511 | * |
| 512 | * |
| 513 | ** |
| 514 | *** |
| 515 | *** |
| 516 | *** |
| 517 | *** |
| 518 | *** |
| 519 | *** |
| 520 | *** |
| 521 | ** |
| 522 | *** |
| 523 | * |
| 524 | ** |
| 526 | *** |
| 527 | ** |
| 528 | ** |
| 529 | ** |
| 530 | *** |
| 531 | *** |
| 532 | ** |
| 533 | * |
| 534 | * |
| 535 | *** |
| 536 | *** |
| 537 | *** |
| 538 | *** |
| 539 | *** |
| 540 | *** |
| 541 | *** |
| 560 | ** |
| 561 | * |
| 562 | *** |
| 563 | ** |
| 564 | *** |
| 578 | ** |
| 579 | * |
| 580 | *** |
| 581 | *** |
| 582 | ** |
| 583 | ** |
| 584 | * |
| 585 | ** |

TABLE 5-continued

In Vitro Potency in the HEK Human IDO-1 Cellular Assay

| Example No. | HEK Human IDO-1 IC$_{50}$ (nM) |
|---|---|
| 586 | * |
| 587 | * |
| 588 | * |
| 589 | * |
| 590 | ** |
| 591 | *** |
| 592 | * |
| 593 | ** |
| 594 | * |
| 595 | * |
| 596 | * |
| 597 | * |
| 608 | *** |
| 609 | *** |
| 610 | * |
| 611 | ** |
| 612 E1 | *** |
| 612 E2 | *** |
| 613 | *** |
| 614 | ** |
| 615 | *** |
| 616 | *** |
| 617 | ** |
| 618 | *** |
| 619 | ** |
| 623 | ** |
| 633 | ** |
| 636 | * |
| 637 E1 | *** |
| 637 E2 | *** |
| 638 | ** |
| 639 | ** |
| 640 | * |
| 641 | * |
| 642 | *** |
| 643 | *** |
| 644 | ** |
| 645 | ** |
| 646 | *** |
| 647 | *** |
| 648 | *** |
| 649 | ** |
| 650 | *** |
| 651 | ** |
| 652 | ** |
| 653 | ** |
| 654 | *** |
| 655 | *** |
| 656 E1 | *** |
| 656 E2 | *** |
| 657 | ** |
| 658 | ** |
| 659 | ** |
| 660 | *** |
| 661 | * |
| 662 | *** |
| 666 E1 | *** |
| 666 E2 | *** |
| 667 E1 | * |
| 667 E2 | * |
| 676 | * |
| 677 | * |
| 678 | * |
| 679 | *** |
| 680 | ** |
| 682 | * |
| 683 | * |
| 684 | ** |
| 686 | *** |
| 687 | ** |
| 688 | * |
| 689 | * |
| 690 | * |
| 691 | *** |
| 692 | ** |

TABLE 5-continued

In Vitro Potency in the HEK Human IDO-1 Cellular Assay

| Example No. | HEK Human IDO-1 IC$_{50}$ (nM) |
|---|---|
| 695 | ** |
| 696 | *** |
| 697 | * |
| 698 | ** |
| 699 | *** |
| 700 | * |
| 701 | ** |
| 702 | *** |
| 703 | *** |
| 704 | ** |
| 705 | *** |
| 706 | *** |
| 707 | ** |
| 708 | *** |
| 709 | *** |
| 710 | *** |
| 711 | *** |
| 712 | *** |
| 714 | *** |
| 715 | ** |
| 716 | * |
| 717 | *** |
| 718 | ** |
| 727 | *** |
| 728 | *** |
| 729 | * |
| 730 | * |
| 731 | ** |
| 732 | ** |
| 733 | ** |
| 734 | * |
| 735 | * |
| 736 | * |
| 737 | * |
| 738 | * |
| 739 | * |
| 740 | * |
| 741 | * |
| 742 | * |
| 743 | * |
| 744 | * |
| 745 | ** |
| 746 | * |
| 747 | |
| 748 | * |
| 754 | * |
| 756 | * |
| 757 | * |
| 758 | * |
| 759 | * |
| 760 | * |
| 761 | ** |
| 763 | * |
| 764 | ** |
| 765 | ** |
| 767 | * |
| 769 | * |
| 771 | ** |
| 773 | ** |
| 773 | ** |
| 774 | * |
| 775 | * |
| 776 | * |
| 777 | * |
| 778 | * |
| 779 | * |
| 780 | *** |
| 781 | * |
| 782 | ** |
| 783 | *** |
| 784 | * |
| 785 | * |
| 786 | * |
| 787 | * |
| 788 | *** |

TABLE 5-continued

In Vitro Potency in the HEK Human IDO-1 Cellular Assay

| Example No. | HEK Human IDO-1 IC$_{50}$ (nM) |
|---|---|
| 789 | * |
| 790 | ** |
| 791 | ** |
| 792 | * |
| 793 | * |
| 794 | ** |
| 796 | * |
| 797 | * |
| 798 | * |
| 799 | * |
| 800 | * |
| 801 | * |
| 802 | * |
| 803 | * |
| 804 | ** |
| 805 | * |
| 806 | * |
| 807 | * |
| 808 | ** |
| 809 | ** |
| 810 | * |
| 811 | * |
| 812 | * |
| 813 | * |
| 814 | * |
| 815 | * |
| 816 | * |
| 817 | * |
| 818 | * |
| 819 | * |
| 820 | *** |
| 821 | ** |
| 822 | * |
| 823 | ** |
| 824 | * |
| 825 | ** |
| 826 | * |
| 827 | * |
| 828 | * |
| 829 | * |
| 830 | * |
| 831 | * |
| 832 | * |
| 833 | * |
| 834 | * |
| 835 | * |
| 836 | ** |
| 837 | * |
| 838 | * |
| 839 | * |
| 840 | ** |
| 841 | * |
| 842 | * |
| 891 | * |
| 892 | ** |
| 893 | * |
| 894 | ** |
| 895 | * |
| 896 | ** |
| 897 | * |
| 898 | * |
| 899 | *** |
| 900 | *** |
| 901 | *** |
| 902 | *** |
| 903 | ** |
| 904 | *** |
| 905 | * |
| 906 | ** |
| 907 | * |
| 908 | ** |
| 927 | ** |
| 949 | *** |
| 950 | *** |
| 951 | *** |
| 952 | *** |
| 953 | * |
| 954 | ** |
| 955 | *** |
| 956 | *** |
| 957 | *** |
| 958 | ** |
| 959 | *** |
| 960 | ** |
| 961 | * |
| 962 | * |
| 963 | * |
| 964 | * |
| 965 | ** |
| 966 | ** |
| 967 | ** |
| 968 | ** |
| 969 | * |
| 970 | |
| 971 | * |
| 972 | *** |
| 973 | ** |
| 974 | ** |
| 975 | ** |
| 976 | ** |
| 977 | NA |
| 978 | ** |
| 979 | NA |
| 980-1 | *** |
| 980-2 | *** |
| 981-1 | *** |
| 981-2 | *** |
| 982-1 | *** |
| 982-2 | *** |
| 983 | *** |
| 984 | *** |
| 985-1 | *** |
| 985-2 | *** |
| 986 | ** |
| 987-1 | ** |
| 987-2 | ** |
| 988 | *** |
| 989-1 | *** |
| 989-2 | *** |
| 990 | ** |
| 991-1 | ** |
| 991-2 | *** |
| 992 | ** |
| 993-1 | ** |
| 993-2 | ** |
| 994 | *** |
| 995-1 | *** |
| 995-2 | *** |
| 996 | * |
| 997-1 | * |
| 997-2 | ** |
| 998 | ** |
| 999-1 | ** |
| 999-2 | ** |
| 1000 | * |
| 1001 | * |
| 1002 | ** |
| 1003 | *** |
| 1004 | *** |
| 1005 | * |
| 1006 | *** |
| 1007-1 | * |
| 1007-2 | * |
| 1008-1 | * |
| 1008-2 | * |
| 1009 | * |
| 1010 | *** |
| 1011 | ** |
| 1012 | ** |
| 1073 | * |

TABLE 5-continued

In Vitro Potency in the HEK Human IDO-1 Cellular Assay

| Example No. | HEK Human IDO-1 IC$_{50}$ (nM) |
|---|---|
| 1074 | * |
| 1075 | * |
| 1076 | ** |
| 1077 | ** |
| 1078 | ** |
| 1079 | ** |
| 1080 | *** |
| 1081 | *** |
| 1082 | *** |
| 1083 | *** |
| 1084 | *** |
| 1085 | *** |
| 1086 | *** |
| 1087 | *** |
| 1088 | ** |
| 1089 | * |
| 1090 | *** |
| 1091 | *** |
| 1092 E1 | *** |
| 1092 E2 | *** |
| 1093 E1 | *** |
| 1093 E2 | *** |
| 1094 E1 | *** |
| 1094 E2 | *** |
| 1095 E1 | *** |
| 1095 E2 | *** |
| 1096 E1 | *** |
| 1096 E2 | *** |
| 1097 E1 | *** |
| 1097 E2 | *** |
| 1098 E1 | *** |
| 1098 E2 | *** |
| 1099 E1 | ** |
| 1099 E2 | ** |
| 1100 E1 | * |
| 1100 E2 | * |
| 1101 E1 | *** |
| 1101 E2 | *** |
| 1102 E1 | *** |
| 1102 E2 | *** |
| 1103 E1 | *** |
| 1103 E2 | *** |
| 1104 | *** |
| 1105 | *** |
| 1106 | *** |
| 1107 | *** |
| 1108 | *** |
| 1109 | *** |
| 1110 | *** |
| 1111 | *** |
| 1112 | *** |
| 1113 | *** |
| 1114 | *** |
| 1115 | *** |
| 1116 | *** |
| 1117 | *** |
| 1118 | *** |
| 1119 | *** |
| 1120 | *** |
| 1121 | *** |
| 1122 | *** |
| 1123 | *** |
| 1124 | *** |
| 1125 | *** |
| 1126 | *** |
| 1127 | *** |
| 1128 | *** |
| 1129 | *** |
| 1130 | *** |
| 1131 | *** |
| 1132 | *** |
| 1133 | *** |
| 1134 | *** |
| 1135 | *** |
| 1136 | *** |
| 1137 | *** |
| 1138 | *** |
| 1139 | *** |
| 1140 | *** |
| 1141 | *** |
| 1142 | *** |
| 1143 | * |
| 1144 | * |
| 1145 | * |
| 1147 | ** |
| 1148 | * |
| 1149 | *** |
| 1151 | * |
| 1152 | *** |
| 1153 | ** |
| 1154 | ** |
| 1155 | *** |
| 1156 | *** |
| 1157 | *** |
| 1158 | ** |
| 1159 | *** |
| 1160 | *** |
| 1161 | *** |
| 1162 | *** |
| 1163 | *** |
| 1164 | *** |
| 1165 | *** |
| 1166 | *** |
| 1167 | *** |
| 1168 | ** |
| 1169 | * |
| 1170 | ** |
| 1171 | * |
| 1172 | ** |
| 1173 | ** |
| 1174 | ** |
| 1175 | ** |
| 1176 | *** |
| 1177 | ** |
| 1178 | ** |
| 1179 | ** |
| 1180 | *** |
| 1181 | ** |
| 1182 | *** |
| 1183 | ** |
| 1184 | ** |
| 1185 | *** |
| 1186 | *** |
| 1187 | *** |
| 1188 | ** |
| 1189 | *** |
| 1190 | *** |
| 1191 | *** |
| 1192 | ** |
| 1193 | ** |
| 1194 | ** |
| 1195 | *** |
| 1196 | * |
| 1197 | ** |
| 1198 | *** |
| 1199 E1 | *** |
| 1199 E2 | *** |
| 1200 | ** |
| 1201 E1 | ** |
| 1201 E2 | ** |
| 1202 | *** |
| 1202 E1 | *** |
| 1202 E2 | *** |
| 1204 | ** |
| 1205 E1 | ** |
| 1205 E2 | ** |
| 1206 | * |
| 1207 E1 | * |
| 1207 E2 | * |
| 1208 | ** |

TABLE 5-continued

In Vitro Potency in the HEK Human IDO-1 Cellular Assay

| Example No. | HEK Human IDO-1 IC$_{50}$ (nM) |
|---|---|
| 1209 | * |
| 1210 | ** |
| 1211 | * |
| 1212 | * |
| 1213 | * |
| 1214 | * |
| 1215 | * |
| 1216 | ** |
| 1217 | *** |
| 1218 | * |
| 1219 | * |
| 1220 | * |
| 1221 | ** |
| 1222 | ** |
| 1223 | * |
| 1124 | * |
| 1125 E1 | *** |
| 1125 E2 | *** |
| 1126 | *** |
| 1127 | *** |
| 1128 | *** |
| 1129 | *** |
| 1230 | ** |
| 1231 | ** |
| 1232 | ** |
| 1233 | *** |
| 1234 | * |
| 1235 | *** |
| 1236 | *** |
| 1237 | ** |
| 1238 | * |
| 1239 | *** |
| 1240 | ** |
| 1241 | ** |
| 1242 | ** |
| 1243 | ** |
| 1244 | *** |
| 1245 | *** |
| 1246 | *** |
| 1247 | *** |
| 1248 | *** |
| 1249 | *** |
| 1250 | *** |
| 1251 | ** |
| 1252 | ** |

TABLE 6

In Vitro Potency in the Hela Human IDO-1 Cellular Assay

| Example No. | Hela Human IDO-1 IC$_{50}$ (nM) |
|---|---|
| 4 | ** |
| 6 E1 | * |
| 6 E2 | ** |
| 7 E1 | * |
| 7 E2 | * |
| 8 E1 | * |
| 8 E2 | ** |
| 12 E1 | *** |
| 12 E2 | *** |
| 13 E1 | ** |
| 13 E2 | ** |
| 14 E1 | * |
| 14 E2 | * |
| 15 | *** |
| 16 | *** |
| 17 | * |
| 18 | * |
| 19 | * |
| 20 | ** |
| 21 | *** |
| 22 | *** |
| 23 | ** |
| 24 | ** |
| 25 | ** |
| 26 | *** |
| 27 | *** |
| 28 | ** |
| 29 | *** |
| 30 | ** |
| 31 | ** |
| 32 | *** |
| 33 E1 | *** |
| 33 E2 | *** |
| 34 | *** |
| 35 | ** |
| 36 | ** |
| 38 | ** |
| 39 | ** |
| 40 E1 | *** |
| 40 E2 | ** |
| 41 E1 | ** |
| 41 E2 | ** |
| 42 | * |
| 43 | * |
| 44 | * |
| 45 | * |
| 46 E1 | * |
| 46 E2 | * |
| 47 E1 | *** |
| 47 E2 | ** |
| 48 E1 | *** |
| 48 E2 | *** |
| 49 | ** |
| 60 E2 | *** |
| 61 | *** |
| 62 | *** |
| 63 | *** |
| 64 | *** |
| 65 | *** |
| 66 | *** |
| 67 | *** |
| 68 | ** |
| 133 | *** |
| 134 | |
| 135 | ** |
| 136 | ** |
| 137 | ** |
| 138 | *** |
| 139 | *** |
| 140 | *** |
| 141 | *** |
| 142 | *** |
| 143 | *** |
| 144 | *** |
| 145 | *** |
| 153 | * |
| 154 | ** |
| 155 | *** |
| 156 | * |
| 157 | * |
| 158 | |
| 168 E1 | * |
| 168 E2 | * |
| 169 | * |
| 170 | *** |
| 171 | * |
| 172 | ** |
| 174 | ** |
| 175 | * |
| 177 | |
| 178 | ** |
| 179 | *** |
| 180 | *** |
| 182 E1 | ** |

TABLE 6-continued

In Vitro Potency in the Hela Human IDO-1 Cellular Assay

| Example No. | Hela Human IDO-1 IC$_{50}$ (nM) |
|---|---|
| 182 E2 | * |
| 183 | ** |
| 184 | *** |
| 185 | *** |
| 186 | *** |
| 187 | ** |
| 188 | * |
| 189 | * |
| 190 | * |
| 243 | ** |
| 244 | ** |
| 245 | * |
| 246 | * |
| 247 | * |
| 248 | ** |
| 249 | * |
| 250 | * |
| 251 E1 | * |
| 251 E2 | * |
| 252 | * |
| 253 | * |
| 254 | |
| 255 E1 | * |
| 255 E2 | * |
| 256 E1 | *** |
| 256 E2 | *** |
| 257 | ** |
| 258 | ** |
| 259 | ** |
| 260 | ** |
| 261 E1 | * |
| 261 E2 | * |
| 262 | * |
| 263 | * |
| 264 E1 | ** |
| 264 E2 | *** |
| 265 E1 | *** |
| 265 E2 | *** |
| 267 | *** |
| 268 | *** |
| 269 | ** |
| 318 E1 | *** |
| 318 E2 | *** |
| 319 | *** |
| 320 | * |
| 321 E1 | *** |
| 321 E2 | *** |
| 322 | *** |
| 323 | *** |
| 324 | ** |
| 325 | *** |
| 326 | ** |
| 327 | * |
| 328 | * |
| 329 | ** |
| 330 | *** |
| 331 | ** |
| 332 | * |
| 333 | * |
| 334 E1 | *** |
| 334 E2 | *** |
| 335 | ** |
| 339 E1 | *** |
| 339 E2 | *** |
| 340 | ** |
| 341 | * |
| 342 | ** |
| 343 | *** |
| 345 | * |
| 346 | ** |
| 347 | *** |
| 348 E1 | * |
| 348 E2 | * |
| 349 | *** |
| 352 | ** |
| 353 | *** |
| 354 | ** |
| 355 | *** |
| 356 | *** |
| 357 | ** |
| 358 | ** |
| 359 | * |
| 360 | * |
| 361 | *** |
| 362 | *** |
| 363 | ** |
| 364 | *** |
| 365 | ** |
| 366 | * |
| 367 | ** |
| 368 | ** |
| 369 | * |
| 370 | ** |
| 371 | ** |
| 372 | ** |
| 380 | ** |
| 381 | ** |
| 382 | ** |
| 383 | * |
| 384 | * |
| 385 | * |
| 386 | * |
| 389 | ** |
| 390 | *** |
| 391 | ** |
| 392 | *** |
| 393 | ** |
| 394 | ** |
| 395 | * |
| 396 | * |
| 397 | * |
| 398 | *** |
| 399 | *** |
| 400 | ** |
| 401 | *** |
| 402 | ** |
| 403 | * |
| 404 | ** |
| 405 | * |
| 406 | * |
| 407 | ** |
| 408 | ** |
| 409 | ** |
| 410 | ** |
| 411 | *** |
| 412 | *** |
| 413 | *** |
| 414 | ** |
| 415 | *** |
| 417 | ** |
| 418 | ** |
| 419 | * |
| 420 | * |
| 421 | * |
| 422 E1 | * |
| 422 E2 | * |
| 423 | * |
| 430 | ** |
| 431 | * |
| 441 | * |
| 442 | * |
| 443 D1 | *** |
| 443 D2 | ** |
| 444 | *** |
| 448 | * |
| 449 | ** |
| 450 | * |
| 451 D1 | ** |
| 451 D2 | * |
| 459 | ** |

TABLE 6-continued

In Vitro Potency in the Hela Human IDO-1 Cellular Assay

| Example No. | Hela Human IDO-1 IC$_{50}$ (nM) |
|---|---|
| 460 | *** |
| 461 | *** |
| 462 | *** |
| 463 | * |
| 464 | *** |
| 465 | *** |
| 466 | *** |
| 467 | ** |
| 502 | ** |
| 503 | *** |
| 504 | *** |
| 505 | ** |
| 506 | * |
| 507 | *** |
| 508 | *** |
| 509 | *** |
| 510 | *** |
| 525 | ** |
| 542 | *** |
| 543 | *** |
| 544 | *** |
| 545 | ** |
| 546 | *** |
| 547 | *** |
| 548 | ** |
| 549 | *** |
| 550 | *** |
| 551 | *** |
| 552 | *** |
| 553 | *** |
| 554 | *** |
| 555 | *** |
| 556 | ** |
| 557 E1 | ** |
| 557 E2 | *** |
| 558 | *** |
| 559 | ** |
| 565 | ** |
| 566 | ** |
| 567 | ** |
| 568 | *** |
| 570 | ** |
| 571 | *** |
| 572 | ** |
| 573 | ** |
| 574 | *** |
| 575 | ** |
| 576 | ** |
| 577 | * |
| 598 | ** |
| 599 | ** |
| 600 | *** |
| 601 | *** |
| 602 E1 | * |
| 602 E2 | * |
| 603 | * |
| 604 | * |
| 605 D1 | * |
| 605 D2 | * |
| 606 | * |
| 607 | * |
| 620 | ** |
| 621 | ** |
| 622 | * |
| 624 | * |
| 625 | *** |
| 626 | ** |
| 627 | *** |
| 628 | *** |
| 629 | ** |
| 630 | ** |
| 631 | ** |
| 632 | ** |
| 634 | ** |
| 635 | * |
| 668 E1 | * |
| 668 E2 | * |
| 669 | * |
| 670 | * |
| 671 E1 | * |
| 671 E2 | * |
| 672 | * |
| 673 | * |
| 674 E1 | ** |
| 674 E2 | * |
| 675 | * |
| 693 | * |
| 749 E1 | * |
| 749 E2 | * |
| 750 | * |
| 751 | * |
| 752 | * |
| 753 | * |
| 843 | *** |
| 844 | *** |
| 845 | ** |
| 846 | *** |
| 847 | *** |
| 848 | *** |
| 849 | * |
| 850 | *** |
| 851 | *** |
| 852 | ** |
| 853 | *** |
| 854 | *** |
| 855 | ** |
| 856 | *** |
| 857 | ** |
| 858 | *** |
| 859 | *** |
| 860 | *** |
| 861 | *** |
| 862 | *** |
| 863 | *** |
| 864 | *** |
| 865 | *** |
| 866 | ** |
| 867 | *** |
| 868 | ** |
| 869 | ** |
| 870 | *** |
| 871 | * |
| 872 | ** |
| 873 | ** |
| 874 | *** |
| 875 | ** |
| 876 | ** |
| 877 | * |
| 878 | * |
| 879 | * |
| 880 | ** |
| 881 | * |
| 882 | ** |
| 883 | ** |
| 884 | *** |
| 885 | * |
| 886 | * |
| 887 | *** |
| 888 | *** |
| 889 | *** |
| 890 | ** |
| 909 | ** |
| 910 | ** |
| 911 | * |
| 912 | *** |
| 913 | *** |
| 914 | * |
| 915 | * |
| 916 | *** |
| 917 | * |

TABLE 6-continued

In Vitro Potency in the Hela Human IDO-1 Cellular Assay

| Example No. | Hela Human IDO-1 IC$_{50}$ (nM) |
|---|---|
| 918 | ** |
| 919 | * |
| 920 | *** |
| 921 | *** |
| 922 | ** |
| 923 | ** |
| 924 | ** |
| 925 | ** |
| 926 | ** |
| 928 E1 | * |
| 928 E2 | * |
| 929 | ** |
| 930 | ** |
| 931 | * |
| 932 | * |
| 933 | * |
| 934 | * |
| 935 | * |
| 936 | * |
| 937 | *** |
| 938 | * |
| 939 | ** |
| 940 | *** |
| 943 | *** |
| 945 D1 | ** |
| 945 D2 | ** |
| 946 D1 | ** |
| 946 D2 | *** |
| 947 D1 | ** |
| 947 D2 | ** |
| 948 D1 | ** |
| 948 D2 | ** |
| 1253 E1 | ** |
| 1253 E2 | *** |
| 1254 | ** |
| 1255 | ** |
| 1256 | * |
| 1257 E1 | *** |
| 1257 E2 | *** |
| 1258 | *** |
| 1259 | ** |
| 1260 | ** |
| 1261 | *** |
| 1262 | ** |
| 1263 | ** |
| 1264 E1 | * |
| 1264 E2 | * |
| 1265 | ** |
| 1266 | ** |
| 1267 | *** |
| 1268 | * |
| 1269 | ** |
| 1270 | ** |
| 1271 | * |
| 1272 | ** |
| 1281 | * |
| 1282 | * |
| 1283 | * |
| 1284 | * |
| 1285 | * |
| 1286 | * |
| 1287 | * |
| 1288 | * |
| 1289 | * |
| 1290 | * |
| 1291 | * |
| 1292 | ** |
| 1293 | * |
| 1294 | * |
| 1295 | ** |
| 1296 | * |
| 1297 | * |
| 1298 | * |
| 1299 | * |
| 1300 | ** |
| 1301 | * |
| 1302 | * |
| 1303 | ** |
| 1304 | ** |
| 1305 | * |
| 1306 | * |
| 1307 | * |
| 1308 | ** |
| 1309 | ** |
| 1310 | * |
| 1311 D1 | * |
| 1311 D2 | * |
| 1312 | * |
| 1313 | * |
| 1314 D1 | * |
| 1314 D2 | * |
| 1315 E1 | * |
| 1315 E2 | * |
| 1316 | * |
| 1317 | * |
| 1318 E1 | * |
| 1318 E2 | * |
| 1319 E1 | ** |
| 1319 E2 | ** |
| 1320 | * |
| 1320 | ** |
| 1322 E1 | * |
| 1322 E2 | * |
| 1325 | ** |
| 1327 | |
| 1328 | * |
| 1329 | *** |
| 1332 | * |
| 1333 | * |
| 1335 | * |
| 1336 D1 | ** |
| 1337 | ** |
| 1338 | ** |
| 1339 | *** |
| 1340 | |
| 1341 | |
| 1342 | ** |
| 1345 | * |
| 1346 | ** |
| 1349 | * |
| 1350 E1 | *** |
| 1350 E2 | *** |
| 1351 | ** |
| 1354 | *** |
| 1357 E1 | * |
| 1357 E2 | ** |
| 1358 | * |
| 1359 | * |
| 1360 | *** |
| 1361 | *** |
| 1362 | *** |
| 1363 | *** |
| 1364 | *** |
| 1366 | * |
| 1368 | * |
| 1376 | *** |
| 1377 | ** |
| 1378 | *** |
| 1379 | *** |
| 1380 | *** |

What is claimed is:

1. A compound of formula I

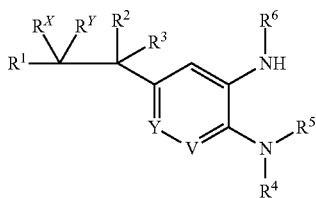

wherein:

Y is N, CH or CF;

V is N, CH or CF;

$R^1$ is —COOH, —COO$C_1$-$C_6$ alkyl, —CONH$_2$, —CN, optionally substituted 5 or 6 membered heterocyclyl having 1-4 ring vertices independently selected from O, N, S, 5 or 6 membered optionally substituted heteroaryl having 1-4 ring vertices independently selected from O, N, S, —NHCONHR$^{13}$, —CONHSO$_2$R$^{14}$, —CONHCOR$^{13}$, —SO$_2$NHCOR$^{13}$, —CONR$^{13}$, —CONHSO$_2$NR$^{13}$R$^{14}$, —SO$_2$NHR$^{13}$, —NHCONHSO$_2$R$^{13}$, —CHCF$_3$OH, —COCF$_3$, —CR$^2$R$^3$OH, or —NHSO$_2$R$^{13}$;

$R^{13}$ is H, optionally substituted $C_1$-$C_{10}$ alkyl, optionally substituted $C_3$-$C_8$ cycloalkyl, optionally substituted $C_2$-$C_{10}$ alkenyl, optionally substituted $C_2$-$C_{10}$ alkynyl, optionally substituted 5-6 membered heterocyclyl having 1-4 ring vertices independently selected from O, N, S, optionally substituted phenyl, or optionally substituted 5-6 membered heteroaryl having 1-4 vertices independently selected from O, N, S;

$R^{14}$ is H, optionally substituted $C_1$-$C_{10}$ alkyl, phenyl, or $C_{3-8}$ cycloalkyl;

$R^2$ and $R^3$ are independently -hydrogen, optionally substituted $C_1$-$C_{10}$ alkyl, optionally substituted $C_{3-8}$ cycloalkyl, or optionally substituted phenyl; or $R^2$ and $R^3$ are taken together with the carbon to which they are attached to form an optionally substituted 3- to 6-membered carbocyclic or heterocyclic ring;

$R^4$ and $R^5$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl containing 0-3 heteroatoms selected form N, S and O, optionally substituted $C_3$-$C_8$ cycloalkyl or optionally substituted heterocyclyl containing 0-3 heteroatoms selected form N, S and O; or $R^4$ and $R^5$ are taken together with the nitrogen to which they are attached to form a 4- to 8-membered optionally substituted heterocyclic ring containing 0-3 additional heteroatoms selected from —N—, —S— and —O—; or $R^4$ and $R^5$ are taken together with the nitrogen to which they are attached to form a 6- to 10-membered optionally substituted heterobicyclic ring containing 0-3 additional heteroatoms selected from —N—, —S—, and —O—;

$R^6$ is optionally substituted 5 or 6 membered aryl, optionally substituted 5 or 6 membered heteroaryl having 1 to 4 ring vertices selected from O, N, S, optionally substituted $C_3$-$C_8$ cycloalkyl optionally substituted 9 to 10 membered fused bicyclic heterocyclyl having 1 to 4 ring vertices independently selected from O, N, S, 9 to 10 membered fused bicyclic heteroaryl having 1 to 4 vertices independently selected from O, N, S or —COR$^7$;

$R^7$ is optionally substituted —CR$^2$R$^3$— 5 or 6 membered aryl, optionally substituted —CR$^2$R$^3$— 5 or 6 membered heteroaryl, —CR$^2$R$^3$— 3 to 6 membered heterocyclyl, optionally substituted 5 or 6 membered aryl, optionally substituted 5 or 6 membered heteroaryl, optionally substituted $C_3$-$C_8$ cycloalkyl, or optionally substituted 3 to 6 membered heterocyclyl; and $R^x$ and $R^y$ are each independently H, optionally substituted $C_1$-$C_{10}$ alkyl, optionally substituted $C_1$-$C_{10}$ alkoxy, or optionally substituted $C_3$-$C_8$ cycloalkyl; or $R^x$ and $R^y$ are taken together with the carbon to which they are attached to form a 3- to 7-membered heterocyclic ring containing 0-3 additional heteroatoms selected from —N—, —S— and —O—;

and/or a stereoisomer, a tautomer or a pharmaceutically acceptable salt thereof.

2. The compound according to claim 1 wherein $R^x$ and $R^y$ are H, methyl, or methoxy.

3. The compound according to claim 1 wherein $R^2$ and $R^3$ are each independently H, methyl, ethyl, methoxymethyl, haloalkyl, or alkoxy.

4. The compound according to claim 1, wherein $R^1$ is —COOH, —CONHSO$_2$R$^{14}$, —NHSO$_2$R$^{14}$, —CHCF$_3$OH, or is selected from the group consisting of

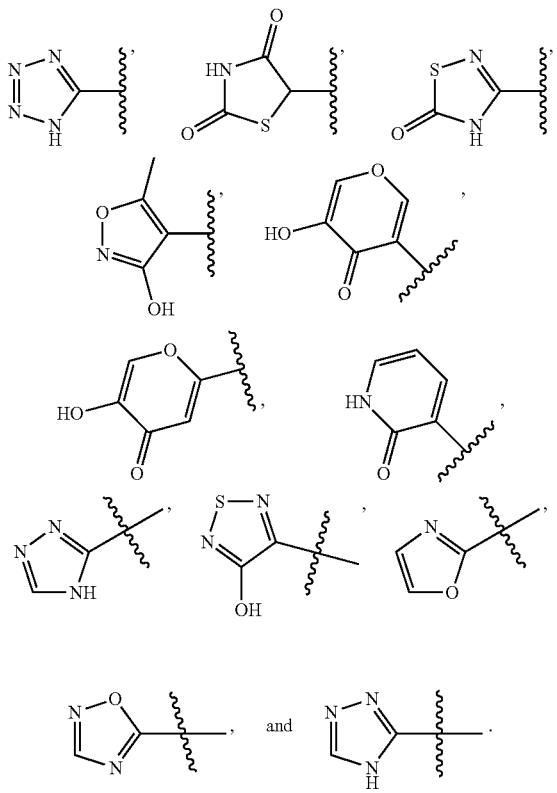

5. The compound according to claim 4, wherein $R^1$ is —COOH, —CONHSO$_2$R$^{14}$, —NHSO$_2$R$^{14}$, —CHCF$_3$OH,

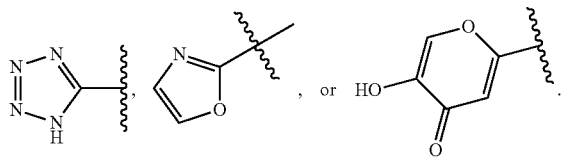

, or

6. The compound according to claim 5 wherein $R^1$ is —COOH.

7. The compound according to claim 1 wherein:
$R^4$ is optionally substituted $C_1$ to $C_6$ alkyl, optionally substituted $C_3$ to $C_6$ cycloalkyl; or selected from the group consisting of optionally substituted tetrahydropyranyl, optionally substituted azetidinyl, optionally substituted morpholinyl, optionally substituted piperidinyl, optionally substituted pyrrolidinyl, optionally substituted piperazinyl, or an optionally substituted heterocyclic ring selected from

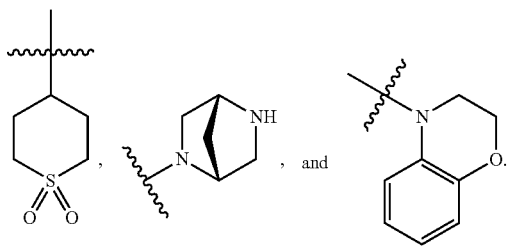 [SMILES: *C1CCS(=O)(=O)CC1 ; "," ; *N1C[C@H]2C[C@@H]1CN2 ; "," ; "and" ; *N1CCOc2ccccc21]

, and

8. The compound according to claim 1, wherein $R^5$ is —H, optionally substituted $C_1$ to $C_6$ alkyl, or optionally substituted $C_3$ to $C_6$ cycloalkyl.

9. The compound according to claim 1, wherein $R^4$ is $C_1$ to $C_6$ alkyl optionally substituted with hydroxyl; $C_3$ to $C_6$ cycloalkyl, optionally substituted with at least one of $C_1$ to $C_6$ alkyl, hydroxyl, and/or alkoxy; azetidinyl optionally substituted with hydroxyl, halo, or alkoxy; tetrahydropyranyl; morpholinyl optionally substituted with at least one of at least one of $C_1$ to $C_6$ alkyl and/or phenyl; piperidinyl optionally substituted with at least one of $C_1$ to $C_6$ alkyl, phenyl and/or benzyl; cyclohexyl; pyrrolidinyl optionally substituted with at least one of —OH, hydroxyalkyl, methoxyalkyl and/or haloalkyl; piperazinyl optionally substituted with at least one of $C_1$ to $C_4$ alkyl and/or —COOR$^{13}$;

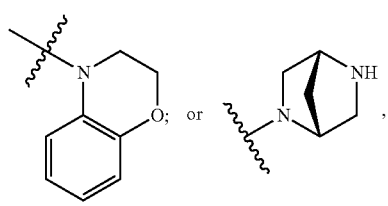 [SMILES: *N1CCOc2ccccc21 ; "or" ; *N1C[C@H]2C[C@@H]1CN2 ; ","]

; or optionally substituted with phenyl, —COOR$_{13}$, alkyl, haloalkyl, or benzyl.

10. The compound according to claim 1, wherein $R^4$ is optionally substituted $C_1$ to $C_6$ alkyl.

11. The compound according to claim 1 wherein $R^4$ is optionally substituted tetrahydropyranyl.

12. The compound according to claim 1 wherein $R^4$ is optionally substituted morpholinyl.

13. The compound according to claim 1 wherein $R^4$ is optionally substituted piperidinyl.

14. The compound according to claim 1 wherein $R^4$ is optionally substituted pyrrolidinyl.

15. The compound according to claim 1, wherein $R^4$ and $R^5$ are taken together with the nitrogen to which they are attached to form an optionally substituted heterocyclyl selected from the group consisting of morpholinyl, piperidinyl, azetidinyl, piperazinyl,

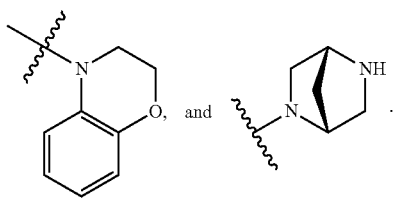 [SMILES: *N1CCOc2ccccc21 ; "and" ; *N1C[C@H]2C[C@@H]1CN2 ; "."]

, and

16. The compound according to claim 1, wherein $R^6$ is optionally substituted phenyl; optionally substituted pyrimidinyl; optionally substituted pyridyl; optionally substituted pyrazinyl, optionally substituted pyridazinyl, an optionally substituted heterocyclic ring selected from the group consisting of

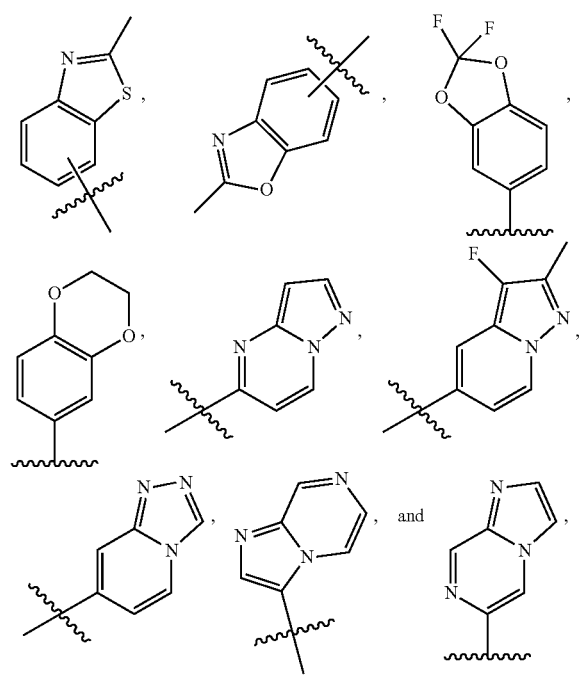

, and or —COR$^7$ wherein $R^7$ is optionally substituted benzyl, —CF$_2$phenyl, —CH$_2$-isoxalyl, or optionally substituted phenyl.

17. The compound according to claim 1, wherein $R^6$ is phenyl optionally substituted with from 1 to 3 substituents selected from $C_1$ to $C_6$ alkyl, —CN, halo, alkoxy, haloalkoxy, and/or —SO$_2$-alkyl.

18. The compound according to claim 1, wherein $R^6$ is pyrimidinyl optionally substituted with at least one of $C_1$ to $C_6$ alkyl, $C_1$ to $C_6$ alkoxy, —CN, and/or amino.

19. The compound according to claim 1, wherein $R^6$ is pyridyl, optionally substituted with at least one of alkoxy, amino, and/or CONH$_2$.

20. The compound according to claim 1, wherein:
Y is CH or CF;
V is CH or CF;
$R^1$ is —COOH;
$R^2$ and $R^3$ are independently hydrogen, optionally substituted $C_1$ to $C_6$ alkyl, $C_3$ to $C_6$ cycloalkyl, phenyl, or $R^2$ and $R^3$ join together with the carbon to which they are attached to form tetrahydropyranyl;
$R^4$ is H, optionally substituted $C_1$ to $C_6$ alkyl, tetrahydropyranyl, optionally substituted cyclohexyl,

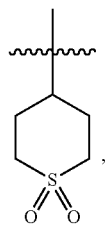

optionally substituted piperazinyl, optionally substituted piperidinyl, optionally substituted pyrrolidinyl, optionally substituted diazabicycloheptanyl, or furanyl; or
$R^4$ and $R^5$ are taken together with the nitrogen to which they are attached to form optionally substituted morpholinyl, optionally substituted piperidinyl, optionally substituted piperazinyl, optionally substituted

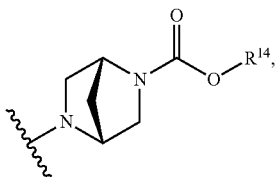

or optionally substituted pyrrolidinyl; and
$R^6$ is optionally substituted phenyl, optionally substituted pyrimidinyl, morpholinyl, or —$COR^7$ wherein $R^7$ is optionally substituted phenyl.

21. A compound that is
(S)-3-(4-((1,1-dioxidotetrahydro-2H-thiopyran-4-yl)(isobutyl)amino)-3-((2-methylbenzo[d]thiazol -5-yl)amino)phenyl)pentanoic acid;
(S)-3-(3-((2,2-difluorobenzo[d][1,3] dioxol-5-yl)amino)-4-((1,1-dioxidotetrahydro -2H-thiopyran-4-yl)(isobutyl)amino)phenyl)pentanoic acid;
(S)-3-(4-(cyclohexyl(2-hydroxy-2-methylpropyl)amino)-3-((4-fluorophenyl) amino)phenyl)pentanoic acid;
(S)-3-(4-(cyclohexyl(2-hydroxy-2-methylpropyl)amino)-3-((4-difluoromethody)phenyl)amino)phenyl)pentanoic acid;
(S)-3-(3-((4-cyanophenyl)amino)-4-(cyclohexyl(2-hydroxy-2-methylpropyl) amino)phenyl)pentanoic acid;
(S)-3-(4-(cyclohexyl(2-hydroxy-2-methylpropyl)amino)-3-((4-ethylphenyl) amino)phenyl)pentanoic acid;
(S)-3-(4-(ethyl(tetrahydro-2H-pyran-4-yl)amino)-3-(p-tolylamino)phenyl)-4-methoxybutanoic acid;
(S)-3-(4-(ethyl(tetrahydro-2H-pyran-4-yl)amino)-3-((4-ethylphenyl)amino)phenyl)-4-methoxybutanoic acid;
(S)-3-(4-(ethyl(tetrahydro-2H-pyran-4-yl)amino)-3-((4-fluorophenyl)amino)phenyl)-4-methoxybutanoic acid;
(S)-3-(3-((4-chlorophenyl) amino)-4-(ethyl(tetrahydro-2H-pyran-4-yl)amino) phenyl)-4-methoxybutanoic acid;
3-(3-((4-chlorophenyl) amino)-4-(cyclohexyl (isobutyl)amino)phenyl) pentanoic acid;
3-(4-(cyclohexyl(isobutyl) amino)-3-((4-ethylphenyl) amino)phenyl)pentanoic acid;
3-(3-((4-chloro-3-fluorophenyl)amino)-4-(cyclohexyl (isobutyl) amino)phenyl)pentanoic acid;
3-(4-(cyclohexyl(isobutyl) amino)-3-((4-fluorophenyl) amino)phenyl)pentanoic acid;
3-(4-(cyclohexyl(isobutyl) amino)-3-((4-(trifluoromethoxy)phenyl) amino)phenyl)pentanoic acid;
3-(4-(cyclohexyl(isobutyl) amino)-3-((4-ethoxyphenyl) amino) phenyl)pentanoic acid;
3-(3-((4-cyanophenyl) amino)-4-(cyclohexyl (isobutyl) amino)phenyl) pentanoic acid;
(R)-3-(3-((2-Ethoxypyrimidin-5-yl)amino)-4-(ethyl(tetrahydro-2H-pyran-4-yl) amino)phenyl)pentanoic acid;
(R)-3-(3-((4-ethoxyphenyl) amino)-4-(ethyl (tetrahydro-2H-pyran-4-yl)amino)phenyl)pentanoic acid;
(R)-3-(4-(ethyl(tetrahydro-2H-pyran-4-yl)amino)-3-((4-(2,2,2-trifluoroethoxy) phenyl)amino)phenyl)pentanoic acid;
(R)-3-(3-((4-(cyclopropylmethoxy) phenyl)amino)-4-(ethyl(tetrahydro-2 H-pyran-4-yl) amino)phenyl)pentanoic acid;
(R)-3-(4-(ethyl(tetrahydro-2H-pyran-4-yl)amino)-3-((4-ethylphenyl)amino) phenyl)pentanoic acid;
(R)-3-(4-(ethyl(tetrahydro-2H-pyran-4-yl)amino)-3-((6-methoxypyridin-3-yl)amino)phenyl)pentanoic acid;
(R)-3-(4-(ethyl(tetrahydro-2 H-pyran-4-yl)amino)-3-((2-methoxypyrimidin-5-yl) amino)phenyl)pentanoic acid;
(R)-3-(3-((2-(cyclopropylmethoxy) pyrimidin-5-yl) amino)-4-(ethyl(tetrahydro-2H-pyran-4-yl) amino) phenyl) pentanoic acid;
and/or a stereoisomer, a tautomer or a pharmaceutically acceptable salt thereof.

22. The compound of claim 21 that is (S)-3-(3-((4-chlorophenyl) amino)-4-(ethyl(tetrahydro-2H-pyran-4-yl) amino) phenyl)-4-methoxybutanoic acid
and/or a stereoisomer, a tautomer or a pharmaceutically acceptable salt thereof.

23. The compound of claim 21 that is 3-(4-(cyclohexyl (isobutyl) amino)-3-((4-ethylphenyl) amino)phenyl)pentanoic acid
and/or a stereoisomer, a tautomer or a pharmaceutically acceptable salt thereof.

24. The compound of claim 21 that is (R)-3-(3-((2-Ethoxypyrimidin-5-yl)amino)-4-(ethyl(tetrahydro-2H-pyran-4-yl)amino)phenyl)pentanoic acid and/or a stereoisomer, a tautomer or a pharmaceutically acceptable salt thereof.

25. The compound of claim 21 that is 3-(4-(cyclohexyl (isobutyl) amino)-3-((4-fluorophenyl) amino)phenyl)pentanoic acid and/or a stereoisomer, a tautomer or a pharmaceutically acceptable salt thereof.

26. A method of inhibiting activity of indoleamine 2,3-dioxygenase comprising contacting said indoleamine 2,3-dioxygenase with a compound according to claim 1 or a pharmaceutically acceptable salt thereof.

27. A pharmaceutical composition comprising one or more compounds of claim 1 and a pharmaceutical carrier.

* * * * *

UNITED STATES PATENT AND TRADEMARK OFFICE
CERTIFICATE OF CORRECTION

PATENT NO. : 9,790,169 B2
APPLICATION NO. : 15/088211
DATED : October 17, 2017
INVENTOR(S) : James Aaron Balog et al.

It is certified that error appears in the above-identified patent and that said Letters Patent is hereby corrected as shown below:

In the Claims

Claim 1, Column 921, Line 34, after "1-4" insert -- ring --.

Claim 1, Column 921, Line 49, delete "form" and insert -- from --, therefor.

Claim 1, Column 921, Line 52, delete "form" and insert -- from --, therefor.

Claim 1, Column 921, Line 65, after "vertices" insert -- independently --.

Claim 1, Column 922, Line 3, before "vertices" insert -- ring --.

Claim 21, Column 925, Line 47, delete "thiazol -5-yl)" and insert -- thiazol-5-yl) --, therefor.

Claim 21, Column 925, Line 50, delete "dioxidotetrahydro -2H-" and insert -- dioxidotetrahydro-2H- --, therefor.

Claim 21, Column 925, Line 55, delete "difluoromethody)" and insert -- difluoromethoxy) --, therefor.

Claim 21, Column 926, Line 27, delete "-2 H-" and insert -- -2H- --, therefor.

Claim 21, Column 926, Line 34 (Approx.), delete "-2 H-" and insert -- -2H- --, therefor.

Signed and Sealed this
Eighth Day of May, 2018

Andrei Iancu
*Director of the United States Patent and Trademark Office*